US012480141B2

(12) United States Patent
Casini et al.

(10) Patent No.: US 12,480,141 B2
(45) Date of Patent: Nov. 25, 2025

(54) TYPE V CAS PROTEINS AND APPLICATIONS THEREOF

(71) Applicant: Alia Therapeutics Srl, Milan (IT)

(72) Inventors: Antonio Casini, Trento (IT); Antonio Carusillo, Trento (IT); Veronica Pinamonti, Trento (IT); Matteo Ciciani, Schio (IT); Maddalena Bosetti, Terre d'Adige (IT)

(73) Assignee: Alia Therapeutics Srl, Milan (IT)

( * ) Notice: Subject to any disclaimer, the term of this patent is extended or adjusted under 35 U.S.C. 154(b) by 0 days.

(21) Appl. No.: 19/232,045

(22) Filed: Jun. 9, 2025

(65) Prior Publication Data

US 2025/0313864 A1 Oct. 9, 2025

Related U.S. Application Data

(63) Continuation of application No. PCT/EP2025/059128, filed on Apr. 3, 2025.

(60) Provisional application No. 63/574,354, filed on Apr. 4, 2024.

(51) Int. Cl.
*C12N 15/90* (2006.01)
*C12N 9/22* (2006.01)
*C12N 15/11* (2006.01)

(52) U.S. Cl.
CPC .......... *C12N 15/907* (2013.01); *C12N 9/226* (2025.05); *C12N 15/11* (2013.01); *C07K 2319/09* (2013.01); *C12N 2310/20* (2017.05)

(58) Field of Classification Search
None
See application file for complete search history.

(56) References Cited

U.S. PATENT DOCUMENTS

| | | | | |
|---|---|---|---|---|
| 9,790,490 | B2 | 10/2017 | Zhang et al. | |
| 11,225,649 | B2 | 1/2022 | Donohoue et al. | |
| 2021/0230677 | A1 | 7/2021 | Wang et al. | |
| 2023/0340537 | A1* | 10/2023 | Zhang | C12N 9/1276 |

FOREIGN PATENT DOCUMENTS

| | | | |
|---|---|---|---|
| EP | 3283625 | B1 | 2/2018 |
| WO | WO2021011829 | A1 | 1/2021 |
| WO | WO2023028444 | A1 | 3/2023 |
| WO | WO2024020346 | A2 | 1/2024 |
| WO | 2024026499 | A2 | 2/2024 |
| WO | WO2025137461 | A1 | 6/2025 |

OTHER PUBLICATIONS

Blanco-Míguez, et al., 2023, "Extending and improving metagenomic taxonomic profiling with uncharacterized species using MetaPhlAn 4," Nature Biotechnology 41(11):1633-1644.
Database RefSeq, 2023 "type V CRISPR-associated protein Cas12a/Cpf1 [uncultured *Mogibacterium* sp.]" NCBI Reference Sequence: WP_288963892.1.

* cited by examiner

*Primary Examiner* — Nancy J Leith
(74) *Attorney, Agent, or Firm* — Biospark Intellectual Property Law

(57) ABSTRACT

Type V Cas proteins, for example Type V Cas proteins referred to as ZWGD, ZJHK, ZIKV, ZZFT, YYAN, ZZGY, ZKBG, ZZKD, ZXPB, ZPPX, ZXHQ, ZQKH, ZRGM, ZTAE, ZSQQ, ZSYN, ZRBH, ZWPU, ZZQE, and ZRXE Type V Cas proteins; gRNAs for Type V Cas proteins; systems comprising Type V Cas proteins and gRNAs; nucleic acids encoding the Type V Cas proteins, gRNAs and systems; particles comprising the foregoing; pharmaceutical compositions of the foregoing; and uses of the foregoing, for example to alter the genomic DNA of a cell.

23 Claims, 22 Drawing Sheets

Specification includes a Sequence Listing.

ZWGD crRNA

ZJHK crRNA

ZIKV crRNA

ZZFT crRNA

YYAN crRNA

ZZGY crRNA

ZKBG crRNA

ZZKD crRNA

ZXPB crRNA

ZPPX crRNA

ZXHQ crRNA

ZQKH crRNA

ZRGM crRNA

ZTAE crRNA

ZSQQ crRNA

ZSYN crRNA

ZRBH crRNA

ZWPU crRNA

ZZQE crRNA

ZRXE crRNA

TYPE V CAS PROTEINS AND APPLICATIONS THEREOF

1. CROSS-REFERENCE TO RELATED APPLICATIONS

This application is a continuation of PCT application no. PCT/EP2025/059128, filed Apr. 3, 2025, which claims the priority benefit of U.S. provisional application No. 63/574,354, filed Apr. 4, 2024, the contents of each of which are incorporated herein in their entireties by reference thereto.

2. SEQUENCE LISTING

The instant application contains a Sequence Listing which has been submitted electronically in XML format and is hereby incorporated by reference in its entirety. Said XML Sequence Listing, created on Mar. 25, 2025, is named ALA-013WO_SL.xml and is 679,601 bytes in size.

3. BACKGROUND

CRISPR-Cas systems (Clustered Regularly Interspaced Short Palindromic Repeats-CRISPR associated proteins) are powerful tools with the potential to treat a variety of genetic diseases. The CRISPR-Cas systems are classified into two classes (Class 1 and 2) that are subdivided into six types (Type 1 through VI). Class 1 (Type I, III and IV) systems use multiple Cas proteins in their CRISPR ribonucleoprotein effector nucleases, and Class 2 systems (Type II, V and VI) use a single Cas protein. Cas9, belonging to Class 2 Type II CRISPR-Cas system, is the most extensively used tool for genome editing.

However, there are some challenges in using CRISPR-Cas9 systems. For example, packaging a large Cas protein such as SpCas9 together with a guide RNA into a single AAV vector (Adeno-associated viral vectors) can be challenging due to the limited packaging capacity of AAVs. Type V Cas proteins such as Cas12a target T-rich sequences, which in principle allow Type V Cas proteins to access different genomic regions as compared to Cas9. Type V Cas proteins typically produce staggered ends when it creates a double stranded DNA cut (while Cas9 creates a blund end), which may be an advantage in certain situations such as during gene insertions and substitutions. Type V Cas proteins also typically produce mid sized deletions at the target site (generally tens of nucleotides) allowing for the removal of target sequences locally (e.g. binding sites for transcription factors, splice sites, etc). In comparison, Cas9 produces relatively small indels (generally insertion or deletion of a few nucleotides). Type V Cas proteins such as Cas12a are typically capable of processing their own crRNA from larger transcripts, which can make multiplexing easier.

Thus, there is a need for new Cas nucleases, especially Type V Cas nucleases.

4. SUMMARY

This disclosure is based, in part, on the discovery of a Type V Cas protein from an unclassified bacterium from the Candidatus Saccharibacteria phylum (referred to herein as “wildtype ZWGD type V Cas”); a Type V Cas protein from an unclassified bacterium from the Clostridiaceae family (referred to herein as “wildtype ZJHK type V Cas”); a Type V Cas protein from an unclassified bacterium from the Firmucutes phylum (referred to herein as “wildtype ZIKV type V Cas”); a Type V Cas protein from an unclassified bacterium from the Bacteroidota phylum (referred to herein as “wildtype ZZFT type V Cas”); a Type V Cas protein from an unclassified bacterium from the Firmicutes phylum (referred to herein as “wildtype YYAN type V Cas”); a Type V Cas protein from an unclassified bacterium from the Succinivibrionaceae family (referred to herein as “wildtype ZZGY type V Cas”); a Type V Cas protein from an unclassified bacterium from the Muribaculaceae family (referred to herein as “wildtype ZKBG type V Cas”); a Type V Cas protein from *Mogibacterium kristiansenii* (referred to herein as “wildtype ZZKD type V Cas”); a Type V Cas protein from an unclassified bacterium from the Bacteroidales order (referred to herein as “wildtype ZXPB type V Cas”); a Type V Cas protein from an unclassified bacterium from the Prevotellaceae family (referred to herein as “wildtype ZPPX type V Cas”); a Type V Cas protein from an unclassified bacterium from the phylum Candidatus Roizmanbacteria (referred to herein as “wildtype ZXHQ type V Cas”); a Type V Cas protein from an unclassified bacterium from the phylum Bacteroidota (referred to herein as “wildtype ZQKH type V Cas”); a Type V Cas protein from an unclassified bacterium from the phylum Firmicutes (referred to herein as “wildtype ZRGM type V Cas”); a Type V Cas protein from an unclassified bacterium from the phylum Kiritimatiellaeota (referred to herein as “wildtype ZTAE type V Cas”); a Type V Cas protein from an unclassified bacterium from the phylum Fibrobacteres (referred to herein as “wildtype ZSQQ type V Cas”); a Type V Cas protein from an unclassified bacterium from the phylum Firmicutes (referred to herein as “wildtype ZSYN type V Cas”); a Type V Cas protein from an unclassified bacterium from the phylum Firmicutes (referred to herein as “wildtype ZRBH type V Cas”); a Type V Cas protein from an unclassified bacterium from the phylum Bacteroidota (referred to herein as “wildtype ZWPU type V Cas”); a Type V Cas protein from an unclassified bacterium from the Prevotellaceae family (referred to herein as “wildtype ZZQE type V Cas”); and a Type V Cas protein from an unclassified bacterium from the phylum Bacteroidota (referred to herein as “wildtype ZRXE type V Cas”).

In one aspect, the disclosure provides Type V Cas proteins whose amino acid sequence comprises an amino acid sequence that is at least 50% identical (e.g., at least 55%, at least 60%, at least 65%, at least 70%, at least 75%, at least 85%, at least 90%, at least 95%, at least 98%, at least 99% identical, or 100% identical) to SEQ ID NO:1 (such proteins referred to herein as “ZWGD Type V Cas proteins”). Exemplary ZWGD Type V Cas protein sequences are set forth in SEQ ID NO:1, SEQ ID NO:2, and SEQ ID NO:3.

In one aspect, the disclosure provides Type V Cas proteins whose amino acid sequence comprises an amino acid sequence that is at least 50% identical (e.g., at least 55%, at least 60%, at least 65%, at least 70%, at least 75%, at least 85%, at least 90%, at least 95%, at least 98%, at least 99% identical, or 100% identical) to SEQ ID NO:7 (such proteins referred to herein as “ZJHK Type V Cas proteins”). Exemplary ZJHK Type V Cas protein sequences are set forth in SEQ ID NO:7, SEQ ID NO:8, and SEQ ID NO:9.

In one aspect, the disclosure provides Type V Cas proteins whose amino acid sequence comprises an amino acid sequence that is at least 50% identical (e.g., at least 55%, at least 60%, at least 65%, at least 70%, at least 75%, at least 85%, at least 90%, at least 95%, at least 98%, at least 99% identical, or 100% identical) to SEQ ID NO:13 (such proteins referred to herein as “ZIKV Type V Cas proteins”). Exemplary ZIKV Type V Cas protein sequences are set forth in SEQ ID NO:13, SEQ ID NO:14, and SEQ ID NO:15.

In one aspect, the disclosure provides Type V Cas proteins whose amino acid sequence comprises an amino acid sequence that is at least 50% identical (e.g., at least 55%, at least 60%, at least 65%, at least 70%, at least 75%, at least 85%, at least 90%, at least 95%, at least 98%, at least 99% identical, or 100% identical) to SEQ ID NO:19 (such proteins referred to herein as "ZZFT Type V Cas proteins"). Exemplary ZZFT Type V Cas protein sequences are set forth in SEQ ID NO:19, SEQ ID NO:20, and SEQ ID NO:21.

In one aspect, the disclosure provides Type V Cas proteins whose amino acid sequence comprises an amino acid sequence that is at least 50% identical (e.g., at least 55%, at least 60%, at least 65%, at least 70%, at least 75%, at least 85%, at least 90%, at least 95%, at least 98%, at least 99% identical, or 100% identical) to SEQ ID NO:25 (such proteins referred to herein as "YYAN Type V Cas proteins"). Exemplary YYAN Type V Cas protein sequences are set forth in SEQ ID NO:25, SEQ ID NO:26, and SEQ ID NO:27.

In one aspect, the disclosure provides Type V Cas proteins whose amino acid sequence comprises an amino acid sequence that is at least 50% identical (e.g., at least 55%, at least 60%, at least 65%, at least 70%, at least 75%, at least 85%, at least 90%, at least 95%, at least 98%, at least 99% identical, or 100% identical) to SEQ ID NO:31 (such proteins referred to herein as "ZZGY Type V Cas proteins"). Exemplary ZZGY Type V Cas protein sequences are set forth in SEQ ID NO:31, SEQ ID NO:32, and SEQ ID NO:33.

In one aspect, the disclosure provides Type V Cas proteins whose amino acid sequence comprises an amino acid sequence that is at least 50% identical (e.g., at least 55%, at least 60%, at least 65%, at least 70%, at least 75%, at least 85%, at least 90%, at least 95%, at least 98%, at least 99% identical, or 100% identical) to SEQ ID NO:37 (such proteins referred to herein as "ZKBG Type V Cas proteins"). Exemplary ZKBG Type V Cas protein sequences are set forth in SEQ ID NO:37, SEQ ID NO:38, and SEQ ID NO:39.

In one aspect, the disclosure provides Type V Cas proteins whose amino acid sequence comprises an amino acid sequence that is at least 50% identical (e.g., at least 55%, at least 60%, at least 65%, at least 70%, at least 75%, at least 85%, at least 90%, at least 95%, at least 98%, at least 99% identical, or 100% identical) to SEQ ID NO:43 (such proteins referred to herein as "ZZKD Type V Cas proteins"). Exemplary ZZKD Type V Cas protein sequences are set forth in SEQ ID NO:43, SEQ ID NO:44, and SEQ ID NO:45.

In one aspect, the disclosure provides Type V Cas proteins whose amino acid sequence comprises an amino acid sequence that is at least 50% identical (e.g., at least 55%, at least 60%, at least 65%, at least 70%, at least 75%, at least 85%, at least 90%, at least 95%, at least 98%, at least 99% identical, or 100% identical) to SEQ ID NO:49 (such proteins referred to herein as "ZXPB Type V Cas proteins"). Exemplary ZXPB Type V Cas protein sequences are set forth in SEQ ID NO:49, SEQ ID NO:50, and SEQ ID NO:51.

In one aspect, the disclosure provides Type V Cas proteins whose amino acid sequence comprises an amino acid sequence that is at least 50% identical (e.g., at least 55%, at least 60%, at least 65%, at least 70%, at least 75%, at least 85%, at least 90%, at least 95%, at least 98%, at least 99% identical, or 100% identical) to SEQ ID NO:55 (such proteins referred to herein as "ZPPX Type V Cas proteins"). Exemplary ZPPX Type V Cas protein sequences are set forth in SEQ ID NO:55, SEQ ID NO:56, and SEQ ID NO:57.

In one aspect, the disclosure provides Type V Cas proteins whose amino acid sequence comprises an amino acid sequence that is at least 50% identical (e.g., at least 55%, at least 60%, at least 65%, at least 70%, at least 75%, at least 85%, at least 90%, at least 95%, at least 98%, at least 99% identical, or 100% identical) to SEQ ID NO:61 (such proteins referred to herein as "ZXHQ Type V Cas proteins"). Exemplary ZXHQ Type V Cas protein sequences are set forth in SEQ ID NO:61, SEQ ID NO:62, and SEQ ID NO:63.

In one aspect, the disclosure provides Type V Cas proteins whose amino acid sequence comprises an amino acid sequence that is at least 50% identical (e.g., at least 55%, at least 60%, at least 65%, at least 70%, at least 75%, at least 85%, at least 90%, at least 95%, at least 98%, at least 99% identical, or 100% identical) to SEQ ID NO:67 (such proteins referred to herein as "ZQKH Type V Cas proteins"). Exemplary ZQKH Type V Cas protein sequences are set forth in SEQ ID NO:67, SEQ ID NO:68, and SEQ ID NO:69.

In one aspect, the disclosure provides Type V Cas proteins whose amino acid sequence comprises an amino acid sequence that is at least 50% identical (e.g., at least 55%, at least 60%, at least 65%, at least 70%, at least 75%, at least 85%, at least 90%, at least 95%, at least 98%, at least 99% identical, or 100% identical) to SEQ ID NO:73 (such proteins referred to herein as "ZRGM Type V Cas proteins"). Exemplary ZRGM Type V Cas protein sequences are set forth in SEQ ID NO:73, SEQ ID NO:74, and SEQ ID NO:75.

In one aspect, the disclosure provides Type V Cas proteins whose amino acid sequence comprises an amino acid sequence that is at least 50% identical (e.g., at least 55%, at least 60%, at least 65%, at least 70%, at least 75%, at least 85%, at least 90%, at least 95%, at least 98%, at least 99% identical, or 100% identical) to SEQ ID NO:79 (such proteins referred to herein as "ZTAE Type V Cas proteins"). Exemplary ZTAE Type V Cas protein sequences are set forth in SEQ ID NO:79, SEQ ID NO:80, and SEQ ID NO:81.

In one aspect, the disclosure provides Type V Cas proteins whose amino acid sequence comprises an amino acid sequence that is at least 50% identical (e.g., at least 55%, at least 60%, at least 65%, at least 70%, at least 75%, at least 85%, at least 90%, at least 95%, at least 98%, at least 99% identical, or 100% identical) to SEQ ID NO:85 (such proteins referred to herein as "ZSQQ Type V Cas proteins"). Exemplary ZSQQ Type V Cas protein sequences are set forth in SEQ ID NO:85, SEQ ID NO:86, and SEQ ID NO:87.

In one aspect, the disclosure provides Type V Cas proteins whose amino acid sequence comprises an amino acid sequence that is at least 50% identical (e.g., at least 55%, at least 60%, at least 65%, at least 70%, at least 75%, at least 85%, at least 90%, at least 95%, at least 98%, at least 99% identical, or 100% identical) to SEQ ID NO:91 (such proteins referred to herein as "ZSYN Type V Cas proteins"). Exemplary ZSYN Type V Cas protein sequences are set forth in SEQ ID NO:91, SEQ ID NO:92, and SEQ ID NO:93.

In one aspect, the disclosure provides Type V Cas proteins whose amino acid sequence comprises an amino acid sequence that is at least 50% identical (e.g., at least 55%, at least 60%, at least 65%, at least 70%, at least 75%, at least 85%, at least 90%, at least 95%, at least 98%, at least 99% identical, or 100% identical) to SEQ ID NO:97 (such proteins referred to herein as "ZRBH Type V Cas proteins"). Exemplary ZRBH Type V Cas protein sequences are set forth in SEQ ID NO:97, SEQ ID NO:98, and SEQ ID NO:99.

In one aspect, the disclosure provides Type V Cas proteins whose amino acid sequence comprises an amino acid sequence that is at least 50% identical (e.g., at least 55%, at least 60%, at least 65%, at least 70%, at least 75%, at least 85%, at least 90%, at least 95%, at least 98%, at least 99% identical, or 100% identical) to SEQ ID NO:103 (such proteins referred to herein as "ZWPU Type V Cas proteins"). Exemplary ZWPU Type V Cas protein sequences are set forth in SEQ ID NO:103, SEQ ID NO:104, and SEQ ID NO:105.

In one aspect, the disclosure provides Type V Cas proteins whose amino acid sequence comprises an amino acid sequence that is at least 50% identical (e.g., at least 55%, at least 60%, at least 65%, at least 70%, at least 75%, at least 85%, at least 90%, at least 95%, at least 98%, at least 99% identical, or 100% identical) to SEQ ID NO:109 (such proteins referred to herein as "ZZQE Type V Cas proteins"). Exemplary ZZQE Type V Cas protein sequences are set forth in SEQ ID NO:109, SEQ ID NO:110, and SEQ ID NO:111.

In one aspect, the disclosure provides Type V Cas proteins whose amino acid sequence comprises an amino acid sequence that is at least 50% identical (e.g., at least 55%, at least 60%, at least 65%, at least 70%, at least 75%, at least 85%, at least 90%, at least 95%, at least 98%, at least 99% identical, or 100% identical) to SEQ ID NO:115 (such proteins referred to herein as "ZRXE Type V Cas proteins"). Exemplary ZRXE Type V Cas protein sequences are set forth in SEQ ID NO:115, SEQ ID NO:116, and SEQ ID NO:117.

In another aspect, the disclosure provides Type V Cas proteins comprising an amino acid sequence having at least 50% (e.g., at least 55%, at least 60%, at least 65%, at least 70%, at least 75%, at least 85%, at least 90%, at least 95%, at least 98%, at least 99%, or 100%) sequence identity to a WED-1 domain, REC1 domain, REC2 domain, WED-II domain, PI domain, WED-III domain, RuvC-I domain, BH domain, RuvC-II domain, NUC domain, or RuvC-III domain of a ZWGD Type V Cas protein, a ZJHK Type V Cas protein, a ZIKV Type V Cas protein, a ZZFT Type V Cas protein, a YYAN Type V Cas protein, a ZZGY Type V Cas protein, a ZKBG Type V Cas protein, a ZZKD Type V Cas protein, a ZXPB Type V Cas protein, a ZPPX Type V Cas protein, a ZXHQ Type V Cas protein, a ZQKH Type V Cas protein, a ZRGM Type V Cas protein, a ZTAE Type V Cas protein, a ZSQQ Type V Cas protein, a ZSYN Type V Cas protein, a ZRBH Type V Cas protein, a ZWPU Type V Cas protein, a ZZQE Type V Cas protein, or a ZRXE Type V Cas protein.

In some embodiments, a Type V Cas protein of the disclosure is a chimeric Type V Cas protein, for example, comprising one or more domains from a ZWGD, ZJHK, ZIKV, ZZFT, YYAN, ZZGY, ZKBG, ZZKD, ZXPB, ZPPX, ZXHQ, ZQKH, ZRGM, ZTAE, ZSQQ, ZSYN, ZRBH, ZWPU, ZZQE, and/or ZRXE Type V Cas protein(s) and one or more domains from a different Type V Cas protein such as AsCas12a.

In some embodiments, the Type V Cas proteins of the disclosure are in the form of a fusion protein, for example, comprising a ZWGD Type V Cas protein, a ZJHK Type V Cas protein, a ZIKV Type V Cas protein, a ZZFT Type V Cas protein, a YYAN Type V Cas protein, a ZZGY Type V Cas protein, a ZKBG Type V Cas protein, a ZZKD Type V Cas protein, a ZXPB Type V Cas protein, a ZPPX Type V Cas protein, a ZXHQ Type V Cas protein, a ZQKH Type V Cas protein, a ZRGM Type V Cas protein, a ZTAE Type V Cas protein, a ZSQQ Type V Cas protein, a ZSYN Type V Cas protein, a ZRBH Type V Cas protein, a ZWPU Type V Cas protein, a ZZQE Type V Cas protein, or a ZRXE Type V Cas protein sequence fused to one or more additional amino acid sequences, for example, one or more nuclear localization signals and/or one or more tags. Other exemplary fusion partners can enable base editing (e.g., where the fusion partner is nucleoside deaminase) or prime editing (e.g., where the fusion partner is a reverse transcriptase).

Exemplary features of Type V Cas proteins of the disclosure are described in Section 6.2 and specific embodiments 1 to 329 and 660 to 671, infra.

In further aspects, the disclosure provides guide (gRNA) molecules and combinations of two or more gRNA molecules. In various embodiments, the disclosure provides gRNAs that can be used with a ZWGD, ZJHK, ZIKV, ZZFT, YYAN, ZZGY, ZKBG, ZZKD, ZXPB, ZPPX, ZXHQ, ZQKH, ZRGM, ZTAE, ZSQQ, ZSYN, ZRBH, ZWPU, ZZQE, or ZRXE Type V Cas protein of the disclosure. Exemplary features of the gRNAs and combinations of gRNAs of the disclosure of the disclosure are described in Section 6.3 and specific embodiments 330 to 578, infra.

In further aspects, the disclosure provides systems comprising a Type V Cas protein of the disclosure and one or more gRNAs. For example, a system can comprise a ribonucleoprotein (RNP) comprising a Type V Cas protein complexed with a gRNA. Exemplary features of systems are described in Section 6.4 and specific embodiments 579 to 594, infra.

In another aspect, the disclosure provides nucleic acids and pluralities of nucleic acids encoding a Type V Cas protein of the disclosure and, optionally, a gRNA. In some embodiments, the nucleic acids comprise a Type V Cas protein of the disclosure operably linked to a heterologous promoter, e.g., a mammalian promoter, for example a human promoter.

In another aspect, the disclosure provides nucleic acids encoding a gRNA, and, optionally, a Type V Cas protein, for example a ZWGD Type V Cas protein, a ZJHK Type V Cas protein, a ZIKV Type V Cas protein, a ZZFT Type V Cas protein, a YYAN Type V Cas protein, a ZZGY Type V Cas protein, a ZKBG Type V Cas protein, a ZZKD Type V Cas protein, a ZXPB Type V Cas protein, a ZPPX Type V Cas protein, a ZXHQ Type V Cas protein, a ZQKH Type V Cas protein, a ZRGM Type V Cas protein, a ZTAE Type V Cas protein, a ZSQQ Type V Cas protein, a ZSYN Type V Cas protein, a ZRBH Type V Cas protein, a ZWPU Type V Cas protein, a ZZQE Type V Cas protein, or a ZRXE Type V Cas protein. Exemplary features of nucleic acids and pluralities of nucleic acids are described in Section 6.5 and specific embodiments 595 to 659, infra.

In further aspects, the disclosure provides particles comprising the Type V Cas proteins, gRNAs, nucleic acids, and systems of the disclosure. Exemplary features of particles of the disclosure are described in Section 6.6 and specific embodiments 672 to 687, infra.

In another aspect, the disclosure provides cells and populations of cells containing or contacted with a Type V Cas protein, gRNA, nucleic acid, plurality of nucleic acids, system, or particle of the disclosure. Exemplary features of such cells and cell populations are described in Section 6.6 and specific embodiments 689 to 699 and 737, infra.

In another aspect, the disclosure provides pharmaceutical compositions comprising a Type V Cas protein, gRNA, nucleic acid, plurality of nucleic acids, system, particle, cell, or population of cells together with one or more excipients. Exemplary features of pharmaceutical compositions are described in Section 6.7 and specific embodiment 688, infra.

In another aspect, the disclosure provides methods of altering cells (e.g., editing the genome of a cell) using the Type V Cas proteins, gRNAs, nucleic acids, systems, particles, and pharmaceutical compositions of the disclosure. Cells altered according to the methods of the disclosure can be used, for example, to treat subjects having a disease or disorder, e.g., genetic disease or disorder. Features of exemplary methods of altering cells are described in Section 6.8 and specific embodiments 700 to 736, infra.

In another aspect, the disclosure provides methods of detecting a target nucleic acid using the Type V Cas proteins, gRNAs, and systems of the disclosure, and use of the foregoing in such methods. Features of exemplary methods of detecting target nucleic acids, and Type V Cas proteins, gRNAs, and systems for use in methods of detecting a target nucleic acid are described in Section 6.9 and specific embodiments 738 to 740, infra.

5. BRIEF DESCRIPTION OF THE FIGURES

FIGS. 1A-1E illustrate exemplary Type V-A Cas protein crRNAs (corresponding DNA sequences shown). Schematic representation of the hairpin structure generated for visualization using RNAplot after in silico folding using RNAalifold v2.4.17 of the crRNA scaffolds (not including the spacer sequence) for ZWGD Type V-A Cas protein (FIG. 1A), ZJHK Type V-A Cas protein (FIG. 1B), ZIKV Type V-A Cas protein (FIG. 1C), ZZFT Type V-A Cas protein (FIG. 1D) and YYAN Type V-A Cas protein (FIG. 1E) are shown. Figures disclose SEQ ID NOS 390-394, respectively, in order of appearance.

FIGS. 2A-2E illustrate exemplary Type V-A Cas protein crRNAs (corresponding DNA sequences shown). Schematic representation of the hairpin structure generated for visualization using RNAplot after in silico folding using RNAalifold v2.4.17 of the crRNA scaffolds (not including the spacer sequence) for ZZGY Type V-A Cas protein (FIG. 2A), ZKBG Type V-A Cas protein (FIG. 2B), ZZKD Type V-A Cas protein (FIG. 2C), ZXPB Type V-A Cas protein (FIG. 2D) or ZPPX Type V-A Cas protein (FIG. 2E). Figures disclose SEQ ID NOS 395-399, respectively, in order of appearance.

Figure 1A:
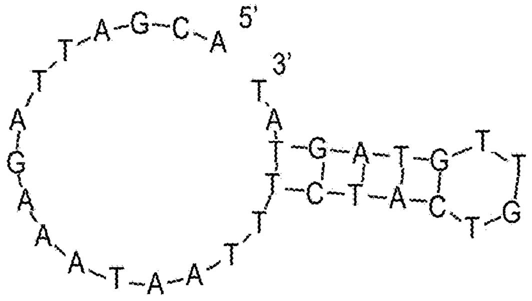
Figure 1B:
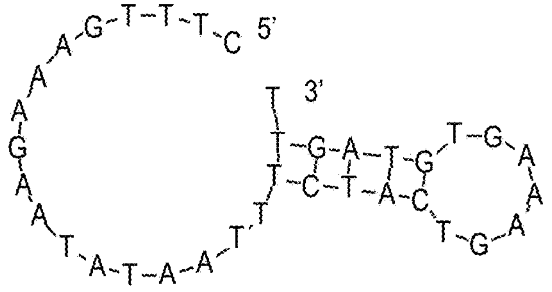
Figure 1C:
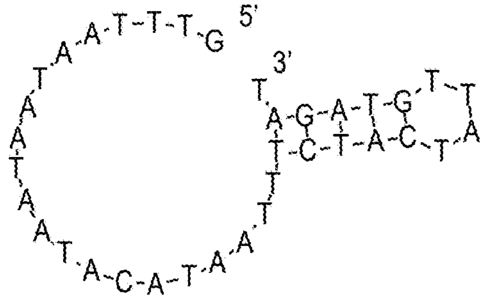
Figure 1D:
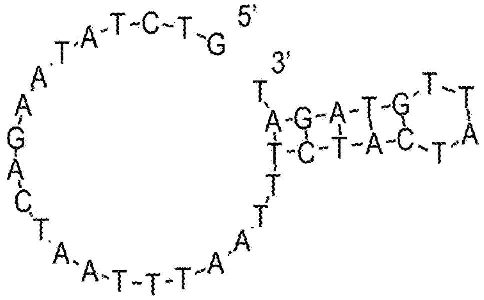
Figure 1E:
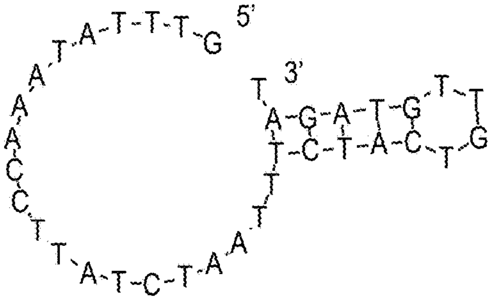
Figure 2A:
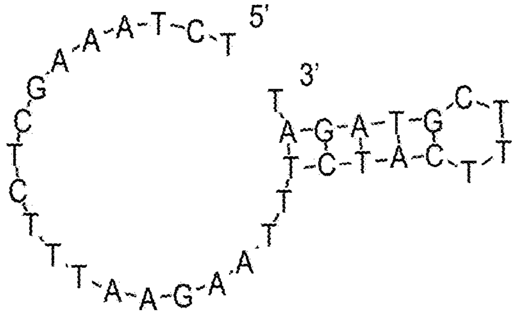
Figure 2B:
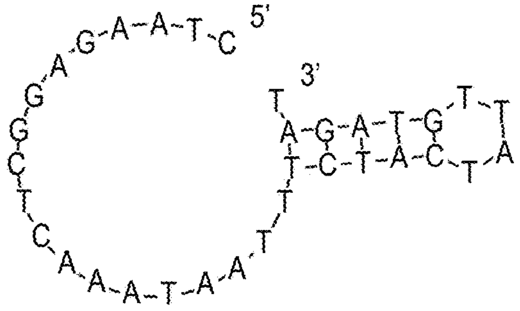
Figure 2C:
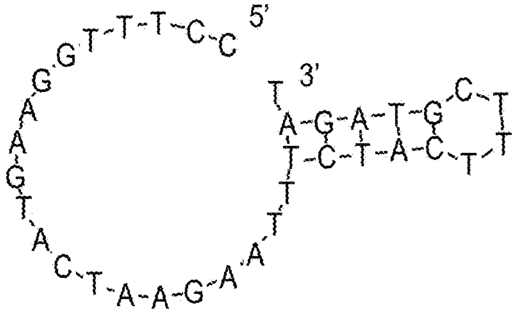
Figure 2D:
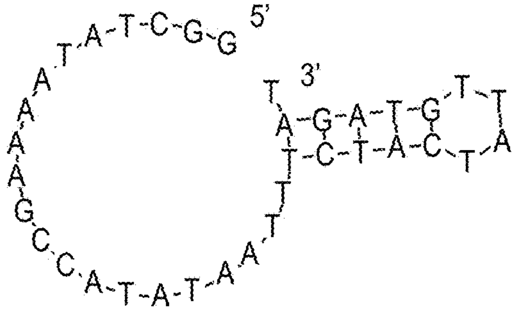
Figure 2E:
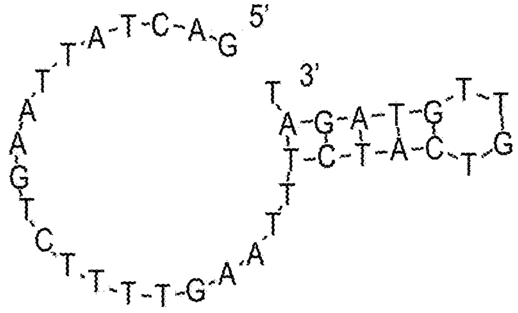
Figure 3A:
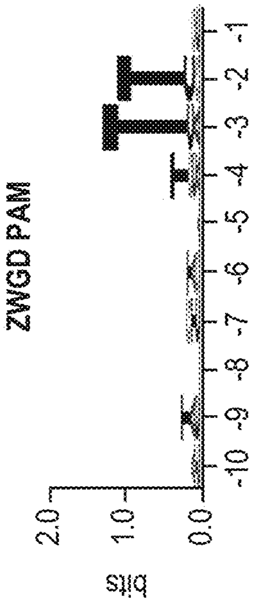
FIGS. 3A-3E illustrate in silico predicted PAM specificities for ZWGD, ZJHK, ZIKV, ZZFT and YYAN Type V-A Cas proteins. PAM sequence logos for ZWGD (FIG. 3A), ZJHK (FIG. 3B), ZIKV (FIG. 3C), ZZFT (FIG. 3D) and YYAN (FIG. 3E) Type V-A Cas proteins are shown.
Figure 3B:
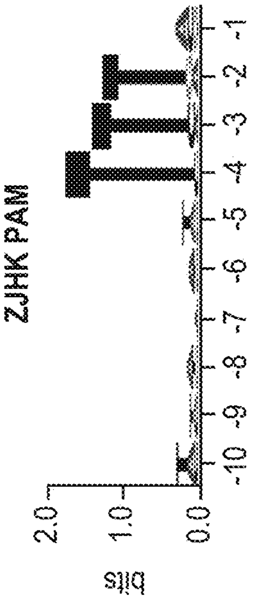
Figure 3C:
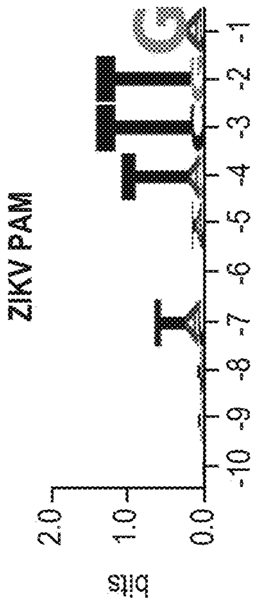
Figure 3D:
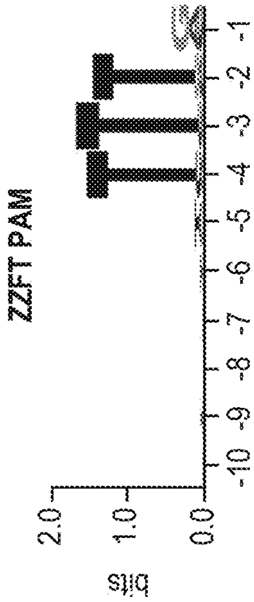
Figure 3E:
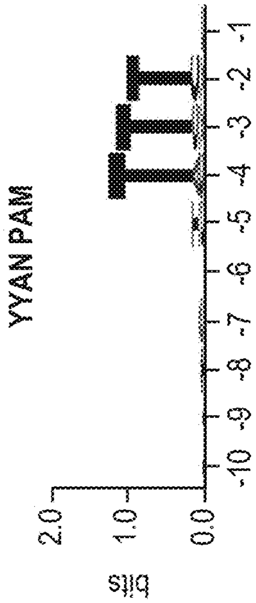
Figure 4A:
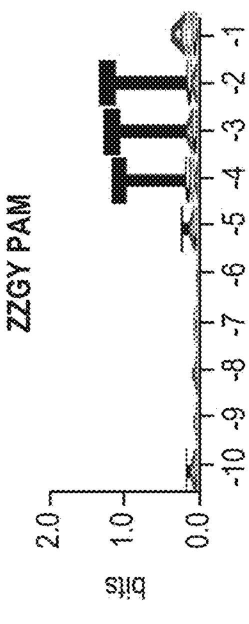
FIGS. 4A-4E illustrate in silico predicted PAM specificities for ZZGY, ZKBG, ZZKD, ZXPB and ZPPX Type V-A Cas proteins. PAM sequence logos for ZZGY (FIG. 4A), ZKGB (FIG. 4B), ZZKD (FIG. 4C), ZXPB (FIG. 4D) and ZPPX (FIG. 4E) Type V-A Cas proteins are shown.
Figure 4B:
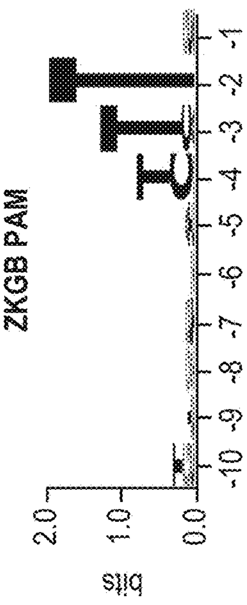
Figure 4C:
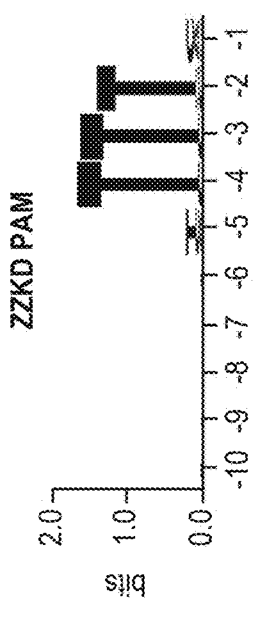
Figure 4D:
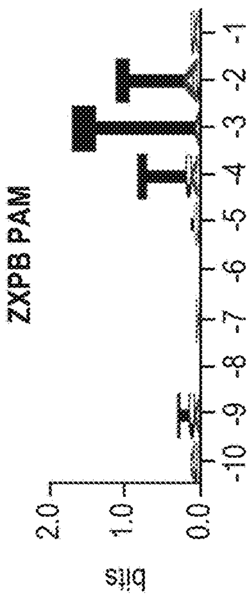
Figure 4E:
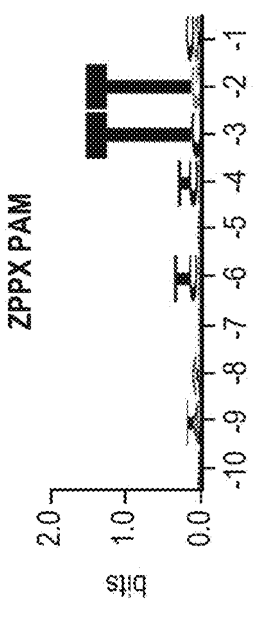
Figure 5:
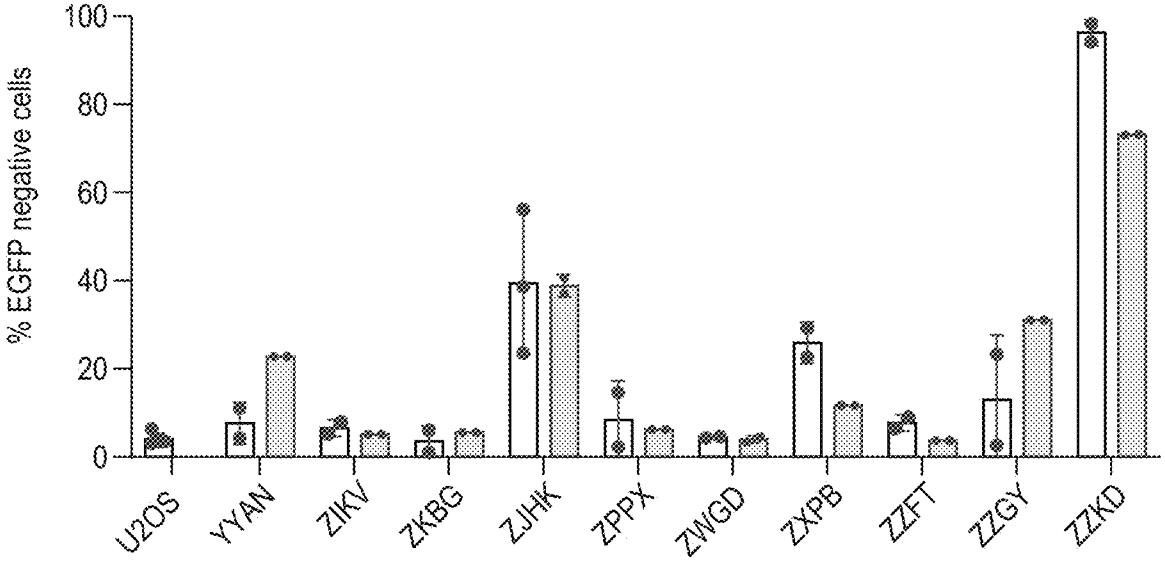

FIG. 5 illustrates activity of Type V-A Cas proteins against an EGFP reporter in mammalian cells. The activity of the selected Type V-A Cas proteins was evaluated after transient electroporation of plasmids encoding each nuclease together with the indicated guide RNAs in U2OS cells stably expressing EGFP. For each Cas protein, 2 different gRNAs targeting the same two positions of the EGFP coding sequence were evaluated. Loss of EGFP fluorescence, expressed as % of EGFP-negative cells, was measured by cytofluorimetry. Data presented as mean±SEM of n≥2 biologically independent runs. Untreated U2OS cells (U2OS sample) are included as a measurement of the background loss of fluorescence.

Figure 6A:
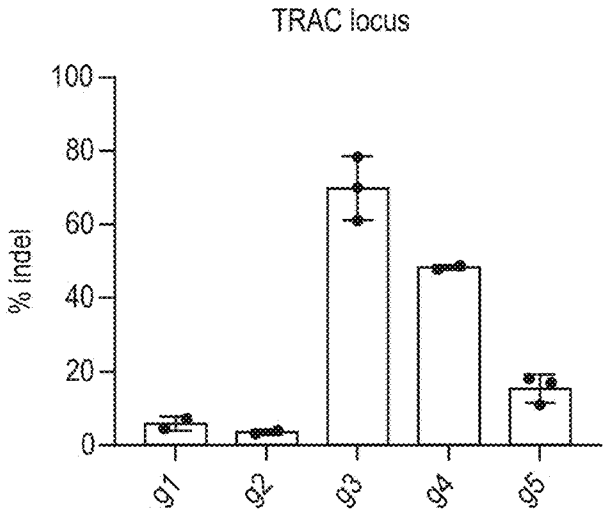
Figure 6B:
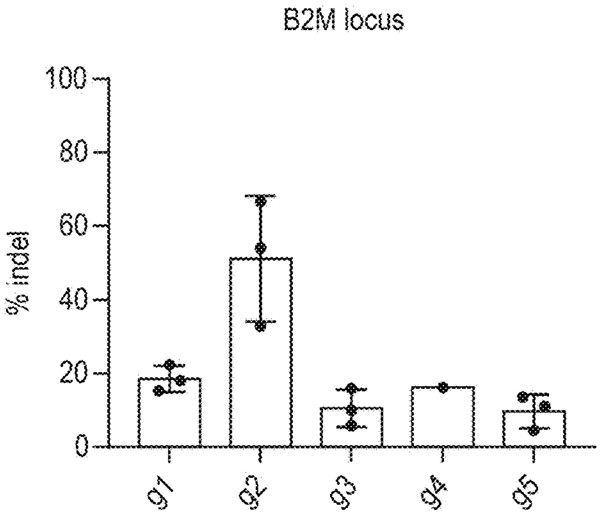
Figure 6C:
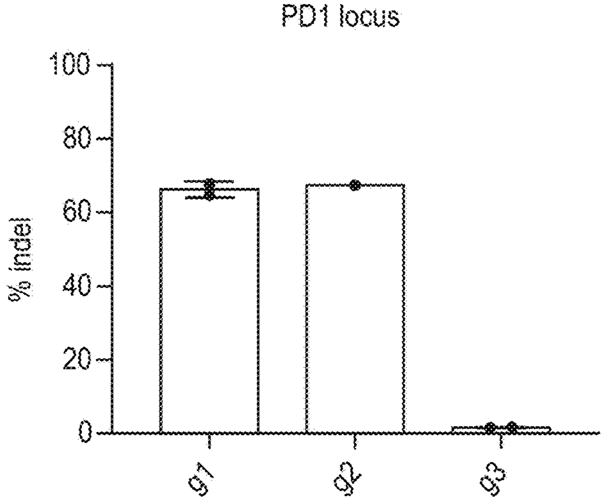
Figure 7A:
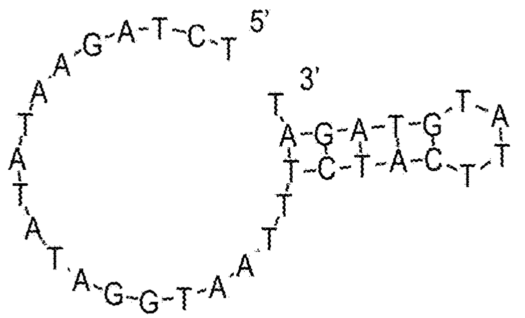
Figure 7B:
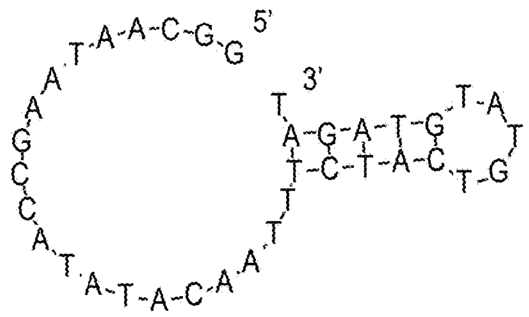
Figure 7C:
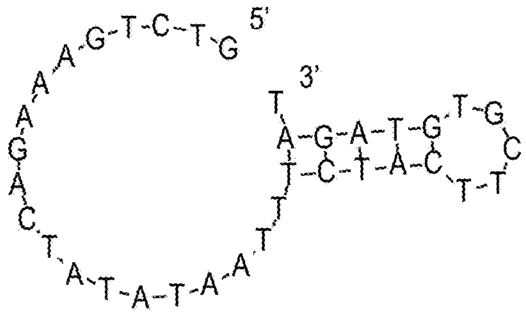
Figure 7D:
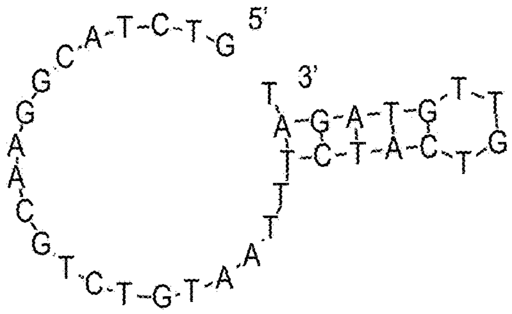
Figure 7E:
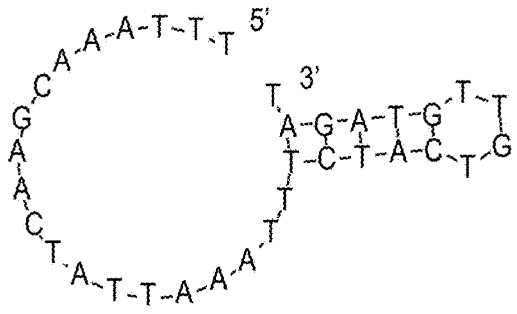
Figure 8A:
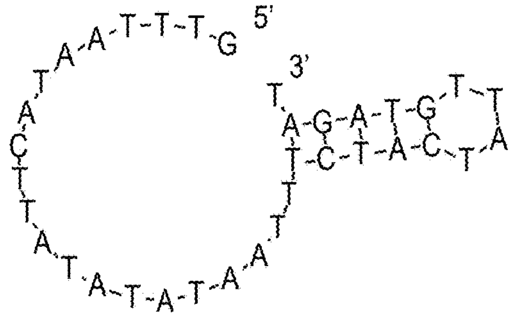
Figure 8B:
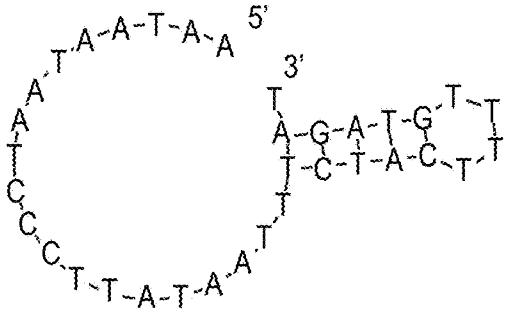
Figure 8C:
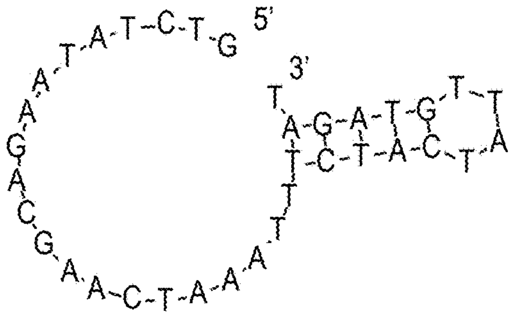
Figure 8D:
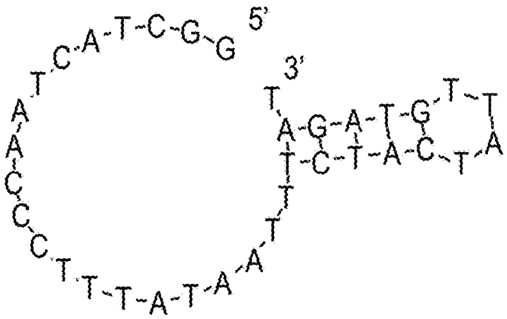
Figure 8E:
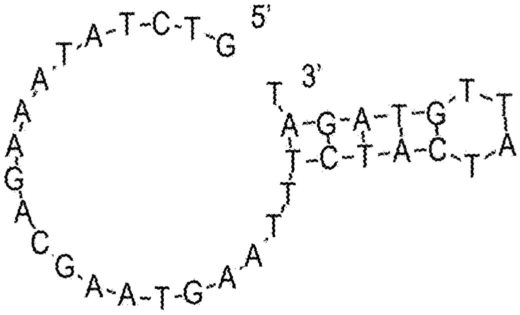

FIGS. 6A-6C illustrate activity of ZZKD Type V-A Cas protein against benchmark endogenous genomic loci in mammalian cells. The activity of ZZKD Type V-A Cas protein was evaluated after transient electroporation of plasmids encoding each nuclease together with the indicated guide RNAs in U2OS cells. Several gRNAs targeting the TRAC (FIG. 6A), B2M (FIG. 6B) and PD1 (FIG. 6C) benchmark loci were evaluated. Editing activity was measured by Sanger chromatogram deconvolution 3 days after transfection. Data presented as mean±SEM of n≥2 biologically independent runs.

FIGS. 7A-7E illustrate exemplary Type V-A Cas protein crRNAs (corresponding DNA sequences shown). Schematic representation of the hairpin structure generated for visualization using RNAplot after in silico folding using RNAalifold v2.4.17 of the crRNA scaffolds (not including the spacer sequence) for ZXHQ Type V-A Cas protein (FIG. 7A), ZQKH Type V-A Cas protein (FIG. 7B), ZRGM Type V-A Cas protein (FIG. 7C), ZTAE Type V-A Cas protein (FIG. 7D) and ZSQQ Type V-A Cas protein (FIG. 7E) are shown. Figures disclose SEQ ID NOS 400-404, respectively, in order of appearance.

FIGS. 8A-8E illustrate exemplary Type V-A Cas protein crRNAs (corresponding DNA sequences shown). Schematic representation of the hairpin structure generated for visualization using RNAplot after in silico folding using RNAalifold v2.4.17 of the crRNA scaffolds (not including the spacer sequence) for ZSYN Type V-A Cas protein (FIG. 8A), ZRBH Type V-A Cas protein (FIG. 8B), ZWPU Type V-A Cas protein (FIG. 8C), ZZQE Type V-A Cas protein (FIG. 8D) and ZRXE Type V-A Cas protein (FIG. 8E) are shown. Figures disclose SEQ ID NOS 405-409, respectively, in order of appearance.

Figure 9:
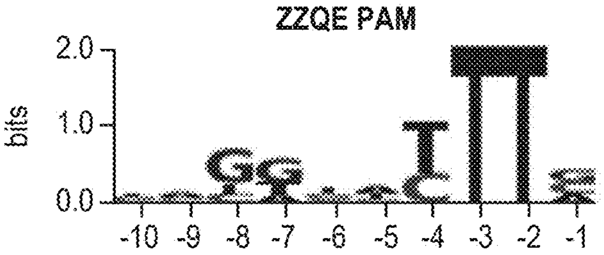

FIG. 9 illustrates in silico prediction of ZZQE Type V-A Cas protein PAM specificity. PAM sequence logo for ZZQE Type V-A Cas protein is shown.

Figure 10:
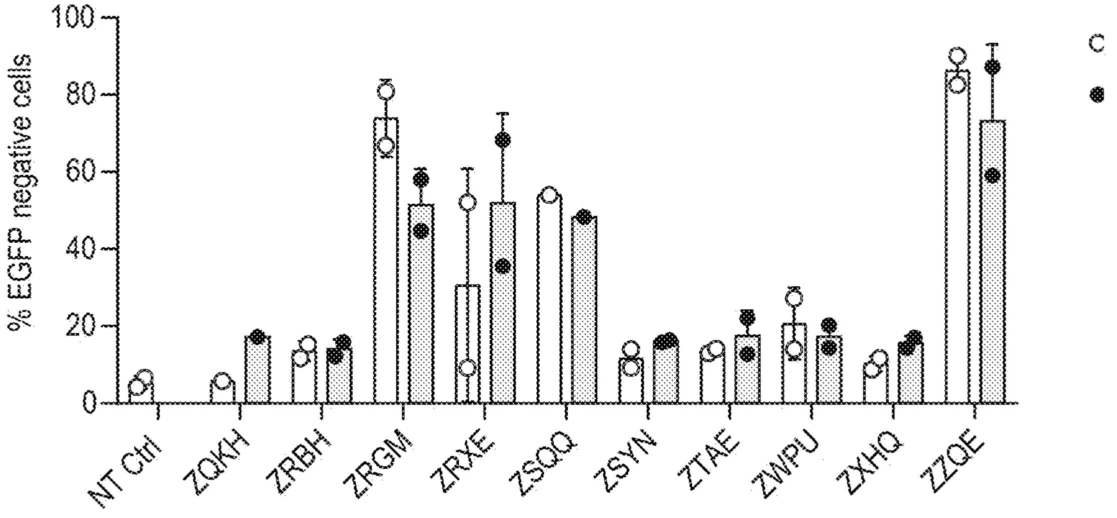

FIG. 10 shows activity of novel Type V-A Cas proteins in human cells. Evaluation of the activity of novel Type V-A Cas protein after transient electroporation in U2OS-EGFP cells. Two different guide RNAs were evaluated (target sequences are common for all proteins) and EGFP downregulation was measured by flow cytometry 5 days post-electroporation. A non-transfected control sample has been included to measure the assay background (NT Ctrl). 23nt spacers were used. Data represented as mean±SD of n=2 independent biological replicates.

Figure 11:
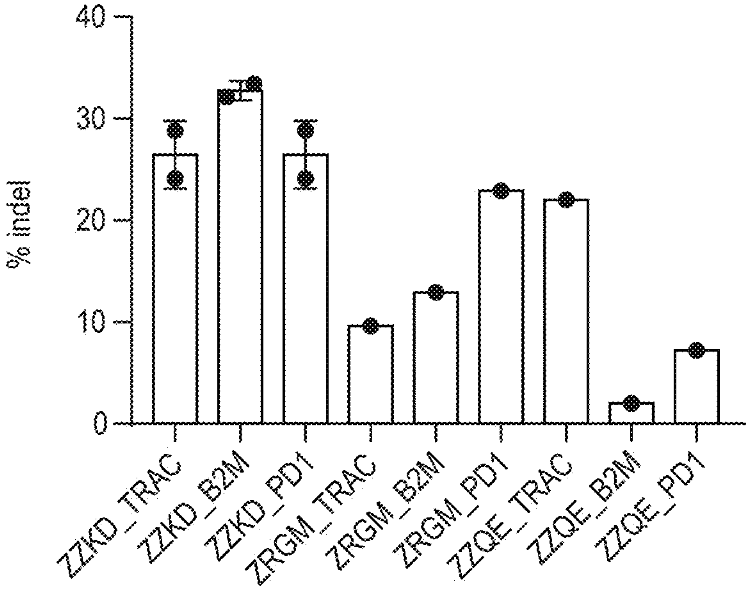

FIG. 11 shows activity of selected Type V-A Cas proteins towards endogenous genomic loci in human cells. The editing activity of ZZKD, ZRGM and ZZQE Type V-A Cas proteins was evaluated for the benchmark TRAC-g3, B2M-g2 and PD1-g2 genomic loci after transient transfection in HEK293T cells. Given the PAM compatibility among the different proteins the same spacers were used (23nt in length). For ZZKD activity on the TRAC locus, data represented as mean±SD of n=3 independent biological replicates.

Figure 12A:
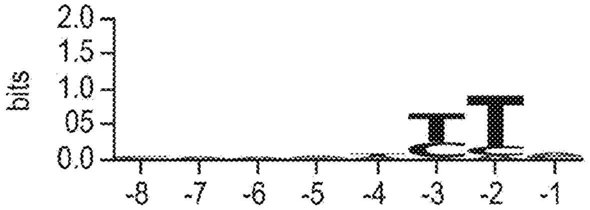
Figure 12B:
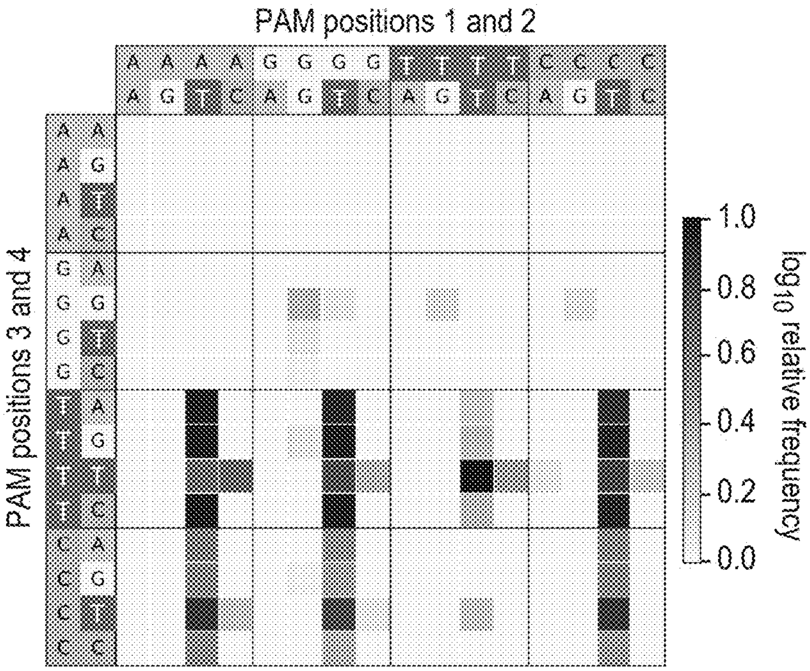
Figure 12C:
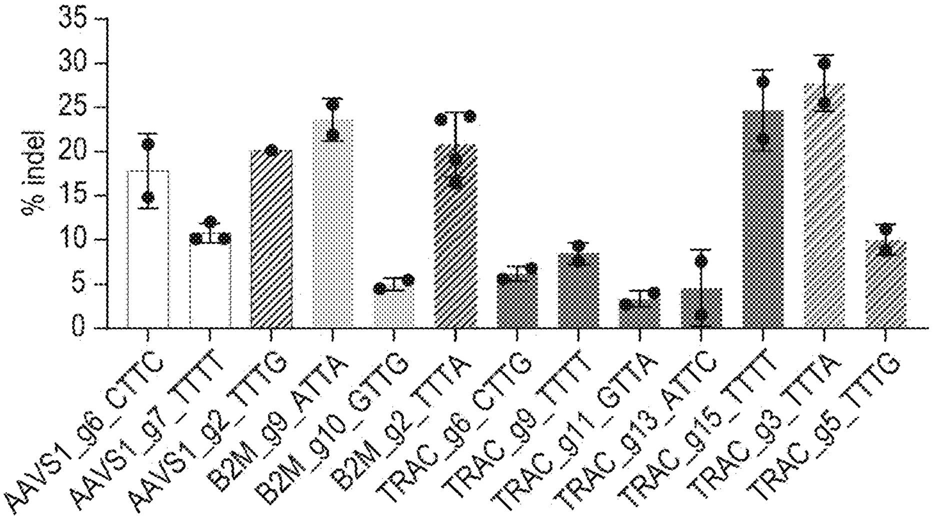

FIGS. 12A-12C show in vitro analysis of PAM preferences of ZZKD Type V-A Cas protein. A PAM sequence logo is shown in FIG. 12A and PAM heatmap is shown in FIG. 12B for ZZKD Type V-A Cas protein FIG. 12C shows validation of the PAM preferences by measurement of indel formation after transient transfection of HEK293T cells using crRNAs associated with PAMs shown to be preferentially cut by the PAM assay. The PAM associated with each guide is reported on the graph. Data represented as mean±SD of n≥2 independent biological replicates.

Figure 13A:
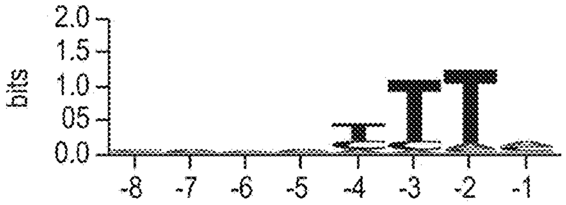
Figure 13B:
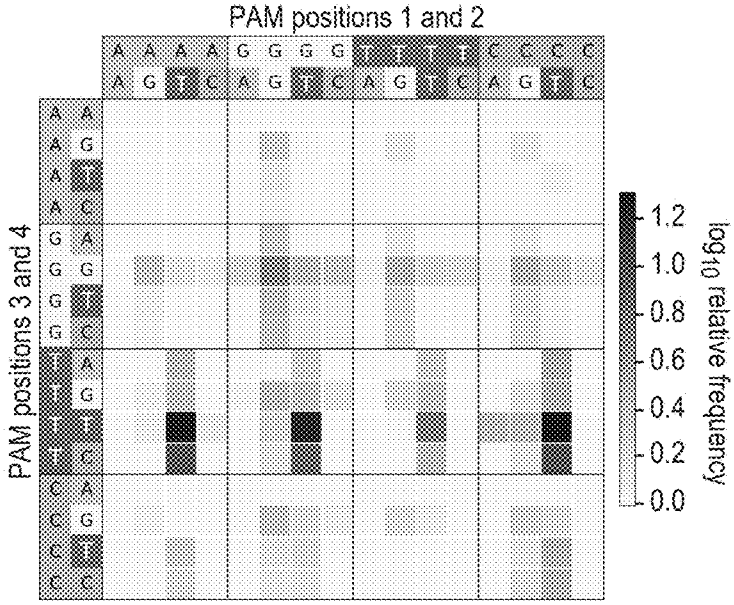
Figure 13C:
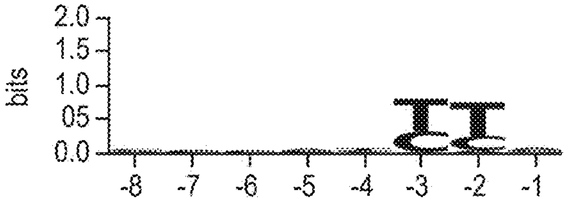
Figure 13D:
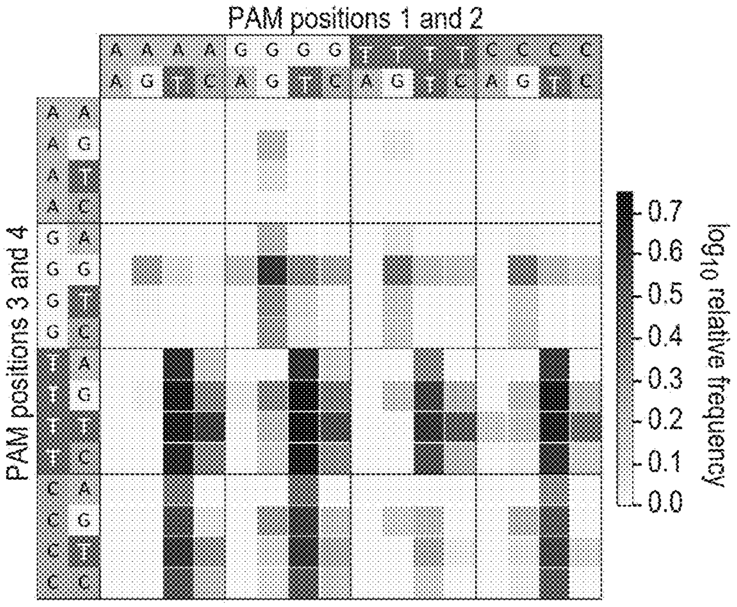

FIGS. 13A-13D show analysis of PAM preferences of ZRGM and ZZQE Type V-A Cas proteins. A PAM sequence logo is shown in FIG. 13A and a PAM heatmap is shown in FIG. 13B for ZRGM Type V-A Cas protein. A PAM sequence logo is shown in FIG. 13C and a PAM heatmap is shown in FIG. 13D for ZZQE Type V-A Cas protein.

Figure 14A:
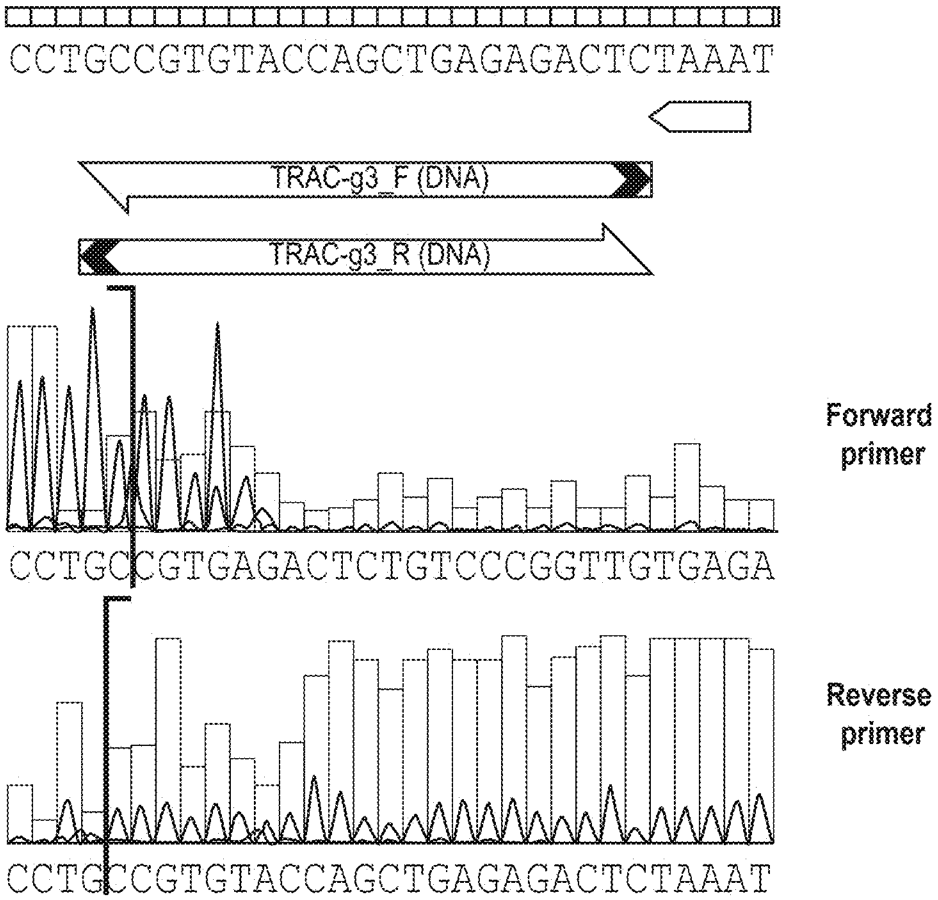
Figure 14B:
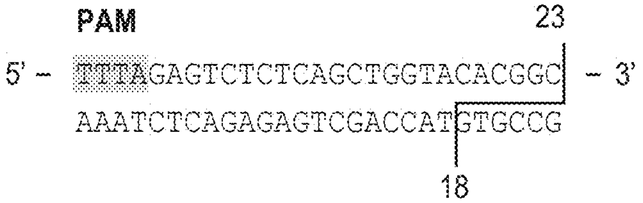

FIGS. 14A-14B illustrate in vitro determination of the double strand break profile of ZZKD Type V-A Cas protein. In vitro cleavage reactions using a PCR-generated target (TRAC-g3) and recombinant ZZKD Type V-A Cas protein were run on an agarose gel and the separated fragments were independently Sanger sequenced using a forward and a reverse primer to sequence both DNA strands. Based on the drop in the chromatographic signal in the two sequencing reactions (FIG. 14A) it was possible to determine that ZZKD type V-A Cas protein produces a 6 nucleotide staggered cut, as indicated by the solid lines in the scheme shown in FIG. 14B. Figure discloses SEQ ID NOS 410-411, 410, and 412, respectively, in order of appearance.

Figure 15:
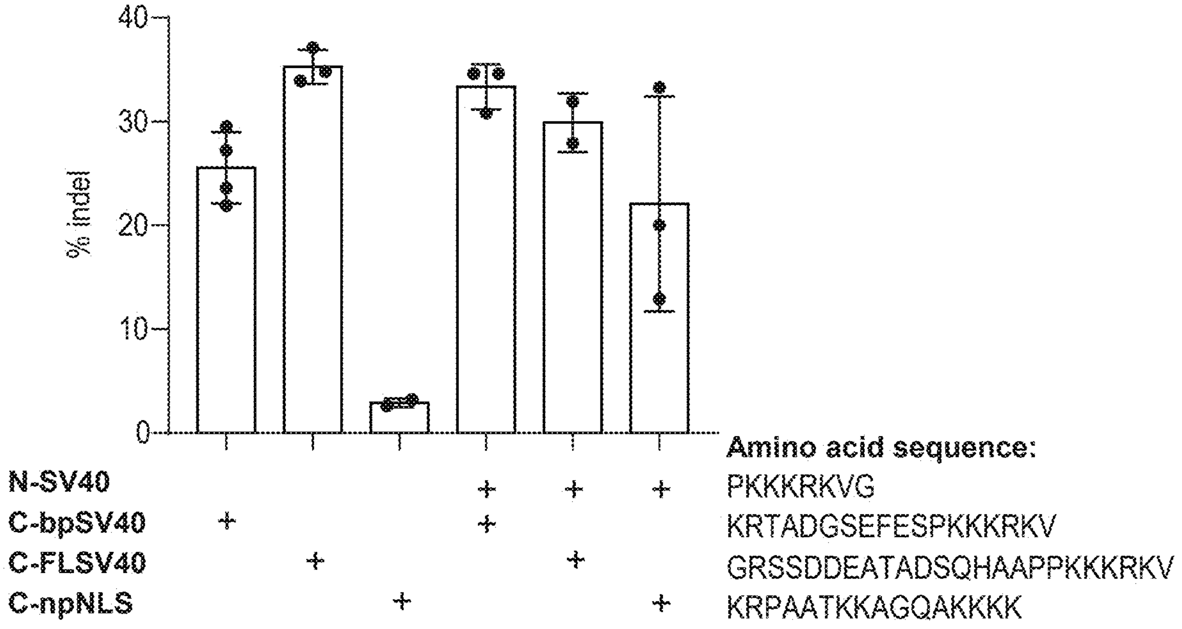

FIG. 15 shows an evaluation of alternative nuclear localization signal (NLS) designs to improve the activity of ZZKD Type V-A Cas protein. FIG. 15 plots indel formation at the TRAC locus (g3) after transient transfection of HEK293T cells with alternative versions of ZZKD Type V-A Cas proteins characterized by different nuclear localization signal sequences positioned either at the N- or the C-terminus of the protein, as indicated on the graph. The amino acid sequence of each evaluated NLS is reported in the figure. Data represented as mean±SD of n≥2 independent biological replicates. Figure discloses SEQ ID NOS 179, 122, 180, and 125, respectively, in order of appearance.

Figure 16A:
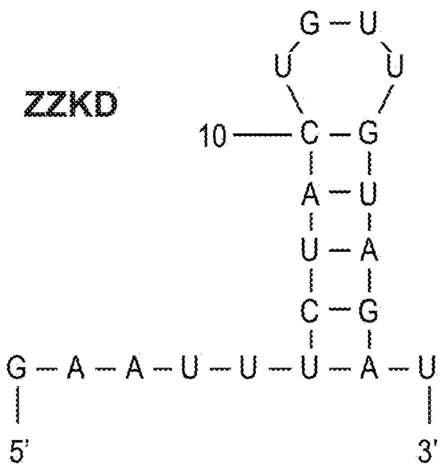
Figure 16B:
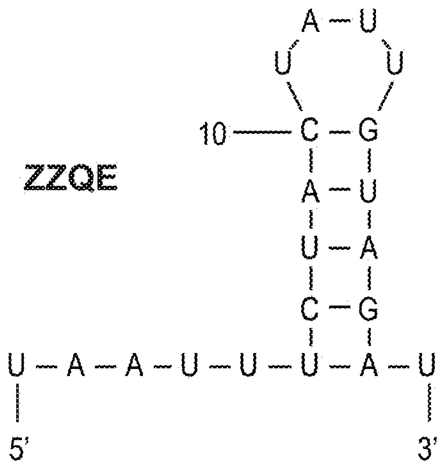
Figure 16C:
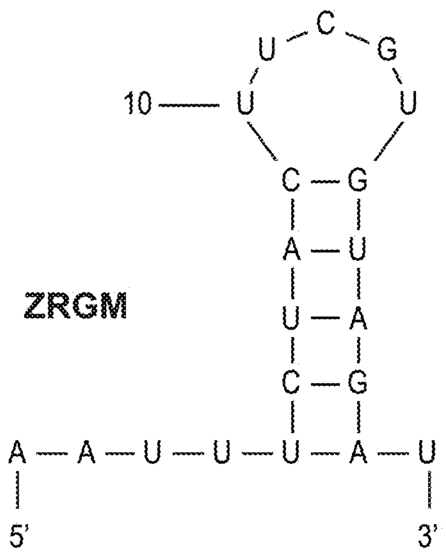

FIGS. 16A-16C show alternative crRNA scaffolds for selected Type V-A Cas proteins. Schematic representation of the hairpin structure generated for visualization using the RNAfold webserver (www.unafold.org) of the crRNA trimmed scaffolds (not including the spacer sequence) for ZZKD Type V-A Cas protein (FIG. 16A) (SEQ ID NO:211), ZZQE Type V-A Cas protein (FIG. 16B) (SEQ ID NO:212) and ZRGM Type V-A Cas protein (FIG. 16C) (SEQ ID NO:213).

Figure 17A:
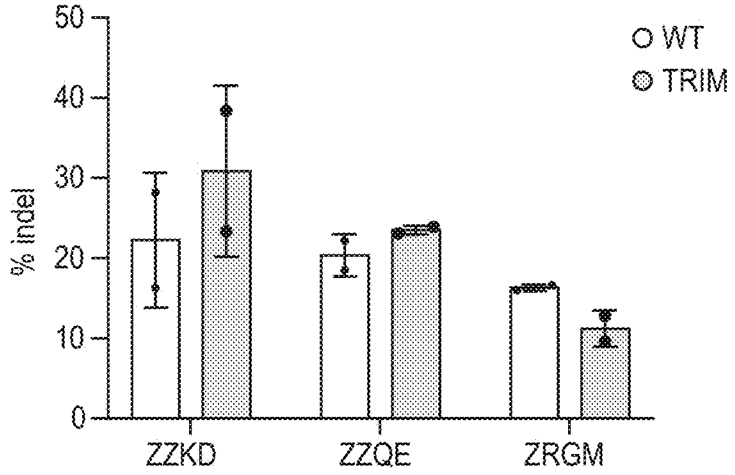
Figure 17B:
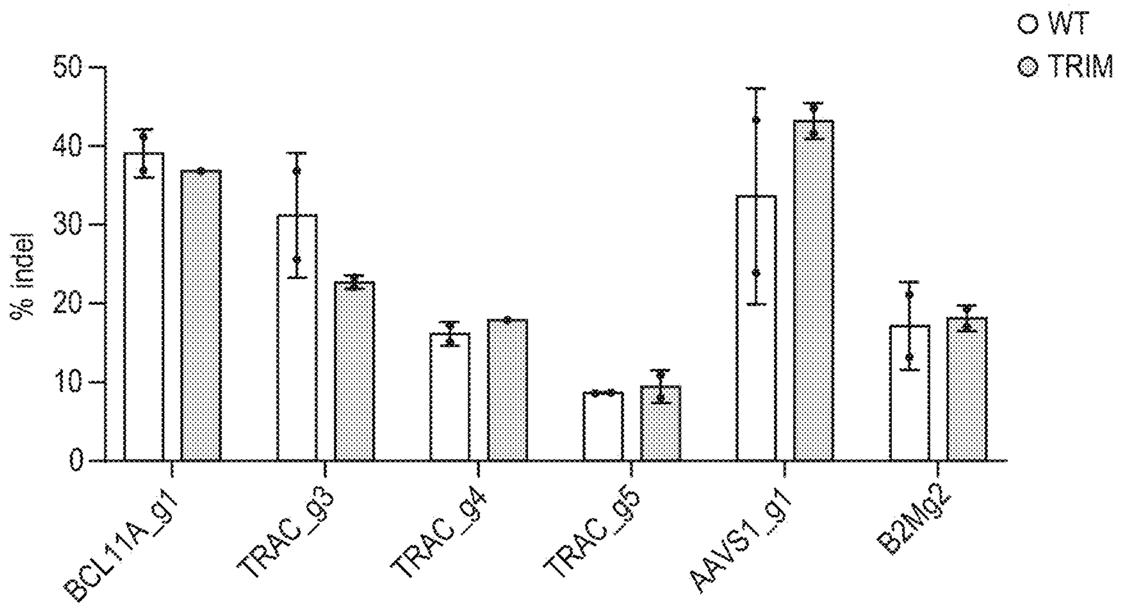

FIGS. 17A-17B show the activity of alternative crRNA scaffolds for selected Type V-A Cas proteins. FIG. 17A shows indel formation measured after transient transfection of HEK293T cells with alternative versions (full-length or trimmed) of the crRNAs targeting the TRAC-g3 locus for ZZKD, ZZQE and ZRGM Type V-A Cas proteins. FIG. 17B shows indel formation measured after transient transfection of HEK293T cells with alternative versions (full-length or trimmed) of ZZKD Type V-A Cas protein crRNAs targeting the BCL11A, TRAC, AAVS1 and B2M loci, as indicated on the graph. Data represented as mean±SD of n=2 independent biological replicates.

Figure 18A:
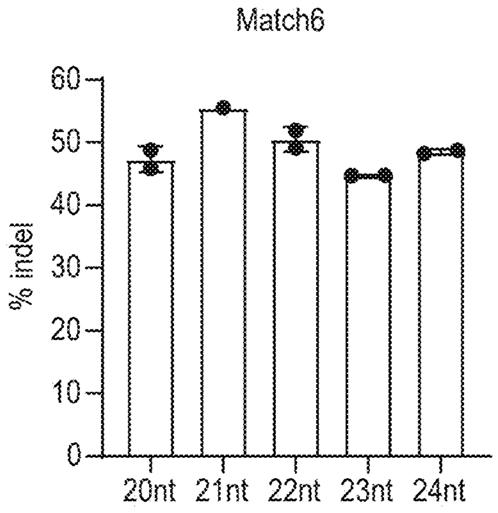
Figure 18B:
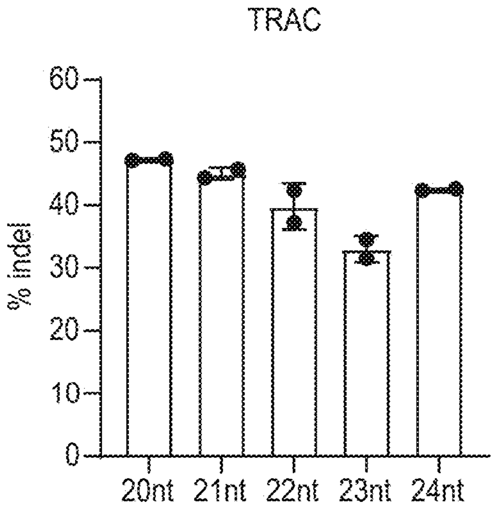

FIGS. 18A-18B illustrate the effect of alternative spacer lengths on ZZKD Type V-A Cas protein editing activity. Indel formation in HEK293T cells after transient transfection of ZZKD Type V-A Cas protein in combination with families of crRNAs characterized by different spacer lengths (from 20nt to 24nt) targeting either the Match6 (FIG. 18A) or the TRAC locus (g3, FIG. 18B). Data represented as mean±SD of n=2 independent biological replicates.

Figure 19:
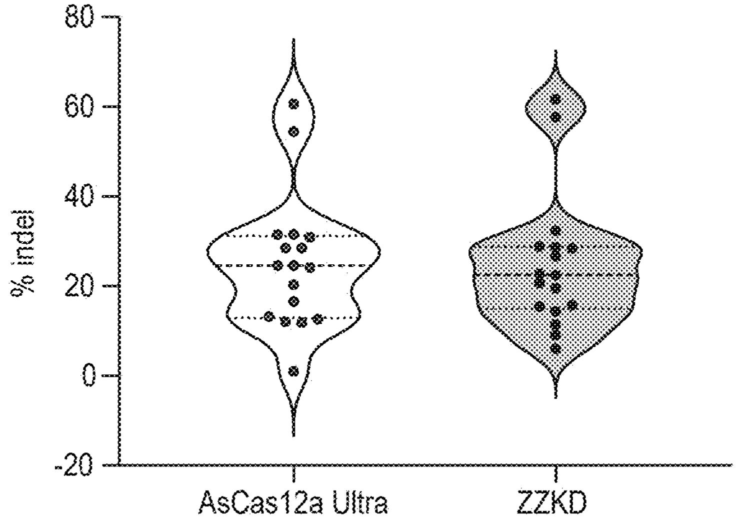
Figure 20A:
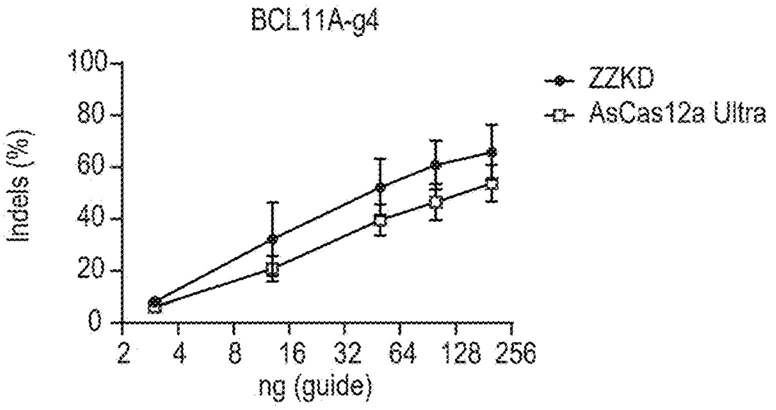
Figure 20B:
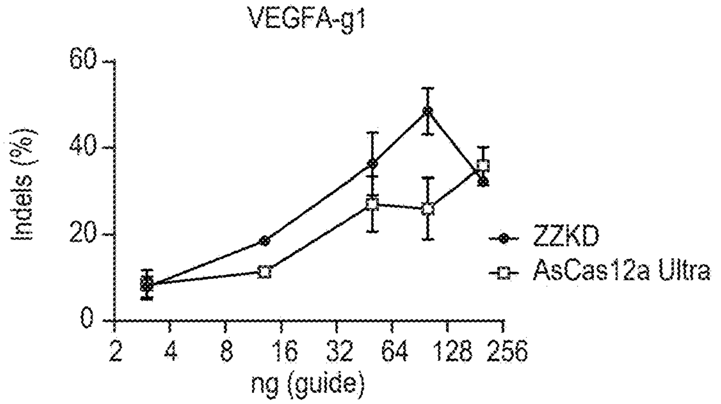
Figure 20C:
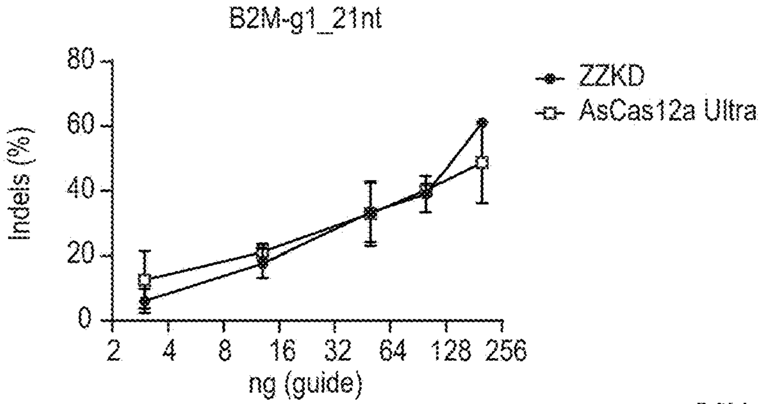
Figure 20D:
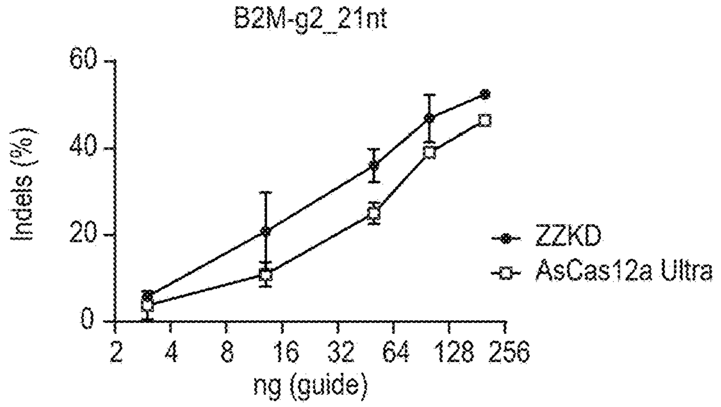

FIG. 19 shows a side-by-side comparison of ZZKD Type V-A Cas protein activity with AsCs12a Ultra. The figure shows a violin plot summarizing the editing activity of ZZKD Type V-A Cas protein and AsCas12a Ultra on a panel of endogenous genomic loci (TRAC, PD1, B2M, EMX1, AAVS1, BCL11a, PCSK9, Match6, VEGFA) after transient transfection of HEK292T cells, using crRNAs for the two nucleases that overlap on each locus. Each point on the graph represents the mean of n=2 independent runs except for B2M-g1_21nt for AsCas12a Ultra (n=1).

FIGS. 20A-20D show activity of ZZKD Type V-A Cas protein in subsaturating conditions. Titration curves obtained by measuring indel formation at the BCL11A-g4 (FIG. 20A), VEGFA-g1 (FIG. 20B), B2M-g1_21nt (FIG. 20C) and B2M-g2_21nt (FIG. 20D) target sites after a 2-fold serial dilution of the amount of ZZKD and crRNA plasmids transiently transfected in HEK293T cells. The activity of AsCas12a Ultra was measured in the same study conditions as a benchmark and is reported on each graph. Data represented as mean±SD of n=2 independent biological replicates.

Figure 21A:
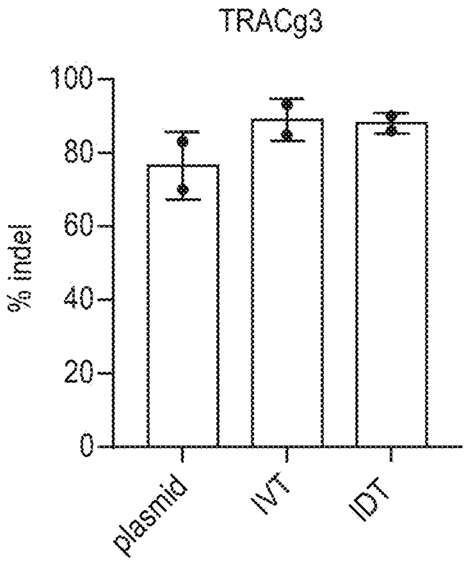
Figure 21B:
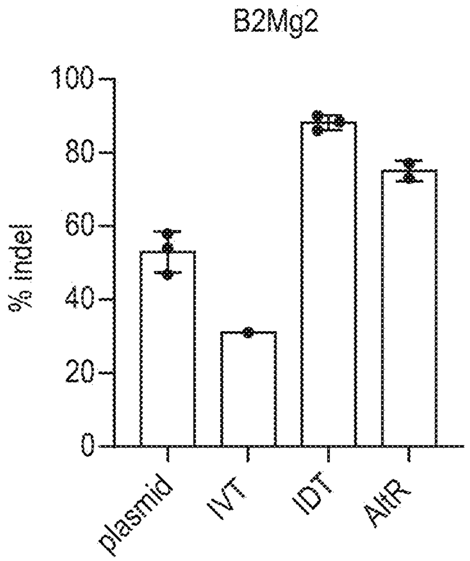
Figure 21C:
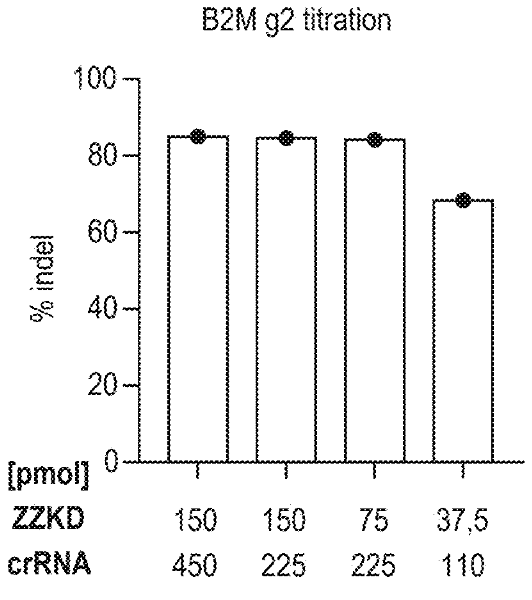

FIGS. 21A-21C show activity of ZZKD Type V-A Cas after direct ribonucleoprotein delivery in human cell lines. Indel formation after ZZKD Type V-A Cas RNP electroporation in U2OS cells to target either the TRAC-g3 locus (FIG. 21A) or the B2M-g2 locus (FIG. 21B). Cells were also transfected with plasmids expressing ZZKD and its crRNA as a positive control. IVT, in vitro transcribed crRNA; syn, unmodified chemically synthesized crRNA; AltR, chemically synthesized crRNA including commercially available AltR modifications from IDT. FIG. 21C shows the results of a titration study in U2OS cells delivering different amounts of recombinant ZZKD and cognate crRNA targeting the B2M-g2 locus by electroporation. The amount (pmol) of recombinant protein and crRNA used in each condition is indicated below each bar. Data represented as mean±SD of n≥2 independent biological replicates, except for B2M-g2 IVT and panel (FIG. 21C) where only one replicate is available.

Figure 22:
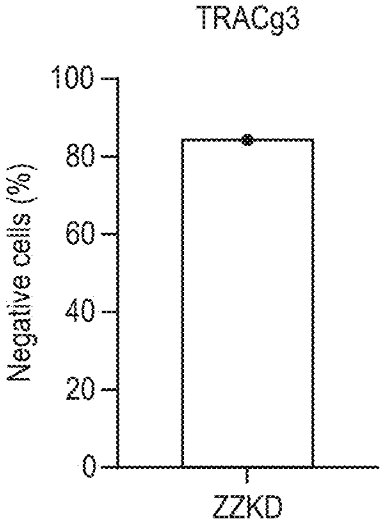

FIG. 22 shows activity of ZZKD Type V-A Cas after direct ribonucleoprotein delivery in primary human T cells. The figure shows percentage of TRAC-negative cells measured by flow cytometry after ZZKD Type V-A Cas RNP electroporation in commercial human primary T cells to target the TRAC-g3 locus.

6. DETAILED DESCRIPTION

In one aspect, the disclosure provides Type V Cas proteins, e.g., a ZWGD Type V Cas protein, a ZJHK Type V Cas protein, a ZIKV Type V Cas protein, a ZZFT Type V Cas protein, a YYAN Type V Cas protein, a ZZGY Type V Cas protein, a ZKBG Type V Cas protein, a ZZKD Type V Cas protein, a ZXPB Type V Cas protein, a ZPPX Type V Cas protein, a ZXHQ Type V Cas protein, a ZQKH Type V Cas protein, a ZRGM Type V Cas protein, a ZTAE Type V Cas protein, a ZSQQ Type V Cas protein, a ZSYN Type V Cas protein, a ZRBH Type V Cas protein, a ZWPU Type V Cas protein, a ZZQE Type V Cas protein, and a ZRXE Type V Cas protein. Type V Cas proteins of the disclosure can be in the form of fusion proteins. Unless required otherwise by context, disclosures relating to Type V Cas proteins encompass Type V Cas proteins which are not fusion proteins and Type V Cas proteins which are in the form of fusion proteins (e.g., Type V Cas protein comprising one or more nuclear localization signals and/or one or more tags).

In some embodiments, a Type V Cas protein of the disclosure comprises an amino acid sequence having at least 50% (e.g., at least 55%, at least 60%, at least 65%, at least 70%, at least 75%, at least 85%, at least 90%, at least 95%, at least 98%, at least 99%, or 100%) sequence identity to a WED-1 domain, REC1 domain, REC2 domain, WED-II domain, PI domain, WED-III domain, RuvC-I domain, BH domain, RuvC-II domain, NUC domain, or RuvC-III domain of a ZWGD Type V Cas protein, a ZJHK Type V Cas protein, a ZIKV Type V Cas protein, a ZZFT Type V Cas protein, a YYAN Type V Cas protein, a ZZGY Type V Cas protein, a ZKBG Type V Cas protein, a ZZKD Type V Cas protein, a ZXPB Type V Cas protein, a ZPPX Type V Cas protein, a ZXHQ Type V Cas protein, a ZQKH Type V Cas protein, a ZRGM Type V Cas protein, a ZTAE Type V Cas protein, a ZSQQ Type V Cas protein, a ZSYN Type V Cas protein, a ZRBH Type V Cas protein, a ZWPU Type V Cas protein, a ZZQE Type V Cas protein, or a ZRXE Type V Cas protein.

In some embodiments, a Type V Cas protein of the disclosure is a chimeric Type V Cas protein, for example, comprising one or more domains from a ZWGD Type V Cas protein and/or a ZJHK Type V Cas protein and/or a ZIKV Type V Cas protein and/or a ZZFT Type V Cas protein and/or a YYAN Type V Cas protein and/or a ZZGY Type V Cas protein and/or a ZKBG Type V Cas protein and/or a ZZKD Type V Cas protein and/or a ZXPB Type V Cas protein and/or a ZPPX Type V Cas protein and/or a ZXHQ Type V Cas protein and/or a ZQKH Type V Cas protein and/or a ZRGM Type V Cas protein and/or a ZTAE Type V Cas protein and/or a ZSQQ Type V Cas protein and/or a ZSYN Type V Cas protein and/or a ZRBH Type V Cas protein and/or a ZWPU Type V Cas protein and/or a ZZQE Type V Cas protein and/or a ZRXE Type V Cas protein, and one or more domains from a different Type V Cas protein such as AsCas12a.

Exemplary features of Type V Cas proteins of the disclosure are described in Section 6.2.

In further aspects, the disclosure provides guide (gRNA) molecules and combinations of guide RNA molecules, for example combinations of two or more gRNAs. Exemplary features of the gRNAs and combinations of gRNAs of the disclosure are further described in Section 6.3.

In further aspects, the disclosure provides systems comprising a Type V Cas protein of the disclosure and one or more gRNAs. Exemplary features of systems are described in Section 6.4.

In further aspects, the disclosure provides nucleic acids and pluralities of nucleic acids encoding a Type V Cas protein of the disclosure and, optionally, a gRNA, and provides nucleic acids encoding a gRNA, of the disclosure and, optionally, a Type V Cas protein. Exemplary features of nucleic and pluralities of nucleic acids of the disclosure are described in Section 6.5.

In further aspects, the disclosure provides particles comprising the Type V Cas proteins, gRNAs, nucleic acids, and systems of the disclosure. Exemplary features of particles of the disclosure are described in Section 6.6.

In another aspect, the disclosure provides cells and populations of cells containing or contacted with a Type V Cas protein, gRNA, nucleic acid, plurality of nucleic acids, system, or particle of the disclosure. Exemplary features of such cells and cell populations are described in Section 6.6.

In another aspect, the disclosure provides pharmaceutical compositions comprising a Type V Cas protein, gRNA, nucleic acid, plurality of nucleic acids, system, particle, cell, or population of cells together with one or more excipients. Exemplary features of pharmaceutical compositions are described in Section 6.7.

In another aspect, the disclosure provides methods of altering cells (e.g., editing the genome of a cell) using the Type V Cas proteins, gRNAs, nucleic acids, systems, particles, and pharmaceutical compositions of the disclosure. Features of exemplary methods of altering cells are described in Section 6.8.

6.1. Definitions

Unless defined otherwise, all technical and scientific terms used herein have the same meaning as commonly understood to one of ordinary skill in the art to which this invention belongs. The following definitions are provided for the full understanding of terms used in this specification.

As used in the specification and claims, the singular form "a," "an," and "the" include plural references unless the context clearly dictates otherwise. For example, the term "an agent" includes a plurality of agents, including mixtures thereof.

Unless indicated otherwise, an "or" conjunction is intended to be used in its correct sense as a Boolean logical operator, encompassing both the selection of features in the alternative (A or B, where the selection of A is mutually exclusive from B) and the selection of features in conjunction (A or B, where both A and B are selected). In some places in the text, the term "and/or" is used for the same purpose, which shall not be construed to imply that "or" is used with reference to mutually exclusive alternatives.

AsCas12a refers to a Cas12a protein having the following amino acid sequence:

```
                                                    (SEQ ID NO: 121)
MTQFEGFTNLYQVSKTLRFELIPQGKTLKHIQEQGFIEEDKARNDHYKELKPIIDRIYKTYADQCLQLVQLD

WENLSAAIDSYRKEKTEETRNALIEEQATYRNAIHDYFIGRTDNLTDAINKRHAEIYKGLFKAELFNGKVLK

QLGTVTTTEHENALLRSFDKFTTYFSGFYENRKNVFSAEDISTAIPHRIVQDNFPKFKENCHIFTRLITAVP

SLREHFENVKKAIGIFVSTSIEEVFSFPFYNQLLTQTQIDLYNQLLGGISREAGTEKIKGLNEVLNLAIQKND

ETAHIIASLPHRFIPLFKQILSDRNTLSFILEEFKSDEEVIQSFCKYKTLLRNENVLETAEALFNELNSIDLTHI

FISHKKLETISSALCDHWDTLRNALYERRISELTGKITKSAKEKVQRSLKHEDINLQEIISAAGKELSEAFKQ

KTSEILSHAHAALDQPLPTTLKKQEEKEILKSQLDSLLGLYHLLDWFAVDESNEVDPEFSARLTGIKLEME

PSLSFYNKARNYATKKPYSVEKFKLNFQMPTLASGWDVNKEKNNGAILFVKNGLYYLGIMPKQKGRYKA

LSFEPTEKTSEGFDKMYYDYFPDAAKMIPKCSTQLKAVTAHFQTHTTPILLSNNFIEPLEITKEIYDLNNPE

KEPKKFQTAYAKKTGDQKGYREALCKWIDFTRDFLSKYTKTTSIDLSSLRPSSQYKDLGEYYAELNPLLY
```

-continued

```
HISFQRIAEKEIMDAVETGKLYLFQIYNKDFAKGHHGKPNLHTLYWTGLFSPENLAKTSIKLNGQAELFYR

PKSRMKRMAHRLGEKMLNKKLKDQKTPIPDTLYQELYDYVNHRLSHDLSDEARALLPNVITKEVSHEIIKD

RRFTSDKFFFHVPITLNYQAANSPSKFNQRVNAYLKEHPETPIIGIDRGERNLIYITVIDSTGKILEQRSLNTI

QQFDYQKKLDNREKERVAARQAWSVVGTIKDLKQGYLSQVIHEIVDLMIHYQAVVVLENLNFGFKSKRTG

IAEKAVYQQFEKMLIDKLNCLVLKDYPAEKVGGVLNPYQLTDQFTSFAKMGTQSGFLFYVPAPYTSKIDPL

TGFVDPFVWKTIKNHESRKHFLEGFDFLHYDVKTGDFILHFKMNRNLSFQRGLPGFMPAWDIVFEKNET

QFDAKGTPFIAGKRIVPVIENHRFTGRYRDLYPANELIALLEEKGIVFRDGSNILPKLLENDDSHAIDTMVAL

IRSVLQMRNSNAATGEDYINSPVRDLNGVCFDSRFQNPEWPMDADANGAYHIALKGQLLLNHLKESKDL

KLQNGISNQDWLAYIQELRN
```

A Type V Cas protein refers to a wild-type or engineered Type V Cas protein. Engineered Type V Cas proteins can also be referred to as Type V Cas variants. For the avoidance of doubt, any disclosure pertaining to a "Type V Cas" or "Type V Cas protein" pertains to wild-type Type V Cas proteins and Type V Cas variants, unless the context dictates otherwise. A Type V Cas protein can have nuclease activity or be catalytically inactive (e.g., as in a dCas).

As used herein, the percentage identity between two nucleotide sequences or between two amino acid sequences is calculated by multiplying the number of matches between a pair of aligned sequences by 100, and dividing by the length of the aligned region. Identity scoring only counts perfect matches and does not consider the degree of similarity of amino acids to one another, nor does it consider substitutions or deletions as matches. For calculation of the percent sequence identity (% sequence identity), two sequences are aligned using the EMBOSS Needle Pairwise Sequence Alignment software tool based on the Needleman and Wunsch algorithm (available at www.ebi.ac.uk/jdispatcher/psa/emboss_needle) with the following parameters: Matrix: BLOSUM62 (for protein sequences) or DNAfull (for DNA sequences); Gap Open: 10; Gap Extend: 0.5; End Gap Penalty: false; End Gap Open: 10; and End Gap Extend: 0.5.

Guide RNA molecule (gRNA) refers to an RNA capable of forming a complex with a Type V Cas protein and which can direct the Type V Cas protein to a target DNA. gRNAs typically comprise a spacer of 15 to 30 nucleotides in length. gRNAs of the disclosure typically comprise a crRNA scaffold region at the 5' end of the molecule and a spacer at the 3' end of the molecule. Various non-limiting examples of crRNA scaffolds are described in Section 6.3.

An gRNA can in some embodiments comprise no uracil base at the 3' end of the gRNA sequence. Alternatively, a gRNA can comprise one or more uracil bases at the 3' end of the sgRNA sequence. For example, a gRNA can comprise 1 uracil (U) at the 3' end of the gRNA sequence, 2 uracil (UU) at the 3' end of the gRNA sequence, 3 uracil (UUU) at the 3' end of the gRNA sequence, 4 uracil (UUUU) at the 3' end of the gRNA sequence, 5 uracil (UUUUU) at the 3' end of the gRNA sequence, 6 uracil (UUUUUU) at the 3' end of the gRNA sequence, 7 uracil (UUUUUUU) at the 3' end of the gRNA sequence, or 8 uracil (UUUUUUUU) at the 3' end of the gRNA sequence. Different length stretches of uracil can be appended at the 3' end of a gRNA as terminators.

A gRNA can in some embodiments comprise a 5' guanine (G) at it's 5' end. A 5'-G can promote efficient transcription from a U6 promoter.

Peptide, protein, and polypeptide are used interchangeably to refer to a natural or synthetic molecule comprising two or more amino acids linked by the carboxyl group of one amino acid to the alpha amino group of another. The amino acids may be natural or synthetic, and can contain chemical modifications such as disulfide bridges, substitution of radioisotopes, phosphorylation, substrate chelation (e.g., chelation of iron or copper atoms), glycosylation, acetylation, formylation, amidation, biotinylation, and a wide range of other modifications. A polypeptide may be attached to other molecules, for instance molecules required for function. Examples of molecules which may be attached to a polypeptide include, without limitation, cofactors, polynucleotides, lipids, metal ions, phosphate, etc. Non-limiting examples of polypeptides include peptide fragments, denatured/unstructured polypeptides, polypeptides having quaternary or aggregated structures, etc. There is expressly no requirement that a polypeptide must contain an intended function; a polypeptide can be functional, non-functional, function for unexpected/unintended purposes, or have unknown function. A polypeptide is comprised of approximately twenty, standard naturally occurring amino acids, although natural and synthetic amino acids which are not members of the standard twenty amino acids may also be used. The standard twenty amino acids include alanine (Ala, A), arginine (Arg, R), asparagine (Asn, N), aspartic acid (Asp, D), cysteine (Cys, C), glutamine (Gln, Q), glutamic acid (Glu, E), glycine (Gly, G), histidine, (His, H), isoleucine (Ile, I), leucine (Leu, L), lysine (Lys, K), methionine (Met, M), phenylalanine (Phe, F), proline (Pro, P), serine (Ser, S), threonine (Thr, T), tryptophan (Trp, W), tyrosine (Tyr, Y), and valine (Val, V). The terms "polypeptide sequence" or "amino acid sequence" are an alphabetical representation of a polypeptide molecule.

Polynucleotide and oligonucleotide are used interchangeably and refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: a gene or gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, primers and gRNAs. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component. A polynucleotide is composed of a specific sequence of four nucleotide bases: adenine (A); cytosine (C); guanine (G); thymine (T); and uracil (U) for thymine (T) when the polynucleotide is RNA. Thus, the term "nucleotide sequence" is the alphabetical representation of a polynucleotide molecule. The letters used in polynucleotide sequences described herein correspond to IUPAC notation. For example, the letter "N" in a nucleotide sequence represents a nucleotide which can be A, T, C, or G in a DNA sequence, or A, U, C, or G in a RNA sequence; the letter "R" in a nucleotide sequence represents a nucleotide which can be A or G; the letter "V" in a nucleotide sequence represents a nucleotide which can be A, C, or G; and the letter "Y" in a nucleotide sequence represents a nucleotide which can be C or T.

Protospacer adjacent motif (PAM) refers to a DNA sequence upstream (e.g., immediately upstream) of a target sequence on the non-target strand recognized by a Type V Cas protein. A PAM sequence is located 5' of the target sequence on the non-target strand.

Spacer refers to a region of a gRNA molecule which is partially or fully complementary to a target sequence found in the + or − strand of genomic DNA. When complexed with a Type V Cas protein, the gRNA directs the Type V Cas to the target sequence in the genomic DNA. A spacer of a Type V Cas gRNA is typically 15 to 30 nucleotides in length (e.g., 20-25 nucleotides). The nucleotide sequence of a spacer can be, but is not necessarily, fully complementary to the target sequence. For example, a spacer can contain one or more mismatches with a target sequence, e.g., the spacer can comprise one, two, or three mismatches with the target sequence.

6.2. Type V Cas Proteins

6.2.1. ZWGD Type V Cas Proteins

In one aspect, the disclosure provides ZWGD Type V Cas proteins. ZWGD Type V Cas proteins can be further classified as Type V-A Cas proteins. The ZWGD Type V Cas proteins typically comprise an amino acid sequence that is at least 50%, at least 55%, at least 60%, at least 65%, at least 70%, at least 75%, at least 85%, at least 90%, or at least 95% identical to SEQ ID NO:1. In some embodiments, the ZWGD Type V Cas proteins comprise an amino acid sequence that is at least 95%, at least 96%, at least 97%, at least 98%, or at least 99% identical to SEQ ID NO:1. In some embodiments, a ZWGD Type V Cas protein comprises an amino acid sequence that is identical to SEQ ID NO:1.

Exemplary ZWGD Type V Cas protein sequences and nucleotide sequences encoding exemplary ZWGD Type V Cas proteins are set forth in Table 1A.

TABLE 1A

ZWGD Type V Cas Sequences

| Name | Sequence | SEQ ID NO. |
|---|---|---|
| Wildtype amino acid sequence (without N-terminal methionine) | VSEKENTPTFNSLTNLYSVSKTLRFELRPQYSTLDHIKDDQIVDKGEELKNHYKTFKKILD<br>QVFSRIINDSLDKTYLDQKYISTYQDLVFKHRDRLTDKDRAELKALKETLKKQIDKSLDHK<br>DKKAIFSDPVNFLIDNESDFADLIGDNRPSIEAFNRQKGYLSGYLQNRANIFDHTTNETSV<br>AFRIVEENLAIFLNNRLTLQHFFEKVADKDGLLKFLQETLSQLGFKLKLEDLLSLDYFNRT<br>LSQPGIDQYNLLISGKALEDGKKMQGINEVLNQYLQQHQEEKLHKIKLKQLYKQILSESK<br>TESFTLDFVEDNKGLAAMLLQFIDFVNKLIEEKMLLLDMIQGLKDSSVSSEFLSRLYLERK<br>NIKRLSNFIYKDYGYIEQSLEENFLSTIEGKITKKALEEHRKQDAFTIHEILVALQKQQYEK<br>DGALESADHLLLPGVVDFLYQNLDCKHSTLLEKVGSEKQPLLDLFNEKQLLEGQDAESH<br>ASKYSDRPFNDHEIKVVKTALDFYKNLQSNFAIFQIPDENLKLDSEFYSEFDEFYQGLKNI<br>IPVYNKSRNFLTKKPFSTEKTKLIFNNPQLLDGWSKSKESDCLGTIFIKDGKYYVGIINSAT<br>NAKNTLFEPNNFANFDQKQYFEKMNLFFLSDLKRDFPKKYFSEKWHNQHPVPADLREK<br>YDYYRIDEHKDERKNDLKYHHQLIAYYQDCLKKDTEWQIYQFKYKAPEEYSDVNEFLSE<br>LTPNTYKMEFNKIPAEYIKKLVDDGKLYFFQIYSKDFSEFAKGKPNLHTLYLKAVFDQKNA<br>EEFNYNYKISGSAEIFYRPASIETRVTHPKNQPIKNKNKNNPKAESVFQYDLCKDRRYMS<br>DKFFLHLPIELNRIPLLANDSSVNSMVNQVVSSRNQNYFLGIDRGERHLIYLVLIDQNGRII<br>KQQTLNQITSSYQEKANNQTVEVITDYHDLLNDKEKLRKKNLQEWQSVENIKELKAGYL<br>SNWVNEIGKIIVEYQPVIMLENLNTGFKNSRIKIEKQVYQKFEKALIDKFNYFMRKDLDSSA<br>IGGLYHALQLTKEYSKQYNGKQNGIIYYIPASYTSNIDPTTGFISAFIQTRYENVEKTKSLIE<br>KFNDITYDAEESLFCFSADYKKFSPEAKLWQQTIWQIYTNGDRIYTFKNKEEWQSKNYIL<br>VEEFKDLFAKYHIDYCRDLKAQILSQTDASFFKQFLFLLRLTLQMRNSRTTELNGTDADT<br>KKRENDYIISPVKNQYGKFYDSRKDYVDWPENADANGAYNIARKGLIMLKHLKEGLPEK<br>RICDISTEEWVQFVEELNK | 1 |
| Wildtype amino acid sequence (with N-terminal methionine) | MVSEKENTPTFNSLTNLYSVSKTLRFELRPQYSTLDHIKDDQIVDKGEELKNHYKTFKKIL<br>DQVFSRIINDSLDKTYLDQKYISTYQDLVFKHRDRLTDKDRAELKALKETLKKQIDKSLDH<br>KDKKAIFSDPVNFLIDNESDFADLIGDNRPSIEAFNRQKGYLSGYLQNRANIFDHTTNETS<br>VAFRIVEENLAIFLNNRLTLQHFFEKVADKDGLLKFLQETLSQLGFKLKLEDLLSLDYFNR<br>TLSQPGIDQYNLLISGKALEDGKKMQGINEVLNQYLQQHQEEKLHKIKLKQLYKQILSES<br>KTESFTLDFVEDNKGLAAMLLQFIDFVNKLIEEKMLLLDMIQGLKDSSVSSEFLSRLYLER<br>KNIKRLSNFIYKDYGYIEQSLEENFLSTIEGKITKKALEEHRKQDAFTIHEILVALQKQQYE<br>KDGALESADHLLLPGVVDFLYQNLDCKHSTLLEKVGSEKQPLLDLFNEKQLLEGQDAES<br>HASKYSDRPFNDHEIKVVKTALDFYKNLQSNFAIFQIPDENLKLDSEFYSEFDEFYQGLK<br>NIIPVYNKSRNFLTKKPFSTEKTKLIFNNPQLLDGWSKSKESDCLGTIFIKDGKYYVGIINS<br>ATNAKNTLFEPNNFANFDQKQYFEKMNLFFLSDLKRDFPKKYFSEKWHNQHPVPADLR<br>EKYDYYRIDEHKDERKNDLKYHHQLIAYYQDCLKKDTEWQIYQFKYKAPEEYSDVNEFL<br>SELTPNTYKMEFNKIPAEYIKKLVDDGKLYFFQIYSKDFSEFAKGKPNLHTLYLKAVFDQK<br>NAEEFNYNYKISGSAEIFYRPASIETRVTHPKNQPIKNKNKNNPKAESVFQYDLCKDRRY<br>MSDKFFLHLPIELNRIPLLANDSSVNSMVNQVVSSRNQNYFLGIDRGERHLIYLVLIDQNG<br>RIIKQQTLNQITSSYQEKANNQTVEVITDYHDLLNDKEKLRKKNLQEWQSVENIKELKAG<br>YLSNVVNEIGKIIVEYQPVIMLENLNTGFKNSRIKIEKQVYQKFEKALIDKFNYFMRKDLDS<br>SAIGGLYHALQLTKEYSKQYNGKQNGIIYYIPASYTSNIDPTTGFISAFIQTRYENVEKTKS | 2 |

TABLE 1A-continued

ZWGD Type V Cas Sequences

| Name | Sequence | SEQ ID NO. |
| --- | --- | --- |
| | LIEKFNDITYDAEESLFCFSADYKKFSPEAKLWQQTIWQIYTNGDRIYTFKNKEEWQSKN<br>YILVEEFKDLFAKYHIDYCRDLKAQILSQTDASFFKQFLFLLRLTLQMRNSRTTELNGTDA<br>DTKKRENDYIISPVKNQYGKFYDSRKDYVDWPENADANGAYNIARKGLIMLKHLKEGLP<br>EKRICDISTEEWVQFVEELNK | |
| Expression construct (with N-terminal methionine, V5-tag and C-terminal NLS) aa sequence | MGVSEKENTPTFNSLTNLYSVSKTLRFELRPQYSTLDHIKDDQIVDKGEELKNHYKTFK<br>KILDQVFSRIINDSLDKTYLDQKYISTYQDLVFKHRDRLTDKDRAELKALKETLKKQIDKS<br>LDHKDKKAIFSDPVNFLIDNESDFADLIGDNRPSIEAFNRQKGYLSGYLQNRANIFDHTT<br>NETSVAFRIVEENLAIFLNNRLTLQHFFEKVADKDGLLKFLQETLSQLGFKLKLEDLLSLD<br>YFNRTLSQPGIDQYNLLISGKALEDGKKMQGINEVLNQYLQQHQEEKLHKIKLKQLYKQI<br>LSESKTESFTLDFVEDNKGLAAMLLQFIDFVNKLIEEKMLLLDMIQGLKDSSVSSEFLSRL<br>YLERKNIKRLSNFIYKDYGYIEQSLEENFLSTIEGKITKKALEEHRKQDAFTIHEILVALQK<br>QQYEKDGALESADHLLLPGVVDFLYQNLDCKHSTLLEKVGSEKQPLLDLFNEKQLLEG<br>QDAESHASKYSDRPFNDHEIKVVKTALDFYKNLQSNFAIFQIPDENLKLDSEFYSEFDEF<br>YQGLKNIIPVYNKSRNFLTKKPFSTEKTKLIFNNPQLLDGWSKSKESDCLGTIFIKDGKYY<br>VGIINSATNAKNTLFEPNNFANFDQKQYFEKMNLFFLSDLKRDFPKKYFSEKWHNQHPV<br>PADLREKYDYYRIDEHKDERKNDLKYHHQLIAYYQDCLKKDTEWQIYQFKYKAPEEYSD<br>VNEFLSELTPNTYKMEFNKIPAEYIKKLVDDGKLYFFQIYSKDFSEFAKGKPNLHTLYLKA<br>VFDQKNAEEFNYNYKISGSAEIFYRPASIETRVTHPKNQPIKNKNKNNPKAESVFQYDLC<br>KDRRYMSDKFFLHLPIELNRIPLLANDSSVNSMVNQVVSSRNQNYFLGIDRGERHLIYLV<br>LIDQNGRIIKQQTLNQITSSYQEKANNQTVEVITDYHDLLNDKEKLRKKNLQEWQSVENI<br>KELKAGYLSNVVNEIGKIIVEYQPVIMLENLNTGFKNSRIKIEKQVYQKFEKALIDKFNYFM<br>RKDLDSSAIGGLYHALQLTKEYSKQYNGKQNGIIYYIPASYTSNIDPTTGFISAFIQTRYE<br>NVEKTKSLIEKFNDITYDAEESLFCFSADYKKFSPEAKLWQQTIWQIYTNGDRIYTFKNK<br>EEWQSKNYILVEEFKDLFAKYHIDYCRDLKAQILSQTDASFFKQFLFLLRLTLQMRNSRT<br>TELNGTDADTKKRENDYIISPVKNQYGKFYDSRKDYVDWPENADANGAYNIARKGLIML<br>KHLKEGLPEKRICDISTEEWVQFVEELNKSRKRTADGSEFESPKKKRKVGSGKPIPNPL<br>LGLDST | 3 |
| Wildtype coding sequence (with N-terminal methionine and stop codon) | ATGGTGTCCGAAAAAGAAAATACACCAACTTTTAATAGTCTAACCAATCTCTATAGTG<br>TTTCAAAGACTCTTAGATTTGAACTTAGGCCACAATATTCAACTCTAGATCACATTAA<br>AGATGACCAAATTGTTGACAAAGGTGAAGAACTAAAAAACCACTACAAAACTTTCAA<br>GAAAATTCTTGATCAGGTCTTTTCAAGGATCATCAACGATAGCCTAGATAAAACCTA<br>TCTTGATCAAAAATATATTTCCACCTACCAAGATCTTGTATTCAAGCATCGAGACCGA<br>CTAACAGACAAAGACCGTGCAGAACTAAAGGCCTTAAAAGAAACACTCAAAAAGCA<br>GATCGACAAAAGCCTCGATCATAAAGATAAAAAAGCTATCTTCAGTGATCCCGTAAA<br>TTTTCTCATCGACAATGAATCGGATTTTGCTGACTTAATTGGTGATAATCGTCCTAGT<br>ATTGAAGCTTTCAACCGTCAAAAAGGTTATCTTTCCGGATATCTCCAAAATCGCGCA<br>AATATCTTCGATCACACCACAAATGAAACTTCAGTCGCGTTTCGTATTGTCGAGGAA<br>AACCTCGCTATCTTTTTAAATAATCGCCTCACATTACAGCATTTTTTCGAGAAAGTTG<br>CAGATAAAGATGGGCTATTAAAATTTTTACAAGAGACACTTTCTCAGTTAGGTTTTAA<br>GTTGAAACTCGAAGACCTTCTTTCCCTTGATTATTTTAATCGTACCCTATCTCAACCC<br>GGCATCGATCAGTATAACCTCCTAATCTCTGGCAAGGCGCTAGAAGATGGAAAGAA<br>AATGCAGGGAATTAATGAGGTCCTCAATCAATATCTCCAACAACATCAAGAAGAGAA<br>GCTACATAAAATCAAACTCAAGCAACTCTATAAGCAGATCCTCTCAGAGTCAAAAAC<br>TGAATCATTTACCCTTGATTTTGTGGAAGATAATAAAGGGCTTGCTGCCATGCTCCT<br>ACAGTTTATCGATTTTGTAAACAAGCTGATTGAAGAGAAAATGCTTCTCCTTGATATG<br>ATTCAGGGGCTAAAAGATAGCTCAGTTTCATCAGAATTTCTTTCACGACTCTATCTT<br>GAACGCAAAAACATCAAGCGTCTTTCGAATTTTATCTATAAAGATTATGGCTATATTG<br>AGCAATCCTTGGAAGAGAACTTTCTCTCGACAATTGAAGGCAAGATTACCAAGAAG<br>GCACTCGAGGAACATCGCAAACAGGATGCTTTCACAATCCATGAAATCTTAGTTGC<br>CCTACAAAAGCAACAATATGAAAAGGATGGAGCTCTAGAGTCCGCAGATCATCTTTT<br>ACTTCCTGGTGTTGTTGACTTCCTCTACCAGAATTTGGATTGCAAACACTCCACTCT<br>ACTTGAAAAAGTCGGGTCAGAAAAACAGCCACTACTCGACCTCTTCAACGAAAAAC<br>AATTATTGGAAGGTCAAGACGCAGAATCTCATGCTTCCAAATATTCTGATCGTCCAT<br>TCAACGACCACGAAATAAAGGTTGTTAAAACTGCTTTGGATTTTTATAAAAATCTACA<br>GAGTAATTTTGCGATCTTTCAAATCCCGGATGAAAACCTTAAACTAGATTCCGAATTT<br>TATTCCGAGTTTGATGAATTTTATCAAGGTCTCAAGAATATTATTCCAGTCTATAACA<br>AGTCCAGAAATTTCCTCACTAAAAAACCATTCTCAACCGAAAAGACCAAGCTCATTT<br>TTAACAACCCGCAACTACTTGACGGATGGAGTAAATCAAAAGAGTCAGATTGTTTAG<br>GCACGATTTTTATTAAAGACGGCAAATATTATGTTGGCATTATTAATAGTGCTACGAA<br>TGCTAAAAATACTTTATTTGAGCCTAACAATTTTGCAAACTTCGACCAAAAACAATAT<br>TTTGAAAAGATGAACCTTTTCTTCCTTTCGGACTTGAAGCGAGATTTTCCTAAGAAAT<br>ATTTTTCTGAAAAGTGGCATAATCAACACCCAGTTCCAGCCGATCTTCGTGAAAAGT<br>ATGATTATTATCGAATCGACGAACATAAGGATGAGCGCAAAAATGATCTAAAATATC<br>ATCATCAACTTATCGCCTATTATCAAGACTGTCTTAAAAAAGACACGGAATGGCAGA<br>TTTATCAATTCAAATATAAGGCCCCTGAAGAATATTCAGATGTCAATGAATTCTTATC<br>CGAGCTTACTCCAAATACCTACAAAATGGAGTTCAATAAAATCCCAGCTGAATATAT<br>CAAAAAGCTTGTTGATGATGGAAAATTATATTTCTTCCAAATTTATTCCAAAGATTTTT<br>CTGAGTTTGCAAAAGGTAAACCAAATCTCCATACTCTCTATCTAAAAGCGGTCTTTG<br>ATCAGAAAAATGCGGAAGAGTTCAACTATAATTATAAAATTTCTGGTAGTGCCGAAA<br>TCTTCTATCGTCCAGCCAGCATTGAAACTCGTGTCACTCATCCAAAAAATCAACCAA<br>TCAAGAATAAGAATAAAAATAATCCAAAGGCTGAATCTGTCTTCCAGTATGATCTTTG<br>TAAAGATCGTCGCTATATGTCAGATAAATTCTTTTTGCATCTTCCGATCGAATTAAAT<br>CGTATTCCGTTACTCGCTAACGACTCCTCGGTAAATAGTATGGTCAATCAAGTCGTT | 4 |

TABLE 1A-continued

| ZWGD Type V Cas Sequences | | |
|---|---|---|
| Name | Sequence | SEQ ID NO. |
| | AGTTCTCGTAATCAGAATTATTTCCTTGGTATTGACCGTGGCGAGAGGCATCTAATT<br>TATCTAGTCCTGATCGATCAAAACGGTAGAATCATTAAACAGCAAACCTTAAATCAG<br>ATCACTAGTTCATACCAAGAAAAAGCCAATAACCAAACGGTTGAAGTTATTACGGAT<br>TATCATGATCTCTTGAATGACAAAGAAAAACTGCGAAAGAAGAATCTCCAAGAGTGG<br>CAATCCGTCGAAAATATCAAGGAGTTAAAGGCTGGGTACCTAAGTAATGTGGTGAA<br>TGAAATCGGTAAGATTATCGTTGAATATCAGCCAGTTATTATGCTGGAAAATCTTAAT<br>ACTGGATTTAAAAACTCACGAATTAAAATTGAGAAACAGGTGTACCAGAAATTTGAG<br>AAGGCGCTCATTGATAAGTTTAACTACTTTATGAGAAAAGATCTCGACTCTTCAGCT<br>ATTGGTGGTCTCTATCACGCTTTGCAGTTGACTAAGGAATACTCTAAGCAGTACAAC<br>GGCAAGCAGAATGGTATCATCTACTATATTCCTGCAAGCTACACTAGTAATATTGAT<br>CCAACTACTGGTTTCATCTCGGCCTTTATACAGACTAGATACGAAAACGTCGAGAAA<br>ACAAAATCCTTAATCGAAAAGTTTAATGATATCACTTATGATGCAGAAGAATCTCTCT<br>TCTGCTTCTCCGCAGATTACAAGAAATTTAGTCCAGAGGCCAAGCTTTGGCAGCAG<br>ACGATTTGGCAGATTTATACTAATGGCGATCGTATTTATACATTTAAGAACAAAGAAG<br>AGTGGCAGAGCAAAAACTACATCCTCGTTGAGGAGTTCAAAGATCTCTTTGCTAAAT<br>ATCACATCGATTATTGCAGGGACCTTAAGGCGCAGATTCTGTCACAAACTGACGCG<br>AGCTTCTTCAAGCAGTTCCTCTTCTTGTTGCGACTAACCTTGCAGATGCGAAATAGT<br>CGCACTACCGAATTAAATGGAACTGATGCTGATACTAAAAAACGTGAGAATGATTAT<br>ATTATTTCTCCAGTTAAGAATCAGTATGGCAAGTTCTATGATTCCCGCAAGGATTAT<br>GTGGACTGGCCAGAAAATGCAGATGCAAATGGCGCATACAATATTGCCAGAAAAGG<br>TCTCATCATGCTAAAACACCTAAAAGAAGGTCTTCCCGAAAAACGTATCTGTGATAT<br>ATCGACTGAAGAATGGGTACAGTTTGTCGAAGAACTAAATAAATAG | |
| Codon optimized coding sequence (no N-terminal methionine, no stop codon) | GTGTCTGAAAAGGAAAACACCCCTACCTTCAACTCTCTGACCAACCTGTACAGCGTT<br>TCTAAAACCCTGCGGTTCGAGCTGCGGCCTCAGTACAGCACCCTGGACCACATCAA<br>GGACGATCAGATCGTGGACAAGGGAGAGGAGCTAAAGAACCACTACAAGACATTC<br>AAAAAAATCCTGGACCAGGTGTTCTCTCGGATCATCAACGACTCTCTGGATAAAACT<br>TACCTGGATCAGAAGTACATCTCCACCTACCAGGATCTGGTGTTCAAGCACAGAGA<br>TAGACTGACAGATAAGGACAGAGCCGAACTGAAGGCCCTGAAGGAGACACTGAAG<br>AAGCAGATCGACAAAAGCCTGGATCACAAAGACAAGAAGGCTATCTTCTCCGACCC<br>TGTGAACTTCCTGATCGACAATGAGAGCGACTTCGCCGACCTGATTGGAGACAACC<br>GGCCCAGCATCGAGGCCTTTAACCGCCAGAAGGGATATCTGTCCGGCTACCTGCA<br>GAATAGAGCCAACATCTTCGATCATACAACCAACGAAACCAGCGTTGCTTTCAGAAT<br>CGTGGAAGAGAACCTCGCCATCTTCCTCAACAACCGCCTGACCCTGCAGCATTTCT<br>TCGAGAAAGTGGCCGACAAAGACGGACTGCTGAAGTTCCTGCAGGAGACACTGAG<br>CCAGCTGGGCTTCAAGCTGAAGCTGGAGGATCTGCTGAGCCTGGATTACTTTAACC<br>GGACACTGAGCCAGCCTGGCATCGACCAATACAACCTGCTGATCAGCGGAAAGGC<br>CCTGGAAGATGGCAAGAAGATGCAGGGCATCAATGAAGTGCTGAACCAGTACCTG<br>CAGCAGCACCAGGAGGAAAAGCTGCACAAAATCAAGCTGAAGCAGCTGTATAAGCA<br>AATCCTGAGCGAAAGCAAGACAGAGAGCTTCACGCTGGACTTCGTGGAGGACAAC<br>AAGGGCCTGGCCGCCATGCTGCTGCAGTTTATCGATTTCGTGAACAAGTTAATAGA<br>AGAGAAGATGCTGCTGCTGGATATGATCCAGGGACTGAAAGACAGCAGTGTGTCCA<br>GCGAGTTCTTGAGCCGGCTTTACCTGGAAAGAAAGAACATCAAGCGGCTGAGCAAC<br>TTCATCTACAAGGACTATGGCTATATCGAGCAGTCCCTGGAAGAAAACTTCCTGAG<br>CACCATCGAGGGCAAGATCACTAAGAAGGCCCTGGAAGAGCATAGAAAACAGGAC<br>GCCTTTACCATTCACGAGATCCTGGTCGCACTGCAGAAACAACAGTACGAAAAGGA<br>CGGCGCCCTAGAGAGCGCCGACCACCTGCTGCTTCCAGGCGTGGTGGATTTCCTC<br>TACCAAAACCTGGACTGTAAGCACAGCACGCTGCTGGAAAAGGTGGGCAGCGAGA<br>AGCAGCCCCTGCTGGATCTTTTCAACGAAAAGCAGCTGCTTGAGGGCCAGGACGC<br>CGAGTCCCACGCCTCTAAGTACAGCGATCGGCCTTTCAACGACCACGAGATCAAG<br>GTGGTGAAAACCGCCCTGGACTTCTACAAGAACCTGCAATCTAACTTTGCTATCTTC<br>CAGATCCCCGACGAAAACCTGAAGCTGGATAGCGAGTTTTACAGCGAGTTTGATGA<br>GTTCTACCAGGGCCTGAAAAATATTATTCCTGTGTACAACAAAAGCCGGAACTTCCT<br>GACAAAAAAGCCGTTCAGCACCGAAAAGACCAAACTGATCTTCAACAACCCCCAGC<br>TGCTCGATGGCTGGAGCAAGAGCAAGGAAAGCGACTGTCTGGGGACCATCTTCAT<br>CAAAGACGGCAAGTACTATGTGGGAATCATCAACAGCGCCACCAACGCTAAGAATA<br>CACTGTTCGAGCCTAACAACTTCGCCAATTTCGACCAAAAACAATACTTCGAGAAGA<br>TGAACCTGTTCTTCCTGAGCGATCTGAAGCGAGACTTCCCCAAGAAGTATTTCTCC<br>GAGAAGTGGCACAACCAGCACCCCGTGCCCGCTGACCTTAGAGAAAAGTACGACT<br>ACTACCGGATCGACGAGCATAAGGATGAGAGAAAGAATGACCTGAAATACCACCAC<br>CAGTTAATCGCCTACTACCAAGACTGCCTGAAAAAGGATACAGAGTGGCAGATCTA<br>CCAGTTCAAGTACAAGGCCCCTGAGGAGTACAGCGACGTGAACGAGTTCCTGAGT<br>GAACTGACCCCTAATACCTACAAGATGGAGTTCAACAAGATTCCTGCCGAGTACATT<br>AAGAAGCTGGTGGATGACGGCAAGCTGTACTTTTTTCAGATATACTCCAAAGACTTT<br>AGCGAATTTGCCAAGGGCAAGCCAAACCTGCACACCCTCTACCTGAAGGCCGTGTT<br>CGACCAGAAGAACGCCGAGGAGTTCAACTACAACTATAAAATATCTGGATCTGCTG<br>AAATCTTTTACAGACCTGCTTCTATCGAGACAAGAGTGACCCACCCTAAGAATCAGC<br>CTATCAAGAACAAGAACAAGAACAATCCTAAGGCTGAAAGCGTGTTCCAGTACGAC<br>CTGTGCAAGGACCGGCGGTACATGTCCGACAAGTTCTTCCTGCACCTTCCCATCGA<br>ACTTAACAGAATCCCTCTGCTGGCTAACGATTCCTCCGTGAATAGCATGGTCAACCA<br>GGTGGTGAGCAGCAGAAACCAGAACTACTTCCTGGGCATCGATAGAGGCGAGAGA<br>CACCTGATCTACCTGGTGCTGATCGACCAGAACGGTAGAATCATCAAGCAACAGAC<br>CCTGAATCAGATTACAAGCAGCTACCAAGAAAAGGCCAACAACCAGACAGTGGAGG<br>TGATCACAGACTACCACGACCTGCTGAACGACAAGGAAAAGCTCAGAAAGAAGAAT<br>CTTCAGGAGTGGCAGTCCGTGGAGAATATCAAAGAGCTGAAGGCCGGCTACCTGA | 5 |

TABLE 1A-continued

| ZWGD Type V Cas Sequences | | |
|---|---|---|
| Name | Sequence | SEQ ID NO. |
| | GCAACGTGGTCAACGAGATCGGCAAGATCATCGTGGAGTACCAGCCTGTGATCAT<br>GCTGGAAAACCTCAACACCGGATTTAAAAACTCAAGAATCAAGATTGAGAAGCAGG<br>TGTACCAGAAGTTCGAGAAGGCCTTAATCGATAAGTTCAATTACTTCATGCGGAAGG<br>ATCTGGACTCTAGCGCCATCGGCGGCCTGTACCACGCCCTGCAGCTGACCAAAGA<br>GTATAGCAAGCAGTACAACGGCAAGCAGAACGGCATCATCTACTACATCCCAGCTT<br>CTTACACCTCTAATATCGACCCCACCACCGGCTTTATTAGCGCCTTCATCCAGACCA<br>GATACGAGAACGTGGAAAAGACCAAGTCTCTGATCGAGAAATTTAATGACATCACCT<br>ACGACGCCGAAGAGTCGCTGTTCTGCTTCAGCGCCGATTACAAGAAATTTTCACCT<br>GAAGCTAAGCTGTGGCAGCAAACCATCTGGCAGATCTATACCAACGGCGACAGAAT<br>CTACACCTTCAAGAACAAGGAAGAGTGGCAAAGCAAGAACTACATTCTGGTGGAGG<br>AGTTTAAGGACCTGTTCGCCAAATACCACATCGACTATTGCAGGGACCTGAAAGCC<br>CAGATCCTGAGCCAGACCGACGCATCTTTTTTCAAGCAGTTTCTCTTCCTGCTGAGA<br>CTGACACTGCAAATGAGAAATAGTCGTACCACAGAGCTGAACGGCACCGACGCCG<br>ACACCAAGAAAAGAGAGAATGACTACATCATCTCTCCAGTGAAAAATCAGTACGGC<br>AAATTCTATGATTCCCGCAAGGACTACGTGGACTGGCCTGAGAACGCCGACGCCAA<br>TGGCGCCTACAACATCGCCAGAAAGGGCCTGATCATGCTGAAGCACCTGAAGGAA<br>GGACTGCCTGAGAAGAGGATCTGCGACATCAGCACAGAAGAATGGGTTCAGTTTGT<br>GGAAGAACTGAACAAG | |
| Expression construct (with N-terminal methionine and stop codon, includes V5-tag and C-terminal NLS) | ATGggcGTGTCTGAAAAGGAAAACACCCCTACCTTCAACTCTCTGACCAACCTGTAC<br>AGCGTTTCTAAAACCCTGCGGTTCGAGCTGCGGCCTCAGTACAGCACCCTGGACC<br>ACATCAAGGACGATCAGATCGTGGACAAGGGAGAGGAGCTAAAGAACCACTACAA<br>GACATTCAAAAAAATCCTGGACCAGGTGTTCTCTCGGATCATCAACGACTCTCTGGA<br>TAAAACTTACCTGGATCAGAAGTACATCTCCACCTACCAGGATCTGGTGTTCAAGCA<br>CAGAGATAGACTGACAGATAAGGACAGAGCCGAACTGAAGGCCCTGAAGGAGACA<br>CTGAAGAAGCAGATCGACAAAAGCCTGGATCACAAAGACAAGAAGGCTATCTTCTC<br>CGACCCTGTGAACTTCCTGATCGACAATGAGAGCGACTTCGCCGACCTGATTGGAG<br>ACAACCGGCCCAGCATCGAGGCCTTTAACCGCCAGAAGGGATATCTGTCCGGCTA<br>CCTGCAGAATAGAGCCAACATCTTCGATCATACAACCAACGAAACCAGCGTTGCTTT<br>CAGAATCGTGGAAGAGAACCTCGCCATCTTCCTCAACAACCGCCTGACCCTGCAGC<br>ATTTCTTCGAGAAAGTGGCCGACAAAGACGGACTGCTGAAGTTCCTGCAGGAGACA<br>CTGAGCCAGCTGGGCTTCAAGCTGAAGCTGGAGGATCTGCTGAGCCTGGATTACTT<br>TAACCGGACACTGAGCCAGCCTGGCATCGACCAATACAACCTGCTGATCAGCGGA<br>AAGGCCCTGGAAGATGGCAAGAAGATGCAGGGCATCAATGAAGTGCTGAACCAGT<br>ACCTGCAGCAGCACCAGGAGGAAAAGCTGCACAAAATCAAGCTGAAGCAGCTGTAT<br>AAGCAAATCCTGAGCGAAAGCAAGACAGAGAGCTTCACGCTGGACTTCGTGGAGG<br>ACAACAAGGGCCTGGCCGCCATGCTGCTGCAGTTTATCGATTTCGTGAACAAGTTA<br>ATAGAAGAGAAGATGCTGCTGCTGGATATGATCCAGGGACTGAAAGACAGCAGTGT<br>GTCCAGCGAGTTCTTGAGCCGGCTTTACCTGGAAAGAAAGAACATCAAGCGGCTGA<br>GCAACTTCATCTACAAGGACTATGGCTATATCGAGCAGTCCCTGGAAGAAAACTTC<br>CTGAGCACCATCGAGGGCAAGATCACTAAGAAGGCCCTGGAAGAGCATAGAAAAC<br>AGGACGCCTTTACCATTCACGAGATCCTGGTCGCACTGCAGAAACAACAGTACGAA<br>AAGGACGGCGCCCTAGAGAGCGCCGACCACCTGCTGCTTCCAGGCGTGGTGGATT<br>TCCTCTACCAAAACCTGGACTGTAAGCACAGCACGCTGCTGGAAAAGGTGGGCAG<br>CGAGAAGCAGCCCCTGCTGGATCTTTTCAACGAAAAGCAGCTGCTTGAGGGCCAG<br>GACGCCGAGTCCCACGCCTCTAAGTACAGCGATCGGCCTTTCAACGACCACGAGA<br>TCAAGGTGGTGAAAACCGCCCTGGACTTCTACAAGAACCTGCAATCTAACTTTGCTA<br>TCTTCCAGATCCCCGACGAAAACCTGAAGCTGGATAGCGAGTTTTACAGCGAGTTT<br>GATGAGTTCTACCAGGGCCTGAAAAATATTATTCCTGTGTACAACAAAAGCCGGAAC<br>TTCCTGACAAAAAAGCCGTTCAGCACCGAAAAGACCAAACTGATCTTCAACAACCC<br>CCAGCTGCTCGATGGCTGGAGCAAGAGCAAGGAAAGCGACTGTCTGGGGACCATC<br>TTCATCAAAGACGGCAAGTACTATGTGGGAATCATCAACAGCGCCACCAACGCTAA<br>GAATACACTGTTCGAGCCTAACAACTTCGCCAATTTCGACCAAAAACAATACTTCGA<br>GAAGATGAACCTGTTCTTCCTGAGCGATCTGAAGCGAGACTTCCCCAAGAAGTATT<br>TCTCCGAGAAGTGGCACAACCAGCACCCCGTGCCCGCTGACCTTAGAGAAAAGTA<br>CGACTACTACCGGATCGACGAGCATAAGGATGAGAGAAAGAATGACCTGAAATACC<br>ACCACCAGTTAATCGCCTACTACCAAGACTGCCTGAAAAAGGATACAGAGTGGCAG<br>ATCTACCAGTTCAAGTACAAGGCCCCTGAGGAGTACAGCGACGTGAACGAGTTCCT<br>GAGTGAACTGACCCCTAATACCTACAAGATGGAGTTCAACAAGATTCCTGCCGAGT<br>ACATTAAGAAGCTGGTGGATGACGGCAAGCTGTACTTTTTTCAGATATACTCCAAAG<br>ACTTTAGCGAATTTGCCAAGGGCAAGCCAAACCTGCACACCCTCTACCTGAAGGCC<br>GTGTTCGACCAGAAGAACGCCGAGGAGTTCAACTACAACTATAAAATATCTGGATCT<br>GCTGAAATCTTTTACAGACCTGCTTCTATCGAGACAAGAGTGACCCACCCTAAGAAT<br>CAGCCTATCAAGAACAAGAACAAGAACAATCCTAAGGCTGAAAGCGTGTTCCAGTA<br>CGACCTGTGCAAGGACCGGCGGTACATGTCCGACAAGTTCTTCCTGCACCTTCCCA<br>TCGAACTTAACAGAATCCCTCTGCTGGCTAACGATTCCTCCGTGAATAGCATGGTCA<br>ACCAGGTGGTGAGCAGCAGAAACCAGAACTACTTCCTGGGCATCGATAGAGGCGA<br>GAGACACCTGATCTACCTGGTGCTGATCGACCAGAACGGTAGAATCATCAAGCAAC<br>AGACCCTGAATCAGATTACAAGCAGCTACCAAGAAAAGGCCAACAACCAGACAGTG<br>GAGGTGATCACAGACTACCACGACCTGCTGAACGACAAGGAAAAGCTCAGAAAGAA<br>GAATCTTCAGGAGTGGCAGTCCGTGGAGAATATCAAAGAGCTGAAGGCCGGCTAC<br>CTGAGCAACGTGGTCAACGAGATCGGCAAGATCATCGTGGAGTACCAGCCTGTGA<br>TCATGCTGGAAAACCTCAACACCGGATTTAAAAACTCAAGAATCAAGATTGAGAAGC<br>AGGTGTACCAGAAGTTCGAGAAGGCCTTAATCGATAAGTTCAATTACTTCATGCGGA<br>AGGATCTGGACTCTAGCGCCATCGGCGGCCTGTACCACGCCCTGCAGCTGACCAA | 6 |

TABLE 1A-continued

| ZWGD Type V Cas Sequences | | |
|---|---|---|
| Name | Sequence | SEQ ID NO. |
| | AGAGTATAGCAAGCAGTACAACGGCAAGCAGAACGGCATCATCTACTACATCCCAG<br>CTTCTTACACCTCTAATATCGACCCCACCACCGGCTTTATTAGCGCCTTCATCCAGA<br>CCAGATACGAGAACGTGGAAAAGACCAAGTCTCTGATCGAGAAATTTAATGACATC<br>ACCTACGACGCCGAAGAGTCGCTGTTCTGCTTCAGCGCCGATTACAAGAAATTTTC<br>ACCTGAAGCTAAGCTGTGGCAGCAAACCATCTGGCAGATCTATACCAACGGCGACA<br>GAATCTACACCTTCAAGAACAAGGAAGAGTGGCAAAGCAAGAACTACATTCTGGTG<br>GAGGAGTTTAAGGACCTGTTCGCCAAATACCACATCGACTATTGCAGGGACCTGAA<br>AGCCCAGATCCTGAGCCAGACCGACGCATCTTTTTTCAAGCAGTTTCTCTTCCTGCT<br>GAGACTGACACTGCAAATGAGAAATAGTCGTACCACAGAGCTGAACGGCACCGAC<br>GCCGACACCAAGAAAAGAGAGAATGACTACATCATCTCTCCAGTGAAAAATCAGTA<br>CGGCAAATTCTATGATTCCCGCAAGGACTACGTGGACTGGCCTGAGAACGCCGAC<br>GCCAATGGCGCCTACAACATCGCCAGAAAGGGCCTGATCATGCTGAAGCACCTGA<br>AGGAAGGACTGCCTGAGAAGAGGATCTGCGACATCAGCACAGAAGAATGGGTTCA<br>GTTTGTGGAAGAACTGAACAAGtctagaAAGCGGACAGCAGACGGCTCCGAATTTGAA<br>AGCCCTAAGAAAAAGAGAAAGGTGggatccGGCAAACCTATCCCCAATCCCCTGCTG<br>GGCCTGGACAGCACCTGA | |

In some embodiments a ZWGD Type V Cas protein comprises an amino acid sequence of SEQ ID NO:1, SEQ ID NO:2, or SEQ ID NO:3. In some embodiments, a ZWGD Type V Cas protein has nickase activity, for example resulting from one or more amino acid substitutions relative to the sequence of SEQ ID NO:1, SEQ ID NO:2, or SEQ ID NO:3. In some embodiments, the one or more amino acid substitutions providing nickase activity comprise a D891 substitution, wherein the position of the D891 substitution is defined with respect to the amino acid numbering of SEQ ID NO:2 (corresponding to amino acid 908 of SEQ ID NO:121). In some embodiments, the one or more amino acid substitutions providing nickase activity comprise an E990 substitution, wherein the position of the E990 substitution is defined with respect to the amino acid numbering of SEQ ID NO:2 (corresponding to amino acid 993 of SEQ ID NO:121). In some embodiments, the one or more amino acid substitutions providing nickase activity comprise a R1200 substitution, wherein the position of the R1200 substitution is defined with respect to the amino acid numbering of SEQ ID NO:2 (corresponding to amino acid 1226 of SEQ ID NO:121). In some embodiments, the one or more amino acid substitutions providing nickase activity comprise a D1248 substitution, wherein the position of the D1248 substitution is defined with respect to the amino acid numbering of SEQ ID NO:2 (corresponding to amino acid 1263 of SEQ ID NO:121). In some embodiments, a ZWGD Type V Cas protein is catalytically inactive, for example due to a R1200 substitution in combination with a D891 substitution, a E990 substitution, and/or D1248 substitution.

6.2.2. ZJHK Type V Cas Proteins

In one aspect, the disclosure provides ZJHK Type V Cas proteins. ZJHK Type V Cas proteins can be further classified as Type V-A Cas proteins. The ZJHK Type V Cas proteins typically comprise an amino acid sequence that is at least 50%, at least 55%, at least 60%, at least 65%, at least 70%, at least 75%, at least 85%, at least 90%, or at least 95% identical to SEQ ID NO:7. In some embodiments, the ZJHK Type V Cas proteins comprise an amino acid sequence that is at least 95%, at least 96%, at least 97%, at least 98%, or at least 99% identical to SEQ ID NO:7. In some embodiments, a ZJHK Type V Cas protein comprises an amino acid sequence that is identical to SEQ ID NO:7.

Exemplary ZJHK Type V Cas protein sequences and nucleotide sequences encoding exemplary ZJHK Type V Cas proteins are set forth in Table 1B.

TABLE 1B

| ZJHK Type V Cas Sequences | | |
|---|---|---|
| Name | Sequence | SEQ ID NO. |
| Wildtype amino acid sequence (without N-terminal methionine) | KSIYENFIGLESKNLTLRFALNPEAKTQENLKLYWDKLRDEERDRAYPIVKKILDKE<br>YQQLISEGLKLLENQNVLDWTELAEYIRTSDLSKKKKEDKRLRKLIAQNLKAHPLV<br>DKLKVKNAFGKNGYLETLPLGKEEKEAVKVFAGFGGFFNNYNKNRENYFSTEEK<br>STAIANRIVNENFSKHFSNVEIVTKIQKEVPELIQIVEAQFKGYDTIFTVNGYNTALS<br>QAGIDTYNEMVAIWNKEANLYAQKAGKLPDGHPLKKKRNYLLSALFKQIGSEKEH<br>LIQIDRFDGDEEVIEALTGVKKMLQEADVFEKLNMLVEDMENWDYSKIYLSAQSLS<br>NVSVFLNNLYEDERENSWNYLDNVLREKWQIELQGKKKGTDLEEAIRKKKQSFY<br>SIEELQEAVNAIEETDKCYNVSKWLLGAMKSERVIEEKKKDVEDFCTQWKNERNS<br>LKETDITALKEYLEQWIFLARYCKSFYANGIEKKEKDEAFYHILEDVLYVLDEVIYFY<br>NKVRNYVTKKPYSLEKMHLKFGHNELANGWSVNKEENYGTAILRRNGKYYLAITN<br>SLNKKMSIPTQLESTGNNYEKMVLNVFPNVFRMIPKCTTGRNDVKSCFERKEPNE<br>YFFIDTPEFVNPFKVTREEYELNKITYDGVKKWQSDYSKNTQDEKGYKEAVTKWI<br>QFCMRFLQSYKSTAIYDYSTLQQPEKYETVDSFYHDVEKILYECHFEYVPANKIEQ<br>LEEEGRIFLFQIYNKDFSENRRPDSKKNLHTLYWEALFSEENRKAKVIQLNGKAEI<br>FRREKSIEHPIVHKAGEVLVNKRTKDGEPIPDDIYKDLSNYFNGRNVTSEKEEYKE<br>CLDKVYTSTKKYDITKDKRFTETKYEFHVPITLNYQADGVKYLNQKILHVLRDNPD<br>VNIIGLDRGERNLISYVVLNREGKIVNNQQGSFNIVGKMDYQKKLYQKEKNRDKE<br>RKTWKNIETIKDLKEGYISQWVHELTDMAIRNNAIIVMEDLNFGFKRGRTKVERQV<br>YQKFELALLKKLHYLVTDKTEGEAMLKPGGVLQGYQLAREVKTLKEIGKQCGCVF | 7 |

TABLE 1B-continued

ZJHK Type V Cas Sequences

| Name | Sequence | SEQ ID NO. |
|---|---|---|
| | YVPPGYTSKIDPTTGFVDVFNMSGVTNREKKKAFFEKFDNMFYDEKRDMFGFSF NYEKFTTYQSSYRNDWTVYSNGSKYVWNSLKRTDELIDVTKELKLLFEKYAIDYR NEALFEQIMSQDTDKNNADFWNKLFWYFRVLLRLRNSSDELDQIVSPVLNQNGE FFETPKKITEKSYLSDYPMDADTNGAYHIALKGLYLIQEKIADESVDLDNKLPKDFY KISNAEWFMFRQKEK | |
| Wildtype amino acid sequence (with N-terminal methionine) | MKSIYENFIGLESKNLTLRFALNPEAKTQENLKLYWDKLRDEERDRAYPIVKKILDK EYQQLISEGLKLLENQNVLDWTELAEYIRTSDLSKKKKEDKRLRKLIAQNLKAHPL VDKLKVKNAFGKNGYLETLPLGKEEKEAVKVFAGFGGFFNNYNKNRENYFSTEE KSTAIANRIVNENFSKHFSNVEIVTKIQKEVPELIQIVEAQFKGYDTIFTVNGYNTAL SQAGIDTYNEMVAIWNKEANLYAQKAGKLPDGHPLKKKRNYLLSALFKQIGSEKE HLIQIDRFDGDEEVIEALTGVKKMLQEADVFEKLNMLVEDMENWDYSKIYLSAQSL SNVSVFLNNLYEDERENSWNYLDNVLREKWQIELQGKKKGTDLEEAIRKKKQSF YSIEELQEAVNAIEETDKCYNVSKWLLGAMKSERVIEEKKKDVEDFCTQWKNERN SLKETDITALKEYLEQWIFLARYCKSFYANGIEKKEKDEAFYHILEDVLYVLDEVIYF YNKVRNYVTKKPYSLEKMHLKFGHNELANGWSVNKEENYGTAILRRNGKYYLAIT NSLNKKMSIPTQLESTGNNYEKMVLNVFPNVFRMIPKCTTGRNDVKSCFERKEPN EYFFIDTPEFVNPFKVTREEYELNKITYDGVKKWQSDYSKNTQDEKGYKEAVTKW IQFCMRFLQSYKSTAIYDYSTLQQPEKYETVDSFYHDVEKILYECHFEYVPANKIE QLEEEGRIFLFQIYNKDFSENRRPDSKKNLHTLYWEALFSEENRKAKVIQLNGKAE IFRREKSIEHPIVHKAGEVLVNKRTKDGEPIPDDIYKDLSNYFNGRNVTSEKEEYKE CLDKVYTSTKKYDITKDKRFTETKYEFHVPITLNYQADGVKYLNQKILHVLRDNPD VNIIGLDRGERNLISYVVLNREGKIVNNQQGSFNIVGKMDYQKKLYQKEKNRDKE RKTWKNIETIKDLKEGYISQWVHELTDMAIRNNAIIVMEDLNFGFKRGRTKVERQV YQKFELALLKKLHYLVTDKTEGEAMLKPGGVLQGYQLAREVKTLKEIGKQCGCVF YVPPGYTSKIDPTTGFVDVFNMSGVTNREKKKAFFEKFDNMFYDEKRDMFGFSF NYEKFTTYQSSYRNDWTVYSNGSKYVWNSLKRTDELIDVTKELKLLFEKYAIDYR NEALFEQIMSQDTDKNNADFWNKLFWYFRVLLRLRNSSDELDQIVSPVLNQNGE FFETPKKITEKSYLSDYPMDADTNGAYHIALKGLYLIQEKIADESVDLDNKLPKDFY KISNAEWFMFRQKEK | 8 |
| Expression construct (with N-terminal methionine, V5-tag and C-terminal NLS) aa sequence | MGKSIYENFIGLESKNLTLRFALNPEAKTQENLKLYWDKLRDEERDRAYPIVKKILD KEYQQLISEGLKLLENQNVLDWTELAEYIRTSDLSKKKKEDKRLRKLIAQNLKAHP LVDKLKVKNAFGKNGYLETLPLGKEEKEAVKVFAGFGGFFNNYNKNRENYFSTE EKSTAIANRIVNENFSKHFSNVEIVTKIQKEVPELIQIVEAQFKGYDTIFTVNGYNTA LSQAGIDTYNEMVAIWNKEANLYAQKAGKLPDGHPLKKKRNYLLSALFKQIGSEK EHLIQIDRFDGDEEVIEALTGVKKMLQEADVFEKLNMLVEDMENWDYSKIYLSAQ SLSNVSVFLNNLYEDERENSWNYLDNVLREKWQIELQGKKKGTDLEEAIRKKKQS FYSIEELQEAVNAIEETDKCYNVSKWLLGAMKSERVIEEKKKDVEDFCTQWKNER NSLKETDITALKEYLEQWIFLARYCKSFYANGIEKKEKDEAFYHILEDVLYVLDEVIY FYNKVRNYVTKKPYSLEKMHLKFGHNELANGWSVNKEENYGTAILRRNGKYYLAI TNSLNKKMSIPTQLESTGNNYEKMVLNVFPNVFRMIPKCTTGRNDVKSCFERKEP NEYFFIDTPEFVNPFKVTREEYELNKITYDGVKKWQSDYSKNTQDEKGYKEAVTK WIQFCMRFLQSYKSTAIYDYSTLQQPEKYETVDSFYHDVEKILYECHFEYVPANKI EQLEEEGRIFLFQIYNKDFSENRRPDSKKNLHTLYWEALFSEENRKAKVIQLNGKA EIFRREKSIEHPIVHKAGEVLVNKRTKDGEPIPDDIYKDLSNYFNGRNVTSEKEEYK ECLDKVYTSTKKYDITKDKRFTETKYEFHVPITLNYQADGVKYLNQKILHVLRDNP DVNIIGLDRGERNLISYVVLNREGKIVNNQQGSFNIVGKMDYQKKLYQKEKNRDK ERKTWKNIETIKDLKEGYISQVVHELTDMAIRNNAIIVMEDLNFGFKRGRTKVERQ VYQKFELALLKKLHYLVTDKTEGEAMLKPGGVLQGYQLAREVKTLKEIGKQCGCV FYVPPGYTSKIDPTTGFVDVFNMSGVTNREKKKAFFEKFDNMFYDEKRDMFGFS FNYEKFTTYQSSYRNDWTVYSNGSKYVWNSLKRTDELIDVTKELKLLFEKYAIDY RNEALFEQIMSQDTDKNNADFWNKLFWYFRVLLRLRNSSDELDQIVSPVLNQNG EFFETPKKITEKSYLSDYPMDADTNGAYHIALKGLYLIQEKIADESVDLDNKLPKDF YKISNAEWFMFRQKEKSRKRTADGSEFESPKKKRKVGSGKPIPNPLLGLDST | 9 |
| Wildtype coding sequence (with N-terminal methionine and stop codon) | ATGAAAAGTATTTATGAAAATTTTATTGGATTGGAGTCAAAAAATTTGACGCTG CGCTTTGCGTTGAATCCAGAAGCTAAGACACAAGAAAATTTGAAGTTGTACTG GGACAAATTGCGTGATGAGGAGAGAGATAGGGCGTATCCAATTGTAAAAAAG ATATTGGATAAGGAATATCAGCAGCTGATTTCGGAAGGACTGAAATTATTAGA GAATCAGAATGTGTTGGATTGGACAGAATTAGCAGAGTATATACGGACAAGTG ATTTAAGTAAGAAGAAAAAAGAAGATAAACGCTTAAGAAAATTAATAGCACAAA ATTTAAAAGCGCATCCGTTAGTTGACAAACTGAAAGTAAAAAATGCATTTGGTA AAAATGGCTATCTTGAAACTTTACCGTTGGGAAAAGAAGAGAAAGAGGCAGTA AAAGTTTTTGCCGGTTTTGGCGGCTTTTTCAATAACTACAATAAAAACAGGGAA AATTATTTTTCAACCGAGGAAAAAAGCACTGCAATCGCAAACCGAATTGTAAAT GAAAATTTTTCAAAACATTTTTCAAATGTAGAAATAGTTACCAAAATTCAAAAGG AAGTGCCAGAATTAATTCAAATCGTGGAAGCACAATTCAAGGGATATGATACT ATCTTTACAGTAAATGGTTATAATACGGCATTGTCACAGGCAGGGATTGATAC ATATAATGAGATGGTTGCAATCTGGAATAAAGAAGCAAATTTGTATGCGCAAA AGGCAGGAAAACTTCCAGATGGACATCCGTTAAAGAAAAAGAGAAATTACTTA TTGTCGGCATTGTTTAAACAGATTGGGAGTGAAAAGGAGCATTTGATTCAAAT TGATAGATTTGATGGAGATGAAGAGGTGATTGAGGCATTGACGGGTGTGAAA AAAATGCTTCAAGAGGCAGATGTATTTGAAAAATTGAATATGCTTGTGGAGGA TATGGAGAATTGGGATTATAGTAAAATATATTTGTCAGCACAGAGTTTATCCAA | 10 |

TABLE 1B-continued

ZJHK Type V Cas Sequences

| Name | Sequence | SEQ ID NO. |
|---|---|---|
| | TGTTTCTGTGTTCCTAAATAATTTATATGAGGATGAACGGGAGAACTCATGGAA<br>TTATCTTGATAATGTCCTAAGAGAAAAATGGCAAATAGAATTACAGGGAAAGAA<br>AAAGGGGACAGATCTGGAAGAAGCGATTCGGAAGAAAAAACAAAGTTTCTATT<br>CAATAGAAGAACTTCAAGAGGCAGTGAATGCCATAGAAGAAACAGATAAATGT<br>TATAATGTATCTAAATGGCTTCTAGGAGCAATGAAAAGCGAAAGGGTAATAGA<br>AGAAAAAAAGAAGGATGTGGAAGATTTTTGCACACAGTGGAAAAATGAAAGAA<br>ACTCGCTGAAAGAGACAGATATAACTGCACTGAAAGAATATCTGGAGCAATGG<br>ATTTTTTTGGCAAGATATTGCAAATCTTTTTATGCAAATGGAATTGAAAAAAAG<br>AAAAAGATGAAGCATTTTATCATATTTTAGAAGATGTGTTGTATGTTTTGGATG<br>AAGTAATATATTTTTATAATAAAGTTCGAAATTATGTAACGAAGAAGCCATATTC<br>TCTTGAAAAAATGCATTTAAAATTTGGTCATAATGAACTGGCAAATGGATGGTC<br>TGTTAACAAAGAAGAGAACTATGGTACGGCAATATTGAGGCGAAATGGCAAAT<br>ACTATTTGGCAATTACAAATTCATTGAATAAAAGATGAGTATTCCCACTCAAT<br>TAGAAAGTACAGGAAATAATTATGAAAAGATGGTATTGAATGTATTCCCAAATG<br>TATTTCGGATGATACCAAAATGTACTACAGGAAGAAATGATGTGAAAAGTTGTT<br>TTGAAAGAAAAGAGCCAAATGAGTATTTCTTTATTGATACACCGGAATTTGTTA<br>ACCCATTTAAAGTTACGCGCGAGGAATATGAGTTAAATAAGATAACTTATGATG<br>GTGTTAAAAAGTGGCAATCTGATTATTCAAAAAATACGCAGGATGAAAAAGGA<br>TACAAAGAGGCAGTGACAAAATGGATTCAGTTTTGTATGCGCTTTTTACAATCT<br>TATAAGAGTACAGCAATATATGATTATTCAACTTTACAGCAACCGGAGAAATAT<br>GAGACGGTGGATTCTTTTTATCATGACGTTGAAAAAATATTATATGAATGTCAT<br>TTTGAGTACGTTCCGGCTAATAAAATAGAGCAGTTGGAAGAAGAAGGAAGAAT<br>TTTTCTGTTTCAGATTTACAACAAAGATTTTTCGGAAAACAGACGCCCGGACA<br>GCAAAAAGAATTTGCATACACTTTATTGGGAGGCATTGTTTTCAGAAGAAAATC<br>GGAAAGCAAAAGTGATACAATTAAATGGCAAAGCTGAAATATTTCGGAGAGAA<br>AAAAGCATTGAACATCCGATTGTTCATAAAGCTGGGGAAGTGTTAGTGAATAA<br>ACGAACGAAAGACGGGGAACCAATACCAGATGATATTTATAAAGATTTGAGCA<br>ACTATTTTAACGGAAGAAATGTAACATCTGAAAAGGAAGAGTATAAGGAATGT<br>CTGGATAAAGTGTATACTTCGACCAAAAAATATGATATTACAAAGGATAAACGT<br>TTTACTGAAACCAAATATGAATTTCATGTTCCGATTACCTTGAACTATCAGGCG<br>GACGGTGTTAAATATTTGAATCAGAAAATACTTCATGTGCTGAGGGATAATCC<br>AGATGTGAATATTATAGGTCTAGATAGAGGCGAGCGTAATCTGATTTCCTACG<br>TAGTATTGAACCGAGAAGGCAAGATTGTTAACAATCAGCAGGGGAGTTTCAAT<br>ATTGTGGGTAAGATGGACTATCAGAAGAAACTGTATCAAAAAGAAAAGAATCG<br>TGACAAAGAACGAAAAACTTGGAAAAATATCGAAACAATAAAGGATTTGAAGG<br>AAGGATATATTTCACAAGTCGTTCATGAATTGACCGATATGGCGATTCGCAAT<br>AATGCAATTATTGTGATGGAAGATCTGAATTTTGGATTTAAAAGGGGACGCAC<br>CAAAGTGGAACGGCAGGTATATCAGAAGTTTGAGCTGGCGCTTCTGAAGAAA<br>TTGCATTATCTGGTTACGGATAAAACAGAAGGTGAGGCTATGCTTAAGCCTGG<br>CGGTGTCCTTCAAGGTTATCAGCTTGCAAGAGAAGTAAAAACCCTAAAAGAAA<br>TCGGAAAGCAATGCGGATGTGTATTTTATGTTCCACCGGGATATACTTCTAAA<br>ATCGATCCAACAACCGGATTTGTTGATGTGTTTAACATGTCAGGTGTTACGAA<br>TCGTGAAAAGAAAAAAGCATTTTTTGAAAAGTTCGATAATATGTTCTATGATGA<br>AAAGCGGGATATGTTTGGATTTTCATTTAACTATGAGAAGTTTACAACATATCA<br>AAGTTCTTATAGAAATGATTGGACTGTATATTCGAATGGAAGCAAATATGTGTG<br>GAACTCTTTAAAAAGGACAGACGAGCTTATTGATGTTACAAAAGAATTGAAACT<br>GCTCTTTGAAAAGTATGCAATTGATTACAGAAACGAAGCATTGTTTGAACAAAT<br>CATGTCCCAAGATACGGATAAAAACAATGCTGACTTTTGGAATAAATTGTTCTG<br>GTATTTTCGTGTTTTGCTCCGTCTGAGAAACAGTTCAGATGAATTAGATCAGAT<br>TGTTTCACCGGTACTTAATCAAAACGGAGAATTTTTTGAAACACCGAAAAAAAT<br>CACGGAGAAAAGTTATTTGTCTGATTATCCGATGGATGCGGATACCAATGGTG<br>CGTATCACATCGCTTTAAAAGGGTTGTATCTCATACAGGAAAAAATTGCAGAT<br>GAGAGCGTAGATTTGGATAACAAATTACCAAAAGATTTTTACAAGATCTCTAAT<br>GCAGAGTGGTTTATGTTTAGGCAGAAGGAGAAGTAA | |
| Codon optimized coding sequence (no N-terminal methionine, no stop codon) | AAGAGCATCTACGAGAACTTCATCGGTCTTGAGAGCAAGAACCTGACACTGA<br>GATTCGCCCTGAACCCTGAGGCTAAAACCCAGGAGAACCTGAAGCTGTACTG<br>GGACAAACTGAGGGACGAAGAAAGAGATAGAGCCTACCCTATCGTGAAAAAA<br>ATCCTCGACAAGGAGTATCAGCAGCTCATCAGCGAGGGCCTGAAACTGCTGG<br>AAAATCAAAACGTGCTGGACTGGACCGAACTGGCCGAGTACATCAGAACCAG<br>CGATCTGTCTAAGAAGAAGAAGGAGGACAAGAGACTGCGCAAGCTGATCGCC<br>CAGAACCTGAAAGCCCACCCCCTGGTCGACAAGCTGAAGGTGAAGAATGCCT<br>TCGGCAAGAACGGCTACCTGGAAACCCTGCCATTAGGAAAGGAAGAAAAAGA<br>GGCCGTGAAGGTGTTTGCCGGATTCGGAGGCTTTTTCAACAACTACAACAAG<br>AATCGGGAGAACTACTTCAGTACCGAGGAGAAGTCCACCGCCATCGCCAACA<br>GAATCGTGAACGAGAACTTCAGCAAGCACTTCAGCAACGTGGAAATCGTTACA<br>AAGATCCAAAAAGAAGTGCCAGAGCTGATTCAAATCGTGGAAGCTCAGTTCAA<br>GGGTTACGACACCATCTTTACCGTGAACGGCTACAACACCGCCCTGAGCCAG<br>GCTGGCATCGACACATACAACGAAATGGTGGCCATCTGGAACAAGGAGGCAA<br>ACCTGTACGCTCAAAAAGCCGGCAAGCTGCCAGACGGCCACCCGCTGAAGA<br>AGAAGCGTAACTACCTGCTGAGCGCCCTCTTCAAACAGATCGGCAGCGAAAA<br>AGAACACCTGATCCAGATCGACAGATTCGACGGCGACGAGGAAGTGATCGAA<br>GCCCTGACTGGCGTGAAAAAGATGCTGCAGGAGGCCGACGTGTTCGAGAAG<br>CTGAACATGCTGGTCGAGGACATGGAAAATTGGGATTACTCCAAGATCTACCT<br>GTCTGCCCAGAGCCTGAGTAACGTGTCCGTGTTCCTGAACAACCTGTATGAA | 11 |

TABLE 1B-continued

| ZJHK Type V Cas Sequences | | |
|---|---|---|
| Name | Sequence | SEQ ID NO. |
| | GATGAACGGGAGAACAGCTGGAACTACCTGGATAACGTGCTGAGAGAGAAGT<br>GGCAGATTGAACTGCAGGGCAAAAAAAAGGGAACAGATCTGGAAGAGGCCAT<br>TAGAAAGAAGAAGCAGAGCTTTTACTCTATCGAGGAACTTCAGGAGGCAGTG<br>AACGCCATCGAGGAAACCGACAAGTGCTACAATGTGTCTAAATGGCTGCTGG<br>GAGCCATGAAGAGCGAGAGAGTGATCGAGGAGAAGAAGAAAGACGTGGAGG<br>ATTTCTGCACACAGTGGAAGAACGAGAGAAACAGCCTCAAGGAAACCGACAT<br>CACCGCCCTGAAGGAGTACCTGGAGCAGTGGATCTTCCTGGCTAGGTACTGC<br>AAGAGCTTCTACGCCAATGGCATCGAAAAGAAAGAGAAGGATGAGGCTTTTA<br>CCACATCCTGGAGGATGTGCTGTACGTGCTGGACGAAGTGATCTACTTCTAC<br>AACAAGGTGCGGAACTACGTGACCAAAAAGCCTTACAGTCTGGAGAAGATGC<br>ACCTGAAGTTCGGCCACAACGAGCTGGCCAACGGCTGGAGCGTGAACAAGG<br>AAGAAAATTACGGCACCGCCATCCTGAGAAGAAACGGCAAGTACTACCTGGC<br>CATCACCAACAGCCTGAACAAGAAAATGAGCATCCCTACCCAGCTGGAGAGC<br>ACAGGAAATAATTATGAGAAGATGGTCCTGAACGTTTTTCCCAACGTGTTCCG<br>GATGATCCCAAAGTGCACCACAGGCAGGAACGACGTGAAGTCATGCTTCGAG<br>AGAAAGGAACCCAACGAGTACTTCTTCATCGACACCCCTGAGTTCGTGAACC<br>CCTTTAAGGTCACACGGGAGGAGTACGAACTGAATAAGATCACCTACGACGG<br>AGTTAAGAAGTGGCAGAGCGACTACAGCAAGAACACACAGGACGAAAAGGGC<br>TATAAGGAAGCCGTGACCAAGTGGATTCAGTTTTGTATGCGGTTCCTGCAGTC<br>TTATAAGAGCACCGCCATATATGACTACAGCACCCTGCAGCAACCTGAAAAAT<br>ACGAAACAGTGGACAGCTTCTATCATGATGTGGAAAAGATCCTGTACGAGTGC<br>CACTTCGAGTACGTGCCCGCTAACAAGATCGAGCAGCTTGAAGAAGAGGGAA<br>GAATCTTCCTGTTCCAGATCTACAACAAGGATTTTTCTGAGAACAGACGGCCT<br>GATAGCAAGAAAAACCTCCACACCCTGTACTGGGAGGCGCTGTTCTCCGAAG<br>AGAATAGAAAGGCCAAGGTGATTCAGCTGAATGGCAAGGCCGAGATCTTCAG<br>ACGGGAGAAATCAATCGAGCACCCTATCGTGCATAAGGCTGGCGAGGTGCTG<br>GTGAACAAGCGGACCAAAGATGGCGAACCTATTCCTGACGACATCTACAAGG<br>ACCTGAGCAACTATTTCAACGGCAGAAACGTTACCTCTGAGAAGGAAGAGTAC<br>AAGGAGTGTCTGGACAAGGTGTACACCAGCACCAAAAAGTACGATATCACCA<br>AGGACAAAAGATTCACCGAGACAAAGTACGAGTTCCACGTGCCTATCACCCT<br>GAACTACCAGGCCGACGGCGTGAAGTACCTGAATCAGAAGATCCTGCACGTG<br>CTGCGGGACAACCCTGATGTTAACATCATCGGCCTGGATAGAGGCGAAAGAA<br>ACCTGATCTCTTATGTTGTGCTGAACAGAGAGGGCAAGATCGTGAACAATCAG<br>CAGGGTTCTTTCAACATCGTGGGCAAAATGGACTACCAGAAAAAGCTGTACCA<br>GAAGGAGAAAAACCGGGATAAAGAACGGAAAACGTGGAAAAACATCGAAACC<br>ATCAAGGACCTGAAGGAGGGCTATATCAGCCAGGTGGTACACGAGCTGACCG<br>ATATGGCCATCCGGAATAACGCGATCATCGTGATGGAAGATCTGAATTTCGGA<br>TTCAAGCGGGGCCGGACCAAGGTGGAACGGCAGGTGTACCAGAAGTTTGAG<br>CTGGCCCTGCTGAAGAAGCTGCACTACCTCGTGACCGACAAGACCGAGGGA<br>GAAGCTATGCTGAAACCCGGCGGCGTGCTGCAAGGCTACCAGCTGGCTAGA<br>GAAGTCAAGACCCTGAAAGAGATCGGCAAGCAGTGCGGCTGTGTGTTCTACG<br>TGCCCCCTGGCTACACAAGCAAGATCGACCCTACAACCGGCTTCGTCGACGT<br>GTTCAACATGTCTGGAGTTACAAACCGCGAGAAAAAGAAAGCCTTTTTCGAAA<br>AATTTGATAACATGTTCTACGACGAGAAGAGAGACATGTTCGGCTTCAGCTTC<br>AATTACGAAAAGTTTACTACCTACCAGAGCAGCTACAGAAACGACTGGACCGT<br>GTACAGCAACGGCAGCAAGTATGTGTGGAACTCCCTTAAGAGAACAGACGAG<br>TTAATTGACGTGACAAAGGAGCTCAAGCTGCTGTTCGAGAAGTACGCCATCG<br>ATTACCGGAACGAAGCTCTGTTTGAGCAGATCATGAGCCAGGATACAGATAA<br>GAACAACGCCGACTTCTGGAACAAACTGTTCTGGTACTTCCGGGTGCTGCTG<br>CGGCTGAGAAATAGCAGCGACGAACTGGACCAAATCGTCAGCCCTGTGCTGA<br>ATCAGAACGGAGAGTTCTTCGAAACCCCTAAGAAAATCACAGAGAAGTCCTAC<br>CTGTCTGATTACCCTATGGACGCCGATACAAACGGCGCCTACCACATCGCCC<br>TGAAGGGCCTGTACCTGATCCAGGAGAAGATCGCTGACGAATCTGTGGACCT<br>GGACAACAAGCTGCCTAAGGACTTCTACAAGATCAGCAACGCCGAGTGGTTC<br>ATGTTTAGACAGAAAGAAAAA | |
| Expression construct (with N-terminal methionine and stop codon, includes V5-tag and C-terminal NLS) | ATGggcAAGAGCATCTACGAGAACTTCATCGGTCTTGAGAGCAAGAACCTGAC<br>ACTGAGATTCGCCCTGAACCCTGAGGCTAAAACCCAGGAGAACCTGAAGCTG<br>TACTGGGACAAACTGAGGGACGAAGAAAGAGATAGAGCCTACCCTATCGTGA<br>AAAAAATCCTCGACAAGGAGTATCAGCAGCTCATCAGCGAGGGCCTGAAACT<br>GCTGGAAAATCAAAACGTGCTGGACTGGACCGAACTGGCCGAGTACATCAGA<br>ACCAGCGATCTGTCTAAGAAGAAGAAGGAGGACAAGAGACTGCGCAAGCTGA<br>TCGCCCAGAACCTGAAAGCCCACCCCCTGGTCGACAAGCTGAAGGTGAAGAA<br>TGCCTTCGGCAAGAACGGCTACCTGGAAACCCTGCCATTAGGAAAGGAAGAA<br>AAAGAGGCCGTGAAGGTGTTTGCCGGATTCGGAGGCTTTTTCAACAACTACA<br>ACAAGAATCGGGAGAACTACTTCAGTACCGAGGAGAAGTCCACCGCCATCGC<br>CAACAGAATCGTGAACGAGAACTTCAGCAAGCACTTCAGCAACGTGGAAATC<br>GTTACAAAGATCCAAAAAGAAGTGCCAGAGCTGATTCAAATCGTGGAAGCTCA<br>GTTCAAGGGTTACGACACCATCTTTACCGTGAACGGCTACAACACCGCCCTG<br>AGCCAGGCTGGCATCGACACATACAACGAAATGGTGGCCATCTGGAACAAGG<br>AGGCAAACCTGTACGCTCAAAAAGCCGGCAAGCTGCCAGACGGCCACCCGC<br>TGAAGAAGAAGCGTAACTACCTGCTGAGCGCCCTCTTCAAACAGATCGGCAG<br>CGAAAAAGAACACCTGATCCAGATCGACAGATTCGACGGCGACGAGGAAGTG<br>ATCGAAGCCCTGACTGGCGTGAAAAAGATGCTGCAGGAGGCCGACGTGTTC<br>GAGAAGCTGAACATGCTGGTCGAGGACATGGAAAATTGGGATTACTCCAAGA | 12 |

TABLE 1B-continued

ZJHK Type V Cas Sequences

| Name | Sequence | SEQ ID NO. |
|---|---|---|
| | TCTACCTGTCTGCCCAGAGCCTGAGTAACGTGTCCGTGTTCCTGAACAACCT<br>GTATGAAGATGAACGGGAGAACAGCTGGAACTACCTGGATAACGTGCTGAGA<br>GAGAAGTGGCAGATTGAACTGCAGGGCAAAAAAAAGGGAACAGATCTGGAAG<br>AGGCCATTAGAAAGAAGAAGCAGAGCTTTTACTCTATCGAGGAACTTCAGGAG<br>GCAGTGAACGCCATCGAGGAAACCGACAAGTGCTACAATGTGTCTAAATGGC<br>TGCTGGGAGCCATGAAGAGCGAGAGAGTGATCGAGGAGAAGAAGAAAGACG<br>TGGAGGATTTCTGCACACAGTGGAAGAACGAGAGAAACAGCCTCAAGGAAAC<br>CGACATCACCGCCCTGAAGGAGTACCTGGAGCAGTGGATCTTCCTGGCTAGG<br>TACTGCAAGAGCTTCTACGCCAATGGCATCGAAAAGAAAGAGAAGGATGAGG<br>CTTTTTACCACATCCTGGAGGATGTGCTGTACGTGCTGGACGAAGTGATCTAC<br>TTCTACAACAAGGTGCGGAACTACGTGACCAAAAAGCCTTACAGTCTGGAGAA<br>GATGCACCTGAAGTTCGGCCACAACGAGCTGGCCAACGGCTGGAGCGTGAA<br>CAAGGAAGAAAATTACGGCACCGCCATCCTGAGAAGAAACGGCAAGTACTAC<br>CTGGCCATCACCAACAGCCTGAACAAGAAAATGAGCATCCCTACCCAGCTGG<br>AGAGCACAGGAAATAATTATGAGAAGATGGTCCTGAACGTTTTTCCCAACGTG<br>TTCCGGATGATCCCAAAGTGCACCACAGGCAGGAACGACGTGAAGTCATGCT<br>TCGAGAGAAAGGAACCCAACGAGTACTTCTTCATCGACACCCCTGAGTTCGT<br>GAACCCCTTTAAGGTCACACGGGAGGAGTACGAACTGAATAAGATCACCTAC<br>GACGGAGTTAAGAAGTGGCAGAGCGACTACAGCAAGAACACACAGGACGAAA<br>AGGGCTATAAGGAAGCCGTGACCAAGTGGATTCAGTTTTGTATGCGGTTCCT<br>GCAGTCTTATAAGAGCACCGCCATATATGACTACAGCACCCTGCAGCAACCT<br>GAAAAATACGAAACAGTGGACAGCTTCTATCATGATGTGGAAAAGATCCTGTA<br>CGAGTGCCACTTCGAGTACGTGCCCGCTAACAAGATCGAGCAGCTTGAAGAA<br>GAGGGAAGAATCTTCCTGTTCCAGATCTACAACAAGGATTTTTCTGAGAACAG<br>ACGGCCTGATAGCAAGAAAAACCTCCACACCCTGTACTGGGAGGCGCTGTTC<br>TCCGAAGAGAATAGAAAGGCCAAGGTGATTCAGCTGAATGGCAAGGCCGAGA<br>TCTTCAGACGGGAGAAATCAATCGAGCACCCTATCGTGCATAAGGCTGGCGA<br>GGTGCTGGTGAACAAGCGGACCAAAGATGGCGAACCTATTCCTGACGACATC<br>TACAAGGACCTGAGCAACTATTTCAACGGCAGAAACGTTACCTCTGAGAAGGA<br>AGAGTACAAGGAGTGTCTGGACAAGGTGTACACCAGCACCAAAAAGTACGAT<br>ATCACCAAGGACAAAAGATTCACCGAGACAAAGTACGAGTTCCACGTGCCTAT<br>CACCCTGAACTACCAGGCCGACGGCGTGAAGTACCTGAATCAGAAGATCCTG<br>CACGTGCTGCGGGACAACCCTGATGTTAACATCATCGGCCTGGATAGAGGCG<br>AAAGAAACCTGATCTCTTATGTTGTGCTGAACAGAGAGGGCAAGATCGTGAAC<br>AATCAGCAGGGTTCTTTCAACATCGTGGGCAAAATGGACTACCAGAAAAAGCT<br>GTACCAGAAGGAGAAAAACCGGGATAAAGAACGGAAAACGTGGAAAAACATC<br>GAAACCATCAAGGACCTGAAGGAGGGCTATATCAGCCAGGTGGTACACGAGC<br>TGACCGATATGGCCATCCGGAATAACGCGATCATCGTGATGGAAGATCTGAA<br>TTTCGGATTCAAGCGGGGCCGGACCAAGGTGGAACGGCAGGTGTACCAGAA<br>GTTTGAGCTGGCCCTGCTGAAGAAGCTGCACTACCTCGTGACCGACAAGACC<br>GAGGGAGAAGCTATGCTGAAACCCGGCGGCGTGCTGCAAGGCTACCAGCTG<br>GCTAGAGAAGTCAAGACCCTGAAAGAGATCGGCAAGCAGTGCGGCTGTGTGT<br>TCTACGTGCCCCCTGGCTACACAAGCAAGATCGACCCTACAACCGGCTTCGT<br>CGACGTGTTCAACATGTCTGGAGTTACAAACCGCGAGAAAAAGAAAGCCTTTT<br>TCGAAAAATTTGATAACATGTTCTACGACGAGAAGAGAGACATGTTCGGCTTC<br>AGCTTCAATTACGAAAAGTTTACTACCTACCAGAGCAGCTACAGAAACGACTG<br>GACCGTGTACAGCAACGGCAGCAAGTATGTGTGGAACTCCCTTAAGAGAACA<br>GACGAGTTAATTGACGTGACAAAGGAGCTCAAGCTGCTGTTCGAGAAGTACG<br>CCATCGATTACCGGAACGAAGCTCTGTTTGAGCAGATCATGAGCCAGGATAC<br>AGATAAGAACAACGCCGACTTCTGGAACAAACTGTTCTGGTACTTCCGGGTG<br>CTGCTGCGGCTGAGAAATAGCAGCGACGAACTGGACCAAATCGTCAGCCCTG<br>TGCTGAATCAGAACGGAGAGTTCTTCGAAACCCCTAAGAAAATCACAGAGAAG<br>TCCTACCTGTCTGATTACCCTATGGACGCCGATACAAACGGCGCCTACCACAT<br>CGCCCTGAAGGGCCTGTACCTGATCCAGGAGAAGATCGCTGACGAATCTGTG<br>GACCTGGACAACAAGCTGCCTAAGGACTTCTACAAGATCAGCAACGCCGAGT<br>GGTTCATGTTTAGACAGAAAGAAAAAtctagaAAGCGGACAGCAGACGGCTCCG<br>AATTTGAAAGCCCTAAGAAAAAGAGAAAGGTGggatccGGCAAACCTATCCCCA<br>ATCCCCTGCTGGGCCTGGACAGCACCTGA | |

In some embodiments a ZJHK Type V Cas protein comprises an amino acid sequence of SEQ ID NO:7, SEQ ID NO:8, or SEQ ID NO:9. In some embodiments, a ZJHK Type V Cas protein has nickase activity, for example resulting from one or more amino acid substitutions relative to the sequence of SEQ ID NO:7, SEQ ID NO:8, or SEQ ID NO:9. In some embodiments, the one or more amino acid substitutions providing nickase activity comprise a D900 substitution, wherein the position of the D900 substitution is defined with respect to the amino acid numbering of SEQ ID NO:8 (corresponding to amino acid 908 of SEQ ID NO:121). In some embodiments, the one or more amino acid substitutions providing nickase activity comprise an E987 substitution, wherein the position of the E987 substitution is defined with respect to the amino acid numbering of SEQ ID NO:8 (corresponding to amino acid 993 of SEQ ID NO:121). In some embodiments, the one or more amino acid substitutions providing nickase activity comprise a R1203 substitution, wherein the position of the R1203 substitution is defined with respect to the amino acid numbering of SEQ ID NO:8 (corresponding to amino acid 1226 of SEQ ID NO:121). In some embodiments, the one or more amino acid substitutions providing nickase activity comprise a D1244 substitution, wherein the position of the D1244 substitution is defined with respect to the amino acid numbering of SEQ ID NO:121 (corresponding to amino acid 1263 of SEQ ID NO:121). In some embodiments, a ZJHK Type V Cas protein is catalytically inactive, for example due to a R1203 substitution in combination with a D900 substitution, a E987 substitution, and/or D1244 substitution.

6.2.3. ZIKV Type V Cas Proteins

In one aspect, the disclosure provides ZIKV Type V Cas proteins. ZIKV Type V Cas proteins can be further classified as Type V-A Cas proteins. The ZIKV Type V Cas proteins typically comprise an amino acid sequence that is at least 50%, at least 55%, at least 60%, at least 65%, at least 70%, at least 75%, at least 85%, at least 90%, or at least 95% identical to SEQ ID NO:13. In some embodiments, the ZIKV Type V Cas proteins comprise an amino acid sequence that is at least 95%, at least 96%, at least 97%, at least 98%, or at least 99% identical to SEQ ID NO:13. In some embodiments, a ZIKV Type V Cas protein comprises an amino acid sequence that is identical to SEQ ID NO:13.

Exemplary ZIKV Type V Cas protein sequences and nucleotide sequences encoding exemplary ACEE Type V Cas proteins are set forth in Table 1C.

TABLE 1C

ZIKV Type V Cas Sequences

| Name | Sequence | SEQ ID NO. |
|---|---|---|
| Wildtype amino acid sequence (without N-terminal methionine) | NIYENFTNMYQVNKTIRMGLKPICKTGENIAKFLEEDKETSDKYKIAKEVIDKENRA<br>FIEDRLKDFSISGLDEYLELLKQKKNLTKNQNKMKKEISTQLTKIQNKMRDEISTQL<br>KGFPQFDNKYKFKYITDKEDIEILKYFKDKKFITFFEEFNTNRKNVYSKENISTSIGH<br>RIVHENLPKFISNFRILNKAIEAFGISKINEDFKNNGINVTVEELNKIDYFNKVLTQSG<br>IDLYNNLIGILNQNINLYNQQQKVKKNKIGKLEILYKQILSKTDKVSFIEEFTEDNQLL<br>ECIDEYFKEKYSLITVDLNNLLENIDTYNLNGIFIKSDKSLGNISNYLYKDWWYISNLI<br>NEEYDYKHKNKVRDDKYYETRKKAIDKIKYFSIGHIDELLKDKNVPMVENYFKEKIN<br>LVVKEFNAYLNKFNEYKFINELKTDEIAVEIIKNLCDSIKNVQGIVKPLIITGNDKDDD<br>FYVEINYIWDELNKFDKIYNMVRNYLTKKDYIEEKIRMMFSKSSFMDGWGKDYGT<br>KKAHIVYHDKNYYLVIVDKKLKLEDIDKLYKPGGDTVHYVYNYQSTENGNIPRKFIY<br>SKGKRFAPSVEKYNLPIEDVIEVYNNEYHTTDYEKKNPEIYKKSLTSLIDYFKIGVN<br>RDMDFEKFDFRLKDSNEYKNIKEFYDNLETCCYKLQEEKVNFNVLEELSYSGKIYL<br>FKIYNKDFSENSKGIPNLHTLYFKMLFDKENLENPIYKLSGKAKMFFRKGSLNLDK<br>KTVDYDKKPIDKKENDKKIKNRRYKVDSFTLHMSIITNFQSYENKNVNETVNRALK<br>YCDDVYAIGIDRGIRNLLYACVVNSKGEIVKQVPLNIINNKDYHNLLAEREEKKKNS<br>RKNWKIIDNIRNLKEGYLSQAIHIITDLMVEYNAVLVLENLNFRFKEKQMKFESNVY<br>QKFEKMLIDKLNFLVDKKLDKNANGGLFNAYQLTEKFTNFKDMKNQNGIIFYIPAW<br>MTSKIDPVTGFTNLFYIKYESIEKAKEFFGKFKSIKFNKVDNYFEFEFDYNDFTDRA<br>QGTRSKWTVCSFGPRIEGFRNPEKNNSWDGREIDITEKIKKLLDDYNVSLDKDIKA<br>QIMDINTKDFFEKFIKYFKLVLQMRNSKTGTDIDYIISPVKNKQNEFFDSRKQNEKM<br>PMDADANGAYNIARKGLMFIDIIKETEDKDLKMPKLFIKNKDWLNYVQKSDL | 13 |
| Wildtype amino acid sequence (with N-terminal methionine) | MNIYENFTNMYQVNKTIRMGLKPICKTGENIAKFLEEDKETSDKYKIAKEVIDKENR<br>AFIEDRLKDFSISGLDEYLELLKQKKNLTKNQNKMKKEISTQLTKIQNKMRDEISTQ<br>LKGFPQFDNKYKFKYITDKEDIEILKYFKDKKFITFFEEFNTNRKNVYSKENISTSIG<br>HRIVHENLPKFISNFRILNKAIEAFGISKINEDFKNNGINVTVEELNKIDYFNKVLTQS<br>GIDLYNNLIGILNQNINLYNQQQKVKKNKIGKLEILYKQILSKTDKVSFIEEFTEDNQL<br>LECIDEYFKEKYSLITVDLNNLLENIDTYNLNGIFIKSDKSLGNISNYLYKDWWYISN<br>LINEEYDYKHKNKVRDDKYYETRKKAIDKIKYFSIGHIDELLKDKNVPMVENYFKEK<br>INLVVKEFNAYLNKFNEYKFINELKTDEIAVEIIKNLCDSIKNVQGIVKPLIITGNDKDD<br>DFYVEINYIWDELNKFDKIYNMVRNYLTKKDYIEEKIRMMFSKSSFMDGWGKDYG<br>TKKAHIVYHDKNYYLVIVDKKLKLEDIDKLYKPGGDTVHYVYNYQSTENGNIPRKFI<br>YSKGKRFAPSVEKYNLPIEDVIEVYNNEYHTTDYEKKNPEIYKKSLTSLIDYFKIGV<br>NRDMDFEKFDFRLKDSNEYKNIKEFYDNLETCCYKLQEEKVNFNVLEELSYSGKI<br>YLFKIYNKDFSENSKGIPNLHTLYFKMLFDKENLENPIYKLSGKAKMFFRKGSLNL<br>DKKTVDYDKKPIDKKENDKKIKNRRYKVDSFTLHMSIITNFQSYENKNVNETVNRA<br>LKYCDDVYAIGIDRGIRNLLYACVVNSKGEIVKQVPLNIINNKDYHNLLAEREEKKK<br>NSRKNWKIIDNIRNLKEGYLSQAIHIITDLMVEYNAVLVLENLNFRFKEKQMKFESN<br>VYQKFEKMLIDKLNFLVDKKLDKNANGGLFNAYQLTEKFTNFKDMKNQNGIIFYIP<br>AWMTSKIDPVTGFTNLFYIKYESIEKAKEFFGKFKSIKFNKVDNYFEFEFDYNDFTD<br>RAQGTRSKWTVCSFGPRIEGFRNPEKNNSWDGREIDITEKIKKLLDDYNVSLDKDI<br>KAQIMDINTKDFFEKFIKYFKLVLQMRNSKTGTDIDYIISPVKNKQNEFFDSRKQNE<br>KMPMDADANGAYNIARKGLMFIDIIKETEDKDLKMPKLFIKNKDWLNYVQKSDL | 14 |
| Expression construct (with N-terminal methionine, V5-tag and C-terminal NLS) aa sequence | MGNIYENFTNMYQVNKTIRMGLKPICKTGENIAKFLEEDKETSDKYKIAKEVIDKEN<br>RAFIEDRLKDFSISGLDEYLELLKQKKNLTKNQNKMKKEISTQLTKIQNKMRDEIST<br>QLKGFPQFDNKYKFKYITDKEDIEILKYFKDKKFITFFEEFNTNRKNVYSKENISTSI<br>GHRIVHENLPKFISNFRILNKAIEAFGISKINEDFKNNGINVTVEELNKIDYFNKVLTQ<br>SGIDLYNNLIGILNQNINLYNQQQKVKKNKIGKLEILYKQILSKTDKVSFIEEFTEDN<br>QLLECIDEYFKEKYSLITVDLNNLLENIDTYNLNGIFIKSDKSLGNISNYLYKDWWYI<br>SNLINEEYDYKHKNKVRDDKYYETRKKAIDKIKYFSIGHIDELLKDKNVPMVENYFK<br>EKINLVVKEFNAYLNKFNEYKFINELKTDEIAVEIIKNLCDSIKNVQGIVKPLIITGNDK<br>DDDFYVEINYIWDELNKFDKIYNMVRNYLTKKDYIEEKIRMMFSKSSFMDGWGKD<br>YGTKKAHIVYHDKNYYLVIVDKKLKLEDIDKLYKPGGDTVHYVYNYQSTENGNIPR<br>KFIYSKGKRFAPSVEKYNLPIEDVIEVYNNEYHTTDYEKKNPEIYKKSLTSLIDYFKI<br>GVNRDMDFEKFDFRLKDSNEYKNIKEFYDNLETCCYKLQEEKVNFNVLEELSYSG<br>KIYLFKIYNKDFSENSKGIPNLHTLYFKMLFDKENLENPIYKLSGKAKMFFRKGSLN<br>LDKKTVDYDKKPIDKKENDKKIKNRRYKVDSFTLHMSIITNFQSYENKNVNETVNR<br>ALKYCDDVYAIGIDRGIRNLLYACVVNSKGEIVKQVPLNIINNKDYHNLLAEREEKK<br>KNSRKNWKIIDNIRNLKEGYLSQAIHIITDLMVEYNAVLVLENLNFRFKEKQMKFES | 15 |

TABLE 1C-continued

ZIKV Type V Cas Sequences

| Name | Sequence | SEQ ID NO. |
|---|---|---|
| | NVYQKFEKMLIDKLNFLVDKKLDKNANGGLFNAYQLTEKFTNFKDMKNQNGIIFYI<br>PAWMTSKIDPVTGFTNLFYIKYESIEKAKEFFGKFKSIKFNKVDNYFEFEFDYNDFT<br>DRAQGTRSKWTVCSFGPRIEGFRNPEKNNSWDGREIDITEKIKKLLDDYNVSLDK<br>DIKAQIMDINTKDFFEKFIKYFKLVLQMRNSKTGTDIDYIISPVKNKQNEFFDSRKQ<br>NEKMPMDADANGAYNIARKGLMFIDIIKETEDKDLKMPKLFIKNKDWLNYVQKSDL<br>SRKRTADGSEFESPKKKRKVGSGKPIPNPLLGLDST | |
| Wildtype coding sequence (with N-terminal methionine and stop codon) | ATGAACATTTACGAAAATTTTACTAATATGTATCAGGTAAATAAGACTATAAGAA<br>TGGGGTTAAAGCCAATATGTAAAACTGGTGAAAATATTGCTAAATTTCTTGAGG<br>AAGATAAGGAAACAAGTGATAAATACAAGATAGCTAAAGAAGTAATTGATAAG<br>GAAAATAGAGCTTTTATAGAGGATAGATTAAAGGATTTTTCAATTTCAGGGTTG<br>GATGAATATTTGGAATTGCTTAAACAAAAAAAGAATTTAACCAAAAATCAAAAT<br>AAAATGAAAAAGGAAATTTCAACACAGTTAACAAAAATACAAAATAAAATGAGA<br>GATGAAATTTCAACACAGTTAAAAGGCTTCCCTCAATTTGATAATAAATATAAA<br>TTCAAATATATTACAGATAAAGAAGATATAGAAATTTTAAAATATTTTAAAGATA<br>AGAAATTTATTACTTTCTTTGAAGAATTTAATACTAATAGAAAAAATGTCTACTC<br>TAAAGAAAATATTTCAACTTCTATTGGACACAGAATTGTTCACGAAAATCTTCC<br>AAAATTTATTTCAAATTTTAGGATTTTAAATAAAGCAATAGAGGCGTTTGGAATA<br>AGTAAAATAAATGAAGATTTTAAGAATAATGGAATTAATGTTACAGTTGAAGAA<br>CTTAATAAAATAGATTATTTTAACAAGGTTTTAACTCAATCAGGAATAGATTTGT<br>ATAATAATTTGATAGGTATTTTAAATCAAAATATAAATCTATATAATCAACAACA<br>GAAAGTAAAAAAGAATAAAATTGGAAAGTTAGAAATATTATATAAGCAAATTTTA<br>AGTAAAACAGATAAAGTATCGTTTATTGAAGAATTTACTGAAGATAACCAACTT<br>TTGGAATGTATTGATGAATATTTTAAAGAAAAATATAGTTTGATAACTGTAGATT<br>TAAATAATTTACTTGAAAATATTGATACTTATAATTTGAATGGTATCTTTATTAAA<br>AGTGATAAGTCCTTGGGAAATATATCTAATTATTTATATAAAGATTGGTGGTAT<br>ATATCAAATCTTATAAACGAAGAATACGATTATAAACATAAGAATAAGGTAAGA<br>GATGATAAGTATTATGAAACAAGAAAAAAAGCTATAGATAAGATTAAATATTTTT<br>CCATAGGACATATTGATGAATTGTTAAAAGATAAAAATGTTCCTATGGTAGAAA<br>ACTATTTCAAAGAAAAGATAAATTTAGTAGTAAAAGAATTTAATGCTTATTTAAA<br>CAAATTTAATGAATATAAGTTTATAAATGAGCTAAAAACTGATGAAATTGCTGT<br>CGAAATAATAAAAAATTTATGTGATTCAATAAAGAATGTACAGGGGATAGTAAA<br>GCCTTTAATAATTACTGGAAATGATAAAGACGATGATTTTTATGTGGAAATCAA<br>TTATATATGGGACGAGCTTAATAAGTTTGATAAAATATATAATATGGTTAGAAAT<br>TATCTTACAAAAAAGGATTACATAGAGGAAAAAATTAGAATGATGTTTTCAAAG<br>AGCAGTTTTATGGATGGTTGGGGAAAAGATTATGGAACAAAAAAAGCACATAT<br>AGTTTATCATGATAAAAATTATTATTTAGTAATAGTAGACAAGAAATTAAAATTA<br>GAGGATATAGATAAATTATATAAACCAGGTGGAGATACTGTACATTATGTATAT<br>AATTACCAATCAACAGAAAATGGAAATATTCCTAGAAAATTCATATATTCTAAG<br>GGTAAAAGATTTGCACCATCTGTAGAAAAATATAATTTACCAATAGAAGATGTT<br>ATCGAAGTGTATAACAATGAATATCATACAACAGATTACGAAAAGAAAAATCCT<br>GAAATTTACAAGAAATCATTAACATCCTTAATTGATTATTTTAAAATAGGGGTAA<br>ATAGGGATATGGATTTTGAAAAATTTGATTTTAGATTAAAAGATTCAAACGAAT<br>ACAAAAATATAAAAGAATTTTATGATAATTTGGAAACTTGTTGCTATAAGTTACA<br>AGAAGAAAAAGTTAATTTTAATGTACTTGAAGAGCTTTCATATAGTGGAAAAAT<br>TTATTTATTTAAAATATACAATAAGGATTTTTCTGAAAATAGCAAAGGAATACCT<br>AATCTTCATACTTTATATTTTAAAATGCTATTTGACAAAGAAAACCTTGAAAATC<br>CGATTTATAAACTTAGTGGAAAGGCTAAAATGTTTTTTAGAAAGGGTAGTCTTA<br>ATTTAGACAAAAAAACTGTTGATTATGATAAAAAGCCAATAGATAAGAAAGAAA<br>ATGACAAAAAAATTAAAAATAGAAGATATAAAGTTGATAGTTTTACATTACATAT<br>GTCAATTATTACGAACTTTCAGTCATATGAAAATAAAAATGTAAATGAAACTGT<br>AAATAGGGCTTTAAAATATTGTGATGATGTTTATGCCATAGGTATAGACAGAG<br>GAATAAGAAATTTATTATATGCTTGTGTAGTAAATTCAAAGGGAGAAATAGTAA<br>AACAAGTTCCTTTAAATATTATAAATAATAAAGATTATCACAATTTACTTGCAGA<br>AAGAGAAGAGAAGAAAAAGAATAGTAGGAAAAATTGGAAAATCATTGATAATA<br>TAAGGAATTTAAAGGAAGGCTATTTAAGTCAGGCCATACATATAATAACTGACC<br>TTATGGTTGAATATAATGCTGTACTTGTTTTAGAGAATTTGAATTTTAGATTTAA<br>AGAAAAACAAATGAAATTTGAAAGTAATGTTTATCAAAAATTTGAAAAGATGCT<br>TATTGATAAATTGAATTTCTTAGTTGATAAAAAGCTTGATAAGAACGCCAATGG<br>TGGATTGTTTAATGCGTATCAATTAACAGAAAAATTTACAAACTTTAAAGATATG<br>AAAAATCAAAATGGTATAATATTTTATATTCCTGCTTGGATGACAAGCAAAATT<br>GACCCAGTTACAGGATTTACAAATTTATTCTATATTAAATATGAGAGTATTGAA<br>AAGGCTAAAGAGTTTTTTGGTAAGTTTAAATCAATAAAATTTAATAAGGTAGAC<br>AACTATTTTGAATTTGAATTTGATTATAATGATTTTACTGACAGAGCTCAAGGTA<br>CAAGGTCTAAATGGACAGTTTGTAGTTTTGGCCCTAGAATTGAAGGTTTTAGA<br>AATCCTGAAAAAAATAATAGTTGGGATGGTAGAGAAATAGATATAACAGAGAA<br>AATTAAAAAATTACTTGATGATTATAATGTATOTTTAGATAAAGATATTAAAGCT<br>CAAATTATGGATATAAATACTAAGGATTTCTTTGAAAAATTTATTAAATATTTTAA<br>ACTTGTATTGCAAATGAGAAACAGTAAAACAGGTACAGATATTGATTATATCAT<br>TTCTCCGGTTAAAAATAAGCAAAATGAATTTTTTGACAGTAGAAAGCAAAATGA<br>AAAAATGCCTATGGATGCAGATGCAAATGGTGCTTATAATATTGCTAGAAAAG<br>GCTTAATGTTTATTGATATAATAAAAGAAACTGAAGATAAAGATTTAAAGATGC<br>CTAAATTGTTCATTAAAAATAAAGATTGGTTAAATTATGTACAAAAGAGTGATTT<br>GTAA | 16 |

TABLE 1C-continued

ZIKV Type V Cas Sequences

| Name | Sequence | SEQ ID NO. |
|---|---|---|
| Codon optimized coding sequence (no N-terminal methionine, no stop codon) | AATATCTATGAGAACTTCACCAACATGTACCAGGTGAACAAGACAATCCGCAT<br>GGGCCTGAAGCCTATCTGTAAAACCGGAGAAAACATCGCCAAGTTCCTGGAG<br>GAGGACAAGGAAACCAGCGACAAGTACAAGATCGCCAAGGAGGTCATCGACA<br>AGGAGAACAGAGCCTTTATCGAGGACAGACTGAAGGACTTCAGCATCAGCGG<br>CCTGGACGAGTACCTGGAACTGCTGAAGCAGAAGAAAAACCTGACAAAGAAC<br>CAGAACAAGATGAAAAAGGAAATCTCCACCCAGCTGACAAAGATCCAGAACAA<br>GATGCGGGACGAGATATCGACACAGCTGAAGGGCTTCCCTCAGTTCGATAAC<br>AAATACAAGTTCAAATATATCACAGACAAGGAGGACATCGAAATCCTCAAGTA<br>CTTCAAGGATAAGAAGTTCATTACATTCTTTGAGGAATTTAATACCAATCGGAA<br>AAACGTGTACAGCAAGGAAAACATCAGCACCTCTATCGGCCATAGAATCGTG<br>CACGAGAACCTGCCAAAGTTCATCAGCAACTTCAGAATCCTGAATAAGGCCAT<br>CGAGGCCTTCGGCATCTCTAAAATCAATGAGGACTTCAAGAACAATGGCATCA<br>ACGTGACCGTAGAAGAACTGAACAAGATCGACTACTTCAACAAGGTCCTGACA<br>CAGAGCGGCATTGACCTGTACAACAACCTGATTGGCATCCTGAACCAGAACA<br>TCAACCTGTACAATCAGCAGCAGAAGGTGAAGAAGAACAAAATCGGAAAGCT<br>GGAAATCCTGTACAAGCAAATCTTGTCCAAAACCGACAAGGTGTCTTTCATTG<br>AGGAGTTCACCGAGGACAACCAGCTGCTGGAGTGCATCGACGAGTACTTTAA<br>AGAGAAATACAGCCTGATCACCGTGGACCTGAACAACCTGCTTGAAAATATCG<br>ACACCTACAATCTCAACGGCATCTTCATCAAATCTGATAAAAGCCTGGGCAAC<br>ATCAGCAACTACCTGTACAAGGATTGGTGGTACATCAGCAACCTGATCAACGA<br>AGAATACGACTACAAGCACAAGAACAAGGTCAGAGATGATAAGTACTACGAGA<br>CAAGAAAGAAGGCCATCGACAAGATCAAGTACTTCTCTATCGGACACATCGAT<br>GAGCTGCTGAAGGACAAGAACGTTCCAATGGTGGAAAACTACTTCAAGGAGA<br>AGATCAACCTGGTCGTGAAGGAGTTCAATGCTTATCTGAACAAGTTCAATGAA<br>TATAAATTCATCAACGAGCTGAAAACAGACGAGATCGCCGTGGAAATCATCAA<br>GAACCTGTGCGACAGCATCAAGAACGTGCAGGGCATCGTGAAGCCCCTGATC<br>ATCACCGGCAACGACAAGGATGATGATTTTTACGTGGAGATCAACTACATCTG<br>GGATGAGCTTAACAAGTTCGACAAAATCTACAACATGGTCAGGAATTACCTAA<br>CCAAGAAGGACTACATCGAGGAAAAGATCAGAATGATGTTTTCCAAGAGCAG<br>CTTTATGGACGGCTGGGGCAAGGACTACGGCACCAAGAAGGCCCACATCGT<br>GTACCACGACAAGAACTACTACCTGGTGATCGTGGACAAGAAGCTGAAACTG<br>GAAGATATCGACAAACTATACAAGCCAGGCGGCGACACAGTTCACTACGTGT<br>ACAACTACCAGTCTACCGAGAACGGAAACATCCCTCGGAAGTTCATCTACTCT<br>AAGGGCAAGCGGTTCGCCCCTAGCGTGGAAAAATATAACCTGCCTATTGAAG<br>ATGTGATTGAGGTGTACAACAACGAGTACCACACCACCGACTATGAGAAAAAG<br>AACCCTGAGATATACAAAAAGTCCCTGACCAGCCTGATCGACTATTTCAAGAT<br>CGGCGTGAACAGAGATATGGACTTCGAGAAGTTTGATTTTCGGCTAAAGGACT<br>CCAACGAATACAAGAACATCAAGGAGTTCTACGATAACCTGGAGACATGCTGC<br>TACAAGCTGCAGGAGGAAAAGGTGAACTTCAACGTGCTGGAGGAACTGAGCT<br>ACAGCGGAAAGATCTACCTGTTCAAGATCTACAACAAAGATTTCAGCGAGAAT<br>AGCAAAGGCATCCCTAACCTGCATACCCTGTACTTCAAAATGCTGTTCGACAA<br>AGAGAACCTGGAGAACCCCATCTACAAGCTGTCTGGAAAAGCTAAGATGTTTT<br>TCAGAAAGGGCAGCCTGAACCTGGACAAAAAAACCGTTGACTATGACAAAAAA<br>CCTATCGATAAGAAGGAAAACGACAAAAAAATCAAGAATAGGCGGTACAAGGT<br>GGACAGCTTCACCCTGCACATGAGCATCATCACCAACTTCCAGAGCTACGAG<br>AACAAGAACGTTAATGAGACTGTGAACCGGGCCCTGAAGTACTGCGACGACG<br>TGTACGCCATCGGCATCGACCGCGGAATCCGGAACCTGCTGTACGCTTGTGT<br>GGTGAACAGCAAGGGCGAGATCGTGAAGCAAGTGCCCCTCAACATCATTAAC<br>AATAAGGATTACCACAACCTGCTGGCCGAGAGAGAAGAAAAGAAGAAAAACA<br>GCAGAAAGAATTGGAAGATCATAGACAACATCAGAAACCTGAAGGAAGGCTA<br>CCTGAGCCAGGCCATCCACATCATCACCGACCTGATGGTGGAATACAACGCC<br>GTGCTGGTGCTGGAGAACCTGAATTTCAGATTCAAGGAGAAGCAGATGAAGT<br>TTGAAAGCAATGTGTACCAAAAATTCGAAAAAATGCTGATCGACAAGCTGAAT<br>TTCCTGGTCGATAAAAAACTGGACAAGAATGCCAATGGCGGACTGTTTAACGC<br>CTATCAGCTGACAGAGAAGTTCACCAACTTTAAGGATATGAAGAATCAGAACG<br>GCATCATCTTCTACATCCCCGCCTGGATGACAAGCAAGATCGATCCCGTGAC<br>CGGCTTCACAAACCTGTTTTATATCAAATACGAGAGCATCGAGAAGGCAAAGG<br>AGTTCTTCGGCAAGTTTAAGTCTATCAAGTTCAATAAGGTGGACAATTATTTCG<br>AGTTCGAGTTCGACTACAACGACTTTACCGACAGAGCTCAAGGCACCAGAAG<br>CAAGTGGACCGTGTGTAGCTTCGGTCCTCGGATCGAGGGCTTCAGAAACCCC<br>GAGAAAAACAATTCCTGGGACGGCAGAGAAATCGACATCACAGAGAAGATCA<br>AGAAGCTGCTGGATGACTACAATGTGAGCCTGGACAAAGACATCAAAGCCCA<br>GATCATGGACATCAACACCAAGGATTTCTTCGAGAAGTTCATCAAGTACTTCA<br>AGCTGGTGCTGCAGATGAGAAACAGCAAGACCGGCACCGACATCGATTACAT<br>TATCTCCCCTGTGAAGAACAAGCAGAACGAGTTTTTCGACTCCAGAAAGCAGA<br>ACGAGAAGATGCCTATGGACGCTGATGCCAACGGCGCCTACAACATCGCTAG<br>AAAGGGGCTGATGTTCATCGATATCATCAAGGAAACAGAGGACAAGGACCTG<br>AAAATGCCTAAGCTGTTCATAAAGAACAAGGATTGGCTGAACTATGTGCAGAA<br>ATCAGATCTG | 17 |
| Expression construct (with N-terminal methionine and stop | ATGggcAATATCTATGAGAACTTCACCAACATGTACCAGGTGAACAAGACAATC<br>CGCATGGGCCTGAAGCCTATCTGTAAAACCGGAGAAAACATCGCCAAGTTCC<br>TGGAGGAGGACAAGGAAACCAGCGACAAGTACAAGATCGCCAAGGAGGTCA<br>TCGACAAGGAGAACAGAGCCTTTATCGAGGACAGACTGAAGGACTTCAGCAT<br>CAGCGGCCTGGACGAGTACCTGGAACTGCTGAAGCAGAAGAAAAACCTGACA | 18 |

TABLE 1C-continued

ZIKV Type V Cas Sequences

| Name | Sequence | SEQ ID NO. |
|---|---|---|
| codon, | AAGAACCAGAACAAGATGAAAAAGGAAATCTCCACCCAGCTGACAAAGATCCA | |
| includes V5- | GAACAAGATGCGGGACGAGATATCGACACAGCTGAAGGGCTTCCCTCAGTTC | |
| tag and C- | GATAACAAATACAAGTTCAAATATATCACAGACAAGGAGGACATCGAAATCCT | |
| terminal NLS) | CAAGTACTTCAAGGATAAGAAGTTCATTACATTCTTTGAGGAATTTAATACCAA | |
| | TCGGAAAAACGTGTACAGCAAGGAAAACATCAGCACCTCTATCGGCCATAGA | |
| | ATCGTGCACGAGAACCTGCCAAAGTTCATCAGCAACTTCAGAATCCTGAATAA | |
| | GGCCATCGAGGCCTTCGGCATCTCTAAAATCAATGAGGACTTCAAGAACAATG | |
| | GCATCAACGTGACCGTAGAAGAACTGAACAAGATCGACTACTTCAACAAGGTC | |
| | CTGACACAGAGCGGCATTGACCTGTACAACAACCTGATTGGCATCCTGAACC | |
| | AGAACATCAACCTGTACAATCAGCAGCAGAAGGTGAAGAAGAACAAAATCGG | |
| | AAAGCTGGAAATCCTGTACAAGCAAATCTTGTCCAAAACCGACAAGGTGTCTT | |
| | TCATTGAGGAGTTCACCGAGGACAACCAGCTGCTGGAGTGCATCGACGAGTA | |
| | CTTTAAAGAGAAATACAGCCTGATCACCGTGGACCTGAACAACCTGCTTGAAA | |
| | ATATCGACACCTACAATCTCAACGGCATCTTCATCAAATCTGATAAAAGCCTG | |
| | GGCAACATCAGCAACTACCTGTACAAGGATTGGTGGTACATCAGCAACCTGAT | |
| | CAACGAAGAATACGACTACAAGCACAAGAACAAGGTCAGAGATGATAAGTACT | |
| | ACGAGACAAGAAAGAAGGCCATCGACAAGATCAAGTACTTCTCTATCGGACA | |
| | CATCGATGAGCTGCTGAAGGACAAGAACGTTCCAATGGTGGAAAACTACTTCA | |
| | AGGAGAAGATCAACCTGGTCGTGAAGGAGTTCAATGCTTATCTGAACAAGTTC | |
| | AATGAATATAAATTCATCAACGAGCTGAAAACAGACGAGATCGCCGTGGAAAT | |
| | CATCAAGAACCTGTGCGACAGCATCAAGAACGTGCAGGGCATCGTGAAGCCC | |
| | CTGATCATCACCGGCAACGACAAGGATGATGATTTTTACGTGGAGATCAACTA | |
| | CATCTGGGATGAGCTTAACAAGTTCGACAAAATCTACAACATGGTCAGGAATT | |
| | ACCTAACCAAGAAGGACTACATCGAGGAAAAGATCAGAATGATGTTTTCCAAG | |
| | AGCAGCTTTATGGACGGCTGGGGCAAGGACTACGGCACCAAGAAGGCCCCAC | |
| | ATCGTGTACCACGACAAGAACTACTACCTGGTGATCGTGGACAAGAAGCTGA | |
| | AACTGGAAGATATCGACAAACTATACAAGCCAGGCGGCGACACAGTTCACTA | |
| | CGTGTACAACTACCAGTCTACCGAGAACGGAAACATCCCTCGGAAGTTCATCT | |
| | ACTCTAAGGGCAAGCGGTTCGCCCCTAGCGTGGAAAAATATAACCTGCCTATT | |
| | GAAGATGTGATTGAGGTGTACAACAACGAGTACCACACCACCGACTATGAGA | |
| | AAAAGAACCCTGAGATATACAAAAAGTCCCTGACCAGCCTGATCGACTATTTC | |
| | AAGATCGGCGTGAACAGAGATATGGACTTCGAGAAGTTTGATTTTCGGCTAAA | |
| | GGACTCCAACGAATACAAGAACATCAAGGAGTTCTACGATAACCTGGAGACAT | |
| | GCTGCTACAAGCTGCAGGAGGAAAAGGTGAACTTCAACGTGCTGGAGGAACT | |
| | GAGCTACAGCGGAAAGATCTACCTGTTCAAGATCTACAACAAAGATTTCAGCG | |
| | AGAATAGCAAAGGCATCCCTAACCTGCATACCCTGTACTTCAAAATGCTGTTC | |
| | GACAAAGAGAACCTGGAGAACCCCATCTACAAGCTGTCTGGAAAAGCTAAGA | |
| | TGTTTTTCAGAAAGGGCAGCCTGAACCTGGACAAAAAAACCGTTGACTATGAC | |
| | AAAAAACCTATCGATAAGAAGGAAAACGACAAAAAAATCAAGAATAGGCGGTA | |
| | CAAGGTGGACAGCTTCACCCTGCACATGAGCATCATCACCAACTTCCAGAGC | |
| | TACGAGAACAAGAACGTTAATGAGACTGTGAACCGGGCCCTGAAGTACTGCG | |
| | ACGACGTGTACGCCATCGGCATCGACCGCGGAATCCGGAACCTGCTGTACG | |
| | CTTGTGTGGTGAACAGCAAGGGCGAGATCGTGAAGCAAGTGCCCCTCAACAT | |
| | CATTAACAATAAGGATTACCACAACCTGCTGGCCGAGAGAGAAGAAAAGAAG | |
| | AAAAACAGCAGAAAGAATTGGAAGATCATAGACAACATCAGAAACCTGAAGGA | |
| | AGGCTACCTGAGCCAGGCCATCCACATCATCACCGACCTGATGGTGGAATAC | |
| | AACGCCGTGCTGGTGCTGGAGAACCTGAATTTCAGATTCAAGGAGAAGCAGA | |
| | TGAAGTTTGAAAGCAATGTGTACCAAAAATTCGAAAAAATGCTGATCGACAAG | |
| | CTGAATTTCCTGGTCGATAAAAAACTGGACAAGAATGCCAATGGCGGACTGTT | |
| | TAACGCCTATCAGCTGACAGAGAAGTTCACCAACTTTAAGGATATGAAGAATC | |
| | AGAACGGCATCATCTTCTACATCCCCGCCTGGATGACAAGCAAGATCGATCC | |
| | CGTGACCGGCTTCACAAACCTGTTTTATATCAAATACGAGAGCATCGAGAAGG | |
| | CAAAGGAGTTCTTCGGCAAGTTTAAGTCTATCAAGTTCAATAAGGTGGACAAT | |
| | TATTTCGAGTTCGAGTTCGACTACAACGACTTTACCGACAGAGCTCAAGGCAC | |
| | CAGAAGCAAGTGGACCGTGTGTAGCTTCGGTCCTCGGATCGAGGGCTTCAGA | |
| | AACCCCGAGAAAAACAATTCCTGGGACGGCAGAGAAATCGACATCACAGAGA | |
| | AGATCAAGAAGCTGCTGGATGACTACAATGTGAGCCTGGACAAAGACATCAA | |
| | AGCCCAGATCATGGACATCAACACCAAGGATTTCTTCGAGAAGTTCATCAAGT | |
| | ACTTCAAGCTGGTGCTGCAGATGAGAAACAGCAAGACCGGCACCGACATCGA | |
| | TTACATTATCTCCCCTGTGAAGAACAAGCAGAACGAGTTTTTCGACTCCAGAA | |
| | AGCAGAACGAGAAGATGCCTATGGACGCTGATGCCAACGGCGCCTACAACAT | |
| | CGCTAGAAAGGGGCTGATGTTCATCGATATCATCAAGGAAACAGAGGACAAG | |
| | GACCTGAAAATGCCTAAGCTGTTCATAAAGAACAAGGATTGGCTGAACTATGT | |
| | GCAGAAATCAGATCTGTctagaAAGCGGACAGCAGACGGCTCCGAATTTGAAAG | |
| | CCCTAAGAAAAAGAGAAAGGTGggatccGGCAAACCTATCCCCAATCCCCTGCT | |
| | GGGCCTGGACAGCACCTGA | |

In some embodiments a ZIKV Type V Cas protein comprises an amino acid sequence of SEQ ID NO:13, SEQ ID NO:14, or SEQ ID NO:15. In some embodiments, a ZIKV Type V Cas protein has nickase activity, for example resulting from one or more amino acid substitutions relative to the sequence of SEQ ID NO:13, SEQ ID NO:14, or SEQ ID NO:15. In some embodiments, the one or more amino acid substitutions providing nickase activity comprise a D814 substitution, wherein the position of the D814 substitution is defined with respect to the amino acid numbering of SEQ ID NO:14 (corresponding to amino acid 908 of SEQ ID NO:121). In some embodiments, the one or more amino acid substitutions providing nickase activity comprise an E899 substitution, wherein the position of the E899 substitution is defined with respect to the amino acid numbering of SEQ ID NO:14 (corresponding to amino acid 993 of SEQ ID NO:121). In some embodiments, the one or more amino acid substitutions providing nickase activity comprise a R1111 substitution, wherein the position of the R1111 substitution is defined with respect to the amino acid numbering of SEQ ID NO:14 (corresponding to amino acid 1226 of SEQ ID NO:121). In some embodiments, the one or more amino acid substitutions providing nickase activity comprise a D1148 substitution, wherein the position of the D1148 substitution is defined with respect to the amino acid numbering of SEQ ID NO:14 (corresponding to amino acid 1263 of SEQ ID NO:121). In some embodiments, a ZIKV Type V Cas protein is catalytically inactive, for example due to a R1111 substitution in combination with a D814 substitution, a E899 substitution, and/or D1148 substitution.

6.2.4. ZZFT Type V Cas Proteins

In one aspect, the disclosure provides ZZFT Type V Cas proteins. ZZFT Type V Cas proteins can be further classified as Type V-A Cas proteins. The ZZFT Type V Cas proteins typically comprise an amino acid sequence that is at least 50%, at least 55%, at least 60%, at least 65%, at least 70%, at least 75%, at least 85%, at least 90%, or at least 95% identical to SEQ ID NO:19. In some embodiments, the ZZFT Type V Cas proteins comprise an amino acid sequence that is at least 95%, at least 96%, at least 97%, at least 98%, or at least 99% identical to SEQ ID NO:19. In some embodiments, a ZZFT Type V Cas protein comprises an amino acid sequence that is identical to SEQ ID NO:19.

Exemplary ZZFT Type V Cas protein sequences and nucleotide sequences encoding exemplary ZZFT Type V Cas proteins are set forth in Table 1D.

TABLE 1D

ZZFT Type V Cas Sequences

| Name | Sequence | SEQ ID NO. |
|---|---|---|
| Wildtype amino acid sequence (without N-terminal methionine) | EISNRFTNKYQVSKTLRFRLEPTGGTDDLLCQAQIIEGDERRNKEAITMKQILDNC<br>HKQIIERVLSDFNFKEHSLEEFFKVYTRNDDDREKDIENLQAKMRKEIAAAFTKQD<br>VTKLFSSKFKDFVERGLIKYASNEKERNIVSRFKGFATYFTGFNTNRLNMYSEEAK<br>STAISFRLINQNLIKFIDNILVYKKVSQTLPSDVLSNIYIDFKAIINTSSLEEFFSINNYN<br>NILTQKQIEIFNAVIGGKKDKDEKIITKGFNQYINEYNQTNKNIRLPKMMRLFNQILS<br>DREGVSARPEPFNNANETISSVRDCFTNEISKQITILSETTSKIESFDIDRIYIKGGE<br>DLRALSNSIYGYFNYIHDRIADKWKHNNPQGKKSPESYQKNLNAYLKGIKSVSLHS<br>IANICGDNKVIEYFRNLGAENTVDFQRENVVSLIDNKYNCASNLLSDAQITDEELRT<br>NSRSIKDLLDAVKSAQRFFRLLCGSGNEPDKDHSFYDEYTPAFEALENSINPLYNK<br>VRSFVTKKDFSTDKFKLNFDSSSFLSGWAKKSEYEKSSAFIFIRDNQYYLGINKCL<br>SKEDIAYLEDSTSSSDTKRVVYMFQKVDATNIPRIFIRSKGSNLAPAVNEFQLPIETI<br>LDIYDNKFFTTSYQKKDRTKWKESLTKLIDYYKLGFSQHKSYADFDLKWKASSEY<br>NDINDFLADVQRFCYRIEFININWDKLIEFTEDGKFYLFRIANKDLSGNSTGLPNLH<br>TIYWKMLFDESNLKDIVYKLSGNAEVFMRYNSLKNPIVHKAGVEIKNKCPFTEKKT<br>SIFDYDIIKDRRYTKDQLELHVPILMNFKSPSAAKGKAFNKECLEYIRNNGIKHIIGID<br>RGERNLLYMVITDLDGNIVEQKSLNQIASNPKLPLFRQDYNKLLKTKADANAQARR<br>DWETIDTVKEIKFGFLSQIVHEIAMAIIKYDAIVVLENLNRGFMQKRGLENNVYQKF<br>EQMLLDKLSYYVDKTKHPEEAGGALHAYQLSDTYANFNSLSKNAMVRQSGFVFY<br>IPAWLTSKIDPVTGFASFLKFHRDDSMATIKSTISKFDCFKYDKECDMFHIRIDYNK<br>FSTSCSGGQRKWDLFTFGDRILAERNTMQNSRYVYQTVNLTSEFKNLFATKDIDI<br>SGNLKDSICKIEDVGFFRKLSQLLSLTLQLRNSNAETGEDFLISPVADKDGNFFDS<br>RNCPDSLPKDADANGAYNIARKGLMLVEQLKRCKDVSKFKPAIKNEDWLDYVQR | 19 |
| Wildtype amino acid sequence (with N-terminal methionine) | MEISNRFTNKYQVSKTLRFRLEPTGGTDDLLCQAQIIEGDERRNKEAITMKQILDN<br>CHKQIIERVLSDFNFKEHSLEEFFKVYTRNDDDREKDIENLQAKMRKEIAAAFTKQ<br>DVTKLFSSKFKDFVERGLIKYASNEKERNIVSRFKGFATYFTGFNTNRLNMYSEEA<br>KSTAISFRLINQNLIKFIDNILVYKKVSQTLPSDVLSNIYIDFKAIINTSSLEEFFSINNY<br>NNILTQKQIEIFNAVIGGKKDKDEKIITKGFNQYINEYNQTNKNIRLPKMMRLFNQIL<br>SDREGVSARPEPFNNANETISSVRDCFTNEISKQITILSETTSKIESFDIDRIYIKGG<br>EDLRALSNSIYGYFNYIHDRIADKWKHNNPQGKKSPESYQKNLNAYLKGIKSVSLH<br>SIANICGDNKVIEYFRNLGAENTVDFQRENVVSLIDNKYNCASNLLSDAQITDEELR<br>TNSRSIKDLLDAVKSAQRFFRLLCGSGNEPDKDHSFYDEYTPAFEALENSINPLYN<br>KVRSFVTKKDFSTDKFKLNFDSSSFLSGWAKKSEYEKSSAFIFIRDNQYYLGINKC<br>LSKEDIAYLEDSTSSSDTKRVVYMFQKVDATNIPRIFIRSKGSNLAPAVNEFQLPIE<br>TILDIYDNKFFTTSYQKKDRTKWKESLTKLIDYYKLGFSQHKSYADFDLKWKASSE<br>YNDINDFLADVQRFCYRIEFININWDKLIEFTEDGKFYLFRIANKDLSGNSTGLPNL<br>HTIYWKMLFDESNLKDIVYKLSGNAEVFMRYNSLKNPIVHKAGVEIKNKCPFTEKK<br>TSIFDYDIIKDRRYTKDQLELHVPILMNFKSPSAAKGKAFNKECLEYIRNNGIKHIIGI<br>DRGERNLLYMVITDLDGNIVEQKSLNQIASNPKLPLFRQDYNKLLKTKADANAQAR<br>RDWETIDTVKEIKFGFLSQIVHEIAMAIIKYDAIVVLENLNRGFMQKRGLENNVYQK<br>FEQMLLDKLSYYVDKTKHPEEAGGALHAYQLSDTYANFNSLSKNAMVRQSGFVF<br>YIPAWLTSKIDPVTGFASFLKFHRDDSMATIKSTISKFDCFKYDKECDMFHIRIDYN<br>KFSTSCSGGQRKWDLFTFGDRILAERNTMQNSRYVYQTVNLTSEFKNLFATKDID<br>ISGNLKDSICKIEDVGFFRKLSQLLSLTLQLRNSNAETGEDFLISPVADKDGNFFDS<br>RNCPDSLPKDADANGAYNIARKGLMLVEQLKRCKDVSKFKPAIKNEDWLDYVQR | 20 |
| Expression construct (with N-terminal methionine, V5-tag and C-terminal NLS) aa sequence | MGEISNRFTNKYQVSKTLRFRLEPTGGTDDLLCQAQIIEGDERRNKEAITMKQILD<br>NCHKQIIERVLSDFNFKEHSLEEFFKVYTRNDDDREKDIENLQAKMRKEIAAAFTK<br>QDVTKLFSSKFKDFVERGLIKYASNEKERNIVSRFKGFATYFTGFNTNRLNMYSE<br>EAKSTAISFRLINQNLIKFIDNILVYKKVSQTLPSDVLSNIYIDFKAIINTSSLEEFFSIN<br>NYNNILTQKQIEIFNAVIGGKKDKDEKIITKGFNQYINEYNQTNKNIRLPKMMRLFN<br>QILSDREGVSARPEPFNNANETISSVRDCFTNEISKQITILSETTSKIESFDIDRIYIK<br>GGEDLRALSNSIYGYFNYIHDRIADKWKHNNPQGKKSPESYQKNLNAYLKGIKSV | 21 |

TABLE 1D-continued

| ZZFT Type V Cas Sequences | | |
|---|---|---|
| Name | Sequence | SEQ ID NO. |
| | SLHSIANICGDNKVIEYFRNLGAENTVDFQRENVVSLIDNKYNCASNLLSDAQITDE<br>ELRTNSRSIKDLLDAVKSAQRFFRLLCGSGNEPDKDHSFYDEYTPAFEALENSINP<br>LYNKVRSFVTKKDFSTDKFKLNFDSSSFLSGWAKKSEYEKSSAFIFIRDNQYYLGI<br>NKCLSKEDIAYLEDSTSSSDTKRVVYMFQKVDATNIPRIFIRSKGSNLAPAVNEFQ<br>LPIETILDIYDNKFFTTSYQKKDRTKWKESLTKLIDYYKLGFSQHKSYADFDLKWKA<br>SSEYNDINDFLADVQRFCYRIEFININWDKLIEFTEDGKFYLFRIANKDLSGNSTGL<br>PNLHTIYWKMLFDESNLKDIVYKLSGNAEVFMRYNSLKNPIVHKAGVEIKNKCPFT<br>EKKTSIFDYDIIKDRRYTKDQLELHVPILMNFKSPSAAKGKAFNKECLEYIRNNGIK<br>HIIGIDRGERNLLYMVITDLDGNIVEQKSLNQIASNPKLPLFRQDYNKLLKTKADAN<br>AQARRDWETIDTVKEIKFGFLSQIVHEIAMAIIKYDAIVVLENLNRGFMQKRGLENN<br>VYQKFEQMLLDKLSYYVDKTKHPEEAGGALHAYQLSDTYANFNSLSKNAMVRQS<br>GFVFYIPAWLTSKIDPVTGFASFLKFHRDDSMATIKSTISKFDCFKYDKECDMFHIR<br>IDYNKFSTSCSGGQRKWDLFTFGDRILAERNTMQNSRYVYQTVNLTSEFKNLFAT<br>KDIDISGNLKDSICKIEDVGFFRKLSQLLSLTLQLRNSNAETGEDFLISPVADKDGN<br>FFDSRNCPDSLPKDADANGAYNIARKGLMLVEQLKRCKDVSKFKPAIKNEDWLD<br>YVQRSRKRTADGSEFESPKKKRKVGSGKPIPNPLLGLDST | |
| Wildtype coding sequence (with N-terminal methionine and stop codon) | ATGGAAATTTCGAACCGATTCACAAACAAGTATCAAGTAAGCAAGACCCTCCG<br>CTTTCGCCTTGAGCCAACCGGAGGTACTGATGATTTACTTTGCCAAGCACAAA<br>TCATCGAGGGAGACGAGCGCCGCAATAAAGAGGCTATAACAATGAAACAGAT<br>TTTGGACAATTGTCACAAACAGATAATTGAGCGCGTATTGTCCGACTTTAATTT<br>TAAAGAGCATTCTCTTGAAGAGTTTTTCAAAGTGTATACCAGAAACGATGATGA<br>CCGCGAAAAGGACATTGAAAATCTCCAAGCAAAAATGCGCAAAGAAATAGCC<br>GCCGCCTTCACCAAACAGGATGTTACGAAACTTTTCTCAAGCAAATTCAAGGA<br>TTTTGTTGAAAGAGGCTTGATTAAATATGCATCAAACGAGAAGGAACGCAACA<br>TCGTTTCCCGCTTCAAAGGTTTTGCCACTTACTTTACAGGGTTCAATACCAATA<br>GACTGAATATGTACTCAGAAGAAGCAAAATCCACAGCTATATCATTCAGATTAA<br>TTAATCAAAACTTGATAAAGTTCATAGACAACATCCTTGTATATAAAAAAGTGT<br>CTCAAACGTTGCCTTCAGATGTGCTATCAAACATTTATATAGACTTTAAGGCAA<br>TCATCAACACATCAAGTCTTGAAGAATTCTTCTCCATAAACAACTACAATAACA<br>TACTCACCCAGAAACAGATTGAGATTTTCAATGCAGTTATCGGAGGTAAAAAA<br>GACAAGGATGAAAAAATAATAACCAAAGGATTCAACCAATATATAAACGAATAC<br>AACCAGACCAATAAAAACATCCGTCTGCCTAAGATGATGCGGTTATTCAATCA<br>AATCCTAAGCGACAGAGAAGGTGTTTCTGCAAGACCAGAGCCATTCAATAACG<br>CGAACGAGACAATCAGTTCCGTCCGTGATTGTTTTACAAACGAAATATCAAAA<br>CAAATAACGATATTGTCTGAAACAACATCCAAAATTGAATCATTCGACATTGAT<br>AGAATTTACATTAAGGGCGGAGAAGATCTGAGAGCATTATCCAACAGTATATA<br>TGGATATTTCAATTATATCCATGACCGTATCGCAGACAAATGGAAACACAACAA<br>TCCTCAGGGCAAAAAGAGCCCCGAAAGCTACCAAAAAAACCTCAACGCATAT<br>CTGAAAGGCATAAAAAGCGTCTCTTTACACAGTATTGCAAACATCTGTGGTGA<br>CAACAAAGTTATTGAGTATTTCAGGAATCTTGGTGCAGAAAACACTGTTGATTT<br>CCAAAGAGAGAACGTTGTATCATTAATCGACAACAAATACAACTGCGCTTCAA<br>ATCTTTTATCCGACGCCCAAATTACGGATGAAGAACTTCGCACAAACAGTCGC<br>TCAATTAAAGACTTGCTTGACGCCGTCAAGAGTGCCCAACGATTTTTCCGTCT<br>ACTGTGCGGTTCTGGCAACGAACCAGACAAAGACCACTCTTTTTATGACGAGT<br>ATACACCAGCATTTGAAGCACTTGAGAATTCAATAAATCCCCTATATAACAAAG<br>TCAGGAGTTTTGTAACCAAAAAAGATTTCTCCACCGATAAATTCAAATTGAATT<br>TCGACAGCAGCAGCTTTCTATCCGGTTGGGCAAAGAAATCAGAATATGAGAA<br>GAGTTCTGCATTTATATTTATTCGCGACAATCAATATTACTTAGGAATAAACAA<br>ATGCCTTAGCAAAGAAGACATTGCCTACCTTGAGGACTCAACAAGCTCATCAG<br>ATACAAAAAGAGTGGTATATATGTTCCAAAAAGTGGACGCCACGAATATTCCC<br>AGAATATTCATCCGTTCCAAAGGTTCCAATTTAGCTCCTGCTGTCAACGAATTC<br>CAACTGCCGATAGAAACCATTCTTGACATTTATGACAATAAGTTCTTCACTACC<br>AGTTATCAGAAAAAAGACCGGACTAAATGGAAAGAATCATTGACCAAACTCAT<br>TGACTATTACAAGCTTGGATTCAGCCAGCACAAGTCATACGCAGATTTCGACT<br>TAAAATGGAAAGCATCCAGTGAATATAACGACATAAATGACTTTCTTGCAGAC<br>GTACAGAGATTCTGCTACAGAATCGAATTTATAAATATCAATTGGGACAAGCT<br>GATAGAATTCACAGAAGATGGCAAATTTTACCTATTCCGCATTGCAAATAAAGA<br>TTTATCAGGCAATAGCACAGGTCTGCCCAATTTGCACACGATTTATTGGAAAA<br>TGCTTTTTGACGAAAGCAACCTCAAAGATATTGTCTATAAATTGTCGGGCAATG<br>CGGAAGTCTTTATGCGCTATAATTCATTAAAAAATCCAATTGTGCATAAAGCGG<br>GAGTGGAGATTAAAAACAAATGCCCTTTTACTGAAAAAAAGACAAGCATATTTG<br>ACTACGACATTATAAAAGACCGTCGCTATACAAAAGATCAGCTTGAACTGCAT<br>GTTCCAATCCTAATGAACTTCAAAAGCCCATCGGCAGCAAAAGGCAAAGCTTT<br>CAACAAAGAATGCTTGGAATACATAAGAAATAATGGTATAAAGCATATTATAGG<br>AATAGACCGAGGTGAACGGAATCTACTTTATATGGTTATAACAGACCTTGACG<br>GCAACATCGTTGAGCAAAAGTCTTTGAACCAAATTGCGAGCAATCCGAAATTG<br>CCTCTTTTCAGACAAGACTACAACAAGCTGCTGAAGACAAAGGCTGATGCAAA<br>CGCACAAGCACGTCGTGATTGGGAAACAATAGACACCGTAAAGGAGATAAAA<br>TTCGGCTTCTTGAGTCAGATTGTACATGAGATAGCAATGGCTATCATAAAATAC<br>GATGCAATTGTTGTTTTGGAGAATCTGAACAGAGGGTTTATGCAGAAACGAGG<br>TCTTGAAAACAACGTCTATCAGAAATTCGAACAAATGCTGCTTGACAAGTTGA<br>GCTACTATGTCGACAAAACGAAACATCCGGAAGAGGCCGGAGGAGCTTTGCA<br>CGCATATCAGCTCTCTGACACTTACGCGAACTTCAATTCTCTGTCGAAGAATG<br>CGATGGTGCGACAGTCGGGTTTTGTTTTCTATATTCCTGCATGGCTTACAAGC | 22 |

TABLE 1D-continued

ZZFT Type V Cas Sequences

| Name | Sequence | SEQ ID NO. |
|---|---|---|
| | AAAATAGACCCCGTCACAGGATTCGCCTCCTTTTTGAAATTTCACAGAGATGA<br>CAGTATGGCAACAATCAAATCTACAATTTCAAAGTTTGATTGTTTCAAATACGA<br>CAAGGAATGCGACATGTTCCACATCCGCATTGACTATAACAAGTTTAGCACAA<br>GCTGCAGCGGAGGTCAACGCAAATGGGACTTGTTCACTTTTGGCGATCGAAT<br>CTTGGCAGAACGCAATACAATGCAAAACAGCAGATATGTTTACCAAACAGTCA<br>ATTTAACTTCTGAATTCAAAAACTTATTTGCCACAAAGGATATCGACATTTCAG<br>GCAACCTGAAGGACTCTATATGCAAAATTGAGGATGTTGGCTTTTTCAGAAAA<br>CTAAGCCAACTCTTGTCACTCACGCTTCAATTACGCAACAGCAATGCTGAAAC<br>AGGAGAAGACTTCTTGATTTCCCCAGTAGCTGACAAAGATGGCAATTTCTTCG<br>ATTCAAGAAACTGTCCCGACTCTCTCCCAAAAGACGCAGATGCCAATGGCGC<br>ATACAACATTGCTAGGAAGGGATTAATGCTTGTCGAGCAATTGAAGAGATGCA<br>AAGATGTATCAAAATTCAAGCCCGCGATAAAAAACGAGGACTGGTTAGACTAT<br>GTTCAACGCTGA | |
| Codon optimized coding sequence (no N-terminal methionine, no stop codon) | GAAATCAGTAATCGGTTTACAAACAAGTACCAGGTGTCTAAGACCCTGCGGTT<br>CAGACTGGAGCCTACAGGCGGGACCGATGACCTGCTGTGCCAGGCCCAGAT<br>CATCGAGGGCGATGAGCGGCGCAACAAAGAAGCCATCACCATGAAACAGATC<br>CTCGACAACTGTCACAAGCAGATCATCGAAAGAGTGCTGTCCGACTTCAACTT<br>CAAAGAGCACTCCCTGGAAGAGTTCTTTAAGGTGTACACACGGAACGACGAT<br>GACAGAGAGAAGGATATCGAGAACCTGCAGGCAAAGATGCGCAAGGAAATCG<br>CCGCCGCCTTTACTAAGCAAGACGTGACAAAACTGTTTTCTTCCAAGTTTAAA<br>GACTTTGTCGAAAGGGGTCTGATCAAGTACGCCAGCAACGAGAAGGAGCGGA<br>ATATCGTGTCCCGGTTCAAGGGCTTTGCCACATACTTCACCGGCTTCAACACA<br>AACCGCCTGAACATGTACAGCGAGGAAGCCAAATCTACGGCCATTAGCTTCC<br>GGCTGATCAACCAGAACCTCATCAAATTCATCGACAATATCCTGGTGTACAAG<br>AAGGTGTCTCAGACCCTCCCTTCTGATGTCCTGAGCAACATCTACATCGACTT<br>CAAGGCCATCATCAATACCAGCAGCCTGGAGGAGTTCTTCTCCATCAACAACT<br>ACAACAACATCCTGACCCAGAAGCAGATCGAGATCTTCAACGCTGTGATCGG<br>CGGAAAGAAGGATAAGGATGAGAAAATTATCACAAAGGGCTTCAACCAGTACA<br>TCAATGAATATAATCAGACCAACAAGAATATCAGACTGCCAAAGATGATGAGA<br>CTGTTCAATCAGATACTGAGCGACCGGGAAGGCGTGTCAGCTAGACCTGAGC<br>CCTTCAACAACGCCAACGAGACAATCAGCTCCGTGAGAGACTGTTTTACAAAC<br>GAAATCAGCAAGCAGATCACCATCCTGTCTGAAACCACCAGTAAGATCGAGA<br>GCTTCGACATCGATAGAATCTACATCAAGGGCGGAGAGGACCTGCGGGCCCT<br>GAGCAACAGCATCTACGGCTACTTCAACTACATCCACGATAGAATCGCTGATA<br>AGTGGAAGCACAACAATCCTCAGGGCAAGAAGAGCCCCGAGAGCTACCAAAA<br>GAATCTGAACGCCTACCTGAAGGGCATAAAGAGCGTGAGCCTGCATTCTATC<br>GCCAACATCTGTGGCGACAACAAGGTGATCGAATATTTTAGAAATCTCGGCGC<br>CGAGAACACAGTGGATTTTCAGAGAGAAAACGTGGTGTCCCTAATTGACAACA<br>AATACAACTGTGCCTCAAACCTGCTGTCCGACGCCCAAATCACCGACGAGGA<br>GCTGAGGACCAACAGCAGAAGCATCAAGGATCTGCTCGACGCCGTGAAGAGT<br>GCCCAGAGATTCTTCAGACTGCTGTGCGGTTCTGGCAATGAGCCTGATAAAG<br>ACCACAGCTTTTATGACGAGTACACCCCTGCTTTCGAGGCCCTGGAAAACAG<br>CATCAACCCCCTGTACAACAAGGTCCGCAGCTTCGTGACCAAAAAGGACTTC<br>AGCACAGACAAGTTCAAACTGAACTTCGACAGCAGCAGCTTCCTGAGCGGAT<br>GGGCCAAGAAAAGCGAGTACGAGAAGAGCAGCGCTTTCATCTTCATCAGGGA<br>TAATCAGTACTACCTGGGAATTAATAAGTGCCTGAGTAAAGAGGACATCGCCT<br>ACCTGGAGGACAGCACCTCTAGCAGCGACACAAAGAGAGTGGTGTACATGTT<br>TCAGAAGGTGGATGCCACCAATATCCCAAGAATCTTCATCAGATCCAAGGGCA<br>GCAACCTGGCCCCTGCTGTGAACGAGTTCCAGCTGCCTATCGAAACCATCCT<br>GGATATCTACGACAACAAGTTCTTCACCACCAGTTACCAGAAGAAGGATAGAA<br>CCAAATGGAAGGAAAGCCTGACCAAGCTGATCGACTACTACAAGCTGGGCTT<br>TAGCCAGCACAAGTCCTATGCCGATTTCGATTTAAAGTGGAAAGCCAGCTCAG<br>AATACAATGACATCAATGATTTCCTGGCCGACGTGCAGAGATTCTGCTACAGA<br>ATTGAGTTCATCAATATCAATTGGGACAAGCTCATCGAGTTCACAGAGGACGG<br>CAAGTTCTACCTGTTTAGAATCGCCAACAAAGACCTGTCTGGCAACAGCACTG<br>GCCTGCCCAATCTGCACACCATCTACTGGAAGATGCTGTTCGACGAGAGCAA<br>CCTGAAGGACATCGTGTACAAGCTGAGCGGCAACGCTGAGGTGTTTATGCGC<br>TACAACAGCCTGAAGAACCCCATTGTGCACAAGGCCGGAGTGGAAATCAAGA<br>ATAAGTGTCCTTTCACCGAGAAGAAAACCAGCATCTTTGACTACGACATTATC<br>AAGGACCGCAGATACACCAAGGACCAGCTGGAACTGCATGTGCCTATCCTGA<br>TGAACTTCAAGTCTCCATCTGCCGCTAAAGGCAAAGCCTTTAACAAGGAGTGC<br>CTGGAATACATCAGAAACAACGGCATCAAGCACATCATCGGCATCGACAGAG<br>GAGAGCGGAATCTGCTTTACATGGTGATCACAGACCTGGACGGCAACATCGT<br>GGAACAGAAGTCTCTGAACCAGATCGCCTCCAATCCAAAGCTGCCTCTGTTCA<br>GACAGGACTACAACAAGCTGCTGAAAACCAAAGCTGACGCCAACGCACAAGC<br>CAGAAGAGACTGGGAGACAATAGACACCGTGAAGGAGATTAAGTTCGGCTTC<br>CTGAGCCAGATCGTGCACGAGATCGCTATGGCCATCATCAAGTACGACGCCA<br>TTGTGGTCCTGGAAAACCTGAACAGAGGCTTCATGCAAAAACGGGGCCTGGA<br>AAACAACGTGTATCAGAAGTTCGAGCAAATGCTCCTCGATAAACTGAGCTACT<br>ATGTCGACAAGACCAAACACCCTGAGGAAGCTGGCGGAGCCCTGCACGCCT<br>ATCAGTTAAGCGATACCTACGCCAACTTCAATTCCTTGAGCAAGAACGCTATG<br>GTGAGACAGTCTGGCTTCGTGTTCTACATCCCCGCCTGGCTGACCAGCAAGA<br>TCGATCCTGTGACCGGCTTCGCCTCTTTCCTGAAGTTCCACAGAGATGATAGC<br>ATGGCCACCATCAAGAGCACCATCTCCAAATTCGACTGCTTCAAGTACGACAA | 23 |

TABLE 1D-continued

| ZZFT Type V Cas Sequences | | |
|---|---|---|
| Name | Sequence | SEQ ID NO. |
| | GGAATGCGACATGTTCCACATCAGAATAGATTACAACAAATTTAGCACTTCAT<br>GCAGCGGTGGCCAGCGGAAGTGGGATCTGTTCACATTCGGAGACAGAATCCT<br>GGCCGAGAGAAACACCATGCAGAACAGTAGATACGTTTACCAGACAGTTAAC<br>CTGACCTCTGAGTTCAAGAACCTGTTCGCCACAAAGGATATCGATATAAGCGG<br>GAACCTGAAGGATAGCATCTGCAAGATCGAGGACGTGGGCTTCTTCCGGAAG<br>CTGAGCCAGCTGCTGAGCCTGACACTACAGCTTCGGAACAGCAACGCTGAAA<br>CCGGAGAAGATTTCCTGATCAGCCCTGTGGCCGACAAGGACGGCAACTTCTT<br>TGACAGCAGAAACTGCCCCGACAGCCTGCCAAAGGATGCAGACGCGAATGG<br>CGCTTATAACATTGCCAGGAAGGGCCTGATGCTGGTGGAGCAACTGAAGCGG<br>TGCAAGGACGTGAGCAAGTTCAAGCCTGCTATCAAGAACGAGGACTGGCTGG<br>ACTACGTGCAGCGG | |
| Expression construct (with N-terminal methionine and stop codon, includes V5-tag and C-terminal NLS) | ATGggcGAAATCAGTAATCGGTTTACAAACAAGTACCAGGTGTCTAAGACCCTG<br>CGGTTCAGACTGGAGCCTACAGGCGGGACCGATGACCTGCTGTGCCAGGCC<br>CAGATCATCGAGGGCGATGAGCGGCGCAACAAAGAAGCCATCACCATGAAAC<br>AGATCCTCGACAACTGTCACAAGCAGATCATCGAAAGAGTGCTGTCCGACTTC<br>AACTTCAAAGAGCACTCCCTGGAAGAGTTCTTTAAGGTGTACACACGGAACGA<br>CGATGACAGAGAGAAGGATATCGAGAACCTGCAGGCAAAGATGCGCAAGGAA<br>ATCGCCGCCGCCTTTACTAAGCAAGACGTGACAAAACTGTTTTCTTCCAAGTT<br>TAAAGACTTTGTCGAAAGGGGTCTGATCAAGTACGCCAGCAACGAGAAGGAG<br>CGGAATATCGTGTCCCGGTTCAAGGGCTTTGCCACATACTTCACCGGCTTCAA<br>CACAAACCGCCTGAACATGTACAGCGAGGAAGCCAAATCTACGGCCATTAGC<br>TTCCGGCTGATCAACCAGAACCTCATCAAATTCATCGACAATATCCTGGTGTA<br>CAAGAAGGTGTCTCAGACCCTCCCTTCTGATGTCCTGAGCAACATCTACATCG<br>ACTTCAAGGCCATCATCAATACCAGCAGCCTGGAGGAGTTCTTCTCCATCAAC<br>AACTACAACAACATCCTGACCCAGAAGCAGATCGAGATCTTCAACGCTGTGAT<br>CGGCGGAAAGAAGGATAAGGATGAGAAAATTATCACAAAGGGCTTCAACCAG<br>TACATCAATGAATATAATCAGACCAACAAGAATATCAGACTGCCAAAGATGAT<br>GAGACTGTTCAATCAGATACTGAGCGACCGGGAAGGCGTGTCAGCTAGACCT<br>GAGCCCTTCAACAACGCCAACGAGACAATCAGCTCCGTGAGAGACTGTTTTA<br>CAAACGAAATCAGCAAGCAGATCACCATCCTGTCTGAAACCACCAGTAAGATC<br>GAGAGCTTCGACATCGATAGAATCTACATCAAGGGCGGAGAGGACCTGCGG<br>GCCCTGAGCAACAGCATCTACGGCTACTTCAACTACATCCACGATAGAATCGC<br>TGATAAGTGGAAGCACAACAATCCTCAGGGCAAGAAGAGCCCCGAGAGCTAC<br>CAAAAGAATCTGAACGCCTACCTGAAGGGCATAAAGAGCGTGAGCCTGCATT<br>CTATCGCCAACATCTGTGGCGACAACAAGGTGATCGAATATTTTAGAAATCTC<br>GGCGCCGAGAACACAGTGGATTTTCAGAGAGAAAACGTGGTGTCCCTAATTG<br>ACAACAAATACAACTGTGCCTCAAACCTGCTGTCCGACGCCCAAATCACCGAC<br>GAGGAGCTGAGGACCAACAGCAGAAGCATCAAGGATCTGCTCGACGCCGTG<br>AAGAGTGCCCAGAGATTCTTCAGACTGCTGTGCGGTTCTGGCAATGAGCCTG<br>ATAAAGACCACAGCTTTTATGACGAGTACACCCCTGCTTTCGAGGCCCTGGAA<br>AACAGCATCAACCCCCTGTACAACAAGGTCCGCAGCTTCGTGACCAAAAAGG<br>ACTTCAGCACAGACAAGTTCAAACTGAACTTCGACAGCAGCAGCTTCCTGAGC<br>GGATGGGCCAAGAAAAGCGAGTACGAGAAGAGCAGCGCTTTCATCTTCATCA<br>GGGATAATCAGTACTACCTGGGAATTAATAAGTGCCTGAGTAAAGAGGACATC<br>GCCTACCTGGAGGACAGCACCTCTAGCAGCGACACAAAGAGAGTGGTGTACA<br>TGTTTCAGAAGGTGGATGCCACCAATATCCCAAGAATCTTCATCAGATCCAAG<br>GGCAGCAACCTGGCCCCTGCTGTGAACGAGTTCCAGCTGCCTATCGAAACCA<br>TCCTGGATATCTACGACAACAAGTTCTTCACCACCAGTTACCAGAAGAAGGAT<br>AGAACCAAATGGAAGGAAAGCCTGACCAAGCTGATCGACTACTACAAGCTGG<br>GCTTTAGCCAGCACAAGTCCTATGCCGATTTCGATTTAAAGTGGAAAGCCAGC<br>TCAGAATACAATGACATCAATGATTTCCTGGCCGACGTGCAGAGATTCTGCTA<br>CAGAATTGAGTTCATCAATATCAATTGGGACAAGCTCATCGAGTTCACAGAGG<br>ACGGCAAGTTCTACCTGTTTAGAATCGCCAACAAAGACCTGTCTGGCAACAGC<br>ACTGGCCTGCCCAATCTGCACACCATCTACTGGAAGATGCTGTTCGACGAGA<br>GCAACCTGAAGGACATCGTGTACAAGCTGAGCGGCAACGCTGAGGTGTTTAT<br>GCGCTACAACAGCCTGAAGAACCCCATTGTGCACAAGGCCGGAGTGGAAATC<br>AAGAATAAGTGTCCTTTCACCGAGAAGAAAACCAGCATCTTTGACTACGACAT<br>TATCAAGGACCGCAGATACACCAAGGACCAGCTGGAACTGCATGTGCCTATC<br>CTGATGAACTTCAAGTCTCCATCTGCCGCTAAAGGCAAAGCCTTTAACAAGGA<br>GTGCCTGGAATACATCAGAAACAACGGCATCAAGCACATCATCGGCATCGAC<br>AGAGGAGAGCGGAATCTGCTTTACATGGTGATCACAGACCTGGACGGCAACA<br>TCGTGGAACAGAAGTCTCTGAACCAGATCGCCTCCAATCCAAAGCTGCCTCT<br>GTTCAGACAGGACTACAACAAGCTGCTGAAAACCAAAGCTGACGCCAACGCA<br>CAAGCCAGAAGAGACTGGGAGACAATAGACACCGTGAAGGAGATTAAGTTCG<br>GCTTCCTGAGCCAGATCGTGCACGAGATCGCTATGGCCATCATCAAGTACGA<br>CGCCATTGTGGTCCTGGAAAACCTGAACAGAGGCTTCATGCAAAAACGGGGC<br>CTGGAAAACAACGTGTATCAGAAGTTCGAGCAAATGCTCCTCGATAAACTGAG<br>CTACTATGTCGACAAGACCAAACACCCTGAGGAAGCTGGCGGAGCCCTGCAC<br>GCCTATCAGTTAAGCGATACCTACGCCAACTTCAATTCCTTGAGCAAGAACGC<br>TATGGTGAGACAGTCTGGCTTCGTGTTCTACATCCCCGCCTGGCTGACCAGC<br>AAGATCGATCCTGTGACCGGCTTCGCCTCTTTCCTGAAGTTCCACAGAGATGA<br>TAGCATGGCCACCATCAAGAGCACCATCTCCAAATTCGACTGCTTCAAGTACG<br>ACAAGGAATGCGACATGTTCCACATCAGAATAGATTACAACAAATTTAGCACTT<br>CATGCAGCGGTGGCCAGCGGAAGTGGGATCTGTTCACATTCGGAGACAGAAT | 24 |

TABLE 1D-continued

| ZZFT Type V Cas Sequences | | |
|---|---|---|
| Name | Sequence | SEQ ID NO. |
| | CCTGGCCGAGAGAAACACCATGCAGAACAGTAGATACGTTTACCAGACAGTT<br>AACCTGACCTCTGAGTTCAAGAACCTGTTCGCCACAAAGGATATCGATATAAG<br>CGGGAACCTGAAGGATAGCATCTGCAAGATCGAGGACGTGGGCTTCTTCCGG<br>AAGCTGAGCCAGCTGCTGAGCCTGACACTACAGCTTCGGAACAGCAACGCTG<br>AAACCGGAGAAGATTTCCTGATCAGCCCTGTGGCCGACAAGGACGGCAACTT<br>CTTTGACAGCAGAAACTGCCCCGACAGCCTGCCAAAGGATGCAGACGCGAAT<br>GGCGCTTATAACATTGCCAGGAAGGGCCTGATGCTGGTGGAGCAACTGAAGC<br>GGTGCAAGGACGTGAGCAAGTTCAAGCCTGCTATCAAGAACGAGGACTGGCT<br>GGACTACGTGCAGCGGtctagaAAGCGGACAGCAGACGGCTCCGAATTTGAAA<br>GCCCTAAGAAAAAGAGAAAGGTGggatccGGCAAACCTATCCCCAATCCCCTGC<br>TGGGCCTGGACAGCACCTGA | |

In some embodiments a ZZFT Type V Cas protein comprises an amino acid sequence of SEQ ID NO:19, SEQ ID NO:20, or SEQ ID NO:21. In some embodiments, a ZZFT Type V Cas protein has nickase activity, for example resulting from one or more amino acid substitutions relative to the sequence of SEQ ID NO:19, SEQ ID NO:20, or SEQ ID NO:21. In some embodiments, the one or more amino acid substitutions providing nickase activity comprise a D856 substitution, wherein the position of the D856 substitution is defined with respect to the amino acid numbering of SEQ ID NO:20 (corresponding to amino acid 908 of SEQ ID NO:121). In some embodiments, the one or more amino acid substitutions providing nickase activity comprise an E949 substitution, wherein the position of the E949 substitution is defined with respect to the amino acid numbering of SEQ ID NO:20 (corresponding to amino acid 993 of SEQ ID NO:121). In some embodiments, the one or more amino acid substitutions providing nickase activity comprise a R1166 substitution, wherein the position of the R1166 substitution is defined with respect to the amino acid numbering of SEQ ID NO:20 (corresponding to amino acid 1226 of SEQ ID NO:121). In some embodiments, the one or more amino acid substitutions providing nickase activity comprise a D1203 substitution, wherein the position of the D1203 substitution is defined with respect to the amino acid numbering of SEQ ID NO:20 (corresponding to amino acid 1263 of SEQ ID NO:121). In some embodiments, a ZZFT Type V Cas protein is catalytically inactive, for example due to a R1166 substitution in combination with a D856 substitution, a E949 substitution, and/or D1203 substitution.

6.2.5. YYAN Type V Cas Proteins

In one aspect, the disclosure provides YYAN Type V Cas proteins. YYAN Type V Cas proteins can be further classified as Type V-A Cas proteins. The YYAN Type V Cas proteins typically comprise an amino acid sequence that is at least 50%, at least 55%, at least 60%, at least 65%, at least 70%, at least 75%, at least 85%, at least 90%, or at least 95% identical to SEQ ID NO:25. In some embodiments, the YYAN Type V Cas proteins comprise an amino acid sequence that is at least 95%, at least 96%, at least 97%, at least 98%, or at least 99% identical to SEQ ID NO:25. In some embodiments, a YYAN Type V Cas protein comprises an amino acid sequence that is identical to SEQ ID NO:25.

Exemplary YYAN Type V Cas protein sequences and nucleotide sequences encoding exemplary YYAN Type V Cas proteins are set forth in Table 1E.

TABLE 1E

| YYAN Type V Cas Sequences | | |
|---|---|---|
| Name | Sequence | SEQ ID NO. |
| Wildtype amino acid sequence (without N-terminal methionine) | KINAFINCYSMSKTLRFKLAPEYETEKNLLEKGFLDRDKLRADDYDLMKKVIDKYHKH<br>FIDKALEGFKFDLLQEYAEAFYSQSADDDGKKLEEIKKKMCKELATCFSKQDEFKLLD<br>KKELVEKLIPAAEFIEDEEKDIAKRFKGFTTYFTGFNENRQNLYAAELKHGTIAFRLIEE<br>NLPAFLYNCKKGVKIFEGLDAVDAETLNNELGEILSIENVKDVLSVEYYNKTLTQNGID<br>VYNRIIGGYTQEDGTKIKGVNEYVNLYNQTHDKKLPSLAKLKKQILSDSYSLSFLPAKF<br>NDDSELLLSLKKFYSTVNEETGLSVEKAIQEMRDVFSHIDDCDLHNVFIDAKFINKVSN<br>DVFGNWSVLIDGINAEYEKLNPFNGKNLDNYEEKRKAFLNKIESYSVDALQAYSGKEE<br>KIADYVQKRAVELYDSVACAYENMSNKVINAREGKVKLYQDDEKTEIIKTFLDAVQEF<br>KKFAEMFCYDGTDGDTTFYGEFANYYGQIAEIIPLYNKCRNYLTKKPYSEDKIKINFDN<br>AELLHGWDANKEKNYLTVLLFKNGSYYLGILDKKHKNVLIKDVPEKTQEEPCFKKMIY<br>KLLPDPKRNMPRIILHAKSNKKLFEPSDEIYRIYETESFKTDIDDCHRLIDFYKESISKYE<br>DWKTFGFKFKETSEYKNIGQFYNEVKEQGYKISFTDIPESYVKDLVNDGKLYLFRLAN<br>KDFSPYSKGKKNLHTMYFEGIFDPENIKEKVYALNGGGELFFRCASLNYDKPTHPKN<br>VPIKNKTYDFRTDNAKKETSTFEYDLIKDKRYTKDQYTLHCPVTLNFKERGIERINDLV<br>RQSLRESDDNYVIGIDRGERNLIYISVIDGKGKIVEQFSMNNLLSGNDVSIDFHKMLET<br>REHERDASRKNWNTIDNIKDLKQGYLSYVVKKICDLVVKYDAIVAMEDLNVGFKHGR<br>EKFERQVYQKFEKALVDKMSYIVNKNASPHSDGGLFRAYQLTNKKYNENEKQNGFIF<br>YVRAWNTSKIDPTTGFVNMLPLKYQSKEKSKEFFDKFEDIFYDENKDMFGFTFRYDD<br>FGINIDHKNEWTAYSNGERIITVRNSFGKWDKAKIVLTPAFKKLFDDYNVDCRGDVKR<br>QIMNVDDKDFFVRLYKLLSYTMQLRNSDDVDDYILSPVVNAEGKFFDSRNSDGSLPC<br>DADANGAYHIAKKAMWAIGKIKEADEESFKKTSLAIDNKTWLEFVQKA | 25 |

TABLE 1E-continued

YYAN Type V Cas Sequences

| Name | Sequence | SEQ ID NO. |
|---|---|---|
| Wildtype amino acid sequence (with N-terminal methionine) | MKINAFINCYSMSKTLRFKLAPEYETEKNLLEKGFLDRDKLRADDYDLMKKVIDKYHK<br>HFIDKALEGFKFDLLQEYAEAFYSQSADDDGKKLEEIKKKMCKELATCFSKQDEFKLL<br>DKKELVEKLIPAAEFIEDEEKDIAKRFKGFTTYFTGFNENRQNLYAAELKHGTIAFRLIE<br>ENLPAFLYNCKKGVKIFEGLDAVDAETLNNELGEILSIENVKDVLSVEYYNKTLTQNGI<br>DVYNRIIGGYTQEDGTKIKGVNEYVNLYNQTHDKKLPSLAKLKKQILSDSYSLSFLPAK<br>FNDDSELLLSLKKFYSTVNEETGLSVEKAIQEMRDVFSHIDDCDLHNVFIDAKFINKVS<br>NDVFGNWSVLIDGINAEYEKLNPFNGKNLDNYEEKRKAFLNKIESYSVDALQAYSGK<br>EEKIADYVQKRAVELYDSVACAYENMSNKVINAREGKVKLYQDDEKTEIIKTFLDAVQ<br>EFKKFAEMFCYDGTDGDTTFYGEFANYYGQIAEIIPLYNKCRNYLTKKPYSEDKIKINF<br>DNAELLHGWDANKEKNYLTVLLFKNGSYYLGILDKKHKNVLIKDVPEKTQEEPCFKK<br>MIYKLLPDPKRNMPRIILHAKSNKKLFEPSDEIYRIYETESFKTDIDDCHRLIDFYKESIS<br>KYEDWKTFGFKFKETSEYKNIGQFYNEVKEQGYKISFTDIPESYVKDLVNDGKLYLFR<br>LANKDFSPYSKGKKNLHTMYFEGIFDPENIKEKVYALNGGGELFFRCASLNYDKPTH<br>PKNVPIKNKTYDFRTDNAKKETSTFEYDLIKDKRYTKDQYTLHCPVTLNFKERGIERIN<br>DLVRQSLRESDDNYVIGIDRGERNLIYISVIDGKGKIVEQFSMNNLLSGNDVSIDFHKM<br>LETREHERDASRKNWNTIDNIKDLKQGYLSYVVKKICDLVVKYDAIVAMEDLNVGFKH<br>GREKFERQVYQKFEKALVDKMSYIVNKNASPHSDGGLFRAYQLTNKKYNENEKQNG<br>FIFYVRAWNTSKIDPTTGFVNMLPLKYQSKEKSKEFFDKFEDIFYDENKDMFGFTFRY<br>DDFGINIDHKNEWTAYSNGERIITVRNSFGKWDKAKIVLTPAFKKLFDDYNVDCRGDV<br>KRQIMNVDDKDFFVRLYKLLSYTMQLRNSDDVDDYILSPVVNAEGKFFDSRNSDGSL<br>PCDADANGAYHIAKKAMWAIGKIKEADEESFKKTSLAIDNKTWLEFVQKA | 26 |
| Expression construct (with N-terminal methionine, V5-tag and C-terminal NLS) aa sequence | MGKINAFINCYSMSKTLRFKLAPEYETEKNLLEKGFLDRDKLRADDYDLMKKVIDKYH<br>KHFIDKALEGFKFDLLQEYAEAFYSQSADDDGKKLEEIKKKMCKELATCFSKQDEFKL<br>LDKKELVEKLIPAAEFIEDEEKDIAKRFKGFTTYFTGFNENRQNLYAAELKHGTIAFRLI<br>EENLPAFLYNCKKGVKIFEGLDAVDAETLNNELGEILSIENVKDVLSVEYYNKTLTQNG<br>IDVYNRIIGGYTQEDGTKIKGVNEYVNLYNQTHDKKLPSLAKLKKQILSDSYSLSFLPA<br>KFNDDSELLLSLKKFYSTVNEETGLSVEKAIQEMRDVFSHIDDCDLHNVFIDAKFINKV<br>SNDVFGNWSVLIDGINAEYEKLNPFNGKNLDNYEEKRKAFLNKIESYSVDALQAYSG<br>KEEKIADYVQKRAVELYDSVACAYENMSNKVINAREGKVKLYQDDEKTEIIKTFLDAV<br>QEFKKFAEMFCYDGTDGDTTFYGEFANYYGQIAEIIPLYNKCRNYLTKKPYSEDKIKIN<br>FDNAELLHGWDANKEKNYLTVLLFKNGSYYLGILDKKHKNVLIKDVPEKTQEEPCFKK<br>MIYKLLPDPKRNMPRIILHAKSNKKLFEPSDEIYRIYETESFKTDIDDCHRLIDFYKESIS<br>KYEDWKTFGFKFKETSEYKNIGQFYNEVKEQGYKISFTDIPESYVKDLVNDGKLYLFR<br>LANKDFSPYSKGKKNLHTMYFEGIFDPENIKEKVYALNGGGELFFRCASLNYDKPTH<br>PKNVPIKNKTYDFRTDNAKKETSTFEYDLIKDKRYTKDQYTLHCPVTLNFKERGIERIN<br>DLVRQSLRESDDNYVIGIDRGERNLIYISVIDGKGKIVEQFSMNNLLSGNDVSIDFHKM<br>LETREHERDASRKNWNTIDNIKDLKQGYLSYVVKKICDLVVKYDAIVAMEDLNVGFKH<br>GREKFERQVYQKFEKALVDKMSYIVNKNASPHSDGGLFRAYQLTNKKYNENEKQNG<br>FIFYVRAWNTSKIDPTTGFVNMLPLKYQSKEKSKEFFDKFEDIFYDENKDMFGFTFRY<br>DDFGINIDHKNEWTAYSNGERIITVRNSFGKWDKAKIVLTPAFKKLFDDYNVDCRGDV<br>KRQIMNVDDKDFFVRLYKLLSYTMQLRNSDDVDDYILSPVVNAEGKFFDSRNSDGSL<br>PCDADANGAYHIAKKAMWAIGKIKEADEESFKKTSLAIDNKTWLEFVQKASRKRTAD<br>GSEFESPKKKRKVGSGKPIPNPLLGLDST | 27 |
| Wildtype coding sequence (with N-terminal methionine and stop codon) | ATGAAAATTAACGCTTTTATCAACTGTTATTCGATGTCCAAGACGTTGCGATTCAA<br>GCTTGCGCCCGAATACGAGACGGAAAAGAACCTTTTGGAAAAGGGATTTCTTGAT<br>CGCGACAAATTGCGCGCGGACGATTATGATTTAATGAAAAAAGTTATCGATAAAT<br>ATCACAAACATTTTATCGATAAAGCGTTGGAAGGTTTCAAATTCGATTTATTGCAA<br>GAGTATGCCGAAGCGTTTTATTCGCAATCGGCCGATGACGACGGCAAAAAACTT<br>GAAGAAATCAAAAAGAAAATGTGCAAGGAGTTGGCGACTTGTTTTTCGAAACAAG<br>ACGAGTTTAAATTACTCGATAAAAAAGAACTGGTCGAAAAACTAATCCCTGCTGCC<br>GAATTTATTGAAGACGAAGAAAAAGATATTGCGAAGAGATTCAAGGGGTTTACGA<br>CCTATTTCACGGGATTCAACGAAAACAGGCAAAACTTATACGCCGCAGAACTGAA<br>ACACGGGACGATTGCGTTCAGATTGATTGAAGAAAATTTGCCTGCATTTTTGTACA<br>ACTGCAAAAAGGGAGTAAAAATATTCGAGGGACTCGACGCAGTCGATGCAGAAA<br>CGCTTAATAATGAACTTGGAGAGATTCTTTCAATCGAAAACGTAAAAGATGTATTA<br>AGCGTAGAGTATTACAATAAAACGCTCACGCAAAACGGCATAGACGTTTACAACC<br>GGATTATAGGCGGCTATACACAGGAAGACGGGACGAAAATCAAAGGTGTCAACG<br>AGTACGTCAATTTGTATAACCAGACGCACGACAAAAAACTTCCGTCGCTCGCAAA<br>ACTCAAAAAACAGATTTTAAGCGACAGTTATTCGTTGTCGTTTTTGCCCGCAAAAT<br>TCAACGACGATTCCGAATTGCTTTTATCGCTTAAAAAGTTTTATTCGACGGTAAAC<br>GAAGAGACCGGTTTAAGCGTAGAAAAGGCGATACAGGAAATGCGCGACGTTTTT<br>TCACACATCGATGACTGTGATTTGCATAACGTTTTTATCGACGCAAAATTTATAAA<br>CAAGGTTTCAAACGACGTTTTCGGGAATTGGAGCGTTTTGATTGACGGCATAAAT<br>GCGGAATATGAGAAACTCAATCCGTTCAACGGGAAAAACCTCGACAATTATGAGG<br>AAAAACGCAAAGCGTTTTTAAACAAGATCGAAAGCTATTCTGTTGACGCGTTGCA<br>GGCATATTCGGGTAAAGAAGAAAAAATCGCCGACTACGTTCAAAAACGTGCGGTC<br>GAACTTTACGATAGTGTCGCATGCGCATATGAGAATATGAGTAATAAGGTAATAAA<br>TGCGCGAGAAGGGAAGGTTAAACTTTATCAGGACGATGAAAAAACCGAAATAATC<br>AAAACGTTTTTGGACGCGGTACAGGAATTCAAAAAGTTTGCCGAGATGTTTTGCT<br>ATGACGGCACCGACGGCGATACGACGTTTTACGGCGAATTTGCGAATTATTACG<br>GACAAATTGCCGAAATTATACCGCTTTACAATAAATGCAGGAACTATTTGACGAAA<br>AAGCCGTATTCCGAAGACAAAATCAAAATAAACTTTGACAACGCTGAGCTTTTGCA | 28 |

TABLE 1E-continued

| YYAN Type V Cas Sequences | | |
|---|---|---|
| Name | Sequence | SEQ ID NO. |
| | TGGATGGGACGCAAACAAAGAAAAGAATTATCTGACTGTATTATTATTTAAAAACG GCAGTTATTATCTCGGTATTCTGGATAAAAAGCATAAGAACGTTTTGATCAAAGAC GTGCCCGAAAAGACGCAGGAGGAGCCGTGTTTCAAGAAAATGATTTACAAATTAC TCCCTGATCCGAAACGAAATATGCCTAGAATAATATTACATGCAAAAAGTAACAAG AAGTTGTTTGAGCCTAGTGATGAGATATATAGGATATATGAAACAGAATCGTTTAA AACTGACATTGACGACTGCCATAGGTTGATTGATTTTTATAAAGAAAGTATAAGCA AGTACGAGGACTGGAAGACGTTCGGGTTCAAGTTCAAAGAAACGAGCGAGTATA AAAACATAGGGCAATTTTATAACGAAGTTAAAGAGCAGGGATATAAGATTTCATTC ACGGATATACCCGAAAGTTACGTCAAAGACTTGGTAAACGACGGGAAACTGTATT TATTCAGGCTTGCTAATAAAGATTTTTCTCCGTACAGCAAGGGCAAAAAGAATTTG CATACGATGTATTTCGAGGGAATATTTGATCCTGAAAACATAAAAGAAAAGGTTTA TGCGCTTAACGGCGGCGGCGAGTTGTTTTTCAGATGCGCGAGCTTGAATTACGA CAAACCGACGCATCCGAAAAACGTACCGATTAAAAACAAAACGTATGATTTCCGC ACCGATAATGCGAAAAAAGAAACAAGCACGTTTGAATACGACCTCATAAAAGATA AGCGATATACGAAAGATCAATACACGTTGCATTGTCCGGTGACGCTTAATTTTAA GGAAAGAGGAATCGAAAGAATAAACGATCTCGTAAGGCAATCGTTGCGTGAAAGT GACGACAACTACGTAATCGGCATTGATCGGGGCGAAAGAAACTTAATTTACATCA GTGTTATCGACGGAAAAGGAAAGATTGTCGAGCAATTCTCGATGAACAATTTGTT AAGCGGTAACGACGTGTCGATAGATTTCCACAAAATGCTCGAAACGCGGGAGCA CGAGCGCGACGCGTCCAGAAAAAACTGGAATACAATCGACAATATCAAAGACTTG AAGCAAGGATATTTAAGTTATGTCGTAAAGAAAATTTGCGACCTTGTCGTAAAATA CGACGCGATTGTCGCAATGGAAGACTTAAACGTCGGGTTCAAGCACGGACGAGA AAAGTTCGAGCGACAGGTATATCAGAAATTTGAAAAAGCACTTGTCGACAAAATG AGTTATATCGTAAACAAGAACGCGTCGCCGCATTCCGACGGAGGTTTGTTCAGG GCATACCAGCTGACCAATAAAAAGTATAATGAAAACGAAAAACAAAACGGTTTTAT TTTCTATGTCAGAGCGTGGAATACCAGTAAGATCGATCCGACGACCGGGTTTGTA AACATGCTTCCGTTAAAATATCAGAGCAAAGAAAAATCAAAAGAATTTTTCGATAA ATTTGAAGATATTTTTTACGATGAAAACAAGGATATGTTCGGTTTTACATTCAGATA TGACGATTTCGGTATAAATATCGATCATAAAAACGAATGGACGGCTTATTCAAACG GCGAACGAATAATCACCGTACGAAATTCGTTCGGCAAGTGGGATAAAGCGAAGA TCGTATTGACGCCGGCATTTAAGAAACTGTTTGACGACTATAACGTGGATTGTCG CGGCGACGTCAAACGACAGATTATGAACGTTGACGACAAAGACTTTTTCGTTAGG TTATATAAGCTTTTGTCGTATACGATGCAGTTGAGAAACTCCGACGATGTTGACGA CTATATTTTGTCGCCCGTCGTTAATGCGGAAGGGAAGTTCTTTGACAGTCGCAAT TCGGACGGCAGTTTGCCTTGCGACGCGGACGCAAACGGAGCGTATCATATTGCC AAAAAGGCAATGTGGGCAATCGGGAAGATAAAAGAAGCGGACGAAGAAAGTTTT AAAAAGACAAGTCTTGCAATCGACAACAAGACGTGGCTTGAATTCGTTCAAAAGG CATAA | |
| Codon optimized coding sequence (no N-terminal methionine, no stop codon) | AAGATCAACGCTTTTATCAACTGTTACAGCATGAGCAAGACCCTGAGATTCAAGC TGGCCCCTGAGTACGAAACCGAGAAGAACCTGCTGGAAAAGGGCTTTCTGGACC GGGACAAGCTGAGAGCCGACGACTACGACCTGATGAAGAAGGTGATAGACAAGT ACCACAAGCACTTCATCGACAAGGCCCTGGAAGGCTTCAAGTTTGACCTGCTGC AAGAATACGCTGAGGCCTTTTACAGCCAGAGCGCCGACGACGACGGCAAGAAGC TCGAAGAGATCAAGAAGAAGATGTGCAAGGAGCTGGCCACATGCTTCAGCAAGC AAGACGAGTTCAAGCTACTGGATAAGAAAGAGCTGGTGGAAAAGCTGATCCCAG CCGCTGAGTTCATCGAGGACGAGGAAAAAGACATTGCCAAGAGATTCAAAGGCT TTACAACCTACTTTACCGGCTTCAATGAAAACAGACAGAATCTGTACGCCGCCGA GCTGAAGCACGGAACAATCGCCTTCAGACTGATCGAGGAGAACTTGCCTGCCTT CCTGTACAATTGCAAGAAGGGTGTTAAGATCTTCGAGGGCCTGGACGCTGTGGA TGCTGAGACTCTCAACAACGAGCTGGGCGAGATCCTGAGCATCGAAAACGTGAA GGACGTGCTGTCCGTGGAGTACTACAACAAAACCCTGACCCAAAACGGCATCGA TGTGTACAATAGAATCATCGGCGGCTACACCCAGGAGGATGGCACCAAGATCAA GGGAGTGAACGAGTACGTGAACCTGTATAACCAGACACACGACAAGAAACTGCC TTCTCTGGCTAAGCTGAAGAAGCAAATCCTGTCTGACTCCTATTCTCTGTCATTCC TGCCCGCCAAGTTTAACGACGACTCTGAGCTCCTGCTCAGCCTGAAGAAGTTTTA CAGCACCGTGAACGAGGAAACAGGACTGAGCGTGGAGAAAGCTATCCAGGAGAT GAGAGATGTGTTCAGCCACATTGACGACTGCGACCTTCACAACGTCTTTATCGAT GCCAAGTTCATCAACAAGGTGAGCAACGACGTGTTCGGCAACTGGTCGGTCCTG ATCGATGGCATCAATGCCGAGTACGAGAAGCTGAACCCCTTCAACGGCAAGAAC CTGGACAACTACGAGGAAAAAAGAAAGGCCTTTCTGAACAAAATCGAGAGCTATA GCGTGGACGCCCTGCAGGCCTACAGCGGCAAGGAAGAGAAGATCGCCGATTAT GTGCAGAAACGGGCCGTTGAACTGTACGACAGCGTGGCTTGTGCTTACGAAAAC ATGAGCAACAAAGTGATCAACGCCCGGGAAGGCAAGGTGAAGCTGTACCAGGAC GACGAAAAGACCGAGATTATCAAGACCTTCCTGGATGCTGTTCAGGAGTTCAAGA AGTTCGCCGAAATGTTCTGCTACGATGGAACAGATGGAGATACCACCTTCTACGG CGAGTTCGCCAATTATTACGGCCAGATCGCCGAGATAATCCCCCTGTACAACAAG TGCAGAAACTATCTGACAAAGAAACCTTACAGCGAGGACAAGATTAAGATCAACT TCGATAACGCGGAACTGCTGCATGGATGGGACGCCAACAAGGAAAAGAACTACC TGACAGTCCTGCTGTTCAAAAATGGATCATATTACCTGGGCATCCTGGATAAAAA GCATAAGAACGTGCTGATTAAGGACGTTCCTGAAAAGACACAGGAAGAGCCCTG TTTCAAAAAAAATGATCTACAAGCTGCTGCCTGATCCCAAGCGGAATATGCCTAGG ATCATCTTGCACGCCAAAAGCAATAAAAAACTGTTCGAGCCTAGCGATGAGATCT ACAGAATCTATGAGACAGAGAGCTTCAAGACCGACATCGACGATTGCCACAGACT GATCGATTTCTACAAGGAATCCATCAGCAAGTACGAGGACTGGAAAACCTTTGGA | 29 |

TABLE 1E-continued

| YYAN Type V Cas Sequences | | |
|---|---|---|
| Name | Sequence | SEQ ID NO. |
| | TTTAAATTCAAAGAAACCAGCGAGTACAAGAACATCGGACAGTTCTACAACGAGG<br>TGAAGGAACAGGGCTACAAGATTAGCTTCACCGACATCCCTGAGAGCTACGTGA<br>AGGATCTGGTGAATGATGGCAAGCTGTATCTGTTTAGACTCGCCAACAAGGATTT<br>CTCTCCATACTCCAAGGGCAAAAAGAACCTGCACACCATGTACTTCGAGGGAATC<br>TTCGACCCCGAAAACATCAAGGAGAAAGTGTACGCCCTGAACGGCGGCGGCGA<br>GCTGTTCTTCCGCTGTGCCTCTCTGAACTACGACAAGCCTACCCACCCCAAGAAC<br>GTGCCTATCAAGAACAAGACCTACGATTTTAGAACCGATAACGCTAAGAAAGAAA<br>CCAGTACATTCGAGTACGACCTGATCAAAGATAAACGGTACACAAAGGACCAGTA<br>CACACTGCACTGCCCTGTGACACTGAATTTCAAGGAGCGTGGAATCGAACGCAT<br>CAACGACCTGGTGCGGCAGAGCCTGCGGGAAAGCGACGACAACTACGTCATCG<br>GCATCGACAGAGGGGAGAGAAATCTGATCTACATCTCTGTGATCGACGGCAAGG<br>GCAAGATCGTCGAGCAGTTCAGCATGAACAACCTGCTGTCCGGCAACGACGTCA<br>GCATCGACTTCCACAAGATGCTGGAAACCAGAGAGCACGAGCGGGACGCCTCCA<br>GAAAGAACTGGAACACCATCGACAACATCAAGGACCTGAAGCAGGGCTACCTGA<br>GTTACGTGGTGAAAAAGATCTGCGACCTGGTCGTGAAGTATGATGCCATCGTGG<br>CTATGGAGGATCTGAACGTGGGCTTTAAACACGGCAGAGAGAAGTTCGAGAGAC<br>AGGTGTACCAGAAGTTTGAGAAAGCCCTGGTGGACAAGATGAGCTACATCGTGA<br>ATAAAAATGCTAGTCCTCACAGCGATGGCGGCCTGTTCAGAGCTTATCAGCTGAC<br>CAACAAGAAATACAACGAGAATGAAAAGCAGAACGGATTCATCTTTTACGTGAGA<br>GCCTGGAATACCAGCAAGATCGACCCAACAACAGGCTTCGTGAACATGTTGCCA<br>CTGAAATACCAATCTAAGGAAAAGTCCAAGGAGTTCTTCGACAAGTTCGAGGATA<br>TCTTCTATGATGAAAACAAAGACATGTTCGGCTTCACCTTCCGGTACGACGACTT<br>CGGCATCAACATCGACCACAAGAATGAATGGACCGCCTACAGCAATGGTGAGCG<br>GATCATCACCGTGCGGAACAGCTTCGGCAAATGGGATAAAGCGAAGATCGTGCT<br>GACCCCTGCTTTTAAGAAGCTGTTCGATGATTACAACGTGGACTGCAGAGGCGA<br>CGTGAAGCGACAGATTATGAACGTGGACGACAAAGATTTCTTCGTGCGGCTGTA<br>CAAGCTGCTGAGCTACACCATGCAGCTGAGAAACAGCGACGACGTGGACGATTA<br>CATCCTGAGCCCCGTGGTGAATGCCGAAGGCAAGTTCTTCGACAGCAGAAACTC<br>TGACGGCTCTCTGCCTTGTGACGCCGATGCCAACGGCGCCTACCACATCGCCAA<br>GAAGGCCATGTGGGCCATCGGCAAGATCAAGGAAGCCGATGAGGAATCTTTTAA<br>GAAAACCTCCCTCGCCATCGACAACAAAACCTGGCTGGAGTTCGTGCAGAAAGC<br>C | |
| Expression construct (with N-terminal methionine and stop codon, includes V5-tag and C-terminal NLS) | ATGggcAAGATCAACGCTTTTATCAACTGTTACAGCATGAGCAAGACCCTGAGATT<br>CAAGCTGGCCCCTGAGTACGAAACCGAGAAGAACCTGCTGGAAAAGGGCTTTCT<br>GGACCGGGACAAGCTGAGAGCCGACGACTACGACCTGATGAAGAAGGTGATAG<br>ACAAGTACCACAAGCACTTCATCGACAAGGCCCTGGAAGGCTTCAAGTTTGACCT<br>GCTGCAAGAATACGCTGAGGCCTTTTACAGCCAGAGCGCCGACGACGACGGCAA<br>GAAGCTCGAAGAGATCAAGAAGAAGATGTGCAAGGAGCTGGCCACATGCTTCAG<br>CAAGCAAGACGAGTTCAAGCTACTGGATAAGAAAGAGCTGGTGGAAAAGCTGAT<br>CCCAGCCGCTGAGTTCATCGAGGACGAGGAAAAAGACATTGCCAAGAGATTCAA<br>AGGCTTTACAACCTACTTTACCGGCTTCAATGAAAACAGACAGAATCTGTACGCC<br>GCCGAGCTGAAGCACGGAACAATCGCCTTCAGACTGATCGAGGAGAACTTGCCT<br>GCCTTCCTGTACAATTGCAAGAAGGGTGTTAAGATCTTCGAGGGCCTGGACGCT<br>GTGGATGCTGAGACTCTCAACAACGAGCTGGGCGAGATCCTGAGCATCGAAAAC<br>GTGAAGGACGTGCTGTCCGTGGAGTACTACAACAAAACCCTGACCCAAAACGGC<br>ATCGATGTGTACAATAGAATCATCGGCGGCTACACCCAGGAGGATGGCACCAAG<br>ATCAAGGGAGTGAACGAGTACGTGAACCTGTATAACCAGACACACGACAAGAAA<br>CTGCCTTCTCTGGCTAAGCTGAAGAAGCAAATCCTGTCTGACTCCTATTCTCTGT<br>CATTCCTGCCCGCCAAGTTTAACGACGACTCTGAGCTCCTGCTCAGCCTGAAGAA<br>GTTTTACAGCACCGTGAACGAGGAAACAGGACTGAGCGTGGAGAAAGCTATCCA<br>GGAGATGAGAGATGTGTTCAGCCACATTGACGACTGCGACCTTCACAACGTCTTT<br>ATCGATGCCAAGTTCATCAACAAGGTGAGCAACGACGTGTTCGGCAACTGGTCG<br>GTCCTGATCGATGGCATCAATGCCGAGTACGAGAAGCTGAACCCCTTCAACGGC<br>AAGAACCTGGACAACTACGAGGAAAAAGAAAGGCCTTTCTGAACAAAATCGAGA<br>GCTATAGCGTGGACGCCCTGCAGGCCTACAGCGGCAAGGAAGAGAAGATCGCC<br>GATTATGTGCAGAAACGGGCCGTTGAACTGTACGACAGCGTGGCTTGTGCTTAC<br>GAAAACATGAGCAACAAAGTGATCAACGCCCGGGAAGGCAAGGTGAAGCTGTAC<br>CAGGACGACGAAAAGACCGAGATTATCAAGACCTTCCTGGATGCTGTTCAGGAG<br>TTCAAGAAGTTCGCCGAAATGTTCTGCTACGATGGAACAGATGGAGATACCACCT<br>TCTACGGCGAGTTCGCCAATTATTACGGCCAGATCGCCGAGATAATCCCCCTGTA<br>CAACAAGTGCAGAAACTATCTGACAAAGAAACCTTACAGCGAGGACAAGATTAAG<br>ATCAACTTCGATAACGCGGAACTGCTGCATGGATGGGACGCCAACAAGGAAAAG<br>AACTACCTGACAGTCCTGCTGTTCAAAAATGGATCATATTACCTGGGCATCCTGG<br>ATAAAAAGCATAAGAACGTGCTGATTAAGGACGTTCCTGAAAAGACACAGGAAGA<br>GCCCTGTTTCAAAAAAATGATCTACAAGCTGCTGCCTGATCCCAAGCGGAATATG<br>CCTAGGATCATCTTGCACGCCAAAAGCAATAAAAAACTGTTCGAGCCTAGCGATG<br>AGATCTACAGAATCTATGAGACAGAGAGCTTCAAGACCGACATCGACGATTGCCA<br>CAGACTGATCGATTTCTACAAGGAATCCATCAGCAAGTACGAGGACTGGAAAACC<br>TTTGGATTTAAATTCAAAGAAACCAGCGAGTACAAGAACATCGGACAGTTCTACAA<br>CGAGGTGAAGGAACAGGGCTACAAGATTAGCTTCACCGACATCCCTGAGAGCTA<br>CGTGAAGGATCTGGTGAATGATGGCAAGCTGTATCTGTTTAGACTCGCCAACAAG<br>GATTTCTCTCCATACTCCAAGGGCAAAAAGAACCTGCACACCATGTACTTCGAGG<br>GAATCTTCGACCCCGAAAACATCAAGGAGAAAGTGTACGCCCTGAACGGCGGCG<br>GCGAGCTGTTCTTCCGCTGTGCCTCTCTGAACTACGACAAGCCTACCCACCCCA | 30 |

TABLE 1E-continued

| YYAN Type V Cas Sequences | | |
|---|---|---|
| Name | Sequence | SEQ ID NO. |
| | AGAACGTGCCTATCAAGAACAAGACCTACGATTTTAGAACCGATAACGCTAAGAA AGAAACCAGTACATTCGAGTACGACCTGATCAAAGATAAACGGTACACAAAGGAC CAGTACACACTGCACTGCCCTGTGACACTGAATTTCAAGGAGCGTGGAATCGAA CGCATCAACGACCTGGTGCGGCAGAGCCTGCGGGAAAGCGACGACAACTACGT CATCGGCATCGACAGAGGGGAGAGAAATCTGATCTACATCTCTGTGATCGACGG CAAGGGCAAGATCGTCGAGCAGTTCAGCATGAACAACCTGCTGTCCGGCAACGA CGTCAGCATCGACTTCCACAAGATGCTGGAAACCAGAGAGCACGAGCGGGACG CCTCCAGAAAGAACTGGAACACCATCGACAACATCAAGGACCTGAAGCAGGGCT ACCTGAGTTACGTGGTGAAAAAGATCTGCGACCTGGTCGTGAAGTATGATGCCAT CGTGGCTATGGAGGATCTGAACGTGGGCTTTAAACACGGCAGAGAGAAGTTCGA GAGACAGGTGTACCAGAAGTTTGAGAAAGCCCTGGTGGACAAGATGAGCTACAT CGTGAATAAAAATGCTAGTCCTCACAGCGATGGCGGCCTGTTCAGAGCTTATCAG CTGACCAACAAGAAATACAACGAGAATGAAAAGCAGAACGGATTCATCTTTTACG TGAGAGCCTGGAATACCAGCAAGATCGACCCAACAACAGGCTTCGTGAACATGT TGCCACTGAAATACCAATCTAAGGAAAAGTCCAAGGAGTTCTTCGACAAGTTCGA GGATATCTTCTATGATGAAAACAAAGACATGTTCGGCTTCACCTTCCGGTACGAC GACTTCGGCATCAACATCGACCACAAGAATGAATGGACCGCCTACAGCAATGGT GAGCGGATCATCACCGTGCGGAACAGCTTCGGCAAATGGGATAAAGCGAAGATC GTGCTGACCCCTGCTTTTAAGAAGCTGTTCGATGATTACAACGTGGACTGCAGAG GCGACGTGAAGCGACAGATTATGAACGTGGACGACAAAGATTTCTTCGTGCGGC TGTACAAGCTGCTGAGCTACACCATGCAGCTGAGAAACAGCGACGACGTGGACG ATTACATCCTGAGCCCCGTGGTGAATGCCGAAGGCAAGTTCTTCGACAGCAGAA ACTCTGACGGCTCTCTGCCTTGTGACGCCGATGCCAACGGCGCCTACCACATCG CCAAGAAGGCCATGTGGGCCATCGGCAAGATCAAGGAAGCCGATGAGGAATCTT TTAAGAAAACCTCCCTCGCCATCGACAACAAAACCTGGCTGGAGTTCGTGCAGAA AGCCtctagaAAGCGGACAGCAGACGGCTCCGAATTTGAAAGCCCTAAGAAAAAGA GAAAGGTGggatccGGCAAACCTATCCCCAATCCCCTGCTGGGCCTGGACAGCAC CTGA | |

In some embodiments a YYAN Type V Cas protein comprises an amino acid sequence of SEQ ID NO:25, SEQ ID NO:26, or SEQ ID NO:27. In some embodiments, a YYAN Type V Cas protein has nickase activity, for example resulting from one or more amino acid substitutions relative to the sequence of SEQ ID NO:25, SEQ ID NO:26, or SEQ ID NO:27. In some embodiments, the one or more amino acid substitutions providing nickase activity comprise a D838 substitution, wherein the position of the D838 substitution is defined with respect to the amino acid numbering of SEQ ID NO:26 (corresponding to amino acid 908 of SEQ ID NO:121). In some embodiments, the one or more amino acid substitutions providing nickase activity comprise an E928 substitution, wherein the position of the E928 substitution is defined with respect to the amino acid numbering of SEQ ID NO:26 (corresponding to amino acid 993 of SEQ ID NO:121). In some embodiments, the one or more amino acid substitutions providing nickase activity comprise a R1135 substitution, wherein the position of the R1135 substitution is defined with respect to the amino acid numbering of SEQ ID NO:26 (corresponding to amino acid 1226 of SEQ ID NO:121). In some embodiments, the one or more amino acid substitutions providing nickase activity comprise a D1170 substitution, wherein the position of the D1170 substitution is defined with respect to the amino acid numbering of SEQ ID NO:26 (corresponding to amino acid 1263 of SEQ ID NO:121). In some embodiments, a YYAN Type V Cas protein is catalytically inactive, for example due to a R1135 substitution in combination with a D838 substitution, a E928 substitution, and/or D1170 substitution.

6.2.6. ZZGY Type V Cas Proteins

In one aspect, the disclosure provides ZZGY Type V Cas proteins. ZZGY Type V Cas proteins can be further classified as Type V-A Cas proteins. The ZZGY Type V Cas proteins typically comprise an amino acid sequence that is at least 50%, at least 55%, at least 60%, at least 65%, at least 70%, at least 75%, at least 85%, at least 90%, or at least 95% identical to SEQ ID NO:31. In some embodiments, the ZZGY Type V Cas proteins comprise an amino acid sequence that is at least 95%, at least 96%, at least 97%, at least 98%, or at least 99% identical to SEQ ID NO:31. In some embodiments, a ZZGY Type V Cas protein comprises an amino acid sequence that is identical to SEQ ID NO:31.

Exemplary ZZGY Type V Cas protein sequences and nucleotide sequences encoding exemplary ZZGY Type V Cas proteins are set forth in Table 1F.

TABLE 1F

| ZZGY Type V Cas Sequences | | |
|---|---|---|
| Name | Sequence | SEQ ID NO. |
| Wildtype amino acid sequence (without N-terminal methionine) | SKLSTFNEHFQKTLTLRNELVPVGKTLENIISSNVLINDEKRSEDYKKAKEIIDSYHREFI EKSLSSVNVDWNDLYSYLSKKEPEDYAQKQKFLEELENILLEKRKIIVKQFEQYVFGS YTDSKGKKTKDLKFENLFKSELFDYLLPNFLKNDEDKKVIGSFNKFTSYFTGFYENRK NLYKSEPLPTAVAYRIVNENFPKFISNKNIFRVWKDNVPQFIEIAKTKLREEGISDLNIEL KFDLTNFNSCLNQTGIDTYNDLIGQLNFAINLECQKDKNLCDLLRKKRSLKMVPLYKQI LSDNDSSFSIDEFDNDESAIKDVISFYKKMIGENCPQRTLSELLHGLSSHDLEKIFVQG | 31 |

TABLE 1F-continued

| ZZGY Type V Cas Sequences | | |
|---|---|---|
| Name | Sequence | SEQ ID NO. |
| | KNLNSVSKNLFGGKNWSLLRDAVIEEKSKEKVFKKVIKSNSTADELDKVLSKEEFSISF<br>LSKVSGKDLSVEIDKFVKKQDELLVENNIQNWPSSLKNSEEKNLIKAPLDFLLNFYRFA<br>QSFSSNNIDKDMSFYADFDESLSSLENVIGLYNKVRNYATKKPYTLEKIKLNFENPNLA<br>SGWSESKENDCLSIILLKEKKYFLGIFNKNNKPNFSEGISHSLSSNGCYRKMRYLLFK<br>GFNKMLPKCAFTGEVKDHFKESSDDFSLFNKDTFISPLVITKEIFDLACSKEKVKKYQK<br>EYEKINRAEYRQSLVKWITFGLKFLSSYKTTTQFDLSNLKRPEEYCDLKEFYEDVDNL<br>TYKIEFLNIKEEDVDALVEKGQLYLFEIRNKDFAKNASGTPNLHTLYFKSIFDSKNLEN<br>GIVKLNGEAEIFYRKKSLKKDDITVHREGSYLVNKVCVDPNSGKTEQIPDKIYENIYAF<br>VNGKSRDLSKEDEVYYAKATIKKATHEIVKDRRFTVDKFFFHCPITINYKSKDKPSKFN<br>DKVLDFLRNNKDINIIGIDRGERNLIYVTVINQNGEIIDCKSFNTIKHQSSTVNYDVDYH<br>NKLQEREKNRKEEKRSWNSITKIADLKEGYLSAVIHEVSLMMVKYNAIVVMENLNQGF<br>KRIRGGIAERSVYQKFEKMLIDKLNYFVIKNENWTNPGGVLNGYQLTNKVSTIKDIGN<br>QCGFLFYVPATYTSKIDPSTGFVNLINFNKYKNSEDRRKLICSFDKICFVQNENLFKFSI<br>DYGKLCPDSKIAIKKWDVFSYGTRIIKENLTTGHIEENPEYDPTEELKSLLSSRGIEYQK<br>GQNLLETIPTSDMTREFWNSLFKIFKAILQMRNSLTNSPIDRLLSPVKGKDGTFFDTDK<br>VEGTKFEKLKDADANGAYNIALKGLLVLEKNDSVESNKDLKNVKKISLEDWLKFVQITL<br>RD | |
| Wildtype amino acid sequence (with N-terminal methionine) | MSKLSTFNEHFQKTLTLRNELVPVGKTLENIISSNVLINDEKRSEDYKKAKEIIDSYHRE<br>FIEKSLSSVNVDWNDLYSYLSKKEPEDYAQKQKFLEELENILLEKRKIIVKQFEQYVFG<br>SYTDSKGKKTKDLKFENLFKSELFDYLLPNFLKNDEDKKVIGSFNKFTSYFTGFYENR<br>KNLYKSEPLPTAVAYRIVNENFPKFISNKNIFRVWKDNVPQFIEIAKTKLREEGISDLNI<br>ELKFDLTNFNSCLNQTGIDTYNDLIGQLNFAINLECQKDKNLCDLLRKKRSLKMVPLYK<br>QILSDNDSSFSIDEFDNDESAIKDVISFYKKMIGENCPQRTLSELLHGLSSHDLEKIFVQ<br>GKNLNSVSKNLFGGKNWSLLRDAVIEEKSKEKVFKKVIKSNSTADELDKVLSKEEFSI<br>SFLSKVSGKDLSVEIDKFVKKQDELLVENNIQNWPSSLKNSEEKNLIKAPLDFLLNFYR<br>FAQSFSSNNIDKDMSFYADFDESLSSLENVIGLYNKVRNYATKKPYTLEKIKLNFENP<br>NLASGWSESKENDCLSIILLKEKKYFLGIFNKNNKPNFSEGISHSLSSNGCYRKMRYL<br>LFKGFNKMLPKCAFTGEVKDHFKESSDDFSLFNKDTFISPLVITKEIFDLACSKEKVKK<br>YQKEYEKINRAEYRQSLVKWITFGLKFLSSYKTTTQFDLSNLKRPEEYCDLKEFYEDV<br>DNLTYKIEFLNIKEEDVDALVEKGQLYLFEIRNKDFAKNASGTPNLHTLYFKSIFDSKNL<br>ENGIVKLNGEAEIFYRKKSLKKDDITVHREGSYLVNKVCVDPNSGKTEQIPDKIYENIY<br>AFVNGKSRDLSKEDEVYYAKATIKKATHEIVKDRRFTVDKFFFHCPITINYKSKDKPSK<br>FNDKVLDFLRNNKDINIIGIDRGERNLIYVTVINQNGEIIDCKSFNTIKHQSSTVNYDVDY<br>HNKLQEREKNRKEEKRSWNSITKIADLKEGYLSAVIHEVSLMMVKYNAIVVMENLNQ<br>GFKRIRGGIAERSVYQKFEKMLIDKLNYFVIKNENWTNPGGVLNGYQLTNKVSTIKDIG<br>NQCGFLFYVPATYTSKIDPSTGFVNLINFNKYKNSEDRRKLICSFDKICFVQNENLFKF<br>SIDYGKLCPDSKIAIKKWDVFSYGTRIIKENLTTGHIEENPEYDPTEELKSLLSSRGIEY<br>QKGQNLLETIPTSDMTREFWNSLFKIFKAILQMRNSLTNSPIDRLLSPVKGKDGTFFDT<br>DKVEGTKFEKLKDADANGAYNIALKGLLVLEKNDSVESNKDLKNVKKISLEDWLKFVQ<br>ITLRD | 32 |
| Expression construct (with N-terminal methionine, V5-tag and C-terminal NLS) aa sequence | MGSKLSTFNEHFQKTLTLRNELVPVGKTLENIISSNVLINDEKRSEDYKKAKEIIDSYHR<br>EFIEKSLSSVNVDWNDLYSYLSKKEPEDYAQKQKFLEELENILLEKRKIIVKQFEQYVF<br>GSYTDSKGKKTKDLKFENLFKSELFDYLLPNFLKNDEDKKVIGSFNKFTSYFTGFYEN<br>RKNLYKSEPLPTAVAYRIVNENFPKFISNKNIFRVWKDNVPQFIEIAKTKLREEGISDLN<br>IELKFDLTNFNSCLNQTGIDTYNDLIGQLNFAINLECQKDKNLCDLLRKKRSLKMVPLY<br>KQILSDNDSSFSIDEFDNDESAIKDVISFYKKMIGENCPQRTLSELLHGLSSHDLEKIFV<br>QGKNLNSVSKNLFGGKNWSLLRDAVIEEKSKEKVFKKVIKSNSTADELDKVLSKEEFS<br>ISFLSKVSGKDLSVEIDKFVKKQDELLVENNIQNWPSSLKNSEEKNLIKAPLDFLLNFY<br>RFAQSFSSNNIDKDMSFYADFDESLSSLENVIGLYNKVRNYATKKPYTLEKIKLNFEN<br>PNLASGWSESKENDCLSIILLKEKKYFLGIFNKNNKPNFSEGISHSLSSNGCYRKMRY<br>LLFKGFNKMLPKCAFTGEVKDHFKESSDDFSLFNKDTFISPLVITKEIFDLACSKEKVK<br>KYQKEYEKINRAEYRQSLVKWITFGLKFLSSYKTTTQFDLSNLKRPEEYCDLKEFYED<br>VDNLTYKIEFLNIKEEDVDALVEKGQLYLFEIRNKDFAKNASGTPNLHTLYFKSIFDSKN<br>LENGIVKLNGEAEIFYRKKSLKKDDITVHREGSYLVNKVCVDPNSGKTEQIPDKIYENI<br>YAFVNGKSRDLSKEDEVYYAKATIKKATHEIVKDRRFTVDKFFFHCPITINYKSKDKPS<br>KFNDKVLDFLRNNKDINIIGIDRGERNLIYVTVINQNGEIIDCKSFNTIKHQSSTVNYDVD<br>YHNKLQEREKNRKEEKRSWNSITKIADLKEGYLSAVIHEVSLMMVKYNAIVVMENLNQ<br>GFKRIRGGIAERSVYQKFEKMLIDKLNYFVIKNENWTNPGGVLNGYQLTNKVSTIKDIG<br>NQCGFLFYVPATYTSKIDPSTGFVNLINFNKYKNSEDRRKLICSFDKICFVQNENLFKF<br>SIDYGKLCPDSKIAIKKWDVFSYGTRIIKENLTTGHIEENPEYDPTEELKSLLSSRGIEY<br>QKGQNLLETIPTSDMTREFWNSLFKIFKAILQMRNSLTNSPIDRLLSPVKGKDGTFFDT<br>DKVEGTKFEKLKDADANGAYNIALKGLLVLEKNDSVESNKDLKNVKKISLEDWLKFVQ<br>ITLRDSRKRTADGSEFESPKKKRKVGSGKPIPNPLLGLDST | 33 |
| Wildtype coding sequence (with N-terminal methionine and stop codon) | ATGTCTAAATTATCAACTTTTAATGAACATTTTCAAAAAACGTTAACTTTAAGAAAC<br>GAACTAGTTCCTGTAGGAAAAACTCTTGAAAATATCATATCTTCAAATGTATTGATA<br>AATGATGAGAAAAGAAGTGAAGATTATAAAAAGGCTAAAGAGATCATAGATTCTTA<br>TCATCGAGAGTTTATAGAGAAATCACTTTCATCAGTAAATGTTGATTGGAATGATC<br>TGTACTCGTATTTATCCAAAAAAGAACCAGAAGACTATGCTCAAAAGCAGAAGTTC<br>CTCGAAGAGTTAGAAAATATTCTCCTTGAAAAGAGAAAAATTATTGTTAAACAGTT<br>TGAGCAATACGTTTTCGGATCATATACAGATTCAAAAGGTAAAAAAACAAAAGATC<br>TAAAATTTGAGAATCTTTTTAAATCAGAGTTGTTTGATTATCTTTTGCCAAATTTCC | 34 |

TABLE 1F-continued

| ZZGY Type V Cas Sequences | | |
|---|---|---|
| Name | Sequence | SEQ ID NO. |
| | TAAAAAATGATGAAGATAAAAAAGTAATAGGTAGTTTTAATAAATTTACATCGTATT<br>TTACAGGTTTTTACGAAAATCGAAAGAATTTATATAAATCAGAGCCATTGCCAACA<br>GCTGTGGCTTATAGAATAGTTAACGAAAACTTTCCTAAATTCATTTCTAATAAAAAT<br>ATCTTTCGCGTGTGGAAAGATAATGTTCCTCAGTTTATAGAAATAGCGAAAACTAA<br>ACTAAGAGAAGAAGGCATTTCTGATTTAAATATAGAATTAAAATTTGATTTAACTAA<br>TTTCAATTCATGCTTAAATCAAACTGGAATTGATACTTACAATGACTTGATAGGTCA<br>ACTCAACTTTGCAATTAACCTTGAATGTCAGAAAGACAAGAATTTATGTGACCTTT<br>TAAGGAAGAAAAGAAGCCTTAAAATGGTACCTCTGTATAAACAGATTTTATCTGAT<br>AATGATTCTTCATTCAGTATTGATGAATTTGATAATGATGAATCGGCAATAAAAGAT<br>GTAATTTCTTTTTATAAGAAAATGATTGGTGAAAATTGTCCTCAACGAACACTATCT<br>GAATTGCTACATGGTTTGTCATCTCACGATCTTGAAAAGATATTTGTTCAAGGTAA<br>AAACTTAAATTCGGTTTCTAAAAATTTATTTGGAGGGAAGAACTGGTCTTTACTAA<br>GGGATGCAGTTATAGAAGAAAAGTCAAAAGAAAAAGTCTTCAAAAAGGTTATAAA<br>GTCAAATTCTACCGCAGATGAATTAGACAAAGTTCTTTCCAAGGAAGAATTTTCAA<br>TTTCATTCTTATCAAAAGTGAGCGGTAAAGATTTATCAGTAGAAATTGATAAATTTG<br>TAAAAAAACAAGACGAACTACTTGTTGAAAATAATATACAAAATTGGCCAAGTTCT<br>CTTAAGAACAGCGAAGAGAAAAATCTCATAAAAGCTCCTTTAGATTTCTTACTTAA<br>TTTTTATAGATTTGCACAATCATTCTCTTCAAATAATATTGATAAGGATATGTCATTT<br>TATGCTGACTTTGATGAATCTCTATCGTCTTTAGAAAATGTAATAGGTCTTTATAAC<br>AAAGTCAGAAACTATGCAACTAAGAAACCTTATACACTCGAAAAGATCAAATTGAA<br>TTTTGAAAATCCAAATTTAGCTTCTGGATGGAGTGAAAGCAAAGAAAATGATTGTT<br>TATCAATTATCTTATTAAAAGAGAAAAAATATTTTTTAGGAATTTTCAACAAAAATAA<br>TAAACCTAATTTTTCTGAAGGCATTTCTCATTCACTTTCTTCAAATGGTTGCTACAG<br>AAAAATGAGGTATTTATTATTCAAGGGATTCAATAAAATGCTTCCTAAATGTGCTTT<br>TACAGGAGAAGTTAAAGATCATTTTAAAGAATCATCGGATGATTTTTCTCTTTTTAA<br>CAAGGATACTTTTATCTCTCCTCTTGTAATTACCAAAGAGATCTTTGATTTAGCATG<br>TAGTAAAGAAAAGGTAAAAAAATATCAAAAAGAATATGAAAAGATCAATCGTGCTG<br>AATATAGACAATCATTGGTTAAGTGGATTACTTTTGGTCTTAAATTTTTGTCATCAT<br>ATAAAACTACAACTCAATTTGATTTATCAAATTTAAAAAGACCTGAAGAATACTGCG<br>ATCTAAAGGAATTTTATGAAGATGTAGATAATCTTACATACAAGATAGAATTTTTAA<br>ATATAAAAGAAGAAGATGTAGATGCATTGGTTGAAAAAGGTCAACTGTATTTATTT<br>GAAATTCGAAATAAAGATTTTGCAAAAAATGCAAGTGGCACTCCTAATCTACATAC<br>TCTCTATTTTAAAAGTATTTTCGATTCGAAAAATTTAGAGAATGGCATTGTCAAGCT<br>TAATGGTGAAGCAGAGATATTTTATAGAAAGAAAAGCTTGAAGAAAGATGACATAA<br>CTGTTCATCGAGAAGGCAGTTATCTTGTAAATAAGGTGTGTGTCGATCCTAATTCT<br>GGAAAAACAGAACAGATTCCTGACAAAATTTATGAAAATATTTATGCTTTCGTAAA<br>TGGTAAATCAAGAGATTTATCTAAGGAGGATGAAGTATATTATGCAAAAGCCACAA<br>TAAAAAAAGCTACCCATGAGATCGTAAAAGATAGACGCTTTACTGTAGATAAATTC<br>TTTTTCCACTGCCCTATTACTATTAACTATAAATCTAAAGATAAACCTTCAAAATTC<br>AATGACAAGGTTTTAGATTTCTTAAGAAATAATAAAGACATCAACATTATAGGCATA<br>GATCGAGGAGAGAGAAATCTTATTTATGTAACTGTAATTAATCAAAATGGCGAAAT<br>TATTGATTGCAAATCATTTAATACTATCAAACATCAGTCTTCAACAGTGAATTACGA<br>TGTTGATTATCACAACAAATTACAAGAAAGAGAAAAAAATAGAAAAGAAGAAAAGA<br>GATCTTGGAATAGTATTACTAAAATTGCAGATCTCAAAGAAGGCTATCTTTCTGCT<br>GTAATTCATGAAGTTTCATTAATGATGGTTAAGTACAATGCCATTGTCGTTATGGA<br>AAATTTGAATCAAGGTTTTAAGAGAATTAGAGGAGGAATTGCTGAAAGATCCGTAT<br>ACCAAAAATTTGAAAAGATGCTGATAGATAAACTGAATTATTTTGTTATAAAAAATG<br>AAAATTGGACAAATCCTGGTGGGGTCCTCAATGGATATCAGTTAACTAACAAAGT<br>GTCTACAATCAAAGATATCGGTAATCAGTGTGGATTTTTATTTTACGTTCCTGCAA<br>CTTATACCTCAAAGATTGATCCTTCTACAGGCTTTGTTAATTTAATTAATTTCAATA<br>AATATAAAAATTCAGAAGATCGAAGAAAACTCATTTGTAGCTTTGACAAGATATGC<br>TTTGTACAGAATGAGAATTTATTTAAATTTTCTATAGATTATGGAAAATTATGCCCA<br>GATAGCAAAATTGCTATAAAAAAATGGGATGTTTTCTCCTACGGAACAAGAATTAT<br>TAAGGAAAATCTAACAACTGGTCATATAGAAGAAAATCCTGAATACGATCCGACA<br>GAAGAGCTTAAATCTCTGCTTTCCTCAAGAGGAATTGAGTATCAAAAAGGTCAAAA<br>TTTACTAGAAACAATACCTACTAGTGATATGACTAGAGAATTTTGGAATTCTCTTTT<br>CAAGATTTTTAAAGCAATTTTACAAATGAGAAACAGTCTAACTAATTCACCAATAGA<br>CAGGCTTTTATCTCCAGTTAAAGGAAAAGATGGAACCTTCTTTGATACAGATAAAG<br>TAGAAGGTACTAAGTTTGAAAAGTTAAAAGACGCTGATGCAAACGGAGCATATAA<br>CATTGCGTTAAAAGGATTGTTAGTCCTCGAGAAAAATGATTCTGTAGAGTCCAATA<br>AGGATCTAAAAAATGTTAAGAAAATTAGTCTTGAGGATTGGTTAAAGTTTGTCCAA<br>ATCACATTAAGAGATTAA | 35 |
| Codon optimized coding sequence (no N-terminal methionine, no stop codon) | AGCAAATTGTCGACCTTCAATGAGCACTTTCAGAAAACCCTGACCCTGCGGAATG<br>AGCTGGTGCCCGTGGGCAAGACACTGGAGAACATCATCAGCTCTAACGTGCTGA<br>TCAACGACGAGAAGCGGTCCGAGGACTACAAAAAGGCCAAGGAAATCATTGACA<br>GCTATCACCGGGAGTTCATCGAGAAAAGCCTGAGCTCTGTGAATGTGGACTGGA<br>ATGATCTGTACAGCTACCTGAGCAAGAAAGAACCCGAGGACTATGCCCAGAAAC<br>AGAAGTTCCTGGAGGAGTTAGAGAACATCCTGCTGGAAAAGAGAAAGATCATCGT<br>GAAGCAGTTCGAGCAGTACGTGTTCGGTTCCTATACCGACAGCAAGGGAAAAAA<br>GACCAAGGACCTGAAATTCGAAAACCTGTTTAAGTCCGAACTCTTTGACTACCTG<br>CTGCCTAACTTCTTGAAAAACGACGAGGATAAGAAGGTGATTGGCTCCTTCAATA<br>AGTTCACCAGCTATTTCACCGGCTTTTACGAGAACAGAAAAAACCTGTACAAGAG<br>CGAGCCTCTGCCTACCGCCGTCGCCTACAGAATCGTGAACGAGAACTTCCCCAA | |

TABLE 1F-continued

ZZGY Type V Cas Sequences

| Name | Sequence | SEQ ID NO. |
| --- | --- | --- |
| | GTTTATCTCTAACAAGAACATCTTTAGAGTGTGGAAGGACAACGTCCCTCAATTCA<br>TCGAGATCGCAAAGACCAAACTGAGAGAAGAAGGCATCTCTGATCTGAACATCGA<br>GCTGAAGTTTGATTTGACAAATTTCAACTCCTGCCTGAATCAGACCGGCATCGAT<br>ACCTACAACGACCTGATCGGCCAGCTGAACTTTGCTATCAACCTCGAATGTCAGA<br>AGGACAAGAACCTTTGTGACCTGCTGCGCAAGAAGCGGAGCCTTAAGATGGTGC<br>CACTGTACAAGCAAATCCTGTCCGACAACGATAGCAGCTTCAGCATCGACGAGTT<br>CGACAATGATGAAAGCGCCATCAAGGACGTTATCAGCTTCTACAAGAAGATGATC<br>GGCGAGAACTGCCCTCAGCGGACCCTGTCTGAGCTGCTGCACGGCCTGTCTAG<br>CCACGATCTGGAGAAAATTTTCGTGCAAGGGAAGAACCTGAACAGCGTGTCCAA<br>GAACCTGTTCGGCGGCAAGAACTGGTCCCTGCTGCGGGACGCCGTGATCGAGG<br>AAAAAAGCAAAGAGAAGGTGTTCAAGAAGGTGATCAAGAGCAACAGCACCGCTG<br>ATGAGCTGGATAAGGTGCTGTCTAAGGAGGAGTTCAGCATCTCTTTCCTATCCAA<br>GGTGTCCGGCAAGGATCTGAGCGTGGAAATCGACAAGTTCGTCAAAAAACAGGA<br>CGAGCTTCTGGTGGAGAACAATATCCAGAACTGGCCTTCTTCTCTCAAGAATAGC<br>GAAGAAAAGAACCTGATCAAGGCCCCTCTGGACTTTTTGTTGAATTTCTACAGGT<br>TCGCCCAGAGCTTCAGCAGCAACAACATCGATAAAGATATGTCCTTCTACGCTGA<br>TTTTGACGAGTCTCTGTCAAGCCTGGAAAATGTGATAGGCCTGTACAACAAAGTG<br>CGGAACTACGCCACCAAGAAACCTTACACACTGGAAAAGATCAAGCTAAACTTCG<br>AGAACCCTAACCTGGCCTCTGGATGGAGTGAGAGCAAGGAAAACGATTGCCTGA<br>GTATCATCCTGCTGAAGGAGAAGAAATACTTCCTGGGCATCTTCAACAAGAACAA<br>CAAGCCCAACTTTTCAGAGGGCATCAGCCACAGCCTGTCAAGCAACGGCTGTTA<br>CCGGAAGATGAGATACCTGCTGTTCAAGGGATTCAACAAGATGCTGCCTAAGTG<br>CGCCTTCACAGGAGAGGTGAAGGACCACTTCAAGGAAAGCTCCGATGACTTCAG<br>CCTGTTCAACAAGGACACCTTCATCAGCCCCCTGGTGATCACCAAGGAAATTTTC<br>GATCTGGCTTGCAGCAAGGAAAAAGTGAAGAAGTACCAAAAAGAATACGAGAAAA<br>TCAACAGAGCCGAGTACCGGCAGTCTCTGGTGAAGTGGATCACCTTTGGCCTGA<br>AGTTTCTGTCTAGCTACAAAACCACCACCCAGTTCGACCTGAGCAATTTGAAGCG<br>CCCCGAGGAATACTGCGACCTGAAAGAATTTTACGAGGACGTGGATAACTTAACC<br>TACAAGATTGAGTTCCTGAACATTAAAGAGGAGGACGTGGACGCTCTGGTCGAG<br>AAAGGCCAGCTGTACCTGTTTGAGATTAGAAACAAGGACTTCGCCAAGAATGCCA<br>GCGGCACGCCCAACCTGCATACACTGTATTTCAAGAGCATCTTCGATAGCAAGAA<br>CCTGGAAAATGGCATCGTGAAACTGAACGGCGAGGCCGAAATTTTCTACAGAAA<br>GAAGAGCCTGAAGAAGGATGATATCACCGTGCACAGAGAGGGAAGCTACCTCGT<br>CAACAAAGTCTGCGTGGACCCTAATTCCGGCAAGACAGAGCAGATCCCAGATAA<br>GATCTACGAGAACATCTACGCCTTCGTCAACGGCAAGTCACGGGACCTGAGCAA<br>GGAGGACGAGGTGTACTACGCCAAAGCCACCATCAAGAAGGCTACCCACGAGAT<br>CGTGAAGGATCGAAGATTCACCGTCGACAAGTTCTTCTTCCACTGCCCCATCACT<br>ATCAACTACAAGAGCAAAGACAAGCCAAGCAAGTTTAACGACAAAGTGCTGGACT<br>TCCTGAGAAATAACAAGGACATCAATATCATCGGCATCGACAGAGGCGAAAGAAA<br>CTTGATCTACGTGACCGTGATCAACCAGAACGGAGAGATCATCGACTGTAAGAG<br>CTTCAATACCATTAAGCACCAGAGCAGCACAGTGAACTACGACGTGGACTACCAC<br>AACAAGCTGCAGGAGCGGGAAAAGAACAGAAAGGAAGAAAAGAGATCTTGGAAC<br>AGCATCACCAAGATCGCCGATCTGAAAGAGGGCTACCTGTCTGCCGTGATTCAC<br>GAGGTTAGCCTGATGATGGTGAAGTACAACGCCATAGTTGTGATGGAAAACCTGA<br>ACCAGGGCTTCAAGAGAATCCGGGGCGGCATCGCCGAACGGAGCGTGTACCAA<br>AAGTTTGAAAAGATGCTCATCGACAAGCTGAACTACTTCGTGATCAAGAACGAGA<br>ACTGGACCAATCCTGGCGGAGTGCTGAATGGATACCAGCTGACAAACAAGGTGT<br>CCACAATCAAGGATATTGGAAATCAGTGCGGCTTCCTGTTCTACGTGCCCGCCAC<br>TTATACATCTAAAATCGATCCTAGCACTGGATTTGTGAACCTGATCAACTTCAACA<br>AGTACAAGAACAGCGAGGACAGAAGGAAGCTGATCTGTAGCTTCGACAAGATCT<br>GCTTTGTGCAGAATGAGAACCTGTTCAAGTTCTCTATCGATTACGGCAAACTGTG<br>CCCTGACAGCAAGATCGCCATCAAAAAGTGGGACGTATTCTCCTATGGCACCAG<br>GATCATCAAGGAAAACCTGACAACAGGCCACATCGAAGAAAATCCAGAGTACGA<br>CCCTACAGAGGAACTGAAATCCCTGCTTTCCAGCAGAGGCATCGAGTACCAGAA<br>GGGCCAAAACCTGCTAGAAACCATCCCTACCAGCGACATGACCAGAGAGTTCTG<br>GAATAGCCTGTTCAAGATCTTCAAGGCCATCCTGCAGATGAGAAACTCTCTGACA<br>AACTCTCCTATCGACCGGCTGCTAAGCCCTGTGAAGGGGAAAGATGGAACCTTC<br>TTCGACACCGACAAGGTGGAAGGCACAAAATTTGAGAAACTGAAGGACGCTGAC<br>GCTAACGGCGCCTACAACATCGCCCTGAAGGGCCTGCTGGTGCTGGAAAAAAAC<br>GACTCTGTCGAGAGCAACAAGGACCTCAAGAACGTGAAGAAAATCTCACTGGAG<br>GACTGGCTGAAATTCGTGCAGATCACACTTAGAGAC | |
| Expression construct (with N-terminal methionine and stop codon, includes V5-tag and C-terminal NLS) | ATGggcAGCAAATTGTCGACCTTCAATGAGCACTTTCAGAAAACCCTGACCCTGCG<br>GAATGAGCTGGTGCCCGTGGGCAAGACACTGGAGAACATCATCAGCTCTAACGT<br>GCTGATCAACGACGAGAAGCGGTCCGAGGACTACAAAAAGGCCAAGGAAATCAT<br>TGACAGCTATCACCGGGAGTTCATCGAGAAAAGCCTGAGCTCTGTGAATGTGGA<br>CTGGAATGATCTGTACAGCTACCTGAGCAAGAAAGAACCCGAGGACTATGCCCA<br>GAAACAGAAGTTCCTGGAGGAGTTAGAGAACATCCTGCTGGAAAAGAGAAAGAT<br>CATCGTGAAGCAGTTCGAGCAGTACGTGTTCGGTTCCTATACCGACAGCAAGGG<br>AAAAAAGACCAAGGACCTGAAATTCGAAAACCTGTTTAAGTCCGAACTCTTTGACT<br>ACCTGCTGCCTAACTTCTTGAAAAACGACGAGGATAAGAAGGTGATTGGCTCCTT<br>CAATAAGTTCACCAGCTATTTCACCGGCTTTTACGAGAACAGAAAAAACCTGTACA<br>AGAGCGAGCCTCTGCCTACCGCCGTCGCCTACAGAATCGTGAACGAGAACTTCC<br>CCAAGTTTATCTCTAACAAGAACATCTTTAGAGTGTGGAAGGACAACGTCCCTCA | 36 |

TABLE 1F-continued

| ZZGY Type V Cas Sequences | | |
|---|---|---|
| Name | Sequence | SEQ ID NO. |
| | ATTCATCGAGATCGCAAAGACCAAACTGAGAGAAGAAGGCATCTCTGATCTGAAC<br>ATCGAGCTGAAGTTTGATTTGACAAATTTCAACTCCTGCCTGAATCAGACCGGCA<br>TCGATACCTACAACGACCTGATCGGCCAGCTGAACTTTGCTATCAACCTCGAATG<br>TCAGAAGGACAAGAACCTTTGTGACCTGCTGCGCAAGAAGCGGAGCCTTAAGAT<br>GGTGCCACTGTACAAGCAAATCCTGTCCGACAACGATAGCAGCTTCAGCATCGA<br>CGAGTTCGACAATGATGAAAGCGCCATCAAGGACGTTATCAGCTTCTACAAGAAG<br>ATGATCGGCGAGAACTGCCCTCAGCGGACCCTGTCTGAGCTGCTGCACGGCCT<br>GTCTAGCCACGATCTGGAGAAAATTTTCGTGCAAGGGAAGAACCTGAACAGCGT<br>GTCCAAGAACCTGTTCGGCGGCAAGAACTGGTCCCTGCTGCGGGACGCCGTGA<br>TCGAGGAAAAAAGCAAAGAGAAGGTGTTCAAGAAGGTGATCAAGAGCAACAGCA<br>CCGCTGATGAGCTGGATAAGGTGCTGTCTAAGGAGGAGTTCAGCATCTCTTTCCT<br>ATCCAAGGTGTCCGGCAAGGATCTGAGCGTGGAAATCGACAAGTTCGTCAAAAA<br>ACAGGACGAGCTTCTGGTGGAGAACAATATCCAGAACTGGCCTTCTTCTCTCAAG<br>AATAGCGAAGAAAAGAACCTGATCAAGGCCCCTCTGGACTTTTTGTTGAATTTCTA<br>CAGGTTCGCCCAGAGCTTCAGCAGCAACAACATCGATAAAGATATGTCCTTCTAC<br>GCTGATTTTGACGAGTCTCTGTCAAGCCTGGAAAATGTGATAGGCCTGTACAACA<br>AAGTGCGGAACTACGCCACCAAGAAACCTTACACACTGGAAAAGATCAAGCTAAA<br>CTTCGAGAACCCTAACCTGGCCTCTGGATGGAGTGAGAGCAAGGAAAACGATTG<br>CCTGAGTATCATCCTGCTGAAGGAGAAGAAATACTTCCTGGGCATCTTCAACAAG<br>AACAACAAGCCCAACTTTTCAGAGGGCATCAGCCACAGCCTGTCAAGCAACGGC<br>TGTTACCGGAAGATGAGATACCTGCTGTTCAAGGGATTCAACAAGATGCTGCCTA<br>AGTGCGCCTTCACAGGAGAGGTGAAGGACCACTTCAAGGAAAGCTCCGATGACT<br>TCAGCCTGTTCAACAAGGACACCTTCATCAGCCCCCTGGTGATCACCAAGGAAAT<br>TTTCGATCTGGCTTGCAGCAAGGAAAAAGTGAAGAAGTACCAAAAAGAATACGAG<br>AAAATCAACAGAGCCGAGTACCGGCAGTCTCTGGTGAAGTGGATCACCTTTGGC<br>CTGAAGTTTCTGTCTAGCTACAAAACCACCACCCAGTTCGACCTGAGCAATTTGA<br>AGCGCCCCGAGGAATACTGCGACCTGAAAGAATTTTACGAGGACGTGGATAACT<br>TAACCTACAAGATTGAGTTCCTGAACATTAAAGAGGAGGACGTGGACGCTCTGGT<br>CGAGAAAGGCCAGCTGTACCTGTTTGAGATTAGAAACAAGGACTTCGCCAAGAAT<br>GCCAGCGGCACGCCCAACCTGCATACACTGTATTTCAAGAGCATCTTCGATAGCA<br>AGAACCTGGAAAATGGCATCGTGAAACTGAACGGCGAGGCCGAAATTTTCTACA<br>GAAAGAAGAGCCTGAAGAAGGATGATATCACCGTGCACAGAGAGGGAAGCTACC<br>TCGTCAACAAAGTCTGCGTGGACCCTAATTCCGGCAAGACAGAGCAGATCCCAG<br>ATAAGATCTACGAGAACATCTACGCCTTCGTCAACGGCAAGTCACGGGACCTGA<br>GCAAGGAGGACGAGGTGTACTACGCCAAAGCCACCATCAAGAAGGCTACCCACG<br>AGATCGTGAAGGATCGAAGATTCACCGTCGACAAGTTCTTCTTCCACTGCCCCAT<br>CACTATCAACTACAAGAGCAAAGACAAGCCAAGCAAGTTTAACGACAAAGTGCTG<br>GACTTCCTGAGAAATAACAAGGACATCAATATCATCGGCATCGACAGAGGCGAAA<br>GAAACTTGATCTACGTGACCGTGATCAACCAGAACGGAGAGATCATCGACTGTAA<br>GAGCTTCAATACCATTAAGCACCAGAGCAGCACAGTGAACTACGACGTGGACTA<br>CCACAACAAGCTGCAGGAGCGGGAAAAGAACAGAAAGGAAGAAAAGAGATCTTG<br>GAACAGCATCACCAAGATCGCCGATCTGAAAGAGGGCTACCTGTCTGCCGTGAT<br>TCACGAGGTTAGCCTGATGATGGTGAAGTACAACGCCATAGTTGTGATGGAAAAC<br>CTGAACCAGGGCTTCAAGAGAATCCGGGGCGGCATCGCCGAACGGAGCGTGTA<br>CCAAAAGTTTGAAAAGATGCTCATCGACAAGCTGAACTACTTCGTGATCAAGAAC<br>GAGAACTGGACCAATCCTGGCGGAGTGCTGAATGGATACCAGCTGACAAACAAG<br>GTGTCCACAATCAAGGATATTGGAAATCAGTGCGGCTTCCTGTTCTACGTGCCCG<br>CCACTTATACATCTAAAATCGATCCTAGCACTGGATTTGTGAACCTGATCAACTTC<br>AACAAGTACAAGAACAGCGAGGACAGAAGGAAGCTGATCTGTAGCTTCGACAAG<br>ATCTGCTTTGTGCAGAATGAGAACCTGTTCAAGTTCTCTATCGATTACGGCAAACT<br>GTGCCCTGACAGCAAGATCGCCATCAAAAAGTGGGACGTATTCTCCTATGGCAC<br>CAGGATCATCAAGGAAAACCTGACAACAGGCCACATCGAAGAAAATCCAGAGTA<br>CGACCCTACAGAGGAACTGAAATCCCTGCTTTCCAGCAGAGGCATCGAGTACCA<br>GAAGGGCCAAAACCTGCTAGAAACCATCCCTACCAGCGACATGACCAGAGAGTT<br>CTGGAATAGCCTGTTCAAGATCTTCAAGGCCATCCTGCAGATGAGAAACTCTCTG<br>ACAAACTCTCCTATCGACCGGCTGCTAAGCCCTGTGAAGGGGAAAGATGGAACC<br>TTCTTCGACACCGACAAGGTGGAAGGCACAAAATTTGAGAAACTGAAGGACGCT<br>GACGCTAACGGCGCCTACAACATCGCCCTGAAGGGCCTGCTGGTGCTGGAAAAA<br>AACGACTCTGTCGAGAGCAACAAGGACCTCAAGAACGTGAAGAAAATCTCACTG<br>GAGGACTGGCTGAAATTCGTGCAGATCACACTTAGAGACtctagaAAGCGGACAGC<br>AGACGGCTCCGAATTTGAAAGCCCTAAGAAAAAGAGAAAGGTGggatccGGCAAAC<br>CTATCCCCAATCCCCTGCTGGGCCTGGACAGCACCTGA | |

In some embodiments a ZZGY Type V Cas protein comprises an amino acid sequence of SEQ ID NO:31, SEQ ID NO:32, or SEQ ID NO:33. In some embodiments, a ZZGY Type V Cas protein has nickase activity, for example resulting from one or more amino acid substitutions relative to the sequence of SEQ ID NO:31, SEQ ID NO:32, or SEQ ID NO:33. In some embodiments, the one or more amino acid substitutions providing nickase activity comprise a D905 substitution, wherein the position of the D905 substitution is defined with respect to the amino acid numbering of SEQ ID NO:32 (corresponding to amino acid 908 of SEQ ID NO:121). In some embodiments, the one or more amino acid substitutions providing nickase activity comprise an E998 substitution, wherein the position of the E998 substitution is defined with respect to the amino acid numbering of SEQ ID NO:32 (corresponding to amino acid 993 of SEQ ID NO:121). In some embodiments, the one or more amino acid substitutions providing nickase activity comprise a R1214 substitution, wherein the position of the R1214 substitution is defined with respect to the amino acid numbering of SEQ ID NO:32 (corresponding to amino acid 1226 of SEQ ID NO:121). In some embodiments, the one or more amino acid substitutions providing nickase activity comprise a D1254 substitution, wherein the position of the D1254 substitution is defined with respect to the amino acid numbering of SEQ ID NO:32 (corresponding to amino acid 1263 of SEQ ID NO:121). In some embodiments, a ZZGY Type V Cas protein is catalytically inactive, for example due to a R1214 substitution in combination with a D905 substitution, a E998 substitution, and/or D1254 substitution.

6.2.7. ZKBG Type V Cas Proteins

In one aspect, the disclosure provides ZKBG Type V Cas proteins. ZKBG Type V Cas proteins can be further classified as Type V-A Cas proteins. The ZKBG Type V Cas proteins typically comprise an amino acid sequence that is at least 50%, at least 55%, at least 60%, at least 65%, at least 70%, at least 75%, at least 85%, at least 90%, or at least 95% identical to SEQ ID NO:37. In some embodiments, the ZKBG Type V Cas proteins comprise an amino acid sequence that is at least 95%, at least 96%, at least 97%, at least 98%, or at least 99% identical to SEQ ID NO:37. In some embodiments, a ZKBG Type V Cas protein comprises an amino acid sequence that is identical to SEQ ID NO:37.

Exemplary ZKBG Type V Cas protein sequences and nucleotide sequences encoding exemplary ZKBG Type V Cas proteins are set forth in Table 1G.

TABLE 1G

ZKBG Type V Cas Sequences

| Name | Sequence | SEQ ID NO. |
|---|---|---|
| Wildtype amino acid sequence (without N-terminal methionine) | KRLIDFTNIYQRSKTLRFRLEPIGKTADYIKNSQSLETDARLAKESKKVKELADEYHKE<br>FIGDVLSSLELPLSKINELWDIYIYIYMSNDTDREIKFKKLQENLRKVIAEAFSKDKRFG<br>NLFKKEIITDILPEFLQDKDDDIKIVNRFKGFTTYFYAFHKNRENMYVSEEKSTAIPYRIV<br>NQNLVKYFDNYKTFKEKVMPLLKDKNIVESIERDFKDILNEKSIEDVFGLANFTHTLCQ<br>ADIEKYNTLIGGLVVKNEKKEIKGINQYINEHNQTSKKGNGIPKLKPLFNQILSDRKSLS<br>FTLDDIKKTSEAIRTIKDEYENLRDKLATIERLIKSIKEYDLAGIYIKMGEDTSTISQHWF<br>GAYYKIIEAIADAWERRNPKKNRESKAYSKYVSSLKSISLQEIDDLKIGEPIENYFATFG<br>TTCSDRTSGVSSLNRIKAAYTEFVNKFPEGFEDGDDCNDAYFKANVEVVKNLLDSIK<br>DFQRFVKPLLGNEDERDKDEAFYGEFVPTYTDMDNIITPLYNRVRNFATKKPYSTDKI<br>KINFENVVLLKGWDKNKESDYASIILMKDGQYFLGVLRNGSKSTLKTILPNTGDCYQK<br>MVYKYFKDIKSNLPRCTTQRKDVKAHFAESSDDYTLLDTKAFVSALTISREVFELYNA<br>PDKEKKFKKEYLKNTNDSIGYANAVSVCKRFCLEFLKKYRSTAIYDLSDVETSVDSFD<br>DLSSFYQEIDKRLYSISFENVSVDSVNELVDNGNMLLFRIANKDFSPNSKGRPNLHTIY<br>WRMLFDPANLKDVVYQLNGNAEIFFRKASVTRTEPTHPANVAIKNKSEYNKQNKPYS<br>TFKYGLIKDRRYTTDQFEFHVPITMNFKQPESSKLQDKLNKQVLDFLKQDGVRHIIGID<br>RGERNLLYLVMVDMEGKIKKQISLNEIAGNPKNPEFKQDFLALLHEREGDRLESRRS<br>WNTIQSIKELKEGYMSLVVHEIANMMLENDAIVVLENLNRSFMQKRGGIEKSVYQKFE<br>KMLIDKLGYIVDKTKDVSDNGGALHAVQLADTFENFNKTQKGAIRQCGFIFYIPAWRT<br>SKIDPVTGFVPMLRCQYESIVESKKFFGKFDSIYYDATGKYFVFQTDFTKFNTESKGGI<br>QKWDICTYGDRIYAPRTKDRNNNPVSERVNLTEEMKSLFVSHNINIQGDIKAGIMQQT<br>DKEFFESLHRLLRLTLQIRNSKKSTGKDYEDYIISPVMGKDGRFFDSRNADATQPKDA<br>DANGAYNIARKGLMLLRQIQAQEKQDLSNGKWLEFAQR | 37 |
| Wildtype amino acid sequence (with N-terminal methionine) | MKRLIDFTNIYQRSKTLRFRLEPIGKTADYIKNSQSLETDARLAKESKKVKELADEYHK<br>EFIGDVLSSLELPLSKINELWDIYIYIYMSNDTDREIKFKKLQENLRKVIAEAFSKDKRFG<br>NLFKKEIITDILPEFLQDKDDDIKIVNRFKGFTTYFYAFHKNRENMYVSEEKSTAIPYRIV<br>NQNLVKYFDNYKTFKEKVMPLLKDKNIVESIERDFKDILNEKSIEDVFGLANFTHTLCQ<br>ADIEKYNTLIGGLVVKNEKKEIKGINQYINEHNQTSKKGNGIPKLKPLFNQILSDRKSLS<br>FTLDDIKKTSEAIRTIKDEYENLRDKLATIERLIKSIKEYDLAGIYIKMGEDTSTISQHWF<br>GAYYKIIEAIADAWERRNPKKNRESKAYSKYVSSLKSISLQEIDDLKIGEPIENYFATFG<br>TTCSDRTSGVSSLNRIKAAYTEFVNKFPEGFEDGDDCNDAYFKANVEVVKNLLDSIK<br>DFQRFVKPLLGNEDERDKDEAFYGEFVPTYTDMDNIITPLYNRVRNFATKKPYSTDKI<br>KINFENVVLLKGWDKNKESDYASIILMKDGQYFLGVLRNGSKSTLKTILPNTGDCYQK<br>MVYKYFKDIKSNLPRCTTQRKDVKAHFAESSDDYTLLDTKAFVSALTISREVFELYNA<br>PDKEKKFKKEYLKNTNDSIGYANAVSVCKRFCLEFLKKYRSTAIYDLSDVETSVDSFD<br>DLSSFYQEIDKRLYSISFENVSVDSVNELVDNGNMLLFRIANKDFSPNSKGRPNLHTIY<br>WRMLFDPANLKDVVYQLNGNAEIFFRKASVTRTEPTHPANVAIKNKSEYNKQNKPYS<br>TFKYGLIKDRRYTTDQFEFHVPITMNFKQPESSKLQDKLNKQVLDFLKQDGVRHIIGID<br>RGERNLLYLVMVDMEGKIKKQISLNEIAGNPKNPEFKQDFLALLHEREGDRLESRRS<br>WNTIQSIKELKEGYMSLVVHEIANMMLENDAIVVLENLNRSFMQKRGGIEKSVYQKFE<br>KMLIDKLGYIVDKTKDVSDNGGALHAVQLADTFENFNKTQKGAIRQCGFIFYIPAWRT<br>SKIDPVTGFVPMLRCQYESIVESKKFFGKFDSIYYDATGKYFVFQTDFTKFNTESKGGI<br>QKWDICTYGDRIYAPRTKDRNNNPVSERVNLTEEMKSLFVSHNINIQGDIKAGIMQQT<br>DKEFFESLHRLLRLTLQIRNSKKSTGKDYEDYIISPVMGKDGRFFDSRNADATQPKDA<br>DANGAYNIARKGLMLLRQIQAQEKQDLSNGKWLEFAQR | 38 |
| Expression construct (with N-terminal methionine, V5-tag and C-terminal NLS) aa sequence | MGKRLIDFTNIYQRSKTLRFRLEPIGKTADYIKNSQSLETDARLAKESKKVKELADEYH<br>KEFIGDVLSSLELPLSKINELWDIYIYIYMSNDTDREIKFKKLQENLRKVIAEAFSKDKRF<br>GNLFKKEIITDILPEFLQDKDDDIKIVNRFKGFTTYFYAFHKNRENMYVSEEKSTAIPYRI<br>VNQNLVKYFDNYKTFKEKVMPLLKDKNIVESIERDFKDILNEKSIEDVFGLANFTHTLC<br>QADIEKYNTLIGGLVVKNEKKEIKGINQYINEHNQTSKKGNGIPKLKPLFNQILSDRKSL<br>SFTLDDIKKTSEAIRTIKDEYENLRDKLATIERLIKSIKEYDLAGIYIKMGEDTSTISQHWF<br>GAYYKIIEAIADAWERRNPKKNRESKAYSKYVSSLKSISLQEIDDLKIGEPIENYFATFG<br>TTCSDRTSGVSSLNRIKAAYTEFVNKFPEGFEDGDDCNDAYFKANVEVVKNLLDSIK | 39 |

TABLE 1G-continued

ZKBG Type V Cas Sequences

| Name | Sequence | SEQ ID NO. |
|---|---|---|
| | DFQRFVKPLLGNEDERDKDEAFYGEFVPTYTDMDNIITPLYNRVRNFATKKPYSTDKI<br>KINFENVVLLKGWDKNKESDYASIILMKDGQYFLGVLRNGSKSTLKTILPNTGDCYQK<br>MVYKYFKDIKSNLPRCTTQRKDVKAHFAESSDDYTLLDTKAFVSALTISREVFELYNA<br>PDKEKKFKKEYLKNTNDSIGYANAVSVCKRFCLEFLKKYRSTAIYDLSDVETSVDSFD<br>DLSSFYQEIDKRLYSISFENVSVDSVNELVDNGNMLLFRIANKDFSPNSKGRPNLHTIY<br>WRMLFDPANLKDVVYQLNGNAEIFFRKASVTRTEPTHPANVAIKNKSEYNKQNKPYS<br>TFKYGLIKDRRYTTDQFEFHVPITMNFKQPESSKLQDKLNKQVLDFLKQDGVRHIIGID<br>RGERNLLYLVMVDMEGKIKKQISLNEIAGNPKNPEFKQDFLALLHEREGDRLESRRS<br>WNTIQSIKELKEGYMSLVVHEIANMMLENDAIVVLENLNRSFMQKRGGIEKSVYQKFE<br>KMLIDKLGYIVDKTKDVSDNGGALHAVQLADTFENFNKTQKGAIRQCGFIFYIPAWRT<br>SKIDPVTGFVPMLRCQYESIVESKKFFGKFDSIYYDATGKYFVFQTDFTKFNTESKGGI<br>QKWDICTYGDRIYAPRTKDRNNNPVSERVNLTEEMKSLFVSHNINIQGDIKAGIMQQT<br>DKEFFESLHRLLRLTLQIRNSKKSTGKDYEDYIISPVMGKDGRFFDSRNADATQPKDA<br>DANGAYNIARKGLMLLRQIQAQEKQDLSNGKWLEFAQRSRKRTADGSEFESPKKKR<br>KVGSGKPIPNPLLGLDST | |
| Wildtype coding sequence (with N-terminal methionine and stop codon) | ATGAAACGCCTAATTGACTTTACAAACATCTATCAGCGATCAAAGACTTTGAGGTT<br>TCGATTGGAGCCTATCGGTAAAACGGCCGACTATATTAAGAATTCTCAGTCCCTC<br>GAAACTGATGCGCGTTTGGCAAAAGAGAGCAAGAAGGTAAAAGAGCTTGCTGAT<br>GAATATCACAAAGAGTTTATTGGAGATGTCCTGTCTTCGTTGGAATTGCCTTTAAG<br>CAAAATCAACGAGTTATGGGATATATATATATATATATATATGTCCAATGATACAGA<br>CCGCGAGATAAAATTCAAAAAACTGCAAGAGAACCTGCGAAAGGTGATTGCAGA<br>GGCTTTTAGTAAGGACAAACGGTTTGGTAATTTATTCAAAAAGGAGATAATCACAG<br>ACATTCTGCCGGAATTCTTGCAAGATAAGGATGATGATATTAAGATCGTAAATAGA<br>TTCAAAGGATTTACCACATATTTTTACGCCTTTCATAAGAATAGGGAAAATATGTAT<br>GTCTCGGAAGAGAAATCGACTGCAATACCATATCGAATTGTGAATCAAAATCTCG<br>TCAAGTATTTTGACAACTACAAGACGTTCAAAGAGAAGGTAATGCCTCTTCTGAAA<br>GACAAGAATATAGTCGAAAGCATAGAGAGAGACTTCAAAGACATCTTGAACGAAA<br>AATCAATAGAGGATGTTTTTGGCCTTGCCAACTTCACTCATACTTTATGTCAGGCT<br>GACATCGAGAAATACAATACGTTGATAGGTGGCCTTGTCGTCAAAAACGAAAAAA<br>AAGAGATTAAAGGTATTAATCAGTACATTAACGAACATAACCAAACGAGTAAAAAA<br>GGGAATGGAATTCCGAAACTAAAGCCGTTGTTCAATCAGATTTTGAGCGATAGAA<br>AATCGTTATCGTTTACCTTAGACGATATCAAAAAAACGTCGGAGGCTATTCGCAC<br>CATTAAGGATGAGTATGAAAATCTCCGAGACAAGTTGGCGACCATCGAAAGGCTT<br>ATTAAGTCTATCAAGGAGTATGATCTTGCAGGTATTTACATCAAGATGGGAGAGG<br>ATACTTCGACAATATCGCAGCATTGGTTTGGTGCGTATTATAAAATCATCGAAGCG<br>ATAGCAGATGCATGGGAACGACGAAATCCGAAGAAAAACAGAGAATCCAAGGCA<br>TATAGCAAGTATGTATCGTCCCTAAAAAGCATCAGTCTCCAAGAAATAGATGATCT<br>CAAAATCGGAGAGCCTATAGAGAACTACTTCGCAACTTTTGGCACGACTTGTTCA<br>GACCGAACAAGTGGAGTTTCTTCGCTCAATAGGATAAAAGCTGCTTATACCGAGT<br>TCGTGAACAAATTTCCTGAAGGATTTGAAGATGGCGATGACTGTAACGATGCCTA<br>CTTTAAGGCTAATGTGGAAGTCGTCAAAAATCTGCTGGATTCAATTAAAGATTTTC<br>AGCGTTTTGTGAAGCCTTTGCTTGGCAATGAGGACGAAAGAGACAAAGACGAGG<br>CATTCTATGGAGAGTTTGTCCCGACATACACAGATATGGATAACATCATAACCCCT<br>CTATACAACCGTGTACGCAATTTTGCCACCAAGAAACCATACTCTACAGACAAGA<br>TAAAAATCAACTTTGAAAACGTAGTATTGCTAAAAGGATGGGACAAAAACAAGGA<br>GTCAGACTACGCATCCATCATATTGATGAAAGACGGACAATACTTTTTAGGGGTA<br>CTCCGTAATGGTTCAAAAAGTACTCTTAAAACCATATTGCCTAACACAGGTGATTG<br>CTATCAAAAAATGGTTTATAAGTATTTTAAGGATATAAAATCAAATCTTCCCCGGTG<br>TACGACCCAGAGGAAAGACGTGAAAGCGCACTTTGCCGAATCGAGCGACGATTA<br>CACTCTTTTAGATACAAAGGCCTTTGTTTCGGCACTGACTATCAGCAGAGAAGTG<br>TTCGAACTATACAATGCCCCCGATAAGGAGAAAAAATTCAAAAAGGAATATTTGAA<br>GAACACAAACGATAGTATAGGCTACGCCAATGCTGTATCCGTATGTAAACGCTTC<br>TGTTTGGAGTTCCTAAAAAAATATCGCAGCACTGCCATATATGATCTTTCGGATGT<br>TGAAACTTCAGTCGATTCGTTTGACGATTTGTCCTCATTCTATCAAGAGATAGACA<br>AAAGGCTGTACAGCATCTCATTCGAAAATGTATCTGTCGATTCCGTCAATGAGCTT<br>GTAGACAATGGCAATATGCTTCTATTCCGTATCGCGAATAAAGATTTTTCGCCTAA<br>CAGCAAGGGCCGTCCCAATCTTCATACTATATATTGGCGAATGCTTTTCGACCCG<br>GCCAACCTGAAGGATGTTGTATATCAGCTCAATGGTAATGCCGAAATATTCTTCC<br>GTAAGGCAAGCGTTACGAGGACGGAGCCTACACATCCGGCTAACGTTGCCATCA<br>AAAACAAGAGCGAATATAACAAACAGAATAAGCCGTATAGTACATTCAAGTACGG<br>TTTAATCAAGGATAGGCGCTACACTACCGACCAGTTCGAGTTTCATGTACCCATC<br>ACAATGAACTTCAAGCAACCAGAGTCGTCTAAACTACAGGACAAGCTCAACAAGC<br>AAGTGCTTGACTTCTTGAAACAGGACGGCGTACGCCATATTATAGGCATTGATCG<br>GGGCGAACGTAATCTGCTATACTTGGTGATGGTAGATATGGAGGGCAAAATCAAA<br>AAACAAATATCACTCAACGAGATAGCCGGTAATCCGAAGAATCCCGAGTTCAAAC<br>AAGACTTCCTTGCACTACTGCACGAGCGCGAAGGTGACCGTTTGGAGTCACGTC<br>GCAGTTGGAACACCATTCAGAGCATTAAAGAACTCAAAGAAGGTTACATGAGCTT<br>GGTGGTTCATGAAATAGCGAATATGATGCTTGAGAATGATGCTATAGTAGTGCTC<br>GAAAATCTGAATCGCTCGTTTATGCAAAAGCGCGGCGGCATAGAAAAGTCTGTAT<br>ACCAAAAGTTCGAAAAGATGCTTATCGACAAGTTGGGATACATCGTGGATAAGAC<br>TAAAGATGTGTCCGACAACGGAGGCGCACTACATGCTGTACAGCTTGCTGATAC<br>GTTTGAAAACTTCAATAAGACCCAAAAAGGAGCTATTCGTCAATGTGGATTCATAT<br>TCTATATTCCTGCATGGCGTACCAGCAAGATTGACCCCGTTACCGGCTTTGTGCC | 40 |

TABLE 1G-continued

| ZKBG Type V Cas Sequences | | |
|---|---|---|
| Name | Sequence | SEQ ID NO. |
| | AATGCTTAGGTGTCAATATGAAAGCATCGTAGAATCCAAAAAATTCTTCGGAAAGT<br>TCGACAGTATATACTACGATGCGACAGGAAAGTATTTTGTCTTCCAAACTGACTTT<br>ACCAAATTCAATACCGAGAGCAAAGGAGGAATCCAAAAATGGGATATATGCACCT<br>ATGGAGACAGAATATATGCTCCTCGCACCAAAGACCGGAATAATAACCCTGTTTC<br>GGAACGTGTAAACCTTACTGAGGAGATGAAATCACTGTTTGTATCGCATAATATCA<br>ATATTCAAGGCGATATCAAAGCCGGAATTATGCAGCAGACAGACAAGGAGTTCTT<br>CGAGTCACTGCATCGATTGCTTCGACTTACGTTGCAAATACGCAATAGCAAAAAA<br>TCTACAGGCAAAGACTATGAAGACTATATCATATCGCCGGTGATGGGCAAGGAC<br>GGTCGTTTCTTTGATTCGCGTAACGCGGATGCTACGCAACCTAAGGATGCAGATG<br>CCAATGGCGCGTACAATATTGCACGCAAAGGCTTGATGCTGCTTCGCCAGATTCA<br>AGCCCAAGAGAAGCAAGACCTATCCAACGGAAAATGGCTTGAATTTGCCCAAAG<br>GTGA | |
| Codon optimized coding sequence (no N-terminal methionine, no stop codon) | AAGCGGCTCATCGACTTCACCAACATCTACCAGCGTTCTAAGACCCTGAGATTCA<br>GACTGGAACCTATCGGCAAGACCGCGGACTACATCAAAAACAGCCAGTCCCTGG<br>AAACAGACGCCAGACTGGCCAAGGAATCCAAGAAAGTGAAGGAACTGGCCGATG<br>AGTACCACAAAGAGTTTATCGGCGACGTGCTGAGCAGCCTGGAGCTGCCCCTGA<br>GCAAAATCAACGAGCTGTGGGACATCTATATCTACATCTACATGAGCAACGACAC<br>CGATCGGGAAATCAAATTTAAGAAGCTCCAGGAGAACCTGCGGAAGGTGATCGC<br>CGAGGCCTTTAGCAAGGATAAGAGATTCGGCAACCTGTTCAAGAAAGAAATCATC<br>ACAGATATCCTGCCCGAGTTCCTGCAAGATAAAGATGACGATATCAAAATCGTGA<br>ACCGGTTCAAGGGTTTTACAACCTACTTCTACGCCTTCCACAAGAATCGGGAAAA<br>CATGTACGTGTCTGAAGAGAAGAGCACAGCCATCCCCTACAGAATCGTGAATCAA<br>AACCTGGTGAAATACTTCGATAACTACAAGACTTTTAAGGAGAAGGTGATGCCTC<br>TGCTGAAGGACAAGAACATCGTCGAAAGCATCGAGCGCGACTTCAAGGACATCC<br>TGAACGAGAAAAGCATCGAGGACGTGTTCGGCCTGGCCAATTTCACCCACACCC<br>TGTGCCAGGCTGACATCGAGAAGTACAACACCTTGATAGGCGGACTGGTGGTGA<br>AGAACGAAAAGAAGGAGATCAAGGGCATCAACCAGTATATTAACGAGCACAACCA<br>GACCTCTAAGAAGGGCAACGGCATCCCAAAGCTGAAGCCTCTGTTTAACCAGAT<br>CCTGAGCGACAGAAAATCTCTCAGCTTCACCCTGGATGATATCAAGAAAACCAGC<br>GAGGCCATCAGAACAATTAAGGACGAGTATGAGAACCTGAGAGATAAGCTGGCC<br>ACAATCGAACGGCTGATCAAGAGCATCAAGGAATACGACCTGGCCGGCATCTAC<br>ATCAAGATGGGCGAGGACACCTCTACCATCTCCCAGCACTGGTTCGGTGCCTAT<br>TACAAGATTATCGAAGCCATCGCCGACGCCTGGGAGAGAAGAAACCCAAAGAAA<br>AACAGAGAGAGCAAGGCCTACAGCAAGTACGTGAGCAGCCTTAAGAGCATCAGC<br>CTGCAGGAGATCGACGACCTGAAGATCGGCGAGCCTATCGAGAATTACTTCGCC<br>ACCTTTGGAACAACATGTAGCGACCGGACATCTGGCGTGAGCTCTCTGAACCGG<br>ATCAAAGCCGCCTACACCGAGTTCGTGAACAAGTTCCCCGAGGGCTTTGAGGAT<br>GGCGATGATTGCAACGACGCTTACTTCAAAGCCAATGTGGAGGTGGTGAAGAAC<br>TTGCTGGATAGCATAAAAGACTTCCAGAGATTTGTGAAGCCTCTACTGGGCAATG<br>AGGACGAGCGGGACAAAGATGAGGCCTTCTACGGCGAGTTCGTTCCTACCTACA<br>CAGATATGGACAACATCATCACGCCTCTGTATAATAGAGTCAGAAACTTCGCTAC<br>CAAGAAGCCTTACAGTACAGACAAGATCAAAATAAACTTCGAAAACGTGGTACTG<br>CTGAAGGGCTGGGATAAGAACAAGGAGAGCGACTATGCCAGCATCATCCTGATG<br>AAGGACGGCCAGTACTTTCTGGGAGTGCTGAGAAACGGATCTAAGAGCACTCTG<br>AAAACCATCCTGCCTAACACCGGTGACTGCTACCAGAAAATGGTGTACAAGTATT<br>TCAAGGATATCAAGTCTAACCTGCCCAGATGCACCACCCAGAGAAAGGACGTGA<br>AGGCACATTTCGCTGAAAGCAGCGATGATTACACCCTGCTTGATACAAAAGCCTT<br>CGTGAGCGCTCTGACGATCTCCAGAGAGGTGTTCGAACTGTACAACGCTCCTGA<br>TAAGGAAAAGAAATTCAAGAAGGAATACCTGAAGAACACCAACGACTCCATCGGC<br>TACGCCAATGCAGTGAGCGTGTGCAAGAGATTCTGCCTGGAGTTCCTGAAAAAG<br>TACCGGAGCACCGCCATCTACGACCTGAGCGATGTTGAAACCTCTGTGGACAGT<br>TTCGACGACCTGAGCAGCTTCTACCAGGAGATCGATAAGAGACTGTACAGCATCA<br>GCTTCGAAAACGTGAGCGTGGACAGCGTGAACGAGCTGGTGGATAACGGCAATA<br>TGCTGCTGTTCAGAATCGCCAACAAGGATTTCTCTCCTAATAGCAAGGGCAGACC<br>TAATCTGCACACAATTTACTGGAGAATGCTGTTCGACCCTGCTAATCTCAAGGAC<br>GTCGTGTACCAACTGAACGGCAATGCCGAAATCTTCTTCCGGAAGGCCAGCGTT<br>ACAAGGACAGAACCAACACACCCCGCCAATGTGGCCATCAAGAACAAGAGCGAG<br>TACAACAAGCAGAACAAACCTTACAGCACCTTCAAGTACGGCCTCATCAAGGACC<br>GGCGATACACCACCGATCAGTTCGAGTTCCACGTGCCTATCACCATGAACTTCAA<br>GCAACCTGAGTCATCTAAGCTGCAGGACAAACTGAATAAGCAAGTGCTGGACTTC<br>CTGAAGCAAGACGGCGTGCGGCACATCATCGGCATCGACCGGGGAGAAAGAAA<br>CCTGCTGTACCTGGTGATGGTCGACATGGAAGGAAAAATCAAGAAGCAGATCAG<br>CCTGAATGAAATCGCCGGAAACCCAAAGAACCCTGAGTTTAAGCAGGACTTCTTA<br>GCTCTGCTGCATGAGAGAGAGGGCGATAGACTGGAGTCCAGAAGAAGTTGGAAC<br>ACCATCCAGAGCATCAAGGAGCTGAAAGAAGGCTACATGTCCCTGGTGGTGCAC<br>GAGATCGCTAACATGATGCTGGAGAATGATGCCATCGTGGTCTTGGAAAACCTTA<br>ACAGATCCTTTATGCAGAAGAGAGGCGGCATTGAGAAAAGCGTGTACCAGAAGT<br>TTGAGAAAATGCTGATCGACAAGCTGGGCTACATCGTGGACAAAACAAAAGATGT<br>GTCAGATAATGGCGGAGCCCTGCACGCCGTGCAGCTGGCTGACACCTTCGAGAA<br>CTTTAACAAGACCCAGAAAGGCGCCATCCGGCAGTGCGGCTTCATCTTTTATATC<br>CCCGCCTGGCGGACAAGCAAAATTGACCCGGTAACCGGCTTTGTGCCCATGCTG<br>AGATGTCAGTACGAATCTATCGTGGAATCCAAGAAGTTCTTTGGCAAATTCGACT<br>CTATCTACTACGACGCCACCGGAAAGTACTTCGTGTTCCAGACCGACTTTACCAA | 41 |

TABLE 1G-continued

ZKBG Type V Cas Sequences

| Name | Sequence | SEQ ID NO. |
| --- | --- | --- |
| | GTTCAACACCGAGTCTAAGGGGGGCATCCAGAAGTGGGACATCTGTACCTACGG<br>AGACAGAATCTACGCCCCTAGAACCAAAGACAGAAATAACAACCCTGTGTCCGAA<br>AGAGTGAACCTGACAGAAGAAATGAAGAGCCTGTTCGTAAGCCACAATATCAACA<br>TCCAGGGCGACATCAAGGCCGGCATTATGCAGCAGACAGACAAGGAGTTCTTCG<br>AGTCGCTGCACAGACTGCTGAGACTGACCCTGCAGATCCGGAACAGCAAGAAAA<br>GCACCGGCAAGGACTACGAGGACTACATTATCAGTCCTGTGATGGGCAAGGACG<br>GAAGATTCTTCGACAGCCGGAACGCCGACGCCACCCAGCCCAAGGACGCCGAC<br>GCAAACGGCGCCTACAACATTGCCAGAAAAGGCCTGATGCTGCTGCGCCAGATC<br>CAGGCCCAGGAGAAGCAGGACCTGTCTAATGGGAAGTGGCTGGAGTTCGCCCA<br>GCGG | |
| Expression construct (with N-terminal methionine and stop codon, includes V5-tag and C-terminal NLS) | ATGggcAAGCGGCTCATCGACTTCACCAACATCTACCAGCGTTCTAAGACCCTGA<br>GATTCAGACTGGAACCTATCGGCAAGACCGCGGACTACATCAAAAACAGCCAGT<br>CCCTGGAAACAGACGCCAGACTGGCCAAGGAATCCAAGAAAGTGAAGGAACTGG<br>CCGATGAGTACCACAAAGAGTTTATCGGCGACGTGCTGAGCAGCCTGGAGCTGC<br>CCCTGAGCAAAATCAACGAGCTGTGGGACATCTATATCTACATCTACATGAGCAA<br>CGACACCGATCGGGAAATCAAATTTAAGAAGCTCCAGGAGAACCTGCGGAAGGT<br>GATCGCCGAGGCCTTTAGCAAGGATAAGAGATTCGGCAACCTGTTCAAGAAAGA<br>AATCATCACAGATATCCTGCCCGAGTTCCTGCAAGATAAAGATGACGATATCAAA<br>ATCGTGAACCGGTTCAAGGGTTTTACAACCTACTTCTACGCCTTCCACAAGAATC<br>GGGAAAACATGTACGTGTCTGAAGAGAAGAGCACAGCCATCCCCTACAGAATCG<br>TGAATCAAAACCTGGTGAAATACTTCGATAACTACAAGACTTTTAAGGAGAAGGT<br>GATGCCTCTGCTGAAGGACAAGAACATCGTCGAAAGCATCGAGCGCGACTTCAA<br>GGACATCCTGAACGAGAAAAGCATCGAGGACGTGTTCGGCCTGGCCAATTTCAC<br>CCACACCCTGTGCCAGGCTGACATCGAGAAGTACAACACCTTGATAGGCGGACT<br>GGTGGTGAAGAACGAAAAGAAGGAGATCAAGGGCATCAACCAGTATATTAACGA<br>GCACAACCAGACCTCTAAGAAGGGCAACGGCATCCCAAAGCTGAAGCCTCTGTT<br>TAACCAGATCCTGAGCGACAGAAAATCTCTCAGCTTCACCCTGGATGATATCAAG<br>AAAACCAGCGAGGCCATCAGAACAATTAAGGACGAGTATGAGAACCTGAGAGAT<br>AAGCTGGCCACAATCGAACGGCTGATCAAGAGCATCAAGGAATACGACCTGGCC<br>GGCATCTACATCAAGATGGGCGAGGACACCTCTACCATCTCCCAGCACTGGTTC<br>GGTGCCTATTACAAGATTATCGAAGCCATCGCCGACGCCTGGGAGAGAAGAAAC<br>CCAAAGAAAAACAGAGAGAGCAAGGCCTACAGCAAGTACGTGAGCAGCCTTAAG<br>AGCATCAGCCTGCAGGAGATCGACGACCTGAAGATCGGCGAGCCTATCGAGAAT<br>TACTTCGCCACCTTTGGAACAACATGTAGCGACCGGACATCTGGCGTGAGCTCT<br>CTGAACCGGATCAAAGCCGCCTACACCGAGTTCGTGAACAAGTTCCCCGAGGGC<br>TTTGAGGATGGCGATGATTGCAACGACGCTTACTTCAAAGCCAATGTGGAGGTG<br>GTGAAGAACTTGCTGGATAGCATAAAAGACTTCCAGAGATTTGTGAAGCCTCTAC<br>TGGGCAATGAGGACGAGCGGGACAAAGATGAGGCCTTCTACGGCGAGTTCGTTC<br>CTACCTACACAGATATGGACAACATCATCACGCCTCTGTATAATAGAGTCAGAAA<br>CTTCGCTACCAAGAAGCCTTACAGTACAGACAAGATCAAAATAAACTTCGAAAAC<br>GTGGTACTGCTGAAGGGCTGGGATAAGAACAAGGAGAGCGACTATGCCAGCATC<br>ATCCTGATGAAGGACGGCCAGTACTTTCTGGGAGTGCTGAGAAACGGATCTAAG<br>AGCACTCTGAAAACCATCCTGCCTAACACCGGTGACTGCTACCAGAAAATGGTGT<br>ACAAGTATTTCAAGGATATCAAGTCTAACCTGCCCAGATGCACCACCCAGAGAAA<br>GGACGTGAAGGCACATTTCGCTGAAAGCAGCGATGATTACACCCTGCTTGATACA<br>AAAGCCTTCGTGAGCGCTCTGACGATCTCCAGAGAGGTGTTCGAACTGTACAAC<br>GCTCCTGATAAGGAAAAGAAATTCAAGAAGGAATACCTGAAGAACACCAACGACT<br>CCATCGGCTACGCCAATGCAGTGAGCGTGTGCAAGAGATTCTGCCTGGAGTTCC<br>TGAAAAAGTACCGGAGCACCGCCATCTACGACCTGAGCGATGTTGAAACCTCTG<br>TGGACAGTTTCGACGACCTGAGCAGCTTCTACCAGGAGATCGATAAGAGACTGT<br>ACAGCATCAGCTTCGAAAACGTGAGCGTGGACAGCGTGAACGAGCTGGTGGATA<br>ACGGCAATATGCTGCTGTTCAGAATCGCCAACAAGGATTTCTCTCCTAATAGCAA<br>GGGCAGACCTAATCTGCACACAATTTACTGGAGAATGCTGTTCGACCCTGCTAAT<br>CTCAAGGACGTCGTGTACCAACTGAACGGCAATGCCGAAATCTTCTTCCGGAAG<br>GCCAGCGTTACAAGGACAGAACCAACACACCCCGCCAATGTGGCCATCAAGAAC<br>AAGAGCGAGTACAACAAGCAGAACAAACCTTACAGCACCTTCAAGTACGGCCTCA<br>TCAAGGACCGGCGATACACCACCGATCAGTTCGAGTTCCACGTGCCTATCACCA<br>TGAACTTCAAGCAACCTGAGTCATCTAAGCTGCAGGACAAACTGAATAAGCAAGT<br>GCTGGACTTCCTGAAGCAAGACGGCGTGCGGCACATCATCGGCATCGACCGGG<br>GAGAAAGAAACCTGCTGTACCTGGTGATGGTCGACATGGAAGGAAAAATCAAGA<br>AGCAGATCAGCCTGAATGAAATCGCCGGAAACCCAAAGAACCCTGAGTTTAAGC<br>AGGACTTCTTAGCTCTGCTGCATGAGAGAGAGGGCGATAGACTGGAGTCCAGAA<br>GAAGTTGGAACACCATCCAGAGCATCAAGGAGCTGAAAGAAGGCTACATGTCCC<br>TGGTGGTGCACGAGATCGCTAACATGATGCTGGAGAATGATGCCATCGTGGTCT<br>TGGAAAACCTTAACAGATCCTTTATGCAGAAGAGAGGCGGCATTGAGAAAAGCGT<br>GTACCAGAAGTTTGAGAAAATGCTGATCGACAAGCTGGGCTACATCGTGGACAAA<br>ACAAAAGATGTGTCAGATAATGGCGGAGCCCTGCACGCCGTGCAGCTGGCTGAC<br>ACCTTCGAGAACTTTAACAAGACCCAGAAAGGCGCCATCCGGCAGTGCGGCTTC<br>ATCTTTTATATCCCCGCCTGGCGGACAAGCAAAATTGACCCGGTAACCGGCTTTG<br>TGCCCATGCTGAGATGTCAGTACGAATCTATCGTGGAATCCAAGAAGTTCTTTGG<br>CAAATTCGACTCTATCTACTACGACGCCACCGGAAAGTACTTCGTGTTCCAGACC<br>GACTTTACCAAGTTCAACACCGAGTCTAAGGGGGGCATCCAGAAGTGGGACATC<br>TGTACCTACGGAGACAGAATCTACGCCCCTAGAACCAAAGACAGAAATAACAACC | 42 |

TABLE 1G-continued

| ZKBG Type V Cas Sequences | | |
|---|---|---|
| Name | Sequence | SEQ ID NO. |
| | CTGTGTCCGAAAGAGTGAACCTGACAGAAGAAATGAAGAGCCTGTTCGTAAGCC<br>ACAATATCAACATCCAGGGCGACATCAAGGCCGGCATTATGCAGCAGACAGACA<br>AGGAGTTCTTCGAGTCGCTGCACAGACTGCTGAGACTGACCCTGCAGATCCGGA<br>ACAGCAAGAAAAGCACCGGCAAGGACTACGAGGACTACATTATCAGTCCTGTGA<br>TGGGCAAGGACGGAAGATTCTTCGACAGCCGGAACGCCGACGCCACCCAGCCC<br>AAGGACGCCGACGCAAACGGCGCCTACAACATTGCCAGAAAAGGCCTGATGCTG<br>CTGCGCCAGATCCAGGCCCAGGAGAAGCAGGACCTGTCTAATGGGAAGTGGCT<br>GGAGTTCGCCCAGCGGtctagaAAGCGGACAGCAGACGGCTCCGAATTTGAAAGC<br>CCTAAGAAAAAGAGAAAGGTGggatccGGCAAACCTATCCCCAATCCCCTGCTGGG<br>CCTGGACAGCACCTGA | |

In some embodiments a ZKBG Type V Cas protein comprises an amino acid sequence of SEQ ID NO:37, SEQ ID NO:38, or SEQ ID NO:39. In some embodiments, a ZKBG Type V Cas protein has nickase activity, for example resulting from one or more amino acid substitutions relative to the sequence of SEQ ID NO:37, SEQ ID NO:38, or SEQ ID NO:39. In some embodiments, the one or more amino acid substitutions providing nickase activity comprise a D885 substitution, wherein the position of the D885 substitution is defined with respect to the amino acid numbering of SEQ ID NO:38 (corresponding to amino acid 908 of SEQ ID NO:121). In some embodiments, the one or more amino acid substitutions providing nickase activity comprise an E978 substitution, wherein the position of the E978 substitution is defined with respect to the amino acid numbering of SEQ ID NO:38 (corresponding to amino acid 993 of SEQ ID NO:121). In some embodiments, the one or more amino acid substitutions providing nickase activity comprise a R1194 substitution, wherein the position of the R1194 substitution is defined with respect to the amino acid numbering of SEQ ID NO:38 (corresponding to amino acid 1226 of SEQ ID NO:121). In some embodiments, the one or more amino acid substitutions providing nickase activity comprise a D1234 substitution, wherein the position of the D1234 substitution is defined with respect to the amino acid numbering of SEQ ID NO:38 (corresponding to amino acid 1263 of SEQ ID NO:121). In some embodiments, a ZKBG Type V Cas protein is catalytically inactive, for example due to a R1194 substitution in combination with a D885 substitution, a E978 substitution, and/or D1234 substitution.

6.2.8. ZZKD Type V Cas Proteins

In one aspect, the disclosure provides ZZKD Type V Cas proteins. ZZKD Type V Cas proteins can be further classified as Type V-A Cas proteins. The ZZKD Type V Cas proteins typically comprise an amino acid sequence that is at least 50%, at least 55%, at least 60%, at least 65%, at least 70%, at least 75%, at least 85%, at least 90%, or at least 95% identical to SEQ ID NO:43. In some embodiments, the ZZKD Type V Cas proteins comprise an amino acid sequence that is at least 95%, at least 96%, at least 97%, at least 98%, or at least 99% identical to SEQ ID NO:43. In some embodiments, a ZZKD Type V Cas protein comprises an amino acid sequence that is identical to SEQ ID NO:43.

Exemplary ZZKD Type V Cas protein sequences and nucleotide sequences encoding exemplary ZZKD Type V Cas proteins are set forth in Table 1H.

TABLE 1H

| ZZKD Type V Cas Sequences | | |
|---|---|---|
| Name | Sequence | SEQ ID NO. |
| Wildtype amino acid sequence (without N-terminal methionine) | AEMFKDFTNLYPVSKTLRFELIPEGETLHYLEKNGVLENDEKRNEDYKKLKKLMDEY<br>YRAYIDEALSNVHLSDLDRYAELYSIQNKSDEENVEFENVQLRLRTQIVGFLESRETY<br>SSLFKKELIEKELPKFFIRREEELNLIKSFKGFTTMCTGFWENRKNMFSAEEKSTAIA<br>YRVVHENLPKFMNNIRIFRLFIDEKLDCSEKLLEKAGVNSLSEVFELDYFNNTLSQRG<br>IELYNCILGGFTEDEKHKIQGVNELINLYNQQTKEKKIPQLQPLYKQILSDTKSLSFLA<br>DAFENDGGVLATVKALYDEFHEEILSERGLISTTLQNIEKYDSKGIFVKNDLTITGLSN<br>SLFGDWKAINGSLNSWYEENVPRKERTEEKHVEVRKAYFKKLKSISLEFIEEAGLSE<br>LRCKYKALLLEKAEAVCDAYKNAEELFSEAYNENTNLIADGKSVEKIKALLDSMKELE<br>AVILMLSGTGEEAERDELFYGEFEKHRFVLNLLDNVFNKTRNYVTKKPYKTEKIKLTF<br>DSPTLLDGWDRNKETSNKSVILMKDGYYYLGIMNKANNKAFENLKDTGGKCYSKM<br>DYKLLPGPNKMLPKVFFAKKNIDYYAPSEDLLQKYKEGTHKKGKKFNLEDCHALIDF<br>FKDSIAKHPEWNEFGFDFSDTKSYRDISDFYKEVSEQGYKISYRNVSVNYIDSLVRE<br>GKLYLFKIYNKDFSPYSKGRPNLHTMYWKALFANKNFENRIYKLNGQAEMFYRKKSI<br>PEDKRVIHSAKEPIDQRRNTDEKSLFDYDIIKDRRYTVDKFQFNVPITMNYTAPGSGR<br>INRKMREAIKNCENMHIIGIDRGERHLLYVTVIDMQGNIKEQFSLNRILSEYKANNVAK<br>SVETDYKTLLTKKEIERQDARKQWKSIENIKELKDGYMSQVVHVIAELMIKYNAIVVM<br>EDLNFGFKRGRQKVERQVYQKFEKALIDKLNYLVDKTASEMENTGLYAALQLTEKF<br>ESFKKMGKQNGGLFYVNAWNTSKMDPTTGFVNLLYPKYESIEKSKAYIEKFKDIQFC<br>DDDEYGKYLAISFDYNDFTEKAKGAKTEWTICSYGKRLYNHRNKDGYWEEQELDLT<br>EEYFNLFEEFGINAASNIKEQVIAQNSADFFRRFMWLLKMTLQIRNSETNGETDYML<br>SPVKNEDGKFFNSDEVKDDTLPENADANGAYNIARKGLLLVERIKDCPDEELDKVDL<br>KVTNLDWMKFAQR | 43 |

TABLE 1H-continued

ZZKD Type V Cas Sequences

| Name | Sequence | SEQ ID NO. |
|---|---|---|
| Wildtype amino acid sequence (with N-terminal methionine) | MAEMFKDFTNLYPVSKTLRFELIPEGETLHYLEKNGVLENDEKRNEDYKKLKKLMDE<br>YYRAYIDEALSNVHLSDLDRYAELYSIQNKSDEENVEFENVQLRLRTQIVGFLESRET<br>YSSLFKKELIEKELPKFFIRREEELNLIKSFKGFTTMCTGFWENRKNMFSAEEKSTAI<br>AYRVVHENLPKFMNNIRIFRLFIDEKLDCSEKLLEKAGVNSLSEVFELDYFNNTLSQR<br>GIELYNCILGGFTEDEKHKIQGVNELINLYNQQTKEKKIPQLQPLYKQILSDTKSLSFL<br>ADAFENDGGVLATVKALYDEFHEEILSERGLISTTLQNIEKYDSKGIFVKNDLTITGLS<br>NSLFGDWKAINGSLNSWYEENVPRKERTEEKHVEVRKAYFKKLKSISLEFIEEAGLS<br>ELRCKYKALLLEKAEAVCDAYKNAEELFSEAYNENTNLIADGKSVEKIKALLDSMKEL<br>EAVILMLSGTGEEAERDELFYGEFEKHRFVLNLLDNVFNKTRNYVTKKPYKTEKIKLT<br>FDSPTLLDGWDRNKETSNKSVILMKDGYYYLGIMNKANNKAFENLKDTGGKCYSKM<br>DYKLLPGPNKMLPKVFFAKKNIDYYAPSEDLLQKYKEGTHKKGKKFNLEDCHALIDF<br>FKDSIAKHPEWNEFGFDFSDTKSYRDISDFYKEVSEQGYKISYRNVSVNYIDSLVRE<br>GKLYLFKIYNKDFSPYSKGRPNLHTMYWKALFANKNFENRIYKLNGQAEMFYRKKSI<br>PEDKRVIHSAKEPIDQRRNTDEKSLFDYDIIKDRRYTVDKFQFNVPITMNYTAPGSGR<br>INRKMREAIKNCENMHIIGIDRGERHLLYVTVIDMQGNIKEQFSLNRILSEYKANNVAK<br>SVETDYKTLLTKKEIERQDARKQWKSIENIKELKDGYMSQVVHVIAELMIKYNAIVVM<br>EDLNFGFKRGRQKVERQVYQKFEKALIDKLNYLVDKTASEMENTGLYAALQLTEKF<br>ESFKKMGKQNGGLFYVNAWNTSKMDPTTGFVNLLYPKYESIEKSKAYIEKFKDIQFC<br>DDDEYGKYLAISFDYNDFTEKAKGAKTEWTICSYGKRLYNHRNKDGYWEEQELDLT<br>EEYFNLFEEFGINAASNIKEQVIAQNSADFFRRFMWLLKMTLQIRNSETNGETDYML<br>SPVKNEDGKFFNSDEVKDDTLPENADANGAYNIARKGLLLVERIKDCPDEELDKVDL<br>KVTNLDWMKFAQR | 44 |
| Expression construct (with N-terminal methionine, V5-tag and C-terminal NLS) aa sequence | MGAEMFKDFTNLYPVSKTLRFELIPEGETLHYLEKNGVLENDEKRNEDYKKLKKLM<br>DEYYRAYIDEALSNVHLSDLDRYAELYSIQNKSDEENVEFENVQLRLRTQIVGFLES<br>RETYSSLFKKELIEKELPKFFIRREEELNLIKSFKGFTTMCTGFWENRKNMFSAEEKS<br>TAIAYRVVHENLPKFMNNIRIFRLFIDEKLDCSEKLLEKAGVNSLSEVFELDYFNNTLS<br>QRGIELYNCILGGFTEDEKHKIQGVNELINLYNQQTKEKKIPQLQPLYKQILSDTKSLS<br>FLADAFENDGGVLATVKALYDEFHEEILSERGLISTTLQNIEKYDSKGIFVKNDLTITG<br>LSNSLFGDWKAINGSLNSWYEENVPRKERTEEKHVEVRKAYFKKLKSISLEFIEEAG<br>LSELRCKYKALLLEKAEAVCDAYKNAEELFSEAYNENTNLIADGKSVEKIKALLDSMK<br>ELEAVILMLSGTGEEAERDELFYGEFEKHRFVLNLLDNVFNKTRNYVTKKPYKTEKIK<br>LTFDSPTLLDGWDRNKETSNKSVILMKDGYYYLGIMNKANNKAFENLKDTGGKCYS<br>KMDYKLLPGPNKMLPKVFFAKKNIDYYAPSEDLLQKYKEGTHKKGKKFNLEDCHALI<br>DFFKDSIAKHPEWNEFGFDFSDTKSYRDISDFYKEVSEQGYKISYRNVSVNYIDSLV<br>REGKLYLFKIYNKDFSPYSKGRPNLHTMYWKALFANKNFENRIYKLNGQAEMFYRK<br>KSIPEDKRVIHSAKEPIDQRRNTDEKSLFDYDIIKDRRYTVDKFQFNVPITMNYTAPG<br>SGRINRKMREAIKNCENMHIIGIDRGERHLLYVTVIDMQGNIKEQFSLNRILSEYKAN<br>NVAKSVETDYKTLLTKKEIERQDARKQWKSIENIKELKDGYMSQVVHVIAELMIKYNA<br>IVVMEDLNFGFKRGRQKVERQVYQKFEKALIDKLNYLVDKTASEMENTGLYAALQLT<br>EKFESFKKMGKQNGGLFYVNAWNTSKMDPTTGFVNLLYPKYESIEKSKAYIEKFKDI<br>QFCDDDEYGKYLAISFDYNDFTEKAKGAKTEWTICSYGKRLYNHRNKDGYWEEQE<br>LDLTEEYFNLFEEFGINAASNIKEQVIAQNSADFFRRFMWLLKMTLQIRNSETNGETD<br>YMLSPVKNEDGKFFNSDEVKDDTLPENADANGAYNIARKGLLLVERIKDCPDEELDK<br>VDLKVTNLDWMKFAQRSRKRTADGSEFESPKKKRKVGSGKPIPNPLLGLDST | 45 |
| Wildtype coding sequence (with N-terminal methionine and stop codon) | ATGGCTGAGATGTTTAAAGATTTTACGAATTTGTATCCTGTTTCAAAAACCTTGC<br>GTTTTGAATTAATTCCTGAAGGGGAAACATTGCATTATCTTGAAAAAAATGGCGT<br>TCTGGAAAACGATGAGAAGCGAAACGAAGATTATAAGAAGTTGAAAAAACTGAT<br>GGATGAATATTACCGTGCATACATCGATGAAGCTTTATCTAATGTTCATCTTTCA<br>GATTTGGATAGATATGCAGAATTATATTCAATTCAGAATAAATCGGATGAAGAAA<br>ATGTAGAATTCGAAAATGTTCAACTGAGATTGAGAACACAAATTGTTGGATTCTT<br>AGAATCCAGAGAAACCTATTCTTCACTTTTCAAAAAAGAACTGATTGAGAAGGAA<br>CTTCCTAAATTCTTTATTCGGAGAGAAGAGGAGCTTAATTTAATCAAATCATTTAA<br>AGGTTTTACAACGATGTGCACCGGCTTCTGGGAAAATCGGAAAAATATGTTTTCT<br>GCCGAAGAAAAATCTACAGCAATAGCATATCGTGTAGTCCATGAAAACCTACCTA<br>AGTTTATGAATAATATAAGAATTTTTCGTTTGTTCATTGATGAAAAGTTGGACTGT<br>TCTGAAAAATTGCTGGAAAAAGCCGGAGTGAATTCTCTGAGTGAAGTGTTTGAA<br>CTTGATTATTTTAACAATACATTATCCCAACGTGGCATTGAATTGTATAACTGTAT<br>ATTGGGCGGATTTACCGAGGATGAAAAGCATAAGATTCAAGGCGTAAACGAATT<br>GATTAATTTGTACAATCAGCAGACAAAAGAGAAGAAGATTCCACAGTTGCAGCC<br>GCTGTACAAGCAGATTCTCAGCGATACCAAGAGCCTTTCATTTCTTGCAGATGC<br>ATTTGAAAACGACGGGGGGGTCTTAGCGACTGTAAAAGCATTATATGATGAATTT<br>CATGAAGAGATTTTGAGCGAAAGGGGATTAATCTCTACGACATTACAGAATATTG<br>AAAAGTATGATTCAAAAGGCATCTTCGTAAAAAACGATTTAACGATTACCGGTTT<br>ATCAAATAGTTTGTTCGGCGACTGGAAGGCTATTAATGGTAGTTTAAATTCGTGG<br>TATGAGGAGAACGTGCCTCGAAAAGAAAGAACTGAAGAGAAACATGTAGAGGTA<br>AGAAAAGCCTATTTTAAAAAGTTAAAATCAATAAGCCTGGAATTTATCGAGGAGG<br>CCGGATTGTCGGAACTCCGTTGCAAATATAAAGCCCTTCTTTTAGAAAAAGCAGA<br>GGCTGTTTGCGATGCGTACAAAAATGCAGAAGAGCTTTTTAGTGAAGCTTATAAT<br>GAAAATACTAACCTTATTGCCGATGGAAAGTCTGTGGAAAAAATAAAAGCGCTAT<br>TGGATTCTATGAAAGAGCTTGAAGCGGTGATTCTTATGCTTTCCGGAACCGGAG<br>AGGAAGCAGAACGGGATGAATTGTTTTACGGCGAATTTGAAAAACATAGGTTCG<br>TATTGAATCTCTTAGACAACGTATTTAATAAAACGAGAAATTACGTAACAAAGAAA | 46 |

TABLE 1H-continued

| ZZKD Type V Cas Sequences | | |
|---|---|---|
| Name | Sequence | SEQ ID NO. |
| | CCATATAAGACTGAGAAGATTAAATTAACATTTGATTCCCCAACGCTGCTAGACG<br>GGTGGGATCGTAATAAAGAAACATCAAACAAGTCCGTGATACTTATGAAAGATG<br>GCTATTATTACCTTGGAATTATGAACAAGGCAAATAACAAAGCCTTTGAGAATTT<br>GAAAGACACAGGCGGGAAATGCTATAGCAAGATGGATTACAAACTTTTGCCTGG<br>ACCAAACAAGATGTTGCCGAAGGTGTTTTTTGCAAAGAAAAACATCGACTATTAT<br>GCACCAAGCGAAGACTTGCTACAGAAATATAAAGAGGGAACACATAAAAAAGGA<br>AAGAAATTTAATCTAGAGGATTGTCACGCGTTAATAGACTTTTTTAAAGACTCAAT<br>TGCAAAGCATCCAGAATGGAACGAGTTTGGATTTGATTTTTCAGATACGAAATCA<br>TATCGAGATATTAGTGATTTCTATAAGGAGGTTTCAGAGCAGGGATACAAAATCA<br>GTTATCGAAATGTATCTGTTAATTACATAGATTCTCTAGTAAGAGAAGGGAAATT<br>GTATTTGTTCAAAATTTATAATAAAGATTTTTCACCGTACAGCAAAGGCAGACCAA<br>ATCTTCATACGATGTATTGGAAAGCGTTATTCGCTAATAAGAATTTTGAAAATCG<br>CATATATAAGTTAAATGGCCAGGCAGAAATGTTCTATCGAAAAAAGAGCATTCCG<br>GAAGACAAGAGGGTGATTCACTCGGCAAAAGAACCAATCGATCAGAGAAGAAAT<br>ACGGATGAAAAGAGCCTCTTTGATTATGACATTATTAAAGATCGGCGATATACTG<br>TGGACAAATTCCAATTTAATGTTCCGATTACGATGAATTACACTGCACCGGGTTC<br>CGGCCGAATTAACAGAAAAATGCGGGAAGCGATTAAGAACTGTGAAAATATGCA<br>TATTATCGGAATAGATAGAGGCGAACGTCATTTGCTGTATGTGACGGTTATCGAT<br>ATGCAGGGAAACATTAAAGAACAGTTTTCATTAAATCGAATCCTGAGTGAGTACA<br>AGGCAAACAATGTGGCTAAAAGTGTCGAAACGGACTACAAAACACTCCTGACAA<br>AAAAAGAAATTGAACGACAGGATGCAAGAAAGCAGTGGAAGAGCATTGAAAATA<br>TTAAGGAATTAAAAGACGGCTACATGAGCCAGGTTGTGCATGTGATTGCCGAAC<br>TCATGATAAAGTACAATGCGATTGTGGTTATGGAGGATTTGAATTTCGGATTCAA<br>GCGAGGAAGACAGAAGGTTGAGAGACAGGTTTACCAGAAGTTTGAGAAGGCAT<br>TAATTGATAAATTGAACTATTTGGTTGATAAAACAGCCTCTGAAATGGAGAACAC<br>CGGTCTGTATGCGGCATTGCAGCTTACAGAAAAATTTGAGAGCTTTAAGAAAAT<br>GGGCAAACAAAATGGTGGATTATTTTATGTAAACGCATGGAATACCAGTAAAATG<br>GATCCAACAACCGGTTTTGTGAACCTTCTCTATCCTAAATATGAGAGCATTGAAA<br>AAAGCAAAGCGTATATTGAGAAATTCAAGGATATTCAGTTTTGTGATGATGACGA<br>ATATGGAAAGTACCTTGCAATATCTTTTGATTATAACGATTTCACGGAGAAGGCA<br>AAGGGCGCAAAAACGGAATGGACCATTTGCTCTTATGGAAAGAGATTGTATAAT<br>CACAGAAATAAAGATGGGTATTGGGAAGAGCAGGAATTGGATCTTACAGAAGAG<br>TATTTCAATCTGTTTGAAGAATTTGGAATTAATGCAGCGTCTAATATTAAAGAACA<br>AGTCATCGCACAGAATTCTGCAGACTTTTTTAGACGGTTTATGTGGCTTTTGAAA<br>ATGACCTTACAGATTAGAAACAGTGAAACAAATGGGGAGACGGATTATATGCTTT<br>CTCCGGTAAAAAATGAAGACGGAAAATTCTTTAATTCAGATGAAGTCAAGGATGA<br>CACGCTTCCGGAAAATGCGGATGCGAATGGTGCATACAACATCGCTAGAAAAG<br>GATTACTGCTTGTGGAAAGAATTAAAGACTGTCCGGACGAAGAACTTGATAAGG<br>TTGATTTGAAGGTAACAAATTTAGATTGGATGAAATTTGCACAGAGGTAA | |
| Codon optimized coding sequence (no N-terminal methionine, no stop codon) | GCCGAAATGTTCAAGGACTTCACCAACCTGTACCCAGTGTCCAAAACCCTCCGG<br>TTCGAATTGATCCCCGAGGGCGAAACACTGCACTACCTAGAAAAGAACGGAGTG<br>CTGGAAAACGACGAGAAGAGAAATGAGGATTACAAGAAGCTGAAGAAACTCATG<br>GATGAATACTACCGGGCCTACATCGACGAGGCCTTATCTAATGTCCACCTGTCC<br>GATCTGGACCGGTACGCCGAACTGTATTCTATCCAGAACAAGAGCGATGAGGA<br>GAACGTGGAGTTCGAGAATGTGCAGCTGCGCCTGAGAACCCAGATCGTGGGCT<br>TCCTGGAAAGCAGAGAAACCTACAGCAGCCTGTTCAAGAAGGAGCTGATCGAAA<br>AAGAACTGCCTAAGTTTTTCATCAGAAGAGAGGAAGAGCTGAACCTGATAAAGA<br>GCTTTAAGGGCTTTACCACTATGTGCACCGGCTTCTGGGAAAATCGGAAGAACA<br>TGTTCAGCGCCGAGGAAAAGTCCACAGCCATCGCCTATAGAGTGGTCCATGAAA<br>ACCTGCCCAAGTTCATGAACAACATTAGAATCTTCCGGCTGTTTATCGACGAGAA<br>GCTGGATTGTAGCGAGAAGCTGCTGGAGAAGGCCGGCGTGAACAGCCTGAGC<br>GAGGTGTTCGAGCTTGACTATTTCAATAACACCCTGAGCCAGAGAGGCATCGAG<br>CTGTACAACTGCATCCTGGGCGGATTCACCGAGGATGAAAAACACAAGATCCAG<br>GGAGTGAACGAGTTGATCAACCTGTACAACCAGCAGACAAAGGAGAAGAAAATT<br>CCTCAGCTGCAACCTCTGTACAAACAGATCCTGTCTGACACGAAGTCGCTGTCC<br>TTTCTGGCTGATGCCTTTGAAAACGACGGAGGAGTGCTGGCTACAGTGAAGGCT<br>TTATATGATGAGTTTCACGAGGAAATCCTGAGCGAGAGAGGCCTGATCAGCACA<br>ACCCTGCAGAACATTGAGAAGTACGATAGTAAGGGCATCTTTGTTAAGAACGAT<br>CTCACCATTACAGGCCTGTCCAACAGCCTGTTTGGAGATTGGAAGGCCATCAAT<br>GGAAGCCTGAACAGCTGGTACGAGGAGAACGTGCCCCGGAAGGAGCGAACAG<br>AAGAGAAACACGTGGAAGTGAGAAAGGCTTATTTTAAGAAGCTGAAGTCTATCA<br>GCCTGGAGTTCATCGAGGAGGCCGGACTGAGCGAGCTGCGGTGCAAGTACAA<br>GGCCCTGCTGCTGGAGAAAGCCGAGGCTGTGTGCGACGCGTACAAGAACGCC<br>GAGGAGCTGTTTAGCGAGGCCTATAATGAGAACACCAATCTGATCGCCGATGG<br>CAAATCTGTGGAAAAAATCAAAGCCCTGCTGGACAGCATGAAGGAGCTGGAGG<br>CCGTGATCCTGATGCTGAGCGGCACAGGCGAGGAGGCCGAGCGGGACGAACT<br>GTTTTATGGCGAGTTCGAAAAACATAGATTCGTGCTGAATCTGCTGGACAACGT<br>GTTCAACAAGACCAGAAACTACGTGACCAAGAAGCCTTACAAGACCGAGAAGAT<br>CAAGCTCACCTTCGACAGCCCTACCCTTCTGGATGGCTGGGACCGTAACAAGG<br>AGACAAGCAACAAGAGCGTGATCCTGATGAAGGATGGCTACTACTACCTGGGC<br>ATCATGAACAAAGCCAACAACAAGGCCTTCGAGAACCTGAAGGACACAGGAGG<br>CAAATGCTACAGCAAGATGGACTACAAGCTGCTGCCTGGCCCTAACAAGATGCT<br>GCCTAAGGTGTTCTTTGCCAAAAAGAACATCGACTACTACGCCCCTAGCGAGGA<br>CCTGCTGCAGAAGTACAAGGAGGGCACCCACAAGAAAGGAAGAAGTTCAATC | 47 |

TABLE 1H-continued

ZZKD Type V Cas Sequences

| Name | Sequence | SEQ ID NO. |
|---|---|---|
| | TTGAGGACTGTCACGCCCTGATCGACTTCTTCAAGGACAGCATCGCTAAACACC<br>CCGAGTGGAACGAGTTCGGCTTCGACTTTTCTGACACCAAGTCTTATAGAGACA<br>TCTCGGATTTCTACAAGGAGGTCAGCGAACAGGGCTACAAGATTAGCTACCGGA<br>ACGTGAGTGTTAACTACATCGACAGTCTGGTGCGGGAAGGTAAGCTGTACCTGT<br>TCAAGATCTACAACAAGGACTTCAGCCCATACTCCAAAGGACGTCCCAACCTGC<br>ACACCATGTACTGGAAAGCCCTGTTCGCCAATAAAAACTTCGAAAACCGGATCT<br>ACAAGCTGAACGGCCAGGCCGAAATGTTCTACAGAAAGAAATCTATCCCTGAAG<br>ATAAGCGGGTGATCCACAGCGCCAAAGAACCTATCGATCAGAGAAGAAACACC<br>GACGAAAAGTCTCTGTTTGACTACGACATCATCAAGGACAGACGGTACACCGTG<br>GACAAGTTCCAGTTCAACGTGCCAATCACAATGAACTACACCGCCCCTGGCAGC<br>GGCAGAATCAACAGAAAGATGCGGGAAGCTATCAAGAATTGCGAGAATATGCAC<br>ATCATCGGCATCGACCGGGGAGAGCGGCACCTGCTGTACGTGACCGTGATCGA<br>CATGCAGGGCAACATCAAAGAACAGTTCTCTCTCAACCGCATCCTGTCTGAGTA<br>CAAGGCCAATAACGTCGCCAAGAGCGTGGAGACAGACTACAAAACACTGCTGA<br>CGAAAAAAGAGATCGAGAGACAGGACGCTAGAAAGCAATGGAAGAGCATCGAA<br>AACATCAAAGAGCTGAAAGACGGCTATATGAGCCAGGTGGTGCACGTGATAGC<br>AGAGCTGATGATCAAGTACAACGCCATAGTTGTGATGGAGGACCTGAATTTCGG<br>CTTCAAGAGAGGCCGGCAAAAGGTGGAGAGACAGGTGTACCAGAAATTCGAGA<br>AGGCCCTGATCGATAAGCTGAATTACCTGGTGGATAAGACAGCTTCCGAGATGG<br>AAAACACCGGCCTGTACGCCGCCCTGCAGCTGACAGAGAAGTTCGAATCCTTC<br>AAGAAGATGGGCAAACAGAACGGCGGCTTGTTCTACGTGAACGCCTGGAACAC<br>CAGCAAGATGGACCCTACCACCGGATTCGTGAACCTGCTGTACCCTAAGTACGA<br>ATCTATCGAAAAGAGCAAGGCCTATATCGAGAAATTCAAGGATATCCAGTTTTGT<br>GACGACGATGAATACGGCAAATACCTGGCAATTTCTTTCGACTACAACGACTTC<br>ACAGAAAAGGCCAAGGGCGCCAAGACCGAGTGGACCATCTGCAGCTACGGCAA<br>AAGACTGTACAACCACAGAAATAAGGACGGCTACTGGGAGGAGCAGGAGCTGG<br>ATCTGACCGAGGAGTACTTCAACCTGTTCGAAGAGTTCGGCATCAACGCTGCCA<br>GCAACATCAAGGAACAAGTGATCGCTCAGAACAGCGCCGATTTCTTCAGAAGAT<br>TCATGTGGCTGCTGAAGATGACCCTGCAGATCAGGAACTCTGAAACTAACGGCG<br>AAACCGATTACATGCTGAGCCCTGTGAAGAACGAGGACGGCAAATTCTTCAACT<br>CTGACGAGGTGAAGGACGACACCCTGCCCGAGAATGCCGACGCCAACGGCGC<br>CTACAACATCGCAAGAAAGGGCCTGCTGCTGGTCGAACGTATCAAGGATTGCC<br>CCGACGAAGAACTAGACAAGGTGGACCTGAAGGTCACCAACCTGGACTGGATG<br>AAATTCGCCCAAAGA | |
| Expression construct (with N-terminal methionine and stop codon, includes V5-tag and C-terminal NLS) | ATGggcGCCGAAATGTTCAAGGACTTCACCAACCTGTACCCAGTGTCCAAAACCC<br>TCCGGTTCGAATTGATCCCCGAGGGCGAAACACTGCACTACCTAGAAAAGAACG<br>GAGTGCTGGAAAACGACGAGAAGAGAAATGAGGATTACAAGAAGCTGAAGAAA<br>CTCATGGATGAATACTACCGGGCCTACATCGACGAGGCCTTATCTAATGTCCAC<br>CTGTCCGATCTGGACCGGTACGCCGAACTGTATTCTATCCAGAACAAGAGCGAT<br>GAGGAGAACGTGGAGTTCGAGAATGTGCAGCTGCGCCTGAGAACCCAGATCGT<br>GGGCTTCCTGGAAAGCAGAGAAACCTACAGCAGCCTGTTCAAGAAGGAGCTGA<br>TCGAAAAAGAACTGCCTAAGTTTTTCATCAGAAGAGAGGAAGAGCTGAACCTGA<br>TAAAGAGCTTTAAGGGCTTTACCACTATGTGCACCGGCTTCTGGGAAAATCGGA<br>AGAACATGTTCAGCGCCGAGGAAAAGTCCACAGCCATCGCCTATAGAGTGGTC<br>CATGAAAACCTGCCCAAGTTCATGAACAACATTAGAATCTTCCGGCTGTTTATCG<br>ACGAGAAGCTGGATTGTAGCGAGAAGCTGCTGGAGAAGGCCGGCGTGAACAG<br>CCTGAGCGAGGTGTTCGAGCTTGACTATTTCAATAACACCCTGAGCCAGAGAGG<br>CATCGAGCTGTACAACTGCATCCTGGGCGGATTCACCGAGGATGAAAAACACAA<br>GATCCAGGGAGTGAACGAGTTGATCAACCTGTACAACCAGCAGACAAAGGAGA<br>AGAAAATTCCTCAGCTGCAACCTCTGTACAAACAGATCCTGTCTGACACGAAGT<br>CGCTGTCCTTTCTGGCTGATGCCTTTGAAAACGACGGAGGAGTGCTGGCTACA<br>GTGAAGGCTTTATATGATGAGTTTCACGAGGAAATCCTGAGCGAGAGAGGCCTG<br>ATCAGCACAACCCTGCAGAACATTGAGAAGTACGATAGTAAGGGCATCTTTGTT<br>AAGAACGATCTCACCATTACAGGCCTGTCCAACAGCCTGTTTGGAGATTGGAAG<br>GCCATCAATGGAAGCCTGAACAGCTGGTACGAGGAGAACGTGCCCCGGAAGGA<br>GCGAACAGAAGAGAAACACGTGGAAGTGAGAAAGGCTTATTTTAAGAAGCTGAA<br>GTCTATCAGCCTGGAGTTCATCGAGGAGGCCGGACTGAGCGAGCTGCGGTGCA<br>AGTACAAGGCCCTGCTGCTGGAGAAAGCCGAGGCTGTGTGCGACGCGTACAAG<br>AACGCCGAGGAGCTGTTTAGCGAGGCCTATAATGAGAACACCAATCTGATCGCC<br>GATGGCAAATCTGTGGAAAAAATCAAAGCCCTGCTGGACAGCATGAAGGAGCT<br>GGAGGCCGTGATCCTGATGCTGAGCGGCACAGGCGAGGAGGCCGAGCGGGAC<br>GAACTGTTTTATGGCGAGTTCGAAAAACATAGATTCGTGCTGAATCTGCTGGAC<br>AACGTGTTCAACAAGACCAGAAACTACGTGACCAAGAAGCCTTACAAGACCGAG<br>AAGATCAAGCTCACCTTCGACAGCCCTACCCTTCTGGATGGCTGGGACCGTAAC<br>AAGGAGACAAGCAACAAGAGCGTGATCCTGATGAAGGATGGCTACTACTACCTG<br>GGCATCATGAACAAAGCCAACAACAAGGCCTTCGAGAACCTGAAGGACACAGG<br>AGGCAAATGCTACAGCAAGATGGACTACAAGCTGCTGCCTGGCCCTAACAAGAT<br>GCTGCCTAAGGTGTTCTTTGCCAAAAAGAACATCGACTACTACGCCCCTAGCGA<br>GGACCTGCTGCAGAAGTACAAGGAGGGCACCCACAAGAAAGGGAAGAAGTTCA<br>ATCTTGAGGACTGTCACGCCCTGATCGACTTCTTCAAGGACAGCATCGCTAAAC<br>ACCCCGAGTGGAACGAGTTCGGCTTCGACTTTTCTGACACCAAGTCTTATAGAG<br>ACATCTCGGATTTCTACAAGGAGGTCAGCGAACAGGGCTACAAGATTAGCTACC<br>GGAACGTGAGTGTTAACTACATCGACAGTCTGGTGCGGGAAGGTAAGCTGTAC<br>CTGTTCAAGATCTACAACAAGGACTTCAGCCCATACTCCAAAGGACGTCCCAAC | 48 |

TABLE 1H-continued

| ZZKD Type V Cas Sequences | | |
|---|---|---|
| Name | Sequence | SEQ ID NO. |
| | CTGCACACCATGTACTGGAAAGCCCTGTTCGCCAATAAAAACTTCGAAAACCGG<br>ATCTACAAGCTGAACGGCCAGGCCGAAATGTTCTACAGAAAGAAATCTATCCCT<br>GAAGATAAGCGGGTGATCCACAGCGCCAAAGAACCTATCGATCAGAGAAGAAA<br>CACCGACGAAAAGTCTCTGTTTGACTACGACATCATCAAGGACAGACGGTACAC<br>CGTGGACAAGTTCCAGTTCAACGTGCCAATCACAATGAACTACACCGCCCCTGG<br>CAGCGGCAGAATCAACAGAAAGATGCGGGAAGCTATCAAGAATTGCGAGAATAT<br>GCACATCATCGGCATCGACCGGGGAGAGCGGCACCTGCTGTACGTGACCGTGA<br>TCGACATGCAGGGCAACATCAAAGAACAGTTCTCTCTCAACCGCATCCTGTCTG<br>AGTACAAGGCCAATAACGTCGCCAAGAGCGTGGAGACAGACTACAAAACACTG<br>CTGACGAAAAAAGAGATCGAGAGACAGGACGCTAGAAAGCAATGGAAGAGCAT<br>CGAAAACATCAAAGAGCTGAAAGACGGCTATATGAGCCAGGTGGTGCACGTGA<br>TAGCAGAGCTGATGATCAAGTACAACGCCATAGTTGTGATGGAGGACCTGAATT<br>TCGGCTTCAAGAGAGGCCGGCAAAAGGTGGAGAGACAGGTGTACCAGAAATTC<br>GAGAAGGCCCTGATCGATAAGCTGAATTACCTGGTGGATAAGACAGCTTCCGAG<br>ATGGAAAACACCGGCCTGTACGCCGCCCTGCAGCTGACAGAGAAGTTCGAATC<br>CTTCAAGAAGATGGGCAAACAGAACGGCGGCTTGTTCTACGTGAACGCCTGGA<br>ACACCAGCAAGATGGACCCTACCACCGGATTCGTGAACCTGCTGTACCCTAAGT<br>ACGAATCTATCGAAAAGAGCAAGGCCTATATCGAGAAATTCAAGGATATCCAGTT<br>TTGTGACGACGATGAATACGGCAAATACCTGGCAATTTCTTTCGACTACAACGA<br>CTTCACAGAAAAGGCCAAGGGCGCCAAGACCGAGTGGACCATCTGCAGCTACG<br>GCAAAAGACTGTACAACCACAGAAATAAGGACGGCTACTGGGAGGAGCAGGAG<br>CTGGATCTGACCGAGGAGTACTTCAACCTGTTCGAAGAGTTCGGCATCAACGCT<br>GCCAGCAACATCAAGGAACAAGTGATCGCTCAGAACAGCGCCGATTTCTTCAGA<br>AGATTCATGTGGCTGCTGAAGATGACCCTGCAGATCAGGAACTCTGAAACTAAC<br>GGCGAAACCGATTACATGCTGAGCCCTGTGAAGAACGAGGACGGCAAATTCTT<br>CAACTCTGACGAGGTGAAGGACGACACCCTGCCCGAGAATGCCGACGCCAACG<br>GCGCCTACAACATCGCAAGAAAGGGCCTGCTGCTGGTCGAACGTATCAAGGAT<br>TGCCCCGACGAAGAACTAGACAAGGTGGACCTGAAGGTCACCAACCTGGACTG<br>GATGAAATTCGCCCAAAGGtctagaAAGCGGACAGCAGACGGCTCCGAATTTGAA<br>AGCCCTAAGAAAAAGAGAAAGGTGggatccGGCAAACCTATCCCCAATCCCCTGC<br>TGGGCCTGGACAGCACCTGA | |

In some embodiments a ZZKD Type V Cas protein comprises an amino acid sequence of SEQ ID NO:43, SEQ ID NO:44, or SEQ ID NO:45. In some embodiments, a ZZKD Type V Cas protein has nickase activity, for example resulting from one or more amino acid substitutions relative to the sequence of SEQ ID NO:43, SEQ ID NO:44, or SEQ ID NO:45. In some embodiments, the one or more amino acid substitutions providing nickase activity comprise a D828 substitution, wherein the position of the D828 substitution is defined with respect to the amino acid numbering of SEQ ID NO:44 (corresponding to amino acid 908 of SEQ ID NO:121). In some embodiments, the one or more amino acid substitutions providing nickase activity comprise an E925 substitution, wherein the position of the E925 substitution is defined with respect to the amino acid numbering of SEQ ID NO:44 (corresponding to amino acid 993 of SEQ ID NO:121). In some embodiments, the one or more amino acid substitutions providing nickase activity comprise a R1138 substitution, wherein the position of the R1138 substitution is defined with respect to the amino acid numbering of SEQ ID NO:44 (corresponding to amino acid 1226 of SEQ ID NO:121). In some embodiments, the one or more amino acid substitutions providing nickase activity comprise a D1176 substitution, wherein the position of the D1176 substitution is defined with respect to the amino acid numbering of SEQ ID NO:44 (corresponding to amino acid 1263 of SEQ ID NO:121). In some embodiments, a ZZKD Type V Cas protein is catalytically inactive, for example due to a R1138 substitution in combination with a D828 substitution, a E925 substitution, and/or D1176 substitution.

6.2.9. ZXPB Type V Cas Proteins

In one aspect, the disclosure provides ZXPB Type V Cas proteins. ZXPB Type V Cas proteins can be further classified as Type V-A Cas proteins. The ZXPB Type V Cas proteins typically comprise an amino acid sequence that is at least 50%, at least 55%, at least 60%, at least 65%, at least 70%, at least 75%, at least 85%, at least 90%, or at least 95% identical to SEQ ID NO:49. In some embodiments, the ZXPB Type V Cas proteins comprise an amino acid sequence that is at least 95%, at least 96%, at least 97%, at least 98%, or at least 99% identical to SEQ ID NO:49. In some embodiments, a ZXPB Type V Cas protein comprises an amino acid sequence that is identical to SEQ ID NO:49.

Exemplary ZXPB Type V Cas protein sequences and nucleotide sequences encoding exemplary ZXPB Type V Cas proteins are set forth in Table 11.

TABLE 11

| ZXPB Type V Cas Sequences | | |
|---|---|---|
| Name | Sequence | SEQ ID NO. |
| Wildtype amino acid sequence | KLEDFTNLYSLSKTLRFELRPIGKTRENIENGGLLRQDEDRAEKYVHIKKLIDEYHKAYI<br>DKQLSGLVLQYADIGKANSLEEYYHSTRKSKDSDKDKIVKIQDNLRKQIVKRLKDSDE<br>FKRIDKKELIQSDLAEFIKPAEDRALIAEFKNFTTYFTGFNENRQNMYSDKAISTAIAYR | 49 |

TABLE 11-continued

ZXPB Type V Cas Sequences

| Name | Sequence | SEQ ID NO. |
|---|---|---|
| (without N-terminal methionine) | LIHENLPKFIDNIETFDRIAGITELYDQTSSDAEIFRLEHFSETLSQKQIDAYNSVMGRY<br>NMLINEYNQTHKQSRLPKFKMLYKQILSDREHPSWLPEQFESDTAVLTAIRECYDDLR<br>IPMANLKTLLEGLGNYDPSGIFLRNDQHLSQISKRLTGDRSSIERSVTEDLLTSRRLNK<br>RKSRTTDEEESRKLFKQKGSLSIGYIADTAKIDVERYFAKLGAINTVTEQSENLFAKAE<br>NARTTADELLANDYPAGKRLVQSNDDIALLKNLLDALMELQWFVKPLLGTGDEAGKD<br>ERFYGEFAQIWEQLDRITPLYNMVRNYVTRKPYSTDKFKLNFESAALLGGWDKNKEP<br>DCLSVILRKDEQYYLGIINKNHKKIFENDILPCEGECYDKMVYKLLPGANKMLPKVFFS<br>ASRIAEFAPSDEVKRIYNDKTFQKGEKFDLNDCRTLIDFYKASIDKHEEWNKFGFEFS<br>DTNNYEDISGFFREVDRQGYKMSFRPVAASYIETLVEEGKLYLFQIYNKDFSAYSKGT<br>PNMHTLYWRMLFDERNLSDVVYQLNGGAELFFRRKSLQNGRPTHPANIPIKNKNSR<br>NDKKESLFDYDLIKDRRYTVDKFQFHVPITLNFKSDGAGRINERVREYLRSADDVHVI<br>GIDRGERNLLYLVVTDMDGNICEQFSLNEICNTDYHSLLDEREHKRMQERQSWQAIE<br>GIKELKEGYLSQVVHRIATLMVKYRAIVVLEDLNFGFMRSRQKVEKSVYQKFEHMLID<br>KLNYLVDKKANPTTPGGLLKAYQLTDKFESFQKLGKQSGFLFYVPAWNTSKIDPATG<br>FVNMLDLGYESIDKAKTLLCKFDSIRYNACKDWFEFALDYDKFGSKATGTRTKWTVC<br>TYGQRIDTYRNKDSQWVSRDVDLTNELKSLFSEHGIDIYSNLKDAIVAQNDKEFFANM<br>QRILKLTMQMRNSKTGTDTDYIVSPVADANGRFFDSRQADATMPKDADANGAYNIAR<br>KGIMLVQQIKQSDDLRTMKFDISNKSWLRFAQHTNQADE | |
| Wildtype amino acid sequence (with N-terminal methionine) | MKLEDFTNLYSLSKTLRFELRPIGKTRENIENGGLLRQDEDRAEKYVHIKKLIDEYHKA<br>YIDKQLSGLVLQYADIGKANSLEEYYHSTRKSKDSDKDKIVKIQDNLRKQIVKRLKDSD<br>EFKRIDKKELIQSDLAEFIKPAEDRALIAEFKNFTTYFTGFNENRQNMYSDKAISTAIAY<br>RLIHENLPKFIDNIETFDRIAGITELYDQTSSDAEIFRLEHFSETLSQKQIDAYNSVMGR<br>YNMLINEYNQTHKQSRLPKFKMLYKQILSDREHPSWLPEQFESDTAVLTAIRECYDDL<br>RIPMANLKTLLEGLGNYDPSGIFLRNDQHLSQISKRLTGDRSSIERSVTEDLLTSRRLN<br>KRKSRTTDEEESRKLFKQKGSLSIGYIADTAKIDVERYFAKLGAINTVTEQSENLFAKA<br>ENARTTADELLANDYPAGKRLVQSNDDIALLKNLLDALMELQWFVKPLLGTGDEAGK<br>DERFYGEFAQIWEQLDRITPLYNMVRNYVTRKPYSTDKFKLNFESAALLGGWDKNKE<br>PDCLSVILRKDEQYYLGIINKNHKKIFENDILPCEGECYDKMVYKLLPGANKMLPKVFF<br>SASRIAEFAPSDEVKRIYNDKTFQKGEKFDLNDCRTLIDFYKASIDKHEEWNKFGFEF<br>SDTNNYEDISGFFREVDRQGYKMSFRPVAASYIETLVEEGKLYLFQIYNKDFSAYSKG<br>TPNMHTLYWRMLFDERNLSDVVYQLNGGAELFFRRKSLQNGRPTHPANIPIKNKNS<br>RNDKKESLFDYDLIKDRRYTVDKFQFHVPITLNFKSDGAGRINERVREYLRSADDVHV<br>IGIDRGERNLLYLVVTDMDGNICEQFSLNEICNTDYHSLLDEREHKRMQERQSWQAIE<br>GIKELKEGYLSQVVHRIATLMVKYRAIVVLEDLNFGFMRSRQKVEKSVYQKFEHMLID<br>KLNYLVDKKANPTTPGGLLKAYQLTDKFESFQKLGKQSGFLFYVPAWNTSKIDPATG<br>FVNMLDLGYESIDKAKTLLCKFDSIRYNACKDWFEFALDYDKFGSKATGTRTKWTVC<br>TYGQRIDTYRNKDSQWVSRDVDLTNELKSLFSEHGIDIYSNLKDAIVAQNDKEFFANM<br>QRILKLTMQMRNSKTGTDTDYIVSPVADANGRFFDSRQADATMPKDADANGAYNIAR<br>KGIMLVQQIKQSDDLRTMKFDISNKSWLRFAQHTNQADE | 50 |
| Expression construct (with N-terminal methionine, V5-tag and C-terminal NLS) aa sequence | MGKLEDFTNLYSLSKTLRFELRPIGKTRENIENGGLLRQDEDRAEKYVHIKKLIDEYHK<br>AYIDKQLSGLVLQYADIGKANSLEEYYHSTRKSKDSDKDKIVKIQDNLRKQIVKRLKDS<br>DEFKRIDKKELIQSDLAEFIKPAEDRALIAEFKNFTTYFTGFNENRQNMYSDKAISTAIA<br>YRLIHENLPKFIDNIETFDRIAGITELYDQTSSDAEIFRLEHFSETLSQKQIDAYNSVMG<br>RYNMLINEYNQTHKQSRLPKFKMLYKQILSDREHPSWLPEQFESDTAVLTAIRECYD<br>DLRIPMANLKTLLEGLGNYDPSGIFLRNDQHLSQISKRLTGDRSSIERSVTEDLLTSRR<br>LNKRKSRTTDEEESRKLFKQKGSLSIGYIADTAKIDVERYFAKLGAINTVTEQSENLFA<br>KAENARTTADELLANDYPAGKRLVQSNDDIALLKNLLDALMELQWFVKPLLGTGDEA<br>GKDERFYGEFAQIWEQLDRITPLYNMVRNYVTRKPYSTDKFKLNFESAALLGGWDK<br>NKEPDCLSVILRKDEQYYLGIINKNHKKIFENDILPCEGECYDKMVYKLLPGANKMLPK<br>VFFSASRIAEFAPSDEVKRIYNDKTFQKGEKFDLNDCRTLIDFYKASIDKHEEWNKFG<br>FEFSDTNNYEDISGFFREVDRQGYKMSFRPVAASYIETLVEEGKLYLFQIYNKDFSAY<br>SKGTPNMHTLYWRMLFDERNLSDVVYQLNGGAELFFRRKSLQNGRPTHPANIPIKN<br>KNSRNDKKESLFDYDLIKDRRYTVDKFQFHVPITLNFKSDGAGRINERVREYLRSADD<br>VHVIGIDRGERNLLYLVVTDMDGNICEQFSLNEICNTDYHSLLDEREHKRMQERQSW<br>QAIEGIKELKEGYLSQVVHRIATLMVKYRAIVVLEDLNFGFMRSRQKVEKSVYQKFEH<br>MLIDKLNYLVDKKANPTTPGGLLKAYQLTDKFESFQKLGKQSGFLFYVPAWNTSKIDP<br>ATGFVNMLDLGYESIDKAKTLLCKFDSIRYNACKDWFEFALDYDKFGSKATGTRTKW<br>TVCTYGQRIDTYRNKDSQWVSRDVDLTNELKSLFSEHGIDIYSNLKDAIVAQNDKEFF<br>ANMQRILKLTMQMRNSKTGTDTDYIVSPVADANGRFFDSRQADATMPKDADANGAY<br>NIARKGIMLVQQIKQSDDLRTMKFDISNKSWLRFAQHTNQADESRKRTADGSEFESP<br>KKKRKVGSGKPIPNPLLGLDST | 51 |
| Wildtype coding sequence (with N-terminal methionine and stop codon) | ATGAAATTAGAAGATTTTACCAACCTGTATTCGTTATCCAAGACTCTGCGTTTCGA<br>ACTGCGGCCGATCGGCAAGACACGTGAAAATATCGAAAACGGAGGCCTTTTGAG<br>GCAGGACGAGGATCGTGCTGAAAAATATGTACACATAAAAAAACTAATCGATGAA<br>TATCATAAAGCATATATCGATAAACAATTGTCGGGTTTAGTGCTGCAATACGCCGA<br>TATCGGTAAAGCCAATTCATTGGAGGAGTATTATCACTCCACAAGAAAGAGCAAA<br>GATTCGGACAAGGATAAGATTGTCAAAATCCAGGATAATCTGCGTAAACAAATTG<br>TCAAACGGTTGAAAGACTCAGACGAATTCAAGCGTATCGATAAAAAAGAGTTGAT<br>TCAATCGGATCTGGCAGAGTTCATAAAACCAGCCGAAGACAGAGCTTTGATTGCC<br>GAATTCAAAAACTTCACAACATATTTTACCGGATTCAATGAAAACAGACAGAACAT<br>GTATTCGGACAAAGCTATATCTACGGCAATAGCTTATCGTCTGATACATGAGAATC | 52 |

TABLE 11-continued

| ZXPB Type V Cas Sequences | | |
|---|---|---|
| Name | Sequence | SEQ ID NO. |
| | TTCCGAAGTTCATAGACAACATAGAGACTTTCGATCGCATCGCCGGTATAACGGA ATTGTACGACCAAACCTCCTCCGATGCCGAAATTTTCCGTCTGGAACATTTTTCG GAAACACTGAGCCAAAAGCAGATCGATGCCTATAACTCCGTTATGGGCAGATATA ACATGCTTATCAATGAGTACAATCAGACGCATAAACAGTCGCGCCTACCTAAATT CAAAATGCTGTACAAACAGATTCTTAGCGACCGCGAACACCCCTCGTGGCTGCC CGAGCAGTTCGAGTCGGACACGGCTGTATTGACAGCCATTCGCGAATGTTACGA TGATCTGCGCATACCTATGGCCAATTTGAAAACGCTTTTAGAGGGGTTGGGCAAC TATGACCCGAGTGGAATATTTTTGCGTAATGACCAACATCTCTCTCAGATATCCAA ACGATTGACAGGTGATCGGAGTAGCATTGAACGTAGCGTAACAGAAGACCTTCT GACATCGAGGAGACTCAACAAGCGAAAAAGCCGCACAACCGACGAGGAGGAATC GAGAAAACTGTTCAAGCAAAAGGGTAGTCTGAGTATAGGCTATATAGCTGACACG GCCAAAATCGATGTCGAAAGATACTTTGCCAAACTCGGTGCAATAAATACGGTAA CGGAGCAGAGCGAGAATCTATTCGCCAAGGCTGAGAATGCCCGCACGACAGCG GATGAGCTGCTCGCAAATGATTACCCGGCAGGCAAGAGGCTCGTTCAGTCCAAC GACGACATAGCATTGCTGAAAAATCTGCTCGATGCTTTAATGGAGCTGCAATGGT TCGTCAAGCCGCTGCTTGGCACGGGGGACGAAGCCGGCAAAGACGAACGTTTC TATGGAGAATTTGCACAGATATGGGAGCAGCTGGATCGTATAACGCCTCTCTATA ACATGGTGCGCAACTATGTTACCCGCAAGCCGTATTCGACCGACAAATTCAAGCT CAACTTTGAGAGCGCAGCGCTTCTCGGCGGCTGGGACAAGAACAAGGAGCCGG ACTGTCTGTCGGTAATCTTACGCAAGGATGAGCAATATTATCTCGGCATAATCAAT AAGAATCACAAAAAGATATTCGAGAACGATATCTTGCCGTGCGAAGGGGAGTGTT ACGACAAAATGGTATATAAACTCCTGCCCGGCGCAAACAAGATGCTGCCGAAAGT ATTCTTCTCGGCTTCGCGTATCGCCGAATTTGCACCGAGCGACGAAGTAAAACG GATATACAATGATAAGACTTTCCAAAAAGGCGAAAAGTTCGACTTGAACGATTGTC GCACACTGATCGACTTCTACAAGGCTTCTATCGACAAACATGAGGAGTGGAACAA GTTTGGATTCGAATTCTCGGATACGAACAATTATGAAGACATAAGCGGATTCTTTC GCGAGGTCGACAGGCAAGGCTATAAAATGTCATTCCGCCCGGTCGCAGCATCGT ATATCGAAACCCTTGTTGAAGAGGGCAAACTCTATCTTTTCCAAATATATAATAAG GATTTTTCGGCATATAGCAAAGGTACTCCCAATATGCACACGCTGTATTGGAGGA TGCTCTTCGACGAGCGCAATCTATCGGATGTCGTATATCAGCTCAACGGCGGAG CAGAGTTGTTCTTCCGAAGAAAGAGTCTTCAAAACGGCCGTCCGACGCATCCGG CAAATATTCCTATCAAAAACAAAAACAGTCGGAATGACAAAAAAGAGAGCCTGTTC GACTACGATTTGATCAAAGACAGACGCTATACTGTGGACAAATTTCAGTTCCATGT CCCGATAACCCTCAATTTCAAGAGCGACGGGGGGGGCAGGATCAACGAGCGTGT AAGGGAATATCTCCGCTCGGCGGACGACGTTCACGTCATAGGCATCGACCGCGG AGAACGCAATCTGCTGTATCTGGTCGTGACGGATATGGACGGCAATATCTGCGA ACAATTCTCGCTCAACGAAATTTGTAATACTGATTATCATTCTTTGTTGGATGAAC GCGAACACAAACGTATGCAGGAGAGACAGAGCTGGCAGGCGATAGAGGGCATC AAGGAGTTGAAAGAAGGTTATCTGTCTCAGGTCGTACACCGAATCGCGACACTCA TGGTTAAATATCGCGCCATTGTCGTACTGGAAGATCTCAACTTCGGCTTCATGCG TAGCCGCCAGAAGGTAGAGAAGTCTGTATACCAGAAATTCGAACACATGCTCATA GATAAGCTCAATTATCTGGTCGACAAGAAAGCCAATCCGACAACGCCGGGCGGT CTGCTAAAAGCCTATCAGTTGACAGACAAATTCGAGAGCTTCCAGAAGCTCGGCA AACAGAGCGGATTTCTATTCTACGTTCCGGCATGGAATACATCGAAGATCGATCC AGCAACCGGATTCGTCAACATGCTCGATCTCGGATACGAGAGCATCGACAAAGC CAAAACACTGCTCTGCAAGTTCGACTCTATACGCTACAATGCGTGCAAAGACTGG TTCGAGTTCGCTCTCGATTACGACAAGTTCGGCAGCAAGGCCACCGGTACCCGC ACGAAATGGACTGTTTGCACCTACGGACAACGTATCGATACTTATCGCAACAAAG ATTCGCAGTGGGTCAGCCGCGACGTCGATTTGACAAATGAGCTGAAATCACTCTT CTCCGAACACGGCATAGACATTTACAGCAATCTGAAAGATGCAATAGTCGCACAA AACGACAAAGAATTTTTCGCGAACATGCAGCGGATATTGAAACTGACCATGCAAA TGCGAAACAGCAAAACGGGTACCGACACAGACTATATCGTCTCGCCCGTCGCCG ATGCCAACGGCAGATTCTTCGACAGCAGGCAGGCCGATGCGACCATGCCCAAAG ATGCGGATGCGAACGGAGCGTATAATATCGCACGTAAGGGCATTATGCTCGTAC AGCAGATCAAGCAGTCCGACGATCTGCGTACAATGAAGTTCGACATAAGCAACAA GAGCTGGCTGCGCTTCGCCCAACATACGAACCAGGCGGACGAGTAA | |
| Codon optimized coding sequence (no N-terminal methionine, no stop codon) | AAGCTGGAGGACTTCACCAATCTGTACTCTCTGAGCAAGACCCTGCGGTTTGAG CTGCGGCCTATCGGCAAGACAAGAGAAAACATCGAAAACGGCGGACTGCTGCGT CAAGACGAGGACAGAGCCGAAAAGTACGTGCATATTAAAAAGCTGATCGATGAAT ACCACAAGGCTTATATCGACAAGCAACTGAGTGGCCTGGTCCTGCAATACGCCG ATATCGGCAAGGCCAATTCTCTGGAGGAGTACTACCACAGCACTAGAAAAAGCAA GGACTCTGACAAGGATAAGATAGTCAAGATCCAGGACAACCTGCGCAAGCAGAT CGTCAAGAGATTGAAGGACAGCGATGAGTTTAAGAGGATCGATAAGAAGGAACT GATCCAGTCTGACCTGGCAGAGTTCATCAAGCCAGCCGAGGACAGGGCCCTGAT AGCCGAGTTCAAGAACTTCACCACCTACTTCACAGGATTCAACGAAAATAGGCAG AACATGTACAGCGATAAGGCTATCAGCACCGCCATCGCCTACCGGCTGATCCAC GAGAACCTGCCTAAGTTCATCGACAACATCGAAACCTTCGACCGGATCGCGGGC ATCACAGAGCTGTATGACCAGACATCCAGCGACGCAGAGATCTTTAGACTGGAG CACTTCAGTGAGACACTGAGCCAGAAGCAGATCGATGCCTATAACAGCGTGATG GGCCGGTACAACATGCTGATCAACGAATATAACCAGACCCACAAGCAATCTCGG CTGCCTAAATTCAAAATGCTGTACAAGCAGATCCTGAGCGACCGGGAGCACCCC AGCTGGCTGCCGGAACAGTTCGAGAGCGACACCGCCGTGCTGACCGCCATCAG AGAGTGTTACGACGACCTGAGAATCCCTATGGCCAACTTAAAAACCCTGCTTGAG | 53 |

TABLE 11-continued

ZXPB Type V Cas Sequences

| Name | Sequence | SEQ ID NO. |
|---|---|---|
| | GGCCTGGGAAATTACGATCCCTCTGGCATCTTCCTGCGGAACGATCAGCACCTG<br>TCTCAGATCAGCAAAAGACTCACCGGAGACAGATCCAGCATCGAACGGAGCGTG<br>ACCGAGGACTTATTAACGAGCCGGAGACTGAACAAAAGAAAGAGCAGAACCACC<br>GATGAAGAGGAAAGCAGAAAGCTGTTCAAGCAAAAAGGCAGCCTGAGCATCGGC<br>TACATCGCCGACACAGCCAAGATCGACGTGGAGAGATACTTCGCCAAGCTGGGA<br>GCCATTAATACCGTGACCGAGCAGTCTGAGAACCTCTTCGCTAAGGCCGAGAAC<br>GCCAGAACCACTGCTGACGAGCTGCTGGCCAACGACTACCCTGCCGGCAAAAGA<br>CTGGTGCAGAGCAACGACGACATCGCTCTGCTGAAGAACCTATTGGACGCCCTG<br>ATGGAACTGCAATGGTTCGTGAAGCCCCTGCTGGGCACCGGCGACGAGGCCGG<br>CAAAGACGAACGGTTCTATGGCGAGTTCGCTCAGATCTGGGAGCAGCTGGATAG<br>AATCACCCCTCTGTACAACATGGTGCGGAATTACGTGACAAGAAAGCCCTACTCC<br>ACAGACAAGTTCAAGCTGAACTTCGAATCTGCCGCCCTGCTGGGCGGATGGGAC<br>AAGAACAAAGAACCTGACTGCCTGTCCGTGATTCTGAGAAAGGACGAGCAGTAC<br>TACCTGGGCATCATCAACAAGAACCACAAGAAGATCTTCGAGAATGACATTCTGC<br>CTTGCGAGGGCGAGTGCTACGACAAGATGGTCTACAAGCTGCTGCCTGGCGCTA<br>ACAAAATGCTGCCTAAGGTGTTCTTTAGCGCCTCCAGAATCGCTGAGTTCGCCCC<br>TTCTGATGAGGTGAAAAGAATTTACAACGATAAGACCTTCCAGAAGGGCGAGAAG<br>TTCGATCTGAACGACTGCAGAACCCTCATCGATTTCTACAAGGCTTCTATCGATAA<br>GCACGAGGAGTGGAATAAATTTGGCTTCGAGTTTAGCGACACCAACAACTACGA<br>GGACATCAGCGGCTTCTTCCGGGAGGTGGACAGACAGGGCTACAAGATGAGCTT<br>TAGACCCGTGGCCGCCAGCTACATCGAAACGTTGGTGGAAGAGGGCAAACTGTA<br>CCTGTTCCAGATCTACAACAAAGATTTCAGCGCCTACAGCAAGGGCACCCCTAAT<br>ATGCACACCCTGTACTGGAGAATGCTGTTTGACGAGCGGAACCTGAGCGACGTG<br>GTGTACCAGCTGAACGGCGGAGCTGAACTGTTCTTTAGACGCAAGTCCCTCCAG<br>AACGGCCGGCCTACACACCCTGCCAACATCCCTATCAAGAACAAGAACAGCAGA<br>AACGATAAAAAGGAATCACTGTTCGACTACGATCTCATCAAGGATCGTAGATACA<br>CAGTGGATAAGTTCCAGTTCCACGTGCCAATCACACTGAATTTCAAGAGCGATGG<br>CGCTGGCAGAATTAACGAGAGAGTGCGGGAGTACCTGAGATCTGCCGATGACGT<br>GCACGTGATCGGCATCGACAGAGGCGAGCGGAACCTGCTGTACCTCGTGGTGA<br>CCGATATGGACGGCAACATCTGCGAACAGTTTAGCCTGAACGAAATCTGTAATAC<br>CGACTACCACAGCCTGTTGGATGAGAGAGAGCACAAAAGAATGCAGGAAAGACA<br>GAGCTGGCAGGCCATCGAGGGAATCAAGGAGCTGAAGGAAGGCTACCTGTCCC<br>AAGTGGTCCACAGAATCGCCACCCTGATGGTGAAGTACAGAGCGATCGTGGTGC<br>TGGAGGACCTGAACTTCGGCTTCATGCGGAGCAGACAGAAAGTGGAAAAAAGCG<br>TGTACCAGAAGTTCGAGCACATGCTGATCGACAAACTGAACTACCTGGTGGACAA<br>GAAAGCCAACCCTACCACACCCGGCGGCCTGCTGAAGGCCTACCAGCTGACAG<br>ACAAGTTCGAGAGCTTCCAGAAGCTGGGCAAGCAGTCTGGATTCCTGTTTTATGT<br>GCCCGCCTGGAACACAAGCAAGATCGACCCTGCTACCGGATTCGTGAACATGCT<br>GGATCTGGGCTATGAGAGCATCGACAAGGCCAAAACCCTGCTGTGCAAGTTTGA<br>CTCCATCAGATACAACGCCTGCAAGGACTGGTTCGAGTTTGCCCTGGACTACGA<br>CAAGTTCGGCAGCAAGGCCACAGGCACACGGACCAAGTGGACAGTGTGCACCT<br>ACGGCCAGCGGATCGATACTTATAGAAACAAGGACAGCCAGTGGGTGTCTCGGG<br>ACGTGGATCTGACCAATGAGCTGAAGAGCCTGTTTTCTGAACATGGCATCGACAT<br>CTACAGCAACCTGAAAGACGCCATCGTGGCCCAAAATGACAAAGAGTTCTTCGC<br>CAACATGCAGAGAATCCTGAAGCTGACCATGCAGATGAGAAATTCTAAAACTGGA<br>ACAGATACAGACTACATTGTGTCCCCTGTTGCCGATGCTAACGGAAGATTCTTCG<br>ACAGCAGACAAGCCGACGCCACCATGCCAAAGGACGCCGACGCCAACGGCGCC<br>TACAACATCGCTAGAAAGGGCATCATGCTGGTTCAGCAGATCAAGCAGAGCGAT<br>GACCTCCGCACCATGAAATTCGACATCAGCAACAAGAGCTGGCTGAGATTCGCC<br>CAGCATACCAACCAGGCCGATGAG | |
| Expression construct (with N-terminal methionine and stop codon, includes V5-tag and C-terminal NLS) | ATGggcAAGCTGGAGGACTTCACCAATCTGTACTCTCTGAGCAAGACCCTGCGGT<br>TTGAGCTGCGGCCTATCGGCAAGACAAGAGAAAACATCGAAAACGGCGGACTGC<br>TGCGTCAAGACGAGGACAGAGCCGAAAAGTACGTGCATATTAAAAAGCTGATCG<br>ATGAATACCACAAGGCTTATATCGACAAGCAACTGAGTGGCCTGGTCCTGCAATA<br>CGCCGATATCGGCAAGGCCAATTCTCTGGAGGAGTACTACCACAGCACTAGAAA<br>AAGCAAGGACTCTGACAAGGATAAGATAGTCAAGATCCAGGACAACCTGCGCAA<br>GCAGATCGTCAAGAGATTGAAGGACAGCGATGAGTTTAAGAGGATCGATAAGAA<br>GGAACTGATCCAGTCTGACCTGGCAGAGTTCATCAAGCCAGCCGAGGACAGGGC<br>CCTGATAGCCGAGTTCAAGAACTTCACCACCTACTTCACAGGATTCAACGAAAAT<br>AGGCAGAACATGTACAGCGATAAGGCTATCAGCACCGCCATCGCCTACCGGCTG<br>ATCCACGAGAACCTGCCTAAGTTCATCGACAACATCGAAACCTTCGACCGGATCG<br>CGGGCATCACAGAGCTGTATGACCAGACATCCAGCGACGCAGAGATCTTTAGAC<br>TGGAGCACTTCAGTGAGACACTGAGCCAGAAGCAGATCGATGCCTATAACAGCG<br>TGATGGGCCGGTACAACATGCTGATCAACGAATATAACCAGACCCACAAGCAATC<br>TCGGCTGCCTAAATTCAAAATGCTGTACAAGCAGATCCTGAGCGACCGGGAGCA<br>CCCCAGCTGGCTGCCGGAACAGTTCGAGAGCGACACCGCCGTGCTGACCGCCA<br>TCAGAGAGTGTTACGACGACCTGAGAATCCCTATGGCCAACTTAAAAACCCTGCT<br>TGAGGGCCTGGGAAATTACGATCCCTCTGGCATCTTCCTGCGGAACGATCAGCA<br>CCTGTCTCAGATCAGCAAAAGACTCACCGGAGACAGATCCAGCATCGAACGGAG<br>CGTGACCGAGGACTTATTAACGAGCCGGAGACTGAACAAAAGAAAGAGCAGAAC<br>CACCGATGAAGAGGAAAGCAGAAAGCTGTTCAAGCAAAAAGGCAGCCTGAGCAT<br>CGGCTACATCGCCGACACAGCCAAGATCGACGTGGAGAGATACTTCGCCAAGCT<br>GGGAGCCATTAATACCGTGACCGAGCAGTCTGAGAACCTCTTCGCTAAGGCCGA | 54 |

TABLE 11-continued

ZXPB Type V Cas Sequences

| Name | Sequence | SEQ ID NO. |
|---|---|---|
| | GAACGCCAGAACCACTGCTGACGAGCTGCTGGCCAACGACTACCCTGCCGGCA<br>AAAGACTGGTGCAGAGCAACGACGACATCGCTCTGCTGAAGAACCTATTGGACG<br>CCCTGATGGAACTGCAATGGTTCGTGAAGCCCCTGCTGGGCACCGGCGACGAG<br>GCCGGCAAAGACGAACGGTTCTATGGCGAGTTCGCTCAGATCTGGGAGCAGCTG<br>GATAGAATCACCCCTCTGTACAACATGGTGCGGAATTACGTGACAAGAAAGCCCT<br>ACTCCACAGACAAGTTCAAGCTGAACTTCGAATCTGCCGCCCTGCTGGGCGGAT<br>GGGACAAGAACAAAGAACCTGACTGCCTGTCCGTGATTCTGAGAAAGGACGAGC<br>AGTACTACCTGGGCATCATCAACAAGAACCACAAGAAGATCTTCGAGAATGACAT<br>TCTGCCTTGCGAGGGCGAGTGCTACGACAAGATGGTCTACAAGCTGCTGCCTGG<br>CGCTAACAAAATGCTGCCTAAGGTGTTCTTTAGCGCCTCCAGAATCGCTGAGTTC<br>GCCCCTTCTGATGAGGTGAAAAGAATTTACAACGATAAGACCTTCCAGAAGGGCG<br>AGAAGTTCGATCTGAACGACTGCAGAACCCTCATCGATTTCTACAAGGCTTCTAT<br>CGATAAGCACGAGGAGTGGAATAAATTTGGCTTCGAGTTTAGCGACACCAACAAC<br>TACGAGGACATCAGCGGCTTCTTCCGGGAGGTGGACAGACAGGGCTACAAGATG<br>AGCTTTAGACCCGTGGCCGCCAGCTACATCGAAACGTTGGTGGAAGAGGGCAAA<br>CTGTACCTGTTCCAGATCTACAACAAAGATTTCAGCGCCTACAGCAAGGGCACCC<br>CTAATATGCACACCCTGTACTGGAGAATGCTGTTTGACGAGCGGAACCTGAGCG<br>ACGTGGTGTACCAGCTGAACGGCGGAGCTGAACTGTTCTTTAGACGCAAGTCCC<br>TCCAGAACGGCCGGCCTACACACCCTGCCAACATCCCTATCAAGAACAAGAACA<br>GCAGAAACGATAAAAAGGAATCACTGTTCGACTACGATCTCATCAAGGATCGTAG<br>ATACACAGTGGATAAGTTCCAGTTCCACGTGCCAATCACACTGAATTTCAAGAGC<br>GATGGCGCTGGCAGAATTAACGAGAGAGTGCGGGAGTACCTGAGATCTGCCGAT<br>GACGTGCACGTGATCGGCATCGACAGAGGCGAGCGGAACCTGCTGTACCTCGT<br>GGTGACCGATATGGACGGCAACATCTGCGAACAGTTTAGCCTGAACGAAATCTG<br>TAATACCGACTACCACAGCCTGTTGGATGAGAGAGAGCACAAAAGAATGCAGGA<br>AAGACAGAGCTGGCAGGCCATCGAGGGAATCAAGGAGCTGAAGGAAGGCTACC<br>TGTCCCAAGTGGTCCACAGAATCGCCACCCTGATGGTGAAGTACAGAGCGATCG<br>TGGTGCTGGAGGACCTGAACTTCGGCTTCATGCGGAGCAGACAGAAAGTGGAAA<br>AAAGCGTGTACCAGAAGTTCGAGCACATGCTGATCGACAAACTGAACTACCTGGT<br>GGACAAGAAAGCCAACCCTACCACACCCGGCGGCCTGCTGAAGGCCTACCAGC<br>TGACAGACAAGTTCGAGAGCTTCCAGAAGCTGGGCAAGCAGTCTGGATTCCTGT<br>TTTATGTGCCCGCCTGGAACACAAGCAAGATCGACCCTGCTACCGGATTCGTGA<br>ACATGCTGGATCTGGGCTATGAGAGCATCGACAAGGCCAAAACCCTGCTGTGCA<br>AGTTTGACTCCATCAGATACAACGCCTGCAAGGACTGGTTCGAGTTTGCCCTGGA<br>CTACGACAAGTTCGGCAGCAAGGCCACAGGCACACGGACCAAGTGGACAGTGT<br>GCACCTACGGCCAGCGGATCGATACTTATAGAAACAAGGACAGCCAGTGGGTGT<br>CTCGGGACGTGGATCTGACCAATGAGCTGAAGAGCCTGTTTTCTGAACATGGCA<br>TCGACATCTACAGCAACCTGAAAGACGCCATCGTGGCCCAAAATGACAAAGAGTT<br>CTTCGCCAACATGCAGAGAATCCTGAAGCTGACCATGCAGATGAGAAATTCTAAA<br>ACTGGAACAGATACAGACTACATTGTGTCCCCTGTTGCCGATGCTAACGGAAGAT<br>TCTTCGACAGCAGACAAGCCGACGCCACCATGCCAAAGGACGCCGACGCCAAC<br>GGCGCCTACAACATCGCTAGAAAGGGCATCATGCTGGTTCAGCAGATCAAGCAG<br>AGCGATGACCTCCGCACCATGAAATTCGACATCAGCAACAAGAGCTGGCTGAGA<br>TTCGCCCAGCATACCAACCAGGCCGATGAGtctagaAAGCGGACAGCAGACGGCTC<br>CGAATTTGAAAGCCCTAAGAAAAAGAGAAAGGTGggatccGGCAAACCTATCCCCA<br>ATCCCCTGCTGGGCCTGGACAGCACCTGA | |

In some embodiments a ZXPB Type V Cas protein comprises an amino acid sequence of SEQ ID NO:49, SEQ ID NO:50, or SEQ ID NO:51. In some embodiments, a ZXPB Type V Cas protein has nickase activity, for example resulting from one or more amino acid substitutions relative to the sequence of SEQ ID NO:49, SEQ ID NO:50, or SEQ ID NO:51. In some embodiments, the one or more amino acid substitutions providing nickase activity comprise a D821 substitution, wherein the position of the D821 substitution is defined with respect to the amino acid numbering of SEQ ID NO:50 (corresponding to amino acid 908 of SEQ ID NO:121). In some embodiments, the one or more amino acid substitutions providing nickase activity comprise an E906 substitution, wherein the position of the E906 substitution is defined with respect to the amino acid numbering of SEQ ID NO:50 (corresponding to amino acid 993 of SEQ ID NO:121). In some embodiments, the one or more amino acid substitutions providing nickase activity comprise a R1116 substitution, wherein the position of the R1116 substitution is defined with respect to the amino acid numbering of SEQ ID NO:50 (corresponding to amino acid 1226 of SEQ ID NO:121). In some embodiments, the one or more amino acid substitutions providing nickase activity comprise a D1153 substitution, wherein the position of the D1153 substitution is defined with respect to the amino acid numbering of SEQ ID NO:50 (corresponding to amino acid 1263 of SEQ ID NO:121). In some embodiments, a ZXPB Type V Cas protein is catalytically inactive, for example due to a R1116 substitution in combination with a D821 substitution, a E906 substitution, and/or D1153 substitution.

6.2.10. ZPPX Type V Cas Proteins

In one aspect, the disclosure provides ZPPX Type V Cas proteins. ZPPX Type V Cas proteins can be further classified as Type V-A Cas proteins. The ZPPX Type V Cas proteins typically comprise an amino acid sequence that is at least 50%, at least 55%, at least 60%, at least 65%, at least 70%, at least 75%, at least 85%, at least 90%, or at least 95% identical to SEQ ID NO:55. In some embodiments, the ZPPX Type V Cas proteins comprise an amino acid sequence that is at least 95%, at least 96%, at least 97%, at least 98%, or at least 99% identical to SEQ ID NO:55. In some embodiments, a ZPPX Type V Cas protein comprises an amino acid sequence that is identical to SEQ ID NO:55.

Exemplary ZPPX Type V Cas protein sequences and nucleotide sequences encoding exemplary ZPPX Type V Cas proteins are set forth in Table 1J.

TABLE 1J

ZPPX Type V Cas Sequences

| Name | Sequence | SEQ ID NO. |
| --- | --- | --- |
| Wildtype amino acid sequence (without N-terminal methionine) | MKDLTGQYSLSKTLRFELKPIGKTLEHIEQKGLLTQDEQRAEEYEQMKGIIDRYHKAFI<br>TMCLRNCKIKVNNTDDELDSLEEYSSLLSKSKRDADDENKLEKIKENLRKQIVNAFKS<br>GNTYGDLFTKELIKNHLPDFVTDEEEKQVVEHFCNFTTYFTGFHDNRKNMYSDKAKS<br>TAIAYRLIHENFPRFFDNLRSFAKISESEVANRFPEIESAFSLYLNVEHIADMFHVDYFP<br>WVLTQEQIDVYNNIIGGKTEEDGTKIQGINEYINLYNQHHPDVKLPFLKPLYKMILSDKV<br>ALSWLPEEFENDEEMLTAINDFYKSVQPVVFGDDENCIRHLLTNIAEYNTDHIYISNDL<br>GLTGISQQLFDQYSIFEDVIKDELRRNVKQTPKEKRNPELLEERIKNLFKKEKSFSISYL<br>DSLIKDKGEDTIESYYAKLGAFDRDGKQTVNLLTQIEMAYIAAKEVLDGKYDNINQSEE<br>ATKYIKDLLDAFKSLQHYIKPLLGSGEEAEKDNVFSSQLLNVWEALDVVTPLYNKVRN<br>WLTRKPYSTKKIKLNFENVQLLGGWPNIEAYSCAIFMKDDNTYYLGILDNAYKTLLRD<br>FPEPAEEKDTIGLMHYLQGGDMGKNIQNLMVVDGKVRKVNGRKEKSGINVGQNIRLE<br>EAKKRYLPTEINRIRKLGTYSVSNPNYNKQDLITIIDYYKPLACEYYASYTFHFKDSSEY<br>NSFAEFTDDINQQAYQLGFVPFSQQYLNKLVDEGKLYLFQIWNKDFSDYSKGTPNMH<br>TLYWKALFDKANLADVVYKLNGRQAEVFYRKRSLQKENTTVHKALQPIKNKNTQNEK<br>STSTFDYDIVKDRRYTVDKFHFHVPITINFKSSGKPNINEHVLDIIRHHGIEHVIGIDRGE<br>RHLLYLSLIDLKGRIIKQMTLNEIKQQTGGNYGTNYKELLAAREGDRAEARRNWKKIE<br>NIKDLKAGYLSQVVHVIAQMMVEYNAIVVLEDLNMGFMRGRQKIERSVYEQFEHMLID<br>KLNFYVDKKKEACAPGGLLHGLQLANKFESFNKLGKQSGCLFYVPAWNTSKIDPVTG<br>FVNMLDARYESVESSRRFFSRFDVIRYNEEKNWFEFTFDYNNFHAKLDGTKTQWTL<br>CTYGSRIKTFRNPAKLNQWDNEEVVLTDEFKKVFANAGINIHGNLKEAICSLAKREHL<br>EPLMHLMKLLLQLRNSKTNSEVDYMLSPVADNGVFYDSRSCNGNLPIDADANGAYNI<br>ARKGLWWVLRQIQDSKPGDKLNLALSNKEWLRFVQEKSNFE | 55 |
| Wildtype amino acid sequence (with N-terminal methionine) | MKDLTGQYSLSKTLRFELKPIGKTLEHIEQKGLLTQDEQRAEEYEQMKGIIDRYHKAFI<br>TMCLRNCKIKVNNTDDELDSLEEYSSLLSKSKRDADDENKLEKIKENLRKQIVNAFKS<br>GNTYGDLFTKELIKNHLPDFVTDEEEKQVVEHFCNFTTYFTGFHDNRKNMYSDKAKS<br>TAIAYRLIHENFPRFFDNLRSFAKISESEVANRFPEIESAFSLYLNVEHIADMFHVDYFP<br>WVLTQEQIDVYNNIIGGKTEEDGTKIQGINEYINLYNQHHPDVKLPFLKPLYKMILSDKV<br>ALSWLPEEFENDEEMLTAINDFYKSVQPVVFGDDENCIRHLLTNIAEYNTDHIYISNDL<br>GLTGISQQLFDQYSIFEDVIKDELRRNVKQTPKEKRNPELLEERIKNLFKKEKSFSISYL<br>DSLIKDKGEDTIESYYAKLGAFDRDGKQTVNLLTQIEMAYIAAKEVLDGKYDNINQSEE<br>ATKYIKDLLDAFKSLQHYIKPLLGSGEEAEKDNVFSSQLLNVWEALDVVTPLYNKVRN<br>WLTRKPYSTKKIKLNFENVQLLGGWPNIEAYSCAIFMKDDNTYYLGILDNAYKTLLRD<br>FPEPAEEKDTIGLMHYLQGGDMGKNIQNLMVVDGKVRKVNGRKEKSGINVGQNIRLE<br>EAKKRYLPTEINRIRKLGTYSVSNPNYNKQDLITIIDYYKPLACEYYASYTFHFKDSSEY<br>NSFAEFTDDINQQAYQLGFVPFSQQYLNKLVDEGKLYLFQIWNKDFSDYSKGTPNMH<br>TLYWKALFDKANLADVVYKLNGRQAEVFYRKRSLQKENTTVHKALQPIKNKNTQNEK<br>STSTFDYDIVKDRRYTVDKFHFHVPITINFKSSGKPNINEHVLDIIRHHGIEHVIGIDRGE<br>RHLLYLSLIDLKGRIIKQMTLNEIKQQTGGNYGTNYKELLAAREGDRAEARRNWKKIE<br>NIKDLKAGYLSQVVHVIAQMMVEYNAIVVLEDLNMGFMRGRQKIERSVYEQFEHMLID<br>KLNFYVDKKKEACAPGGLLHGLQLANKFESFNKLGKQSGCLFYVPAWNTSKIDPVTG<br>FVNMLDARYESVESSRRFFSRFDVIRYNEEKNWFEFTFDYNNFHAKLDGTKTQWTL<br>CTYGSRIKTFRNPAKLNQWDNEEVVLTDEFKKVFANAGINIHGNLKEAICSLAKREHL<br>EPLMHLMKLLLQLRNSKTNSEVDYMLSPVADNGVFYDSRSCNGNLPIDADANGAYNI<br>ARKGLWVLRQIQDSKPGDKLNLALSNKEWLRFVQEKSNFE | 56 |
| Expression construct (with N-terminal methionine, V5-tag and C-terminal NLS) aa sequence | MGKDLTGQYSLSKTLRFELKPIGKTLEHIEQKGLLTQDEQRAEEYEQMKGIIDRYHKA<br>FITMCLRNCKIKVNNTDDELDSLEEYSSLLSKSKRDADDENKLEKIKENLRKQIVNAFK<br>SGNTYGDLFTKELIKNHLPDFVTDEEEKQVVEHFCNFTTYFTGFHDNRKNMYSDKAK<br>STAIAYRLIHENFPRFFDNLRSFAKISESEVANRFPEIESAFSLYLNVEHIADMFHVDYF<br>PVVLTQEQIDVYNNIIGGKTEEDGTKIQGINEYINLYNQHHPDVKLPFLKPLYKMILSDK<br>VALSWLPEEFENDEEMLTAINDFYKSVQPVVFGDDENCIRHLLTNIAEYNTDHIYISND<br>LGLTGISQQLFDQYSIFEDVIKDELRRNVKQTPKEKRNPELLEERIKNLFKKEKSFSISY<br>LDSLIKDKGEDTIESYYAKLGAFDRDGKQTVNLLTQIEMAYIAAKEVLDGKYDNINQSE<br>EATKYIKDLLDAFKSLQHYIKPLLGSGEEAEKDNVFSSQLLNVWEALDVVTPLYNKVR<br>NWLTRKPYSTKKIKLNFENVQLLGGWPNIEAYSCAIFMKDDNTYYLGILDNAYKTLLR<br>DFPEPAEEKDTIGLMHYLQGGDMGKNIQNLMVVDGKVRKVNGRKEKSGINVGQNIR<br>LEEAKKRYLPTEINRIRKLGTYSVSNPNYNKQDLITIIDYYKPLACEYYASYTFHFKDSS<br>EYNSFAEFTDDINQQAYQLGFVPFSQQYLNKLVDEGKLYLFQIWNKDFSDYSKGTPN<br>MHTLYWKALFDKANLADVVYKLNGRQAEVFYRKRSLQKENTTVHKALQPIKNKNTQ<br>NEKSTSTFDYDIVKDRRYTVDKFHFHVPITINFKSSGKPNINEHVLDIIRHHGIEHVIGID<br>RGERHLLYLSLIDLKGRIIKQMTLNEIKQQTGGNYGTNYKELLAAREGDRAEARRNWK<br>KIENIKDLKAGYLSQVVHVIAQMMVEYNAIVVLEDLNMGFMRGRQKIERSVYEQFEH<br>MLIDKLNFYVDKKKEACAPGGLLHGLQLANKFESFNKLGKQSGCLFYVPAWNTSKID<br>PVTGFVNMLDARYESVESSRRFFSRFDVIRYNEEKNWFEFTFDYNNFHAKLDGTKT<br>QWTLCTYGSRIKTFRNPAKLNQWDNEEVVLTDEFKKVFANAGINIHGNLKEAICSLAK<br>REHLEPLMHLMKLLLQLRNSKTNSEVDYMLSPVADNGVFYDSRSCNGNLPIDADAN<br>GAYNIARKGLWVLRQIQDSKPGDKLNLALSNKEWLRFVQEKSNFESRKRTADGSEF<br>ESPKKKRKVGSGKPIPNPLLGLDST | 57 |

TABLE 1J-continued

ZPPX Type V Cas Sequences

| Name | Sequence | SEQ ID NO. |
|---|---|---|
| Wildtype coding sequence (with N-terminal methionine and stop codon) | ATGAAAGACCTGACAGGGCAATATAGCCTGTCGAAAACTTTACGATTTGAGTTAA<br>AACCTATCGGTAAAACTCTTGAGCACATTGAGCAAAAAGGACTCTTGACACAGGA<br>CGAACAAAGAGCAGAAGAGTACGAGCAAATGAAAGGTATCATCGACCGATATCA<br>CAAGGCATTTATTACCATGTGTTTGAGAAACTGCAAAATCAAGGTAAATAATACAG<br>ACGACGAATTAGACTCATTAGAAGAATACTCCTCATTACTTTCCAAAAGTAAAAGA<br>GATGCTGATGATGAGAACAAATTGGAAAAGATTAAGGAAAATCTTCGCAAGCAAA<br>TCGTCAATGCTTTCAAAAGCGGCAACACTTATGGCGACTTGTTCACAAAGGAACT<br>GATTAAGAATCATCTGCCCGACTTCGTCACAGACGAGGAAGAAAAGCAAGTGGT<br>GGAGCATTTCTGCAATTTTACCACATATTTTACGGGTTTCCACGACAACCGCAAAA<br>ACATGTACTCAGATAAGGCTAAATCCACGGCAATAGCCTATCGCCTGATACATGA<br>GAATTTCCCTCGGTTTTTTGACAATCTTCGCTCTTTTGCAAAGATTTCAGAAAGCG<br>AGGTGGCAAATCGGTTCCCTGAGATAGAATCTGCTTTCTCTCTGTATCTCAACGT<br>GGAACACATCGCCGACATGTTCCACGTTGACTATTTCCCAGTTGTTCTTACCCAA<br>GAACAAATTGATGTGTATAATAATATTATTGGAGGCAAGACGGAAGAAGATGGGA<br>CAAAAATACAGGGCATCAATGAATACATCAACCTTTATAACCAACATCACCCAGAT<br>GTAAAGTTGCCGTTCTTGAAACCTCTATACAAGATGATTCTTAGCGACAAGGTTG<br>CGCTTTCATGGTTGCCGGAGGAGTTTGAGAATGATGAAGAGATGTTGACGGCCA<br>TAAATGATTTTTACAAGTCAGTTCAGCCTGTCGTTTTCGGGGATGACGAGAATTGT<br>ATCCGTCATCTTCTGACGAATATTGCCGAATACAATACGGATCACATATACATTTC<br>AAACGATTTAGGATTGACTGGAATATCCCAGCAATTGTTCGACCAATACAGCATCT<br>TTGAAGACGTCATTAAAGATGAGTTGAGGCGTAATGTCAAACAGACGCCCAAAGA<br>GAAACGCAATCCTGAATTGTTGGAAGAAAGAATAAAGAACTTGTTCAAGAAAGAG<br>AAGAGTTTCTCCATCTCTTACCTGGACTCTCTCATTAAGGATAAGGGTGAGGATA<br>CGATCGAGTCTTATTATGCCAAACTTGGTGCGTTTGACAGAGACGGTAAGCAAAC<br>AGTGAATTTGCTCACGCAAATTGAAATGGCATACATAGCGGCAAAGGAGGTGCTT<br>GATGGTAAGTATGACAACATTAACCAGTCTGAAGAAGCAACGAAATATATTAAAGA<br>TCTTCTTGATGCGTTCAAGTCTTTGCAACACTACATCAAACCGCTGTTAGGTAGTG<br>GCGAAGAAGCAGAAAAGGATAATGTGTTTAGTTCGCAACTGCTCAATGTTTGGGA<br>GGCGTTAGACGTTGTGACTCCTCTTTATAACAAAGTTCGCAACTGGCTCACACGC<br>AAGCCTTACTCAACAAAAAAGATAAAGCTGAACTTTGAGAATGTCCAACTGCTTG<br>GCGGCTGGCCAAATATAGAAGCGTATTCATGTGCTATTTTTATGAAGGATGATAAT<br>ACTTACTATCTTGGAATACTGGACAATGCATATAAAACTTTATTAAGAGATTTTCCA<br>GAGCCTGCCGAAGAGAAGGATACTATTGGGCTAATGCATTACCTCCAAGGAGGC<br>GATATGGGAAAAAATATTCAGAATTTGATGGTGGTAGATGGAAAGGTTCGGAAAG<br>TTAATGGGCGCAAAGAGAAGTCAGGAATTAATGTTGGGCAGAATATTCGATTAGA<br>AGAAGCAAAAAAGAGATACCTGCCAACAGAAATCAATAGAATAAGGAAGTTGGGA<br>ACGTATTCTGTTTCAAATCCAAATTATAACAAACAAGATTTGATAACCATAATCGAT<br>TATTACAAGCCACTGGCTTGTGAATACTATGCTTCCTATACATTCCATTTCAAGGA<br>TTCTTCCGAGTATAATTCGTTCGCGGAGTTTACAGACGATATCAATCAGCAAGCG<br>TATCAACTTGGGTTTGTACCTTTTTCTCAACAATACTTAAACAAACTTGTAGACGAA<br>GGCAAACTCTACCTTTTCCAAATATGGAATAAAGATTTCTCTGATTATAGTAAAGG<br>CACTCCCAATATGCATACCCTTTATTGGAAGGCGCTCTTTGATAAAGCAAATCTTG<br>CCGATGTTGTCTACAAACTTAATGGTCGTCAGGCAGAGGTGTTCTATCGGAAAAG<br>AAGCCTCCAAAAAGAGAATACGACTGTGCACAAAGCATTGCAGCCTATAAAGAAT<br>AAAAACACGCAGAATGAGAAAAGCACCAGTACGTTTGACTATGACATCGTAAAAG<br>ATCGTCGTTATACAGTTGATAAATTCCATTTCCATGTGCCCATTACTATTAACTTTA<br>AGTCATCTGGAAAACCTAATATCAATGAACACGTTTTAGATATTATCCGTCACCAT<br>GGCATTGAGCATGTCATCGGAATCGACCGTGGCGAGCGCCATCTATTATATCTTT<br>CTCTTATAGATCTCAAGGGAAGAATAATCAAGCAAATGACGCTTAATGAGATAAAG<br>CAGCAAACAGGCGGTAACTATGGCACAAATTATAAAGAACTCTTGGCCGCAAGAG<br>AAGGCGATCGTGCGGAAGCGCGTCGTAACTGGAAAAAGATAGAGAATATTAAAG<br>ACCTTAAAGCTGGCTATCTCAGTCAGGTTGTACATGTGATAGCCCAAATGATGGT<br>GGAATACAATGCCATCGTTGTGCTCGAAGACCTCAATATGGGCTTTATGCGTGGG<br>CGGCAGAAAATCGAGCGGAGCGTATACGAGCAGTTCGAACACATGCTGATAGAT<br>AAGTTGAACTTCTATGTTGATAAGAAAAAGGAAGCATGTGCCCCCGGAGGTCTGC<br>TTCATGGTCTCCAATTAGCCAATAAATTTGAGAGCTTCAATAAGCTTGGGAAACAG<br>AGCGGTTGCCTTTTTTATGTACCGGCATGGAATACCAGCAAAATAGATCCTGTCA<br>CAGGGTTTGTCAATATGCTTGATGCACGCTATGAAAGTGTAGAAAGTTCGCGCCG<br>CTTCTTCTCTCGTTTCGATGTTATTCGTTACAATGAGGAAAAGAATTGGTTTGAAT<br>TTACTTTTGATTATAATAACTTCCATGCAAAGTTGGACGGGACAAAAACCCAATGG<br>ACGCTTTGCACATACGGCAGTCGCATCAAAACATTCCGCAACCCCGCAAAACTCA<br>ATCAATGGGATAATGAAGAGGTGGTTCTTACCGATGAATTTAAGAAGGTATTTGC<br>CAATGCTGGTATCAATATTCATGGGAATTTGAAAGAGGCCATTTGCTCTCTTGCTA<br>AACGGGAGCATTTAGAACCGTTGATGCATTTGATGAAACTGCTTTTACAGTTGCG<br>CAACAGCAAGACCAACTCAGAGGTCGACTATATGCTTTCTCCTGTGGCAGATAAT<br>GGCGTGTTTTACGACAGCCGTTCTTGCAATGGCAATTTGCCTATAGATGCCGATG<br>CCAATGGGGCATACAACATTGCCCGGAAAGGATTATGGGTTTTGCGCCAAATTCA<br>GGACTCTAAGCCTGGCGACAAACTGAATTTGGCTTTGTCGAACAAGGAATGGTTG<br>CGATTTGTTCAAGAAAAGAGCAACTTTGAATAA | 58 |
| Codon optimized coding | AAGGATCTGACAGGCCAGTACAGCCTCTCTAAGACCCTCAGATTTGAACTGAAGC<br>CTATCGGCAAGACCCTGGAGCACATCGAGCAAAAGGGCCTGCTGACCCAGGAC<br>GAGCAGAGAGCCGAGGAATACGAGCAGATGAAGGGAATTATTGACAGATACCAC | 59 |

TABLE 1J-continued

ZPPX Type V Cas Sequences

| Name | Sequence | SEQ ID NO. |
|---|---|---|
| sequence (no N-terminal methionine, no stop codon) | AAGGCCTTCATCACTATGTGCCTGAGAAATTGCAAGATCAAGGTGAACAACACCG<br>ACGATGAGCTGGACAGCCTGGAAGAGTACAGCAGCCTGCTGTCAAAGTCTAAGC<br>GGGACGCCGACGACGAGAACAAACTGGAGAAGATCAAGGAAAACCTGAGAAAG<br>CAGATCGTCAATGCCTTCAAGAGCGGAAACACCTACGGCGATCTGTTCACCAAG<br>GAGCTGATCAAGAACCACCTCCCCGATTTTGTGACCGACGAGGAAGAAAAGCAG<br>GTGGTGGAACACTTCTGCAACTTCACCACCTACTTCACCGGCTTTCACGACAACC<br>GCAAGAACATGTACAGCGACAAGGCCAAGAGCACAGCCATCGCCTACAGACTGA<br>TCCACGAGAACTTTCCAAGATTTTTCGATAATCTGCGGAGCTTTGCCAAGATCTC<br>CGAATCTGAAGTGGCCAACAGATTCCCAGAAATCGAGAGCGCCTTTAGCCTGTA<br>CCTGAATGTGGAACATATCGCCGATATGTTCCACGTGGACTACTTCCCAGTGGTG<br>CTGACCCAGGAGCAGATTGACGTGTACAACAACATCATCGGAGGCAAGACCGAG<br>GAAGATGGCACAAAGATTCAGGGCATCAACGAGTATATCAACCTGTACAACCAAC<br>ACCATCCTGACGTCAAACTGCCCTTCCTGAAGCCTCTGTATAAGATGATCCTGAG<br>CGACAAGGTGGCCCTGAGCTGGCTGCCTGAAGAGTTCGAGAACGACGAGGAAA<br>TGCTGACCGCCATCAATGATTTCTACAAGTCTGTGCAGCCTGTGGTGTTCGGCGA<br>TGACGAGAACTGTATCAGACACCTGCTGACAAACATCGCCGAGTACAACACCGAT<br>CACATTTACATCAGCAATGACCTGGGACTGACTGGCATCTCTCAGCAGCTGTTCG<br>ACCAGTACTCTATCTTCGAAGATGTGATCAAGGACGAGCTACGGCGGAACGTGA<br>AGCAAACACCTAAGGAGAAGCGGAACCCCGAACTGCTGGAAGAGAGAATCAAGA<br>ACCTGTTCAAGAAAGAAAAGAGCTTCTCCATCAGCTACCTGGATAGCCTGATCAA<br>GGACAAAGGAGAAGATACCATCGAGAGCTACTACGCCAAGCTGGGCGCCTTCGA<br>CAGAGATGGCAAGCAGACAGTGAACCTGCTCACCCAGATCGAGATGGCCTACAT<br>CGCCGCTAAGGAAGTGCTGGATGGCAAGTACGACAACATCAACCAGAGCGAGGA<br>AGCTACAAAGTACATCAAGGATCTGCTTGACGCCTTCAAGAGCCTGCAGCACTAC<br>ATCAAGCCCCTGCTGGGCAGCGGCGAGGAGGCCGAAAAAGACAACGTGTTCAG<br>CAGCCAGCTCCTGAACGTGTGGGAGGCTCTGGACGTGGTGACGCCTCTGTACAA<br>CAAGGTCAGAAATTGGCTGACAAGAAAGCCCTACAGTACCAAGAAAATCAAACTG<br>AACTTCGAGAATGTTCAACTGCTGGGCGGATGGCCTAACATCGAGGCCTATAGC<br>TGCGCCATTTTTATGAAAGACGACAACACCTACTACTTAGGCATCCTGGACAACG<br>CCTATAAAACACTACTTCGGGACTTTCCTGAACCTGCTGAAGAAAAGGACACAAT<br>CGGCCTGATGCACTACCTGCAAGGAGGCGACATGGGCAAGAACATCCAGAACCT<br>GATGGTCGTCGACGGGAAGGTGCGGAAGGTGAACGGCCGTAAGGAAAAGTCCG<br>GCATCAACGTGGGCCAGAATATCCGGCTGGAGGAGGCCAAGAAGAGATACCTG<br>CCTACAGAGATCAACAGAATCAGAAAGCTGGGCACCTACTCTGTGAGCAACCCTA<br>ATTATAACAAGCAGGATCTGATTACAATCATCGACTACTACAAGCCACTGGCCTG<br>CGAGTACTACGCCTCTTATACATTCCACTTCAAGGACAGCAGCGAGTACAACAGC<br>TTCGCCGAGTTCACCGATGATATCAACCAGCAGGCCTACCAGTTGGGCTTCGTG<br>CCTTTCTCCCAGCAATACCTCAACAAACTGGTGGACGAGGGCAAGCTGTACCTGT<br>TCCAGATCTGGAATAAGGACTTCTCTGACTACTCTAAGGGCACCCCCAACATGCA<br>CACCCTGTACTGGAAGGCCCTGTTTGACAAGGCCAATCTGGCTGATGTGGTTTAC<br>AAGCTGAACGGCAGACAGGCCGAGGTGTTTTACAGAAAGAGAAGCCTGCAGAAA<br>GAGAACACAACCGTGCACAAGGCTCTGCAGCCCATCAAGAATAAGAACACACAG<br>AACGAGAAATCTACCAGCACATTCGATTACGATATCGTGAAGGACAGAAGATACA<br>CCGTGGACAAGTTCCATTTCCACGTTCCTATCACCATCAACTTCAAGTCCAGCGG<br>CAAGCCTAACATCAACGAGCATGTGCTGGATATCATCAGACACCACGGCATCGA<br>GCACGTGATCGGCATCGACCGCGGCGAAAGGCACCTGCTGTACCTGTCCCTGAT<br>CGACCTGAAAGGACGGATCATAAAGCAGATGACCCTTAACGAGATCAAACAACA<br>GACCGGCGGCAACTACGGCACAAACTACAAAGAGCTGCTGGCCGCCAGAGAAG<br>GCGACAGAGCCGAGGCTAGAAGAAACTGGAAGAAAATCGAGAACATCAAGGACC<br>TGAAGGCCGGCTACCTGAGCCAGGTGGTGCACGTGATTGCTCAGATGATGGTGG<br>AATACAACGCCATTGTAGTGCTGGAGGACCTGAACATGGGCTTCATGAGAGGCA<br>GACAGAAGATCGAGAGAAGCGTGTACGAGCAGTTCGAGCACATGCTGATTGACA<br>AGCTGAACTTCTACGTGGACAAAAAGAAGGAAGCATGCGCCCCTGGCGGACTTC<br>TGCACGGCCTGCAGCTGGCCAACAAATTCGAGTCTTTCAACAAACTGGGCAAGC<br>AATCCGGCTGTCTGTTCTACGTGCCCGCCTGGAACACCAGCAAGATCGATCCTG<br>TGACCGGATTCGTGAACATGCTGGACGCCCGGTACGAGAGCGTGGAGAGCTCC<br>CGGCGGTTCTTCTCCAGATTTGACGTGATCAGATACAACGAGGAGAAGAACTGG<br>TTCGAGTTCACCTTTGATTATAACAACTTCCACGCCAAACTGGATGGCACCAAGA<br>CCCAGTGGACACTGTGCACCTACGGCAGCAGAATCAAGACCTTTAGAAATCCTG<br>CTAAGCTGAATCAGTGGGACAATGAAGAGGTGGTTCTGACCGACGAATTTAAGAA<br>GGTGTTCGCCAACGCCGGAATCAATATCCACGGCAACCTGAAGGAAGCTATCTG<br>CAGCCTGGCCAAAAGAGAGCACCTGGAACCTCTGATGCACCTGATGAAACTGCT<br>GCTGCAACTTCGGAATAGCAAAACCAACAGCGAGGTCGACTACATGCTGTCTCC<br>AGTGGCCGATAATGGAGTGTTCTACGACAGCAGAAGCTGTAACGGTAACCTGCC<br>TATCGACGCCGACGCCAACGGAGCCTACAATATCGCTAGAAAAGGTCTGTGGGT<br>CCTCAGGCAAATCCAGGATAGCAAGCCCGGCGACAAGCTGAACCTGGCTCTGAG<br>CAACAAGGAATGGCTGCGATTTGTACAGGAGAAAAGCAATTTCGAG | |
| Expression construct (with N-terminal methionine and stop codon, | ATGggcAAGGATCTGACAGGCCAGTACAGCCTCTCTAAGACCCTCAGATTTGAACT<br>GAAGCCTATCGGCAAGACCCTGGAGCACATCGAGCAAAAGGGCCTGCTGACCCA<br>GGACGAGCAGAGAGCCGAGGAATACGAGCAGATGAAGGGAATTATTGACAGATA<br>CCACAAGGCCTTCATCACTATGTGCCTGAGAAATTGCAAGATCAAGGTGAACAAC<br>ACCGACGATGAGCTGGACAGCCTGGAAGAGTACAGCAGCCTGCTGTCAAAGTCT<br>AAGCGGGACGCCGACGACGAGAACAAACTGGAGAAGATCAAGGAAAACCTGAG | 60 |

TABLE 1J-continued

| ZPPX Type V Cas Sequences | | |
|---|---|---|
| Name | Sequence | SEQ ID NO. |
| includes V5-<br>tag and C-<br>terminal NLS) | AAAGCAGATCGTCAATGCCTTCAAGAGCGGAAACACCTACGGCGATCTGTTCAC<br>CAAGGAGCTGATCAAGAACCACCTCCCCGATTTTGTGACCGACGAGGAAGAAAA<br>GCAGGTGGTGGAACACTTCTGCAACTTCACCACCTACTTCACCGGCTTTCACGAC<br>AACCGCAAGAACATGTACAGCGACAAGGCCAAGAGCACAGCCATCGCCTACAGA<br>CTGATCCACGAGAACTTTCCAAGATTTTTCGATAATCTGCGGAGCTTTGCCAAGA<br>TCTCCGAATCTGAAGTGGCCAACAGATTCCCAGAAATCGAGAGCGCCTTTAGCCT<br>GTACCTGAATGTGGAACATATCGCCGATATGTTCCACGTGGACTACTTCCCAGTG<br>GTGCTGACCCAGGAGCAGATTGACGTGTACAACAACATCATCGGAGGCAAGACC<br>GAGGAAGATGGCACAAAGATTCAGGGCATCAACGAGTATATCAACCTGTACAACC<br>AACACCATCCTGACGTCAAACTGCCCTTCCTGAAGCCTCTGTATAAGATGATCCT<br>GAGCGACAAGGTGGCCCTGAGCTGGCTGCCTGAAGAGTTCGAGAACGACGAGG<br>AAATGCTGACCGCCATCAATGATTTCTACAAGTCTGTGCAGCCTGTGGTGTTCGG<br>CGATGACGAGAACTGTATCAGACACCTGCTGACAAACATCGCCGAGTACAACAC<br>CGATCACATTTACATCAGCAATGACCTGGGACTGACTGGCATCTCTCAGCAGCTG<br>TTCGACCAGTACTCTATCTTCGAAGATGTGATCAAGGACGAGCTACGGCGGAAC<br>GTGAAGCAAACACCTAAGGAGAAGCGGAACCCCGAACTGCTGGAAGAGAGAATC<br>AAGAACCTGTTCAAGAAAGAAAAGAGCTTCTCCATCAGCTACCTGGATAGCCTGA<br>TCAAGGACAAAGGAGAAGATACCATCGAGAGCTACTACGCCAAGCTGGGCGCCT<br>TCGACAGAGATGGCAAGCAGACAGTGAACCTGCTCACCCAGATCGAGATGGCCT<br>ACATCGCCGCTAAGGAAGTGCTGGATGGCAAGTACGACAACATCAACCAGAGCG<br>AGGAAGCTACAAAGTACATCAAGGATCTGCTTGACGCCTTCAAGAGCCTGCAGC<br>ACTACATCAAGCCCCTGCTGGGCAGCGGCGAGGAGGCCGAAAAAGACAACGTG<br>TTCAGCAGCCAGCTCCTGAACGTGTGGGAGGCTCTGGACGTGGTGACGCCTCTG<br>TACAACAAGGTCAGAAATTGGCTGACAAGAAAGCCCTACAGTACCAAGAAAATCA<br>AACTGAACTTCGAGAATGTTCAACTGCTGGGCGGATGGCCTAACATCGAGGCCT<br>ATAGCTGCGCCATTTTTATGAAAGACGACAACACCTACTACTTAGGCATCCTGGA<br>CAACGCCTATAAAACACTACTTCGGGACTTTCCTGAACCTGCTGAAGAAAAGGAC<br>ACAATCGGCCTGATGCACTACCTGCAAGGAGGCGACATGGGCAAGAACATCCAG<br>AACCTGATGGTCGTCGACGGGAAGGTGCGGAAGGTGAACGGCCGTAAGGAAAA<br>GTCCGGCATCAACGTGGGCCAGAATATCCGGCTGGAGGAGGCCAAGAAGAGAT<br>ACCTGCCTACAGAGATCAACAGAATCAGAAAGCTGGGCACCTACTCTGTGAGCA<br>ACCCTAATTATAACAAGCAGGATCTGATTACAATCATCGACTACTACAAGCCACTG<br>GCCTGCGAGTACTACGCCTCTTATACATTCCACTTCAAGGACAGCAGCGAGTACA<br>ACAGCTTCGCCGAGTTCACCGATGATATCAACCAGCAGGCCTACCAGTTGGGCT<br>TCGTGCCTTTCTCCCAGCAATACCTCAACAAACTGGTGGACGAGGGCAAGCTGT<br>ACCTGTTCCAGATCTGGAATAAGGACTTCTCTGACTACTCTAAGGGCACCCCCAA<br>CATGCACACCCTGTACTGGAAGGCCCTGTTTGACAAGGCCAATCTGGCTGATGT<br>GGTTTACAAGCTGAACGGCAGACAGGCCGAGGTGTTTTACAGAAAGAGAAGCCT<br>GCAGAAAGAGAACACAACCGTGCACAAGGCTCTGCAGCCCATCAAGAATAAGAA<br>CACACAGAACGAGAAATCTACCAGCACATTCGATTACGATATCGTGAAGGACAGA<br>AGATACACCGTGGACAAGTTCCATTTCCACGTTCCTATCACCATCAACTTCAAGTC<br>CAGCGGCAAGCCTAACATCAACGAGCATGTGCTGGATATCATCAGACACCACGG<br>CATCGAGCACGTGATCGGCATCGACCGCGGCGAAAGGCACCTGCTGTACCTGTC<br>CCTGATCGACCTGAAAGGACGGATCATAAAGCAGATGACCCTTAACGAGATCAAA<br>CAACAGACCGGCGGCAACTACGGCACAAACTACAAAGAGCTGCTGGCCGCCAG<br>AGAAGGCGACAGAGCCGAGGCTAGAAGAAACTGGAAGAAAATCGAGAACATCAA<br>GGACCTGAAGGCCGGCTACCTGAGCCAGGTGGTGCACGTGATTGCTCAGATGAT<br>GGTGGAATACAACGCCATTGTAGTGCTGGAGGACCTGAACATGGGCTTCATGAG<br>AGGCAGACAGAAGATCGAGAGAAGCGTGTACGAGCAGTTCGAGCACATGCTGAT<br>TGACAAGCTGAACTTCTACGTGGACAAAAAGAAGGAAGCATGCGCCCCTGGCGG<br>ACTTCTGCACGGCCTGCAGCTGGCCAACAAATTCGAGTCTTTCAACAAACTGGGC<br>AAGCAATCCGGCTGTCTGTTCTACGTGCCCGCCTGGAACACCAGCAAGATCGAT<br>CCTGTGACCGGATTCGTGAACATGCTGGACGCCCGGTACGAGAGCGTGGAGAG<br>CTCCCGGCGGTTCTTCTCCAGATTTGACGTGATCAGATACAACGAGGAGAAGAA<br>CTGGTTCGAGTTCACCTTTGATTATAACAACTTCCACGCCAAACTGGATGGCACC<br>AAGACCCAGTGGACACTGTGCACCTACGGCAGCAGAATCAAGACCTTTAGAAAT<br>CCTGCTAAGCTGAATCAGTGGGACAATGAAGAGGTGGTTCTGACCGACGAATTTA<br>AGAAGGTGTTCGCCAACGCCGGAATCAATATCCACGGCAACCTGAAGGAAGCTA<br>TCTGCAGCCTGGCCAAAAGAGAGCACCTGGAACCTCTGATGCACCTGATGAAAC<br>TGCTGCTGCAACTTCGGAATAGCAAAACCAACAGCGAGGTCGACTACATGCTGT<br>CTCCAGTGGCCGATAATGGAGTGTTCTACGACAGCAGAAGCTGTAACGGTAACC<br>TGCCTATCGACGCCGACGCCAACGGAGCCTACAATATCGCTAGAAAAGGTCTGT<br>GGGTCCTCAGGCAAATCCAGGATAGCAAGCCCGGCGACAAGCTGAACCTGGCT<br>CTGAGCAACAAGGAATGGCTGCGATTTGTACAGGAGAAAAGCAATTTCGAGtctaga<br>AAGCGGACAGCAGACGGCTCCGAATTTGAAAGCCCTAAGAAAAAGAGAAAGGTG<br>ggatccGGCAAACCTATCCCCAATCCCCTGCTGGGCCTGGACAGCACCTGA | |

In some embodiments a ZPPX Type V Cas protein comprises an amino acid sequence of SEQ ID NO:55, SEQ ID NO:56, or SEQ ID NO:57. In some embodiments, a ZPPX Type V Cas protein has nickase activity, for example resulting from one or more amino acid substitutions relative to the sequence of SEQ ID NO:55, SEQ ID NO:56, or SEQ ID NO:57. In some embodiments, the one or more amino acid substitutions providing nickase activity comprise a D877 substitution, wherein the position of the D877 substitution is defined with respect to the amino acid numbering of SEQ ID NO:56 (corresponding to amino acid 908 of SEQ ID NO:121). In some embodiments, the one or more amino acid substitutions providing nickase activity comprise an E969 substitution, wherein the position of the E969 substitution is defined with respect to the amino acid numbering of SEQ ID NO:56 (corresponding to amino acid 993 of SEQ ID NO:121). In some embodiments, the one or more amino acid substitutions providing nickase activity comprise a R1181 substitution, wherein the position of the R1181 substitution is defined with respect to the amino acid numbering of SEQ ID NO:56 (corresponding to amino acid 1226 of SEQ ID NO:121). In some embodiments, the one or more amino acid substitutions providing nickase activity comprise a D1217 substitution, wherein the position of the D1217 substitution is defined with respect to the amino acid numbering of SEQ ID NO:56 (corresponding to amino acid 1263 of SEQ ID NO:121). In some embodiments, a ZPPX Type V Cas protein is catalytically inactive, for example due to a R1181 substitution in combination with a D877 substitution, a E969 substitution, and/or D1217 substitution.

6.2.11. ZXHQ Type V Cas Proteins

In one aspect, the disclosure provides ZXHQ Type V Cas proteins. ZXHQ Type V Cas proteins can be further classified as Type V-A Cas proteins. The ZXHQ Type V Cas proteins typically comprise an amino acid sequence that is at least 50%, at least 55%, at least 60%, at least 65%, at least 70%, at least 75%, at least 85%, at least 90%, or at least 95% identical to SEQ ID NO:61. In some embodiments, the ZXHQ Type V Cas proteins comprise an amino acid sequence that is at least 95%, at least 96%, at least 97%, at least 98%, or at least 99% identical to SEQ ID NO:61. In some embodiments, a ZXHQ Type V Cas protein comprises an amino acid sequence that is identical to SEQ ID NO:61.

Exemplary ZXHQ Type V Cas protein sequences and nucleotide sequences encoding exemplary ZXHQ Type V Cas proteins are set forth in Table 1K.

TABLE 1K

ZXHQ Type V Cas Sequences

| Name | Sequence | SEQ ID NO. |
|---|---|---|
| Wildtype amino acid sequence (without N-terminal methionine) | TNTSIFKTFTNQYSLSKTLRFELRPHPMTSGLDDIISLDTGIKKLYENEMKPLFDEL HFEFISQSLVQVSFPSEKLEVLLNKYRSLKDQKAKNIEKELEGPLQELRTIITDTFES TGNNWKKEWLQQGFKIKSSGYKVLTEEGILEVLSVRKKDKADAINKFKGFFTYFS GFNMNRENYYSSEDKKTAVAYRVINENLIRYMDNILLLQNVLAKAPEFKKFEDILSL TTFGKYINQEGITTYNNNVVATINLELNTYHQHNPKIFSRLPKLKLLYKQIGSPKED KRIFTIEKRTEWQSLEDLIQKQNKVVEHEKKNVEILSNLKAAYISFFTNTDETILSEV YFNKRSLNTISSFWFTGGWQTLLLKLKEFKLANQNKDGDIVVPKALSLAELKQVLD SLEEQDPAVNHLFKEMYSDCYKENLWQTFIAIWQCEITSKFNLLEGYIQECNAVKE DTFDKKKHKNIIKNICDTYLDIEQISKYIIVHESLPKYDALYDAVILYLQESSLRSYYD AFRNLISKRPVNEEKVKLNFQNSTLLDGWDMNKESANLCVLLKNNIGEYFLAVMN KKSNMVFDQKKNSALYSAGNESSFQKLEYKLLPGPNKMLPKVIFAKSNEKYFIIPE EIVQIREEESFKKGKKFDKHALKTWIRFMQESIEKYPGWKTFDFTFKKPEEYEDVS KFYKDVEEQGYKLNWKDINEEELLSLVEQKKVYLFQIKSKDIGETKEHGNKNLHTL LFLELLKPENTSRLKLLGGGEMFYRAPSMEKVYKTVNEKQVLDSKGNPILEAKRY YEPKFFLHFPIQVKGSENGYKTEMNPKILRAISTSKEVNIIGIDRGEKHLLYYYVIKP DGTPITQGSLNTISLGLDKNQNPRLVDERTFKILERDSKGKPSKISDFESTGKKVD YIDYHNILTYYETKRNIARRSWDTIGAIKNFKEGYLSQAIHQIYQLMLKYNAVVVLE DLNTEFKAKRTAKVEKSVYEKFEIALAKKLNHLIIKGTDPAEAGSVINPYQLTPAITA DTLSDFKKSKQWGPLFYIRANYTSTTDPITGWRKHIYIPSGASDKEIKTYFCKQGE KEPLIQISYDTALTAFAFTYTHEGKEWTLHATKDTQRMRYDSKKRKMEPVEIFDRL RELFIDFSFEESLTDQLEATLSFDWKTLAFLWTMLNQIRNTDREAEGNDGDFIQSP VAPFYDSRDPENKTNGLPVNGDANGAFNIARKGAILIKRIQEYAKKDPTFEKMREK DGLNLYISDAEWDTEIS | 61 |
| Wildtype amino acid sequence (with N-terminal methionine) | MTNTSIFKTFTNQYSLSKTLRFELRPHPMTSGLDDIISLDTGIKKLYENEMKPLFDE LHFEFISQSLVQVSFPSEKLEVLLNKYRSLKDQKAKNIEKELEGPLQELRTIITDTFE STGNNWKKEWLQQGFKIKSSGYKVLTEEGILEVLSVRKKDKADAINKFKGFFTYF SGFNMNRENYYSSEDKKTAVAYRVINENLIRYMDNILLLQNVLAKAPEFKKFEDIL SLTTFGKYINQEGITTYNNNVVATINLELNTYHQHNPKIFSRLPKLKLLYKQIGSPKE DKRIFTIEKRTEWQSLEDLIQKQNKVVEHEKKNVEILSNLKAAYISFFTNTDETILSE VYFNKRSLNTISSFWFTGGWQTLLLKLKEFKLANQNKDGDIVVPKALSLAELKQVL DSLEEQDPAVNHLFKEMYSDCYKENLWQTFIAIWQCEITSKFNLLEGYIQECNAV KEDTFDKKKHKNIIKNICDTYLDIEQISKYIIVHESLPKYDALYDAVILYLQESSLRSY YDAFRNLISKRPVNEEKVKLNFQNSTLLDGWDMNKESANLCVLLKNNIGEYFLAV MNKKSNMVFDQKKNSALYSAGNESSFQKLEYKLLPGPNKMLPKVIFAKSNEKYFII PEEIVQIREEESFKKGKKFDKHALKTWIRFMQESIEKYPGWKTFDFTFKKPEEYED VSKFYKDVEEQGYKLNWKDINEEELLSLVEQKKVYLFQIKSKDIGETKEHGNKNLH TLLFLELLKPENTSRLKLLGGGEMFYRAPSMEKVYKTVNEKQVLDSKGNPILEAK RYYEPKFFLHFPIQVKGSENGYKTEMNPKILRAISTSKEVNIIGIDRGEKHLLYYYVI KPDGTPITQGSLNTISLGLDKNQNPRLVDERTFKILERDSKGKPSKISDFESTGKK VDYIDYHNILTYYETKRNIARRSWDTIGAIKNFKEGYLSQAIHQIYQLMLKYNAVVV LEDLNTEFKAKRTAKVEKSVYEKFEIALAKKLNHLIIKGTDPAEAGSVINPYQLTPAI TADTLSDFKKSKQWGPLFYIRANYTSTTDPITGWRKHIYIPSGASDKEIKTYFCKQ GEKEPLIQISYDTALTAFAFTYTHEGKEWTLHATKDTQRMRYDSKKRKMEPVEIF DRLRELFIDFSFEESLTDQLEATLSFDWKTLAFLWTMLNQIRNTDREAEGNDGDFI QSPVAPFYDSRDPENKTNGLPVNGDANGAFNIARKGAILIKRIQEYAKKDPTFEKM REKDGLNLYISDAEWDTEIS | 62 |
| Expression construct (with N-terminal methionine, | MGSGTNTSIFKTFTNQYSLSKTLRFELRPHPMTSGLDDIISLDTGIKKLYENEMKPL FDELHFEFISQSLVQVSFPSEKLEVLLNKYRSLKDQKAKNIEKELEGPLQELRTIITD TFESTGNNWKKEWLQQGFKIKSSGYKVLTEEGILEVLSVRKKDKADAINKFKGFF TYFSGFNMNRENYYSSEDKKTAVAYRVINENLIRYMDNILLLQNVLAKAPEFKKFE | 63 |

TABLE 1K-continued

ZXHQ Type V Cas Sequences

| Name | Sequence | SEQ ID NO. |
| --- | --- | --- |
| V5-tag and C-terminal NLS) aa sequence | DILSLTTFGKYINQEGITTYNNNVVATINLELNTYHQHNPKIFSRLPKLKLLYKQIGS<br>PKEDKRIFTIEKRTEWQSLEDLIQKQNKVVEHEKKNVEILSNLKAAYISFFTNTDETI<br>LSEVYFNKRSLNTISSFWFTGGWQTLLLKLKEFKLANQNKDGDIVVPKALSLAELK<br>QVLDSLEEQDPAVNHLFKEMYSDCYKENLWQTFIAIWQCEITSKFNLLEGYIQEC<br>NAVKEDTFDKKKHKNIIKNICDTYLDIEQISKYIIVHESLPKYDALYDAVILYLQESSL<br>RSYYDAFRNLISKRPVNEEKVKLNFQNSTLLDGWDMNKESANLCVLLKNNIGEYF<br>LAVMNKKSNMVFDQKKNSALYSAGNESSFQKLEYKLLPGPNKMLPKVIFAKSNEK<br>YFIIPEEIVQIREEESFKKGKKFDKHALKTWIRFMQESIEKYPGWKTFDFTFKKPEE<br>YEDVSKFYKDVEEQGYKLNWKDINEEELLSLVEQKKVYLFQIKSKDIGETKEHGN<br>KNLHTLLFLELLKPENTSRLKLLGGGEMFYRAPSMEKVYKTVNEKQVLDSKGNPIL<br>EAKRYYEPKFFLHFPIQVKGSENGYKTEMNPKILRAISTSKEVNIIGIDRGEKHLLY<br>YYVIKPDGTPITQGSLNTISLGLDKNQNPRLVDERTFKILERDSKGKPSKISDFEST<br>GKKVDYIDYHNILTYYETKRNIARRSWDTIGAIKNFKEGYLSQAIHQIYQLMLKYNA<br>WVVLEDLNTEFKAKRTAKVEKSVYEKFEIALAKKLNHLIIKGTDPAEAGSVINPYQL<br>TPAITADTLSDFKKSKQWGPLFYIRANYTSTTDPITGWRKHIYIPSGASDKEIKTYF<br>CKQGEKEPLIQISYDTALTAFAFTYTHEGKEWTLHATKDTQRMRYDSKKRKMEPV<br>EIFDRLRELFIDFSFEESLTDQLEATLSFDWKTLAFLWTMLNQIRNTDREAEGNDG<br>DFIQSPVAPFYDSRDPENKTNGLPVNGDANGAFNIARKGAILIKRIQEYAKKDPTF<br>EKMREKDGLNLYISDAEWDTEISSRKRTADGSEFESPKKKRKVGSGKPIPNPLLG<br>LDST | |
| Wildtype coding sequence (with N-terminal methionine and stop codon) | ATGACTAACACATCTATTTTCAAAACCTTCACTAATCAATATTCACTTTCAAAAA<br>CGTTGCGGTTTGAGTTGAGACCTCATCCGATGACTAGTGGTCTAGATGATATC<br>ATTTCATTAGATACTGGCATAAAAAAATTGTATGAAAACGAGATGAAGCCGCTA<br>TTTGATGAACTTCATTTTGAATTTATCTCTCAGTCGCTAGTTCAAGTATCATTCC<br>CTTCAGAAAAACTGGAAGTTTTGCTAAACAAGTATAGGTCTCTTAAGGATCAG<br>AAAGCTAAAAATATAGAAAAAGAACTGGAAGGCCCATTACAGGAACTAAGAAC<br>AATTATTACTGACACCTTTGAATCCACTGGTAACAACTGGAAAAAAGAATGGCT<br>ACAACAAGGGTTTAAAATCAAAAGCTCGGGATACAAAGTACTAACAGAAGAGG<br>GAATATTAGAAGTATTGTCTGTTCGTAAAAAAGATAAAGCGGATGCAATCAATA<br>AATTTAAAGGATTCTTCACGTACTTTTCAGGGTTTAACATGAACCGTGAAAATT<br>ATTATTCATCGGAAGATAAAAAAACAGCTGTAGCGTATAGGGTAATTAATGAAA<br>ACCTTATCCGGTATATGGATAACATTCTCCTCCTTCAGAATGTTTTAGCAAAAG<br>CTCCTGAGTTTAAAAAGTTTGAAGATATTTTAAGTCTTACTACATTTGGAAAATA<br>CATAAATCAGGAAGGAATAACTACATATAATAATAACGTAGTTGCAACAATTAA<br>TCTTGAACTTAATACGTACCATCAGCATAATCCAAAAATCTTTTCTCGCCTGCC<br>AAAGTTAAAATTGCTTTATAAACAAATTGGTTCACCAAAAGAGGACAAACGCAT<br>TTTTACTATTGAAAAAAGAACGGAATGGCAGAGTTTGGAAGACTTAATACAAAA<br>ACAGAATAAAGTTGTTGAACACGAAAAAAAGAATGTTGAAATCCTGTCAAATTT<br>GAAAGCAGCATACATTTCTTTTTTCACGAACACAGATGAAACAATCTTAAGCGA<br>GGTATATTTCAATAAGCGTTCTCTTAATACAATTTCTTCTTTCTGGTTTACGGGT<br>GGCTGGCAAACACTGCTTCTTAAACTAAAAGAGTTTAAATTGGCCAATCAAAA<br>CAAAGATGGTGATATAGTAGTCCCTAAAGCATTATCCCTTGCTGAACTAAAAC<br>AGGTGCTTGATTCGTTAGAAGAGCAAGACCCTGCTGTTAATCATTTATTTAAG<br>GAAATGTACTCAGATTGTTACAAAGAAAACCTATGGCAGACCTTTATAGCTATC<br>TGGCAATGTGAAATTACATCAAAATTTAACCTGCTCGAAGGGTATATTCAAGAA<br>TGTAATGCTGTTAAAGAAGACACCTTTGATAAAAAAAAGCATAAAAATATTATC<br>AAAAACATCTGCGATACATACCTGGATATTGAGCAGATATCAAAATACATAATA<br>GTACATGAAAGTCTTCCTAAATATGATGCGCTATATGATGCGGTAATACTTTAT<br>TTGCAGGAATCTTCTTTACGCAGTTATTACGATGCCTTCCGCAACCTTATTAGC<br>AAGCGACCTGTTAACGAAGAAAAAGTTAAGCTCAACTTTCAGAACTCTACCCT<br>GCTTGATGGCTGGGATATGAATAAAGAAAGCGCTAACTTATGCGTATTACTGA<br>AAAACAATATAGGTGAATACTTCCTTGCTGTAATGAATAAAAAGAGCAACATGG<br>TTTTTGATCAGAAGAAAAACTCTGCCCTTTACTCTGCTGGGAATGAAAGTAGTT<br>TTCAGAAGCTGGAGTATAAACTGTTGCCTGGGCCTAACAAAATGCTGCCAAAA<br>GTAATTTTTGCAAAATCGAACGAAAAATATTTCATCATACCGGAAGAAATTGTG<br>CAGATTAGAGAAGAAGAATCGTTTAAAAAAGGAAAAAAATTTGATAAGCATGC<br>ATTGAAAACGTGGATCAGGTTTATGCAGGAATCAATTGAAAAATACCCAGGTT<br>GGAAGACATTCGACTTTACCTTTAAAAAACCGGAAGAGTACGAAGATGTCAGC<br>AAGTTCTATAAAGATGTAGAAGAACAGGGGTATAAACTAAACTGGAAAGATAT<br>TAACGAGGAAGAGCTCCTGTCACTTGTAGAACAAAAAAAAGTATATCTGTTTC<br>AGATAAAAAGCAAAGATATCGGAGAAACAAAGGAGCACGGCAACAAGAACCT<br>TCACACATTGTTATTTTTAGAACTCCTCAAACCGGAAAATACCAGCAGGTTAAA<br>GCTACTGGGCGGTGGCGAAATGTTTTATCGTGCGCCAAGTATGGAAAAGGTA<br>TACAAAACCGTAAATGAAAAACAGGTTCTGGATTCAAAAGGTAACCCCATTTTA<br>GAAGCAAAACGGTACTATGAACCAAAGTTTTTCCTTCACTTCCCTATTCAGGTC<br>AAAGGGAGCGAAAATGGTTATAAAACAGAAATGAATCCGAAAATATTGCGGGC<br>AATTAGCACTTCAAAAGAAGTAAATATAATAGGAATAGACCGTGGAGAAAAGC<br>ATTTACTCTATTATTACGTTATAAAGCCAGACGGAACTCCAATTACTCAAGGAA<br>GCCTGAATACAATTAGTTTAGGTTTAGATAAAAATCAAAATCCCAGACTTGTTG<br>ACGAGCGTACCTTCAAGATTTTGGAGAGAGATTCCAAGGGAAAACCATCAAAA<br>ATATCAGATTTTGAATCTACAGGGAAAAAAGTTGATTACATAGATTATCACAAT<br>ATACTTACCTATTACGAAACAAAACGCAATATAGCACGCCGTTCGTGGGATAC<br>TATTGGGGCAATAAAAAACTTTAAAGAGGGGTACTTGTCTCAGGCGATTCACC<br>AGATTTATCAGCTTATGTTGAAGTATAACGCTGTGGTAGTTTTGGAAGATCTTA | 64 |

TABLE 1K-continued

ZXHQ Type V Cas Sequences

| Name | Sequence | SEQ ID NO. |
|---|---|---|
| | ATACGGAGTTTAAGGCAAAACGAACCGCAAAAGTTGAAAAATCCGTGTACGAA<br>AAGTTTGAAATTGCCCTTGCTAAAAAACTGAACCACTTAATTATTAAAGGAACT<br>GACCCTGCAGAAGCAGGAAGCGTAATAAATCCGTATCAGCTTACTCCAGCAAT<br>TACAGCTGATACATTAAGCGACTTTAAGAAATCAAAACAATGGGGTCCGCTTT<br>TCTATATTAGAGCAAACTATACCTCTACGACTGACCCTATAACCGGCTGGCGT<br>AAACACATATATATCCCGTCCGGAGCTTCAGATAAAGAAATTAAAACATATTTC<br>TGTAAACAGGGCGAAAAAGAACCTTTGATTCAGATTTCATATGATACAGCGCT<br>TACCGCGTTTGCATTTACCTATACCCATGAAGGCAAAGAATGGACATTACACG<br>CAACGAAAGATACTCAGCGTATGCGTTATGACAGTAAGAAGCGGAAGATGGA<br>ACCCGTAGAAATATTTGATAGACTACGAGAGCTTTTTATAGATTTTAGTTTCGA<br>AGAATCGTTAACAGATCAACTAGAAGCAACACTTTCCTTTGACTGGAAAACAC<br>TGGCCTTTTTGTGGACAATGTTAAACCAGATACGTAATACCGACAGAGAAGCA<br>GAAGGGAATGACGGTGACTTTATTCAGTCTCCGGTTGCTCCGTTTTATGATAG<br>TCGAGATCCGGAAAATAAAACAAATGGACTTCCTGTTAACGGAGATGCTAATG<br>GGGCTTTCAATATAGCCAGAAAAGGTGCAATCCTGATAAAACGTATTCAAGAA<br>TATGCAAAAAAAGACCCCACCTTTGAAAAGATGAGAGAAAAAGATGGTCTCAA<br>TTTGTATATATCTGATGCAGAGTGGGATACAGAAATAAGCTAA | |
| Codon optimized coding sequence (no N-terminal methionine, no stop codon) | ACAAACACTAGCATCTTCAAGACATTCACCAACCAATACAGCCTCTCCAAGAC<br>CCTGCGGTTTGAGCTCAGACCCCACCCTATGACCTCCGGCCTGGACGACATC<br>ATCAGCCTGGACACCGGAATCAAAAAGCTGTACGAGAACGAAATGAAGCCTC<br>TGTTCGACGAGCTGCACTTCGAGTTCATCAGCCAGAGCCTGGTCCAGGTCAG<br>CTTCCCTAGCGAGAAGCTCGAAGTGCTGCTGAACAAGTACCGGAGCCTGAAG<br>GACCAGAAAGCTAAGAACATCGAGAAGGAACTGGAGGGCCCCCTGCAGGAG<br>CTGAGAACCATCATCACCGACACCTTCGAGAGCACCGGCAACAACTGGAAGA<br>AAGAGTGGCTGCAGCAGGGGTTCAAGATCAAAAGCAGTGGATACAAGGTGCT<br>GACAGAGGAGGGCATCCTGGAAGTGCTTTCCGTGCGGAAGAAGGATAAGGC<br>CGATGCTATAAACAAGTTCAAAGGATTCTTCACCTACTTCAGCGGCTTCAACA<br>TGAACAGAGAGAACTACTACAGCAGCGAAGATAAAAAAACAGCCGTGGCCTA<br>CAGAGTGATCAACGAGAACCTGATCCGGTACATGGATAACATCCTGCTCCTG<br>CAGAACGTGCTGGCCAAAGCCCCTGAGTTCAAGAAATTTGAAGATATCCTGA<br>GTCTGACCACCTTCGGCAAGTACATCAACCAGGAGGGCATCACAACCTACAA<br>CAACAACGTTGTGGCCACCATCAACCTGGAGCTGAACACCTACCACCAGCAC<br>AACCCAAAAATCTTCAGCAGACTGCCCAAACTGAAGCTGCTGTACAAGCAGAT<br>CGGTTCTCCAAAGGAGGACAAGCGCATCTTCACCATCGAGAAGAGAACAGAA<br>TGGCAGAGCCTGGAGGACCTGATCCAGAAGCAGAACAAGGTCGTGGAACAC<br>GAAAAGAAGAACGTGGAGATCCTGTCTAATCTGAAGGCCGCCTATATCAGCTT<br>CTTCACAAACACCGACGAAACCATCCTGTCTGAGGTGTACTTCAACAAGAGAA<br>GCCTGAATACGATCAGCAGCTTCTGGTTCACCGGCGGATGGCAAACCCTGCT<br>GCTGAAACTGAAGGAATTTAAGCTGGCTAATCAGAACAAAGACGGCGATATC<br>GTGGTTCCCAAGGCCCTGAGCCTGGCCGAGCTGAAGCAGGTGCTGGACTCC<br>CTGGAAGAGCAGGACCCCGCCGTGAATCACCTGTTCAAGGAAATGTACAGCG<br>ACTGCTACAAGGAAAACCTGTGGCAAACATTTATCGCCATCTGGCAATGTGAA<br>ATCACAAGCAAGTTCAACCTGCTGGAGGGCTATATCCAAGAGTGCAACGCCG<br>TGAAAGAGGACACCTTTGACAAGAAAAAGCACAAAAACATCATCAAGAACATC<br>TGCGACACGTACCTGGACATTGAGCAGATCAGTAAGTACATCATCGTGCACG<br>AAAGCCTGCCTAAATACGACGCCCTCTATGATGCCGTCATCCTGTACCTGCAG<br>GAGTCTAGTCTGCGGTCCTACTACGACGCCTTTAGAAACCTGATTTCTAAGCG<br>GCCAGTGAACGAGGAAAAGGTGAAGCTGAATTTCCAGAATAGCACCCTGCTG<br>GATGGCTGGGACATGAATAAAGAAAGCGCCAATCTTTGTGTGCTGCTGAAGA<br>ACAACATCGGAGAGTACTTTCTGGCCGTGATGAACAAAAAAAGCAACATGGTT<br>TTTGACCAGAAAAAAAACAGCGCCCTGTATAGCGCTGGCAATGAATCTAGCTT<br>CCAGAAGCTGGAGTACAAGCTGTTGCCCGGCCCTAACAAGATGCTGCCTAAG<br>GTGATCTTTGCCAAGTCCAATGAGAAGTACTTCATCATCCCTGAGGAGATCGT<br>GCAGATCAGGGAGGAAGAGAGCTTCAAGAAAGGCAAAAAATTCGATAAGCAC<br>GCGCTGAAAACCTGGATCAGATTCATGCAGGAGTCTATCGAGAAGTATCCTG<br>GCTGGAAAAACCTTTGACTTCACATTCAAAAAGCCTGAGGAATACGAGGATGTG<br>TCCAAGTTCTACAAAGACGTGGAAGAGCAGGGCTACAAACTGAACTGGAAGG<br>ATATCAACGAGGAAGAACTGCTGAGCCTGGTGGAACAGAAGAAGGTGTACCT<br>TTTTCAGATCAAGTCCAAAGACATAGGCGAGACAAAGGAACACGGAAATAAGA<br>ACCTGCACACCCTGCTCTTCCTAGAATTGCTGAAGCCTGAGAACACAAGTCG<br>GCTGAAGCTGTTGGGCGGCGGAGAAATGTTCTACCGGGCCCCTTCTATGGAA<br>AAAGTCTACAAAACAGTGAACGAGAAGCAGGTGCTGGATTCTAAAGGCAACC<br>CTATCCTGGAGGCCAAGCGCTACTACGAGCCTAAGTTTTTTCTGCATTTCCCC<br>ATCCAGGTGAAGGGCTCTGAGAACGGCTATAAGACCGAGATGAACCCCAAAA<br>TCCTCAGAGCCATCAGCACCAGCAAGGAAGTGAACATCATTGGCATCGACAG<br>AGGCGAGAAGCACCTGCTGTACTATTACGTGATCAAGCCCGACGGAACACCT<br>ATCACCCAGGGCAGCCTGAACACCATCTCCCTGGGCCTTGATAAGAATCAAA<br>ATCCTAGACTGGTGGACGAGAGAACCTTCAAGATCCTGGAAAGAGATAGCAA<br>GGGCAAGCCAAGCAAGATCTCAGATTTTGAAAGCACAGGCAAGAAGGTCGAC<br>TACATCGACTACCACAACATCCTGACATACTATGAAACCAAGAGAAATATCGC<br>CAGAAGAAGCTGGGACACAATTGGCGCCATCAAGAATTTCAAGGAGGGATAC<br>CTCTCTCAGGCCATCCACCAGATCTACCAGCTGATGCTGAAATATAACGCCGT<br>GGTGGTGCTAGAGGACCTGAACACCGAGTTCAAGGCAAAGAGAACCGCCAA<br>GGTGGAAAAAAAGCGTGTACGAAAAGTTTGAGATAGCTCTGGCCAAGAAGCTG | 65 |

TABLE 1K-continued

ZXHQ Type V Cas Sequences

| Name | Sequence | SEQ ID NO. |
|---|---|---|
| | AATCACCTGATCATCAAGGGCACCGACCCAGCCGAGGCCGGATCTGTGATCA<br>ACCCTTACCAGCTGACCCCTGCTATTACAGCCGACACACTGAGCGATTTCAAG<br>AAGAGCAAACAATGGGGCCCTCTGTTCTACATCCGGGCCAACTACACCAGCA<br>CAACCGACCCTATCACAGGCTGGAGAAAGCACATCTACATCCCCAGCGGAGC<br>CAGTGACAAGGAAATCAAGACCTACTTCTGCAAGCAGGGCGAGAAGGAGCCT<br>CTGATCCAGATTAGCTACGACACCGCCCTGACCGCCTTCGCCTTCACATACA<br>CCCACGAAGGCAAGGAGTGGACCCTACATGCCACAAAGGATACCCAAAGAAT<br>GCGGTACGACAGCAAGAAGAGAAAGATGGAACCCGTGGAAATCTTCGACAGA<br>CTGAGAGAGCTGTTCATCGACTTCTCTTTCGAGGAAAGCCTGACCGACCAGC<br>TGGAGGCAACCCTGTCCTTCGACTGGAAAACCCTGGCTTTTCTGTGGACAAT<br>GCTGAATCAGATCAGAAACACCGATAGAGAGGCTGAAGGCAACGACGGCGA<br>CTTCATCCAGTCTCCTGTGGCCCCTTTCTATGATAGCCGGGACCCAGAGAAC<br>AAGACCAATGGCCTGCCCGTTAACGGCGACGCCAACGGCGCCTTCAACATCG<br>CTAGAAAGGGGGCTATCCTGATCAAGAGAATCCAGGAATACGCCAAGAAGGA<br>CCCTACATTCGAGAAGATGCGGGAAAAGGACGGTTTAAACCTGTACATCAGC<br>GATGCTGAGTGGGATACCGAGATCAGC | |
| Expression construct (with N-terminal methionine and stop codon, includes V5-tag and C-terminal NLS) | ATGggctccggaACAAACACTAGCATCTTCAAGACATTCACCAACCAATACAGCCT<br>CTCCAAGACCCTGCGGTTTGAGCTCAGACCCCACCCTATGACCTCCGGCCTG<br>GACGACATCATCAGCCTGGACACCGGAATCAAAAAGCTGTACGAGAACGAAA<br>TGAAGCCTCTGTTCGACGAGCTGCACTTCGAGTTCATCAGCCAGAGCCTGGT<br>CCAGGTCAGCTTCCCTAGCGAGAAGCTCGAAGTGCTGCTGAACAAGTACCGG<br>AGCCTGAAGGACCAGAAAGCTAAGAACATCGAGAAGGAACTGGAGGGCCCC<br>CTGCAGGAGCTGAGAACCATCATCACCGACACCTTCGAGAGCACCGGCAACA<br>ACTGGAAGAAAGAGTGGCTGCAGCAGGGGTTCAAGATCAAAAGCAGTGGATA<br>CAAGGTGCTGACAGAGGAGGGCATCCTGGAAGTGCTTTCCGTGCGGAAGAA<br>GGATAAGGCCGATGCTATAAACAAGTTCAAAGGATTCTTCACCTACTTCAGCG<br>GCTTCAACATGAACAGAGAGAACTACTACAGCAGCGAAGATAAAAAAACAGCC<br>GTGGCCTACAGAGTGATCAACGAGAACCTGATCCGGTACATGGATAACATCC<br>TGCTCCTGCAGAACGTGCTGGCCAAAGCCCCTGAGTTCAAGAAATTTGAAGA<br>TATCCTGAGTCTGACCACCTTCGGCAAGTACATCAACCAGGAGGGCATCACA<br>ACCTACAACAACAACGTTGTGGCCACCATCAACCTGGAGCTGAACACCTACC<br>ACCAGCACAACCCAAAAATCTTCAGCAGACTGCCCAAACTGAAGCTGCTGTAC<br>AAGCAGATCGGTTCTCCAAAGGAGGACAAGCGCATCTTCACCATCGAGAAGA<br>GAACAGAATGGCAGAGCCTGGAGGACCTGATCCAGAAGCAGAACAAGGTCG<br>TGGAACACGAAAAGAAGAACGTGGAGATCCTGTCTAATCTGAAGGCCGCCTA<br>TATCAGCTTCTTCACAAACACCGACGAAACCATCCTGTCTGAGGTGTACTTCA<br>ACAAGAGAAGCCTGAATACGATCAGCAGCTTCTGGTTCACCGGCGGATGGCA<br>AACCCTGCTGCTGAAACTGAAGGAATTTAAGCTGGCTAATCAGAACAAAGACG<br>GCGATATCGTGGTTCCCAAGGCCCTGAGCCTGGCCGAGCTGAAGCAGGTGC<br>TGGACTCCCTGGAAGAGCAGGACCCCGCCGTGAATCACCTGTTCAAGGAAAT<br>GTACAGCGACTGCTACAAGGAAAACCTGTGGCAAACATTTATCGCCATCTGG<br>CAATGTGAAATCACAAGCAAGTTCAACCTGCTGGAGGGCTATATCCAAGAGTG<br>CAACGCCGTGAAAGAGGACACCTTTGACAAGAAAAAGCACAAAAACATCATCA<br>AGAACATCTGCGACACGTACCTGGACATTGAGCAGATCAGTAAGTACATCATC<br>GTGCACGAAAGCCTGCCTAAATACGACGCCCTCTATGATGCCGTCATCCTGT<br>ACCTGCAGGAGTCTAGTCTGCGGTCCTACTACGACGCCTTTAGAAACCTGATT<br>TCTAAGCGGCCAGTGAACGAGGAAAAGGTGAAGCTGAATTTCCAGAATAGCA<br>CCCTGCTGGATGGCTGGGACATGAATAAAGAAAGCGCCAATCTTTGTGTGCT<br>GCTGAAGAACAACATCGGAGAGTACTTTCTGGCCGTGATGAACAAAAAAAGC<br>AACATGGTTTTTGACCAGAAAAAAAACAGCGCCCTGTATAGCGCTGGCAATGA<br>ATCTAGCTTCCAGAAGCTGGAGTACAAGCTGTTGCCCGGCCCTAACAAGATG<br>CTGCCTAAGGTGATCTTTGCCAAGTCCAATGAGAAGTACTTCATCATCCCTGA<br>GGAGATCGTGCAGATCAGGGAGGAAGAGAGCTTCAAGAAAGGCAAAAAATTC<br>GATAAGCACGCGCTGAAAACCTGGATCAGATTCATGCAGGAGTCTATCGAGA<br>AGTATCCTGGCTGGAAAACCTTTGACTTCACATTCAAAAAGCCTGAGGAATAC<br>GAGGATGTGTCCAAGTTCTACAAAGACGTGGAAGAGCAGGGCTACAAACTGA<br>ACTGGAAGGATATCAACGAGGAAGAACTGCTGAGCCTGGTGGAACAGAAGAA<br>GGTGTACCTTTTTCAGATCAAGTCCAAAGACATAGGCGAGACAAAGGAACAC<br>GGAAATAAGAACCTGCACACCCTGCTCTTCCTAGAATTGCTGAAGCCTGAGAA<br>CACAAGTCGGCTGAAGCTGTTGGGCGGCGGAGAAATGTTCTACCGGGCCCC<br>TTCTATGGAAAAAGTCTACAAAACAGTGAACGAGAAGCAGGTGCTGGATTCTA<br>AAGGCAACCCTATCCTGGAGGCCAAGCGCTACTACGAGCCTAAGTTTTTTCTG<br>CATTTCCCCATCCAGGTGAAGGGCTCTGAGAACGGCTATAAGACCGAGATGA<br>ACCCCAAAATCCTCAGAGCCATCAGCACCAGCAAGGAAGTGAACATCATTGG<br>CATCGACAGAGGCGAGAAGCACCTGCTGTACTATTACGTGATCAAGCCCGAC<br>GGAACACCTATCACCCAGGGCAGCCTGAACACCATCTCCCTGGGCCTTGATA<br>AGAATCAAAATCCTAGACTGGTGGACGAGAGAACCTTCAAGATCCTGGAAAG<br>AGATAGCAAGGGCAAGCCAAGCAAGATCTCAGATTTTGAAAGCACAGGCAAG<br>AAGGTCGACTACATCGACTACCACAACATCCTGACATACTATGAAACCAAGAG<br>AAATATCGCCAGAAGAAGCTGGGACACAATTGGCGCCATCAAGAATTTCAAG<br>GAGGGATACCTCTCTCAGGCCATCCACCAGATCTACCAGCTGATGCTGAAAT<br>ATAACGCCGTGGTGGTGCTAGAGGACCTGAACACCGAGTTCAAGGCAAAGAG<br>AACCGCCAAGGTGGAAAAAAGCGTGTACGAAAAGTTTGAGATAGCTCTGGCC<br>AAGAAGCTGAATCACCTGATCATCAAGGGCACCGACCCAGCCGAGGCCGGAT | 66 |

TABLE 1K-continued

| ZXHQ Type V Cas Sequences | | |
|---|---|---|
| Name | Sequence | SEQ ID NO. |
| | CTGTGATCAACCCTTACCAGCTGACCCCTGCTATTACAGCCGACACACTGAG<br>CGATTTCAAGAAGAGCAAACAATGGGGCCCTCTGTTCTACATCCGGGCCAAC<br>TACACCAGCACAACCGACCCTATCACAGGCTGGAGAAAGCACATCTACATCC<br>CCAGCGGAGCCAGTGACAAGGAAATCAAGACCTACTTCTGCAAGCAGGGCGA<br>GAAGGAGCCTCTGATCCAGATTAGCTACGACACCGCCCTGACCGCCTTCGCC<br>TTCACATACACCCACGAAGGCAAGGAGTGGACCCTACATGCCACAAAGGATA<br>CCCAAAGAATGCGGTACGACAGCAAGAAGAGAAAGATGGAACCCGTGGAAAT<br>CTTCGACAGACTGAGAGAGCTGTTCATCGACTTCTCTTTCGAGGAAAGCCTGA<br>CCGACCAGCTGGAGGCAACCCTGTCCTTCGACTGGAAAACCCTGGCTTTTCT<br>GTGGACAATGCTGAATCAGATCAGAAACACCGATAGAGAGGCTGAAGGCAAC<br>GACGGCGACTTCATCCAGTCTCCTGTGGCCCCTTTCTATGATAGCCGGGACC<br>CAGAGAACAAGACCAATGGCCTGCCCGTTAACGGCGACGCCAACGGCGCCT<br>TCAACATCGCTAGAAAGGGGGCTATCCTGATCAAGAGAATCCAGGAATACGC<br>CAAGAAGGACCCTACATTCGAGAAGATGCGGGAAAAGGACGGTTTAAACCTG<br>T<br>ACATCAGCGATGCTGAGTGGGATACCGAGATCAGCtctagaAAGCGGACAGCAG<br>ACGGCTCCGAATTTGAAAGCCCTAAGAAAAAGAGAAAGGTGggatccGGCAAAC<br>CTATCCCCAATCCCCTGCTGGGCCTGGACAGCACCTGA | |

In some embodiments a ZXHQ Type V Cas protein comprises an amino acid sequence of SEQ ID NO:61, SEQ ID NO:62, or SEQ ID NO:63. In some embodiments, a ZXHQ Type V Cas protein has nickase activity, for example resulting from one or more amino acid substitutions relative to the sequence of SEQ ID NO:61, SEQ ID NO:62, or SEQ ID NO:63. In some embodiments, the one or more amino acid substitutions providing nickase activity comprise a D836 substitution, wherein the position of the D836 substitution is defined with respect to the amino acid numbering of SEQ ID NO:62 (corresponding to amino acid 908 of SEQ ID NO:121). In some embodiments, the one or more amino acid substitutions providing nickase activity comprise an E963 substitution, wherein the position of the E963 substitution is defined with respect to the amino acid numbering of SEQ ID NO:62 (corresponding to amino acid 993 of SEQ ID NO:121). In some embodiments, the one or more amino acid substitutions providing nickase activity comprise a R1172 substitution, wherein the position of the R1172 substitution is defined with respect to the amino acid numbering of SEQ ID NO:62 (corresponding to amino acid 1226 of SEQ ID NO:121). In some embodiments, the one or more amino acid substitutions providing nickase activity comprise a D1211 substitution, wherein the position of the D1211 substitution is defined with respect to the amino acid numbering of SEQ ID NO:62 (corresponding to amino acid 1263 of SEQ ID NO:121). In some embodiments, a ZXHQ Type V Cas protein is catalytically inactive, for example due to a R1172 substitution in combination with a D836 substitution, a E963 substitution, and/or D1211 substitution.

6.2.12. ZQKH Type V Cas Proteins

In one aspect, the disclosure provides ZQKH Type V Cas proteins. ZQKH Type V Cas proteins can be further classified as Type V-A Cas proteins. The ZQKH Type V Cas proteins typically comprise an amino acid sequence that is at least 50%, at least 55%, at least 60%, at least 65%, at least 70%, at least 75%, at least 85%, at least 90%, or at least 95% identical to SEQ ID NO:67. In some embodiments, the ZQKH Type V Cas proteins comprise an amino acid sequence that is at least 95%, at least 96%, at least 97%, at least 98%, or at least 99% identical to SEQ ID NO:67. In some embodiments, a ZQKH Type V Cas protein comprises an amino acid sequence that is identical to SEQ ID NO:67.

Exemplary ZQKH Type V Cas protein sequences and nucleotide sequences encoding exemplary ZQKH Type V Cas proteins are set forth in Table 1L.

TABLE 1L

| ZQKH Type V Cas Sequences | | |
|---|---|---|
| Name | Sequence | SEQ ID NO. |
| Wildtype amino acid sequence (without N-terminal methionine) | AYQVVKCLINDYCQNEIIAPQLQKVSCDNTWIVKLREFQEAANWEAQKIIQQDLIGIINK<br>KLPKKFNSKALIEAIPDYLQGKSKEDLQRMLSGIHDYEIKVKNQNLQVAWNNGLEDFC<br>NLCYQQFRGFSGYLDALSENLKFLFSGRKNGIAYRIVYQNLVTFERNRRAYESLILINE<br>TFRVQDEALLLNYSSSLTQEGINTYNERIGQLVKNLKEFGDTDRSFRNWHRRFKKLN<br>KQILSPRVAPPWLARAYRSDEEMVMSLQSFLDEFNPLKPRLKQLIANLESYDEHIYYF<br>RKSLSLLSVTLRNDYKALDEELSIPQEQANCRSLSLSWIPFRQELINEIERIIDSSYTDIE<br>KCLASASEYLNTERAKRNDYRLDNTVSFTIKKLMDVFLSLYRAVKPLTGTGEEEDRNE<br>DFYDEFTTIWDVLQYVQKLYNAVFAWLNKKPYENNSYPAYLDEFTLLKNWKEKAAYI<br>KRNGKFYFIMFNGIDEQDIIEHRGDSAILYHVESQSPDRIKANLTKQFVFSKKANAGKG<br>RPNPSKAKFVRDNPEFQADWERVKTEAYKVAGNTEALAHAIRYFQRCLQSHPDYNR<br>FPFNFRPANDYTSLDDFVDSIKDKLFMMEETAINWSYVRQLAEEGTIYLFKLYNKDYA<br>KNRVGGSKPNLHTLYWEAMFSSENLRENNIKLEEPKLFYREVATNRDGELNMRLIPH<br>RYATDQLELHVPIHLNVNATASSDINMMVLDAIREGSIENVIGIDRGERNLLYYSVLRL<br>SDGEIVDQKSLNITFNDVDYHAKLSTKEEEIHDEQREWKAKTSIRKLKEGYLSQAIHQL<br>TSLIVKYHAVVVLEDLSEDFYSKRQKINKQIYQIFEKRLIEKLSYFVDKDAAEGQAGNIY<br>SALQLSSPNLVRKDNKKIFQNGIVFFVPPEYTSAIDPVTGFCNLFDKNRVRNICELLYR | 67 |

TABLE 1L-continued

ZQKH Type V Cas Sequences

| Name | Sequence | SEQ ID NO. |
|---|---|---|
| | FENICYNRKNDRFEFTWDYRNVMTYTRLEQDNISHLWTACSLGNRIEWSGSERNKN<br>RRCEIVNLTQSMKVLFEKHGIQYQTGKDVREAVCSIRNNDFKKELKRLFFLMLSLRNS<br>IVDGKVKKDYILSPVQNQRGSFFDSREYEELDNPKLPKCGDANGAYNIARKGILTIRKL<br>ENGNEKALTLDEWVISTQKGNIRM | |
| Wildtype amino acid sequence (with N-terminal methionine) | MAYQVVKCLINDYCQNEIIAPQLQKVSCDNTWIVKLREFQEAANWEAQKIIQQDLIGII<br>NKKLPKKFNSKALIEAIPDYLQGKSKEDLQRMLSGIHDYEIKVKNQNLQVAWNNGLED<br>FCNLCYQQFRGFSGYLDALSENLKFLFSGRKNGIAYRIVYQNLVTFERNRRAYESLILI<br>NETFRVQDEALLLNYSSSLTQEGINTYNERIGQLVKNLKEFGDTDRSFRNWHRRFKK<br>LNKQILSPRVAPPWLARAYRSDEEMVMSLQSFLDEFNPLKPRLKQLIANLESYDEHIY<br>YFRKSLSLLSVTLRNDYKALDEELSIPQEQANCRSLSLSWIPFRQELINEIERIIDSSYT<br>DIEKCLASASEYLNTERAKRNDYRLDNTVSFTIKKLMDVFLSLYRAVKPLTGTGEEED<br>RNEDFYDEFTTIWDVLQYVQKLYNAVFAWLNKKPYENNSYPAYLDEFTLLKNWKEKA<br>AYIKRNGKFYFIMFNGIDEQDIIEHRGDSAILYHVESQSPDRIKANLTKQFVFSKKANA<br>GKGRPNPSKAKFVRDNPEFQADWERVKTEAYKVAGNTEALAHAIRYFQRCLQSHPD<br>YNRFPFNFRPANDYTSLDDFVDSIKDKLFMMEETAINWSYVRQLAEEGTIYLFKLYNK<br>DYAKNRVGGSKPNLHTLYWEAMFSSENLRENNIKLEEPKLFYREVATNRDGELNMR<br>LIPHRYATDQLELHVPIHLNVNATASSDINMMVLDAIREGSIENVIGIDRGERNLLYYSV<br>LRLSDGEIVDQKSLNITFNDVDYHAKLSTKEEEIHDEQREWKAKTSIRKLKEGYLSQAI<br>HQLTSLIVKYHAVVVLEDLSEDFYSKRQKINKQIYQIFEKRLIEKLSYFVDKDAAEGQA<br>GNIYSALQLSSPNLVRKDNKKIFQNGIVFFVPPEYTSAIDPVTGFCNLFDKNRVRNICE<br>LLYRFENICYNRKNDRFEFTWDYRNVMTYTRLEQDNISHLWTACSLGNRIEWSGSER<br>NKNRRCEIVNLTQSMKVLFEKHGIQYQTGKDVREAVCSIRNNDFKKELKRLFFLMLSL<br>RNSIVDGKVKKDYILSPVQNQRGSFFDSREYEELDNPKLPKCGDANGAYNIARKGILT<br>IRKLENGNEKALTLDEWVISTQKGNIRM | 68 |
| Expression construct (with N-terminal methionine, V5-tag and C-terminal NLS) aa sequence | MGSGAYQVVKCLINDYCQNEIIAPQLQKVSCDNTWIVKLREFQEAANWEAQKIIQQDL<br>IGIINKKLPKKFNSKALIEAIPDYLQGKSKEDLQRMLSGIHDYEIKVKNQNLQVAWNNG<br>LEDFCNLCYQQFRGFSGYLDALSENLKFLFSGRKNGIAYRIVYQNLVTFERNRRAYE<br>SLILINETFRVQDEALLLNYSSSLTQEGINTYNERIGQLVKNLKEFGDTDRSFRNWHR<br>RFKKLNKQILSPRVAPPWLARAYRSDEEMVMSLQSFLDEFNPLKPRLKQLIANLESYD<br>EHIYYFRKSLSLLSVTLRNDYKALDEELSIPQEQANCRSLSLSWIPFRQELINEIERIIDS<br>SYTDIEKCLASASEYLNTERAKRNDYRLDNTVSFTIKKLMDVFLSLYRAVKPLTGTGE<br>EEDRNEDFYDEFTTIWDVLQYVQKLYNAVFAWLNKKPYENNSYPAYLDEFTLLKNWK<br>EKAAYIKRNGKFYFIMFNGIDEQDIIEHRGDSAILYHVESQSPDRIKANLTKQFVFSKKA<br>NAGKGRPNPSKAKFVRDNPEFQADWERVKTEAYKVAGNTEALAHAIRYFQRCLQSH<br>PDYNRFPFNFRPANDYTSLDDFVDSIKDKLFMMEETAINWSYVRQLAEEGTIYLFKLY<br>NKDYAKNRVGGSKPNLHTLYWEAMFSSENLRENNIKLEEPKLFYREVATNRDGELN<br>MRLIPHRYATDQLELHVPIHLNVNATASSDINMMVLDAIREGSIENVIGIDRGERNLLYY<br>SVLRLSDGEIVDQKSLNITFNDVDYHAKLSTKEEEIHDEQREWKAKTSIRKLKEGYLS<br>QAIHQLTSLIVKYHAVVVLEDLSEDFYSKRQKINKQIYQIFEKRLIEKLSYFVDKDAAEG<br>QAGNIYSALQLSSPNLVRKDNKKIFQNGIVFFVPPEYTSAIDPVTGFCNLFDKNRVRNI<br>CELLYRFENICYNRKNDRFEFTWDYRNVMTYTRLEQDNISHLWTACSLGNRIEWSGS<br>ERNKNRRCEIVNLTQSMKVLFEKHGIQYQTGKDVREAVCSIRNNDFKKELKRLFFLML<br>SLRNSIVDGKVKKDYILSPVQNQRGSFFDSREYEELDNPKLPKCGDANGAYNIARKGI<br>LTIRKLENGNEKALTLDEWVISTQKGNIRMSRKRTADGSEFESPKKKRKVGSGKPIPN<br>PLLGLDST | 69 |
| Wildtype coding sequence (with N-terminal methionine and stop codon) | ATGGCATACCAAGTGGTTAAATGCCTAATCAACGACTATTGCCAGAATGAAATCAT<br>TGCACCTCAATTGCAGAAAGTTTCCTGTGATAACACTTGGATTGTAAAACTTCGCG<br>AGTTTCAAGAGGCTGCCAATTGGGAAGCCCAAAAAATTATCCAGCAAGATCTTAT<br>TGGTATCATAAACAAGAAACTTCCTAAAAAGTTCAATAGCAAGGCATTGATAGAAG<br>CCATTCCTGACTATTTACAAGGCAAGTCTAAAGAAGATCTGCAACGTATGTTGAGT<br>GGTATACATGACTATGAGATTAAGGTAAAAAATCAGAACCTTCAGGTGGCTTGGA<br>ATAATGGGTTAGAAGATTTTTGTAACCTCTGCTATCAACAATTTAGAGGATTTTCT<br>GGCTATCTTGACGCTTTATCTGAGAACCTGAAATTTCTATTCTCGGGCAGAAAAAA<br>TGGTATAGCCTATAGAATAGTGTATCAGAACCTTGTTACATTTGAGAGGAATAGGA<br>GAGCTTATGAATCCCTAATATTAATAAATGAGACTTTTAGGGTACAAGATGAGGCT<br>CTACTTCTTAATTACTCCAGTAGTCTGACCCAAGAAGGTATCAACACCTATAATGA<br>ACGAATAGGGCAACTTGTCAAAAATCTGAAAGAATTTGGCGATACAGACAGATCT<br>TTCAGAAACTGGCATCGCCGATTCAAGAAACTGAACAAGCAAATCCTAAGCCCTC<br>GTGTTGCTCCACCTTGGTTGGCACGCGCCTACAGAAGCGATGAAGAGATGGTGA<br>TGTCGCTACAGTCTTTTCTCGACGAGTTCAATCCATTAAAACCTCGTTTGAAGCAA<br>CTTATTGCTAATCTGGAATCTTACGATGAGCATATCTATTACTTCCGCAAGTCTCT<br>TTCTCTATTATCGGTGACCTTGAGGAATGATTATAAGGCACTTGATGAAGAACTCT<br>CAATACCACAAGAACAGGCCAATTGCAGAAGTTTAAGCCTTTCGTGGATTCCGTT<br>TCGCCAAGAATTGATAAACGAAATAGAACGAATTATTGACAGTTCATATACAGACA<br>TAGAGAAGTGTCTTGCCTCTGCCTCGGAATATCTGAACACGGAGAGAGCAAAAC<br>GGAACGACTATCGTCTAGATAATACTGTGTCTTTCACAATCAAGAAACTGATGGA<br>CGTATTCCTGTCATTGTATCGTGCGGTGAAGCCTCTGACTGGAACAGGAGAGGA<br>GGAGGATCGAAACGAGGACTTCTATGATGAGTTTACAACAATCTGGGATGTGCTT<br>CAATATGTACAAAAACTTTATAATGCAGTTTTTGCATGGCTGAACAAGAAGCCTTA<br>TGAGAACAACAGCTATCCTGCCTATTTGGACGAGTTTACACTTCTTAAAAACTGGA<br>AGGAGAAAGCCGCGTATATAAAACGGAATGGGAAGTTCTATTTTATCATGTTCAAT | 70 |

TABLE 1L-continued

ZQKH Type V Cas Sequences

| Name | Sequence | SEQ ID NO. |
|---|---|---|
| | GGTATTGATGAACAAGACATTATCGAGCATCGAGGTGATTCTGCAATCTTGTATC ATGTGGAAAGTCAATCCCCCGATAGGATTAAGGCAAATCTCACCAAACAATTTGT TTTTTCCAAAAAAGCAAATGCAGGAAAGGGGCGACCAAATCCTTCTAAAGCCAAA TTCGTGCGTGACAATCCAGAATTCCAAGCTGACTGGGAACGTGTGAAAACTGAAG CATATAAAGTAGCTGGAAACACAGAAGCGCTTGCTCATGCCATTCGATATTTTCAA CGCTGCCTTCAATCACATCCTGACTATAATAGGTTTCCGTTCAATTTTAGACCAGC GAATGACTACACTAGTTTAGATGATTTTGTTGACTCCATTAAAGACAAATTGTTTAT GATGGAAGAAACTGCTATTAACTGGTCGTATGTGAGGCAATTAGCAGAAGAAGGA ACAATTTACTTGTTTAAACTCTACAATAAAGATTATGCCAAGAATAGAGTTGGCGG GTCTAAACCCAACTTGCATACGCTCTATTGGGAGGCGATGTTCAGCTCTGAGAAC CTTCGTGAAAATAATATAAAGTTGGAGGAACCCAAACTCTTCTATCGTGAAGTTGC AACTAACCGTGATGGTGAATTGAATATGCGCTTGATACCTCACAGATATGCAACA GACCAACTTGAGCTGCATGTTCCAATTCACTTAAATGTGAATGCAACCGCTTCAA GCGATATAAATATGATGGTGTTGGATGCAATACGAGAAGGGAGTATTGAAAATGT CATTGGTATTGACCGTGGAGAGAGGAACCTTCTCTACTATTCAGTCTTGCGGTTG TCAGATGGTGAAATTGTTGACCAAAAAAGTTTGAATATTACTTTCAATGATGTTGA CTACCACGCCAAACTGTCGACTAAAGAGGAGGAAATCCATGACGAACAAAGAGA ATGGAAAGCAAAAACAAGTATTCGGAAACTGAAAGAAGGATACCTTAGTCAAGCT ATCCACCAACTAACATCGCTGATTGTCAAGTACCATGCTGTGGTAGTGCTAGAAG ACTTATCAGAGGACTTCTATTCGAAGCGCCAGAAGATAAACAAGCAAATCTATCA GATATTTGAAAAAAGGCTGATAGAAAAACTGAGTTATTTTGTCGATAAGGATGCTG CAGAAGGTCAGGCAGGCAATATATATTCAGCATTGCAGTTGTCAAGCCCCAACTT GGTGAGGAAAGATAATAAAAAAATCTTTCAGAACGGCATCGTCTTTTTTGTGCCAC CTGAATATACAAGTGCCATTGACCCTGTAACAGGGTTCTGCAATCTCTTTGACAA GAATCGGGTAAGAAATATTTGCGAACTTCTCTACAGATTTGAAAACATCTGCTATA ATAGGAAAAATGACCGATTTGAGTTCACATGGGACTATCGTAATGTTATGACTTAT ACGCGTCTGGAGCAGGACAATATTTCACATCTTTGGACAGCATGCTCTTTAGGAA ACAGGATTGAATGGTCTGGTAGCGAACGTAATAAAAACAGAAGGTGCGAAATTGT AAACCTTACGCAATCTATGAAAGTTTTGTTGAAAAACATGGTATCCAATACCAAA CAGGAAAAGATGTAAGGGAGGCTGTATGCAGCATAAGAAACAACGATTTTAAAAA AGAATTGAAGCGCCTGTTCTTCTTGATGTTATCTTTAAGGAATAGCATTGTTGATG GAAAAGTGAAAAAAGACTATATATTATCCCCCGTTCAGAACCAACGAGGCAGTTT TTTCGATAGTAGAGAATATGAAGAGTTGGACAATCCAAAACTCCCTAAATGTGGA GATGCAAATGGCGCATATAATATTGCAAGGAAAGGGATACTGACAATTAGAAAGT TGGAAAATGGCAATGAAAAGGCATTAACCCTTGATGAGTGGGTTATTTCTACGCA AAAAGGGAATATACGCATGTAA | |
| Codon optimized coding sequence (no N-terminal methionine, no stop codon) | GCCTACCAGGTGGTGAAATGCCTGATTAACGACTACTGCCAGAACGAGATCATC GCCCCTCAGCTGCAAAAGGTGAGCTGCGACAATACCTGGATCGTGAAGCTCAGA GAGTTCCAGGAGGCCGCAAACTGGGAAGCCCAGAAGATCATCCAGCAGGACCT GATCGGCATTATCAATAAGAAACTGCCTAAGAAATTCAACTCTAAGGCCCTGATC GAGGCTATACCTGATTACCTCCAGGGCAAGAGCAAGGAAGATCTGCAGAGAATG CTGTCCGGCATCCACGACTATGAGATCAAGGTGAAGAACCAGAACCTGCAGGTA GCTTGGAACAATGGCCTGGAAGATTTCTGTAACTTGTGCTACCAACAATTTAGAG GCTTTTCCGGCTACCTTGATGCTCTGTCAGAAAATCTGAAGTTCCTGTTCAGCGG CAGAAAAAACGGCATCGCCTACAGGATCGTCTACCAGAACCTGGTGACCTTCGA GCGGAACCGGAGAGCTTACGAGAGCCTGATCCTGATCAACGAGACATTTAGAGT GCAGGACGAGGCCCTGCTGCTCAACTACTCTAGCTCTCTGACACAGGAGGGAAT CAACACGTACAACGAGCGGATCGGCCAGCTGGTGAAGAACCTGAAGGAGTTCG GCGACACCGACCGGAGCTTTCGGAACTGGCACAGACGGTTCAAGAAACTGAACA AGCAGATCCTGAGCCCTAGAGTGGCCCCTCCTTGGCTGGCTCGTGCCTACAGAA GCGATGAGGAAATGGTGATGAGCCTGCAGAGCTTCCTGGATGAGTTCAACCCTC TGAAACCTAGACTCAAACAGCTGATCGCCAATCTGGAGTCCTACGACGAGCACAT CTACTACTTCAGAAAGTCCCTGTCTCTGCTGTCAGTGACACTGAGGAACGACTAT AAGGCACTGGATGAAGAGCTGAGCATCCCTCAGGAGCAGGCCAACTGCAGATCT CTTAGCCTGAGCTGGATTCCTTTCAGACAGGAACTGATCAACGAGATCGAGAGAA TCATCGATAGCAGCTACACAGACATTGAGAAGTGCCTGGCCAGCGCCTCCGAGT ACCTGAACACCGAGAGAGCCAAGAGAAACGACTACCGGCTAGATAATACCGTGT CCTTCACCATCAAGAAGCTGATGGACGTGTTCCTGAGCCTGTACCGCGCCGTGA AGCCTCTGACCGGAACAGGCGAAGAGGAGGACAGAAATGAAGATTTCTACGACG AGTTCACCACCATCTGGGATGTGCTGCAATACGTGCAGAAGCTGTACAACGCTGT TTTCGCCTGGCTGAACAAGAAGCCCTACGAGAACAATAGCTACCCTGCCTACCTG GATGAATTTACCCTGCTGAAGAACTGGAAGGAAAAGGCCGCCTACATCAAGAGG AATGGAAAATTCTACTTCATCATGTTCAACGGCATCGACGAGCAGGATATCATCG AACACAGAGGAGATTCTGCCATCCTGTACCATGTGGAAAGCCAGAGCCCTGATA GAATCAAGGCCAATCTGACCAAGCAGTTCGTGTTCAGCAAGAAAGCCAATGCCG GCAAGGGCCGGCCCAATCCCAGCAAGGCCAAGTTCGTGAGAGATAACCCCGAG TTTCAGGCCGACTGGGAGCGGGTGAAAACCGAGGCCTACAAGGTGGCCGGAAA CACCGAGGCCCTGGCCCACGCCATCAGATACTTCCAAAGATGCCTGCAAAGCCA CCCCGATTATAATCGGTTCCCCTTCAACTTCAGACCTGCCAACGACTACACATCT CTGGATGACTTCGTGGACAGCATCAAGGACAAGCTGTTCATGATGGAAGAAACC GCCATCAACTGGAGTTATGTGAGACAGCTGGCCGAAGAAGGCACAATCTACCTG TTCAAGCTGTATAACAAAGACTACGCCAAGAACCGGGTGGGCGGCAGCAAGCCT AACCTGCACACCCTGTACTGGGAGGCCATGTTCAGCTCTGAGAATCTGAGAGAA | 71 |

TABLE 1L-continued

ZQKH Type V Cas Sequences

| Name | Sequence | SEQ ID NO. |
|---|---|---|
| | AACAACATCAAACTGGAAGAACCCAAACTGTTCTACAGAGAGGTGGCCACAAACC<br>GGGACGGCGAGCTGAACATGAGACTGATCCCCCACAGATACGCCACCGACCAG<br>CTGGAACTGCACGTGCCTATCCACCTGAATGTGAACGCCACAGCCAGCAGCGAC<br>ATCAACATGATGGTCCTTGATGCCATCCGGGAAGGATCTATTGAGAACGTGATCG<br>GCATCGACCGGGGAGAACGGAACCTGCTGTACTACAGCGTCCTGCGACTGTCC<br>GACGGCGAGATCGTGGACCAGAAGAGCCTGAATATCACCTTTAACGATGTGGAC<br>TACCACGCAAAGTTGTCTACCAAGGAGGAAGAAATCCATGATGAGCAGAGAGAG<br>TGGAAAGCCAAGACCTCCATCAGAAAGCTGAAGGAAGGTTACCTGTCTCAGGCT<br>ATCCACCAGCTGACCAGCCTGATCGTGAAGTACCACGCTGTGGTAGTGCTGGAA<br>GATCTGAGCGAAGATTTCTACAGCAAGCGGCAGAAAATCAACAAGCAGATCTACC<br>AGATTTTCGAGAAAAGACTTATCGAGAAGCTGAGCTACTTTGTGGACAAAGACGC<br>CGCCGAGGGCCAGGCAGGCAACATCTACAGCGCCCTGCAGCTGAGCTCCCCAA<br>ATCTGGTGAGAAAGGACAACAAGAAGATCTTCCAGAACGGCATCGTGTTCTTCGT<br>GCCACCTGAGTACACGAGTGCGATTGACCCCGTGACCGGCTTCTGCAACCTGTT<br>TGACAAGAACAGAGTGCGCAATATCTGTGAGCTGCTCTACAGATTCGAAAACATT<br>TGCTACAACAGAAAGAATGACCGGTTTGAGTTCACATGGGACTATAGAAACGTGA<br>TGACCTACACCAGACTTGAGCAGGACAACATCTCTCACCTGTGGACCGCTTGTAG<br>CCTCGGCAACCGGATCGAGTGGAGCGGCTCTGAAAGAAATAAGAACAGAAGATG<br>CGAGATCGTGAACCTGACACAAAGCATGAAGGTCCTGTTTGAGAAGCACGGCAT<br>CCAGTACCAGACCGGCAAGGACGTGCGGGAAGCTGTGTGTAGTATCAGAAACAA<br>CGACTTTAAGAAAGAACTGAAGAGACTGTTTTTCCTGATGCTGAGCCTGCGTAAC<br>AGCATCGTGGATGGAAAGGTGAAAAAGGACTACATCCTGAGCCCAGTGCAAAAC<br>CAGCGGGGTAGCTTTTTCGACTCCAGAGAATATGAAGAACTGGACAACCCGAAG<br>TTGCCTAAGTGCGGGGACGCCAACGGCGCCTACAACATCGCCAGAAAAGGAATC<br>CTGACAATCAGAAAGCTGGAGAACGGCAACGAGAAAGCCCTGACCCTGGACGAA<br>TGGGTGATCAGCACCCAGAAGGGCAACATCAGAATG | |
| Expression construct (with N-terminal methionine and stop codon, includes V5-tag and C-terminal NLS) | ATGggctccggaGCCTACCAGGTGGTGAAATGCCTGATTAACGACTACTGCCAGAAC<br>GAGATCATCGCCCCTCAGCTGCAAAAGGTGAGCTGCGACAATACCTGGATCGTG<br>AAGCTCAGAGAGTTCCAGGAGGCCGCAAACTGGGAAGCCCAGAAGATCATCCAG<br>CAGGACCTGATCGGCATTATCAATAAGAAACTGCCTAAGAAATTCAACTCTAAGG<br>CCCTGATCGAGGCTATACCTGATTACCTCCAGGGCAAGAGCAAGGAAGATCTGC<br>AGAGAATGCTGTCCGGCATCCACGACTATGAGATCAAGGTGAAGAACCAGAACC<br>TGCAGGTAGCTTGGAACAATGGCCTGGAAGATTTCTGTAACTTGTGCTACCAACA<br>ATTTAGAGGCTTTTCCGGCTACCTTGATGCTCTGTCAGAAAATCTGAAGTTCCTGT<br>TCAGCGGCAGAAAAAACGGCATCGCCTACAGGATCGTCTACCAGAACCTGGTGA<br>CCTTCGAGCGGAACCGGAGAGCTTACGAGAGCCTGATCCTGATCAACGAGACAT<br>TTAGAGTGCAGGACGAGGCCCTGCTGCTCAACTACTCTAGCTCTCTGACACAGG<br>AGGGAATCAACACGTACAACGAGCGGATCGGCCAGCTGGTGAAGAACCTGAAG<br>GAGTTCGGCGACACCGACCGGAGCTTTCGGAACTGGCACAGACGGTTCAAGAAA<br>CTGAACAAGCAGATCCTGAGCCCTAGAGTGGCCCCTCCTTGGCTGGCTCGTGCC<br>TACAGAAGCGATGAGGAAATGGTGATGAGCCTGCAGAGCTTCCTGGATGAGTTC<br>AACCCTCTGAAACCTAGACTCAAACAGCTGATCGCCAATCTGGAGTCCTACGACG<br>AGCACATCTACTACTTCAGAAAGTCCCTGTCTCTGCTGTCAGTGACACTGAGGAA<br>CGACTATAAGGCACTGGATGAAGAGCTGAGCATCCCTCAGGAGCAGGCCAACTG<br>CAGATCTCTTAGCCTGAGCTGGATTCCTTTCAGACAGGAACTGATCAACGAGATC<br>GAGAGAATCATCGATAGCAGCTACACAGACATTGAGAAGTGCCTGGCCAGCGCC<br>TCCGAGTACCTGAACACCGAGAGAGCCAAGAGAAACGACTACCGGCTAGATAAT<br>ACCGTGTCCTTCACCATCAAGAAGCTGATGGACGTGTTCCTGAGCCTGTACCGC<br>GCCGTGAAGCCTCTGACCGGAACAGGCGAAGAGGAGGACAGAAATGAAGATTTC<br>TACGACGAGTTCACCACCATCTGGGATGTGCTGCAATACGTGCAGAAGCTGTAC<br>AACGCTGTTTTCGCCTGGCTGAACAAGAAGCCCTACGAGAACAATAGCTACCCTG<br>CCTACCTGGATGAATTTACCCTGCTGAAGAACTGGAAGGAAAAGGCCGCCTACAT<br>CAAGAGGAATGGAAAATTCTACTTCATCATGTTCAACGGCATCGACGAGCAGGAT<br>ATCATCGAACACAGAGGAGATTCTGCCATCCTGTACCATGTGGAAAGCCAGAGC<br>CCTGATAGAATCAAGGCCAATCTGACCAAGCAGTTCGTGTTCAGCAAGAAAGCCA<br>ATGCCGGCAAGGGCCGGCCCAATCCCAGCAAGGCCAAGTTCGTGAGAGATAAC<br>CCCGAGTTTCAGGCCGACTGGGAGCGGGTGAAAACCGAGGCCTACAAGGTGGC<br>CGGAAACACCGAGGCCCTGGCCCACGCCATCAGATACTTCCAAAGATGCCTGCA<br>AAGCCACCCCGATTATAATCGGTTCCCCTTCAACTTCAGACCTGCCAACGACTAC<br>ACATCTCTGGATGACTTCGTGGACAGCATCAAGGACAAGCTGTTCATGATGGAAG<br>AAACCGCCATCAACTGGAGTTATGTGAGACAGCTGGCCGAAGAAGGCACAATCT<br>ACCTGTTCAAGCTGTATAACAAAGACTACGCCAAGAACCGGGTGGGCGGCAGCA<br>AGCCTAACCTGCACACCCTGTACTGGGAGGCCATGTTCAGCTCTGAGAATCTGA<br>GAGAAAACAACATCAAACTGGAAGAACCCAAACTGTTCTACAGAGAGGTGGCCA<br>CAAACCGGGACGGCGAGCTGAACATGAGACTGATCCCCCACAGATACGCCACC<br>GACCAGCTGGAACTGCACGTGCCTATCCACCTGAATGTGAACGCCACAGCCAGC<br>AGCGACATCAACATGATGGTCCTTGATGCCATCCGGGAAGGATCTATTGAGAAC<br>GTGATCGGCATCGACCGGGGAGAACGGAACCTGCTGTACTACAGCGTCCTGCG<br>ACTGTCCGACGGCGAGATCGTGGACCAGAAGAGCCTGAATATCACCTTTAACGA<br>TGTGGACTACCACGCAAAGTTGTCTACCAAGGAGGAAGAAATCCATGATGAGCA<br>GAGAGAGTGGAAAGCCAAGACCTCCATCAGAAAGCTGAAGGAAGGTTACCTGTC<br>TCAGGCTATCCACCAGCTGACCAGCCTGATCGTGAAGTACCACGCTGTGGTAGT<br>GCTGGAAGATCTGAGCGAAGATTTCTACAGCAAGCGGCAGAAAATCAACAAGCA | 72 |

TABLE 1L-continued

ZQKH Type V Cas Sequences

| Name | Sequence | SEQ ID NO. |
|---|---|---|
| | GATCTACCAGATTTTCGAGAAAAGACTTATCGAGAAGCTGAGCTACTTTGTGGAC<br>AAAGACGCCGCCGAGGGCCAGGCAGGCAACATCTACAGCGCCCTGCAGCTGAG<br>CTCCCCAAATCTGGTGAGAAAGGACAACAAGAAGATCTTCCAGAACGGCATCGT<br>GTTCTTCGTGCCACCTGAGTACACGAGTGCGATTGACCCCGTGACCGGCTTCTG<br>CAACCTGTTTGACAAGAACAGAGTGCGCAATATCTGTGAGCTGCTCTACAGATTC<br>GAAAACATTTGCTACAACAGAAAGAATGACCGGTTTGAGTTCACATGGGACTATA<br>GAAACGTGATGACCTACACCAGACTTGAGCAGGACAACATCTCTCACCTGTGGA<br>CCGCTTGTAGCCTCGGCAACCGGATCGAGTGGAGCGGCTCTGAAAGAAATAAGA<br>ACAGAAGATGCGAGATCGTGAACCTGACACAAAGCATGAAGGTCCTGTTTGAGA<br>AGCACGGCATCCAGTACCAGACCGGCAAGGACGTGCGGGAAGCTGTGTGTAGT<br>ATCAGAAACAACGACTTTAAGAAAGAACTGAAGAGACTGTTTTTCCTGATGCTGA<br>GCCTGCGTAACAGCATCGTGGATGGAAAGGTGAAAAAGGACTACATCCTGAGCC<br>CAGTGCAAAACCAGCGGGGTAGCTTTTTCGACTCCAGAGAATATGAAGAACTGG<br>ACAACCCGAAGTTGCCTAAGTGCGGGGACGCCAACGGCGCCTACAACATCGCCA<br>GAAAAGGAATCCTGACAATCAGAAAGCTGGAGAACGGCAACGAGAAAGCCCTGA<br>CCCTGGACGAATGGGTGATCAGCACCCAGAAGGGCAACATCAGAATGtctagaAAG<br>CGGACAGCAGACGGCTCCGAATTTGAAAGCCCTAAGAAAAAGAGAAAGGTGggat<br>ccGGCAAACCTATCCCCAATCCCCTGCTGGGCCTGGACAGCACCTGA | |

In some embodiments a ZQKH Type V Cas protein comprises an amino acid sequence of SEQ ID NO:67, SEQ ID NO:68, or SEQ ID NO:69. In some embodiments, a ZQKH Type V Cas protein has nickase activity, for example resulting from one or more amino acid substitutions relative to the sequence of SEQ ID NO:67, SEQ ID NO:68, or SEQ ID NO:69. In some embodiments, the one or more amino acid substitutions providing nickase activity comprise a D744 substitution, wherein the position of the D744 substitution is defined with respect to the amino acid numbering of SEQ ID NO:68 (corresponding to amino acid 908 of SEQ ID NO:121). In some embodiments, the one or more amino acid substitutions providing nickase activity comprise an E831 substitution, wherein the position of the E831 substitution is defined with respect to the amino acid numbering of SEQ ID NO:68 (corresponding to amino acid 993 of SEQ ID NO:121). In some embodiments, the one or more amino acid substitutions providing nickase activity comprise a R1048 substitution, wherein the position of the R1048 substitution is defined with respect to the amino acid numbering of SEQ ID NO:68 (corresponding to amino acid 1226 of SEQ ID NO:121). In some embodiments, the one or more amino acid substitutions providing nickase activity comprise a D1091 substitution, wherein the position of the D1091 substitution is defined with respect to the amino acid numbering of SEQ ID NO:68 (corresponding to amino acid 1263 of SEQ ID NO:121). In some embodiments, a ZQKH Type V Cas protein is catalytically inactive, for example due to a R1048 substitution in combination with a D744 substitution, a E831 substitution, and/or D1091 substitution.

6.2.13. ZRGM Type V Cas Protein

In one aspect, the disclosure provides ZRGM Type V Cas proteins. ZRGM Type V Cas proteins can be further classified as Type V-A Cas proteins. The ZRGM Type V Cas proteins typically comprise an amino acid sequence that is at least 50%, at least 55%, at least 60%, at least 65%, at least 70%, at least 75%, at least 85%, at least 90%, or at least 95% identical to SEQ ID NO:73. In some embodiments, the ZRGM Type V Cas proteins comprise an amino acid sequence that is at least 95%, at least 96%, at least 97%, at least 98%, or at least 99% identical to SEQ ID NO:73. In some embodiments, a ZRGM Type V Cas protein comprises an amino acid sequence that is identical to SEQ ID NO:73.

Exemplary ZRGM Type V Cas protein sequences and nucleotide sequences encoding exemplary ZRGM Type V Cas proteins are set forth in Table 1M.

TABLE 1M

ZRGM Type V Cas Sequences

| Name | Sequence | SEQ ID NO. |
|---|---|---|
| Wildtype amino acid sequence (without N-terminal methionine) | ERMYEEFRNCYSVRKTLSFKAIPTEETKKHLQLQWEVLGDEIRFENYDKMKMVLDQ<br>LHQSYISRKLDNIGEENQKKIVEILEKLVLVMKKIDTTHQKDKEKAQNQLQSLQASLR<br>KEIGMFFPKNEWQQLQGKNVFKKDGVLSEYNISEENKKNIQCYDGFMTFFKKYNET<br>RANIYSTEEKSTAITFRIVNDNLPKYVRNADNYEQIKKLIPEALEEVEKTYPNLTNYFSI<br>KNYLKYWSQKGIETYNTVIGEINKQVNLVVQQRKDSKFRKYKMQVLYQQILSDREE<br>QSFVYQQDQEVFAAVNELAELVNGSAFNEAIELLKSPNINENEIFIPYAKLAEVSIKMK<br>MGWNGLEEAFINDLQQQYPKKDHEKLVQKLKKEKKVFSLNEIKDVVMKIEHEEDWK<br>FVSLLDCVEDYQKQLTETRDAYVEYAKTYAGSTGTSLQGNDVAPIKAFLDSCLQLVR<br>WCKLFEYSDLYGNRDKIFYGGAESIILALDSLISVYNKTRNYVTMRPGQARKMHLMF<br>NYPEFGDGFSNSKVDSYGTILLREGKKYYLAVIKKGIKVLLEDTINENDSYERLSYML<br>FPDVKKMIPKCSISTKKVKEHFENSDDDYTIRKGESYAKELLVKKEDYDLYFVNLYDD<br>KKMFQKDYLSKTGDKKGYRQALERWIRFCIRFLQAYKSTKDYDLSELEPISNFRSLD<br>EFYDKLDTLLYKIEWKTISREQIKQMESSGQLFLFELYNKDFSEHAKGKKNLFTLYW<br>EQIFCEENLKQPVIKLCGGAEMFYRKVAIQKKYVHKKDSILVDKTYVDQNGVRKTLP<br>DTIYKEWSDFMNKKITSVSQEASKYKGLVNCHEAKYDITKDKRYTEDQFEFHVPITL<br>NYSALGKGQLNDSVLDCLCQKEKYNVIGIDRGERNLLAYCVVNQDGQILEQGTFNKI | 73 |

TABLE 1M-continued

| Name | Sequence | SEQ ID NO. |
|---|---|---|
| ZRGM Type V Cas Sequences | | |
| | VGGNKQEVDYKQKLQEKEVNRQQARKEWKNIGKIKELKNGYLSQVIYQLTQMMVK YDAIVVMEDLNVGFKRGRFKVERQVYQKFEKALIDKLNYLVTKKDENQYGIEGSVSN AYQLTEKIKSFKDIGKQNGMIFYVPAGYTSKIDPTTGFVDVLNRTGLTNAKARKAFFE NFDDINYSKEDNMFAFSFDYSKFKTFQEMHRKKWTVYTNGKKYIYSKKERKEKQID VTELMKEELRKVGITEYDNLYSQITNVEDDKEHADFWKSLQFVFDRTMQLRSSQIDN GEDNLEDKIISPVKNAEGVFYESNGNYGDTSQPADADTNGAFHIARKGLLLAENVKK TGRGANGKWNSSVKNISNKDWFAFVQK | |
| Wildtype amino acid sequence (with N-terminal methionine) | MERMYEEFRNCYSVRKTLSFKAIPTEETKKHLQLQWEVLGDEIRFENYDKMKMVLD QLHQSYISRKLDNIGEENQKKIVEILEKLVLVMKKIDTTHQKDKEKAQNQLQSLQASL RKEIGMFFPKNEWQQLQGKNVFKKDGVLSEYNISEENKKNIQCYDGFMTFFKKYNE TRANIYSTEEKSTAITFRIVNDNLPKYVRNADNYEQIKKLIPEALEEVEKTYPNLTNYF SIKNYLKYWSQKGIETYNTVIGEINKQVNLVVQQRKDSKFRKYKMQVLYQQILSDRE EQSFVYQQDQEVFAAVNELAELVNGSAFNEAIELLKSPNINENEIFIPYAKLAEVSIKM KMGWNGLEEAFINDLQQQYPKKDHEKLVQKLKKEKKVFSLNEIKDVVMKIEHEEDW KFVSLLDCVEDYQKQLTETRDAYVEYAKTYAGSTGTSLQGNDVAPIKAFLDSCLQLV RWCKLFEYSDLYGNRDKIFYGGAESIILALDSLISVYNKTRNYVTMRPGQARKMHLM FNYPEFGDGFSNSKVDSYGTILLREGKKYYLAVIKKGIKVLLEDTINENDSYERLSYM LFPDVKKMIPKCSISTKKVKEHFENSDDDYTIRKGESYAKELLVKKEDYDLYFVNLYD DKKMFQKDYLSKTGDKKGYRQALERWIRFCIRFLQAYKSTKDYDLSELEPISNFRSL DEFYDKLDTLLYKIEWKTISREQIKQMESSGQLFLFELYNKDFSEHAKGKKNLFTLY WEQIFCEENLKQPVIKLCGGAEMFYRKVAIQKKYVHKKDSILVDKTYVDQNGVRKTL PDTIYKEWSDFMNKKITSVSQEASKYKGLVNCHEAKYDITKDKRYTEDQFEFHVPIT LNYSALGKGQLNDSVLDCLCQKEKYNVIGIDRGERNLLAYCVVNQDGQILEQGTEN KIVGGNKQEVDYKQKLQEKEVNRQQARKEWKNIGKIKELKNGYLSQVIYQLTQMMV KYDAIVVMEDLNVGFKRGRFKVERQVYQKFEKALIDKLNYLVTKKDENQYGIEGSVS NAYQLTEKIKSFKDIGKQNGMIFYVPAGYTSKIDPTTGFVDVLNRTGLTNAKARKAFF ENFDDINYSKEDNMFAFSFDYSKFKTFQEMHRKKWTVYTNGKKYIYSKKERKEKQI DVTELMKEELRKVGITEYDNLYSQITNVEDDKEHADFWKSLQFVFDRTMQLRSSQID NGEDNLEDKIISPVKNAEGVFYESNGNYGDTSQPADADTNGAFHIARKGLLLAENVK KTGRGANGKWNSSVKNISNKDWFAFVQK | 74 |
| Expression construct (with N-terminal methionine, V5-tag and C-terminal NLS) aa sequence | MGSGERMYEEFRNCYSVRKTLSFKAIPTEETKKHLQLQWEVLGDEIRFENYDKMK MVLDQLHQSYISRKLDNIGEENQKKIVEILEKLVLVMKKIDTTHQKDKEKAQNQLQSL QASLRKEIGMFFPKNEWQQLQGKNVFKKDGVLSEYNISEENKKNIQCYDGFMTFFK KYNETRANIYSTEEKSTAITFRIVNDNLPKYVRNADNYEQIKKLIPEALEEVEKTYPNL TNYFSIKNYLKYWSQKGIETYNTVIGEINKQVNLVVQQRKDSKFRKYKMQVLYQQIL SDREEQSFVYQQDQEVFAAVNELAELVNGSAFNEAIELLKSPNINENEIFIPYAKLAE VSIKMKMGWNGLEEAFINDLQQQYPKKDHEKLVQKLKKEKKVFSLNEIKDVVMKIEH EEDWKFVSLLDCVEDYQKQLTETRDAYVEYAKTYAGSTGTSLQGNDVAPIKAFLDS CLQLVRWCKLFEYSDLYGNRDKIFYGGAESIILALDSLISVYNKTRNYVTMRPGQAR KMHLMFNYPEFGDGFSNSKVDSYGTILLREGKKYYLAVIKKGIKVLLEDTINENDSYE RLSYMLFPDVKKMIPKCSISTKKVKEHFENSDDDYTIRKGESYAKELLVKKEDYDLYF VNLYDDKKMFQKDYLSKTGDKKGYRQALERWIRFCIRFLQAYKSTKDYDLSELEPIS NFRSLDEFYDKLDTLLYKIEWKTISREQIKQMESSGQLFLFELYNKDFSEHAKGKKNL FTLYWEQIFCEENLKQPVIKLCGGAEMFYRKVAIQKKYVHKKDSILVDKTYVDQNGV RKTLPDTIYKEWSDFMNKKITSVSQEASKYKGLVNCHEAKYDITKDKRYTEDQFEFH VPITLNYSALGKGQLNDSVLDCLCQKEKYNVIGIDRGERNLLAYCVVNQDGQILEQG TFNKIVGGNKQEVDYKQKLQEKEVNRQQARKEWKNIGKIKELKNGYLSQVIYQLTQ MMVKYDAIVVMEDLNVGFKRGRFKVERQVYQKFEKALIDKLNYLVTKKDENQYGIE GSVSNAYQLTEKIKSFKDIGKQNGMIFYVPAGYTSKIDPTTGFVDVLNRTGLTNAKA RKAFFENFDDINYSKEDNMFAFSFDYSKFKTFQEMHRKKWTVYTNGKKYIYSKKER KEKQIDVTELMKEELRKVGITEYDNLYSQITNVEDDKEHADFWKSLQFVFDRTMQLR SSQIDNGEDNLEDKIISPVKNAEGVFYESNGNYGDTSQPADADTNGAFHIARKGLLL AENVKKTGRGANGKWNSSVKNISNKDWFAFVQKSRKRTADGSEFESPKKKRKVG SGKPIPNPLLGLDST | 75 |
| Wildtype coding sequence (with N-terminal methionine and stop codon) | ATGGAGAGAATGTACGAAGAATTTAGAAATTGTTATTCAGTACGAAAAACATTGT CATTTAAGGCAATCCCAACAGAGGAAACAAAAAAACATTTACAATTACAATGGGA AGTGTTGGGGGATGAGATACGTTTTGAAAACTATGATAAAATGAAAATGGTTTTG GATCAACTTCATCAATCATATATTTCGAGAAAATTAGATAATATAGGAGAAGAAAA TCAAAAAAAGATAGTTGAAATCTTAGAGAAACTCGTATTAGTTATGAAAAAGATA GATACTACGCATCAAAAGGATAAAGAGAAAGCGCAAAATCAGCTTCAATCGTTA CAAGCTTCATTAAGGAAAGAAATAGGAATGTTTTTTCCTAAAAACGAATGGCAAC AATTACAGGGAAAAAATGTATTTAAGAAGGATGGGGTACTAAGCGAGTATAACAT TTCGGAAGAGAATAAGAAAAATATTCAATGTTATGATGGTTTTATGACATTCTTTA AAAAATATAATGAAACTAGAGCAAATATATATAGTACAGAGGAAAAAAGCACGGC AATCACTTTTCGAATTGTGAATGATAATCTTCCAAAATATGTGAGAAATGCGGAT AATTACGAACAGATTAAAAAATTAATTCCTGAAGCTCTTGAAGAAGTAGAAAAAA CATACCCAAATTTGACGAATTATTTCTCGATTAAAAACTATTTGAAGTATTGGAGT CAGAAGGGGATTGAAACATACAATACTGTTATTGGAGAAATAAATAAGCAGGTTA ATCTTGTAGTACAACAAAGAAAAGATTCGAAATTTAGAAAATACAAGATGCAGGT GTTGTATCAACAAATTCTAAGTGATAGAGAGGAACAGTCTTTTGTGTATCAACAG GATCAGGAAGTTTTTGCTGCTGTTAATGAACTTGCAGAACTTGTGAACGGTAGT GCTTTTAACGAGGCAATTGAATTGTTGAAATCACCTAATATTAACGAAAATGAGA | 76 |

TABLE 1M-continued

| ZRGM Type V Cas Sequences | | |
|---|---|---|
| Name | Sequence | SEQ ID NO. |
| | TATTTATTCCCTATGCAAAATTAGCAGAAGTATCCATAAAAATGAAAATGGGATG<br>GAATGGATTAGAGGAGGCTTTTATAAACGATTTGCAACAGCAGTATCCAAAGAA<br>GGATCATGAAAAATTGGTGCAAAAATTAAAAAAAGAGAAAAAAGTTTTTTCTTTGA<br>ATGAAATTAAAGATGTTGTTATGAAAATTGAACATGAAGAAGATTGGAAATTTGTT<br>AGTTTGCTGGATTGTGTTGAGGATTATCAAAAACAGTTGACAGAGACAAGAGAT<br>GCATATGTGGAATATGCAAAAACTTATGCAGGTTCAACCGGTACATCATTACAAG<br>GAAATGATGTAGCACCGATAAAAGCATTTTTAGATAGTTGTTTGCAATTGGTACG<br>ATGGTGTAAGTTGTTTGAATATTCTGATTTGTATGGAAATCGAGATAAAATATTTT<br>ATGGAGGAGCAGAGTCGATTATACTTGCATTAGATTCCTTAATATCTGTGTATAA<br>TAAAACAAGAAATTATGTGACTATGCGACCGGGGCAGGCTAGAAAAATGCATTT<br>AATGTTTAATTATCCGGAATTCGGTGATGGCTTTAGTAATAGTAAAGTGGATTCT<br>TATGGTACGATTTTGCTTCGTGAAGGAAAGAAATATTATTTAGCTGTTATTAAAAA<br>AGGCATAAAAGTCTTGCTGGAAGATACCATAAATGAAAATGACAGTTATGAACGT<br>TTGAGTTATATGTTGTTTCCTGATGTAAAAAAAATGATACCGAAATGTTCTATTAG<br>TACGAAGAAAGTTAAAGAACATTTTGAAAATTCGGATGATGATTATACGATTCGT<br>AAAGGTGAATCTTATGCAAAAGAATTACTTGTGAAAAAAGAAGATTATGACCTTT<br>ACTTTGTAAATCTTTATGATGATAAGAAGATGTTTCAAAAGGACTATTTGAGTAAA<br>ACTGGAGATAAAAAAGGATATAGACAGGCGTTAGAACGCTGGATACGTTTTTGC<br>ATTCGATTTTTACAAGCTTATAAGAGTACAAAGGATTATGATCTCAGTGAATTAGA<br>GCCAATTTCGAATTTTCGTTCCTTAGATGAGTTTTATGATAAATTGGATACTTTGT<br>TATACAAGATAGAGTGGAAAACAATTTCAAGAGAACAAATTAAGCAAATGGAGTC<br>ATCTGGTCAGTTGTTTTTATTTGAATTATATAACAAAGATTTCTCTGAACATGCAA<br>AAGGAAAGAAAAATTTATTTACATTGTATTGGGAACAGATTTTCTGTGAAGAGAA<br>TTTAAAACAGCCAGTGATTAAACTTTGTGGCGGGGCAGAGATGTTTTATCGTAAG<br>GTTGCCATTCAAAAAAAATATGTACATAAAAAAGACTCCATTTTGGTGGATAAAA<br>CGTATGTGGATCAGAATGGAGTCAGAAAAACACTTCCGGATACTATATATAAAGA<br>GTGGTCGGATTTTATGAATAAAAAGATAACATCTGTCAGCCAGGAGGCAAGTAA<br>ATATAAAGGTTTGGTTAATTGTCATGAGGCAAAATATGATATTACAAAAGATAAAA<br>GATATACGGAAGATCAATTTGAGTTTCATGTGCCAATTACTTTAAATTATTCAGCA<br>TTAGGAAAAGGGCAATTAAATGATAGTGTTCTGGATTGTCTATGTCAGAAAGAAA<br>AATATAATGTGATAGGAATTGACCGTGGAGAAAGAAACTTGTTGGCTTACTGTGT<br>CGTAAATCAAGATGGACAGATTTTAGAACAAGGGACATTTAATAAGATTGTAGGT<br>GGAAATAAACAGGAAGTAGATTACAAACAGAAGTTACAGGAGAAAGAAGTAAAT<br>CGACAACAAGCAAGAAAAGAGTGGAAAAATATTGGAAAAATTAAAGAATTAAAGA<br>ACGGTTATTTGTCTCAGGTTATTTATCAACTGACGCAAATGATGGTAAAATATGA<br>TGCTATTGTTGTTATGGAAGATTTGAATGTTGGCTTTAAACGTGGTCGATTTAAG<br>GTGGAACGACAGGTTTACCAGAAATTTGAAAAAGCGCTGATTGACAAATTAAATT<br>ATTTAGTAACTAAAAAAGATGAAAATCAATATGGAATAGAGGGTAGCGTAAGCAA<br>TGCATATCAACTGACAGAAAAAATCAAATCATTTAAAGATATTGGCAAACAAAAC<br>GGGATGATATTTTATGTGCCAGCGGGATATACCTCTAAAATAGATCCTACAACAG<br>GATTTGTGGATGTGCTAAATCGAACAGGATTAACAAATGCCAAAGCCAGAAAAG<br>CGTTCTTTGAAAATTTTGATGATATTAACTATTCAAAAGAAGATAATATGTTTGCC<br>TTTTCTTTTGATTATAGCAAGTTTAAGACATTTCAAGAAATGCATAGAAAAAAATG<br>GACAGTTTACACAAATGGTAAAAAGTACATTTATTCAAAAAAAGAACGAAAAGAA<br>AAACAAATTGATGTTACTGAGTTGATGAAAGAAGAATTGAGAAAAGTAGGAATTA<br>CAGAGTATGATAATCTTTATTCGCAAATTACTAATGTGGAAGATGATAAAGAACA<br>TGCAGATTTTTGGAAATCTTTACAGTTTGTATTTGATAGAACGATGCAGTTGAGA<br>AGTAGTCAAATTGACAATGGAGAGGATAATCTTGAGGATAAGATTATATCTCCGG<br>TGAAAAATGCAGAGGGTGTATTTTATGAATCAAATGGAAATTATGGTGACACTTC<br>ACAACCTGCAGATGCAGATACAAATGGTGCTTTTCATATTGCAAGGAAGGGATT<br>ACTACTTGCAGAAAATGTGAAAAAAACAGGTAGAGGAGCAAATGGAAAATGGAA<br>TTCTTCTGTAAAAAATATTTCTAATAAGGATTGGTTTGCATTTGTTCAAAAATAA | |
| Codon optimized coding sequence (no N-terminal methionine, no stop codon) | GAACGGATGTACGAGGAGTTCAGAAACTGCTACTCCGTGCGGAAAACACTGTC<br>CTTCAAAGCCATCCCTACCGAGGAGACAAAGAAGCACCTGCAGCTGCAGTGGG<br>AAGTGCTCGGCGACGAGATTAGATTTGAGAATTATGATAAGATGAAAATGGTGC<br>TGGACCAGCTGCACCAGTCTTACATCAGCCGGAAGCTGGACAACATCGGCGAG<br>GAGAACCAGAAAAAGATTGTAGAAATCCTGGAGAAGCTGGTGCTGGTGATGAAG<br>AAGATCGATACAACCCACCAGAAGGACAAGGAGAAGGCCCAGAATCAACTGCA<br>GAGCCTGCAGGCTTCCCTGCGGAAGGAAATTGGTATGTTTTTCCCAAAGAACGA<br>GTGGCAGCAGCTGCAGGGCAAAAACGTGTTCAAGAAGGACGGCGTTCTCAGCG<br>AATACAACATCAGCGAGGAAAACAAGAAGAACATCCAGTGTTACGACGGCTTTA<br>TGACCTTCTTCAAGAAGTACAACGAGACACGGGCCAATATCTATTCTACGGAGG<br>AAAAGAGCACCGCCATCACCTTCAGGATCGTGAATGATAATCTGCCTAAGTATG<br>TGCGAAACGCTGACAACTACGAGCAGATAAAGAAGCTGATCCCCGAAGCTCTG<br>GAAGAAGTCGAAAAGACCTATCCTAATCTGACCAACTACTTCAGCATCAAGAACT<br>ATCTGAAGTACTGGAGCCAGAAGGGGATCGAAACATACAACACCGTGATCGGC<br>GAGATCAACAAGCAGGTGAACCTGGTGGTCCAACAGAGAAAGGACAGCAAGTT<br>CAGGAAGTACAAAATGCAGGTGCTGTACCAGCAGATCCTATCCGACAGAGAGG<br>AGCAGAGCTTCGTGTACCAGCAGGACCAGGAGGTGTTCGCCGCCGTGAACGAG<br>CTGGCCGAGCTGGTGAATGGCAGCGCCTTCAATGAAGCTATCGAATTGCTGAAA<br>AGCCCAAACATCAACGAGAATGAGATTTTCATCCCCTACGCCAAGCTCGCCGAG<br>GTGTCTATCAAGATGAAAATGGGATGGAACGGCCTGGAGGAGGCCTTCATCAA<br>CGATCTGCAGCAACAATACCCCAAGAAAGACCACGAAAAATTGGTTCAGAAGCT<br>GAAGAAAGAGAAGAAGGTGTTTAGCCTGAATGAAATCAAGGATGTGGTCATGAA | 77 |

TABLE 1M-continued

| ZRGM Type V Cas Sequences | | |
|---|---|---|
| Name | Sequence | SEQ ID NO. |
| | GATCGAACACGAGGAAGATTGGAAATTCGTGAGCCTGCTGGACTGCGTGGAGG<br>ATTACCAGAAGCAGCTTACAGAGACAAGAGATGCCTACGTGGAGTACGCTAAGA<br>CATACGCCGGCAGCACAGGCACCAGCCTGCAGGGCAACGACGTGGCCCCTAT<br>CAAGGCCTTCCTGGACTCCTGCCTGCAACTGGTGCGGTGGTGCAAGCTGTTCG<br>AGTACAGCGACCTGTACGGCAACAGAGACAAGATCTTCTACGGAGGCGCCGAG<br>AGCATCATCCTGGCCCTGGATAGCCTGATTTCCGTGTACAACAAAACCAGAAAC<br>TACGTGACCATGCGGCCTGGCCAGGCCAGAAAAATGCACCTGATGTTCAACTAC<br>CCCGAGTTTGGCGACGGCTTCAGCAACAGCAAAGTGGATTCTTACGGCACCAT<br>CCTGCTGAGAGAAGGCAAGAAGTACTACCTGGCTGTGATCAAGAAGGGCATCA<br>AAGTGCTGCTGGAGGACACCATTAACGAGAATGACTCTTACGAGCGGCTGTCCT<br>ACATGCTGTTCCCCGACGTGAAAAAGATGATCCCTAAGTGCAGCATCAGTACCA<br>AGAAGGTGAAAGAGCATTTCGAGAACAGCGACGACGACTACACCATCAGAAAG<br>GGCGAGAGCTATGCCAAGGAGCTGCTGGTGAAGAAGGAAGATTACGACCTGTA<br>TTTCGTGAACCTGTACGACGACAAAAAGATGTTCCAGAAAGACTACCTGAGCAA<br>AACCGGCGACAAGAAGGGATACAGACAGGCCCTGGAGAGGTGGATCAGATTCT<br>GCATCAGATTCCTGCAGGCTTACAAGTCTACAAAGGATTATGACCTGTCTGAACT<br>GGAACCTATCAGCAACTTCAGAAGCCTGGACGAGTTCTACGATAAGCTGGACAC<br>CCTACTGTACAAGATCGAGTGGAAAACCATCTCCAGAGAGCAGATCAAGCAAAT<br>GGAATCCTCTGGCCAGCTCTTCCTGTTCGAGTTGTACAACAAGGACTTCTCTGA<br>ACACGCCAAGGGAAAGAAGAACCTGTTCACCCTGTACTGGGAGCAAATTTTTG<br>TGAAGAGAACCTGAAGCAGCCTGTGATCAAGCTGTGCGGCGGAGCCGAGATGT<br>TCTACAGAAAGGTTGCCATCCAGAAAAAGTACGTGCACAAGAAGGACAGCATCC<br>TGGTAGACAAGACCTACGTGGATCAGAACGGCGTTCGCAAGACCCTGCCTGAT<br>ACCATCTACAAGGAATGGTCCGACTTCATGAACAAAAAGATCACCAGCGTGTCC<br>CAAGAAGCCTCTAAATACAAGGGCCTGGTGAACTGTCACGAGGCCAAGTACGA<br>CATCACCAAGGACAAGAGATACACCGAAGATCAATTCGAATTTCACGTGCCAAT<br>CACACTGAACTACAGCGCCCTCGGAAAAGGTCAGCTGAACGACAGCGTGCTGG<br>ACTGCCTGTGTCAGAAAGAGAAGTACAACGTGATTGGAATCGACCGGGGAGAA<br>AGAAACCTGCTGGCCTACTGCGTGGTGAACCAGGATGGCCAGATCCTGGAACA<br>GGGCACCTTCAACAAGATCGTGGGCGGCAATAAGCAGGAGGTGGACTATAAGC<br>AGAAACTGCAGGAGAAGGAGGTGAATAGACAGCAGGCCAGGAAGGAGTGGAA<br>GAACATCGGCAAGATCAAGGAGTTGAAAAACGGCTACCTGAGCCAAGTAATCTA<br>CCAGCTGACACAGATGATGGTGAAGTACGATGCCATCGTGGTGATGGAAGATCT<br>GAACGTGGGCTTTAAGAGAGGCAGATTCAAGGTTGAGCGGCAGGTGTACCAGA<br>AGTTCGAAAAGGCTCTGATCGATAAGCTGAATTATCTGGTCACCAAGAAGGACG<br>AGAACCAATACGGGATCGAGGGCAGCGTTTCGAATGCCTACCAGCTGACCGAG<br>AAAATCAAGAGCTTCAAAGACATCGGAAAACAGAACGGCATGATCTTCTACGTG<br>CCTGCTGGCTATACAAGCAAAATCGACCCTACGACCGGATTCGTCGATGTGCTG<br>AACAGAACCGGCCTGACAAACGCCAAGGCTAGAAAAGCCTTCTTCGAGAATTTT<br>GACGACATCAACTACTCTAAGGAGGACAACATGTTCGCCTTCAGCTTCGATTAC<br>AGCAAGTTCAAGACCTTTCAGGAAATGCATAGAAAAAAGTGGACAGTGTACACA<br>AACGGAAAAAAATACATCTACAGCAAGAAGGAACGGAAGGAAAAGCAGATAGAC<br>GTGACCGAACTGATGAAAGAAGAGCTGAGAAAGGTGGGCATAACCGAGTACGA<br>CAACCTCTACAGCCAGATCACCAACGTGGAAGATGATAAGGAGCACGCCGACTT<br>TTGGAAGTCTCTGCAGTTCGTGTTCGACAGAACAATGCAGCTGAGAAGCAGCCA<br>GATCGACAACGGCGAGGACAATCTGGAAGATAAGATCATTTCACCTGTGAAAAA<br>CGCCGAGGGCGTGTTCTATGAAAGCAACGGCAACTACGGCGATACGAGCCAGC<br>CCGCCGACGCGGACACCAACGGCGCCTTCCACATCGCGCGGAAGGGCCTGCT<br>GCTCGCCGAGAATGTGAAGAAAACCGGAAGAGGCGCCAATGGCAAATGGAATA<br>GCAGCGTGAAGAACATCTCTAACAAGGATTGGTTCGCCTTTGTGCAGAAA | |
| Expression<br>construct (with<br>N-terminal<br>methionine<br>and stop<br>codon,<br>includes V5-<br>tag and C-<br>terminal NLS) | ATGggctccggaGAACGGATGTACGAGGAGTTCAGAAACTGCTACTCCGTGCGGAA<br>AACACTGTCCTTCAAAGCCATCCCTACCGAGGAGACAAAGAAGCACCTGCAGCT<br>GCAGTGGGAAGTGCTCGGCGACGAGATTAGATTTGAGAATTATGATAAGATGAA<br>AATGGTGCTGGACCAGCTGCACCAGTCTTACATCAGCCGGAAGCTGGACAACA<br>TCGGCGAGGAGAACCAGAAAAAGATTGTAGAAATCCTGGAGAAGCTGGTGCTG<br>GTGATGAAGAAGATCGATACAACCCACCAGAAGGACAAGGAGAAGGCCCAGAA<br>TCAACTGCAGAGCCTGCAGGCTTCCCTGCGGAAGGAAATTGGTATGTTTTTCCC<br>AAAGAACGAGTGGCAGCAGCTGCAGGGCAAAAACGTGTTCAAGAAGGACGGCG<br>TTCTCAGCGAATACAACATCAGCGAGGAAAACAAGAAGAACATCCAGTGTTACG<br>ACGGCTTTATGACCTTCTTCAAGAAGTACAACGAGACACGGGCCAATATCTATTC<br>TACGGAGGAAAAGAGCACCGCCATCACCTTCAGGATCGTGAATGATAATCTGCC<br>TAAGTATGTGCGAAACGCTGACAACTACGAGCAGATAAAGAAGCTGATCCCCGA<br>AGCTCTGGAAGAAGTCGAAAAGACCTATCCTAATCTGACCAACTACTTCAGCAT<br>CAAGAACTATCTGAAGTACTGGAGCCAGAAGGGGATCGAAACATACAACACCGT<br>GATCGGCGAGATCAACAAGCAGGTGAACCTGGTGGTCCAACAGAGAAAGGACA<br>GCAAGTTCAGGAAGTACAAAATGCAGGTGCTGTACCAGCAGATCCTATCCGACA<br>GAGAGGAGCAGAGCTTCGTGTACCAGCAGGACCAGGAGGTGTTCGCCGCCGT<br>GAACGAGCTGGCCGAGCTGGTGAATGGCAGCGCCTTCAATGAAGCTATCGAAT<br>TGCTGAAAAGCCCAAACATCAACGAGAATGAGATTTTCATCCCCTACGCCAAGC<br>TCGCCGAGGTGTCTATCAAGATGAAAATGGGATGGAACGGCCTGGAGGAGGCC<br>TTCATCAACGATCTGCAGCAACAATACCCCAAGAAAGACCACGAAAAATTGGTT<br>CAGAAGCTGAAGAAAGAGAAGAAGGTGTTTAGCCTGAATGAAATCAAGGATGTG<br>GTCATGAAGATCGAACACGAGGAAGATTGGAAATTCGTGAGCCTGCTGGACTG<br>CGTGGAGGATTACCAGAAGCAGCTTACAGAGACAAGAGATGCCTACGTGGAGT | 78 |

TABLE 1M-continued

ZRGM Type V Cas Sequences

| Name | Sequence | SEQ ID NO. |
|---|---|---|
| | ACGCTAAGACATACGCCGGCAGCACAGGCACCAGCCTGCAGGGCAACGACGT<br>GGCCCCTATCAAGGCCTTCCTGGACTCCTGCCTGCAACTGGTGCGGTGGTGCA<br>AGCTGTTCGAGTACAGCGACCTGTACGGCAACAGAGACAAGATCTTCTACGGA<br>GGCGCCGAGAGCATCATCCTGGCCCTGGATAGCCTGATTTCCGTGTACAACAA<br>AACCAGAAACTACGTGACCATGCGGCCTGGCCAGGCCAGAAAAATGCACCTGA<br>TGTTCAACTACCCCGAGTTTGGCGACGGCTTCAGCAACAGCAAAGTGGATTCTT<br>ACGGCACCATCCTGCTGAGAGAAGGCAAGAAGTACTACCTGGCTGTGATCAAG<br>AAGGGCATCAAAGTGCTGCTGGAGGACACCATTAACGAGAATGACTCTTACGAG<br>CGGCTGTCCTACATGCTGTTCCCCGACGTGAAAAAGATGATCCCTAAGTGCAGC<br>ATCAGTACCAAGAAGGTGAAAGAGCATTTCGAGAACAGCGACGACGACTACACC<br>ATCAGAAAGGGCGAGAGCTATGCCAAGGAGCTGCTGGTGAAGAAGGAAGATTA<br>CGACCTGTATTTCGTGAACCTGTACGACGACAAAAAGATGTTCCAGAAAGACTA<br>CCTGAGCAAAACCGGCGACAAGAAGGGATACAGACAGGCCCTGGAGAGGTGG<br>ATCAGATTCTGCATCAGATTCCTGCAGGCTTACAAGTCTACAAAGGATTATGACC<br>TGTCTGAACTGGAACCTATCAGCAACTTCAGAAGCCTGGACGAGTTCTACGATA<br>AGCTGGACACCCTACTGTACAAGATCGAGTGGAAAACCATCTCCAGAGAGCAGA<br>TCAAGCAAATGGAATCCTCTGGCCAGCTCTTCCTGTTCGAGTTGTACAACAAGG<br>ACTTCTCTGAACACGCCAAGGGAAAGAAGAACCTGTTCACCCTGTACTGGGAGC<br>AAATTTTTTGTGAAGAGAACCTGAAGCAGCCTGTGATCAAGCTGTGCGGCGGAG<br>CCGAGATGTTCTACAGAAAGGTTGCCATCCAGAAAAAGTACGTGCACAAGAAGG<br>ACAGCATCCTGGTAGACAAGACCTACGTGGATCAGAACGGCGTTCGCAAGACC<br>CTGCCTGATACCATCTACAAGGAATGGTCCGACTTCATGAACAAAAAGATCACC<br>AGCGTGTCCCAAGAAGCCTCTAAATACAAGGGCCTGGTGAACTGTCACGAGGC<br>CAAGTACGACATCACCAAGGACAAGAGATACACCGAAGATCAATTCGAATTTCA<br>CGTGCCAATCACACTGAACTACAGCGCCCTCGGAAAAGGTCAGCTGAACGACA<br>GCGTGCTGGACTGCCTGTGTCAGAAAGAGAAGTACAACGTGATTGGAATCGAC<br>CGGGGAGAAAGAAACCTGCTGGCCTACTGCGTGGTGAACCAGGATGGCCAGAT<br>CCTGGAACAGGGCACCTTCAACAAGATCGTGGGCGGCAATAAGCAGGAGGTGG<br>ACTATAAGCAGAAACTGCAGGAGAAGGAGGTGAATAGACAGCAGGCCAGGAAG<br>GAGTGGAAGAACATCGGCAAGATCAAGGAGTTGAAAAACGGCTACCTGAGCCA<br>AGTAATCTACCAGCTGACACAGATGATGGTGAAGTACGATGCCATCGTGGTGAT<br>GGAAGATCTGAACGTGGGCTTTAAGAGAGGCAGATTCAAGGTTGAGCGGCAGG<br>TGTACCAGAAGTTCGAAAAGGCTCTGATCGATAAGCTGAATTATCTGGTCACCA<br>AGAAGGACGAGAACCAATACGGGATCGAGGGCAGCGTTTCGAATGCCTACCAG<br>CTGACCGAGAAAATCAAGAGCTTCAAAGACATCGGAAAACAGAACGGCATGATC<br>TTCTACGTGCCTGCTGGCTATACAAGCAAAATCGACCCTACGACCGGATTCGTC<br>GATGTGCTGAACAGAACCGGCCTGACAAACGCCAAGGCTAGAAAAGCCTTCTTC<br>GAGAATTTTGACGACATCAACTACTCTAAGGAGGACAACATGTTCGCCTTCAGC<br>TTCGATTACAGCAAGTTCAAGACCTTTCAGGAAATGCATAGAAAAAAGTGGACA<br>GTGTACACAAACGGAAAAAAATACATCTACAGCAAGAAGGAACGGAAGGAAAAG<br>CAGATAGACGTGACCGAACTGATGAAAGAAGAGCTGAGAAAGGTGGGCATAAC<br>CGAGTACGACAACCTCTACAGCCAGATCACCAACGTGGAAGATGATAAGGAGC<br>ACGCCGACTTTTGGAAGTCTCTGCAGTTCGTGTTCGACAGAACAATGCAGCTGA<br>GAAGCAGCCAGATCGACAACGGCGAGGACAATCTGGAAGATAAGATCATTTCAC<br>CTGTGAAAAACGCCGAGGGCGTGTTCTATGAAAGCAACGGCAACTACGGCGAT<br>ACGAGCCAGCCCGCCGACGCGGACACCAACGGCGCCTTCCACATCGCGCGGA<br>AGGGCCTGCTGCTCGCCGAGAATGTGAAGAAAACCGGAAGAGGCGCCAATGG<br>CAAATGGAATAGCAGCGTGAAGAACATCTCTAACAAGGATTGGTTCGCCTTTGT<br>GCAGAAAtctagaAAGCGGACAGCAGACGGCTCCGAATTTGAAAGCCCTAAGAAA<br>AAGAGAAAGGTGggatccGGCAAACCTATCCCCAATCCCCTGCTGGGCCTGGACA<br>GCACCTGA | |

In some embodiments a ZRGM Type V Cas protein comprises an amino acid sequence of SEQ ID NO:73, SEQ ID NO:74, or SEQ ID NO:75. In some embodiments, a ZRGM Type V Cas protein has nickase activity, for example resulting from one or more amino acid substitutions relative to the sequence of SEQ ID NO:73, SEQ ID NO:74, or SEQ ID NO:75. In some embodiments, the one or more amino acid substitutions providing nickase activity comprise a D890 substitution, wherein the position of the D890 substitution is defined with respect to the amino acid numbering of SEQ ID NO:74 (corresponding to amino acid 908 of SEQ ID NO:121). In some embodiments, the one or more amino acid substitutions providing nickase activity comprise an E980 substitution, wherein the position of the E980 substitution is defined with respect to the amino acid numbering of SEQ ID NO:74 (corresponding to amino acid 993 of SEQ ID NO:121). In some embodiments, the one or more amino acid substitutions providing nickase activity comprise a R1194 substitution, wherein the position of the R1194 substitution is defined with respect to the amino acid numbering of SEQ ID NO:74 (corresponding to amino acid 1226 of SEQ ID NO:121). In some embodiments, the one or more amino acid substitutions providing nickase activity comprise a D1237 substitution, wherein the position of the D1237 substitution is defined with respect to the amino acid numbering of SEQ ID NO:74 (corresponding to amino acid 1263 of SEQ ID NO:121). In some embodiments, a ZRGM Type V Cas protein is catalytically inactive, for example due to a R1194 substitution in combination with a D890 substitution, a E980 substitution, and/or D1237 substitution.

6.2.14. ZTAE Type V Cas Protein

In one aspect, the disclosure provides ZTAE Type V Cas proteins. ZTAE Type V Cas proteins can be further classified as Type V-A Cas proteins. The ZTAE Type V Cas proteins typically comprise an amino acid sequence that is at least 50%, at least 55%, at least 60%, at least 65%, at least 70%, at least 75%, at least 85%, at least 90%, or at least 95% identical to SEQ ID NO:79. In some embodiments, the ZTAE Type V Cas proteins comprise an amino acid sequence that is at least 95%, at least 96%, at least 97%, at least 98%, or at least 99% identical to SEQ ID NO:79. In some embodiments, a ZTAE Type V Cas protein comprises an amino acid sequence that is identical to SEQ ID NO:79.

Exemplary ZTAE Type V Cas protein sequences and nucleotide sequences encoding exemplary ZTAE Type V Cas proteins are set forth in Table 1N.

TABLE 1N

ZTAE Type V Cas Sequences

| Name | Sequence | SEQ ID NO. |
|---|---|---|
| Wildtype amino acid sequence (without N-terminal methionine) | SFESFTNVYPVSKTLRFELRPVGATAEKLKESGILEHDTKRGKEYATLKDLLDEQHKE LLADALKPERVKNALKPNSGKSKKDKLVEENYITEDGEIRWETLAAAMEAFRAGEVE KNVLEAIQTQFRKLIVTILKADERYPGLTASTPSAVIKTLLKQDVHPEAVETFAKFACYF TGFQENRKNIYAEEKQATAVATRVVHDNFAKFHTQSKIIGVIKNKYPEILQSVEMELM DELGGMKITDIFSINSYSKWMTQEGIDFINKIIGGYSPSVGVKVRGLNEFINLYRQQHE EANADRRNLAKMPMLFKQILSDISTRSFIPVMFENDAELKDSIEAFLTGLNDFELNAQK FNVVVALGNLFQKIVPCEGIFLDAALMEKVSKTATGDWSLLAQSMEAYAETAFTRAK DRDAWLRKNYYSLSELSQVPILKNTDEGMLKFELSAYWSGEKMESFVKGIMDAELA MKPVLASIGQKTEEVRLRDRIDDVVKIKGYLDSIQNFLHHLKPFCAPTELNRDADFYS DFDALYNQLVLVIPLYNCVRNYVTQKVTEVQKLRLKFDAPTLADGWDANKENDNKAV LFEKDGLYFLGILNPNLKAKDRPVFEHESNVTKKSCYRKIVYKLLPGPNKMLPKVFFA DSNRTLYHPSKSLLDRYHNGEYKKGDSFDIKFCHELIDYFKASISIHPDWKEFGFQFS ATKTYESIDGFYREVEEQGYKVNFAFVRADLIDKYVESGSLFLFQLYNKDFSCASSGK PNLHTLYWKSLFAKENLDEPILKLCGGAELFFRPVAIQKPYVHTLGEKLVNRRLGEHG KGEAIPERVHKELVDYYNHRVSVLSHDGKAFKDKVVVRDVAHSITKDRRFSEAKFFF HVPIMFNRTASKSAKFNDKVVDYLKTTQNVNVIGLDRGERNLIYLTMVNLHGKLIEQR SFNLVNGVDYHSKLDLREKERMDARVNWENIGGIKDLKTGYLSAVVHEIAKMMVTNN AIVVLEDLNFGFKRGRFKVEKQVYQKFEKMLIDKLNFLMFKECNQAALGGVRRAYQL TDKFVSFEKLGKQTGFLFYVPAGYTSKIDPTTGFTNLFNTKKCTNAEGRKVFFEAMN SIIYDGSRKSFAFSFDYGNPVFRASQTSFKKEWTVYSADTRIVYNRGEKTVNTIHPTQI LHDALCALGIDVHDGLNVLNVVRETPADKIHAKFFSDLFYAFDRTLQMRNSVSGTDE DYIQSPVLNATGEFFDSRKADSTLPQDADANGAYHIALKGLLLLQRMKDIGSDIKLDLS IKHEDWFAFAQKRCQR | 79 |
| Wildtype amino acid sequence (with N-terminal methionine) | MSFESFTNVYPVSKTLRFELRPVGATAEKLKESGILEHDTKRGKEYATLKDLLDEQHK ELLADALKPERVKNALKPNSGKSKKDKLVEENYITEDGEIRWETLAAAMEAFRAGEV EKNVLEAIQTQFRKLIVTILKADERYPGLTASTPSAVIKTLLKQDVHPEAVETFAKFACY FTGFQENRKNIYAEEKQATAVATRVVHDNFAKFHTQSKIIGVIKNKYPEILQSVEMELM DELGGMKITDIFSINSYSKWMTQEGIDFINKIIGGYSPSVGVKVRGLNEFINLYRQQHE EANADRRNLAKMPMLFKQILSDISTRSFIPVMFENDAELKDSIEAFLTGLNDFELNAQK FNVVVALGNLFQKIVPCEGIFLDAALMEKVSKTATGDWSLLAQSMEAYAETAFTRAK DRDAWLRKNYYSLSELSQVPILKNTDEGMLKFELSAYWSGEKMESFVKGIMDAELA MKPVLASIGQKTEEVRLRDRIDDVVKIKGYLDSIQNFLHHLKPFCAPTELNRDADFYS DFDALYNQLVLVIPLYNCVRNYVTQKVTEVQKLRLKFDAPTLADGWDANKENDNKAV LFEKDGLYFLGILNPNLKAKDRPVFEHESNVTKKSCYRKIVYKLLPGPNKMLPKVFFA DSNRTLYHPSKSLLDRYHNGEYKKGDSFDIKFCHELIDYFKASISIHPDWKEFGFQFS ATKTYESIDGFYREVEEQGYKVNFAFVRADLIDKYVESGSLFLFQLYNKDFSCASSGK PNLHTLYWKSLFAKENLDEPILKLCGGAELFFRPVAIQKPYVHTLGEKLVNRRLGEHG KGEAIPERVHKELVDYYNHRVSVLSHDGKAFKDKVVVRDVAHSITKDRRFSEAKFFF HVPIMFNRTASKSAKFNDKVVDYLKTTQNVNVIGLDRGERNLIYLTMVNLHGKLIEQR SFNLVNGVDYHSKLDLREKERMDARVNWENIGGIKDLKTGYLSAVVHEIAKMMVTNN AIVVLEDLNFGFKRGRFKVEKQVYQKFEKMLIDKLNFLMFKECNQAALGGVRRAYQL TDKFVSFEKLGKQTGFLFYVPAGYTSKIDPTTGFTNLFNTKKCTNAEGRKVFFEAMN SIIYDGSRKSFAFSFDYGNPVFRASQTSFKKEWTVYSADTRIVYNRGEKTVNTIHPTQI LHDALCALGIDVHDGLNVLNVVRETPADKIHAKFFSDLFYAFDRTLQMRNSVSGTDE DYIQSPVLNATGEFFDSRKADSTLPQDADANGAYHIALKGLLLLQRMKDIGSDIKLDLS IKHEDWFAFAQKRCQR | 80 |
| Expression construct (with N-terminal methionine, V5-tag and C-terminal NLS) aa sequence | MGSGSFESFTNVYPVSKTLRFELRPVGATAEKLKESGILEHDTKRGKEYATLKDLLDE QHKELLADALKPERVKNALKPNSGKSKKDKLVEENYITEDGEIRWETLAAAMEAFRA GEVEKNVLEAIQTQFRKLIVTILKADERYPGLTASTPSAVIKTLLKQDVHPEAVETFAKF ACYFTGFQENRKNIYAEEKQATAVATRVVHDNFAKFHTQSKIIGVIKNKYPEILQSVEM ELMDELGGMKITDIFSINSYSKWMTQEGIDFINKIIGGYSPSVGVKVRGLNEFINLYRQ QHEEANADRRNLAKMPMLFKQILSDISTRSFIPVMFENDAELKDSIEAFLTGLNDFELN AQKFNVVVALGNLFQKIVPCEGIFLDAALMEKVSKTATGDWSLLAQSMEAYAETAFT RAKDRDAWLRKNYYSLSELSQVPILKNTDEGMLKFELSAYWSGEKMESFVKGIMDA ELAMKPVLASIGQKTEEVRLRDRIDDVVKIKGYLDSIQNFLHHLKPFCAPTELNRDADF YSDFDALYNQLVLVIPLYNCVRNYVTQKVTEVQKLRLKFDAPTLADGWDANKENDNK AVLFEKDGLYFLGILNPNLKAKDRPVFEHESNVTKKSCYRKIVYKLLPGPNKMLPKVF FADSNRTLYHPSKSLLDRYHNGEYKKGDSFDIKFCHELIDYFKASISIHPDWKEFGFQ FSATKTYESIDGFYREVEEQGYKVNFAFVRADLIDKYVESGSLFLFQLYNKDFSCASS GKPNLHTLYWKSLFAKENLDEPILKLCGGAELFFRPVAIQKPYVHTLGEKLVNRRLGE HGKGEAIPERVHKELVDYYNHRVSVLSHDGKAFKDKVVVRDVAHSITKDRRFSEAKF FFHVPIMFNRTASKSAKFNDKVVDYLKTTQNVNVIGLDRGERNLIYLTMVNLHGKLIE QRSFNLVNGVDYHSKLDLREKERMDARVNWENIGGIKDLKTGYLSAVVHEIAKMMVT NNAIVVLEDLNFGFKRGRFKVEKQVYQKFEKMLIDKLNFLMFKECNQAALGGVRRAY QLTDKFVSFEKLGKQTGFLFYVPAGYTSKIDPTTGFTNLFNTKKCTNAEGRKVFFEAM | 81 |

TABLE 1N-continued

| ZTAE Type V Cas Sequences | | |
|---|---|---|
| Name | Sequence | SEQ ID NO. |
| | NSIIYDGSRKSFAFSFDYGNPVFRASQTSFKKEWTVYSADTRIVYNRGEKTVNTIHPT<br>QILHDALCALGIDVHDGLNVLNVVRETPADKIHAKFFSDLFYAFDRTLQMRNSVSGTD<br>EDYIQSPVLNATGEFFDSRKADSTLPQDADANGAYHIALKGLLLLQRMKDIGSDIKLDL<br>SIKHEDWFAFAQKRCQRSRKRTADGSEFESPKKKRKVGSGKPIPNPLLGLDST | |
| Wildtype coding sequence (with N-terminal methionine and stop codon) | ATGAGTTTTGAATCATTCACTAACGTTTATCCCGTTTCCAAGACTTTGCGCTTTGA<br>GCTGAGGCCCGTTGGTGCAACTGCAGAGAAGCTTAAGGAAAGTGGTATCCTTGA<br>GCATGATACGAAACGAGGTAAGGAATATGCGACTCTCAAGGATCTGCTTGATGAG<br>CAACATAAGGAGTTACTTGCTGACGCCCTAAAACCTGAACGTGTGAAGAATGCGC<br>TTAAGCCCAATAGTGGTAAGAGTAAAAAAGATAAATTGGTTGAAGAGAATTACATT<br>ACGGAAGACGGGGAGATTCGATGGGAAACTCTTGCGGCTGCGATGGAGGCATTT<br>CGCGCCGGTGAGGTAGAGAAAAATGTGCTTGAAGCAATACAGACGCAATTTAGA<br>AAGCTGATTGTAACGATACTGAAGGCGGATGAGCGGTATCCGGGACTGACAGCT<br>TCAACGCCTTCGGCTGTCATTAAGACTCTTCTTAAGCAGGATGTTCATCCAGAAG<br>CAGTAGAGACATTTGCAAAATTTGCCTGTTATTTTACCGGTTTTCAGGAAAATCGG<br>AAGAATATCTATGCGGAAGAAAAGCAAGCAACTGCAGTTGCAACGCGAGTTGTTC<br>ATGATAATTTCGCAAAGTTCCATACACAATCGAAAATAATAGGTGTCATAAAGAAT<br>AAATATCCAGAAATCCTTCAGTCGGTAGAAATGGAATTGATGGACGAATTAGGTG<br>GGATGAAAATCACTGATATCTTTTCTATCAACAGCTATTCCAAATGGATGACGCAA<br>GAAGGGATAGACTTTATTAATAAGATTATAGGTGGCTATAGCCCATCTGTTGGTGT<br>GAAGGTGCGTGGTCTGAACGAGTTCATTAATCTTTATCGGCAGCAGCATGAAGAG<br>GCAAATGCAGATCGGCGGAATCTCGCAAAAATGCCGATGCTGTTTAAACAAATTT<br>TAAGTGATATTTCGACACGATCATTCATTCCGGTGATGTTTGAAAATGATGCGGAA<br>CTAAAGGATTCAATAGAAGCATTCTTGACAGGTCTGAATGATTTTGAGTTGAATGC<br>TCAGAAGTTTAACGTTGTCGTTGCATTAGGTAATCTTTTCCAAAAAATTGTGCCTT<br>GCGAAGGTATTTTCTTGGATGCAGCATTGATGGAAAAAGTTTCGAAGACGGCTAC<br>AGGAGATTGGAGTCTTCTTGCTCAGTCGATGGAGGCGTATGCAGAGACAGCATT<br>CACAAGAGCAAAAGACCGAGACGCATGGCTAAGGAAAAATTATTATTCGCTGTCC<br>GAGCTGAGCCAAGTTCCGATTTTGAAGAACACTGATGAAGGAATGTTGAAGTTTG<br>AACTATCTGCCTATTGGTCAGGCGAAAAGATGGAAAGTTTTGTTAAAGGAATCAT<br>GGATGCTGAATTGGCAATGAAACCAGTTCTTGCCAGCATTGGTCAGAAAACCGAA<br>GAGGTGCGTCTTCGTGATCGGATTGACGATGTCGTAAAAATCAAGGGATATCTTG<br>ATTCAATTCAGAATTTTTTACATCACCTAAAACCGTTTTGTGCTCCAACTGAATTGA<br>ATCGTGATGCGGATTTTTATTCTGACTTTGACGCATTGTATAATCAGCTTGTACTG<br>GTTATACCGCTTTATAACTGTGTCCGCAATTACGTGACACAGAAAGTGACAGAGG<br>TTCAGAAACTGAGGCTAAAGTTTGATGCCCCTACATTGGCGGACGGATGGGACG<br>CGAATAAAGAAAATGATAATAAGGCAGTTCTGTTTGAAAAGGACGGGCTATATTTT<br>CTTGGAATCCTGAATCCTAACCTGAAGGCGAAAGATCGTCCAGTCTTTGAGCATG<br>AAAGTAATGTTACAAAGAAATCTTGTTATCGCAAGATTGTCTATAAACTTTTGCCA<br>GGACCAAATAAAATGCTTCCCAAGGTCTTTTTTGCTGATTCCAATAGGACACTGTA<br>CCATCCTTCCAAGTCGTTGCTGGATCGTTATCACAACGGTGAATACAAGAAAGGC<br>GATTCATTCGACATCAAATTCTGTCATGAATTGATTGATTATTTTAAAGCCTCGATT<br>AGTATTCACCCCGATTGGAAGGAATTCGGTTTCCAATTCAGTGCGACAAAAACAT<br>ATGAGAGCATTGATGGTTTTTATCGTGAGGTTGAGGAGCAAGGATATAAAGTTAA<br>TTTTGCTTTTGTAAGGGCGGATTTAATTGACAAATATGTGGAAAGTGGAAGTTTGT<br>TCCTTTTCCAATTGTATAACAAGGATTTCTCTTGTGCGTCATCTGGGAAGCCAAAC<br>CTCCACACGCTTTACTGGAAGAGCCTCTTTGCAAAAGAAAACCTTGATGAGCCGA<br>TTCTGAAGTTGTGTGGGGGTGCAGAGCTATTCTTCCGCCCAGTTGCAATCCAGAA<br>GCCGTATGTACATACCTTGGGAGAAAAGTTGGTCAATCGCAGGCTTGGCGAGCA<br>CGGTAAGGGAGAGGCAATCCCGGAGAGAGTTCACAAGGAACTCGTGGACTACTA<br>CAACCATCGTGTGTCGGTGCTGAGTCATGATGGGAAGGCATTTAAAGACAAGGTT<br>GTTGTTCGGGATGTCGCACATTCGATTACAAAAGATCGTCGATTCTCAGAGGCAA<br>AGTTTTTTTTCCATGTTCCGATCATGTTTAACCGTACAGCATCGAAGAGTGCAAAG<br>TTTAACGACAAAGTTGTGGACTATCTCAAGACCACTCAGAATGTAAACGTTATCG<br>GGTTGGATCGAGGAGAAAGAAATCTGATTTATCTGACAATGGTAAATTTGCACGG<br>AAAGCTGATAGAGCAGCGTAGTTTCAACCTAGTTAATGGTGTGGATTATCATTCAA<br>AGCTAGATTTGCGAGAAAAGGAGCGCATGGACGCACGCGTTAATTGGGAGAACA<br>TTGGGGGAATTAAAGATCTTAAGACCGGATATCTTTCCGCGGTTGTTCATGAGAT<br>TGCGAAGATGATGGTGACGAATAATGCCATTGTTGTCTTGGAGGACTTGAACTTC<br>GGTTTCAAACGTGGGCGGTTCAAGGTTGAGAAACAGGTCTATCAGAAGTTTGAGA<br>AGATGCTGATTGATAAACTGAATTTCCTGATGTTCAAGGAATGCAATCAAGCGGC<br>TCTCGGTGGTGTTCGCCGTGCATATCAATTGACGGATAAATTCGTGAGTTTTGAA<br>AAACTTGGTAAACAAACGGGTTTCCTGTTTTATGTTCCGGCGGGCTACACATCGA<br>AGATTGATCCAACAACTGGATTCACCAACCTCTTCAACACGAAAAAATGCACTAAT<br>GCCGAAGGTCGGAAGGTCTTCTTTGAGGCGATGAACTCTATCATATATGACGGAT<br>CAAGGAAGTCGTTTGCGTTCTCATTTGATTACGGCAACCCAGTTTTTAGAGCAAG<br>TCAAACGAGTTTTAAAAAAGAATGGACCGTCTATTCCGCTGATACGCGCATTGTC<br>TACAATCGTGGCGAGAAAACTGTTAATACGATCCATCCGACACAAATTCTTCATGA<br>TGCTTTGTGTGCACTCGGCATTGACGTTCATGACGGATTGAACGTCTTGAACGTA<br>GTTCGTGAGACGCCAGCGGACAAGATTCATGCTAAGTTTTTCTCAGACTTGTTCT<br>ATGCGTTTGATCGTACACTTCAGATGCGTAACAGTGTTTCAGGAACAGATGAAGA<br>CTATATCCAATCGCCTGTTTTGAATGCGACAGGTGAGTTTTTTGATTCGCGGAAA<br>GCAGACAGTACTCTTCCGCAGGATGCCGATGCCAATGGTGCCTACCACATCGCA<br>TTAAAGGGACTTTTGCTGCTACAACGCATGAAAGATATTGGCAGTGATATCAAGC | 82 |

TABLE 1N-continued

| ZTAE Type V Cas Sequences | | |
|---|---|---|
| Name | Sequence | SEQ ID NO. |
| | TTGATCTATCCATTAAGCATGAGGACTGGTTTGCGTTTGCACAAAAGCGTTGCCA GAGATAA | |
| Codon optimized coding sequence (no N-terminal methionine, no stop codon) | AGCTTCGAGTCTTTCACTAACGTATACCCTGTGTCTAAAACCCTGCGTTTTGAACT GCGGCCTGTGGGCGCCACTGCCGAGAAGCTGAAGGAGAGCGGCATCCTGGAGC ACGATACCAAGCGGGGCAAGGAATACGCTACACTGAAGGACCTGCTGGACGAG CAGCACAAAGAGCTACTGGCCGACGCCCTGAAGCCAGAGAGAGTGAAGAACGC CCTGAAGCCCAACAGCGGCAAGTCCAAAAAGGACAAGCTGGTCGAAGAGAACTA CATTACAGAAGATGGAGAGATCAGATGGGAGACACTGGCCGCTGCTATGGAGGC CTTCAGAGCTGGCGAAGTGGAGAAGAACGTGCTGGAAGCGATCCAGACACAGTT TCGGAAGCTGATCGTGACCATCCTGAAAGCCGACGAGAGATACCCTGGACTGAC CGCCTCTACACCTAGCGCCGTCATCAAGACCTTGCTGAAGCAGGACGTGCACCC CGAGGCCGTAGAGACATTCGCTAAATTTGCCTGTTACTTCACCGGCTTTCAGGAA AACAGAAAGAATATCTACGCCGAAGAAAAACAGGCCACCGCCGTGGCCACACGG GTTGTCCACGACAACTTCGCCAAATTTCACACCCAGTCTAAGATTATCGGCGTGA TCAAAAACAAGTACCCCGAGATCCTGCAGAGCGTCGAGATGGAACTGATGGACG AACTTGGGGGAATGAAGATCACCGATATCTTCAGTATCAACAGCTACAGCAAGTG GATGACCCAGGAGGGAATCGACTTCATCAACAAAATCATCGGCGGCTACAGCCC TAGCGTGGGCGTCAAAGTGAGAGGCCTGAACGAGTTCATCAACCTGTACAGACA GCAGCACGAGGAAGCCAACGCCGACCGGCGGAACCTGGCTAAGATGCCTATGC TGTTTAAACAAATTCTGAGCGACATCAGCACCCGGAGCTTCATCCCTGTGATGTT CGAGAATGACGCCGAGCTCAAGGACAGCATCGAGGCCTTCCTGACAGGCCTGAA TGATTTCGAGCTGAACGCTCAGAAGTTCAACGTTGTGGTGGCCCTGGGGAACCT GTTTCAGAAGATTGTGCCTTGTGAAGGCATCTTCCTGGACGCTGCCCTGATGGAA AAGGTTTCCAAGACAGCTACAGGCGACTGGAGCCTGCTCGCACAGTCTATGGAA GCCTACGCCGAAACAGCCTTTACAAGAGCCAAGGACCGGGACGCCTGGCTGAG AAAGAATTACTACAGCCTGTCCGAGCTGAGCCAGGTGCCAATCCTGAAGAACACT GATGAGGGCATGCTGAAGTTCGAGCTGAGCGCCTACTGGTCCGGCGAGAAAATG GAATCTTTCGTGAAGGGCATCATGGACGCCGAGCTGGCCATGAAGCCAGTGCTG GCCAGCATCGGCCAGAAAACCGAAGAGGTGCGGCTGAGAGATAGAATCGACGA CGTGGTGAAGATCAAGGGCTACCTGGACAGCATCCAGAATTTCCTGCACCACCT GAAGCCTTTCTGTGCCCCTACCGAGCTGAACCGGGACGCCGACTTCTACTCTGA CTTCGATGCTCTGTACAATCAACTGGTGCTGGTGATTCCCCTGTACAACTGCGTG AGAAACTACGTCACCCAAAAGGTTACCGAGGTGCAGAAGCTGCGCCTCAAGTTC GATGCACCTACCCTGGCCGATGGATGGGACGCCAATAAAGAGAATGACAACAAA GCCGTCCTGTTCGAGAAAGACGGCCTGTATTTCCTCGGCATCCTCAACCCTAACC TGAAAGCCAAGGACCGGCCTGTGTTCGAACATGAAAGCAACGTGACCAAGAAGT CATGCTACCGGAAGATTGTGTACAAACTGCTGCCAGGCCCTAACAAGATGCTGC CTAAGGTGTTCTTTGCCGATAGCAACAGGACACTGTACCACCCTAGCAAGAGCCT GCTGGACCGGTATCACAACGGCGAGTACAAGAAGGGCGATAGCTTTGATATCAA GTTTTGCCACGAGCTGATCGACTACTTCAAGGCCTCTATCTCTATTCACCCTGAC TGGAAGGAGTTCGGCTTTCAATTTTCTGCCACAAAGACCTACGAGTCTATCGACG GCTTCTATAGAGAGGTGGAAGAGCAGGGCTACAAGGTGAACTTCGCCTTTGTGC GTGCTGACCTGATCGATAAGTACGTGGAAAGCGGCTCCCTGTTCCTGTTCCAGC TCTATAACAAGGACTTCAGCTGTGCCTCTAGCGGCAAGCCGAATCTTCATACACT GTACTGGAAAAGCCTGTTCGCCAAGGAGAACCTGGACGAGCCTATACTGAAGCT GTGCGGCGGCGCCGAGCTGTTCTTCAGACCCGTGGCGATCCAGAAACCCTACG TGCACACATTGGGCGAAAAGCTGGTGAATAGACGGCTCGGCGAGCACGGCAAG GGCGAGGCTATCCCTGAGCGGGTGCACAAGGAACTGGTGGACTACTACAACCAC AGAGTGAGCGTGCTCAGTCACGATGGAAAGGCCTTCAAGGACAAGGTGGTGGTT CGGGACGTGGCCCACAGCATCACCAAGGACCGACGGTTTAGCGAGGCCAAGTT CTTCTTCCACGTGCCCATCATGTTTAACCGGACCGCCAGCAAGAGCGCCAAGTT CAACGACAAGGTGGTGGACTACCTGAAAACCACCCAAAACGTGAACGTGATCGG ACTGGACAGAGGTGAAAGAAACCTGATCTACCTCACAATGGTGAACCTGCATGG CAAGCTCATCGAGCAGCGGAGCTTCAACCTGGTGAATGGCGTGGACTACCATTC TAAGCTGGATCTGCGCGAGAAGGAACGTATGGATGCTAGAGTGAACTGGGAGAA TATCGGCGGCATAAAGGATCTGAAAACCGGCTACCTGAGCGCCGTGGTGCACGA GATCGCCAAAATGATGGTGACAAACAACGCCATCGTGGTGCTGGAAGATCTGAA CTTTGGATTCAAGAGAGGCAGATTCAAAGTGGAAAAGCAGGTGTACCAGAAATTC GAGAAGATGCTGATCGACAAACTGAACTTCCTGATGTTCAAAGAGTGCAACCAGG CCGCCCTGGGCGGCGTGCGGCGGGCCTATCAGCTGACCGACAAGTTCGTGAGC TTCGAGAAGCTGGGAAAGCAGACCGGCTTCCTGTTCTATGTGCCCGCCGGCTAT ACAAGCAAAATCGATCCTACAACCGGTTTCACCAACCTGTTCAATACCAAGAAAT GCACCAACGCCGAGGGAAGAAAGGTGTTCTTCGAGGCTATGAACAGCATCATCT ACGACGGCTCCAGAAAATCTTTCGCCTTTAGCTTCGACTACGGCAACCCCGTGTT TCGAGCCTCCCAGACCAGCTTCAAGAAGGAATGGACCGTGTACAGCGCCGATAC AAGAATCGTGTATAATCGGGGCGAAAAGACCGTAAACACCATCCACCCTACCCA GATCCTGCACGACGCCCTGTGCGCCTTGGGAATCGACGTGCACGATGGGTTAAA TGTCTTGAACGTCGTGAGAGAGACACCCGCTGATAAGATCCACGCCAAGTTCTTC AGCGATCTCTTCTACGCCTTCGACAGAACCCTGCAGATGAGGAACTCTGTGAGC | 83 |

TABLE 1N-continued

ZTAE Type V Cas Sequences

| Name | Sequence | SEQ ID NO. |
|---|---|---|
| | GGGACCGACGAAGATTACATCCAGAGCCCTGTGCTGAATGCTACCGGCGAGTTC<br>TTTGACAGCAGAAAAGCCGACAGCACCCTGCCCCAGGACGCAGACGCTAATGGA<br>GCCTACCACATCGCCCTGAAGGGCCTGCTGCTCCTGCAGAGAATGAAGGATATC<br>GGCTCAGATATCAAGCTGGATCTGTCTATTAAGCACGAGGATTGGTTCGCCTTCG<br>CTCAGAAGCGGTGCCAGAGA | |
| Expression construct (with N-terminal methionine and stop codon, includes V5-tag and C-terminal NLS) | ATGggctccggaAGCTTCGAGTCTTTCACTAACGTATACCCTGTGTCTAAAACCCTGC<br>GTTTTGAACTGCGGCCTGTGGGCGCCACTGCCGAGAAGCTGAAGGAGAGCGGC<br>ATCCTGGAGCACGATACCAAGCGGGGCAAGGAATACGCTACACTGAAGGACCTG<br>CTGGACGAGCAGCACAAAGAGCTACTGGCCGACGCCCTGAAGCCAGAGAGAGT<br>GAAGAACGCCCTGAAGCCCAACAGCGGCAAGTCCAAAAAGGACAAGCTGGTCGA<br>AGAGAACTACATTACAGAAGATGGAGAGATCAGATGGGAGACACTGGCCGCTGC<br>TATGGAGGCCTTCAGAGCTGGCGAAGTGGAGAAGAACGTGCTGGAAGCGATCCA<br>GACACAGTTTCGGAAGCTGATCGTGACCATCCTGAAAGCCGACGAGAGATACCC<br>TGGACTGACCGCCTCTACACCTAGCGCCGTCATCAAGACCTTGCTGAAGCAGGA<br>CGTGCACCCCGAGGCCGTAGAGACATTCGCTAAATTTGCCTGTTACTTCACCGG<br>CTTTCAGGAAAACAGAAAGAATATCTACGCCGAAGAAAAACAGGCCACCGCCGT<br>GGCCACACGGGTTGTCCACGACAACTTCGCCAAATTTCACACCCAGTCTAAGATT<br>ATCGGCGTGATCAAAAACAAGTACCCCGAGATCCTGCAGAGCGTCGAGATGGAA<br>CTGATGGACGAACTTGGGGGAATGAAGATCACCGATATCTTCAGTATCAACAGCT<br>ACAGCAAGTGGATGACCCAGGAGGGAATCGACTTCATCAACAAAATCATCGGCG<br>GCTACAGCCCTAGCGTGGGCGTCAAAGTGAGAGGCCTGAACGAGTTCATCAACC<br>TGTACAGACAGCAGCACGAGGAAGCCAACGCCGACCGGCGGAACCTGGCTAAG<br>ATGCCTATGCTGTTTAAACAAATTCTGAGCGACATCAGCACCCGGAGCTTCATCC<br>CTGTGATGTTCGAGAATGACGCCGAGCTCAAGGACAGCATCGAGGCCTTCCTGA<br>CAGGCCTGAATGATTTCGAGCTGAACGCTCAGAAGTTCAACGTTGTGGTGGCCC<br>TGGGGAACCTGTTTCAGAAGATTGTGCCTTGTGAAGGCATCTTCCTGGACGCTG<br>CCCTGATGGAAAAGGTTTCCAAGACAGCTACAGGCGACTGGAGCCTGCTCGCAC<br>AGTCTATGGAAGCCTACGCCGAAACAGCCTTTACAAGAGCCAAGGACCGGGACG<br>CCTGGCTGAGAAAGAATTACTACAGCCTGTCCGAGCTGAGCCAGGTGCCAATCC<br>TGAAGAACACTGATGAGGGCATGCTGAAGTTCGAGCTGAGCGCCTACTGGTCCG<br>GCGAGAAAATGGAATCTTTCGTGAAGGGCATCATGGACGCCGAGCTGGCCATGA<br>AGCCAGTGCTGGCCAGCATCGGCCAGAAAACCGAAGAGGTGCGGCTGAGAGAT<br>AGAATCGACGACGTGGTGAAGATCAAGGGCTACCTGGACAGCATCCAGAATTTC<br>CTGCACCACCTGAAGCCTTTCTGTGCCCCTACCGAGCTGAACCGGGACGCCGAC<br>TTCTACTCTGACTTCGATGCTCTGTACAATCAACTGGTGCTGGTGATTCCCCTGTA<br>CAACTGCGTGAGAAACTACGTCACCCAAAAGGTTACCGAGGTGCAGAAGCTGCG<br>CCTCAAGTTCGATGCACCTACCCTGGCCGATGGATGGGACGCCAATAAAGAGAA<br>TGACAACAAAGCCGTCCTGTTCGAGAAAGACGGCCTGTATTTCCTCGGCATCCTC<br>AACCCTAACCTGAAAGCCAAGGACCGGCCTGTGTTCGAACATGAAAGCAACGTG<br>ACCAAGAAGTCATGCTACCGGAAGATTGTGTACAAACTGCTGCCAGGCCCTAACA<br>AGATGCTGCCTAAGGTGTTCTTTGCCGATAGCAACAGGACACTGTACCACCCTAG<br>CAAGAGCCTGCTGGACCGGTATCACAACGGCGAGTACAAGAAGGGCGATAGCTT<br>TGATATCAAGTTTTGCCACGAGCTGATCGACTACTTCAAGGCCTCTATCTCTATTC<br>ACCCTGACTGGAAGGAGTTCGGCTTTCAATTTTCTGCCACAAAGACCTACGAGTC<br>TATCGACGGCTTCTATAGAGAGGTGGAAGAGCAGGGCTACAAGGTGAACTTCGC<br>CTTTGTGCGTGCTGACCTGATCGATAAGTACGTGGAAAGCGGCTCCCTGTTCCT<br>GTTCCAGCTCTATAACAAGGACTTCAGCTGTGCCTCTAGCGGCAAGCCGAATCTT<br>CATACACTGTACTGGAAAAGCCTGTTCGCCAAGGAGAACCTGGACGAGCCTATA<br>CTGAAGCTGTGCGGCGGCGCCGAGCTGTTCTTCAGACCCGTGGCGATCCAGAA<br>ACCCTACGTGCACACATTGGGCGAAAAGCTGGTGAATAGACGGCTCGGCGAGCA<br>CGGCAAGGGCGAGGCTATCCCTGAGCGGGTGCACAAGGAACTGGTGGACTACT<br>ACAACCACAGAGTGAGCGTGCTCAGTCACGATGGAAAGGCCTTCAAGGACAAGG<br>TGGTGGTTCGGGACGTGGCCCACAGCATCACCAAGGACCGACGGTTTAGCGAG<br>GCCAAGTTCTTCTTCCACGTGCCCATCATGTTTAACCGGACCGCCAGCAAGAGC<br>GCCAAGTTCAACGACAAGGTGGTGGACTACCTGAAAACCACCCAAAACGTGAAC<br>GTGATCGGACTGGACAGAGGTGAAAGAAACCTGATCTACCTCACAATGGTGAAC<br>CTGCATGGCAAGCTCATCGAGCAGCGGAGCTTCAACCTGGTGAATGGCGTGGAC<br>TACCATTCTAAGCTGGATCTGCGCGAGAAGGAACGTATGGATGCTAGAGTGAACT<br>GGGAGAATATCGGCGGCATAAAGGATCTGAAAACCGGCTACCTGAGCGCCGTG<br>GTGCACGAGATCGCCAAAATGATGGTGACAAACAACGCCATCGTGGTGCTGGAA<br>GATCTGAACTTTGGATTCAAGAGAGGCAGATTCAAAGTGGAAAAGCAGGTGTACC<br>AGAAATTCGAGAAGATGCTGATCGACAAACTGAACTTCCTGATGTTCAAAGAGTG<br>CAACCAGGCCGCCCTGGGCGGCGTGCGGCGGGCCTATCAGCTGACCGACAAGT<br>TCGTGAGCTTCGAGAAGCTGGGAAAGCAGACCGGCTTCCTGTTCTATGTGCCCG<br>CCGGCTATACAAGCAAAATCGATCCTACAACCGGTTTCACCAACCTGTTCAATAC<br>CAAGAAATGCACCAACGCCGAGGGAAGAAAGGTGTTCTTCGAGGCTATGAACAG<br>CATCATCTACGACGGCTCCAGAAAATCTTTCGCCTTTAGCTTCGACTACGGCAAC<br>CCCGTGTTTCGAGCCTCCCAGACCAGCTTCAAGAAGGAATGGACCGTGTACAGC<br>GCCGATACAAGAATCGTGTATAATCGGGGCGAAAAGACCGTAAACACCATCCAC<br>CCTACCCAGATCCTGCACGACGCCCTGTGCGCCTTGGGAATCGACGTGCACGAT<br>GGGTTAAATGTCTTGAACGTCGTGAGAGAGACACCCGCTGATAAGATCCACGCC<br>AAGTTCTTCAGCGATCTCTTCTACGCCTTCGACAGAACCCTGCAGATGAGGAACT<br>CTGTGAGCGGGACCGACGAAGATTACATCCAGAGCCCTGTGCTGAATGCTACCG | 84 |

TABLE 1N-continued

| ZTAE Type V Cas Sequences | | |
|---|---|---|
| Name | Sequence | SEQ ID NO. |
| | GCGAGTTCTTTGACAGCAGAAAAGCCGACAGCACCCTGCCCCAGGACGCAGAC<br>GCTAATGGAGCCTACCACATCGCCCTGAAGGGCCTGCTGCTCCTGCAGAGAATG<br>AAGGATATCGGCTCAGATATCAAGCTGGATCTGTCTATTAAGCACGAGGATTGGT<br>TCGCCTTCGCTCAGAAGCGGTGCCAGAGAtctagaAAGCGGACAGCAGACGGCTC<br>CGAATTTGAAAGCCCTAAGAAAAAGAGAAAGGTGggatccGGCAAACCTATCCCCA<br>ATCCCCTGCTGGGCCTGGACAGCACCTGA | |

In some embodiments a ZTAE Type V Cas protein comprises an amino acid sequence of SEQ ID NO:79, SEQ ID NO:80, or SEQ ID NO:81. In some embodiments, a ZTAE Type V Cas protein has nickase activity, for example resulting from one or more amino acid substitutions relative to the sequence of SEQ ID NO:79, SEQ ID NO:80, or SEQ ID NO:81. In some embodiments, the one or more amino acid substitutions providing nickase activity comprise a D905 substitution, wherein the position of the D905 substitution is defined with respect to the amino acid numbering of SEQ ID NO:80 (corresponding to amino acid 908 of SEQ ID NO:121). In some embodiments, the one or more amino acid substitutions providing nickase activity comprise an E990 substitution, wherein the position of the E990 substitution is defined with respect to the amino acid numbering of SEQ ID NO:80 (corresponding to amino acid 993 of SEQ ID NO:121). In some embodiments, the one or more amino acid substitutions providing nickase activity comprise a R1206 substitution, wherein the position of the R1206 substitution is defined with respect to the amino acid numbering of SEQ ID NO:80 (corresponding to amino acid 1226 of SEQ ID NO:121). In some embodiments, the one or more amino acid substitutions providing nickase activity comprise a D1243 substitution, wherein the position of the D1243 substitution is defined with respect to the amino acid numbering of SEQ ID NO:80 (corresponding to amino acid 1263 of SEQ ID NO:121). In some embodiments, a ZTAE Type V Cas protein is catalytically inactive, for example due to a R1206 substitution in combination with a D905 substitution, a E990 substitution, and/or D1243 substitution.

6.2.15. ZSQQ Type V Cas Protein

In one aspect, the disclosure provides ZSQQ Type V Cas proteins. ZSQQ Type V Cas proteins can be further classified as Type V-A Cas proteins. The ZSQQ Type V Cas proteins typically comprise an amino acid sequence that is at least 50%, at least 55%, at least 60%, at least 65%, at least 70%, at least 75%, at least 85%, at least 90%, or at least 95% identical to SEQ ID NO:85. In some embodiments, the ZSQQ Type V Cas proteins comprise an amino acid sequence that is at least 95%, at least 96%, at least 97%, at least 98%, or at least 99% identical to SEQ ID NO:85. In some embodiments, a ZSQQ Type V Cas protein comprises an amino acid sequence that is identical to SEQ ID NO:85.

Exemplary ZSQQ Type V Cas protein sequences and nucleotide sequences encoding exemplary ZSQQ Type V Cas proteins are set forth in Table 10.

TABLE 10

| ZSQQ Type V Cas Sequences | | |
|---|---|---|
| Name | Sequence | SEQ ID NO. |
| Wildtype amino acid sequence (without N-terminal methionine) | STINKFCGQGNGYSRSITLRNKLIPIGKTEENLKWFLEKDLERAIAYPEIKNLIDNIHRS<br>VIEDTLSKVALNWNEIFNTLAAYQNEKDKKKKAAIKKDLEKLQGCARKKIVDTFKKNP<br>DYEKLFKEGLFKELLPELIKTAPVSEIEDKTKALECFNRFSTYFTGFHENRKNMYSED<br>AKSTAISYRIVNENFPKFFANIKLYNYLKEKFPQIIINTEESLKDYLKGKKLDSVFSIDGF<br>NDVLAQSGIDFYNTVIGGISGEAGTEKTQGLNEKINLARQQLPKDEKDKLRGKMVDL<br>FKQILSDRETSSFIPTGFENKKEVYSTVKKFSEIVVEKSVSKVKEIFTQNEEYNLNEIF<br>VPAKSLTNFSQNIFGNWSILSEGLFLLEKDNVKKQLSEKQIETLHKEIAKKDCSFTEL<br>QNAYERWCAENSVDATKNINRYFSIVDLRTKNDSFEKEEINILDEITNAFSKIDFDDIH<br>DLQQEKEAATPIKNYLDEVQNLYHHLKLVDYRGEERKDANFYSKLDYILRKDRKDYL<br>NLAEVVPLYNKVRNFVTKKPGEVKKIKMMFDCSSLLGGWGTDYETKEAHIFIDSGKY<br>YLGIINEKLSKDDVELLKKSSERMITKVIYDFQKPDNKNTPRLFIRSKGTNYAPAVFQY<br>NLPIESVIDIYDRGLFKTEYRKINSKVYKESLIKMIDYFKMGFERHESYKHYKFCWKE<br>SSKYNDIGEFYKDVINSCYQLNFEKVNYENLLKLVENNKLFLFQIYNKDFAEKKSGKK<br>NLHTLYWENLFSEENLKDVCLKLNGEAELFWRKASLDKGKVIVHRMGSILVNRTTSE<br>GKSIPEDIYQEIYQYKNKMKDKISDEAKSLLDSGTVICKEATHDITKDKRFTEDTYLFH<br>CPITMNFKATDKKNKEFNNHVLEVLKENPDVKIIGLDRGERHLIYLSLINQKGEIELQK<br>TLNLVEQVRNDKTVKVDYQEKLVHKEGDRDKARKNWQTIGNIKELKEGYLSAVVHEI<br>AMLMVENNAIVVMEDLNFGFKRGRFAVERQIYQKFENMLIEKLNYLVFKDKNATEPG<br>GVLNAYQLTNKSANVTDVYKQCGWLFYIPAAYTSKIDPKTGFANLFITKGLTNVEKK<br>KEFFDKFDSIRYDSKEDCFVFGFDYAKLCDNASFRKKWEVYTRGERLVYNKDKHKN<br>EPINPTEELKGIFDAFDINWNTDDNFIDSVQTIQAEKANAKFFDILLRMFNATLQMRN<br>SKTNSSASEDDYLISPVKAEDGTFFDTREELKKGKDAKLPIDSDANGAYHIALKGLFL<br>LENDFNRDEKGVIQNISNADWFKFVQEKKYKD | 85 |

TABLE 10-continued

ZSQQ Type V Cas Sequences

| Name | Sequence | SEQ ID NO. |
|---|---|---|
| Wildtype amino acid sequence (with N-terminal methionine) | MSTINKFCGQGNGYSRSITLRNKLIPIGKTEENLKWFLEKDLERAIAYPEIKNLIDNIHR<br>SVIEDTLSKVALNWNEIFNTLAAYQNEKDKKKKAAIKKDLEKLQGCARKKIVDTFKKN<br>PDYEKLFKEGLFKELLPELIKTAPVSEIEDKTKALECFNRFSTYFTGFHENRKNMYSE<br>DAKSTAISYRIVNENFPKFFANIKLYNYLKEKFPQIIINTEESLKDYLKGKKLDSVFSID<br>GFNDVLAQSGIDFYNTVIGGISGEAGTEKTQGLNEKINLARQQLPKDEKDKLRGKMV<br>DLFKQILSDRETSSFIPTGFENKKEVYSTVKKFSEIVVEKSVSKVKEIFTQNEEYNLNE<br>IFVPAKSLTNFSQNIFGNWSILSEGLFLLEKDNVKKQLSEKQIETLHKEIAKKDCSFTE<br>LQNAYERWCAENSVDATKNINRYFSIVDLRTKNDSFEKEEINILDEITNAFSKIDFDDI<br>HDLQQEKEAATPIKNYLDEVQNLYHHLKLVDYRGEERKDANFYSKLDYILRKDRKDY<br>LNLAEVVPLYNKVRNFVTKKPGEVKKIKMMFDCSSLLGGWGTDYETKEAHIFIDSGK<br>YYLGIINEKLSKDDVELLKKSSERMITKVIYDFQKPDNKNTPRLFIRSKGTNYAPAVFQ<br>YNLPIESVIDIYDRGLFKTEYRKINSKVYKESLIKMIDYFKMGFERHESYKHYKFCWK<br>ESSKYNDIGEFYKDVINSCYQLNFEKVNYENLLKLVENNKLFLFQIYNKDFAEKKSGK<br>KNLHTLYWENLFSEENLKDVCLKLNGEAELFWRKASLDKGKVIVHRMGSILVNRTTS<br>EGKSIPEDIYQEIYQYKNKMKDKISDEAKSLLDSGTVICKEATHDITKDKRFTEDTYLF<br>HCPITMNFKATDKKNKEFNNHVLEVLKENPDVKIIGLDRGERHLIYLSLINQKGEIELQ<br>KTLNLVEQVRNDKTVKVDYQEKLVHKEGDRDKARKNWQTIGNIKELKEGYLSAVVH<br>EIAMLMVENNAIVVMEDLNFGFKRGRFAVERQIYQKFENMLIEKLNYLVFKDKNATE<br>PGGVLNAYQLTNKSANVTDVYKQCGWLFYIPAAYTSKIDPKTGFANLFITKGLTNVE<br>KKKEFFDKFDSIRYDSKEDCFVFGFDYAKLCDNASFRKKWEVYTRGERLVYNKDKH<br>KNEPINPTEELKGIFDAFDINWNTDDNFIDSVQTIQAEKANAKFFDILLRMFNATLQM<br>RNSKTNSSASEDDYLISPVKAEDGTFFDTREELKKGKDAKLPIDSDANGAYHIALKG<br>LFLLENDFNRDEKGVIQNISNADWFKFVQEKKYKD | 86 |
| Expression construct (with N-terminal methionine, V5-tag and C-terminal NLS) aa sequence | MGSGSTINKFCGQGNGYSRSITLRNKLIPIGKTEENLKWFLEKDLERAIAYPEIKNLID<br>NIHRSVIEDTLSKVALNWNEIFNTLAAYQNEKDKKKKAAIKKDLEKLQGCARKKIVDT<br>FKKNPDYEKLFKEGLFKELLPELIKTAPVSEIEDKTKALECFNRFSTYFTGFHENRKN<br>MYSEDAKSTAISYRIVNENFPKFFANIKLYNYLKEKFPQIIINTEESLKDYLKGKKLDSV<br>FSIDGFNDVLAQSGIDFYNTVIGGISGEAGTEKTQGLNEKINLARQQLPKDEKDKLRG<br>KMVDLFKQILSDRETSSFIPTGFENKKEVYSTVKKFSEIVVEKSVSKVKEIFTQNEEY<br>NLNEIFVPAKSLTNFSQNIFGNWSILSEGLFLLEKDNVKKQLSEKQIETLHKEIAKKDC<br>SFTELQNAYERWCAENSVDATKNINRYFSIVDLRTKNDSFEKEEINILDEITNAFSKID<br>FDDIHDLQQEKEAATPIKNYLDEVQNLYHHLKLVDYRGEERKDANFYSKLDYILRKD<br>RKDYLNLAEVVPLYNKVRNFVTKKPGEVKKIKMMFDCSSLLGGWGTDYETKEAHIFI<br>DSGKYYLGIINEKLSKDDVELLKKSSERMITKVIYDFQKPDNKNTPRLFIRSKGTNYA<br>PAVFQYNLPIESVIDIYDRGLFKTEYRKINSKVYKESLIKMIDYFKMGFERHESYKHYK<br>FCWKESSKYNDIGEFYKDVINSCYQLNFEKVNYENLLKLVENNKLFLFQIYNKDFAE<br>KKSGKKNLHTLYWENLFSEENLKDVCLKLNGEAELFWRKASLDKGKVIVHRMGSIL<br>VNRTTSEGKSIPEDIYQEIYQYKNKMKDKISDEAKSLLDSGTVICKEATHDITKDKRFT<br>EDTYLFHCPITMNFKATDKKNKEFNNHVLEVLKENPDVKIIGLDRGERHLIYLSLINQK<br>GEIELQKTLNLVEQVRNDKTVKVDYQEKLVHKEGDRDKARKNWQTIGNIKELKEGY<br>LSAVVHEIAMLMVENNAIVVMEDLNFGFKRGRFAVERQIYQKFENMLIEKLNYLVFK<br>DKNATEPGGVLNAYQLTNKSANVTDVYKQCGWLFYIPAAYTSKIDPKTGFANLFITK<br>GLTNVEKKKEFFDKFDSIRYDSKEDCFVFGFDYAKLCDNASFRKKWEVYTRGERLV<br>YNKDKHKNEPINPTEELKGIFDAFDINWNTDDNFIDSVQTIQAEKANAKFFDILLRMF<br>NATLQMRNSKTNSSASEDDYLISPVKAEDGTFFDTREELKKGKDAKLPIDSDANGAY<br>HIALKGLFLLENDFNRDEKGVIQNISNADWFKFVQEKKYKDSRKRTADGSEFESPKK<br>KRKVGSGKPIPNPLLGLDST | 87 |
| Wildtype coding sequence (with N-terminal methionine and stop codon) | ATGTCAACTATTAACAAATTTTGTGGACAGGGGAATGGGTATTCTCGTTCAATTA<br>CTTTGAGGAATAAGTTAATTCCTATTGGAAAAACTGAAGAAAATTTGAAATGGTTT<br>TTAGAAAAAGATTTGGAAAGGGCAATTGCTTATCCGGAGATAAAGAATCTTATAG<br>ATAATATTCATCGTAGTGTAATTGAGGATACTTTATCCAAAGTTGCTTTGAATTGG<br>AATGAAATATTCAATACACTTGCTGCTTATCAAAATGAAAAAGATAAAAAAAAGAA<br>AGCAGCAATAAAAAAGGATTTGGAGAAATTACAAGGTTGTGCAAGAAAGAAAATA<br>GTTGATACTTTTAAAAAGAATCCTGATTATGAAAAATTGTTTAAGGAAGGATTATT<br>CAAAGAACTATTACCTGAGTTAATAAAAACTGCTCCTGTTAGTGAAATAGAAGAT<br>AAAACAAAAGCTTTGGAATGTTTTAATAGATTTAGTACATATTTTACAGGATTTCA<br>TGAAAATAGAAAAAATATGTATAGCGAAGATGCAAAATCAACTGCAATAAGTTAC<br>CGTATTGTAAATGAGAATTTCCCCAAATTTTTTGCAAATATAAAGTTATATAATTAT<br>TTAAAAGAAAAGTTTCCACAAATTATTATTAATACAGAAGAATCTTTAAAAGATTAT<br>CTAAAAGGTAAAAAACTTGATTCTGTATTTAGTATTGATGGATTTAATGATGTTTT<br>AGCTCAAAGTGGAATCGATTTTTATAATACAGTAATTGGTGGAATTTCTGGTGAA<br>GCCGGAACAGAAAAGACTCAAGGATTAAATGAAAAAATCAATCTTGCAAGACAA<br>CAATTACCAAAAGATGAAAAAGATAAACTTCGTGGAAAAATGGTTGATTTATTTAA<br>GCAGATTTTAAGTGATAGAGAAACATCTTCGTTTATTCCAACTGGTTTTGAAAATA<br>AAAAAGAAGTTTATTCTACTGTAAAGAAATTTAGTGAAATTGTTGTTGAAAAGTCT<br>GTTTCAAAAGTAAAAGAAATTTTTACACAAAATGAAGAATATAATCTTAATGAAAT<br>CTTTGTTCCAGCAAAATCATTAACAAATTTTTCTCAAAATATTTTTGGAAATTGGT<br>CTATTTTATCAGAAGGGTTATTTTTGCTTGAAAAAGATAATGTTAAAAAACAATTA<br>TCTGAAAAACAAATTGAAACATTACACAAAGAAATTGCAAAAAAAGATTGTTCTTT<br>TACTGAACTACAAAATGCTTATGAAAGATGGTGTGCTGAAAATAGTGTTGATGCA<br>ACAAAAAATATCAATAGGTATTTTTCAATAGTTGATTTAAGAACAAAAAATGATTC<br>GTTTGAAAAAGAAGAAATTAATATTTTGGATGAAATTACAAATGCTTTTTCAAAAA | 88 |

TABLE 10-continued

| ZSQQ Type V Cas Sequences | | |
|---|---|---|
| Name | Sequence | SEQ ID NO. |
| | TTGATTTTGATGATATTCATGATTTACAACAAGAAAAAGAAGCTGCAACACCAATA<br>AAAAATTATTTGGATGAAGTTCAAAATCTTTATCATCACTTAAAACTTGTTGATTAT<br>CGTGGTGAAGAACGAAAGGATGCAAACTTTTATTCAAAGCTAGATTATATATTAA<br>GGAAAGATAGGAAAGATTACCTTAATCTTGCTGAAGTTGTACCTTTGTATAACAA<br>AGTTCGTAATTTTGTAACAAAGAAACCTGGTGAAGTAAAAAAGATTAAAATGATG<br>TTTGATTGTAGTTCTTTATTAGGGGGGTGGGGAACTGATTACGAAACAAAAGAA<br>GCTCATATTTTTATTGATTCTGGAAAATATTATTTGGGAATTATAAACGAAAAATT<br>ATCAAAAGATGATGTTGAGTTATTAAAAAAATCAAGTGAAAGAATGATAACAAAA<br>GTAATTTATGATTTTCAGAAACCTGATAATAAAAATACACCTCGTTTATTTATTCG<br>TTCAAAAGGAACAAATTATGCACCTGCTGTTTTTCAATATAATTTACCAATAGAAT<br>CTGTTATTGATATTTATGATAGAGGATTGTTTAAAACCGAATATAGAAAAATCAAT<br>TCAAAAGTTTACAAAGAATCATTAATAAAAATGATTGATTATTTCAAGATGGGCTT<br>TGAAAGACATGAATCATATAAGCATTATAAATTCTGTTGGAAGGAATCTTCAAAAT<br>ATAATGATATTGGTGAATTTTACAAGGATGTGATAAATTCATGCTATCAATTAAAT<br>TTCGAAAAAGTGAATTATGAAAATTTATTAAAATTGGTTGAAAACAATAAATTATT<br>CCTTTTCCAAATATATAACAAAGATTTTGCAGAAAAAAAATCTGGAAAGAAAAATC<br>TTCATACTTTGTATTGGGAAAATCTTTTTAGTGAAGAAAACTTGAAAGATGTTTGC<br>TTAAAATTGAATGGTGAAGCTGAACTTTTCTGGCGCAAAGCAAGTTTAGACAAAG<br>GAAAAGTTATAGTTCATAGAATGGGTTCTATTCTTGTAAATAGAACTACATCTGAA<br>GGTAAATCAATTCCAGAAGATATTTATCAGGAAATTTATCAATATAAAAATAAAAT<br>GAAAGATAAAATTTCTGATGAAGCAAAAAGTCTTTTAGATTCAGGAACAGTTATTT<br>GTAAAGAAGCAACTCACGATATTACAAAAGACAAGCGCTTTACAGAAGATACATA<br>TCTTTTCCATTGTCCAATTACAATGAACTTTAAAGCAACTGATAAAAAAAATAAAG<br>AATTTAATAATCATGTTCTTGAAGTTTTAAAAGAAAATCCAGATGTTAAAATTATTG<br>GTCTTGACCGTGGTGAAAGACATTTGATTTATCTTTCTTTGATTAATCAAAAAGGT<br>GAAATTGAACTTCAAAAAACATTGAATCTTGTAGAACAAGTTAGAAATGATAAAAC<br>TGTAAAAGTAGATTATCAAGAAAAACTTGTACATAAAGAAGGCGACAGAGACAAA<br>GCTCGTAAAAACTGGCAAACAATTGGAAATATCAAAGAACTAAAAGAAGGTTATT<br>TATCTGCTGTTGTTCATGAAATTGCAATGTTGATGGTAGAAAATAATGCAATTGTT<br>GTAATGGAAGATTTGAATTTTGGATTTAAACGTGGTCGATTTGCTGTAGAAAGAC<br>AAATTTATCAAAAGTTTGAAAATATGCTCATTGAAAAACTTAATTATCTTGTGTTTA<br>AGGATAAAAATGCTACAGAACCAGGTGGTGTCCTTAATGCATATCAATTAACAAA<br>TAAATCTGCAAATGTAACTGACGTTTATAAACAATGTGGATGGCTTTTCTATATTC<br>CAGCAGCGTATACTTCAAAAATTGATCCAAAAACAGGTTTTGCAAATTTATTCATA<br>ACAAAAGGATTAACAAATGTAGAAAAGAAAAAAGAATTCTTTGATAAATTCGATTC<br>CATTCGTTATGACTCAAAAGAAGACTGTTTTGTATTTGGTTTTGATTATGCAAAAC<br>TTTGTGATAATGCAAGTTTTAGAAAAAAATGGGAAGTATACACAAGAGGGGAAAG<br>ATTAGTTTACAATAAAGATAAACATAAAAATGAACCTATTAATCCAACAGAAGAAT<br>TAAAAGGAATTTTTGATGCATTCGATATAAATTGGAATACGGATGATAATTTTATT<br>GATTCCGTACAGACAATACAAGCAGAAAAAGCAAATGCCAAATTCTTTGATATTC<br>TTTTGCGAATGTTTAATGCAACTCTTCAAATGCGAAATTCAAAAACAAATTCTTCA<br>GCATCAGAAGATGATTATTTGATATCTCCGGTAAAAGCAGAGGATGGAACATTCT<br>TTGATACTCGTGAAGAATTAAAGAAAGGCAAAGATGCAAAACTTCCTATAGATTC<br>AGATGCAAACGGAGCTTATCATATTGCACTAAAAGGACTTTTCTTACTTGAAAAT<br>GACTTCAATAGAGATGAAAAAGGTGTGATTCAGAATATCTCCAACGCCGATTGG<br>TTTAAGTTTGTGCAGGAGAAAAAATACAAAGATTAA | |
| Codon optimized coding sequence (no N-terminal methionine, no stop codon) | AGCACCATCAACAAATTCTGCGGCCAGGGCAACGGCTACAGCAGAAGCATCAC<br>CCTGCGGAACAAACTGATCCCTATCGGCAAGACTGAGGAGAACCTGAAGTGGT<br>TCCTGGAGAAGGACCTGGAGCGGGCTATCGCCTACCCCGAGATTAAAAACCTT<br>ATCGACAATATCCACAGAAGCGTGATAGAGGATACCCTGAGCAAGGTCGCCCT<br>GAACTGGAATGAGATCTTCAACACCCTGGCCGCCTACCAGAACGAGAAAGATAA<br>GAAAAAGAAGGCCGCTATCAAGAAGGACCTGGAGAAGTTGCAAGGATGTGCGA<br>GAAAGAAAATCGTGGATACCTTCAAGAAGAACCCTGATTATGAGAAACTGTTTAA<br>AGAGGGACTGTTCAAGGAGCTGCTGCCTGAACTGATCAAGACCGCCCCTGTGA<br>GCGAAATTGAAGATAAAACCAAAGCCCTGGAGTGCTTCAACCGGTTCTCCACAT<br>ACTTCACCGGCTTCCACGAAAATCGCAAAAATATGTACAGCGAGGACGCGAAGA<br>GCACCGCCATCTCCTACCGGATCGTGAACGAGAACTTCCCCAAGTTCTTCGCTA<br>ATATCAAGCTGTACAACTACCTCAAGGAAAAATTTCCACAGATTATCATCAACAC<br>AGAAGAGTCTCTGAAGGATTACCTGAAGGGCAAGAAGCTGGATTCCGTGTTCTC<br>CATCGACGGGTTCAATGACGTGCTGGCCCAGAGCGGCATAGACTTCTACAACA<br>CCGTGATCGGTGGCATCTCAGGAGAGGCCGGCACAGAAAAGACCCAGGGCCT<br>GAATGAGAAGATCAACCTAGCCAGACAGCAGCTGCCTAAGGATGAGAAGGACA<br>AGCTAAGAGGCAAGATGGTCGACCTGTTCAAGCAGATTCTGAGCGATAGAGAAA<br>CCAGCAGCTTCATCCCTACTGGCTTCGAGAATAAGAAGGAAGTGTACTCTACCG<br>TGAAGAAGTTCAGCGAAATCGTGGTCGAAAAAAGCGTGTCCAAGGTGAAGGAG<br>ATCTTCACTCAGAACGAAGAGTACAATCTGAACGAGATCTTCGTGCCTGCGAAG<br>AGCCTGACCAATTTTAGCCAGAACATCTTTGGCAACTGGAGCATCCTTTCTGAA<br>GGCCTGTTCCTGCTGGAAAAGGACAACGTGAAGAAACAGCTGAGTGAGAAACA<br>AATCGAGACACTCCATAAGGAGATCGCCAAGAAGGACTGCAGCTTTACCGAACT<br>GCAGAACGCCTACGAGCGGTGGTGCGCCGAGAACTCCGTGGACGCCACCAAG<br>AACATTAACAGATACTTCAGCATCGTCGACCTGAGAACCAAGAATGACTCCTTC<br>GAGAAGGAAGAGATCAATATCCTTGATGAGATAACCAACGCCTTCTCTAAGATT<br>GACTTCGACGATATCCACGATCTGCAGCAAGAGAAGGAGGCCGCCACCCCTAT<br>CAAGAACTACCTGGACGAGGTTCAAAACCTGTACCACCACCTGAAGCTGGTGGA | 89 |

TABLE 10-continued

ZSQQ Type V Cas Sequences

| Name | Sequence | SEQ ID NO. |
|---|---|---|
| | CTACAGAGGTGAGGAACGAAAGGACGCTAACTTCTACTCTAAACTGGACTATAT<br>CCTGAGAAAGGACAGAAAGGACTACCTGAACCTGGCCGAAGTGGTGCCATTGT<br>ACAACAAGGTTAGAAACTTCGTGACCAAGAAGCCTGGCGAGGTGAAAAAGATCA<br>AGATGATGTTCGACTGCAGCAGCCTGCTGGGCGGATGGGGCACAGATTACGAG<br>ACAAAAGAGGCCCACATTTTCATCGACTCCGGCAAGTATTACCTTGGAATCATCA<br>ACGAGAAGTTGTCAAAAGATGACGTGGAGCTGCTGAAGAAGAGCAGCGAACGG<br>ATGATCACAAAGGTGATCTACGATTTCCAAAAGCCCGATAACAAGAATACACCTA<br>GACTGTTCATCAGGAGCAAGGGCACAAATTATGCTCCTGCTGTTTTCCAATACAA<br>TCTGCCAATAGAGTCTGTGATCGATATTTACGACCGTGGCCTGTTTAAGACCGA<br>GTACAGAAAAATCAACAGCAAGGTGTACAAGGAGAGCCTGATTAAGATGATCGA<br>TTACTTCAAGATGGGCTTTGAGAGACACGAGAGCTACAAGCACTACAAGTTTTG<br>CTGGAAGGAATCTAGCAAGTACAACGACATCGGCGAATTTTACAAGGATGTGAT<br>TAACTCTTGTTACCAGCTGAACTTCGAGAAGGTGAACTATGAGAACCTCCTGAA<br>GTTAGTGGAAAACAACAAGCTGTTCCTGTTTCAGATCTACAACAAGGATTTTGCC<br>GAAAAGAAAAGCGGTAAGAAGAACCTGCACACCCTGTACTGGGAGAACCTGTTT<br>TCTGAGGAGAACCTGAAGGACGTTTGTCTGAAGCTGAATGGCGAGGCCGAGCT<br>GTTCTGGCGGAAGGCTTCTCTGGACAAGGGCAAGGTGATCGTGCACAGAATGG<br>GCTCTATCCTGGTGAACAGAACAACAAGCGAGGGCAAGTCAATCCCTGAGGAC<br>ATCTACCAGGAGATCTATCAGTACAAGAACAAAATGAAGGATAAGATCAGCGAC<br>GAAGCCAAAAGCCTGCTGGACAGCGGCACCGTGATCTGTAAAGAAGCCACCCA<br>CGACATCACCAAGGACAAACGGTTCACAGAGGACACCTACCTGTTCCACTGCCC<br>TATCACCATGAACTTCAAGGCCACCGACAAGAAAAACAAAGAGTTCAACAACCA<br>CGTGCTGGAAGTGCTGAAAGAGAATCCCGACGTGAAGATCATCGGCCTGGACA<br>GAGGCGAACGGCACCTGATCTACCTGAGCCTGATCAACCAGAAGGGCGAGATC<br>GAGCTGCAGAAAACCCTGAATCTGGTGGAACAGGTGCGGAACGACAAAACCGT<br>GAAGGTGGACTACCAGGAGAAGCTGGTGCATAAGGAAGGCGACCGCGACAAA<br>GCCAGAAAGAACTGGCAGACAATCGGAAACATCAAGGAACTGAAGGAGGGCTA<br>CCTGTCTGCCGTGGTGCACGAAATCGCCATGCTGATGGTGGAAAACAACGCCA<br>TCGTGGTGATGGAGGACCTGAACTTCGGCTTCAAGAGAGGCAGATTCGCCGTG<br>GAACGGCAGATCTACCAGAAGTTCGAGAACATGCTGATCGAAAAGCTGAACTAC<br>CTAGTGTTCAAGGACAAGAACGCCACCGAACCTGGCGGCGTGCTGAATGCGTA<br>TCAGCTCACCAACAAGAGCGCCAACGTCACCGACGTGTACAAACAGTGCGGCT<br>GGCTGTTCTACATCCCCGCCGCTTATACAAGCAAGATCGACCCCAAGACCGGAT<br>TCGCCAACCTGTTCATCACAAAGGGACTGACAAACGTGGAAAAGAAGAAGGAGT<br>TCTTCGATAAGTTCGACAGCATCCGGTACGACAGCAAAGAGGACTGCTTTGTGT<br>TCGGCTTCGACTACGCCAAGCTGTGCGACAACGCCTCCTTTAGAAAGAAGTGG<br>GAAGTTTACACCAGAGGAGAGAGGCTGGTCTACAACAAAGACAAGCACAAAAAC<br>GAACCTATCAACCCCACCGAGGAGCTGAAGGGCATCTTCGATGCTTTTGATATT<br>AACTGGAACACCGACGACAACTTCATTGATTCAGTGCAGACCATCCAGGCCGAG<br>AAGGCCAACGCCAAGTTCTTTGACATCCTGCTGAGAATGTTCAACGCCACACTG<br>CAGATGAGAAACAGCAAGACTAACTCCTCTGCCAGCGAGGACGACTACCTGATC<br>AGCCCTGTCAAAGCCGAGGATGGCACCTTCTTCGACACAAGAGAGGAATTAAAG<br>AAGGGCAAAGATGCCAAGCTGCCGATCGACAGCGACGCTAATGGCGCCTACCA<br>CATCGCCCTGAAAGGACTGTTCCTGCTGGAAAATGACTTTAACCGGGACGAGAA<br>GGGAGTGATCCAAAATATCAGCAACGCTGATTGGTTCAAGTTTGTGCAGGAGAA<br>GAAATACAAGGAT | |
| Expression construct (with N-terminal methionine and stop codon, includes V5-tag and C-terminal NLS) | ATGggctccggaAGCACCATCAACAAATTCTGCGGCCAGGGCAACGGCTACAGCAG<br>AAGCATCACCCTGCGGAACAAACTGATCCCTATCGGCAAGACTGAGGAGAACCT<br>GAAGTGGTTCCTGGAGAAGGACCTGGAGCGGGCTATCGCCTACCCCGAGATTA<br>AAAACCTTATCGACAATATCCACAGAAGCGTGATAGAGGATACCCTGAGCAAGG<br>TCGCCCTGAACTGGAATGAGATCTTCAACACCCTGGCCGCCTACCAGAACGAG<br>AAAGATAAGAAAAAGAAGGCCGCTATCAAGAAGGACCTGGAGAAGTTGCAAGG<br>ATGTGCGAGAAAGAAAATCGTGGATACCTTCAAGAAGAACCCTGATTATGAGAA<br>ACTGTTTAAAGAGGGACTGTTCAAGGAGCTGCTGCCTGAACTGATCAAGACCGC<br>CCCTGTGAGCGAAATTGAAGATAAAACCAAAGCCCTGGAGTGCTTCAACCGGTT<br>CTCCACATACTTCACCGGCTTCCACGAAAATCGCAAAAATATGTACAGCGAGGA<br>CGCGAAGAGCACCGCCATCTCCTACCGGATCGTGAACGAGAACTTCCCCAAGT<br>TCTTCGCTAATATCAAGCTGTACAACTACCTCAAGGAAAAATTTCCACAGATTAT<br>CATCAACACAGAAGAGTCTCTGAAGGATTACCTGAAGGGCAAGAAGCTGGATTC<br>CGTGTTCTCCATCGACGGGTTCAATGACGTGCTGGCCCAGAGCGGCATAGACT<br>TCTACAACACCGTGATCGGTGGCATCTCAGGAGAGGCCGGCACAGAAAAGACC<br>CAGGGCCTGAATGAGAAGATCAACCTAGCCAGACAGCAGCTGCCTAAGGATGA<br>GAAGGACAAGCTAAGAGGCAAGATGGTCGACCTGTTCAAGCAGATTCTGAGCG<br>ATAGAGAAACCAGCAGCTTCATCCCTACTGGCTTCGAGAATAAGAAGGAAGTGT<br>ACTCTACCGTGAAGAAGTTCAGCGAAATCGTGGTCGAAAAAAGCGTGTCCAAGG<br>TGAAGGAGATCTTCACTCAGAACGAAGAGTACAATCTGAACGAGATCTTCGTGC<br>CTGCGAAGAGCCTGACCAATTTTAGCCAGAACATCTTTGGCAACTGGAGCATCC<br>TTTCTGAAGGCCTGTTCCTGCTGGAAAAGGACAACGTGAAGAAACAGCTGAGTG<br>AGAAACAAATCGAGACACTCCATAAGGAGATCGCCAAGAAGGACTGCAGCTTTA<br>CCGAACTGCAGAACGCCTACGAGCGGTGGTGCGCCGAGAACTCCGTGGACGC<br>CACCAAGAACATTAACAGATACTTCAGCATCGTCGACCTGAGAACCAAGAATGA<br>CTCCTTCGAGAAGGAAGAGATCAATATCCTTGATGAGATAACCAACGCCTTCTCT<br>AAGATTGACTTCGACGATATCCACGATCTGCAGCAAGAGAAGGAGGCCGCCAC<br>CCCTATCAAGAACTACCTGGACGAGGTTCAAAACCTGTACCACCACCTGAAGCT | 90 |

TABLE 10-continued

ZSQQ Type V Cas Sequences

| Name | Sequence | SEQ ID NO. |
|---|---|---|
| | GGTGGACTACAGAGGTGAGGAACGAAAGGACGCTAACTTCTACTCTAAACTGGA<br>CTATATCCTGAGAAAGGACAGAAAGGACTACCTGAACCTGGCCGAAGTGGTGC<br>CATTGTACAACAAGGTTAGAAACTTCGTGACCAAGAAGCCTGGCGAGGTGAAAA<br>AGATCAAGATGATGTTCGACTGCAGCAGCCTGCTGGGCGGATGGGGCACAGAT<br>TACGAGACAAAAGAGGCCCACATTTTCATCGACTCCGGCAAGTATTACCTTGGA<br>ATCATCAACGAGAAGTTGTCAAAAGATGACGTGGAGCTGCTGAAGAAGAGCAGC<br>GAACGGATGATCACAAAGGTGATCTACGATTTCCAAAAGCCCGATAACAAGAAT<br>ACACCTAGACTGTTCATCAGGAGCAAGGGCACAAATTATGCTCCTGCTGTTTTC<br>CAATACAATCTGCCAATAGAGTCTGTGATCGATATTTACGACCGTGGCCTGTTTA<br>AGACCGAGTACAGAAAAATCAACAGCAAGGTGTACAAGGAGAGCCTGATTAAGA<br>TGATCGATTACTTCAAGATGGGCTTTGAGAGACACGAGAGCTACAAGCACTACA<br>AGTTTTGCTGGAAGGAATCTAGCAAGTACAACGACATCGGCGAATTTTACAAGG<br>ATGTGATTAACTCTTGTTACCAGCTGAACTTCGAGAAGGTGAACTATGAGAACCT<br>CCTGAAGTTAGTGGAAAACAACAAGCTGTTCCTGTTTCAGATCTACAACAAGGAT<br>TTTGCCGAAAAGAAAAGCGGTAAGAAGAACCTGCACACCCTGTACTGGGAGAAC<br>CTGTTTTCTGAGGAGAACCTGAAGGACGTTTGTCTGAAGCTGAATGGCGAGGCC<br>GAGCTGTTCTGGCGGAAGGCTTCTCTGGACAAGGGCAAGGTGATCGTGCACAG<br>AATGGGCTCTATCCTGGTGAACAGAACAACAAGCGAGGGCAAGTCAATCCCTGA<br>GGACATCTACCAGGAGATCTATCAGTACAAGAACAAAATGAAGGATAAGATCAG<br>CGACGAAGCCAAAAGCCTGCTGGACAGCGGCACCGTGATCTGTAAAGAAGCCA<br>CCCACGACATCACCAAGGACAAACGGTTCACAGAGGACACCTACCTGTTCCACT<br>GCCCTATCACCATGAACTTCAAGGCCACCGACAAGAAAAACAAAGAGTTCAACA<br>ACCACGTGCTGGAAGTGCTGAAAGAGAATCCCGACGTGAAGATCATCGGCCTG<br>GACAGAGGCGAACGGCACCTGATCTACCTGAGCCTGATCAACCAGAAGGGCGA<br>GATCGAGCTGCAGAAAACCCTGAATCTGGTGGAACAGGTGCGGAACGACAAAA<br>CCGTGAAGGTGGACTACCAGGAGAAGCTGGTGCATAAGGAAGGCGACCGCGA<br>CAAAGCCAGAAAGAACTGGCAGACAATCGGAAACATCAAGGAACTGAAGGAGG<br>GCTACCTGTCTGCCGTGGTGCACGAAATCGCCATGCTGATGGTGGAAAACAAC<br>GCCATCGTGGTGATGGAGGACCTGAACTTCGGCTTCAAGAGAGGCAGATTCGC<br>CGTGGAACGGCAGATCTACCAGAAGTTCGAGAACATGCTGATCGAAAAGCTGAA<br>CTACCTAGTGTTCAAGGACAAGAACGCCACCGAACCTGGCGGCGTGCTGAATG<br>CGTATCAGCTCACCAACAAGAGCGCCAACGTCACCGACGTGTACAAACAGTGC<br>GGCTGGCTGTTCTACATCCCCGCCGCTTATACAAGCAAGATCGACCCCAAGACC<br>GGATTCGCCAACCTGTTCATCACAAAGGGACTGACAAACGTGGAAAAGAAGAAG<br>GAGTTCTTCGATAAGTTCGACAGCATCCGGTACGACAGCAAAGAGGACTGCTTT<br>GTGTTCGGCTTCGACTACGCCAAGCTGTGCGACAACGCCTCCTTTAGAAAGAAG<br>TGGGAAGTTTACACCAGAGGAGAGAGGCTGGTCTACAACAAAGACAAGCACAA<br>AAACGAACCTATCAACCCCACCGAGGAGCTGAAGGGCATCTTCGATGCTTTTGA<br>TATTAACTGGAACACCGACGACAACTTCATTGATTCAGTGCAGACCATCCAGGC<br>CGAGAAGGCCAACGCCAAGTTCTTTGACATCCTGCTGAGAATGTTCAACGCCAC<br>ACTGCAGATGAGAAACAGCAAGACTAACTCCTCTGCCAGCGAGGACGACTACCT<br>GATCAGCCCTGTCAAAGCCGAGGATGGCACCTTCTTCGACACAAGAGAGGAATT<br>AAAGAAGGGCAAAGATGCCAAGCTGCCGATCGACAGCGACGCTAATGGCGCCT<br>ACCACATCGCCCTGAAAGGACTGTTCCTGCTGGAAAATGACTTTAACCGGGACG<br>AGAAGGGAGTGATCCAAAATATCAGCAACGCTGATTGGTTCAAGTTTGTGCAGG<br>AGAAGAAATACAAGGATtctagaAAGCGGACAGCAGACGGCTCCGAATTTGAAAGC<br>CCTAAGAAAAAGAGAAAGGTGggatccGGCAAACCTATCCCCAATCCCCTGCTGG<br>GCCTGGACAGCACCTGA | |

In some embodiments a ZSQQ Type V Cas protein comprises an amino acid sequence of SEQ ID NO:85, SEQ ID NO:86, or SEQ ID NO:87. In some embodiments, a ZSQQ Type V Cas protein has nickase activity, for example resulting from one or more amino acid substitutions relative to the sequence of SEQ ID NO:85, SEQ ID NO:86, or SEQ ID NO:87. In some embodiments, the one or more amino acid substitutions providing nickase activity comprise a D913 substitution, wherein the position of the D913 substitution is defined with respect to the amino acid numbering of SEQ ID NO:86 (corresponding to amino acid 908 of SEQ ID NO:121). In some embodiments, the one or more amino acid substitutions providing nickase activity comprise an E1006 substitution, wherein the position of the E1006 substitution is defined with respect to the amino acid numbering of SEQ ID NO:86 (corresponding to amino acid 993 of SEQ ID NO:121). In some embodiments, the one or more amino acid substitutions providing nickase activity comprise a R1219 substitution, wherein the position of the R1219 substitution is defined with respect to the amino acid numbering of SEQ ID NO:86 (corresponding to amino acid 1226 of SEQ ID NO:121). In some embodiments, the one or more amino acid substitutions providing nickase activity comprise a D1264 substitution, wherein the position of the D1264 substitution is defined with respect to the amino acid numbering of SEQ ID NO:86 (corresponding to amino acid 1263 of SEQ ID NO:121). In some embodiments, a ZSQQ Type V Cas protein is catalytically inactive, for example due to a R1219 substitution in combination with a D913 substitution, a E1006 substitution, and/or D1264 substitution.

6.2.16. ZSYN Type V Cas Protein

In one aspect, the disclosure provides ZSYN Type V Cas proteins. ZSYN Type V Cas proteins can be further classified as Type V-A Cas proteins. The ZSYN Type V Cas proteins typically comprise an amino acid sequence that is at least 50%, at least 55%, at least 60%, at least 65%, at least 70%, at least 75%, at least 85%, at least 90%, or at least 95% identical to SEQ ID NO:91. In some embodiments, the ZSYN Type V Cas proteins comprise an amino acid sequence that is at least 95%, at least 96%, at least 97%, at least 98%, or at least 99% identical to SEQ ID NO:91. In some embodiments, a ZSYN Type V Cas protein comprises an amino acid sequence that is identical to SEQ ID NO:91.

Exemplary ZSYN Type V Cas protein sequences and nucleotide sequences encoding exemplary ZSYN Type V Cas proteins are set forth in Table 1P.

TABLE 1P

ZSYN Type V Cas Sequences

| Name | Sequence | SEQ ID NO. |
|---|---|---|
| Wildtype amino acid sequence (without N-terminal methionine) | GKFFETDEFIGQYSINKTLRFELIPQGKTKELLNNYMNDNSKIKQDILRADEKNNFKEVI<br>DEYYRELIHDALTDEDIFSITPLVKDAYELYIASRKNTSDSSKKEYRDVKNKIRKEIANILN<br>KYKTIYGLDKFANIYKSESDKSVDDDESDNDDLDEKNTTNDDNAKSEDKRIYKWLNKK<br>LRLKQISNEEYDRYYKSLNEYHGFTTGLQGLQNNKENMFSSENKSTAIAFRIIDDNMEK<br>YFSNILLLEFIKNKYKDLYEKIEEKANKMNVECFTKYFTQEGIDEYNQMIGRSIEEEYAK<br>GINQEINLYKQSKGLNNKEIRTLSPLYKQILSKTSQNEIIVFKNDKETLEYIKNICDYIIEED<br>IFGKMNHLIKTNLIDMCTGIYIKRNELSNISFKLYNDWGLLDRIICDYANEFKTKKEKNEF<br>EKLNKEVISLNLLNDIFNKYKETRGNDTDLKEIVEYFKNVDEKMIEDEYSKIKSILNLERID<br>IDRRVPSKDEEKGGEGFEQICMIKTFLDLLLESIHIYKPLSLIKNGEKVEIYNYNENFYNE<br>YDILFSQLDNIINLYNKVRNYFSKKTYSKEKIKIYFSKPTLLNGWDVNKEISNYSIILRKDE<br>EYFLAIMNSDNKIFTNERLEENCAITENNEECYEKMVYKQISDSNKMFSKVFFSEKNKKI<br>YMPSEEIKNIRKNKTHLKVANNKDSQTKWIKFMIECYYKHPEWSKYFDINFKKPEEYES<br>IVEFYNQVNEKIYNIKFVNIKCDYINSMVDSGELYLFKIYNKDFSKNKKKSGTDNLHTMY<br>WKLLFSKENMNCGVYKLNGQAEVFFRKASLPDKITHERNKEIDNKNPIKDKKTSTFTY<br>DLKKDKRFMEDKFFFHCPITINYKGLNAKDKEIRKYNEKINKFIAGNPDINIIGIDRGERH<br>LLYYTIINQKGEILKQSTLNNVGIEGRDKDYQELLSNKEKERHLARKSWGTIGNIKELKE<br>GYLSIWVHELAKLVKEYNAIIVLENLNAGFKRGRTKVEKQVYQKFELALIKKLNYLVFKN<br>ENIQNKGGYLKGLQLTQPFDTFKDIGNQSGIIYYVIPSYTSKICPTTGFIDVIKPQYESVE<br>KAKELFSKFKRIYFDNNKKCFIFEFMYKDFGRDYGLDKIWSICTLGEKRYYYDSKNKVS<br>NVINVTESIISILQEKNINYINSDNIIDEILQYSDVKLYKELLFNLKVVLQMRYTKSGTNNE<br>DDFILSPVLDENDKAFCSLNAKETEPQNADANGAYHIAMKGLNAIMSIKNGNVDRDINN<br>LENWINFIQKFHIGK | 91 |
| Wildtype amino acid sequence (with N-terminal methionine) | MGKFFETDEFIGQYSINKTLRFELIPQGKTKELLNNYMNDNSKIKQDILRADEKNNFKEV<br>IDEYYRELIHDALTDEDIFSITPLVKDAYELYIASRKNTSDSSKKEYRDVKNKIRKEIANIL<br>NKYKTIYGLDKFANIYKSESDKSVDDDESDNDDLDEKNTTNDDNAKSEDKRIYKWLNK<br>KLRLKQISNEEYDRYYKSLNEYHGFTTGLQGLQNNKENMFSSENKSTAIAFRIIDDNME<br>KYFSNILLLEFIKNKYKDLYEKIEEKANKMNVECFTKYFTQEGIDEYNQMIGRSIEEEYA<br>KGINQEINLYKQSKGLNNKEIRTLSPLYKQILSKTSQNEIIVFKNDKETLEYIKNICDYIIEE<br>DIFGKMNHLIKTNLIDMCTGIYIKRNELSNISFKLYNDWGLLDRIICDYANEFKTKKEKNE<br>FEKLNKEVISLNLLNDIFNKYKETRGNDTDLKEIVEYFKNVDEKMIEDEYSKIKSILNLERI<br>DIDRRVPSKDEEKGGEGFEQICMIKTFLDLLLESIHIYKPLSLIKNGEKVEIYNYNENFYN<br>EYDILFSQLDNIINLYNKVRNYFSKKTYSKEKIKIYFSKPTLLNGWDVNKEISNYSIILRKD<br>EEYFLAIMNSDNKIFTNERLEENCAITENNEECYEKMVYKQISDSNKMFSKVFFSEKNK<br>KIYMPSEEIKNIRKNKTHLKVANNKDSQTKWIKFMIECYYKHPEWSKYFDINFKKPEEY<br>ESIVEFYNQVNEKIYNIKFVNIKCDYINSMVDSGELYLFKIYNKDFSKNKKKSGTDNLHT<br>MYWKLLFSKENMNCGVYKLNGQAEVFFRKASLPDKITHERNKEIDNKNPIKDKKTSTF<br>TYDLKKDKRFMEDKFFFHCPITINYKGLNAKDKEIRKYNEKINKFIAGNPDINIIGIDRGE<br>RHLLYYTIINQKGEILKQSTLNNVGIEGRDKDYQELLSNKEKERHLARKSWGTIGNIKEL<br>KEGYLSIWVHELAKLVKEYNAIIVLENLNAGFKRGRTKVEKQVYQKFELALIKKLNYLVF<br>KNENIQNKGGYLKGLQLTQPFDTFKDIGNQSGIIYYVIPSYTSKICPTTGFIDVIKPQYES<br>VEKAKELFSKFKRIYFDNNKKCFIFEFMYKDFGRDYGLDKIWSICTLGEKRYYYDSKNK<br>VSNVINVTESIISILQEKNINYINSDNIIDEILQYSDVKLYKELLFNLKVVLQMRYTKSGTN<br>NEDDFILSPVLDENDKAFCSLNAKETEPQNADANGAYHIAMKGLNAIMSIKNGNVDRDI<br>NNLENWINFIQKFHIGK | 92 |
| Expression construct (with N-terminal methionine, V5-tag and C-terminal NLS) aa sequence | MGSGGKFFETDEFIGQYSINKTLRFELIPQGKTKELLNNYMNDNSKIKQDILRADEKNN<br>FKEVIDEYYRELIHDALTDEDIFSITPLVKDAYELYIASRKNTSDSSKKEYRDVKNKIRKEI<br>ANILNKYKTIYGLDKFANIYKSESDKSVDDDESDNDDLDEKNTTNDDNAKSEDKRIYKW<br>LNKKLRLKQISNEEYDRYYKSLNEYHGFTTGLQGLQNNKENMFSSENKSTAIAFRIIDD<br>NMEKYFSNILLLEFIKNKYKDLYEKIEEKANKMNVECFTKYFTQEGIDEYNQMIGRSIEE<br>EYAKGINQEINLYKQSKGLNNKEIRTLSPLYKQILSKTSQNEIIVFKNDKETLEYIKNICDY<br>IIEEDIFGKMNHLIKTNLIDMCTGIYIKRNELSNISFKLYNDWGLLDRIICDYANEFKTKKE<br>KNEFEKLNKEVISLNLLNDIFNKYKETRGNDTDLKEIVEYFKNVDEKMIEDEYSKIKSILN<br>LERIDIDRRVPSKDEEKGGEGFEQICMIKTFLDLLLESIHIYKPLSLIKNGEKVEIYNYNEN<br>FYNEYDILFSQLDNIINLYNKVRNYFSKKTYSKEKIKIYFSKPTLLNGWDVNKEISNYSIIL<br>RKDEEYFLAIMNSDNKIFTNERLEENCAITENNEECYEKMVYKQISDSNKMFSKVFFSE<br>KNKKIYMPSEEIKNIRKNKTHLKVANNKDSQTKWIKFMIECYYKHPEWSKYFDINFKKP<br>EEYESIVEFYNQVNEKIYNIKFVNIKCDYINSMVDSGELYLFKIYNKDFSKNKKKSGTDN<br>LHTMYWKLLFSKENMNCGVYKLNGQAEVFFRKASLPDKITHERNKEIDNKNPIKDKKT<br>STFTYDLKKDKRFMEDKFFFHCPITINYKGLNAKDKEIRKYNEKINKFIAGNPDINIIGIDR<br>GERHLLYYTIINQKGEILKQSTLNNVGIEGRDKDYQELLSNKEKERHLARKSWGTIGNIK<br>ELKEGYLSIWVHELAKLVKEYNAIIVLENLNAGFKRGRTKVEKQVYQKFELALIKKLNYLV<br>FKNENIQNKGGYLKGLQLTQPFDTFKDIGNQSGIIYYVIPSYTSKICPTTGFIDVIKPQYE<br>SVEKAKELFSKFKRIYFDNNKKCFIFEFMYKDFGRDYGLDKIWSICTLGEKRYYYDSKN<br>KVSNVINVTESIISILQEKNINYINSDNIIDEILQYSDVKLYKELLFNLKVVLQMRYTKSGTN<br>NEDDFILSPVLDENDKAFCSLNAKETEPQNADANGAYHIAMKGLNAIMSIKNGNVDRDI<br>NNLENWINFIQKFHIGKSRKRTADGSEFESPKKKRKVGSGKPIPNPLLGLDST | 93 |

TABLE 1P-continued

| ZSYN Type V Cas Sequences | | |
|---|---|---|
| Name | Sequence | SEQ ID NO. |
| Wildtype coding sequence (with N-terminal methionine and stop codon) | ATGGGTAAATTTTTTGAAACAGATGAATTTATTGGACAGTATTCAATAAATAAAACAT<br>TACGATTCGAATTGATACCACAAGGTAAGACAAAGGAATTACTAAATAATTATATGA<br>ATGATAACAGCAAAATTAAACAGGATATTTTAAGAGCAGATGAAAAGAATAATTTTA<br>AAGAAGTAATTGATGAATATTATCGAGAGTTGATTCATGATGCTTTAACAGATGAAG<br>ATATTTTTTCCATTACACCATTAGTAAAGGATGCATATGAATTATATATTGCTTCTAG<br>AAAAAATACTTCTGATAGTTCTAAAAAAGAATATAGAGATGTTAAAAATAAAATTAG<br>GAAAGAAATAGCAAACATTCTTAATAAATATAAGACGATTTATGGACTAGATAAATT<br>TGCAAATATATATAAATCCGAGAGTGATAAAAGTGTAGATGATGATGAATCTGATAA<br>TGATGATTTAGATGAGAAAAATACTACTAATGATGATAATGCAAAATCAGAAGATAA<br>AAGGATATACAAATGGCTAAATAAAAAATTAAGATTAAAACAAATTTCTAACGAGGA<br>ATATGATAGATACTACAAATCTTTAAATGAATATCATGGTTTTACAACAGGTCTGCA<br>AGGATTACAAAATAATAAAGAAAATATGTTCTCTTCAGAAAACAAAAGTACGGCAAT<br>AGCATTTCGAATAATAGATGACAATATGGAAAAATATTTTTCAAATATACTGTTATTA<br>GAATTTATTAAAAACAAATATAAAGATTTATATGAAAAAATTGAAGAAAAAGCAAATA<br>AAATGAATGTGGAATGTTTTACTAAATATTTTACACAAGAGGGTATAGATGAATATA<br>ATCAAATGATAGGTAGAAGTATAGAAGAAGAATATGCAAAAGGTATAAATCAAGAA<br>ATAAATCTTTATAAACAATCAAAAGGATTAAATAATAAAGAAATTAGGACATTATCTC<br>CATTGTATAAGCAAATATTATCAAAGACTTCACAAAATGAAATAATAGTATTCAAAAA<br>TGATAAAGAAACTTTAGAATACATCAAGAATATATGTGATTATATAATAGAAGAAGA<br>TATATTTGGAAAGATGAATCATTTAATTAAAACAAATTTGATTGATATGTGTACTGGT<br>ATATATATAAAAAGAAATGAATTATCGAATATTTCATTTAAACTTTATAATGATTGGG<br>GATTACTAGATAGAATAATATGTGATTATGCAAATGAATTTAAGACAAAAAAAGAAA<br>AGAACGAATTTGAAAAATTAAATAAAGAAGTAATTTCACTTAATCTTTTAAATGATAT<br>ATTTAATAAATATAAGGAAACAAGAGGGAATGATACAGATTTAAAAGAAATAGTAGA<br>ATATTTTAAAAATGTAGATGAAAAAATGATAGAGGATGAATACTCTAAAATAAAAAG<br>TATTTTAAATTTAGAAAGAATAGATATTGATAGAAGAGTACCAAGCAAAGATGAAGA<br>AAAAGGTGGAGAAGGATTTGAACAAATTTGTATGATAAAAACATTTTTAGATTTATT<br>GCTTGAGAGTATACATATTTACAAACCATTAAGTTTAATTAAAAATGGAGAGAAAGT<br>GGAGATATATAATTATAATGAAAATTTTTACAATGAATATGATATATTGTTTTCACAA<br>TTAGATAATATAATTAACTTATATAATAAAGTCAGAAATTATTTTTCTAAAAAAACATA<br>TTCAAAAGAAAAAATCAAGATATATTTTTCTAAGCCAACGTTATTAAATGGATGGGA<br>TGTAAATAAAGAAATATCAAATTATTCGATTATTTTGAGAAAAGATGAAGAATATTTC<br>CTAGCCATAATGAATAGTGATAATAAGATTTTTACTAATGAAAGATTGGAAGAAAAT<br>TGCGCAATTACAGAAAATAATGAAGAGTGTTATGAAAAAATGGTATATAAACAAATA<br>TCCGATTCAAATAAGATGTTTTCAAAAGTGTTTTTTTCAGAAAAAAACAAAAAAATAT<br>ATATGCCTTCAGAAGAAATTAAAAATATTAGAAAAAATAAAACACATTTGAAAGTAG<br>CAAATAATAAAGACTCACAAACAAAATGGATTAAATTTATGATTGAATGCTATTATAA<br>ACATCCTGAATGGAGTAAATATTTTGATATAAATTTTAAAAAGCCTGAAGAATATGA<br>ATCAATAGTTGAATTTTATAATCAAGTAAATGAAAAAATATATAATATAAAATTTGTA<br>AATATTAAATGTGATTATATAAATAGTATGGTTGATAGTGGAGAATTGTATTTGTTTA<br>AAATATATAATAAGGATTTTTCAAAAAATAAGAAAAAATCTGGAACAGATAATTTACA<br>CACTATGTATTGGAAATTATTATTTTCAAAAGAAAATATGAATTGTGGTGTATACAAA<br>TTAAATGGACAAGCAGAAGTGTTTTTTAGGAAAGCTTCTTTACCTGATAAAATTACA<br>CATGAAAGAAATAAAGAAATAGATAATAAAAATCCAATAAAAGATAAAAAAACAAGT<br>ACATTTACTTATGATTTAAAGAAAGATAAAAGATTCATGGAAGATAAATTCTTCTTTC<br>ATTGCCCAATAACAATAAATTATAAAGGATTAAATGCAAAAGATAAAGAAATAAGAA<br>AATATAATGAGAAAATAAACAAATTTATTGCTGGTAACCCAGATATAAATATTATCG<br>GAATAGATCGTGGTGAACGACATTTGCTATATTATACGATAATAAATCAAAAGGGT<br>GAAATATTAAAACAGTCAACATTAAATAATGTTGGTATTGAAGGGCGTGATAAAGAT<br>TATCAAGAATTATTATCTAATAAAGAGAAAGAACGTCACTTAGCTAGAAAAAGTTGG<br>GGAACAATAGGTAATATAAAAGAACTTAAAGAAGGATATTTATCAATTGTAGTACAT<br>GAATTAGCTAAATTAGTAAAGGAATATAATGCAATAATTGTTCTAGAAAATTTGAAT<br>GCTGGATTTAAAAGGGGAAGAACTAAAGTTGAAAAACAAGTATATCAAAAATTTGA<br>ACTTGCATTGATAAAGAAACTTAATTATTTAGTATTTAAAAACGAAAATATTCAAAAT<br>AAAGGTGGTTATTTAAAAGGATTACAATTAACTCAGCCATTTGATACTTTTAAAGAT<br>ATTGGAAATCAATCTGGTATAATTTATTATGTTATTCCATCATATACATCGAAAATAT<br>GTCCTACTACAGGCTTTATAGATGTAATTAAGCCACAATATGAAAGTGTTGAAAAAG<br>CCAAAGAATTATTTTCTAAATTTAAGCGTATATATTTCGATAATAATAAAAAATGTTT<br>TATATTTGAATTTATGTATAAAGACTTTGGTAGAGATTATGGTTTAGATAAAATATGG<br>AGTATATGTACACTTGGAGAAAAAAGATATTATTATGATTCTAAAAATAAAGTATCAA<br>ATGTAATAAATGTAACAGAATCAATAATTAGTATATTACAAGAAAAAAACATAAATTA<br>TATAAATTCAGACAATATCATAGATGAAATTTTACAATATAGTGATGTTAAGTTGTAT<br>AAAGAATTATTATTTAATTTAAAAGTTGTTTTACAAATGAGATATACGAAGAGTGGTA<br>CAAATAATGAAGATGATTTTATTCTATCACCAGTATTAGATGAAAATGATAAGGCAT<br>TTTGTTCACTTAATGCAAAAGAAACAGAACCTCAAAATGCAGATGCAAACGGTGCA<br>TATCATATTGCTATGAAAGGTTTAAATGCAATAATGAGCATTAAGAATGGTAATGTA<br>GATAGAGATATTAACAATTTAGAAAATTGGATAAATTTTATACAAAAGTTTCATATAG<br>GTAAATAA | 94 |
| Codon optimized coding sequence (no N-terminal | GGCAAGTTCTTTGAAACCGACGAGTTCATCGGACAGTACAGTATCAACAAAACACT<br>GAGGTTCGAGCTCATCCCTCAAGGCAAGACCAAGGAACTGCTGAACAACTATATG<br>AACGACAACAGTAAGATCAAGCAGGACATCCTGCGGGCCGACGAGAAGAACAATT<br>TCAAGGAAGTGATCGACGAGTATTATAGAGAGTTGATCCACGACGCCCTGACCGA<br>CGAGGACATCTTTTCCATCACCCCTCTCGTCAAGGACGCCTACGAGCTGTACATC | 95 |

TABLE 1P-continued

| ZSYN Type V Cas Sequences | | |
|---|---|---|
| Name | Sequence | SEQ ID NO. |
| methionine, no stop codon) | GCCTCCAGAAAAAACACCAGCGACTCCAGCAAGAAGGAGTATCGGGACGTGAAAA<br>ATAAGATTAGAAAAGAGATCGCTAACATCCTGAACAAGTACAAGACAATCTACGGC<br>CTGGACAAGTTCGCCAATATCTACAAGTCTGAGAGCGACAAGAGCGTTGATGATG<br>ACGAATCTGATAACGATGACTTGGACGAGAAGAATACCACCAACGACGATAATGC<br>CAAGTCTGAGGACAAGCGGATCTATAAGTGGCTGAATAAGAAGCTGAGACTGAAG<br>CAGATCTCCAACGAAGAATACGACCGGTACTACAAGTCCCTGAACGAATACCACG<br>GGTTCACAACAGGACTGCAGGGCCTGCAGAACAACAAGGAAAACATGTTCAGCAG<br>CGAGAACAAGAGCACCGCCATCGCCTTTAGAATCATCGATGACAACATGGAAAAG<br>TATTTTTCTAACATCCTGCTCCTGGAGTTCATCAAAAACAAGTACAAAGATCTGTAC<br>GAGAAGATCGAGGAGAAGGCCAACAAGATGAACGTGGAATGCTTCACCAAGTACT<br>TCACCCAGGAGGGCATCGACGAGTACAATCAGATGATTGGCAGAAGCATTGAGGA<br>AGAATACGCCAAGGGCATCAACCAGGAGATCAACCTGTATAAGCAGAGCAAGGGT<br>CTAAACAATAAGGAGATCAGAACACTGAGCCCCCTGTACAAGCAGATCCTGTCCA<br>AGACCAGCCAGAACGAAATCATCGTGTTCAAAAACGACAAGGAAACCCTGGAATA<br>CATCAAGAATATCTGTGATTACATTATCGAGGAGGACATCTTCGGAAAGATGAACC<br>ACCTGATCAAAACCAACCTGATCGACATGTGCACCGGAATCTACATTAAGAGAAAC<br>GAGCTGAGCAACATCTCTTTCAAGCTCTACAACGACTGGGGCCTGCTGGACAGAA<br>TTATCTGTGACTACGCCAACGAGTTCAAGACAAAGAAGGAAAAGAATGAGTTCGAG<br>AAGCTGAACAAAGAGGTGATCTCTCTGAACCTGCTCAACGATATTTTCAACAAATA<br>CAAGGAAACCAGAGGCAATGATACAGACCTGAAGGAAATCGTGGAATACTTTAAAA<br>ACGTCGACGAGAAAATGATTGAGGACGAGTACAGCAAGATCAAGAGCATACTTAA<br>TCTGGAACGCATCGACATCGACCGTAGAGTGCCAAGCAAGGACGAGGAAAAGGG<br>CGGCGAAGGCTTTGAGCAGATCTGCATGATCAAGACGTTCCTGGATCTGCTGTTG<br>GAGAGCATCCACATCTACAAGCCTCTGTCTCTGATCAAGAACGGCGAGAAGGTGG<br>AAATCTACAATTATAACGAGAACTTCTACAACGAGTACGACATCCTGTTCAGCCAG<br>CTGGATAACATTATAAATCTGTACAATAAGGTGCGGAACTACTTCAGCAAGAAAAC<br>CTACAGCAAAGAGAAAATCAAAATCTATTTCTCCAAACCCACCCTGCTGAACGGAT<br>GGGACGTGAACAAGGAGATCAGCAACTACTCTATCATCCTGAGAAAAGACGAAGA<br>GTACTTTCTGGCAATTATGAACAGCGACAACAAGATCTTCACGAATGAGAGGCTGG<br>AAGAAAACTGCGCCATCACCGAGAATAATGAAGAATGTTACGAGAAAATGGTGTAC<br>AAGCAAATCTCTGACTCTAACAAGATGTTCAGCAAGGTGTTTTTCAGCGAGAAAAA<br>CAAGAAGATCTACATGCCCAGCGAAGAGATCAAGAATATCAGAAAGAACAAGACC<br>CATCTCAAGGTGGCCAACAATAAGGATTCTCAAACAAAGTGGATCAAGTTCATGAT<br>CGAGTGCTACTATAAACACCCTGAGTGGAGTAAGTACTTCGATATCAACTTCAAGA<br>AACCTGAAGAATATGAAAGCATCGTGGAATTTTACAACCAGGTGAACGAGAAGATC<br>TACAACATCAAGTTCGTGAATATCAAATGCGACTACATCAACAGCATGGTGGATTC<br>GGGAGAGCTGTACCTGTTCAAGATCTACAACAAGGACTTCTCTAAGAACAAGAAAA<br>AAAGTGGCACAGATAACCTGCACACCATGTATTGGAAGCTGCTGTTTAGCAAAGAA<br>AACATGAATTGCGGCGTGTACAAGCTGAACGGCCAGGCCGAGGTGTTCTTCAGAA<br>AGGCCAGCCTGCCTGATAAGATCACACACGAAAGAAATAAGGAGATCGACAACAA<br>AAATCCTATCAAGGACAAGAAAACCAGCACCTTCACATACGACCTGAAGAAAGATA<br>AGCGGTTCATGGAAGATAAGTTCTTCTTCCACTGCCCCATAACCATCAACTACAAG<br>GGCCTTAACGCCAAGGACAAGGAGATCAGAAAGTACAACGAAAAGATCAACAAAT<br>TCATCGCTGGCAACCCCGACATCAACATCATAGGCATCGACCGGGGCGAACGGC<br>ACCTGCTGTACTACACCATCATCAACCAGAAGGGAGAGATCCTGAAGCAATCTACA<br>CTGAACAACGTGGGCATCGAGGGCAGAGACAAAGATTACCAGGAGCTGCTGAGC<br>AACAAGGAAAAGGAAAGACACCTCGCTAGAAAGAGCTGGGGCACCATCGGCAAC<br>ATAAAAGAACTGAAGGAAGGCTACCTGAGCATCGTGGTGCACGAGCTGGCCAAGC<br>TCGTGAAGGAGTACAACGCCATCATCGTGCTGGAGAATCTGAACGCCGGCTTCAA<br>GAGAGGCAGAACCAAGGTGGAAAAACAGGTCTACCAGAAGTTTGAGCTGGCCCT<br>GATCAAGAAGCTGAACTACCTCGTGTTCAAGAACGAGAACATCCAGAACAAGGGA<br>GGCTACCTGAAGGGACTGCAACTGACACAGCCTTTCGACACCTTTAAGGATATCG<br>GCAACCAGAGCGGCATCATCTACTACGTGATCCCCAGCTACACAAGCAAAATTTGT<br>CCAACAACCGGCTTCATCGACGTGATCAAACCTCAGTACGAGTCTGTGGAAAAGG<br>CCAAGGAGCTGTTCTCCAAATTCAAACGGATTTACTTCGACAACAACAAGAAGTGC<br>TTTATCTTCGAATTTATGTACAAAGATTTCGGCAGAGATTACGGTCTGGACAAGATC<br>TGGAGCATCTGTACCCTGGGCGAGAAGAGATACTACTACGACAGCAAGAACAAGG<br>TTTCCAATGTGATCAACGTGACCGAGAGCATCATCAGCATCCTGCAGGAGAAGAA<br>CATCAACTACATCAACAGCGACAACATCATCGACGAGATCCTGCAGTACAGCGAC<br>GTGAAGCTGTATAAGGAGCTGCTTTTTAACCTGAAGGTGGTGCTGCAGATGCGGT<br>ACACCAAGAGCGGCACCAATAACGAGGACGACTTCATTCTGTCTCCTGTGCTGGA<br>CGAGAACGACAAGGCCTTCTGCAGCCTGAACGCTAAGGAAACAGAGCCTCAGAAT<br>GCTGATGCTAATGGCGCCTATCATATCGCCATGAAGGGACTGAACGCCATCATGT<br>CCATCAAGAACGGCAACGTGGATAGAGATATTAACAACCTGGAAAACTGGATCAA<br>CTTCATCCAGAAATTCCACATCGGGAAG | |

TABLE 1P-continued

ZSYN Type V Cas Sequences

| Name | Sequence | SEQ ID NO. |
|---|---|---|
| Expression construct (with N-terminal methionine and stop codon, includes V5-tag and C-terminal NLS) | ATGggctccggaGGCAAGTTCTTTGAAACCGACGAGTTCATCGGACAGTACAGTATCA<br>ACAAAACACTGAGGTTCGAGCTCATCCCTCAAGGCAAGACCAAGGAACTGCTGAA<br>CAACTATATGAACGACAACAGTAAGATCAAGCAGGACATCCTGCGGGCCGACGAG<br>AAGAACAATTTCAAGGAAGTGATCGACGAGTATTATAGAGAGTTGATCCACGACGC<br>CCTGACCGACGAGGACATCTTTTCCATCACCCCTCTCGTCAAGGACGCCTACGAG<br>CTGTACATCGCCTCCAGAAAAAACACCAGCGACTCCAGCAAGAAGGAGTATCGGG<br>ACGTGAAAAATAAGATTAGAAAAGAGATCGCTAACATCCTGAACAAGTACAAGACA<br>ATCTACGGCCTGGACAAGTTCGCCAATATCTACAAGTCTGAGAGCGACAAGAGCG<br>TTGATGATGACGAATCTGATAACGATGACTTGGACGAGAAGAATACCACCAACGAC<br>GATAATGCCAAGTCTGAGGACAAGCGGATCTATAAGTGGCTGAATAAGAAGCTGA<br>GACTGAAGCAGATCTCCAACGAAGAATACGACCGGTACTACAAGTCCCTGAACGA<br>ATACCACGGGTTCACAACAGGACTGCAGGGCCTGCAGAACAACAAGGAAAACATG<br>TTCAGCAGCGAGAACAAGAGCACCGCCATCGCCTTTAGAATCATCGATGACAACA<br>TGGAAAAGTATTTTTCTAACATCCTGCTCCTGGAGTTCATCAAAAACAAGTACAAAG<br>ATCTGTACGAGAAGATCGAGGAGAAGGCCAACAAGATGAACGTGGAATGCTTCAC<br>CAAGTACTTCACCCAGGAGGGCATCGACGAGTACAATCAGATGATTGGCAGAAGC<br>ATTGAGGAAGAATACGCCAAGGGCATCAACCAGGAGATCAACCTGTATAAGCAGA<br>GCAAGGGTCTAAACAATAAGGAGATCAGAACACTGAGCCCCCTGTACAAGCAGAT<br>CCTGTCCAAGACCAGCCAGAACGAAATCATCGTGTTCAAAAACGACAAGGAAACC<br>CTGGAATACATCAAGAATATCTGTGATTACATTATCGAGGAGGACATCTTCGGAAA<br>GATGAACCACCTGATCAAAACCAACCTGATCGACATGTGCACCGGAATCTACATTA<br>AGAGAAACGAGCTGAGCAACATCTCTTTCAAGCTCTACAACGACTGGGGCCTGCT<br>GGACAGAATTATCTGTGACTACGCCAACGAGTTCAAGACAAAGAAGGAAAAGAAT<br>GAGTTCGAGAAGCTGAACAAAGAGGTGATCTCTCTGAACCTGCTCAACGATATTTT<br>CAACAAATACAAGGAAACCAGAGGCAATGATACAGACCTGAAGGAAATCGTGGAA<br>TACTTTAAAAACGTCGACGAGAAAATGATTGAGGACGAGTACAGCAAGATCAAGAG<br>CATACTTAATCTGGAACGCATCGACATCGACCGTAGAGTGCCAAGCAAGGACGAG<br>GAAAAGGGCGGCGAAGGCTTTGAGCAGATCTGCATGATCAAGACGTTCCTGGATC<br>TGCTGTTGGAGAGCATCCACATCTACAAGCCTCTGTCTCTGATCAAGAACGGCGA<br>GAAGGTGGAAATCTACAATTATAACGAGAACTTCTACAACGAGTACGACATCCTGT<br>TCAGCCAGCTGGATAACATTATAAATCTGTACAATAAGGTGCGGAACTACTTCAGC<br>AAGAAAACCTACAGCAAAGAGAAAATCAAAATCTATTTCTCCAAACCCACCCTGCT<br>GAACGGATGGGACGTGAACAAGGAGATCAGCAACTACTCTATCATCCTGAGAAAA<br>GACGAAGAGTACTTTCTGGCAATTATGAACAGCGACAACAAGATCTTCACGAATGA<br>GAGGCTGGAAGAAAACTGCGCCATCACCGAGAATAATGAAGAATGTTACGAGAAA<br>ATGGTGTACAAGCAAATCTCTGACTCTAACAAGATGTTCAGCAAGGTGTTTTTCAG<br>CGAGAAAAACAAGAAGATCTACATGCCCAGCGAAGAGATCAAGAATATCAGAAAG<br>AACAAGACCCATCTCAAGGTGGCCAACAATAAGGATTCTCAAACAAAGTGGATCAA<br>GTTCATGATCGAGTGCTACTATAAACACCCTGAGTGGAGTAAGTACTTCGATATCA<br>ACTTCAAGAAACCTGAAGAATATGAAAGCATCGTGGAATTTTACAACCAGGTGAAC<br>GAGAAGATCTACAACATCAAGTTCGTGAATATCAAATGCGACTACATCAACAGCAT<br>GGTGGATTCGGGAGAGCTGTACCTGTTCAAGATCTACAACAAGGACTTCTCTAAG<br>AACAAGAAAAAAAGTGGCACAGATAACCTGCACACCATGTATTGGAAGCTGCTGTT<br>TAGCAAAGAAAACATGAATTGCGGCGTGTACAAGCTGAACGGCCAGGCCGAGGT<br>GTTCTTCAGAAAGGCCAGCCTGCCTGATAAGATCACACACGAAAGAAATAAGGAG<br>ATCGACAACAAAAATCCTATCAAGGACAAGAAAACCAGCACCTTCACATACGACCT<br>GAAGAAAGATAAGCGGTTCATGGAAGATAAGTTCTTCTTCCACTGCCCCATAACCA<br>TCAACTACAAGGGCCTTAACGCCAAGGACAAGGAGATCAGAAAGTACAACGAAAA<br>GATCAACAAATTCATCGCTGGCAACCCCGACATCAACATCATAGGCATCGACCGG<br>GGCGAACGGCACCTGCTGTACTACACCATCATCAACCAGAAGGGAGAGATCCTGA<br>AGCAATCTACACTGAACAACGTGGGCATCGAGGGCAGAGACAAAGATTACCAGGA<br>GCTGCTGAGCAACAAGGAAAAGGAAAGACACCTCGCTAGAAAGAGCTGGGGCAC<br>CATCGGCAACATAAAAGAACTGAAGGAAGGCTACCTGAGCATCGTGGTGCACGAG<br>CTGGCCAAGCTCGTGAAGGAGTACAACGCCATCATCGTGCTGGAGAATCTGAACG<br>CCGGCTTCAAGAGAGGCAGAACCAAGGTGGAAAAACAGGTCTACCAGAAGTTTGA<br>GCTGGCCCTGATCAAGAAGCTGAACTACCTCGTGTTCAAGAACGAGAACATCCAG<br>AACAAGGGAGGCTACCTGAAGGGACTGCAACTGACACAGCCTTTCGACACCTTTA<br>AGGATATCGGCAACCAGAGCGGCATCATCTACTACGTGATCCCCAGCTACACAAG<br>CAAAATTTGTCCAACAACCGGCTTCATCGACGTGATCAAACCTCAGTACGAGTCTG<br>TGGAAAAGGCCAAGGAGCTGTTCTCCAAATTCAAACGGATTTACTTCGACAACAAC<br>AAGAAGTGCTTTATCTTCGAATTTATGTACAAAGATTTCGGCAGAGATTACGGTCT<br>GGACAAGATCTGGAGCATCTGTACCCTGGGCGAGAAGAGATACTACTACGACAGC<br>AAGAACAAGGTTTCCAATGTGATCAACGTGACCGAGAGCATCATCAGCATCCTGC<br>AGGAGAAGAACATCAACTACATCAACAGCGACAACATCATCGACGAGATCCTGCA<br>GTACAGCGACGTGAAGCTGTATAAGGAGCTGCTTTTTAACCTGAAGGTGGTGCTG<br>CAGATGCGGTACACCAAGAGCGGCACCAATAACGAGGACGACTTCATTCTGTCTC<br>CTGTGCTGGACGAGAACGACAAGGCCTTCTGCAGCCTGAACGCTAAGGAAACAGA<br>GCCTCAGAATGCTGATGCTAATGGCGCCTATCATATCGCCATGAAGGGACTGAAC<br>GCCATCATGTCCATCAAGAACGGCAACGTGGATAGAGATATTAACAACCTGGAAAA<br>CTGGATCAACTTCATCCAGAAATTCCACATCGGGAAGtctagaAAGCGGACAGCAGA<br>CGGCTCCGAATTTGAAAGCCCTAAGAAAAAGAGAAAGGTGggatccGGCAAACCTAT<br>CCCCAATCCCCTGCTGGGCCTGGACAGCACCTGA | 96 |

In some embodiments a ZSYN Type V Cas protein comprises an amino acid sequence of SEQ ID NO:91, SEQ ID NO:92, or SEQ ID NO:93. In some embodiments, a ZSYN Type V Cas protein has nickase activity, for example resulting from one or more amino acid substitutions relative to the sequence of SEQ ID NO:91, SEQ ID NO:92, or SEQ ID NO:93. In some embodiments, the one or more amino acid substitutions providing nickase activity comprise a D902 substitution, wherein the position of the D902 substitution is defined with respect to the amino acid numbering of SEQ ID NO:92 (corresponding to amino acid 908 of SEQ ID NO:121). In some embodiments, the one or more amino acid substitutions providing nickase activity comprise an E991 substitution, wherein the position of the E991 substitution is defined with respect to the amino acid numbering of SEQ ID NO:92 (corresponding to amino acid 993 of SEQ ID NO:121). In some embodiments, the one or more amino acid substitutions providing nickase activity comprise a R1200 substitution, wherein the position of the R1200 substitution is defined with respect to the amino acid numbering of SEQ ID NO:92 (corresponding to amino acid 1226 of SEQ ID NO:121). In some embodiments, the one or more amino acid substitutions providing nickase activity comprise a D1239 substitution, wherein the position of the D1239 substitution is defined with respect to the amino acid numbering of SEQ ID NO:92 (corresponding to amino acid 1263 of SEQ ID NO:121). In some embodiments, a ZSYN Type V Cas protein is catalytically inactive, for example due to a R1200 substitution in combination with a D902 substitution, a E991 substitution, and/or D1239 substitution.

6.2.17. ZRBH Type V Cas Protein

In one aspect, the disclosure provides ZRBH Type V Cas proteins. ZRBH Type V Cas proteins can be further classified as Type V-A Cas proteins. The ZRBH Type V Cas proteins typically comprise an amino acid sequence that is at least 50%, at least 55%, at least 60%, at least 65%, at least 70%, at least 75%, at least 85%, at least 90%, or at least 95% identical to SEQ ID NO:97. In some embodiments, the ZRBH Type V Cas proteins comprise an amino acid sequence that is at least 95%, at least 96%, at least 97%, at least 98%, or at least 99% identical to SEQ ID NO:97. In some embodiments, a ZRBH Type V Cas protein comprises an amino acid sequence that is identical to SEQ ID NO:97.

Exemplary ZRBH Type V Cas protein sequences and nucleotide sequences encoding exemplary ZRBH Type V Cas proteins are set forth in Table 1Q.

TABLE 1Q

ZRBH Type V Cas Sequences

| Name | Sequence | SEQ ID NO. |
|---|---|---|
| Wildtype amino acid sequence (without N-terminal methionine) | EFDNSFVNRYPLSKTLSFSLLPVGSTEANFEKKLLLQEDEKRAAEYILVKSYIDRYHKAY IESVLSKVVLDGINNYAQLYCKNNKTEQDIKRLEQLEGSFRKQISKSLKSDARYKLIYKK EMLEKLLPEFLDNEEEKARVISFENFTTYFTGFHTNRENMYTDEAKSTAVSFRCINDNL PKFLDNISVFKWVTAFLSESDINELKADFSGLLGCSLEEMFTPDYFSFVLSQSGIERYN NVIGGYTCSDGEKVKGLNEYINLYNQKLQHGEKKLPLLKRLFKQILSDTESVSFIPEKLE NDDAVISAINGFCNIKIENETFFEILDKTKCLFSNLNEFDSAGVYITNGFAVTDISNAVFG TWDVISEAWKKEYAKAIPLKNIAKADAYYEKQGKAYKAIKSFSVSELQRLANTTEGKAA YKHNGDISAYFSETVCFAVQDIFEKYSSSKALFASPYKNEKRLFKNNEAIALIKDFLDSIK NLEKLIKPFNGSGRENDKDESFYGEFTACYERLSKIDLLYDKVRNYMTQKPYSGDKIKL NFENPQFLNGWDRNKERDYRTVLLRKGGYYYLAIMDKSNNRIFEDLPEPKNGEDCYE KIDYKLLPGPNKMLPKVFFAASNIDYFAPSEQILKIRQKETFKKGVNFNIDDCHAFIDFLK ESIEKHDEWCKYGFEFKDTSDYNNIGEFYKDVREQGYSISFRNVPESYINSCVNSGSL YLFQIYNKDFSPYSKGTKSLHTLYFEMLFDERNLKNVVYQLNGGAEMFYRKASIKERD KIVHPANIPIKNKNPDNPKAESVFEYDIIKDRRFTERQFSLHIPVTLNFKGSGGSANLNA DVRRAIRGADENYVIGIDRGERNLLYITVINSKGEIVEQIPGNVIINGKQVVDYHKLLDAK EKERLAARQNWTTVENIKELKEGYLSVIIHNICELVKKYNAVIAMEDLSSGFKNSRVKVE KQVYQKFEKMLTEKLNFLVDKKADVQSRGGLLQAYQLTNSTKDYKRAGSQDGIVFYV PAWLTSKIDPVTGFVDLLKPKYTSVQEAKELFSNFEAVEYIPEEDLFSFTFDYSKFPRC SVAYRNKWTVYSNGERIYTFRDKNSNNEYVSKTVALTTEFKSLFDEYSVYYRDNLKSQ ILCQDKVDFFKQLIRLLSLTMQMRNSISNSAVDYLISPVKDKNGNFFDSRKSIKNLPENA DANGAYNIAKKALWAIGQIKEADENDLMKVKLSVSNKEWLKYVQEVE | 97 |
| Wildtype amino acid sequence (with N-terminal methionine) | MEFDNSFVNRYPLSKTLSFSLLPVGSTEANFEKKLLLQEDEKRAAEYILVKSYIDRYHK AYIESVLSKVVLDGINNYAQLYCKNNKTEQDIKRLEQLEGSFRKQISKSLKSDARYKLIY KKEMLEKLLPEFLDNEEEKARVISFENFTTYFTGFHTNRENMYTDEAKSTAVSFRCIND NLPKFLDNISVFKWVTAFLSESDINELKADFSGLLGCSLEEMFTPDYFSFVLSQSGIER YNNVIGGYTCSDGEKVKGLNEYINLYNQKLQHGEKKLPLLKRLFKQILSDTESVSFIPEK LENDDAVISAINGFCNIKIENETFFEILDKTKCLFSNLNEFDSAGVYITNGFAVTDISNAVF GTWDVISEAWKKEYAKAIPLKNIAKADAYYEKQGKAYKAIKSFSVSELQRLANTTEGKA AYKHNGDISAYFSETVCFAVQDIFEKYSSSKALFASPYKNEKRLFKNNEAIALIKDFLDSI KNLEKLIKPFNGSGRENDKDESFYGEFTACYERLSKIDLLYDKVRNYMTQKPYSGDKIK LNFENPQFLNGWDRNKERDYRTVLLRKGGYYYLAIMDKSNNRIFEDLPEPKNGEDCY EKIDYKLLPGPNKMLPKVFFAASNIDYFAPSEQILKIRQKETFKKGVNFNIDDCHAFIDFL KESIEKHDEWCKYGFEFKDTSDYNNIGEFYKDVREQGYSISFRNVPESYINSCVNSGS LYLFQIYNKDFSPYSKGTKSLHTLYFEMLFDERNLKNVVYQLNGGAEMFYRKASIKER DKIVHPANIPIKNKNPDNPKAESVFEYDIIKDRRFTERQFSLHIPVTLNFKGSGGSANLN ADVRRAIRGADENYVIGIDRGERNLLYITVINSKGEIVEQIPGNVIINGKQVVDYHKLLDA KEKERLAARQNWTTVENIKELKEGYLSVIIHNICELVKKYNAVIAMEDLSSGFKNSRVKV EKQVYQKFEKMLTEKLNFLVDKKADVQSRGGLLQAYQLTNSTKDYKRAGSQDGIVFY VPAWLTSKIDPVTGFVDLLKPKYTSVQEAKELFSNFEAVEYIPEEDLFSFTFDYSKFPR CSVAYRNKWTVYSNGERIYTFRDKNSNNEYVSKTVALTTEFKSLFDEYSVYYRDNLKS QILCQDKVDFFKQLIRLLSLTMQMRNSISNSAVDYLISPVKDKNGNFFDSRKSIKNLPEN ADANGAYNIAKKALWAIGQIKEADENDLMKVKLSVSNKEWLKYVQEVE | 98 |

TABLE 1Q-continued

ZRBH Type V Cas Sequences

| Name | Sequence | SEQ ID NO. |
|---|---|---|
| Expression construct (with N-terminal methionine, V5-tag and C-terminal NLS) aa sequence | MGSGEFDNSFVNRYPLSKTLSFSLLPVGSTEANFEKKLLLQEDEKRAAEYILVKSYIDR<br>YHKAYIESVLSKVVLDGINNYAQLYCKNNKTEQDIKRLEQLEGSFRKQISKSLKSDARY<br>KLIYKKEMLEKLLPEFLDNEEEKARVISFENFTTYFTGFHTNRENMYTDEAKSTAVSFR<br>CINDNLPKFLDNISVFKWVTAFLSESDINELKADFSGLLGCSLEEMFTPDYFSFVLSQS<br>GIERYNNVIGGYTCSDGEKVKGLNEYINLYNQKLQHGEKKLPLLKRLFKQILSDTESVS<br>FIPEKLENDDAVISAINGFCNIKIENETFFEILDKTKCLFSNLNEFDSAGVYITNGFAVTDI<br>SNAVFGTWDVISEAWKKEYAKAIPLKNIAKADAYYEKQGKAYKAIKSFSVSELQRLANT<br>TEGKAAYKHNGDISAYFSETVCFAVQDIFEKYSSSKALFASPYKNEKRLFKNNEAIALIK<br>DFLDSIKNLEKLIKPFNGSGRENDKDESFYGEFTACYERLSKIDLLYDKVRNYMTQKPY<br>SGDKIKLNFENPQFLNGWDRNKERDYRTVLLRKGGYYYLAIMDKSNNRIFEDLPEPKN<br>GEDCYEKIDYKLLPGPNKMLPKVFFAASNIDYFAPSEQILKIRQKETFKKGVNFNIDDCH<br>AFIDFLKESIEKHDEWCKYGFEFKDTSDYNNIGEFYKDVREQGYSISFRNVPESYINSC<br>VNSGSLYLFQIYNKDFSPYSKGTKSLHTLYFEMLFDERNLKNVVYQLNGGAEMFYRKA<br>SIKERDKIVHPANIPIKNKNPDNPKAESVFEYDIIKDRRFTERQFSLHIPVTLNFKGSGGS<br>ANLNADVRRAIRGADENYVIGIDRGERNLLYITVINSKGEIVEQIPGNVIINGKQVVDYHK<br>LLDAKEKERLAARQNWTTVENIKELKEGYLSVIIHNICELVKKYNAVIAMEDLSSGFKNS<br>RVKVEKQVYQKFEKMLTEKLNFLVDKKADVQSRGGLLQAYQLTNSTKDYKRAGSQD<br>GIVFYVPAWLTSKIDPVTGFVDLLKPKYTSVQEAKELFSNFEAVEYIPEEDLFSFTFDYS<br>KFPRCSVAYRNKWTVYSNGERIYTFRDKNSNNEYVSKTVALTTEFKSLFDEYSVYYRD<br>NLKSQILCQDKVDFFKQLIRLLSLTMQMRNSISNSAVDYLISPVKDKNGNFFDSRKSIKN<br>LPENADANGAYNIAKKALWAIGQIKEADENDLMKVKLSVSNKEWLKYVQEVESRKRTA<br>DGSEFESPKKKRKVGSGKPIPNPLLGLDST | 99 |
| Wildtype coding sequence (with N-terminal methionine and stop codon) | ATGGAATTCGACAATAGCTTTGTTAACCGATACCCTTTATCAAAAACACTAAGCTTC<br>AGTTTGCTTCCTGTTGGCAGTACCGAAGCAAATTTTGAGAAAAAACTGTTGCTGCA<br>GGAGGACGAAAAAAGAGCCGCGGAATATATTTTGGTGAAGTCATACATTGACAGA<br>TACCATAAAGCCTATATTGAATCGGTTTTATCAAAGGTTGTGCTTGACGGCATAAAT<br>AACTATGCACAGCTGTACTGCAAGAACAACAAAACCGAACAGGATATCAAACGACT<br>GGAGCAGCTTGAAGGTTCATTTAGAAAGCAGATTTCAAAGAGCTTGAAATCCGATG<br>CCCGTTATAAGTTGATTTATAAAAAAGAAATGCTTGAAAAGCTTTTGCCTGAGTTTC<br>TTGATAATGAAGAAGAAAAGGCGAGGGTAATATCTTTTGAAAACTTTACAACATATT<br>TCACAGGCTTTCATACCAATAGAGAAAATATGTATACCGACGAAGCAAAATCCACT<br>GCGGTGTCCTTCAGATGTATAAATGATAATTTACCAAAATTTCTTGATAATATTTCA<br>GTTTTTAAATGGGTTACGGCATTTTTGAGCGAAAGTGATATCAACGAATTAAAGGC<br>GGATTTTTCAGGTCTGTTAGGTTGTTCGCTTGAAGAAATGTTTACACCGGATTATTT<br>TTCCTTTGTGTTATCTCAAAGCGGGATAGAAAGATATAACAATGTTATCGGCGGTT<br>ACACATGTTCTGACGGTGAAAAAGTTAAGGGACTAAATGAATACATAAATTTATACA<br>ACCAAAAGTTACAACACGGTGAAAAAAAGCTCCCGCTTTTAAAACGCTTGTTCAAG<br>CAGATATTGAGTGATACCGAAAGTGTATCCTTTATTCCGGAAAAGCTTGAAAACGA<br>CGATGCTGTTATTTCTGCGATAAACGGATTTTGTAATATCAAAATTGAAAACGAAAC<br>ATTCTTTGAAATTCTTGATAAAACTAAATGCTTGTTTTCAAATTTAAATGAGTTTGAC<br>AGCGCCGGTGTATATATTACCAACGGTTTTGCTGTAACCGATATTTCAAATGCTGT<br>TTTCGGTACTTGGGATGTTATTTCGGAAGCGTGGAAAAAGGAGTATGCGAAAGCA<br>ATCCCGCTTAAAAATATCGCCAAGGCAGATGCATATTACGAAAAGCAGGGCAAGG<br>CGTATAAGGCAATTAAAAGCTTTTCGGTAAGCGAGCTTCAAAGGCTGGCCAACACA<br>ACAGAAGGGAAGGCGGCATATAAGCACAACGGAGATATTTCTGCATATTTTTCGGA<br>AACTGTTTGCTTTGCGGTTCAAGATATATTTGAAAAATACAGTAGTTCAAAAGCCCT<br>TTTTGCGTCGCCCTATAAAAATGAAAAGCGGCTCTTCAAAAACAATGAGGCTATAG<br>CGCTGATTAAGGATTTTCTTGACAGCATCAAAAATCTGGAAAAGCTTATTAAACCAT<br>TTAACGGCTCCGGTAGAGAAAACGATAAGGACGAAAGCTTCTACGGTGAATTTAC<br>CGCTTGCTACGAGAGGCTTTCTAAAATTGACCTGCTATATGATAAGGTTCGCAACT<br>ATATGACACAAAAACCTTATTCCGGGGACAAGATAAAGTTGAATTTTGAAAATCCG<br>CAATTTCTAAATGGTTGGGACAGGAACAAAGAGCGGGATTACAGAACTGTTCTCTT<br>AAGAAAAGGCGGGTATTACTACCTTGCTATTATGGATAAAAGCAACAACAGGATTT<br>TTGAAGATTTGCCGGAGCCCAAAAACGGCGAGGATTGTTATGAAAAAATAGACTAC<br>AAGCTTCTGCCGGGACCGAATAAGATGTTGCCAAAGGTGTTTTTTGCCGCGAGCA<br>ATATTGATTATTTTGCACCCTCTGAGCAAATTTTGAAAATTAGACAGAAAGAAACCT<br>TTAAGAAGGGTGTGAATTTTAATATTGATGATTGCCATGCTTTCATAGACTTCCTTA<br>AAGAGTCTATAGAAAAACACGATGAGTGGTGCAAGTATGGGTTCGAATTTAAAGAT<br>ACTTCAGATTATAACAACATCGGTGAATTTTATAAAGATGTAAGGGAGCAGGGCTA<br>TTCTATCAGCTTTAGAAATGTGCCTGAGTCTTATATAAATTCTTGCGTTAATTCCGG<br>TTCACTTTACCTTTTCCAAATCTACAACAAGGATTTTTCACCTTACAGCAAAGGGAC<br>CAAGAGTTTGCACACATTGTATTTTGAAATGCTTTTTGATGAAAGGAACCTTAAGAA<br>TGTTGTTTATCAGCTTAACGGCGGTGCAGAGATGTTTTACCGCAAAGCAAGTATTA<br>AGGAAAGGGATAAAATAGTACACCCTGCTAATATTCCGATAAAAAATAAAAATCCC<br>GATAACCCAAAAGCTGAAAGTGTTTTTGAGTATGACATCATAAAGGACAGACGCTT<br>TACTGAAAGACAGTTCTCTTTGCATATTCCTGTTACGCTCAATTTTAAAGGCTCGGG<br>CGGCTCTGCAAATCTTAATGCTGATGTGCGCAGAGCCATAAGAGGCGCTGATGAA<br>AACTATGTTATAGGTATAGACAGAGGAGAAAGAAATTTGCTTTACATCACCGTAATA<br>AACAGTAAAGGTGAAATTGTTGAGCAGATTCCGGGCAATGTAATAATCAACGGAAA<br>ACAAGTGGTCGATTATCACAAGCTGCTTGATGCCAAAGAAAAAGAGCGTCTTGCA<br>GCACGGCAAAACTGGACAACGGTTGAAAATATCAAGGAGCTTAAAGAGGGCTATT<br>TGAGCGTAATCATACACAATATTTGTGAACTTGTAAAAAAATACAATGCTGTTATTG<br>CTATGGAGGATCTTTCTTCCGGTTTTAAAAACAGCAGGGTTAAAGTAGAAAAACAG | 100 |

TABLE 1Q-continued

| ZRBH Type V Cas Sequences | | |
|---|---|---|
| Name | Sequence | SEQ ID NO. |
| | GTTTATCAGAAATTTGAAAAAATGCTTACCGAAAAGCTTAATTTTCTTGTTGATAAAA<br>AAGCTGATGTTCAAAGCAGGGGAGGACTTCTGCAGGCATATCAGTTAACAAACAG<br>CACCAAGGATTATAAGCGGGCAGGCTCACAAGACGGTATTGTTTTCTATGTTCCG<br>GCGTGGCTTACAAGCAAAATCGATCCCGTTACGGGTTTTGTTGATTTGCTTAAGCC<br>TAAGTATACAAGTGTGCAGGAAGCAAAGGAGCTGTTTTCAAATTTTGAAGCTGTTG<br>AATATATCCCTGAGGAGGATTTGTTCAGCTTTACTTTTGATTATTCGAAATTTCCCC<br>GTTGCTCCGTAGCTTACCGTAACAAATGGACTGTATACTCAAACGGCGAAAGAATT<br>TATACATTCAGGGATAAAAACAGCAATAATGAATATGTTAGCAAAACAGTTGCTCTT<br>ACAACGGAGTTTAAATCCTTGTTTGACGAATACAGCGTTTATTACCGCGATAACCTT<br>AAATCGCAGATTCTATGTCAAGATAAAGTCGATTTCTTCAAACAGCTAATTCGGTTA<br>CTGTCTTTGACAATGCAAATGCGAAACAGTATTTCAAATTCAGCAGTAGATTATCTG<br>ATTTCTCCGGTTAAGGATAAAAACGGAAATTTCTTTGACAGCCGGAAAAGTATAAA<br>AAATCTTCCGGAAAATGCAGATGCTAACGGTGCTTACAACATTGCCAAAAAGGCTC<br>TTTGGGCAATCGGGCAAATAAAGGAAGCGGATGAGAATGATTTAATGAAGGTCAA<br>GCTGTCTGTTTCAAACAAGGAATGGCTTAAATATGTGCAGGAGGTAGAATGA | |
| Codon optimized coding sequence (no N-terminal methionine, no stop codon) | GAATTTGATAACTCTTTCGTGAATAGATATCCTCTGAGCAAGACCCTGAGCTTCAG<br>TCTGCTGCCAGTGGGCAGCACCGAAGCCAACTTCGAAAAAAAGCTGCTGCTGCAG<br>GAGGACGAAAAGAGAGCCGCCGAGTACATCCTGGTGAAAAGCTACATCGACAGAT<br>ACCACAAGGCCTACATCGAGAGCGTGCTGAGCAAGGTGGTGCTGGACGGCATCA<br>ACAACTATGCCCAGCTGTACTGCAAGAACAACAAGACCGAACAGGACATCAAGCG<br>GCTGGAGCAGCTGGAGGGCAGCTTCAGAAAGCAGATCTCTAAAAGCCTGAAGTCC<br>GACGCCAGATACAAGCTGATCTACAAAAAGGAGATGCTGGAAAAGCTCCTGCCTG<br>AGTTCCTGGACAACGAGGAAGAAAAGGCTAGAGTGATCAGCTTCGAGAACTTTAC<br>AACCTACTTCACTGGCTTCCACACCAACCGGGAAAACATGTACACCGATGAGGCC<br>AAGTCTACGGCCGTTTCCTTTAGGTGTATCAACGATAACCTGCCAAAGTTCCTGGA<br>CAACATCAGCGTATTCAAGTGGGTCACCGCCTTTCTGAGCGAGTCTGACATCAAC<br>GAACTGAAGGCCGATTTCAGCGGCCTGTTGGGCTGCTCCCTGGAAGAGATGTTCA<br>CCCCTGATTACTTCAGCTTCGTGCTGTCTCAGAGCGGCATCGAGAGATACAACAA<br>CGTGATCGGCGGATACACCTGTAGCGATGGCGAGAAAGTCAAAGGACTTAATGAG<br>TACATCAACCTGTATAACCAGAAGCTGCAACACGGCGAAAAGAAACTGCCCCTGC<br>TCAAGCGGCTGTTCAAGCAGATTCTGTCAGACACCGAGAGCGTGTCCTTCATCCC<br>CGAGAAACTGGAAAATGATGACGCCGTGATCTCCGCCATTAACGGATTTTGTAATA<br>TCAAGATCGAGAATGAAACATTCTTCGAGATCCTGGACAAGACCAAGTGCCTGTTC<br>AGCAATCTGAACGAGTTCGACTCTGCCGGAGTGTACATCACCAACGGCTTCGCAG<br>TGACAGACATCAGCAACGCCGTGTTCGGCACCTGGGACGTCATCAGCGAAGCCT<br>GGAAGAAAGAGTACGCCAAAGCTATCCCCCTGAAGAACATCGCTAAGGCCGACGC<br>CTACTATGAGAAGCAGGGCAAGGCCTACAAGGCCATCAAGAGCTTCTCTGTAAGC<br>GAACTGCAGAGACTGGCCAACACCACGGAGGGAAAGGCCGCCTACAAGCACAAC<br>GGCGACATCAGCGCCTATTTCAGCGAGACAGTCTGCTTCGCTGTGCAGGATATCT<br>TCGAGAAGTATAGCAGCAGCAAGGCCCTGTTCGCCAGCCCCTATAAGAACGAGAA<br>GCGGCTGTTCAAGAACAATGAGGCAATCGCTCTGATTAAGGACTTCCTGGATAGC<br>ATCAAGAACCTGGAGAAGCTGATTAAGCCATTCAACGGCAGCGGCAGAGAGAACG<br>ACAAGGACGAGAGCTTTTACGGCGAGTTCACCGCCTGCTACGAGCGGCTGAGCA<br>AAATCGATCTGCTGTACGACAAGGTGCGGAACTACATGACACAGAAACCTTACAG<br>CGGCGATAAGATCAAGCTGAACTTCGAGAATCCTCAGTTCCTGAACGGATGGGAT<br>AGAAACAAGGAGCGGGATTACAGAACAGTGCTGCTGAGAAAGGGAGGTTATTACT<br>ACCTGGCCATCATGGACAAGAGCAACAACCGGATCTTCGAGGATCTGCCTGAGCC<br>TAAGAATGGTGAGGACTGCTACGAAAAAATCGATTACAAGCTGCTGCCTGGCCCT<br>AACAAGATGCTGCCCAAAGTGTTCTTCGCCGCTAGTAACATCGACTACTTCGCCCC<br>TAGCGAACAGATCCTCAAAATCCGGCAGAAGGAAACCTTCAAAAAGGGCGTGAAC<br>TTCAACATTGACGACTGTCACGCCTTCATCGACTTCCTGAAGGAATCTATCGAGAA<br>GCACGACGAGTGGTGCAAGTACGGCTTCGAGTTTAAGGACACCAGCGACTACAAC<br>AATATAGGCGAGTTCTACAAGGACGTGCGGGAACAGGGCTACAGCATCTCTTTTC<br>GGAATGTGCCCGAGTCCTACATCAACAGCTGCGTGAACTCTGGCTCTCTGTACCT<br>GTTTCAGATCTACAACAAAGATTTTAGCCCTTACTCTAAGGGCACAAAGAGCCTGC<br>ACACCCTGTACTTTGAAATGCTGTTTGACGAGCGCAACCTGAAGAACGTGGTGTAT<br>CAGCTGAATGGTGGCGCTGAGATGTTCTACAGAAAGGCCAGCATCAAGGAAAGAG<br>ACAAGATCGTGCACCCCGCCAACATCCCTATCAAGAACAAGAACCCCGACAACCC<br>TAAGGCCGAGAGCGTGTTCGAATACGACATTATCAAGGACAGAAGATTCACCGAA<br>CGGCAGTTCTCCCTGCACATCCCTGTGACCCTGAACTTCAAAGGCTCTGGCGGAT<br>CTGCCAACCTGAACGCCGACGTTAGGCGGGCTATCAGAGGCGCCGATGAGAACT<br>ACGTGATCGGCATCGACCGGGGCGAGAGGAACCTGCTGTACATCACAGTGATCA<br>ATAGCAAGGGCGAGATCGTGGAACAAATCCCAGGCAACGTGATCATCAACGGCAA<br>GCAAGTGGTGGACTACCACAAGCTGCTGGATGCTAAAGAGAAGGAAAGACTGGCT<br>GCCAGACAGAACTGGACAACAGTTGAAAACATCAAGGAACTGAAGGAAGGCTACC<br>TGTCCGTGATCATCCACAACATCTGCGAGCTGGTGAAAAAGTACAACGCTGTGAT<br>CGCTATGGAGGACCTGAGCAGCGGCTTCAAGAACAGCCGCGTGAAGGTGGAAAA<br>GCAGGTATACCAGAAGTTCGAAAAAATGCTGACCGAGAAACTGAACTTCCTGGTG<br>GACAAGAAAGCCGATGTGCAAAGCAGAGGCGGCCTGCTGCAGGCCTACCAGCTG<br>ACAAATAGCACAAAGGATTACAAGCGGGCCGGCAGCCAAGACGGCATCGTGTTCT<br>ACGTGCCTGCCTGGCTGACAAGCAAAATTGACCCTGTGACCGGCTTTGTGGACCT<br>GCTGAAACCTAAATACACCAGCGTTCAGGAGGCCAAAGAGCTGTTCAGCAACTTC<br>GAGGCCGTCGAGTACATCCCCGAGGAGGACCTGTTCAGCTTCACCTTCGACTACA | 101 |

TABLE 1Q-continued

ZRBH Type V Cas Sequences

| Name | Sequence | SEQ ID NO. |
|---|---|---|
| | GCAAGTTCCCCAGATGCAGCGTGGCCTACAGAAACAAGTGGACCGTGTACAGTAA<br>CGGAGAGAGAATCTACACATTCAGAGATAAGAACAGCAACAACGAATACGTGTCC<br>AAGACAGTTGCCCTGACCACCGAGTTTAAAAGCCTCTTCGACGAATATAGCGTGTA<br>CTACCGAGACAACCTGAAGAGTCAGATTTTGTGCCAGGATAAGGTGGATTTCTTCA<br>AGCAACTTATCAGACTGCTGTCCCTGACCATGCAGATGAGAAACAGCATCAGCAA<br>CAGCGCCGTGGACTACCTGATCTCCCCTGTGAAGGATAAGAATGGCAATTTTTTC<br>GACAGCAGAAAGAGCATCAAGAACCTGCCTGAGAACGCCGACGCCAACGGCGCC<br>TACAACATTGCTAAGAAGGCTCTGTGGGCCATCGGTCAGATCAAAGAGGCTGATG<br>AGAATGACCTGATGAAGGTGAAGCTGTCCGTGTCTAATAAAGAGTGGCTGAAGTA<br>CGTGCAGGAGGTGGAA | |
| Expression<br>construct (with<br>N-terminal<br>methionine<br>and stop<br>codon,<br>includes V5-<br>tag and C-<br>terminal NLS) | ATGggctccggaGAATTTGATAACTCTTTCGTGAATAGATATCCTCTGAGCAAGACCCT<br>GAGCTTCAGTCTGCTGCCAGTGGGCAGCACCGAAGCCAACTTCGAAAAAAAGCTG<br>CTGCTGCAGGAGGACGAAAAGAGAGCCGCCGAGTACATCCTGGTGAAAAGCTAC<br>ATCGACAGATACCACAAGGCCTACATCGAGAGCGTGCTGAGCAAGGTGGTGCTG<br>GACGGCATCAACAACTATGCCCAGCTGTACTGCAAGAACAACAAGACCGAACAGG<br>ACATCAAGCGGCTGGAGCAGCTGGAGGGCAGCTTCAGAAAGCAGATCTCTAAAAG<br>CCTGAAGTCCGACGCCAGATACAAGCTGATCTACAAAAAGGAGATGCTGGAAAAG<br>CTCCTGCCTGAGTTCCTGGACAACGAGGAAGAAAAGGCTAGAGTGATCAGCTTCG<br>AGAACTTTACAACCTACTTCACTGGCTTCCACACCAACCGGGAAAACATGTACACC<br>GATGAGGCCAAGTCTACGGCCGTTTCCTTTAGGTGTATCAACGATAACCTGCCAAA<br>GTTCCTGGACAACATCAGCGTATTCAAGTGGGTCACCGCCTTTCTGAGCGAGTCT<br>GACATCAACGAACTGAAGGCCGATTTCAGCGGCCTGTTGGGCTGCTCCCTGGAAG<br>AGATGTTCACCCCTGATTACTTCAGCTTCGTGCTGTCTCAGAGCGGCATCGAGAG<br>ATACAACAACGTGATCGGCGGATACACCTGTAGCGATGGCGAGAAAGTCAAAGGA<br>CTTAATGAGTACATCAACCTGTATAACCAGAAGCTGCAACACGGCGAAAAGAAACT<br>GCCCCTGCTCAAGCGGCTGTTCAAGCAGATTCTGTCAGACACCGAGAGCGTGTCC<br>TTCATCCCCGAGAAACTGGAAAATGATGACGCCGTGATCTCCGCCATTAACGGATT<br>TTGTAATATCAAGATCGAGAATGAAACATTCTTCGAGATCCTGGACAAGACCAAGT<br>GCCTGTTCAGCAATCTGAACGAGTTCGACTCTGCCGGAGTGTACATCACCAACGG<br>CTTCGCAGTGACAGACATCAGCAACGCCGTGTTCGGCACCTGGGACGTCATCAGC<br>GAAGCCTGGAAGAAAGAGTACGCCAAAGCTATCCCCCTGAAGAACATCGCTAAGG<br>CCGACGCCTACTATGAGAAGCAGGGCAAGGCCTACAAGGCCATCAAGAGCTTCTC<br>TGTAAGCGAACTGCAGAGACTGGCCAACACCACGGAGGGAAAGGCCGCCTACAA<br>GCACAACGGCGACATCAGCGCCTATTTCAGCGAGACAGTCTGCTTCGCTGTGCAG<br>GATATCTTCGAGAAGTATAGCAGCAGCAAGGCCCTGTTCGCCAGCCCCTATAAGA<br>ACGAGAAGCGGCTGTTCAAGAACAATGAGGCAATCGCTCTGATTAAGGACTTCCT<br>GGATAGCATCAAGAACCTGGAGAAGCTGATTAAGCCATTCAACGGCAGCGGCAGA<br>GAGAACGACAAGGACGAGAGCTTTTACGGCGAGTTCACCGCCTGCTACGAGCGG<br>CTGAGCAAAATCGATCTGCTGTACGACAAGGTGCGGAACTACATGACACAGAAAC<br>CTTACAGCGGCGATAAGATCAAGCTGAACTTCGAGAATCCTCAGTTCCTGAACGG<br>ATGGGATAGAAACAAGGAGCGGGATTACAGAACAGTGCTGCTGAGAAAGGGAGG<br>TTATTACTACCTGGCCATCATGGACAAGAGCAACAACCGGATCTTCGAGGATCTGC<br>CTGAGCCTAAGAATGGTGAGGACTGCTACGAAAAAATCGATTACAAGCTGCTGCC<br>TGGCCCTAACAAGATGCTGCCCAAAGTGTTCTTCGCCGCTAGTAACATCGACTACT<br>TCGCCCCTAGCGAACAGATCCTCAAAATCCGGCAGAAGGAAACCTTCAAAAAGGG<br>CGTGAACTTCAACATTGACGACTGTCACGCCTTCATCGACTTCCTGAAGGAATCTA<br>TCGAGAAGCACGACGAGTGGTGCAAGTACGGCTTCGAGTTTAAGGACACCAGCG<br>ACTACAACAATATAGGCGAGTTCTACAAGGACGTGCGGGAACAGGGCTACAGCAT<br>CTCTTTTCGGAATGTGCCCGAGTCCTACATCAACAGCTGCGTGAACTCTGGCTCTC<br>TGTACCTGTTTCAGATCTACAACAAAGATTTTAGCCCTTACTCTAAGGGCACAAAG<br>AGCCTGCACACCCTGTACTTTGAAATGCTGTTTGACGAGCGCAACCTGAAGAACG<br>TGGTGTATCAGCTGAATGGTGGCGCTGAGATGTTCTACAGAAAGGCCAGCATCAA<br>GGAAAGAGACAAGATCGTGCACCCCGCCAACATCCCTATCAAGAACAAGAACCCC<br>GACAACCCTAAGGCCGAGAGCGTGTTCGAATACGACATTATCAAGGACAGAAGAT<br>TCACCGAACGGCAGTTCTCCCTGCACATCCCTGTGACCCTGAACTTCAAAGGCTC<br>TGGCGGATCTGCCAACCTGAACGCCGACGTTAGGCGGGCTATCAGAGGCGCCGA<br>TGAGAACTACGTGATCGGCATCGACCGGGGCGAGAGGAACCTGCTGTACATCAC<br>AGTGATCAATAGCAAGGGCGAGATCGTGGAACAAATCCCAGGCAACGTGATCATC<br>AACGGCAAGCAAGTGGTGGACTACCACAAGCTGCTGGATGCTAAAGAGAAGGAAA<br>GACTGGCTGCCAGACAGAACTGGACAACAGTTGAAAACATCAAGGAACTGAAGGA<br>AGGCTACCTGTCCGTGATCATCCACAACATCTGCGAGCTGGTGAAAAAGTACAAC<br>GCTGTGATCGCTATGGAGGACCTGAGCAGCGGCTTCAAGAACAGCCGCGTGAAG<br>GTGGAAAAGCAGGTATACCAGAAGTTCGAAAAAATGCTGACCGAGAAACTGAACT<br>TCCTGGTGGACAAGAAAGCCGATGTGCAAAGCAGAGGCGGCCTGCTGCAGGCCT<br>ACCAGCTGACAAATAGCACAAAGGATTACAAGCGGGCCGGCAGCCAAGACGGCA<br>TCGTGTTCTACGTGCCTGCCTGGCTGACAAGCAAAATTGACCCTGTGACCGGCTT<br>TGTGGACCTGCTGAAACCTAAATACACCAGCGTTCAGGAGGCCAAAGAGCTGTTC<br>AGCAACTTCGAGGCCGTCGAGTACATCCCCGAGGAGGACCTGTTCAGCTTCACCT<br>TCGACTACAGCAAGTTCCCCAGATGCAGCGTGGCCTACAGAAACAAGTGGACCGT<br>GTACAGTAACGGAGAGAGAATCTACACATTCAGAGATAAGAACAGCAACAACGAAT<br>ACGTGTCCAAGACAGTTGCCCTGACCACCGAGTTTAAAAGCCTCTTCGACGAATAT<br>AGCGTGTACTACCGAGACAACCTGAAGAGTCAGATTTTGTGCCAGGATAAGGTGG<br>ATTTCTTCAAGCAACTTATCAGACTGCTGTCCCTGACCATGCAGATGAGAAACAGC | 102 |

TABLE 1Q-continued

| ZRBH Type V Cas Sequences | | |
|---|---|---|
| Name | Sequence | SEQ ID NO. |
| | ATCAGCAACAGCGCCGTGGACTACCTGATCTCCCCTGTGAAGGATAAGAATGGCA<br>ATTTTTTCGACAGCAGAAAGAGCATCAAGAACCTGCCTGAGAACGCCGACGCCAA<br>CGGCGCCTACAACATTGCTAAGAAGGCTCTGTGGGCCATCGGTCAGATCAAAGAG<br>GCTGATGAGAATGACCTGATGAAGGTGAAGCTGTCCGTGTCTAATAAAGAGTGGC<br>TGAAGTACGTGCAGGAGGTGGAAtctagaAAGCGGACAGCAGACGGCTCCGAATTT<br>GAAAGCCCTAAGAAAAAGAGAAAGGTGggatccGGCAAACCTATCCCCAATCCCCTG<br>CTGGGCCTGGACAGCACCTGA | |

In some embodiments a ZRBH Type V Cas protein comprises an amino acid sequence of SEQ ID NO:97, SEQ ID NO:98, or SEQ ID NO:99. In some embodiments, a ZRBH Type V Cas protein has nickase activity, for example resulting from one or more amino acid substitutions relative to the sequence of SEQ ID NO:97, SEQ ID NO:98, or SEQ ID NO:99. In some embodiments, the one or more amino acid substitutions providing nickase activity comprise a D851 substitution, wherein the position of the D851 substitution is defined with respect to the amino acid numbering of SEQ ID NO:98 (corresponding to amino acid 908 of SEQ ID NO:121). In some embodiments, the one or more amino acid substitutions providing nickase activity comprise an E940 substitution, wherein the position of the E940 substitution is defined with respect to the amino acid numbering of SEQ ID NO:98 (corresponding to amino acid 993 of SEQ ID NO:121). In some embodiments, the one or more amino acid substitutions providing nickase activity comprise a R1152 substitution, wherein the position of the R1152 substitution is defined with respect to the amino acid numbering of SEQ ID NO:98 (corresponding to amino acid 1226 of SEQ ID NO:121). In some embodiments, the one or more amino acid substitutions providing nickase activity comprise a D1189 substitution, wherein the position of the D1189 substitution is defined with respect to the amino acid numbering of SEQ ID NO:98 (corresponding to amino acid 1263 of SEQ ID NO:121). In some embodiments, a ZRBH Type V Cas protein is catalytically inactive, for example due to a R1152 substitution in combination with a D851 substitution, a E940 substitution, and/or D1152 substitution.

6.2.18. ZWPU Type V Cas Protein

In one aspect, the disclosure provides ZWPU Type V Cas proteins. ZWPU Type V Cas proteins can be further classified as Type V-A Cas proteins. The ZWPU Type V Cas proteins typically comprise an amino acid sequence that is at least 50%, at least 55%, at least 60%, at least 65%, at least 70%, at least 75%, at least 85%, at least 90%, or at least 95% identical to SEQ ID NO:103. In some embodiments, the ZWPU Type V Cas proteins comprise an amino acid sequence that is at least 95%, at least 96%, at least 97%, at least 98%, or at least 99% identical to SEQ ID NO:103. In some embodiments, a ZWPU Type V Cas protein comprises an amino acid sequence that is identical to SEQ ID NO:103.

Exemplary ZWPU Type V Cas protein sequences and nucleotide sequences encoding exemplary ZWPU Type V Cas proteins are set forth in Table 1R.

TABLE 1R

| ZWPU Type V Cas Sequences | | |
|---|---|---|
| Name | Sequence | SEQ ID NO. |
| Wildtype amino acid sequence (without N-terminal methionine) | KAETNLTELVNLYSLQKTLRFELIPQGKTLENIEKNGILTQDNQRADDYEKVKKLIDEY<br>HKHHIEISLDDCRLEGLEEYKELYEKKDDLKKIQENLRKQIVKSLTENERYKDKRLFSD<br>KLFKEDLPNYLKDREQDKALVKKFEKFTTYFTGFNENRKNMYSSEDKPTSIAYRLIHE<br>NLPKFIDNLHIFDKIKETTIKDDFDKIVEKLNKHLKIHIKSFDEIFSIEYFNKTLSQKQIDNY<br>NNIIGGMSFENGTKIQGLNEYINRYNQKQEDKHQKLPCVKTLYKQILSDREKISWIPEQ<br>FDDDKQMAESISNLYNEMLPIIKDDLLPLMANIGDYDLSKIFISNDSALTTISQRIFGAYN<br>VYTLAIIEKLKSDKPKSKRQSESKYLDEIDKNFKNMKSFSIAKLNNAVKGKYDKTIENYI<br>KVFGAFDEEENLLQRLETAYNEAEPILNNIEDRCKNINQDKDAVEKIKTLLDALKDIQH<br>FAKLLLCDNDETEIDAEFYNKLHDIVVKLDKITPIYNMVRNYVTKKPYSEEKIKLNFEKS<br>TLLGGWDLNKEKNNLSVILRKDNLYYLGIMKKDNNKIFDSTNIKTDGVCFEKMEYKLL<br>PDPKKMLPKVFFSKKCSKDFNPNDKILEIKENESFKKTSSNFNIEQCRKLIDFYKESIN<br>KHKDWQKFNFQFSDTKTYNDINEFYNEVEKQGYKISFCKISEDYINELVKDNKLYLFKI<br>WNKDFSKYSKGTPNTHTLYWKQIFAPENINNVVYKLNGQAEIFFRQASISQKNVIKHL<br>ANKPVKNKNIKNEKKESTFSYDLVKDKRFTMDKFHFHVPITINFKAKGINNTNPIVNNLI<br>RQNKIEHIIGIDRGERHLLYLSLIDLKGNIIEQKSLNEIINNYNGNEYKTDYHTLLDDKEK<br>ERKDARLSWNTIENIKELKDGYMSQWVHIISQMIVKYNAIVVLEDLNHGFVRGRQKIEK<br>QVYEKFEHKLIDKLNYYVDKNADSNAVGGLYNALQLTNPFDSFEKLGKQSGCLFYIPA<br>WKTSKIDPVTGFINMFTNLKYESVEKSKKFFSKFDDIRYNKEKNRFEFDVSFDKFDSD<br>FVRITQESKLHWTLCSVGQRIELVKENNGYKPNEINLTDAFKSVFNTNKIEINTAKLNR<br>EIGKINDTAFFKELMRLMKLLLQMRNSKPNSIEKNDDYIISPVADENGVFFDSSKVEDN<br>GNLPKDADANGAYNIARKGLYVIHQIKQSEDDKKIDFKDFNPRWLKFIQQKLYLND | 103 |

TABLE 1R-continued

ZWPU Type V Cas Sequences

| Name | Sequence | SEQ ID NO. |
|---|---|---|
| Wildtype amino acid sequence (with N-terminal methionine) | MKAETNLTELVNLYSLQKTLRFELIPQGKTLENIEKNGILTQDNQRADDYEKVKKLIDE<br>YHKHHIEISLDDCRLEGLEEYKELYEKKDDLKKIQENLRKQIVKSLTENERYKDKRLFS<br>DKLFKEDLPNYLKDREQDKALVKKFEKFTTYFTGFNENRKNMYSSEDKPTSIAYRLIH<br>ENLPKFIDNLHIFDKIKETTIKDDFDKIVEKLNKHLKIHIKSFDEIFSIEYFNKTLSQKQIDN<br>YNNIIGGMSFENGTKIQGLNEYINRYNQKQEDKHQKLPCVKTLYKQILSDREKISWIPE<br>QFDDDKQMAESISNLYNEMLPIIKDDLLPLMANIGDYDLSKIFISNDSALTTISQRIFGAY<br>NVYTLAIIEKLKSDKPKSKRQSESKYLDEIDKNFKNMKSFSIAKLNNAVKGKYDKTIEN<br>YIKVFGAFDEEENLLQRLETAYNEAEPILNNIEDRCKNINQDKDAVEKIKTLLDALKDIQ<br>HFAKLLLCDNDETEIDAEFYNKLHDIWVKLDKITPIYNMVRNYVTKKPYSEEKIKLNFEK<br>STLLGGWDLNKEKNNLSVILRKDNLYYLGIMKKDNNKIFDSTNIKTDGVCFEKMEYKL<br>LPDPKKMLPKVFFSKKCSKDFNPNDKILEIKENESFKKTSSNFNIEQCRKLIDFYKESIN<br>KHKDWQKFNFQFSDTKTYNDINEFYNEVEKQGYKISFCKISEDYINELVKDNKLYLFKI<br>WNKDFSKYSKGTPNTHTLYWKQIFAPENINNVVYKLNGQAEIFFRQASISQKNVIKHL<br>ANKPVKNKNIKNEKKESTFSYDLVKDKRFTMDKFHFHVPITINFKAKGINNTNPIVNNLI<br>RQNKIEHIIGIDRGERHLLYLSLIDLKGNIIEQKSLNEIINNYNGNEYKTDYHTLLDDKEK<br>ERKDARLSWNTIENIKELKDGYMSQWVHIISQMIVKYNAIVVLEDLNHGFVRGRQKIEK<br>QVYEKFEHKLIDKLNYYVDKNADSNAVGGLYNALQLTNPFDSFEKLGKQSGCLFYIPA<br>WKTSKIDPVTGFINMFTNLKYESVEKSKKFFSKFDDIRYNKEKNRFEFDVSFDKFDSD<br>FVRITQESKLHWTLCSVGQRIELVKENNGYKPNEINLTDAFKSVFNTNKIEINTAKLNR<br>EIGKINDTAFFKELMRLMKLLLQMRNSKPNSIEKNDDYIISPVADENGVFFDSSKVEDN<br>GNLPKDADANGAYNIARKGLYVIHQIKQSEDDKKIDFKDFNPRWLKFIQQKLYLND | 104 |
| Expression construct (with N-terminal methionine, V5-tag and C-terminal NLS) aa sequence | MGSGKAETNLTELVNLYSLQKTLRFELIPQGKTLENIEKNGILTQDNQRADDYEKVKK<br>LIDEYHKHHIEISLDDCRLEGLEEYKELYEKKDDLKKIQENLRKQIVKSLTENERYKDK<br>RLFSDKLFKEDLPNYLKDREQDKALVKKFEKFTTYFTGFNENRKNMYSSEDKPTSIAY<br>RLIHENLPKFIDNLHIFDKIKETTIKDDFDKIVEKLNKHLKIHIKSFDEIFSIEYFNKTLSQK<br>QIDNYNNIIGGMSFENGTKIQGLNEYINRYNQKQEDKHQKLPCVKTLYKQILSDREKIS<br>WIPEQFDDDKQMAESISNLYNEMLPIIKDDLLPLMANIGDYDLSKIFISNDSALTTISQRI<br>FGAYNVYTLAIIEKLKSDKPKSKRQSESKYLDEIDKNFKNMKSFSIAKLNNAVKGKYDK<br>TIENYIKVFGAFDEEENLLQRLETAYNEAEPILNNIEDRCKNINQDKDAVEKIKTLLDAL<br>KDIQHFAKLLLCDNDETEIDAEFYNKLHDIWVKLDKITPIYNMVRNYVTKKPYSEEKIKL<br>NFEKSTLLGGWDLNKEKNNLSVILRKDNLYYLGIMKKDNNKIFDSTNIKTDGVCFEKM<br>EYKLLPDPKKMLPKVFFSKKCSKDFNPNDKILEIKENESFKKTSSNFNIEQCRKLIDFY<br>KESINKHKDWQKFNFQFSDTKTYNDINEFYNEVEKQGYKISFCKISEDYINELVKDNKL<br>YLFKIWNKDFSKYSKGTPNTHTLYWKQIFAPENINNVVYKLNGQAEIFFRQASISQKN<br>VIKHLANKPVKNKNIKNEKKESTFSYDLVKDKRFTMDKFHFHVPITINFKAKGINNTNPI<br>VNNLIRQNKIEHIIGIDRGERHLLYLSLIDLKGNIIEQKSLNEIINNYNGNEYKTDYHTLLD<br>DKEKERKDARLSWNTIENIKELKDGYMSQVVHIISQMIVKYNAIVVLEDLNHGFVRGR<br>QKIEKQVYEKFEHKLIDKLNYYVDKNADSNAVGGLYNALQLTNPFDSFEKLGKQSGC<br>LFYIPAWKTSKIDPVTGFINMFTNLKYESVEKSKKFFSKFDDIRYNKEKNRFEFDVSFD<br>KFDSDFVRITQESKLHWTLCSVGQRIELVKENNGYKPNEINLTDAFKSVENTNKIEINT<br>AKLNREIGKINDTAFFKELMRLMKLLLQMRNSKPNSIEKNDDYIISPVADENGVFFDSS<br>KVEDNGNLPKDADANGAYNIARKGLYVIHQIKQSEDDKKIDFKDFNPRWLKFIQQKLY<br>LNDSRKRTADGSEFESPKKKRKVGSGKPIPNPLLGLDST | 105 |
| Wildtype coding sequence (with N-terminal methionine and stop codon) | ATGAAAGCAGAAACAAATCTGACAGAATTAGTGAATCTGTATTCATTGCAGAAAAC<br>ACTTCGTTTTGAATTAATCCCACAGGGCAAAACATTAGAAAACATTGAGAAAAATG<br>GTATTCTTACACAAGATAACCAAAGAGCAGACGATTACGAAAAAGTCAAAAAACTT<br>ATTGATGAGTATCATAAGCACCATATTGAAATAAGTCTTGACGATTGTCGCCTTGA<br>AGGTTTAGAGGAATATAAAGAACTCTACGAAAAGAAAGATGATTTGAAAAAAATTC<br>AAGAGAATCTACGAAAACAAATCGTTAAAAGTTTAACGGAGAACGAAAGGTATAA<br>AGACAAACGTCTATTCTCTGATAAACTCTTCAAAGAAGATCTTCCGAATTATCTAA<br>AAGATAGAGAACAAGACAAAGCTCTTGTTAAAAAATTTGAAAAATTCACCACATAT<br>TTTACTGGATTTAACGAAAACAGAAAAAATATGTATTCTTCCGAAGACAAACCTAC<br>CTCAATTGCTTATAGATTAATCCATGAAAATTTACCTAAGTTTATAGACAATTTACA<br>TATTTTTGATAAAATTAAAGAAACAACAATCAAAGATGATTTTGATAAGATTGTTGA<br>AAAATTAAACAAGCATCTAAAAATTCATATCAAATCATTTGACGAAATTTTCTCTAT<br>TGAATATTTCAATAAAACTCTTAGCCAAAAACAAATAGACAATTATAACAATATAAT<br>TGGAGGAATGTCTTTTGAGAATGGTACAAAGATACAAGGCTTAAACGAATATATTA<br>ATCGTTACAATCAAAAGCAGGAAGATAAACATCAAAAACTTCCTTGCGTCAAAACA<br>CTTTATAAGCAAATACTCAGTGATAGAGAAAAAATATCGTGGATTCCAGAACAATT<br>TGATGATGATAAACAAATGGCAGAAAGTATTTCGAATTTGTACAATGAAATGCTTC<br>CAATTATTAAAGATGATCTACTTCCGCTAATGGCTAATATAGGCGATTATGATCTT<br>AGCAAAATATTTATCTCCAACGACTCTGCTTTAACAACAATATCTCAACGAATTTTT<br>GGAGCTTACAACGTTTACACTCTTGCAATAATAGAAAAATTAAAAAGTGATAAACC<br>TAAATCAAAAAGACAATCCGAGTCTAAGTATTTAGACGAAATTGACAAAAACTTCA<br>AAAATATGAAAAGTTTCAGTATTGCAAAACTAAACAATGCCGTAAAAGGCAAATAC<br>GATAAAACAATAGAAAATTATATCAAGGTTTTCGGGGCTTTTGACGAAGAAGAGAA<br>CTTGCTACAACGATTAGAAACAGCCTATAACGAAGCTGAGCCTATACTTAATAATA<br>TAGAAGACAGATGCAAAAATATTAATCAAGACAAAGATGCTGTTGAAAAGATTAAA<br>ACATTATTAGATGCTTTGAAAGATATTCAACATTTTGCAAAACTTCTATTATGTGAT<br>AACGACGAAACTGAAATAGATGCGGAGTTTTATAATAAATTACATGATATATGGGT<br>AAAATTGGACAAGATAACACCTATATATAATATGGTGAGAAATTATGTTACAAAGA<br>AACCTTATTCAGAAGAAAAAATCAAATTGAATTTTGAAAAATCTACACTATTAGGC | 106 |

TABLE 1R-continued

ZWPU Type V Cas Sequences

| Name | Sequence | SEQ ID NO. |
| --- | --- | --- |
| | GGCTGGGATTTGAACAAAGAAAAAAATAATTTATCAGTTATACTCCGCAAAGATAA<br>TTTGTATTACTTAGGGATTATGAAAAAAGATAATAACAAAATCTTTGATAGTACAAA<br>TATCAAAACCGATGGCGTTTGTTTTGAGAAAATGGAATACAAACTACTTCCTGATC<br>CAAAGAAAATGCTGCCAAAGGTATTCTTTTCAAAAAAATGTTCAAAGGACTTTAAC<br>CCGAACGACAAAATATTAGAAATTAAGGAAAATGAAAGTTTCAAGAAAACAAGCA<br>GTAATTTCAATATTGAGCAATGTCGTAAATTAATAGACTTCTATAAAGAATCTATCA<br>ATAAACATAAAGATTGGCAAAAATTTAATTTCCAATTCTCTGACACTAAAACTTACA<br>ATGACATAAACGAATTTTACAACGAAGTTGAAAAACAAGGTTATAAAATATCTTTTT<br>GTAAAATTTCTGAGGATTATATAAATGAGTTGGTGAAAGACAATAAACTTTATTTGT<br>TTAAGATTTGGAACAAAGACTTTTCAAAATATAGCAAAGGAACTCCAAATACGCAC<br>ACTCTTTATTGGAAACAAATATTTGCACCTGAAAATATCAACAATGTCGTATATAAA<br>CTAAACGGACAAGCCGAAATATTTTTTAGGCAAGCAAGTATTTCTCAAAAAAACGT<br>TATCAAACATTTGGCAAACAAACCTGTTAAAAACAAGAATATAAAAAACGAAAAAA<br>AGGAAAGTACGTTCAGTTATGATTTAGTAAAAGATAAACGTTTTACTATGGATAAA<br>TTCCATTTCCACGTACCGATTACTATTAATTTCAAGGCAAAAGGAATAAATAATAC<br>CAATCCTATTGTCAATAATCTAATTCGTCAAAACAAGATAGAACATATTATTGGTAT<br>AGATAGAGGCGAAAGGCATTTGCTTTATCTTTCTCTTATAGATTTGAAAGGAAATA<br>TCATTGAACAAAAGTCGTTGAATGAAATCATAAACAACTACAATGGCAATGAATAT<br>AAAACAGATTACCATACCTTGCTTGATGATAAGGAAAAAGAAAGAAAAGATGCCC<br>GACTTTCGTGGAATACTATTGAAAATATCAAAGAACTCAAAGACGGGTATATGAG<br>CCAAGTTGTGCATATTATCTCACAAATGATTGTGAAGTACAATGCAATAGTTGTTT<br>TGGAAGACCTTAATCATGGCTTTGTTCGTGGTCGCCAGAAGATAGAAAAACAAGT<br>TTATGAAAAATTTGAGCATAAACTTATTGATAAACTAAACTATTATGTCGATAAGAA<br>TGCCGATAGCAATGCCGTTGGAGGACTTTACAATGCTTTGCAACTAACAAATCCA<br>TTTGATAGTTTTGAAAAATTAGGAAAACAAAGCGGCTGTTTATTCTATATCCCTGC<br>TTGGAAAACAAGTAAGATTGATCCCGTTACTGGATTTATTAATATGTTTACAAATCT<br>CAAATACGAATCAGTGGAAAAATCAAAGAAGTTCTTTTCAAAGTTTGACGATATTA<br>GATACAATAAAGAAAAAAATAGGTTTGAATTTGATGTTTCATTTGATAAATTCGATA<br>GTGATTTTGTCCGTATTACACAGGAAAGTAAATTACATTGGACGCTTTGCAGTGTT<br>GGTCAGCGTATAGAATTAGTAAAAGAGAATAATGGTTATAAACCTAATGAAATAAA<br>TTTAACTGATGCTTTCAAATCAGTGTTTAATACTAATAAAATAGAGATAAACACTGC<br>TAAACTGAATAGAGAGATTGGTAAAATCAATGATACAGCGTTTTTCAAGGAACTTA<br>TGCGTTTAATGAAATTGTTATTACAAATGAGAAATAGTAAGCCAAATTCAATAGAG<br>AAGAACGACGATTATATTATCTCTCCTGTTGCAGACGAAAATGGAGTATTCTTTGA<br>CAGCAGTAAAGTTGAAGACAATGGCAATTTGCCAAAAGATGCCGATGCCAACGG<br>AGCATACAATATTGCTCGCAAAGGCTTGTATGTAATACACCAAATAAAGCAAAGC<br>GAAGATGATAAAAAAATCGATTTCAAAGATTTCAACCCACGTTGGTTAAAATTCAT<br>TCAGCAAAAACTATATTTGAATGATTGA | |
| Codon optimized coding sequence (no N-terminal methionine, no stop codon) | AAGGCCGAGACAAACCTGACAGAACTCGTGAACCTGTACAGCCTGCAAAAAACC<br>CTGAGATTTGAGCTCATCCCCCAGGGCAAGACCCTTGAGAACATCGAGAAGAAC<br>GGTATCCTGACCCAGGACAATCAGAGAGCCGACGACTACGAGAAGGTGAAAAAA<br>CTGATCGACGAGTACCACAAGCACCACATCGAGATCAGCCTGGACGATTGCAGA<br>CTGGAAGGCCTGGAAGAATACAAGGAACTGTATGAGAAGAAGGATGACCTAAAG<br>AAAATCCAGGAAAACCTGAGAAAGCAGATCGTGAAGTCCCTCACTGAGAACGAA<br>CGGTACAAGGACAAAAGACTCTTCTCAGATAAGCTGTTCAAGGAAGATCTGCCTA<br>ATTACCTGAAGGACAGAGAACAGGACAAGGCCCTGGTAAAAAAGTTCGAGAAGT<br>TCACCACCTACTTCACCGGCTTCAACGAAAACCGCAAAAACATGTACAGCAGCGA<br>GGATAAGCCCACCAGCATCGCTTATAGACTGATCCACGAGAACCTGCCTAAGTTC<br>ATCGACAACCTGCACATCTTTGATAAGATCAAGGAAACCACCATCAAGGACGATT<br>TCGATAAGATCGTGGAAAAGCTGAATAAACACCTGAAGATCCACATCAAATCCTT<br>CGACGAGATCTTTTCTATTGAATACTTCAACAAGACACTGAGTCAAAAGCAAATCG<br>ACAACTACAACAACATCATCGGCGGAATGAGCTTCGAGAATGGCACCAAGATCCA<br>GGGCCTGAATGAGTACATCAACAGATACAACCAGAAACAAGAGGACAAGCATCA<br>AAAGCTGCCTTGCGTGAAAACCCTGTACAAGCAGATCCTGAGCGACAGAGAGAA<br>GATTTCCTGGATTCCTGAACAGTTCGATGACGACAAACAGATGGCCGAGAGCATC<br>AGCAATCTGTACAACGAGATGCTGCCAATCATCAAGGACGACCTGCTGCCTCTGA<br>TGGCCAACATTGGCGACTACGACCTGAGCAAAATCTTCATCAGCAATGACAGCG<br>CCCTGACAACCATCTCGCAGCGGATCTTCGGAGCTTACAACGTGTACACCCTGG<br>CCATCATTGAGAAGCTGAAGTCTGATAAGCCTAAGAGCAAGCGGCAGTCTGAGT<br>CTAAGTACCTGGACGAGATCGACAAGAACTTCAAGAACATGAAGTCTTTTAGCAT<br>CGCCAAGCTGAACAACGCCGTGAAGGGCAAGTATGACAAGACAATCGAAAATTA<br>CATCAAGGTGTTTGGCGCCTTTGATGAGGAGGAGAATCTCCTGCAGAGGCTGGA<br>AACAGCCTATAACGAGGCCGAGCCTATCCTGAACAACATCGAGGACAGATGCAA<br>AAACATCAATCAAGACAAGGATGCCGTGGAAAAGATCAAGACCTTACTGGACGCT<br>CTGAAAGATATCCAGCACTTTGCCAAGTTACTGCTGTGCGACAATGACGAAACCG<br>AGATTGACGCCGAGTTCTACAACAAGCTGCACGACATCTGGGTGAAGCTGGACA<br>AAATCACACCAATCTACAACATGGTGCGGAACTACGTGACCAAGAAGCCCTACTC<br>TGAAGAGAAAATCAAGCTGAACTTCGAAAAGTCTACACTGCTGGGCGGCTGGGA<br>TCTGAACAAGGAAAAGAACAATCTGAGCGTGATCCTGAGAAAGGACAACCTGTAC<br>TACCTGGGCATCATGAAGAAAGACAACAACAAGATCTTCGACTCCACAAACATCA<br>AGACCGACGGCGTTTGTTTCGAGAAGATGGAATATAAGCTGTTACCTGACCCTAA<br>AAAGATGCTGCCCAAGGTGTTCTTCTCAAAGAAATGCAGCAAGGATTTCAATCCT<br>AACGACAAGATCCTGGAGATCAAAGAGAACGAATCTTTCAAGAAAACCTCTAGCA | 107 |

TABLE 1R-continued

| ZWPU Type V Cas Sequences | | |
|---|---|---|
| Name | Sequence | SEQ ID NO. |
| | ACTTTAATATCGAGCAGTGCAGAAAACTGATCGACTTTTACAAGGAGTCCATCAAT<br>AAGCACAAAGACTGGCAGAAATTCAACTTTCAGTTCAGCGATACCAAGACCTACA<br>ACGATATCAACGAGTTCTACAACGAGGTGGAAAAACAGGGCTACAAAATTAGCTT<br>CTGCAAGATCAGCGAGGACTACATCAATGAGCTGGTTAAGGACAACAAACTGTAC<br>CTGTTTAAGATCTGGAACAAGGATTTCAGTAAGTACAGCAAGGGGACCCCTAACA<br>CCCACACCCTGTACTGGAAGCAGATCTTCGCCCCTGAGAACATCAACAACGTCG<br>TGTACAAGCTGAACGGACAGGCCGAGATCTTCTTCAGACAAGCATCTATCTCCCA<br>GAAGAACGTCATCAAGCACCTAGCTAATAAGCCAGTGAAAAACAAGAACATCAAG<br>AACGAGAAGAAGGAGAGCACCTTCAGCTACGATCTTGTTAAGGACAAGCGGTTTA<br>CAATGGACAAGTTCCACTTCCACGTGCCAATCACCATAAACTTTAAGGCCAAGGG<br>CATCAACAACACCAATCCTATTGTCAACAACCTGATCCGGCAGAACAAGATTGAA<br>CACATCATCGGCATCGACAGAGGCGAGAGACACCTGCTGTATCTGAGCCTGATC<br>GATCTGAAGGGCAACATCATAGAACAGAAGAGCCTGAACGAGATCATCAACAATT<br>ACAACGGCAATGAGTACAAGACCGATTACCATACCTTGCTGGATGACAAGGAAAA<br>GGAGAGAAAGGATGCTAGACTGAGCTGGAACACCATCGAAAATATCAAGGAACT<br>GAAAGATGGCTACATGAGCCAGGTGGTGCACATCATCAGTCAGATGATCGTGAA<br>ATACAACGCCATTGTGGTCCTGGAGGATCTCAACCACGGCTTCGTGCGGGGCAG<br>ACAGAAGATCGAGAAGCAGGTGTATGAAAAATTTGAACACAAGCTGATCGACAAG<br>CTGAATTACTACGTGGACAAGAATGCTGACAGCAACGCCGTGGGAGGACTGTAC<br>AATGCCCTGCAGCTGACAAACCCCTTCGACAGCTTCGAGAAGCTGGGCAAGCAG<br>AGCGGCTGTCTGTTTTACATCCCCGCCTGGAAAACAAGTAAGATCGATCCTGTGA<br>CCGGATTCATCAACATGTTCACCAACCTGAAGTACGAATCTGTGGAAAAGAGCAA<br>AAAGTTCTTCAGCAAGTTCGATGACATCAGATACAACAAGGAGAAAAACCGATTC<br>GAGTTCGACGTGTCCTTCGACAAGTTCGACTCCGACTTCGTGCGGATCACCCAG<br>GAGAGCAAACTGCATTGGACCTTGTGTAGCGTGGGCCAGAGAATCGAACTGGTC<br>AAGGAAAACAACGGATACAAGCCTAACGAAATCAACCTGACAGATGCTTTCAAGA<br>GCGTGTTCAACACAAACAAGATCGAGATCAACACCGCCAAACTGAATCGGGAAAT<br>CGGAAAAATCAACGACACAGCTTTCTTCAAGGAACTGATGCGGCTGATGAAGCTG<br>CTCCTGCAGATGAGAAACAGCAAGCCCAACTCCATCGAAAAGAACGATGATTACA<br>TCATCAGCCCTGTGGCCGATGAGAACGGCGTGTTCTTTGACAGCAGCAAAGTGG<br>AGGACAATGGCAACCTGCCAAAGGACGCCGATGCCAACGGCGCCTACAACATCG<br>CCAGGAAGGGCCTGTATGTGATCCACCAGATTAAGCAGTCTGAGGACGACAAGA<br>AGATCGACTTTAAGGACTTCAACCCCAGATGGCTGAAGTTCATCCAGCAGAAGCT<br>GTACCTGAACGAT | |
| Expression construct (with N-terminal methionine and stop codon, includes V5-tag and C-terminal NLS) | ATGggctccggaAAGGCCGAGACAAACCTGACAGAACTCGTGAACCTGTACAGCCTG<br>CAAAAAACCCTGAGATTTGAGCTCATCCCCCAGGGCAAGACCCTTGAGAACATC<br>GAGAAGAACGGTATCCTGACCCAGGACAATCAGAGAGCCGACGACTACGAGAAG<br>GTGAAAAAACTGATCGACGAGTACCACAAGCACCACATCGAGATCAGCCTGGAC<br>GATTGCAGACTGGAAGGCCTGGAAGAATACAAGGAACTGTATGAGAAGAAGGAT<br>GACCTAAAGAAAATCCAGGAAAACCTGAGAAAGCAGATCGTGAAGTCCCTCACTG<br>AGAACGAACGGTACAAGGACAAAAGACTCTTCTCAGATAAGCTGTTCAAGGAAGA<br>TCTGCCTAATTACCTGAAGGACAGAGAACAGGACAAGGCCCTGGTAAAAAAGTTC<br>GAGAAGTTCACCACCTACTTCACCGGCTTCAACGAAAACCGCAAAAACATGTACA<br>GCAGCGAGGATAAGCCCACCAGCATCGCTTATAGACTGATCCACGAGAACCTGC<br>CTAAGTTCATCGACAACCTGCACATCTTTGATAAGATCAAGGAAACCACCATCAA<br>GGACGATTTCGATAAGATCGTGGAAAAGCTGAATAAACACCTGAAGATCCACATC<br>AAATCCTTCGACGAGATCTTTTCTATTGAATACTTCAACAAGACACTGAGTCAAAA<br>GCAAATCGACAACTACAACAACATCATCGGCGGAATGAGCTTCGAGAATGGCAC<br>CAAGATCCAGGGCCTGAATGAGTACATCAACAGATACAACCAGAAACAAGAGGA<br>CAAGCATCAAAAGCTGCCTTGCGTGAAAACCCTGTACAAGCAGATCCTGAGCGA<br>CAGAGAGAAGATTTCCTGGATTCCTGAACAGTTCGATGACGACAAACAGATGGCC<br>GAGAGCATCAGCAATCTGTACAACGAGATGCTGCCAATCATCAAGGACGACCTG<br>CTGCCTCTGATGGCCAACATTGGCGACTACGACCTGAGCAAAATCTTCATCAGCA<br>ATGACAGCGCCCTGACAACCATCTCGCAGCGGATCTTCGGAGCTTACAACGTGT<br>ACACCCTGGCCATCATTGAGAAGCTGAAGTCTGATAAGCCTAAGAGCAAGCGGC<br>AGTCTGAGTCTAAGTACCTGGACGAGATCGACAAGAACTTCAAGAACATGAAGTC<br>TTTTAGCATCGCCAAGCTGAACAACGCCGTGAAGGGCAAGTATGACAAGACAATC<br>GAAAATTACATCAAGGTGTTTGGCGCCTTTGATGAGGAGGAGAATCTCCTGCAGA<br>GGCTGGAAACAGCCTATAACGAGGCCGAGCCTATCCTGAACAACATCGAGGACA<br>GATGCAAAAACATCAATCAAGACAAGGATGCCGTGGAAAAGATCAAGACCTTACT<br>GGACGCTCTGAAAGATATCCAGCACTTTGCCAAGTTACTGCTGTGCGACAATGAC<br>GAAACCGAGATTGACGCCGAGTTCTACAACAAGCTGCACGACATCTGGGTGAAG<br>CTGGACAAAATCACACCAATCTACAACATGGTGCGGAACTACGTGACCAAGAAGC<br>CCTACTCTGAAGAGAAAATCAAGCTGAACTTCGAAAAGTCTACACTGCTGGGCGG<br>CTGGGATCTGAACAAGGAAAAGAACAATCTGAGCGTGATCCTGAGAAAGGACAA<br>CCTGTACTACCTGGGCATCATGAAGAAAGACAACAACAAGATCTTCGACTCCACA<br>AACATCAAGACCGACGGCGTTTGTTTCGAGAAGATGGAATATAAGCTGTTACCTG<br>ACCCTAAAAAGATGCTGCCCAAGGTGTTCTTCTCAAAGAAATGCAGCAAGGATTT<br>CAATCCTAACGACAAGATCCTGGAGATCAAAGAGAACGAATCTTTCAAGAAAACC<br>TCTAGCAACTTTAATATCGAGCAGTGCAGAAAACTGATCGACTTTTACAAGGAGT<br>CCATCAATAAGCACAAAGACTGGCAGAAATTCAACTTTCAGTTCAGCGATACCAA<br>GACCTACAACGATATCAACGAGTTCTACAACGAGGTGGAAAAACAGGGCTACAAA<br>ATTAGCTTCTGCAAGATCAGCGAGGACTACATCAATGAGCTGGTTAAGGACAACA | 108 |

TABLE 1R-continued

| ZWPU Type V Cas Sequences | | |
|---|---|---|
| Name | Sequence | SEQ ID NO. |
| | AACTGTACCTGTTTAAGATCTGGAACAAGGATTTCAGTAAGTACAGCAAGGGGAC<br>CCCTAACACCCACACCCTGTACTGGAAGCAGATCTTCGCCCCTGAGAACATCAAC<br>AACGTCGTGTACAAGCTGAACGGACAGGCCGAGATCTTCTTCAGACAAGCATCTA<br>TCTCCCAGAAGAACGTCATCAAGCACCTAGCTAATAAGCCAGTGAAAAACAAGAA<br>CATCAAGAACGAGAAGAAGGAGAGCACCTTCAGCTACGATCTTGTTAAGGACAA<br>GCGGTTTACAATGGACAAGTTCCACTTCCACGTGCCAATCACCATAAACTTTAAG<br>GCCAAGGGCATCAACAACACCAATCCTATTGTCAACAACCTGATCCGGCAGAACA<br>AGATTGAACACATCATCGGCATCGACAGAGGCGAGAGACACCTGCTGTATCTGA<br>GCCTGATCGATCTGAAGGGCAACATCATAGAACAGAAGAGCCTGAACGAGATCA<br>TCAACAATTACAACGGCAATGAGTACAAGACCGATTACCATACCTTGCTGGATGA<br>CAAGGAAAAGGAGAGAAAGGATGCTAGACTGAGCTGGAACACCATCGAAAATAT<br>CAAGGAACTGAAAGATGGCTACATGAGCCAGGTGGTGCACATCATCAGTCAGAT<br>GATCGTGAAATACAACGCCATTGTGGTCCTGGAGGATCTCAACCACGGCTTCGT<br>GCGGGGCAGACAGAAGATCGAGAAGCAGGTGTATGAAAAATTTGAACACAAGCT<br>GATCGACAAGCTGAATTACTACGTGGACAAGAATGCTGACAGCAACGCCGTGGG<br>AGGACTGTACAATGCCCTGCAGCTGACAAACCCCTTCGACAGCTTCGAGAAGCT<br>GGGCAAGCAGAGCGGCTGTCTGTTTTACATCCCCGCCTGGAAAACAAGTAAGAT<br>CGATCCTGTGACCGGATTCATCAACATGTTCACCAACCTGAAGTACGAATCTGTG<br>GAAAAGAGCAAAAAGTTCTTCAGCAAGTTCGATGACATCAGATACAACAAGGAGA<br>AAAACCGATTCGAGTTCGACGTGTCCTTCGACAAGTTCGACTCCGACTTCGTGCG<br>GATCACCCAGGAGAGCAAACTGCATTGGACCTTGTGTAGCGTGGGCCAGAGAAT<br>CGAACTGGTCAAGGAAAACAACGGATACAAGCCTAACGAAATCAACCTGACAGAT<br>GCTTTCAAGAGCGTGTTCAACACAAACAAGATCGAGATCAACACCGCCAAACTGA<br>ATCGGGAAATCGGAAAAATCAACGACACAGCTTTCTTCAAGGAACTGATGCGGCT<br>GATGAAGCTGCTCCTGCAGATGAGAAACAGCAAGCCCAACTCCATCGAAAAGAA<br>CGATGATTACATCATCAGCCCTGTGGCCGATGAGAACGGCGTGTTCTTTGACAG<br>CAGCAAAGTGGAGGACAATGGCAACCTGCCAAAGGACGCCGATGCCAACGGCG<br>CCTACAACATCGCCAGGAAGGGCCTGTATGTGATCCACCAGATTAAGCAGTCTG<br>AGGACGACAAGAAGATCGACTTTAAGGACTTCAACCCCAGATGGCTGAAGTTCAT<br>CCAGCAGAAGCTGTACCTGAACGATtctagaAAGCGGACAGCAGACGGCTCCGAAT<br>TTGAAAGCCCTAAGAAAAAGAGAAAGGTGggatccGGCAAACCTATCCCCAATCCC<br>CTGCTGGGCCTGGACAGCACCTGA | |

In some embodiments a ZWPU Type V Cas protein comprises an amino acid sequence of SEQ ID NO:103, SEQ ID NO:104, or SEQ ID NO:105. In some embodiments, a ZWPU Type V Cas protein has nickase activity, for example resulting from one or more amino acid substitutions relative to the sequence of SEQ ID NO:103, SEQ ID NO:104, or SEQ ID NO:105. In some embodiments, the one or more amino acid substitutions providing nickase activity comprise a D845 substitution, wherein the position of the D845 substitution is defined with respect to the amino acid numbering of SEQ ID NO:104 (corresponding to amino acid 908 of SEQ ID NO:121). In some embodiments, the one or more amino acid substitutions providing nickase activity comprise an E938 substitution, wherein the position of the E938 substitution is defined with respect to the amino acid numbering of SEQ ID NO:104 (corresponding to amino acid 993 of SEQ ID NO:121). In some embodiments, the one or more amino acid substitutions providing nickase activity comprise a R1153 substitution, wherein the position of the R1153 substitution is defined with respect to the amino acid numbering of SEQ ID NO:104 (corresponding to amino acid 1226 of SEQ ID NO:121). In some embodiments, the one or more amino acid substitutions providing nickase activity comprise a D1195 substitution, wherein the position of the D1195 substitution is defined with respect to the amino acid numbering of SEQ ID NO:104 (corresponding to amino acid 1263 of SEQ ID NO:121). In some embodiments, a ZWPU Type V Cas protein is catalytically inactive, for example due to a R1153 substitution in combination with a D845 substitution, a E938 substitution, and/or D1195 substitution.

6.2.19. ZZQE Type V Cas Protein

In one aspect, the disclosure provides ZZQE Type V Cas proteins. ZZQE Type V Cas proteins can be further classified as Type V-A Cas proteins. The ZZQE Type V Cas proteins typically comprise an amino acid sequence that is at least 50%, at least 55%, at least 60%, at least 65%, at least 70%, at least 75%, at least 85%, at least 90%, or at least 95% identical to SEQ ID NO:109. In some embodiments, the ZZQE Type V Cas proteins comprise an amino acid sequence that is at least 95%, at least 96%, at least 97%, at least 98%, or at least 99% identical to SEQ ID NO:109. In some embodiments, a ZZQE Type V Cas protein comprises an amino acid sequence that is identical to SEQ ID NO:109.

Exemplary ZZQE Type V Cas protein sequences and nucleotide sequences encoding exemplary ZZQE Type V Cas proteins are set forth in Table 1S.

TABLE 1S

| ZZQE Type V Cas Sequences | | |
|---|---|---|
| Name | Sequence | SEQ ID NO. |
| Wildtype amino acid | DMKSLNSFQNQYSLSKTLRFQLIPQGKTLDNINESRILEEDQHRSESYKLVKKIIDDYH<br>KAYIEQALGSFELKIASDSKNDSLEEFYSQYIAERKEDKAKKLFEKTQDNLRKQISKKL | 109 |

TABLE 1S-continued

ZZQE Type V Cas Sequences

| Name | Sequence | SEQ ID NO. |
| --- | --- | --- |
| sequence (without N-terminal methionine) | KQGEAYKRLFGKELIQEDLLEFVATDPEADSKKRLIEEFKDFTTYFIGFHENRKNMYA<br>EEAQSTAIAYRIIHENLPKFIDNIRTFEELAKSSIADVLPQVYEDFKAYLKVESVKELFSL<br>DYFNTVLTQKQLDIYNAVIGGKSLDENSRIQGLNEYINLYNQQHKDKKLPFLKPLFKQI<br>LSDRNSLSWLPEAFDNDKQVLQAVHDCYTSLLESVFHKDGLQQLLQSLPTYNLKGIY<br>LRNDLSMTNVSQKLLGDWGAITRAVKEKLQKENPAKKRESDEAYQERINKIFKQAGS<br>YSLDYINQALEATDQTNIKVEDYFINMGVDNEQKEPLFQRVAQAYNQASDLLEKEYPA<br>NKNLMQDKESIEHIKFLLDNLKAVQHFIKPLLGDGNEADKDNRFYGELTALWNELDQV<br>TRLYNKVRNYMTRKPYSVDKIKINFKNSTLLNGWDRNKERDNTAVILRKDGKFYLAIM<br>HKEHNKVFEKFPVGTKDSDFEKMEYKLLPGANKMLPKVFFSKSRIDEFKPSAELLQK<br>YQMGTHKKGELFSLNDCHSLIDFFKASIEKHDDWKQFNFHFSPTSSYEDLSGFYREV<br>EQQGYKLTFKSVDADYINKMVDEGKIFLFQIYNKDFSEHSKGTPNLHTLYWKMLFDE<br>RNLQNVVYKLNGEAEVFFRKKSLTYTRPTHPKKEPIKNKNVQNAKKESIFDYDLIKNK<br>RFTVDSFQFHVPITMNFKSEGRSNLNERVNEFLRQNNDAHIIGIDRGERHLLYLVVIDR<br>HGNIVEQFSLNSIINEYQGNTYATNYHDLLDKREKEREEARESWQSIENIKELKEGYL<br>SQVVHKIADLMVKYHAIVVLEDLNMGFMRGRQKVEKQVYQKFEKMLIDKLNYLVDKK<br>QDAETDGGLLKAYQLTNQFESFQKLGKQSGFLFYVPAWNTSKIDPCTGFTNLLDTRY<br>ESIEKAKKFFQTFNAIRYNAAQGYFEFELDYNKFNKRADGTQTLWTLCTYGPRIETLR<br>STEDNNKWTSKEVDLTDELKKHFYHYGIKLDADLKEAIGQQTDKPFFTNLLHLLKLTL<br>QMRNSKIGTEVDYLISPIRNEDGTFYDSRQGNKSLPANADANGAYNIARKGLWVINQI<br>KQTPQDQKPKLAITNKEWLQFAQEKPYLKD | |
| Wildtype amino acid sequence (with N-terminal methionine) | MDMKSLNSFQNQYSLSKTLRFQLIPQGKTLDNINESRILEEDQHRSESYKLVKKIIDDY<br>HKAYIEQALGSFELKIASDSKNDSLEEFYSQYIAERKEDKAKKLFEKTQDNLRKQISKK<br>LKQGEAYKRLFGKELIQEDLLEFVATDPEADSKKRLIEEFKDFTTYFIGFHENRKNMYA<br>EEAQSTAIAYRIIHENLPKFIDNIRTFEELAKSSIADVLPQVYEDFKAYLKVESVKELFSL<br>DYFNTVLTQKQLDIYNAVIGGKSLDENSRIQGLNEYINLYNQQHKDKKLPFLKPLFKQI<br>LSDRNSLSWLPEAFDNDKQVLQAVHDCYTSLLESVFHKDGLQQLLQSLPTYNLKGIY<br>LRNDLSMTNVSQKLLGDWGAITRAVKEKLQKENPAKKRESDEAYQERINKIFKQAGS<br>YSLDYINQALEATDQTNIKVEDYFINMGVDNEQKEPLFQRVAQAYNQASDLLEKEYPA<br>NKNLMQDKESIEHIKFLLDNLKAVQHFIKPLLGDGNEADKDNRFYGELTALWNELDQV<br>TRLYNKVRNYMTRKPYSVDKIKINFKNSTLLNGWDRNKERDNTAVILRKDGKFYLAIM<br>HKEHNKVFEKFPVGTKDSDFEKMEYKLLPGANKMLPKVFFSKSRIDEFKPSAELLQK<br>YQMGTHKKGELFSLNDCHSLIDFFKASIEKHDDWKQFNFHFSPTSSYEDLSGFYREV<br>EQQGYKLTFKSVDADYINKMVDEGKIFLFQIYNKDFSEHSKGTPNLHTLYWKMLFDE<br>RNLQNVVYKLNGEAEVFFRKKSLTYTRPTHPKKEPIKNKNVQNAKKESIFDYDLIKNK<br>RFTVDSFQFHVPITMNFKSEGRSNLNERVNEFLRQNNDAHIIGIDRGERHLLYLVVIDR<br>HGNIVEQFSLNSIINEYQGNTYATNYHDLLDKREKEREEARESWQSIENIKELKEGYL<br>SQVVHKIADLMVKYHAIVVLEDLNMGFMRGRQKVEKQVYQKFEKMLIDKLNYLVDKK<br>QDAETDGGLLKAYQLTNQFESFQKLGKQSGFLFYVPAWNTSKIDPCTGFTNLLDTRY<br>ESIEKAKKFFQTFNAIRYNAAQGYFEFELDYNKFNKRADGTQTLWTLCTYGPRIETLR<br>STEDNNKWTSKEVDLTDELKKHFYHYGIKLDADLKEAIGQQTDKPFFTNLLHLLKLTL<br>QMRNSKIGTEVDYLISPIRNEDGTFYDSRQGNKSLPANADANGAYNIARKGLWVINQI<br>KQTPQDQKPKLAITNKEWLQFAQEKPYLKD | 110 |
| Expression construct (with N-terminal methionine, V5-tag and C-terminal NLS) aa sequence | MGSGDMKSLNSFQNQYSLSKTLRFQLIPQGKTLDNINESRILEEDQHRSESYKLVKKII<br>DDYHKAYIEQALGSFELKIASDSKNDSLEEFYSQYIAERKEDKAKKLFEKTQDNLRKQI<br>SKKLKQGEAYKRLFGKELIQEDLLEFVATDPEADSKKRLIEEFKDFTTYFIGFHENRKN<br>MYAEEAQSTAIAYRIIHENLPKFIDNIRTFEELAKSSIADVLPQVYEDFKAYLKVESVKE<br>LFSLDYFNTVLTQKQLDIYNAVIGGKSLDENSRIQGLNEYINLYNQQHKDKKLPFLKPL<br>FKQILSDRNSLSWLPEAFDNDKQVLQAVHDCYTSLLESVFHKDGLQQLLQSLPTYNL<br>KGIYLRNDLSMTNVSQKLLGDWGAITRAVKEKLQKENPAKKRESDEAYQERINKIFKQ<br>AGSYSLDYINQALEATDQTNIKVEDYFINMGVDNEQKEPLFQRVAQAYNQASDLLEK<br>EYPANKNLMQDKESIEHIKFLLDNLKAVQHFIKPLLGDGNEADKDNRFYGELTALWNE<br>LDQVTRLYNKVRNYMTRKPYSVDKIKINFKNSTLLNGWDRNKERDNTAVILRKDGKF<br>YLAIMHKEHNKVFEKFPVGTKDSDFEKMEYKLLPGANKMLPKVFFSKSRIDEFKPSAE<br>LLQKYQMGTHKKGELFSLNDCHSLIDFFKASIEKHDDWKQFNFHFSPTSSYEDLSGF<br>YREVEQQGYKLTFKSVDADYINKMVDEGKIFLFQIYNKDFSEHSKGTPNLHTLYWKM<br>LFDERNLQNVVYKLNGEAEVFFRKKSLTYTRPTHPKKEPIKNKNVQNAKKESIFDYDLI<br>KNKRFTVDSFQFHVPITMNFKSEGRSNLNERVNEFLRQNNDAHIIGIDRGERHLLYLV<br>VIDRHGNIVEQFSLNSIINEYQGNTYATNYHDLLDKREKEREEARESWQSIENIKELKE<br>GYLSQVVHKIADLMVKYHAIVVLEDLNMGFMRGRQKVEKQVYQKFEKMLIDKLNYLV<br>DKKQDAETDGGLLKAYQLTNQFESFQKLGKQSGFLFYVPAWNTSKIDPCTGFTNLLD<br>TRYESIEKAKKFFQTFNAIRYNAAQGYFEFELDYNKFNKRADGTQTLWTLCTYGPRIE<br>TLRSTEDNNKWTSKEVDLTDELKKHFYHYGIKLDADLKEAIGQQTDKPFFTNLLHLLK<br>LTLQMRNSKIGTEVDYLISPIRNEDGTFYDSRQGNKSLPANADANGAYNIARKGLWVI<br>NQIKQTPQDQKPKLAITNKEWLQFAQEKPYLKDSRKRTADGSEFESPKKKRKVGSG<br>KPIPNPLLGLDST | 111 |
| Wildtype coding sequence (with N-terminal | ATGGATATGAAAAGTTTAAACAGCTTTCAGAACCAGTATTCCCTATCCAAGACCCT<br>CCGGTTTCAGCTAATACCCCAGGGTAAAACTTTGGATAACATTAACGAGAGCAGA<br>ATATTGGAGGAAGACCAACACCGAAGCGAAAGCTACAAGTTGGTCAAGAAAATCA<br>TTGACGACTATCACAAGGCCTACATCGAACAAGCCCTGGGCAGTTTCGAACTCAA | 112 |

TABLE 1S-continued

| ZZQE Type V Cas Sequences | | |
|---|---|---|
| Name | Sequence | SEQ ID NO. |
| methionine and stop codon) | AATTGCCAGTGACTCTAAAAACGATTCGTTAGAGGAGTTCTACTCGCAGTATATTG<br>CCGAACGGAAAGAAGATAAAGCCAAAAAACTTTTCGAAAAGACGCAAGACAACTT<br>GCGAAAGCAAATCTCCAAGAAATTAAAGCAGGGCGAAGCCTACAAGCGGTTGTTT<br>GGCAAGGAACTCATTCAAGAAGACCTGCTGGAGTTTGTAGCTACCGACCCTGAG<br>GCTGATAGCAAAAAGCGTCTGATTGAAGAATTCAAGGACTTCACCACCTACTTTAT<br>CGGATTCCACGAGAACCGAAAGAACATGTATGCTGAGGAAGCCCAATCCACAGC<br>AATTGCCTACCGCATCATTCACGAGAACCTGCCGAAGTTCATTGATAACATACGC<br>ACCTTCGAAGAACTTGCTAAAAGTTCCATTGCCGACGTCCTGCCACAGGTTTATG<br>AAGATTTCAAAGCGTACTTAAAGGTCGAATCGGTCAAAGAACTTTTCAGTCTGGA<br>CTATTTCAATACCGTCTTGACCCAAAAGCAGCTTGACATTTACAATGCGGTTATCG<br>GCGGTAAGTCGTTAGATGAGAACAGCCGCATCCAGGGGCTCAACGAGTATATCA<br>ACCTGTACAACCAGCAGCACAAGGACAAAAAGTTACCCTTCTTAAAACCCTTGTT<br>CAAGCAAATTCTGAGCGACCGCAACAGCCTTTCGTGGTTGCCCGAAGCTTTCGA<br>CAATGACAAGCAGGTACTTCAGGCTGTACACGACTGCTACACCTCGCTATTGGAG<br>AGCGTATTCCACAAAGACGGCCTGCAACAGTTGCTACAGTCACTGCCTACCTACA<br>ACCTGAAGGGCATTTACCTGCGCAACGACCTTTCCATGACCAACGTTTCTCAAAA<br>ACTATTGGGCGATTGGGGAGCTATTACACGTGCCGTTAAAGAAAAACTACAAAAA<br>GAAAATCCTGCCAAAAAACGAGAGTCGGACGAAGCCTACCAAGAACGCATCAAC<br>AAGATATTCAAGCAAGCCGGCAGCTACTCTTTAGATTACATCAACCAAGCGCTCG<br>AAGCAACAGACCAGACCAATATCAAAGTCGAAGACTACTTCATCAACATGGGCGT<br>AGACAACGAGCAAAAAGAGCCCCTGTTCCAGCGTGTAGCGCAAGCCTACAATCA<br>GGCCAGCGATTTGCTTGAAAAGGAATATCCCGCAAACAAAAATCTGATGCAGGAT<br>AAAGAAAGCATCGAGCACATCAAATTCTTGCTCGATAACCTCAAAGCCGTTCAAC<br>ACTTTATAAAGCCCCTGCTCGGCGATGGTAACGAGGCTGATAAAGATAATCGTTT<br>TTACGGAGAACTTACAGCGCTGTGGAACGAATTAGACCAGGTAACGCGCCTGTA<br>TAACAAGGTGCGAAACTACATGACCCGCAAGCCCTACTCGGTTGATAAAATCAAG<br>ATTAACTTTAAGAACTCAACTCTACTTAATGGCTGGGACAGAAATAAGGAACGTGA<br>CAATACCGCTGTTATTCTGCGCAAAGACGGCAAGTTCTATCTGGCCATTATGCAT<br>AAAGAACACAATAAGGTGTTCGAAAAATTCCCGGTCGGAACAAAGGATTCTGACT<br>TCGAGAAAATGGAGTATAAGTTACTTCCGGGCGCCAATAAAATGCTTCCGAAGGT<br>TTTCTTCTCTAAATCGCGTATCGATGAGTTTAAGCCCAGCGCCGAACTTCTCCAAA<br>AGTACCAGATGGGTACCCACAAAAAGGGCGAACTCTTCAGTCTGAACGACTGCC<br>ATTCTCTGATTGACTTCTTTAAGGCTTCTATTGAAAAGCATGACGATTGGAAACAG<br>TTTAACTTCCATTTCTCACCCACTTCGAGCTACGAAGACTTGAGCGGATTTTACAG<br>AGAGGTTGAACAGCAGGGGTACAAACTGACCTTCAAATCCGTTGACGCCGACTA<br>TATCAACAAAATGGTTGACGAGGGCAAAATCTTTCTCTTCCAGATTTACAATAAAG<br>ACTTCTCGGAACATAGCAAAGGCACCCCCAACCTGCATACGCTCTACTGGAAAAT<br>GCTCTTTGACGAACGCAACCTGCAGAACGTGGTCTACAAACTGAACGGCGAGGC<br>CGAAGTCTTCTTCCGGAAGAAGAGTCTTACCTACACCCGTCCTACGCACCCCAAG<br>AAAGAGCCTATCAAGAACAAGAACGTTCAGAATGCCAAAAAGGAAAGCATCTTCG<br>ACTACGACCTGATTAAAAACAAACGCTTTACGGTCGACTCCTTCCAGTTCCACGT<br>TCCCATCACGATGAACTTCAAGAGCGAAGGACGCTCCAACCTGAACGAGCGGGT<br>CAACGAGTTTTTACGCCAGAACAACGATGCCCACATCATTGGCATTGACCGGGG<br>CGAACGCCATTTGCTCTACCTGGTGGTTATTGACCGGCACGGAAACATTGTGGAA<br>CAATTTTCGCTCAACTCTATCATCAACGAATATCAGGGTAATACGTACGCCACCAA<br>CTACCACGACTTGTTGGATAAGCGCGAAAAGGAAAGAGAGGAAGCACGCGAAAG<br>CTGGCAGAGTATTGAGAATATTAAAGAACTGAAAGAAGGATACTTGAGCCAGGTG<br>GTGCATAAAATTGCCGACCTCATGGTAAAGTATCATGCCATCGTGGTGCTCGAAG<br>ACTTGAATATGGGCTTCATGCGCGGACGCCAGAAGGTAGAAAAGCAGGTCTATC<br>AGAAGTTTGAAAAAATGCTGATAGACAAGTTAAACTATCTGGTTGACAAGAAGCAA<br>GATGCCGAAACCGACGGCGGTCTGCTCAAGGCATACCAACTGACCAACCAGTTC<br>GAAAGTTTCCAGAAGTTAGGCAAGCAGAGCGGTTTCCTCTTCTATGTGCCTGCCT<br>GGAACACCAGCAAAATTGACCCCTGCACCGGATTTACCAACCTGCTCGACACTC<br>GATACGAGAGCATCGAAAAGGCCAAAAAGTTCTTTCAAACTTTCAATGCCATCCG<br>CTACAATGCTGCGCAGGGGTACTTTGAGTTCGAACTGGATTACAATAAATTCAAC<br>AAGCGGGCCGATGGTACACAAACCCTATGGACGCTCTGCACCTACGGCCCACGC<br>ATCGAAACACTCCGAAGCACCGAGGATAATAACAAGTGGACAAGCAAAGAGGTT<br>GATTTGACCGACGAATTGAAAAAGCACTTCTACCACTATGGCATTAAGCTGGATG<br>CCGACCTGAAGGAAGCCATCGGCCAACAAACCGACAAACCTTTCTTCACCAACTT<br>GCTCCATCTGCTCAAACTAACACTGCAAATGCGAAACAGCAAAATCGGCACGGA<br>GGTTGACTACCTCATTTCGCCAATTCGCAATGAAGACGGAACGTTCTACGACAGC<br>CGACAAGGCAACAAATCATTGCCTGCCAATGCCGATGCCAATGGTGCCTACAAC<br>ATTGCCCGAAAGGGTTTATGGGTAATTAACCAGATAAAACAAACACCTCAAGACC<br>AAAAGCCCAAGTTAGCTATTACCAACAAGGAATGGCTGCAATTTGCTCAAGAGAA<br>GCCCTACCTTAAGGATTGA | |
| Codon optimized coding sequence (no N-terminal methionine, no stop codon) | GACATGAAGAGCCTGAACTCTTTTCAGAACCAATACTCTCTGAGCAAAACCCTGC<br>GGTTCCAGCTGATCCCTCAGGGCAAGACACTGGATAATATCAACGAGAGCAGAA<br>TCCTGGAAGAGGATCAGCACAGAAGCGAGTCATATAAACTGGTGAAGAAGATCAT<br>TGACGACTATCACAAGGCCTACATCGAGCAGGCCCTGGGCAGCTTCGAGCTGAA<br>AATTGCCTCCGATAGCAAGAACGACAGCCTGGAGGAGTTCTACTCTCAGTACATT<br>GCGGAGAGAAAGGAGGACAAGGCCAAGAAGCTGTTCGAAAAGACCCAGGACAA<br>TCTGAGAAAGCAGATCTCCAAGAAGCTGAAACAGGGTGAAGCCTACAAACGGCT<br>GTTCGGCAAAGAACTGATCCAGGAGGACCTGCTGGAGTTCGTGGCCACAGATCC | 113 |

TABLE 1S-continued

| ZZQE Type V Cas Sequences | | |
|---|---|---|
| Name | Sequence | SEQ ID NO. |
| | TGAGGCCGACTCTAAGAAGAGACTGATCGAAGAGTTCAAGGACTTTACCACCTAC<br>TTCATCGGATTTCACGAAAATAGAAAGAACATGTACGCCGAGGAGGCTCAGAGCA<br>CAGCTATTGCCTACAGAATCATCCACGAGAACCTGCCAAAGTTTATCGATAATATC<br>AGAACCTTCGAGGAACTGGCCAAGAGCAGCATCGCCGACGTGCTGCCCCAGGT<br>CTACGAGGACTTTAAGGCCTACCTGAAGGTGGAAAGCGTGAAAGAACTGTTCTCT<br>CTGGATTATTTCAACACCGTGCTGACACAGAAACAACTGGACATCTACAATGCCG<br>TGATCGGCGGAAAAAGCCTGGACGAGAACAGCAGAATCCAGGGCCTGAACGAG<br>TACATCAACCTCTACAACCAGCAGCATAAGGACAAGAAGCTGCCTTTCCTGAAGC<br>CCCTGTTCAAGCAAATCCTGTCCGATAGAAACAGCCTGTCCTGGCTGCCTGAGG<br>CCTTCGACAACGACAAGCAGGTGCTGCAGGCCGTGCACGACTGCTACACCAGCC<br>TGCTGGAATCTGTGTTCCACAAGGACGGCCTGCAACAGCTGCTGCAGAGCCTCC<br>CAACCTACAACTTAAAAGGCATCTACCTGCGGAACGACCTTAGCATGACCAATGT<br>GTCCCAGAAGCTGCTGGGCGATTGGGGCGCTATCACCAGAGCCGTGAAGGAAA<br>AGCTGCAGAAGGAAAACCCTGCCAAGAAGAGAGAGTCGGACGAGGCCTACCAG<br>GAGCGGATCAACAAGATCTTCAAGCAGGCCGGCTCATATTCACTGGATTACATCA<br>ACCAGGCCCTCGAAGCCACAGACCAGACAAACATCAAAGTGGAGGACTACTTTA<br>TCAACATGGGCGTGGATAATGAGCAGAAAGAGCCTCTGTTTCAAAGGGTGGCCC<br>AGGCCTATAACCAGGCCAGCGACCTGCTGGAAAAAGAATACCCCGCTAACAAGA<br>ATCTGATGCAGGACAAGGAGAGCATCGAGCACATCAAATTCCTGCTCGACAACCT<br>TAAGGCCGTGCAGCACTTCATCAAGCCTCTGCTGGGAGATGGCAACGAAGCCGA<br>CAAGGACAACAGATTCTACGGCGAGCTAACCGCCCTGTGGAACGAACTTGACCA<br>GGTGACCCGCCTGTACAACAAGGTGCGGAATTACATGACCAGGAAGCCTTACAG<br>CGTGGACAAGATCAAAATCAACTTCAAGAACAGCACCCTGCTGAACGGATGGGA<br>CAGAAACAAGGAACGGGACAACACAGCTGTCATCCTGAGAAAGGACGGCAAGTT<br>CTACCTCGCCATCATGCACAAGGAACACAACAAGGTCTTTGAGAAGTTTCCTGTG<br>GGCACTAAGGATTCTGACTTCGAGAAGATGGAATACAAGCTGCTGCCCGGCGCC<br>AACAAGATGCTGCCTAAGGTTTTCTTTAGCAAGAGCAGAATCGACGAGTTCAAGC<br>CATCTGCCGAGCTGCTGCAGAAGTACCAGATGGGAACTCACAAGAAGGGAGAAC<br>TGTTCAGCCTGAACGATTGCCACAGCCTGATCGACTTCTTCAAAGCCTCTATCGA<br>GAAGCACGATGATTGGAAGCAGTTCAACTTCCATTTCAGCCCTACCAGCAGCTAC<br>GAGGACCTGAGCGGCTTCTACCGGGAGGTGGAACAGCAGGGCTACAAGCTGAC<br>CTTCAAGAGCGTGGACGCTGATTACATCAATAAGATGGTCGATGAAGGCAAAATC<br>TTCCTGTTCCAGATCTACAACAAGGATTTTAGCGAGCACAGCAAGGGCACACCTA<br>ACCTGCACACCCTGTACTGGAAGATGCTGTTCGACGAGAGAAACCTGCAGAACG<br>TGGTGTACAAGCTGAACGGCGAAGCTGAGGTGTTCTTTCGGAAGAAGAGCCTGA<br>CCTACACACGCCCCACCCACCCTAAGAAGGAGCCTATCAAGAACAAAAACGTGC<br>AGAACGCTAAAAAGGAAAGCATCTTCGATTACGACCTGATCAAGAACAAAAGATT<br>CACAGTGGATTCTTTCCAGTTCCACGTGCCTATCACAATGAACTTCAAATCTGAG<br>GGCAGAAGCAACCTGAATGAGAGGGTGAACGAGTTCCTGAGACAAAACAACGAT<br>GCCCACATCATCGGAATCGACAGAGGCGAAAGGCATCTGCTGTACCTGGTGGTG<br>ATTGATAGACACGGCAACATCGTGGAACAATTTAGCCTGAACAGCATAATCAATG<br>AGTACCAAGGCAATACCTACGCCACAAACTATCACGACCTCCTGGACAAGAGAG<br>AGAAGGAGCGGGAAGAGGCCAGAGAGTCCTGGCAGTCTATCGAGAACATCAAG<br>GAGCTCAAAGAAGGCTACCTGAGTCAGGTGGTGCACAAAATCGCCGACCTGATG<br>GTGAAGTATCACGCCATCGTGGTGCTGGAGGACCTGAACATGGGCTTCATGAGA<br>GGCCGACAGAAGGTAGAGAAGCAGGTTTACCAGAAATTCGAGAAGATGCTGATT<br>GACAAGCTGAACTATCTGGTGGACAAAAAGCAAGATGCTGAAACCGACGGCGGC<br>CTGCTCAAGGCCTACCAACTGACCAACCAGTTCGAGAGCTTCCAGAAGCTGGGC<br>AAACAGTCTGGCTTCCTGTTTTACGTGCCCGCCTGGAACACCAGCAAGATCGATC<br>CCTGTACAGGCTTCACCAACCTGCTGGACACCCGATACGAGAGCATCGAAAAAG<br>CAAAGAAGTTCTTCCAAACATTCAACGCCATAAGATACAACGCTGCTCAGGGGTA<br>TTTTGAGTTCGAGCTCGACTACAACAAGTTTAACAAGCGGGCCGATGGCACCCA<br>GACCCTGTGGACACTGTGCACCTACGGACCTAGAATCGAAACCCTGCGGAGCAC<br>AGAGGACAACAACAAGTGGACCAGCAAAGAGGTGGACCTGACAGACGAGCTGAA<br>GAAACACTTCTACCACTACGGCATCAAGTTGGATGCCGACCTGAAAGAGGCCAT<br>CGGCCAGCAAACAGACAAGCCCTTCTTCACCAACCTGCTGCACCTGCTGAAGCT<br>GACACTGCAGATGAGAAACAGCAAGATCGGAACCGAGGTGGACTACCTGATTAG<br>CCCCATCAGAAACGAAGATGGCACCTTCTACGACAGCAGACAGGGAAACAAGAG<br>CCTGCCTGCTAATGCGGACGCCAATGGCGCCTACAACATCGCTAGAAAAGGCCT<br>CTGGGTCATCAACCAGATCAAACAGACCCCTCAGGATCAGAAACCTAAGCTGGC<br>CATCACCAATAAGGAGTGGCTGCAGTTCGCCCAGGAGAAACCATACCTGAAAGA<br>C | |
| Expression construct (with N-terminal methionine and stop codon, includes V5-tag and C-terminal NLS) | ATGggctccggaGACATGAAGAGCCTGAACTCTTTTCAGAACCAATACTCTCTGAGCA<br>AAACCCTGCGGTTCCAGCTGATCCCTCAGGGCAAGACACTGGATAATATCAACG<br>AGAGCAGAATCCTGGAAGAGGATCAGCACAGAAGCGAGTCATATAAACTGGTGA<br>AGAAGATCATTGACGACTATCACAAGGCCTACATCGAGCAGGCCCTGGGCAGCT<br>TCGAGCTGAAAATTGCCTCCGATAGCAAGAACGACAGCCTGGAGGAGTTCTACT<br>CTCAGTACATTGCGGAGAGAAAGGAGGACAAGGCCAAGAAGCTGTTCGAAAAGA<br>CCCAGGACAATCTGAGAAAGCAGATCTCCAAGAAGCTGAAACAGGGTGAAGCCT<br>ACAAACGGCTGTTCGGCAAAGAACTGATCCAGGAGGACCTGCTGGAGTTCGTGG<br>CCACAGATCCTGAGGCCGACTCTAAGAAGAGACTGATCGAAGAGTTCAAGGACT<br>TTACCACCTACTTCATCGGATTTCACGAAAATAGAAAGAACATGTACGCCGAGGA<br>GGCTCAGAGCACAGCTATTGCCTACAGAATCATCCACGAGAACCTGCCAAAGTTT | 114 |

TABLE 1S-continued

| ZZQE Type V Cas Sequences | | |
|---|---|---|
| Name | Sequence | SEQ ID NO. |
| | ATCGATAATATCAGAACCTTCGAGGAACTGGCCAAGAGCAGCATCGCCGACGTG<br>CTGCCCCAGGTCTACGAGGACTTTAAGGCCTACCTGAAGGTGGAAAGCGTGAAA<br>GAACTGTTCTCTCTGGATTATTTCAACACCGTGCTGACACAGAAACAACTGGACA<br>TCTACAATGCCGTGATCGGCGGAAAAAGCCTGGACGAGAACAGCAGAATCCAGG<br>GCCTGAACGAGTACATCAACCTCTACAACCAGCAGCATAAGGACAAGAAGCTGC<br>CTTTCCTGAAGCCCCTGTTCAAGCAAATCCTGTCCGATAGAAACAGCCTGTCCTG<br>GCTGCCTGAGGCCTTCGACAACGACAAGCAGGTGCTGCAGGCCGTGCACGACT<br>GCTACACCAGCCTGCTGGAATCTGTGTTCCACAAGGACGGCCTGCAACAGCTGC<br>TGCAGAGCCTCCCAACCTACAACTTAAAAGGCATCTACCTGCGGAACGACCTTAG<br>CATGACCAATGTGTCCCAGAAGCTGCTGGGCGATTGGGGCGCTATCACCAGAGC<br>CGTGAAGGAAAAGCTGCAGAAGGAAAACCCTGCCAAGAAGAGAGAGTCGGACG<br>AGGCCTACCAGGAGCGGATCAACAAGATCTTCAAGCAGGCCGGCTCATATTCAC<br>TGGATTACATCAACCAGGCCCTCGAAGCCACAGACCAGACAAACATCAAAGTGG<br>AGGACTACTTTATCAACATGGGCGTGGATAATGAGCAGAAAGAGCCTCTGTTTCA<br>AAGGGTGGCCCAGGCCTATAACCAGGCCAGCGACCTGCTGGAAAAAGAATACCC<br>CGCTAACAAGAATCTGATGCAGGACAAGGAGAGCATCGAGCACATCAAATTCCT<br>GCTCGACAACCTTAAGGCCGTGCAGCACTTCATCAAGCCTCTGCTGGGAGATGG<br>CAACGAAGCCGACAAGGACAACAGATTCTACGGCGAGCTAACCGCCCTGTGGAA<br>CGAACTTGACCAGGTGACCCGCCTGTACAACAAGGTGCGGAATTACATGACCAG<br>GAAGCCTTACAGCGTGGACAAGATCAAAATCAACTTCAAGAACAGCACCCTGCTG<br>AACGGATGGGACAGAAACAAGGAACGGGACAACACAGCTGTCATCCTGAGAAAG<br>GACGGCAAGTTCTACCTCGCCATCATGCACAAGGAACACAACAAGGTCTTTGAGA<br>AGTTTCCTGTGGGCACTAAGGATTCTGACTTCGAGAAGATGGAATACAAGCTGCT<br>GCCCGGCGCCAACAAGATGCTGCCTAAGGTTTTCTTTAGCAAGAGCAGAATCGA<br>CGAGTTCAAGCCATCTGCCGAGCTGCTGCAGAAGTACCAGATGGGAACTCACAA<br>GAAGGGAGAACTGTTCAGCCTGAACGATTGCCACAGCCTGATCGACTTCTTCAAA<br>GCCTCTATCGAGAAGCACGATGATTGGAAGCAGTTCAACTTCCATTTCAGCCCTA<br>CCAGCAGCTACGAGGACCTGAGCGGCTTCTACCGGGAGGTGGAACAGCAGGGC<br>TACAAGCTGACCTTCAAGAGCGTGGACGCTGATTACATCAATAAGATGGTCGATG<br>AAGGCAAAATCTTCCTGTTCCAGATCTACAACAAGGATTTTAGCGAGCACAGCAA<br>GGGCACACCTAACCTGCACACCCTGTACTGGAAGATGCTGTTCGACGAGAGAAA<br>CCTGCAGAACGTGGTGTACAAGCTGAACGGCGAAGCTGAGGTGTTCTTTCGGAA<br>GAAGAGCCTGACCTACACACGCCCCACCCACCCTAAGAAGGAGCCTATCAAGAA<br>CAAAAACGTGCAGAACGCTAAAAAGGAAAGCATCTTCGATTACGACCTGATCAAG<br>AACAAAAGATTCACAGTGGATTCTTTCCAGTTCCACGTGCCTATCACAATGAACTT<br>CAAATCTGAGGGCAGAAGCAACCTGAATGAGAGGGTGAACGAGTTCCTGAGACA<br>AAACAACGATGCCCACATCATCGGAATCGACAGAGGCGAAAGGCATCTGCTGTA<br>CCTGGTGGTGATTGATAGACACGGCAACATCGTGGAACAATTTAGCCTGAACAG<br>CATAATCAATGAGTACCAAGGCAATACCTACGCCACAAACTATCACGACCTCCTG<br>GACAAGAGAGAGAAGGAGCGGGAAGAGGCCAGAGAGTCCTGGCAGTCTATCGA<br>GAACATCAAGGAGCTCAAAGAAGGCTACCTGAGTCAGGTGGTGCACAAAATCGC<br>CGACCTGATGGTGAAGTATCACGCCATCGTGGTGCTGGAGGACCTGAACATGGG<br>CTTCATGAGAGGCCGACAGAAGGTAGAGAAGCAGGTTTACCAGAAATTCGAGAA<br>GATGCTGATTGACAAGCTGAACTATCTGGTGGACAAAAAGCAAGATGCTGAAACC<br>GACGGCGGCCTGCTCAAGGCCTACCAACTGACCAACCAGTTCGAGAGCTTCCAG<br>AAGCTGGGCAAACAGTCTGGCTTCCTGTTTTACGTGCCCGCCTGGAACACCAGC<br>AAGATCGATCCCTGTACAGGCTTCACCAACCTGCTGGACACCCGATACGAGAGC<br>ATCGAAAAAGCAAAGAAGTTCTTCCAAACATTCAACGCCATAAGATACAACGCTG<br>CTCAGGGGTATTTTGAGTTCGAGCTCGACTACAACAAGTTTAACAAGCGGGCCGA<br>TGGCACCCAGACCCTGTGGACACTGTGCACCTACGGACCTAGAATCGAAACCCT<br>GCGGAGCACAGAGGACAACAACAAGTGGACCAGCAAAGAGGTGGACCTGACAG<br>ACGAGCTGAAGAAACACTTCTACCACTACGGCATCAAGTTGGATGCCGACCTGAA<br>AGAGGCCATCGGCCAGCAAACAGACAAGCCCTTCTTCACCAACCTGCTGCACCT<br>GCTGAAGCTGACACTGCAGATGAGAAACAGCAAGATCGGAACCGAGGTGGACTA<br>CCTGATTAGCCCCATCAGAAACGAAGATGGCACCTTCTACGACAGCAGACAGGG<br>AAACAAGAGCCTGCCTGCTAATGCGGACGCCAATGGCGCCTACAACATCGCTAG<br>AAAAGGCCTCTGGGTCATCAACCAGATCAAACAGACCCCTCAGGATCAGAAACCT<br>AAGCTGGCCATCACCAATAAGGAGTGGCTGCAGTTCGCCCAGGAGAAACCATAC<br>CTGAAAGACtctagaAAGCGGACAGCAGACGGCTCCGAATTTGAAAGCCCTAAGAA<br>AAAGAGAAAGGTGggatccGGCAAACCTATCCCCAATCCCCTGCTGGGCCTGGACA<br>GCACCTGA | |

In some embodiments a ZZQE Type V Cas protein comprises an amino acid sequence of SEQ ID NO:109, SEQ ID NO:110, or SEQ ID NO:111. In some embodiments, a ZZQE Type V Cas protein has nickase activity, for example resulting from one or more amino acid substitutions relative to the sequence of SEQ ID NO:109, SEQ ID NO:110, or SEQ ID NO:111. In some embodiments, the one or more amino acid substitutions providing nickase activity comprise a D859 substitution, wherein the position of the D859 substitution is defined with respect to the amino acid numbering of SEQ ID NO:110 (corresponding to amino acid 908 of SEQ ID NO:121). In some embodiments, the one or more amino acid substitutions providing nickase activity comprise an E952 substitution, wherein the position of the E952 substitution is defined with respect to the amino acid numbering of SEQ ID NO:110 (corresponding to amino acid 993 of SEQ ID NO:121). In some embodiments, the one or more amino acid substitutions providing nickase activity comprise a R1164 substitution, wherein the position of the R1164 substitution is defined with respect to the amino acid numbering of SEQ ID NO:110 (corresponding to amino acid 1226 of SEQ ID NO:121). In some embodiments, the one or more amino acid substitutions providing nickase activity comprise a D1201 substitution, wherein the position of the D1201 substitution is defined with respect to the amino acid numbering of SEQ ID NO:110 (corresponding to amino acid 1263 of SEQ ID NO:121). In some embodiments, a ZZQE Type V Cas protein is catalytically inactive, for example due to a R1164 substitution in combination with a D859 substitution, a E952 substitution, and/or D1201 substitution.

6.2.20. ZRXE Type V Cas Protein

In one aspect, the disclosure provides ZRXE Type V Cas proteins. ZRXE Type V Cas proteins can be further classified as Type V-A Cas proteins. The ZRXE Type V Cas proteins typically comprise an amino acid sequence that is at least 50%, at least 55%, at least 60%, at least 65%, at least 70%, at least 75%, at least 85%, at least 90%, or at least 95% identical to SEQ ID NO:115. In some embodiments, the ZRXE Type V Cas proteins comprise an amino acid sequence that is at least 95%, at least 96%, at least 97%, at least 98%, or at least 99% identical to SEQ ID NO:115. In some embodiments, a ZRXE Type V Cas protein comprises an amino acid sequence that is identical to SEQ ID NO:115.

Exemplary ZRXE Type V Cas protein sequences and nucleotide sequences encoding exemplary ZRXE Type V Cas proteins are set forth in Table 1T.

TABLE 1T

ZRXE Type V Cas Sequences

| Name | Sequence | SEQ ID NO. |
| --- | --- | --- |
| Wildtype amino acid sequence (without N-terminal methionine) | KAFENFTGLYPLSKTLRFELKPIGKTLEYIEKHGILDKDKHRANSYVKVKDIIDRYHK<br>QFIEDSLSDSDFKLKYENKGKKESLEEYFYYYKLRNRDDKQKKDFDEIQKNLRKQI<br>ASQLKKQDRFKRIDKKELIKEDLLEFVSDDNERNLINEFKDFTTYFTGFHENRQNMY<br>SDEAKSTAIAYRLIHENLPKFIDNISVFERVAATDVADCFAQIYSDFEEYLNVNDISEI<br>FRLDYYTEILTQTQIDAYNLIIGGRSEGNIKIKGLNEYINLYNQQQKDKSQRLPKLKSL<br>FKQILSDRNAISWLPESFENDNQLLEKLESCYQSFNETYDDKKSIFVRFRELLLTISD<br>YEMDKIFLRNDLQLTDISQKMFGSYSIISRSLLEDLKRGTSRKSKKETDESFEERLR<br>NIIKNQDSFAIGTIDSSLQQMDVEEYKKSICDYFPNLSVDDKGDDIFDRIVKAYSEVK<br>DLLNSPYPSDKNLAQEDDDIDKIKNLLESMKDLQKFVKPLCGKGNESDKDERFYGE<br>FTALYEELDKITPLYNMVRNYLTRKPYSTEKIKLNFDNAQLLNGWDLNKESDNTSVI<br>LRKDGLYYLAIMNKKHNKVFEKNKLQSDGVCFEKMEYKLLPGANKMLPKVFFSKS<br>RIDEFGPSQRLLDSYQNETHKKGDKFNIEDCHELIDFFKRSIDKHEDWSKFSFSFS<br>DTKTYEDLSGFYREVEHQGYILSFVNVSVDYVNSLVDEGKIYLFQIYNKDFSPFSKG<br>TPNMHTLYWKMLFDEENLKDVVYKLNGQAEVFFRKSSIKYDKPTHPANLPIDNKNV<br>SNHKKRSVFEYDLVKDKRYTVDKFQFHVPVTINFKSDGNGNINPLVNDYIKKSDDL<br>HVIGIDRGERHLLYLTVIDMKGNIKKQFSLNEIVNEYKGNTYSTNYHDLLEKREDKR<br>DKERKEWKTIETIKELKEGYLSQVIHKITELMVEYNAIIVLEDLNLGFMRGRQKVEKS<br>VYQKFEKMLIDKLNYLADKKKEPEDLGGVLKAYQLANKFESFQKMGKQSGFLFYT<br>QAWNTSKIDPVTGFVNLFDTHYENILKSKNFFSKFDLIKYNSDKDWFEFSFDYNNF<br>TTKAEGTKTKWTLCTFGNRIISFRNPDNNMQWDGKEINLTEEFKLFFEKFGININSD<br>LHAEILKQDKKDFFEGLLHLLKLTLQMRNSKTRTDIDYMQSPVADENGVLYNSNKC<br>GKSLPENADANGAYNIARKGLMIIDKIKKSDNLNKIDLTISNKEWLVFAQNKPYLKN | 115 |
| Wildtype amino acid sequence (with N-terminal methionine) | MKAFENFTGLYPLSKTLRFELKPIGKTLEYIEKHGILDKDKHRANSYVKVKDIIDRYH<br>KQFIEDSLSDSDFKLKYENKGKKESLEEYFYYYKLRNRDDKQKKDFDEIQKNLRKQ<br>IASQLKKQDRFKRIDKKELIKEDLLEFVSDDNERNLINEFKDFTTYFTGFHENRQNM<br>YSDEAKSTAIAYRLIHENLPKFIDNISVFERVAATDVADCFAQIYSDFEEYLNVNDISE<br>IFRLDYYTEILTQTQIDAYNLIIGGRSEGNIKIKGLNEYINLYNQQQKDKSQRLPKLKS<br>LFKQILSDRNAISWLPESFENDNQLLEKLESCYQSFNETYDDKKSIFVRFRELLLTIS<br>DYEMDKIFLRNDLQLTDISQKMFGSYSIISRSLLEDLKRGTSRKSKKETDESFEERL<br>RNIIKNQDSFAIGTIDSSLQQMDVEEYKKSICDYFPNLSVDDKGDDIFDRIVKAYSEV<br>KDLLNSPYPSDKNLAQEDDDIDKIKNLLESMKDLQKFVKPLCGKGNESDKDERFYG<br>EFTALYEELDKITPLYNMVRNYLTRKPYSTEKIKLNFDNAQLLNGWDLNKESDNTS<br>VILRKDGLYYLAIMNKKHNKVFEKNKLQSDGVCFEKMEYKLLPGANKMLPKVFFSK<br>SRIDEFGPSQRLLDSYQNETHKKGDKFNIEDCHELIDFFKRSIDKHEDWSKFSFSFS<br>DTKTYEDLSGFYREVEHQGYILSFVNVSVDYVNSLVDEGKIYLFQIYNKDFSPFSKG<br>TPNMHTLYWKMLFDEENLKDVVYKLNGQAEVFFRKSSIKYDKPTHPANLPIDNKNV<br>SNHKKRSVFEYDLVKDKRYTVDKFQFHVPVTINFKSDGNGNINPLVNDYIKKSDDL<br>HVIGIDRGERHLLYLTVIDMKGNIKKQFSLNEIVNEYKGNTYSTNYHDLLEKREDKR<br>DKERKEWKTIETIKELKEGYLSQVIHKITELMVEYNAIIVLEDLNLGFMRGRQKVEKS<br>VYQKFEKMLIDKLNYLADKKKEPEDLGGVLKAYQLANKFESFQKMGKQSGFLFYT<br>QAWNTSKIDPVTGFVNLFDTHYENILKSKNFFSKFDLIKYNSDKDWFEFSFDYNNF<br>TTKAEGTKTKWTLCTFGNRIISFRNPDNNMQWDGKEINLTEEFKLFFEKFGININSD<br>LHAEILKQDKKDFFEGLLHLLKLTLQMRNSKTRTDIDYMQSPVADENGVLYNSNKC<br>GKSLPENADANGAYNIARKGLMIIDKIKKSDNLNKIDLTISNKEWLVFAQNKPYLKN | 116 |
| Expression construct (with N-terminal methionine, V5-tag and C-terminal NLS) aa sequence | MGSGKAFENFTGLYPLSKTLRFELKPIGKTLEYIEKHGILDKDKHRANSYVKVKDIID<br>RYHKQFIEDSLSDSDFKLKYENKGKKESLEEYFYYYKLRNRDDKQKKDFDEIQKNL<br>RKQIASQLKKQDRFKRIDKKELIKEDLLEFVSDDNERNLINEFKDFTTYFTGFHENR<br>QNMYSDEAKSTAIAYRLIHENLPKFIDNISVFERVAATDVADCFAQIYSDFEEYLNVN<br>DISEIFRLDYYTEILTQTQIDAYNLIIGGRSEGNIKIKGLNEYINLYNQQQKDKSQRLP<br>KLKSLFKQILSDRNAISWLPESFENDNQLLEKLESCYQSFNETYDDKKSIFVRFREL<br>LLTISDYEMDKIFLRNDLQLTDISQKMFGSYSIISRSLLEDLKRGTSRKSKKETDESF<br>EERLRNIIKNQDSFAIGTIDSSLQQMDVEEYKKSICDYFPNLSVDDKGDDIFDRIVKA<br>YSEVKDLLNSPYPSDKNLAQEDDDIDKIKNLLESMKDLQKFVKPLCGKGNESDKDE | 117 |

TABLE 1T-continued

ZRXE Type V Cas Sequences

| Name | Sequence | SEQ ID NO. |
|---|---|---|
| | RFYGEFTALYEELDKITPLYNMVRNYLTRKPYSTEKIKLNFDNAQLLNGWDLNKES<br>DNTSVILRKDGLYYLAIMNKKHNKVFEKNKLQSDGVCFEKMEYKLLPGANKMLPKV<br>FFSKSRIDEFGPSQRLLDSYQNETHKKGDKFNIEDCHELIDFFKRSIDKHEDWSKFS<br>FSFSDTKTYEDLSGFYREVEHQGYILSFVNVSVDYVNSLVDEGKIYLFQIYNKDFSP<br>FSKGTPNMHTLYWKMLFDEENLKDVVYKLNGQAEVFFRKSSIKYDKPTHPANLPID<br>NKNVSNHKKRSVFEYDLVKDKRYTVDKFQFHVPVTINFKSDGNGNINPLVNDYIKK<br>SDDLHVIGIDRGERHLLYLTVIDMKGNIKKQFSLNEIVNEYKGNTYSTNYHDLLEKR<br>EDKRDKERKEWKTIETIKELKEGYLSQVIHKITELMVEYNAIIVLEDLNLGFMRGRQK<br>VEKSVYQKFEKMLIDKLNYLADKKKEPEDLGGVLKAYQLANKFESFQKMGKQSGF<br>LFYTQAWNTSKIDPVTGFVNLFDTHYENILKSKNFFSKFDLIKYNSDKDWFEFSFDY<br>NNFTTKAEGTKTKWTLCTFGNRIISFRNPDNNMQWDGKEINLTEEFKLFFEKFGINI<br>NSDLHAEILKQDKKDFFEGLLHLLKLTLQMRNSKTRTDIDYMQSPVADENGVLYNS<br>NKCGKSLPENADANGAYNIARKGLMIIDKIKKSDNLNKIDLTISNKEWLVFAQNKPYL<br>KNSRKRTADGSEFESPKKKRKVGSGKPIPNPLLGLDST | |
| Wildtype coding sequence (with N-terminal methionine and stop codon) | ATGAAAGCATTTGAGAATTTTACAGGATTGTATCCTCTTTCTAAAACATTAAGAT<br>TTGAGCTGAAACCGATTGGAAAGACATTGGAATATATTGAGAAGCATGGTATTC<br>TTGATAAGGATAAACACAGAGCAAATAGTTATGTTAAGGTCAAGGATATAATTG<br>ACAGATATCATAAACAATTTATTGAAGACTCGTTAAGTGATAGTGATTTTAAACT<br>TAAATATGAAAACAAAGGAAAGAAAGAATCATTAGAAGAATATTTCTATTATTAT<br>AAATTAAGAAATAGAGACGACAAACAGAAGAAAGATTTTGATGAAATTCAAAAG<br>AATCTTAGAAAACAGATTGCAAGTCAATTAAAGAAACAAGATCGTTTTAAAAGAA<br>TTGATAAAAAGGAACTTATAAAGGAAGATCTTTTAGAATTTGTTAGTGATGATAA<br>TGAAAGGAATCTTATTAATGAATTTAAAGATTTCACGACATATTTTACAGGTTTT<br>CACGAAAACAGACAAAATATGTATTCTGATGAAGCCAAATCAACTGCGATAGCG<br>TATAGACTGATACATGAGAATCTTCCTAAATTTATAGATAACATTTCAGTTTTTGA<br>AAGAGTTGCTGCTACAGATGTGGCTGATTGTTTTGCACAAATCTATTCTGATTTT<br>GAGGAATATCTGAATGTAAATGATATATCTGAAATTTTTAGATTAGACTATTATA<br>CGGAAATATTAACTCAGACACAGATTGATGCTTATAATCTGATAATTGGAGGAC<br>GTTCTGAGGGCAATATTAAAATAAAAGGTTTGAACGAATATATTAATCTGTATAA<br>TCAACAGCAGAAAGACAAGTCTCAACGGTTGCCAAAACTGAAGTCTTTGTTTAA<br>ACAGATTTTGAGTGATAGAAATGCTATATCTTGGTTGCCAGAATCGTTTGAAAAT<br>GATAATCAACTCTTGGAAAAGTTGGAGAGTTGTTATCAGTCTTTTAATGAAACAT<br>ATGACGATAAGAAGTCAATATTTGTAAGGTTTAGAGAATTATTGTTGACTATATC<br>TGATTATGAAATGGATAAAATATTTCTTCGTAATGATTTGCAGTTGACAGATATT<br>TCACAAAAGATGTTCGGTAGTTATAGTATTATTTCAAGGTCTTTATTGGAAGATT<br>TAAAGAGAGGTACATCTCGTAAATCAAAGAAGGAAACTGATGAAAGTTTTGAAG<br>AAAGGTTGAGAAATATTATCAAAAACCAAGATAGTTTTGCCATTGGAACAATAG<br>ATTCGTCTTTGCAACAAATGGATGTTGAAGAATACAAGAAATCTATTTGTGATTA<br>TTTCCCTAATTTATCTGTTGATGACAAAGGAGATGATATTTTTGATAGAATAGTA<br>AAAGCGTATTCGGAGGTTAAAGACTTGTTGAATTCTCCGTATCCGTCAGATAAA<br>AACCTTGCTCAAGAAGATGATGATATTGATAAGATTAAAAATCTTTTAGAGTCAA<br>TGAAAGATCTTCAGAAGTTTGTGAAACCTCTCTGTGGAAAAGGAAATGAATCTG<br>ATAAAGATGAGCGTTTCTATGGTGAGTTTACGGCTTTATATGAAGAATTAGACA<br>AGATAACACCATTATATAATATGGTGAGAAATTATCTTACTCGCAAACCGTATTC<br>TACGGAAAAGATAAAGTTAAACTTTGACAATGCTCAACTTTTGAATGGATGGGA<br>TTTAAATAAAGAAAGTGATAATACGAGTGTCATATTGCGTAAAGACGGATTGTAT<br>TATCTTGCCATCATGAACAAGAAGCATAATAAAGTCTTCGAGAAAAATAAATTAC<br>AGTCAGATGGTGTTTGCTTTGAAAAAATGGAGTATAAATTACTTCCTGGTGCAA<br>ACAAGATGCTTCCAAAAGTTTTCTTCTCTAAATCAAGGATAGATGAGTTTGGAC<br>CTTCTCAAAGATTGTTGGACAGTTATCAGAATGAAACTCATAAAAAAGGTGATA<br>AATTCAATATTGAAGATTGCCATGAATTGATAGATTTTTTCAAAAGGTCTATTGA<br>TAAACATGAGGATTGGAGTAAATTTAGCTTTAGTTTCTCAGATACTAAGACATAT<br>GAAGATTTAAGCGGATTTTACAGAGAAGTTGAGCATCAGGGTTATATACTTTCT<br>TTTGTAAATGTTTCTGTAGATTATGTAAATAGTTTGGTAGATGAAGGAAAGATAT<br>ATTTATTTCAAATTTATAATAAAGATTTCTCGCCATTTAGCAAAGGAACTCCAAAT<br>ATGCATACTTTGTATTGGAAAATGCTTTTTGATGAAGAAAATCTGAAAGATGTGG<br>TGTATAAATTGAATGGTCAGGCAGAAGTGTTTTTCAGGAAATCCAGTATAAAGT<br>ATGATAAACCGACTCATCCTGCTAATTTGCCTATTGATAATAAAAATGTATCTAA<br>CCATAAGAAACGGAGTGTCTTTGAGTATGATTTGGTCAAAGATAAGAGATATAC<br>GGTTGATAAATTCCAGTTTCATGTTCCTGTAACAATCAATTTTAAAAGTGATGGA<br>AATGGAAATATCAATCCTCTCGTCAATGATTATATCAAAAAGTCTGATGATTTGC<br>ATGTGATTGGTATCGACAGGGGAGAGCGTCATCTTTTGTATCTTACGGTCATAG<br>ATATGAAAGGTAATATCAAGAAGCAGTTTTCATTGAATGAAATCGTCAATGAATA<br>TAAAGGAAATACATATAGTACCAATTATCATGATTTGTTGGAAAAACGCGAGGA<br>CAAACGTGATAAGGAAAGAAAAGAATGGAAAACTATAGAAACCATCAAGGAGTT<br>GAAAGAAGGTTATCTCAGCCAGGTTATTCATAAAATAACGGAATTGATGGTTGA<br>ATATAATGCAATCATTGTGCTGGAGGATCTTAATTTAGGATTTATGCGTGGGCG<br>ACAAAAGGTGGAGAAGTCTGTTTATCAAAAGTTTGAAAAGATGTTGATTGATAA<br>ACTGAATTATCTTGCTGATAAAAAGAAAGAACCGGAAGATTTGGGTGGTGTGTT<br>GAAGGCATATCAACTGGCAAATAAGTTTGAAAGTTTTCAAAAAATGGGAAAACA<br>ATCAGGTTTCTTATTCTATACCCAAGCATGGAATACAAGTAAGATAGATCCGGT<br>TACTGGTTTTGTTAATCTTTTTGACACACATTATGAGAATATCTTAAAGTCTAAAA<br>ATTTCTTCTCTAAGTTTGATTTGATAAAGTATAATTCTGATAAAGATTGGTTCGA<br>GTTTTCTTTTGATTATAATAATTTTACAACTAAAGCAGAAGGTACAAAAACAAAAT | 118 |

TABLE 1T-continued

| ZRXE Type V Cas Sequences | | |
| --- | --- | --- |
| Name | Sequence | SEQ ID NO. |
| | GGACATTATGTACCTTTGGAAATAGAATAATATCATTCCGTAATCCTGATAATAA<br>TATGCAATGGGATGGAAAAGAAATTAATCTTACTGAAGAATTCAAGTTATTCTTT<br>GAGAAATTTGGAATCAATATTAATTCTGATTTGCATGCGGAAATATTAAAACAAG<br>ATAAAAAAGACTTCTTTGAAGGTCTTTTGCATTTGTTGAAATTGACATTGCAGAT<br>GCGTAATAGTAAGACTCGCACTGATATAGATTATATGCAGTCTCCTGTAGCAGA<br>CGAAAACGGAGTGTTATACAATAGTAATAAATGTGGTAAATCCTTGCCAGAAAA<br>TGCTGATGCTAACGGTGCGTATAATATTGCAAGAAAAGGTCTTATGATAATTGA<br>CAAAATAAAGAAGTCTGATAATCTGAATAAAATAGATCTTACGATCTCTAATAAG<br>GAGTGGTTGGTATTCGCACAAAATAAACCATATTTGAAGAATTGA | |
| Codon optimized coding sequence (no N-terminal methionine, no stop codon) | AAGGCCTTCGAGAACTTCACCGGCCTGTATCCCCTCTCTAAAACCCTGAGATTT<br>GAGCTGAAGCCAATCGGCAAGACCCTCGAATACATTGAGAAGCACGGCATCCT<br>GGACAAGGACAAGCACAGAGCCAATAGCTACGTGAAGGTGAAGGACATCATC<br>GACAGATACCACAAACAGTTCATCGAGGACTCTCTGTCTGATAGCGACTTCAA<br>GCTAAAGTACGAGAACAAAGGCAAGAAGGAGAGCCTGGAAGAGTACTTCTACT<br>ACTACAAGCTGCGGAACCGGGATGATAAGCAAAAGAAAGATTTTGATGAGATC<br>CAGAAGAACCTGAGAAAACAAATCGCCAGCCAGCTCAAAAAACAGGACAGATT<br>CAAGCGGATCGACAAGAAAGAACTGATCAAGGAAGATCTGCTGGAGTTCGTGA<br>GCGACGACAATGAAAGAAACCTGATCAACGAGTTCAAGGATTTTACTACATACT<br>TTACCGGCTTCCACGAGAACCGGCAGAACATGTACTCTGATGAGGCCAAGTCC<br>ACCGCCATCGCTTATAGACTGATTCACGAGAATCTGCCTAAGTTCATCGATAAC<br>ATAAGCGTGTTCGAGCGGGTCGCAGCTACAGATGTGGCCGACTGCTTCGCCC<br>AGATCTACTCCGATTTCGAGGAATACCTGAACGTGAACGACATCAGCGAGATC<br>TTCAGACTGGACTACTATACAGAAATCCTGACCCAGACCCAGATCGACGCCTA<br>CAATCTGATCATTGGCGGCAGAAGCGAGGGCAACATCAAAATTAAAGGCTTGA<br>ACGAGTACATCAATCTGTACAACCAGCAGCAGAAAGACAAGAGCCAAAGACTG<br>CCCAAGCTGAAGAGCCTGTTTAAACAGATCCTGAGCGACAGAAATGCCATATC<br>TTGGTTGCCTGAGTCTTTCGAGAACGATAACCAGCTGCTGGAGAAGCTGGAGA<br>GCTGCTACCAGAGCTTCAACGAAACCTACGACGACAAGAAGTCTATCTTTGTTA<br>GATTTAGAGAACTGCTGCTGACAATCTCTGACTACGAGATGGACAAAATCTTCC<br>TGAGAAATGACCTGCAGCTGACCGACATCTCCCAAAAAATGTTCGGATCTTACA<br>GCATCATCTCCCGGAGCCTGTTAGAGGATCTCAAGAGAGGAACCAGCCGGAA<br>GTCAAAGAAGGAAACAGACGAGAGCTTCGAAGAACGGCTGCGCAACATTATCA<br>AGAATCAGGACTCCTTTGCCATCGGCACCATCGATAGCAGCCTGCAGCAGATG<br>GACGTGGAAGAGTACAAGAAATCCATCTGCGACTATTTCCCTAATCTGAGTGTT<br>GACGACAAGGGCGATGACATATTTGACAGAATCGTGAAAGCCTATAGCGAGGT<br>GAAGGACCTGCTGAACTCCCCTTACCCTAGCGACAAGAACCTGGCTCAGGAG<br>GACGACGACATCGACAAGATCAAAAACCTGCTGGAAAGCATGAAGGACCTGCA<br>GAAGTTCGTCAAGCCTCTGTGTGGCAAGGGCAACGAGAGCGATAAGGATGAA<br>AGGTTCTACGGCGAGTTCACAGCCCTGTACGAGGAACTGGACAAGATCACCCC<br>TCTGTACAATATGGTGCGGAACTACCTGACAAGAAAGCCATACTCTACCGAGA<br>AGATCAAACTGAACTTCGACAACGCCCAGCTGCTGAACGGATGGGACCTGAAT<br>AAAGAGAGCGACAACACCAGCGTCATCCTGCGTAAGGATGGCCTGTACTACCT<br>GGCCATCATGAACAAGAAGCACAACAAGGTGTTCGAGAAGAACAAGCTCCAAA<br>GCGATGGCGTGTGCTTCGAGAAGATGGAGTACAAGCTGCTGCCTGGCGCCAA<br>CAAGATGCTGCCAAAGGTGTTCTTCTCTAAGAGCAGAATCGATGAGTTCGGCC<br>CTTCTCAGAGACTGCTGGACAGCTACCAGAACGAAACCCACAAGAAGGGCGA<br>CAAATTCAACATCGAGGACTGTCACGAGCTGATCGACTTTTTCAAAAGAAGCAT<br>CGACAAACATGAAGATTGGAGCAAGTTTTCTTTTAGCTTCAGCGACACCAAGAC<br>CTACGAGGACCTGAGCGGCTTCTACAGAGAAGTAGAACACCAGGGCTACATCC<br>TGAGCTTTGTGAACGTGAGCGTGGATTACGTGAACAGCCTGGTGGACGAGGG<br>AAAGATCTACTTATTTCAGATCTACAACAAGGATTTCAGCCCTTTCTCTAAGGG<br>CACCCCTAACATGCACACACTGTACTGGAAGATGCTGTTCGACGAGGAAAACC<br>TGAAGGATGTGGTGTACAAGCTGAATGGCCAGGCCGAAGTGTTCTTCAGAAAG<br>TCCTCTATCAAGTACGACAAACCTACCCATCCTGCCAATCTCCCCATCGATAAC<br>AAGAACGTGAGCAACCACAAGAAGCGGAGCGTGTTCGAGTACGACCTGGTGA<br>AGGACAAACGTTACACCGTGGATAAGTTCCAGTTCCACGTGCCCGTGACCATC<br>AACTTCAAGAGCGATGGCAACGGCAATATCAACCCCCTGGTGAACGACTACAT<br>CAAGAAGAGCGACGATCTACACGTGATCGGCATCGACAGAGGAGAACGGCAC<br>CTGCTGTACCTGACGGTGATCGACATGAAGGGCAACATCAAGAAACAATTTAG<br>CCTGAACGAGATCGTGAACGAATATAAGGGCAATACCTACAGCACCAACTACC<br>ACGACCTGCTGGAGAAACGGGAAGATAAGAGAGATAAGGAGAGAAAGGAATG<br>GAAAACCATTGAAACAATCAAGGAACTGAAAGAAGGATATCTGAGCCAGGTGA<br>TCCACAAGATCACCGAGCTGATGGTGGAGTACAACGCCATCATCGTCCTGGAG<br>GACCTGAACCTGGGCTTCATGAGAGGGAGACAGAAGGTGGAGAAGTCCGTAT<br>ACCAGAAATTTGAAAAGATGCTGATCGACAAGCTGAACTACCTGGCTGACAAG<br>AAAAAGGAACCTGAGGACCTTGGAGGCGTCCTGAAGGCCTACCAGCTGGCCA<br>ACAAATTCGAATCTTTCCAAAAGATGGGCAAACAGAGCGGCTTTCTGTTTTACA<br>CCCAGGCTTGGAACACCAGCAAGATCGACCCCGTGACGGGCTTCGTGAACCT<br>CTTCGATACACATTACGAGAACATCCTGAAGAGCAAGAATTTCTTCAGCAAGTT<br>CGATCTCATCAAATATAACAGCGATAAAGATTGGTTCGAGTTCTCGTTCGACTA<br>CAACAATTTCACCACCAAGGCCGAGGGCACCAAAACAAAGTGGACACTGTGCA<br>CCTTCGGAAACAGAATCATCAGCTTTAGAAACCCTGACAACAACATGCAGTGG<br>GATGGCAAGGAGATCAACCTGACAGAGGAGTTCAAGCTGTTCTTCGAGAAGTT<br>CGGCATCAACATCAACTCCGACCTGCACGCTGAGATCCTGAAGCAAGACAAGA | 119 |

TABLE 1T-continued

ZRXE Type V Cas Sequences

| Name | Sequence | SEQ ID NO. |
|---|---|---|
| | AGGACTTCTTCGAGGGCCTGCTGCACCTGCTGAAACTGACACTCCAGATGCGG<br>AACAGCAAGACGAGGACCGATATCGACTACATGCAGAGCCCCGTGGCCGACG<br>AGAATGGGGTGCTGTACAACTCCAACAAATGCGGCAAGAGCCTGCCCGAGAA<br>CGCCGATGCCAACGGAGCCTACAACATCGCTAGAAAGGGACTGATGATCATTG<br>ACAAGATCAAGAAGTCTGACAACCTGAACAAGATCGATCTGACTATCTCTAACA<br>AGGAATGGCTGGTGTTCGCCCAGAACAAGCCTTACCTGAAAAAT | |
| Expression construct (with N-terminal methionine and stop codon, includes V5-tag and C-terminal NLS) | ATGggctccggaAAGGCCTTCGAGAACTTCACCGGCCTGTATCCCCTCTCTAAAAC<br>CCTGAGATTTGAGCTGAAGCCAATCGGCAAGACCCTCGAATACATTGAGAAGC<br>ACGGCATCCTGGACAAGGACAAGCACAGAGCCAATAGCTACGTGAAGGTGAA<br>GGACATCATCGACAGATACCACAAACAGTTCATCGAGGACTCTCTGTCTGATA<br>GCGACTTCAAGCTAAAGTACGAGAACAAAGGCAAGAAGGAGAGCCTGGAAGA<br>GTACTTCTACTACTACAAGCTGCGGAACCGGGATGATAAGCAAAAGAAAGATTT<br>TGATGAGATCCAGAAGAACCTGAGAAAACAAATCGCCAGCCAGCTCAAAAAAC<br>AGGACAGATTCAAGCGGATCGACAAGAAAGAACTGATCAAGGAAGATCTGCTG<br>GAGTTCGTGAGCGACGACAATGAAAGAAACCTGATCAACGAGTTCAAGGATTT<br>TACTACATACTTTACCGGCTTCCACGAGAACCGGCAGAACATGTACTCTGATGA<br>GGCCAAGTCCACCGCCATCGCTTATAGACTGATTCACGAGAATCTGCCTAAGT<br>TCATCGATAACATAAGCGTGTTCGAGCGGGTCGCAGCTACAGATGTGGCCGAC<br>TGCTTCGCCCAGATCTACTCCGATTTCGAGGAATACCTGAACGTGAACGACAT<br>CAGCGAGATCTTCAGACTGGACTACTATACAGAAATCCTGACCCAGACCCAGA<br>TCGACGCCTACAATCTGATCATTGGCGGCAGAAGCGAGGGCAACATCAAAATT<br>AAAGGCTTGAACGAGTACATCAATCTGTACAACCAGCAGCAGAAAGACAAGAG<br>CCAAAGACTGCCCAAGCTGAAGAGCCTGTTTAAACAGATCCTGAGCGACAGAA<br>ATGCCATATCTTGGTTGCCTGAGTCTTTCGAGAACGATAACCAGCTGCTGGAG<br>AAGCTGGAGAGCTGCTACCAGAGCTTCAACGAAACCTACGACGACAAGAAGTC<br>TATCTTTGTTAGATTTAGAGAACTGCTGCTGACAATCTCTGACTACGAGATGGA<br>CAAAATCTTCCTGAGAAATGACCTGCAGCTGACCGACATCTCCCAAAAAATGTT<br>CGGATCTTACAGCATCATCTCCCGGAGCCTGTTAGAGGATCTCAAGAGAGGAA<br>CCAGCCGGAAGTCAAAGAAGGAAACAGACGAGAGCTTCGAAGAACGGCTGCG<br>CAACATTATCAAGAATCAGGACTCCTTTGCCATCGGCACCATCGATAGCAGCCT<br>GCAGCAGATGGACGTGGAAGAGTACAAGAAATCCATCTGCGACTATTTCCCTA<br>ATCTGAGTGTTGACGACAAGGGCGATGACATATTTGACAGAATCGTGAAAGCC<br>TATAGCGAGGTGAAGGACCTGCTGAACTCCCCTTACCCTAGCGACAAGAACCT<br>GGCTCAGGAGGACGACGACATCGACAAGATCAAAAACCTGCTGGAAAGCATG<br>AAGGACCTGCAGAAGTTCGTCAAGCCTCTGTGTGGCAAGGGCAACGAGAGCG<br>ATAAGGATGAAAGGTTCTACGGCGAGTTCACAGCCCTGTACGAGGAACTGGAC<br>AAGATCACCCCTCTGTACAATATGGTGCGGAACTACCTGACAAGAAAGCCATA<br>CTCTACCGAGAAGATCAAACTGAACTTCGACAACGCCCAGCTGCTGAACGGAT<br>GGGACCTGAATAAAGAGAGCGACAACACCAGCGTCATCCTGCGTAAGGATGG<br>CCTGTACTACCTGGCCATCATGAACAAGAAGCACAACAAGGTGTTCGAGAAGA<br>ACAAGCTCCAAAGCGATGGCGTGTGCTTCGAGAAGATGGAGTACAAGCTGCTG<br>CCTGGCGCCAACAAGATGCTGCCAAAGGTGTTCTTCTCTAAGAGCAGAATCGA<br>TGAGTTCGGCCCTTCTCAGAGACTGCTGGACAGCTACCAGAACGAAACCCACA<br>AGAAGGGCGACAAATTCAACATCGAGGACTGTCACGAGCTGATCGACTTTTTC<br>AAAAGAAGCATCGACAAACATGAAGATTGGAGCAAGTTTTCTTTTAGCTTCAGC<br>GACACCAAGACCTACGAGGACCTGAGCGGCTTCTACAGAGAAGTAGAACACCA<br>GGGCTACATCCTGAGCTTTGTGAACGTGAGCGTGGATTACGTGAACAGCCTGG<br>TGGACGAGGGAAAGATCTACTTATTTCAGATCTACAACAAGGATTTCAGCCCTT<br>TCTCTAAGGGCACCCCTAACATGCACACACTGTACTGGAAGATGCTGTTCGAC<br>GAGGAAAACCTGAAGGATGTGGTGTACAAGCTGAATGGCCAGGCCGAAGTGT<br>TCTTCAGAAAGTCCTCTATCAAGTACGACAAACCTACCCATCCTGCCAATCTCC<br>CCATCGATAACAAGAACGTGAGCAACCACAAGAAGCGGAGCGTGTTCGAGTAC<br>GACCTGGTGAAGGACAAACGTTACACCGTGGATAAGTTCCAGTTCCACGTGCC<br>CGTGACCATCAACTTCAAGAGCGATGGCAACGGCAATATCAACCCCCTGGTGA<br>ACGACTACATCAAGAAGAGCGACGATCTACACGTGATCGGCATCGACAGAGGA<br>GAACGGCACCTGCTGTACCTGACGGTGATCGACATGAAGGGCAACATCAAGAA<br>ACAATTTAGCCTGAACGAGATCGTGAACGAATATAAGGGCAATACCTACAGCA<br>CCAACTACCACGACCTGCTGGAGAAACGGGAAGATAAGAGAGATAAGGAGAG<br>AAAGGAATGGAAAACCATTGAAACAATCAAGGAACTGAAAGAAGGATATCTGA<br>GCCAGGTGATCCACAAGATCACCGAGCTGATGGTGGAGTACAACGCCATCATC<br>GTCCTGGAGGACCTGAACCTGGGCTTCATGAGAGGGAGACAGAAGGTGGAGA<br>AGTCCGTATACCAGAAATTTGAAAAGATGCTGATCGACAAGCTGAACTACCTGG<br>CTGACAAGAAAAAGGAACCTGAGGACCTTGGAGGCGTCCTGAAGGCCTACCA<br>GCTGGCCAACAAATTCGAATCTTTCCAAAAGATGGGCAAACAGAGCGGCTTTC<br>TGTTTTACACCCAGGCTTGGAACACCAGCAAGATCGACCCCGTGACGGGCTTC<br>GTGAACCTCTTCGATACACATTACGAGAACATCCTGAAGAGCAAGAATTTCTTC<br>AGCAAGTTCGATCTCATCAAATATAACAGCGATAAAGATTGGTTCGAGTTCTCG<br>TTCGACTACAACAATTTCACCACCAAGGCCGAGGGCACCAAAACAAAGTGGAC<br>ACTGTGCACCTTCGGAAACAGAATCATCAGCTTTAGAAACCCTGACAACAACAT<br>GCAGTGGGATGGCAAGGAGATCAACCTGACAGAGGAGTTCAAGCTGTTCTTCG<br>AGAAGTTCGGCATCAACATCAACTCCGACCTGCACGCTGAGATCCTGAAGCAA<br>GACAAGAAGGACTTCTTCGAGGGCCTGCTGCACCTGCTGAAACTGACACTCCA<br>GATGCGGAACAGCAAGACGAGGACCGATATCGACTACATGCAGAGCCCCGTG<br>GCCGACGAGAATGGGGTGCTGTACAACTCCAACAAATGCGGCAAGAGCCTGC | 120 |

TABLE 1T-continued

| ZRXE Type V Cas Sequences | | |
|---|---|---|
| Name | Sequence | SEQ ID NO. |
| | CCGAGAACGCCGATGCCAACGGAGCCTACAACATCGCTAGAAAGGGACTGAT GATCATTGACAAGATCAAGAAGTCTGACAACCTGAACAAGATCGATCTGACTAT CTCTAACAAGGAATGGCTGGTGTTCGCCCAGAACAAGCCTTACCTGAAAAATtct agaAAGCGGACAGCAGACGGCTCCGAATTTGAAAGCCCTAAGAAAAAGAGAAA GGTGggatccGGCAAACCTATCCCCAATCCCCTGCTGGGCCTGGACAGCACCTG A | |

In some embodiments a ZRXE Type V Cas protein comprises an amino acid sequence of SEQ ID NO:115, SEQ ID NO:116, or SEQ ID NO:117. In some embodiments, a ZRXE Type V Cas protein has nickase activity, for example resulting from one or more amino acid substitutions relative to the sequence of SEQ ID NO:115, SEQ ID NO:116, or SEQ ID NO:117. In some embodiments, the one or more amino acid substitutions providing nickase activity comprise a D862 substitution, wherein the position of the D862 substitution is defined with respect to the amino acid numbering of SEQ ID NO:116 (corresponding to amino acid 908 of SEQ ID NO:121). In some embodiments, the one or more amino acid substitutions providing nickase activity comprise an E955 substitution, wherein the position of the E955 substitution is defined with respect to the amino acid numbering of SEQ ID NO:116 (corresponding to amino acid 993 of SEQ ID NO:121). In some embodiments, the one or more amino acid substitutions providing nickase activity comprise a R1167 substitution, wherein the position of the R1167 substitution is defined with respect to the amino acid numbering of SEQ ID NO:116 (corresponding to amino acid 1226 of SEQ ID NO:121). In some embodiments, the one or more amino acid substitutions providing nickase activity comprise a D1204 substitution, wherein the position of the D1204 substitution is defined with respect to the amino acid numbering of SEQ ID NO:116 (corresponding to amino acid 1263 of SEQ ID NO:121). In some embodiments, a ZRXE Type V Cas protein is catalytically inactive, for example due to a R1167 substitution in combination with a D862 substitution, a E955 substitution, and/or D1204 substitution.

6.2.21. Fusion and Chimeric Proteins

The disclosure provides Type V Cas proteins, e.g., a ZWGD Type V Cas protein, a ZJHK Type V Cas protein, a ZIKV Type V Cas protein, a ZZFT Type V Cas protein, a YYAN Type V Cas protein, a ZZGY Type V Cas protein, a ZKBG Type V Cas protein, a ZZKD Type V Cas protein, a ZXPB Type V Cas protein, a ZPPX Type V Cas protein, a ZXHQ Type V Cas protein, a ZQKH Type V Cas protein, a ZRGM Type V Cas protein, a ZTAE Type V Cas protein, a ZSQQ Type V Cas protein, a ZSYN Type V Cas protein, a ZRBH Type V Cas protein, a ZWPU Type V Cas protein, a ZZQE Type V Cas protein, and a ZRXE Type V Cas protein, which are in the form of fusion proteins comprising a Type V Cas protein sequence fused with one or more additional amino acid sequences, such as one or more nuclear localization signals and/or one or more non-native tags. Fusion proteins can also comprise an amino acid sequence of, for example, a nucleoside deaminase, a reverse transcriptase, a transcriptional activator (e.g., VP64), a transcriptional repressor (e.g., Krüppel associated box (KRAB)), a histone-modifying protein, an integrase, or a recombinase. Fusion proteins can include linker sequences joining different portions of the fusion protein. For example, glycine-serine linkers such as GS, SG, or GS or SG repeats, (e.g., GSGS (SEQ ID NO:259)). In some embodiments, one or more fusion partners (e.g., an adenosine deaminase or cytidine deaminase) is/are positioned N-terminal to a Type V Cas protein sequence. In some embodiments, one or more fusion partners (e.g., an adenosine deaminase or cytidine deaminase) is/are positioned C-terminal to a Type V Cas protein sequence.

In some embodiments, a fusion protein of the disclosure comprises a means for localizing the Type V Cas protein to the nucleus, for example a nuclear localization signal.

Non-limiting examples of nuclear localization signals include KRTADGSEFESPKKKRKV (SEQ ID NO:122), PKKKRKV (SEQ ID NO:123), PKKKRRV (SEQ ID NO:124), KRPAATKKAGQAKKKK (SEQ ID NO:125), YGRKKRRQRRR (SEQ ID NO:126), RKKRRQRRR (SEQ ID NO:127), PAAKRVKLD (SEQ ID NO:128), RQRRNELKRSP (SEQ ID NO:129), VSRKRPRP (SEQ ID NO:130), PPKKARED (SEQ ID NO:131), PQPKKKPL (SEQ ID NO:132), SALIKKKKKMAP (SEQ ID NO:133), PKQKKRK (SEQ ID NO:134), RKLKKKIKKL (SEQ ID NO:135), REKKKFLKRR (SEQ ID NO:136), KRKGDEVDGVDEVAKKKSKK (SEQ ID NO:137), RKCLQAGMNLEARKTKK (SEQ ID NO:138), NQSSNFGPMKGGNFGGRSSGPYGGGGQYFAKPRNQGGY (SEQ ID NO:139), RMRIZFKNKGKDTAELRRRRVEVSVELRKAKKDEQILKRRNV (SEQ ID NO:140), and SSDDEATADSQHAAPPKKKRKV (SEQ ID NO:178). Additional non-limiting examples of nuclear localization signals include PKKKRKVG (SEQ ID NO:179) and GRSSDDEATADSQHAAPPKKKRKV (SEQ ID NO:180).

Exemplary fusion partners include protein tags (e.g., V5-tag (e.g., having the sequence GKPIPNPLLGLDST (SEQ ID NO:141) or IPNPLLGLD (SEQ ID NO:142)), FLAG-tag, myc-tag, HA-tag, GST-tag, polyHis-tag, MBP-tag), protein domains, transcription modulators, enzymes acting on small molecule substrates, DNA, RNA and protein modification enzymes (e.g., adenosine deaminase, cytidine deaminase, guanosyl transferase, DNA methyltransferase, RNA methyltransferases, DNA demethylases, RNA demethylases, dioxygenases, polyadenylate polymerases, pseudouridine synthases, acetyltransferases, deacetylase, ubiquitin-ligases, deubiquitinases, kinases, phosphatases, NEDD8-ligases, de-NEDDylases, SUMO-ligases, deSUMOylases, histone deacetylases, reverse transcriptases, histone acetyltransferases histone methyltransferases, histone demethylases), protein DNA binding domains, RNA binding proteins, polypeptide sequences with specific biological functions (e.g., nuclear localization signals, mitochondrial localization signals, plastid localization signals, subcellular localization signals, destabilizing signals, Geminin destruction box motifs), and biological tethering domains (e.g., MS2, Csy4 and lambda N protein). Various Type V Cas fusion proteins are described in Ribeiro et al., 2018, In. J. Genomics, Article ID: 1652567; Jayavaradhan, et al., 2019, Nat Commun 10:2866; Xiao et al., 2019, The CRISPR Journal, 2(1):51-63; Mali et al., 2013, Nat Methods. 10(10):957-63; U.S. Pat. Nos. 9,322,037, and 9,388,430. In some embodiments, a fusion partner is an adenosine deaminase. An exemplary adenosine deaminase is the tRNA adenosine deaminase (TadA) moiety contained in the adenine base editor ABE8e (Richter, 2020, Nature Biotechnology 38:883-891). The TadA moiety of ABE8e comprises the following amino acid sequence:

(SEQ ID NO: 143)
SEVEFSHEYWMRHALTLAKRARDEREVPVGAVLVLNNRVIGEGWNRAI

GLHDPTAHAEIMALRQGGLVMQNYRLIDATLYVTFEPCVMCAGAMIHS

RIGRVVFGVRNSKRGAAGSLMNVLNYPGMNHRVEITEGILADECAALL

CDFYRMPRQVFNAQKKAQSSIN

In some embodiments, an adenosine deaminase fusion partner comprises an amino acid sequence having at least 50%, at least 60%, at least 70%, at least 80%, at least 90%, at least 95%, at least 97%, at least 98%, at least 99% amino acid sequence identity with SEQ ID NO:143.

Type V Cas proteins of the disclosure in the form of a fusion protein comprising an adenosine deaminase can be used, for example, as an adenine base editor (ABE) to change an "A" to a "G" in DNA. Type V Cas proteins of the disclosure in the form of a fusion protein comprising a cytidine deaminase can be used, for example, as a cytosine base editor (CBE) to change a "C" to a "T" in DNA.

In some embodiments, a fusion protein of the disclosure comprises a means for deaminating adenosine, for example an adenosine deaminase, e.g., a TadA variant. In some embodiments, a fusion protein of the disclosure comprises a means for deaminating cytidine, for example a cytidine deaminase, e.g., cytidine deaminase 1 (CDA1) or an apolipoprotein B mRNA-editing complex (APOBEC) family deaminase (see, e.g., Cheng et al., 2019, Nat Commun. 10(1):3612; Gehrke et al., 2018, Nat Biotechnol. 36(10): 977-982; Komor et al., 2016, Nature 533(7603):420-424, Porto and Komor, 2023, PLOS Biol 21(4):e3002071, the contents of each of which are incorporated herein by reference in their entireties).

Exemplary deaminases that can be used in fusion proteins of the disclosure are set forth in Table 2.

TABLE 2

| Name | Amino Acid Sequence | SEQ ID NO | Note | Addgene catalog #/ DOI reference |
|---|---|---|---|---|
| APOBEC1 | SSETGPVAVDPTLRRRIEPHEFEVFFDPRELRKET<br>CLLYEINWGGRHSIWRHTSQNTNKHVEVNFIEKFT<br>TERYFCPNTRCSITWFLSWSPCGECSRAITEFLSR<br>YPHVTLFIYIARLYHHADPRNRQGLRDLISSGVTIQI<br>MTEQESGYCWRNFVNYSPSNEAHWPRYPHLWV<br>RLYVLELYCIILGLPPCLNILRRKQPQLTFFTIALQS<br>CHYQRLPPHILWATGLK | 214 | | #87437 |
| evoAPOBEC | SSKTGPVAVDPTLRRRIEPHEFEVFFDPRELRKET<br>CLLYEINWGGRHSIWRHTSQNTNKHVEVNFIEKFT<br>TERYFCPNTRCSITWFLSWSPCGECSRAITEFLSR<br>YPNVTLFIYIARLYHLANPRNRQGLRDLISSGVTIQI<br>MTEQESGYCWHNFVNYSPSNESHWPRYPHLWV<br>RLYVLELYCIILGLPPCLNILRRKQSQLTSFTIALQS<br>CHYQRLPPHILWATGLK | 215 | APOBEC1<br>E4K H109N<br>H122L<br>D124N<br>R154H<br>A165S P201S<br>F205S | #122611 |
| YE1 | SSETGPVAVDPTLRRRIEPHEFEVFFDPRELRKET<br>CLLYEINWGGRHSIWRHTSQNTNKHVEVNFIEKFT<br>TERYFCPNTRCSITWFLSYSPCGECSRAITEFLSR<br>YPHVTLFIYIARLYHHADPENRQGLRDLISSGVTIQI<br>MTEQESGYCWRNFVNYSPSNEAHWPRYPHLWV<br>RLYVLELYCIILGLPPCLNILRRKQPQLTFFTIALQS<br>CHYQRLPPHILWATGLK | 216 | APOBEC1<br>W90Y<br>R126E | #138155 |
| FERNY | SFERNYDPRELRKETYLLYEIKWGKSGKLWRHWC<br>QNNRTQHAEVYFLENIFNARRFNPSTHCSITWYLS<br>WSPCAECSQKIVDFLKEHPNVNLEIYVARLYYHED<br>ERNRQGLRDLVNSGVTIRIMDLPDYNYCWKTFVS<br>DQGGDEDYWPGHFAPWIKQYSLKL | 217 | | #157944 |
| ppAPOBEC1 | TSEKGPSTGDPTLRRRIESWEFDVFYDPRELRKE<br>TCLLYEIKWGMSRKIWRSSGKNTTNHVEVNFIKKF<br>TSERRFHSSISCSITWFLSWSPCWECSQAIREFLS<br>QHPGVTLVIYVARLFWHMDQRNRQGLRDLVNSG<br>VTIQIMRASEYYHCWRNFVNYPPGDEAHWPQYPP<br>LWMMLYALELHCIILSLPPCLKISRRWQNHLAFFRL<br>HLQNCHYQTIPPHILLATGLIHPSVTWRLK | 218 | | #138349 |
| amAPOBEC1 | ADSSEKMRGQYISRDTFEKNYKPIDGTKEAHLLCE<br>IKWGKYGKPWLHWCQNQRMNIHAEDYFMNNIFK<br>AKKHPVHCYVTWYLSWSPCADCASKIVKFLEERP<br>YLKLTIYVAQLYYHTEEENRKGLRLLRSKKVIIRVM<br>DISDYNYCWKVFVSNQNGNEDYWPLQFDPWVKE<br>NYSRLLDIFWESKCRSPNPW | 219 | | #138342 |

TABLE 2-continued

| Name | Amino Acid Sequence | SEQ ID NO | Note | Addgene catalog #/ DOI reference |
|---|---|---|---|---|
| Anc689 | SSETGPVAVDPTLRRRIEPHEFEVFFDPRELRKET CLLYEIKWGTSHKIWRHSSKNTTKHVEVNFIEKFT SERHFCPSTSCSITWFLSWSPCGECSKAITEFLSQ HPNVTLVIYVARLYHHMDQQNRQGLRDLVNSGVT IQIMTAPEYDYCWRNFVNYPPGKEAHWPRYPPLW MKLYALELHAGILGLPPCLNILRRKQPQLTFFTIALQ SCHYQRLPPHILWATGLK | 220 | | #163526 |
| APOBEC A3A | EASPASGPRHLMDPHIFTSNFNNGIGRHKTYLCYE VERLDNGTSVKMDQHRGFLHNQAKNLLCGFYGR HAELRFLDLVPSLQLDPAQIYRVTWFISWSPCFSW GCAGEVRAFLQENTHVRLRIFAARIYDYDPLYKEA LQMLRDAGAQVSIMTYDEFKHCWDTFVDHQGCP FQPWDGLDEHSQALSGRLRAILQNQGN | 221 | | #113410 |
| APOBEC3 eA3A | EASPASGPRHLMDPHIFTSNFNNGIGRHKTYLCYE VERLDNGTSVKMDQHRGFLHGQAKNLLCGFYGR HAELRFLDLVPSLQLDPAQIYRVTWFISWSPCFSW GCAGEVRAFLQENTHVRLRIFAARIYDYDPLYKEA LQMLRDAGAQVSIMTYDEFKHCWDTFVDHQGCP FQPWDGLDEHSQALSGRLRAILQNQGN | 222 | APOBEC A3A N57G | #131315 |
| APOBEC A3B | NPQIRNPMERMYRDTFYDNFENEPILYGRSYTWL CYEVKIKRGRSNLLWDTGVFRGQVYFKPQYHAEM CFLSWFCGNQLPAYKCFQITWFVSWTPCPDCVAK LAEFLSEHPNVTLTISAARLYYYWERDYRRALCRL SQAGARVKIMDYEEFAYCWENFVYNEGQQFMPW YKFDENYAFLHRTLKEILRYLMDPDTFTFNFNNDP LVLRRRQTYLCYEVERLDNGTWVLMDQHMGFLC NEAKNLLCGFYGRHAELRFLDLVPSLQLDPAQIYR VTWFISWSPCFSWGCAGEVRAFLQENTHVRLRIF AARIYDYDPLYKEALQMLRDAGAQVSIMTYDEFEY CWDTFVYRQGCPFQPWDGLEEHSQALSGRLRAI LQNQGN | 223 | | #113411 |
| APOBEC A3C | NPQIRNPMKAMYPGTFYFQFKNLWEANDRNETW LCFTVEGIKRRSVVSWKTGVFRNQVDSETHCHAE RCFLSWFCDDILSPNTKYQVTWYTSWSPCPDCA GEVAEFLARHSNVNLTIFTARLYYFQYPCYQEGLR SLSQEGVAVEIMDYEDFKYCWENFVYNDNEPFKP WKGLKTNFRLLKRRLRESLQ | 224 | | #113412 #119136 |
| APOBEC A3D | NPQIRNPMERMYRDTFYDNFENEPILYGRSYTWL CYEVKIKRGRSNLLWDTGVFRGPVLPKRQSNHRQ EVYFRFENHAEMCFLSWFCGNRLPANRRFQITWF VSWNPCLPCVVKVTKFLAEHPNVTLTISAARLYYY RDRDWRWVLLRLHKAGARVKIMDYEDFAYCWEN FVCNEGQPFMPWYKFDDNYASLHRTLKEILRNPM EAMYPHIFYFHFKNLLKACGRNESWLCFTMEVTK HHSAVFRKRGVFRNQVDPETHCHAERCFLSWFC DDILSPNTNYEVTWYTSWSPCPECAGEVAEFLAR HSNVNLTIFTARLCYFWDTDYQEGLCSLSQEGAS VKIMGYKDFVSCWKNFVYSDDEPFKPWKGLQTNF RLLKRRLREILQ | 225 | | #119137 |
| APOBEC A3F | KPHFRNTVERMYRDTFSYNFYNRPILSRRNTVWL CYEVKTKGPSRPRLDAKIFRGQVYSQPEHHAEMC FLSWFCGNQLPAYKCFQITWFVSWTPCPDCVAKL AEFLAEHPNVTLTISAARLYYYWERDYRRALCRLS QAGARVKIMDDEEFAYCWENFVYSEGQPFMPWY KFDDNYAFLHRTLKEILRNPMEAMYPHIFYFHFKN LRKAYGRNESWLCFTMEVVKHHSPVSWKRGVFR NQVDPETHCHAERCFLSWFCDDILSPNTNYEVTW YTSWSPCPECAGEVAEFLARHSNVNLTIFTARLYY FWDTDYQEGLRSLSQEGASVEIMGYKDFKYCWE NFVYNDDEPFKPWKGLKYNFLFLDSKLQEILE | 226 | | #119138 |
| APOBEC A3G | KPHFRNTVERMYRDTFSYNFYNRPILSRRNTVWL CYEVKTKGPSRPPLDAKIFRGQVYSELKYHPEMR FFHWFSKWRKLHRDQEYEVTWYISWSPCTKCTR DMATFLAEDPKVTLTIFVARLYYFWDPDYQEALRS LCQKRDGPRATMKIMNYDEFQHCWSKFVYSQRE LFEPWNNLPKYYILLHIMLGEILRHSMDPPTFTFNF NNEPWVRGRHETYLCYEVERMHNDTWVLLNQRR GFLCNQAPHKHGFLEGRHAELCFLDVIPFWKLDL | 227 | | #119139 |

TABLE 2-continued

| Name | Amino Acid Sequence | SEQ ID NO | Note | Addgene catalog #/ DOI reference |
| --- | --- | --- | --- | --- |
| | DQDYRVTCFTSWSPCFSCAQEMAKFISKNKHVSLCIFTARIYDDQGRCQEGLRTLAEAGAKISIMTYSEFKHCWDTFVDHQGCPFQPWDGLDEHSQDLSGRLRAILQNQEN | | | |
| APOBEC A3H | ALLTAETFRLQFNNKRRLRRPYYPRKALLCYQLTPQNGSTPTRGYFENKKKCHAEICFINEIKSMGLDETQCYQVTCYLTWSPCSSCAWELVDFIKAHDHLNLGIFASRLYYHWCKPQQKGLRLLCGSQVPVEVMGFPEFADCWENFVDHEKPLSFNPYKMLEELDKNSRAIKRRLERIKQS | 228 | | #119140 |
| RrA3F | KPQIRDHRPNPMEAMYPHIFYFHFENLEKAYGRNETWLCFTVEIIKQYLPVPWKKGVFRNQVDPETHCHAEKCFLSWFCNNTLSPKKNYQVTWYTSWSPCPECAGEVAEFLAEHSNVKLTIYTARLYYFWDTDYQEGLRSLSEEGASVEIMDYEDFQYCWENFVYDDGEPFKRWKGLKYNFQSLTRRLREILQ | 229 | | #138340 |
| ss-APOBEC-3b | DPQRLRQWPGPGPASRGGYGQRPRIRNPEEWFHELSPRTFSFHFRNLRFASGRNRSYICCQVEGKNCFFQGIFQNQVPPDPPCHAELCFLSWFQSWGLSPDEHYYVTWFISWSPCCECAAKVAQFLEENRNVSLSLSAARLYYFWKSESREGLRRLSDLGAQVGIMSFQDFQHCWNNFVHNLGMPFQPWKKLHKNYQRLVTELKQILREEPATYGSPQAQGKVRIGSTAAGLRHSHSHTRSEAHLRPNHSSRQHRILNPPREARARTCVLVDASWICYR | 230 | | #138343 |
| AID | DSLLMNRRKFLYQFKNVRWAKGRRETYLCYVVKRRDSATSFSLDFGYLRNKNGCHVELLFLRYISDWDLDPGRCYRVTWFTSWSPCYDCARHVADFLRGNPNLSLRIFTARLYFCEDRKAEPEGLRRLHRAGVQIAIMTFKDYFYCWNTFVENHERTFKAWEGLHENSVRLSRQLRRILLPLYEVDDLRDAFRTLGL | 231 | | #100803 |
| AIDmono | DPATFTYQFKNVRWAKGRRETYLCYVVKRRDSATSFSLDFGYLRNKNGCHVELLFLRYISDWDLDPGRCYRVTWFTSWSPCYDCARHVADFLRGNPNLSLRIFTARLYFCEDRKAEPEGLRRLAEAGVQIAIMTFKDYFYCWNTFVENHERTFKAWEGLHENSVRLSRQLRRILQ | 232 | | DOI: 10.1016/j. celrep.2018. 09.090 |
| AID-3c | DPATFTYQFKNVRWAKGRRETYLCYVVKRRDSATSFSLDFGYLRNKNGCHVELLFLRYISDWDLDPGRCYRVTWFTSWSPCYDCARHVADFLRGNPNLSLRIFTARLYYFQYPCYQEGLRRLHRAGVQIAIMTFKDYFYCWNTFVENHERTFKAWEGLHENSVRLSRQLRRILQ | 233 | | DOI: 10.1016/j. celrep.2018. 09.090 |
| AID-3f | DPATFTYQFKNVRWAKGRRETYLCYVVKRRDSATSFSLDFGYLRNKNGCHVELLFLRYISDWDLDPGRCYRVTWFTSWSPCYDCARHVADFLRGNPNLSLRIFTARLYYFWDTDYQEGLRRLHRAGVQIAIMTFKDYFYCWNTFVENHERTFKAWEGLHENSVRLSRQLRRILQ | 234 | | DOI: 10.1016/j. celrep.2018. 09.090 |
| PmCDA1 | TDAEYVRIHEKLDIYTFKKQFFNNKKSVSHRCYVLFELKRRGERRACFWGYAVNKPQSGTERGIHAEIFSIRKVEEYLRDNPGQFTINWYSSWSPCADCAEKILEWYNQELRGNGHTLKIWACKLYYEKNARNQIGLWNLRDNGVGLNVMVSEHYQCCRKIFIQSSHNQLNENRWLEKTLKRAEKRRSELSIMIQVKILHTTKSPAV | 235 | | #100804 |
| ABE7.10 | **SEVEFSHEYWMRHALTLAKRAWDEREVPVGAVLVHNNRVIGEGWNRPIGRHDPTAHAEIMALRQGGLVMQNYRLIDATLYVTLEPCVMCAGAMIHSRIGRVVFGARDAKTGAAGSLMDVLHHPGMNHRVEITEGILADECAALLSDFFRMRRQEIKAQKKAQSSTD***SGGSSGGSSGSETPGTSESATPESSGGSSGGSSEVEFSHEYWMRHALTLAKRARDEREVPVGAVLVLNNRVIGEGWNRAIGLHDPTAHAEIMALRQGGLVMQNYRLIDATLYVTFEPCVMCAGAMIHSRIGRVVFGVRNAKTGAAGSLMDVLHYPGMNHRVEITEGILADECAALLCYFFRMPRQVFNAQKKAQSSTD* | 236 | **TadA** + *TadA** (with linker) | #102919 |

TABLE 2-continued

| Name | Amino Acid Sequence | SEQ ID NO | Note | Addgene catalog #/ DOI reference |
|---|---|---|---|---|
| ABE8e | SEVEFSHEYWMRHALTLAKRARDEREVPVGAVLVLNNRVIGEGWNRAIGLHDPTAHAEIMALRQGGLVMQNYRLIDATLYVTFEPCVMCAGAMIHSRIGRVVFGVRNSKRGAAGSLMNVLNYPGMNHRVEITEGILADECAALLCDFYRMPRQVFNAQKKAQSSIN | 237 | | #138489 |
| miniABE7.10 | SEVEFSHEYWMRHALTLAKRARDEREVPVGAVLVLNNRVIGEGWNRAIGLHDPTAHAEIMALRQGGLVMQNYRLIDATLYVTFEPCVMCAGAMIHSRIGRVVFGVRNAKTGAAGSLMDVLHYPGMNHRVEITEGILADECAALLCYFFRMPRQVFNAQKKAQSSTD | 238 | | DOI: 10.1038/ s41587-019-0236-6 |
| ABE6.3 | **SEVEFSHEYWMRHALTLAKRAWDEREVPVGAVLVHNNRVIGEGWNRPIGRHDPTAHAEIMALRQGGLVMQNYRLIDATLYVTLEPCVMCAGAMIHSRIGRVVFGARDAKTGAAGSLMDVLHHPGMNHRVEITEGILADECAALLSDFFRMRRQEIKAQKKAQSSTD***SGGSSGGSSGSETPGTSESATPESSGGSSGGSSEVEFSHEYWMRHALTLAKRAWDEREVPVGAVLVLNNRVIGEGWNRSIGLHDPTAHAEIMALRQGGLVMQNYRLIDATLYVTFEPCVMCAGAMIHSRIGRVVFGVRNAKTGAAGSLMDVLHYPGMNHRVEITEGILADECAALLCYFFRMRRQVFNAQKKAQSSTD* | 239 | **TadA** + *TadA** (with linker) | #102916 |
| ABE7.8 | **SEVEFSHEYWMRHALTLAKRAWDEREVPVGAVLVHNNRVIGEGWNRPIGRHDPTAHAEIMALRQGGLVMQNYRLIDATLYVTLEPCVMCAGAMIHSRIGRVVFGARDAKTGAAGSLMDVLHHPGMNHRVEITEGILADECAALLSDFFRMRRQEIKAQKKAQSSTD***SGGSSGGSSGSETPGTSESATPESSGGSSGGSSEVEFSHEYWMRHALTLAKRALDEREVPVGAVLVLNNRVIGEGWNRAIGLHDPTAHAEIMALRQGGLVMQNYRLIDATLYVTFEPCVMCAGAMIHSRIGRVVFGVRNAKTGAAGSLMDVLHYPGMNHRVEITEGILADECNALLCYFFRMRRQVFNAQKKAQSSTD* | 240 | **TadA** + *TadA** (with linker) | #102917 |
| ABE7.9 | **SEVEFSHEYWMRHALTLAKRAWDEREVPVGAVLVHNNRVIGEGWNRPIGRHDPTAHAEIMALRQGGLVMQNYRLIDATLYVTLEPCVMCAGAMIHSRIGRVVFGARDAKTGAAGSLMDVLHHPGMNHRVEITEGILADECAALLSDFFRMRRQEIKAQKKAQSSTD***SGGSSGGSSGSETPGTSESATPESSGGSSGGSSEVEFSHEYWMRHALTLAKRALDEREVPVGAVLVLNNRVIGEGWNRAIGLHDPTAHAEIMALRQGGLVMQNYRLIDATLYVTFEPCVMCAGAMIHSRIGRVVFGVRNAKTGAAGSLMDVLHYPGMNHRVEITEGILADECNALLCYFFRMPRQVFNAQKKAQSSTD* | 241 | **TadA** + *TadA** (with linker) | #194843 |
| ABE8.8-m | SEVEFSHEYWMRHALTLAKRARDEREVPVGAVLVLNNRVIGEGWNRAIGLHDPTAHAEIMALRQGGLVMQNYRLIDATLYVTFEPCVMCAGAMIHSRIGRVVFGVRNAKTGAAGSLMDVLHHPGMNHRVEITEGILADECAALLCRFFRMPRRVFNAQKKAQSSTD | 242 | ABE8 variant | DOI: 10.1038/ s41587-020-0491-6 |
| ABE8.8-d | SEVEFSHEYWMRHALTLAKRAWDEREVPVGAVLVHNNRVIGEGWNRPIGRHDPTAHAEIMALRQGGLVMQNYRLIDATLYVTLEPCVMCAGAMIHSRIGRVVFGARDAKTGAAGSLMDVLHHPGMNHRVEITEGILADECAALLSDFFRMRRQEIKAQKKAQSSTDSGGSSGGSSGSETPGTSESATPESSGGSSGGSSEVEFSHEYWMRHALTLAKRARDEREVPVGAVLVLNNRVIGEGWNRAIGLHDPTAHAEIMALRQGGLVMQNYRLIDATLYVTFEPCVMCAGAMIHSRIGRVVFGVRNAKTGAAGSLMDVLHHPGMNHRVEITEGILADECAALLCRFFRMPRRVFNAQKKAQSSTD | 243 | ABE8 variant | DOI: 10.1038/ s41587-020-0491-6 |
| ABE8.13-m | SEVEFSHEYWMRHALTLAKRARDEREVPVGAVLVLNNRVIGEGWNRAIGLHDPTAHAEIMALRQGGLVMQNYRLYDATLYVTFEPCVMCAGAMIHSRIGRVVFGVRNAKTGAAGSLMDVLHHPGMNHRVEITEGILADECAALLCRFFRMPRRVFNAQKKAQSSTD | 244 | ABE8 variant | DOI: 10.1038/ s41587-020-0491-6 |

TABLE 2-continued

| Name | Amino Acid Sequence | SEQ ID NO | Note | Addgene catalog #/ DOI reference |
|---|---|---|---|---|
| ABE8.13-d | SEVEFSHEYWMRHALTLAKRAWDEREVPVGAVL VHNNRVIGEGWNRPIGRHDPTAHAEIMALRQGGL VMQNYRLIDATLYVTLEPCVMCAGAMIHSRIGRVV FGARDAKTGAAGSLMDVLHHPGMNHRVEITEGIL ADECAALLSDFFRMRRQEIKAQKKAQSSTDSGGS SGGSSGSETPGTSESATPESSGGSSGGSSEVEF SHEYWMRHALTLAKRARDEREVPVGAVLVLNNRV IGEGWNRAIGLHDPTAHAEIMALRQGGLVMQNYR LYDATLYVTFEPCVMCAGAMIHSRIGRVVFGVRNA KTGAAGSLMDVLHHPGMNHRVEITEGILADECAAL LCRFFRMPRRVFNAQKKAQSSTD | 245 | ABE8 variant | DOI: 10.1038/ s41587-020- 0491-6 |
| ABE8.17-m | SEVEFSHEYWMRHALTLAKRARDEREVPVGAVLV LNNRVIGEGWNRAIGLHDPTAHAEIMALRQGGLV MQNYRLIDATLYSTFEPCVMCAGAMIHSRIGRVVF GVRNAKTGAAGSLMDVLHYPGMNHRVEITEGILA DECAALLCYFFRMPRRVFNAQKKAQSSTD | 246 | ABE8 variant | DOI: 10.1038/ s41587-020- 0491-6 |
| ABE8.17-d | SEVEFSHEYWMRHALTLAKRAWDEREVPVGAVL VHNNRVIGEGWNRPIGRHDPTAHAEIMALRQGGL VMQNYRLIDATLYVTLEPCVMCAGAMIHSRIGRVV FGARDAKTGAAGSLMDVLHHPGMNHRVEITEGIL ADECAALLSDFFRMRRQEIKAQKKAQSSTDSGGS SGGSSGSETPGTSESATPESSGGSSGGSSEVEF SHEYWMRHALTLAKRARDEREVPVGAVLVLNNRV IGEGWNRAIGLHDPTAHAEIMALRQGGLVMQNYR LIDATLYSTFEPCVMCAGAMIHSRIGRVVFGVRNA KTGAAGSLMDVLHYPGMNHRVEITEGILADECAAL LCYFFRMPRRVFNAQKKAQSSTD | 247 | ABE8 variant | DOI: 10.1038/ s41587-020- 0491-6 |
| ABE8.20-m | SEVEFSHEYWMRHALTLAKRARDEREVPVGAVLV LNNRVIGEGWNRAIGLHDPTAHAEIMALRQGGLV MQNYRLYDATLYSTFEPCVMCAGAMIHSRIGRVV FGVRNAKTGAAGSLMDVLHHPGMNHRVEITEGIL ADECAALLCRFFRMPRRVFNAQKKAQSSTD | 248 | ABE8 variant | DOI: 10.1038/ s41587-020- 0491-6 |
| ABE8.20-d | SEVEFSHEYWMRHALTLAKRAWDEREVPVGAVL VHNNRVIGEGWNRPIGRHDPTAHAEIMALRQGGL VMQNYRLIDATLYVTLEPCVMCAGAMIHSRIGRVV FGARDAKTGAAGSLMDVLHHPGMNHRVEITEGIL ADECAALLSDFFRMRRQEIKAQKKAQSSTDSGGS SGGSSGSETPGTSESATPESSGGSSGGSSEVEF SHEYWMRHALTLAKRARDEREVPVGAVLVLNNRV IGEGWNRAIGLHDPTAHAEIMALRQGGLVMQNYR LYDATLYSTFEPCVMCAGAMIHSRIGRVVFGVRNA KTGAAGSLMDVLHHPGMNHRVEITEGILADECAAL LCRFFRMPRRVFNAQKKAQSSTD | 249 | ABE8 variant | DOI: 10.1038/ s41587-020- 0491-6 |

In some embodiments, a deaminase fusion partner comprises an amino acid sequence having at least 50%, at least 60%, at least 70%, at least 80%, at least 90%, at least 95%, at least 97%, at least 98%, at least 99%, or 100% amino acid sequence identity to an amino acid sequence set forth in Table 2. The amino acid sequences shown in Table 2 are shown without an N-terminal methionine; an N-terminal methionine can be added, for example when the deaminase amino acid sequence is at the N-terminal end of the molecule.

In some embodiments, a fusion protein of the disclosure comprises a deaminase, e.g., as described in Table 2 and a uracil glycosylase inhibitor (UGI) domain (e.g., as described in Wu et al., 2022, Mol. Cell 82(23):4487-4502, the contents of which are incorporated herein by reference in their entireties.) An exemplary UGI domain comprises the amino acid sequence (SEQ ID NO: 250)
TNLSDIIEKETGKQLVIQESILMLPEEVEEVIGNKPESDILVHTAYDE

STDENVMLLTSDAPEYKPWALVIQDSNGENKIKML

Type V Cas proteins of the disclosure in the form of a fusion protein comprising a transcriptional repressor or an effector domain thereof can be used, for example, to silence genes via epigenome editing (see, e.g., Cappelluti et al., 2024 Nature 627:416-423, the contents of which are incorporated herein by reference in their entireties). Exemplary effector domains are described in Table 3.

TABLE 3

| Name | Amino Acid Sequence | SEQ ID NO |
|---|---|---|
| KRAB | ALSPQHSAVTQGSIIKNKEGMDAKSLTAWSRTLVTFKDVFVDFTREEWKLLDTAQQI VYRNVMLENYKNLVSLGYQLTKPDVILRLEKGEEPWLVEREIHQETHPDSETAFEIKS SV | 251 |
| KRAB alternative | SRTLVTFKDVFVDFTREEWKLLDTAQQIVYRNVMLENYKNLVSLGYQLTKPDVILRLE KGEEPWLV | 252 |
| cdDNMT3A | GTYGLLRRREDWPSRLQMFFANNHDQEFDPPKVYPPVPAEKRKPIRVLSLFDGIAT GLLVLKDLGIQVDRYIASEVCEDSITVGMVRHQGKIMYVGDVRSVTQKHIQEWGPFD LVIGGSPCNDLSIVNPARKGLYEGTGRLFFEFYRLLHDARPKEGDDRPFFWLFENVV AMGVSDKRDISRFLESNPVMIDAKEVSAAHRARYFWGNLPGMNRPLASTVNDKLEL QECLEHGRIAKFSKVRTITTRSNSIKQGKDQHFPVFMNEKEDILWCTEMERVFGFPV HYTDVSNMSRLARQRLLGRSWSVPVIRHLFAPLKEYFACV | 253 |
| DNMT3L | AAIPALDPEAEPSMDVILVGSSELSSSVSPGTGRDLIAYEVKANQRNIEDICICCGSLQ VHTQHPLFEGGICAPCKDKFLDALFLYDDDGYQSYCSICCSGETLLICGNPDCTRCY CFECVDSLVGPGTSGKVHAMSNWVCYLCLPSSRSGLLQRRRKWRSQLKAFYDRE SENPLEMFETVPVWRRQPVRVLSLFEDIKKELTSLGFLESGSDPGQLKHVVDVTDT VRKDVEEWGPFDLVYGATPPLGHTCDRPPSWYLFQFHRLLQYARPKPGSPRPFFW MFVDNLVLNKEDLDVASRFLEMEPVTIPDVHGGSLQNAVRVWSNIPAIRSRHWALVS EEELSLLAQNKQSSKLAAKWPTKLVKNCFLPLREYFKYFSTELTSSL | 254 |
| DNMT3A-DNMT3L dimer | NHDQEFDPPKVYPPVPAEKRKPIRVLSLFDGIATGLLVLKDLGIQVDRYIASEVCEDSI TVGMVRHQGKIMYVGDVRSVTQKHIQEWGPFDLVIGGSPCNDLSIVNPARKGLYEG TGRLFFEFYRLLHDARPKEGDDRPFFWLFENVVAMGVSDKRDISRFLESNPVMIDA KEVSAAHRARYFWGNLPGMNRPLASTVNDKLELQECLEHGRIAKFSKVRTITTRSN SIKQGKDQHFPVFMNEKEDILWCTEMERVFGFPVHYTDVSNMSRLARQRLLGRSW SVPVIRHLFAPLKEYFACVSSGNSNANSRGPSFSSGLVPLSLRGSHMAAIPALDPEA EPSMDVILVGSSELSSSVSPGTGRDLIAYEVKANQRNIEDICICCGSLQVHTQHPLFE GGICAPCKDKFLDALFLYDDDGYQSYCSICCSGETLLICGNPDCTRCYCFECVDSLV GPGTSGKVHAMSNWVCYLCLPSSRSGLLQRRRKWRSQLKAFYDRESENPLEMFE TVPVWRRQPVRVLSLFEDIKKELTSLGFLESGSDPGQLKHVVDVTDTVRKDVEEWG PFDLVYGATPPLGHTCDRPPSWYLFQFHRLLQYARPKPGSPRPFFWMFVDNLVLNK EDLDVASRFLEMEPVTIPDVHGGSLQNAVRVWSNIPAIRSRHWALVSEEELSLLAQN KQSSKLAAKWPTKLVKNCFLPLREYFKYFSTELTSSL | 255 |

In some embodiments, an effector domain fusion partner comprises an amino acid sequence having at least 50%, at least 60%, at least 70%, at least 80%, at least 90%, at least 95%, at least 97%, at least 98%, at least 99%, or 100% amino acid sequence identity to an amino acid sequence set forth in Table 3. The amino acid sequences shown in Table 3 are shown without an N-terminal methionine; an N-terminal methionine can be added, for example when the effector domain amino acid sequence is at the N-terminal end of the molecule.

In some embodiments, a fusion protein of the disclosure comprises a means for synthesizing DNA from a single-stranded template, for example a reverse transcriptase, e.g., a MMLV reverse transcriptase (see, WO 2021/226558, the contents of which are incorporated herein by reference in their entireties). An exemplary reverse transcriptase comprises the amino acid sequence (SEQ ID NO: 256)

TLNIEDEYRLHETSKEPDVSLGSTWLSDFPQAWAETGGMGLAVRQAPLIIPLKATSTPVSIKQYPMSQEA

RLGIKPHIQRLLDQGILVPCQSPWNTPLLPVKKPGTNDYRPVQDLREVNKRVEDIHPTVPNPYNLLSGLPP

SHQWYTVLDLKDAFFCLRLHPTSQPLFAFEWRDPEMGISGQLTWTRLPQGFKNSPTLFNEALHRDLADF

RIQHPDLILLQYVDDLLLAATSELDCQQGTRALLQTLGNLGYRASAKKAQICQKQVKYLGYLLKEGQRWL

TEARKETVMGQPTPKTPRQLREFLGKAGFCRLFIPGFAEMAAPLYPLTKPGTLFNWGPDQQKAYQEIKQ

ALLTAPALGLPDLTKPFELFVDEKQGYAKGVLTQKLGPWRRPVAYLSKKLDPVAAGWPPCLRMVAAIAVLT

KDAGKLTMGQPLVILAPHAVEALVKQPPDRWLSNARMTHYQALLLDTDRVQFGPVVALNPATLLPLPEEG

LQHNCLDILAEAHGTRPDLTDQPLPDADHTWYTDGSSLLQEGQRKAGAAVTTETEVIWAKALPAGTSAQ

RAELIALTQALKMAEGKKLNVYTDSRYAFATAHIHGEIYRRRGWLTSEGKEIKNKDEILALLKALFLPKRLSII

HCPGHQKGHSAEARGNRMADQAARKAAITETPDTSTLLIENSSP (see, Chen et al., 2021, Cell 184(22): 5635-5652, the contents of which are incorporated herein by reference in their entireties).

Another exemplary reverse transcriptase comprises the amino acid sequence (SEQ ID NO: 257)

ISSSKHTLSQMNKVSNIVKEPELPDIYKEFKDITADTNTEKLPKPIKGLEFEVELTQENYRLPIRNYPLTPVK

MQAMNDEINQGLKGGIIRESKAINACPVIFVPRKEGTLRMVVDYRPLNKYVKPNVYPLPLIEQLLAKIQGST

IFTKLDLKSAYHQIRVRKGDEHKLAFRCPRGVFEYLVMPYGIKTAPAHFQYFINTILGEAKESHVVCYMDDI

LIHSKSESEHVKHVKDVLQKLKNANLIINQAKCEFHQSQVKFLGYHISEKGLTPCQENIDKVLQWKQPKNQ

KELRQFLGQVNYLRKFIPKTSQLTHPLNKLLKKDVRWKWTPTQTQAIENIKQCLVSPPVLRHFDFSKKILLE

TDVSDVAVGAVLSQKHDDDKYYPVGYYSAKMSKAQLNYSVSDKEMLAIIKSLEHWRHYLESTIEPFKILTD

HRNLIGRITNESEPENKRLARWQLFLQDFNFEINYRPGSANHIADALSRIVDETEPIPKDNEDNSINFVNQI

SIS (see, Doman et al., 2023, Cell 186(18): 3983-4002, the contents of which are incorporated herein by reference in their entireties).

In some embodiments, a reverse transcriptase fusion partner comprises an amino acid sequence having at least 50%, at least 60%, at least 70%, at least 80%, at least 90%, at least 95%, at least 97%, at least 98%, at least 99%, or 100% amino acid sequence identity to SEQ ID NO:256 or SEQ ID NO:257.

Type V Cas proteins of the disclosure in the form of a fusion protein comprising a reverse transcriptase (RT) can be used as a prime editor to carry out precise DNA editing without double-stranded DNA breaks.

In some embodiments, a Type V Cas protein described herein can be used for prime editing, e.g., with different Circular RNA-mediated Prime Editors (CPEs) for various editing scenarios: for example a nickase-dependent CPE (niCPE), a nuclease-dependent CPE (nuCPE), a split nickase-dependent CPE (sniCPE), or a split nuclease-dependent CPE (snuCPE) (Liang et al., 2004, Nature Biotechnology doi.org/10.1038/s41587-023-02095-x).

In some embodiments, a fusion protein of the disclosure comprises one or more nuclear localization signals positioned N-terminal and/or C-terminal to a Type V Cas protein sequence (e.g., a Type V Cas protein comprising an amino acid sequence set forth in Section 6.2). In some embodiments, a fusion protein of the disclosure comprises a C-terminal nuclear localization signal, for example having the sequence KRTADGSEFESPKKKRKV (SEQ ID NO:122). In some embodiments, a fusion protein of the disclosure comprises a N-terminal nuclear localization signal, for example having the sequence KRTADGSEFESPKKKRKV (SEQ ID NO:122). In some embodiments, a fusion protein of the disclosure comprises a N-terminal and a C-terminal nuclear localization signal, for example each having the sequence KRTADGSEFESPKKKRKV (SEQ ID NO:122).

The disclosure provides chimeric Type V Cas proteins comprising one or more domains of an ZWGD Type V Cas protein and one or more domains of one or more different proteins (e.g., one or more different Type V Cas proteins); a chimeric Type V Cas proteins comprising one or more domains of an ZJHK Type V Cas protein and one or more domains of one or more different proteins (e.g., one or more different Type V Cas proteins); a chimeric Type V Cas proteins comprising one or more domains of an ZIKV Type V Cas protein and one or more domains of one or more different proteins (e.g., one or more different Type V Cas proteins); a chimeric Type V Cas proteins comprising one or more domains of an ZZFT Type V Cas protein and one or more domains of one or more different proteins (e.g., one or more different Type V Cas proteins); a chimeric Type V Cas proteins comprising one or more domains of an YYAN Type V Cas protein and one or more domains of one or more different proteins (e.g., one or more different Type V Cas proteins); a chimeric Type V Cas proteins comprising one or more domains of an ZZGY Type V Cas protein and one or more domains of one or more different proteins (e.g., one or more different Type V Cas proteins); a chimeric Type V Cas proteins comprising one or more domains of an ZKBG Type V Cas protein and one or more domains of one or more different proteins (e.g., one or more different Type V Cas proteins); a chimeric Type V Cas proteins comprising one or more domains of an ZZKD Type V Cas protein and one or more domains of one or more different proteins (e.g., one or more different Type V Cas proteins); a chimeric Type V Cas proteins comprising one or more domains of an ZXPB Type V Cas protein and one or more domains of one or more different proteins (e.g., one or more different Type V Cas proteins); a chimeric Type V Cas proteins comprising one or more domains of an ZPPX Type V Cas protein and one or more domains of one or more different proteins (e.g., one or more different Type V Cas proteins); a chimeric Type V Cas proteins comprising one or more domains of an ZXHQ Type V Cas protein and one or more domains of one or more different proteins (e.g., one or more different Type V Cas proteins); a chimeric Type V Cas proteins comprising one or more domains of an ZQKH Type V Cas protein and one or more domains of one or more different proteins (e.g., one or more different Type V Cas proteins); a chimeric Type V Cas proteins comprising one or more domains of an ZRGM Type V Cas protein and one or more domains of one or more different proteins (e.g., one or more different Type V Cas proteins); a chimeric Type V Cas proteins comprising one or more domains of an ZTAE Type V Cas protein and one or more domains of one or more different proteins (e.g., one or more different Type V Cas proteins); a chimeric Type V Cas proteins comprising one or more domains of an ZSQQ Type V Cas protein and one or more domains of one or more different proteins (e.g., one or more different Type V Cas proteins); a chimeric Type V Cas proteins comprising one or more domains of an ZSYN Type V Cas protein and one or more domains of one or more different proteins (e.g., one or more different Type V Cas proteins); a chimeric Type V Cas proteins comprising one or more domains of an ZRBH Type V Cas protein and one or more domains of one or more different proteins (e.g., one or more different Type V Cas proteins); a chimeric Type V Cas proteins comprising one or more domains of an ZWPU Type V Cas protein and one or more domains of one or more different proteins (e.g., one or more different Type V Cas proteins); a chimeric Type V Cas proteins comprising one or more domains of an ZZQE Type V Cas protein and one or more domains of one or more different proteins (e.g., one or more different Type V Cas proteins); a chimeric Type V Cas proteins comprising one or more domains of an ZRXE Type V Cas protein and one or more domains of one or more different proteins (e.g., one or more different Type V Cas proteins).

The domain structures of the Type V Cas proteins described herein were inferred by multiple alignment with the amino acid sequences of Type V Cas proteins for which the crystal structure is known and for which it is thus possible to define the boundaries of each functional domain. The domains identified in Type V Cas proteins are: wedge (WED) domain (WED-1 domain, WED-II domain, WED-III domain), the RuvC catalytic domain (discontinuous, represented by RuvC-I domain, RuvC-II domain, RuvCIII domain), recognition (REC) domain (REC1 domain, REC2 domain), PAM-interacting domain (PI domain), bridge helix (BH domain), and nuclease (NUC) domain, Table 4 below report the amino acid positions corresponding to the boundaries between different functional domains in full-length wild-type ZWGD (SEQ ID NO:2), ZJHK (SEQ ID NO:8), ZIKV (SEQ ID NO:14), ZZFT (SEQ ID NO:20), YYAN (SEQ ID NO:26), ZZGY (SEQ ID NO:32), ZKBG (SEQ ID NO:38), ZZKD (SEQ ID NO:44), ZXPB (SEQ ID NO:50), ZPPX (SEQ ID NO:56), ZXHQ (SEQ ID NO:62), ZQKH (SEQ ID NO:68), ZRGM (SEQ ID NO:74), ZTAE (SEQ ID NO:80), ZSQQ (SEQ ID NO:86), ZSYN (SEQ ID NO:92), ZRBH (SEQ ID NO:98), ZWPU (SEQ ID NO:104), ZZQE (SEQ ID NO:110), and ZRXE (SEQ ID NO:116) Type V Cas proteins.

TABLE 4

Amino Acid Positions of Domains of Exemplified Type V Cas Proteins

| Type V Cas | WED-I | REC1 | REC2 | WED-II | PI | WED-III | RuvC-I | BH | RuvC-II | NUC | RuvC-III |
|---|---|---|---|---|---|---|---|---|---|---|---|
| ZRGM | 1-24 | 25-291 | 292-506 | 507-574 | 575-699 | 700-866 | 867-926 | 927-943 | 944-1053 | 1054-1235 | 1236-1284 |
| ZZGY | 1-23 | 24-307 | 308-518 | 519-590 | 591-710 | 711-880 | 881-944 | 945-961 | 962-1070 | 1071-1252 | 1253-1302 |
| ZRXE | 1-23 | 24-304 | 305-545 | 546-615 | 616-706 | 707-838 | 839-901 | 902-918 | 919-1026 | 1027-1202 | 1203-1252 |
| ZRBH | 1-23 | 24-294 | 295-531 | 532-602 | 603-693 | 694-827 | 828-886 | 887-903 | 904-1011 | 1012-1187 | 1188-1235 |
| ZSYN | 1-26 | 27-340 | 341-573 | 574-649 | 650-740 | 741-873 | 874-937 | 938-954 | 955-1062 | 1063-1237 | 1238-1283 |
| ZKBG | 1-23 | 24-302 | 303-530 | 531-599 | 600-723 | 724-857 | 858-924 | 925-941 | 942-1053 | 1054-1232 | 1233-1271 |
| ZXHQ | 1-26 | 27-289 | 290-524 | 525-600 | 601-691 | 692-811 | 812-909 | 910-926 | 927-1039 | 1040-1209 | 1210-1262 |
| ZZQE | 1-25 | 26-307 | 308-542 | 543-612 | 613-703 | 704-835 | 836-898 | 899-915 | 916-1023 | 1024-1199 | 1200-1249 |
| YYAN | 1-22 | 23-291 | 292-517 | 518-589 | 590-677 | 678-814 | 815-874 | 875-891 | 892-997 | 998-1168 | 1169-1215 |
| ZQKH | 1-25 | 26-248 | 249-443 | 444-504 | 505-609 | 610-720 | 721-777 | 778-794 | 795-904 | 905-1089 | 1090-1133 |
| ZZFT | 1-23 | 24-296 | 297-524 | 525-595 | 596-698 | 699-829 | 830-895 | 896-912 | 913-1024 | 1025-1201 | 1202-1245 |
| ZIKV | 1-23 | 24-281 | 282-496 | 497-564 | 565-667 | 668-790 | 791-845 | 846-862 | 863-970 | 971-1146 | 1147-1195 |
| ZWPU | 1-26 | 27-296 | 297-526 | 527-596 | 597-688 | 689-821 | 822-884 | 885-901 | 902-1009 | 1010-1193 | 1194-1243 |
| ZPPX | 1-20 | 21-299 | 300-536 | 537-606 | 607-719 | 720-853 | 854-915 | 916-932 | 933-1040 | 1041-1215 | 1216-1264 |
| ZZKD | 1-24 | 25-290 | 291-513 | 514-582 | 583-673 | 674-804 | 805-871 | 872-888 | 889-996 | 997-1174 | 1175-1220 |
| ZSQQ | 1-26 | 27-309 | 310-548 | 549-617 | 618-720 | 721-887 | 888-952 | 953-969 | 970-1077 | 1078-1262 | 1263-1310 |
| ZJHK | 1-24 | 25-285 | 286-515 | 516-585 | 586-710 | 711-876 | 877-933 | 934-950 | 951-1061 | 1062-1242 | 1243-1294 |
| ZWGD | 1-30 | 31-310 | 311-563 | 564-638 | 639-732 | 733-867 | 868-936 | 937-953 | 954-1060 | 1061-1246 | 1247-1292 |
| ZTAE | 1-22 | 23-322 | 323-550 | 551-624 | 625-715 | 716-881 | 882-936 | 937-953 | 954-1061 | 1062-1241 | 1242-1289 |
| ZXPB | 1-22 | 23-275 | 276-504 | 505-574 | 575-665 | 666-797 | 798-852 | 853-869 | 870-977 | 978-1151 | 1152-1201 |

A chimeric Type V Cas protein can comprise one of more of the following domains (e.g., one or more, two or more, three or more, four or more, five or more, six or more, seven or more) from a ZWGD Type V Cas protein, a ZJHK Type V Cas protein, a ZIKV Type V Cas protein, a ZZFT Type V Cas protein, a YYAN Type V Cas protein, a ZZGY Type V Cas protein, a ZKBG Type V Cas protein, a ZZKD Type V Cas protein, a ZXPB Type V Cas protein, a ZPPX Type V Cas protein, a ZXHQ Type V Cas protein, a ZQKH Type V Cas protein, a ZRGM Type V Cas protein, a ZTAE Type V Cas protein, a ZSQQ Type V Cas protein, a ZSYN Type V Cas protein, a ZRBH Type V Cas protein, a ZWPU Type V Cas protein, a ZZQE Type V Cas protein, and/or a ZRXE Type V Cas protein, and one or more domains from one or more other proteins, for example Cas12a: WED-1 domain, REC1 domain, REC2 domain, WED-II domain, PI domain, WED-III domain, RuvC-I domain, BH domain, RuvC-II domain, NUC domain, or RuvC-III domain. For example, the PID domain can be swapped between different Type V Cas proteins to change the PAM specificity of the resulting chimeric protein (which is given by the donor PID domain). Swapping of other domains or portions of them is also within the scope of the disclosure (e.g., through protein shuffling).

In some embodiments, a Type V Cas protein of the disclosure comprises one, two, three, four, five, six, seven, or eight of a WED-1 domain, REC1 domain, REC2 domain, WED-II domain, PI domain, WED-III domain, RuvC-I domain, BH domain, RuvC-II domain, NUC domain, or RuvC-III domain arranged in the N-terminal to C-terminal direction. In some embodiments, all domains are from one Type V Cas protein as described herein, e.g., ZWGD, ZJHK, ZIKV), ZZFT, YYAN, ZZGY, ZKBG, ZZKD, ZXPB, ZPPX, ZXHQ, ZQKH, ZRGM, ZTAE, ZSQQ, ZSYN, ZRBH, ZWPU, ZZQE, or ZRXE. In other embodiments, one or more domains (e.g., one domain), e.g., a PID domain, is from another Type V Cas protein, for example a Cas12a protein from *Alicyclobacillus acidoterrestris, Bacillus thermoamylovorans, Lachnospiraceae bacterium* (e.g., LbCas12a, NCBI Reference Sequence WP_051666128.1), *Acidaminococcus* sp. BV3L6 (e.g., AsCas12a, NCBI Reference Sequence WP_021736722.1), *Arcobacter butzleri* L348 (e.g., AbCas12a, GeneBank ID: JAIQ01000039.1), *Agathobacter rectalis* strain 2789STDY5834884 (e.g., ArCas12a, GeneBank ID: CZAJ01000001.1), *Bacteroidetes oraltaxon* 274 str. F0058 (e.g., BoCas12a, GeneBank ID: NZ_GG774890.1), *Butyrivibrio* sp. NC3005 (e.g., BsCas12a, GeneBank ID: NZ_AUKC01000013.1), Candidate division WS6 bacterium GW2011_GWA2_37_6 US52_C0007 (e.g., C6Cas12a, GeneBank ID: LBTH01000007.1), *Helcococcus kunzii* ATCC 51366 (e.g., HkCas12a, GeneBank ID: JH601088.1/AGEI01000022.1), *Lachnospira pectinoschiza* strain 2789STDY5834836 (e.g., LpCas12a, GeneBank ID: CZAK01000004), *Oribacterium* sp. NK2B42 (e.g., OsCas12a, GeneBank ID: NZ_KE384190.1), *Pseudobutyrivibrio ruminis* CF1b (e.g., PrCas12a, GeneBank ID: NZ_KE384121.1), *Proteocatella sphenisci* DSM 23131 (e.g., PsCas12a, GeneBank ID: NZ_KE384028.1), *Pseudobutyrivibrio xylanivorans* strain DSM 10317 (e.g., PxCas12a, GeneBank ID: FMWK01000002.1), *Sneathia amniistrain* SN35 (e.g., SaCas12a, GeneBank ID: CP011280.1), *Francisella novicida*, or *Leptotrichia shahii*. In addition, one or more amino acid substitutions can be introduced in one or more domains to modify the properties of the resulting nuclease in terms of editing activity, targeting specificity or PAM recognition specificity. For example, one or more amino acid substitutions can be introduced to provide nickase activity. Exemplary amino acid substitutions in Cas12a providing nickase activity are the D908, E993, R1226 and D1263. Corresponding substitutions can be introduced into the Type V Cas nucleases of the disclosure to provide nickases and catalytically inactive Cas proteins. Positions corresponding to such Cas12a positions for Type V Cas proteins of the disclosure as shown in Table 5. Nickases and catalytically inactive Type V Cas proteins of the disclosure can be used, for example, in base editors comprising a cytosine or adenosine deaminase fusion partner. Catalytically inactive Type V Cas proteins can also be used, for example, as fusion partners for transcriptional activators or repressors.

TABLE 5

| Type V Cas Protein | Position corresponding to D908 of AsCas12a | Position corresponding to E993 of AsCas12a | Position corresponding to R1226 of AsCas12a | Position corresponding to D1263 of AsCas12a | Reference SEQ ID NO defining amino acid numbering |
|---|---|---|---|---|---|
| ZWGD | 891 | 990 | 1200 | 1248 | 2 |
| ZJHK | 900 | 987 | 1203 | 1244 | 8 |
| ZIKV | 814 | 899 | 1111 | 1148 | 14 |
| ZZFT | 856 | 949 | 1166 | 1203 | 20 |
| YYAN | 838 | 928 | 1135 | 1170 | 26 |
| ZZGY | 905 | 998 | 1214 | 1254 | 32 |
| ZKBG | 885 | 978 | 1194 | 1234 | 38 |
| ZZKD | 828 | 925 | 1138 | 1176 | 44 |
| ZXPB | 821 | 906 | 1116 | 1153 | 50 |
| ZPPX | 877 | 969 | 1181 | 1217 | 56 |
| ZXHQ | 836 | 963 | 1172 | 1211 | 62 |
| ZQKH | 744 | 831 | 1048 | 1091 | 68 |
| ZRGM | 890 | 980 | 1194 | 1237 | 74 |
| ZTAE | 905 | 990 | 1206 | 1243 | 80 |
| ZSQQ | 913 | 1006 | 1219 | 1264 | 86 |
| ZSYN | 902 | 991 | 1200 | 1239 | 92 |
| ZRBH | 851 | 940 | 1152 | 1189 | 98 |
| ZWPU | 845 | 938 | 1153 | 1195 | 104 |
| ZZQE | 859 | 952 | 1164 | 1201 | 110 |
| ZRXE | 862 | 955 | 1167 | 1204 | 116 |

6.3. Guide RNAs

The disclosure provides crRNA scaffolds and gRNA molecules that can be used with Type V Cas proteins of the disclosure to edit genomic DNA, for example mammalian DNA, e.g., human DNA. gRNAs of the disclosure typically comprise a spacer of 15 to 30 nucleotides in length. The spacer can be positioned 3' of a crRNA scaffold to form a full gRNA.

An exemplary crRNA scaffold sequence that can be used for ZWGD Type V Cas gRNAs comprises (SEQ ID NO: 144)
ACGAUUAGAAAUAAUUUCUACUGUUGUAGAU.

An exemplary crRNA scaffold sequence that can be used for ZJHK Type V Cas gRNAs comprises (SEQ ID NO: 145)
CUUUGAAAGAAUAUAAUUUCUACUGAAAGUGUAGAU.

An exemplary crRNA scaffold sequence that can be used for ZIKV Type V Cas gRNAs comprises (SEQ ID NO: 146)
GUUUAAUAAUAAUACAUAAUUUCUACUAUUGUAGAU.

An exemplary crRNA scaffold sequence that can be used for ZZFT Type V Cas gRNAs comprises (SEQ ID NO: 147)
GUCUAUAAGACUAAUUUAAUUUCUACUAUUGUAGAU.

An exemplary crRNA scaffold sequence that can be used for YYAN Type V Cas gRNAs comprises (SEQ ID NO: 148)
GUUUAUAAACCUUAUCUAAUUUCUACUGUUGUAGAU.

An exemplary crRNA scaffold sequence that can be used for ZZGY Type V Cas gRNAs comprises (SEQ ID NO: 149)
UCUAAAGCUCUUUAAGAAUUUCUACUUUCGUAGAU.

An exemplary crRNA scaffold sequence that can be used for ZKBG Type V Cas gRNAs comprises (SEQ ID NO: 150)
CUAAGAGGCUCAAAUAAUUUCUACUAUUGUAGAU.

An exemplary crRNA scaffold sequence that can be used for ZZKD Type V Cas gRNAs comprises (SEQ ID NO: 151)
CCUUUGGAAGUACUAAGAAUUUCUACUGUUGUAGAU.

An exemplary crRNA scaffold sequence that can be used for ZZKD Type V Cas gRNAs comprises (SEQ ID NO: 211)
GAAUUUCUACUGUUGUAGAU.

An exemplary crRNA scaffold sequence that can be used for ZXPB Type V Cas gRNAs comprises (SEQ ID NO: 152)
GGCUAUAAAAGCCAUAUAAUUUCUACUAUUGUAGAU.

An exemplary crRNA scaffold sequence that can be used for ZPPX Type V Cas gRNAs comprises (SEQ ID NO: 153)
GACUAUUAAGUCUUUUGAAUUUCUACUGUUGUAGAU.

An exemplary crRNA scaffold sequence that can be used for ZXHQ Type V Cas gRNAs comprises (SEQ ID NO: 154)
UCUAGAAUAUAUAGGUAAUUUCUACUUAUGUAGAU.

An exemplary crRNA scaffold sequence that can be used for ZQKH Type V Cas gRNAs comprises (SEQ ID NO: 155)
GGCAAUAAGCCAUAUACAAUUUCUACUGUAUGUAGAU.

An exemplary crRNA scaffold sequence that can be used for ZRGM Type V Cas gRNAs comprises (SEQ ID NO: 156)
GUCUGAAAGACUAUAUAAUUUCUACUUCGUGUAGAU.

An exemplary crRNA scaffold sequence that can be used for ZRGM Type V Cas gRNAs comprises (SEQ ID NO: 213)
AAUUUCUACUUCGUGUAGAU.

-continued

An exemplary crRNA scaffold sequence that can be used for ZTAE Type V Cas gRNAs comprises (SEQ ID NO: 157)
GUCUACGGAACGUCUGUAAUUUCUACUGUUGUAGAU.

An exemplary crRNA scaffold sequence that can be used for ZSQQ Type V Cas gRNAs comprises (SEQ ID NO: 158)
UUUAAACGAACUAUUAAAUUUCUACUGUUGUAGAU.

An exemplary crRNA scaffold sequence that can be used for ZSYN Type V Cas gRNAs comprises (SEQ ID NO: 159)
GUUUAAUACUUAUAUAUAAUUUCUACUAUUGUAGAU.

An exemplary crRNA scaffold sequence that can be used for ZRBH Type V Cas gRNAs comprises (SEQ ID NO: 160)
AAUAAUAAUCCCUUAUAAUUUCUACUUUUGUAGAU.

An exemplary crRNA scaffold sequence that can be used for ZWPU Type V Cas gRNAs comprises (SEQ ID NO: 161)
GUCUAUAAGACGAACUAAAUUUCUACUAUUGUAGAU.

An exemplary crRNA scaffold sequence that can be used for ZZQE Type V Cas gRNAs comprises (SEQ ID NO: 162)
GGCUACUAAGCCUUUAUAAUUUCUACUAUUGUAGAU.

An exemplary crRNA scaffold sequence that can be used for ZZQE Type V Cas gRNAs comprises (SEQ ID NO: 212)
UAAUUUCUACUAUUGUAGAU.

An exemplary crRNA scaffold sequence that can be used for ZRXE Type V Cas gRNAs comprises (SEQ ID NO: 163)
GUCUAUAAAGACGAAUGAAUUUCUACUAUUGUAGAU.

Type V Cas gRNAs of the disclosure are generally 40-70 nucleotides long (e.g., 50 to 60 nucleotides long, 55 to 65 nucleotides long, or 55 to 60 nucleotides long), but gRNAs of other lengths are also contemplated. For example, a crRNA scaffold described herein can be trimmed to a shorter length or extended at the 5' end (e.g., as described in Park et al., 2018, Nature Communications, 9:3313), which can be helpful for enhancing gene editing efficacy. Additionally, gRNAs of the disclosure can optionally be chemically modified, which can be useful, for example, to enhance serum stability of a gRNA (see, e.g., Park et al., 2018, Nature Communications, 9:3313). Chemical modifications are further discussed in Section 6.3.2.

Further optimization of the structure can be obtained by introducing targeted base changes into the stems of the gRNA to increase their stability and folding. Such base changes will preferably correspond to the introduction of G:C couples, which are known to generate the strongest Watson-Crick pairing. For the sake of clarity, these substitutions can consist in the introduction of a G or a C in a specific position of a stem together with a complementary substitution in another position of the gRNA sequence which is predicted to base pair with the former, for example according to available bioinformatic tools for RNA folding such as UNAfold or RNAfold.

Stem-loop trimming can also be exploited to stabilize desired secondary structures by removing portions of the guide RNA producing unwanted secondary structures through annealing with other regions of the RNA molecule 6.3.1. Spacers The spacer sequence is partially or fully complementary to a target sequence found in a genomic DNA sequence, for example a human genomic DNA sequence. For example, a spacer sequence can be partially or fully complementary to a nucleotide sequence in a gene having a disease causing mutation. A spacer that is partially complementary to a target sequence can have, for example, one, two, or three mismatches with the target sequence.

gRNAs of the disclosure can comprise a spacer that is 15 to 30 nucleotides in length (e.g., 15 to 25, 16 to 24, 17 to 23, 18 to 22, 19 to 21, 18 to 30, 20 to 28, 22 to 26, or 23 to 25 nucleotides in length). In some embodiments, a spacer is 15 nucleotides in length. In other embodiments, a spacer is 16 nucleotides in length. In other embodiments, a spacer is 17 nucleotides in length. In other embodiments, a spacer is 18 nucleotides in length. In other embodiments, a spacer is 19 nucleotides in length. In other embodiments, a spacer is 20 nucleotides in length. In other embodiments, a spacer is 21 nucleotides in length. In other embodiments, a spacer is 22 nucleotides in length. In other embodiments, a spacer is 23 nucleotides in length. In other embodiments, a spacer is 24 nucleotides in length. In other embodiments, a spacer is 25 nucleotides in length. In other embodiments, a spacer is 26 nucleotides in length. In other embodiments, a spacer is 27 nucleotides in length. In other embodiments, a spacer is 28 nucleotides in length. In other embodiments, a spacer is 29 nucleotides in length. In other embodiments, a spacer is 30 nucleotides in length.

Type V Cas endonucleases require a specific sequence, called a protospacer adjacent motif (PAM) that is upstream (e.g., directly upstream) of the target sequence on the non-target strand. Thus, spacer sequences for targeting a gene of interest can be identified by scanning the gene for PAM sequences recognized by the Type V Cas protein.

Exemplary PAM sequences for Type V Cas proteins of the disclosure are shown in Table 6A-4B. In addition, TTTV is a canonical PAM sequence for Type V-A Cas proteins, and it expected that Type V Cas proteins of the disclosure can recognize the TTTV PAM.

TABLE 6A

| Exemplary Type V Cas Protein PAM Sequences (in silico determined) | |
|---|---|
| Cas Protein | PAM Sequence |
| ZWGD | TTN |
| ZJHK | TTTN |
| ZIKV | TTTR |
| ZZFT | TTTN, TTTR |
| YYAN | TTTN |
| ZZGY | TTTN, TTTR |
| ZKBG | YTTN |
| ZZKD | TTTN |
| ZXPB | TTTN |
| ZPPX | YTTN, TTN |
| ZZQE | YTTV |

TABLE 6B

| Exemplary Type V Cas Protein PAM Sequences (in vitro determined) | |
|---|---|
| Cas protein | PAM Sequence |
| ZZKD | NTTV, VTTV, NCTV, TTTT |
| ZRGM | YTTV |
| ZZQE | NYYN, NTTN, NCTV |

Section 7 describes exemplary sequences that can be used to target B2M, TRAC and PD1 genes. Section 7 further describes exemplary sequences that can be used to target AAVS1, BCL11A, EMX1, PCSK9, VEGFA, and Match6 genomic sequences. Exemplary spacer sequences that can be used in gRNAs of the disclosure are set forth in Table 7. In some embodiments, a gRNA of the disclosure comprises a spacer sequence targeting TRAC. In some embodiments, a gRNA of the disclosure comprises a spacer sequence targeting B2M. In some embodiments, a gRNA of the disclosure comprises a spacer sequence targeting PD1. In some embodiments, a gRNA of the disclosure comprises a spacer sequence targeting AAVS1. In some embodiments, a gRNA of the disclosure comprises a spacer sequence targeting BCL11A. In some embodiments, a gRNA of the disclosure comprises a spacer sequence targeting EMX1. In some embodiments, a gRNA of the disclosure comprises a spacer sequence targeting PCSK9. In some embodiments, a gRNA of the disclosure comprises a spacer sequence targeting VEGFA. In some embodiments, a gRNA of the disclosure comprises a spacer sequence targeting Match6.

TABLE 7

| Exemplary Spacer Sequences Targeting Endogenous Genomic Loci | | | |
|---|---|---|---|
| Guide ID | Target | Spacer (5'→3') | SEQ ID NO. |
| B2M-g1 | B2M | UGGCCUGGAGGCUAUCCAGCGUG | 164 |
| B2M-g2 | B2M | CUCACGUCAUCCAGCAGAGAAUG | 165 |
| B2M-g3 | B2M | ACUUUCCAUUCUCUGCUGGAUGA | 166 |
| B2M-g4 | B2M | CUGAAUUGCUAUGUGUCUGGGUU | 167 |
| B2M-g5 | B2M | AAUUCUCUCUCCAUUCUUCAGUA | 168 |
| B2M-g8 | B2M | GUGUCAAGCUAUAUCAGGCACCA | 181 |
| B2M-g9 | B2M | AUGUGUCUUUUCCCGAUAUUCCU | 182 |
| B2M-g1_21 nt | B2M | UGGCCUGGAGGCUAUCCAGCG | 183 |
| TRAC-g1 | TRAC | AGAAUCAAAAUCGGUGAAUAGGC | 169 |
| TRAC-g2 | TRAC | UGACACAUUUGUUUGAGAAUCAA | 170 |
| TRAC-g3 | TRAC | GAGUCUCUCAGCUGGUACACGGC | 171 |
| TRAC-g4 | TRAC | UCUGUGAUAUACACAUCAGAAUC | 172 |
| TRAC-g5 | TRAC | AUUCUCAAACAAAUGUGUCACAA | 173 |
| TRAC-g6 | TRAC | UCACUGGAUUUAGAGUCUCUCAG | 184 |
| TRAC-g9 | TRAC | GAUUCUCAAACAAAUGUGUCACA | 185 |
| TRAC-g11 | TRAC | AAGAGGGAAAUGAGAUCAUGUCC | 186 |
| TRAC-g13 | TRAC | ACCGAUUUUGAUUCUCAAACAAA | 187 |
| TRAC-g15 | TRAC | GUCUGUGAUAUACACAUCAGAAU | 188 |

TABLE 7-continued

Exemplary Spacer Sequences Targeting Endogenous Genomic Loci

| Guide ID | Target | Spacer (5'→3') | SEQ ID NO. |
|---|---|---|---|
| TRAC g3_20 nt | TRAC | GAGUCUCUCAGCUGGUACAC | 189 |
| TRAC g3_21 nt | TRAC | GAGUCUCUCAGCUGGUACACG | 190 |
| TRAC g3_22 nt | TRAC | GAGUCUCUCAGCUGGUACACGG | 191 |
| TRAC g3_24 nt | TRAC | GAGUCUCUCAGCUGGUACACGGCA | 192 |
| PD1-g1 | PD1 | CCUUCCGCUCACCUCCGCCUGAG | 174 |
| PD1-g2 | PD1 | GCACGAAGCUCUCCGAUGUGUUG | 175 |
| PD1-g3 | PD1 | AUCUGCGCCUUGGGGGCCAGGGA | 176 |
| PD1-g4 | PD1 | GAACUGGCCGGCUGGCCUGGGUG | 177 |
| AAVS1-g1 | AAVS1 | AUUUGGGCAGCUCCCCUACCCCC | 193 |
| AAVS1-g2 | AAVS1 | GGCAGCUCCCCUACCCCCCUUAC | 194 |
| AAVS1-g6 | AAVS1 | CAGGGGUCCGAGAGCUCAGCUAG | 195 |
| AAVS1-g7 | AAVS1 | AUCUGUCCCCUCCACCCCACAGU | 196 |
| EMX1-g2 | EMX1 | UACUUUGUCCUCCGGUUCUGGAA | 197 |
| EMX1-g3 | EMX1 | UCCUCCGGUUCUGGAACCACACC | 198 |
| BCL11A-g1 | BCL11A | AGCCAUCUCACUACAGAUAACUC | 199 |
| BCL11A-g2 | BCL11A | AAGCUAGUCUAGUGCAAGCUAAC | 200 |
| BCL11A-g3 | BCL11A | GCCUCUGAUUAGGGUGGGGGCGU | 201 |
| BCL11A-g4 | BCL11A | UCACAGGCUCCAGGAAGGGUU | 202 |
| PCSK9-g1 | PCSK9 | UCUGCCACCCACCUCCUCACCUU | 203 |
| PCSK9-g2 | PSCK9 | CAGGUCAUCACAGUUGGGGCCAC | 204 |
| VEGFA-g1 | VEGFA | GAGAGUGAGGACGUGUGUGUC | 205 |
| Match6_20 nt | Match6 | GGGUGAUCAGACCCAACAGC | 206 |
| Match6_21 nt | Match6 | GGGUGAUCAGACCCAACAGCA | 207 |
| Match6_22 nt | Match6 | GGGUGAUCAGACCCAACAGCAG | 208 |
| Match6_23 nt | Match6 | GGGUGAUCAGACCCAACAGCAGG | 209 |
| Match6_24 nt | Match6 | GGGUGAUCAGACCCAACAGCAGGU | 210 |

In some embodiments, a gRNA of the disclosure has a spacer whose nucleotide sequence comprises 15 or more consecutive nucleotides from a sequence shown in Table 7. In some embodiments, a gRNA of the disclosure has a spacer whose nucleotide sequence comprises 16 or more consecutive nucleotides from a sequence shown in Table 7. In some embodiments, a gRNA of the disclosure has a spacer whose nucleotide sequence comprises 17 or more consecutive nucleotides from a sequence shown in Table 7. In some embodiments, a gRNA of the disclosure has a spacer whose nucleotide sequence comprises 18 or more consecutive nucleotides from a sequence shown in Table 7. In some embodiments, a gRNA of the disclosure has a spacer whose nucleotide sequence comprises 19 or more consecutive nucleotides from a sequence shown in Table 7. In some embodiments, a gRNA of the disclosure has a spacer whose nucleotide sequence comprises 20 or more consecutive nucleotides from a sequence shown in Table 7. In some embodiments, a gRNA of the disclosure has a spacer whose nucleotide sequence comprises 21 or more consecutive nucleotides from a sequence shown in Table 7. In some embodiments, a gRNA of the disclosure has a spacer whose nucleotide sequence comprises 22 or more consecutive nucleotides from a sequence shown in Table 7. In some embodiments, a gRNA of the disclosure has a spacer whose nucleotide sequence comprises 23 or more consecutive nucleotides from a sequence shown in Table 5. In some embodiments, a gRNA of the disclosure has a spacer whose nucleotide sequence comprises a sequence shown in Table 7.

6.3.2. Modified gRNA Molecules

Guide RNAs can be readily synthesized by chemical means, enabling a number of modifications to be readily incorporated, as described in the art. The disclosed gRNA (e.g., sgRNA) molecules can be unmodified or can contain any one or more of an array of chemical modifications.

While chemical synthetic procedures are continually expanding, purifications of such RNAs by procedures such as high-performance liquid chromatography (HPLC, which avoids the use of gels such as PAGE) tends to become more challenging as polynucleotide lengths increase significantly beyond a hundred or so nucleotides. One approach that can be used for generating chemically modified RNAs of greater length is to produce two or more molecules that are ligated together. Much longer RNAs, such as those encoding a Type V Cas endonuclease, are more readily generated enzymatically. While fewer types of modifications are available for use in enzymatically produced RNAs, there are still modifications that can be used to, for instance, enhance stability, reduce the likelihood or degree of innate immune response, and/or enhance other attributes, as described herein and in the art.

By way of illustration of various types of modifications, especially those used frequently with smaller chemically synthesized RNAs, modifications can comprise one or more nucleotides modified at the 2' position of the sugar, for instance a 2'-O-alkyl, 2'-O-alkyl-O-alkyl, or 2'-fluoro-modified nucleotide. In some examples, RNA modifications can comprise 2'-fluoro, 2'-amino or 2'-O-methyl modifications on the ribose of pyrimidines, abasic residues, or an inverted base at the 3' end of the RNA. Such modifications can be routinely incorporated into oligonucleotides and these oligonucleotides have been shown to have a higher Tm (thus, higher target binding affinity) than 2'-deoxyoligonucleotides against a given target.

A number of nucleotide and nucleoside modifications have been shown to make the oligonucleotide into which they are incorporated more resistant to nuclease digestion than the native oligonucleotide; these modified oligos survive intact for a longer time than unmodified oligonucleotides. Specific examples of modified oligonucleotides include those comprising modified backbones, for example, phosphorothioates, phosphotriesters, methyl phosphonates, short chain alkyl or cycloalkyl intersugar linkages or short chain heteroatomic or heterocyclic intersugar linkages. Some oligonucleotides are oligonucleotides with phosphorothioate backbones and those with heteroatom backbones, particularly $CH_2$—NH—O—$CH_2$, CH, ~N($CH_3$)—O—$CH_2$ (known as a methylene (methylimino) or MMI backbone), $CH_2$—O—N($CH_3$)—$CH_2$, $CH_2$—N($CH_3$)—N($CH_3$)—$CH_2$ and O—N($CH_3$)—$CH_2$—$CH_2$ backbones, wherein the native phosphodiester backbone is represented as O—P—O—CH); amide backbones (see De Mesmaeker et al. 1995, Ace. Chem. Res., 28:366-374); morpholino backbone structures (see U.S. Pat. No. 5,034,506); peptide nucleic acid (PNA) backbone (wherein the phosphodiester backbone of the oligonucleotide is replaced with a polyamide backbone, the nucleotides being bound directly or indirectly to the aza nitrogen atoms of the polyamide backbone, see Nielsen et al., 1991, Science 254:1497). Phosphorus-containing linkages include, but are not limited to, phosphorothioates, chiral phosphorothioates, phosphorodithioates, phosphotriesters, aminoalkylphosphotriesters, methyl and other alkyl phosphonates comprising 3'alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'; see U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050.

Morpholino-based oligomeric compounds are described in Braasch and David Corey, 2002, Biochemistry, 41(14): 4503-4510; Genesis, Volume 30, Issue 3, (2001); Heasman, 2002, Dev. Biol., 243:209-214; Nasevicius et al., 2000, Nat. Genet., 26:216-220; Lacerra et al., 2000, Proc. Natl. Acad. Sci., 97: 9591-9596; and U.S. Pat. No. 5,034,506.

Cyclohexenyl nucleic acid oligonucleotide mimetics are described in Wang et al., 2000, J. Am. Chem. Soc., 122: 8595-8602.

Modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These comprise those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S, and $CH_2$ component parts; see U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439.

One or more substituted sugar moieties can also be included, e.g., one of the following at the 2' position: OH, SH, $SCH_3$, F, OCN, $OCH_3$, $OCH_3O(CH_2)n\ CH_3$, $O(CH_2)n\ NH_2$, or $O(CH_2)n\ CH_3$, where n is from 1 to about 10; $C_1$ to $C_{10}$ lower alkyl, alkoxyalkoxy, substituted lower alkyl, alkaryl or aralkyl; Cl; Br; CN; $CF_3$; $OCF_3$; O-, S-, or bi-alkyl; O-, S-, or N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. In some aspects, a modification includes 2'-methoxyethoxy (2'-O—$CH_2CH_2OCH_3$, also known as 2'-O-(2-methoxyethyl)) (Martin et al., 1995, Helv. Chim. Acta, 78, 486). Other modifications include 2'-methoxy (2'-O—$CH_3$), 2'-propoxy (2'-$OCH_2\ CH_2CH_3$) and 2'-fluoro (2'-F). Similar modifications can also be made at other positions on the oligonucleotide, particularly the 3' position of the sugar on the 3' terminal nucleotide and the 5' position of 5' terminal nucleotide. Oligonucleotides can also have sugar mimetics, such as cyclobutyls in place of the pentofuranosyl group.

In some examples, both a sugar and an internucleoside linkage (in the backbone) of the nucleotide units can be replaced with novel groups. The base units can be maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide can be replaced with an amide containing backbone, for example, an aminoethylglycine backbone.

The nucleobases can be retained and bound directly or indirectly to aza nitrogen atoms of the amide portion of the backbone. Representative U.S. patents that teach the preparation of PNA compounds include, but are not limited to, U.S. Pat. Nos. 5,539,082; 5,714,331; and 5,719,262. Further teaching of PNA compounds can be found in Nielsen et al., 1991, Science, 254: 1497-1500.

RNAs such as guide RNAs can also include, additionally or alternatively, nucleobase (often referred to in the art simply as "base") modifications or substitutions. As used herein, "unmodified" or "natural" nucleobases include adenine (A), guanine (G), thymine (T), cytosine (C), and uracil (U). Modified nucleobases include nucleobases found only infrequently or transiently in natural nucleic acids, e.g., hypoxanthine, 6-methyladenine, 5-Me pyrimidines, particularly 5-methylcytosine (also referred to as 5-methyl-2' deoxy cytosine and often referred to in the art as 5-Me-C), 5-hydroxymethylcytosine (HMC), glycosyl HMC and gentobiosyl HMC, as well as synthetic nucleobases, e.g., 2-aminoadenine, 2-(methylamino) adenine, 2-(imidazolylalkyl) adenine, 2-(aminoalklyamino) adenine or other heterosubstituted alkyladenines, 2-thiouracil, 2-thiothymine, 5-bromouracil, 5-hydroxymethyluracil, 8-azaguanine, 7-deazaguanine, N6 (6-aminohexyl) adenine, and 2,6-diaminopurine. Komberg, A., DNA Replication, W. H. Freeman & Co., San Francisco, pp. 75-77 (1980); Gebeyehu et al., Nucl. Acids Res. 15:4513 (1997). A "universal" base known in the art, e.g., inosine, can also be included. 5-Me-C substitutions have been shown to increase nucleic acid duplex stability by about 0.6-1.2° C. (Sanghvi, Y. S., in Crooke, S. T. and Lebleu, B., eds., Antisense Research and Applications, CRC Press, Boca Raton, 1993, pp. 276-278) and are aspects of base substitutions.

Modified nucleobases can comprise other synthetic and natural nucleobases, such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudo-uracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylquanine and 7-methyladenine, 8-azaguanine and 8-azaadenine, 7-deazaguanine and 7-deazaadenine, and 3-deazaguanine and 3-deazaadenine.

Further, nucleobases can comprise those disclosed in U.S. Pat. No. 3,687,808, those disclosed in 'The Concise Encyclopedia of Polymer Science and Engineering', 858-859, Kroschwitz, J. I., ed. John Wiley & Sons, 1990, those disclosed by Englisch et al., Angewandle Chemie, International Edition', 1991, 30, p. 613, and those disclosed by Sanghvi, Y. S., Chapter 15, Antisense Research and Applications', 289-302, Crooke, S. T. and Lebleu, B. ea., CRC Press, 1993. Certain of these nucleobases can be useful for increasing the binding affinity of the oligomeric compounds of the invention. These include 5-substituted pyrimidines, 6-azapyrimidines and N-2, N-6 and O-6 substituted purines, comprising 2-aminopropyladenine, 5-propynyluracil and 5-propynylcytosine. 5-methylcytosine substitutions have been shown to increase nucleic acid duplex stability by about 0.6-1.2° C. (Sanghvi, Y. S., Crooke, S. T. and Lebleu, B., eds, 'Antisense Research and Applications', CRC Press, Boca Raton, 1993, 276-278) and are aspects of base substitutions, even more particularly when combined with 2'-O-methoxyethyl sugar modifications. Modified nucleobases are described in U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,596,091; 5,614,617; 5,681,941; 5,750,692; 5,763,588; 5,830,653; 6,005,096; and U.S. Patent Application Publication 2003/0158403.

Thus, a modified gRNA can include, for example, one or more non-natural sugars, internucleotide linkages and/or bases. It is not necessary for all positions in a given gRNA to be uniformly modified, and in fact more than one of the aforementioned modifications can be incorporated in a single oligonucleotide, or even in a single nucleoside within an oligonucleotide.

The guide RNAs and/or mRNA (or DNA) encoding an endonuclease can be chemically linked to one or more moieties or conjugates that enhance the activity, cellular distribution, or cellular uptake of the oligonucleotide. Such moieties comprise, but are not limited to, lipid moieties such as a cholesterol moiety (Letsinger et al. 1989, Proc. Natl. Acad. Sci. USA, 86: 6553-6556); cholic acid (Manoharan et al, 1994, Bioorg. Med. Chem. Let., 4: 1053-1060); a thioether, e.g., hexyl-S-tritylthiol (Manoharan et al, 1992, Ann. N. Y. Acad. Sci., 660: 306-309; Manoharan et al., 1993, Bioorg. Med. Chem. Let., 3: 2765-2770); a thiocholesterol (Oberhauser et al., 1992, Nucl. Acids Res., 20: 533-538); an aliphatic chain, e.g., dodecandiol or undecyl residues (Kabanov et al, 1990, FEBS Lett., 259: 327-330; Svinarchuk et al, 1993, Biochimie, 75: 49-54); a phospholipid, e.g., di-hexadecyl-rac-glycerol or triethylammonium 1,2-di-O-hexadecyl-rac-glycero-3-H-phosphonate (Manoharan et al., 1995, Tetrahedron Lett., 36: 3651-3654; and Shea et al, 1990, Nucl. Acids Res., 18: 3777-3783); a polyamine or a polyethylene glycol chain (Mancharan et al, 1995, Nucleosides & Nucleotides, 14: 969-973); adamantane acetic acid (Manoharan et al, 1995, Tetrahedron Lett., 36: 3651-3654); a palmityl moiety (Mishra et al., 1995, Biochim. Biophys. Acta, 1264: 229-237); or an octadecylamine or hexylamino-carbonyl-t oxycholesterol moiety (Crooke et al, 1996, J. Pharmacol. Exp. Ther., 277: 923-937). See also U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

Sugars and other moieties can be used to target proteins and complexes comprising nucleotides, such as cationic polysomes and liposomes, to particular sites. For example, hepatic cell directed transfer can be mediated via asialoglycoprotein receptors (ASGPRs); see, e.g., Hu, et al., 2014, Protein Pept Lett. 21(10):1025-30. Other systems known in the art and regularly developed can be used to target biomolecules of use in the present case and/or complexes thereof to particular target cells of interest.

Targeting moieties or conjugates can include conjugate groups covalently bound to functional groups, such as primary or secondary hydroxyl groups. Conjugate groups of the present disclosure include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this present disclosure, include groups that improve uptake, enhance resistance to degradation, and/or strengthen sequence-specific hybridization with the target nucleic acid. Groups that enhance the pharmacokinetic properties, in the context of this disclosure, include groups that improve uptake, distribution, metabolism or excretion of the compounds of the present disclosure. Representative conjugate groups are disclosed in International Patent Application Publication WO1993007883, and U.S. Pat. No. 6,287,860. Conjugate moieties include, but are not limited to, lipid moieties such as a cholesterol moiety, cholic acid, a thioether, e.g., hexyl-5-trityl thiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxy cholesterol moiety. See, e.g., U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

A large variety of modifications have been developed and applied to enhance RNA stability, reduce innate immune responses, and/or achieve other benefits that can be useful in connection with the introduction of polynucleotides into human cells, as described herein; see, e.g., the reviews by Whitehead K A et al., 2011, Annual Review of Chemical and Biomolecular Engineering, 2: 77-96; Gaglione and Messere, 2010, Mini Rev Med Chem, 10(7):578-95; Chernolovskaya et al, 2010, Curr Opin Mol Ther., 12(2): 158-67; Deleavey et al., 2009, Curr Protoc Nucleic Acid Chem Chapter 16: Unit 16.3; Behlke, 2008, Oligonucleotides 18(4):305-19; Fucini et al, 2012, Nucleic Acid Ther 22(3): 205-210; Bremsen et al, 2012, Front Genet 3:154.

6.4. Systems

The disclosure provides systems comprising a Type V Cas protein of the disclosure (e.g., as described in Section 6.2) and a means for targeting the Type V Cas protein to a target genomic sequence. The means for targeting the Type V Cas protein to a target genomic sequence can be a guide RNA (gRNA) (e.g., as described in Section 6.3).

The disclosure also provides systems comprising a Type V Cas protein of the disclosure (e.g., as described in Section 6.2) and a gRNA (e.g., as described in Section 6.3). The systems can comprise a ribonucleoprotein particle (RNP) in which a Type V Cas protein is complexed with a gRNA. Systems of the disclosure can in some embodiments further comprise genomic DNA complexed with the Type V Cas protein and the gRNA. Accordingly, the disclosure provides systems comprising a Type V Cas protein, a genomic DNA, and gRNA, all complexed with one another.

The systems of the disclosure can exist within a cell (whether the cell is in vivo, ex vivo, or in vitro) or outside a cell (e.g., in a particle our outside of a particle).

6.5. Nucleic Acids

The disclosure provides nucleic acids (e.g., DNA or RNA) encoding Type V Cas proteins (e.g., a ZWGD Type V Cas protein, a ZJHK Type V Cas protein, a ZIKV Type V Cas protein, a ZZFT Type V Cas protein, a YYAN Type V Cas protein, a ZZGY Type V Cas protein, a ZKBG Type V Cas protein, a ZZKD Type V Cas protein, a ZXPB Type V Cas protein, a ZPPX Type V Cas protein, a ZXHQ Type V Cas protein, a ZQKH Type V Cas protein, a ZRGM Type V Cas protein, a ZTAE Type V Cas protein, a ZSQQ Type V Cas protein, a ZSYN Type V Cas protein, a ZRBH Type V Cas protein, a ZWPU Type V Cas protein, a ZZQE Type V Cas protein, or a ZRXE Type V Cas protein), nucleic acids encoding gRNAs of the disclosure (e.g., a single gRNA or combination of gRNAs), nucleic acids encoding both Type V Cas proteins and gRNAs, and pluralities of nucleic acids, for example comprising a nucleic acid encoding a Type V Cas protein and a gRNA.

A nucleic acid encoding a Type V Cas protein and/or gRNA can be, for example, a plasmid or a viral genome (e.g., a lentivirus, retrovirus, adenovirus, or adeno-associated virus genome). Plasmids can be, for example, plasmids for producing virus particles, e.g., lentivirus particles, or plasmids for propagating the Type V Cas and gRNA coding sequences in bacterial (e.g., *E. coli*) or eukaryotic (e.g., yeast) cells.

A nucleic acid encoding a Type V Cas protein can, in some embodiments, further encode a gRNA. Alternatively, a gRNA can be encoded by a separate nucleic acid (e.g., DNA or mRNA).

Nucleic acids encoding a Type V Cas protein can be codon optimized, e.g., where at least one non-common codon or less-common codon has been replaced by a codon that is common in a host cell. For example, a codon optimized nucleic acid can direct the synthesis of an optimized messenger mRNA, e.g., optimized for expression in a mammalian expression system. As an example, if the intended target nucleic acid is within a human cell, a human codon-optimized polynucleotide encoding Type V Cas can be used for producing a Type V Cas polypeptide. Exemplary codon-optimized sequences are shown in Tables 1A to 1T.

Nucleic acids of the disclosure, e.g., plasmids and viral vectors, can comprise one or more regulatory elements such as promoters, enhancers, and other expression control elements (e.g., transcription termination signals, such as polyadenylation signals and poly-U sequences). Such regulatory elements are described, for example, in Goeddel, 1990, GENE EXPRESSION TECHNOLOGY: METHODS IN ENZYMOLOGY 185, Academic Press, San Diego, Calif. Regulatory elements include those that direct constitutive expression of a nucleotide sequence in many types of host cell and those that direct expression of the nucleotide sequence only in certain host cells (e.g., tissue-specific regulatory sequences). A tissue-specific promoter may direct expression primarily in a desired tissue of interest or in particular cell types. Regulatory elements may also direct expression in a temporal-dependent manner, such as in a cell-cycle dependent or developmental stage-dependent manner, which may or may not also be tissue or cell-type specific. In some embodiments, a nucleic acid of the disclosure comprises one or more pol III promoter (e.g., 1, 2, 3, 4, 5, or more pol III promoters), one or more pol II promoters (e.g., 1, 2, 3, 4, 5, or more pol II promoters), one or more pol I promoters (e.g., 1, 2, 3, 4, 5, or more pol I promoters), or combinations thereof, e.g., to express a Type V Cas protein and a gRNA separately. Examples of pol III promoters include, but are not limited to, U6 and H1 promoters. Examples of pol II promoters include, but are not limited to, the retroviral Rous Sarcoma virus (RSV) LTR promoter (optionally with the RSV enhancer), the cytomegalovirus (CMV) promoter (optionally with the CMV enhancer) (see, e.g., Boshart et al, 1985, Cell 41:521-530), the SV40 promoter, the dihydrofolate reductase promoter, the β-actin promoter, the phosphoglycerol kinase (PGK) promoter, and EF1α promoters (for example, full length EF1α promoter and the EFS promoter, which is a short, intron-less form of the full EF1α promoter). Exemplary enhancer elements include WPRE; CMV enhancers; the R-U5' segment in LTR of HTLV-I; SV40 enhancer; and the intron sequence between exons 2 and 3 of rabbit β-globin. It will be appreciated by those skilled in the art that the design of an expression vector can depend on such factors as the choice of the host cell, the level of expression desired, etc.

The term "vector" refers to a polynucleotide molecule capable of transporting another nucleic acid to which it has been linked. One type of polynucleotide vector includes a "plasmid", which refers to a circular double-stranded DNA loop into which additional nucleic acid segments are or can be ligated. Another type of polynucleotide vector is a viral vector; wherein additional nucleic acid segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome.

In some examples, vectors can be capable of directing the expression of nucleic acids to which they are operably linked. Such vectors can be referred to herein as "recombinant expression vectors", or more simply "expression vectors", which serve equivalent functions.

The term "operably linked" means that the nucleotide sequence of interest is linked to regulatory sequence(s) in a manner that allows for expression of the nucleotide sequence. The term "regulatory sequence" is intended to include, for example, promoters, enhancers and other expression control elements (e.g., polyadenylation signals). Such regulatory sequences are well known in the art and are described, for example, in Goeddel; Gene Expression Technology: Methods in Enzymology 185, Academic Press, San Diego, CA (1990). Regulatory sequences include those that direct constitutive expression of a nucleotide sequence in many types of host cells, and those that direct expression of the nucleotide sequence only in certain host cells (e.g., tissue-specific regulatory sequences). It will be appreciated by those skilled in the art that the design of the expression vector can depend on such factors as the choice of the target cell, the level of expression desired, and the like.

Vectors can include, but are not limited to, viral vectors based on vaccinia virus, poliovirus, adenovirus, adeno-associated virus (e.g., AAV2, AAV5, AAV7m8, AAV8, AAV9, AAVrh8r, AAVrh10), SV40, herpes simplex virus, human immunodeficiency virus, retrovirus (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus) and other recombinant vectors. Other vectors contemplated for eukaryotic target cells include, but are not limited to, the vectors pXTI, pSG5, pSVK3, pBPV, pMSG, and pSVLSV40 (Pharmacia). Additional vectors contemplated for eukaryotic target cells include, but are not limited to, the vectors pCTx-I, pCTx-2, and pCTx-3. Other vectors can be used so long as they are compatible with the host cell.

In some examples, a vector can comprise one or more transcription and/or translation control elements. Depending on the host/vector system utilized, any of a number of suitable transcription and translation control elements, including constitutive and inducible promoters, transcription enhancer elements, transcription terminators, etc. can be used in the expression vector. The vector can be a self-inactivating vector that either inactivates the viral sequences or the components of the CRISPR machinery or other elements.

Non-limiting examples of suitable eukaryotic promoters (promoters functional in a eukaryotic cell) include those from cytomegalovirus (CMV) immediate early, herpes simplex virus (HSV) thymidine kinase, early and late SV40, long terminal repeats (LTRs) from retrovirus, human elongation factor-I promoters (for example, the full EF1α promoter and the EFS promoter), a hybrid construct comprising the cytomegalovirus (CMV) enhancer fused to the chicken beta-actin promoter (CAG), murine stem cell virus promoter (MSCV), phosphoglycerate kinase-1 locus promoter (PGK), and mouse metallothionein-l.

An expression vector can also contain a ribosome binding site for translation initiation and a transcription terminator. The expression vector can also comprise appropriate sequences for amplifying expression. The expression vector can also include nucleotide sequences encoding non-native tags (e.g., histidine tag, hemagglutinin tag, green fluorescent protein, etc.) that are fused to the site-directed polypeptide, thus resulting in a fusion protein.

A promoter can be an inducible promoter (e.g., a heat shock promoter, tetracycline-regulated promoter, steroid-regulated promoter, metal-regulated promoter, estrogen receptor-regulated promoter, etc.). The promoter can be a constitutive promoter (e.g., CMV promoter, UBC promoter). In some cases, the promoter can be a spatially restricted and/or temporally restricted promoter (e.g., a tissue specific promoter, for example a human RHO promoter or human rhodopsin kinase promoter (hGRK), a cell type specific promoter, etc.).

6.6. Particles and Cells

The disclosure further provides particles comprising a Type V Cas protein of the disclosure (e.g., a ZWGD Type V Cas protein, a ZJHK Type V Cas protein, a ZIKV Type V Cas protein, a ZZFT Type V Cas protein, a YYAN Type V Cas protein, a ZZGY Type V Cas protein, a ZKBG Type V Cas protein, a ZZKD Type V Cas protein, a ZXPB Type V Cas protein, a ZPPX Type V Cas protein, a ZXHQ Type V Cas protein, a ZQKH Type V Cas protein, a ZRGM Type V Cas protein, a ZTAE Type V Cas protein, a ZSQQ Type V Cas protein, a ZSYN Type V Cas protein, a ZRBH Type V Cas protein, a ZWPU Type V Cas protein, a ZZQE Type V Cas protein, or a ZRXE Type V Cas protein), particles comprising a gRNA of the disclosure, particles comprising a system of the disclosure, and particles comprising a nucleic acid or plurality of nucleic acids of the disclosure. The particles can in some embodiments comprise or further comprise a gRNA, or a nucleic acid encoding the gRNA (e.g., DNA or mRNA). For example, the particles can comprise a RNP of the disclosure. Exemplary particles include lipid nanoparticles, vesicles, viral-like particles (VLPs) and gold nanoparticles. See, e.g., WO 2020/012335, the contents of which are incorporated herein by reference in their entireties, which describes vesicles that can be used to deliver gRNA molecules and Type V Cas proteins to cells (e.g., complexed together as a RNP).

The disclosure provides particles (e.g., virus particles) comprising a nucleic acid encoding a Type V Cas protein of the disclosure. The particles can further comprise a nucleic acid encoding a gRNA. Alternatively, a nucleic acid encoding a Type V Cas protein can further encode a gRNA.

The disclosure further provides pluralities of particles (e.g., pluralities of virus particles). Such pluralities can include a particle encoding a Type V Cas protein and a different particle encoding a gRNA. For example, a plurality of particles can comprise a virus particle (e.g., an AAV2, AAV5, AAV7m8, AAV8, AAV9, AAVrh8r, or AAVrh10 virus particle) encoding a Type V Cas protein and a second virus particle (e.g., an AAV2, AAV5, AAV7m8, AAV8, AAV9, AAVrh8r, or AAVrh10 virus particle) encoding a gRNA. Alternatively, a plurality of particles can comprise a plurality of virus particles where each particle encodes a Type V Cas protein and a gRNA.

The disclosure further provides cells and populations of cells (e.g., ex vivo cells and populations of cells) that can comprise a Type V Cas protein (e.g., introduced to the cell as a RNP) or a nucleic acid encoding the Type V Cas protein (e.g., DNA or mRNA) (optionally also encoding a gRNA). The disclosure further provides cells and populations of cells comprising a gRNA of the disclosure (optionally complexed with a Type V Cas protein) or a nucleic acid encoding the gRNA (e.g., DNA or mRNA) (optionally also encoding a Type V Cas protein). The cells and populations of cells can be, for example, human cells such as a stem cell, e.g., a hematopoietic stem cell (HSC), a pluripotent stem cell, an induced pluripotent stem cell (iPS), or an embryonic stem cell. In some embodiments, the cells and populations of cells are T cells. Methods for introducing proteins and nucleic acids to cells are known in the art. For example, a RNP can be produced by mixing a Type V Cas protein and one or more guide RNAs in an appropriate buffer. An RNP can be introduced to a cell, for example, via electroporation and other methods known in the art.

The cell populations of the disclosure can be cells in which gene editing by the systems of the disclosure has taken place, or cells in which the components of a system of the disclosure have been introduced or expressed but gene editing has not taken place, or a combination thereof. A cell population can comprise, for example, a population in which at least 1%, at least 5%, at least 10%, at least 15%, at least 20%, at least 30%, at least 40%, at least 50%, at least 60%, or at least 70% of the cells have undergone gene editing by a system of the disclosure.

6.7. Pharmaceutical Compositions

Also disclosed herein are pharmaceutical formulations and medicaments comprising a Type V Cas protein, gRNA, nucleic acid or plurality of nucleic acids, system, particle, or plurality of particles of the disclosure together with a pharmaceutically acceptable excipient.

Suitable excipients include, but are not limited to, salts, diluents, (e.g., Tris-HCl, acetate, phosphate), preservatives (e.g., Thimerosal, benzyl alcohol, parabens), binders, fillers, solubilizers, disintegrants, sorbents, solvents, pH modifying agents, antioxidants, antinfective agents, suspending agents, wetting agents, viscosity modifiers, tonicity agents, stabilizing agents, and other components and combinations thereof. Suitable pharmaceutically acceptable excipients can be selected from materials which are generally recognized as safe (GRAS), and may be administered to an individual without causing undesirable biological side effects or unwanted interactions. Suitable excipients and their formulations are described in Remington's Pharmaceutical Sciences, 16th ed. 1980, Mack Publishing Co. In addition, such compositions can be complexed with polyethylene glycol (PEG), metal ions, or incorporated into polymeric compounds such as polyacetic acid, polyglycolic acid, hydrogels, etc., or incorporated into liposomes, microemulsions, micelles, unilamellar or multilamellar vesicles, erythrocyte ghosts or spheroblasts. Suitable dosage forms for administration, e.g., parenteral administration, include solutions, suspensions, and emulsions.

The components of the pharmaceutical formulation can be dissolved or suspended in a suitable solvent such as, for example, water, Ringer's solution, phosphate buffered saline (PBS), or isotonic sodium chloride. The formulation may also be a sterile solution, suspension, or emulsion in a nontoxic, parenterally acceptable diluent or solvent such as 1,3-butanediol.

In some cases, formulations can include one or more tonicity agents to adjust the isotonic range of the formulation. Suitable tonicity agents are well known in the art and include glycerin, mannitol, sorbitol, sodium chloride, and other electrolytes. In some cases, the formulations can be buffered with an effective amount of buffer necessary to maintain a pH suitable for parenteral administration. Suitable buffers are well known by those skilled in the art and some examples of useful buffers are acetate, borate, carbonate, citrate, and phosphate buffers.

In some embodiments, the formulation can be distributed or packaged in a liquid form, or alternatively, as a solid, obtained, for example by lyophilization of a suitable liquid formulation, which can be reconstituted with an appropriate carrier or diluent prior to administration. In some embodiments, the formulations can comprise a guide RNA and a Type V Cas protein in a pharmaceutically effective amount sufficient to edit a gene in a cell. The pharmaceutical compositions can be formulated for medical and/or veterinary use.

6.8. Methods of Altering a Cell

The disclosure further provides methods of using the Type V Cas proteins, gRNAs, nucleic acids (including pluralities of nucleic acids), systems, and particles (including pluralities of particles) of the disclosure for altering cells.

In one aspect, a method of altering a cell comprises contacting a eukaryotic cell (e.g., a human cell) with a nucleic acid, particle, system or pharmaceutical composition described herein.

Contacting a cell with a disclosed nucleic acid, particle, system or pharmaceutical composition can be achieved by any method known in the art and can be performed in vivo, ex vivo, or in vitro. In some embodiments, the methods can include obtaining one or more cells from a subject prior to contacting the cell(s) with a herein disclosed nucleic acid, particle, system or pharmaceutical composition. In some embodiments, the methods can further comprise returning or implanting the contacted cell or a progeny thereof to the subject.

Type V Cas and gRNA, as well as nucleic acids encoding Type V Cas and gRNAs can be delivered to a cell by any means known in the art, for example, by viral or non-viral delivery vehicles, electroporation or lipid nanoparticles.

A polynucleotide encoding Type V Cas and a gRNA, can be delivered to a cell (ex vivo or in vivo) by a lipid nanoparticle (LNP). LNPs can have, for example, a diameter of less than 1000 nm, 500 nm, 250 nm, 200 nm, 150 nm, 100 nm, 75 nm, 50 nm, or 25 nm. Alternatively, a nanoparticle can range in size from 1-1000 nm, 1-500 nm, 1-250 nm, 25-200 nm, 25-100 nm, 35-75 nm, or 25-60 nm. LNPs can be made from cationic, anionic, neutral lipids, and combinations thereof. Neutral lipids, such as the fusogenic phospholipid DOPE or the membrane component cholesterol, can be included in LNPs as 'helper lipids' to enhance transfection activity and nanoparticle stability.

LNPs can also be comprised of hydrophobic lipids, hydrophilic lipids, or both hydrophobic and hydrophilic lipids. Lipids and combinations of lipids that are known in the art can be used to produce a LNP. Examples of lipids used to produce LNPs are: DOTMA, DOSPA, DOTAP, DMRIE, DC-cholesterol, DOTAP-cholesterol, GAP-DMORIE-DPyPE, and GL67A-DOPE-DMPE-polyethylene glycol (PEG). Examples of cationic lipids are: 98N12-5, C12-200, DLin-KC2-DMA (KC2), DLin-MC3-DMA (MC3), XTC, MD1, and 7C1. Examples of neutral lipids are: DPSC, DPPC, POPC, DOPE, and SM. Examples of PEG-modified lipids are: PEG-DMG, PEG-CerCI4, and PEG-CerC20. Lipids can be combined in any number of molar ratios to produce a LNP. In addition, the polynucleotide(s) can be combined with lipid(s) in a wide range of molar ratios to produce a LNP.

Type V Cas and/or gRNAs can be delivered to a cell via an adeno-associated viral vector (e.g., of an AAV2, AAV5, AAV7m8, AAV8, AAV9, AAVrh8r, or AAVrh10 serotype), or by another viral vector. Other viral vectors include, but are not limited to lentivirus, adenovirus, alphavirus, enterovirus, pestivirus, baculovirus, herpesvirus, Epstein Barr virus, papovavirus, poxvirus, vaccinia virus, and herpes simplex virus. In some embodiments, a Type V Cas mRNA is formulated in a lipid nanoparticle, while a sgRNA is delivered to a cell in an AAV or other viral vector. In some embodiments, one or more AAV vectors (e.g., one or more AAV2, AAV5, AAV7m8, AAV8, AAV9, AAVrh8r, or AAVrh10 serotype) are used to deliver both a sgRNA and a Type V Cas. In some embodiments, a Type V Cas and a sgRNA are delivered using separate vectors. In other embodiments, a Type V Cas and a sgRNA are delivered using a single vector. BNK Type V Cas and AIK Type V Cas, with their relatively small size, can be delivered with a gRNA (e.g., sgRNA) using a single AAV vector.

Compositions and methods for delivering Type V Cas and gRNAs to a cell and/or subject are further described in PCT Patent Application Publications WO 2019/102381, WO 2020/012335, and WO 2020/053224, each of which is incorporated by reference herein in its entirety.

DNA cleavage can result in a single-strand break (SSB) or double-strand break (DSB) at particular locations within the DNA molecule. Such breaks can be and regularly are repaired by natural, endogenous cellular processes, such as homology-dependent repair (HDR) and non-homologous end-joining (NHEJ). These repair processes can edit the targeted polynucleotide by introducing a mutation, thereby resulting in a polynucleotide having a sequence which differs from the polynucleotide's sequence prior to cleavage by a Type V Cas.

NHEJ and HDR DNA repair processes consist of a family of alternative pathways. Non-homologous end-joining (NHEJ) refers to the natural, cellular process in which a double-stranded DNA-break is repaired by the direct joining of two non-homologous DNA segments. See, e.g. Cahill et al., 2006, Front. Biosci. 11:1958-1976. DNA repair by non-homologous end-joining is error-prone and frequently results in the untemplated addition or deletion of DNA sequences at the site of repair. Thus, NHEJ repair mechanisms can introduce mutations into the coding sequence which can disrupt gene function. NHEJ directly joins the DNA ends resulting from a double-strand break, sometimes with a modification of the polynucleotide sequence such as a loss of or addition of nucleotides in the polynucleotide sequence. The modification of the polynucleotide sequence can disrupt (or perhaps enhance) gene expression.

Homology-dependent repair (HDR) utilizes a homologous sequence, or donor sequence, as a template for inserting a defined DNA sequence at the break point. The homologous sequence can be in the endogenous genome, such as a sister chromatid. Alternatively, the donor can be an exogenous nucleic acid, such as a plasmid, a single-strand oligonucleotide, a double-stranded oligonucleotide, a duplex oligonucleotide or a virus, that has regions of high homology with the nuclease-cleaved locus, but which can also contain additional sequence or sequence changes including deletions that can be incorporated into the cleaved target locus.

A third repair mechanism includes microhomology-mediated end joining (MMEJ), also referred to as "Alternative NHEJ (ANHEJ)", in which the genetic outcome is similar to NHEJ in that small deletions and insertions can occur at the cleavage site. MMEJ can make use of homologous sequences of a few base pairs flanking the DNA break site to drive a more favored DNA end joining repair outcome. In some instances, it may be possible to predict likely repair outcomes based on analysis of potential microhomologies at the site of the DNA break.

Modifications of a cleaved polynucleotide by HDR, NHEJ, and/or ANHEJ can result in, for example, mutations, deletions, alterations, integrations, gene correction, gene replacement, gene tagging, transgene insertion, nucleotide deletion, gene disruption, translocations and/or gene mutation. The aforementioned process outcomes are examples of editing a polynucleotide.

When performing prime editing, e.g., with a prime editor comprising a Type V Cas protein of the disclosure that comprises a reverse transcriptase, a DNA mismatch repair (MMR) inhibitor can be used in conjunction with the prime editor. Use of MMR inhibitors have been reported to enhance efficiency of prime editing (see, e.g., Chen et al., 2021 Cell 184(22):5635-5652, the contents of which are incorporated herein by reference in their entireties). An exemplary MMR inhibitor is MLH1dn, having the amino acid sequence (SEQ ID NO: 258)

SFVAGVIRRLDETVVNRIAAGEVIQRPANAIKEMIENCLDAKSTSIQVIVKEGGLKLIQIQDNGTGIRKEDLDI

VCERFTTSKLQSFEDLASISTYGFRGEALASISHVAHVTITTKTADGKCAYRASYSDGKLKAPPKPCAGNQ

GTQITVEDLFYNIATRRKALKNPSEEYGKILEVVGRYSVHNAGISFSVKKQGETVADVRTLPNASTVDNIRS

IFGNAVSRELIEIGCEDKTLAFKMNGYISNANYSVKKCIFLLFINHRLVESTSLRKAIETVYAAYLPKNTHPFL

YLSLEISPQNVDVNVHPTKHEVHFLHEESILERVQQHIESKLLGSNSSRMYFTQTLLPGLAGPSGEMVKS

TTSLTSSSTSGSSDKVYAHQMVRTDSREQKLDAFLQPLSKPLSSQPQAIVTEDKTDISSGRARQQDEEML

ELPAPAEVAAKNQSLEGDTTKGTSEMSEKRGPTSSNPRKRHREDSDVEMVEDDSRKEMTAACTPRRRII

NLTSVLSLQEEINEQGHEVLREMLHNHSFVGCVNPQWALAQHQTKLYLLNTTKLSEELFYQILIYDFANFG

VLRLSEPAPLFDLAMLALDSPESGWTEEDGPKEGLAEYIVEFLKKKAEMLADYFSLEIDEEGNLIGLPLLID

NYVPPLEGLPIFILRLATEVNWDEEKECFESLSKECAMFYSIRKQYISEESTLSGQQSEVPGSIPNSWKWT

VEHIVYKALRSHILPPKHFTEDGNILQLANLPDLYKVF.

In some embodiments, an MMR inhibitor is provided in trans with a prime editor.

Advantages of ex vivo cell therapy approaches include the ability to conduct a comprehensive analysis of the therapeutic prior to administration. Nuclease-based therapeutics can have some level of off-target effects. Performing gene correction ex vivo allows a method user to characterize the corrected cell population prior to implantation, including identifying any undesirable off-target effects. Where undesirable effects are observed, a method user may opt not to implant the cells or cell progeny, may further edit the cells, or may select new cells for editing and analysis. Other advantages include ease of genetic correction in iPSCs compared to other primary cell sources. iPSCs are prolific, making it easy to obtain the large number of cells that will be required for a cell-based therapy. Furthermore, iPSCs are an ideal cell type for performing clonal isolations. This allows screening for the correct genomic correction, without risking a decrease in viability.

Although certain cells present an attractive target for ex vivo treatment and therapy, increased efficacy in delivery may permit direct in vivo delivery to such cells. Ideally the targeting and editing is directed to the relevant cells. Cleavage in other cells can also be prevented by the use of promoters only active in certain cell types and/or developmental stages.

Additional promoters are inducible, and therefore can be temporally controlled if the nuclease is delivered as a plasmid. The amount of time that delivered protein and RNA remain in the cell can also be adjusted using treatments or domains added to change the half-life. In vivo treatment would eliminate a number of treatment steps, but a lower rate of delivery can require higher rates of editing. In vivo treatment can eliminate problems and losses from ex vivo treatment and engraftment.

An advantage of in vivo gene therapy can be the ease of therapeutic production and administration. The same therapeutic approach and therapy has the potential to be used to treat more than one patient, for example a number of patients who share the same or similar genotype or allele. In contrast, ex vivo cell therapy typically requires using a subject's own cells, which are isolated, manipulated and returned to the same patient.

Progenitor cells (also referred to as stem cells herein) are capable of both proliferation and giving rise to more progenitor cells, which in turn have the ability to generate a large number of cells that can in turn give rise to differentiated or differentiable daughter cells. The daughter cells themselves can be induced to proliferate and produce progeny that subsequently differentiate into one or more mature cell types, while also retaining one or more cells with parental developmental potential. The term "stem cell" refers then to a cell with the capacity or potential, under particular circumstances, to differentiate to a more specialized or differentiated phenotype, and which retains the capacity, under certain circumstances, to proliferate without substantially differentiating. In one aspect, the term progenitor or stem cell refers to a generalized mother cell whose descendants (progeny) specialize, often in different directions, by differentiation, e.g., by acquiring completely individual characters, as occurs in progressive diversification of embryonic cells and tissues. Cellular differentiation is a complex process typically occurring through many cell divisions. A differentiated cell can derive from a multipotent cell that itself is derived from a multipotent cell, and so on. While each of these multipotent cells can be considered stem cells, the range of cell types that each can give rise to can vary considerably. Some differentiated cells also have the capacity to give rise to cells of greater developmental potential. Such capacity can be natural or can be induced artificially upon treatment with various factors. In many biological instances, stem cells can also be "multipotent" because they can produce progeny of more than one distinct cell type, but this is not required.

Human cells described herein can be induced pluripotent stem cells (IPSCs). An advantage of using iPSCs in the methods of the disclosure is that the cells can be derived from the same subject to which the progenitor cells are to be administered. That is, a somatic cell can be obtained from a subject, reprogrammed to an induced pluripotent stem cell, and then differentiated into a progenitor cell to be administered to the subject (e.g., an autologous cell). Because progenitors are essentially derived from an autologous source, the risk of engraftment rejection or allergic response can be reduced compared to the use of cells from another subject or group of subjects. In addition, the use of iPSCs negates the need for cells obtained from an embryonic source. Thus, in one aspect, the stem cells used in the disclosed methods are not embryonic stem cells.

Methods are known in the art that can be used to generate pluripotent stem cells from somatic cells. Pluripotent stem cells generated by such methods can be used in the method of the disclosure.

Reprogramming methodologies for generating pluripotent cells using defined combinations of transcription factors have been described. Mouse somatic cells can be converted to ES cell-like cells with expanded developmental potential by the direct transduction of Oct4, Sox2, Klf4, and c-Myc; see, e.g., Takahashi and Yamanaka, 2006, Cell 126(4):663-76. iPSCs resemble ES cells, as they restore the pluripotency-associated transcriptional circuitry and much of the epigenetic landscape. In addition, mouse iPSCs satisfy all the standard assays for pluripotency: specifically, in vitro differentiation into cell types of the three germ layers, teratoma formation, contribution to chimeras, germline transmission (see, e.g., Maherali and Hochedlinger, 2008, Cell Stem Cell. 3(6):595-605), and tetraploid complementation.

Human iPSCs can be obtained using similar transduction methods, and the transcription factor trio, OCT4, SOX2, and NANOG, has been established as the core set of transcription factors that govern pluripotency; see, e.g., 2014, Budniatzky and Gepstein, Stem Cells Transl Med. 3(4):448-57; Barrett et al, 2014, Stem Cells Trans Med 3: 1-6 sctm.2014-0121; Focosi et al, 2014, Blood Cancer Journal 4: e211. The production of iPSCs can be achieved by the introduction of nucleic acid sequences encoding stem cell-associated genes into an adult, somatic cell, historically using viral vectors.

iPSCs can be generated or derived from terminally differentiated somatic cells, as well as from adult stem cells, or somatic stem cells. That is, a non-pluripotent progenitor cell can be rendered pluripotent or multipotent by reprogramming. In such instances, it may not be necessary to include as many reprogramming factors as required to reprogram a terminally differentiated cell. Further, reprogramming can be induced by the non-viral introduction of reprogramming factors, e.g., by introducing the proteins themselves, or by introducing nucleic acids that encode the reprogramming factors, or by introducing messenger RNAs that upon translation produce the reprogramming factors (see e.g., Warren et al., 2010, Cell Stem Cell, 7 (5): 618-30. Reprogramming can be achieved by introducing a combination of nucleic acids encoding stem cell-associated genes, including, for example, Oct-4 (also known as Oct-3/4 or Pouf51), SoxI, Sox2, Sox3, Sox 15, Sox 18, NANOG, KIfI, KIf2, KIf4, KIf5, NR5A2, c-Myc, 1-Myc, n-Myc, Rem2, Tert, and LIN28. Reprogramming using the methods and compositions described herein can further comprise introducing one or more of Oct-3/4, a member of the Sox family, a member of the Klf family, and a member of the Myc family to a somatic cell. The methods and compositions described herein can further comprise introducing one or more of each of Oct-4, Sox2, Nanog, c-MYC and Klf4 for reprogramming. As noted above, the exact method used for reprogramming is not necessarily critical to the methods and compositions described herein. However, where cells differentiated from the reprogrammed cells are to be used in, e.g., human therapy, in one aspect the reprogramming is not affected by a method that alters the genome. Thus, in such examples, reprogramming can be achieved, e.g., without the use of viral or plasmid vectors.

Efficiency of reprogramming (the number of reprogrammed cells) derived from a population of starting cells can be enhanced by the addition of various agents, e.g., small molecules, as shown by Shi et al., 2008, Cell-Stem Cell 2:525-528; Huangfu et al., 2008, Nature Biotechnology 26(7):795-797; and Marson et al., 2008, Cell-Stem Cell 3: 132-135. Thus, an agent or combination of agents that enhance the efficiency or rate of induced pluripotent stem cell production can be used in the production of patient-specific or disease-specific iPSCs. Some non-limiting examples of agents that enhance reprogramming efficiency include soluble Wnt, Wnt conditioned media, BIX-01294 (a G9a histone methyltransferase), PD0325901 (a MEK inhibitor), DNA methyltransferase inhibitors, histone deacetylase (HD AC) inhibitors, valproic acid, 5'-azacytidine, dexamethasone, suberoylanilide, hydroxamic acid (SAHA), vitamin C, and trichostatin (TSA), among others. Other non-limiting examples of reprogramming enhancing agents include: Suberoylanilide Hydroxamic Acid (SAHA (e.g., MK0683, vorinostat) and other hydroxamic acids), BML-210, Depudecin (e.g., (−)-Depudecin), HC Toxin, Nullscript (4-(1,3-Dioxo-IH,3H-benzo[de]isoquinolin-2-yl)-N-hydroxybutanamide), Phenylbutyrate (e.g., sodium phenylbutyrate) and Valproic Acid ((VP A) and other short chain fatty acids), Scriptaid, Suramin Sodium, Trichostatin A (TSA), APHA Compound 8, Apicidin, Sodium Butyrate, pi valoyloxy methyl butyrate (Pivanex, AN-9), Trapoxin B, Chlamydocin, Depsipeptide (also known as FR901228 or FK228), benzamides (e.g., CI-994 (e.g., N-acetyl dinaline) and MS-27-275), MGCD0103, NVP-LAQ-824, CBHA (m-carboxycinnaminic acid bishydroxamic acid), JNJ16241199, Tubacin, A-161906, proxamide, oxamflatin, 3-C1-UCHA (e.g., 6-(3-chlorophenylureido) caproic hydroxamic acid), AOE (2-amino-8-oxo-9, 10-epoxy decanoic acid), CHAP31 and CHAP 50. Other reprogramming enhancing agents include, for example, dominant negative forms of the HDACs (e.g, catalytically inactive forms), siRNA inhibitors of the HDACs, and antibodies that specifically bind to the HDACs. Such inhibitors are available, e.g., from BIOMOL International, Fukasawa, Merck Biosciences, Novartis, Gloucester Pharmaceuticals, Titan Pharmaceuticals, MethylGene, and Sigma Aldrich.

To confirm the induction of pluripotent stem cells, isolated clones can be tested for the expression of a stem cell marker. Such expression in a cell derived from a somatic cell identifies the cells as induced pluripotent stem cells. Stem cell markers can be selected from the non-limiting group including SSEA3, SSEA4, CD9, Nanog, FbxI5, EcatI, EsgI, Eras, Gdfi, Fgf4, Cripto, DaxI, Zpf296, Slc2a3, RexI, UtfI, and NatI. In one case, for example, a cell that expresses Oct4 or Nanog is identified as pluripotent. Methods for detecting the expression of such markers can include, for example, RT-PCR and immunological methods that detect the presence of the encoded polypeptides, such as Western blots or flow cytometric analyses. Detection can involve not only RT-PCR, but also detection of protein markers. Intracellular markers can be best identified via RT-PCR, or protein detection methods such as immunocytochemistry, while cell surface markers are readily identified, e.g., by immunocytochemistry.

Pluripotency of isolated cells can be confirmed by tests evaluating the ability of the iPSCs to differentiate into cells of each of the three germ layers. As one example, teratoma formation in nude mice can be used to evaluate the pluripotent character of the isolated clones. The cells can be introduced into nude mice and histology and/or immunohistochemistry can be performed on a tumor arising from the cells. The growth of a tumor comprising cells from all three germ layers, for example, further indicates that the cells are pluripotent stem cells.

Patient-specific iPS cells or cell line can be created. There are many established methods in the art for creating patient specific iPS cells, e.g., as described in Takahashi and Yamanaka 2006; Takahashi, Tanabe et al. 2007. For example, the creating step can comprise: a) isolating a somatic cell, such as a skin cell or fibroblast, from the patient; and b) introducing a set of pluripotency-associated genes into the somatic cell in order to induce the cell to become a pluripotent stem cell. The set of pluripotency-associated genes can be one or more of the genes selected from the group consisting of OCT4, SOX1, SOX2, SOX3, SOX15, SOX18, NANOG, KLF1, KLF2, KLF4, KLF5, c-MYC, n-MYC, REM2, TERT and LIN28.

In some aspects, a biopsy or aspirate of a subject's bone marrow can be performed. A biopsy or aspirate is a sample of tissue or fluid taken from the body. There are many different kinds of biopsies or aspirates. Nearly all of them involve using a sharp tool to remove a small amount of tissue. If the biopsy will be on the skin or other sensitive area, numbing medicine can be applied first. A biopsy or aspirate can be performed according to any of the known methods in the art. For example, in a bone marrow aspirate, a large needle is used to enter the pelvis bone to collect bone marrow.

In some aspects, a mesenchymal stem cell can be isolated from a subject. Mesenchymal stem cells can be isolated according to any method known in the art, such as from a subject's bone marrow or peripheral blood. For example, marrow aspirate can be collected into a syringe with heparin. Cells can be washed and centrifuged on a Percoll™ density gradient. Cells, such as blood cells, liver cells, interstitial cells, macrophages, mast cells, and thymocytes, can be separated using density gradient centrifugation media, Percoll™. The cells can then be cultured in Dulbecco's modified Eagle's medium (DMEM) (low glucose) containing 10% fetal bovine serum (FBS) (Pittinger et. al., 1999, Science 284: 143-147).

6.8.1. Exemplary Genomic Targets

The Type V Cas proteins and gRNAs of the disclosure can be used to alter various genomic targets. In some aspects, the methods of altering a cell are methods for altering a CCR5, EMX1, Fas, FANCF, HBB, ZSCAN2, Chr6, ADAMTSL1, B2M, CXCR4, PD1, DNMT1, Match8, TRAC, TRBC, VEGFAsite2, VEGFAsite3, CACNA, HEKsite3, HEKsite4, Chr8, BCR, ATM, HBG1, HPRT, IL2RG, NF1, USH2A, RHO, BcLenh, or CTFR genomic sequence. In some aspects, the methods of altering a cell are methods of altering a TRAC, B2M, PD1, or LAG3 genomic sequence. Reference sequences of RHO, TRAC, B2M, PD1, and LAG3 are available in public databases, for example those maintained by NCBI. For example, RHO has the NCBI gene ID: 6010; TRAC has the NCBI gene ID: 28755; B2M has the NCBI gene ID: 567; PD1 has the NCBI gene ID: 5133; and LAG3 has the NCBI gene ID: 3902.

In some embodiments, the methods of altering a cell are methods for altering a hemoglobin subunit beta (HBB) gene. HBB mutations are associated with β-thalassemia and SCD. Dever et al., 2016 Nature 539 (7629): 384-389.

In some embodiments, the methods of altering a cell are methods for altering a CCR5 gene. CCR5 has demonstrated involvement in several different disease states including, but not limited to, human immunodeficiency virus (HIV) and acquired immune deficiency syndrome (AIDS). WO 2018/119359 describes CCR5 editing by CRISPR-Cas to make loss of function CCR5 in order to provide protection against HIV infection, decrease one or more symptoms of HIV infection, halt or delay progression of HIV to AIDS, and/or decrease one or more symptoms of AIDS.

In some embodiments, the methods of altering a cell are methods for altering a PD1, B2M gene, TRAC gene, or a combination thereof. CAR-T cells having PD1, B2M and TRAC genes disrupted by CRISPR-Type V Cas have demonstrated enhanced activity in preclinical glioma models. Choi et al., 2019, Journal for Immuno Therapy of Cancer 7:309.

In some embodiments, the methods of altering a cell are methods for altering an USH2A gene. Mutations in the USH2A gene can cause Usher syndrome type 2A, which is characterized by progressive hearing and vision loss.

In some embodiments, the methods of altering a cell are methods for altering a RHO gene. Mutations in the RHO gene can cause retinitis pigmentosa (RP).

Targeting of (one or more of) human TRAC, human B2M, human PD1, and human LAG3 genes can be used, for example, in the engineering of chimeric antigen receptor (CAR) T cells. For example, CRISPR/Cas technology has been used to deliver CAR-encoding DNA sequences to loci such as TRAC and PD1 (see, e.g., Eyquem et al., 2017, Nature 543 (7643): 113-117; Hu et al., 2023, eClinicalMedicine 60:102010), while TRAC, B2M, PD1, and LAG3 knockout CAR T-cells have been reported (see, e.g., Dimitri et al., 2022, Molecular Cancer 21:78; Liu et al., 2016, Cell Research 27:154-157; Ren et al., 2017, Clin Cancer Res. 23 (9): 2255-2266; Zhang et al., 2017, Front Med. 11 (4): 554-562). Thus, the Type V Cas proteins and TRAC, B2M, PD1, and LAG3 guides of the disclosure can be used for targeted knock-in of an exogenous DNA sequence to a desired genomic site in a human cell and/or knock-out of TRAC, B2M, PD1, or LAG3 in a human cell, for example a human T cell. In some embodiments, T cells are edited ex vivo to produce CAR-T cells and subsequently administered to a subject in need of CAR-T cell therapy.

In some embodiments, the methods of altering a cell are methods for altering a DNMT1 gene. Mutations in the DNMT1 gene can cause DNMT1-related disorder, which is a degenerative disorder of the central and peripheral nervous systems. DNMT1-related disorder is characterized by sensory impairment, loss of sweating, dementia, and hearing loss.

Additional exemplary targets include AVS1, BCL11A, PCSK9, and VEGFA. In some embodiments, the methods of altering a cell are methods for altering an AVS1 gene. AVS1 can be used as a safe harbor locus to insert an transgene of interest (see, e.g., Gu et al., 2022, Methods Mol Biol. 2495:99-114). In some embodiments, the methods of altering a cell are methods for altering a BCL11A gene. Editing BCL11A has been identified in the art a target for treatment of sickle cell disease and β-Thalassemia (see, e.g., Frangoul et al., 2021, N Eng J Med 384:252-260). In some embodiments, the methods of altering a cell are methods for altering a PCSK9 gene. PCSK9 has been identified in the art as a target for treatment of hypercholesterolemia (see, e.g., Hoekstra & Van Eck, 2024, Current Atherosclerosis Reports, 26:139-146). In some embodiments, the methods of altering a cell are methods for altering a VEGFA gene. VEGFA has been identified in the art as a target for treatment of eye diseases such as age-related macular degeneration (see, e.g., Park et al., 2023, Scientific Reports 13:3715).

6.9. Methods of Detecting Target Nucleic Acids

The disclosure further provides methods of using the Type V Cas proteins, gRNAs, and systems of the disclosure for detecting target nucleic acids (e.g., nucleic acids from pathogens, for example viruses, bacteria, or parasites). Nucleic acid detection methods using Cas12a are described in the art (see, e.g., Kaminski et al., 2021, Nature Biomedical Engineering 5:643-656; Sashital, 2018, Genome Med. 10:32, each of which is incorporated herein by reference in its entirety), and such methods can be extended to the Type V Cas proteins of the disclosure. Nucleic acid detection methods typically take advantage of collateral cleavage activity of Type V Cas proteins. For example, target binding of Type V Cas proteins such as Cas12a activates collateral cleavage activity toward single-stranded DNA, and this activity can be exploited in a detection assay by supplying a single-stranded reporter nucleic acid, for example a reporter nucleic acid comprising a quenched fluorescent reporter. Type V Cas protein binding to the target nucleic acid leads to cleavage of the reporter nucleic acid. Detection of the fluorescent reporter following cleavage of the reporter nucleic acid allows for detection and, optionally, quantification of the target nucleic acid.

7. EXAMPLES

7.1. Materials and Methods

7.1.1. Plasmids and Cell Lines

Plasmids: Type V-A Cas proteins were expressed in mammalian cells from a plasmid vector characterized by a EF1alpha-driven cassette. Each Type V-A Cas protein coding sequence was human codon-optimized and modified by the addition of an SV5 tag and a bipartite nuclear localization signal at the C-terminus. Additional constructs containing different NLS configurations (discussed in Section 7.4.2) were generated using standard cloning techniques. The crRNA were expressed from a U6-driven cassette located on an independent plasmid construct. The human codon-optimized coding sequence of the Type V-A Cas proteins, as well as their crRNA scaffolds, were obtained by synthesis from Twist Bioscience. Spacer sequences (20-24 nt long) were cloned into the crRNA plasmid as annealed DNA oligonucleotides (Eurofins Genomics) using a double BsaI site present in the plasmid. The list of spacer sequences and relative cloning oligonucleotides used in the present example is reported in Table 8. In all cases in which the crRNA scaffold did not contain a matching native 5'-G, this nucleotide was appended upstream the scaffold sequence in order to allow efficient transcription from a U6 promoter. Unless otherwise stated in all studies, full-length crRNAs were used.

TABLE 8

Spacer sequences and oligonucleotides relative to crRNAs for Type V-A Cas proteins

| Guide ID | Target | Spacer (5'>3') | SEQ ID NO: | PAM (5'>3') | Oligo 1 (5'>3') | SEQ ID NO: | Oligo 2 (5'>3') | SEQ ID NO: |
|---|---|---|---|---|---|---|---|---|
| EGFP-g1 | EGFP | CGUCGCCGUCCAGCUCGACCAGG | 260 | TTTA | agatCGTCGCCGTCCAGCTCGACCAGG | 262 | AaaaCCTGGTCGAGCTGGACGGCGACG | 308 |
| EGFP-g2 | EGFP | CUCAGGGGGGACUGGGUGCUCAG | 261 | TTTG | agatCTCAGGGCGGACTGGGTGCTCAG | 263 | AaaaCTGAGCACCCAGTCCGCCCTGAG | 309 |
| B2M-g1 | B2M | UGGCCUGGAGGCUAUCCAGCGUG | 164 | TTTC | agatTGGCCTGGAGGCTATCCAGCGTG | 264 | aaaaCACGCTGGATAGCCTCCAGGCCA | 310 |
| B2M-g2 | B2M | CUCACGUCAUCCAGCAGAGAAUG | 165 | TTTC | agatCTCACGTCATCCAGCAGAGAATG | 265 | aaaaCATTCTCTGCTGGATGACGTGAG | 311 |
| B2M-g3 | B2M | ACUUUCCAUUCUCUGCUGGAUGA | 166 | TTTG | agatACTTTCCATTCTCTGCTGGATGA | 266 | aaaaTCATCCAGCAGAGAATGGAAAGT | 312 |
| B2M-g4 | B2M | CUGAAUUGCUAUGUGUCUGGGUU | 167 | TTTC | agatCTGAATTGCTATGTGTCTGGGTT | 267 | aaaaAACCCAGACACATAGCAATTCAG | 313 |
| B2M-g5 | B2M | AAUUCUCUCUCCAUUCUUCAGUA | 168 | TTTC | agatAATTCTCTCTCCATTCTTCAGTA | 268 | aaaaTACTGAAGAATGGAGAGAGAATT | 314 |
| TRAC-g1 | TRAC | AGAAUCAAAAUCGGUGAAUAGGC | 169 | TTTA | agatAGAATCAAAATCGGTGAATAGGC | 269 | aaaaGCCTATTCACCGATTTTGATTCT | 315 |
| TRAC-g2 | TRAC | UGACACAUUUGUUUGAGAAUCAA | 170 | TTTG | agatTGACACATTTGTTTGAGAATCAA | 270 | aaaaTTGATTCTCAAACAAATGTGTCA | 316 |
| TRAC-g3 | TRAC | GAGUCUCUCAGCUGGUACACGGC | 171 | TTTA | agatGAGTCTCTCAGCTGGTACACGGC | 271 | aaaaGCCGTGTACCAGCTGAGAGACTC | 317 |
| TRAC-g4 | TRAC | UCUGUGAUAUACACAUCAGAAUC | 172 | TTTG | agatTCTGTGATATACACATCAGAATC | 272 | aaaaGATTCTGATGTGTATATCACAGA | 318 |
| TRAC-g5 | TRAC | AUUCUCAAACAAAUGUGUCACAA | 173 | TTTG | agatATTCTCAAACAAATGTGTCACAA | 273 | aaaaTTGTGACACATTTGTTTGAGAAT | 319 |
| PD1-g1 | PD1 | CCUUCCGCUCACCUCCGCCUGAG | 174 | TTTC | agatCCTTCCGCTCACCTCCGCCTGAG | 274 | aaaaCTCAGGCGGAGGTGAGCGGAAGG | 320 |
| PD1-g2 | PD1 | GCACGAAGCUCUCCGAUGUGUUG | 175 | TTTA | agatGCACGAAGCTCTCCGATGTGTTG | 275 | aaaaCAACACATCGGAGAGCTTCGTGC | 321 |
| PD1-g3 | PD1 | AUCUGCGCCUUGGGGGCCAGGGA | 176 | TTTG | agatATCTGCGCCTTGGGGGCCAGGGA | 276 | aaaaTCCCTGGCCCCCAAGGCGCAGAT | 322 |

TABLE 8-continued

Spacer sequences and oligonucleotides relative to crRNAs for Type V-A Cas proteins

| Guide ID | Target | Spacer (5'>3') | SEQ ID NO: | PAM (5'>3') | Oligo 1 (5'>3') | SEQ ID NO: | Oligo 2 (5'>3') | SEQ ID NO: |
|---|---|---|---|---|---|---|---|---|
| PD1-g4 | PD1 | GAACUGGCCGG CUGGCCUGGGU G | 177 | TTTG | agatGAACTGGCCG GCTGGCCTGGGTG | 277 | aaaaCACCCAGGCC AGCCGGCCAGTTC | 323 |
| AAVS1-g6 | AAVS1 | CAGGGGUCCGA GAGCUCAGCUAG | 195 | CTTC | agatCAGGGGTCCG AGAGCTCAGCTAG | 278 | aaaaCTAGCTGAGCT CTCGGACCCCTG | 324 |
| AAVS1-g7 | AAVS1 | AUCUGUCCCCUC CACCCCACAGU | 196 | TTTT | agatATCTGTCCCCT CCACCCCACAGT | 279 | aaaaACTGTGGGGT GGAGGGGACAGAT | 325 |
| AAVS1-g2 | AAVS1 | GGCAGCUCCCCU ACCCCCCUUAC | 194 | TTTG | agatGGCAGCTCCC CTACCCCCCTTAC | 280 | aaaaGTAAGGGGGG TAGGGGAGCTGCC | 326 |
| B2M-g8 | B2M | GUGUCAAGCUAU AUCAGGCACCA | 181 | CTTG | agatGTGTCAAGCT ATATCAGGCACCA | 281 | aaaaTGGTGCCTGAT ATAGCTTGACAC | 327 |
| B2M-g9 | B2M | AUGUGUCUUUUC CCGAUAUUCCU | 182 | ATTA | agatATGTGTCTTTT CCCGATATTCCT | 282 | aaaaAGGAATATCGG GAAAAGACACAT | 328 |
| TRAC-g6 | TRAC | UCACUGGAUUUA GAGUCUCUCAG | 184 | CTTG | agatTCACTGGATTT AGAGTCTCTCAG | 283 | aaaaCTGAGAGACTC TAAATCCAGTGA | 329 |
| TRAC-g9 | TRAC | GAUUCUCAAACA AAUGUGUCACA | 185 | TTTT | agatGATTCTCAAAC AAATGTGTCACA | 284 | aaaaTCACTGGATTT AGAGTCTCTCAG | 330 |
| TRAC-g11 | TRAC | AAGAGGGAAAUG AGAUCAUGUCC | 186 | GTTA | agatAAGAGGGAAA TGAGATCATGTCC | 285 | aaaaGGACATGATCT CATTTCCCTCTT | 331 |
| TRAC-g13 | TRAC | ACCGAUUUUGAU UCUCAAACAAA | 187 | ATTC | agatACCGATTTTGA TTCTCAAACAAA | 286 | aaaaTTTGTTTGAGA ATCAAAATCGGT | 332 |
| TRAC-g15 | TRAC | GUCUGUGAUAUA CACAUCAGAAU | 188 | TTTT | agatGTCTGTGATAT ACACATCAGAAT | 287 | aaaaATTCTGATGTG TATATCACAGAC | 333 |
| BCL11A-g1 | BCL11A | AGCCAUCUCACU ACAGAUAACUC | 199 | TTTC | agatAGCCATCTCA CTACAGATAACTC | 288 | aaaaGAGTTATCTGT AGTGAGATGGCT | 334 |
| AAVS1-g1 | AAVS1 | AUUUGGGCAGCU CCCCUACCCCC | 193 | TTTC | agatATTTGGGCAG CTCCCCTACCCCC | 289 | aaaaGGGGGTAGGG GAGCTGCCCAAAT | 335 |
| EMX1-g2 | EMX1 | UACUUUGUCCUC CGGUUCUGGAA | 197 | TTTG | agatTACTTTGTCCT CCGGTTCTGGAA | 290 | aaaaTTCCAGAACCG GAGGACAAAGTA | 336 |
| EMX1-g3 | EMX1 | UCCUCCGGUUCU GGAACCACACC | 198 | TTTG | agatTCCTCCGGTT CTGGAACCACACC | 291 | aaaaGGTGTGGTTCC AGAACCGGAGGA | 337 |
| BCL11A-g2 | BCL11A | AAGCUAGUCUAG UGCAAGCUAAC | 200 | TTTG | agatAAGCTAGTCTA GTGCAAGCTAAC | 292 | aaaaGTTAGCTTGCA CTAGACTAGCTT | 338 |
| BCL11A-g3 | BCL11A | GCCUCUGAUUAG GGUGGGGGCGU | 201 | TTTG | agatGCCTCTGATTA GGGTGGGGGCGT | 293 | aaaaACGCCCCCAC CCTAATCAGAGGC | 339 |
| PCSK9-g1 | PCSK9 | UCUGCCACCCAC CUCCUCACCUU | 203 | TTTC | agatTCTGCCACCC ACCTCCTCACCTT | 294 | aaaaAAGGTGAGGA GGTGGGTGGCAGA | 340 |
| PCSK9-g2 | PSCK9 | CAGGUCAUCACA GUUGGGGCCAC | 204 | TTTC | agatCAGGTCATCA CAGTTGGGGCCAC | 295 | aaaaGTGGCCCCAA CTGTGATGACCTG | 341 |
| BCL11A-g4 | BCL11A | UCACAGGCUCCA GGAAGGGUU | 202 | TTTA | agatTCACAGGCTC CAGGAAGGGTT | 296 | aaaaAACCCTTCCTG GAGCCTGTGA | 342 |
| VEGFA-g1 | VEGFA | GAGAGUGAGGAC GUGUGUGUC | 205 | CTTC | agatGAGAGTGAGG ACGTGTGTGTC | 297 | aaaaGACACACACGT CCTCACTCTC | 343 |
| B2M-g1_21nt | B2M | UGGCCUGGAGG CUAUCCAGCG | 183 | TTTC | agatTGGCCTGGAG GCTATCCAGCG | 298 | aaaaCGCTGGATAGC CTCCAGGCCA | 344 |
| TRAC g3_20 nt | TRAC | GAGUCUCUCAGC UGGUACAC | 189 | TTTA | AGATGAGTCTCTC AGCTGGTACAC | 299 | AAAAGTGTACCAGC TGAGAGACTC | 345 |
| TRAC g3_21 nt | TRAC | GAGUCUCUCAGC UGGUACACG | 190 | TTTA | AGATGAGTCTCTC AGCTGGTACACG | 300 | AAAACGTGTACCAG CTGAGAGACTC | 346 |

TABLE 8-continued

Spacer sequences and oligonucleotides relative to crRNAs for Type V-A Cas proteins

| Guide ID | Target | Spacer (5'>3') | SEQ ID NO: | PAM (5'>3') | Oligo 1 (5'>3') | SEQ ID NO: | Oligo 2 (5'>3') | SEQ ID NO: |
|---|---|---|---|---|---|---|---|---|
| TRAC g3_22 nt | TRAC | GAGUCUCUCAGCUGGUACACGG | 191 | TTTA | AGATGAGTCTCTCAGCTGGTACACGG | 301 | AAAACCGTGTACCAGCTGAGAGACTC | 347 |
| TRAC g3_24 nt | TRAC | GAGUCUCUCAGCUGGUACACGGCA | 192 | TTTA | AGATGAGTCTCTCAGCTGGTACACGGCA | 302 | AAAATGCCGTGTACCAGCTGAGAGACTC | 348 |
| Match6_ 20 nt | Match6 | GGGUGAUCAGACCCAACAGC | 206 | TTTG | AGATGGGTGATCAGACCCAACAGC | 303 | AAAAGCTGTTGGGTCTGATCACCC | 349 |
| Match6_ 21 nt | Match6 | GGGUGAUCAGACCCAACAGCA | 207 | TTTG | AGATGGGTGATCAGACCCAACAGCA | 304 | AAAATGCTGTTGGGTCTGATCACCC | 350 |
| Match6 22 nt | Match6 | GGGUGAUCAGACCCAACAGCAG | 208 | TTTG | AGATGGGTGATCAGACCCAACAGCAG | 305 | AAAACTGCTGTTGGGTCTGATCACCC | 351 |
| Match6_ 23 nt | Match6 | GGGUGAUCAGACCCAACAGCAGG | 209 | TTTG | AGATGGGTGATCAGACCCAACAGCAGG | 306 | AAAATGCTGTTGGGTCTGATCACCC | 350 |
| Match6_ 24 nt | Match6 | GGGUGAUCAGACCCAACAGCAGGU | 210 | TTTG | AGATGGGTGATCAGACCCAACAGCAGGT | 307 | AAAAACCTGCTGTTGGGTCTGATCACCC | 352 |

Cell lines: U2OS-EGFP cells, harboring a single integrated copy of an EGFP reporter gene, and wild-type U2OS and HEK293T cells were cultured in DMEM (Life Technologies) supplemented with 10% FBS (Life Technologies), 2 mM L-Glutamine (Life Technologies) and penicillin/streptomycin (Thermo Fisher). All cells were incubated at 37° C. and 5% $CO_2$ in a humidified atmosphere. All cells tested mycoplasma negative (PlasmoTest, Invivogen).

7.1.2. Identification of Novel Type V-A Cas Molecules from Metagenomic Samples

Type V CRISPR-Cas loci were predicted using CRISPRCasTyper (Russel, J., Pinilla-Redondo, R., Mayo-Muñoz, D., Shah, S. A. & Sørensen, S. J. CRISPRCasTyper: Automated Identification, Annotation, and Classification of CRISPR-Cas Loci. CRISPR J 3, 462-469 (2020)) version 1.8.0, starting from a collection of >1M metagenome-assembled genomes (MAGs) and reference genomes (Blanco-Míguez, A. et al. Extending and improving metagenomic taxonomic profiling with uncharacterized species using MetaPhlAn 4. Nat. Biotechnol. 41, 1633-1644 (2023)). A total of 14,568 Type V Cas proteins were recovered. Type V Cas proteins were clustered at 60% sequence identity and 60% sequence coverage using MMseq2 (Steinegger, M. & Söding, J. MMseqs2 enables sensitive protein sequence searching for the analysis of massive data sets. Nat. Biotechnol. 35, 1026-1028 (2017)) version 13.45111 (-c 0.6--cov-mode 5--min-seq-id 0.6--cluster-reassign) and aligned using mafft (Katoh, K. & Standley, D. M. MAFFT multiple sequence alignment software version 7: improvements in performance and usability. Mol. Biol. Evol. 30, 772-780 (2013)) version 7.490 (--maxiterate 100). The resulting alignment was trimmed using TrimAl (Capella-Gutiérrez, S., Silla-Martínez, J. M. & Gabaldón, T. trimAI: a tool for automated alignment trimming in large-scale phylogenetic analyses. Bioinformatics 25, 1972-1973 (2009)) version 1.4.rev15 (-gappyout) and used to generate a phylogenetic tree using IQ-TREE 2 (Minh, B. Q. et al. IQ-TREE 2: New Models and Efficient Methods for Phylogenetic Inference in the Genomic Era. Mol. Biol. Evol. 37, 1530-1534 (2020)) version 2.0.3 (-B 1000) and automatic model selection (Kalyaanamoorthy, S., Minh, B. Q., Wong, T. K. F., von Haeseler, A. & Jermiin, L. S. ModelFinder: fast model selection for accurate phylogenetic estimates. Nat. Methods 14, 587-589 (2017)), which was visualized using GraPhlAn (Asnicar, F., Weingart, G., Tickle, T. L., Huttenhower, C. & Segata, N. Compact graphical representation of phylogenetic data and metadata with GraPhlAn. PeerJ 3, e1029 (2015)) version 1.1.3. PAM predictions were performed using PAMpredict (Ciciani, M. et al. Automated identification of sequence-tailored Cas9 proteins using massive metagenomic data. Nat. Commun. 13, 6474 (2022)), clustering Type V-A Cas proteins at 90% sequence identity. For selected Type V-A Cas proteins, crRNAs resulting from MinCED predictions (Bland, C. et al. CRISPR recognition tool (CRT): a tool for automatic detection of clustered regularly interspaced palindromic repeats. BMC Bioinformatics 8, 209 (2007)) were manually checked for conservation of the 3' end sequence. The structure of the 3' end was checked by aligning the crRNAs using Clustal Omega (Sievers, F. et al. Fast, scalable generation of high-quality protein multiple sequence alignments using Clustal Omega. Mol. Syst. Biol. 7, 539 (2011)) version 1.2.4, generating a consensus secondary structure with RNAalifold version 2.4.17 (-p-r-d2--noLP) (Lorenz, R. et al. ViennaRNA Package 2.0. Algorithms Mol. Biol. 6, 26 (2011)) and analyzing the resulting structure with R2R (Weinberg, Z. & Breaker, R. R. R2R—software to speed the depiction of aesthetic consensus RNA secondary structures. BMC Bioinformatics 12, 3 (2011)) version 1.0.6.

7.1.3. PAM Assay

An in vitro PAM evaluation of the novel Type V-A Cas proteins was performed according to a modified version of the protocol from Karvelis, Young and Siksnys (Karvelis et al., 2019, Methods in Enzymology 616:219-240). The gRNAs to perform the assay were obtained by in vitro transcription using the HighYield™ T7 RNA Synthesis Kit (Jena Bioscience) starting from a PCR template generated by amplification from each gRNA expression construct. The primers used to generate the IVT templates are reported in Table 9. In vitro transcribed gRNAs were subsequently purified using the MEGAClear™ Transcription Clean-up kit (Thermo Fisher Scientific). HEK293T cells were transfected 48 hours before the study with nuclease-expressing plasmids, and protein lysates were collected and used for RNP complex formation. The complex was assembled by combining 20 μL of the supernatant containing the soluble Type V-A Cas proteins with 1 μL of RiboLock™ RNase Inhibitor (Thermo Fisher Scientific) and 2 μg of guide RNAs (previously transcribed in vitro). The RNP complex was used to digest 1 μg of a PAM plasmid DNA library (containing a defined target sequence flanked at the 5'-end by a randomized 8 nucleotide PAM sequence) for 1 hour at 37° C.

A double stranded DNA adapter (Table 10) was ligated to the DNA ends generated by the targeted Type V-A Cas protein cleavage and the final ligation product was purified using CleanNGS™ SPRI beads.

One round of a two-step PCR (Phusion™ HF DNA polymerase, Thermo Fisher Scientific) was performed to enrich the sequences that were cut using a set of forward primers annealing on the adapter and a reverse primer designed on the plasmid backbone downstream of the PAM (Table 11). A second round of PCR was performed to attach the Illumina indexes and adapters. PCR products were purified using the GeneJet™ PCR Purification Kit (Thermo Fisher Scientific).

The library was analysed with a 71-bp single read sequencing, using a flow cell v2 micro, on an Illumina MiSeq™ sequencer.

PAM sequences were extracted from Illumina MiSeq reads and used to generate PAM sequence logos, using Logomaker version 0.8. PAM heatmaps were used to display PAM enrichment, computed dividing the frequency of PAM sequences in the cleaved library by the frequency of the same sequences in a control uncleaved library.

TABLE 9

Sequences of the primers used for PCR amplification of gRNAs used as templates for in vitro transcription

| Primer name | Sequence (5' → 3') | SEQ ID NO: |
|---|---|---|
| ZZKD_PAMassay_F | CCTCTAATACGACTCACTATAGCCTTTGGAAGTACTAAGAATTTCTAC TGTTGTAGATAGGTGAAGTTCGAGGGCGACGAA | 353 |
| ZZKD_PAMassay_R | TTCGTCGCCCTCGAACTTCACCTATCTACAACAGTAGAAATTCTTAGT ACTTCCAAAGGCTATAGTGAGTCGTATTAGAGG | 354 |
| ZZQE_PAMassay_F | cctcTAATACGACTCACTATAGGCTACTAAGCCTTTATAATTTCTACTAT TGTAGATAGGTGAAGTTCGAGGGCGACgaa | 355 |
| ZZQE_PAMassay_R | ttcGTCGCCCTCGAACTTCACCTATCTACAATAGTAGAAATTATAAAGG CTTAGTAGCCTATAGTGAGTCGTATTAgagg | 356 |
| ZRGM_PAMassay_F | cctcTAATACGACTCACTATAGTCTGAAAGACTATATAATTTCTACTTCG TGTAGATAGGTGAAGTTCGAGGGCGACgaa | 357 |
| ZRGM_PAMassay_R | ttcGTCGCCCTCGAACTTCACCTATCTACACGAAGTAGAAATTATATAG TCTTTCAGACTATAGTGAGTCGTATTAgagg | 358 |

TABLE 10

Sequences of the two oligonucleotides used to prepare the dsDNA adapter for the in vitro PAM assay

| Name | Sequence (5' → 3') | SEQ ID NO: |
|---|---|---|
| Oligo UP | CGGCATTCCTGCTGAACCGCTCTTCCGATCT | 359 |
| Oligo BOTTOM | GATCGGAAGAGCGGTTCAGCAGGAATGCCG | 360 |

TABLE 11

| Sequences of the primers used for NGS library preparation in the in vitro PAM assay | | |
|---|---|---|
| Primer name | Sequence (5'→3') | SEQ ID NO: |
| F4a | TCGTCGGCAGCGTCAGATGTGTATAAGAGACAGC TGCTGAACCGCTCTTCCGATC | 361 |
| F4b | TCGTCGGCAGCGTCAGATGTGTATAAGAGACAGT AAGACTGCTGAACCGCTCTTCCGATC | 362 |
| F4c | TCGTCGGCAGCGTCAGATGTGTATAAGAGACAGG CTAGACCTAATGTGATCTGCTGAACCGCTCTTCC GATC | 363 |
| R3 | GTCTCGTGGGCTCGGAGATGTGTATAAGAGACAG TCTGCGTTCTGATTTAATCTGTATCAGGC | 364 |

7.1.4. In Vitro Cleavage Assays

In vitro cleavage assays were performed using an RNP complex targeting a PCR product. Briefly, the RNP was assembled combining 105.7 pmol of synthetic RNA with 35 pmol of protein (ratio 3:1) and the complex was incubated 15 min at room temperature (approximately 20-22° C.). Two ug of PCR template was diluted in 90 µl of R buffer (10 Mm Tris-HCl PH 7.5; 10 mM NaCl; 1 mM DTT) and mixed with 9 µl of RNP complex. The reaction was incubated at 37° C. for 1 hour and then run on 1% agarose gel. Digested bands were gel-extracted and purified using a commercial kit (Macherey-Nagel), and sent for Sanger sequencing using the primers TRAC_ex1 forward and TRAC_ex1 reverse reported in Table 12.

7.1.5. Cell Line Transfections

For studies in HEK293T cells, 100,000 cells were plated in a 24 well plate. 24 hours later, cells were transfected with 500 ng of nuclease-expressing plasmid and 250 ng of sgRNA-expressing plasmid using Mirus TransIT™-LT1 according to the manufacturer's instructions. After 15-30 minutes of incubation at room temperature, the mixture was added drop-wise on HEK293T cultures.

To perform editing studies, 200,000 U2OS-EGFP cells were nucleofected with 500 ng of nuclease-expressing plasmid and 250 ng of sgRNA-expressing plasmid containing a guide designed to target EGFP using the 4D-Nucleofector™ SE Kit (Lonza), DN-100 program, according to the manufacturer's protocol. After electroporation, cells were plated in a 24-well plate. EGFP knock-out was analyzed 4 days after nucleofection using a BD FACSymphony™ A1 (BD) flow cytometer.

7.1.6. RNP Electroporation 200,000 U2OS cells were electroporated with RNP complexes (450 pmol of crRNAs+150 pmol of recombinant ZZKD Type V-A Cas protein) pre-formed at room temperature for 20 minutes using the 4D-Nucleofector™ SE Kit (Lonza), DN-100 program, according to the manufacturer's protocol. For RNP electroporation studies in primary human T cells, commercial lots were purchased from CGT preclinical. Briefly, a vial of $10\times10^6$ T cells, was thawed and incubated in RPMI+100 U/mL IL-2 (ImmunoTools). Four hours later, the T cells were counted, spun down, and resuspended in 5 mL of activation media (RPMI+IL-2 100 U/mL+100 µL TransAct T cell activator from Miltenyi Biotech), resulting in 10 million cells at a concentration of 2 million cells/mL. Three days post-activation, activated T cells were electroporated using Lonza 4D-Nucleofector™, EO115 program, with a pre-assembled RNP complex generated by mixing 450 pmol of the ZZKD Type V-A Cas protein and 150 pmol of the sgRNA and kept at room temperature for 20 minutes before electroporation. KO efficiency was evaluated 4 days post-electroporation by staining the T cells with an anti-human TCR alpha/beta chain antibody (BioLegend) for 30 minutes at 4° C. and quantifying the percentage of negative cells via flow cytometry. The recombinant ZZKD Type V-A protein was custom-produced by Origene, starting from a 6-His tagged (SEQ ID NO: 365) bacterial expression construct generated by gene synthesis (Twist Bioscience), while synthetic guide RNAs were purchased from IDT.

7.1.7. Evaluation of Gene Editing

Three days after transfection cells were collected and DNA was extracted using the QuickExtract™ DNA Extraction Solution (Lucigen) according to the manufacturer's instructions. To amplify the target loci, PCR reactions were performed using the HOT FIREPol™ polymerase (Solis BioDyne) and the oligonucleotides listed in Table 12. The amplified products were purified, sent for Sanger sequencing (EasyRun service, Microsynth) and analyzed with the TIDE web tool (shinyapps.datacurators.nl/tide/) to quantify indels. The forward primers used for generating the amplicons were also exploited for Sanger sequencing reactions.

TABLE 12

| Primers used to amplify target loci for Sanger sequencing | | | | |
|---|---|---|---|---|
| Target | Forward oligo (5'>3') | SEQ ID NO: | Reverse oligo (5'>3') | SEQ ID NO: |
| TRAC_ex1 | CATCACGAGCAGCTGGTTTC | 366 | TGGCAATGGATAAGGCCGAG | 378 |
| B2M_ex1 | CTCTAACCTGGCACTGCGTC | 367 | GGTGCTAGGACATGCGAACTTAG | 379 |
| B2M_ex2 | TGGCCAGAGTGGAAATGGAA | 368 | TGTATTTGTGCAAGTGCTGCT | 380 |
| PD1_ex1 | CACTGCCTCTGTCACTCTCG | 369 | TGGGGCTCCCATCCTTA | 381 |
| PD1_ex2 | CCTCACGTAGAAGGAAGAGGC | 370 | AGAGATGCCGGTCACCATTC | 382 |
| PD1_ex3_F | AATGGTGACCGGCATCTCTG | 371 | AAGGCACAGTGGATCATGCA | 383 |
| AAVS1 | CCTTATATTCCCAGGGCCGG | 372 | GAGAAAGGGAGTAGAGGCGG | 384 |
| VEGFA_2 | ACTTTGATGTCTGCAGGCCA | 373 | GAGCCTCAGCCCTTCCAC | 385 |
| EMX1 | ATTTCGGACTACCCTGAGGAG | 374 | GGAATCTACCACCCCAGGCTCT | 386 |

TABLE 12-continued

| Primers used to amplify target loci for Sanger sequencing | | | | |
|---|---|---|---|---|
| Target | Forward oligo (5'>3') | SEQ ID NO: | Reverse oligo (5'>3') | SEQ ID NO: |
| Match6 | TGCTAGACTTGCTGCTCCTT | 375 | TGAAGGGATTGTGCTGGTGT | 387 |
| PCSK9 | TGAACTTCAGCTCCTGCACA | 376 | TGCAGTTCCCAGTACGTTCC | 388 |
| BCL11A | GCATCACAACAGGCAGAGAAT GTC | 377 | TATGACGTCAGGGGGAGGCAAG TC | 389 |

7.2. Example 1: Identification and Characterization of Novel Type V-A Cas Molecules This Example describes studies performed to identify and characterize ZWGD, ZJHK, ZIKV, ZZFT, YYAN, ZZGY, ZKBG, ZZKD, ZXPB, and ZPPX TYPE V-A Cas proteins.

7.2.1. Identification of the crRNAs of Novel Type V-A Cas Proteins crRNA sequences for the selected Type V-A Cas proteins were identified in silico by extracting the repeat region of the CRISPR arrays associated with each nuclease, as described in the Materials & Methods (Section 7.1). The secondary structures of the identified cRNAs for each of the Type V-A Cas proteins are reported in FIGS. 1A-1E and FIGS. 2A-2E.

7.2.2. In Silico Prediction of the PAM Specificity of Novel Type V-A Cas Proteins An in silico PAM prediction pipeline (as reported above in the Materials & Methods (Section 7.1)) has been used to predict the PAM recognition specificity of the novel Type V-A Cas proteins. Table 13 reported here below contains the PAM preferences as predicted by the algorithm. The predicted PAM logos for each enzyme are reported in FIGS. 3A-3E and 4A-4E.

TABLE 13

| In silico predicted PAM sequences for selected Type V-A Cas proteins | |
|---|---|
| Type V-A Cas protein | Predicted PAM (5'-3') |
| ZWGD Type V-A Cas | TTTN, TTN |
| ZJHK Type V-A Cas | TTTN, TTTV |
| ZIKV Type V-A Cas | TTTR, TNNTTTR, DNNTTTR |
| ZZFT Type V-A Cas | TTTR |
| YYAN Type V-A Cas | TTTN |
| ZZGY Type V-A Cas | TTTN, TTTR |
| ZKBG Type V-A Cas | YTTN, TTTN |
| ZZKD Type V-A Cas | TTTN, TTTV |
| ZXPB Type V-A Cas | TTTN, DTTN, DTDN |
| ZPPX Type V-A Cas | YTTN, TTTN |

7.2.3. Evaluation of Type V-A Cas Proteins Editing Activity Using an EGFP Reporter System By exploiting the knowledge on their predicted PAM sequences and their identified crRNAs, the ability to cleave selected targets in mammalian cells of the selected Type V-A Cas proteins was investigated. An EGFP reporter system was used as it allowed an easier readout on the editing activity, based on the loss of fluorescence of treated cells quantitatively measured by cytofluorimetry. Two gRNAs targeting the EGFP coding sequence were designed exploiting PAMs which, based on the in silico prediction, were compatible for all the Type V-A Cas proteins and tested in U2OS cells stably expressing a single copy of an EGFP reporter by transient electroporation. Surprisingly, as reported in FIG. 5, some of the evaluated guides in combination with their respective Type V-A Cas protein were able to significantly downregulate EGFP expression in target cells. In particular, ZZKD Type V-A Cas protein showed very high activity with both of the guides (>70 and >95% EGFP KO); additionally, ZJHK, ZZGY, ZXPB and YYAN Type V-A Cas proteins showed appreciable knock-out activity (>20% EGFP KO) with at least one of the gRNAs. The remaining Type V-A Cas proteins did not show editing levels above the background of the assay against the currently evaluated targets in the EGFP coding sequence. These data clearly demonstrate that several of the selected Type V-A Cas proteins were able to modify very efficiently genetic targets in mammalian cells and can thus be exploited to edit the mammalian genome.

7.2.4. Evaluation of ZZKD Type V-A Cas Protein Editing Activity on Benchmark Genomic Loci in Mammalian Cells To further validate the editing activity of the highest performing candidate Type V-A Cas protein in the EGFP assay, ZZKD, guide RNAs were designed to target the B2M, TRAC and PD1 benchmark genomic loci in human cells. U2OS cells were electroporated with plasmids encoding ZZKD Type V-A Cas and the selected gRNAs and indel formation was measured by Sanger chromatogram deconvolution on extracted genomic DNA. Strikingly, for all three target loci it was possible to identify at least one gRNA showing high levels of genomic modification (>40%, see FIG. 6A-C) and except for the B2M target locus more than one well performing guide was identified (g3-g4 for the TRAC locus, g1-g2 for the PD1 locus).

Overall these data clearly demonstrate that ZZKD Type V-A is proficient in editing the human genome at several target sites.

7.3. Example 2: Further Characterization of Novel Type V-A Cas Molecules

This Example describes studies performed to further characterize Type V-A Cas proteins identified in Example 1.

7.3.1. Evaluation of Additional Type V-A Cas Proteins Editing Activity Using an EGFP Reporter System Leveraging on the conserved nature of PAM preferences among Type V-A Cas proteins, guide RNAs targeting the EGFP coding sequence were designed for novel Type V-A Cas proteins isolated from the human microbiome to evaluate their activity in human cells. An EGFP reporter system was used as it allowed an easier readout on the editing activity, based on the loss of fluorescence of treated cells quantitatively measured by cytofluorimetry. Two gRNAs targeting the EGFP coding sequence were designed and evaluated in U2OS cells stably expressing a single copy of the EGFP reporter by transient electroporation. As reported in FIG. 10, while most of the evaluated nucleases showed relatively low levels of EGFP downregulation in this particular assay (close to the detection limit of the assay), some of the selected enzymes were particularly proficient in editing their target sequence. In particular, ZZQE Type V-A Cas protein showed very high activity with both of the evaluated guides (>60% EGFP KO), followed by ZRGM, ZSQQ and ZRXE Type V-A Cas proteins which showed appreciable knock-out activity (>40% EGFP KO) with at least one of the evaluated gRNAs. These data clearly demonstrate that several of the selected Type V-A Cas proteins were able to very efficiently modify genetic targets in mammalian cells and can thus be exploited to modify the genome of mammalian cells.

7.3.2. Evaluation of Novel Type V-A Cas Proteins Editing Activity on Benchmark Genomic Loci in Mammalian Cells The evaluation of the editing activity of the top performing Type V-A Cas proteins from the EGFP reporter assay KO, ZZKD, ZRGM and ZZQE, was extended to endogenous genomic loci. Guide RNAs were designed to target the B2M (g2), TRAC (g3) and PD1 (g2) benchmark genomic loci in human cells. HEK293T cells were lipofected with plasmids encoding ZZKD, ZRGM and ZZQE Type V-A Cas proteins and the selected gRNAs and indel formation was measured by Sanger chromatogram deconvolution on extracted genomic DNA. Strikingly, for all three target loci all evaluated Type V-A Cas proteins were able to produce appreciable levels of indels, with some variability depending on the target (FIG. 11).

Overall, these data clearly demonstrate that among the selected Type V-A Cas proteins, ZZKD is the most efficient in editing the human genome at several target sites.

7.3.3. In Vitro Determination of the PAM Specificity of Top-Performing Novel Type V-A Cas Proteins After a first evaluation of their activity in mammalian cells, the PAM preferences of the top performing Type V-A Cas proteins were determined using a well-established in vitro assay. Briefly, ZZKD, ZRGM and ZZQE Type V-A Cas proteins were expressed in HEK293T cells to generate cell lysates which were then used in an in vitro cleavage reaction where a plasmid library including a known target flanked by a randomized 8 nt sequence was cut based on PAM recognition preferences by ribonucleoprotein complexes generated using the cell-expressed nucleases and an in vitro transcribed gRNA targeting the library. Cleaved plasmids were then recovered by amplification and sequenced to determine which PAM sequences were preferentially cleaved (see Materials and Methods for more details). These results confirmed the predicted PAM preferences for ZZKD and ZZQE (see FIG. 4C and FIG. 9, respectively), and in general confirmed the possibility to recognize the TTTV PAM which was used in the initial editing evaluation studies, but showed also additional recognition capabilities. The PAM logos and heatmaps for all the selected Type V-A Cas proteins are reported in FIG. 12A-12B, and FIGS. 13A-13D, while a summary of the in vitro determined PAMs are included in Table 14.

TABLE 14

In vitro determined PAM sequences for selected Type V-A Cas proteins

| Type V-A Cas protein | PAM (5'-3') |
|---|---|
| ZZKD Type V-A Cas | NTTV, VTTV, NCTV, TTTT |
| ZRGM Type V-A Cas | YTTV |
| ZZQE Type V-A Cas | NYYN, NTTN, NCTV |

To further confirm the PAM preferences determined for ZZKD Type V-A Cas, a panel of guide RNAs targeting loci flanked by a VTTV and TTTT PAMs was selected and the editing efficacy of ZZKD towards these loci was evaluated after transient transfection in HEK293T cells. As shown in FIG. 12C, many of the evaluated guides showed efficient editing of the target locus demonstrating the possibility for ZZKD to recognize such PAMs, as indicated by the in vitro assay.

7.4. Example 3: Further Characterization of ZZKD Type V-A Cas Protein

This example describes additional studies to characterize ZZKD Type V-A Cas protein.

7.4.1. Evaluation of the Cleavage Profile of ZZKD Type V-A Cas Protein

To further characterize the enzymatic activity of ZZKD Type V-A Cas protein, its cleavage profile was investigated in vitro. Recombinant ZZKD was used to digest in vitro a dsDNA target obtained by PCR amplification of a known target region (TRAC locus, g3). The digestion products were separated on agarose gel and independently Sanger sequenced. Based on the two chromatographic profiles (FIG. 14A), it was possible to determine where the two DNA strands were cut: a staggered double strand break was produced, with the non-target strand cut 23nt downstream (5'>3') of the PAM and the target strand cut 18nt upstream (5'>3'). This is in line with what was observed for other well characterized Type V-A Cas proteins.

7.4.2. Evaluation of Different Nuclear Localization Signals (NLS) for ZZKD Type V-A Cas Protein In order to further improve the editing activity of the ZZKD Type V-A Cas protein, alternative types and positioning of nuclear localization signals were evaluated. The amino acid sequence of the different NLS evaluated as well as the relative position are indicated in Table 15 below.

TABLE 15

Nuclear localization signals evaluated in the example

| Name | Position | Amino acid sequence | SEQ ID |
|---|---|---|---|
| SV40 | N-term | PKKKRKVG | 179 |
| bpNLS | C-term | KRTADGSEFESPKKKRKV | 122 |

TABLE 15-continued

| Nuclear localization signals evaluated in the example | | | |
|---|---|---|---|
| Name | Position | Amino acid sequence | SEQ ID |
| FL-SV40 | C-term | GRSSDDEATADSQHAAPPKKKRKV | 180 |
| npNLS | C-term | KRPAATKKAGQAKKKK | 125 |

As shown in FIG. 15, when the effect on editing activity of the different NLS designs was evaluated by transient transfection in HEK293T cells using the TRAC benchmark locus (g3) as a target, most of the constructs showed high editing levels with the exception of the single npNLS at the C-terminus, as indicated on the graph. Among all evaluated constructs, the FL-SV40 C-term performed particularly well and was thus used in subsequent studies.

7.5. Example 4: Novel Type V-A Cas Protein Alternative crRNA Scaffolds

Alternative trimmed scaffolds were evaluated for the top performing identified Type V-A Cas proteins (ZZKD, ZRGM, ZZQE). The editing activity of these enzymes was evaluated using the standard full length scaffold (36 nt) in comparison to a shorter 20nt scaffold, which nevertheless preserves a conserved stem-loop structure shared among the different crRNAs (FIGS. 16A-16C), using the TRAC locus (g3) as a benchmark. After transient transfection in HEK293T cells, indels were measured at the target locus revealing similar editing levels with both versions of the crRNA for all the evaluated nucleases (FIG. 17A). To further confirm this finding, ZZKD Type V-A Cas protein was evaluated on an extended panel of loci including additional guides on TRAC, BCL11A, AAVS1 and B2M. These studies confirmed a similar activity for both versions of the scaffold (FIG. 17B), in accordance with previously generated data. Overall, this demonstrates that truncating the 5'-end of the crRNA scaffold does not negatively influence the editing activity of these Type V-A Cas proteins after transfection in human cells.

7.6. Example 5: Evaluation of ZZKD Type V-A Cas Protein Spacer Length

With the aim of further improving the editing activity of ZZKD Type V-A Cas, different spacer lengths were evaluated to determine which favored the highest target modification. crRNAs with spacer lengths ranging from 20nt to 24nt were evaluated by targeting the TRAC (g3) and Match6 (see, Kleinstiver et al., 2016, Nat Biotechnol. 34 (8): 869-74) benchmark loci by transient transfection in HEK293T cells. While appreciable editing levels were observed for all the evaluated lengths (FIGS. 18A-18B), shorter spacers were generally offering higher activity, with 21nt being the most preferred length.

7.7. Example 6: Side-by-Side Comparison of ZZKD Type V-A Cas Protein Activity with the Commercially Available Benchmark AsCas12a Ultra To characterize in depth the editing activity of ZZKD Type V-A Cas, indel formation was compared to the commercially available benchmark AsCas12a Ultra (Zhang et al., 2021, Nat. comms. 12:3908), on a panel of endogenous loci in HEK293T cells after transient transfection. A total of 17 crRNAs targeting multiple genomic loci (TRAC, PD1, EMX1, AAVS1, BCL11A, PCSK9, Match6, VEGFA) were evaluated. Notably, given the PAM compatibility between ZZKD and AsCas12a Ultra, the crRNAs were fully overlapping in all cases. As shown by the violin plots of FIG. 19, summarizing the editing data, the performance of the two nucleases was generally comparable, with ZZKD outperforming AsCas12a Ultra at some loci. The editing levels for each target site for the two nucleases are reported in Table 16 below.

TABLE 16

Editing levels on endogenous target loci after transient transfection of HEK293T cells (mean ± SD)

| Target site | ZZKD Type V-A Cas | AsCas12a Ultra |
|---|---|---|
| B2M_g2 | 16.50 ± 0.99 | 22.45 ± 3.3 |
| TRAC_g3 | 28.45 ± 1.77 | 28.35 ± 1.6 |
| PD1_g2 | 28.45 ± 1.22 | 26.45 ± 3.3 |
| BCL11A_g1 | 30.85 ± 0.35 | 26.65 ± 1.1 |
| BCL11A_g2 | 24.10 ± 2.12 | 22.7 ± 0.3 |
| BCL11A_g3 | 12.05 ± 3.04 | 19.55 ± 1.1 |
| PCSK9_g1 | 24.60 ± 4.24 | 11.4 ± 0.1 |
| PCSK9_g3 | 13.20 ± 4.95 | 15.7 ± 1.6 |
| AAVS1_g1 | 12.60 ± 0.71 | 15.5 ± 5.7 |
| AAVS1_g2 | 31.55 ± 1.20 | 20.7 ± 0.8 |
| AAVS1_g3 | 11.85 ± 0.07 | 9.05 ± 0.1 |
| Match6 | 28.70 ± 0.28 | 28.65 ± 2.5 |
| BCL11A_g4 | 60.65 ± 8.27 | 57.65 ± 3.5 |
| VEGFA_g1 | 33.75 ± 3.18 | 32.35 ± 0.6 |
| EMX1_g2 | 0.95 ± 0.78 | 6 ± 0.4 |
| EMX1_g3 | 20.35 ± 0.35 | 14.35 ± 3.5 |
| B2M_g1_21nt | 54.50 ± 9.19 | 61.6 |

Further to these editing studies, titration studies, where the amounts of transfected nuclease and guide RNA are progressively lowered to better measure differences in the editing activity, were performed on a selection of target loci (BCL11A-g4, B2M-g1 and B2M-g2, VEGFA-g1) in HEK293T cells. As shown in FIGS. 20A-20D, all titration curves showed generally comparable editing activities of the two proteins, with the general tendency for ZZKD Type V-A Cas to perform better than the AsCas12a Ultra benchmark (see for example VEGFA-g1 in FIG. 20B).

Overall, these data demonstrate that ZZKD Type V-A Cas protein is able to match or outperform the editing activity of the current state-of-the-art commercial AsCas12 Ultra benchmark.

7.8. Example 7: Type V-A Cas Protein Activity after Direct Protein Delivery in Cells To demonstrate the efficacy of ZZKD Type V-A Cas protein using alternative delivery modalities, direct ribonucleoprotein (RNP) complex delivery to target cells by electroporation was performed. To this aim, recombinant ZZKD was produced in bacteria and was purified by multiple rounds of chromatography using standard techniques, while crRNAs were obtained either from IDT (chemical synthesis) or through in vitro transcription using the T7 RNA polymerase. The activity of the RNP was initially evaluated in U2OS cells using guides targeting the TRAC (FIG. 21A) and B2M (FIG. 21B) loci. The observed editing activity was generally higher than that of the corresponding electroporated plasmid and, among the different types of crRNA evaluated, the synthetic crRNAs performed better. An AltR-modified guide (a chemical modification available from IDT) targeting B2M was also included in the panel showing editing levels close to the unmodified synthetic guide. Additionally, a titration study using B2M-g2 crRNA was performed by lowering progressively the amount of either recombinant ZZKD or corresponding crRNA and also changing the protein: crRNA ratio from 1:3 to 1:1.5 in order to more stringently evaluate ZZKD potency. As shown in FIG. 21C, in most of the conditions evaluated ZZKD Type V-A Cas protein preserved high levels of editing activity indicating high potency even at low concentrations.

To further confirm the activity of ZZKD Type V-A Cas as RNP, human commercial primary T cells were electroporated with the complex including a guide targeting the TRAC locus (g3). As shown in FIG. 22, ZZKD was able to produce approximately 80% of TRAC-negative cells as measured by cytofluorimetry, demonstrating high editing activity.

Overall, these data show not only that ZZKD Type V-A Cas protein is compatible with direct protein delivery in multiple cell types including hard-to-edit primary T cells but that ZZKD is also highly potent and can be used at low concentrations to obtain efficient target modification.

8. SPECIFIC EMBODIMENTS

The present disclosure is exemplified by the specific embodiments below.

1. A Type V Cas protein comprising an amino acid sequence having at least 50% sequence identity to:
   - (a) the amino acid sequence of a WED-1 domain of a reference protein sequence;
   - (b) the amino acid sequence of a REC1 domain of a reference protein sequence;
   - (c) the amino acid sequence of a REC2 domain of a reference protein sequence;
   - (d) the amino acid sequence of a WED-II domain of a reference protein sequence;
   - (e) the amino acid sequence of a PI domain of a reference protein sequence;
   - (f) the amino acid sequence of a WED-III domain of a reference protein sequence;
   - (g) the amino acid sequence of a RuvC-I domain of a reference protein sequence;
   - (h) the amino acid sequence of a BH domain of a reference protein sequence;
   - (i) the amino acid sequence of a RuvC-II domain of a reference protein sequence;
   - (j) the amino acid sequence of a NUC domain of a reference protein sequence;
   - (k) the amino acid sequence of a RuvC-III domain of a reference protein sequence; or
   - (l) the amino acid sequence of the full length of a reference protein sequence;

wherein the reference protein sequence is SEQ ID NO:1, SEQ ID NO:2, SEQ ID NO:7, SEQ ID NO:8, SEQ ID NO:13, SEQ ID NO:14, SEQ ID NO:19, SEQ ID NO:20, SEQ ID NO:25, SEQ ID NO:26, SEQ ID NO:31, SEQ ID NO:32, SEQ ID NO:37, SEQ ID NO:38, SEQ ID NO:43, SEQ ID NO:44, SEQ ID NO:49, SEQ ID NO:50, SEQ ID NO:55, SEQ ID NO:56, SEQ ID NO:61, SEQ ID NO:62, SEQ ID NO:67, SEQ ID NO:68, SEQ ID NO:73, SEQ ID NO:74, SEQ ID NO:79, SEQ ID NO:80, SEQ ID NO:85, SEQ ID NO:86, SEQ ID NO:91, SEQ ID NO:92, SEQ ID NO:97, SEQ ID NO:98, SEQ ID NO:103, SEQ ID NO:104, SEQ ID NO:109, SEQ ID NO:110, SEQ ID NO:115, or SEQ ID NO:116.

2. The Type V Cas protein of embodiment 1, wherein the amino acid sequence of the Type V Cas protein comprises an amino acid sequence that is at least 50% identical to the amino acid sequence of the WED-I domain of the reference protein sequence.

3. The Type V Cas protein of embodiment 1, wherein the amino acid sequence of the Type V Cas protein comprises an amino acid sequence that is at least 55% identical to the amino acid sequence of the WED-I domain of the reference protein sequence.

4. The Type V Cas protein of embodiment 1, wherein the amino acid sequence of the Type V Cas protein comprises an amino acid sequence that is at least 60% identical to the amino acid sequence of the WED-I domain of the reference protein sequence.

5. The Type V Cas protein of embodiment 1, wherein the amino acid sequence of the Type V Cas protein comprises an amino acid sequence that is at least 65% identical to the amino acid sequence of the WED-I domain of the reference protein sequence.

6. The Type V Cas protein of embodiment 1, wherein the amino acid sequence of the Type V Cas protein comprises an amino acid sequence that is at least 70% identical to the amino acid sequence of the WED-I domain of the reference protein sequence.

7. The Type V Cas protein of embodiment 1, wherein the amino acid sequence of the Type V Cas protein comprises an amino acid sequence that is at least 75% identical to the amino acid sequence of the WED-I domain of the reference protein sequence.

8. The Type V Cas protein of embodiment 1, wherein the amino acid sequence of the Type V Cas protein comprises an amino acid sequence that is at least 80% identical to the amino acid sequence of the WED-I domain of the reference protein sequence.

9. The Type V Cas protein of embodiment 1, wherein the amino acid sequence of the Type V Cas protein comprises an amino acid sequence that is at least 85% identical to the amino acid sequence of the WED-I domain of the reference protein sequence.

10. The Type V Cas protein of embodiment 1, wherein the amino acid sequence of the Type V Cas protein comprises an amino acid sequence that is at least 90% identical to the amino acid sequence of the WED-I domain of the reference protein sequence.

11. The Type V Cas protein of embodiment 1, wherein the amino acid sequence of the Type V Cas protein comprises an amino acid sequence that is at least 95% identical to the amino acid sequence of the WED-I domain of the reference protein sequence.

12. The Type V Cas protein of embodiment 1, wherein the amino acid sequence of the Type V Cas protein comprises an amino acid sequence that is at least 96% identical to the amino acid sequence of the WED-I domain of the reference protein sequence.

13. The Type V Cas protein of embodiment 1, wherein the amino acid sequence of the Type V Cas protein comprises an amino acid sequence that is at least 97% identical to the amino acid sequence of the WED-I domain of the reference protein sequence.

14. The Type V Cas protein of embodiment 1, wherein the amino acid sequence of the Type V Cas protein comprises an amino acid sequence that is at least 98% identical to the amino acid sequence of the WED-I domain of the reference protein sequence.

15. The Type V Cas protein of embodiment 1, wherein the amino acid sequence of the Type V Cas protein comprises an amino acid sequence that is at least 99% identical to the amino acid sequence of the WED-I domain of the reference protein sequence.

16. The Type V Cas protein of embodiment 1, wherein the amino acid sequence of the Type V Cas protein comprises an amino acid sequence that is identical to the amino acid sequence of the WED-I domain of the reference protein sequence.

17. The Type V Cas protein of any one of embodiments 1 to 16, wherein the amino acid sequence of the Type V Cas protein comprises an amino acid sequence that is at least 50% identical to the amino acid sequence of the REC1 domain of the reference protein sequence.

18. The Type V Cas protein of any one of embodiments 1 to 16, wherein the amino acid sequence of the Type V Cas protein comprises an amino acid sequence that is at least 55% identical to the amino acid sequence of the REC1 domain of the reference protein sequence.

19. The Type V Cas protein of any one of embodiments 1 to 16, wherein the amino acid sequence of the Type V Cas protein comprises an amino acid sequence that is at least 60% identical to the amino acid sequence of the REC1 domain of the reference protein sequence.

20. The Type V Cas protein of any one of embodiments 1 to 16, wherein the amino acid sequence of the Type V Cas protein comprises an amino acid sequence that is at least 65% identical to the amino acid sequence of the REC1 domain of the reference protein sequence.

21. The Type V Cas protein of any one of embodiments 1 to 16, wherein the amino acid sequence of the Type V Cas protein comprises an amino acid sequence that is at least 70% identical to the amino acid sequence of the REC1 domain of the reference protein sequence.

22. The Type V Cas protein of any one of embodiments 1 to 16, wherein the amino acid sequence of the Type V Cas protein comprises an amino acid sequence that is at least 75% identical to the amino acid sequence of the REC1 domain of the reference protein sequence.

23. The Type V Cas protein of any one of embodiments 1 to 16, wherein the amino acid sequence of the Type V Cas protein comprises an amino acid sequence that is at least 80% identical to the amino acid sequence of the REC1 domain of the reference protein sequence.

24. The Type V Cas protein of any one of embodiments 1 to 16, wherein the amino acid sequence of the Type V Cas protein comprises an amino acid sequence that is at least 85% identical to the amino acid sequence of the REC1 domain of the reference protein sequence.

25. The Type V Cas protein of any one of embodiments 1 to 16, wherein the amino acid sequence of the Type V Cas protein comprises an amino acid sequence that is at least 90% identical to the amino acid sequence of the REC1 domain of the reference protein sequence.

26. The Type V Cas protein of any one of embodiments 1 to 16, wherein the amino acid sequence of the Type V Cas protein comprises an amino acid sequence that is at least 95% identical to the amino acid sequence of the REC1 domain of the reference protein sequence.

27. The Type V Cas protein of any one of embodiments 1 to 16, wherein the amino acid sequence of the Type V Cas protein comprises an amino acid sequence that is at least 96% identical to the amino acid sequence of the REC1 domain of the reference protein sequence.

28. The Type V Cas protein of any one of embodiments 1 to 16, wherein the amino acid sequence of the Type V Cas protein comprises an amino acid sequence that is at least 97% identical to the amino acid sequence of the REC1 domain of the reference protein sequence.

29. The Type V Cas protein of any one of embodiments 1 to 16, wherein the amino acid sequence of the Type V Cas protein comprises an amino acid sequence that is at least 98% identical to the amino acid sequence of the REC1 domain of the reference protein sequence.

30. The Type V Cas protein of any one of embodiments 1 to 16, wherein the amino acid sequence of the Type V Cas protein comprises an amino acid sequence that is at least 99% identical to the amino acid sequence of the REC1 domain of the reference protein sequence.

31. The Type V Cas protein of any one of embodiments 1 to 16, wherein the amino acid sequence of the Type V Cas protein comprises an amino acid sequence that is identical to the amino acid sequence of the REC1 domain of the reference protein sequence.

32. The Type V Cas protein of any one of embodiments 1 to 31, wherein the amino acid sequence of the Type V Cas protein comprises an amino acid sequence that is at least 50% identical to the amino acid sequence of the REC2 domain of the reference protein sequence.

33. The Type V Cas protein of any one of embodiments 1 to 31, wherein the amino acid sequence of the Type V Cas protein comprises an amino acid sequence that is at least 55% identical to the amino acid sequence of the REC2 domain of the reference protein sequence.

34. The Type V Cas protein of any one of embodiments 1 to 31, wherein the amino acid sequence of the Type V Cas protein comprises an amino acid sequence that is at least 60% identical to the amino acid sequence of the REC2 domain of the reference protein sequence.

35. The Type V Cas protein of any one of embodiments 1 to 31, wherein the amino acid sequence of the Type V Cas protein comprises an amino acid sequence that is at least 65% identical to the amino acid sequence of the REC2 domain of the reference protein sequence.

36. The Type V Cas protein of any one of embodiments 1 to 31, wherein the amino acid sequence of the Type V Cas protein comprises an amino acid sequence that is at least 70% identical to the amino acid sequence of the REC2 domain of the reference protein sequence.

37. The Type V Cas protein of any one of embodiments 1 to 31, wherein the amino acid sequence of the Type V Cas protein comprises an amino acid sequence that is at least 75% identical to the amino acid sequence of the REC2 domain of the reference protein sequence.

38. The Type V Cas protein of any one of embodiments 1 to 31, wherein the amino acid sequence of the Type V Cas protein comprises an amino acid sequence that is at least 80% identical to the amino acid sequence of the REC2 domain of the reference protein sequence.

39. The Type V Cas protein of any one of embodiments 1 to 31, wherein the amino acid sequence of the Type V Cas protein comprises an amino acid sequence that is at least 85% identical to the amino acid sequence of the REC2 domain of the reference protein sequence.

40. The Type V Cas protein of any one of embodiments 1 to 31, wherein the amino acid sequence of the Type V Cas protein comprises an amino acid sequence that is at least 90% identical to the amino acid sequence of the REC2 domain of the reference protein sequence.

41. The Type V Cas protein of any one of embodiments 1 to 31, wherein the amino acid sequence of the Type V Cas protein comprises an amino acid sequence that is at least 95% identical to the amino acid sequence of the REC2 domain of the reference protein sequence.

42. The Type V Cas protein of any one of embodiments 1 to 31, wherein the amino acid sequence of the Type V Cas protein comprises an amino acid sequence that is at least 96% identical to the amino acid sequence of the REC2 domain of the reference protein sequence.

43. The Type V Cas protein of any one of embodiments 1 to 31, wherein the amino acid sequence of the Type V Cas protein comprises an amino acid sequence that is at least 97% identical to the amino acid sequence of the REC2 domain of the reference protein sequence.

44. The Type V Cas protein of any one of embodiments 1 to 31, wherein the amino acid sequence of the Type V Cas protein comprises an amino acid sequence that is at least 98% identical to the amino acid sequence of the REC2 domain of the reference protein sequence.

45. The Type V Cas protein of any one of embodiments 1 to 31, wherein the amino acid sequence of the Type V Cas protein comprises an amino acid sequence that is at least 99% identical to the amino acid sequence of the REC2 domain of the reference protein sequence.

46. The Type V Cas protein of any one of embodiments 1 to 31, wherein the amino acid sequence of the Type V Cas protein comprises an amino acid sequence that is identical to the amino acid sequence of the REC2 domain of the reference protein sequence.

47. The Type V Cas protein of any one of embodiments 1 to 46, wherein the amino acid sequence of the Type V Cas protein comprises an amino acid sequence that is at least 50% identical to the amino acid sequence of the WED-II domain of the reference protein sequence.

48. The Type V Cas protein of any one of embodiments 1 to 46, wherein the amino acid sequence of the Type V Cas protein comprises an amino acid sequence that is at least 55% identical to the amino acid sequence of the WED-II domain of the reference protein sequence.

49. The Type V Cas protein of any one of embodiments 1 to 46, wherein the amino acid sequence of the Type V Cas protein comprises an amino acid sequence that is at least 60% identical to the amino acid sequence of the WED-II domain of the reference protein sequence.

50. The Type V Cas protein of any one of embodiments 1 to 46, wherein the amino acid sequence of the Type V Cas protein comprises an amino acid sequence that is at least 65% identical to the amino acid sequence of the WED-II domain of the reference protein sequence.

51. The Type V Cas protein of any one of embodiments 1 to 46, wherein the amino acid sequence of the Type V Cas protein comprises an amino acid sequence that is at least 70% identical to the amino acid sequence of the WED-II domain of the reference protein sequence.

52. The Type V Cas protein of any one of embodiments 1 to 46, wherein the amino acid sequence of the Type V Cas protein comprises an amino acid sequence that is at least 75% identical to the amino acid sequence of the WED-II domain of the reference protein sequence.

53. The Type V Cas protein of any one of embodiments 1 to 46, wherein the amino acid sequence of the Type V Cas protein comprises an amino acid sequence that is at least 80% identical to the amino acid sequence of the WED-II domain of the reference protein sequence.

54. The Type V Cas protein of any one of embodiments 1 to 46, wherein the amino acid sequence of the Type V Cas protein comprises an amino acid sequence that is at least 85% identical to the amino acid sequence of the WED-II domain of the reference protein sequence.

55. The Type V Cas protein of any one of embodiments 1 to 46, wherein the amino acid sequence of the Type V Cas protein comprises an amino acid sequence that is at least 90% identical to the amino acid sequence of the WED-II domain of the reference protein sequence.

56. The Type V Cas protein of any one of embodiments 1 to 46, wherein the amino acid sequence of the Type V Cas protein comprises an amino acid sequence that is at least 95% identical to the amino acid sequence of the WED-II domain of the reference protein sequence.

57. The Type V Cas protein of any one of embodiments 1 to 46, wherein the amino acid sequence of the Type V Cas protein comprises an amino acid sequence that is at least 96% identical to the amino acid sequence of the WED-II domain of the reference protein sequence.

58. The Type V Cas protein of any one of embodiments 1 to 46, wherein the amino acid sequence of the Type V Cas protein comprises an amino acid sequence that is at least 97% identical to the amino acid sequence of the WED-II domain of the reference protein sequence.

59. The Type V Cas protein of any one of embodiments 1 to 46, wherein the amino acid sequence of the Type V Cas protein comprises an amino acid sequence that is at least 98% identical to the amino acid sequence of the WED-II domain of the reference protein sequence.

60. The Type V Cas protein of any one of embodiments 1 to 46, wherein the amino acid sequence of the Type V Cas protein comprises an amino acid sequence that is at least 99% identical to the amino acid sequence of the WED-II domain of the reference protein sequence.

61. The Type V Cas protein of any one of embodiments 1 to 46, wherein the amino acid sequence of the Type V Cas protein comprises an amino acid sequence that is identical to the amino acid sequence of the WED-II domain of the reference protein sequence.

62. The Type V Cas protein of any one of embodiments 1 to 61, wherein the amino acid sequence of the Type V Cas protein comprises an amino acid sequence that is at least 50% identical to the amino acid sequence of the PI domain of the reference protein sequence.

63. The Type V Cas protein of any one of embodiments 1 to 61, wherein the amino acid sequence of the Type V Cas protein comprises an amino acid sequence that is at least 55% identical to the amino acid sequence of the PI domain of the reference protein sequence.

64. The Type V Cas protein of any one of embodiments 1 to 61, wherein the amino acid sequence of the Type V Cas protein comprises an amino acid sequence that is at least 60% identical to the amino acid sequence of the PI domain of the reference protein sequence.

65. The Type V Cas protein of any one of embodiments 1 to 61, wherein the amino acid sequence of the Type V Cas protein comprises an amino acid sequence that is at least 65% identical to the amino acid sequence of the PI domain of the reference protein sequence.

66. The Type V Cas protein of any one of embodiments 1 to 61, wherein the amino acid sequence of the Type V Cas protein comprises an amino acid sequence that is at least 70% identical to the amino acid sequence of the PI domain of the reference protein sequence.

67. The Type V Cas protein of any one of embodiments 1 to 61, wherein the amino acid sequence of the Type V Cas protein comprises an amino acid sequence that is at least 75% identical to the amino acid sequence of the PI domain of the reference protein sequence.

68. The Type V Cas protein of any one of embodiments 1 to 61, wherein the amino acid sequence of the Type V Cas protein comprises an amino acid sequence that is at least 80% identical to the amino acid sequence of the PI domain of the reference protein sequence.

69. The Type V Cas protein of any one of embodiments 1 to 61, wherein the amino acid sequence of the Type V Cas protein comprises an amino acid sequence that is at least 85% identical to the amino acid sequence of the PI domain of the reference protein sequence.

70. The Type V Cas protein of any one of embodiments 1 to 61, wherein the amino acid sequence of the Type V Cas protein comprises an amino acid sequence that is at least 90% identical to the amino acid sequence of the PI domain of the reference protein sequence.

71. The Type V Cas protein of any one of embodiments 1 to 61, wherein the amino acid sequence of the Type V Cas protein comprises an amino acid sequence that is at least 95% identical to the amino acid sequence of the PI domain of the reference protein sequence.

72. The Type V Cas protein of any one of embodiments 1 to 61, wherein the amino acid sequence of the Type V Cas protein comprises an amino acid sequence that is at least 96% identical to the amino acid sequence of the PI domain of the reference protein sequence.

73. The Type V Cas protein of any one of embodiments 1 to 61, wherein the amino acid sequence of the Type V Cas protein comprises an amino acid sequence that is at least 97% identical to the amino acid sequence of the PI domain of the reference protein sequence.

74. The Type V Cas protein of any one of embodiments 1 to 61, wherein the amino acid sequence of the Type V Cas protein comprises an amino acid sequence that is at least 98% identical to the amino acid sequence of the PI domain of the reference protein sequence.

75. The Type V Cas protein of any one of embodiments 1 to 61, wherein the amino acid sequence of the Type V Cas protein comprises an amino acid sequence that is at least 99% identical to the amino acid sequence of the PI domain of the reference protein sequence.

76. The Type V Cas protein of any one of embodiments 1 to 61, wherein the amino acid sequence of the Type V Cas protein comprises an amino acid sequence that is identical to the amino acid sequence of the PI domain of the reference protein sequence.

77. The Type V Cas protein of any one of embodiments 1 to 76, wherein the amino acid sequence of the Type V Cas protein comprises an amino acid sequence that is at least 50% identical to the amino acid sequence of the WED-III domain of the reference protein sequence.

78. The Type V Cas protein of any one of embodiments 1 to 76, wherein the amino acid sequence of the Type V Cas protein comprises an amino acid sequence that is at least 55% identical to the amino acid sequence of the WED-III domain of the reference protein sequence.

79. The Type V Cas protein of any one of embodiments 1 to 76, wherein the amino acid sequence of the Type V Cas protein comprises an amino acid sequence that is at least 60% identical to the amino acid sequence of the WED-III domain of the reference protein sequence.

80. The Type V Cas protein of any one of embodiments 1 to 76, wherein the amino acid sequence of the Type V Cas protein comprises an amino acid sequence that is at least 65% identical to the amino acid sequence of the WED-III domain of the reference protein sequence.

81. The Type V Cas protein of any one of embodiments 1 to 76, wherein the amino acid sequence of the Type V Cas protein comprises an amino acid sequence that is at least 70% identical to the amino acid sequence of the WED-III domain of the reference protein sequence.

82. The Type V Cas protein of any one of embodiments 1 to 76, wherein the amino acid sequence of the Type V Cas protein comprises an amino acid sequence that is at least 75% identical to the amino acid sequence of the WED-III domain of the reference protein sequence.

83. The Type V Cas protein of any one of embodiments 1 to 76, wherein the amino acid sequence of the Type V Cas protein comprises an amino acid sequence that is at least 80% identical to the amino acid sequence of the WED-III domain of the reference protein sequence.

84. The Type V Cas protein of any one of embodiments 1 to 76, wherein the amino acid sequence of the Type V Cas protein comprises an amino acid sequence that is at least 85% identical to the amino acid sequence of the WED-III domain of the reference protein sequence.

85. The Type V Cas protein of any one of embodiments 1 to 76, wherein the amino acid sequence of the Type V Cas protein comprises an amino acid sequence that is at least 90% identical to the amino acid sequence of the WED-III domain of the reference protein sequence.

86. The Type V Cas protein of any one of embodiments 1 to 76, wherein the amino acid sequence of the Type V Cas protein comprises an amino acid sequence that is at least 95% identical to the amino acid sequence of the WED-III domain of the reference protein sequence.

87. The Type V Cas protein of any one of embodiments 1 to 76, wherein the amino acid sequence of the Type V Cas protein comprises an amino acid sequence that is at least 96% identical to the amino acid sequence of the WED-III domain of the reference protein sequence.

88. The Type V Cas protein of any one of embodiments 1 to 76, wherein the amino acid sequence of the Type V Cas protein comprises an amino acid sequence that is at least 97% identical to the amino acid sequence of the WED-III domain of the reference protein sequence.

89. The Type V Cas protein of any one of embodiments 1 to 76, wherein the amino acid sequence of the Type V Cas protein comprises an amino acid sequence that is at least 98% identical to the amino acid sequence of the WED-III domain of the reference protein sequence.

90. The Type V Cas protein of any one of embodiments 1 to 76, wherein the amino acid sequence of the Type V Cas protein comprises an amino acid sequence that is at least 99% identical to the amino acid sequence of the WED-III domain of the reference protein sequence.

91. The Type V Cas protein of any one of embodiments 1 to 76, wherein the amino acid sequence of the Type V Cas protein comprises an amino acid sequence that is identical to the amino acid sequence of the WED-III domain of the reference protein sequence.

92. The Type V Cas protein of any one of embodiments 1 to 91, wherein the amino acid sequence of the Type V Cas protein comprises an amino acid sequence that is at least 50% identical to the amino acid sequence of the RuvC-I domain of the reference protein sequence.

93. The Type V Cas protein of any one of embodiments 1 to 91, wherein the amino acid sequence of the Type V Cas protein comprises an amino acid sequence that is at least 55% identical to the amino acid sequence of the RuvC-I domain of the reference protein sequence.

94. The Type V Cas protein of any one of embodiments 1 to 91, wherein the amino acid sequence of the Type V Cas protein comprises an amino acid sequence that is at least 60% identical to the amino acid sequence of the RuvC-I domain of the reference protein sequence.

95. The Type V Cas protein of any one of embodiments 1 to 91, wherein the amino acid sequence of the Type V Cas protein comprises an amino acid sequence that is at least 65% identical to the amino acid sequence of the RuvC-I domain of the reference protein sequence.

96. The Type V Cas protein of any one of embodiments 1 to 91, wherein the amino acid sequence of the Type V Cas protein comprises an amino acid sequence that is at least 70% identical to the amino acid sequence of the RuvC-I domain of the reference protein sequence.

97. The Type V Cas protein of any one of embodiments 1 to 91, wherein the amino acid sequence of the Type V Cas protein comprises an amino acid sequence that is at least 75% identical to the amino acid sequence of the RuvC-I domain of the reference protein sequence.

98. The Type V Cas protein of any one of embodiments 1 to 91, wherein the amino acid sequence of the Type V Cas protein comprises an amino acid sequence that is at least 80% identical to the amino acid sequence of the RuvC-I domain of the reference protein sequence.

99. The Type V Cas protein of any one of embodiments 1 to 91, wherein the amino acid sequence of the Type V Cas protein comprises an amino acid sequence that is at least 85% identical to the amino acid sequence of the RuvC-I domain of the reference protein sequence.

100. The Type V Cas protein of any one of embodiments 1 to 91, wherein the amino acid sequence of the Type V Cas protein comprises an amino acid sequence that is at least 90% identical to the amino acid sequence of the RuvC-I domain of the reference protein sequence.

101. The Type V Cas protein of any one of embodiments 1 to 91, wherein the amino acid sequence of the Type V Cas protein comprises an amino acid sequence that is at least 95% identical to the amino acid sequence of the RuvC-I domain of the reference protein sequence.

102. The Type V Cas protein of any one of embodiments 1 to 91, wherein the amino acid sequence of the Type V Cas protein comprises an amino acid sequence that is at least 96% identical to the amino acid sequence of the RuvC-I domain of the reference protein sequence.

103. The Type V Cas protein of any one of embodiments 1 to 91, wherein the amino acid sequence of the Type V Cas protein comprises an amino acid sequence that is at least 97% identical to the amino acid sequence of the RuvC-I domain of the reference protein sequence.

104. The Type V Cas protein of any one of embodiments 1 to 91, wherein the amino acid sequence of the Type V Cas protein comprises an amino acid sequence that is at least 98% identical to the amino acid sequence of the RuvC-I domain of the reference protein sequence.

105. The Type V Cas protein of any one of embodiments 1 to 91, wherein the amino acid sequence of the Type V Cas protein comprises an amino acid sequence that is at least 99% identical to the amino acid sequence of the RuvC-I domain of the reference protein sequence.

106. The Type V Cas protein of any one of embodiments 1 to 91, wherein the amino acid sequence of the Type V Cas protein comprises an amino acid sequence that is identical to the amino acid sequence of the RuvC-I domain of the reference protein sequence.

107. The Type V Cas protein of any one of embodiments 1 to 106, wherein the amino acid sequence of the Type V Cas protein comprises an amino acid sequence that is at least 50% identical to the amino acid sequence of the BH domain of the reference protein sequence.

108. The Type V Cas protein of any one of embodiments 1 to 106, wherein the amino acid sequence of the Type V Cas protein comprises an amino acid sequence that is at least 55% identical to the amino acid sequence of the BH domain of the reference protein sequence.

109. The Type V Cas protein of any one of embodiments 1 to 106, wherein the amino acid sequence of the Type V Cas protein comprises an amino acid sequence that is at least 60% identical to the amino acid sequence of the BH domain of the reference protein sequence.

110. The Type V Cas protein of any one of embodiments 1 to 106, wherein the amino acid sequence of the Type V Cas protein comprises an amino acid sequence that is at least 65% identical to the amino acid sequence of the BH domain of the reference protein sequence.

111. The Type V Cas protein of any one of embodiments 1 to 106, wherein the amino acid sequence of the Type V Cas protein comprises an amino acid sequence that is at least 70% identical to the amino acid sequence of the BH domain of the reference protein sequence.

112. The Type V Cas protein of any one of embodiments 1 to 106, wherein the amino acid sequence of the Type V Cas protein comprises an amino acid sequence that is at least 75% identical to the amino acid sequence of the BH domain of the reference protein sequence.

113. The Type V Cas protein of any one of embodiments 1 to 106, wherein the amino acid sequence of the Type V Cas protein comprises an amino acid sequence that is at least 80% identical to the amino acid sequence of the BH domain of the reference protein sequence.

114. The Type V Cas protein of any one of embodiments 1 to 106, wherein the amino acid sequence of the Type V Cas protein comprises an amino acid sequence that is at least 85% identical to the amino acid sequence of the BH domain of the reference protein sequence.

115. The Type V Cas protein of any one of embodiments 1 to 106, wherein the amino acid sequence of the Type V Cas protein comprises an amino acid sequence that is at least 90% identical to the amino acid sequence of the BH domain of the reference protein sequence.

116. The Type V Cas protein of any one of embodiments 1 to 106, wherein the amino acid sequence of the Type V Cas protein comprises an amino acid sequence that is at least 95% identical to the amino acid sequence of the BH domain of the reference protein sequence.

117. The Type V Cas protein of any one of embodiments 1 to 106, wherein the amino acid sequence of the Type V Cas protein comprises an amino acid sequence that is at least 96% identical to the amino acid sequence of the BH domain of the reference protein sequence.

118. The Type V Cas protein of any one of embodiments 1 to 106, wherein the amino acid sequence of the Type V Cas protein comprises an amino acid sequence that is at least 97% identical to the amino acid sequence of the BH domain of the reference protein sequence.

119. The Type V Cas protein of any one of embodiments 1 to 106, wherein the amino acid sequence of the Type V Cas protein comprises an amino acid sequence that is at least 98% identical to the amino acid sequence of the BH domain of the reference protein sequence.

120. The Type V Cas protein of any one of embodiments 1 to 106, wherein the amino acid sequence of the Type V Cas protein comprises an amino acid sequence that is at least 99% identical to the amino acid sequence of the BH domain of the reference protein sequence.

121. The Type V Cas protein of any one of embodiments 1 to 106, wherein the amino acid sequence of the Type V Cas protein comprises an amino acid sequence that is identical to the amino acid sequence of the BH domain of the reference protein sequence.

122. The Type V Cas protein of any one of embodiments 1 to 121, wherein the amino acid sequence of the Type V Cas protein comprises an amino acid sequence that is at least 50% identical to the amino acid sequence of the RuvC-II domain of the reference protein sequence.

123. The Type V Cas protein of any one of embodiments 1 to 121, wherein the amino acid sequence of the Type V Cas protein comprises an amino acid sequence that is at least 55% identical to the amino acid sequence of the RuvC-II domain of the reference protein sequence.

124. The Type V Cas protein of any one of embodiments 1 to 121, wherein the amino acid sequence of the Type V Cas protein comprises an amino acid sequence that is at least 60% identical to the amino acid sequence of the RuvC-II domain of the reference protein sequence.

125. The Type V Cas protein of any one of embodiments 1 to 121, wherein the amino acid sequence of the Type V Cas protein comprises an amino acid sequence that is at least 65% identical to the amino acid sequence of the RuvC-II domain of the reference protein sequence.

126. The Type V Cas protein of any one of embodiments 1 to 121, wherein the amino acid sequence of the Type V Cas protein comprises an amino acid sequence that is at least 70% identical to the amino acid sequence of the RuvC-II domain of the reference protein sequence.

127. The Type V Cas protein of any one of embodiments 1 to 121, wherein the amino acid sequence of the Type V Cas protein comprises an amino acid sequence that is at least 75% identical to the amino acid sequence of the RuvC-II domain of the reference protein sequence.

128. The Type V Cas protein of any one of embodiments 1 to 121, wherein the amino acid sequence of the Type V Cas protein comprises an amino acid sequence that is at least 80% identical to the amino acid sequence of the RuvC-II domain of the reference protein sequence.

129. The Type V Cas protein of any one of embodiments 1 to 121, wherein the amino acid sequence of the Type V Cas protein comprises an amino acid sequence that is at least 85% identical to the amino acid sequence of the RuvC-II domain of the reference protein sequence.

130. The Type V Cas protein of any one of embodiments 1 to 121, wherein the amino acid sequence of the Type V Cas protein comprises an amino acid sequence that is at least 90% identical to the amino acid sequence of the RuvC-II domain of the reference protein sequence.

131. The Type V Cas protein of any one of embodiments 1 to 121, wherein the amino acid sequence of the Type V Cas protein comprises an amino acid sequence that is at least 95% identical to the amino acid sequence of the RuvC-II domain of the reference protein sequence.

132. The Type V Cas protein of any one of embodiments 1 to 121, wherein the amino acid sequence of the Type V Cas protein comprises an amino acid sequence that is at least 96% identical to the amino acid sequence of the RuvC-II domain of the reference protein sequence.

133. The Type V Cas protein of any one of embodiments 1 to 121, wherein the amino acid sequence of the Type V Cas protein comprises an amino acid sequence that is at least 97% identical to the amino acid sequence of the RuvC-II domain of the reference protein sequence.

134. The Type V Cas protein of any one of embodiments 1 to 121, wherein the amino acid sequence of the Type V Cas protein comprises an amino acid sequence that is at least 98% identical to the amino acid sequence of the RuvC-II domain of the reference protein sequence.

135. The Type V Cas protein of any one of embodiments 1 to 121, wherein the amino acid sequence of the Type V Cas protein comprises an amino acid sequence that is at least 99% identical to the amino acid sequence of the RuvC-II domain of the reference protein sequence.

136. The Type V Cas protein of any one of embodiments 1 to 121, wherein the amino acid sequence of the Type V Cas protein comprises an amino acid sequence that is identical to the amino acid sequence of the RuvC-II domain of the reference protein sequence.

137. The Type V Cas protein of any one of embodiments 1 to 136, wherein the amino acid sequence of the Type V Cas protein comprises an amino acid sequence that is at least 50% identical to the amino acid sequence of the NUC domain of the reference protein sequence.

138. The Type V Cas protein of any one of embodiments 1 to 136, wherein the amino acid sequence of the Type V Cas protein comprises an amino acid sequence that is at least 55% identical to the amino acid sequence of the NUC domain of the reference protein sequence.

139. The Type V Cas protein of any one of embodiments 1 to 136, wherein the amino acid sequence of the Type V Cas protein comprises an amino acid sequence that is at least 60% identical to the amino acid sequence of the NUC domain of the reference protein sequence.

140. The Type V Cas protein of any one of embodiments 1 to 136, wherein the amino acid sequence of the Type V Cas protein comprises an amino acid sequence that is at least 65% identical to the amino acid sequence of the NUC domain of the reference protein sequence.

141. The Type V Cas protein of any one of embodiments 1 to 136, wherein the amino acid sequence of the Type V Cas protein comprises an amino acid sequence that is at least 70% identical to the amino acid sequence of the NUC domain of the reference protein sequence.

142. The Type V Cas protein of any one of embodiments 1 to 136, wherein the amino acid sequence of the Type V Cas protein comprises an amino acid sequence that is at least 75% identical to the amino acid sequence of the NUC domain of the reference protein sequence.

143. The Type V Cas protein of any one of embodiments 1 to 136, wherein the amino acid sequence of the Type V Cas protein comprises an amino acid sequence that is at least 80% identical to the amino acid sequence of the NUC domain of the reference protein sequence.

144. The Type V Cas protein of any one of embodiments 1 to 136, wherein the amino acid sequence of the Type V Cas protein comprises an amino acid sequence that is at least 85% identical to the amino acid sequence of the NUC domain of the reference protein sequence.

145. The Type V Cas protein of any one of embodiments 1 to 136, wherein the amino acid sequence of the Type V Cas protein comprises an amino acid sequence that is at least 90% identical to the amino acid sequence of the NUC domain of the reference protein sequence.

146. The Type V Cas protein of any one of embodiments 1 to 136, wherein the amino acid sequence of the Type V Cas protein comprises an amino acid sequence that is at least 95% identical to the amino acid sequence of the NUC domain of the reference protein sequence.

147. The Type V Cas protein of any one of embodiments 1 to 136, wherein the amino acid sequence of the Type V Cas protein comprises an amino acid sequence that is at least 96% identical to the amino acid sequence of the NUC domain of the reference protein sequence.

148. The Type V Cas protein of any one of embodiments 1 to 136, wherein the amino acid sequence of the Type V Cas protein comprises an amino acid sequence that is at least 97% identical to the amino acid sequence of the NUC domain of the reference protein sequence.

149. The Type V Cas protein of any one of embodiments 1 to 136, wherein the amino acid sequence of the Type V Cas protein comprises an amino acid sequence that is at least 98% identical to the amino acid sequence of the NUC domain of the reference protein sequence.

150. The Type V Cas protein of any one of embodiments 1 to 136, wherein the amino acid sequence of the Type V Cas protein comprises an amino acid sequence that is at least 99% identical to the amino acid sequence of the NUC domain of the reference protein sequence.

151. The Type V Cas protein of any one of embodiments 1 to 136, wherein the amino acid sequence of the Type V Cas protein comprises an amino acid sequence that is identical to the amino acid sequence of the NUC domain of the reference protein sequence.

152. The Type V Cas protein of any one of embodiments 1 to 151, wherein the amino acid sequence of the Type V Cas protein comprises an amino acid sequence that is at least 50% identical to the amino acid sequence of the RuvC-III domain of the reference protein sequence.

153. The Type V Cas protein of any one of embodiments 1 to 151, wherein the amino acid sequence of the Type V Cas protein comprises an amino acid sequence that is at least 55% identical to the amino acid sequence of the RuvC-III domain of the reference protein sequence.

154. The Type V Cas protein of any one of embodiments 1 to 151, wherein the amino acid sequence of the Type V Cas protein comprises an amino acid sequence that is at least 60% identical to the amino acid sequence of the RuvC-III domain of the reference protein sequence.

155. The Type V Cas protein of any one of embodiments 1 to 151, wherein the amino acid sequence of the Type V Cas protein comprises an amino acid sequence that is at least 65% identical to the amino acid sequence of the RuvC-III domain of the reference protein sequence.

156. The Type V Cas protein of any one of embodiments 1 to 151, wherein the amino acid sequence of the Type V Cas protein comprises an amino acid sequence that is at least 70% identical to the amino acid sequence of the RuvC-III domain of the reference protein sequence.

157. The Type V Cas protein of any one of embodiments 1 to 151, wherein the amino acid sequence of the Type V Cas protein comprises an amino acid sequence that is at least 75% identical to the amino acid sequence of the RuvC-III domain of the reference protein sequence.

158. The Type V Cas protein of any one of embodiments 1 to 151, wherein the amino acid sequence of the Type V Cas protein comprises an amino acid sequence that is at least 80% identical to the amino acid sequence of the RuvC-III domain of the reference protein sequence.

159. The Type V Cas protein of any one of embodiments 1 to 151, wherein the amino acid sequence of the Type V Cas protein comprises an amino acid sequence that is at least 85% identical to the amino acid sequence of the RuvC-III domain of the reference protein sequence.

160. The Type V Cas protein of any one of embodiments 1 to 151, wherein the amino acid sequence of the Type V Cas protein comprises an amino acid sequence that is at least 90% identical to the amino acid sequence of the RuvC-III domain of the reference protein sequence.

161. The Type V Cas protein of any one of embodiments 1 to 151, wherein the amino acid sequence of the Type V Cas protein comprises an amino acid sequence that is at least 95% identical to the amino acid sequence of the RuvC-III domain of the reference protein sequence.

162. The Type V Cas protein of any one of embodiments 1 to 151, wherein the amino acid sequence of the Type V Cas protein comprises an amino acid sequence that is at least 96% identical to the amino acid sequence of the RuvC-III domain of the reference protein sequence.

163. The Type V Cas protein of any one of embodiments 1 to 151, wherein the amino acid sequence of the Type V Cas protein comprises an amino acid sequence that is at least 97% identical to the amino acid sequence of the RuvC-III domain of the reference protein sequence.

164. The Type V Cas protein of any one of embodiments 1 to 151, wherein the amino acid sequence of the Type V Cas protein comprises an amino acid sequence that is at least 98% identical to the amino acid sequence of the RuvC-III domain of the reference protein sequence.

165. The Type V Cas protein of any one of embodiments 1 to 151, wherein the amino acid sequence of the Type V Cas protein comprises an amino acid sequence that is at least 99% identical to the amino acid sequence of the RuvC-III domain of the reference protein sequence.

166. The Type V Cas protein of any one of embodiments 1 to 151, wherein the amino acid sequence of the Type V Cas protein comprises an amino acid sequence that is identical to the amino acid sequence of the RuvC-III domain of the reference protein sequence.

167. The Type V Cas protein of embodiment 1, wherein the amino acid sequence of the Type V Cas protein comprises an amino acid sequence that is at least 55% identical to the full length of the reference protein sequence.

168. The Type V Cas protein of embodiment 1, wherein the amino acid sequence of the Type V Cas protein comprises an amino acid sequence that is at least 60% identical to the full length of the reference protein sequence.

169. The Type V Cas protein of embodiment 1, wherein the amino acid sequence of the Type V Cas protein comprises an amino acid sequence that is at least 65% identical to the full length of the reference protein sequence.

170. The Type V Cas protein of embodiment 1, wherein the amino acid sequence of the Type V Cas protein comprises an amino acid sequence that is at least 70% identical to the full length of the reference protein sequence.

171. The Type V Cas protein of embodiment 1, wherein the amino acid sequence of the Type V Cas protein comprises an amino acid sequence that is at least 75% identical to the full length of the reference protein sequence.

172. The Type V Cas protein of embodiment 1, wherein the amino acid sequence of the Type V Cas protein comprises an amino acid sequence that is at least 80% identical to the full length of the reference protein sequence.

173. The Type V Cas protein of embodiment 1, wherein the amino acid sequence of the Type V Cas protein comprises an amino acid sequence that is at least 85% identical to the full length of the reference protein sequence.

174. The Type V Cas protein of embodiment 1, wherein the amino acid sequence of the Type V Cas protein comprises an amino acid sequence that is at least 90% identical to the full length of the reference protein sequence.

175. The Type V Cas protein of embodiment 1, wherein the amino acid sequence of the Type V Cas protein comprises an amino acid sequence that is at least 95% identical to the full length of the reference protein sequence.

176. The Type V Cas protein of embodiment 1, wherein the amino acid sequence of the Type V Cas protein comprises an amino acid sequence that is at least 96% identical to the full length of the reference protein sequence.

177. The Type V Cas protein of embodiment 1, wherein the amino acid sequence of the Type V Cas protein comprises an amino acid sequence that is at least 97% identical to the full length of the reference protein sequence.

178. The Type V Cas protein of embodiment 1, wherein the amino acid sequence of the Type V Cas protein comprises an amino acid sequence that is at least 98% identical to the full length of the reference protein sequence.

179. The Type V Cas protein of embodiment 1, wherein the amino acid sequence of the Type V Cas protein comprises an amino acid sequence that is at least 99% identical to the full length of the reference protein sequence.

180. The Type V Cas protein of embodiment 1, wherein the amino acid sequence of the Type V Cas protein comprises an amino acid sequence that is identical to the full length of the reference protein sequence.

181. The Type V Cas protein of any one of embodiments 1 to 180, which is a chimeric Type V Cas protein.

182. The Type V Cas protein of any one of embodiments 1 to 181, which is a fusion protein.

183. The Type V Cas protein of embodiment 182, which comprises one or more nuclear localization signals.

184. The Type V Cas protein of embodiment 183, which comprises two or more nuclear localization signals.

185. The Type V Cas protein of embodiment 183 or embodiment 184, which comprises an N-terminal nuclear localization signal.

186. The Type V Cas protein of any one of embodiments 183 to 185, which comprises a C-terminal nuclear localization signal.

187. The Type V Cas protein of any one of embodiments 183 to 186, which comprises an N-terminal nuclear localization signal and a C-terminal nuclear localization signal.

188. The Type V Cas protein of any one of embodiments 183 to 187, wherein the amino acid sequence of one or more of the nuclear localization signals comprises the amino acid sequence (SEQ ID NO: 122)
KRTADGSEFESPKKKRKV, (SEQ ID NO: 123)
PKKKRKV, (SEQ ID NO: 124)
PKKKRRV, (SEQ ID NO: 125)
KRPAATKKAGQAKKKK, (SEQ ID NO: 126)
YGRKKRRQRRR, (SEQ ID NO: 127)
RKKRRQRRR, (SEQ ID NO: 128)
PAAKRVKLD, -continued (SEQ ID NO: 129)
RQRRNELKRSP, (SEQ ID NO: 130)
VSRKRPRP, (SEQ ID NO: 131)
PPKKARED, (SEQ ID NO: 132)
PQPKKKPL, (SEQ ID NO: 133)
SALIKKKKKMAP, (SEQ ID NO: 134)
PKQKKRK, (SEQ ID NO: 135)
RKLKKKIKKL, (SEQ ID NO: 136)
REKKKFLKRR, (SEQ ID NO: 137)
KRKGDEVDGVDEVAKKKSKK, (SEQ ID NO: 138)
RKCLQAGMNLEARKTKK, (SEQ ID NO: 139)
NQSSNFGPMKGGNFGGRSSGPYGGGGQYFAKPRNQGGY, (SEQ ID NO: 140)
RMRIZFKNKGKDTAELRRRRVEVSVELRKAKKDEQILKRRNV,
or (SEQ ID NO: 178)
SSDDEATADSQHAAPPKKKRKV.

189. The Type V Cas protein of embodiment 188, wherein the amino acid sequence of one or more of the nuclear localization signals comprises the amino acid sequence KRTADGSEFESPKKKRKV (SEQ ID NO:122).

190. The Type V Cas protein of embodiment 188, wherein the amino acid sequence of one or more of the nuclear localization signals comprises the amino acid sequence PKKKRKV (SEQ ID NO:123).

191. The Type V Cas protein of embodiment 188, wherein the amino acid sequence of one or more of the nuclear localization signals comprises the amino acid sequence PKKKRRV (SEQ ID NO:124).

192. The Type V Cas protein of embodiment 188, wherein the amino acid sequence of one or more of the nuclear localization signals comprises the amino acid sequence KRPAATKKAGQAKKKK (SEQ ID NO:125).

193. The Type V Cas protein of embodiment 188, wherein the amino acid sequence of one or more of the nuclear localization signals comprises the amino acid sequence YGRKKRRQRRR (SEQ ID NO:126).

194. The Type V Cas protein of embodiment 188, wherein the amino acid sequence of one or more of the nuclear localization signals comprises the amino acid sequence RKKRRQRRR (SEQ ID NO:127).

195. The Type V Cas protein of embodiment 188, wherein the amino acid sequence of one or more of the nuclear localization signals comprises the amino acid sequence PAAKRVKLD (SEQ ID NO:128).

196. The Type V Cas protein of embodiment 188, wherein the amino acid sequence of one or more of the nuclear localization signals comprises the amino acid sequence RQRRNELKRSP (SEQ ID NO:129).

197. The Type V Cas protein of embodiment 188, wherein the amino acid sequence of one or more of the nuclear localization signals comprises the amino acid sequence VSRKRPRP (SEQ ID NO:130).

198. The Type V Cas protein of embodiment 188, wherein the amino acid sequence of one or more of the nuclear localization signals comprises the amino acid sequence PPKKARED (SEQ ID NO:131).

199. The Type V Cas protein of embodiment 188, wherein the amino acid sequence of one or more of the nuclear localization signals comprises the amino acid sequence PQPKKKPL (SEQ ID NO:132).

200. The Type V Cas protein of embodiment 188, wherein the amino acid sequence of one or more of the nuclear localization signals comprises the amino acid sequence SALIKKKKKMAP (SEQ ID NO:133).

201. The Type V Cas protein of embodiment 188, wherein the amino acid sequence of one or more of the nuclear localization signals comprises the amino acid sequence PKQKKRK (SEQ ID NO:134).

202. The Type V Cas protein of embodiment 188, wherein the amino acid sequence of one or more of the nuclear localization signals comprises the amino acid sequence RKLKKKIKKL (SEQ ID NO:135).

203. The Type V Cas protein of embodiment 188, wherein the amino acid sequence of one or more of the nuclear localization signals comprises the amino acid sequence REKKKFLKRR (SEQ ID NO:136).

204. The Type V Cas protein of embodiment 188, wherein the amino acid sequence of one or more of the nuclear localization signals comprises the amino acid sequence (SEQ ID NO: 137)
KRKGDEVDGVDEVAKKKSKK.

205. The Type V Cas protein of embodiment 188, wherein the amino acid sequence of one or more of the nuclear localization signals comprises the amino acid sequence RKCLQAGMNLEARKTKK (SEQ ID NO:138).

206. The Type V Cas protein of embodiment 188, wherein the amino acid sequence of one or more of the nuclear localization signals comprises the amino acid sequence (SEQ ID NO: 139)
NQSSNFGPMKGGNFGGRSSGPYGGGGQYFAKPRNQGGY.

207. The Type V Cas protein of embodiment 188, wherein the amino acid sequence of one or more of the nuclear localization signals comprises the amino acid sequence (SEQ ID NO: 140)
RMRIZFKNKGKDTAELRRRRVEVSVELRKAKKDEQILKRRNV.

208. The Type V Cas protein of embodiment 188, wherein the amino acid sequence of one or more of the nuclear localization signals comprises the amino acid sequence (SEQ ID NO: 178)
SSDDEATADSQHAAPPKKKRKV.

209. The Type V Cas protein of any one of embodiments 183 to 187, wherein the amino acid sequence of one or more of the nuclear localization signals comprises the amino acid sequence (SEQ ID NO: 179)
PKKKRKVG.

210. The Type V Cas protein of any one of embodiments 183 to 187, wherein the amino acid sequence of one or more of the nuclear localization signals comprises the amino acid sequence (SEQ ID NO: 180)
GRSSDDEATADSQHAAPPKKKRKV.

211. The Type V Cas protein of any one of embodiments 183 to 210, wherein the amino acid sequence of each nuclear localization signal is the same.

212. The Type V Cas protein of any one of embodiments 181 to 211, which comprises a fusion partner which is a DNA, RNA or protein modification enzyme, optionally wherein the DNA, RNA or protein modification enzyme is an adenosine deaminase, a cytidine deaminase, a reverse transcriptase, a guanosyl transferase, a DNA methyltransferase, a RNA methyltransferase, a DNA demethylase, a RNA demethylase, a dioxygenase, a polyadenylate polymerase, a pseudouridine synthase, an acetyltransferase, a deacetylase, a ubiquitin-ligase, a deubiquitinase, a kinase, a phosphatase, a NEDD8-ligase, a de-NEDDylase, a SUMO-ligase, a deSUMOylase, a histone deacetylase, a histone acetyltransferase, a histone methyltransferase, or a histone demethylase.

213. The Type V Cas protein of any one of embodiments 181 to 212, which comprises a means for deaminating a nucleobase, optionally wherein the means for deaminating a nucleobase is a deaminase, e.g., an adenosine deaminase or cytidine deaminase.

214. The Type V Cas protein of any one of embodiments 181 to 213, which comprises a fusion partner comprising a deaminase, optionally wherein the deaminase is an adenosine deaminase or cytidine deaminase.

215. The Type V Cas protein of embodiment 214, wherein the amino acid sequence of the deaminase comprises an amino acid sequence having at least 50%, at least 60%, at least 70%, at least 80%, at least 90%, at least 95%, at least 97%, at least 98%, at least 99%, or 100% sequence identity to any one of SEQ ID NOS: 214-249.

216. The Type V Cas protein of any one of embodiments 181 to 212, which comprises a means for deaminating adenosine, optionally wherein the means for deaminating adenosine is an adenosine deaminase.

217. The Type V Cas protein of any one of embodiments 181 to 212, which comprises a fusion partner which is an adenosine deaminase, optionally wherein the amino acid sequence of the adenosine deaminase comprises an amino acid sequence having at least 50%, at least 60%, at least 70%, at least 80%, at least 90%, at least 95%, at least 97%, at least 98%, at least 99%, or 100% sequence identity with SEQ ID NO:166, optionally wherein the adenosine deaminase is the adenosine deaminase moiety contained in the adenine base editor ABE8e.

218. The Type V Cas protein of any one of embodiments 181 to 212, which comprises a means for deaminating cytidine, optionally wherein the means for deaminating cytidine is a cytidine deaminase.

219. The Type V Cas protein of any one of embodiments 181 to 212, which comprises a fusion partner which is a cytidine deaminase.

220. The Type V Cas protein of any one of embodiments 181 to 219, which comprises a fusion partner comprising a UGI domain, optionally wherein the amino acid sequence of the UGI domain comprises an amino acid sequence having at least 50%, at least 60%, at least 70%, at least 80%, at least 90%, at least 95%, at least 97%, at least 98%, at least 99%, or 100% sequence identity to SEQ ID NO:250.

221. The Type V Cas protein of any one of embodiments 181 to 220, which comprises a means for repressing gene expression, optionally wherein the means for repressing gene expression comprises a transcriptional repressor or effector domain thereof.

222. The Type V Cas protein of any one of embodiments 181 to 220, which comprises a fusion partner comprising a transcriptional repressor or effector domain thereof.

223. The Type V Cas protein of embodiment 221 or embodiment 222, wherein the amino acid sequence of the transcriptional repressor or effector domain thereof comprises an amino acid sequence having at least 50%, at least 60%, at least 70%, at least 80%, at least 90%, at least 95%, at least 97%, at least 98%, at least 99%, or 100% sequence identity to any one of SEQ ID NOS: 251-255.

224. The Type V Cas protein of any one of embodiments 181 to 212, which comprises a means for synthesizing DNA from a single-stranded template, optionally wherein the means for synthesizing DNA from a single-stranded template is a reverse transcriptase.

225. The Type V Cas protein of any one of embodiments 181 to 212, which comprises a fusion partner which is a reverse transcriptase.

226. The Type V Cas protein of embodiment 224 or embodiment 225, wherein the amino acid sequence of the reverse transcriptase comprises an amino acid sequence having at least 50%, at least 60%, at least 70%, at least 80%, at least 90%, at least 95%, at least 97%, at least 98%, at least 99%, or 100% sequence identity to SEQ ID NO:256 or SEQ ID NO:257.

227. The Type V Cas protein of any one of embodiments 181 to 225, which comprises a tag. 228. The Type V Cas protein of embodiment 226, wherein the tag is a SV5 tag, optionally wherein the SV5 tag comprises the amino acid sequence GKPIPNPLLGLDST (SEQ ID NO:141) or IPNPLLGLD (SEQ ID NO:142).

229. The Type V Cas protein of any one of embodiments 1 to 228, wherein the reference protein sequence is SEQ ID NO:1.

230. The Type V Cas protein of embodiment 229, whose amino acid sequence comprises the amino acid sequence of SEQ ID NO:1.

231. The Type V Cas protein of any one of embodiments 1 to 228, wherein the reference protein sequence is SEQ ID NO:2.

232. The Type V Cas protein of any one of embodiments 229 to 231, whose amino acid sequence comprises the amino acid sequence of SEQ ID NO:2.

233. The Type V Cas protein of embodiment 229 or embodiment 230, whose amino acid sequence comprises the amino acid sequence of SEQ ID NO:3.

234. The Type V Cas protein of any one of embodiments 1 to 228, wherein the reference protein sequence is SEQ ID NO:7.

235. The Type V Cas protein of embodiment 234, whose amino acid sequence comprises the amino acid sequence of SEQ ID NO:7.

236. The Type V Cas protein of any one of embodiments 1 to 228, wherein the reference protein sequence is SEQ ID NO:8.

237. The Type V Cas protein of any one of embodiments 234 to 236, whose amino acid sequence comprises the amino acid sequence of SEQ ID NO:8.

238. The Type V Cas protein of embodiment 234 or embodiment 235, whose amino acid sequence comprises the amino acid sequence of SEQ ID NO:9.

239. The Type V Cas protein of any one of embodiments 1 to 228, wherein the reference protein sequence is SEQ ID NO:13.

240. The Type V Cas protein of embodiment 239, whose amino acid sequence comprises the amino acid sequence of SEQ ID NO:13.

241. The Type V Cas protein of any one of embodiments 1 to 228, wherein the reference protein sequence is SEQ ID NO:14.

242. The Type V Cas protein of any one of embodiments 239 to 241, whose amino acid sequence comprises the amino acid sequence of SEQ ID NO:14.

243. The Type V Cas protein of embodiment 239 or embodiment 240, whose amino acid sequence comprises the amino acid sequence of SEQ ID NO:15.

244. The Type V Cas protein of any one of embodiments 1 to 228, wherein the reference protein sequence is SEQ ID NO:19.

245. The Type V Cas protein of embodiment 244, whose amino acid sequence comprises the amino acid sequence of SEQ ID NO:19.

246. The Type V Cas protein of any one of embodiments 1 to 228, wherein the reference protein sequence is SEQ ID NO:20.

247. The Type V Cas protein of any one of embodiments 244 to 246, whose amino acid sequence comprises the amino acid sequence of SEQ ID NO:20.

248. The Type V Cas protein of embodiment 244 or embodiment 245, whose amino acid sequence comprises the amino acid sequence of SEQ ID NO:21.

249. The Type V Cas protein of any one of embodiments 1 to 228, wherein the reference protein sequence is SEQ ID NO:25.

250. The Type V Cas protein of embodiment 249, whose amino acid sequence comprises the amino acid sequence of SEQ ID NO:25.

251. The Type V Cas protein of any one of embodiments 1 to 228, wherein the reference protein sequence is SEQ ID NO:26.

252. The Type V Cas protein of any one of embodiments 249 to 251, whose amino acid sequence comprises the amino acid sequence of SEQ ID NO:26.

253. The Type V Cas protein of embodiment 250 or embodiment 251, whose amino acid sequence comprises the amino acid sequence of SEQ ID NO:27.

254. The Type V Cas protein of any one of embodiments 1 to 228, wherein the reference protein sequence is SEQ ID NO:31.

255. The Type V Cas protein of embodiment 254, whose amino acid sequence comprises the amino acid sequence of SEQ ID NO:31.

256. The Type V Cas protein of any one of embodiments 1 to 228, wherein the reference protein sequence is SEQ ID NO:32.

257. The Type V Cas protein of any one of embodiments 255 to 256, whose amino acid sequence comprises the amino acid sequence of SEQ ID NO:32.

258. The Type V Cas protein of embodiment 254 or embodiment 255, whose amino acid sequence comprises the amino acid sequence of SEQ ID NO:33.

259. The Type V Cas protein of any one of embodiments 1 to 228, wherein the reference protein sequence is SEQ ID NO:37.

260. The Type V Cas protein of embodiment 259, whose amino acid sequence comprises the amino acid sequence of SEQ ID NO:37.

261. The Type V Cas protein of any one of embodiments 1 to 228, wherein the reference protein sequence is SEQ ID NO:38.

262. The Type V Cas protein of any one of embodiments 259 to 261, whose amino acid sequence comprises the amino acid sequence of SEQ ID NO:38.

263. The Type V Cas protein of embodiment 259 or embodiment 260, whose amino acid sequence comprises the amino acid sequence of SEQ ID NO:39.

264. The Type V Cas protein of any one of embodiments 1 to 228, wherein the reference protein sequence is SEQ ID NO:43.

265. The Type V Cas protein of embodiment 264, whose amino acid sequence comprises the amino acid sequence of SEQ ID NO:43.

266. The Type V Cas protein of any one of embodiments 1 to 228, wherein the reference protein sequence is SEQ ID NO:44.

267. The Type V Cas protein of any one of embodiments 264 to 266, whose amino acid sequence comprises the amino acid sequence of SEQ ID NO:44.

268. The Type V Cas protein of embodiment 264 or embodiment 265, whose amino acid sequence comprises the amino acid sequence of SEQ ID NO:45.

269. The Type V Cas protein of any one of embodiments 1 to 228, wherein the reference protein sequence is SEQ ID NO:49.

270. The Type V Cas protein of embodiment 269, whose amino acid sequence comprises the amino acid sequence of SEQ ID NO:49.

271. The Type V Cas protein of any one of embodiments 1 to 228, wherein the reference protein sequence is SEQ ID NO:50.

272. The Type V Cas protein of any one of embodiments 269 to 271, whose amino acid sequence comprises the amino acid sequence of SEQ ID NO:50.

273. The Type V Cas protein of embodiment 269 or embodiment 270, whose amino acid sequence comprises the amino acid sequence of SEQ ID NO:51.

274. The Type V Cas protein of any one of embodiments 1 to 228, wherein the reference protein sequence is SEQ ID NO:55.

275. The Type V Cas protein of embodiment 274, whose amino acid sequence comprises the amino acid sequence of SEQ ID NO:55.

276. The Type V Cas protein of any one of embodiments 1 to 228, wherein the reference protein sequence is SEQ ID NO:56.

277. The Type V Cas protein of any one of embodiments 274 to 276, whose amino acid sequence comprises the amino acid sequence of SEQ ID NO:56.

278. The Type V Cas protein of embodiment 274 or embodiment 275, whose amino acid sequence comprises the amino acid sequence of SEQ ID NO:57.

279. The Type V Cas protein of any one of embodiments 1 to 228, wherein the reference protein sequence is SEQ ID NO:61.

280. The Type V Cas protein of embodiment 279, whose amino acid sequence comprises the amino acid sequence of SEQ ID NO:61.

281. The Type V Cas protein of any one of embodiments 1 to 228, wherein the reference protein sequence is SEQ ID NO:62.

282. The Type V Cas protein of any one of embodiments 279 to 281, whose amino acid sequence comprises the amino acid sequence of SEQ ID NO:62.

283. The Type V Cas protein of embodiment 279 or embodiment 280, whose amino acid sequence comprises the amino acid sequence of SEQ ID NO:63.

284. The Type V Cas protein of any one of embodiments 1 to 228, wherein the reference protein sequence is SEQ ID NO:67.

285. The Type V Cas protein of embodiment 284, whose amino acid sequence comprises the amino acid sequence of SEQ ID NO:67.

286. The Type V Cas protein of any one of embodiments 1 to 228, wherein the reference protein sequence is SEQ ID NO:68.

287. The Type V Cas protein of any one of embodiments 284 to 286, whose amino acid sequence comprises the amino acid sequence of SEQ ID NO:68.

288. The Type V Cas protein of embodiment 284 or embodiment 285, whose amino acid sequence comprises the amino acid sequence of SEQ ID NO:69.

289. The Type V Cas protein of any one of embodiments 1 to 228, wherein the reference protein sequence is SEQ ID NO:73.

290. The Type V Cas protein of embodiment 289, whose amino acid sequence comprises the amino acid sequence of SEQ ID NO:73.

291. The Type V Cas protein of any one of embodiments 1 to 228, wherein the reference protein sequence is SEQ ID NO:74.

292. The Type V Cas protein of any one of embodiments 289 to 291, whose amino acid sequence comprises the amino acid sequence of SEQ ID NO:74.

293. The Type V Cas protein of embodiment 289 or embodiment 290, whose amino acid sequence comprises the amino acid sequence of SEQ ID NO:75.

294. The Type V Cas protein of any one of embodiments 1 to 228, wherein the reference protein sequence is SEQ ID NO:79.

295. The Type V Cas protein of embodiment 294, whose amino acid sequence comprises the amino acid sequence of SEQ ID NO:79.

296. The Type V Cas protein of any one of embodiments 1 to 228, wherein the reference protein sequence is SEQ ID NO:80.

297. The Type V Cas protein of any one of embodiments 294 to 296, whose amino acid sequence comprises the amino acid sequence of SEQ ID NO:80.

298. The Type V Cas protein of embodiment 294 or embodiment 295, whose amino acid sequence comprises the amino acid sequence of SEQ ID NO:81.

299. The Type V Cas protein of any one of embodiments 1 to 228, wherein the reference protein sequence is SEQ ID NO:85.

300. The Type V Cas protein of embodiment 299, whose amino acid sequence comprises the amino acid sequence of SEQ ID NO:85.

301. The Type V Cas protein of any one of embodiments 1 to 228, wherein the reference protein sequence is SEQ ID NO:86.

302. The Type V Cas protein of any one of embodiments 299 to 301, whose amino acid sequence comprises the amino acid sequence of SEQ ID NO:86.

303. The Type V Cas protein of embodiment 299 or embodiment 300, whose amino acid sequence comprises the amino acid sequence of SEQ ID NO:87.

304. The Type V Cas protein of any one of embodiments 1 to 228, wherein the reference protein sequence is SEQ ID NO:91.

305. The Type V Cas protein of embodiment 304, whose amino acid sequence comprises the amino acid sequence of SEQ ID NO:91.

306. The Type V Cas protein of any one of embodiments 1 to 228, wherein the reference protein sequence is SEQ ID NO:92.

307. The Type V Cas protein of any one of embodiments 304 to 306, whose amino acid sequence comprises the amino acid sequence of SEQ ID NO:92.

308. The Type V Cas protein of embodiment 304 or embodiment 305, whose amino acid sequence comprises the amino acid sequence of SEQ ID NO:93.

309. The Type V Cas protein of any one of embodiments 1 to 228, wherein the reference protein sequence is SEQ ID NO:97.

310. The Type V Cas protein of embodiment 309, whose amino acid sequence comprises the amino acid sequence of SEQ ID NO:97.

311. The Type V Cas protein of any one of embodiments 1 to 228, wherein the reference protein sequence is SEQ ID NO:98.

312. The Type V Cas protein of any one of embodiments 309 to 311, whose amino acid sequence comprises the amino acid sequence of SEQ ID NO:98.

313. The Type V Cas protein of embodiment 309 or embodiment 310, whose amino acid sequence comprises the amino acid sequence of SEQ ID NO:99.

314. The Type V Cas protein of any one of embodiments 1 to 228, wherein the reference protein sequence is SEQ ID NO:103.

315. The Type V Cas protein of embodiment 314, whose amino acid sequence comprises the amino acid sequence of SEQ ID NO:103.

316. The Type V Cas protein of any one of embodiments 1 to 228, wherein the reference protein sequence is SEQ ID NO:104.

317. The Type V Cas protein of any one of embodiments 314 to 316, whose amino acid sequence comprises the amino acid sequence of SEQ ID NO:104.

318. The Type V Cas protein of embodiment 314 or embodiment 315, whose amino acid sequence comprises the amino acid sequence of SEQ ID NO:105.

319. The Type V Cas protein of any one of embodiments 1 to 228, wherein the reference protein sequence is SEQ ID NO:109.

320. The Type V Cas protein of embodiment 319, whose amino acid sequence comprises the amino acid sequence of SEQ ID NO:109.

321. The Type V Cas protein of any one of embodiments 1 to 228, wherein the reference protein sequence is SEQ ID NO:110.

322. The Type V Cas protein of any one of embodiments 319 to 321, whose amino acid sequence comprises the amino acid sequence of SEQ ID NO:110.

323. The Type V Cas protein of embodiment 319 or embodiment 320, whose amino acid sequence comprises the amino acid sequence of SEQ ID NO:111.

324. The Type V Cas protein of any one of embodiments 1 to 228, wherein the reference protein sequence is SEQ ID NO:115.

325. The Type V Cas protein of embodiment 324, whose amino acid sequence comprises the amino acid sequence of SEQ ID NO:115.

326. The Type V Cas protein of any one of embodiments 1 to 228, wherein the reference protein sequence is SEQ ID NO:116.

327. The Type V Cas protein of any one of embodiments 324 to 326, whose amino acid sequence comprises the amino acid sequence of SEQ ID NO:116.

328. The Type V Cas protein of embodiment 324 or embodiment 325, whose amino acid sequence comprises the amino acid sequence of SEQ ID NO:117.

329. A Type V Cas protein whose amino acid sequence is identical to a Type V Cas protein of any one of embodiments 1 to 328 except for one or more amino acid substitutions relative to the reference sequence that provide nickase activity, optionally wherein the one or more amino acid substitutions comprise a substitution (e.g., alanine substitution) at a position corresponding to position D908 of Cas12a, E993 of Cas12a, R1226 of Cas12a, or D1263 of Cas12a (e.g., as shown in Table 5), or a combination thereof.

330. A ZWGD Type V Cas guide RNA (gRNA) molecule.

331. A ZJHK Type V Cas guide RNA (gRNA) molecule.

332. A ZIKV Type V Cas guide RNA (gRNA) molecule.

333. A ZZFT Type V Cas guide RNA (gRNA) molecule.

334. A YYAN Type V Cas guide RNA (gRNA) molecule.

335. A ZZGY Type V Cas guide RNA (gRNA) molecule.

336. A ZKBG Type V Cas guide RNA (gRNA) molecule.

337. A ZZKD Type V Cas guide RNA (gRNA) molecule.

338. A ZXPB Type V Cas guide RNA (gRNA) molecule.

339. A ZPPX Type V Cas guide RNA (gRNA) molecule.

340. A ZXHQ Type V Cas guide RNA (gRNA) molecule.

341. A ZQKH Type V Cas guide RNA (gRNA) molecule.

342. A ZRGM Type V Cas guide RNA (gRNA) molecule.

343. A ZTAE Type V Cas guide RNA (gRNA) molecule.

344. A ZSQQ Type V Cas guide RNA (gRNA) molecule.

345. A ZSYN Type V Cas guide RNA (gRNA) molecule.

346. A ZRBH Type V Cas guide RNA (gRNA) molecule.

347. A ZWPU Type V Cas guide RNA (gRNA) molecule.

348. A ZZQE Type V Cas guide RNA (gRNA) molecule.

349. A ZRXE Type V Cas guide RNA (gRNA) molecule.

350. The gRNA of any one of embodiments 330 to 349, which is a gRNA for editing a human B2M gene.

351. The gRNA of any one of embodiments 330 to 349, which is a gRNA for editing a human TRAC gene.

352. The gRNA of any one of embodiments 330 to 349, which is a gRNA for editing a human PD1 gene.

353. The gRNA of any one of embodiments 330 to 349, which is a gRNA for editing a human AAVS1 genomic sequence.

354. The gRNA of any one of embodiments 330 to 349, which is a gRNA for editing a human EMX1 gene.

355. The gRNA of any one of embodiments 330 to 349, which is a gRNA for editing a human BCL11A gene.

356. The gRNA of any one of embodiments 330 to 349, which is a gRNA for editing a human PCSK9 gene.

357. The gRNA of any one of embodiments 330 to 349, which is a gRNA for editing a human VEGF gene.

358. The gRNA of any one of embodiments 330 to 349, which is a gRNA for editing a human Match6 genomic sequence.

359. A guide RNA (gRNA) molecule for editing a human B2M gene comprising a spacer whose nucleotide sequence comprises 15 or more consecutive nucleotides of a reference sequence or comprises a nucleotide sequence that is at least 85% identical to the reference sequence, wherein the reference sequence is selected from SEQ ID NOs: 164-168 and 181-183.

360. A guide RNA (gRNA) molecule for editing a human TRAC gene comprising a spacer whose nucleotide sequence comprises 15 or more consecutive nucleotides of a reference sequence or comprises a nucleotide sequence that is at least 85% identical to the reference sequence, wherein the reference sequence is selected from SEQ ID NOs: 169-173 and 184-192.

361. A guide RNA (gRNA) molecule for editing a human PD1 gene comprising a spacer whose nucleotide sequence comprises 15 or more consecutive nucleotides of a reference sequence or comprises a nucleotide sequence that is at least 85% identical to the reference sequence, wherein the reference sequence is selected from SEQ ID NOs: 174-177.

362. A guide RNA (gRNA) molecule for editing a human AAVS1 genomic sequence comprising a spacer whose nucleotide sequence comprises 15 or more consecutive nucleotides of a reference sequence or comprises a nucleotide sequence that is at least 85% identical to the reference sequence, wherein the reference sequence is selected from SEQ ID NOs: 193-196.

363. A guide RNA (gRNA) molecule for editing a human EMX1 genomic sequence comprising a spacer whose nucleotide sequence comprises 15 or more consecutive nucleotides of a reference sequence or comprises a nucleotide sequence that is at least 85% identical to the reference sequence, wherein the reference sequence is selected from SEQ ID NOs: 197-198.

364. A guide RNA (gRNA) molecule for editing a human BCL11A genomic sequence comprising a spacer whose nucleotide sequence comprises 15 or more consecutive nucleotides of a reference sequence or comprises a nucleotide sequence that is at least 85% identical to the reference sequence, wherein the reference sequence is selected from SEQ ID NOs: 199-202.

365. A guide RNA (gRNA) molecule for editing a human PCSK9 genomic sequence comprising a spacer whose nucleotide sequence comprises 15 or more consecutive nucleotides of a reference sequence or comprises a nucleotide sequence that is at least 85% identical to the reference sequence, wherein the reference sequence is selected from SEQ ID NOs: 203-204.

366. A guide RNA (gRNA) molecule for editing a human VEGF genomic sequence comprising a spacer whose nucleotide sequence comprises 15 or more consecutive nucleotides of a reference sequence or comprises a nucleotide sequence that is at least 85% identical to the reference sequence, wherein the reference sequence is SEQ ID NO:205.

367. A guide RNA (gRNA) molecule for editing a human Match6 genomic sequence comprising a spacer whose nucleotide sequence comprises 15 or more consecutive nucleotides of a reference sequence or comprises a nucleotide sequence that is at least 85% identical to the reference sequence, wherein the reference sequence is selected from SEQ ID NOs: 206-210.

368. The gRNA of any one of embodiments 353 to 367, which comprises a spacer that is 15 to 30 nucleotides in length.

369. The gRNA of embodiment 368, wherein the spacer is 18 to 30 nucleotides in length.

370. The gRNA of embodiment 368, wherein the spacer is 20 to 28 nucleotides in length.

371. The gRNA of embodiment 368, wherein the spacer is 22 to 26 nucleotides in length.

372. The gRNA of embodiment 368, wherein the spacer is 23 to 25 nucleotides in length.

373. The gRNA of embodiment 368, wherein the spacer is 22 to 25 nucleotides in length.

374. The gRNA of embodiment 368, wherein the spacer is 15 to 25 nucleotides in length.

375. The gRNA of embodiment 368, wherein the spacer is 16 to 24 nucleotides in length.

376. The gRNA of embodiment 368, wherein the spacer is 17 to 23 nucleotides in length.

377. The gRNA of embodiment 368, wherein the spacer is 18 to 22 nucleotides in length.

378. The gRNA of embodiment 368, wherein the spacer is 19 to 21 nucleotides in length.

379. The gRNA of embodiment 368, wherein the spacer is 25 nucleotides in length.

380. The gRNA of embodiment 368, wherein the spacer is 24 nucleotides in length.

381. The gRNA of embodiment 368, wherein the spacer is 23 nucleotides in length.

382. The gRNA of embodiment 368, wherein the spacer is 22 nucleotides in length.

383. The gRNA of embodiment 368, wherein the spacer is 21 nucleotides in length.

384. The gRNA of embodiment 368, wherein the spacer is 20 nucleotides in length.

385. The gRNA of any one of embodiments 359 to 384, wherein the spacer comprises 16 or more consecutive nucleotides of the reference sequence.

386. The gRNA of any one of embodiments 359 to 384, wherein the spacer comprises 17 or more consecutive nucleotides of the reference sequence.

387. The gRNA of any one of embodiments 359 to 384, wherein the spacer comprises 18 or more consecutive nucleotides of the reference sequence.

388. The gRNA of any one of embodiments 359 to 384, wherein the spacer comprises 19 or more consecutive nucleotides of the reference sequence.

389. The gRNA of any one of embodiments 359 to 384, wherein the spacer comprises 20 or more consecutive nucleotides of the reference sequence.

390. The gRNA of any one of embodiments 359 to 384, wherein the spacer comprises 21 or more consecutive nucleotides of the reference sequence.

391. The gRNA of any one of embodiments 359 to 384, wherein the spacer comprises 22 or more consecutive nucleotides of the reference sequence.

392. The gRNA of any one of embodiments 359 to 384, wherein the spacer comprises 23 consecutive nucleotides of the reference sequence.

393. The gRNA of any one of embodiments 359 to 384, wherein the spacer comprises a nucleotide sequence that is at least 90% identical to the reference sequence.

394. The gRNA of embodiment 393, wherein the spacer comprises a nucleotide sequence that is at least 95% identical to the reference sequence.

395. The gRNA of any one of embodiments 359 to 384, wherein the spacer comprises a nucleotide sequence that has one mismatch relative to the reference sequence.

396. The gRNA of any one of embodiments 359 to 384, wherein the spacer comprises a nucleotide sequence that has two mismatches relative to the reference sequence.

397. The gRNA of any one of embodiments 359 to 367, wherein the spacer comprises the reference sequence.

398. The gRNA of any one of embodiments 359 and 368 to 397 when depending from embodiment 359, wherein the reference sequence is SEQ ID NO:164.

399. The gRNA of any one of embodiments 359 and 368 to 397 when depending from embodiment 359, wherein the reference sequence is SEQ ID NO:165.

400. The gRNA of any one of embodiments 359 and 368 to 397 when depending from embodiment 359, wherein the reference sequence is SEQ ID NO:166.

401. The gRNA of any one of embodiments 359 and 368 to 397 when depending from embodiment 359, wherein the reference sequence is SEQ ID NO:167.

402. The gRNA of any one of embodiments 359 and 368 to 397 when depending from embodiment 359, wherein the reference sequence is SEQ ID NO:168.

403. The gRNA of any one of embodiments 359 and 368 to 397 when depending from embodiment 359, wherein the reference sequence is SEQ ID NO:181.

404. The gRNA of any one of embodiments 359 and 368 to 397 when depending from embodiment 359, wherein the reference sequence is SEQ ID NO:182.

405. The gRNA of any one of embodiments 359 and 368 to 397 when depending from embodiment 359, wherein the reference sequence is SEQ ID NO:183.

406. The gRNA of any one of embodiments 360 and 368 to 397 when depending from embodiment 360, wherein the reference sequence is SEQ ID NO:169.

407. The gRNA of any one of embodiments 360 and 368 to 397 when depending from embodiment 360, wherein the reference sequence is SEQ ID NO:170.

408. The gRNA of any one of embodiments 360 and 368 to 397 when depending from embodiment 360, wherein the reference sequence is SEQ ID NO:171.

409. The gRNA of any one of embodiments 360 and 368 to 397 when depending from embodiment 360, wherein the reference sequence is SEQ ID NO:172.

410. The gRNA of any one of embodiments 360 and 368 to 397 when depending from embodiment 360, wherein the reference sequence is SEQ ID NO:173.

411. The gRNA of any one of embodiments 360 and 368 to 397 when depending from embodiment 360, wherein the reference sequence is SEQ ID NO:184.

412. The gRNA of any one of embodiments 360 and 368 to 397 when depending from embodiment 360, wherein the reference sequence is SEQ ID NO:185.

413. The gRNA of any one of embodiments 360 and 368 to 397 when depending from embodiment 360, wherein the reference sequence is SEQ ID NO:186.

414. The gRNA of any one of embodiments 360 and 368 to 397 when depending from embodiment 360, wherein the reference sequence is SEQ ID NO:187.

415. The gRNA of any one of embodiments 360 and 368 to 397 when depending from embodiment 360, wherein the reference sequence is SEQ ID NO:188.

416. The gRNA of any one of embodiments 360 and 368 to 397 when depending from embodiment 360, wherein the reference sequence is SEQ ID NO:189.

417. The gRNA of any one of embodiments 360 and 368 to 397 when depending from embodiment 360, wherein the reference sequence is SEQ ID NO:190.

418. The gRNA of any one of embodiments 360 and 368 to 397 when depending from embodiment 360, wherein the reference sequence is SEQ ID NO:191.

419. The gRNA of any one of embodiments 360 and 368 to 397 when depending from embodiment 360, wherein the reference sequence is SEQ ID NO:192.

420. The gRNA of any one of embodiments 361 and 368 to 397 when depending from embodiment 361, wherein the reference sequence is SEQ ID NO:174.

421. The gRNA of any one of embodiments 361 and 368 to 397 when depending from embodiment 361, wherein the reference sequence is SEQ ID NO:175.

422. The gRNA of any one of embodiments 361 and 368 to 397 when depending from embodiment 361, wherein the reference sequence is SEQ ID NO:176.

423. The gRNA of any one of embodiments 361 and 368 to 397 when depending from embodiment 361, wherein the reference sequence is SEQ ID NO:177.

424. The gRNA of any one of embodiments 362 and 368 to 397 when depending from embodiment 362, wherein the reference sequence is SEQ ID NO:193.

425. The gRNA of any one of embodiments 362 and 368 to 397 when depending from embodiment 362, wherein the reference sequence is SEQ ID NO:194.

426. The gRNA of any one of embodiments 362 and 368 to 397 when depending from embodiment 362, wherein the reference sequence is SEQ ID NO:195.

427. The gRNA of any one of embodiments 362 and 368 to 397 when depending from embodiment 362, wherein the reference sequence is SEQ ID NO:196.

428. The gRNA of any one of embodiments 363 and 368 to 397 when depending from embodiment 363, wherein the reference sequence is SEQ ID NO:197.

429. The gRNA of any one of embodiments 363 and 368 to 397 when depending from embodiment 363, wherein the reference sequence is SEQ ID NO:198.

430. The gRNA of any one of embodiments 364 and 368 to 397 when depending from embodiment 364, wherein the reference sequence is SEQ ID NO:199.

431. The gRNA of any one of embodiments 364 and 368 to 397 when depending from embodiment 364, wherein the reference sequence is SEQ ID NO:200.

432. The gRNA of any one of embodiments 364 and 368 to 397 when depending from embodiment 364, wherein the reference sequence is SEQ ID NO:201.

433. The gRNA of any one of embodiments 364 and 368 to 397 when depending from embodiment 364, wherein the reference sequence is SEQ ID NO:202.

434. The gRNA of any one of embodiments 365 and 368 to 397 when depending from embodiment 365, wherein the reference sequence is SEQ ID NO:203.

435. The gRNA of any one of embodiments 365 and 368 to 397 when depending from embodiment 365, wherein the reference sequence is SEQ ID NO:204.

436. The gRNA of any one of embodiments 366 and 368 to 397 when depending from embodiment 366, wherein the reference sequence is SEQ ID NO:205.

437. The gRNA of any one of embodiments 367 and 368 to 397 when depending from embodiment 367, wherein the reference sequence is SEQ ID NO:206.

438. The gRNA of any one of embodiments 367 and 368 to 397 when depending from embodiment 367, wherein the reference sequence is SEQ ID NO:207.

439. The gRNA of any one of embodiments 367 and 368 to 397 when depending from embodiment 367, wherein the reference sequence is SEQ ID NO:208.

440. The gRNA of any one of embodiments 367 and 368 to 397 when depending from embodiment 367, wherein the reference sequence is SEQ ID NO:209.

441. The gRNA of any one of embodiments 367 and 368 to 397 when depending from embodiment 367, wherein the reference sequence is SEQ ID NO:210.

442. A gRNA comprising a spacer and a crRNA scaffold, which is optionally a gRNA according to any one of embodiments 330 to 441, wherein:

(a) the spacer is positioned 3' to the crRNA scaffold; and (b) the nucleotide sequence of the crRNA scaffold comprises a nucleotide sequence that is at least 50% identical to a reference scaffold sequence, wherein the reference scaffold sequence is selected from SEQ ID NOS: 144-163 and 211-213.

443. A gRNA comprising a means for binding a target mammalian genomic sequence and a crRNA scaffold, optionally wherein the means for binding a target mammalian genomic sequence is a spacer, wherein:

(a) the means for binding a target genomic sequence is positioned 3' to the crRNA scaffold; and (b) the nucleotide sequence of the crRNA scaffold comprises a nucleotide sequence that is at least 50% identical to a reference scaffold sequence, wherein the reference scaffold sequence is selected from SEQ ID NOS: 144-163 and 211-213.

444. The gRNA of embodiment 442 or 443, wherein the crRNA scaffold comprises a nucleotide sequence that is at least 55% identical to the reference scaffold sequence.

445. The gRNA of embodiment 444, wherein the crRNA scaffold comprises a nucleotide sequence that is at least 60% identical to the reference scaffold sequence.

446. The gRNA of embodiment 444, wherein the crRNA scaffold comprises a nucleotide sequence that is at least 65% identical to the reference scaffold sequence.

447. The gRNA of embodiment 444, wherein the crRNA scaffold comprises a nucleotide sequence that is at least 70% identical to the reference scaffold sequence.

448. The gRNA of embodiment 444, wherein the crRNA scaffold comprises a nucleotide sequence that is at least 75% identical to the reference scaffold sequence.

449. The gRNA of embodiment 444, wherein the crRNA scaffold comprises a nucleotide sequence that is at least 80% identical to the reference scaffold sequence.

450. The gRNA of embodiment 444, wherein the crRNA scaffold comprises a nucleotide sequence that is at least 85% identical to the reference scaffold sequence.

451. The gRNA of embodiment 444, wherein the crRNA scaffold comprises a nucleotide sequence that is at least 90% identical to the reference scaffold sequence.

452. The gRNA of embodiment 444, wherein the crRNA scaffold comprises a nucleotide sequence that is at least 95% identical to the reference scaffold sequence.

453. The gRNA of embodiment 444, wherein the crRNA scaffold comprises a nucleotide sequence that is at least 96% identical to the reference scaffold sequence.

454. The gRNA of embodiment 444, wherein the crRNA scaffold comprises a nucleotide sequence that is at least 97% identical to the reference scaffold sequence.

455. The gRNA of embodiment 444, wherein the crRNA scaffold comprises a nucleotide sequence that is at least 98% identical to the reference scaffold sequence.

456. The gRNA of embodiment 444, wherein the crRNA scaffold comprises a nucleotide sequence that is at least 99% identical to the reference scaffold sequence.

457. The gRNA of embodiment 444, wherein the crRNA scaffold comprises a nucleotide sequence that has no more than 5 nucleotide mismatches with the reference scaffold sequence.

458. The gRNA of embodiment 444, wherein the crRNA scaffold comprises a nucleotide sequence that has no more than 4 nucleotide mismatches with the reference scaffold sequence.

459. The gRNA of embodiment 444, wherein the crRNA scaffold comprises a nucleotide sequence that has no more than 3 nucleotide mismatches with the reference scaffold sequence.

460. The gRNA of embodiment 444, wherein the crRNA scaffold comprises a nucleotide sequence that has no more than 2 nucleotide mismatches with the reference scaffold sequence.

461. The gRNA of embodiment 444, wherein the crRNA scaffold comprises a nucleotide sequence that has no more than 1 nucleotide mismatches with the reference scaffold sequence.

462. The gRNA of embodiment 442 or embodiment 443, wherein the crRNA scaffold comprises a nucleotide sequence that is 100% identical to the reference scaffold sequence.

463. The gRNA of any one of embodiments 442 to 462, wherein the reference scaffold sequence is SEQ ID NO:144.

464. The gRNA of any one of embodiments 442 to 462, wherein the reference scaffold sequence is SEQ ID NO:145.

465. The gRNA of any one of embodiments 442 to 462, wherein the reference scaffold sequence is SEQ ID NO:146.

466. The gRNA of any one of embodiments 442 to 462, wherein the reference scaffold sequence is SEQ ID NO:147.

467. The gRNA of any one of embodiments 442 to 462, wherein the reference scaffold sequence is SEQ ID NO:148.

468. The gRNA of any one of embodiments 442 to 462, wherein the reference scaffold sequence is SEQ ID NO:149.

469. The gRNA of any one of embodiments 442 to 462, wherein the reference scaffold sequence is SEQ ID NO:150.

470. The gRNA of any one of embodiments 442 to 462, wherein the reference scaffold sequence is SEQ ID NO:151.

471. The gRNA of any one of embodiments 442 to 462, wherein the reference scaffold sequence is SEQ ID NO:152.

472. The gRNA of any one of embodiments 442 to 462, wherein the reference scaffold sequence is SEQ ID NO:153.

473. The gRNA of any one of embodiments 442 to 462, wherein the reference scaffold sequence is SEQ ID NO:154.

474. The gRNA of any one of embodiments 442 to 462, wherein the reference scaffold sequence is SEQ ID NO:155.

475. The gRNA of any one of embodiments 442 to 462, wherein the reference scaffold sequence is SEQ ID NO:156.

476. The gRNA of any one of embodiments 442 to 462, wherein the reference scaffold sequence is SEQ ID NO:157.

477. The gRNA of any one of embodiments 442 to 462, wherein the reference scaffold sequence is SEQ ID NO:158.

478. The gRNA of any one of embodiments 442 to 462, wherein the reference scaffold sequence is SEQ ID NO:159.

479. The gRNA of any one of embodiments 442 to 462, wherein the reference scaffold sequence is SEQ ID NO:160.

480. The gRNA of any one of embodiments 442 to 462, wherein the reference scaffold sequence is SEQ ID NO:161.

481. The gRNA of any one of embodiments 442 to 462, wherein the reference scaffold sequence is SEQ ID NO:162.

482. The gRNA of any one of embodiments 442 to 462, wherein the reference scaffold sequence is SEQ ID NO:163.

483. The gRNA of any one of embodiments 442 to 462, wherein the reference scaffold sequence is SEQ ID NO:211.

484. The gRNA of any one of embodiments 442 to 462, wherein the reference scaffold sequence is SEQ ID NO:212.

485. The gRNA of any one of embodiments 442 to 462, wherein the reference scaffold sequence is SEQ ID NO:213.

486. The gRNA of any one of embodiments 442 to 485, wherein the gRNA comprises 1 to 8 uracils at its 3' end.

487. The gRNA of embodiment 486, wherein the gRNA comprises 1 uracil at its 3' end.

488. The gRNA of embodiment 486, wherein the gRNA comprises 2 uracils at its 3' end.

489. The gRNA of embodiment 486, wherein the gRNA comprises 3 uracils at its 3' end.

490. The gRNA of embodiment 486, wherein the gRNA comprises 4 uracils at its 3' end.

491. The gRNA of embodiment 486, wherein the gRNA comprises 5 uracils at its 3' end.

492. The gRNA of embodiment 486, wherein the gRNA comprises 6 uracils at its 3' end.

493. The gRNA of embodiment 486, wherein the gRNA comprises 7 uracils at its 3' end.

494. The gRNA of embodiment 486, wherein the gRNA comprises 8 uracils at its 3' end.

495. The gRNA of any one of embodiments 442 to 494, which comprises a 5' guanine.

496. The gRNA of any one of embodiments 442 to 495, wherein the nucleotide sequence of the spacer is partially or fully complementary to a target mammalian genomic sequence.

497. The gRNA of embodiment 496, wherein the target mammalian genomic sequence is downstream of a protospacer adjacent motif (PAM) sequence in the non-target strand recognized by a Type V Cas protein, optionally wherein the Type V Cas protein is a Type V Cas protein according to any one of embodiments 1 to 329.

498. The gRNA of embodiment 497, wherein the PAM sequence is TTN.

499. The gRNA of embodiment 497, wherein the PAM sequence is TTTN, e.g., TTTA, TTTT, TTTG, or TTTC.

500. The gRNA of embodiment 497, wherein the PAM sequence is TTTR.

501. The gRNA of embodiment 497, wherein the PAM sequence is YTTN, e.g., CTTC or CTTG.

502. The gRNA of embodiment 497, wherein the PAM sequence is YTTV.

503. The gRNA of embodiment 497, wherein the PAM sequence is NTTV.

504. The gRNA of embodiment 497, wherein the PAM sequence is VTTV, e.g., ATTA, or GTTA, or ATTC.

505. The gRNA of embodiment 497, wherein the PAM sequence is NCTV.

506. The gRNA of embodiment 497, wherein the PAM sequence is DTTN.

507. The gRNA of embodiment 497, wherein the PAM sequence is DTDN.

508. The gRNA of embodiment 497, wherein the PAM sequence is TTTT.

509. The gRNA of embodiment 497, wherein the PAM sequence is NYYN.

510. The gRNA of embodiment 497, wherein the PAM sequence is NTTN.

511. A gRNA comprising a spacer whose sequence comprises SEQ ID NO:164.

512. A gRNA comprising a spacer whose sequence comprises SEQ ID NO:165.

513. A gRNA comprising a spacer whose sequence comprises SEQ ID NO:166.

514. A gRNA comprising a spacer whose sequence comprises SEQ ID NO:167.

515. A gRNA comprising a spacer whose sequence comprises SEQ ID NO:168.

516. A gRNA comprising a spacer whose sequence comprises SEQ ID NO:169.

517. A gRNA comprising a spacer whose sequence comprises SEQ ID NO:170.

518. A gRNA comprising a spacer whose sequence comprises SEQ ID NO:171.

519. A gRNA comprising a spacer whose sequence comprises SEQ ID NO:172.

520. A gRNA comprising a spacer whose sequence comprises SEQ ID NO:173.

521. A gRNA comprising a spacer whose sequence comprises SEQ ID NO:174.

522. A gRNA comprising a spacer whose sequence comprises SEQ ID NO:175.

523. A gRNA comprising a spacer whose sequence comprises SEQ ID NO:176.

524. A gRNA comprising a spacer whose sequence comprises SEQ ID NO:177.

525. A gRNA comprising a spacer whose sequence comprises SEQ ID NO:181.

526. A gRNA comprising a spacer whose sequence comprises SEQ ID NO:182.

527. A gRNA comprising a spacer whose sequence comprises SEQ ID NO:183.

528. A gRNA comprising a spacer whose sequence comprises SEQ ID NO:184.

529. A gRNA comprising a spacer whose sequence comprises SEQ ID NO:185.

530. A gRNA comprising a spacer whose sequence comprises SEQ ID NO:186.

531. A gRNA comprising a spacer whose sequence comprises SEQ ID NO:187.

532. A gRNA comprising a spacer whose sequence comprises SEQ ID NO:188.

533. A gRNA comprising a spacer whose sequence comprises SEQ ID NO:189.

534. A gRNA comprising a spacer whose sequence comprises SEQ ID NO:190.

535. A gRNA comprising a spacer whose sequence comprises SEQ ID NO:191.

536. A gRNA comprising a spacer whose sequence comprises SEQ ID NO:192.

537. A gRNA comprising a spacer whose sequence comprises SEQ ID NO:193.

538. A gRNA comprising a spacer whose sequence comprises SEQ ID NO:194.

539. A gRNA comprising a spacer whose sequence comprises SEQ ID NO:195.

540. A gRNA comprising a spacer whose sequence comprises SEQ ID NO:196.

541. A gRNA comprising a spacer whose sequence comprises SEQ ID NO:197.

542. A gRNA comprising a spacer whose sequence comprises SEQ ID NO:198.

543. A gRNA comprising a spacer whose sequence comprises SEQ ID NO:199.

544. A gRNA comprising a spacer whose sequence comprises SEQ ID NO:200.

545. A gRNA comprising a spacer whose sequence comprises SEQ ID NO:201.

546. A gRNA comprising a spacer whose sequence comprises SEQ ID NO:202.

547. A gRNA comprising a spacer whose sequence comprises SEQ ID NO:203.

548. A gRNA comprising a spacer whose sequence comprises SEQ ID NO:204.

549. A gRNA comprising a spacer whose sequence comprises SEQ ID NO:205.

550. A gRNA comprising a spacer whose sequence comprises SEQ ID NO:206.

551. A gRNA comprising a spacer whose sequence comprises SEQ ID NO:207.

552. A gRNA comprising a spacer whose sequence comprises SEQ ID NO:208.

553. A gRNA comprising a spacer whose sequence comprises SEQ ID NO:209.

554. A gRNA comprising a spacer whose sequence comprises SEQ ID NO:210.

555. A gRNA comprising a spacer whose sequence comprises SEQ ID NO:211.

556. The gRNA of any one of embodiments 511 to 555, wherein the spacer is positioned 3' to a scaffold whose sequence comprises the sequence of SEQ ID NO:144.

557. The gRNA of any one of embodiments 511 to 555, wherein the spacer is positioned 3' to a scaffold whose sequence comprises the sequence of SEQ ID NO:145.

558. The gRNA of any one of embodiments 511 to 555, wherein the spacer is positioned 3' to a scaffold whose sequence comprises the sequence of SEQ ID NO:146.

559. The gRNA of any one of embodiments 511 to 555, wherein the spacer is positioned 3' to a scaffold whose sequence comprises the sequence of SEQ ID NO:147.

560. The gRNA of any one of embodiments 511 to 555, wherein the spacer is positioned 3' to a scaffold whose sequence comprises the sequence of SEQ ID NO:148.

561. The gRNA of any one of embodiments 511 to 555, wherein the spacer is positioned 3' to a scaffold whose sequence comprises the sequence of SEQ ID NO:149.

562. The gRNA of any one of embodiments 511 to 555, wherein the spacer is positioned 3' to a scaffold whose sequence comprises the sequence of SEQ ID NO:150.

563. The gRNA of any one of embodiments 511 to 555, wherein the spacer is positioned 3' to a scaffold whose sequence comprises the sequence of SEQ ID NO:151.

564. The gRNA of any one of embodiments 511 to 555, wherein the spacer is positioned 3' to a scaffold whose sequence comprises the sequence of SEQ ID NO:152.

565. The gRNA of any one of embodiments 511 to 555, wherein the spacer is positioned 3' to a scaffold whose sequence comprises the sequence of SEQ ID NO:153.

566. The gRNA of any one of embodiments 511 to 555, wherein the spacer is positioned 3' to a scaffold whose sequence comprises the sequence of SEQ ID NO:154.

567. The gRNA of any one of embodiments 511 to 555, wherein the spacer is positioned 3' to a scaffold whose sequence comprises the sequence of SEQ ID NO:155.

568. The gRNA of any one of embodiments 511 to 555, wherein the spacer is positioned 3' to a scaffold whose sequence comprises the sequence of SEQ ID NO:156.

569. The gRNA of any one of embodiments 511 to 555, wherein the spacer is positioned 3' to a scaffold whose sequence comprises the sequence of SEQ ID NO:157.

570. The gRNA of any one of embodiments 511 to 555, wherein the spacer is positioned 3' to a scaffold whose sequence comprises the sequence of SEQ ID NO:158.

571. The gRNA of any one of embodiments 511 to 555, wherein the spacer is positioned 3' to a scaffold whose sequence comprises the sequence of SEQ ID NO:159.

572. The gRNA of any one of embodiments 511 to 555, wherein the spacer is positioned 3' to a scaffold whose sequence comprises the sequence of SEQ ID NO:160.

573. The gRNA of any one of embodiments 511 to 555, wherein the spacer is positioned 3' to a scaffold whose sequence comprises the sequence of SEQ ID NO:161.

574. The gRNA of any one of embodiments 511 to 555, wherein the spacer is positioned 3' to a scaffold whose sequence comprises the sequence of SEQ ID NO:162.

575. The gRNA of any one of embodiments 511 to 555, wherein the spacer is positioned 3' to a scaffold whose sequence comprises the sequence of SEQ ID NO:163.

576. The gRNA of any one of embodiments 511 to 555, wherein the spacer is positioned 3' to a scaffold whose sequence comprises the sequence of SEQ ID NO:211

577. The gRNA of any one of embodiments 511 to 555, wherein the spacer is positioned 3' to a scaffold whose sequence comprises the sequence of SEQ ID NO:212.

578. The gRNA of any one of embodiments 511 to 555, wherein the spacer is positioned 3' to a scaffold whose sequence comprises the sequence of SEQ ID NO:213.

579. A system comprising the Type V Cas protein of any one of embodiments 1 to 329 and a guide RNA (gRNA) comprising a spacer sequence, optionally wherein the gRNA is a gRNA according to any one of embodiments 330 to 578.

580. A system comprising the Type V Cas protein of any one of embodiments 1 to 329 and a means for targeting the Type V Cas protein to a target genomic sequence, optionally wherein the means for targeting the Type V Cas protein to a target genomic sequence is a guide RNA (gRNA) molecule, optionally as described in in any one of embodiments 330 to 578, optionally wherein the gRNA molecule comprises a spacer partially or fully complementary to a target mammalian genomic sequence.

581. The system of embodiment 580, wherein the spacer sequence is partially or fully complementary to a target mammalian genomic sequence.

582. The system of any one of embodiments 580 to 581, wherein the target mammalian genomic sequence is a human genomic sequence.

583. The system of embodiment 582, wherein the target mammalian genomic sequence is a CCR5, EMX1, Fas, FANCF, HBB, ZSCAN2, Chr6, ADAMTSL1, B2M, CXCR4, PD1, DNMT1, Match8, TRAC, TRBC, VEGFA-site2, VEGFAsite3, CACNA, HEKsite3, HEKsite4, Chr8, BCR, ATM, HBG1, HPRT, IL2RG, NF1, USH2A, RHO, BcLenh, or CTFR genomic sequence. 584. The system of embodiment 582, wherein the target mammalian genomic sequence is a RHO genomic sequence.

585. The system of embodiment 582, wherein the target mammalian genomic sequence is a TRAC genomic sequence.

586. The system of embodiment 582, wherein the target mammalian genomic sequence is a B2M genomic sequence.

587. The system of embodiment 582, wherein the target mammalian genomic sequence is a PD1 genomic sequence.

588. The system of embodiment 582, wherein the target mammalian genomic sequence is an AAVS1 genomic sequence.

589. The system of embodiment 582, wherein the target mammalian genomic sequence is an EMX1 genomic sequence.

590. The system of embodiment 582, wherein the target mammalian genomic sequence is an BCL11A genomic sequence.

591. The system of embodiment 582, wherein the target mammalian genomic sequence is an PCSK9 genomic sequence.

592. The system of embodiment 582, wherein the target mammalian genomic sequence is an VEGFA genomic sequence.

593. The system of embodiment 582, wherein the target mammalian genomic sequence is an Match6 genomic sequence.

594. The system of any one of embodiments 579 to 593, which is a ribonucleoprotein (RNP) comprising the Type V Cas protein complexed to the gRNA or means for targeting the Type V Cas protein to a target genomic sequence.

595. A nucleic acid encoding the Type V Cas protein of any one of embodiments 1 to 329, optionally wherein the nucleotide sequence encoding the Type V Cas protein is operably linked to a promoter that is heterologous to the Type V Cas protein.

596. The nucleic acid of embodiment 595, wherein the nucleotide sequence encoding the Type V Cas protein is codon optimized for expression in human cells.

597. The nucleic acid of embodiment 596, wherein when the reference protein sequence is SEQ ID NO:1 or SEQ ID NO:2, the nucleotide sequence encoding the Type V Cas protein comprises a nucleotide sequence that is at least 80%, at least 85%, at least 90%, at least 95%, at least 96%, at least 97%, at least 98%, at least 99%, or 100% identical to the nucleotide sequence of SEQ ID NO:5 or SEQ ID NO:6.

598. The nucleic acid of embodiment 596, wherein when the reference protein sequence is SEQ ID NO:7 or SEQ ID NO:8, the nucleotide sequence encoding the Type V Cas protein comprises a nucleotide sequence that is at least 80%, at least 85%, at least 90%, at least 95%, at least 96%, at least 97%, at least 98%, at least 99%, or 100% identical to the nucleotide sequence of SEQ ID NO:11 or SEQ ID NO:12.

599. The nucleic acid of embodiment 596, wherein when the reference protein sequence is SEQ ID NO:13 or SEQ ID NO:14, the nucleotide sequence encoding the Type V Cas protein comprises a nucleotide sequence that is at least 80%, at least 85%, at least 90%, at least 95%, at least 96%, at least 97%, at least 98%, at least 99%, or 100% identical to the nucleotide sequence of SEQ ID NO:17 or SEQ ID NO:18.

600. The nucleic acid of embodiment 596, wherein when the reference protein sequence is SEQ ID NO:19 or SEQ ID NO:20, the nucleotide sequence encoding the Type V Cas protein comprises a nucleotide sequence that is at least 80%, at least 85%, at least 90%, at least 95%, at least 96%, at least 97%, at least 98%, at least 99%, or 100% identical to the nucleotide sequence of SEQ ID NO:23 or SEQ ID NO:24.

601. The nucleic acid of embodiment 596, wherein when the reference protein sequence is SEQ ID NO:25 or SEQ ID NO:26, the nucleotide sequence encoding the Type V Cas protein comprises a nucleotide sequence that is at least 80%, at least 85%, at least 90%, at least 95%, at least 96%, at least 97%, at least 98%, at least 99%, or 100% identical to the nucleotide sequence of SEQ ID NO:29 or SEQ ID NO:30.

602. The nucleic acid of embodiment 596, wherein when the reference protein sequence is SEQ ID NO:31 or SEQ ID NO:32, the nucleotide sequence encoding the Type V Cas protein comprises a nucleotide sequence that is at least 80%, at least 85%, at least 90%, at least 95%, at least 96%, at least 97%, at least 98%, at least 99%, or 100% identical to the nucleotide sequence of SEQ ID NO:35 or SEQ ID NO:36.

603. The nucleic acid of embodiment 596, wherein when the reference protein sequence is SEQ ID NO:37 or SEQ ID NO:38, the nucleotide sequence encoding the Type V Cas protein comprises a nucleotide sequence that is at least 80%, at least 85%, at least 90%, at least 95%, at least 96%, at least 97%, at least 98%, at least 99%, or 100% identical to the nucleotide sequence of SEQ ID NO:41 or SEQ ID NO:42.

604. The nucleic acid of embodiment 596, wherein when the reference protein sequence is SEQ ID NO:43 or SEQ ID NO:44, the nucleotide sequence encoding the Type V Cas protein comprises a nucleotide sequence that is at least 80%, at least 85%, at least 90%, at least 95%, at least 96%, at least 97%, at least 98%, at least 99%, or 100% identical to the nucleotide sequence of SEQ ID NO:47 or SEQ ID NO:48.

605. The nucleic acid of embodiment 596, wherein when the reference protein sequence is SEQ ID NO:49 or SEQ ID NO:50, the nucleotide sequence encoding the Type V Cas protein comprises a nucleotide sequence that is at least 80%, at least 85%, at least 90%, at least 95%, at least 96%, at least 97%, at least 98%, at least 99%, or 100% identical to the nucleotide sequence of SEQ ID NO:53 or SEQ ID NO:54.

606. The nucleic acid of embodiment 596, wherein when the reference protein sequence is SEQ ID NO:55 or SEQ ID NO:56, the nucleotide sequence encoding the Type V Cas protein comprises a nucleotide sequence that is at least 80%, at least 85%, at least 90%, at least 95%, at least 96%, at least 97%, at least 98%, at least 99%, or 100% identical to the nucleotide sequence of SEQ ID NO:59 or SEQ ID NO:60.

607. The nucleic acid of embodiment 596, wherein when the reference protein sequence is SEQ ID NO:61 or SEQ ID NO:62, the nucleotide sequence encoding the Type V Cas protein comprises a nucleotide sequence that is at least 80%, at least 85%, at least 90%, at least 95%, at least 96%, at least 97%, at least 98%, at least 99%, or 100% identical to the nucleotide sequence of SEQ ID NO:65 or SEQ ID NO:66.

608. The nucleic acid of embodiment 596, wherein when the reference protein sequence is SEQ ID NO:67 or SEQ ID NO:68, the nucleotide sequence encoding the Type V Cas protein comprises a nucleotide sequence that is at least 80%, at least 85%, at least 90%, at least 95%, at least 96%, at least 97%, at least 98%, at least 99%, or 100% identical to the nucleotide sequence of SEQ ID NO:71 or SEQ ID NO:72.

609. The nucleic acid of embodiment 596, wherein when the reference protein sequence is SEQ ID NO:73 or SEQ ID NO:74, the nucleotide sequence encoding the Type V Cas protein comprises a nucleotide sequence that is at least 80%, at least 85%, at least 90%, at least 95%, at least 96%, at least 97%, at least 98%, at least 99%, or 100% identical to the nucleotide sequence of SEQ ID NO:77 or SEQ ID NO:78.

610. The nucleic acid of embodiment 596, wherein when the reference protein sequence is SEQ ID NO:79 or SEQ ID NO:80, the nucleotide sequence encoding the Type V Cas protein comprises a nucleotide sequence that is at least 80%, at least 85%, at least 90%, at least 95%, at least 96%, at least 97%, at least 98%, at least 99%, or 100% identical to the nucleotide sequence of SEQ ID NO:83 or SEQ ID NO:84.

611. The nucleic acid of embodiment 596, wherein when the reference protein sequence is SEQ ID NO:85 or SEQ ID NO:86, the nucleotide sequence encoding the Type V Cas protein comprises a nucleotide sequence that is at least 80%, at least 85%, at least 90%, at least 95%, at least 96%, at least 97%, at least 98%, at least 99%, or 100% identical to the nucleotide sequence of SEQ ID NO:89 or SEQ ID NO:90.

612. The nucleic acid of embodiment 596, wherein when the reference protein sequence is SEQ ID NO:91 or SEQ ID NO:92, the nucleotide sequence encoding the Type V Cas protein comprises a nucleotide sequence that is at least 80%, at least 85%, at least 90%, at least 95%, at least 96%, at least 97%, at least 98%, at least 99%, or 100% identical to the nucleotide sequence of SEQ ID NO:95 or SEQ ID NO:96.

613. The nucleic acid of embodiment 596, wherein when the reference protein sequence is SEQ ID NO:97 or SEQ ID NO:98, the nucleotide sequence encoding the Type V Cas protein comprises a nucleotide sequence that is at least 80%, at least 85%, at least 90%, at least 95%, at least 96%, at least 97%, at least 98%, at least 99%, or 100% identical to the nucleotide sequence of SEQ ID NO:101 or SEQ ID NO:102.

614. The nucleic acid of embodiment 596, wherein when the reference protein sequence is SEQ ID NO:103 or SEQ ID NO:104, the nucleotide sequence encoding the Type V Cas protein comprises a nucleotide sequence that is at least 80%, at least 85%, at least 90%, at least 95%, at least 96%, at least 97%, at least 98%, at least 99%, or 100% identical to the nucleotide sequence of SEQ ID NO:107 or SEQ ID NO:108.

615. The nucleic acid of embodiment 596, wherein when the reference protein sequence is SEQ ID NO:109 or SEQ ID NO:110, the nucleotide sequence encoding the Type V Cas protein comprises a nucleotide sequence that is at least 80%, at least 85%, at least 90%, at least 95%, at least 96%, at least 97%, at least 98%, at least 99%, or 100% identical to the nucleotide sequence of SEQ ID NO:113 or SEQ ID NO:114.

616. The nucleic acid of embodiment 596, wherein when the reference protein sequence is SEQ ID NO:115 or SEQ ID NO:116, the nucleotide sequence encoding the Type V Cas protein comprises a nucleotide sequence that is at least 80%, at least 85%, at least 90%, at least 95%, at least 96%, at least 97%, at least 98%, at least 99%, or 100% identical to the nucleotide sequence of SEQ ID NO:119 or SEQ ID NO:120.

617. The nucleic acid of any one of embodiments embodiment 595 to 616, which is a plasmid.

618. The nucleic acid of any one of embodiments embodiment 595 to 616, which is a viral genome.

619. The nucleic acid of embodiment 618, wherein the viral genome is an adeno-associated virus (AAV) genome.

620. The nucleic acid of embodiment 619, wherein the AAV genome is an AAV2, AAV5, AAV7m8, AAV8, AAV9, AAVrh8r, or AAVrh10 genome.

621. The nucleic acid of embodiment 620, wherein the AAV genome is an AAV2 genome.

622. The nucleic acid of embodiment 620, wherein the AAV genome is an AAV5 genome.

623. The nucleic acid of embodiment 620, wherein the AAV genome is an AAV7m8 genome.

624. The nucleic acid of embodiment 620, wherein the AAV genome is an AAV8 genome.

625. The nucleic acid of embodiment 620, wherein the AAV genome is an AAV9 genome.

626. The nucleic acid of embodiment 620, wherein the AAV genome is an AAVrh8r genome.

627. The nucleic acid of embodiment 620, wherein the AAV genome is an AAVrh10 genome.

628. The nucleic acid of any one of embodiments 595 to 627, further encoding a gRNA, optionally wherein the gRNA is a gRNA according to any one of embodiments 330 to 578.

629. A nucleic acid encoding the gRNA of any one of embodiments 330 to 578.

630. The nucleic acid of embodiment 629, which is a plasmid.

631. The nucleic acid of embodiment 629, which is a viral genome.

632. The nucleic acid of embodiment 631, wherein the viral genome is an adeno-associated virus (AAV) genome.

633. The nucleic acid of embodiment 632, wherein the AAV genome is a AAV2, AAV5, AAV7m8, AAV8, AAV9, AAVrh8r, or AAVrh10 genome.

634. The nucleic acid of embodiment 633, wherein the AAV genome is an AAV2 genome.

635. The nucleic acid of embodiment 633, wherein the AAV genome is an AAV5 genome.

636. The nucleic acid of embodiment 633, wherein the AAV genome is an AAV7m8 genome.

637. The nucleic acid of embodiment 633, wherein the AAV genome is an AAV8 genome.

638. The nucleic acid of embodiment 633, wherein the AAV genome is an AAV9 genome.

639. The nucleic acid of embodiment 633, wherein the AAV genome is an AAVrh8r genome.

640. The nucleic acid of embodiment 633, wherein the AAV genome is an AAVrh10 genome.

641. The nucleic acid of any one of embodiments 629 to 640, further encoding a Type V Cas protein, optionally wherein the Type V Cas protein is a Type V Cas protein according to any one of embodiments 1 to 329.

642. A nucleic acid encoding the Type V Cas protein and gRNA of the system of any one of embodiments 579 to 594.

643. The nucleic acid of embodiment 642, wherein the nucleotide sequence encoding the Type V Cas protein is codon optimized for expression in human cells.

644. The nucleic acid of embodiment 642 or embodiment 643, which is a plasmid.

645. The nucleic acid of embodiment 642 or embodiment 643, which is a viral genome.

646. The nucleic acid of embodiment 645, wherein the viral genome is an adeno-associated virus (AAV) genome.

647. The nucleic acid of embodiment 646, wherein the AAV genome is an AAV2, AAV5, AAV7m8, AAV8, AAV9, AAVrh8r, or AAVrh10 genome.

648. The nucleic acid of embodiment 647, wherein the AAV genome is an AAV2 genome.

649. The nucleic acid of embodiment 647, wherein the AAV genome is an AAV5 genome.

650. The nucleic acid of embodiment 647, wherein the AAV genome is an AAV7m8 genome.

651. The nucleic acid of embodiment 647, wherein the AAV genome is an AAV8 genome.

652. The nucleic acid of embodiment 647, wherein the AAV genome is an AAV9 genome.

653. The nucleic acid of embodiment 647, wherein the AAV genome is an AAVrh8r genome.

654. The nucleic acid of embodiment 647, wherein the AAV genome is an AAVrh10 genome.

655. A plurality of nucleic acids comprising separate nucleic acids encoding the Type V Cas protein and gRNA of the system of any one of embodiments 579 to 594.

656. The plurality of nucleic acid of embodiment 655, wherein the separate nucleic acids encoding the Type V Cas protein and gRNA are plasmids.

657. The plurality of nucleic acids of embodiment 655, wherein the separate nucleic acids encoding the Type V Cas protein and gRNA are viral genomes.

658. The plurality of nucleic acids of embodiment 657, wherein the viral genomes are adeno-associated virus (AAV) genomes.

659. The plurality of nucleic acids of embodiment 658, wherein the AAV genomes the encoding the Type V Cas protein and gRNA are independently an AAV2, AAV5, AAV7m8, AAV8, AAV9, AAVrh8r, or AAVrh10 genome.

660. A Type V Cas protein according to any one of embodiments 1 to 329, a gRNA according to any one of embodiments 330 to 578, a system according to of any one of embodiments 579 to 594, a nucleic acid according to any one of embodiments 595 to 654, a plurality of nucleic acids according to of any one of embodiments 655 to 659, particle according to any one of embodiments 672 to 687, or pharmaceutical composition according to embodiment 688 for use in a method of editing a human genomic sequence.

661. The Type V Cas protein, gRNA, system, nucleic acid, a plurality of nucleic acids, particle, or pharmaceutical composition for use according to embodiment 660, wherein the human genomic sequence is a CCR5, EMX1, Fas, FANCF, HBB, ZSCAN2, Chr6, ADAMTSL1, B2M, CXCR4, PD1, DNMT1, Match8, TRAC, TRBC, VEGFAsite2, VEGFAsite3, CACNA, HEKsite3, HEKsite4, Chr8, BCR, ATM, HBG1, HPRT, IL2RG, NF1, USH2A, RHO, BcLenh, or CTFR genomic sequence.

662. The Type V Cas protein, gRNA, combination of gRNAs, system, nucleic acid, a plurality of nucleic acids, particle, or pharmaceutical composition for use according to embodiment 660, wherein the human genomic sequence is a RHO genomic sequence, optionally wherein the RHO genomic sequence has a pathogenic mutation.

663. The Type V Cas protein, gRNA, combination of gRNAs, system, nucleic acid, a plurality of nucleic acids, particle, or pharmaceutical composition for use according to embodiment 660, wherein the human genomic sequence is a TRAC genomic sequence, optionally wherein the human genomic sequence is in a T cell.

664. The Type V Cas protein, gRNA, combination of gRNAs, system, nucleic acid, a plurality of nucleic acids, particle, or pharmaceutical composition for use according to embodiment 660, wherein the human genomic sequence is a B2M genomic sequence, optionally wherein the human genomic sequence is in a T cell.

665. The Type V Cas protein, gRNA, combination of gRNAs, system, nucleic acid, a plurality of nucleic acids, particle, or pharmaceutical composition for use according to embodiment 660, wherein the human genomic sequence is a PD1 genomic sequence, optionally wherein the human genomic sequence is in a T cell.

666. The Type V Cas protein, gRNA, combination of gRNAs, system, nucleic acid, a plurality of nucleic acids, particle, or pharmaceutical composition for use according to embodiment 660, wherein the human genomic sequence is a LAG3 genomic sequence, optionally wherein the human genomic sequence is in a T cell.

667. The Type V Cas protein, gRNA, combination of gRNAs, system, nucleic acid, a plurality of nucleic acids, particle, or pharmaceutical composition for use according to embodiment 660, wherein the human genomic sequence is a AAVS1 genomic sequence, optionally wherein the human genomic sequence is in a T cell.

668. The Type V Cas protein, gRNA, combination of gRNAs, system, nucleic acid, a plurality of nucleic acids, particle, or pharmaceutical composition for use according to embodiment 660, wherein the human genomic sequence is an EMX1 genomic sequence.

669. The Type V Cas protein, gRNA, combination of gRNAs, system, nucleic acid, a plurality of nucleic acids, particle, or pharmaceutical composition for use according to embodiment 660, wherein the human genomic sequence is a BCL11A genomic sequence.

670. The Type V Cas protein, gRNA, combination of gRNAs, system, nucleic acid, a plurality of nucleic acids, particle, or pharmaceutical composition for use according to embodiment 660, wherein the human genomic sequence is a PCSK9 genomic sequence.

671. The Type V Cas protein, gRNA, combination of gRNAs, system, nucleic acid, a plurality of nucleic acids, particle, or pharmaceutical composition for use according to embodiment 660, wherein the human genomic sequence is a Match6 genomic sequence.

672. A particle comprising a Type V Cas protein according to any one of embodiments 1 to 329, a gRNA according to any one of embodiments 330 to 578, a system according to of any one of embodiments 579 to 594, a nucleic acid according to any one of embodiments 595 to 654, or a plurality of nucleic acids according to of any one of embodiments 655 to 659.

673. The particle of embodiment 667, which is a lipid nanoparticle, a vesicle, a gold nanoparticle, a viral-like particle (VLP) or a viral particle.

674. The particle of embodiment 673, which is a lipid nanoparticle.

675. The particle of embodiment 673, which is a vesicle.

676. The particle of embodiment 673, which is a gold nanoparticle.

677. The particle of embodiment 673, which is a viral-like particle (VLP).

678. The particle of embodiment 673, which is a viral particle.

679. The particle of embodiment 677, which is an adeno-associated virus (AAV) particle.

680. The particle of embodiment 679, wherein the AAV particle is an AAV2, AAV5, AAV7m8, AAV8, AAV9, AAVrh8r, or AAVrh10 particle.

681. The particle of embodiment 680, wherein the AAV particle is an AAV2 particle.

682. The particle of embodiment 680, wherein the AAV particle is an AAV5 particle.

683. The particle of embodiment 680, wherein the AAV particle is an AAV7m8 particle.

684. The particle of embodiment 680, wherein the AAV particle is an AAV8 particle.

685. The particle of embodiment 680, wherein the AAV particle is an AAV9 particle.

686. The particle of embodiment 680, wherein the AAV particle is an AAVrh8r particle.

687. The particle of embodiment 680, wherein the AAV particle is an AAVrh10 particle.

688. A pharmaceutical composition comprising a Type V Cas protein according to any one of embodiments 1 to 329, a gRNA according to any one of embodiments 330 to 578, a system according to of any one of embodiments 579 to 594, a nucleic acid according to any one of embodiments 595 to 654, a plurality of nucleic acids according to of any one of embodiments 655 to 659, or a particle according to any one of embodiments 667 to 687 and at least one pharmaceutically acceptable excipient.

689. A cell comprising a Type V Cas protein according to any one of embodiments 1 to 329, a gRNA according to any one of embodiments 330 to 578, a system according to of any one of embodiments 579 to 594, a nucleic acid according to any one of embodiments 595 to 654, a plurality of nucleic acids according to of any one of embodiments 655 to 659, or a particle according to any one of embodiments 667 to 687.

690. The cell of embodiment 689, which is a human cell.

691. The cell of embodiment 689 or embodiment 690, wherein the cell is a hematopoietic progenitor cell.

692. The cell of any one of embodiments 689 to 691, which is a stem cell.

693. The cell of embodiment 692, wherein the stem cell is a hematopoietic stem cell (HSC), a pluripotent stem cell, or an induced pluripotent stem cell (iPS).

694. The cell of embodiment 693, wherein the stem cell is an embryonic stem cell.

695. The cell of embodiment 689 or embodiment 690, which is a T cell.

696. The cell of embodiment 689 or embodiment 690, which is a retinal cell.

697. The cell of embodiment 689 or embodiment 690, which is a photoreceptor cell.

698. The cell of any one of embodiments 689 to 697, which is an ex vivo cell.

699. A population of cells according to any one of embodiments 689 to 698.

700. A method for altering a cell, the method comprising contacting the cell with a Type V Cas protein according to any one of embodiments 1 to 329, a gRNA according to any one of embodiments 330 to 578, a system according to of any one of embodiments 579 to 594, a nucleic acid according to any one of embodiments 595 to 654, a plurality of nucleic acids according to of any one of embodiments 655 to 659, or a particle according to any one of embodiments 667 to 687, or a pharmaceutical composition according to embodiment 688.

701. The method of embodiment 700, which comprises contacting the cell with the Type V Cas protein of any one of embodiments 1 to 329.

702. The method of embodiment 700, which comprises contacting the cell with the gRNA of any one of embodiments 330 to 578.

703. The method of embodiment 700, which comprises contacting the cell with the system of any one of embodiments 579 to 594.

704. The method of embodiment 703, which comprises electroporation of the cell prior to contacting the cell with the system.

705. The method of embodiment 703, which comprises lipid-mediated delivery of the system to the cell, optionally wherein the lipid-mediated delivery is cationic lipid-mediated delivery.

706. The method of embodiment 703, which comprises polymer-mediated delivery of the system to the cell.

707. The method of embodiment 703, which comprises delivery of the system to the cell by lipofection.

708. The method of embodiment 703, which comprises delivery of the system to the cell by nucleofection.

709. The method of embodiment 700, which comprises contacting the cell with the nucleic acid of any one of embodiments 595 to 654.

710. The method of embodiment 700, which comprises contacting the cell with the plurality of nucleic acids of any one of embodiments 655 to 659.

711. The method of embodiment 700, which comprises contacting the cell with the particle of any one of embodiments 667 to 687.

712. The method of embodiment 700, which comprises contacting the cell with the pharmaceutical composition of embodiment 688.

713. The method of any one of embodiments 700 to 712, further comprising contacting the cell with a DNA mismatch repair (MMR) inhibitor or nucleic acid encoding the MMR inhibitor, optionally wherein the MMR inhibitor comprises an amino acid sequence having at least 50%, at least 60%, at least 70%, at least 80%, at least 90%, at least 95%, at least 97%, at least 98%, at least 99%, or 100% sequence identity to SEQ ID NO:258.

714. The method of any one of embodiments 700 to 713, wherein the contacting alters a CCR5, EMX1, Fas, FANCF, HBB, ZSCAN2, Chr6, ADAMTSL1, B2M, CXCR4, PD1, DNMT1, Match8, TRAC, TRBC, VEGFAsite2, VEGFA-site3, CACNA, HEKsite3, HEKsite4, Chr8, BCR, ATM, HBG1, HPRT, IL2RG, NF1, USH2A, RHO, BcLenh, or CTFR genomic sequence 715. The method of any one of embodiments 700 to 713, wherein the contacting alters a RHO genomic sequence.

716. The method of any one of embodiments 700 to 713, wherein the contacting alters a TRAC genomic sequence.

717. The method of any one of embodiments 700 to 713, wherein the contacting alters a B2M genomic sequence.

718. The method of any one of embodiments 700 to 713, wherein the contacting alters a PD1 genomic sequence.

719. The method of any one of embodiments 700 to 713, wherein the contacting alters a LAG3 genomic sequence.

720. The method of any one of embodiments 700 to 713, wherein the contacting alters a AAVS1 genomic sequence.

721. The method of any one of embodiments 700 to 713, wherein the contacting alters an EMX1 genomic sequence.

722. The method of any one of embodiments 700 to 713, wherein the contacting alters a BCLA11A genomic sequence.

723. The method of any one of embodiments 700 to 713, wherein the contacting alters a PCSK9 genomic sequence.

724. The method of any one of embodiments 700 to 713, wherein the contacting alters a VEGFA genomic sequence.

725. The method of any one of embodiments 700 to 713, wherein the contacting alters a Match6 genomic sequence.

726. The method of any one of embodiments 700 to 725, wherein the cell is a human cell.

727. The method of any one of embodiments 700 to 726, wherein the cell is a hematopoietic progenitor cell.

728. The method of any one of embodiments 700 to 727, wherein the cell is a stem cell.

729. The method of embodiment 728, wherein the stem cell is a hematopoietic stem cell (HSC), a pluripotent stem cell, or an induced pluripotent stem cell (iPS).

730. The method of embodiment 729, wherein the stem cell is an embryonic stem cell.

731. The method of any one of embodiments 700 to 725, wherein the cell is a retinal cell. 732. The method of any one of embodiments 700 to 725, wherein the cell is a photoreceptor cell.

733. The method of any one of embodiments 700 to 725, wherein the cell is a T cell.

734. The method of any one of embodiments 700 to 733, wherein the contacting is in vitro.

735. The method of embodiment 731, further comprising transplanting the cell to a subject.

736. The method of any one of embodiments 700 to 730, wherein the contacting is in vivo in a subject.

737. A cell or population of cells produced by the method of any one of embodiments 700 to 734.

738. A Type V Cas protein according to any one of embodiments 1 to 329, the gRNA according to any one of embodiments 330 to 578, or the system of any one of embodiments 579 to 594 for use in a nucleic acid detection assay.

739. A method of detecting a target nucleic acid, comprising (a) combining a test sample with the Type V Cas protein of any one of embodiments 1 to 329, a gRNA comprising a spacer which is partially or fully complementary to a nucleotide sequence present in the target nucleic acid, and a reporter nucleic acid, and (b) detecting cleavage of the reporter nucleic acid, if any, whereby cleavage of the reporter nucleic acid indicates that the target nucleic acid is present in the test sample.

740. The method of embodiment 739, wherein the reporter nucleic acid comprises a quenched fluorescent reporter moiety.

9. CITATION OF REFERENCES

All publications, patents, patent applications and other documents cited in this application are hereby incorporated by reference in their entireties for all purposes to the same extent as if each individual publication, patent, patent application or other document were individually indicated to be incorporated by reference for all purposes. In the event that there is an inconsistency between the teachings of one or more of the references incorporated herein and the present disclosure, the teachings of the present specification are intended.

What is claimed is:

1. A fusion protein comprising:

(a) a Type V Cas amino acid sequence comprising an amino acid sequence that is at least 98% identical to the full length of SEQ ID NO:43 or SEQ ID NO:44; and (b) one or more nuclear localization signals.

2. The fusion protein of claim 1, wherein the Type V Cas amino acid sequence comprises an amino acid sequence that is at least 99% identical to the full length of SEQ ID NO:43.

3. The fusion protein of claim 1, wherein the Type V Cas amino acid sequence comprises an amino acid sequence that is identical to SEQ ID NO:43.

4. The fusion protein of claim 1, wherein the Type V Cas amino acid sequence comprises an amino acid sequence that is identical to SEQ ID NO:44.

5. The fusion protein of claim 1, which comprises a C-terminal nuclear localization signal.

6. The fusion protein of claim 1, which comprises an N-terminal nuclear localization signal.

7. The fusion protein of claim 1, which comprises a nuclear localization signal comprising the amino acid sequence KRTADGSEFESPKKKRKV (SEQ ID NO:122), PKKKRKV (SEQ ID NO:123), PKKKRRV (SEQ ID NO:124), KRPAATKKAGQAKKKK (SEQ ID NO:125), YGRKKRRQRRR (SEQ ID NO:126), RKKRRQRRR (SEQ ID NO:127), PAAKRVKLD (SEQ ID NO:128), RQRRNELKRSP (SEQ ID NO:129), VSRKRPRP (SEQ ID NO:130), PPKKARED (SEQ ID NO:131), PQPKKKPL (SEQ ID NO:132), SALIKKKKKMAP (SEQ ID NO:133), PKQKKRK (SEQ ID NO:134), RKLKKKIKKL (SEQ ID NO:135), REKKKFLKRR (SEQ ID NO:136), KRKGDEVDGVDEVAKKKSKK (SEQ ID NO:137), RKCLQAGMNLEARKTKK (SEQ ID NO:138), NQSSNFGPMKGGNFGGRSSGPYGGGGQYFAK-PRNQGGY (SEQ ID NO:139), RMRIZFKNKGKDTAEL-RRRRVEVSVELRKAKKDEQILKRRNV (SEQ ID NO:140), or SSDDEATADSQHAAPPKKKRKV (SEQ ID NO:178).

8. The fusion protein of claim 1, which comprises a nuclear localization signal comprising the amino acid sequence GRSSDDEATADSQHAAPPKKKRKV (SEQ ID NO:180).

9. The fusion protein of claim 1, wherein the fusion protein comprises a Type V Cas amino acid sequence that is identical to SEQ ID NO:44 and a C-terminal nuclear localization signal comprising the amino acid sequence GRSSD-DEATADSQHAAPPKKKRKV (SEQ ID NO:180).

10. A system comprising the fusion protein of claim 1 and a guide RNA (gRNA) comprising a spacer positioned 3' to a crRNA scaffold and capable of forming a complex with the fusion protein and directing the fusion protein to a target DNA.

11. The system of claim 10, wherein the nucleotide sequence of the spacer is complementary to a target mammalian genomic sequence that is downstream of a NTTV, VTTV, NCTV, or TTTT protospacer adjacent motif (PAM) sequence.

12. The system of claim 10, wherein the crRNA scaffold comprises a nucleotide sequence that is at least 90% identical to SEQ ID NO:151 or SEQ ID NO:211.

13. The system of claim 12, wherein the crRNA scaffold comprises a nucleotide sequence that is identical to SEQ ID NO:151 or SEQ ID NO:211.

14. The system of claim 10, which is a ribonucleoprotein (RNP) comprising the fusion protein complexed to the gRNA.

15. A nucleic acid encoding the fusion protein of claim 1.

16. The nucleic acid of claim 15, wherein the nucleotide sequence encoding the fusion protein is codon optimized for expression in human cells.

17. An adeno-associated virus (AAV) genome comprising the nucleic acid of claim 15.

18. An adeno-associated virus (AAV) particle comprising the AAV genome of claim 17.

19. An ex vivo human cell comprising the system of claim 10.

20. The ex vivo human cell of claim 19, which is a hematopoietic stem cell (HSC), pluripotent stem cell or an induced pluripotent stem cell (iPS).

21. A method for altering a cell comprising contacting the cell with the system of claim 10, wherein the contacting alters a genomic sequence of the cell.

22. An ex vivo human cell comprising the fusion protein of claim 1.

23. The ex vivo human cell of claim 22, which is a hematopoietic stem cell (HSC), pluripotent stem cell or an induced pluripotent stem cell (iPS).

* * * * *

SEQUENCE LISTING

```
Sequence total quantity: 412
SEQ ID NO: 1           moltype = AA  length = 1291
FEATURE                Location/Qualifiers
source                 1..1291
                       mol_type = protein
                       organism = unidentified
SEQUENCE: 1
VSEKENTPTF NSLTNLYSVS KTLRFELRPQ YSTLDHIKDD QIVDKGEELK NHYKTFKKIL  60
DQVFSRIIND SLDKTYLDQK YISTYQDLVF KHRDRLTDKD RAELKALKET LKKQIDKSLD  120
HKDKKAIFSD PVNFLIDNES DFADLIGDNR PSIEAFNRQK GYLSGYLQNR ANIFDHTTNE  180
TSVAFRIVEE NLAIFLNNRL TLQHFFEKVA DKDGLLKFLQ ETLSQLGFKL KLEDLLSLDY  240
FNRTLSQPGI DQYNLLISGK ALEDGKKMQG INEVLNQYLQ QHQEEKLHKI KLKQLYKQIL  300
SESKTESFTL DFVEDNKGLA AMLLQFIDFV NKLIEEKMLL LDMIQGLKDS SVSSEFLSRL  360
YLERKNIKRL SNFIYKDYGY IEQSLEENFL STIEGKITKK ALEEHRKQDA FTIHEILVAL  420
QKQQYEKDGA LESADHLLLP GVVDFLYQNL DCKHSTLLEK VGSEKQPLLD LFNEKQLLEG  480
QDAESHASKY SDRPFNDHEI KVVKTALDFY KNLQSNFAIF QIPDENLKLD SEFYSEFDEF  540
YQGLKNIIPV YNKSRNFLTK KPFSTEKTKL IFNNPQLLDG WSKSKESDCL GTIFIKDGKY  600
YVGIINSATN AKNTLFEPNN FANFDQKQYF EKMNLFFLSD LKRDFPKKYF SEKWHNQHPV  660
PADLREKYDY YRIDEHKDER KNDLKYHHQL IAYYQDCLKK DTEWQIYQFK YKAPEEYSDV  720
NEFLSELTPN TYKMEFNKIP AEYIKKLVDD GKLYFFQIYS KDFSEFAKGK PNLHTLYLKA  780
VFDQKNAEEF NYNYKISGSA EIFYRPASIE TRVTHPKNQP IKNKNKNNPK AESVFQYDLC  840
KDRRYMSDKF FLHLPIELNR IPLLANDSSV NSMVNQVVSS RNQNYFLGID RGERHLIYLV  900
LIDQNGRIIK QQTLNQITSS YQEKANNQTV EVITDYHDLL NDKEKLRKKN LQEWQSVENI  960
KELKAGYLSN VVNEIGKIIV EYQPVIMLEN LNTGFKNSRI KIEKQVYQKF EKALIDKFNY  1020
FMRKDLDSSA IGGLYHALQL TKEYSKQYNG KQNGIIYYIP ASYTSNIDPT TGFISAFIQT  1080
RYENVEKTKS LIEKFNDITY DAEESLFCFS ADYKKFSPEA KLWQQTIWQI YTNGDRIYTF  1140
KNKEEWQSKN YILVEEFKDL FAKYHIDYCR DLKAQILSQT DASFFKQFLF LLRLTLQMRN  1200
SRTTELNGTD ADTKKRENDY IISPVKNQYG KFYDSRKDYV DWPENADANG AYNIARKGLI  1260
MLKHLKEGLP EKRICDISTE EWVQFVEELN K                                1291

SEQ ID NO: 2           moltype = AA  length = 1292
FEATURE                Location/Qualifiers
source                 1..1292
                       mol_type = protein
                       organism = unidentified
SEQUENCE: 2
MVSEKENTPT FNSLTNLYSV SKTLRFELRP QYSTLDHIKD DQIVDKGEEL KNHYKTFKKI  60
LDQVFSRIIN DSLDKTYLDQ KYISTYQDLV FKHRDRLTDK DRAELKALKE TLKKQIDKSL  120
DHKDKKAIFS DPVNFLIDNE SDFADLIGDN RPSIEAFNRQ KGYLSGYLQN RANIFDHTTN  180
ETSVAFRIVE ENLAIFLNNR LTLQHFFEKV ADKDGLLKFL QETLSQLGFK LKLEDLLSLD  240
YFNRTLSQPG IDQYNLLISG KALEDGKKMQ GINEVLNQYL QQHQEEKLHK IKLKQLYKQI  300
LSESKTESFT LDFVEDNKGL AAMLLQFIDF VNKLIEEKML LLDMIQGLKD SSVSSEFLSR  360
LYLERKNIKR LSNFIYKDYG YIEQSLEENF LSTIEGKITK KALEEHRKQD AFTIHEILVA  420
LQKQQYEKDG ALESADHLLL PGVVDFLYQN LDCKHSTLLE KVGSEKQPLL DLFNEKQLLE  480
GQDAESHASK YSDRPFNDHE IKVVKTALDF YKNLQSNFAI FQIPDENLKL DSEFYSEFDE  540
FYQGLKNIIP VYNKSRNFLT KKPFSTEKTK LIFNNPQLLD GWSKSKESDC LGTIFIKDGK  600
YYVGIINSAT NAKNTLFEPN NFANFDQKQY FEKMNLFFLS DLKRDFPKKY FSEKWHNQHP  660
VPADLREKYD YYRIDEHKDE RKNDLKYHHQ LIAYYQDCLK KDTEWQIYQF KYKAPEEYSD  720
VNEFLSELTP NTYKMEFNKI PAEYIKKLVD DGKLYFFQIY SKDFSEFAKG KPNLHTLYLK  780
AVFDQKNAEE FNYNYKISGS AEIFYRPASI ETRVTHPKNQ PIKNKNKNNP KAESVFQYDL  840
CKDRRYMSDK FFLHLPIELN RIPLLANDSS VNSMVNQVVS SRNQNYFLGI DRGERHLIYL  900
VLIDQNGRII KQQTLNQITS SYQEKANNQT VEVITDYHDL LNDKEKLRKK NLQEWQSVEN  960
IKELKAGYLS NVVNEIGKII VEYQPVIMLE NLNTGFKNSR IKIEKQVYQK FEKALIDKFN  1020
YFMRKDLDSS AIGGLYHALQ LTKEYSKQYN GKQNGIIYYI PASYTSNIDP TTGFISAFIQ  1080
TRYENVEKTK SLIEKFNDIT YDAEESLFCF SADYKKFSPE AKLWQQTIWQ IYTNGDRIYT  1140
FKNKEEWQSK NYILVEEFKD LFAKYHIDYC RDLKAQILSQ TDASFFKQFL FLLRLTLQMR  1200
NSRTTELNGT DADTKKREND YIISPVKNQY GKFYDSRKDY VDWPENADAN GAYNIARKGL  1260
IMLKHLKEGL PEKRICDIST EEWVQFVEEL NK                               1292

SEQ ID NO: 3           moltype = AA  length = 1329
FEATURE                Location/Qualifiers
source                 1..1329
                       mol_type = protein
                       organism = synthetic construct
SEQUENCE: 3
MGVSEKENTP TFNSLTNLYS VSKTLRFELR PQYSTLDHIK DDQIVDKGEE LKNHYKTFKK  60
ILDQVFSRII NDSLDKTYLD QKYISTYQDL VFKHRDRLTD KDRAELKALK ETLKKQIDKS  120
LDHKDKKAIF SDPVNFLIDN ESDFADLIGD NRPSIEAFNR QKGYLSGYLQ NRANIFDHTT  180
NETSVAFRIV EENLAIFLNN RLTLQHFFEK VADKDGLLKF LQETLSQLGF KLKLEDLLSL  240
DYFNRTLSQP GIDQYNLLIS GKALEDGKKM QGINEVLNQY LQQHQEEKLH KIKLKQLYKQ  300
ILSESKTESF TLDFVEDNKG LAAMLLQFID FVNKLIEEKM LLLDMIQGLK DSSVSSEFLS  360
RLYLERKNIK RLSNFIYKDY GYIEQSLEEN FLSTIEGKIT KKALEEHRKQ DAFTIHEILV  420
ALQKQQYEKD GALESADHLL LPGVVDFLYQ NLDCKHSTLL EKVGSEKQPL LDLFNEKQLL  480
EGQDAESHAS KYSDRPFNDH EIKVVKTALD FYKNLQSNFA IFQIPDENLK LDSEFYSEFD  540
EFYQGLKNII PVYNKSRNFL TKKPFSTEKT KLIFNNPQLL DGWSKSKESD CLGTIFIKDG  600
KYYVGIINSA TNAKNTLFEP NNFANFDQKQ YFEKMNLFFL SDLKRDFPKK YFSEKWHNQH  660
PVPADLREKY DYYRIDEHKD ERKNDLKYHH QLIAYYQDCL KKDTEWQIYQ FKYKAPEEYS  720
DVNEFLSELT PNTYKMEFNK IPAEYIKKLV DDGKLYFFQI YSKDFSEFAK GKPNLHTLYL  780
```

```
KAVFDQKNAE EFNYNYKISG SAEIFYRPAS IETRVTHPKN QPIKNKNKNN PKAESVFQYD  840
LCKDRRYMSD KFFLHLPIEL NRIPLLANDS SVNSMVNQVV SSRNQNYFLG IDRGERHLIY  900
LVLIDQNGRI IKQQTLNQIT SSYQEKANNQ TVEVITDYHD LLNDKEKLRK KNLQEWQSVE  960
NIKELKAGYL SNVVNEIGKI IVEYQPVIML ENLNTGFKNS RIKIEKQVYQ KFEKALIDKF  1020
NYFMRKDLDS SAIGGLYHAL QLTKEYSKQY NGKQNGIIYY IPASYTSNID PTTGFISAFI  1080
QTRYENVEKT KSLIEKFNDI TYDAEESLFC FSADYKKFSP EAKLWQQTIW QIYTNGDRIY  1140
TFKNKEEWQS KNYILVEEFK DLFAKYHIDY CRDLKAQILS QTDASFFKQF LFLLRLTLQM  1200
RNSRTTELNG TDADTKKREN DYIISPVKNQ YGKFYDSRKD YVDWPENADA NGAYNIARKG  1260
LIMLKHLKEG LPEKRICDIS TEEWVQFVEE LNKSRKRTAD GSEFESPKKK RKVGSGKPIP  1320
NPLLGLDST                                                    1329

SEQ ID NO: 4           moltype = DNA  length = 3879
FEATURE                Location/Qualifiers
source                 1..3879
                       mol_type = unassigned DNA
                       organism = unidentified
SEQUENCE: 4
atggtgtccg aaaaagaaaa tacaccaact tttaatagtc taaccaatct ctatagtgtt  60
tcaaagactc ttagatttga acttaggcca caatattcaa ctctagatca cattaaagat  120
gaccaaattg ttgacaaagg tgaagaacta aaaaaccact acaaaacttt caagaaaatt  180
cttgatcagg tcttttcaag gatcatcaac gatagcctag ataaaaccta tcttgatcaa  240
aaatatattt ccacctacca agatcttgta ttcaagcatc gagaccgact aacagacaaa  300
gaccgtgcag aactaaaggc cttaaaagaa acactcaaaa agcagatcga caaaagcctc  360
gatcataaag ataaaaaagc tatcttcagt gatcccgtaa attttctcat cgacaatgaa  420
tcggattttg ctgacttaat tggtgataat cgtcctagta ttgaagcttt caaccgtcaa  480
aaaggttatc tttccggata tctccaaaat cgcgcaaata tcttcgatca caccacaaat  540
gaaacttcag tcgcgtttcg tattgtcgag gaaaacctcg ctatcttttt aaataatcgc  600
ctcacattac agcatttttt cgagaaagtt gcagataaag atgggctatt aaaattttta  660
caagagacac tttctcagtt aggttttaag ttgaaactcg aagaccttct ttcccttgat  720
tattttaatc gtaccctatc tcaacccggc atcgatcagt ataacctcct aatctctggc  780
aaggcgctag aagatggaaa gaaaatgcag ggaattaatg aggtcctcaa tcaatatctc  840
caacaacatc aagaagagaa gctacataaa atcaaactca agcaactcta taagcagatc  900
ctctcagagt caaaaaactga atcatttacc cttgattttg tggaagataa taaagggctt  960
gctgccatgc tcctacagtt tatcgatttt gtaaacaagc tgattgaaga gaaaatgctt  1020
ctccttgata tgattcaggg gctaaaagat agctcagttt catcagaatt tctttcacga  1080
ctctatcttg aacgcaaaaa catcaagcgt ctttcgaatt ttatctataa agattatggc  1140
tatattgagc aatccttgga agagaacttt ctctcgacaa ttgaaggcaa gattaccaag  1200
aaggcactcg aggaacatcg caaacaggat gctttcacaa tccatgaaat cttagttgcc  1260
ctacaaaagc aacaatatga aaggatgga gctctagagt ccgcagatca tcttttactt  1320
cctggtgttg ttgacttcct ctaccagaat ttggattgca aacactccac tctacttgaa  1380
aaagtcgggt cagaaaaaca gccactactc gacctcttca acgaaaaaca attattggaa  1440
ggtcaagacg cagaatctca tgcttccaaa tattctgatc gtccattcaa cgaccacgaa  1500
ataaaggttg ttaaaactgc tttggatttt tataaaaatc tacagagtaa ttttgcgatc  1560
tttcaaatcc cggatgaaaa ccttaaacta gattccgaat tttattccga gtttgatgaa  1620
ttttatcaag gtctcaagaa tattattcca gtctataaca agtccagaaa tttcctcact  1680
aaaaaaccat tctcaaccga aaagaccaag ctcattttta acaacccgca actacttgac  1740
ggatggagta aatcaaaaga gtcagattgt ttaggcacga tttttattaa agacggcaaa  1800
tattatgttg gcattattaa tagtgctacg aatgctaaaa atactttatt tgagcctaac  1860
aattttgcaa acttcgacca aaaacaatat tttgaaaaga tgaacctttt cttcctttcg  1920
gacttgaagc gagattttcc taagaaatat ttttctgaaa agtggcataa tcaacaccca  1980
gttccagccg atcttcgtga aaagtatgat tattatcgaa tcgacgaaca taaggatgag  2040
cgcaaaaatg atctaaaata tcatcatcaa cttatcgcct attatcaaga ctgtcttaaa  2100
aaagacacgg aatggcagat ttatcaattc aaatataagg cccctgaaga atattcagat  2160
gtcaatgaat tcttatccga gcttactcca aatacctaca aaatggagtt caataaaatc  2220
ccagctgaat atatcaaaaa gcttgttgat gatggaaaat tatatttctt ccaaatttat  2280
tccaaagatt tttctgagtt tgcaaaaggt aaaccaaatc tccatactct ctatctaaaa  2340
gcggtctttg atcagaaaaa tgcggaagag ttcaactata attataaaat ttctggtagt  2400
gccgaaatct tctatcgtcc agccagcatt gaaactcgtg tcactcatcc aaaaaatcaa  2460
ccaatcaaga ataagaataa aaataatcca aaggctgaat ctgtcttcca gtatgatctt  2520
tgtaaagatc gtcgctatat gtcagataaa ttctttttgc atcttccgat cgaattaaat  2580
cgtattccgt tactcgctaa cgactcctcg gtaaatagta tggtcaatca agtcgttagt  2640
tctcgtaatc agaattattt ccttggtatt gaccgtggcg agaggcatct aatttatcta  2700
gtcctgatcg atcaaaacgg tagaatcatt aaacagcaaa ccttaaatca gatcactagt  2760
tcataccaag aaaaagccaa taaccaaacg gttgaagtta ttacggatta tcatgatctc  2820
ttgaatgaca aagaaaaact gcgaaagaag aatctccaag agtggcaatc cgtcgaaaat  2880
atcaaggagt taaaggctgg gtacctaagt aatgtggtga atgaaatcgg taagattatc  2940
gttgaatatc agccagttat tatgctggaa aatcttaata ctggatttaa aaactcacga  3000
attaaaattg agaaacaggt gtaccagaaa tttgagaagg cgctcattga taagtttaac  3060
tactttatga gaaaagatct cgactcttca gctattggtg gtctctatca cgctttgcag  3120
ttgactaagg aatactctaa gcagtacaac ggcaagcaga atggtatcat ctactatatt  3180
cctgcaagct acactagtaa tattgatcca actactggtt tcatctcggc ctttatacag  3240
actagatacg aaaacgtcga gaaaacaaaa tccttaatcg aaaagtttaa tgatatcact  3300
tatgatgcag aagaatctct cttctgcttc tccgcagatt acaagaaatt tagtccagag  3360
gccaagcttt ggcagcagac gatttggcag atttatacta atggcgatcg tatttataca  3420
tttaagaaca aagaagagtg gcagagcaaa aactacatcc tcgttgagga gttcaaagat  3480
ctctttgcta aatatcacat cgattattgc agggacctta aggcgcagat tctgtcacaa  3540
actgacgcga gcttcttcaa gcagttcctc ttcttgttgc gactaacctt gcagatgcga  3600
aatagtcgca ctaccgaatt aaatggaact gatgctgata ctaaaaaacg tgagaatgat  3660
tatattattt ctccagttaa gaatcagtat ggcaagttct atgattcccg caaggattat  3720
```

```
gtggactggc cagaaaatgc agatgcaaat ggcgcataca atattgccag aaaaggtctc  3780
atcatgctaa aacacctaaa agaaggtctt cccgaaaaac gtatctgtga tatatcgact  3840
gaagaatggg tacagtttgt cgaagaacta aataaatag                         3879

SEQ ID NO: 5           moltype = DNA  length = 3873
FEATURE                Location/Qualifiers
source                 1..3873
                       mol_type = other DNA
                       organism = synthetic construct
SEQUENCE: 5
gtgtctgaaa aggaaaacac ccctaccttc aactctctga ccaacctgta cagcgtttct  60
aaaaccctgc ggttcgagct gcggcctcag tacagcaccc tggaccacat caaggacgat  120
cagatcgtgg acaagggaga ggagctaaag aaccactaca agacattcaa aaaaatcctg  180
gaccaggtgt tctctcggat catcaacgac tctctggata aacttacct ggatcagaag  240
tacatctcca cctaccagga tctggtgttc aagcacagag atagactgac agataaggac  300
agagccgaac tgaaggccct gaaggagaca ctgaagaagc agatcgacaa aagcctggat  360
cacaaagaca agaaggctat cttctccgac cctgtgaact tcctgatcga caatgagagc  420
gacttcgccg acctgattgg agacaaccgg cccagcatcg aggcctttaa ccgccagaag  480
ggatatctgt ccggctacct gcagaataga gccaacatct tcgatcatac aaccaacgaa  540
accagcgttg ctttcagaat cgtggaagag aacctcgcca tcttcctcaa caaccgcctg  600
accctgcagc atttcttcga gaaagtggcc gacaaagacg gactgctgaa gttcctgcag  660
gagacactga gccagctggg cttcaagctg aagctggagg atctgctgag cctggattac  720
tttaaccgga cactgagcca gcctggcatc gaccaataca acctgctgat cagcggaaag  780
gccctggaag atggcaagaa gatgcagggc atcaatgaag tgctgaacca gtacctgcag  840
cagcaccagg aggaaaagct gcacaaaatc aagctgaagc agctgtataa gcaaatcctg  900
agcgaaagca agacagagag cttcacgctg gacttcgtgg aggacaacaa gggcctggcc  960
gccatgctgc tgcagtttat cgatttcgtg aacaagttaa tagaagagaa gatgctgctg  1020
ctggatatga tccagggact gaaagacagc agtgtgtcca gcgagttctt gagccggctt  1080
tacctggaaa gaaagaacat caagcggctg agcaacttca tctacaagga ctatggctat  1140
atcgagcagt ccctggaaga aaacttcctg agcaccatcg agggcaagat cactaagaag  1200
gccctggaag agcatagaaa acaggacgcc tttaccattc acgagatcct ggtcgcactg  1260
cagaaacaac agtacgaaaa ggacggcgcc ctagagagcg ccgaccacct gctgcttcca  1320
ggcgtggtgg atttcctcta ccaaaacctg gactgtaagc acagcacgct gctggaaaag  1380
gtgggcagcg agaagcagcc cctgctggat cttttcaacg aaaagcagct gcttgagggc  1440
caggacgccg agtcccacgc ctctaagtac agcgatcggc ctttcaacga ccacgagatc  1500
aaggtggtga aaaccgccct ggacttctac aagaacctgc aatctaactt tgctatcttc  1560
cagatccccg acgaaaacct gaagctggat agcgagtttt acagcgagtt tgatgagttc  1620
taccagggcc tgaaaaatat tattcctgtg tacaacaaaa gccggaactt cctgacaaaa  1680
aagccgttca gcaccgaaaa gaccaaactg atcttcaaca acccccagct gctcgatggc  1740
tggagcaaga gcaaggaaag cgactgtctg gggaccatct tcatcaaaga cggcaagtac  1800
tatgtgggaa tcatcaacag cgccaccaac gctaagaata cactgttcga gcctaacaac  1860
ttcgccaatt tcgaccaaaa acaatacttc gagaagatga acctgttctt cctgagcgat  1920
ctgaagcgag acttccccaa gaagtatttc tccgagaagt ggcacaacca gcaccccgtg  1980
cccgctgacc ttagagaaaa gtacgactac taccggatcg acgagcataa ggatgagaga  2040
aagaatgacc tgaaatacca ccaccagtta atcgcctact accaagactg cctgaaaaag  2100
gatacagagt ggcagatcta ccagttcaag tacaaggccc ctgaggagta cagcgacgtg  2160
aacgagttcc tgagtgaact gacccctaat acctacaaga tggagttcaa caagattcct  2220
gccgagtaca ttaagaagct ggtggatgac ggcaagctgt actttttttca gatatactcc  2280
aaagacttta gcgaatttgc caagggcaag ccaaacctgc acaccctcta cctgaaggcc  2340
gtgttcgacc agaagaacgc cgaggagttc aactacaact ataaaatatc tggatctgct  2400
gaaatctttt acagacctgc ttctatcgag acaagagtga cccaccctaa gaatcagcct  2460
atcaagaaca agaacaagaa caatcctaag gctgaaagcg tgttccagta cgacctgtgc  2520
aaggaccggc ggtacatgtc cgacaagttc ttcctgcacc ttcccatcga acttaacaga  2580
atccctctgc tggctaacga ttcctccgtg aatagcatgg tcaaccaggt ggtgagcagc  2640
agaaaccaga actacttcct gggcatcgat agaggcgaga gacacctgat ctacctggtg  2700
ctgatcgacc agaacggtag aatcatcaag caacagaccc tgaatcagat tacaagcagc  2760
taccaagaaa aggccaacaa ccagacagtg gaggtgatca cagactacca cgacctgctg  2820
aacgacaagg aaaagctcag aaagaagaat cttcaggagt ggcagtccgt ggagaatatc  2880
aaagagctga aggccggcta cctgagcaac gtggtcaacg agatcggcaa gatcatcgtg  2940
gagtaccagc ctgtgatcat gctggaaaac ctcaacaccg gatttaaaaa ctcaagaatc  3000
aagattgaga agcaggtgta ccagaagttc gagaaggcct taatcgataa gttcaattac  3060
ttcatgcgga aggatctgga ctctagcgcc atcggcggcc tgtaccacgc cctgcagctg  3120
accaaagagt atagcaagca gtacaacggc aagcagaacg gcatcatcta ctacatccca  3180
gcttcttaca cctctaatat cgaccccacc accggcttta ttagcgcctt catccagacc  3240
agatacgaga acgtggaaaa gaccaagtct ctgatcgaga aatttaatga catcacctac  3300
gacgccgaag agtcgctgtt ctgcttcagc gccgattaca agaaattttc acctgaagct  3360
aagctgtggc agcaaaccat ctggcagatc tataccaacg gcgacagaat ctacaccttc  3420
aagaacaagg aagagtggca aagcaagaac tacattctgg tggaggagtt taaggacctg  3480
ttcgccaaat accacatcga ctattgcagg gacctgaaag cccagatcct gagccagacc  3540
gacgcatctt ttttcaagca gtttctcttc ctgctgagac tgacactgca aatgagaaat  3600
agtcgtacca cagagctgaa cggcaccgac gccgacacca agaaaagaga gaatgactac  3660
atcatctctc cagtgaaaaa tcagtacggc aaattctatg attcccgcaa ggactacgtg  3720
gactggcctg agaacgccga cgccaatggc gcctacaaca tcgccagaaa gggcctgatc  3780
atgctgaagc acctgaagga aggactgcct gagaagagga tctgcgacat cagcacagaa  3840
gaatgggttc agtttgtgga agaactgaac aag                              3873

SEQ ID NO: 6           moltype = DNA  length = 3990
FEATURE                Location/Qualifiers
source                 1..3990
```

```
                         mol_type = other DNA
                         organism = synthetic construct
SEQUENCE: 6
atgggcgtgt ctgaaaagga aaacacccct accttcaact ctctgaccaa cctgtacagc  60
gtttctaaaa ccctgcggtt cgagctgcgg cctcagtaca gcaccctgga ccacatcaag  120
gacgatcaga tcgtggacaa gggagaggag ctaaagaacc actacaagac attcaaaaaa  180
atcctggacc aggtgttctc tcggatcatc aacgactctc tggataaaac ttacctggat  240
cagaagtaca tctccaccta ccaggatctg gtgttcaagc acagagatag actgacagat  300
aaggacagag ccgaactgaa ggccctgaag gagacactga agaagcagat cgacaaaagc  360
ctggatcaca aagacaagaa ggctatcttc tccgaccctg tgaacttcct gatcgacaat  420
gagagcgact tcgccgacct gattggagac aaccggccca gcatcgaggc ctttaaccgc  480
cagaagggat atctgtccgg ctacctgcag aatagagcca acatcttcga tcatacaacc  540
aacgaaacca gcgttgcttt cagaatcgtg gaagagaacc tcgccatctt cctcaacaac  600
cgcctgaccc tgcagcattt cttcgagaaa gtggccgaca aagacggact gctgaagttc  660
ctgcaggaga cactgagcca gctgggcttc aagctgaagc tggaggatct gctgagcctg  720
gattacttta accggacact gagccagcct ggcatcgacc aatacaacct gctgatcagc  780
ggaaaggccc tggaagatgg caagaagatg cagggcatca atgaagtgct gaaccagtac  840
ctgcagcagc accaggagga aaagctgcac aaaatcaagc tgaagcagct gtataagcaa  900
atcctgagcg aaagcaagac agagagcttc acgctggact tcgtggagga caacaagggc  960
ctggccgcca tgctgctgca gtttatcgat ttcgtgaaca agttaataga agagaagatg  1020
ctgctgctgg atatgatcca gggactgaaa gacagcagtg tgtccagcga gttcttgagc  1080
cggctttacc tggaaagaaa gaacatcaag cggctgagca acttcatcta caaggactat  1140
ggctatatcg agcagtccct ggaagaaaac ttcctgagca ccatcgaggg caagatcact  1200
aagaaggccc tggaagagca tagaaaacag gacgccttta ccattcacga gatcctggtc  1260
gcactgcaga aacaacagta cgaaaaggac ggcgccctag agagcgccga ccacctgctg  1320
cttccaggcg tggtggattt cctctaccaa aacctggact gtaagcacag cacgctgctg  1380
gaaaaggtgg gcagcgagaa gcagcccctg ctggatcttt tcaacgaaaa gcagctgctt  1440
gagggccagg acgccgagtc ccacgcctct aagtacagcg atcggccttt caacgaccac  1500
gagatcaagg tggtgaaaac cgccctggac ttctacaaga acctgcaatc taactttgct  1560
atcttccaga tccccgacga aaacctgaag ctggatagcg agttttacag cgagtttgat  1620
gagttctacc agggcctgaa aaatattatt cctgtgtaca acaaaagccg gaacttcctg  1680
acaaaaaagc cgttcagcac cgaaaagacc aaactgatct tcaacaaccc ccagctgctc  1740
gatggctgga gcaagagcaa ggaaagcgac tgtctgggga ccatcttcat caaagacggc  1800
aagtactatg tgggaatcat caacagcgcc accaacgcta agaatacact gttcgagcct  1860
aacaacttcg ccaatttcga ccaaaaacaa tacttcgaga agatgaacct gttcttcctg  1920
agcgatctga agcgagactt ccccaagaag tatttctccg agaagtggca caaccagcac  1980
cccgtgcccg ctgaccttag agaaaagtac gactactacc ggatcgacga gcataaggat  2040
gagagaaaga atgacctgaa ataccaccac cagttaatcg cctactacca agactgcctg  2100
aaaaaggata cagagtggca gatctaccag ttcaagtaca aggcccctga ggagtacagc  2160
gacgtgaacg agttcctgag tgaactgacc cctaatacct acaagatgga gttcaacaag  2220
attcctgccg agtacattaa gaagctggtg gatgacggca agctgtactt ttttcagata  2280
tactccaaag actttagcga atttgccaag ggcaagccaa acctgcacac cctctacctg  2340
aaggccgtgt tcgaccagaa gaacgccgag gagttcaact acaactataa aatatctgga  2400
tctgctgaaa tcttttacag acctgcttct atcgagacaa gagtgaccca ccctaagaat  2460
cagcctatca agaacaagaa caagaacaat cctaaggctg aaagcgtgtt ccagtacgac  2520
ctgtgcaagg accggcggta catgtccgac aagttcttcc tgcaccttcc catcgaactt  2580
aacagaatcc ctctgctggc taacgattcc tccgtgaata gcatggtcaa ccaggtggtg  2640
agcagcagaa accagaacta cttcctgggc atcgatagag gcgagagaca cctgatctac  2700
ctggtgctga tcgaccagaa cggtagaatc atcaagcaac agaccctgaa tcagattaca  2760
agcagctacc aagaaaaggc caacaaccag acagtggagg tgatcacaga ctaccacgac  2820
ctgctgaacg acaaggaaaa gctcagaaag aagaatcttc aggagtggca gtccgtggag  2880
aatatcaaag agctgaaggc cggctacctg agcaacgtgg tcaacgagat cggcaagatc  2940
atcgtggagt accagcctgt gatcatgctg gaaaacctca acaccggatt taaaaactca  3000
agaatcaaga ttgagaagca ggtgtaccag aagttcgaga aggccttaat cgataagttc  3060
aattacttca tgcggaagga tctggactct agcgccatcg gcggcctgta ccacgccctg  3120
cagctgacca aagagtatag caagcagtac aacggcaagc agaacggcat catctactac  3180
atcccagctt cttacacctc taatatcgac cccaccaccg gctttattag cgccttcatc  3240
cagaccagat acgagaacgt ggaaaagacc aagtctctga tcgagaaatt taatgacatc  3300
acctacgacg ccgaagagtc gctgttctgc ttcagcgccg attacaagaa attttcacct  3360
gaagctaagc tgtggcagca aaccatctgg cagatctata ccaacggcga cagaatctac  3420
accttcaaga acaaggaaga gtggcaaagc aagaactaca ttctggtgga ggagtttaag  3480
gacctgttcg ccaaatacca catcgactat tgcagggacc tgaaagccca gatcctgagc  3540
cagaccgacg catctttttt caagcagttt ctcttcctgc tgagactgac actgcaaatg  3600
agaaatagtc gtaccacaga gctgaacggc accgacgccg acaccaagaa aagagagaat  3660
gactacatca tctctccagt gaaaaatcag tacggcaaat tctatgattc ccgcaaggac  3720
tacgtggact ggcctgagaa cgccgacgcc aatggcgcct acaacatcgc cagaaagggc  3780
ctgatcatgc tgaagcacct gaaggaagga ctgcctgaga agaggatctg cgacatcagc  3840
acagaagaat gggttcagtt tgtggaagaa ctgaacaagt ctagaaagcg gacagcagac  3900
ggctccgaat ttgaaagccc taagaaaaag agaaaggtgg gatccggcaa acctatcccc  3960
aatcccctgc tgggcctgga cagcacctga                                  3990

SEQ ID NO: 7             moltype = AA  length = 1293
FEATURE                  Location/Qualifiers
source                   1..1293
                         mol_type = protein
                         organism = unidentified
SEQUENCE: 7
KSIYENFIGL ESKNLTLRFA LNPEAKTQEN LKLYWDKLRD EERDRAYPIV KKILDKEYQQ  60
LISEGLKLLE NQNVLDWTEL AEYIRTSDLS KKKKEDKRLR KLIAQNLKAH PLVDKLKVKN  120
```

```
AFGKNGYLET LPLGKEEKEA VKVFAGFGGF FNNYNKNREN YFSTEEKSTA IANRIVNENF  180
SKHFSNVEIV TKIQKEVPEL IQIVEAQFKG YDTIFTVNGY NTALSQAGID TYNEMVAIWN  240
KEANLYAQKA GKLPDGHPLK KKRNYLLSAL FKQIGSEKEH LIQIDRFDGD EEVIEALTGV  300
KKMLQEADVF EKLNMLVEDM ENWDYSKIYL SAQSLSNVSV FLNNLYEDER ENSWNYLDNV  360
LREKWQIELQ GKKKGTDLEE AIRKKKQSFY SIEELQEAVN AIEETDKCYN VSKWLLGAMK  420
SERVIEEKKK DVEDFCTQWK NERNSLKETD ITALKEYLEQ WIFLARYCKS FYANGIEKKE  480
KDEAFYHILE DVLYVLDEVI YFYNKVRNYV TKKPYSLEKM HLKFGHNELA NGWSVNKEEN  540
YGTAILRRNG KYYLAITNSL NKKMSIPTQL ESTGNNYEKM VLNVFPNVFR MIPKCTTGRN  600
DVKSCFERKE PNEYFFIDTP EFVNPFKVTR EEYELNKITY DGVKKWQSDY SKNTQDEKGY  660
KEAVTKWIQF CMRFLQSYKS TAIYDYSTLQ QPEKYETVDS FYHDVEKILY ECHFEYVPAN  720
KIEQLEEEGR IFLFQIYNKD FSENRRPDSK KNLHTLYWEA LFSEENRKAK VIQLNGKAEI  780
FRREKSIEHP IVHKAGEVLV NKRTKDGEPI PDDIYKDLSN YFNGRNVTSE KEEYKECLDK  840
VYTSTKKYDI TKDKRFTETK YEFHVPITLN YQADGVKYLN QKILHVLRDN PDVNIIGLDR  900
GERNLISYVV LNREGKIVNN QQGSFNIVGK MDYQKKLYQK EKNRDKERKT WKNIETIKDL  960
KEGYISQVVH ELTDMAIRNN AIIVMEDLNF GFKRGRTKVE RQVYQKFELA LLKKLHYLVT  1020
DKTEGEAMLK PGGVLQGYQL AREVKTLKEI GKQCGCVFYV PPGYTSKIDP TTGFVDVFNM  1080
SGVTNREKKK AFFEKFDNMF YDEKRDMFGF SFNYEKFTTY QSSYRNDWTV YSNGSKYVWN  1140
SLKRTDELID VTKELKLLFE KYAIDYRNEA LFEQIMSQDT DKNNADFWNK LFWYFRVLLR  1200
LRNSSDELDQ IVSPVLNQNG EFFETPKKIT EKSYLSDYPM DADTNGAYHI ALKGLYLIQE  1260
KIADESVDLD NKLPKDFYKI SNAEWFMFRQ KEK                               1293

SEQ ID NO: 8           moltype = AA  length = 1294
FEATURE                Location/Qualifiers
source                 1..1294
                       mol_type = protein
                       organism = unidentified
SEQUENCE: 8
MKSIYENFIG LESKNLTLRF ALNPEAKTQE NLKLYWDKLR DEERDRAYPI VKKILDKEYQ  60
QLISEGLKLL ENQNVLDWTE LAEYIRTSDL SKKKKEDKRL RKLIAQNLKA HPLVDKLKVK  120
NAFGKNGYLE TLPLGKEEKE AVKVFAGFGG FFNNYNKNRE NYFSTEEKST AIANRIVNEN  180
FSKHFSNVEI VTKIQKEVPE LIQIVEAQFK GYDTIFTVNG YNTALSQAGI DTYNEMVAIW  240
NKEANLYAQK AGKLPDGHPL KKKRNYLLSA LFKQIGSEKE HLIQIDRFDG DEEVIEALTG  300
VKKMLQEADV FEKLNMLVED MENWDYSKIY LSAQSLSNVS VFLNNLYEDE RENSWNYLDN  360
VLREKWQIEL QGKKKGTDLE EAIRKKKQSF YSIEELQEAV NAIEETDKCY NVSKWLLGAM  420
KSERVIEEKK KDVEDFCTQW KNERNSLKET DITALKEYLE QWIFLARYCK SFYANGIEKK  480
EKDEAFYHIL EDVLYVLDEV IYFYNKVRNY VTKKPYSLEK MHLKFGHNEL ANGWSVNKEE  540
NYGTAILRRN GKYYLAITNS LNKKMSIPTQ LESTGNNYEK MVLNVFPNVF RMIPKCTTGR  600
NDVKSCFERK EPNEYFFIDT PEFVNPFKVT REEYELNKIT YDGVKKWQSD YSKNTQDEKG  660
YKEAVTKWIQ FCMRFLQSYK STAIYDYSTL QQPEKYETVD SFYHDVEKIL YECHFEYVPA  720
NKIEQLEEEG RIFLFQIYNK DFSENRRPDS KKNLHTLYWE ALFSEENRKA KVIQLNGKAE  780
IFRREKSIEH PIVHKAGEVL VNKRTKDGEP IPDDIYKDLS NYFNGRNVTS EKEEYKECLD  840
KVYTSTKKYD ITKDKRFTET KYEFHVPITL NYQADGVKYL NQKILHVLRD NPDVNIIGLD  900
RGERNLISYV VLNREGKIVN NQQGSFNIVG KMDYQKKLYQ KEKNRDKERK TWKNIETIKD  960
LKEGYISQVV HELTDMAIRN NAIIVMEDLN FGFKRGRTKV ERQVYQKFEL ALLKKLHYLV  1020
TDKTEGEAML KPGGVLQGYQ LAREVKTLKE IGKQCGCVFY VPPGYTSKID PTTGFVDVFN  1080
MSGVTNREKK KAFFEKFDNM FYDEKRDMFG FSFNYEKFTT YQSSYRNDWT VYSNGSKYVW  1140
NSLKRTDELI DVTKELKLLF EKYAIDYRNE ALFEQIMSQD TDKNNADFWN KLFWYFRVLL  1200
RLRNSSDELD QIVSPVLNQN GEFFETPKKI TEKSYLSDYP MDADTNGAYH IALKGLYLIQ  1260
EKIADESVDL DNKLPKDFYK ISNAEWFMFR QKEK                              1294

SEQ ID NO: 9           moltype = AA  length = 1331
FEATURE                Location/Qualifiers
source                 1..1331
                       mol_type = protein
                       organism = synthetic construct
SEQUENCE: 9
MGKSIYENFI GLESKNLTLR FALNPEAKTQ ENLKLYWDKL RDEERDRAYP IVKKILDKEY  60
QQLISEGLKL LENQNVLDWT ELAEYIRTSD LSKKKKEDKR LRKLIAQNLK AHPLVDKLKV  120
KNAFGKNGYL ETLPLGKEEK EAVKVFAGFG GFFNNYNKNR ENYFSTEEKS TAIANRIVNE  180
NFSKHFSNVE IVTKIQKEVP ELIQIVEAQF KGYDTIFTVN GYNTALSQAG IDTYNEMVAI  240
WNKEANLYAQ KAGKLPDGHP LKKKRNYLLS ALFKQIGSEK EHLIQIDRFD GDEEVIEALT  300
GVKKMLQEAD VFEKLNMLVE DMENWDYSKI YLSAQSLSNV SVFLNNLYED ERENSWNYLD  360
NVLREKWQIE LQGKKKGTDL EEAIRKKKQS FYSIEELQEA VNAIEETDKC YNVSKWLLGA  420
MKSERVIEEK KKDVEDFCTQ WKNERNSLKE TDITALKEYL EQWIFLARYC KSFYANGIEK  480
KEKDEAFYHI LEDVLYVLDE VIYFYNKVRN YVTKKPYSLE KMHLKFGHNE LANGWSVNKE  540
ENYGTAILRR NGKYYLAITN SLNKKMSIPT QLESTGNNYE KMVLNVFPNV FRMIPKCTTG  600
RNDVKSCFER KEPNEYFFID TPEFVNPFKV TREEYELNKI TYDGVKKWQS DYSKNTQDEK  660
GYKEAVTKWI QFCMRFLQSY KSTAIYDYST LQQPEKYETV DSFYHDVEKI LYECHFEYVP  720
ANKIEQLEEE GRIFLFQIYN KDFSENRRPD SKKNLHTLYW EALFSEENRK AKVIQLNGKA  780
EIFRREKSIE HPIVHKAGEV LVNKRTKDGE PIPDDIYKDL SNYFNGRNVT SEKEEYKECL  840
DKVYTSTKKY DITKDKRFTE TKYEFHVPIT LNYQADGVKY LNQKILHVLR DNPDVNIIGL  900
DRGERNLISY VVLNREGKIV NNQQGSFNIV GKMDYQKKLY QKEKNRDKER KTWKNIETIK  960
DLKEGYISQV VHELTDMAIR NNAIIVMEDL NFGFKRGRTK VERQVYQKFE LALLKKLHYL  1020
VTDKTEGEAM LKPGGVLQGY QLAREVKTLK EIGKQCGCVF YVPPGYTSKI DPTTGFVDVF  1080
NMSGVTNREK KKAFFEKFDN MFYDEKRDMF GFSFNYEKFT TYQSSYRNDW TVYSNGSKYV  1140
WNSLKRTDEL IDVTKELKLL FEKYAIDYRN EALFEQIMSQ DTDKNNADFW NKLFWYFRVL  1200
LRLRNSSDEL DQIVSPVLNQ NGEFFETPKK ITEKSYLSDY PMDADTNGAY HIALKGLYLI  1260
QEKIADESVD LDNKLPKDFY KISNAEWFMF RQKEKSRKRT ADGSEFESPK KKRKVGSGKP  1320
IPNPLLGLDS T                                                       1331
```

```
SEQ ID NO: 10          moltype = DNA  length = 3885
FEATURE                Location/Qualifiers
source                 1..3885
                       mol_type = unassigned DNA
                       organism = unidentified
SEQUENCE: 10
atgaaaagta tttatgaaaa ttttattgga ttggagtcaa aaaatttgac gctgcgcttt  60
gcgttgaatc cagaagctaa gacacaagaa aatttgaagt tgtactggga caaattgcgt  120
gatgaggaga gagatagggc gtatccaatt gtaaaaaaga tattggataa ggaatatcag  180
cagctgattt cggaaggact gaaattatta gagaatcaga atgtgttgga ttggacagaa  240
ttagcagagt atatacggac aagtgattta agtaagaaga aaaaagaaga taaacgctta  300
agaaaattaa tagcacaaaa tttaaaagcg catccgttag ttgacaaact gaaagtaaaa  360
aatgcatttg gtaaaaatgg ctatcttgaa actttaccgt tgggaaaaga agagaaagag  420
gcagtaaaag tttttgccgg ttttggcggc tttttcaata actacaataa aaacagggaa  480
aattattttt caaccgagga aaaaagcact gcaatcgcaa accgaattgt aaatgaaaat  540
ttttcaaaac atttttcaaa tgtagaaata gttaccaaaa ttcaaaagga agtgccagaa  600
ttaattcaaa tcgtggaagc acaattcaag ggatatgata ctatctttac agtaaatggt  660
tataatacgg cattgtcaca ggcagggatt gatacatata atgagatggt tgcaatctgg  720
aataaagaag caaatttgta tgcgcaaaag gcaggaaaac ttccagatgg acatccgtta  780
aagaaaaaga gaaattactt attgtcggca ttgtttaaac agattgggag tgaaaaggag  840
catttgattc aaattgatag atttgatgga gatgaagagg tgattgaggc attgacgggt  900
gtgaaaaaaa tgcttcaaga ggcagatgta tttgaaaaat tgaatatgct tgtggaggat  960
atggagaatt gggattatag taaaatatat ttgtcagcac agagtttatc caatgtttct  1020
gtgttcctaa ataatttata tgaggatgaa cgggagaact catggaatta tcttgataat  1080
gtcctaagag aaaaatggca aatagaatta cagggaaaga aaaaggggac agatctggaa  1140
gaagcgattc ggaagaaaaa acaaagtttc tattcaatag aagaacttca agaggcagtg  1200
aatgccatag aagaaacaga taaatgttat aatgtatcta aatggcttct aggagcaatg  1260
aaaagcgaaa gggtaataga agaaaaaaag aaggatgtgg aagatttttg cacacagtgg  1320
aaaaatgaaa gaaactcgct gaaagagaca gatataactg cactgaaaga atatctggag  1380
caatggattt ttttggcaag atattgcaaa tctttttatg caaatggaat tgaaaaaaaa  1440
gaaaaagatg aagcatttta tcatatttta gaagatgtgt tgtatgtttt ggatgaagta  1500
atatattttt ataataaagt tcgaaattat gtaacgaaga agccatattc tcttgaaaaa  1560
atgcatttaa aatttggtca taatgaactg gcaaatggat ggtctgttaa caaagaagag  1620
aactatggta cggcaatatt gaggcgaaat ggcaaatact atttggcaat tacaaattca  1680
ttgaataaaa agatgagtat tcccactcaa ttagaaagta caggaaataa ttatgaaaag  1740
atggtattga atgtattccc aaatgtattt cggatgatac caaaatgtac tacaggaaga  1800
aatgatgtga aagttgtttt tgaaagaaaa gagccaaatg agtatttctt tattgataca  1860
ccggaatttg ttaacccatt taaagttacg cgcgaggaat atgagttaaa taagataact  1920
tatgatggtg ttaaaaagtg gcaatctgat tattcaaaaa atacgcagga tgaaaaagga  1980
tacaaagagg cagtgacaaa atggattcag ttttgtatgc gctttttaca atcttataag  2040
agtacagcaa tatatgatta ttcaacttta cagcaaccgg agaaatatga gacggtggat  2100
tctttttatc atgacgttga aaaaatatta tatgaatgtc attttgagta cgttccggct  2160
aataaaatag agcagttgga agaagaagga agaatttttc tgtttcagat ttacaacaaa  2220
gatttttcgg aaaacagacg cccggacagc aaaaagaatt tgcatacact ttattgggag  2280
gcattgtttt cagaagaaaa tcggaaagca aaagtgatac aattaaatgg caaagctgaa  2340
atatttcgga gagaaaaaag cattgaacat ccgattgttc ataaagctgg ggaagtgtta  2400
gtgaataaac gaacgaaaga cggggaacca ataccagatg atatttataa agatttgagc  2460
aactatttta acggaagaaa tgtaacatct gaaaaggaag agtataagga atgtctggat  2520
aaagtgtata cttcgaccaa aaaatatgat attacaaagg ataaacgttt tactgaaacc  2580
aaatatgaat ttcatgttcc gattaccttg aactatcagg cggacggtgt taaatatttg  2640
aatcagaaaa tacttcatgt gctgagggat aatccagatg tgaatattat aggtctagat  2700
agaggcgagc gtaatctgat ttcctacgta gtattgaacc gagaaggcaa gattgttaac  2760
aatcagcagg ggagtttcaa tattgtgggt aagatggact atcagaagaa actgtatcaa  2820
aaagaaaaga atcgtgacaa agaacgaaaa acttggaaaa atatcgaaac aataaaggat  2880
ttgaaggaag gatatatttc acaagtcgtt catgaattga ccgatatggc gattcgcaat  2940
aatgcaatta ttgtgatgga agatctgaat tttggattta aaaggggacg caccaaagtg  3000
gaacggcagg tatatcagaa gtttgagctg gcgcttctga agaaattgca ttatctggtt  3060
acggataaaa cagaaggtga ggctatgctt aagcctggcg gtgtccttca aggttatcag  3120
cttgcaagag aagtaaaaac cctaaaagaa atcggaaagc aatgcggatg tgtattttat  3180
gttccaccgg gatatacttc taaaatcgat ccaacaaccg gatttgttga tgtgtttaac  3240
atgtcaggtg ttacgaatcg tgaaaagaaa aaagcatttt ttgaaaagtt cgataatatg  3300
ttctatgatg aaaagcggga tatgtttgga ttttcattta actatgagaa gtttacaaca  3360
tatcaaagtt cttatagaaa tgattggact gtatattcga atggaagcaa atatgtgtgg  3420
aactctttaa aaaggacaga cgagcttatt gatgttacaa aagaattgaa actgctcttt  3480
gaaaagtatg caattgatta cagaaacgaa gcattgtttg aacaaatcat gtcccaagat  3540
acggataaaa acaatgctga cttttggaat aaattgttct ggtattttcg tgttttgctc  3600
cgtctgagaa acagttcaga tgaattagat cagattgttt caccggtact taatcaaaac  3660
ggagaatttt ttgaaacacc gaaaaaaatc acggagaaaa gttatttgtc tgattatccg  3720
atggatgcgg ataccaatgg tgcgtatcac atcgctttaa aagggttgta tctcatacag  3780
gaaaaaattg cagatgagag cgtagatttg gataacaaat taccaaaaga tttttacaag  3840
atctctaatg cagagtggtt tatgtttagg cagaaggaga agtaa                 3885

SEQ ID NO: 11          moltype = DNA  length = 3879
FEATURE                Location/Qualifiers
source                 1..3879
                       mol_type = other DNA
                       organism = synthetic construct
SEQUENCE: 11
```

```
aagagcatct acgagaactt catcggtctt gagagcaaga acctgacact gagattcgcc  60
ctgaaccctg aggctaaaac ccaggagaac ctgaagctgt actgggacaa actgagggac  120
gaagaaagag atagagccta ccctatcgtg aaaaaaatcc tcgacaagga gtatcagcag  180
ctcatcagcg agggcctgaa actgctggaa aatcaaaacg tgctggactg gaccgaactg  240
gccgagtaca tcagaaccag cgatctgtct aagaagaaga aggaggacaa gagactgcgc  300
aagctgatcg cccagaacct gaaagcccac cccctggtcg acaagctgaa ggtgaagaat  360
gccttcggca agaacggcta cctggaaacc ctgccattag gaaaggaaga aaaagaggcc  420
gtgaaggtgt ttgccggatt cggaggcttt ttcaacaact acaacaagaa tcgggagaac  480
tacttcagta ccgaggagaa gtccaccgcc atcgccaaca gaatcgtgaa cgagaacttc  540
agcaagcact tcagcaacgt ggaaatcgtt acaaagatcc aaaaagaagt gccagagctg  600
attcaaatcg tggaagctca gttcaagggt tacgacacca tctttaccgt gaacggctac  660
aacaccgccc tgagccaggc tggcatcgac acatacaacg aaatggtggc catctggaac  720
aaggaggcaa acctgtacgc tcaaaaagcc ggcaagctgc cagacggcca cccgctgaag  780
aagaagcgta actacctgct gagcgccctc ttcaaacaga tcggcagcga aaaagaacac  840
ctgatccaga tcgacagatt cgacggcgac gaggaagtga tcgaagccct gactggcgtg  900
aaaaagatgc tgcaggaggc cgacgtgttc gagaagctga acatgctggt cgaggacatg  960
gaaaattggg attactccaa gatctacctg tctgcccaga gcctgagtaa cgtgtccgtg  1020
ttcctgaaca acctgtatga agatgaacgg gagaacagct ggaactacct ggataacgtg  1080
ctgagagaga agtggcagat tgaactgcag ggcaaaaaaa agggaacaga tctggaagag  1140
gccattagaa agaagaagca gagcttttac tctatcgagg aacttcagga ggcagtgaac  1200
gccatcgagg aaaccgacaa gtgctacaat gtgtctaaat ggctgctggg agccatgaag  1260
agcgagagag tgatcgagga gaagaagaaa gacgtggagg atttctgcac acagtggaag  1320
aacgagagaa acagcctcaa ggaaaccgac atcaccgccc tgaaggagta cctggagcag  1380
tggatcttcc tggctaggta ctgcaagagc ttctacgcca atggcatcga aaagaaagag  1440
aaggatgagg ctttttacca catcctggag gatgtgctgt acgtgctgga cgaagtgatc  1500
tacttctaca acaaggtgcg gaactacgtg accaaaaagc cttacagtct ggagaagatg  1560
cacctgaagt tcggccacaa cgagctggcc aacggctgga gcgtgaacaa ggaagaaaat  1620
tacggcaccg ccatcctgag aagaaacggc aagtactacc tggccatcac caacagcctg  1680
aacaagaaaa tgagcatccc tacccagctg gagagcacag gaaataatta tgagaagatg  1740
gtcctgaacg tttttcccaa cgtgttccgg atgatcccaa agtgcaccac aggcaggaac  1800
gacgtgaagt catgcttcga gagaaaggaa cccaacgagt acttcttcat cgacacccct  1860
gagttcgtga acccctttaa ggtcacacgg gaggagtacg aactgaataa gatcacctac  1920
gacggagtta agaagtggca gagcgactac agcaagaaca cacaggacga aaagggctat  1980
aaggaagccg tgaccaagtg gattcagttt tgtatgcggt tcctgcagtc ttataagagc  2040
accgccatat atgactacag caccctgcag caacctgaaa aatacgaaac agtggacagc  2100
ttctatcatg atgtggaaaa gatcctgtac gagtgccact tcgagtacgt gcccgctaac  2160
aagatcgagc agcttgaaga agagggaaga atcttcctgt tccagatcta caacaaggat  2220
ttttctgaga acagacggcc tgatagcaag aaaaacctcc acaccctgta ctgggaggcg  2280
ctgttctccg aagagaatag aaaggccaag gtgattcagc tgaatggcaa ggccgagatc  2340
ttcagacggg agaaatcaat cgagcaccct atcgtgcata aggctggcga ggtgctggtg  2400
aacaagcgga ccaaagatgg cgaacctatt cctgacgaca tctacaagga cctgagcaac  2460
tatttcaacg gcagaaacgt tacctctgag aaggaagagt acaaggagtg tctggacaag  2520
gtgtacacca gcaccaaaaa gtacgatatc accaaggaca aaagattcac cgagacaaag  2580
tacgagttcc acgtgcctat caccctgaac taccaggccg acggcgtgaa gtacctgaat  2640
cagaagatcc tgcacgtgct gcgggacaac cctgatgtta acatcatcgg cctggataga  2700
ggcgaaagaa acctgatctc ttatgttgtg ctgaacagag agggcaagat cgtgaacaat  2760
cagcagggtt ctttcaacat cgtgggcaaa atggactacc agaaaaagct gtaccagaag  2820
gagaaaaacc gggataaaga acggaaaacg tggaaaaaca tcgaaaccat caaggacctg  2880
aaggagggct atatcagcca ggtggtacac gagctgaccg atatggccat ccggaataac  2940
gcgatcatcg tgatggaaga tctgaatttc ggattcaagc ggggccggac caaggtggaa  3000
cggcaggtgt accagaagtt tgagctggcc ctgctgaaga agctgcacta cctcgtgacc  3060
gacaagaccg agggagaagc tatgctgaaa cccggcggcg tgctgcaagg ctaccagctg  3120
gctagagaag tcaagaccct gaaagagatc ggcaagcagt gcggctgtgt gttctacgtg  3180
ccccctggct acacaagcaa gatcgaccct acaaccggct tcgtcgacgt gttcaacatg  3240
tctggagtta caaaccgcga gaaaaagaaa gccttttttcg aaaaatttga taacatgttc  3300
tacgacgaga agagagacat gttcggcttc agcttcaatt acgaaaagtt tactacctac  3360
cagagcagct acagaaacga ctggaccgtg tacagcaacg gcagcaagta tgtgtggaac  3420
tcccttaaga gaacagacga gttaattgac gtgacaaagg agctcaagct gctgttcgag  3480
aagtacgcca tcgattaccg gaacgaagct ctgtttgagc agatcatgag ccaggataca  3540
gataagaaca acgccgactt ctggaacaaa ctgttctggt acttccgggt gctgctgcgg  3600
ctgagaaata gcagcgacga actggaccaa atcgtcagcc ctgtgctgaa tcagaacgga  3660
gagttcttcg aaacccctaa gaaaatcaca gagaagtcct acctgtctga ttaccctatg  3720
gacgccgata caaacggcgc ctaccacatc gccctgaagg gcctgtacct gatccaggag  3780
aagatcgctg acgaatctgt ggacctggac aacaagctgc ctaaggactt ctacaagatc  3840
agcaacgccg agtggttcat gtttagacag aaagaaaaa                         3879

SEQ ID NO: 12          moltype = DNA  length = 3996
FEATURE                Location/Qualifiers
source                 1..3996
                       mol_type = other DNA
                       organism = synthetic construct
SEQUENCE: 12
atgggcaaga gcatctacga gaacttcatc ggtcttgaga gcaagaacct gacactgaga  60
ttcgccctga accctgaggc taaaacccag gagaacctga agctgtactg ggacaaactg  120
agggacgaag aaagagatag agcctaccct atcgtgaaaa aaatcctcga caaggagtat  180
cagcagctca tcagcgaggg cctgaaactg ctggaaaatc aaaacgtgct ggactggacc  240
gaactggccg agtacatcag aaccagcgat ctgtctaaga agaagaagga ggacaagaga  300
ctgcgcaagc tgatcgccca gaacctgaaa gcccaccccc tggtcgacaa gctgaaggtg  360
aagaatgcct tcggcaagaa cggctacctg gaaaccctgc cattaggaaa ggaagaaaaa  420
```

-continued

```
gaggccgtga aggtgtttgc cggattcgga ggctttttca acaactacaa caagaatcgg  480
gagaactact tcagtaccga ggagaagtcc accgccatcg ccaacagaat cgtgaacgag  540
aacttcagca agcacttcag caacgtggaa atcgttacaa agatccaaaa agaagtgcca  600
gagctgattc aaatcgtgga agctcagttc aagggttacg acaccatctt taccgtgaac  660
ggctacaaca ccgccctgag ccaggctggc atcgacacat acaacgaaat ggtggccatc  720
tggaacaagg aggcaaacct gtacgctcaa aaagccggca agctgccaga cggccacccg  780
ctgaagaaga agcgtaacta cctgctgagc gccctcttca aacagatcgg cagcgaaaaa  840
gaacacctga tccagatcga cagattcgac ggcgacgagg aagtgatcga agccctgact  900
ggcgtgaaaa agatgctgca ggaggccgac gtgttcgaga agctgaacat gctggtcgag  960
gacatggaaa attgggatta ctccaagatc tacctgtctg cccagagcct gagtaacgtg  1020
tccgtgttcc tgaacaacct gtatgaagat gaacgggaga acagctggaa ctacctggat  1080
aacgtgctga gagagaagtg gcagattgaa ctgcagggca aaaaaaaggg aacagatctg  1140
gaagaggcca ttagaaagaa gaagcagagc ttttactcta tcgaggaact tcaggaggca  1200
gtgaacgcca tcgaggaaac cgacaagtgc tacaatgtgt ctaaatggct gctgggagcc  1260
atgaagagcg agagagtgat cgaggagaag aagaaagacg tggaggattt ctgcacacag  1320
tggaagaacg agagaaacag cctcaaggaa accgacatca ccgccctgaa ggagtacctg  1380
gagcagtgga tcttcctggc taggtactgc aagagcttct acgccaatgg catcgaaaag  1440
aaagagaagg atgaggcttt ttaccacatc ctggaggatg tgctgtacgt gctggacgaa  1500
gtgatctact tctacaacaa ggtgcggaac tacgtgacca aaaagcctta cagtctggag  1560
aagatgcacc tgaagttcgg ccacaacgag ctggccaacg gctggagcgt gaacaaggaa  1620
gaaaattacg gcaccgccat cctgagaaga aacggcaagt actacctggc catcaccaac  1680
agcctgaaca agaaaatgag catccctacc cagctggaga gcacaggaaa taattatgag  1740
aagatggtcc tgaacgtttt tcccaacgtg ttccggatga tcccaaagtg caccacaggc  1800
aggaacgacg tgaagtcatg cttcgagaga aaggaaccca acgagtactt cttcatcgac  1860
acccctgagt tcgtgaaccc ctttaaggtc acacgggagg agtacgaact gaataagatc  1920
acctacgacg gagttaagaa gtggcagagc gactacagca agaacacaca ggacgaaaag  1980
ggctataagg aagccgtgac caagtggatt cagttttgta tgcggttcct gcagtcttat  2040
aagagcaccg ccatatatga ctacagcacc ctgcagcaac ctgaaaaata cgaaacagtg  2100
gacagcttct atcatgatgt ggaaaagatc ctgtacgagt gccacttcga gtacgtgccc  2160
gctaacaaga tcgagcagct tgaagaagag ggaagaatct tcctgttcca gatctacaac  2220
aaggattttt ctgagaacag acggcctgat agcaagaaaa acctccacac cctgtactgg  2280
gaggcgctgt tctccgaaga gaatagaaag gccaaggtga ttcagctgaa tggcaaggcc  2340
gagatcttca gacgggagaa atcaatcgag caccctatcg tgcataaggc tggcgaggtg  2400
ctggtgaaca agcggaccaa agatggcgaa cctattcctg acgacatcta caaggacctg  2460
agcaactatt tcaacggcag aaacgttacc tctgagaagg aagagtacaa ggagtgtctg  2520
gacaaggtgt acaccagcac caaaaagtac gatatcacca aggacaaaag attcaccgag  2580
acaaagtacg agttccacgt gcctatcacc ctgaactacc aggccgacgg cgtgaagtac  2640
ctgaatcaga agatcctgca cgtgctgcgg gacaaccctg atgttaacat catcggcctg  2700
gatagaggcg aaagaaacct gatctcttat gttgtgctga acagagaggg caagatcgtg  2760
aacaatcagc agggttcttt caacatcgtg ggcaaaatgg actaccagaa aaagctgtac  2820
cagaaggaga aaaaccggga taaagaacgg aaaacgtgga aaaacatcga aaccatcaag  2880
gacctgaagg agggctatat cagccaggtg gtacacgagc tgaccgatat ggccatccgg  2940
aataacgcga tcatcgtgat ggaagatctg aatttcggat tcaagcgggg ccggaccaag  3000
gtggaacggc aggtgtacca gaagtttgag ctggccctgc tgaagaagct gcactacctc  3060
gtgaccgaca agaccgaggg agaagctatg ctgaaacccg gcggcgtgct gcaaggctac  3120
cagctggcta gagaagtcaa gaccctgaaa gagatcggca agcagtgcgg ctgtgtgttc  3180
tacgtgcccc ctggctacac aagcaagatc gaccctacaa ccggcttcgt cgacgtgttc  3240
aacatgtctg gagttacaaa ccgcgagaaa aagaaagcct ttttcgaaaa atttgataac  3300
atgttctacg acgagaagag agacatgttc ggcttcagct tcaattacga aaagtttact  3360
acctaccaga gcagctacag aaacgactgg accgtgtaca gcaacggcag caagtatgtg  3420
tggaactccc ttaagagaac agacgagtta attgacgtga caaaggagct caagctgctg  3480
ttcgagaagt acgccatcga ttaccggaac gaagctctgt ttgagcagat catgagccag  3540
gatacagata agaacaacgc cgacttctgg aacaaactgt tctggtactt ccgggtgctg  3600
ctgcggctga gaaatagcag cgacgaactg gaccaaatcg tcagccctgt gctgaatcag  3660
aacggagagt tcttcgaaac ccctaagaaa atcacagaga agtcctacct gtctgattac  3720
cctatggacg ccgatacaaa cggcgcctac cacatcgccc tgaagggcct gtacctgatc  3780
caggagaaga tcgctgacga atctgtggac ctggacaaca agctgcctaa ggacttctac  3840
aagatcagca acgccgagtg gttcatgttt agacagaaag aaaaatctag aaagcggaca  3900
gcagacggct ccgaatttga aagccctaag aaaaagagaa aggtgggatc cggcaaacct  3960
atccccaatc ccctgctggg cctggacagc acctga                           3996

SEQ ID NO: 13          moltype = AA  length = 1194
FEATURE                Location/Qualifiers
source                 1..1194
                       mol_type = protein
                       organism = unidentified
SEQUENCE: 13
NIYENFTNMY QVNKTIRMGL KPICKTGENI AKFLEEDKET SDKYKIAKEV IDKENRAFIE  60
DRLKDFSISG LDEYLELLKQ KKNLTKNQNK MKKEISTQLT KIQNKMRDEI STQLKGFPQF  120
DNKYKFKYIT DKEDIEILKY FKDKKFITFF EEFNTNRKNV YSKENISTSI GHRIVHENLP  180
KFISNFRILN KAIEAFGISK INEDFKNNGI NVTVEELNKI DYFNKVLTQS GIDLYNNLIG  240
ILNQNINLYN QQQKVKKNKI GKLEILYKQI LSKTDKVSFI EEFTEDNQLL ECIDEYFKEK  300
YSLITVDLNN LLENIDTYNL NGIFIKSDKS LGNISNYLYK DWWYISNLIN EEYDYKHKNK  360
VRDDKYYETR KKAIDKIKYF SIGHIDELLK DKNVPMVENY FKEKINLVVK EFNAYLNKFN  420
EYKFINELKT DEIAVEIIKN LCDSIKNVQG IVKPLIITGN DKDDDFYVEI NYIWDELNKF  480
DKIYNMVRNY LTKKDYIEEK IRMMFSKSSF MDGWGKDYGT KKAHIVYHDK NYYLVIVDKK  540
LKLEDIDKLY KPGGDTVHYV YNYQSTENGN IPRKFIYSKG KRFAPSVEKY NLPIEDVIEV  600
YNNEYHTTDY EKKNPEIYKK SLTSLIDYFK IGVNRDMDFE KFDFRLKDSN EYKNIKEFYD  660
NLETCCYKLQ EEKVNFNVLE ELSYSGKIYL FKIYNKDFSE NSKGIPNLHT LYFKMLFDKE  720
```

```
NLENPIYKLS GKAKMFFRKG SLNLDKKTVD YDKKPIDKKE NDKKIKNRRY KVDSFTLHMS  780
IITNFQSYEN KNVNETVNRA LKYCDDVYAI GIDRGIRNLL YACVVNSKGE IVKQVPLNII  840
NNKDYHNLLA EREEKKKNSR KNWKIIDNIR NLKEGYLSQA IHIITDLMVE YNAVLVLENL  900
NFRFKEKQMK FESNVYQKFE KMLIDKLNFL VDKKLDKNAN GGLFNAYQLT EKFTNFKDMK  960
NQNGIIFYIP AWMTSKIDPV TGFTNLFYIK YESIEKAKEF FGKFKSIKFN KVDNYFEFEF  1020
DYNDFTDRAQ GTRSKWTVCS FGPRIEGFRN PEKNNSWDGR EIDITEKIKK LLDDYNVSLD  1080
KDIKAQIMDI NTKDFFEKFI KYFKLVLQMR NSKTGTDIDY IISPVKNKQN EFFDSRKQNE  1140
KMPMDADANG AYNIARKGLM FIDIIKETED KDLKMPKLFI KNKDWLNYVQ KSDL        1194

SEQ ID NO: 14          moltype = AA  length = 1195
FEATURE                Location/Qualifiers
source                 1..1195
                       mol_type = protein
                       organism = unidentified
SEQUENCE: 14
MNIYENFTNM YQVNKTIRMG LKPICKTGEN IAKFLEEDKE TSDKYKIAKE VIDKENRAFI  60
EDRLKDFSIS GLDEYLELLK QKKNLTKNQN KMKKEISTQL TKIQNKMRDE ISTQLKGFPQ  120
FDNKYKFKYI TDKEDIEILK YFKDKKFITF FEEFNTNRKN VYSKENISTS IGHRIVHENL  180
PKFISNFRIL NKAIEAFGIS KINEDFKNNG INVTVEELNK IDYFNKVLTQ SGIDLYNNLI  240
GILNQNINLY NQQQKVKKNK IGKLEILYKQ ILSKTDKVSF IEEFTEDNQL LECIDEYFKE  300
KYSLITVDLN NLLENIDTYN LNGIFIKSDK SLGNISNYLY KDWWYISNLI NEEYDYKHKN  360
KVRDDKYYET RKKAIDKIKY FSIGHIDELL KDKNVPMVEN YFKEKINLVV KEFNAYLNKF  420
NEYKFINELK TDEIAVEIIK NLCDSIKNVQ GIVKPLIITG NDKDDDFYVE INYIWDELNK  480
FDKIYNMVRN YLTKKDYIEE KIRMMFSKSS FMDGWGKDYG TKKAHIVYHD KNYYLVIVDK  540
KLKLEDIDKL YKPGGDTVHY VYNYQSTENG NIPRKFIYSK GKRFAPSVEK YNLPIEDVIE  600
VYNNEYHTTD YEKKNPEIYK KSLTSLIDYF KIGVNRDMDF EKFDFRLKDS NEYKNIKEFY  660
DNLETCCYKL QEEKVNFNVL EELSYSGKIY LFKIYNKDFS ENSKGIPNLH TLYFKMLFDK  720
ENLENPIYKL SGKAKMFFRK GSLNLDKKTV DYDKKPIDKK ENDKKIKNRR YKVDSFTLHM  780
SIITNFQSYE NKNVNETVNR ALKYCDDVYA IGIDRGIRNL LYACVVNSKG EIVKQVPLNI  840
INNKDYHNLL AEREEKKKNS RKNWKIIDNI RNLKEGYLSQ AIHIITDLMV EYNAVLVLEN  900
LNFRFKEKQM KFESNVYQKF EKMLIDKLNF LVDKKLDKNA NGGLFNAYQL TEKFTNFKDM  960
KNQNGIIFYI PAWMTSKIDP VTGFTNLFYI KYESIEKAKE FFGKFKSIKF NKVDNYFEFE  1020
FDYNDFTDRA QGTRSKWTVC SFGPRIEGFR NPEKNNSWDG REIDITEKIK KLLDDYNVSL  1080
DKDIKAQIMD INTKDFFEKF IKYFKLVLQM RNSKTGTDID YIISPVKNKQ NEFFDSRKQN  1140
EKMPMDADAN GAYNIARKGL MFIDIIKETE DKDLKMPKLF IKNKDWLNYV QKSDL       1195

SEQ ID NO: 15          moltype = AA  length = 1232
FEATURE                Location/Qualifiers
source                 1..1232
                       mol_type = protein
                       organism = synthetic construct
SEQUENCE: 15
MGNIYENFTN MYQVNKTIRM GLKPICKTGE NIAKFLEEDK ETSDKYKIAK EVIDKENRAF  60
IEDRLKDFSI SGLDEYLELL KQKKNLTKNQ NKMKKEISTQ LTKIQNKMRD EISTQLKGFP  120
QFDNKYKFKY ITDKEDIEIL KYFKDKKFIT FFEEFNTNRK NVYSKENIST SIGHRIVHEN  180
LPKFISNFRI LNKAIEAFGI SKINEDFKNN GINVTVEELN KIDYFNKVLT QSGIDLYNNL  240
IGILNQNINL YNQQQKVKKN KIGKLEILYK QILSKTDKVS FIEEFTEDNQ LLECIDEYFK  300
EKYSLITVDL NNLLENIDTY NLNGIFIKSD KSLGNISNYL YKDWWYISNL INEEYDYKHK  360
NKVRDDKYYE TRKKAIDKIK YFSIGHIDEL LKDKNVPMVE NYFKEKINLV VKEFNAYLNK  420
FNEYKFINEL KTDEIAVEII KNLCDSIKNV QGIVKPLIIT GNDKDDDFYV EINYIWDELN  480
KFDKIYNMVR NYLTKKDYIE EKIRMMFSKS SFMDGWGKDY GTKKAHIVYH DKNYYLVIVD  540
KKLKLEDIDK LYKPGGDTVH YVYNYQSTEN GNIPRKFIYS KGKRFAPSVE KYNLPIEDVI  600
EVYNNEYHTT DYEKKNPEIY KKSLTSLIDY FKIGVNRDMD FEKFDFRLKD SNEYKNIKEF  660
YDNLETCCYK LQEEKVNFNV LEELSYSGKI YLFKIYNKDF SENSKGIPNL HTLYFKMLFD  720
KENLENPIYK LSGKAKMFFR KGSLNLDKKT VDYDKKPIDK KENDKKIKNR RYKVDSFTLH  780
MSIITNFQSY ENKNVNETVN RALKYCDDVY AIGIDRGIRN LLYACVVNSK GEIVKQVPLN  840
IINNKDYHNL LAEREEKKKN SRKNWKIIDN IRNLKEGYLS QAIHIITDLM VEYNAVLVLE  900
NLNFRFKEKQ MKFESNVYQK FEKMLIDKLN FLVDKKLDKN ANGGLFNAYQ LTEKFTNFKD  960
MKNQNGIIFY IPAWMTSKID PVTGFTNLFY IKYESIEKAK EFFGKFKSIK FNKVDNYFEF  1020
EFDYNDFTDR AQGTRSKWTV CSFGPRIEGF RNPEKNNSWD GREIDITEKI KKLLDDYNVS  1080
LDKDIKAQIM DINTKDFFEK FIKYFKLVLQ MRNSKTGTDI DYIISPVKNK QNEFFDSRKQ  1140
NEKMPMDADA NGAYNIARKG LMFIDIIKET EDKDLKMPKL FIKNKDWLNY VQKSDLSRKR  1200
TADGSEFESP KKKRKVGSGK PIPNPLLGLD ST                                1232

SEQ ID NO: 16          moltype = DNA  length = 3588
FEATURE                Location/Qualifiers
source                 1..3588
                       mol_type = unassigned DNA
                       organism = unidentified
SEQUENCE: 16
atgaacattt acgaaaattt tactaatatg tatcaggtaa ataagactat aagaatgggg  60
ttaaagccaa tatgtaaaac tggtgaaaat attgctaaat ttcttgagga agataaggaa  120
acaagtgata aatacaagat agctaaagaa gtaattgata aggaaaatag agcttttata  180
gaggatagat taaaggattt ttcaatttca gggttggatg aatatttgga attgcttaaa  240
caaaaaaaga atttaaccaa aaatcaaaat aaaatgaaaa aggaaatttc aacacagtta  300
acaaaaatac aaaataaaat gagagatgaa atttcaacac agttaaaagg cttccctcaa  360
tttgataata aatataaatt caaatatatt acagataaag aagatataga aattttaaaa  420
tattttaaag ataagaaatt tattactttc tttgaagaat ttaatactaa tagaaaaaat  480
gtctactcta aagaaaatat ttcaacttct attggacaca gaattgttca cgaaaatctt  540
```

```
ccaaaattta tttcaaattt taggatttta aataaagcaa tagaggcgtt tggaataagt  600
aaaataaatg aagattttaa gaataatgga attaatgtta cagttgaaga acttaataaa  660
atagattatt ttaacaaggt tttaactcaa tcaggaatag atttgtataa taatttgata  720
ggtattttaa atcaaaatat aaatctatat aatcaacaac agaaagtaaa aaagaataaa  780
attggaaagt tagaaatatt atataagcaa attttaagta aaacagataa agtatcgttt  840
attgaagaat ttactgaaga taaccaactt ttggaatgta ttgatgaata ttttaaagaa  900
aaatatagtt tgataactgt agatttaaat aatttacttg aaaatattga tacttataat  960
ttgaatggta tctttattaa aagtgataag tccttgggaa atatatctaa ttatttatat  1020
aaagattggt ggtatatatc aaatcttata aacgaagaat acgattataa acataagaat  1080
aaggtaagag atgataagta ttatgaaaca agaaaaaaag ctatagataa gattaaatat  1140
ttttccatag gacatattga tgaattgtta aaagataaaa atgttcctat ggtagaaaac  1200
tatttcaaag aaaagataaa tttagtagta aaagaattta atgcttattt aaacaaattt  1260
aatgaatata agtttataaa tgagctaaaa actgatgaaa ttgctgtcga aataataaaa  1320
aatttatgtg attcaataaa gaatgtacag gggatagtaa agcctttaat aattactgga  1380
aatgataaag acgatgattt ttatgtggaa atcaattata tatgggacga gcttaataag  1440
tttgataaaa tatataatat ggttagaaat tatcttacaa aaaaggatta catagaggaa  1500
aaaattagaa tgatgtttct aaagagcagt tttatggatg gttggggaaa agattatgga  1560
acaaaaaaag cacatatagt ttatcatgat aaaaattatt atttagtaat agtagacaag  1620
aaattaaaat tagaggatat agataaatta tataaaccag gtggagatac tgtacattat  1680
gtatataatt accaatcaac agaaaatgga aatattccta gaaaattcat atattctaag  1740
ggtaaaagat ttgcaccatc tgtagaaaaa tataatttac caatagaaga tgttatcgaa  1800
gtgtataaca atgaatatca tacaacagat tacgaaaaga aaaatcctga aatttacaag  1860
aaatcattaa catccttaat tgattatttt aaaatagggg taaataggga tatggatttt  1920
gaaaaatttg attttagatt aaaagattca aacgaataca aaaatataaa agaattttat  1980
gataatttgg aaacttgttg ctataagtta caagaagaaa aagttaattt taatgtactt  2040
gaagagcttt catatagtgg aaaaatttat ttatttaaaa tatacaataa ggatttttct  2100
gaaaatagca aaggaatacc taatcttcat actttatatt ttaaaatgct atttgacaaa  2160
gaaaaccttg aaaatccgat ttataaactt agtggaaagg ctaaaatgtt ttttagaaag  2220
ggtagtctta atttagacaa aaaaactgtt gattatgata aaaagccaat agataagaaa  2280
gaaaatgaca aaaaaattaa aaatagaaga tataaagttg atagttttac attacatatg  2340
tcaattatta cgaactttca gtcatatgaa aataaaaatg taaatgaaac tgtaaatagg  2400
gctttaaaat attgtgatga tgtttatgcc ataggtatag acagaggaat aagaaattta  2460
ttatatgctt gtgtagtaaa ttcaaaggga gaaatagtaa aacaagttcc tttaaatatt  2520
ataaataata aagattatca caatttactt gcagaaagag aagagaagaa aaagaatagt  2580
aggaaaaatt ggaaaatcat tgataatata aggaatttaa aggaaggcta tttaagtcag  2640
gccatacata taataactga ccttatggtt gaatataatg ctgtacttgt tttagagaat  2700
ttgaatttta gatttaaaga aaaacaaatg aaatttgaaa gtaatgttta tcaaaaattt  2760
gaaaagatgc ttattgataa attgaatttc ttagttgata aaaagcttga taagaacgcc  2820
aatggtggat tgtttaatgc gtatcaatta acagaaaaat ttacaaactt taaagatatg  2880
aaaaatcaaa atggtataat attttatatt cctgcttgga tgacaagcaa aattgaccca  2940
gttacaggat ttacaaattt attctatatt aaatatgaga gtattgaaaa ggctaaagag  3000
ttttttggta agtttaaatc aataaaattt aataaggtag acaactattt tgaatttgaa  3060
tttgattata atgattttac tgacagagct caaggtacaa ggtctaaatg gacagtttgt  3120
agttttggcc ctagaattga aggttttaga aatcctgaaa aaaataatag ttgggatggt  3180
agagaaatag atataacaga gaaaattaaa aaattacttg atgattataa tgtatcttta  3240
gataaagata ttaaagctca aattatggat ataaatacta aggatttctt tgaaaaattt  3300
attaaatatt ttaaacttgt attgcaaatg agaaacagta aaacaggtac agatattgat  3360
tatatcattt ctccggttaa aaataagcaa aatgaatttt ttgacagtag aaagcaaaat  3420
gaaaaaatgc ctatggatgc agatgcaaat ggtgcttata atattgctag aaaaggctta  3480
atgtttattg atataataaa agaaactgaa gataaagatt taaagatgcc taaattgttc  3540
attaaaaata aagattggtt aaattatgta caaaagagtg atttgtaa               3588
```

```
SEQ ID NO: 17          moltype = DNA  length = 3582
FEATURE                Location/Qualifiers
source                 1..3582
                       mol_type = other DNA
                       organism = synthetic construct
SEQUENCE: 17
aatatctatg agaacttcac caacatgtac caggtgaaca agacaatccg catgggcctg  60
aagcctatct gtaaaaccgg agaaaacatc gccaagttcc tggaggagga caaggaaacc  120
agcgacaagt acaagatcgc caaggaggtc atcgacaagg agaacagagc ctttatcgag  180
gacagactga aggacttcag catcagcggc ctggacgagt acctggaact gctgaagcag  240
aagaaaaacc tgacaaagaa ccagaacaag atgaaaaagg aaatctccac ccagctgaca  300
aagatccaga acaagatgcg ggacgagata tcgacacagc tgaagggctt ccctcagttc  360
gataacaaat acaagttcaa atatatcaca gacaaggagg acatcgaaat cctcaagtac  420
ttcaaggata agaagttcat tacattcttt gaggaattta ataccaatcg gaaaaacgtg  480
tacagcaagg aaaacatcag cacctctatc ggccatagaa tcgtgcacga gaacctgcca  540
aagttcatca gcaacttcag aatcctgaat aaggccatcg aggccttcgg catctctaaa  600
atcaatgagg acttcaagaa caatggcatc aacgtgaccg tagaagaact gaacaagatc  660
gactacttca acaaggtcct gacacagagc ggcattgacc tgtacaacaa cctgattggc  720
atcctgaacc agaacatcaa cctgtacaat cagcagcaga aggtgaagaa gaacaaaatc  780
ggaaagctgg aaatcctgta caagcaaatc ttgtccaaaa ccgacaaggt gtctttcatt  840
gaggagttca ccgaggacaa ccagctgctg gagtgcatcg acgagtactt taaagagaaa  900
tacagcctga tcaccgtgga cctgaacaac ctgcttgaaa atatcgacac ctacaatctc  960
aacggcatct tcatcaaatc tgataaaagc ctgggcaaca tcagcaacta cctgtacaag  1020
gattggtggt acatcagcaa cctgatcaac gaagaatacg actacaagca caagaacaag  1080
gtcagagatg ataagtacta cgagacaaga aagaaggcca tcgacaagat caagtacttc  1140
tctatcggac acatcgatga gctgctgaag gacaagaacg ttccaatggt ggaaaactac  1200
ttcaaggaga agatcaacct ggtcgtgaag gagttcaatg cttatctgaa caagttcaat  1260
```

```
gaatataaat tcatcaacga gctgaaaaca gacgagatcg ccgtggaaat catcaagaac  1320
ctgtgcgaca gcatcaagaa cgtgcagggc atcgtgaagc ccctgatcat caccggcaac  1380
gacaaggatg atgattttta cgtggagatc aactacatct gggatgagct taacaagttc  1440
gacaaaatct acaacatggt caggaattac ctaaccaaga aggactacat cgaggaaaag  1500
atcagaatga tgttttccaa gagcagcttt atggacggct ggggcaagga ctacggcacc  1560
aagaaggccc acatcgtgta ccacgacaag aactactacc tggtgatcgt ggacaagaag  1620
ctgaaactgg aagatatcga caaactatac aagccaggcg gcgacacagt tcactacgtg  1680
tacaactacc agtctaccga gaacggaaac atccctcgga agttcatcta ctctaagggc  1740
aagcggttcg cccctagcgt ggaaaaatat aacctgccta ttgaagatgt gattgaggtg  1800
tacaacaacg agtaccacac caccgactat gagaaaaaga accctgagat atacaaaaag  1860
tccctgacca gcctgatcga ctatttcaag atcggcgtga acagagatat ggacttcgag  1920
aagtttgatt ttcggctaaa ggactccaac gaatacaaga acatcaagga gttctacgat  1980
aacctggaga catgctgcta caagctgcag gaggaaaagg tgaacttcaa cgtgctggag  2040
gaactgagct acagcggaaa gatctacctg ttcaagatct acaacaaaga tttcagcgag  2100
aatagcaaag gcatccctaa cctgcatacc ctgtacttca aaatgctgtt cgacaaagag  2160
aacctggaga accccatcta caagctgtct ggaaaagcta agatgttttt cagaaagggc  2220
agcctgaacc tggacaaaaa aaccgttgac tatgacaaaa aacctatcga taagaaggaa  2280
aacgacaaaa aaatcaagaa taggcggtac aaggtggaca gcttcaccct gcacatgagc  2340
atcatcacca acttccagag ctacgagaac aagaacgtta atgagactgt gaaccgggcc  2400
ctgaagtact gcgacgacgt gtacgccatc ggcatcgacc gcggaatccg gaacctgctg  2460
tacgcttgtg tggtgaacag caagggcgag atcgtgaagc aagtgcccct caacatcatt  2520
aacaataagg attaccacaa cctgctggcc gagagagaag aaaagaagaa aaacagcaga  2580
aagaattgga agatcataga caacatcaga aacctgaagg aaggctacct gagccaggcc  2640
atccacatca tcaccgacct gatggtggaa tacaacgccg tgctggtgct ggagaacctg  2700
aatttcagat tcaaggagaa gcagatgaag tttgaaagca atgtgtacca aaaattcgaa  2760
aaaatgctga tcgacaagct gaatttcctg gtcgataaaa aactggacaa gaatgccaat  2820
ggcggactgt ttaacgccta tcagctgaca gagaagttca ccaactttaa ggatatgaag  2880
aatcagaacg gcatcatctt ctacatcccc gcctggatga caagcaagat cgatcccgtg  2940
accggcttca caaacctgtt ttatatcaaa tacgagagca tcgagaaggc aaaggagttc  3000
ttcggcaagt ttaagtctat caagttcaat aaggtggaca attatttcga gttcgagttc  3060
gactacaacg actttaccga cagagctcaa ggcaccagaa gcaagtggac cgtgtgtagc  3120
ttcggtcctc ggatcgaggg cttcagaaac cccgagaaaa acaattcctg ggacggcaga  3180
gaaatcgaca tcacagagaa gatcaagaag ctgctggatg actacaatgt gagcctggac  3240
aaagacatca aagcccagat catggacatc aacaccaagg atttcttcga gaagttcatc  3300
aagtacttca agctggtgct gcagatgaga aacagcaaga ccggcaccga catcgattac  3360
attatctccc ctgtgaagaa caagcagaac gagtttttcg actccagaaa gcagaacgag  3420
aagatgccta tggacgctga tgccaacggc gcctacaaca tcgctagaaa ggggctgatg  3480
ttcatcgata tcatcaagga aacagaggac aaggacctga aaatgcctaa gctgttcata  3540
aagaacaagg attggctgaa ctatgtgcag aaatcagatc tg                     3582

SEQ ID NO: 18           moltype = DNA  length = 3699
FEATURE                 Location/Qualifiers
source                  1..3699
                        mol_type = other DNA
                        organism = synthetic construct
SEQUENCE: 18
atgggcaata tctatgagaa cttcaccaac atgtaccagg tgaacaagac aatccgcatg  60
ggcctgaagc ctatctgtaa aaccggagaa aacatcgcca agttcctgga ggaggacaag  120
gaaaccagcg acaagtacaa gatcgccaag gaggtcatcg acaaggagaa cagagccttt  180
atcgaggaca gactgaagga cttcagcatc agcggcctgg acgagtacct ggaactgctg  240
aagcagaaga aaaacctgac aaagaaccag aacaagatga aaaaggaaat ctccacccag  300
ctgacaaaga tccagaacaa gatgcgggac gagatatcga cacagctgaa gggcttccct  360
cagttcgata acaaatacaa gttcaaatat atcacagaca aggaggacat cgaaatcctc  420
aagtacttca aggataagaa gttcattaca ttctttgagg aatttaatac caatcggaaa  480
aacgtgtaca gcaaggaaaa catcagcacc tctatcggcc atagaatcgt gcacgagaac  540
ctgccaaagt tcatcagcaa cttcagaatc ctgaataagg ccatcgaggc cttcggcatc  600
tctaaaatca atgaggactt caagaacaat ggcatcaacg tgaccgtaga agaactgaac  660
aagatcgact acttcaacaa ggtcctgaca cagagcggca ttgacctgta caacaacctg  720
attggcatcc tgaaccagaa catcaacctg tacaatcagc agcagaaggt gaagaagaac  780
aaaatcggaa agctggaaat cctgtacaag caaatcttgt ccaaaaccga caaggtgtct  840
ttcattgagg agttcaccga ggacaaccag ctgctggagt gcatcgacga gtactttaaa  900
gagaaataca gcctgatcac cgtggacctg aacaacctgc ttgaaaatat cgacacctac  960
aatctcaacg gcatcttcat caaatctgat aaaagcctgg gcaacatcag caactacctg  1020
tacaaggatt ggtggtacat cagcaacctg atcaacgaag aatacgacta caagcacaag  1080
aacaaggtca gagatgataa gtactacgag acaagaaaga aggccatcga caagatcaag  1140
tacttctcta tcggacacat cgatgagctg ctgaaggaca agaacgttcc aatggtggaa  1200
aactacttca aggagaagat caacctggtc gtgaaggagt tcaatgctta tctgaacaag  1260
ttcaatgaat ataaattcat caacgagctg aaaacagacg agatcgccgt ggaaatcatc  1320
aagaacctgt gcgacagcat caagaacgtg cagggcatcg tgaagcccct gatcatcacc  1380
ggcaacgaca aggatgatga tttttacgtg gagatcaact acatctggga tgagcttaac  1440
aagttcgaca aaatctacaa catggtcagg aattacctaa ccaagaagga ctacatcgag  1500
gaaaagatca gaatgatgtt ttccaagagc agctttatgg acggctgggg caaggactac  1560
ggcaccaaga aggcccacat cgtgtaccac gacaagaact actacctggt gatcgtggac  1620
aagaagctga aactggaaga tatcgacaaa ctatacaagc caggcggcga cacagttcac  1680
tacgtgtaca actaccagtc taccgagaac ggaaacatcc ctcggaagtt catctactct  1740
aagggcaagc ggttcgcccc tagcgtggaa aaatataacc tgcctattga agatgtgatt  1800
gaggtgtaca acaacgagta ccacaccacc gactatgaga aaaagaaccc tgagatatac  1860
aaaaagtccc tgaccagcct gatcgactat ttcaagatcg gcgtgaacag agatatggac  1920
ttcgagaagt ttgattttcg gctaaaggac tccaacgaat acaagaacat caaggagttc  1980
```

```
tacgataacc tggagacatg ctgctacaag ctgcaggagg aaaaggtgaa cttcaacgtg  2040
ctggaggaac tgagctacag cggaaagatc tacctgttca agatctacaa caaagatttc  2100
agcgagaata gcaaaggcat ccctaacctg catacccctgt acttcaaaat gctgttcgac  2160
aaagagaacc tggagaaccc catctacaag ctgtctggaa aagctaagat gtttttcaga  2220
aagggcagcc tgaacctgga caaaaaaacc gttgactatg acaaaaaacc tatcgataag  2280
aaggaaaacg acaaaaaaat caagaatagg cggtacaagg tggacagctt caccctgcac  2340
atgagcatca tcaccaactt ccagagctac gagaacaaga acgttaatga gactgtgaac  2400
cgggccctga agtactgcga cgacgtgtac gccatcggca tcgaccgcgg aatccggaac  2460
ctgctgtacg cttgtgtggt gaacagcaag ggcgagatcg tgaagcaagt gcccctcaac  2520
atcattaaca ataaggatta ccacaacctg ctggccgaga gagaagaaaa gaagaaaaac  2580
agcagaaaga attggaagat catagacaac atcagaaacc tgaaggaagg ctacctgagc  2640
caggccatcc acatcatcac cgacctgatg gtggaataca acgccgtgct ggtgctggag  2700
aacctgaatt tcagattcaa ggagaagcag atgaagtttg aaagcaatgt gtaccaaaaa  2760
ttcgaaaaaa tgctgatcga caagctgaat ttcctggtcg ataaaaaact ggacaagaat  2820
gccaatggcg gactgtttaa cgcctatcag ctgacagaga agttcaccaa ctttaaggat  2880
atgaagaatc agaacggcat catcttctac atccccgcct ggatgacaag caagatcgat  2940
cccgtgaccg gcttcacaaa cctgttttat atcaaatacg agagcatcga gaaggcaaag  3000
gagttcttcg gcaagtttaa gtctatcaag ttcaataagg tggacaatta tttcgagttc  3060
gagttcgact acaacgactt taccgacaga gctcaaggca ccagaagcaa gtggaccgtg  3120
tgtagcttcg gtcctcggat cgagggcttc agaaaccccg agaaaaacaa ttcctgggac  3180
ggcagagaaa tcgacatcac agagaagatc aagaagctgc tggatgacta caatgtgagc  3240
ctggacaaag acatcaaagc ccagatcatg gacatcaaca ccaaggattt cttcgagaag  3300
ttcatcaagt acttcaagct ggtgctgcag atgagaaaca gcaagaccgg caccgacatc  3360
gattacatta tctcccctgt gaagaacaag cagaacgagt ttttcgactc cagaaagcag  3420
aacgagaaga tgcctatgga cgctgatgcc aacggcgcct acaacatcgc tagaaagggg  3480
ctgatgttca tcgatatcat caaggaaaca gaggacaagg acctgaaaat gcctaagctg  3540
ttcataaaga acaaggattg gctgaactat gtgcagaaat cagatctgtc tagaaagcgg  3600
acagcagacg gctccgaatt tgaaagccct aagaaaaaga gaaaggtggg atccggcaaa  3660
cctatcccca atcccctgct gggcctggac agcacctga                         3699

SEQ ID NO: 19          moltype = AA  length = 1244
FEATURE                Location/Qualifiers
source                 1..1244
                       mol_type = protein
                       organism = unidentified
SEQUENCE: 19
EISNRFTNKY QVSKTLRFRL EPTGGTDDLL CQAQIIEGDE RRNKEAITMK QILDNCHKQI  60
IERVLSDFNF KEHSLEEFFK VYTRNDDDRE KDIENLQAKM RKEIAAAFTK QDVTKLFSSK  120
FKDFVERGLI KYASNEKERN IVSRFKGFAT YFTGFNTNRL NMYSEEAKST AISFRLINQN  180
LIKFIDNILV YKKVSQTLPS DVLSNIYIDF KAIINTSSLE EFFSINNYNN ILTQKQIEIF  240
NAVIGGKKDK DEKIITKGFN QYINEYNQTN KNIRLPKMMR LFNQILSDRE GVSARPEPFN  300
NANETISSVR DCFTNEISKQ ITILSETTSK IESFDIDRIY IKGGEDLRAL SNSIYGYFNY  360
IHDRIADKWK HNNPQGKKSP ESYQKNLNAY LKGIKSVSLH SIANICGDNK VIEYFRNLGA  420
ENTVDFQREN VVSLIDNKYN CASNLLSDAQ ITDEELRTNS RSIKDLLDAV KSAQRFFRLL  480
CGSGNEPDKD HSFYDEYTPA FEALENSINP LYNKVRSFVT KKDFSTDKFK LNFDSSSFLS  540
GWAKKSEYEK SSAFIFIRDN QYYLGINKCL SKEDIAYLED STSSSDTKRV VYMFQKVDAT  600
NIPRIFIRSK GSNLAPAVNE FQLPIETILD IYDNKFFTTS YQKKDRTKWK ESLTKLIDYY  660
KLGFSQHKSY ADFDLKWKAS SEYNDINDFL ADVQRFCYRI EFININWDKL IEFTEDGKFY  720
LFRIANKDLS GNSTGLPNLH TIYWKMLFDE SNLKDIVYKL SGNAEVFMRY NSLKNPIVHK  780
AGVEIKNKCP FTEKKTSIFD YDIIKDRRYT KDQLELHVPI LMNFKSPSAA KGKAFNKECL  840
EYIRNNGIKH IIGIDRGERN LLYMVITDLD GNIVEQKSLN QIASNPKLPL FRQDYNKLLK  900
TKADANAQAR RDWETIDTVK EIKFGFLSQI VHEIAMAIIK YDAIVVLENL NRGFMQKRGL  960
ENNVYQKFEQ MLLDKLSYYV DKTKHPEEAG GALHAYQLSD TYANFNSLSK NAMVRQSGFV  1020
FYIPAWLTSK IDPVTGFASF LKFHRDDSMA TIKSTISKFD CFKYDKECDM FHIRIDYNKF  1080
STSCSGGQRK WDLFTFGDRI LAERNTMQNS RYVYQTVNLT SEFKNLFATK DIDISGNLKD  1140
SICKIEDVGF FRKLSQLLSL TLQLRNSNAE TGEDFLISPV ADKDGNFFDS RNCPDSLPKD  1200
ADANGAYNIA RKGLMLVEQL KRCKDVSKFK PAIKNEDWLD YVQR                  1244

SEQ ID NO: 20          moltype = AA  length = 1245
FEATURE                Location/Qualifiers
source                 1..1245
                       mol_type = protein
                       organism = unidentified
SEQUENCE: 20
MEISNRFTNK YQVSKTLRFR LEPTGGTDDL LCQAQIIEGD ERRNKEAITM KQILDNCHKQ  60
IIERVLSDFN FKEHSLEEFF KVYTRNDDDR EKDIENLQAK MRKEIAAAFT KQDVTKLFSS  120
KFKDFVERGL IKYASNEKER NIVSRFKGFA TYFTGFNTNR LNMYSEEAKS TAISFRLINQ  180
NLIKFIDNIL VYKKVSQTLP SDVLSNIYID FKAIINTSSL EEFFSINNYN NILTQKQIEI  240
FNAVIGGKKD KDEKIITKGF NQYINEYNQT NKNIRLPKMM RLFNQILSDR EGVSARPEPF  300
NNANETISSV RDCFTNEISK QITILSETTS KIESFDIDRI YIKGGEDLRA LSNSIYGYFN  360
YIHDRIADKW KHNNPQGKKS PESYQKNLNA YLKGIKSVSL HSIANICGDN KVIEYFRNLG  420
AENTVDFQRE NVVSLIDNKY NCASNLLSDA QITDEELRTN SRSIKDLLDA VKSAQRFFRL  480
LCGSGNEPDK DHSFYDEYTP AFEALENSIN PLYNKVRSFV TKKDFSTDKF KLNFDSSSFL  540
SGWAKKSEYE KSSAFIFIRD NQYYLGINKC LSKEDIAYLE DSTSSSDTKR VVYMFQKVDA  600
TNIPRIFIRS KGSNLAPAVN EFQLPIETIL DIYDNKFFTT SYQKKDRTKW KESLTKLIDY  660
YKLGFSQHKS YADFDLKWKA SSEYNDINDF LADVQRFCYR IEFININWDK LIEFTEDGKF  720
YLFRIANKDL SGNSTGLPNL HTIYWKMLFD ESNLKDIVYK LSGNAEVFMR YNSLKNPIVH  780
KAGVEIKNKC PFTEKKTSIF DYDIIKDRRY TKDQLELHVP ILMNFKSPSA AKGKAFNKEC  840
LEYIRNNGIK HIIGIDRGER NLLYMVITDL DGNIVEQKSL NQIASNPKLP LFRQDYNKLL  900
```

-continued

```
KTKADANAQA RRDWETIDTV KEIKFGFLSQ IVHEIAMAII KYDAIVVLEN LNRGFMQKRG  960
LENNVYQKFE QMLLDKLSYY VDKTKHPEEA GGALHAYQLS DTYANFNSLS KNAMVRQSGF  1020
VFYIPAWLTS KIDPVTGFAS FLKFHRDDSM ATIKSTISKF DCFKYDKECD MFHIRIDYNK  1080
FSTSCSGGQR KWDLFTFGDR ILAERNTMQN SRYVYQTVNL TSEFKNLFAT KDIDISGNLK  1140
DSICKIEDVG FFRKLSQLLS LTLQLRNSNA ETGEDFLISP VADKDGNFFD SRNCPDSLPK  1200
DADANGAYNI ARKGLMLVEQ LKRCKDVSKF KPAIKNEDWL DYVQR                  1245

SEQ ID NO: 21          moltype = AA  length = 1282
FEATURE                Location/Qualifiers
source                 1..1282
                       mol_type = protein
                       organism = synthetic construct
SEQUENCE: 21
MGEISNRFTN KYQVSKTLRF RLEPTGGTDD LLCQAQIIEG DERRNKEAIT MKQILDNCHK  60
QIIERVLSDF NFKEHSLEEF FKVYTRNDDD REKDIENLQA KMRKEIAAAF TKQDVTKLFS  120
SKFKDFVERG LIKYASNEKE RNIVSRFKGF ATYFTGFNTN RLNMYSEEAK STAISFRLIN  180
QNLIKFIDNI LVYKKVSQTL PSDVLSNIYI DFKAIINTSS LEEFFSINNY NNILTQKQIE  240
IFNAVIGGKK DKDEKIITKG FNQYINEYNQ TNKNIRLPKM MRLFNQILSD REGVSARPEP  300
FNNANETISS VRDCFTNEIS KQITILSETT SKIESFDIDR IYIKGGEDLR ALSNSIYGYF  360
NYIHDRIADK WKHNNPQGKK SPESYQKNLN AYLKGIKSVS LHSIANICGD NKVIEYFRNL  420
GAENTVDFQR ENVVSLIDNK YNCASNLLSD AQITDEELRT NSRSIKDLLD AVKSAQRFFR  480
LLCGSGNEPD KDHSFYDEYT PAFEALENSI NPLYNKVRSF VTKKDFSTDK FKLNFDSSSF  540
LSGWAKKSEY EKSSAFIFIR DNQYYLGINK CLSKEDIAYL EDSTSSSDTK RVVYMFQKVD  600
ATNIPRIFIR SKGSNLAPAV NEFQLPIETI LDIYDNKFFT TSYQKKDRTK WKESLTKLID  660
YYKLGFSQHK SYADFDLKWK ASSEYNDIND FLADVQRFCY RIEFININWD KLIEFTEDGK  720
FYLFRIANKD LSGNSTGLPN LHTIYWKMLF DESNLKDIVY KLSGNAEVFM RYNSLKNPIV  780
HKAGVEIKNK CPFTEKKTSI FDYDIIKDRR YTKDQLELHV PILMNFKSPS AAKGKAFNKE  840
CLEYIRNNGI KHIIGIDRGE RNLLYMVITD LDGNIVEQKS LNQIASNPKL PLFRQDYNKL  900
LKTKADANAQ ARRDWETIDT VKEIKFGFLS QIVHEIAMAI IKYDAIVVLE NLNRGFMQKR  960
GLENNVYQKF EQMLLDKLSY YVDKTKHPEE AGGALHAYQL SDTYANFNSL SKNAMVRQSG  1020
FVFYIPAWLT SKIDPVTGFA SFLKFHRDDS MATIKSTISK FDCFKYDKEC DMFHIRIDYN  1080
KFSTSCSGGQ RKWDLFTFGD RILAERNTMQ NSRYVYQTVN LTSEFKNLFA TKDIDISGNL  1140
KDSICKIEDV GFFRKLSQLL SLTLQLRNSN AETGEDFLIS PVADKDGNFF DSRNCPDSLP  1200
KDADANGAYN IARKGLMLVE QLKRCKDVSK FKPAIKNEDW LDYVQRSRKR TADGSEFESP  1260
KKKRKVGSGK PIPNPLLGLD ST                                          1282

SEQ ID NO: 22          moltype = DNA  length = 3738
FEATURE                Location/Qualifiers
source                 1..3738
                       mol_type = unassigned DNA
                       organism = unidentified
SEQUENCE: 22
atggaaattt cgaaccgatt cacaaacaag tatcaagtaa gcaagaccct ccgctttcgc  60
cttgagccaa ccggaggtac tgatgattta ctttgccaag cacaaatcat cgagggagac  120
gagcgccgca ataaagaggc tataacaatg aaacagattt tggacaattg tcacaaacag  180
ataattgagc gcgtattgtc cgactttaat tttaaagagc attctcttga agagtttttc  240
aaagtgtata ccagaaacga tgatgaccgc gaaaaggaca ttgaaaatct ccaagcaaaa  300
atgcgcaaag aaatagccgc cgccttcacc aaacaggatg ttacgaaact tttctcaagc  360
aaattcaagg attttgttga aagaggcttg attaaatatg catcaaacga gaaggaacgc  420
aacatcgttt cccgcttcaa aggttttgcc acttacttta cagggttcaa taccaataga  480
ctgaatatgt actcagaaga agcaaaatcc acagctatat cattcagatt aattaatcaa  540
aacttgataa agttcataga caacatcctt gtatataaaa aagtgtctca aacgttgcct  600
tcagatgtgc tatcaaacat ttatatagac tttaaggcaa tcatcaacac atcaagtctt  660
gaagaattct tctccataaa caactacaat aacatactca cccagaaaca gattgagatt  720
ttcaatgcag ttatcggagg taaaaaagac aaggatgaaa aaataataac caaaggattc  780
aaccaatata taaacgaata caaccagacc aataaaaaca tccgtctgcc taagatgatg  840
cggttattca atcaaatcct aagcgacaga gaaggtgttt ctgcaagacc agagccattc  900
aataacgcga acgagacaat cagttccgtc cgtgattgtt ttacaaacga aatatcaaaa  960
caaataacga tattgtctga aacaacatcc aaaattgaat cattcgacat tgatagaatt  1020
tacattaagg gcggagaaga tctgagagca ttatccaaca gtatatatgg atatttcaat  1080
tatatccatg accgtatcgc agacaaatgg aaacacaaca atcctcaggg caaaaagagc  1140
cccgaaagct accaaaaaaa cctcaacgca tatctgaaag gcataaaaag cgtctcttta  1200
cacagtattg caaacatctg tggtgacaac aaagttattg agtatttcag gaatcttggt  1260
gcagaaaaca ctgttgattt ccaaagagag aacgttgtat cattaatcga caacaaatac  1320
aactgcgctt caaatctttt atccgacgcc caaattacgg atgaagaact tcgcacaaac  1380
agtcgctcaa ttaaagactt gcttgacgcc gtcaagagtg cccaacgatt tttccgtcta  1440
ctgtgcggtt ctggcaacga accagacaaa gaccactctt tttatgacga gtatacacca  1500
gcatttgaag cacttgagaa ttcaataaat cccctatata acaaagtcag gagttttgta  1560
accaaaaaag atttctccac cgataaattc aaattgaatt tcgacagcag cagctttcta  1620
tccggttggg caaagaaatc agaatatgag aagagttctg catttatatt tattcgcgac  1680
aatcaatatt acttaggaat aaacaaatgc cttagcaaag aagacattgc ctaccttgag  1740
gactcaacaa gctcatcaga tacaaaaaga gtggtatata tgttccaaaa agtggacgcc  1800
acgaatattc ccagaatatt catccgttcc aaaggttcca atttagctcc tgctgtcaac  1860
gaattccaac tgccgataga aaccattctt gacatttatg acaataagtt cttcactacc  1920
agttatcaga aaaaagaccg gactaaatgg aaagaatcat tgaccaaact cattgactat  1980
tacaagcttg gattcagcca gcacaagtca tacgcagatt tcgacttaaa atggaaagca  2040
tccagtgaat ataacgacat aaatgacttt cttgcagacg tacagagatt ctgctacaga  2100
atcgaattta taaatatcaa ttgggacaag ctgatagaat tcacagaaga tggcaaattt  2160
tacctattcc gcattgcaaa taaagattta tcaggcaata gcacaggtct gcccaatttg  2220
```

```
cacacgattt attggaaaat gctttttgac gaaagcaacc tcaaagatat tgtctataaa  2280
ttgtcgggca atgcggaagt ctttatgcgc tataattcat taaaaaatcc aattgtgcat  2340
aaagcgggag tggagattaa aaacaaatgc ccttttactg aaaaaaagac aagcatattt  2400
gactacgaca ttataaaaga ccgtcgctat acaaaagatc agcttgaact gcatgttcca  2460
atcctaatga acttcaaaag cccatcggca gcaaaaggca aagctttcaa caaagaatgc  2520
ttggaataca taagaaataa tggtataaag catattatag gaatagaccg aggtgaacgg  2580
aatctacttt atatggttat aacagacctt gacggcaaca tcgttgagca aaagtctttg  2640
aaccaaattg cgagcaatcc gaaattgcct cttttcagac aagactacaa caagctgctg  2700
aagacaaagg ctgatgcaaa cgcacaagca cgtcgtgatt gggaaacaat agacaccgta  2760
aaggagataa aattcggctt cttgagtcag attgtacatg agatagcaat ggctatcata  2820
aaatacgatg caattgttgt tttggagaat ctgaacagag ggtttatgca gaaacgaggt  2880
cttgaaaaca acgtctatca gaaattcgaa caaatgctgc ttgacaagtt gagctactat  2940
gtcgacaaaa cgaaacatcc ggaagaggcc ggaggagctt tgcacgcata tcagctctct  3000
gacacttacg cgaacttcaa ttctctgtcg aagaatgcga tggtgcgaca gtcgggtttt  3060
gttttctata ttcctgcatg gcttacaagc aaaatagacc ccgtcacagg attcgcctcc  3120
tttttgaaat ttcacagaga tgacagtatg gcaacaatca aatctacaat ttcaaagttt  3180
gattgtttca aatacgacaa ggaatgcgac atgttccaca tccgcattga ctataacaag  3240
tttagcacaa gctgcagcgg aggtcaacgc aaatgggact tgttcacttt tggcgatcga  3300
atcttggcag aacgcaatac aatgcaaaac agcagatatg tttaccaaac agtcaattta  3360
acttctgaat tcaaaaactt atttgccaca aaggatatcg acatttcagg caacctgaag  3420
gactctatat gcaaaattga ggatgttggc tttttcagaa aactaagcca actcttgtca  3480
ctcacgcttc aattacgcaa cagcaatgct gaaacaggag aagacttctt gatttcccca  3540
gtagctgaca aagatggcaa tttcttcgat tcaagaaact gtcccgactc tctcccaaaa  3600
gacgcagatg ccaatggcgc atacaacatt gctaggaagg gattaatgct tgtcgagcaa  3660
ttgaagagat gcaaagatgt atcaaaattc aagcccgcga taaaaaacga ggactggtta  3720
gactatgttc aacgctga                                                3738
```

```
SEQ ID NO: 23          moltype = DNA  length = 3732
FEATURE                Location/Qualifiers
source                 1..3732
                       mol_type = other DNA
                       organism = synthetic construct
SEQUENCE: 23
gaaatcagta atcggtttac aaacaagtac caggtgtcta agaccctgcg gttcagactg  60
gagcctacag gcgggaccga tgacctgctg tgccaggccc agatcatcga gggcgatgag  120
cggcgcaaca aagaagccat caccatgaaa cagatcctcg acaactgtca caagcagatc  180
atcgaaagag tgctgtccga cttcaacttc aaagagcact ccctggaaga gttctttaag  240
gtgtacacac ggaacgacga tgacagagag aaggatatcg agaacctgca ggcaaagatg  300
cgcaaggaaa tcgccgccgc ctttactaag caagacgtga caaaactgtt ttcttccaag  360
tttaaagact ttgtcgaaag gggtctgatc aagtacgcca gcaacgagaa ggagcggaat  420
atcgtgtccc ggttcaaggg ctttgccaca tacttcaccg gcttcaacac aaaccgcctg  480
aacatgtaca gcgaggaagc caaatctacg gccattagct tccggctgat caaccagaac  540
ctcatcaaat tcatcgacaa tatcctggtg tacaagaagg tgtctcagac cctcccttct  600
gatgtcctga gcaacatcta catcgacttc aaggccatca tcaataccag cagcctggag  660
gagttcttct ccatcaacaa ctacaacaac atcctgaccc agaagcagat cgagatcttc  720
aacgctgtga tcggcggaaa gaaggataag gatgagaaaa ttatcacaaa gggcttcaac  780
cagtacatca atgaatataa tcagaccaac aagaatatca gactgccaaa gatgatgaga  840
ctgttcaatc agatactgag cgaccgggaa ggcgtgtcag ctagacctga gcccttcaac  900
aacgccaacg agacaatcag ctccgtgaga gactgtttta caaacgaaat cagcaagcag  960
atcaccatcc tgtctgaaac caccagtaag atcgagagct tcgacatcga tagaatctac  1020
atcaagggcg gagaggacct gcgggccctg agcaacagca tctacggcta cttcaactac  1080
atccacgata gaatcgctga taagtggaag cacaacaatc ctcagggcaa gaagagcccc  1140
gagagctacc aaaagaatct gaacgcctac ctgaagggca taaagagcgt gagcctgcat  1200
tctatcgcca acatctgtgg cgacaacaag gtgatcgaat attttagaaa tctcggcgcc  1260
gagaacacag tggattttca gagagaaaac gtggtgtccc taattgacaa caaatacaac  1320
tgtgcctcaa acctgctgtc cgacgcccaa atcaccgacg aggagctgag gaccaacagc  1380
agaagcatca aggatctgct cgacgccgtg aagagtgccc agagattctt cagactgctg  1440
tgcggttctg gcaatgagcc tgataaagac cacagctttt atgacgagta cacccctgct  1500
ttcgaggccc tggaaaacag catcaacccc ctgtacaaca aggtccgcag cttcgtgacc  1560
aaaaaggact tcagcacaga caagttcaaa ctgaacttcg acagcagcag cttcctgagc  1620
ggatgggcca agaaaagcga gtacgagaag agcagcgctt tcatcttcat cagggataat  1680
cagtactacc tgggaattaa taagtgcctg agtaaagagg acatcgccta cctggaggac  1740
agcacctcta gcagcgacac aaagagagtg gtgtacatgt ttcagaaggt ggatgccacc  1800
aatatcccaa gaatcttcat cagatccaag ggcagcaacc tggcccctgc tgtgaacgag  1860
ttccagctgc ctatcgaaac catcctggat atctacgaca acaagttctt caccaccagt  1920
taccagaaga aggatagaac caaatggaag gaaagcctga ccaagctgat cgactactac  1980
aagctgggct ttagccagca caagtcctat gccgatttcg atttaaagtg gaaagccagc  2040
tcagaataca atgacatcaa tgatttcctg gccgacgtgc agagattctg ctacagaatt  2100
gagttcatca atatcaattg ggacaagctc atcgagttca cagaggacgg caagttctac  2160
ctgtttagaa tcgccaacaa agacctgtct ggcaacagca ctggcctgcc caatctgcac  2220
accatctact ggaagatgct gttcgacgag agcaacctga aggacatcgt gtacaagctg  2280
agcggcaacg ctgaggtgtt tatgcgctac aacagcctga agaaccccat tgtgcacaag  2340
gccggagtgg aaatcaagaa taagtgtcct ttcaccgaga agaaaaccag catctttgac  2400
tacgacatta tcaaggaccg cagatacacc aaggaccagc tggaactgca tgtgcctatc  2460
ctgatgaact tcaagtctcc atctgccgct aaaggcaaag cctttaacaa ggagtgcctg  2520
gaatacatca gaaacaacgg catcaagcac atcatcggca tcgacagagg agagcggaat  2580
ctgctttaca tggtgatcac agacctggac ggcaacatcg tggaacagaa gtctctgaac  2640
cagatcgcct ccaatccaaa gctgcctctg ttcagacagg actacaacaa gctgctgaaa  2700
accaaagctg acgccaacgc acaagccaga agagactggg agacaataga caccgtgaag  2760
```

```
gagattaagt tcggcttcct gagccagatc gtgcacgaga tcgctatggc catcatcaag  2820
tacgacgcca ttgtggtcct ggaaaacctg aacagaggct tcatgcaaaa acggggcctg  2880
gaaaacaacg tgtatcagaa gttcgagcaa atgctcctcg ataaactgag ctactatgtc  2940
gacaagacca aacaccctga ggaagctggc ggagccctgc acgcctatca gttaagcgat  3000
acctacgcca acttcaattc cttgagcaag aacgctatgg tgagacagtc tggcttcgtg  3060
ttctacatcc ccgcctggct gaccagcaag atcgatcctg tgaccggctt cgcctctttc  3120
ctgaagttcc acagagatga tagcatggcc accatcaaga gcaccatctc caaattcgac  3180
tgcttcaagt acgacaagga atgcgacatg ttccacatca gaatagatta caacaaattt  3240
agcacttcat gcagcggtgg ccagcggaag tgggatctgt tcacattcgg agacagaatc  3300
ctggccgaga gaaacaccat gcagaacagt agatacgttt accagacagt taacctgacc  3360
tctgagttca agaacctgtt cgccacaaag gatatcgata taagcgggaa cctgaaggat  3420
agcatctgca agatcgagga cgtgggcttc ttccggaagc tgagccagct gctgagcctg  3480
acactacagc ttcggaacag caacgctgaa accggagaag atttcctgat cagccctgtg  3540
gccgacaagg acggcaactt ctttgacagc agaaactgcc ccgacagcct gccaaaggat  3600
gcagacgcga atggcgctta taacattgcc aggaagggcc tgatgctggt ggagcaactg  3660
aagcggtgca aggacgtgag caagttcaag cctgctatca agaacgagga ctggctggac  3720
tacgtgcagc gg                                                      3732

SEQ ID NO: 24          moltype = DNA  length = 3849
FEATURE                Location/Qualifiers
source                 1..3849
                       mol_type = other DNA
                       organism = synthetic construct
SEQUENCE: 24
atgggcgaaa tcagtaatcg gtttacaaac aagtaccagg tgtctaagac cctgcggttc  60
agactggagc ctacaggcgg gaccgatgac ctgctgtgcc aggcccagat catcgagggc  120
gatgagcggc gcaacaaaga agccatcacc atgaaacaga tcctcgacaa ctgtcacaag  180
cagatcatcg aaagagtgct gtccgacttc aacttcaaag agcactccct ggaagagttc  240
tttaaggtgt acacacggaa cgacgatgac agagagaagg atatcgagaa cctgcaggca  300
aagatgcgca aggaaatcgc cgccgccttt actaagcaag acgtgacaaa actgttttct  360
tccaagttta aagactttgt cgaaaggggt ctgatcaagt acgccagcaa cgagaaggag  420
cggaatatcg tgtcccggtt caagggcttt gccacatact tcaccggctt caacacaaac  480
cgcctgaaca tgtacagcga ggaagccaaa tctacggcca ttagcttccg gctgatcaac  540
cagaacctca tcaaattcat cgacaatatc ctggtgtaca agaaggtgtc tcagaccctc  600
ccttctgatg tcctgagcaa catctacatc gacttcaagg ccatcatcaa taccagcagc  660
ctggaggagt tcttctccat caacaactac aacaacatcc tgacccagaa gcagatcgag  720
atcttcaacg ctgtgatcgg cggaaagaag gataaggatg agaaaattat cacaaagggc  780
ttcaaccagt acatcaatga atataatcag accaacaaga atatcagact gccaaagatg  840
atgagactgt tcaatcagat actgagcgac cgggaaggcg tgtcagctag acctgagccc  900
ttcaacaacg ccaacgagac aatcagctcc gtgagagact gttttacaaa cgaaatcagc  960
aagcagatca ccatcctgtc tgaaaccacc agtaagatcg agagcttcga catcgataga  1020
atctacatca agggcggaga ggacctgcgg gccctgagca acagcatcta cggctacttc  1080
aactacatcc acgatagaat cgctgataag tggaagcaca acaatcctca gggcaagaag  1140
agccccgaga gctaccaaaa gaatctgaac gcctacctga agggcataaa gagcgtgagc  1200
ctgcattcta tcgccaacat ctgtggcgac aacaaggtga tcgaatattt tagaaatctc  1260
ggcgccgaga acacagtgga ttttcagaga gaaaacgtgg tgtccctaat tgacaacaaa  1320
tacaactgtg cctcaaacct gctgtccgac gcccaaatca ccgacgagga gctgaggacc  1380
aacagcagaa gcatcaagga tctgctcgac gccgtgaaga gtgcccagag attcttcaga  1440
ctgctgtgcg gttctggcaa tgagcctgat aaagaccaca gcttttatga cgagtacacc  1500
cctgctttcg aggccctgga aaacagcatc aacccccctgt acaacaaggt ccgcagcttc  1560
gtgaccaaaa aggacttcag cacagacaag ttcaaactga acttcgacag cagcagcttc  1620
ctgagcggat gggccaagaa aagcgagtac gagaagagca gcgctttcat cttcatcagg  1680
gataatcagt actacctggg aattaataag tgcctgagta aagaggacat cgcctacctg  1740
gaggacagca cctctagcag cgacacaaag agagtggtgt acatgtttca gaaggtggat  1800
gccaccaata tcccaagaat cttcatcaga tccaagggca gcaacctggc ccctgctgtg  1860
aacgagttcc agctgcctat cgaaaccatc ctggatatct acgacaacaa gttcttcacc  1920
accagttacc agaagaagga tagaaccaaa tggaaggaaa gcctgaccaa gctgatcgac  1980
tactacaagc tgggctttag ccagcacaag tcctatgccg atttcgattt aaagtggaaa  2040
gccagctcag aatacaatga catcaatgat ttcctggccg acgtgcagag attctgctac  2100
agaattgagt tcatcaatat caattgggac aagctcatcg agttcacaga ggacggcaag  2160
ttctacctgt ttagaatcgc caacaaagac ctgtctggca acagcactgg cctgcccaat  2220
ctgcacacca tctactggaa gatgctgttc gacgagagca acctgaagga catcgtgtac  2280
aagctgagcg gcaacgctga ggtgtttatg cgctacaaca gcctgaagaa ccccattgtg  2340
cacaaggccg gagtggaaat caagaataag tgtcctttca ccgagaagaa aaccagcatc  2400
tttgactacg acattatcaa ggaccgcaga tacaccaagg accagctgga actgcatgtg  2460
cctatcctga tgaacttcaa gtctccatct gccgctaaag gcaaagcctt taacaaggag  2520
tgcctggaat acatcagaaa caacggcatc aagcacatca tcggcatcga cagaggagag  2580
cggaatctgc tttacatggt gatcacagac ctggacggca acatcgtgga acagaagtct  2640
ctgaaccaga tcgcctccaa tccaaagctg cctctgttca gacaggacta caacaagctg  2700
ctgaaaacca aagctgacgc caacgcacaa gccagaagag actgggagac aatagacacc  2760
gtgaaggaga ttaagttcgg cttcctgagc cagatcgtgc acgagatcgc tatggccatc  2820
atcaagtacg acgccattgt ggtcctggaa aacctgaaca gaggcttcat gcaaaaacgg  2880
ggcctggaaa acaacgtgta tcagaagttc gagcaaatgc tcctcgataa actgagctac  2940
tatgtcgaca agaccaaaca ccctgaggaa gctggcggag ccctgcacgc ctatcagtta  3000
agcgatacct acgccaactt caattccttg agcaagaacg ctatggtgag acagtctggc  3060
ttcgtgttct acatccccgc ctggctgacc agcaagatcg atcctgtgac cggcttcgcc  3120
tctttcctga agttccacag agatgatagc atggccacca tcaagagcac catctccaaa  3180
ttcgactgct tcaagtacga caaggaatgc gacatgttcc acatcagaat agattacaac  3240
aaatttagca cttcatgcag cggtggccag cggaagtggg atctgttcac attcggagac  3300
```

```
agaatcctgg ccgagagaaa caccatgcag aacagtagat acgtttacca gacagttaac  3360
ctgacctctg agttcaagaa cctgttcgcc acaaaggata tcgatataag cgggaacctg  3420
aaggatagca tctgcaagat cgaggacgtg ggcttcttcc ggaagctgag ccagctgctg  3480
agcctgacac tacagcttcg gaacagcaac gctgaaaccg gagaagattt cctgatcagc  3540
cctgtggccg acaaggacgg caacttcttt gacagcagaa actgccccga cagcctgcca  3600
aaggatgcag acgcgaatgg cgcttataac attgccagga agggcctgat gctggtggag  3660
caactgaagc ggtgcaagga cgtgagcaag ttcaagcctg ctatcaagaa cgaggactgg  3720
ctggactacg tgcagcggtc tagaaagcgg acagcagacg gctccgaatt tgaaagccct  3780
aagaaaaaga gaaaggtggg atccggcaaa cctatcccca atcccctgct gggcctggac  3840
agcacctga                                                         3849

SEQ ID NO: 25           moltype = AA  length = 1214
FEATURE                 Location/Qualifiers
source                  1..1214
                        mol_type = protein
                        organism = unidentified
SEQUENCE: 25
KINAFINCYS MSKTLRFKLA PEYETEKNLL EKGFLDRDKL RADDYDLMKK VIDKYHKHFI  60
DKALEGFKFD LLQEYAEAFY SQSADDDGKK LEEIKKKMCK ELATCFSKQD EFKLLDKKEL  120
VEKLIPAAEF IEDEEKDIAK RFKGFTTYFT GFNENRQNLY AAELKHGTIA FRLIEENLPA  180
FLYNCKKGVK IFEGLDAVDA ETLNNELGEI LSIENVKDVL SVEYYNKTLT QNGIDVYNRI  240
IGGYTQEDGT KIKGVNEYVN LYNQTHDKKL PSLAKLKKQI LSDSYSLSFL PAKFNDDSEL  300
LLSLKKFYST VNEETGLSVE KAIQEMRDVF SHIDDCDLHN VFIDAKFINK VSNDVFGNWS  360
VLIDGINAEY EKLNPFNGKN LDNYEEKRKA FLNKIESYSV DALQAYSGKE EKIADYVQKR  420
AVELYDSVAC AYENMSNKVI NAREGKVKLY QDDEKTEIIK TFLDAVQEFK KFAEMFCYDG  480
TDGDTTFYGE FANYYGQIAE IIPLYNKCRN YLTKKPYSED KIKINFDNAE LLHGWDANKE  540
KNYLTVLLFK NGSYYLGILD KKHKNVLIKD VPEKTQEEPC FKKMIYKLLP DPKRNMPRII  600
LHAKSNKKLF EPSDEIYRIY ETESFKTDID DCHRLIDFYK ESISKYEDWK TFGFKFKETS  660
EYKNIGQFYN EVKEQGYKIS FTDIPESYVK DLVNDGKLYL FRLANKDFSP YSKGKKNLHT  720
MYFEGIFDPE NIKEKVYALN GGGELFFRCA SLNYDKPTHP KNVPIKNKTY DFRTDNAKKE  780
TSTFEYDLIK DKRYTKDQYT LHCPVTLNFK ERGIERINDL VRQSLRESDD NYVIGIDRGE  840
RNLIYISVID GKGKIVEQFS MNNLLSGNDV SIDFHKMLET REHERDASRK NWNTIDNIKD  900
LKQGYLSYVV KKICDLVVKY DAIVAMEDLN VGFKHGREKF ERQVYQKFEK ALVDKMSYIV  960
NKNASPHSDG GLFRAYQLTN KKYNENEKQN GFIFYVRAWN TSKIDPTTGF VNMLPLKYQS  1020
KEKSKEFFDK FEDIFYDENK DMFGFTFRYD DFGINIDHKN EWTAYSNGER IITVRNSFGK  1080
WDKAKIVLTP AFKKLFDDYN VDCRGDVKRQ IMNVDDKDFF VRLYKLLSYT MQLRNSDDVD  1140
DYILSPVVNA EGKFFDSRNS DGSLPCDADA NGAYHIAKKA MWAIGKIKEA DEESFKKTSL  1200
AIDNKTWLEF VQKA                                                   1214

SEQ ID NO: 26           moltype = AA  length = 1215
FEATURE                 Location/Qualifiers
source                  1..1215
                        mol_type = protein
                        organism = unidentified
SEQUENCE: 26
MKINAFINCY SMSKTLRFKL APEYETEKNL LEKGFLDRDK LRADDYDLMK KVIDKYHKHF  60
IDKALEGFKF DLLQEYAEAF YSQSADDDGK KLEEIKKKMC KELATCFSKQ DEFKLLDKKE  120
LVEKLIPAAE FIEDEEKDIA KRFKGFTTYF TGFNENRQNL YAAELKHGTI AFRLIEENLP  180
AFLYNCKKGV KIFEGLDAVD AETLNNELGE ILSIENVKDV LSVEYYNKTL TQNGIDVYNR  240
IIGGYTQEDG TKIKGVNEYV NLYNQTHDKK LPSLAKLKKQ ILSDSYSLSF LPAKFNDDSE  300
LLLSLKKFYS TVNEETGLSV EKAIQEMRDV FSHIDDCDLH NVFIDAKFIN KVSNDVFGNW  360
SVLIDGINAE YEKLNPFNGK NLDNYEEKRK AFLNKIESYS VDALQAYSGK EEKIADYVQK  420
RAVELYDSVA CAYENMSNKV INAREGKVKL YQDDEKTEII KTFLDAVQEF KKFAEMFCYD  480
GTDGDTTFYG EFANYYGQIA EIIPLYNKCR NYLTKKPYSE DKIKINFDNA ELLHGWDANK  540
EKNYLTVLLF KNGSYYLGIL DKKHKNVLIK DVPEKTQEEP CFKKMIYKLL PDPKRNMPRI  600
ILHAKSNKKL FEPSDEIYRI YETESFKTDI DDCHRLIDFY KESISKYEDW KTFGFKFKET  660
SEYKNIGQFY NEVKEQGYKI SFTDIPESYV KDLVNDGKLY LFRLANKDFS PYSKGKKNLH  720
TMYFEGIFDP ENIKEKVYAL NGGGELFFRC ASLNYDKPTH PKNVPIKNKT YDFRTDNAKK  780
ETSTFEYDLI KDKRYTKDQY TLHCPVTLNF KERGIERIND LVRQSLRESD DNYVIGIDRG  840
ERNLIYISVI DGKGKIVEQF SMNNLLSGND VSIDFHKMLE TREHERDASR KNWNTIDNIK  900
DLKQGYLSYV VKKICDLVVK YDAIVAMEDL NVGFKHGREK FERQVYQKFE KALVDKMSYI  960
VNKNASPHSD GGLFRAYQLT NKKYNENEKQ NGFIFYVRAW NTSKIDPTTG FVNMLPLKYQ  1020
SKEKSKEFFD KFEDIFYDEN KDMFGFTFRY DDFGINIDHK NEWTAYSNGE RIITVRNSFG  1080
KWDKAKIVLT PAFKKLFDDY NVDCRGDVKR QIMNVDDKDF FVRLYKLLSY TMQLRNSDDV  1140
DDYILSPVVN AEGKFFDSRN SDGSLPCDAD ANGAYHIAKK AMWAIGKIKE ADEESFKKTS  1200
LAIDNKTWLE FVQKA                                                  1215

SEQ ID NO: 27           moltype = AA  length = 1252
FEATURE                 Location/Qualifiers
source                  1..1252
                        mol_type = protein
                        organism = synthetic construct
SEQUENCE: 27
MGKINAFINC YSMSKTLRFK LAPEYETEKN LLEKGFLDRD KLRADDYDLM KKVIDKYHKH  60
FIDKALEGFK FDLLQEYAEA FYSQSADDDG KKLEEIKKKM CKELATCFSK QDEFKLLDKK  120
ELVEKLIPAA EFIEDEEKDI AKRFKGFTTY FTGFNENRQN LYAAELKHGT IAFRLIEENL  180
PAFLYNCKKG VKIFEGLDAV DAETLNNELG EILSIENVKD VLSVEYYNKT LTQNGIDVYN  240
RIIGGYTQED GTKIKGVNEY VNLYNQTHDK KLPSLAKLKK QILSDSYSLS FLPAKFNDDS  300
ELLLSLKKFY STVNEETGLS VEKAIQEMRD VFSHIDDCDL HNVFIDAKFI NKVSNDVFGN  360
```

```
WSVLIDGINA EYEKLNPFNG KNLDNYEEKR KAFLNKIESY SVDALQAYSG KEEKIADYVQ  420
KRAVELYDSV ACAYENMSNK VINAREGKVK LYQDDEKTEI IKTFLDAVQE FKKFAEMFCY  480
DGTDGDTTFY GEFANYYGQI AEIIPLYNKC RNYLTKKPYS EDKIKINFDN AELLHGWDAN  540
KEKNYLTVLL FKNGSYYLGI LDKKHKNVLI KDVPEKTQEE PCFKKMIYKL LPDPKRNMPR  600
IILHAKSNKK LFEPSDEIYR IYETESFKTD IDDCHRLIDF YKESISKYED WKTFGFKFKE  660
TSEYKNIGQF YNEVKEQGYK ISFTDIPESY VKDLVNDGKL YLFRLANKDF SPYSKGKKNL  720
HTMYFEGIFD PENIKEKVYA LNGGGELFFR CASLNYDKPT HPKNVPIKNK TYDFRTDNAK  780
KETSTFEYDL IKDKRYTKDQ YTLHCPVTLN FKERGIERIN DLVRQSLRES DDNYVIGIDR  840
GERNLIYISV IDGKGKIVEQ FSMNNLLSGN DVSIDFHKML ETREHERDAS RKNWNTIDNI  900
KDLKQGYLSY VVKKICDLVV KYDAIVAMED LNVGFKHGRE KFERQVYQKF EKALVDKMSY  960
IVNKNASPHS DGGLFRAYQL TNKKYNENEK QNGFIFYVRA WNTSKIDPTT GFVNMLPLKY  1020
QSKEKSKEFF DKFEDIFYDE NKDMFGFTFR YDDFGINIDH KNEWTAYSNG ERIITVRNSF  1080
GKWDKAKIVL TPAFKKLFDD YNVDCRGDVK RQIMNVDDKD FFVRLYKKLS YTMQLRNSDD  1140
VDDYILSPVV NAEGKFFDSR NSDGSLPCDA DANGAYHIAK KAMWAIGKIK EADEESFKKT  1200
SLAIDNKTWL EFVQKASRKR TADGSEFESP KKKRKVGSGK PIPNPLLGLD ST          1252

SEQ ID NO: 28          moltype = DNA  length = 3648
FEATURE                Location/Qualifiers
source                 1..3648
                       mol_type = unassigned DNA
                       organism = unidentified
SEQUENCE: 28
atgaaaatta acgcttttat caactgttat tcgatgtcca agacgttgcg attcaagctt  60
gcgcccgaat acgagacgga aaagaacctt ttggaaaagg gatttcttga tcgcgacaaa  120
ttgcgcgcgg acgattatga tttaatgaaa aaagttatcg ataaatatca caaacatttt  180
atcgataaag cgttggaagg tttcaaattc gatttattgc aagagtatgc cgaagcgttt  240
tattcgcaat cggccgatga cgacggcaaa aaacttgaag aaatcaaaaa gaaaatgtgc  300
aaggagttgg cgacttgttt ttcgaaacaa gacgagttta aattactcga taaaaaagaa  360
ctggtcgaaa aactaatccc tgctgccgaa tttattgaag acgaagaaaa agatattgcg  420
aagagattca aggggtttac gacctatttc acgggattca acgaaaacag gcaaaactta  480
tacgccgcag aactgaaaca cgggacgatt gcgttcagat tgattgaaga aaatttgcct  540
gcatttttgt acaactgcaa aaagggagta aaaatattcg agggactcga cgcagtcgat  600
gcagaaacgc ttaataatga acttggagag attctttcaa tcgaaaacgt aaaagatgta  660
ttaagcgtag agtattacaa taaaacgctc acgcaaaacg gcatagacgt ttacaaccgg  720
attataggcg gctatacaca ggaagacggg acgaaaatca aaggtgtcaa cgagtacgtc  780
aatttgtata accagacgca cgacaaaaaa cttccgtcgc tcgcaaaact caaaaaacag  840
attttaagcg acagttattc gttgtcgttt ttgcccgcaa aattcaacga cgattccgaa  900
ttgcttttat cgcttaaaaa gttttattcg acggtaaacg aagagaccgg tttaagcgta  960
gaaaaggcga tacaggaaat gcgcgacgtt ttttcacaca tcgatgactg tgatttgcat  1020
aacgttttta tcgacgcaaa atttataaac aaggtttcaa acgacgtttt cgggaattgg  1080
agcgttttga ttgacggcat aaatgcggaa tatgagaaac tcaatccgtt caacgggaaa  1140
aacctcgaca attatgagga aaaacgcaaa gcgtttttaa acaagatcga aagctattct  1200
gttgacgcgt tgcaggcata ttcgggtaaa gaagaaaaaa tcgccgacta cgttcaaaaa  1260
cgtgcggtcg aactttacga tagtgtcgca tgcgcatatg agaatatgag taataaggta  1320
ataaatgcgc gagaagggaa ggttaaactt tatcaggacg atgaaaaaac cgaaataatc  1380
aaaacgtttt tggacgcggt acaggaattc aaaaagtttg ccgagatgtt ttgctatgac  1440
ggcaccgacg gcgatacgac gttttacggc gaatttgcga attattacgg acaaattgcc  1500
gaaattatac cgctttacaa taaatgcagg aactatttga cgaaaaagcc gtattccgaa  1560
gacaaaatca aaataaactt tgacaacgct gagcttttgc atggatggga cgcaaacaaa  1620
gaaaagaatt atctgactgt attattattt aaaaacggca gttattatct cggtattctg  1680
gataaaaagc ataagaacgt tttgatcaaa gacgtgcccg aaaagacgca ggaggagccg  1740
tgtttcaaga aaatgattta caaattactc cctgatccga aacgaaatat gcctagaata  1800
atattacatg caaaaagtaa caagaagttg tttgagccta gtgatgagat atataggata  1860
tatgaaacag aatcgtttaa aactgacatt gacgactgcc ataggttgat tgatttttat  1920
aaagaaagta taagcaagta cgaggactgg aagacgttcg ggttcaagtt caaagaaacg  1980
agcgagtata aaaacatagg gcaattttat aacgaagtta aagagcaggg atataagatt  2040
tcattcacgg atatacccga aagttacgtc aaagacttgg taaacgacgg gaaactgtat  2100
ttattcaggc ttgctaataa agatttttct ccgtacagca agggcaaaaa gaatttgcat  2160
acgatgtatt tcgagggaat atttgatcct gaaaacataa aagaaaaggt ttatgcgctt  2220
aacggcggcg gcgagttgtt tttcagatgc gcgagcttga attacgacaa accgacgcat  2280
ccgaaaaacg taccgattaa aaacaaaacg tatgatttcc gcaccgataa tgcgaaaaaa  2340
gaaacaagca cgtttgaata cgacctcata aaagataagc gatatacgaa agatcaatac  2400
acgttgcatt gtccggtgac gcttaatttt aaggaaagag gaatcgaaag aataaacgat  2460
ctcgtaaggc aatcgttgcg tgaaagtgac gacaactacg taatcggcat tgatcggggc  2520
gaaagaaact taatttacat cagtgttatc gacggaaaag gaaagattgt cgagcaattc  2580
tcgatgaaca atttgttaag cggtaacgac gtgtcgatag atttccacaa aatgctcgaa  2640
acgcgggagc acgagcgcga cgcgtccaga aaaaactgga atacaatcga caatatcaaa  2700
gacttgaagc aaggatattt aagttatgtc gtaaagaaaa tttgcgacct tgtcgtaaaa  2760
tacgacgcga ttgtcgcaat ggaagactta aacgtcgggt tcaagcacgg acgagaaaag  2820
ttcgagcgac aggtatatca gaaatttgaa aaagcacttg tcgacaaaat gagttatatc  2880
gtaaacaaga acgcgtcgcc gcattccgac ggaggtttgt tcagggcata ccagctgacc  2940
aataaaaagt ataatgaaaa cgaaaaacaa aacggtttta ttttctatgt cagagcgtgg  3000
aataccagta agatcgatcc gacgaccggg tttgtaaaca tgcttccgtt aaaatatcag  3060
agcaaagaaa aatcaaaaga atttttcgat aaatttgaag atattttttta cgatgaaaac  3120
aaggatatgt tcggttttac attcagatat gacgatttcg gtataaatat cgatcataaa  3180
aacgaatgga cggcttattc aaacggcgaa cgaataatca ccgtacgaaa ttcgttcggc  3240
aagtgggata aagcgaagat cgtattgacg ccggcattta agaaactgtt tgacgactat  3300
aacgtggatt gtcgcggcga cgtcaaacga cagattatga acgttgacga caaagacttt  3360
ttcgttaggt tatataagct tttgtcgtat acgatgcagt tgagaaactc cgacgatgtt  3420
```

```
gacgactata ttttgtcgcc cgtcgttaat gcggaaggga agttctttga cagtcgcaat  3480
tcggacggca gtttgccttg cgacgcggac gcaaacggag cgtatcatat tgccaaaaag  3540
gcaatgtggg caatcgggaa gataaaagaa gcggacgaag aaagttttaa aaagacaagt  3600
cttgcaatcg acaacaagac gtggcttgaa ttcgttcaaa aggcataa              3648

SEQ ID NO: 29           moltype = DNA  length = 3642
FEATURE                 Location/Qualifiers
source                  1..3642
                        mol_type = other DNA
                        organism = synthetic construct
SEQUENCE: 29
aagatcaacg cttttatcaa ctgttacagc atgagcaaga ccctgagatt caagctggcc  60
cctgagtacg aaaccgagaa gaacctgctg gaaaagggct ttctggaccg ggacaagctg  120
agagccgacg actacgacct gatgaagaag gtgatagaca agtaccacaa gcacttcatc  180
gacaaggccc tggaaggctt caagtttgac ctgctgcaag aatacgctga ggcctttttac  240
agccagagcg ccgacgacga cggcaagaag ctcgaagaga tcaagaagaa gatgtgcaag  300
gagctggcca catgcttcag caagcaagac gagttcaagc tactggataa gaaagagctg  360
gtggaaaagc tgatcccagc cgctgagttc atcgaggacg aggaaaaaga cattgccaag  420
agattcaaag gctttacaac ctactttacc ggcttcaatg aaaacagaca gaatctgtac  480
gccgccgagc tgaagcacgg aacaatcgcc ttcagactga tcgaggagaa cttgcctgcc  540
ttcctgtaca attgcaagaa gggtgttaag atcttcgagg gcctggacgc tgtggatgct  600
gagactctca acaacgagct gggcgagatc ctgagcatcg aaaacgtgaa ggacgtgctg  660
tccgtggagt actacaacaa aaccctgacc caaaacggca tcgatgtgta caatagaatc  720
atcggcggct acacccagga ggatggcacc aagatcaagg gagtgaacga gtacgtgaac  780
ctgtataacc agacacacga caagaaactg ccttctctgg ctaagctgaa gaagcaaatc  840
ctgtctgact cctattctct gtcattcctg cccgccaagt ttaacgacga ctctgagctc  900
ctgctcagcc tgaagaagtt ttacagcacc gtgaacgagg aaacaggact gagcgtggag  960
aaagctatcc aggagatgag agatgtgttc agccacattg acgactgcga ccttcacaac  1020
gtctttatcg atgccaagtt catcaacaag gtgagcaacg acgtgttcgg caactggtcg  1080
gtcctgatcg atggcatcaa tgccgagtac gagaagctga acccccttcaa cggcaagaac  1140
ctggacaact acgaggaaaa aagaaaggcc tttctgaaca aaatcgagag ctatagcgtg  1200
gacgccctgc aggcctacag cggcaaggaa gagaagatcg ccgattatgt gcagaaacgg  1260
gccgttgaac tgtacgacag cgtggcttgt gcttacgaaa acatgagcaa caaagtgatc  1320
aacgccccggg aaggcaaggt gaagctgtac caggacgacg aaaagaccga gattatcaag  1380
accttcctgg atgctgttca ggagttcaag aagttcgccg aaatgttctg ctacgatgga  1440
acagatggag ataccacctt ctacggcgag ttcgccaatt attacggcca gatcgccgag  1500
ataatccccc tgtacaacaa gtgcagaaac tatctgacaa agaaacctta cagcgaggac  1560
aagattaaga tcaacttcga taacgcggaa ctgctgcatg gatgggacgc caacaaggaa  1620
aagaactacc tgacagtcct gctgttcaaa aatggatcat attacctggg catcctggat  1680
aaaaagcata agaacgtgct gattaaggac gttcctgaaa agacacagga agagccctgt  1740
ttcaaaaaaa tgatctacaa gctgctgcct gatcccaagc ggaatatgcc taggatcatc  1800
ttgcacgcca aagcaataa aaaactgttc gagcctagcg atgagatcta cagaatctat  1860
gagacagaga gcttcaagac cgacatcgac gattgccaca gactgatcga tttctacaag  1920
gaatccatca gcaagtacga ggactggaaa acctttggat ttaaattcaa agaaaccagc  1980
gagtacaaga acatcggaca gttctacaac gaggtgaagg aacagggcta caagattagc  2040
ttcaccgaca tccctgagag ctacgtgaag gatctggtga atgatggcaa gctgtatctg  2100
tttagactcg ccaacaagga tttctctcca tactccaagg gcaaaaagaa cctgcacacc  2160
atgtacttcg agggaatctt cgaccccgaa aacatcaagg agaaagtgta cgccctgaac  2220
ggcggcggcg agctgttctt ccgctgtgcc tctctgaact acgacaagcc tacccacccc  2280
aagaacgtgc ctatcaagaa caagacctac gattttagaa ccgataacgc taagaaagaa  2340
accagtacat tcgagtacga cctgatcaaa gataaacggt acacaaagga ccagtacaca  2400
ctgcactgcc ctgtgacact gaatttcaag gagcgtggaa tcgaacgcat caacgacctg  2460
gtgcggcaga gcctgcggga aagcgacgac aactacgtca tcggcatcga cagaggggag  2520
agaaatctga tctacatctc tgtgatcgac ggcaagggca agatcgtcga gcagttcagc  2580
atgaacaacc tgctgtccgg caacgacgtc agcatcgact tccacaagat gctggaaacc  2640
agagagcacg agcgggacgc ctccagaaag aactggaaca ccatcgacaa catcaaggac  2700
ctgaagcagg gctacctgag ttacgtggtg aaaaagatct gcgacctggt cgtgaagtat  2760
gatgccatcg tggctatgga ggatctgaac gtgggcttta aacacggcag agagaagttc  2820
gagagacagg tgtaccagaa gtttgagaaa gccctggtgg acaagatgag ctacatcgtg  2880
aataaaaatg ctagtcctca cagcgatggc ggcctgttca gagcttatca gctgaccaac  2940
aagaaataca acgagaatga aaagcagaac ggattcatct tttacgtgag agcctggaat  3000
accagcaaga tcgacccaac aacaggcttc gtgaacatgt tgccactgaa ataccaatct  3060
aaggaaaagt ccaaggagtt cttcgacaag ttcgaggata tcttctatga tgaaaacaaa  3120
gacatgttcg gcttcacctt ccggtacgac gacttcggca tcaacatcga ccacaagaat  3180
gaatggaccg cctacagcaa tggtgagcgg atcatcaccg tgcggaacag cttcggcaaa  3240
tgggataaag cgaagatcgt gctgacccct gcttttaaga agctgttcga tgattacaac  3300
gtggactgca gaggcgacgt gaagcgacag attatgaacg tggacgacaa agatttcttc  3360
gtgcggctgt acaagctgct gagctacacc atgcagctga gaaacagcga cgacgtggac  3420
gattacatcc tgagccccgt ggtgaatgcc gaaggcaagt tcttcgacag cagaaactct  3480
gacggctctc tgccttgtga cgccgatgcc aacggcgcct accacatcgc caagaaggcc  3540
atgtgggcca tcggcaagat caaggaagcc gatgaggaat cttttaagaa aacctccctc  3600
gccatcgaca acaaaacctg gctggagttc gtgcagaaag cc                    3642

SEQ ID NO: 30           moltype = DNA  length = 3759
FEATURE                 Location/Qualifiers
source                  1..3759
                        mol_type = other DNA
                        organism = synthetic construct
SEQUENCE: 30
```

```
atgggcaaga tcaacgcttt tatcaactgt tacagcatga gcaagaccct gagattcaag  60
ctggcccctg agtacgaaac cgagaagaac ctgctggaaa agggctttct ggaccgggac  120
aagctgagag ccgacgacta cgacctgatg aagaaggtga tagacaagta ccacaagcac  180
ttcatcgaca aggccctgga aggcttcaag tttgacctgc tgcaagaata cgctgaggcc  240
ttttacagcc agagcgccga cgacgacggc aagaagctcg aagagatcaa gaagaagatg  300
tgcaaggagc tggccacatg cttcagcaag caagacgagt tcaagctact ggataagaaa  360
gagctggtgg aaaagctgat cccagccgct gagttcatcg aggacgagga aaaagacatt  420
gccaagagat tcaaaggctt tacaacctac tttaccggct tcaatgaaaa cagacagaat  480
ctgtacgccg ccgagctgaa gcacggaaca atcgccttca gactgatcga ggagaacttg  540
cctgccttcc tgtacaattg caagaagggt gttaagatct tcgagggcct ggacgctgtg  600
gatgctgaga ctctcaacaa cgagctgggc gagatcctga gcatcgaaaa cgtgaaggac  660
gtgctgtccg tggagtacta caacaaaacc ctgacccaaa acggcatcga tgtgtacaat  720
agaatcatcg gcggctacac ccaggaggat ggcaccaaga tcaagggagt gaacgagtac  780
gtgaacctgt ataaccagac acacgacaag aaactgcctt ctctggctaa gctgaagaag  840
caaatcctgt ctgactccta ttctctgtca ttcctgcccg ccaagtttaa cgacgactct  900
gagctcctgc tcagcctgaa gaagttttac agcaccgtga acgaggaaac aggactgagc  960
gtggagaaag ctatccagga gatgagagat gtgttcagcc acattgacga ctgcgacctt  1020
cacaacgtct ttatcgatgc caagttcatc aacaaggtga gcaacgacgt gttcggcaac  1080
tggtcggtcc tgatcgatgg catcaatgcc gagtacgaga agctgaaccc cttcaacggc  1140
aagaacctgg acaactacga ggaaaaaaga aaggcctttc tgaacaaaat cgagagctat  1200
agcgtggacg ccctgcaggc ctacagcggc aaggaagaga agatcgccga ttatgtgcag  1260
aaacgggccg ttgaactgta cgacagcgtg gcttgtgctt acgaaaacat gagcaacaaa  1320
gtgatcaacg cccgggaagg caaggtgaag ctgtaccagg acgacgaaaa gaccgagatt  1380
atcaagacct tcctggatgc tgttcaggag ttcaagaagt tcgccgaaat gttctgctac  1440
gatggaacag atggagatac caccttctac ggcgagttcg ccaattatta cggccagatc  1500
gccgagataa tcccccctgta caacaagtgc agaaactatc tgacaaagaa accttacagc  1560
gaggacaaga ttaagatcaa cttcgataac gcggaactgc tgcatggatg ggacgccaac  1620
aaggaaaaga actacctgac agtcctgctg ttcaaaaatg gatcatatta cctgggcatc  1680
ctggataaaa agcataagaa cgtgctgatt aaggacgttc ctgaaaagac acaggaagag  1740
ccctgtttca aaaaaatgat ctacaagctg ctgcctgatc ccaagcggaa tatgcctagg  1800
atcatcttgc acgccaaaag caataaaaaa ctgttcgagc ctagcgatga gatctacaga  1860
atctatgaga cagagagctt caagaccgac atcgacgatt gccacagact gatcgatttc  1920
tacaaggaat ccatcagcaa gtacgaggac tggaaaacct ttggatttaa attcaaagaa  1980
accagcgagt acaagaacat cggacagttc tacaacgagg tgaaggaaca gggctacaag  2040
attagcttca ccgacatccc tgagagctac gtgaaggatc tggtgaatga tggcaagctg  2100
tatctgttta gactcgccaa caaggatttc tctccatact ccaagggcaa aaagaacctg  2160
cacaccatgt acttcgaggg aatcttcgac cccgaaaaca tcaaggagaa agtgtacgcc  2220
ctgaacggcg gcggcgagct gttcttccgc tgtgcctctc tgaactacga caagcctacc  2280
caccccaaga acgtgcctat caagaacaag acctacgatt ttagaaccga taacgctaag  2340
aaagaaacca gtacattcga gtacgacctg atcaaagata aacggtacac aaaggaccag  2400
tacacactgc actgccctgt gacactgaat ttcaaggagc gtggaatcga acgcatcaac  2460
gacctggtgc ggcagagcct gcgggaaagc gacgacaact acgtcatcgg catcgacaga  2520
ggggagagaa atctgatcta catctctgtg atcgacggca agggcaagat cgtcgagcag  2580
ttcagcatga acaacctgct gtccggcaac gacgtcagca tcgacttcca caagatgctg  2640
gaaaccagag agcacgagcg ggacgcctcc agaaagaact ggaacaccat cgacaacatc  2700
aaggacctga agcagggcta cctgagttac gtggtgaaaa agatctgcga cctggtcgtg  2760
aagtatgatg ccatcgtggc tatggaggat ctgaacgtgg gctttaaaca cggcagagag  2820
aagttcgaga gacaggtgta ccagaagttt gagaaagccc tggtggacaa gatgagctac  2880
atcgtgaata aaaatgctag tcctcacagc gatggcggcc tgttcagagc ttatcagctg  2940
accaacaaga aatacaacga gaatgaaaag cagaacggat tcatctttta cgtgagagcc  3000
tggaatacca gcaagatcga cccaacaaca ggcttcgtga acatgttgcc actgaaatac  3060
caatctaagg aaaagtccaa ggagttcttc gacaagttcg aggatatctt ctatgatgaa  3120
aacaaagaca tgttcggctt caccttccgg tacgacgact tcggcatcaa catcgaccac  3180
aagaatgaat ggaccgccta cagcaatggt gagcggatca tcaccgtgcg gaacagcttc  3240
ggcaaatggg ataaagcgaa gatcgtgctg acccctgctt ttaagaagct gttcgatgat  3300
tacaacgtgg actgcagagg cgacgtgaag cgacagatta tgaacgtgga cgacaaagat  3360
ttcttcgtgc ggctgtacaa gctgctgagc tacaccatgc agctgagaaa cagcgacgac  3420
gtggacgatt acatcctgag ccccgtggtg aatgccgaag gcaagttctt cgacagcaga  3480
aactctgacg gctctctgcc ttgtgacgcc gatgccaacg gcgcctacca catcgccaag  3540
aaggccatgt gggccatcgg caagatcaag gaagccgatg aggaatcttt taagaaaacc  3600
tccctcgcca tcgacaacaa aacctggctg gagttcgtgc agaaagcctc tagaaagcgg  3660
acagcagacg gctccgaatt tgaaagccct aagaaaaaga gaaaggtggg atccggcaaa  3720
cctatcccca atcccctgct gggcctggac agcacctga                        3759
```

```
SEQ ID NO: 31          moltype = AA  length = 1301
FEATURE                Location/Qualifiers
source                 1..1301
                       mol_type = protein
                       organism = unidentified
SEQUENCE: 31
SKLSTFNEHF QKTLTLRNEL VPVGKTLENI ISSNVLINDE KRSEDYKKAK EIIDSYHREF  60
IEKSLSSVNV DWNDLYSYLS KKEPEDYAQK QKFLEELENI LLEKRKIIVK QFEQYVFGSY  120
TDSKGKKTKD LKFENLFKSE LFDYLLPNFL KNDEDKKVIG SFNKFTSYFT GFYENRKNLY  180
KSEPLPTAVA YRIVNENFPK FISNKNIFRV WKDNVPQFIE IAKTKLREEG ISDLNIELKF  240
DLTNFNSCLN QTGIDTYNDL IGQLNFAINL ECQKDKNLCD LLRKKRSLKM VPLYKQILSD  300
NDSSFSIDEF DNDESAIKDV ISFYKKMIGE NCPQRTLSEL LHGLSSHDLE KIFVQGKNLN  360
SVSKNLFGGK NWSLLRDAVI EEKSKEKVFK KVIKSNSTAD ELDKVLSKEE FSISFLSKVS  420
GKDLSVEIDK FVKKQDELLV ENNIQNWPSS LKNSEEKNLI KAPLDFLLNF YRFAQSFSSN  480
NIDKDMSFYA DFDESLSSLE NVIGLYNKVR NYATKKPYTL EKIKLNFENP NLASGWSESK  540
```

-continued

ENDCLSIILL KEKKYFLGIF NKNNKPNFSE GISHSLSSNG CYRKMRYLLF KGFNKMLPKC 600
AFTGEVKDHF KESSDDFSLF NKDTFISPLV ITKEIFDLAC SKEKVKKYQK EYEKINRAEY 660
RQSLVKWITF GLKFLSSYKT TTQFDLSNLK RPEEYCDLKE FYEDVDNLTY KIEFLNIKEE 720
DVDALVEKGQ LYLFEIRNKD FAKNASGTPN LHTLYFKSIF DSKNLENGIV KLNGEAEIFY 780
RKKSLKKDDI TVHREGSYLV NKVCVDPNSG KTEQIPDKIY ENIYAFVNGK SRDLSKEDEV 840
YYAKATIKKA THEIVKDRRF TVDKFFFHCP ITINYKSKDK PSKFNDKVLD FLRNNKDINI 900
IGIDRGERNL IYVTVINQNG EIIDCKSFNT IKHQSSTVNY DVDYHNKLQE REKNRKEEKR 960
SWNSITKIAD LKEGYLSAVI HEVSLMMVKY NAIVVMENLN QGFKRIRGGI AERSVYQKFE 1020
KMLIDKLNYF VIKNENWTNP GGVLNGYQLT NKVSTIKDIG NQCGFLFYVP ATYTSKIDPS 1080
TGFVNLINFN KYKNSEDRRK LICSFDKICF VQNENLFKFS IDYGKLCPDS KIAIKKWDVF 1140
SYGTRIIKEN LTTGHIEENP EYDPTEELKS LLSSRGIEYQ KGQNLLETIP TSDMTREFWN 1200
SLFKIFKAIL QMRNSLTNSP IDRLLSPVKG KDGTFFDTDK VEGTKFEKLK DADANGAYNI 1260
ALKGLLVLEK NDSVESNKDL KNVKKISLED WLKFVQITLR D 1301

SEQ ID NO: 32 moltype = AA length = 1302
FEATURE Location/Qualifiers
source 1..1302
mol_type = protein
organism = unidentified
SEQUENCE: 32
MSKLSTFNEH FQKTLTLRNE LVPVGKTLEN IISSNVLIND EKRSEDYKKA KEIIDSYHRE 60
FIEKSLSSVN VDWNDLYSYL SKKEPEDYAQ KQKFLEELEN ILLEKRKIIV KQFEQYVFGS 120
YTDSKGKKTK DLKFENLFKS ELFDYLLPNF LKNDEDKKVI GSFNKFTSYF TGFYENRKNL 180
YKSEPLPTAV AYRIVNENFP KFISNKNIFR VWKDNVPQFI EIAKTKLREE GISDLNIELK 240
FDLTNFNSCL NQTGIDTYND LIGQLNFAIN LECQKDKNLC DLLRKKRSLK MVPLYKQILS 300
DNDSSFSIDE FDNDESAIKD VISFYKKMIG ENCPQRTLSE LLHGLSSHDL EKIFVQGKNL 360
NSVSKNLFGG KNWSLLRDAV IEEKSKEKVF KKVIKSNSTA DELDKVLSKE EFSISFLSKV 420
SGKDLSVEID KFVKKQDELL VENNIQNWPS SLKNSEEKNL IKAPLDFLLN FYRFAQSFSS 480
NNIDKDMSFY ADFDESLSSL ENVIGLYNKV RNYATKKPYT LEKIKLNFEN PNLASGWSES 540
KENDCLSIIL LKEKKYFLGI FNKNNKPNFS EGISHSLSSN GCYRKMRYLL FKGFNKMLPK 600
CAFTGEVKDH FKESSDDFSL FNKDTFISPL VITKEIFDLA CSKEKVKKYQ KEYEKINRAE 660
YRQSLVKWIT FGLKFLSSYK TTTQFDLSNL KRPEEYCDLK EFYEDVDNLT YKIEFLNIKE 720
EDVDALVEKG QLYLFEIRNK DFAKNASGTP NLHTLYFKSI FDSKNLENGI VKLNGEAEIF 780
YRKKSLKKDD ITVHREGSYL VNKVCVDPNS GKTEQIPDKI YENIYAFVNG KSRDLSKEDE 840
VYYAKATIKK ATHEIVKDRR FTVDKFFFHC PITINYKSKD KPSKFNDKVL DFLRNNKDIN 900
IIGIDRGERN LIYVTVINQN GEIIDCKSFN TIKHQSSTVN YDVDYHNKLQ EREKNRKEEK 960
RSWNSITKIA DLKEGYLSAV IHEVSLMMVK YNAIVVMENL NQGFKRIRGG IAERSVYQKF 1020
EKMLIDKLNY FVIKNENWTN PGGVLNGYQL TNKVSTIKDI GNQCGFLFYV PATYTSKIDP 1080
STGFVNLINF NKYKNSEDRR KLICSFDKIC FVQNENLFKF SIDYGKLCPD SKIAIKKWDV 1140
FSYGTRIIKE NLTTGHIEEN PEYDPTEELK SLLSSRGIEY QKGQNLLETI PTSDMTREFW 1200
NSLFKIFKAI LQMRNSLTNS PIDRLLSPVK GKDGTFFDTD KVEGTKFEKL KDADANGAYN 1260
IALKGLLVLE KNDSVESNKD LKNVKKISLE DWLKFVQITL RD 1302

SEQ ID NO: 33 moltype = AA length = 1339
FEATURE Location/Qualifiers
source 1..1339
mol_type = protein
organism = synthetic construct
SEQUENCE: 33
MGSKLSTFNE HFQKTLTLRN ELVPVGKTLE NIISSNVLIN DEKRSEDYKK AKEIIDSYHR 60
EFIEKSLSSV NVDWNDLYSY LSKKEPEDYA QKQKFLEELE NILLEKRKII VKQFEQYVFG 120
SYTDSKGKKT KDLKFENLFK SELFDYLLPN FLKNDEDKKV IGSFNKFTSY FTGFYENRKN 180
LYKSEPLPTA VAYRIVNENF PKFISNKNIF RVWKDNVPQF IEIAKTKLRE EGISDLNIEL 240
KFDLTNFNSC LNQTGIDTYN DLIGQLNFAI NLECQKDKNL CDLLRKKRSL KMVPLYKQIL 300
SDNDSSFSID EFDNDESAIK DVISFYKKMI GENCPQRTLS ELLHGLSSHD LEKIFVQGKN 360
LNSVSKNLFG GKNWSLLRDA VIEEKSKEKV FKKVIKSNST ADELDKVLSK EEFSISFLSK 420
VSGKDLSVEI DKFVKKQDEL LVENNIQNWP SSLKNSEEKN LIKAPLDFLL NFYRFAQSFS 480
SNNIDKDMSF YADFDESLSS LENVIGLYNK VRNYATKKPY TLEKIKLNFE NPNLASGWSE 540
SKENDCLSII LLKEKKYFLG IFNKNNKPNF SEGISHSLSS NGCYRKMRYL LFKGFNKMLP 600
KCAFTGEVKD HFKESSDDFS LFNKDTFISP LVITKEIFDL ACSKEKVKKY QKEYEKINRA 660
EYRQSLVKWI TFGLKFLSSY KTTTQFDLSN LKRPEEYCDL KEFYEDVDNL TYKIEFLNIK 720
EEDVDALVEK GQLYLFEIRN KDFAKNASGT PNLHTLYFKS IFDSKNLENG IVKLNGEAEI 780
FYRKKSLKKD DITVHREGSY LVNKVCVDPN SGKTEQIPDK IYENIYAFVN GKSRDLSKED 840
EVYYAKATIK KATHEIVKDR RFTVDKFFFH CPITINYKSK DKPSKFNDKV LDFLRNNKDI 900
NIIGIDRGER NLIYVTVINQ NGEIIDCKSF NTIKHQSSTV NYDVDYHNKL QEREKNRKEE 960
KRSWNSITKI ADLKEGYLSA VIHEVSLMMV KYNAIVVMEN LNQGFKRIRG GIAERSVYQK 1020
FEKMLIDKLN YFVIKNENWT NPGGVLNGYQ LTNKVSTIKD IGNQCGFLFY VPATYTSKID 1080
PSTGFVNLIN FNKYKNSEDR RKLICSFDKI CFVQNENLFK FSIDYGKLCP DSKIAIKKWD 1140
VFSYGTRIIK ENLTTGHIEE NPEYDPTEEL KSLLSSRGIE YQKGQNLLET IPTSDMTREF 1200
WNSLFKIFKA ILQMRNSLTN SPIDRLLSPV KGKDGTFFDT DKVEGTKFEK LKDADANGAY 1260
NIALKGLLVL EKNDSVESNK DLKNVKKISL EDWLKFVQIT LRDSRKRTAD GSEFESPKKK 1320
RKVGSGKPIP NPLLGLDST 1339

SEQ ID NO: 34 moltype = DNA length = 3909
FEATURE Location/Qualifiers
source 1..3909
mol_type = unassigned DNA
organism = unidentified
SEQUENCE: 34

```
atgtctaaat tatcaacttt taatgaacat tttcaaaaaa cgttaacttt aagaaacgaa  60
ctagttcctg taggaaaaac tcttgaaaat atcatatctt caaatgtatt gataaatgat  120
gagaaaagaa gtgaagatta taaaaaggct aaagagatca tagattctta tcatcgagag  180
tttatagaga aatcactttc atcagtaaat gttgattgga atgatctgta ctcgtattta  240
tccaaaaaag aaccagaaga ctatgctcaa aagcagaagt tcctcgaaga gttagaaaat  300
attctccttg aaaagagaaa aattattgtt aaacagtttg agcaatacgt tttcggatca  360
tatacagatt caaaaggtaa aaaaacaaaa gatctaaaat ttgagaatct ttttaaatca  420
gagttgtttg attatctttt gccaaatttc ctaaaaaatg atgaagataa aaaagtaata  480
ggtagtttta ataaatttac atcgtatttt acaggttttt acgaaaatcg aaagaattta  540
tataaatcag agccattgcc aacagctgtg gcttatagaa tagttaacga aaactttcct  600
aaattcattt ctaataaaaa tatctttcgc gtgtggaaag ataatgttcc tcagtttata  660
gaaatagcga aactaaact aagagaagaa ggcatttctg atttaaatat agaattaaaa  720
tttgatttaa ctaatttcaa ttcatgctta aatcaaactg gaattgatac ttacaatgac  780
ttgataggtc aactcaactt tgcaattaac cttgaatgtc agaaagacaa gaatttatgt  840
gaccttttaa ggaagaaaag aagccttaaa atggtacctc tgtataaaca gattttatct  900
gataatgatt cttcattcag tattgatgaa tttgataatg atgaatcggc aataaaagat  960
gtaatttctt tttataagaa aatgattggt gaaaattgtc ctcaacgaac actatctgaa  1020
ttgctacatg gtttgtcatc tcacgatctt gaaaagatat ttgttcaagg taaaaactta  1080
aattcggttt ctaaaaattt atttggaggg aagaactggt ctttactaag ggatgcagtt  1140
atagaagaaa agtcaaaaga aaaagtcttc aaaaaggtta taaagtcaaa ttctaccgca  1200
gatgaattag acaaagttct ttccaaggaa gaattttcaa tttcattctt atcaaaagtg  1260
agcggtaaag atttatcagt agaaattgat aaatttgtaa aaaaacaaga cgaactactt  1320
gttgaaaata atatacaaaa ttggccaagt tctcttaaga acagcgaaga gaaaaatctc  1380
ataaaagctc ctttagattt cttacttaat ttttatagat ttgcacaatc attctcttca  1440
aataatattg ataaggatat gtcattttat gctgactttg atgaatctct atcgtcttta  1500
gaaaatgtaa taggtcttta taacaaagtc agaaactatg caactaagaa accttataca  1560
ctcgaaaaga tcaaattgaa ttttgaaaat ccaaatttag cttctggatg gagtgaaagc  1620
aaagaaaatg attgtttatc aattatctta ttaaaagaga aaaaatattt tttaggaatt  1680
ttcaacaaaa ataataaacc taatttttct gaaggcattt ctcattcact ttcttcaaat  1740
ggttgctaca gaaaaatgag gtatttatta ttcaagggat tcaataaaat gcttcctaaa  1800
tgtgctttta caggagaagt taaagatcat tttaaagaat catcggatga tttttctctt  1860
tttaacaagg atacttttat ctctcctctt gtaattacca aagagatctt tgatttagca  1920
tgtagtaaag aaaaggtaaa aaaatatcaa aaagaatatg aaaagatcaa tcgtgctgaa  1980
tatagacaat cattggttaa gtggattact tttggtctta aatttttgtc atcatataaa  2040
actacaactc aatttgattt atcaaattta aaaagacctg aagaatactg cgatctaaag  2100
gaattttatg aagatgtaga taatcttaca tacaagatag aatttttaaa tataaaagaa  2160
gaagatgtag atgcattggt tgaaaaaggt caactgtatt tatttgaaat tcgaaataaa  2220
gattttgcaa aaaatgcaag tggcactcct aatctacata ctctctattt taaaagtatt  2280
ttcgattcga aaaatttaga gaatggcatt gtcaagctta atggtgaagc agagatattt  2340
tatagaaaga aaagcttgaa gaaagatgac ataactgttc atcgagaagg cagttatctt  2400
gtaaataagg tgtgtgtcga tcctaattct ggaaaaacag aacagattcc tgacaaaatt  2460
tatgaaaata tttatgcttt cgtaaatggt aaatcaagag atttatctaa ggaggatgaa  2520
gtatattatg caaaagccac aataaaaaaa gctacccatg agatcgtaaa agatagacgc  2580
tttactgtag ataaattctt tttccactgc cctattacta ttaactataa atctaaagat  2640
aaaccttcaa aattcaatga caaggtttta gatttcttaa gaaataataa agacatcaac  2700
attataggca tagatcgagg agagagaaat cttatttatg taactgtaat taatcaaaat  2760
ggcgaaatta ttgattgcaa atcatttaat actatcaaac atcagtcttc aacagtgaat  2820
tacgatgttg attatcacaa caaattacaa gaaagagaaa aaaatagaaa agaagaaaag  2880
agatcttgga atagtattac taaaattgca gatctcaaag aaggctatct ttctgctgta  2940
attcatgaag tttcattaat gatggttaag tacaatgcca ttgtcgttat ggaaaatttg  3000
aatcaaggtt ttaagagaat tagaggagga attgctgaaa gatccgtata ccaaaaattt  3060
gaaaagatgc tgatagataa actgaattat tttgttataa aaatgaaaa ttggacaaat  3120
cctggtgggg tcctcaatgg atatcagtta actaacaaag tgtctacaat caaagatatc  3180
ggtaatcagt gtggattttt attttacgtt cctgcaactt atacctcaaa gattgatcct  3240
tctacaggct ttgttaattt aattaatttc aataaatata aaaattcaga agatcgaaga  3300
aaactcattt gtagctttga caagatatgc tttgtacaga atgagaattt atttaaattt  3360
tctatagatt atggaaaatt atgcccagat agcaaaattg ctataaaaaa atgggatgtt  3420
ttctcctacg gaacaagaat tattaaggaa aatctaacaa ctggtcatat agaagaaaat  3480
cctgaatacg atccgacaga agagcttaaa tctctgcttt cctcaagagg aattgagtat  3540
caaaaaggtc aaaatttact agaaacaata cctactagtg atatgactag agaattttgg  3600
aattctcttt tcaagatttt taaagcaatt ttacaaatga gaaacagtct aactaattca  3660
ccaatagaca ggcttttatc tccagttaaa ggaaaagatg gaaccttctt tgatacagat  3720
aaagtagaag gtactaagtt tgaaaagtta aaagacgctg atgcaaacgg agcatataac  3780
attgcgttaa aaggattgtt agtcctcgag aaaaatgatt ctgtagagtc caataaggat  3840
ctaaaaaatg ttaagaaaat tagtcttgag gattggttaa agtttgtcca aatcacatta  3900
agagattaa                                                         3909
```

```
SEQ ID NO: 35          moltype = DNA  length = 3903
FEATURE                Location/Qualifiers
source                 1..3903
                       mol_type = other DNA
                       organism = synthetic construct
SEQUENCE: 35
agcaaattgt cgaccttcaa tgagcacttt cagaaaaccc tgaccctgcg gaatgagctg  60
gtgcccgtgg gcaagacact ggagaacatc atcagctcta acgtgctgat caacgacgag  120
aagcggtccg aggactacaa aaaggccaag gaaatcattg acagctatca ccgggagttc  180
atcgagaaaa gcctgagctc tgtgaatgtg gactggaatg atctgtacag ctacctgagc  240
aagaaagaac ccgaggacta tgcccagaaa cagaagttcc tggaggagtt agagaacatc  300
ctgctggaaa agagaaagat catcgtgaag cagttcgagc agtacgtgtt cggttcctat  360
```

```
accgacagca agggaaaaaa gaccaaggac ctgaaattcg aaaacctgtt taagtccgaa  420
ctctttgact acctgctgcc taacttcttg aaaaacgacg aggataagaa ggtgattggc  480
tccttcaata agttcaccag ctatttcacc ggcttttacg agaacagaaa aaacctgtac  540
aagagcgagc ctctgcctac cgccgtcgcc tacagaatcg tgaacgagaa cttccccaag  600
tttatctcta acaagaacat ctttagagtg tggaaggaca acgtccctca attcatcgag  660
atcgcaaaga ccaaactgag agaagaaggc atctctgatc tgaacatcga gctgaagttt  720
gatttgacaa atttcaactc ctgcctgaat cagaccggca tcgataccta caacgacctg  780
atcggccagc tgaactttgc tatcaacctc gaatgtcaga aggacaagaa cctttgtgac  840
ctgctgcgca agaagcggag ccttaagatg gtgccactgt acaagcaaat cctgtccgac  900
aacgatagca gcttcagcat cgacgagttc gacaatgatg aaagcgccat caaggacgtt  960
atcagcttct acaagaagat gatcggcgag aactgccctc agcggaccct gtctgagctg  1020
ctgcacggcc tgtctagcca cgatctggag aaaatttcg tgcaagggaa gaacctgaac  1080
agcgtgtcca agaacctgtt cggcggcaag aactggtccc tgctgcggga cgccgtgatc  1140
gaggaaaaaa gcaaagagaa ggtgttcaag aaggtgatca agagcaacag caccgctgat  1200
gagctggata aggtgctgtc taaggaggag ttcagcatct ctttcctatc caaggtgtcc  1260
ggcaaggatc tgagcgtgga aatcgacaag ttcgtcaaaa aacaggacga gcttctggtg  1320
gagaacaata tccagaactg gccttcttct ctcaagaata gcgaagaaaa gaacctgatc  1380
aaggcccctc tggacttttt gttgaatttc tacaggttcg cccagagctt cagcagcaac  1440
aacatcgata aagatatgtc cttctacgct gattttgacg agtctctgtc aagcctggaa  1500
aatgtgatag gcctgtacaa caaagtgcgg aactacgcca ccaagaaacc ttacacactg  1560
gaaaagatca agctaaactt cgagaaccct aacctggcct ctggatggag tgagagcaag  1620
gaaaacgatt gcctgagtat catcctgctg aaggagaaga aatacttcct gggcatcttc  1680
aacaagaaca acaagcccaa cttttcagag ggcatcagcc acagcctgtc aagcaacggc  1740
tgttaccgga agatgagata cctgctgttc aagggattca acaagatgct gcctaagtgc  1800
gccttcacag gagaggtgaa ggaccacttc aaggaaagct ccgatgactt cagcctgttc  1860
aacaaggaca ccttcatcag cccccctggtg atcaccaagg aaattttcga tctggcttgc  1920
agcaaggaaa aagtgaagaa gtaccaaaaa gaatacgaga aaatcaacag agccgagtac  1980
cggcagtctc tggtgaagtg gatcaccttt ggcctgaagt ttctgtctag ctacaaaacc  2040
accacccagt tcgacctgag caatttgaag cgcccccgagg aatactgcga cctgaaagaa  2100
ttttacgagg acgtggataa cttaacctac aagattgagt tcctgaacat taaagaggag  2160
gacgtggacg ctctggtcga gaaaggccag ctgtacctgt ttgagattag aaacaaggac  2220
ttcgccaaga atgccagcgg cacgcccaac ctgcatacac tgtatttcaa gagcatcttc  2280
gatagcaaga acctggaaaa tggcatcgtg aaactgaacg gcgaggccga aatttctac  2340
agaaagaaga gcctgaagaa ggatgatatc accgtgcaca gagagggaag ctacctcgtc  2400
aacaaagtct gcgtggaccc taattccggc aagacagagc agatcccaga taagatctac  2460
gagaacatct acgccttcgt caacggcaag tcacgggacc tgagcaagga ggacgaggtg  2520
tactacgcca aagccaccat caagaaggct acccacgaga tcgtgaagga tcgaagattc  2580
accgtcgaca agttcttctt ccactgcccc atcactatca actacaagag caaagacaag  2640
ccaagcaagt ttaacgacaa agtgctggac ttcctgagaa ataacaagga catcaatatc  2700
atcggcatcg acagaggcga aagaaacttg atctacgtga ccgtgatcaa ccagaacgga  2760
gagatcatcg actgtaagag cttcaatacc attaagcacc agagcagcac agtgaactac  2820
gacgtggact accacaacaa gctgcaggag cgggaaaaga acagaaagga agaaaagaga  2880
tcttggaaca gcatcaccaa gatcgccgat ctgaaagagg gctacctgtc tgccgtgatt  2940
cacgaggtta gcctgatgat ggtgaagtac aacgccatag ttgtgatgga aaacctgaac  3000
cagggcttca agagaatccg gggcggcatc gccgaacgga gcgtgtacca aaagtttgaa  3060
aagatgctca tcgacaagct gaactacttc gtgatcaaga acgagaactg gaccaatcct  3120
ggcggagtgc tgaatggata ccagctgaca aacaaggtgt ccacaatcaa ggatattgga  3180
aatcagtgcg gcttcctgtt ctacgtgccc gccacttata catctaaaat cgatcctagc  3240
actggatttg tgaacctgat caacttcaac aagtacaaga acagcgagga cagaaggaag  3300
ctgatctgta gcttcgacaa gatctgcttt gtgcagaatg agaacctgtt caagttctct  3360
atcgattacg gcaaactgtg ccctgacagc aagatcgcca tcaaaaagtg ggacgtattc  3420
tcctatggca ccaggatcat caaggaaaac ctgacaacag gccacatcga agaaaatcca  3480
gagtacgacc ctacagagga actgaaatcc ctgctttcca gcagaggcat cgagtaccag  3540
aagggccaaa acctgctaga aaccatccct accagcgaca tgaccagaga gttctggaat  3600
agcctgttca agatcttcaa ggccatcctg cagatgagaa actctctgac aaactctcct  3660
atcgaccggc tgctaagccc tgtgaagggg aaagatggaa ccttcttcga caccgacaag  3720
gtggaaggca caaaatttga gaaactgaag gacgctgacg ctaacggcgc ctacaacatc  3780
gccctgaagg gcctgctggt gctggaaaaa aacgactctg tcgagagcaa caaggacctc  3840
aagaacgtga agaaaatctc actggaggac tggctgaaat tcgtgcagat cacacttaga  3900
gac                                                                3903
```

```
SEQ ID NO: 36          moltype = DNA  length = 4020
FEATURE                Location/Qualifiers
source                 1..4020
                       mol_type = other DNA
                       organism = synthetic construct
SEQUENCE: 36
atgggcagca aattgtcgac cttcaatgag cactttcaga aaaccctgac cctgcggaat  60
gagctggtgc ccgtgggcaa gacactggag aacatcatca gctctaacgt gctgatcaac  120
gacgagaagc ggtccgagga ctacaaaaag gccaaggaaa tcattgacag ctatcaccgg  180
gagttcatcg agaaaagcct gagctctgtg aatgtggact ggaatgatct gtacagctac  240
ctgagcaaga aagaacccga ggactatgcc cagaaacaga agttcctgga ggagttagag  300
aacatcctgc tggaaaagag aaagatcatc gtgaagcagt tcgagcagta cgtgttcggt  360
tcctataccg acagcaaggg aaaaaagacc aaggacctga aattcgaaaa cctgtttaag  420
tccgaactct ttgactacct gctgcctaac ttcttgaaaa acgacgagga taagaaggtg  480
attggctcct tcaataagtt caccagctat ttcaccggct tttacgagaa cagaaaaaac  540
ctgtacaaga gcgagcctct gcctaccgcc gtcgcctaca gaatcgtgaa cgagaacttc  600
cccaagttta tctctaacaa gaacatcttt agagtgtgga aggacaacgt ccctcaattc  660
atcgagatcg caaagaccaa actgagagaa gaaggcatct ctgatctgaa catcgagctg  720
```

```
aagtttgatt tgacaaattt caactcctgc ctgaatcaga ccggcatcga tacctacaac  780
gacctgatcg gccagctgaa ctttgctatc aacctcgaat gtcagaagga caagaacctt  840
tgtgacctgc tgcgcaagaa gcggagcctt aagatggtgc cactgtacaa gcaaatcctg  900
tccgacaacg atagcagctt cagcatcgac gagttcgaca atgatgaaag cgccatcaag  960
gacgttatca gcttctacaa gaagatgatc ggcgagaact gccctcagcg gaccctgtct  1020
gagctgctgc acggcctgtc tagccacgat ctggagaaaa ttttcgtgca agggaagaac  1080
ctgaacagcg tgtccaagaa cctgttcggc ggcaagaact ggtccctgct gcgggacgcc  1140
gtgatcgagg aaaaaagcaa agagaaggtg ttcaagaagg tgatcaagag caacagcacc  1200
gctgatgagc tggataaggt gctgtctaag gaggagttca gcatctcttt cctatccaag  1260
gtgtccggca aggatctgag cgtggaaatc gacaagttcg tcaaaaaaca ggacgagctt  1320
ctggtggaga acaatatcca gaactggcct tcttctctca agaatagcga agaaaagaac  1380
ctgatcaagg cccctctgga ctttttgttg aatttctaca ggttcgccca gagcttcagc  1440
agcaacaaca tcgataaaga tatgtccttc tacgctgatt ttgacgagtc tctgtcaagc  1500
ctggaaaatg tgataggcct gtacaacaaa gtgcggaact acgccaccaa gaaaccttac  1560
acactggaaa agatcaagct aaacttcgag aaccctaacc tggcctctgg atggagtgag  1620
agcaaggaaa acgattgcct gagtatcatc ctgctgaagg agaagaaata cttcctgggc  1680
atcttcaaca agaacaacaa gcccaacttt tcagagggca tcagccacag cctgtcaagc  1740
aacggctgtt accggaagat gagatacctg ctgttcaagg gattcaacaa gatgctgcct  1800
aagtgcgcct tcacaggaga ggtgaaggac cacttcaagg aaagctccga tgacttcagc  1860
ctgttcaaca aggacacctt catcagcccc ctggtgatca ccaaggaaat tttcgatctg  1920
gcttgcagca aggaaaaagt gaagaagtac caaaaagaat acgagaaaat caacagagcc  1980
gagtaccggc agtctctggt gaagtggatc acctttggcc tgaagtttct gtctagctac  2040
aaaaccacca cccagttcga cctgagcaat ttgaagcgcc ccgaggaata ctgcgacctg  2100
aaagaatttt acgaggacgt ggataactta acctacaaga ttgagttcct gaacattaaa  2160
gaggaggacg tggacgctct ggtcgagaaa ggccagctgt acctgtttga gattagaaac  2220
aaggacttcg ccaagaatgc cagcggcacg cccaacctgc atacactgta tttcaagagc  2280
atcttcgata gcaagaacct ggaaaatggc atcgtgaaac tgaacggcga ggccgaaatt  2340
ttctacagaa agaagagcct gaagaaggat gatatcaccg tgcacagaga gggaagctac  2400
ctcgtcaaca aagtctgcgt ggaccctaat tccggcaaga cagagcagat cccagataag  2460
atctacgaga acatctacgc cttcgtcaac ggcaagtcac gggacctgag caaggaggac  2520
gaggtgtact acgccaaagc caccatcaag aaggctaccc acgagatcgt gaaggatcga  2580
agattcaccg tcgacaagtt cttcttccac tgccccatca ctatcaacta caagagcaaa  2640
gacaagccaa gcaagtttaa cgacaaagtg ctggacttcc tgagaaataa caaggacatc  2700
aatatcatcg gcatcgacag aggcgaaaga aacttgatct acgtgaccgt gatcaaccag  2760
aacggagaga tcatcgactg taagagcttc aataccatta agcaccagag cagcacagtg  2820
aactacgacg tggactacca caacaagctg caggagcggg aaaagaacag aaaggaagaa  2880
aagagatctt ggaacagcat caccaagatc gccgatctga aagagggcta cctgtctgcc  2940
gtgattcacg aggttagcct gatgatggtg aagtacaacg ccatagttgt gatggaaaac  3000
ctgaaccagg gcttcaagag aatccggggc ggcatcgccg aacggagcgt gtaccaaaag  3060
tttgaaaaga tgctcatcga caagctgaac tacttcgtga tcaagaacga gaactggacc  3120
aatcctggcg gagtgctgaa tggataccag ctgacaaaca aggtgtccac aatcaaggat  3180
attggaaatc agtgcggctt cctgttctac gtgcccgcca cttatacatc taaaatcgat  3240
cctagcactg gatttgtgaa cctgatcaac ttcaacaagt acaagaacag cgaggacaga  3300
aggaagctga tctgtagctt cgacaagatc tgctttgtgc agaatgagaa cctgttcaag  3360
ttctctatcg attacggcaa actgtgccct gacagcaaga tcgccatcaa aaagtgggac  3420
gtattctcct atggcaccag gatcatcaag gaaaacctga caacaggcca catcgaagaa  3480
aatccagagt acgaccctac agaggaactg aaatccctgc tttccagcag aggcatcgag  3540
taccagaagg gccaaaacct gctagaaacc atccctacca gcgacatgac cagagagttc  3600
tggaatagcc tgttcaagat cttcaaggcc atcctgcaga tgagaaactc tctgacaaac  3660
tctcctatcg accggctgct aagccctgtg aaggggaaag atggaacctt cttcgacacc  3720
gacaaggtgg aaggcacaaa atttgagaaa ctgaaggacg ctgacgctaa cggcgcctac  3780
aacatcgccc tgaagggcct gctggtgctg gaaaaaaacg actctgtcga gagcaacaag  3840
gacctcaaga acgtgaagaa aatctcactg gaggactggc tgaaattcgt gcagatcaca  3900
cttagagact ctagaaagcg gacagcagac ggctccgaat ttgaaagccc taagaaaaag  3960
agaaaggtgg gatccggcaa acctatcccc aatcccctgc tgggcctgga cagcacctga  4020
```

```
SEQ ID NO: 37           moltype = AA  length = 1270
FEATURE                 Location/Qualifiers
source                  1..1270
                        mol_type = protein
                        organism = unidentified
SEQUENCE: 37
KRLIDFTNIY QRSKTLRFRL EPIGKTADYI KNSQSLETDA RLAKESKKVK ELADEYHKEF  60
IGDVLSSLEL PLSKINELWD IYIYIYMSND TDREIKFKKL QENLRKVIAE AFSKDKRFGN  120
LFKKEIITDI LPEFLQDKDD DIKIVNRFKG FTTYFYAFHK NRENMYVSEE KSTAIPYRIV  180
NQNLVKYFDN YKTFKEKVMP LLKDKNIVES IERDFKDILN EKSIEDVFGL ANFTHTLCQA  240
DIEKYNTLIG GLVVKNEKKE IKGINQYINE HNQTSKKGNG IPKLKPLFNQ ILSDRKSLSF  300
TLDDIKKTSE AIRTIKDEYE NLRDKLATIE RLIKSIKEYD LAGIYIKMGE DTSTISQHWF  360
GAYYKIIEAI ADAWERRNPK KNRESKAYSK YVSSLKSISL QEIDDLKIGE PIENYFATFG  420
TTCSDRTSGV SSLNRIKAAY TEFVNKFPEG FEDGDDCNDA YFKANVEVVK NLLDSIKDFQ  480
RFVKPLLGNE DERDKDEAFY GEFVPTYTDM DNIITPLYNR VRNFATKKPY STDKIKINFE  540
NVVLLKGWDK NKESDYASII LMKDGQYFLG VLRNGSKSTL KTILPNTGDC YQKMVYKYFK  600
DIKSNLPRCT TQRKDVKAHF AESSDDYTLL DTKAFVSALT ISREVFELYN APDKEKKFKK  660
EYLKNTNDSI GYANAVSVCK RFCLEFLKKY RSTAIYDLSD VETSVDSFDD LSSFYQEIDK  720
RLYSISFENV SVDSVNELVD NGNMLLFRIA NKDFSPNSKG RPNLHTIYWR MLFDPANLKD  780
VVYQLNGNAE IFFRKASVTR TEPTHPANVA IKNKSEYNKQ NKPYSTFKYG LIKDRRYTTD  840
QFEFHVPITM NFKQPESSKL QDKLNKQVLD FLKQDGVRHI IGIDRGERNL LYLVMVDMEG  900
KIKKQISLNE IAGNPKNPEF KQDFLALLHE REGDRLESRR SWNTIQSIKE LKEGYMSLVV  960
HEIANMMLEN DAIVVLENLN RSFMQKRGGI EKSVYQKFEK MLIDKLGYIV DKTKDVSDNG  1020
```

```
GALHAVQLAD TFENFNKTQK GAIRQCGFIF YIPAWRTSKI DPVTGFVPML RCQYESIVES  1080
KKFFGKFDSI YYDATGKYFV FQTDFTKFNT ESKGGIQKWD ICTYGDRIYA PRTKDRNNNP  1140
VSERVNLTEE MKSLFVSHNI NIQGDIKAGI MQQTDKEFFE SLHRLLRLTL QIRNSKKSTG  1200
KDYEDYIISP VMGKDGRFFD SRNADATQPK DADANGAYNI ARKGLMLLRQ IQAQEKQDLS  1260
NGKWLEFAQR                                                         1270

SEQ ID NO: 38          moltype = AA  length = 1271
FEATURE                Location/Qualifiers
source                 1..1271
                       mol_type = protein
                       organism = unidentified
SEQUENCE: 38
MKRLIDFTNI YQRSKTLRFR LEPIGKTADY IKNSQSLETD ARLAKESKKV KELADEYHKE  60
FIGDVLSSLE LPLSKINELW DIYIYIYMSN DTDREIKFKK LQENLRKVIA EAFSKDKRFG  120
NLFKKEIITD ILPEFLQDKD DDIKIVNRFK GFTTYFYAFH KNRENMYVSE EKSTAIPYRI  180
VNQNLVKYFD NYKTFKEKVM PLLKDKNIVE SIERDFKDIL NEKSIEDVFG LANFTHTLCQ  240
ADIEKYNTLI GGLVVKNEKK EIKGINQYIN EHNQTSKKGN GIPKLKPLFN QILSDRKSLS  300
FTLDDIKKTS EAIRTIKDEY ENLRDKLATI ERLIKSIKEY DLAGIYIKMG EDTSTISQHW  360
FGAYYKIIEA IADAWERRNP KKNRESKAYS KYVSSLKSIS LQEIDDLKIG EPIENYFATF  420
GTTCSDRTSG VSSLNRIKAA YTEFVNKFPE GFEDGDDCND AYFKANVEVV KNLLDSIKDF  480
QRFVKPLLGN EDERDKDEAF YGEFVPTYTD MDNIITPLYN RVRNFATKKP YSTDKIKINF  540
ENVVLLKGWD KNKESDYASI ILMKDGQYFL GVLRNGSKST LKTILPNTGD CYQKMVYKYF  600
KDIKSNLPRC TTQRKDVKAH FAESSDDYTL LDTKAFVSAL TISREVFELY NAPDKEKKFK  660
KEYLKNTNDS IGYANAVSVC KRFCLEFLKK YRSTAIYDLS DVETSVDSFD DLSSFYQEID  720
KRLYSISFEN VSVDSVNELV DNGNMLLFRI ANKDFSPNSK GRPNLHTIYW RMLFDPANLK  780
DVVYQLNGNA EIFFRKASVT RTEPTHPANV AIKNKSEYNK QNKPYSTFKY GLIKDRRYTT  840
DQFEFHVPIT MNFKQPESSK LQDKLNKQVL DFLKQDGVRH IIGIDRGERN LLYLVMVDME  900
GKIKKQISLN EIAGNPKNPE FKQDFLALLH EREGDRLESR RSWNTIQSIK ELKEGYMSLV  960
VHEIANMMLE NDAIVVLENL NRSFMQKRGG IEKSVYQKFE KMLIDKLGYI VDKTKDVSDN  1020
GGALHAVQLA DTFENFNKTQ KGAIRQCGFI FYIPAWRTSK IDPVTGFVPM LRCQYESIVE  1080
SKKFFGKFDS IYYDATGKYF VFQTDFTKFN TESKGGIQKW DICTYGDRIY APRTKDRNNN  1140
PVSERVNLTE EMKSLFVSHN INIQGDIKAG IMQQTDKEFF ESLHRLLRLT LQIRNSKKST  1200
GKDYEDYIIS PVMGKDGRFF DSRNADATQP KDADANGAYN IARKGLMLLR QIQAQEKQDL  1260
SNGKWLEFAQ R                                                       1271

SEQ ID NO: 39          moltype = AA  length = 1308
FEATURE                Location/Qualifiers
source                 1..1308
                       mol_type = protein
                       organism = synthetic construct
SEQUENCE: 39
MGKRLIDFTN IYQRSKTLRF RLEPIGKTAD YIKNSQSLET DARLAKESKK VKELADEYHK  60
EFIGDVLSSL ELPLSKINEL WDIYIYIYMS NDTDREIKFK KLQENLRKVI AEAFSKDKRF  120
GNLFKKEIIT DILPEFLQDK DDDIKIVNRF KGFTTYFYAF HKNRENMYVS EEKSTAIPYR  180
IVNQNLVKYF DNYKTFKEKV MPLLKDKNIV ESIERDFKDI LNEKSIEDVF GLANFTHTLC  240
QADIEKYNTL IGGLVVKNEK KEIKGINQYI NEHNQTSKKG NGIPKLKPLF NQILSDRKSL  300
SFTLDDIKKT SEAIRTIKDE YENLRDKLAT IERLIKSIKE YDLAGIYIKM GEDTSTISQH  360
WFGAYYKIIE AIADAWERRN PKKNRESKAY SKYVSSLKSI SLQEIDDLKI GEPIENYFAT  420
FGTTCSDRTS GVSSLNRIKA AYTEFVNKFP EGFEDGDDCN DAYFKANVEV VKNLLDSIKD  480
FQRFVKPLLG NEDERDKDEA FYGEFVPTYT DMDNIITPLY NRVRNFATKK PYSTDKIKIN  540
FENVVLLKGW DKNKESDYAS IILMKDGQYF LGVLRNGSKS TLKTILPNTG DCYQKMVYKY  600
FKDIKSNLPR CTTQRKDVKA HFAESSDDYT LLDTKAFVSA LTISREVFEL YNAPDKEKKF  660
KKEYLKNTND SIGYANAVSV CKRFCLEFLK KYRSTAIYDL SDVETSVDSF DDLSSFYQEI  720
DKRLYSISFE NVSVDSVNEL VDNGNMLLFR IANKDFSPNS KGRPNLHTIY WRMLFDPANL  780
KDVVYQLNGN AEIFFRKASV TRTEPTHPAN VAIKNKSEYN KQNKPYSTFK YGLIKDRRYT  840
TDQFEFHVPI TMNFKQPESS KLQDKLNKQV LDFLKQDGVR HIIGIDRGER NLLYLVMVDM  900
EGKIKKQISL NEIAGNPKNP EFKQDFLALL HEREGDRLES RRSWNTIQSI KELKEGYMSL  960
VVHEIANMML ENDAIVVLEN LNRSFMQKRG GIEKSVYQKF EKMLIDKLGY IVDKTKDVSD  1020
NGGALHAVQL ADTFENFNKT QKGAIRQCGF IFYIPAWRTS KIDPVTGFVP MLRCQYESIV  1080
ESKKFFGKFD SIYYDATGKY FVFQTDFTKF NTESKGGIQK WDICTYGDRI YAPRTKDRNN  1140
NPVSERVNLT EEMKSLFVSH NINIQGDIKA GIMQQTDKEF FESLHRLLRL TLQIRNSKKS  1200
TGKDYEDYII SPVMGKDGRF FDSRNADATQ PKDADANGAY NIARKGLMLL RQIQAQEKQD  1260
LSNGKWLEFA QRSRKRTADG SEFESPKKKR KVGSGKPIPN PLLGLDST               1308

SEQ ID NO: 40          moltype = DNA  length = 3816
FEATURE                Location/Qualifiers
source                 1..3816
                       mol_type = unassigned DNA
                       organism = unidentified
SEQUENCE: 40
atgaaacgcc taattgactt tacaaacatc tatcagcgat caaagacttt gaggtttcga  60
ttggagccta tcggtaaaac ggccgactat attaagaatt ctcagtccct cgaaactgat  120
gcgcgtttgg caaaagagag caagaaggta aaagagcttg ctgatgaata tcacaaagag  180
tttattggag atgtcctgtc ttcgttggaa ttgcctttaa gcaaaatcaa cgagttatgg  240
gatatatata tatatatata tatgtccaat gatacagacc gcgagataaa attcaaaaaa  300
ctgcaagaga acctgcgaaa ggtgattgca gaggctttta gtaaggacaa acggtttggt  360
aatttattca aaaaggagat aatcacagac attctgccgg aattcttgca agataaggat  420
gatgatatta agatcgtaaa tagattcaaa ggatttacca catattttta cgcctttcat  480
aagaataggg aaaatatgta tgtctcggaa gagaaatcga ctgcaatacc atatcgaatt  540
```

```
gtgaatcaaa atctcgtcaa gtattttgac aactacaaga cgttcaaaga gaaggtaatg  600
cctcttctga aagacaagaa tatagtcgaa agcatagaga gagacttcaa agacatcttg  660
aacgaaaaat caatagagga tgtttttggc cttgccaact tcactcatac tttatgtcag  720
gctgacatcg agaaatacaa tacgttgata ggtggccttg tcgtcaaaaa cgaaaaaaaa  780
gagattaaag gtattaatca gtacattaac gaacataacc aaacgagtaa aaaagggaat  840
ggaattccga aactaaagcc gttgttcaat cagattttga gcgatagaaa atcgttatcg  900
tttaccttag acgatatcaa aaaaacgtcg gaggctattc gcaccattaa ggatgagtat  960
gaaaatctcc gagacaagtt ggcgaccatc gaaaggctta ttaagtctat caaggagtat  1020
gatcttgcag gtatttacat caagatggga gaggatactt cgacaatatc gcagcattgg  1080
tttggtgcgt attataaaat catcgaagcg atagcagatg catgggaacg acgaaatccg  1140
aagaaaaaca gagaatccaa ggcatatagc aagtatgtat cgtccctaaa aagcatcagt  1200
ctccaagaaa tagatgatct caaaatcgga gagcctatag agaactactt cgcaactttt  1260
ggcacgactt gttcagaccg aacaagtgga gtttcttcgc tcaataggat aaaagctgct  1320
tataccgagt tcgtgaacaa atttcctgaa ggatttgaag atggcgatga ctgtaacgat  1380
gcctacttta aggctaatgt ggaagtcgtc aaaaatctgc tggattcaat taaagatttt  1440
cagcgttttg tgaagccttt gcttggcaat gaggacgaaa gagacaaaga cgaggcattc  1500
tatggagagt ttgtcccgac atacacagat atggataaca tcataacccc tctatacaac  1560
cgtgtacgca attttgccac caagaaacca tactctacag acaagataaa aatcaacttt  1620
gaaaacgtag tattgctaaa aggatgggac aaaaacaagg agtcagacta cgcatccatc  1680
atattgatga aagacggaca atactttta ggggtactcc gtaatggttc aaaaagtact  1740
cttaaaacca tattgcctaa cacaggtgat tgctatcaaa aaatggttta taagtatttt  1800
aaggatataa aatcaaatct tccccggtgt acgacccaga ggaaagacgt gaaagcgcac  1860
tttgccgaat cgagcgacga ttacactctt ttagatacaa aggcctttgt ttcggcactg  1920
actatcagca gagaagtgtt cgaactatac aatgcccccg ataaggagaa aaaattcaaa  1980
aaggaatatt tgaagaacac aaacgatagt ataggctacg ccaatgctgt atccgtatgt  2040
aaacgcttct gtttggagtt cctaaaaaaa tatcgcagca ctgccatata tgatctttcg  2100
gatgttgaaa cttcagtcga ttcgtttgac gatttgtcct cattctatca agagatagac  2160
aaaaggctgt acagcatctc attcgaaaat gtatctgtcg attccgtcaa tgagcttgta  2220
gacaatggca atatgcttct attccgtatc gcgaataaag atttttcgcc taacagcaag  2280
ggccgtccca atcttcatac tatatattgg cgaatgcttt tcgacccggc caacctgaag  2340
gatgttgtat atcagctcaa tggtaatgcc gaaatattct tccgtaaggc aagcgttacg  2400
aggacggagc ctacacatcc ggctaacgtt gccatcaaaa acaagagcga atataacaaa  2460
cagaataagc cgtatagtac attcaagtac ggtttaatca aggataggcg ctacactacc  2520
gaccagttcg agtttcatgt acccatcaca atgaacttca agcaaccaga gtcgtctaaa  2580
ctacaggaca agctcaacaa gcaagtgctt gacttcttga aacaggacgg cgtacgccat  2640
attataggca ttgatcgggg cgaacgtaat ctgctatact tggtgatggt agatatggag  2700
ggcaaaatca aaaaacaaat atcactcaac gagatagccg gtaatccgaa gaatcccgag  2760
ttcaaacaag acttccttgc actactgcac gagcgcgaag gtgaccgttt ggagtcacgt  2820
cgcagttgga acaccattca gagcattaaa gaactcaaag aaggttacat gagcttggtg  2880
gttcatgaaa tagcgaatat gatgcttgag aatgatgcta tagtagtgct cgaaaatctg  2940
aatcgctcgt ttatgcaaaa gcgcggcggc atagaaaagt ctgtatacca aaagttcgaa  3000
aagatgctta tcgacaagtt gggatacatc gtggataaga ctaaagatgt gtccgacaac  3060
ggaggcgcac tacatgctgt acagcttgct gatacgtttg aaaacttcaa taagacccaa  3120
aaaggagcta ttcgtcaatg tggattcata ttctatattc ctgcatggcg taccagcaag  3180
attgaccccg ttaccggctt tgtgccaatg cttaggtgtc aatatgaaag catcgtagaa  3240
tccaaaaaat tcttcggaaa gttcgacagt atatactacg atgcgacagg aaagtatttt  3300
gtcttccaaa ctgactttac caaattcaat accgagagca aaggaggaat ccaaaaatgg  3360
gatatatgca cctatggaga cagaatatat gctcctcgca ccaaagaccg gaataataac  3420
cctgtttcgg aacgtgtaaa ccttactgag gagatgaaat cactgtttgt atcgcataat  3480
atcaatattc aaggcgatat caaagccgga attatgcagc agacagacaa ggagttcttc  3540
gagtcactgc atcgattgct tcgacttacg ttgcaaatac gcaatagcaa aaaatctaca  3600
ggcaaagact atgaagacta tatcatatcg ccggtgatgg gcaaggacgg tcgtttcttt  3660
gattcgcgta acgcggatgc tacgcaacct aaggatgcag atgccaatgg cgcgtacaat  3720
attgcacgca aaggcttgat gctgcttcgc cagattcaag cccaagagaa gcaagaccta  3780
tccaacggaa aatggcttga atttgcccaa aggtga                          3816
```

```
SEQ ID NO: 41          moltype = DNA  length = 3810
FEATURE                Location/Qualifiers
source                 1..3810
                       mol_type = other DNA
                       organism = synthetic construct
SEQUENCE: 41
aagcggctca tcgacttcac caacatctac cagcgttcta agaccctgag attcagactg  60
gaacctatcg gcaagaccgc ggactacatc aaaaacagcc agtccctgga aacagacgcc  120
agactggcca aggaatccaa gaaagtgaag gaactggccg atgagtacca caaagagttt  180
atcggcgacg tgctgagcag cctggagctg cccctgagca aatcaacgaa gctgtgggac  240
atctatatct acatctacat gagcaacgac accgatcggg aaatcaaatt taagaagctc  300
caggagaacc tgcggaaggt gatcgccgag gcctttagca aggataagag attcggcaac  360
ctgttcaaga aagaaatcat cacagatatc ctgcccgagt tcctgcaaga taaagatgac  420
gatatcaaaa tcgtgaaccg gttcaagggt tttacaacct acttctacgc cttccacaag  480
aatcgggaaa acatgtacgt gtctgaagag aagagcacag ccatccccta cagaatcgtg  540
aatcaaaacc tggtgaaata cttcgataac tacaagactt ttaaggagaa ggtgatgcct  600
ctgctgaagg acaagaacat cgtcgaaagc atcgagcgcg acttcaagga catcctgaac  660
gagaaaagca tcgaggacgt gttcggcctg gccaatttca cccacaccct gtgccaggct  720
gacatcgaga agtacaacac cttgataggc ggactggtgg tgaagaacga aaagaaggag  780
atcaagggca tcaaccagta tattaacgag cacaaccaga cctctaagaa gggcaacggc  840
atcccaaagc tgaagcctct gtttaaccag atcctgagcg acagaaaatc tctcagcttc  900
accctggatg atatcaagaa aaccagcgag gccatcagaa caattaagga cgagtatgag  960
aacctgagag ataagctggc cacaatcgaa cggctgatca agagcatcaa ggaatacgac  1020
```

```
ctggccggca tctacatcaa gatgggcgag gacacctcta ccatctccca gcactggttc  1080
ggtgcctatt acaagattat cgaagccatc gccgacgcct gggagagaag aaacccaaag  1140
aaaaacagag agagcaaggc ctacagcaag tacgtgagca gccttaagag catcagcctg  1200
caggagatcg acgacctgaa gatcggcgag cctatcgaga attacttcgc cacctttgga  1260
acaacatgta gcgaccggac atctggcgtg agctctctga accggatcaa agccgcctac  1320
accgagttcg tgaacaagtt ccccgagggc tttgaggatg gcgatgattg caacgacgct  1380
tacttcaaag ccaatgtgga ggtggtgaag aacttgctgg atagcataaa agacttccag  1440
agatttgtga agcctctact gggcaatgag gacgagcggg acaaagatga ggccttctac  1500
ggcgagttcg ttcctaccta cacagatatg gacaacatca tcacgcctct gtataataga  1560
gtcagaaact tcgctaccaa gaagccttac agtacagaca agatcaaaat aaacttcgaa  1620
aacgtggtac tgctgaaggg ctgggataag aacaaggaga gcgactatgc cagcatcatc  1680
ctgatgaagg acggccagta ctttctggga gtgctgagaa acggatctaa gagcactctg  1740
aaaaccatcc tgcctaacac cggtgactgc taccagaaaa tggtgtacaa gtatttcaag  1800
gatatcaagt ctaacctgcc cagatgcacc acccagagaa aggacgtgaa ggcacatttc  1860
gctgaaagca gcgatgatta caccctgctt gatacaaaag ccttcgtgag cgctctgacg  1920
atctccagag aggtgttcga actgtacaac gctcctgata aggaaaagaa attcaagaag  1980
gaatacctga agaacaccaa cgactccatc ggctacgcca atgcagtgag cgtgtgcaag  2040
agattctgcc tggagttcct gaaaaagtac cggagcaccg ccatctacga cctgagcgat  2100
gttgaaacct ctgtggacag tttcgacgac ctgagcagct tctaccagga gatcgataag  2160
agactgtaca gcatcagctt cgaaaacgtg agcgtggaca gcgtgaacga gctggtggat  2220
aacggcaata tgctgctgtt cagaatcgcc aacaaggatt tctctcctaa tagcaagggc  2280
agacctaatc tgcacacaat ttactggaga atgctgttcg accctgctaa tctcaaggac  2340
gtcgtgtacc aactgaacgg caatgccgaa atcttcttcc ggaaggccag cgttacaagg  2400
acagaaccaa cacaccccgc caatgtggcc atcaagaaca agagcgagta caacaagcag  2460
aacaaacctt acagcacctt caagtacggc ctcatcaagg accggcgata caccaccgat  2520
cagttcgagt tccacgtgcc tatcaccatg aacttcaagc aacctgagtc atctaagctg  2580
caggacaaac tgaataagca agtgctggac ttcctgaagc aagacggcgt gcggcacatc  2640
atcggcatcg accggggaga aagaaacctg ctgtacctgg tgatggtcga catggaagga  2700
aaaatcaaga agcagatcag cctgaatgaa atcgccggaa acccaaagaa ccctgagttt  2760
aagcaggact tcttagctct gctgcatgag agagagggcg atagactgga gtccagaaga  2820
agttggaaca ccatccagag catcaaggag ctgaaagaag gctacatgtc cctggtggtg  2880
cacgagatcg ctaacatgat gctggagaat gatgccatcg tggtcttgga aaaccttaac  2940
agatccttta tgcagaagag aggcggcatt gagaaaagcg tgtaccagaa gtttgagaaa  3000
atgctgatcg acaagctggg ctacatcgtg gacaaaacaa aagatgtgtc agataatggc  3060
ggagccctgc acgccgtgca gctggctgac accttcgaga actttaacaa gacccagaaa  3120
ggcgccatcc ggcagtgcgg cttcatcttt tatatccccg cctggcggac aagcaaaatt  3180
gacccggtaa ccggctttgt gcccatgctg agatgtcagt acgaatctat cgtggaatcc  3240
aagaagttct ttggcaaatt cgactctatc tactacgacg ccaccggaaa gtacttcgtg  3300
ttccagaccg actttaccaa gttcaacacc gagtctaagg ggggcatcca gaagtgggac  3360
atctgtacct acggagacag aatctacgcc cctagaacca aagacagaaa taacaaccct  3420
gtgtccgaaa gagtgaacct gacagaagaa atgaagagcc tgttcgtaag ccacaatatc  3480
aacatccagg gcgacatcaa ggccggcatt atgcagcaga cagacaagga gttcttcgag  3540
tcgctgcaca gactgctgag actgaccctg cagatccgga acagcaagaa aagcaccggc  3600
aaggactacg aggactacat tatcagtcct gtgatgggca aggacggaag attcttcgac  3660
agccggaacg ccgacgccac ccagcccaag gacgccgacg caaacggcgc ctacaacatt  3720
gccagaaaag gcctgatgct gctgcgccag atccaggccc aggagaagca ggacctgtct  3780
aatgggaagt ggctggagtt cgcccagcgg                                   3810

SEQ ID NO: 42           moltype = DNA  length = 3927
FEATURE                 Location/Qualifiers
source                  1..3927
                        mol_type = other DNA
                        organism = synthetic construct
SEQUENCE: 42
atgggcaagc ggctcatcga cttcaccaac atctaccagc gttctaagac cctgagattc  60
agactggaac ctatcggcaa gaccgcggac tacatcaaaa acagccagtc cctggaaaca  120
gacgccagac tggccaagga atccaagaaa gtgaaggaac tggccgatga gtaccacaaa  180
gagtttatcg gcgacgtgct gagcagcctg gagctgcccc tgagcaaaat caacgagctg  240
tgggacatct atatctacat ctacatgagc aacgacaccg atcgggaaat caaatttaag  300
aagctccagg agaacctgcg gaaggtgatc gccgaggcct ttagcaagga taagagattc  360
ggcaacctgt tcaagaaaga aatcatcaca gatatcctgc ccgagttcct gcaagataaa  420
gatgacgata tcaaaatcgt gaaccggttc aagggtttta caacctactt ctacgccttc  480
cacaagaatc gggaaaacat gtacgtgtct gaagagaaga gcacagccat cccctacaga  540
atcgtgaatc aaaacctggt gaaatacttc gataactaca agacttttaa ggagaaggtg  600
atgcctctgc tgaaggacaa gaacatcgtc gaaagcatcg agcgcgactt caaggacatc  660
ctgaacgaga aagcatcgga ggacgtgttc ggcctggcca atttcaccca caccctgtgc  720
caggctgaca tcgagaagta caacaccttg ataggcggac tggtggtgaa gaacgaaaag  780
aaggagatca agggcatcaa ccagtatatt aacgagcaca accagacctc taagaagggc  840
aacggcatcc caaagctgaa gcctctgttt aaccagatcc tgagcgacag aaaatctctc  900
agcttcaccc tggatgatat caagaaaacc agcgaggcca tcagaacaat taaggacgag  960
tatgagaacc tgagagataa gctggccaca atcgaacggc tgatcaagag catcaaggaa  1020
tacgacctgg ccggcatcta catcaagatg ggcgaggaca cctctaccat ctcccagcac  1080
tggttcggtg cctattacaa gattatcgaa gccatcgccg acgcctggga gagaagaaac  1140
ccaaagaaaa acagagagag caaggcctac agcaagtacg tgagcagcct taagagcatc  1200
agcctgcagg agatcgacga cctgaagatc ggcgagccta tcgagaatta cttcgccacc  1260
tttggaacaa catgtagcga ccggacatct ggcgtgagct ctctgaaccg gatcaaagcc  1320
gcctacaccg agttcgtgaa caagttcccc gagggctttg aggatggcga tgattgcaac  1380
gacgcttact tcaaagccaa tgtggaggtg gtgaagaact tgctggatag cataaaagac  1440
ttccagagat ttgtgaagcc tctactgggc aatgaggacg agcgggacaa agatgaggcc  1500
```

```
ttctacggcg agttcgttcc tacctacaca gatatggaca acatcatcac gcctctgtat  1560
aatagagtca gaaacttcgc taccaagaag ccttacagta cagacaagat caaaataaac  1620
ttcgaaaacg tggtactgct gaagggctgg gataagaaca aggagagcga ctatgccagc  1680
atcatcctga tgaaggacgg ccagtacttt ctgggagtgc tgagaaacgg atctaagagc  1740
actctgaaaa ccatcctgcc taacaccggt gactgctacc agaaaatggt gtacaagtat  1800
ttcaaggata tcaagtctaa cctgcccaga tgcaccaccc agagaaagga cgtgaaggca  1860
catttcgctg aaagcagcga tgattacacc ctgcttgata caaaagcctt cgtgagcgct  1920
ctgacgatct ccagagaggt gttcgaactg tacaacgctc ctgataagga aaagaaattc  1980
aagaaggaat acctgaagaa caccaacgac tccatcggct acgccaatgc agtgagcgtg  2040
tgcaagagat tctgcctgga gttcctgaaa aagtaccgga gcaccgccat ctacgacctg  2100
agcgatgttg aaacctctgt ggacagtttc gacgacctga gcagcttcta ccaggagatc  2160
gataagagac tgtacagcat cagcttcgaa aacgtgagcg tggacagcgt gaacgagctg  2220
gtggataacg gcaatatgct gctgttcaga atcgccaaca aggatttctc tcctaatagc  2280
aagggcagac ctaatctgca cacaatttac tggagaatgc tgttcgaccc tgctaatctc  2340
aaggacgtcg tgtaccaact gaacggcaat gccgaaatct tcttccggaa ggccagcgtt  2400
acaaggacag aaccaacaca ccccgccaat gtggccatca agaacaagag cgagtacaac  2460
aagcagaaca aaccttacag caccttcaag tacggcctca tcaaggaccg gcgatacacc  2520
accgatcagt tcgagttcca cgtgcctatc accatgaact tcaagcaacc tgagtcatct  2580
aagctgcagg acaaactgaa taagcaagtg ctggacttcc tgaagcaaga cggcgtgcgg  2640
cacatcatcg gcatcgaccg gggagaaaga aacctgctgt acctggtgat ggtcgacatg  2700
gaaggaaaaa tcaagaagca gatcagcctg aatgaaatcg ccggaaaccc aaagaaccct  2760
gagtttaagc aggacttctt agctctgctg catgagagag agggcgatag actggagtcc  2820
agaagaagtt ggaacaccat ccagagcatc aaggagctga aagaaggcta catgtccctg  2880
gtggtgcacg agatcgctaa catgatgctg gagaatgatg ccatcgtggt cttggaaaac  2940
cttaacagat cctttatgca gaagagaggc ggcattgaga aaagcgtgta ccagaagttt  3000
gagaaaatgc tgatcgacaa gctgggctac atcgtggaca aaacaaaaga tgtgtcagat  3060
aatggcggag ccctgcacgc cgtgcagctg gctgacacct tcgagaactt taacaagacc  3120
cagaaaggcg ccatccggca gtgcggcttc atcttttata tccccgcctg gcggacaagc  3180
aaaattgacc cggtaaccgg ctttgtgccc atgctgagat gtcagtacga atctatcgtg  3240
gaatccaaga agttctttgg caaattcgac tctatctact acgacgccac cggaaagtac  3300
ttcgtgttcc agaccgactt taccaagttc aacaccgagt ctaagggggg catccagaag  3360
tgggacatct gtacctacgg agacagaatc tacgccccta gaaccaaaga cagaaataac  3420
aaccctgtgt ccgaaagagt gaacctgaca gaagaaatga agagcctgtt cgtaagccac  3480
aatatcaaca tccagggcga catcaaggcc ggcattatgc agcagacaga caaggagttc  3540
ttcgagtcgc tgcacagact gctgagactg accctgcaga tccggaacag caagaaaagc  3600
accggcaagg actacgagga ctacattatc agtcctgtga tgggcaagga cggaagattc  3660
ttcgacagcc ggaacgccga cgccacccag cccaaggacg ccgacgcaaa cggcgcctac  3720
aacattgcca gaaaaggcct gatgctgctg cgccagatcc aggcccagga gaagcaggac  3780
ctgtctaatg ggaagtggct ggagttcgcc cagcggtcta gaaagcggac agcagacggc  3840
tccgaatttg aaagccctaa gaaaaagaga aaggtgggat ccggcaaacc tatccccaat  3900
cccctgctgg gcctggacag cacctga                                     3927

SEQ ID NO: 43          moltype = AA  length = 1219
FEATURE                Location/Qualifiers
source                 1..1219
                       mol_type = protein
                       organism = unidentified
SEQUENCE: 43
AEMFKDFTNL YPVSKTLRFE LIPEGETLHY LEKNGVLEND EKRNEDYKKL KKLMDEYYRA  60
YIDEALSNVH LSDLDRYAEL YSIQNKSDEE NVEFENVQLR LRTQIVGFLE SRETYSSLFK  120
KELIEKELPK FFIRREEELN LIKSFKGFTT MCTGFWENRK NMFSAEEKST AIAYRVVHEN  180
LPKFMNNIRI FRLFIDEKLD CSEKLLEKAG VNSLSEVFEL DYFNNTLSQR GIELYNCILG  240
GFTEDEKHKI QGVNELINLY NQQTKEKKIP QLQPLYKQIL SDTKSLSFLA DAFENDGGVL  300
ATVKALYDEF HEEILSERGL ISTTLQNIEK YDSKGIFVKN DLTITGLSNS LFGDWKAING  360
SLNSWYEENV PRKERTEEKH VEVRKAYFKK LKSISLEFIE EAGLSELRCK YKALLLEKAE  420
AVCDAYKNAE ELFSEAYNEN TNLIADGKSV EKIKALLDSM KELEAVILML SGTGEEAERD  480
ELFYGEFEKH RFVLNLLDNV FNKTRNYVTK KPYKTEKIKL TFDSPTLLDG WDRNKETSNK  540
SVILMKDGYY YLGIMNKANN KAFENLKDTG GKCYSKMDYK LLPGPNKMLP KVFFAKKNID  600
YYAPSEDLLQ KYKEGTHKKG KKFNLEDCHA LIDFFKDSIA KHPEWNEFGF DFSDTKSYRD  660
ISDFYKEVSE QGYKISYRNV SVNYIDSLVR EGKLYLFKIY NKDFSPYSKG RPNLHTMYWK  720
ALFANKNFEN RIYKLNGQAE MFYRKKSIPE DKRVIHSAKE PIDQRRNTDE KSLFDYDIIK  780
DRRYTVDKFQ FNVPITMNYT APGSGRINRK MREAIKNCEN MHIIGIDRGE RHLLYVTVID  840
MQGNIKEQFS LNRILSEYKA NNVAKSVETD YKTLLTKKEI ERQDARKQWK SIENIKELKD  900
GYMSQVVHVI AELMIKYNAI VVMEDLNFGF KRGRQKVERQ VYQKFEKALI DKLNYLVDKT  960
ASEMENTGLY AALQLTEKFE SFKKMGKQNG GLFYVNAWNT SKMDPTTGFV NLLYPKYESI  1020
EKSKAYIEKF KDIQFCDDDE YGKYLAISFD YNDFTEKAKG AKTEWTICSY GKRLYNHRNK  1080
DGYWEEQELD LTEEYFNLFE EFGINAASNI KEQVIAQNSA DFFRRFMWLL KMTLQIRNSE  1140
TNGETDYMLS PVKNEDGKFF NSDEVKDDTL PENADANGAY NIARKGLLLV ERIKDCPDEE  1200
LDKVDLKVTN LDWMKFAQR                                                1219

SEQ ID NO: 44          moltype = AA  length = 1220
FEATURE                Location/Qualifiers
source                 1..1220
                       mol_type = protein
                       organism = unidentified
SEQUENCE: 44
MAEMFKDFTN LYPVSKTLRF ELIPEGETLH YLEKNGVLEN DEKRNEDYKK LKKLMDEYYR  60
AYIDEALSNV HLSDLDRYAE LYSIQNKSDE ENVEFENVQL RLRTQIVGFL ESRETYSSLF  120
KKELIEKELP KFFIRREEEL NLIKSFKGFT TMCTGFWENR KNMFSAEEKS TAIAYRVVHE  180
```

```
NLPKFMNNIR IFRLFIDEKL DCSEKLLEKA GVNSLSEVFE LDYFNNTLSQ RGIELYNCIL  240
GGFTEDEKHK IQGVNELINL YNQQTKEKKI PQLQPLYKQI LSDTKSLSFL ADAFENDGGV  300
LATVKALYDE FHEEILSERG LISTTLQNIE KYDSKGIFVK NDLTITGLSN SLFGDWKAIN  360
GSLNSWYEEN VPRKERTEEK HVEVRKAYFK KLKSISLEFI EEAGLSELRC KYKALLLEKA  420
EAVCDAYKNA EELFSEAYNE NTNLIADGKS VEKIKALLDS MKELEAVILM LSGTGEEAER  480
DELFYGEFEK HRFVLNLLDN VFNKTRNYVT KKPYKTEKIK LTFDSPTLLD GWDRNKETSN  540
KSVILMKDGY YYLGIMNKAN NKAFENLKDT GGKCYSKMDY KLLPGPNKML PKVFFAKKNI  600
DYYAPSEDLL QKYKEGTHKK GKKFNLEDCH ALIDFFKDSI AKHPEWNEFG FDFSDTKSYR  660
DISDFYKEVS EQGYKISYRN VSVNYIDSLV REGKLYLFKI YNKDFSPYSK GRPNLHTMYW  720
KALFANKNFE NRIYKLNGQA EMFYRKKSIP EDKRVIHSAK EPIDQRRNTD EKSLFDYDII  780
KDRRYTVDKF QFNVPITMNY TAPGSGRINR KMREAIKNCE NMHIIGIDRG ERHLLYVTVI  840
DMQGNIKEQF SLNRILSEYK ANNVAKSVET DYKTLLTKKE IERQDARKQW KSIENIKELK  900
DGYMSQVVHV IAELMIKYNA IVVMEDLNFG FKRGRQKVER QVYQKFEKAL IDKLNYLVDK  960
TASEMENTGL YAALQLTEKF ESFKKMGKQN GGLFYVNAWN TSKMDPTTGF VNLLYPKYES  1020
IEKSKAYIEK FKDIQFCDDD EYGKYLAISF DYNDFTEKAK GAKTEWTICS YGKRLYNHRN  1080
KDGYWEEQEL DLTEEYFNLF EEFGINAASN IKEQVIAQNS ADFFRRFMWL LKMTLQIRNS  1140
ETNGETDYML SPVKNEDGKF FNSDEVKDDT LPENADANGA YNIARKGLLL VERIKDCPDE  1200
ELDKVDLKVT NLDWMKFAQR                                             1220

SEQ ID NO: 45          moltype = AA  length = 1257
FEATURE                Location/Qualifiers
source                 1..1257
                       mol_type = protein
                       organism = synthetic construct
SEQUENCE: 45
MGAEMFKDFT NLYPVSKTLR FELIPEGETL HYLEKNGVLE NDEKRNEDYK KLKKLMDEYY  60
RAYIDEALSN VHLSDLDRYA ELYSIQNKSD EENVEFENVQ LRLRTQIVGF LESRETYSSL  120
FKKELIEKEL PKFFIRREEE LNLIKSFKGF TTMCTGFWEN RKNMFSAEEK STAIAYRVVH  180
ENLPKFMNNI RIFRLFIDEK LDCSEKLLEK AGVNSLSEVF ELDYFNNTLS QRGIELYNCI  240
LGGFTEDEKH KIQGVNELIN LYNQQTKEKK IPQLQPLYKQ ILSDTKSLSF LADAFENDGG  300
VLATVKALYD EFHEEILSER GLISTTLQNI EKYDSKGIFV KNDLTITGLS NSLFGDWKAI  360
NGSLNSWYEE NVPRKERTEE KHVEVRKAYF KKLKSISLEF IEEAGLSELR CKYKALLLEK  420
AEAVCDAYKN AEELFSEAYN ENTNLIADGK SVEKIKALLD SMKELEAVIL MLSGTGEEAE  480
RDELFYGEFE KHRFVLNLLD NVFNKTRNYV TKKPYKTEKI KLTFDSPTLL DGWDRNKETS  540
NKSVILMKDG YYYLGIMNKA NNKAFENLKD TGGKCYSKMD YKLLPGPNKM LPKVFFAKKN  600
IDYYAPSEDL LQKYKEGTHK KGKKFNLEDC HALIDFFKDS IAKHPEWNEF GFDFSDTKSY  660
RDISDFYKEV SEQGYKISYR NVSVNYIDSL VREGKLYLFK IYNKDFSPYS KGRPNLHTMY  720
WKALFANKNF ENRIYKLNGQ AEMFYRKKSI PEDKRVIHSA KEPIDQRRNT DEKSLFDYDI  780
IKDRRYTVDK FQFNVPITMN YTAPGSGRIN RKMREAIKNC ENMHIIGIDR GERHLLYVTV  840
IDMQGNIKEQ FSLNRILSEY KANNVAKSVE TDYKTLLTKK EIERQDARKQ WKSIENIKEL  900
KDGYMSQVVH VIAELMIKYN AIVVMEDLNF GFKRGRQKVE RQVYQKFEKA LIDKLNYLVD  960
KTASEMENTG LYAALQLTEK FESFKKMGKQ NGGLFYVNAW NTSKMDPTTG FVNLLYPKYE  1020
SIEKSKAYIE KFKDIQFCDD DEYGKYLAIS FDYNDFTEKA KGAKTEWTIC SYGKRLYNHR  1080
NKDGYWEEQE LDLTEEYFNL FEEFGINAAS NIKEQVIAQN SADFFRRFMW LLKMTLQIRN  1140
SETNGETDYM LSPVKNEDGK FFNSDEVKDD TLPENADANG AYNIARKGLL LVERIKDCPD  1200
EELDKVDLKV TNLDWMKFAQ RSRKRTADGS EFESPKKKRK VGSGKPIPNP LLGLDST     1257

SEQ ID NO: 46          moltype = DNA  length = 3663
FEATURE                Location/Qualifiers
source                 1..3663
                       mol_type = unassigned DNA
                       organism = unidentified
SEQUENCE: 46
atggctgaga tgtttaaaga ttttacgaat ttgtatcctg tttcaaaaac cttgcgtttt  60
gaattaattc ctgaagggga aacattgcat tatcttgaaa aaaatggcgt tctggaaaac  120
gatgagaagc gaaacgaaga ttataagaag ttgaaaaaac tgatggatga atattaccgt  180
gcatacatcg atgaagcttt atctaatgtt catctttcag atttggatag atatgcagaa  240
ttatattcaa ttcagaataa atcggatgaa gaaaatgtag aattcgaaaa tgttcaactg  300
agattgagaa cacaaattgt tggattctta gaatccagag aaacctattc ttcacttttc  360
aaaaaagaac tgattgagaa ggaacttcct aaattcttta ttcggagaga agaggagctt  420
aatttaatca aatcatttaa aggttttaca acgatgtgca ccggcttctg ggaaaatcgg  480
aaaaatatgt ttctgccga agaaaaatct acagcaatag catatcgtgt agtccatgaa  540
aacctaccta agtttatgaa taatataaga atttttcgtt tgttcattga tgaaaagttg  600
gactgttctg aaaaattgct ggaaaaagcc ggagtgaatt ctctgagtga agtgtttgaa  660
cttgattatt ttaacaatac attatcccaa cgtggcattg aattgtataa ctgtatattg  720
ggcggattta ccgaggatga aaagcataag attcaaggcg taaacgaatt gattaatttg  780
tacaatcagc agacaaaaga gaagaagatt ccacagttgc agccgctgta caagcagatt  840
ctcagcgata ccaagagcct ttcatttctt gcagatgcat ttgaaaacga cggggggtc  900
ttagcgactg taaaagcatt atatgatgaa tttcatgaag agattttgag cgaaagggga  960
ttaatctcta cgacattaca gaatattgaa aagtatgatt caaaaggcat cttcgtaaaa  1020
aacgatttaa cgattaccgg tttatcaaat agtttgttcg gcgactggaa ggctattaat  1080
ggtagtttaa attcgtggta tgaggagaac gtgcctcgaa aagaaagaac tgaagagaaa  1140
catgtagagg taagaaaagc ctattttaaa aagttaaaat caataagcct ggaatttatc  1200
gaggaggccg gattgtcgga actccgttgc aaatataaag cccttctttt agaaaaagca  1260
gaggctgttt gcgatgcgta caaaaatgca gaagagcttt ttagtgaagc ttataatgaa  1320
aatactaacc ttattgccga tggaaagtct gtggaaaaaa taaaagcgct attggattct  1380
atgaaagagc ttgaagcggt gattcttatg ctttccggaa ccggagagga agcagaacgg  1440
gatgaattgt tttacggcga atttgaaaaa cataggttcg tattgaatct cttagacaac  1500
gtatttaata aaacgagaaa ttacgtaaca aagaaaccat ataagactga gaagattaaa  1560
```

```
ttaacatttg attccccaac gctgctagac gggtgggatc gtaataaaga aacatcaaac  1620
aagtccgtga tacttatgaa agatggctat tattaccttg gaattatgaa caaggcaaat  1680
aacaaagcct ttgagaattt gaaagacaca ggcgggaaat gctatagcaa gatggattac  1740
aaacttttgc ctggaccaaa caagatgttg ccgaaggtgt tttttgcaaa gaaaaacatc  1800
gactattatg caccaagcga agacttgcta cagaaatata aagagggaac acataaaaaa  1860
ggaaagaaat ttaatctaga ggattgtcac gcgttaatag actttttttaa agactcaatt  1920
gcaaagcatc cagaatggaa cgagtttgga tttgattttt cagatacgaa atcatatcga  1980
gatattagtg atttctataa ggaggtttca gagcagggat acaaaatcag ttatcgaaat  2040
gtatctgtta attacataga ttctctagta agagaaggga aattgtattt gttcaaaatt  2100
tataataaag atttttcacc gtacagcaaa ggcagaccaa atcttcatac gatgtattgg  2160
aaagcgttat tcgctaataa gaattttgaa aatcgcatat ataagttaaa tggccaggca  2220
gaaatgttct atcgaaaaaa gagcattccg gaagacaaga gggtgattca ctcggcaaaa  2280
gaaccaatcg atcagagaag aaatacggat gaaaagagcc tctttgatta tgacattatt  2340
aaagatcggc gatatactgt ggacaaattc caatttaatg ttccgattac gatgaattac  2400
actgcaccgg gttccggccg aattaacaga aaaatgcggg aagcgattaa gaactgtgaa  2460
aatatgcata ttatcggaat agatagaggc gaacgtcatt tgctgtatgt gacggttatc  2520
gatatgcagg gaaacattaa agaacagttt tcattaaatc gaatcctgag tgagtacaag  2580
gcaaacaatg tggctaaaag tgtcgaaacg gactacaaaa cactcctgac aaaaaaagaa  2640
attgaacgac aggatgcaag aaagcagtgg aagagcattg aaaatattaa ggaattaaaa  2700
gacggctaca tgagccaggt tgtgcatgtg attgccgaac tcatgataaa gtacaatgcg  2760
attgtggtta tggaggattt gaatttcgga ttcaagcgag gaagacagaa ggttgagaga  2820
caggtttacc agaagtttga gaaggcatta attgataaat tgaactattt ggttgataaa  2880
acagcctctg aaatggagaa caccggtctg tatgcggcat tgcagcttac agaaaaattt  2940
gagagcttta agaaaaatggg caaacaaaat ggtggattat tttatgtaaa cgcatggaat  3000
accagtaaaa tggatccaac aaccggtttt gtgaaccttc tctatcctaa atatgagagc  3060
attgaaaaaa gcaaagcgta tattgagaaa ttcaaggata ttcagttttg tgatgatgac  3120
gaatatggaa agtaccttgc aatatctttt gattataacg atttcacgga gaaggcaaag  3180
ggcgcaaaaa cggaatggac catttgctct tatggaaaga gattgtataa tcacagaaat  3240
aaagatgggt attgggaaga gcaggaattg gatcttacag aagagtattt caatctgttt  3300
gaagaatttg gaattaatgc agcgtctaat attaaagaac aagtcatcgc acagaattct  3360
gcagactttt ttagacggtt tatgtggctt ttgaaaatga ccttacagat tagaaacagt  3420
gaaacaaatg gggagacgga ttatatgctt tctccggtaa aaaatgaaga cggaaaattc  3480
tttaattcag atgaagtcaa ggatgacacg cttccggaaa atgcggatgc gaatggtgca  3540
tacaacatcg ctagaaaagg attactgctt gtggaaagaa ttaaagactg tccggacgaa  3600
gaacttgata aggttgattt gaaggtaaca aatttagatt ggatgaaatt tgcacagagg  3660
taa                                                                3663
```

```
SEQ ID NO: 47          moltype = DNA  length = 3657
FEATURE                Location/Qualifiers
source                 1..3657
                       mol_type = other DNA
                       organism = synthetic construct
SEQUENCE: 47
gccgaaatgt tcaaggactt caccaacctg tacccagtgt ccaaaaccct ccggttcgaa  60
ttgatccccg agggcgaaac actgcactac ctagaaaaga acggagtgct ggaaaacgac  120
gagaagagaa atgaggatta caagaagctg aagaaactca tggatgaata ctaccgggcc  180
tacatcgacg aggccttatc taatgtccac ctgtccgatc tggaccggta cgccgaactg  240
tattctatcc agaacaagag cgatgaggag aacgtggagt tcgagaatgt gcagctgcgc  300
ctgagaaccc agatcgtggg cttcctggaa agcagagaaa cctacagcag cctgttcaag  360
aaggagctga tcgaaaaaga actgcctaag tttttcatca gaagagagga agagctgaac  420
ctgataaaga gctttaaggg ctttaccact atgtgcaccg gcttctggga aaatcggaag  480
aacatgttca gcgccgagga aaagtccaca gccatcgcct atagagtggt ccatgaaaac  540
ctgcccaagt tcatgaacaa cattagaatc ttccggctgt ttatcgacga gaagctggat  600
tgtagcgaga agctgctgga gaaggccgc gtgaacagcc tgagcgaggt gttcgagctt  660
gactatttca ataacaccct gagccagaga ggcatcgagc tgtacaactg catcctgggc  720
ggattcaccg aggatgaaaa acacaagatc cagggagtga acgagttgat caacctgtac  780
aaccagcaga caaaggagaa gaaaattcct cagctgcaac ctctgtacaa acagatcctg  840
tctgacacga agtcgctgtc ctttctggct gatgcctttg aaaacgacgg aggagtgctg  900
gctacagtga aggctttata tgatgagttt cacgaggaaa tcctgagcga gagaggcctg  960
atcagcacaa ccctgcagaa cattgagaag tacgatagta agggcatctt tgttaagaac  1020
gatctcacca ttacaggcct gtccaacagc ctgtttggag attggaaggc catcaatgga  1080
agcctgaaca gctggtacga ggagaacgtg ccccggaagg agcgaacaga agagaaacac  1140
gtggaagtga gaaaggctta ttttaagaag ctgaagtcta tcagcctgga gttcatcgag  1200
gaggccggac tgagcgagct gcggtgcaag tacaaggccc tgctgctgga gaaagccgag  1260
gctgtgtgcg acgcgtacaa gaacgccgag gagctgttta gcgaggccta taatgagaac  1320
accaatctga tcgccgatgg caaatctgtg gaaaaaatca aagccctgct ggacagcatg  1380
aaggagctgg aggccgtgat cctgatgctg agcggcacag gcgaggaggc cgagcgggac  1440
gaactgtttt atggcgagtt cgaaaaacat agattcgtgc tgaatctgct ggacaacgtg  1500
ttcaacaaga ccagaaacta cgtgaccaag aagccttaca agaccgagaa gatcaagctc  1560
accttcgaca gccctaccct tctggatggc tgggaccgta acaaggagac aagcaacaag  1620
agcgtgatcc tgatgaagga tggctactac tacctgggca tcatgaacaa agccaacaac  1680
aaggccttcg agaacctgaa ggacacagga ggcaaatgct acagcaagat ggactacaag  1740
ctgctgcctg gccctaacaa gatgctgcct aaggtgttct ttgccaaaaa gaacatcgac  1800
tactacgccc ctagcgagga cctgctgcag aagtacaagg agggcaccca caagaaaggg  1860
aagaagttca atcttgagga ctgtcacgcc ctgatcgact tcttcaagga cagcatcgct  1920
aaacaccccg agtggaacga gttcggcttc gacttttctg acaccaagtc ttatagagac  1980
atctcggatt tctacaagga ggtcagcgaa cagggctaca agattagcta ccggaacgtg  2040
agtgttaact acatcgacag tctggtgcgg gaaggtaagc tgtacctgtt caagatctac  2100
aacaaggact tcagcccata ctccaaagga cgtcccaacc tgcacaccat gtactggaaa  2160
```

```
gccctgttcg ccaataaaaa cttcgaaaac cggatctaca agctgaacgg ccaggccgaa  2220
atgttctaca gaaagaaatc tatccctgaa gataagcggg tgatccacag cgccaaagaa  2280
cctatcgatc agagaagaaa caccgacgaa aagtctctgt ttgactacga catcatcaag  2340
gacagacggt acaccgtgga caagttccag ttcaacgtgc caatcacaat gaactacacc  2400
gcccctggca gcggcagaat caacagaaag atgcgggaag ctatcaagaa ttgcgagaat  2460
atgcacatca tcggcatcga ccggggagag cggcacctgc tgtacgtgac cgtgatcgac  2520
atgcagggca acatcaaaga acagttctct ctcaaccgca tcctgtctga gtacaaggcc  2580
aataacgtcg ccaagagcgt ggagacagac tacaaaacac tgctgacgaa aaaagagatc  2640
gagagacagg acgctagaaa gcaatggaag agcatcgaaa acatcaaaga gctgaaagac  2700
ggctatatga gccaggtggt gcacgtgata gcagagctga tgatcaagta caacgccata  2760
gttgtgatgg aggacctgaa tttcggcttc aagagaggcc ggcaaaaggt ggagagacag  2820
gtgtaccaga aattcgagaa ggccctgatc gataagctga attacctggt ggataagaca  2880
gcttccgaga tggaaaacac cggcctgtac gccgccctgc agctgacaga gaagttcgaa  2940
tccttcaaga agatgggcaa acagaacggc ggcttgttct acgtgaacgc ctggaacacc  3000
agcaagatgg accctaccac cggattcgtg aacctgctgt accctaagta cgaatctatc  3060
gaaaagagca aggcctatat cgagaaattc aaggatatcc agttttgtga cgacgatgaa  3120
tacggcaaat acctggcaat ttctttcgac tacaacgact tcacagaaaa ggccaagggc  3180
gccaagaccg agtggaccat ctgcagctac ggcaaaagac tgtacaacca cagaaataag  3240
gacggctact gggaggagca ggagctggat ctgaccgagg agtacttcaa cctgttcgaa  3300
gagttcggca tcaacgctgc cagcaacatc aaggaacaag tgatcgctca gaacagcgcc  3360
gatttcttca gaagattcat gtggctgctg aagatgaccc tgcagatcag gaactctgaa  3420
actaacggcg aaaccgatta catgctgagc cctgtgaaga acgaggacgg caaattcttc  3480
aactctgacg aggtgaagga cgacaccctg cccgagaatg ccgacgccaa cggcgcctac  3540
aacatcgcaa gaaagggcct gctgctggtc gaacgtatca aggattgccc cgacgaagaa  3600
ctagacaagg tggacctgaa ggtcaccaac ctggactgga tgaaattcgc ccaaaga     3657
```

```
SEQ ID NO: 48           moltype = DNA  length = 3774
FEATURE                 Location/Qualifiers
source                  1..3774
                        mol_type = other DNA
                        organism = synthetic construct
SEQUENCE: 48
atgggcgccg aaatgttcaa ggacttcacc aacctgtacc cagtgtccaa aaccctccgg  60
ttcgaattga tccccgaggg cgaaacactg cactacctag aaaagaacgg agtgctggaa  120
aacgacgaga agagaaatga ggattacaag aagctgaaga aactcatgga tgaatactac  180
cgggcctaca tcgacgaggc cttatctaat gtccacctgt ccgatctgga ccggtacgcc  240
gaactgtatt ctatccagaa caagagcgat gaggagaacg tggagttcga gaatgtgcag  300
ctgcgcctga gaacccagat cgtgggcttc ctggaaagca gagaaaccta cagcagcctg  360
ttcaagaagg agctgatcga aaaagaactg cctaagtttt tcatcagaag agaggaagag  420
ctgaacctga taaagagctt taagggcttt accactatgt gcaccggctt ctgggaaaat  480
cggaagaaca tgttcagcgc cgaggaaaag tccacagcca tcgcctatag agtggtccat  540
gaaaacctgc ccaagttcat gaacaacatt agaatcttcc ggctgtttat cgacgagaag  600
ctggattgta gcgagaagct gctggagaag gccggcgtga acagcctgag cgaggtgttc  660
gagcttgact atttcaataa caccctgagc cagagaggca tcgagctgta caactgcatc  720
ctgggcggat tcaccgagga tgaaaaacac aagatccagg gagtgaacga gttgatcaac  780
ctgtacaacc agcagacaaa ggagaagaaa attcctcagc tgcaacctct gtacaaacag  840
atcctgtctg acacgaagtc gctgtccttt ctggctgatg cctttgaaaa cgacggagga  900
gtgctggcta cagtgaaggc tttatatgat gagtttcacg aggaaatcct gagcgagaga  960
ggcctgatca gcacaaccct gcagaacatt gagaagtacg atagtaaggg catctttgtt  1020
aagaacgatc tcaccattac aggcctgtcc aacagcctgt ttggagattg gaaggccatc  1080
aatggaagcc tgaacagctg gtacgaggag aacgtgcccc ggaaggagcg aacagaagag  1140
aaacacgtgg aagtgagaaa ggcttatttt aagaagctga agtctatcag cctggagttc  1200
atcgaggagg ccggactgag cgagctgcgg tgcaagtaca aggccctgct gctggagaaa  1260
gccgaggctg tgtgcgacgc gtacaagaac gccgaggagc tgtttagcga ggcctataat  1320
gagaacacca atctgatcgc cgatggcaaa tctgtggaaa aaatcaaagc cctgctggac  1380
agcatgaagg agctggaggc cgtgatcctg atgctgagcg gcacaggcga ggaggccgag  1440
cgggacgaac tgttttatgg cgagttcgaa aaacatagat tcgtgctgaa tctgctggac  1500
aacgtgttca acaagaccag aaactacgtg accaagaagc cttacaagac cgagaagatc  1560
aagctcacct tcgacagccc taccttctgg gatggctggg accgtaacaa ggagacaagc  1620
aacaagagcg tgatcctgat gaaggatggc tactactacc tgggcatcat gaacaaagcc  1680
aacaacaagg ccttcgagaa cctgaaggac acaggaggca aatgctacag caagatggac  1740
tacaagctgc tgcctggccc taacaagatg ctgcctaagg tgttctttgc caaaaagaac  1800
atcgactact acgcccctag cgaggacctg ctgcagaagt acaaggaggg cacccacaag  1860
aaagggaaga agttcaatct tgaggactgt cacgccctga tcgacttctt caaggacagc  1920
atcgctaaac accccgagtg gaacgagttc ggcttcgact ttctgacac caagtcttat  1980
agagacatct cggatttcta caaggaggtc agcgaacagg gctacaagat tagctaccgg  2040
aacgtgagtg ttaactacat cgacagtctg gtgcgggaag gtaagctgta cctgttcaag  2100
atctacaaca aggacttcag cccatactcc aaaggacgtc ccaacctgca caccatgtac  2160
tggaaagccc tgttcgccaa taaaaacttc gaaaaccgga tctacaagct gaacggccag  2220
gccgaaatgt tctacagaaa gaaatctatc cctgaagata agcgggtgat ccacagcgcc  2280
aaagaaccta tcgatcagag aagaaacacc gacgaaaagt ctctgtttga ctacgacatc  2340
atcaaggaca gacggtacac cgtggacaag ttccagttca acgtgccaat cacaatgaac  2400
tacaccgccc ctggcagcgg cagaatcaac agaaagatgc gggaagctat caagaattgc  2460
gagaatatgc acatcatcgg catcgaccgg ggagagcggc acctgctgta cgtgaccgtg  2520
atcgacatgc agggcaacat caaagaacag ttctctctca accgcatcct gtctgagtac  2580
aaggccaata acgtcgccaa gagcgtggag acagactaca aaacactgct gacgaaaaaa  2640
gagatcgaga gacaggacgc tagaaagcaa tggaagagca tcgaaaacat caaagagctg  2700
aaagacggct atatgagcca ggtggtgcac gtgatagcag agctgatgat caagtacaac  2760
gccatagttg tgatggagga cctgaatttc ggcttcaaga gaggccggca aaaggtggag  2820
```

```
agacaggtgt accagaaatt cgagaaggcc ctgatcgata agctgaatta cctggtggat  2880
aagacagctt ccgagatgga aaacaccggc ctgtacgccg ccctgcagct gacagagaag  2940
ttcgaatcct tcaagaagat gggcaaacag aacggcggct tgttctacgt gaacgcctgg  3000
aacaccagca agatggaccc taccaccgga ttcgtgaacc tgctgtaccc taagtacgaa  3060
tctatcgaaa agagcaaggc ctatatcgag aaattcaagg atatccagtt ttgtgacgac  3120
gatgaatacg gcaaatacct ggcaatttct ttcgactaca acgacttcac agaaaaggcc  3180
aagggcgcca agaccgagtg gaccatctgc agctacggca aaagactgta caaccacaga  3240
aataaggacg gctactggga ggagcaggag ctggatctga ccgaggagta cttcaacctg  3300
ttcgaagagt tcggcatcaa cgctgccagc aacatcaagg aacaagtgat cgctcagaac  3360
agcgccgatt tcttcagaag attcatgtgg ctgctgaaga tgaccctgca gatcaggaac  3420
tctgaaacta acggcgaaac cgattacatg ctgagccctg tgaagaacga ggacggcaaa  3480
ttcttcaact ctgacgaggt gaaggacgac accctgcccg agaatgccga cgccaacggc  3540
gcctacaaca tcgcaagaaa gggcctgctg ctggtcgaac gtatcaagga ttgccccgac  3600
gaagaactag acaaggtgga cctgaaggtc accaacctgg actggatgaa attcgcccaa  3660
aggtctagaa agcggacagc agacggctcc gaatttgaaa gccctaagaa aaagagaaag  3720
gtgggatccg gcaaacctat ccccaatccc ctgctgggcc tggacagcac ctga        3774

SEQ ID NO: 49          moltype = AA  length = 1200
FEATURE                Location/Qualifiers
source                 1..1200
                       mol_type = protein
                       organism = unidentified
SEQUENCE: 49
KLEDFTNLYS LSKTLRFELR PIGKTRENIE NGGLLRQDED RAEKYVHIKK LIDEYHKAYI  60
DKQLSGLVLQ YADIGKANSL EEYYHSTRKS KDSDKDKIVK IQDNLRKQIV KRLKDSDEFK  120
RIDKKELIQS DLAEFIKPAE DRALIAEFKN FTTYFTGFNE NRQNMYSDKA ISTAIAYRLI  180
HENLPKFIDN IETFDRIAGI TELYDQTSSD AEIFRLEHFS ETLSQKQIDA YNSVMGRYNM  240
LINEYNQTHK QSRLPKFKML YKQILSDREH PSWLPEQFES DTAVLTAIRE CYDDLRIPMA  300
NLKTLLEGLG NYDPSGIFLR NDQHLSQISK RLTGDRSSIE RSVTEDLLTS RRLNKRKSRT  360
TDEEESRKLF KQKGSLSIGY IADTAKIDVE RYFAKLGAIN TVTEQSENLF AKAENARTTA  420
DELLANDYPA GKRLVQSNDD IALLKNLLDA LMELQWFVKP LLGTGDEAGK DERFYGEFAQ  480
IWEQLDRITP LYNMVRNYVT RKPYSTDKFK LNFESAALLG GWDKNKEPDC LSVILRKDEQ  540
YYLGIINKNH KKIFENDILP CEGECYDKMV YKLLPGANKM LPKVFFSASR IAEFAPSDEV  600
KRIYNDKTFQ KGEKFDLNDC RTLIDFYKAS IDKHEEWNKF GFEFSDTNNY EDISGFFREV  660
DRQGYKMSFR PVAASYIETL VEEGKLYLFQ IYNKDFSAYS KGTPNMHTLY WRMLFDERNL  720
SDVVYQLNGG AELFFRRKSL QNGRPTHPAN IPIKNKNSRN DKKESLFDYD LIKDRRYTVD  780
KFQFHVPITL NFKSDGAGRI NERVREYLRS ADDVHVIGID RGERNLLYLV VTDMDGNICE  840
QFSLNEICNT DYHSLLDERE HKRMQERQSW QAIEGIKELK EGYLSQVVHR IATLMVKYRA  900
IVVLEDLNFG FMRSRQKVEK SVYQKFEHML IDKLNYLVDK KANPTTPGGL LKAYQLTDKF  960
ESFQKLGKQS GFLFYVPAWN TSKIDPATGF VNMLDLGYES IDKAKTLLCK FDSIRYNACK  1020
DWFEFALDYD KFGSKATGTR TKWTVCTYGQ RIDTYRNKDS QWVSRDVDLT NELKSLFSEH  1080
GIDIYSNLKD AIVAQNDKEF FANMQRILKL TMQMRNSKTG TDTDYIVSPV ADANGRFFDS  1140
RQADATMPKD ADANGAYNIA RKGIMLVQQI KQSDDLRTMK FDISNKSWLR FAQHTNQADE  1200

SEQ ID NO: 50          moltype = AA  length = 1201
FEATURE                Location/Qualifiers
source                 1..1201
                       mol_type = protein
                       organism = unidentified
SEQUENCE: 50
MKLEDFTNLY SLSKTLRFEL RPIGKTRENI ENGGLLRQDE DRAEKYVHIK KLIDEYHKAY  60
IDKQLSGLVL QYADIGKANS LEEYYHSTRK SKDSDKDKIV KIQDNLRKQI VKRLKDSDEF  120
KRIDKKELIQ SDLAEFIKPA EDRALIAEFK NFTTYFTGFN ENRQNMYSDK AISTAIAYRL  180
IHENLPKFID NIETFDRIAG ITELYDQTSS DAEIFRLEHF SETLSQKQID AYNSVMGRYN  240
MLINEYNQTH KQSRLPKFKM LYKQILSDRE HPSWLPEQFE SDTAVLTAIR ECYDDLRIPM  300
ANLKTLLEGL GNYDPSGIFL RNDQHLSQIS KRLTGDRSSI ERSVTEDLLT SRRLNKRKSR  360
TTDEEESRKL FKQKGSLSIG YIADTAKIDV ERYFAKLGAI NTVTEQSENL FAKAENARTT  420
ADELLANDYP AGKRLVQSND DIALLKNLLD ALMELQWFVK PLLGTGDEAG KDERFYGEFA  480
QIWEQLDRIT PLYNMVRNYV TRKPYSTDKF KLNFESAALL GGWDKNKEPD CLSVILRKDE  540
QYYLGIINKN HKKIFENDIL PCEGECYDKM VYKLLPGANK MLPKVFFSAS RIAEFAPSDE  600
VKRIYNDKTF QKGEKFDLND CRTLIDFYKA SIDKHEEWNK FGFEFSDTNN YEDISGFFRE  660
VDRQGYKMSF RPVAASYIET LVEEGKLYLF QIYNKDFSAY SKGTPNMHTL YWRMLFDERN  720
LSDVVYQLNG GAELFFRRKS LQNGRPTHPA NIPIKNKNSR NDKKESLFDY DLIKDRRYTV  780
DKFQFHVPIT LNFKSDGAGR INERVREYLR SADDVHVIGI DRGERNLLYL VVTDMDGNIC  840
EQFSLNEICN TDYHSLLDER EHKRMQERQS WQAIEGIKEL KEGYLSQVVH RIATLMVKYR  900
AIVVLEDLNF GFMRSRQKVE KSVYQKFEHM LIDKLNYLVD KKANPTTPGG LLKAYQLTDK  960
FESFQKLGKQ SGFLFYVPAW NTSKIDPATG FVNMLDLGYE SIDKAKTLLC KFDSIRYNAC  1020
KDWFEFALDY DKFGSKATGT RTKWTVCTYG QRIDTYRNKD SQWVSRDVDL TNELKSLFSE  1080
HGIDIYSNLK DAIVAQNDKE FFANMQRILK LTMQMRNSKT GTDTDYIVSP VADANGRFFD  1140
SRQADATMPK DADANGAYNI ARKGIMLVQQ IKQSDDLRTM KFDISNKSWL RFAQHTNQAD  1200
E                                                                 1201

SEQ ID NO: 51          moltype = AA  length = 1238
FEATURE                Location/Qualifiers
source                 1..1238
                       mol_type = protein
                       organism = synthetic construct
SEQUENCE: 51
MGKLEDFTNL YSLSKTLRFE LRPIGKTREN IENGGLLRQD EDRAEKYVHI KKLIDEYHKA  60
```

```
YIDKQLSGLV LQYADIGKAN SLEEYYHSTR KSKDSDKDKI VKIQDNLRKQ IVKRLKDSDE  120
FKRIDKKELI QSDLAEFIKP AEDRALIAEF KNFTTYFTGF NENRQNMYSD KAISTAIAYR  180
LIHENLPKFI DNIETFDRIA GITELYDQTS SDAEIFRLEH FSETLSQKQI DAYNSVMGRY  240
NMLINEYNQT HKQSRLPKFK MLYKQILSDR EHPSWLPEQF ESDTAVLTAI RECYDDLRIP  300
MANLKTLLEG LGNYDPSGIF LRNDQHLSQI SKRLTGDRSS IERSVTEDLL TSRRLNKRKS  360
RTTDEEESRK LFKQKGSLSI GYIADTAKID VERYFAKLGA INTVTEQSEN LFAKAENART  420
TADELLANDY PAGKRLVQSN DDIALLKNLL DALMELQWFV KPLLGTGDEA GKDERFYGEF  480
AQIWEQLDRI TPLYNMVRNY VTRKPYSTDK FKLNFESAAL LGGWDKNKEP DCLSVILRKD  540
EQYYLGIINK NHKKIFENDI LPCEGECYDK MVYKLLPGAN KMLPKVFFSA SRIAEFAPSD  600
EVKRIYNDKT FQKGEKFDLN DCRTLIDFYK ASIDKHEEWN KFGFEFSDTN NYEDISGFFR  660
EVDRQGYKMS FRPVAASYIE TLVEEGKLYL FQIYNKDFSA YSKGTPNMHT LYWRMLFDER  720
NLSDVVYQLN GGAELFFRRK SLQNGRPTHP ANIPIKNKNS RNDKKESLFD YDLIKDRRYT  780
VDKFQFHVPI TLNFKSDGAG RINERVREYL RSADDVHVIG IDRGERNLLY LVVTDMDGNI  840
CEQFSLNEIC NTDYHSLLDE REHKRMQERQ SWQAIEGIKE LKEGYLSQVV HRIATLMVKY  900
RAIVVLEDLN FGFMRSRQKV EKSVYQKFEH MLIDKLNYLV DKKANPTTPG GLLKAYQLTD  960
KFESFQKLGK QSGFLFYVPA WNTSKIDPAT GFVNMLDLGY ESIDKAKTLL CKFDSIRYNA  1020
CKDWFEFALD YDKFGSKATG TRTKWTVCTY GQRIDTYRNK DSQWVSRDVD LTNELKSLFS  1080
EHGIDIYSNL KDAIVAQNDK EFFANMQRIL KLTMQMRNSK TGTDTDYIVS PVADANGRFF  1140
DSRQADATMP KDADANGAYN IARKGIMLVQ QIKQSDDLRT MKFDISNKSW LRFAQHTNQA  1200
DESRKRTADG SEFESPKKKR KVGSGKPIPN PLLGLDST                         1238

SEQ ID NO: 52          moltype = DNA  length = 3606
FEATURE                Location/Qualifiers
source                 1..3606
                       mol_type = unassigned DNA
                       organism = unidentified
SEQUENCE: 52
atgaaattag aagattttac caacctgtat tcgttatcca agactctgcg tttcgaactg  60
cggccgatcg gcaagacacg tgaaaatatc gaaaacggag gccttttgag gcaggacgag  120
gatcgtgctg aaaaatatgt acacataaaa aaactaatcg atgaatatca taaagcatat  180
atcgataaac aattgtcggg tttagtgctg caatacgccg atatcggtaa agccaattca  240
ttggaggagt attatcactc cacaagaaag agcaaagatt cggacaagga taagattgtc  300
aaaatccagg ataatctgcg taaacaaatt gtcaaacggt tgaaagactc agacgaattc  360
aagcgtatcg ataaaaaaga gttgattcaa tcggatctgg cagagttcat aaaaccagcc  420
gaagacagag ctttgattgc cgaattcaaa aacttcacaa catattttac cggattcaat  480
gaaaacagac agaacatgta ttcggacaaa gctatatcta cggcaatagc ttatcgtctg  540
atacatgaga atcttccgaa gttcatagac aacatagaga ctttcgatcg catcgccggt  600
ataacggaat tgtacgacca aacctcctcc gatgccgaaa ttttccgtct ggaacatttt  660
tcggaaacac tgagccaaaa gcagatcgat gcctataact ccgttatggg cagatataac  720
atgcttatca atgagtacaa tcagacgcat aaacagtcgc gcctacctaa attcaaaatg  780
ctgtacaaac agattcttag cgaccgcgaa cacccctcgt ggctgcccga gcagttcgag  840
tcggacacgg ctgtattgac agccattcgc gaatgttacg atgatctgcg catacctatg  900
gccaatttga aaacgctttt agaggggttg ggcaactatg acccgagtgg aatatttttg  960
cgtaatgacc aacatctctc tcagatatcc aaacgattga caggtgatcg gagtagcatt  1020
gaacgtagcg taacagaaga ccttctgaca tcgaggagac tcaacaagcg aaaaagccgc  1080
acaaccgacg aggaggaatc gagaaaactg ttcaagcaaa agggtagtct gagtataggc  1140
tatatagctg acacggccaa aatcgatgtc gaaagatact ttgccaaact cggtgcaata  1200
aatacggtaa cggagcagag cgagaatcta ttcgccaagg ctgagaatgc ccgcacgaca  1260
gcggatgagc tgctcgcaaa tgattacccg gcaggcaaga ggctcgttca gtccaacgac  1320
gacatagcat tgctgaaaaa tctgctcgat gctttaatgg agctgcaatg gttcgtcaag  1380
ccgctgcttg gcacggggga cgaagccggc aaagacgaac gtttctatgg agaatttgca  1440
cagatatggg agcagctgga tcgtataacg cctctctata acatggtgcg caactatgtt  1500
acccgcaagc cgtattcgac cgacaaattc aagctcaact ttgagagcgc agcgcttctc  1560
ggcggctggg acaagaacaa ggagccggac tgtctgtcgg taatcttacg caaggatgag  1620
caatattatc tcggcataat caataagaat cacaaaaaga tattcgagaa cgatatcttg  1680
ccgtgcgaag ggagtgttta cgacaaaatg gtatataaac tcctgcccgg cgcaaacaag  1740
atgctgccga aagtattctt ctcggcttcg cgtatcgccg aatttgcacc gagcgacgaa  1800
gtaaaacgga tatacaatga taagactttc caaaaaggcg aaaagttcga cttgaacgat  1860
tgtcgcacac tgatcgactt ctacaaggct tctatcgaca aacatgagga gtggaacaag  1920
tttggattcg aattctcgga tacgaacaat tatgaagaca taagcggatt ctttcgcgag  1980
gtcgacaggc aaggctataa aatgtcattc cgcccggtcg cagcatcgta tatcgaaacc  2040
cttgttgaag agggcaaact ctatcttttc caaatatata ataaggattt ttcggcatat  2100
agcaaaggta ctcccaatat gcacacgctg tattggagga tgctcttcga cgagcgcaat  2160
ctatcggatg tcgtatatca gctcaacggc ggagcagagt tgttcttccg aagaaagagt  2220
cttcaaaacg gccgtccgac gcatccggca aatattccta tcaaaaacaa aaacagtcgg  2280
aatgacaaaa aagagagcct gttcgactac gatttgatca aagacagacg ctatactgtg  2340
gacaaatttc agttccatgt cccgataacc ctcaatttca agagcgacgg ggcgggcagg  2400
atcaacgagc gtgtaaggga atatctccgc tcggcggacg acgttcacgt catagcatc  2460
gaccgcggag aacgcaatct gctgtatctg gtcgtgacgg atatggacgg caatatctgc  2520
gaacaattct cgctcaacga aatttgtaat actgattatc attctttgtt ggatgaacgc  2580
gaacacaaac gtatgcagga gagacagagc tggcaggcga tagagggcat caaggagttg  2640
aaagaaggtt atctgtctca ggtcgtacac cgaatcgcga cactcatggt taaatatcgc  2700
gccattgtcg tactggaaga tctcaacttc ggcttcatgc gtagccgcca gaaggtagag  2760
aagtctgtat accagaaatt cgaacacatg ctcatagata agctcaatta tctggtcgac  2820
aagaaagcca atccgacaac gccgggcggt ctgctaaaag cctatcagtt gacagacaaa  2880
ttcgagagct tccagaagct cggcaaacag agcggatttc tattctacgt tccggcatgg  2940
aatacatcga agatcgatcc agcaaccgga ttcgtcaaca tgctcgatct cggatacgag  3000
agcatcgaca aagccaaaac actgctctgc aagttcgact ctatacgcta caatgcgtgc  3060
aaagactggt tcgagttcgc tctcgattac gacaagttcg gcagcaaggc caccggtacc  3120
```

```
cgcacgaaat ggactgtttg cacctacgga caacgtatcg atacttatcg caacaaagat  3180
tcgcagtggg tcagccgcga cgtcgatttg acaaatgagc tgaaatcact cttctccgaa  3240
cacggcatag acatttacag caatctgaaa gatgcaatag tcgcacaaaa cgacaaagaa  3300
tttttcgcga acatgcagcg gatattgaaa ctgaccatgc aaatgcgaaa cagcaaaacg  3360
ggtaccgaca cagactatat cgtctcgccc gtcgccgatg ccaacggcag attcttcgac  3420
agcaggcagg ccgatgcgac catgcccaaa gatgcggatg cgaacggagc gtataatatc  3480
gcacgtaagg gcattatgct cgtacagcag atcaagcagt ccgacgatct gcgtacaatg  3540
aagttcgaca taagcaacaa gagctggctg cgcttcgccc aacatacgaa ccaggcggac  3600
gagtaa                                                             3606

SEQ ID NO: 53           moltype = DNA  length = 3600
FEATURE                 Location/Qualifiers
source                  1..3600
                        mol_type = other DNA
                        organism = synthetic construct
SEQUENCE: 53
aagctggagg acttcaccaa tctgtactct ctgagcaaga ccctgcggtt tgagctgcgg  60
cctatcggca agacaagaga aaacatcgaa aacggcggac tgctgcgtca agacgaggac  120
agagccgaaa agtacgtgca tattaaaaag ctgatcgatg aataccacaa ggcttatatc  180
gacaagcaac tgagtggcct ggtcctgcaa tacgccgata tcggcaaggc caattctctg  240
gaggagtact accacagcac tagaaaaagc aaggactctg acaaggataa gatagtcaag  300
atccaggaca acctgcgcaa gcagatcgtc aagagattga aggacagcga tgagtttaag  360
aggatcgata agaaggaact gatccagtct gacctggcag agttcatcaa gccagccgag  420
gacagggccc tgatagccga gttcaagaac ttcaccacct acttcacagg attcaacgaa  480
aataggcaga acatgtacag cgataaggct atcagcaccg ccatcgccta ccggctgatc  540
cacgagaacc tgcctaagtt catcgacaac atcgaaacct tcgaccggat cgcgggcatc  600
acagagctgt atgaccagac atccagcgac gcagagatct ttagactgga gcacttcagt  660
gagacactga gccagaagca gatcgatgcc tataacagcg tgatgggccg gtacaacatg  720
ctgatcaacg aatataacca gacccacaag caatctcggc tgcctaaatt caaaatgctg  780
tacaagcaga tcctgagcga ccgggagcac cccagctggc tgccggaaca gttcgagagc  840
gacaccgccg tgctgaccgc catcagagag tgttacgacg acctgagaat ccctatggcc  900
aacttaaaaa ccctgcttga gggcctggga aattacgatc cctctggcat cttcctgcgg  960
aacgatcagc acctgtctca gatcagcaaa agactcaccg gagacagatc cagcatcgaa  1020
cggagcgtga ccgaggactt attaacgagc cggagactga acaaaagaaa gagcagaacc  1080
accgatgaag aggaaagcag aaagctgttc aagcaaaaag gcagcctgag catcggctac  1140
atcgccgaca cagccaagat cgacgtggag agatacttcg ccaagctggg agccattaat  1200
accgtgaccg agcagtctga gaacctcttc gctaaggccg agaacgccag aaccactgct  1260
gacgagctgc tggccaacga ctaccctgcc ggcaaaagac tggtgcagag caacgacgac  1320
atcgctctgc tgaagaacct attggacgcc ctgatggaac tgcaatggtt cgtgaagccc  1380
ctgctgggca ccggcgacga ggccggcaaa gacgaacggt tctatggcga gttcgctcag  1440
atctgggagc agctggatag aatcacccct ctgtacaaca tggtgcggaa ttacgtgaca  1500
agaaagccct actccacaga caagttcaag ctgaacttcg aatctgccgc cctgctgggc  1560
ggatgggaca agaacaaaga acctgactgc ctgtccgtga ttctgagaaa ggacgagcag  1620
tactacctgg gcatcatcaa caagaaccac aagaagatct tcgagaatga cattctgcct  1680
tgcgagggcg agtgctacga caagatggtc tacaagctgc tgcctggcgc taacaaaatg  1740
ctgcctaagg tgttctttag cgcctccaga atcgctgagt tcgccccttc tgatgaggtg  1800
aaaagaattt acaacgataa gaccttccag aagggcgaga agttcgatct gaacgactgc  1860
agaaccctca tcgatttcta caaggcttct atcgataagc acgaggagtg gaataaattt  1920
ggcttcgagt ttagcgacac caacaactac gaggacatca gcggcttctt ccgggaggtg  1980
gacagacagg gctacaagat gagctttaga cccgtggccg ccagctacat cgaaacgttg  2040
gtggaagagg gcaaactgta cctgttccag atctacaaca aagatttcag cgcctacagc  2100
aagggcaccc ctaatatgca caccctgtac tggagaatgc tgtttgacga gcggaacctg  2160
agcgacgtgg tgtaccagct gaacggcgga gctgaactgt tctttagacg caagtccctc  2220
cagaacggcc ggcctacaca ccctgccaac atccctatca agaacaagaa cagcagaaac  2280
gataaaaagg aatcactgtt cgactacgat ctcatcaagg atcgtagata cacagtggat  2340
aagttccagt tccacgtgcc aatcacactg aatttcaaga gcgatggcgc tggcagaatt  2400
aacgagagag tgcgggagta cctgagatct gccgatgacg tgcacgtgat cggcatcgac  2460
agaggcgagc ggaacctgct gtacctcgtg gtgaccgata tggacggcaa catctgcgaa  2520
cagtttagcc tgaacgaaat ctgtaatacc gactaccaca gcctgttgga tgagagagag  2580
cacaaaagaa tgcaggaaag acagagctgg caggccatcg agggaatcaa ggagctgaag  2640
gaaggctacc tgtcccaagt ggtccacaga atcgccaccc tgatggtgaa gtacagagcg  2700
atcgtggtgc tggaggacct gaacttcggc ttcatgcgga gcagacagaa agtggaaaaa  2760
agcgtgtacc agaagttcga gcacatgctg atcgacaaac tgaactacct ggtggacaag  2820
aaagccaacc ctaccacacc cggcggcctg ctgaaggcct accagctgac agacaagttc  2880
gagagcttcc agaagctggg caagcagtct ggattcctgt tttatgtgcc cgcctggaac  2940
acaagcaaga tcgaccctgc taccggattc gtgaacatgc tggatctggg ctatgagagc  3000
atcgacaagg ccaaaaccct gctgtgcaag tttgactcca tcagatacaa cgcctgcaag  3060
gactggttcg agtttgccct ggactacgac aagttcggca gcaaggccac aggcacacgg  3120
accaagtgga cagtgtgcac ctacggccag cggatcgata cttatagaaa caaggacagc  3180
cagtgggtgt ctcgggacgt ggatctgacc aatgagctga agagcctgtt ttctgaacat  3240
ggcatcgaca tctacagcaa cctgaaagac gccatcgtgg cccaaaatga caaagagttc  3300
ttcgccaaca tgcagagaat cctgaagctg accatgcaga tgagaaattc taaaactgga  3360
acagatacag actacattgt gtcccctgtt gccgatgcta acggaagatt cttcgacagc  3420
agacaagccg acgccaccat gccaaaggac gccgacgcca acggcgccta caacatcgct  3480
agaaagggca tcatgctggt tcagcagatc aagcagagcg atgacctccg caccatgaaa  3540
ttcgacatca gcaacaagag ctggctgaga ttcgcccagc ataccaacca ggccgatgag  3600

SEQ ID NO: 54           moltype = DNA  length = 3717
FEATURE                 Location/Qualifiers
```

```
source                  1..3717
                        mol_type = other DNA
                        organism = synthetic construct
SEQUENCE: 54
atgggcaagc tggaggactt caccaatctg tactctctga gcaagaccct gcggtttgag  60
ctgcggccta tcggcaagac aagagaaaac atcgaaaacg gcggactgct gcgtcaagac  120
gaggacagag ccgaaaagta cgtgcatatt aaaaagctga tcgatgaata ccacaaggct  180
tatatcgaca agcaactgag tggcctggtc ctgcaatacg ccgatatcgg caaggccaat  240
tctctggagg agtactacca cagcactaga aaaagcaagg actctgacaa ggataagata  300
gtcaagatcc aggacaacct gcgcaagcag atcgtcaaga gattgaagga cagcgatgag  360
tttaagagga tcgataagaa ggaactgatc cagtctgacc tggcagagtt catcaagcca  420
gccgaggaca gggccctgat agccgagttc aagaacttca ccacctactt cacaggattc  480
aacgaaaata ggcagaacat gtacagcgat aaggctatca gcaccgccat cgcctaccgg  540
ctgatccacg agaacctgcc taagttcatc gacaacatcg aaaccttcga ccggatcgcg  600
ggcatcacag agctgtatga ccagacatcc agcgacgcag agatctttag actggagcac  660
ttcagtgaga cactgagcca gaagcagatc gatgcctata acagcgtgat gggccggtac  720
aacatgctga tcaacgaata taaccagacc cacaagcaat ctcggctgcc taaattcaaa  780
atgctgtaca agcagatcct gagcgaccgg gagcacccca gctggctgcc ggaacagttc  840
gagagcgaca ccgccgtgct gaccgccatc agagagtgtt acgacgacct gagaatccct  900
atggccaact taaaaaccct gcttgagggc ctgggaaatt acgatccctc tggcatcttc  960
ctgcggaacg atcagcacct gtctcagatc agcaaaagac tcaccggaga cagatccagc  1020
atcgaacgga gcgtgaccga ggacttatta acgagccgga gactgaacaa aagaaagagc  1080
agaaccaccg atgaagagga aagcagaaag ctgttcaagc aaaaaggcag cctgagcatc  1140
ggctacatcg ccgacacagc caagatcgac gtggagagat acttcgccaa gctgggagcc  1200
attaataccg tgaccgagca gtctgagaac ctcttcgcta aggccgagaa cgccagaacc  1260
actgctgacg agctgctggc caacgactac cctgccggca aaagactggt gcagagcaac  1320
gacgacatcg ctctgctgaa gaacctattg gacgccctga tggaactgca atggttcgtg  1380
aagcccctgc tgggcaccgg cgacgaggcc ggcaaagacg aacggttcta tggcgagttc  1440
gctcagatct gggagcagct ggatagaatc accccctctgt acaacatggt gcggaattac  1500
gtgacaagaa agccctactc cacagacaag ttcaagctga acttcgaatc tgccgccctg  1560
ctgggcggat gggacaagaa caaagaacct gactgcctgt ccgtgattct gagaaaggac  1620
gagcagtact acctgggcat catcaacaag aaccacaaga agatcttcga gaatgacatt  1680
ctgccttgcg agggcgagtg ctacgacaag atggtctaca agctgctgcc tggcgctaac  1740
aaaatgctgc ctaaggtgtt ctttagcgcc tccagaatcg ctgagttcgc cccttctgat  1800
gaggtgaaaa gaatttacaa cgataagacc ttccagaagg gcgagaagtt cgatctgaac  1860
gactgcagaa ccctcatcga tttctacaag gcttctatcg ataagcacga ggagtggaat  1920
aaatttggct tcgagtttag cgacaccaac aactacgagg acatcagcgg cttcttccgg  1980
gaggtggaca gacagggcta caagatgagc tttagacccg tggccgccag ctacatcgaa  2040
acgttggtgg aagagggcaa actgtacctg ttccagatct acaacaaaga tttcagcgcc  2100
tacagcaagg gcacccctaa tatgcacacc ctgtactgga gaatgctgtt tgacgagcgg  2160
aacctgagcg acgtggtgta ccagctgaac ggcggagctg aactgttctt tagacgcaag  2220
tccctccaga acggccggcc tacacaccct gccaacatcc ctatcaagaa caagaacagc  2280
agaaacgata aaaaggaatc actgttcgac tacgatctca tcaaggatcg tagatacaca  2340
gtggataagt tccagttcca cgtgccaatc acactgaatt tcaagagcga tggcgctggc  2400
agaattaacg agagagtgcg ggagtacctg agatctgccg atgacgtgca cgtgatcggc  2460
atcgacagag gcgagcggaa cctgctgtac ctcgtggtga ccgatatgga cggcaacatc  2520
tgcgaacagt ttagcctgaa cgaaatctgt aataccgact accacagcct gttggatgag  2580
agagagcaca aaagaatgca ggaaagacag agctggcagg ccatcgaggg aatcaaggag  2640
ctgaaggaag gctacctgtc ccaagtggtc cacagaatcg ccaccctgat ggtgaagtac  2700
agagcgatcg tggtgctgga ggacctgaac ttcggcttca tgcggagcag acagaaagtg  2760
gaaaaaagcg tgtaccagaa gttcgagcac atgctgatcg acaaactgaa ctacctggtg  2820
gacaagaaag ccaaccctac cacacccggc ggcctgctga aggcctacca gctgacagac  2880
aagttcgaga gcttccagaa gctgggcaag cagtctggat tcctgtttta tgtgcccgcc  2940
tggaacacaa gcaagatcga ccctgctacc ggattcgtga acatgctgga tctgggctat  3000
gagagcatcg acaaggccaa aaccctgctg tgcaagtttg actccatcgg atacaacgcc  3060
tgcaaggact ggttcgagtt tgccctggac tacgacaagt tcggcagcaa ggccacaggc  3120
acacggacca agtggacagt gtgcacctac ggccagcgga tcgatactta tagaaacaag  3180
gacagccagt gggtgtctcg ggacgtggat ctgaccaatg agctgaagag cctgttttct  3240
gaacatggca tcgacatcta cagcaacctg aaagacgcca tcgtggccca aaatgacaaa  3300
gagttcttcg ccaacatgca gagaatcctg aagctgacca tgcagatgag aaattctaaa  3360
actggaacag atacagacta cattgtgtcc cctgttgccg atgctaacgg aagattcttc  3420
gacagcagac aagccgacgc caccatgcca aaggacgccg acgccaacgg cgcctacaac  3480
atcgctagaa agggcatcat gctggttcag cagatcaagc agagcgatga cctccgcacc  3540
atgaaattcg acatcagcaa caagagctgg ctgagattcg cccagcatac caaccaggcc  3600
gatgagtcta gaaagcggac agcagacggc tccgaatttg aaagccctaa gaaaaagaga  3660
aaggtgggat ccggcaaacc tatcccccaat cccctgctgg gcctggacag cacctga  3717

SEQ ID NO: 55           moltype = AA  length = 1264
FEATURE                 Location/Qualifiers
source                  1..1264
                        mol_type = protein
                        organism = unidentified
SEQUENCE: 55
MKDLTGQYSL SKTLRFELKP IGKTLEHIEQ KGLLTQDEQR AEEYEQMKGI IDRYHKAFIT  60
MCLRNCKIKV NNTDDELDSL EEYSSLLSKS KRDADDENKL EKIKENLRKQ IVNAFKSGNT  120
YGDLFTKELI KNHLPDFVTD EEEKQVVEHF CNFTTYFTGF HDNRKNMYSD KAKSTAIAYR  180
LIHENFPRFF DNLRSFAKIS ESEVANRFPE IESAFSLYLN VEHIADMFHV DYFPVVLTQE  240
QIDVYNNIIG GKTEEDGTKI QGINEYINLY NQHHPDVKLP FLKPLYKMIL SDKVALSWLP  300
EEFENDEEML TAINDFYKSV QPVVFGDDEN CIRHLLTNIA EYNTDHIYIS NDLGLTGISQ  360
```

```
QLFDQYSIFE DVIKDELRRN VKQTPKEKRN PELLEERIKN LFKKEKSFSI SYLDSLIKDK  420
GEDTIESYYA KLGAFDRDGK QTVNLLTQIE MAYIAAKEVL DGKYDNINQS EEATKYIKDL  480
LDAFKSLQHY IKPLLGSGEE AEKDNVFSSQ LLNVWEALDV VTPLYNKVRN WLTRKPYSTK  540
KIKLNFENVQ LLGGWPNIEA YSCAIFMKDD NTYYLGILDN AYKTLLRDFP EPAEEKDTIG  600
LMHYLQGGDM GKNIQNLMVV DGKVRKVNGR KEKSGINVGQ NIRLEEAKKR YLPTEINRIR  660
KLGTYSVSNP NYNKQDLITI IDYYKPLACE YYASYTFHFK DSSEYNSFAE FTDDINQQAY  720
QLGFVPFSQQ YLNKLVDEGK LYLFQIWNKD FSDYSKGTPN MHTLYWKALF DKANLADVVY  780
KLNGRQAEVF YRKRSLQKEN TTVHKALQPI KNKNTQNEKS TSTFDYDIVK DRRYTVDKFH  840
FHVPITINFK SSGKPNINEH VLDIIRHHGI EHVIGIDRGE RHLLYLSLID LKGRIIKQMT  900
LNEIKQQTGG NYGTNYKELL AAREGDRAEA RRNWKKIENI KDLKAGYLSQ VVHVIAQMMV  960
EYNAIVVLED LNMGFMRGRQ KIERSVYEQF EHMLIDKLNF YVDKKKEACA PGGLLHGLQL  1020
ANKFESFNKL GKQSGCLFYV PAWNTSKIDP VTGFVNMLDA RYESVESSRR FFSRFDVIRY  1080
NEEKNWFEFT FDYNNFHAKL DGTKTQWTLC TYGSRIKTFR NPAKLNQWDN EEVVLTDEFK  1140
KVFANAGINI HGNLKEAICS LAKREHLEPL MHLMKLLLQL RNSKTNSEVD YMLSPVADNG  1200
VFYDSRSCNG NLPIDADANG AYNIARKGLW VLRQIQDSKP GDKLNLALSN KEWLRFVQEK  1260
SNFE                                                              1264

SEQ ID NO: 56          moltype = AA  length = 1264
FEATURE                Location/Qualifiers
source                 1..1264
                       mol_type = protein
                       organism = unidentified
SEQUENCE: 56
MKDLTGQYSL SKTLRFELKP IGKTLEHIEQ KGLLTQDEQR AEEYEQMKGI IDRYHKAFIT  60
MCLRNCKIKV NNTDDELDSL EEYSSLLSKS KRDADDENKL EKIKENLRKQ IVNAFKSGNT  120
YGDLFTKELI KNHLPDFVTD EEEKQVVEHF CNFTTYFTGF HDNRKNMYSD KAKSTAIAYR  180
LIHENFPRFF DNLRSFAKIS ESEVANRFPE IESAFSLYLN VEHIADMFHV DYFPVVLTQE  240
QIDVYNNIIG GKTEEDGTKI QGINEYINLY NQHHPDVKLP FLKPLYKMIL SDKVALSWLP  300
EEFENDEEML TAINDFYKSV QPVVFGDDEN CIRHLLTNIA EYNTDHIYIS NDLGLTGISQ  360
QLFDQYSIFE DVIKDELRRN VKQTPKEKRN PELLEERIKN LFKKEKSFSI SYLDSLIKDK  420
GEDTIESYYA KLGAFDRDGK QTVNLLTQIE MAYIAAKEVL DGKYDNINQS EEATKYIKDL  480
LDAFKSLQHY IKPLLGSGEE AEKDNVFSSQ LLNVWEALDV VTPLYNKVRN WLTRKPYSTK  540
KIKLNFENVQ LLGGWPNIEA YSCAIFMKDD NTYYLGILDN AYKTLLRDFP EPAEEKDTIG  600
LMHYLQGGDM GKNIQNLMVV DGKVRKVNGR KEKSGINVGQ NIRLEEAKKR YLPTEINRIR  660
KLGTYSVSNP NYNKQDLITI IDYYKPLACE YYASYTFHFK DSSEYNSFAE FTDDINQQAY  720
QLGFVPFSQQ YLNKLVDEGK LYLFQIWNKD FSDYSKGTPN MHTLYWKALF DKANLADVVY  780
KLNGRQAEVF YRKRSLQKEN TTVHKALQPI KNKNTQNEKS TSTFDYDIVK DRRYTVDKFH  840
FHVPITINFK SSGKPNINEH VLDIIRHHGI EHVIGIDRGE RHLLYLSLID LKGRIIKQMT  900
LNEIKQQTGG NYGTNYKELL AAREGDRAEA RRNWKKIENI KDLKAGYLSQ VVHVIAQMMV  960
EYNAIVVLED LNMGFMRGRQ KIERSVYEQF EHMLIDKLNF YVDKKKEACA PGGLLHGLQL  1020
ANKFESFNKL GKQSGCLFYV PAWNTSKIDP VTGFVNMLDA RYESVESSRR FFSRFDVIRY  1080
NEEKNWFEFT FDYNNFHAKL DGTKTQWTLC TYGSRIKTFR NPAKLNQWDN EEVVLTDEFK  1140
KVFANAGINI HGNLKEAICS LAKREHLEPL MHLMKLLLQL RNSKTNSEVD YMLSPVADNG  1200
VFYDSRSCNG NLPIDADANG AYNIARKGLW VLRQIQDSKP GDKLNLALSN KEWLRFVQEK  1260
SNFE                                                              1264

SEQ ID NO: 57          moltype = AA  length = 1301
FEATURE                Location/Qualifiers
source                 1..1301
                       mol_type = protein
                       organism = synthetic construct
SEQUENCE: 57
MGKDLTGQYS LSKTLRFELK PIGKTLEHIE QKGLLTQDEQ RAEEYEQMKG IIDRYHKAFI  60
TMCLRNCKIK VNNTDDELDS LEEYSSLLSK SKRDADDENK LEKIKENLRK QIVNAFKSGN  120
TYGDLFTKEL IKNHLPDFVT DEEEKQVVEH FCNFTTYFTG FHDNRKNMYS DKAKSTAIAY  180
RLIHENFPRF FDNLRSFAKI SESEVANRFP EIESAFSLYL NVEHIADMFH VDYFPVVLTQ  240
EQIDVYNNII GGKTEEDGTK IQGINEYINL YNQHHPDVKL PFLKPLYKMI LSDKVALSWL  300
PEEFENDEEM LTAINDFYKS VQPVVFGDDE NCIRHLLTNI AEYNTDHIYI SNDLGLTGIS  360
QQLFDQYSIF EDVIKDELRR NVKQTPKEKR NPELLEERIK NLFKKEKSFS ISYLDSLIKD  420
KGEDTIESYY AKLGAFDRDG KQTVNLLTQI EMAYIAAKEV LDGKYDNINQ SEEATKYIKD  480
LLDAFKSLQH YIKPLLGSGE EAEKDNVFSS QLLNVWEALD VVTPLYNKVR NWLTRKPYST  540
KKIKLNFENV QLLGGWPNIE AYSCAIFMKD DNTYYLGILD NAYKTLLRDF PEPAEEKDTI  600
GLMHYLQGGD MGKNIQNLMV VDGKVRKVNG RKEKSGINVG QNIRLEEAKK RYLPTEINRI  660
RKLGTYSVSN PNYNKQDLIT IIDYYKPLAC EYYASYTFHF KDSSEYNSFA EFTDDINQQA  720
YQLGFVPFSQ QYLNKLVDEG KLYLFQIWNK DFSDYSKGTP NMHTLYWKAL FDKANLADVV  780
YKLNGRQAEV FYRKRSLQKE NTTVHKALQP IKNKNTQNEK STSTFDYDIV KDRRYTVDKF  840
HFHVPITINF KSSGKPNINE HVLDIIRHHG IEHVIGIDRG ERHLLYLSLI DLKGRIIKQM  900
TLNEIKQQTG GNYGTNYKEL LAAREGDRAE ARRNWKKIEN IKDLKAGYLS QVVHVIAQMM  960
VEYNAIVVLE DLNMGFMRGR QKIERSVYEQ FEHMLIDKLN FYVDKKKEAC APGGLLHGLQ  1020
LANKFESFNK LGKQSGCLFY VPAWNTSKID PVTGFVNMLD ARYESVESSR RFFSRFDVIR  1080
YNEEKNWFEF TFDYNNFHAK LDGTKTQWTL CTYGSRIKTF RNPAKLNQWD NEEVVLTDEF  1140
KKVFANAGIN IHGNLKEAIC SLAKREHLEP LMHLMKLLLQ LRNSKTNSEV DYMLSPVADN  1200
GVFYDSRSCN GNLPIDADAN GAYNIARKGL WVLRQIQDSK PGDKLNLALS NKEWLRFVQE  1260
KSNFESRKRT ADGSEFESPK KKRKVGSGKP IPNPLLGLDS T                     1301

SEQ ID NO: 58          moltype = DNA  length = 3795
FEATURE                Location/Qualifiers
source                 1..3795
                       mol_type = unassigned DNA
```

organism = unidentified
SEQUENCE: 58
atgaaagacc tgacagggca atatagcctg tcgaaaactt tacgatttga gttaaaacct 60
atcggtaaaa ctcttgagca cattgagcaa aaaggactct tgacacagga cgaacaaaga 120
gcagaagagt acgagcaaat gaaaggtatc atcgaccgat atcacaaggc atttattacc 180
atgtgtttga gaaactgcaa aatcaaggta aataatacag acgacgaatt agactcatta 240
gaagaatact cctcattact ttccaaaagt aaaagagatg ctgatgatga gaacaaattg 300
gaaaagatta aggaaaatct tcgcaagcaa atcgtcaatg ctttcaaaag cggcaacact 360
tatggcgact tgttcacaaa ggaactgatt aagaatcatc tgcccgactt cgtcacagac 420
gaggaagaaa agcaagtggt ggagcatttc tgcaatttta ccacatattt tacgggtttc 480
cacgacaacc gcaaaaacat gtactcagat aaggctaaat ccacggcaat agcctatcgc 540
ctgatacatg agaatttccc tcggtttttt gacaatcttc gctcttttgc aaagatttca 600
gaaagcgagg tggcaaatcg gttccctgag atagaatctg ctttctctct gtatctcaac 660
gtggaacaca tcgccgacat gttccacgtt gactatttcc cagttgttct tacccaagaa 720
caaattgatg tgtataataa tattattgga ggcaagacgg aagaagatgg gacaaaaata 780
cagggcatca atgaatacat caacctttat aaccaacatc acccagatgt aaagttgccg 840
ttcttgaaac ctctatacaa gatgattctt agcgacaagg ttgcgctttc atggttgccg 900
gaggagtttg agaatgatga agagatgttg acggccataa atgattttta caagtcagtt 960
cagcctgtcg ttttcgggga tgacgagaat tgtatccgtc atcttctgac gaatattgcc 1020
gaatacaata cggatcacat atacatttca aacgatttag gattgactgg aatatcccag 1080
caattgttcg accaatacag catctttgaa gacgtcatta aagatgagtt gaggcgtaat 1140
gtcaaacaga cgcccaaaga gaaacgcaat cctgaattgt tggaagaaag aataaagaac 1200
ttgttcaaga aagagaagag tttctccatc tcttacctgg actctctcat taaggataag 1260
ggtgaggata cgatcgagtc ttattatgcc aaacttggtg cgtttgacag agacggtaag 1320
caaacagtga atttgctcac gcaaattgaa atggcataca tagcggcaaa ggaggtgctt 1380
gatggtaagt atgacaacat taaccagtct gaagaagcaa cgaaatatat taaagatctt 1440
cttgatgcgt tcaagtcttt gcaacactac atcaaaccgc tgttaggtag tggcgaagaa 1500
gcagaaaagg ataatgtgtt tagttcgcaa ctgctcaatg tttgggaggc gttagacgtt 1560
gtgactcctc tttataacaa agttcgcaac tggctcacac gcaagcctta ctcaacaaaa 1620
aagataaagc tgaactttga gaatgtccaa ctgcttggcg gctggccaaa tatagaagcg 1680
tattcatgtg ctatttttat gaaggatgat aatacttact atcttggaat actggacaat 1740
gcatataaaa ctttattaag agattttcca gagcctgccg aagagaagga tactattggg 1800
ctaatgcatt acctccaagg aggcgatatg ggaaaaaata ttcagaattt gatggtggta 1860
gatggaaagg ttcggaaagt taatgggcgc aaagagaagt caggaattaa tgttgggcag 1920
aatattcgat tagaagaagc aaaaaagaga tacctgccaa cagaaatcaa tagaataagg 1980
aagttgggaa cgtattctgt ttcaaatcca aattataaca aacaagattt gataaccata 2040
atcgattatt acaagccact ggcttgtgaa tactatgctt cctatacatt ccatttcaag 2100
gattcttccg agtataattc gttcgcggag tttacagacg atatcaatca gcaagcgtat 2160
caacttgggt ttgtaccttt ttctcaacaa tacttaaaca aacttgtaga cgaaggcaaa 2220
ctctaccttt tccaaatatg gaataaagat ttctctgatt atagtaaagg cactcccaat 2280
atgcataccc tttattggaa ggcgctcttt gataaagcaa atcttgccga tgttgtctac 2340
aaacttaatg gtcgtcaggc agaggtgttc tatcggaaaa gaagcctcca aaaagagaat 2400
acgactgtgc acaaagcatt gcagcctata aagaataaaa acacgcagaa tgagaaaagc 2460
accagtacgt ttgactatga catcgtaaaa gatcgtcgtt atacagttga taaattccat 2520
ttccatgtgc ccattactat taactttaag tcatctggaa aacctaatat caatgaacac 2580
gttttagata ttatccgtca ccatggcatt gagcatgtca tcggaatcga ccgtggcgag 2640
cgccatctat tatatctttc tcttatagat ctcaagggaa gaataatcaa gcaaatgacg 2700
cttaatgaga taaagcagca aacaggcggt aactatggca caaattataa agaactcttg 2760
gccgcaagag aaggcgatcg tgcggaagcg cgtcgtaact ggaaaaagat agagaatatt 2820
aaagacctta aagctggcta tctcagtcag gttgtacatg tgatagccca aatgatggtg 2880
gaatacaatg ccatcgttgt gctcgaagac ctcaatatgg gctttatgcg tgggcggcag 2940
aaaatcgagc ggagcgtata cgagcagttc gaacacatgc tgatagataa gttgaacttc 3000
tatgttgata agaaaaagga agcatgtgcc cccggaggtc tgcttcatgg tctccaatta 3060
gccaataaat ttgagagctt caataagctt gggaaacaga gcggttgcct tttttatgta 3120
ccggcatgga ataccagcaa aatagatcct gtcacagggt ttgtcaatat gcttgatgca 3180
cgctatgaaa gtgtagaaag ttcgcgccgc ttcttctctc gtttcgatgt tattcgttac 3240
aatgaggaaa agaattggtt tgaatttact tttgattata ataacttcca tgcaaagttg 3300
gacgggacaa aaacccaatg gacgctttgc acatacggca gtcgcatcaa aacattccgc 3360
aaccccgcaa aactcaatca atgggataat gaagaggtgg ttcttaccga tgaatttaag 3420
aaggtatttg ccaatgctgg tatcaatatt catgggaatt tgaaagaggc catttgctct 3480
cttgctaaac gggagcattt agaaccgttg atgcatttga tgaaactgct tttacagttg 3540
cgcaacagca agaccaactc agaggtcgac tatatgcttt ctcctgtggc agataatggc 3600
gtgttttacg acagccgttc ttgcaatggc aatttgccta tagatgccga tgccaatggg 3660
gcatacaaca ttgcccggaa aggattatgg gttttgcgcc aaattcagga ctctaagcct 3720
ggcgacaaac tgaatttggc tttgtcgaac aaggaatggt tgcgatttgt tcaagaaaag 3780
agcaactttg aataa 3795

SEQ ID NO: 59 moltype = DNA length = 3789
FEATURE Location/Qualifiers
source 1..3789
mol_type = other DNA
organism = synthetic construct
SEQUENCE: 59
aaggatctga caggccagta cagcctctct aagaccctca gatttgaact gaagcctatc 60
ggcaagaccc tggagcacat cgagcaaaag ggcctgctga cccaggacga gcagagagcc 120
gaggaatacg agcagatgaa gggaattatt gacagatacc acaaggcctt catcactatg 180
tgcctgagaa attgcaagat caaggtgaac aacaccgacg atgagctgga cagcctggaa 240
gagtacagca gcctgctgtc aaagtctaag cgggacgccg acgacgagaa caaactggag 300
aagatcaagg aaaacctgag aaagcagatc gtcaatgcct tcaagagcgg aaacacctac 360

```
ggcgatctgt tcaccaagga gctgatcaag aaccacctcc ccgattttgt gaccgacgag  420
gaagaaaagc aggtggtgga acacttctgc aacttcacca cctacttcac cggctttcac  480
gacaaccgca agaacatgta cagcgacaag gccaagagca cagccatcgc ctacagactg  540
atccacgaga actttccaag atttttcgat aatctgcgga gctttgccaa gatctccgaa  600
tctgaagtgg ccaacagatt cccagaaatc gagagcgcct ttagcctgta cctgaatgtg  660
gaacatatcg ccgatatgtt ccacgtggac tacttcccag tggtgctgac ccaggagcag  720
attgacgtgt acaacaacat catcggaggc aagaccgagg aagatggcac aaagattcag  780
ggcatcaacg agtatatcaa cctgtacaac caacaccatc ctgacgtcaa actgcccttc  840
ctgaagcctc tgtataagat gatcctgagc gacaaggtgg ccctgagctg gctgcctgaa  900
gagttcgaga acgacgagga aatgctgacc gccatcaatg atttctacaa gtctgtgcag  960
cctgtggtgt tcggcgatga cgagaactgt atcagacacc tgctgacaaa catcgccgag  1020
tacaacaccg atcacattta catcagcaat gacctgggac tgactggcat ctctcagcag  1080
ctgttcgacc agtactctat cttcgaagat gtgatcaagg acgagctacg gcggaacgtg  1140
aagcaaacac ctaaggagaa gcggaacccc gaactgctgg aagagagaat caagaacctg  1200
ttcaagaaag aaaagagctt ctccatcagc tacctggata gcctgatcaa ggacaaagga  1260
gaagatacca tcgagagcta ctacgccaag ctgggcgcct tcgacagaga tggcaagcag  1320
acagtgaacc tgctcaccca gatcgagatg gcctacatcg ccgctaagga agtgctggat  1380
ggcaagtacg acaacatcaa ccagagcgag gaagctacaa agtacatcaa ggatctgctt  1440
gacgccttca agagcctgca gcactacatc aagcccctgc tgggcagcgg cgaggaggcc  1500
gaaaaagaca acgtgttcag cagccagctc ctgaacgtgt gggaggctct ggacgtggtg  1560
acgcctctgt acaacaaggt cagaaattgg ctgacaagaa agccctacag taccaagaaa  1620
atcaaactga acttcgagaa tgttcaactg ctgggcggat ggcctaacat cgaggcctat  1680
agctgcgcca tttttatgaa agacgacaac acctactact taggcatcct ggacaacgcc  1740
tataaaacac tacttcggga ctttcctgaa cctgctgaag aaaaggacac aatcggcctg  1800
atgcactacc tgcaaggagg cgacatgggc aagaacatcc agaacctgat ggtcgtcgac  1860
gggaaggtgc ggaaggtgaa cggccgtaag gaaaagtccg gcatcaacgt gggccagaat  1920
atccggctgg aggaggccaa gaagagatac ctgcctacag agatcaacag aatcagaaag  1980
ctgggcacct actctgtgag caaccctaat tataacaagc aggatctgat tacaatcatc  2040
gactactaca agccactggc ctgcgagtac tacgcctctt atacattcca cttcaaggac  2100
agcagcgagt acaacagctt cgccgagttc accgatgata tcaaccagca ggcctaccag  2160
ttgggcttcg tgcctttctc ccagcaatac ctcaacaaac tggtggacga gggcaagctg  2220
tacctgttcc agatctggaa taaggacttc tctgactact ctaagggcac ccccaacatg  2280
cacaccctgt actggaaggc cctgtttgac aaggccaatc tggctgatgt ggtttacaag  2340
ctgaacggca gacaggccga ggtgttttac agaaagagaa gcctgcagaa agagaacaca  2400
accgtgcaca aggctctgca gcccatcaag aataagaaca cacagaacga gaaatctacc  2460
agcacattcg attacgatat cgtgaaggac agaagataca ccgtggacaa gttccatttc  2520
cacgttccta tcaccatcaa cttcaagtcc agcggcaagc ctaacatcaa cgagcatgtg  2580
ctggatatca tcagacacca cggcatcgag cacgtgatcg gcatcgaccg cggcgaaagg  2640
cacctgctgt acctgtccct gatcgacctg aaaggacgga tcataaagca gatgaccctt  2700
aacgagatca aacaacagac cggcggcaac tacggcacaa actacaaaga gctgctggcc  2760
gccagagaag gcgacagagc cgaggctaga agaaactgga agaaaatcga gaacatcaag  2820
gacctgaagg ccggctacct gagccaggtg gtgcacgtga ttgctcagat gatggtggaa  2880
tacaacgcca ttgtagtgct ggaggacctg aacatgggct tcatgagagg cagacagaag  2940
atcgagagaa gcgtgtacga gcagttcgag cacatgctga ttgacaagct gaacttctac  3000
gtggacaaaa agaaggaagc atgcgcccct ggcggacttc tgcacggcct gcagctggcc  3060
aacaaattcg agtctttcaa caaactgggc aagcaatccg gctgtctgtt ctacgtgccc  3120
gcctggaaca ccagcaagat cgatcctgtg accggattcg tgaacatgct ggacgcccgg  3180
tacgagagcg tggagagctc ccggcggttc ttctccagat ttgacgtgat cagatacaac  3240
gaggagaaga actggttcga gttcaccttt gattataaca acttccacgc caaactggat  3300
ggcaccaaga cccagtggac actgtgcacc tacggcagca gaatcaagac ctttagaaat  3360
cctgctaagc tgaatcagtg ggacaatgaa gaggtggttc tgaccgacga atttaagaag  3420
gtgttcgcca acgccggaat caatatccac ggcaacctga aggaagctat ctgcagcctg  3480
gccaaaagag agcacctgga acctctgatg cacctgatga aactgctgct gcaacttcgg  3540
aatagcaaaa ccaacagcga ggtcgactac atgctgtctc cagtggccga taatggagtg  3600
ttctacgaca gcagaagctg taacggtaac ctgcctatcg acgccgacgc caacggagcc  3660
tacaatatcg ctagaaaagg tctgtgggtc ctcaggcaaa tccaggatag caagcccggc  3720
gacaagctga acctggctct gagcaacaag gaatggctgc gatttgtaca ggagaaaagc  3780
aatttcgag                                                          3789
```

```
SEQ ID NO: 60           moltype = DNA  length = 3906
FEATURE                 Location/Qualifiers
source                  1..3906
                        mol_type = other DNA
                        organism = synthetic construct
SEQUENCE: 60
atgggcaagg atctgacagg ccagtacagc ctctctaaga ccctcagatt tgaactgaag  60
cctatcggca agaccctgga gcacatcgag caaaagggcc tgctgaccca ggacgagcag  120
agagccgagg aatacgagca gatgaaggga attattgaca gataccacaa ggccttcatc  180
actatgtgcc tgagaaattg caagatcaag gtgaacaaca ccgacgatga gctggacagc  240
ctggaagagt acagcagcct gctgtcaaag tctaagcggg acgccgacga cgagaacaaa  300
ctggagaaga tcaaggaaaa cctgagaaag cagatcgtca atgccttcaa gagcggaaac  360
acctacggcg atctgttcac caaggagctg atcaagaacc acctccccga ttttgtgacc  420
gacgaggaag aaaagcaggt ggtggaacac ttctgcaact tcaccaccta cttcaccggc  480
tttcacgaca accgcaagaa catgtacagc gacaaggcca agagcacagc catcgcctac  540
agactgatcc acgagaactt tccaagattt ttcgataatc tgcggagctt tgccaagatc  600
tccgaatctg aagtggccaa cagattccca gaaatcgaga gcgcctttag cctgtacctg  660
aatgtggaac atatcgccga tatgttccac gtggactact tcccagtggt gctgacccag  720
gagcagattg acgtgtacaa caacatcatc ggaggcaaga ccgaggaaga tggcacaaag  780
attcagggca tcaacgagta tatcaacctg tacaaccaac accatcctga cgtcaaactg  840
```

```
ccccttcctga agcctctgta taagatgatc ctgagcgaca aggtggccct gagctggctg  900
cctgaagagt tcgagaacga cgaggaaatg ctgaccgcca tcaatgattt ctacaagtct  960
gtgcagcctg tggtgttcgg cgatgacgag aactgtatca gacacctgct gacaaacatc  1020
gccgagtaca acaccgatca catttacatc agcaatgacc tgggactgac tggcatctct  1080
cagcagctgt tcgaccagta ctctatcttc gaagatgtga tcaaggacga gctacggcgg  1140
aacgtgaagc aaacacctaa ggagaagcgg aaccccgaac tgctggaaga gagaatcaag  1200
aacctgttca agaaagaaaa gagcttctcc atcagctacc tggatagcct gatcaaggac  1260
aaaggagaag ataccatcga gagctactac gccaagctgg gcgccttcga cagagatggc  1320
aagcagacag tgaacctgct cacccagatc gagatggcct acatcgccgc taaggaagtg  1380
ctggatggca agtacgacaa catcaaccag agcgaggaag ctacaaagta catcaaggat  1440
ctgcttgacg ccttcaagag cctgcagcac tacatcaagc ccctgctggg cagcggcgag  1500
gaggccgaaa aagacaacgt gttcagcagc cagctcctga acgtgtggga ggctctggac  1560
gtggtgacgc ctctgtacaa caaggtcaga aattggctga caagaaagcc ctacagtacc  1620
aagaaaatca aactgaactt cgagaatgtt caactgctgg gcggatggcc taacatcgag  1680
gcctatagct gcgccatttt tatgaaagac gacaacacct actacttagg catcctggac  1740
aacgcctata aacactact tcgggacttt cctgaacctg ctgaagaaaa ggacacaatc  1800
ggcctgatgc actacctgca aggaggcgac atgggcaaga acatccagaa cctgatggtc  1860
gtcgacggga aggtgcggaa ggtgaacggc cgtaaggaaa agtccggcat caacgtgggc  1920
cagaatatcc ggctggagga ggccaagaag agatacctgc ctacagagat caacagaatc  1980
agaaagctgg gcacctactc tgtgagcaac cctaattata acaagcagga tctgattaca  2040
atcatcgact actacaagcc actggcctgc gagtactacg cctcttatac attccacttc  2100
aaggacagca gcgagtacaa cagcttcgcc gagttcaccg atgatatcaa ccagcaggcc  2160
taccagttgg gcttcgtgcc tttctcccag caatacctca acaaactggt ggacgagggc  2220
aagctgtacc tgttccagat ctggaataag gacttctctg actactctaa gggcaccccc  2280
aacatgcaca ccctgtactg gaaggccctg tttgacaagg ccaatctggc tgatgtggtt  2340
tacaagctga acggcagaca ggccgaggtg ttttacagaa agagaagcct gcagaaagag  2400
aacacaaccg tgcacaaggc tctgcagccc atcaagaata agaacacaca gaacgagaaa  2460
tctaccagca cattcgatta cgatatcgtg aaggacagaa gatacaccgt ggacaagttc  2520
catttccacg ttcctatcac catcaacttc aagtccagcg gcaagcctaa catcaacgag  2580
catgtgctgg atatcatcag acaccacggc atcgagcacg tgatcggcat cgaccgcggc  2640
gaaaggcacc tgctgtacct gtccctgatc gacctgaaag gacggatcat aaagcagatg  2700
acccttaacg agatcaaaca acagaccggc ggcaactacg gcacaaacta caaagagctg  2760
ctggccgcca gagaaggcga cagagccgag gctagaagaa actggaagaa aatcgagaac  2820
atcaaggacc tgaaggccgg ctacctgagc caggtggtgc acgtgattgc tcagatgatg  2880
gtggaataca acgccattgt agtgctggag gacctgaaca tgggcttcat gagaggcaga  2940
cagaagatcg agagaagcgt gtacgagcag ttcgagcaca tgctgattga caagctgaac  3000
ttctacgtgg acaaaaagaa ggaagcatgc gcccctggcg gacttctgca cggcctgcag  3060
ctggccaaca aattcgagtc tttcaacaaa ctgggcaagc aatccggctg tctgttctac  3120
gtgcccgcct ggaacaccag caagatcgat cctgtgaccg gattcgtgaa catgctggac  3180
gcccggtacg agagcgtgga gagctcccgg cggttcttct ccagatttga cgtgatcaga  3240
tacaacgagg agaagaactg gttcgagttc acctttgatt ataacaactt ccacgccaaa  3300
ctggatggca ccaagaccca gtggacactg tgcacctacg gcagcagaat caagaccttt  3360
agaaatcctg ctaagctgaa tcagtgggac aatgaagagg tggttctgac cgacgaattt  3420
aagaaggtgt tcgccaacgc cggaatcaat atccacggca acctgaagga agctatctgc  3480
agcctggcca aaagagagca cctggaacct ctgatgcacc tgatgaaact gctgctgcaa  3540
cttcggaata gcaaaaccaa cagcgaggtc gactacatgc tgtctccagt ggccgataat  3600
ggagtgttct acgacagcag aagctgtaac ggtaacctgc ctatcgacgc cgacgccaac  3660
ggagcctaca atatcgctag aaaaggtctg tgggtcctca ggcaaatcca ggatagcaag  3720
cccggcgaca agctgaacct ggctctgagc aacaaggaat ggctgcgatt tgtacaggag  3780
aaaagcaatt tcgagtctag aaagcggaca gcagacggct ccgaatttga aagccctaag  3840
aaaaagagaa aggtgggatc cggcaaacct atccccaatc ccctgctggg cctggacagc  3900
acctga                                                             3906

SEQ ID NO: 61           moltype = AA  length = 1261
FEATURE                 Location/Qualifiers
source                  1..1261
                        mol_type = protein
                        organism = unidentified
SEQUENCE: 61
TNTSIFKTFT NQYSLSKTLR FELRPHPMTS GLDDIISLDT GIKKLYENEM KPLFDELHFE  60
FISQSLVQVS FPSEKLEVLL NKYRSLKDQK AKNIEKELEG PLQELRTIIT DTFESTGNNW  120
KKEWLQQGFK IKSSGYKVLT EEGILEVLSV RKKDKADAIN KFKGFFTYFS GFNMNRENYY  180
SSEDKKTAVA YRVINENLIR YMDNILLLQN VLAKAPEFKK FEDILSLTTF GKYINQEGIT  240
TYNNNVVATI NLELNTYHQH NPKIFSRLPK LKLLYKQIGS PKEDKRIFTI EKRTEWQSLE  300
DLIQKQNKVV EHEKKNVEIL SNLKAAYISF FTNTDETILS EVYFNKRSLN TISSFWFTGG  360
WQTLLLKLKE FKLANQNKDG DIVVPKALSL AELKQVLDSL EEQDPAVNHL FKEMYSDCYK  420
ENLWQTFIAI WQCEITSKFN LLEGYIQECN AVKEDTFDKK KHKNIIKNIC DTYLDIEQIS  480
KYIIVHESLP KYDALYDAVI LYLQESSLRS YYDAFRNLIS KRPVNEEKVK LNFQNSTLLD  540
GWDMNKESAN LCVLLKNNIG EYFLAVMNKK SNMVFDQKKN SALYSAGNES SFQKLEYKLL  600
PGPNKMLPKV IFAKSNEKYF IIPEEIVQIR EEESFKKGKK FDKHALKTWI RFMQESIEKY  660
PGWKTFDFTF KKPEEYEDVS KFYKDVEEQG YKLNWKDINE EELLSLVEQK KVYLFQIKSK  720
DIGETKEHGN KNLHTLLFLE LLKPENTSRL KLLGGGEMFY RAPSMEKVYK TVNEKQVLDS  780
KGNPILEAKR YYEPKFFLHF PIQVKGSENG YKTEMNPKIL RAISTSKEVN IIGIDRGEKH  840
LLYYYVIKPD GTPITQGSLN TISLGLDKNQ NPRLVDERTF KILERDSKGK PSKISDFEST  900
GKKVDYIDYH NILTYYETKR NIARRSWDTI GAIKNFKEGY LSQAIHQIYQ LMLKYNAVVV  960
LEDLNTEFKA KRTAKVEKSV YEKFEIALAK KLNHLIIKGT DPAEAGSVIN PYQLTPAITA  1020
DTLSDFKKSK QWGPLFYIRA NYTSTTDPIT GWRKHIYIPS GASDKEIKTY FCKQGEKEPL  1080
IQISYDTALT AFAFTYTHEG KEWTLHATKD TQRMRYDSKK RKMEPVEIFD RLRELFIDFS  1140
FEESLTDQLE ATLSFDWKTL AFLWTMLNQI RNTDREAEGN DGDFIQSPVA PFYDSRDPEN  1200
```

```
KTNGLPVNGD ANGAFNIARK GAILIKRIQE YAKKDPTFEK MREKDGLNLY ISDAEWDTEI  1260
S                                                                  1261

SEQ ID NO: 62           moltype = AA  length = 1262
FEATURE                 Location/Qualifiers
source                  1..1262
                        mol_type = protein
                        organism = unidentified
SEQUENCE: 62
MTNTSIFKTF TNQYSLSKTL RFELRPHPMT SGLDDIISLD TGIKKLYENE MKPLFDELHF  60
EFISQSLVQV SFPSEKLEVL LNKYRSLKDQ KAKNIEKELE GPLQELRTII TDTFESTGNN  120
WKKEWLQQGF KIKSSGYKVL TEEGILEVLS VRKKDKADAI NKFKGFFTYF SGFNMNRENY  180
YSSEDKKTAV AYRVINENLI RYMDNILLLQ NVLAKAPEFK KFEDILSLTT FGKYINQEGI  240
TTYNNNVVAT INLELNTYHQ HNPKIFSRLP KLKLLYKQIG SPKEDKRIFT IEKRTEWQSL  300
EDLIQKQNKV VEHEKKNVEI LSNLKKAAYIS FFTNTDETIL SEVYFNKRSL NTISSFWFTG  360
GWQTLLLKLK EFKLANQNKD GDIVVPKALS LAELKQVLDS LEEQDPAVNH LFKEMYSDCY  420
KENLWQTFIA IWQCEITSKF NLLEGYIQEC NAVKEDTFDK KKHKNIIKNI CDTYLDIEQI  480
SKYIIVHESL PKYDALYDAV ILYLQESSLR SYYDAFRNLI SKRPVNEEKV KLNFQNSTLL  540
DGWDMNKESA NLCVLLKNNI GEYFLAVMNK KSNMVFDQKK NSALYSAGNE SSFQKLEYKL  600
LPGPNKMLPK VIFAKSNEKY FIIPEEIVQI REEESFKKGK KFDKHALKTW IRFMQESIEK  660
YPGWKTFDFT FKKPEEYEDV SKFYKDVEEQ GYKLNWKDIN EEELLSLVEQ KKVYLFQIKS  720
KDIGETKEHG NKNLHTLLFL ELLKPENTSR LKLLGGGEMF YRAPSMEKVY KTVNEKQVLD  780
SKGNPILEAK RYYEPKFFLH FPIQVKGSEN GYKTEMNPKI LRAISTSKEV NIIGIDRGEK  840
HLLYYYVIKP DGTPITQGSL NTISLGLDKN QNPRLVDERT FKILERDSKG KPSKISDFES  900
TGKKVDYIDY HNILTYYETK RNIARRSWDT IGAIKNFKEG YLSQAIHQIY QLMLKYNAVV  960
VLEDLNTEFK AKRTAKVEKS VYEKFEIALA KKLNHLIIKG TDPAEAGSVI NPYQLTPAIT  1020
ADTLSDFKKS KQWGPLFYIR ANYTSTTDPI TGWRKHIYIP SGASDKEIKT YFCKQGEKEP  1080
LIQISYDTAL TAFAFTYTHE GKEWTLHATK DTQRMRYDSK KRKMEPVEIF DRLRELFIDF  1140
SFEESLTDQL EATLSFDWKT LAFLWTMLNQ IRNTDREAEG NDGDFIQSPV APFYDSRDPE  1200
NKTNGLPVNG DANGAFNIAR KGAILIKRIQ EYAKKDPTFE KMREKDGLNL YISDAEWDTE  1260
IS                                                                 1262

SEQ ID NO: 63           moltype = AA  length = 1301
FEATURE                 Location/Qualifiers
source                  1..1301
                        mol_type = protein
                        organism = synthetic construct
SEQUENCE: 63
MGSGTNTSIF KTFTNQYSLS KTLRFELRPH PMTSGLDDII SLDTGIKKLY ENEMKPLFDE  60
LHFEFISQSL VQVSFPSEKL EVLLNKYRSL KDQKAKNIEK ELEGPLQELR TIITDTFEST  120
GNNWKKEWLQ QGFKIKSSGY KVLTEEGILE VLSVRKKDKA DAINKFKGFF TYFSGFNMNR  180
ENYYSSEDKK TAVAYRVINE NLIRYMDNIL LLQNVLAKAP EFKKFEDILS LTTFGKYINQ  240
EGITTYNNNV VATINLELNT YHQHNPKIFS RLPKLKLLYK QIGSPKEDKR IFTIEKRTEW  300
QSLEDLIQKQ NKVVEHEKKN VEILSNLKAA YISFFTNTDE TILSEVYFNK RSLNTISSFW  360
FTGGWQTLLL KLKEFKLANQ NKDGDIVVPK ALSLAELKQV LDSLEEQDPA VNHLFKEMYS  420
DCYKENLWQT FIAIWQCEIT SKFNLLEGYI QECNAVKEDT FDKKKHKNII KNICDTYLDI  480
EQISKYIIVH ESLPKYDALY DAVILYLQES SLRSYYDAFR NLISKRPVNE EKVKLNFQNS  540
TLLDGWDMNK ESANLCVLLK NNIGEYFLAV MNKKSNMVFD QKKNSALYSA GNESSFQKLE  600
YKLLPGPNKM LPKVIFAKSN EKYFIIPEEI VQIREEESFK KGKKFDKHAL KTWIRFMQES  660
IEKYPGWKTF DFTFKKPEEY EDVSKFYKDV EEQGYKLNWK DINEEELLSL VEQKKVYLFQ  720
IKSKDIGETK EHGNKNLHTL LFLELLKPEN TSRLKLLGGG EMFYRAPSME KVYKTVNEKQ  780
VLDSKGNPIL EAKRYYEPKF FLHFPIQVKG SENGYKTEMN PKILRAISTS KEVNIIGIDR  840
GEKHLLYYYV IKPDGTPITQ GSLNTISLGL DKNQNPRLVD ERTFKILERD SKGKPSKISD  900
FESTGKKVDY IDYHNILTYY ETKRNIARRS WDTIGAIKNF KEGYLSQAIH QIYQLMLKYN  960
AVVVLEDLNT EFKAKRTAKV EKSVYEKFEI ALAKKLNHLI IKGTDPAEAG SVINPYQLTP  1020
AITADTLSDF KKSKQWGPLF YIRANYTSTT DPITGWRKHI YIPSGASDKE IKTYFCKQGE  1080
KEPLIQISYD TALTAFAFTY THEGKEWTLH ATKDTQRMRY DSKKRKMEPV EIFDRLRELF  1140
IDFSFEESLT DQLEATLSFD WKTLAFLWTM LNQIRNTDRE AEGNDGDFIQ SPVAPFYDSR  1200
DPENKTNGLP VNGDANGAFN IARKGAILIK RIQEYAKKDP TFEKMREKDG LNLYISDAEW  1260
DTEISSRKRT ADGSEFESPK KKRKVGSGKP IPNPLLGLDS T                      1301

SEQ ID NO: 64           moltype = DNA  length = 3789
FEATURE                 Location/Qualifiers
source                  1..3789
                        mol_type = unassigned DNA
                        organism = unidentified
SEQUENCE: 64
atgactaaca catctatttt caaaaccttc actaatcaat attcactttc aaaaacgttg  60
cggtttgagt tgagacctca tccgatgact agtggtctag atgatatcat ttcattagat  120
actggcataa aaaaattgta tgaaaacgag atgaagccgc tatttgatga acttcatttt  180
gaatttatct ctcagtcgct agttcaagta tcattccctt cagaaaaact ggaagttttg  240
ctaaacaagt ataggtctct taaggatcag aaagctaaaa atatagaaaa agaactggaa  300
ggcccattac aggaactaag aacaattatt actgacacct ttgaatccac tggtaacaac  360
tggaaaaaag aatggctaca acaagggttt aaaatcaaaa gctcgggata caaagtacta  420
acagaagagg gaatattaga agtattgtct gttcgtaaaa aagataaagc ggatgcaatc  480
aataaattta aaggattctt cacgtacttt tcagggttta acatgaaccg tgaaaattat  540
tattcatcgg aagataaaaa aacagctgta gcgtataggg taattaatga aaaccttatc  600
cggtatatgg ataacattct cctccttcag aatgttttag caaaagctcc tgagtttaaa  660
aagtttgaag atattttaag tcttactaca tttggaaaat acataaatca ggaaggaata  720
```

```
actacatata ataataacgt agttgcaaca attaatcttg aacttaatac gtaccatcag  780
cataatccaa aaatcttttc tcgcctgcca aagttaaaat tgctttataa acaaattggt  840
tcaccaaaag aggacaaacg catttttact attgaaaaaa gaacggaatg gcagagtttg  900
gaagacttaa tacaaaaaca gaataaagtt gttgaacacg aaaaaaagaa tgttgaaatc  960
ctgtcaaatt tgaaagcagc atacatttct tttttcacga acacagatga aacaatctta  1020
agcgaggtat atttcaataa gcgttctctt aatacaattt cttctttctg gtttacgggt  1080
ggctggcaaa cactgcttct taaactaaaa gagtttaaat tggccaatca aaacaaagat  1140
ggtgatatag tagtccctaa agcattatcc cttgctgaac taaaacaggt gcttgattcg  1200
ttagaagagc aagaccctgc tgttaatcat ttatttaagg aaatgtactc agattgttac  1260
aaagaaaacc tatggcagac ctttatagct atctggcaat gtgaaattac atcaaaattt  1320
aacctgctcg aagggtatat tcaagaatgt aatgctgtta aagaagacac ctttgataaa  1380
aaaaagcata aaaatattat caaaaacatc tgcgatacat acctggatat tgagcagata  1440
tcaaaataca taatagtaca tgaaagtctt cctaaatatg atgcgctata tgatgcggta  1500
atactttatt tgcaggaatc ttctttacgc agttattacg atgccttccg caaccttatt  1560
agcaagcgac ctgttaacga agaaaaagtt aagctcaact ttcagaactc taccctgctt  1620
gatggctggg atatgaataa agaaagcgct aacttatgcg tattactgaa aaacaatata  1680
ggtgaatact tccttgctgt aatgaataaa aagagcaaca tggtttttga tcagaagaaa  1740
aactctgccc tttactctgc tgggaatgaa agtagtttc agaagctgga gtataaactg  1800
ttgcctgggc ctaacaaaat gctgccaaaa gtaatttttg caaaatcgaa cgaaaaatat  1860
ttcatcatac cggaagaaat tgtgcagatt agagaagaag aatcgtttaa aaaaggaaaa  1920
aaatttgata agcatgcatt gaaaacgtgg atcaggttta tgcaggaatc aattgaaaaa  1980
tacccaggtt ggaagacatt cgactttacc tttaaaaaac cggaagagta cgaagatgtc  2040
agcaagttct ataaagatgt agaagaacag gggtataaac taaactggaa agatattaac  2100
gaggaagagc tcctgtcact tgtagaacaa aaaaaagtat atctgtttca gataaaaagc  2160
aaagatatcg gagaaacaaa ggagcacggc aacaagaacc ttcacacatt gttattttta  2220
gaactcctca aaccggaaaa taccagcagg ttaaagctac tgggcggtgg cgaaatgttt  2280
tatcgtgcgc caagtatgga aaaggtatac aaaaccgtaa atgaaaaaca ggttctggat  2340
tcaaaaggta accccatttt agaagcaaaa cggtactatg aaccaaagtt tttccttcac  2400
ttccctattc aggtcaaagg gagcgaaaat ggttataaaa cagaaatgaa tccgaaaata  2460
ttgcgggcaa ttagcacttc aaaagaagta aatataatag gaatagaccg tggagaaaag  2520
catttactct attattacgt tataaagcca gacggaactc caattactca aggaagcctg  2580
aatacaatta gtttaggttt agataaaaat caaaatccca gacttgttga cgagcgtacc  2640
ttcaagattt tggagagaga ttccaaggga aaaccatcaa aaatatcaga ttttgaatct  2700
acagggaaaa aagttgatta catagattat cacaatatac ttacctatta cgaaacaaaa  2760
cgcaatatag cacgccgttc gtgggatact attggggcaa taaaaaactt taaagagggg  2820
tacttgtctc aggcgattca ccagatttat cagcttatgt tgaagtataa cgctgtggta  2880
gttttggaag atcttaatac ggagtttaag gcaaaacgaa ccgcaaaagt tgaaaaatcc  2940
gtgtacgaaa agtttgaaat tgcccttgct aaaaaactga accacttaat tattaaagga  3000
actgaccctg cagaagcagg aagcgtaata aatccgtatc agcttactcc agcaattaca  3060
gctgatacat taagcgactt taagaaatca aaacaatggg gtccgctttt ctatattaga  3120
gcaaactata cctctacgac tgaccctata accggctggc gtaaacacat atatatcccg  3180
tccggagctt cagataaaga aattaaaaca tatttctgta aacagggcga aaaagaacct  3240
ttgattcaga tttcatatga tacagcgctt accgcgtttg catttaccta tacccatgaa  3300
ggcaaagaat ggacattaca cgcaacgaaa gatactcagc gtatgcgtta tgacagtaag  3360
aagcggaaga tggaacccgt agaaatattt gatagactac gagagctttt tatagatttt  3420
agtttcgaag aatcgttaac agatcaacta gaagcaacac tttcctttga ctggaaaaca  3480
ctggcctttt tgtggacaat gttaaaccag atacgtaata ccgacagaga agcagaaggg  3540
aatgacggtg actttattca gtctccggtt gctccgtttt atgatagtcg agatccggaa  3600
aataaaacaa atggacttcc tgttaacgga gatgctaatg gggctttcaa tatagccaga  3660
aaaggtgcaa tcctgataaa acgtattcaa gaatatgcaa aaaaagaccc cacctttgaa  3720
aagatgagag aaaaagatgg tctcaatttg tatatatctg atgcagagtg ggatacagaa  3780
ataagctaa                                                         3789

SEQ ID NO: 65          moltype = DNA  length = 3783
FEATURE                Location/Qualifiers
source                 1..3783
                       mol_type = other DNA
                       organism = synthetic construct
SEQUENCE: 65
acaaacacta gcatcttcaa gacattcacc aaccaataca gcctctccaa gaccctgcgg  60
tttgagctca gaccccaccc tatgacctcc ggcctggacg acatcatcag cctggacacc  120
ggaatcaaaa agctgtacga gaacgaaatg aagcctctgt tcgacgagct gcacttcgag  180
ttcatcagcc agagcctggt ccaggtcagc ttccctagcg agaagctcga agtgctgctg  240
aacaagtacc ggagcctgaa ggaccagaaa gctaagaaca tcgagaagga actggagggc  300
cccctgcagg agctgagaac catcatcacc gacaccttcg agagcaccgg caacaactgg  360
aagaaagagt ggctgcagca ggggttcaag atcaaaagca gtggatacaa ggtgctgaca  420
gaggagggca tcctggaagt gctttccgtg cggaagaagg ataaggccga tgctataaac  480
aagttcaaag gattcttcac ctacttcagc ggcttcaaca tgaacagaga gaactactac  540
agcagcgaag ataaaaaaac agccgtggcc tacagagtga tcaacgagaa cctgatccgg  600
tacatggata acatcctgct cctgcagaac gtgctggcca aagcccctga gttcaagaaa  660
tttgaagata tcctgagtct gaccaccttc ggcaagtaca tcaaccagga gggcatcaca  720
acctacaaca acaacgttgt ggccaccatc aacctggagc tgaacaccta ccaccagcac  780
aacccaaaaa tcttcagcag actgcccaaa ctgaagctgc tgtacaagca gatcggttct  840
ccaaaggagg acaagcgcat cttcaccatc gagaagagaa cagaatggca gagcctggag  900
gacctgatcc agaagcagaa caaggtcgtg gaacacgaaa agaagaacgt ggagatcctg  960
tctaatctga aggccgccta tatcagcttc ttcacaaaca ccgacgaaac catcctgtct  1020
gaggtgtact tcaacaagag aagcctgaat acgatcagca gcttctggtt caccggcgga  1080
tggcaaaccc tgctgctgaa actgaaggaa tttaagctgg ctaatcagaa caaagacggc  1140
gatatcgtgg ttcccaaggc cctgagcctg gccgagctga agcaggtgct ggactccctg  1200
```

```
gaagagcagg accccgccgt gaatcacctg ttcaaggaaa tgtacagcga ctgctacaag  1260
gaaaacctgt ggcaaacatt tatcgccatc tggcaatgtg aaatcacaag caagttcaac  1320
ctgctggagg gctatatcca agagtgcaac gccgtgaaag aggacacctt tgacaagaaa  1380
aagcacaaaa acatcatcaa gaacatctgc gacacgtacc tggacattga gcagatcagt  1440
aagtacatca tcgtgcacga aagcctgcct aaatacgacg ccctctatga tgccgtcatc  1500
ctgtacctgc aggagtctag tctgcggtcc tactacgacg cctttagaaa cctgatttct  1560
aagcggccag tgaacgagga aaaggtgaag ctgaatttcc agaatagcac cctgctggat  1620
ggctgggaca tgaataaaga aagcgccaat ctttgtgtgc tgctgaagaa caacatcgga  1680
gagtactttc tggccgtgat gaacaaaaaa agcaacatgg tttttgacca gaaaaaaaac  1740
agcgccctgt atagcgctgg caatgaatct agcttccaga agctggagta caagctgttg  1800
cccggcccta acaagatgct gcctaaggtg atctttgcca agtccaatga gaagtacttc  1860
atcatccctg aggagatcgt gcagatcagg gaggaagaga gcttcaagaa aggcaaaaaa  1920
ttcgataagc acgcgctgaa aacctggatc agattcatgc aggagtctat cgagaagtat  1980
cctggctgga aaacctttga cttcacattc aaaaagcctg aggaatacga ggatgtgtcc  2040
aagttctaca aagacgtgga agagcagggc tacaaactga actggaagga tatcaacgag  2100
gaagaactgc tgagcctggt ggaacagaag aaggtgtacc tttttcagat caagtccaaa  2160
gacataggcg agacaaagga acacggaaat aagaacctgc acaccctgct cttcctagaa  2220
ttgctgaagc ctgagaacac aagtcggctg aagctgttgg gcggcggaga aatgttctac  2280
cgggcccctt ctatggaaaa agtctacaaa acagtgaacg agaagcaggt gctggattct  2340
aaaggcaacc ctatcctgga ggccaagcgc tactacgagc ctaagttttt tctgcatttc  2400
cccatccagg tgaagggctc tgagaacggc tataagaccg agatgaaccc caaaatcctc  2460
agagccatca gcaccagcaa ggaagtgaac atcattggca tcgacagagg cgagaagcac  2520
ctgctgtact attacgtgat caagcccgac ggaacaccta tcacccaggg cagcctgaac  2580
accatctccc tgggccttga taagaatcaa aatcctagac tggtggacga gagaaccttc  2640
aagatcctgg aaagagatag caagggcaag ccaagcaaga tctcagattt tgaaagcaca  2700
ggcaagaagg tcgactacat cgactaccac aacatcctga catactatga aaccaagaga  2760
aatatcgcca gaagaagctg ggacacaatt ggcgccatca agaatttcaa ggagggatac  2820
ctctctcagg ccatccacca gatctaccag ctgatgctga aatataacgc cgtggtggtg  2880
ctagaggacc tgaacaccga gttcaaggca aagagaaccg ccaaggtgga aaaaagcgtg  2940
tacgaaaagt ttgagatagc tctggccaag aagctgaatc acctgatcat caagggcacc  3000
gacccagccg aggccggatc tgtgatcaac ccttaccagc tgacccctgc tattacagcc  3060
gacacactga gcgatttcaa gaagagcaaa caatggggcc ctctgttcta catccgggcc  3120
aactacacca gcacaaccga ccctatcaca ggctggagaa agcacatcta catccccagc  3180
ggagccagtg acaaggaaat caagacctac ttctgcaagc agggcgagaa ggagcctctg  3240
atccagatta gctacgacac cgccctgacc gccttcgcct tcacatacac ccacgaaggc  3300
aaggagtgga ccctacatgc cacaaaggat acccaaagaa tgcggtacga cagcaagaag  3360
agaaagatgg aacccgtgga aatcttcgac agactgagag agctgttcat cgacttctct  3420
ttcgaggaaa gcctgaccga ccagctggag gcaaccctgt ccttcgactg gaaaaccctg  3480
gcttttctgt ggacaatgct gaatcagatc agaaacaccg atagagaggc tgaaggcaac  3540
gacggcgact tcatccagtc tcctgtggcc cctttctatg atagccggga cccagagaac  3600
aagaccaatg gcctgcccgt taacggcgac gccaacggcg ccttcaacat cgctagaaag  3660
ggggctatcc tgatcaagag aatccaggaa tacgccaaga aggaccctac attcgagaag  3720
atgcgggaaa aggacggttt aaacctgtac atcagcgatg ctgagtggga taccgagatc  3780
agc                                                                3783

SEQ ID NO: 66           moltype = DNA  length = 3906
FEATURE                 Location/Qualifiers
source                  1..3906
                        mol_type = other DNA
                        organism = synthetic construct
SEQUENCE: 66
atgggctccg gaacaaacac tagcatcttc aagacattca ccaaccaata cagcctctcc  60
aagaccctgc ggtttgagct cagaccccac cctatgacct ccggcctgga cgacatcatc  120
agcctggaca ccggaatcaa aaagctgtac gagaacgaaa tgaagcctct gttcgacgag  180
ctgcacttcg agttcatcag ccagagcctg gtccaggtca gcttccctag cgagaagctc  240
gaagtgctgc tgaacaagta ccggagcctg aaggaccaga aagctaagaa catcgagaag  300
gaactggagg gccccctgca ggagctgaga accatcatca ccgacacctt cgagagcacc  360
ggcaacaact ggaagaaaga gtggctgcag caggggttca agatcaaaag cagtggatac  420
aaggtgctga cagaggaggg catcctggaa gtgctttccg tgcggaagaa ggataaggcc  480
gatgctataa acaagttcaa aggattcttc acctacttca gcggcttcaa catgaacaga  540
gagaactact acagcagcga agataaaaaa acagccgtgg cctacagagt gatcaacgag  600
aacctgatcc ggtacatgga taacatcctg ctcctgcaga acgtgctggc caaagcccct  660
gagttcaaga aatttgaaga tatcctgagt ctgaccacct tcggcaagta catcaaccag  720
gagggcatca caacctacaa caacaacgtt gtggccacca tcaacctgga gctgaacacc  780
taccaccagc acaacccaaa aatcttcagc agactgccca aactgaagct gctgtacaag  840
cagatcggtt ctccaaagga ggacaagcgc atcttcacca tcgagaagag aacagaatgg  900
cagagcctgg aggacctgat ccagaagcag aacaaggtcg tggaacacga aaagaagaac  960
gtggagatcc tgtctaatct gaaggccgcc tatatcagct tcttcacaaa caccgacgaa  1020
accatcctgt ctgaggtgta cttcaacaag agaagcctga atacgatcag cagcttctgg  1080
ttcaccggcg gatggcaaac cctgctgctg aaactgaagg aatttaagct ggctaatcag  1140
aacaaagacg gcgatatcgt ggttcccaag gccctgagcc tggccgagct gaagcaggtg  1200
ctggactccc tggaagagca ggaccccgcc gtgaatcacc tgttcaagga aatgtacagc  1260
gactgctaca aggaaaacct gtggcaaaca tttatcgcca tctggcaatg tgaaatcaca  1320
agcaagttca acctgctgga gggctatatc caagagtgca acgccgtgaa agaggacacc  1380
tttgacaaga aaaagcacaa aaacatcatc aagaacatct gcgacacgta cctggacatt  1440
gagcagatca gtaagtacat catcgtgcac gaaagcctgc ctaaatacga cgccctctat  1500
gatgccgtca tcctgtacct gcaggagtct agtctgcggt cctactacga cgcctttaga  1560
aacctgattt ctaagcggcc agtgaacgag gaaaaggtga agctgaattt ccagaatagc  1620
accctgctgg atggctggga catgaataaa gaaagcgcca atctttgtgt gctgctgaag  1680
```

-continued

```
aacaacatcg gagagtactt tctggccgtg atgaacaaaa aaagcaacat ggtttttgac  1740
cagaaaaaaa acagcgccct gtatagcgct ggcaatgaat ctagcttcca gaagctggag  1800
tacaagctgt tgcccggccc taacaagatg ctgcctaagg tgatctttgc caagtccaat  1860
gagaagtact tcatcatccc tgaggagatc gtgcagatca gggaggaaga gagcttcaag  1920
aaaggcaaaa aattcgataa gcacgcgctg aaaacctgga tcagattcat gcaggagtct  1980
atcgagaagt atcctggctg gaaaaccttt gacttcacat tcaaaaagcc tgaggaatac  2040
gaggatgtgt ccaagttcta caaagacgtg gaagagcagg gctacaaact gaactggaag  2100
gatatcaacg aggaagaact gctgagcctg gtggaacaga agaaggtgta ccttttttcag  2160
atcaagtcca aagacatagg cgagacaaag gaacacggaa ataagaacct gcacaccctg  2220
ctcttcctag aattgctgaa gcctgagaac acaagtcggc tgaagctgtt gggcggcgga  2280
gaaatgttct accgggcccc ttctatggaa aaagtctaca aaacagtgaa cgagaagcag  2340
gtgctggatt ctaaaggcaa ccctatcctg gaggccaagc gctactacga gcctaagttt  2400
tttctgcatt tccccatcca ggtgaagggc tctgagaacg gctataagac cgagatgaac  2460
cccaaaatcc tcagagccat cagcaccagc aaggaagtga acatcattgg catcgacaga  2520
ggcgagaagc acctgctgta ctattacgtg atcaagcccg acggaacacc tatcacccag  2580
ggcagcctga acaccatctc cctgggcctt gataagaatc aaaatcctag actggtggac  2640
gagagaacct tcaagatcct ggaaagagat agcaagggca agccaagcaa gatctcagat  2700
tttgaaagca caggcaagaa ggtcgactac atcgactacc acaacatcct gacatactat  2760
gaaaccaaga gaaatatcgc cagaagaagc tgggacacaa ttggcgccat caagaatttc  2820
aaggagggat acctctctca ggccatccac cagatctacc agctgatgct gaaatataac  2880
gccgtggtgg tgctagagga cctgaacacc gagttcaagg caaagagaac cgccaaggtg  2940
gaaaaaagcg tgtacgaaaa gtttgagata gctctggcca agaagctgaa tcacctgatc  3000
atcaagggca ccgacccagc cgaggccgga tctgtgatca acccttacca gctgacccct  3060
gctattacag ccgacacact gagcgatttc aagaagagca aacaatgggg ccctctgttc  3120
tacatccggg ccaactacac cagcacaacc gaccctatca caggctggag aaagcacatc  3180
tacatcccca gcggagccag tgacaaggaa atcaagacct acttctgcaa gcagggcgag  3240
aaggagcctc tgatccagat tagctacgac accgccctga ccgccttcgc cttcacatac  3300
acccacgaag gcaaggagtg gaccctacat gccacaaagg atacccaaag aatgcggtac  3360
gacagcaaga agagaaagat ggaacccgtg gaaatcttcg acagactgag agagctgttc  3420
atcgacttct ctttcgagga aagcctgacc gaccagctgg aggcaaccct gtccttcgac  3480
tggaaaaccc tggcttttct gtggacaatg ctgaatcaga tcagaaacac cgatagagag  3540
gctgaaggca acgacggcga cttcatccag tctcctgtgg ccccttcta tgatagccgg  3600
gacccagaga acaagaccaa tggcctgccc gttaacggcg acgccaacgg cgccttcaac  3660
atcgctagaa agggggctat cctgatcaag agaatccagg aatacgccaa gaaggaccct  3720
acattcgaga agatgcggga aaaggacggt ttaaacctgt acatcagcga tgctgagtgg  3780
gataccgaga tcagctctag aaagcggaca gcagacggct ccgaatttga aagccctaag  3840
aaaaagagaa aggtgggatc cggcaaacct atccccaatc ccctgctggg cctggacagc  3900
acctga                                                              3906
```

```
SEQ ID NO: 67          moltype = AA  length = 1132
FEATURE                Location/Qualifiers
source                 1..1132
                       mol_type = protein
                       organism = unidentified
SEQUENCE: 67
AYQVVKCLIN DYCQNEIIAP QLQKVSCDNT WIVKLREFQE AANWEAQKII QQDLIGIINK  60
KLPKKFNSKA LIEAIPDYLQ GKSKEDLQRM LSGIHDYEIK VKNQNLQVAW NNGLEDFCNL  120
CYQQFRGFSG YLDALSENLK FLFSGRKNGI AYRIVYQNLV TFERNRRAYE SLILINETFR  180
VQDEALLLNY SSSLTQEGIN TYNERIGQLV KNLKEFGDTD RSFRNWHRRF KKLNKQILSP  240
RVAPPWLARA YRSDEEMVMS LQSFLDEFNP LKPRLKQLIA NLESYDEHIY YFRKSLSLLS  300
VTLRNDYKAL DEELSIPQEQ ANCRSLSLSW IPFRQELINE IERIIDSSYT DIEKCLASAS  360
EYLNTERAKR NDYRLDNTVS FTIKKLMDVF LSLYRAVKPL TGTGEEEDRN EDFYDEFTTI  420
WDVLQYVQKL YNAVFAWLNK KPYENNSYPA YLDEFTLLKN WKEKAAYIKR NGKFYFIMFN  480
GIDEQDIIEH RGDSAILYHV ESQSPDRIKA NLTKQFVFSK KANAGKGRPN PSKAKFVRDN  540
PEFQADWERV KTEAYKVAGN TEALAHAIRY FQRCLQSHPD YNRFPFNFRP ANDYTSLDDF  600
VDSIKDKLFM MEETAINWSY VRQLAEEGTI YLFKLYNKDY AKNRVGGSKP NLHTLYWEAM  660
FSSENLRENN IKLEEPKLFY REVATNRDGE LNMRLIPHRY ATDQLELHVP IHLNVNATAS  720
SDINMMVLDA IREGSIENVI GIDRGERNLL YYSVLRLSDG EIVDQKSLNI TFNDVDYHAK  780
LSTKEEEIHD EQREWKAKTS IRKLKEGYLS QAIHQLTSLI VKYHAVVVLE DLSEDFYSKR  840
QKINKQIYQI FEKRLIEKLS YFVDKDAAEG QAGNIYSALQ LSSPNLVRKD NKKIFQNGIV  900
FFVPPEYTSA IDPVTGFCNL FDKNRVRNIC ELLYRFENIC YNRKNDRFEF TWDYRNVMTY  960
TRLEQDNISH LWTACSLGNR IEWSGSERNK NRRCEIVNLT QSMKVLFEKH GIQYQTGKDV  1020
REAVCSIRNN DFKKELKRLF FLMLSLRNSI VDGKVKKDYI LSPVQNQRGS FFDSREYEEL  1080
DNPKLPKCGD ANGAYNIARK GILTIRKLEN GNEKALTLDE WVISTQKGNI RM          1132
```

```
SEQ ID NO: 68          moltype = AA  length = 1133
FEATURE                Location/Qualifiers
source                 1..1133
                       mol_type = protein
                       organism = unidentified
SEQUENCE: 68
MAYQVVKCLI NDYCQNEIIA PQLQKVSCDN TWIVKLREFQ EAANWEAQKI IQQDLIGIIN  60
KKLPKKFNSK ALIEAIPDYL QGKSKEDLQR MLSGIHDYEI KVKNQNLQVA WNNGLEDFCN  120
LCYQQFRGFS GYLDALSENL KFLFSGRKNG IAYRIVYQNL VTFERNRRAY ESLILINETF  180
RVQDEALLLN YSSSLTQEGI NTYNERIGQL VKNLKEFGDT DRSFRNWHRR FKKLNKQILS  240
PRVAPPWLAR AYRSDEEMVM SLQSFLDEFN PLKPRLKQLI ANLESYDEHI YYFRKSLSLL  300
SVTLRNDYKA LDEELSIPQE QANCRSLSLS WIPFRQELIN EIERIIDSSY TDIEKCLASA  360
SEYLNTERAK RNDYRLDNTV SFTIKKLMDV FLSLYRAVKP LTGTGEEEDR NEDFYDEFTT  420
IWDVLQYVQK LYNAVFAWLN KKPYENNSYP AYLDEFTLLK NWKEKAAYIK RNGKFYFIMF  480
```

```
NGIDEQDIIE HRGDSAILYH VESQSPDRIK ANLTKQFVFS KKANAGKGRP NPSKAKFVRD  540
NPEFQADWER VKTEAYKVAG NTEALAHAIR YFQRCLQSHP DYNRFPFNFR PANDYTSLDD  600
FVDSIKDKLF MMEETAINWS YVRQLAEEGT IYLFKLYNKD YAKNRVGGSK PNLHTLYWEA  660
MFSSENLREN NIKLEEPKLF YREVATNRDG ELNMRLIPHR YATDQLELHV PIHLNVNATA  720
SSDINMMVLD AIREGSIENV IGIDRGERNL LYYSVLRLSD GEIVDQKSLN ITFNDVDYHA  780
KLSTKEEEIH DEQREWKAKT SIRKLKEGYL SQAIHQLTSL IVKYHAVVVL EDLSEDFYSK  840
RQKINKQIYQ IFEKRLIEKL SYFVDKDAAE GQAGNIYSAL QLSSPNLVRK DNKKIFQNGI  900
VFFVPPEYTS AIDPVTGFCN LFDKNRVRNI CELLYRFENI CYNRKNDRFE FTWDYRNVMT  960
YTRLEQDNIS HLWTACSLGN RIEWSGSERN KNRRCEIVNL TQSMKVLFEK HGIQYQTGKD  1020
VREAVCSIRN NDFKKELKRL FFLMLSLRNS IVDGKVKKDY ILSPVQNQRG SFFDSREYEE  1080
LDNPKLPKCG DANGAYNIAR KGILTIRKLE NGNEKALTLD EWVISTQKGN IRM         1133

SEQ ID NO: 69          moltype = AA  length = 1172
FEATURE                Location/Qualifiers
source                 1..1172
                       mol_type = protein
                       organism = synthetic construct
SEQUENCE: 69
MGSGAYQVVK CLINDYCQNE IIAPQLQKVS CDNTWIVKLR EFQEAANWEA QKIIQQDLIG  60
IINKKLPKKF NSKALIEAIP DYLQGKSKED LQRMLSGIHD YEIKVKNQNL QVAWNNGLED  120
FCNLCYQQFR GFSGYLDALS ENLKFLFSGR KNGIAYRIVY QNLVTFERNR RAYESLILIN  180
ETFRVQDEAL LLNYSSSLTQ EGINTYNERI GQLVKNLKEF GDTDRSFRNW HRRFKKLNKQ  240
ILSPRVAPPW LARAYRSDEE MVMSLQSFLD EFNPLKPRLK QLIANLESYD EHIYYFRKSL  300
SLLSVTLRND YKALDEELSI PQEQANCRSL SLSWIPFRQE LINEIERIID SSYTDIEKCL  360
ASASEYLNTE RAKRNDYRLD NTVSFTIKKL MDVFLSLYRA VKPLTGTGEE EDRNEDFYDE  420
FTTIWDVLQY VQKLYNAVFA WLNKKPYENN SYPAYLDEFT LLKNWKEKAA YIKRNGKFYF  480
IMFNGIDEQD IIEHRGDSAI LYHVESQSPD RIKANLTKQF VFSKKANAGK GRPNPSKAKF  540
VRDNPEFQAD WERVKTEAYK VAGNTEALAH AIRYFQRCLQ SHPDYNRFPF NFRPANDYTS  600
LDDFVDSIKD KLFMMEETAI NWSYVRQLAE EGTIYLFKLY NKDYAKNRVG GSKPNLHTLY  660
WEAMFSSENL RENNIKLEEP KLFYREVATN RDGELNMRLI PHRYATDQLE LHVPIHLNVN  720
ATASSDINMM VLDAIREGSI ENVIGIDRGE RNLLYYSVLR LSDGEIVDQK SLNITFNDVD  780
YHAKLSTKEE EIHDEQREWK AKTSIRKLKE GYLSQAIHQL TSLIVKYHAV VVLEDLSEDF  840
YSKRQKINKQ IYQIFEKRLI EKLSYFVDKD AAEGQAGNIY SALQLSSPNL VRKDNKKIFQ  900
NGIVFFVPPE YTSAIDPVTG FCNLFDKNRV RNICELLYRF ENICYNRKND RFEFTWDYRN  960
VMTYTRLEQD NISHLWTACS LGNRIEWSGS ERNKNRRCEI VNLTQSMKVL FEKHGIQYQT  1020
GKDVREAVCS IRNNDFKKEL KRLFFLMLSL RNSIVDGKVK KDYILSPVQN QRGSFFDSRE  1080
YEELDNPKLP KCGDANGAYN IARKGILTIR KLENGNEKAL TLDEWVISTQ KGNIRMSRKR  1140
TADGSEFESP KKKRKVGSGK PIPNPLLGLD ST                               1172

SEQ ID NO: 70          moltype = DNA  length = 3402
FEATURE                Location/Qualifiers
source                 1..3402
                       mol_type = unassigned DNA
                       organism = unidentified
SEQUENCE: 70
atggcatacc aagtggttaa atgcctaatc aacgactatt gccagaatga aatcattgca  60
cctcaattgc agaaagtttc ctgtgataac acttggattg taaaacttcg cgagtttcaa  120
gaggctgcca attgggaagc ccaaaaaatt atccagcaag atcttattgg tatcataaac  180
aagaaacttc ctaaaaagtt caatagcaag gcattgatag aagccattcc tgactattta  240
caaggcaagt ctaaagaaga tctgcaacgt atgttgagtg gtatacatga ctatgagatt  300
aaggtaaaaa atcagaacct tcaggtggct tggaataatg ggttagaaga tttttgtaac  360
ctctgctatc aacaatttag aggattttct ggctatcttg acgctttatc tgagaacctg  420
aaatttctat tctcgggcag aaaaaatggt atagcctata gaatagtgta tcagaacctt  480
gttacatttg agaggaatag gagagcttat gaatccctaa tattaataaa tgagactttt  540
agggtacaag atgaggctct acttcttaat tactccagta gtctgaccca agaaggtatc  600
aacacctata atgaacgaat agggcaactt gtcaaaaatc tgaaagaatt tggcgataca  660
gacagatctt tcagaaactg gcatcgccga ttcaagaaac tgaacaagca aatcctaagc  720
cctcgtgttg ctccaccttg gttggcacgc gcctacagaa gcgatgaaga gatggtgatg  780
tcgctacagt cttttctcga cgagttcaat ccattaaaac ctcgtttgaa gcaacttatt  840
gctaatctgg aatcttacga tgagcatatc tattacttcc gcaagtctct ttctctatta  900
tcggtgacct tgaggaatga ttataaggca cttgatgaag aactctcaat accacaagaa  960
caggccaatt gcagaagttt aagcctttcg tggattccgt ttcgccaaga attgataaac  1020
gaaatagaac gaattattga cagttcatat acagacatag agaagtgtct tgcctctgcc  1080
tcggaatatc tgaacacgga gagagcaaaa cggaacgact atcgtctaga taatactgtg  1140
tctttcacaa tcaagaaact gatggacgta ttcctgtcat tgtatcgtgc ggtgaagcct  1200
ctgactggaa caggagagga ggaggatcga aacgaggact tctatgatga gtttacaaca  1260
atctgggatg tgcttcaata tgtacaaaaa ctttataatg cagtttttgc atggctgaac  1320
aagaagcctt atgagaacaa cagctatcct gcctatttgg acgagtttac acttcttaaa  1380
aactggaagg agaaagccgc gtatataaaa cggaatggga agttctattt tatcatgttc  1440
aatggtattg atgaacaaga cattatcgag catcgaggtg attctgcaat cttgtatcat  1500
gtggaaagtc aatcccccga taggattaag gcaaatctca ccaaacaatt tgttttttcc  1560
aaaaaagcaa atgcaggaaa ggggcgacca aatccttcta aagccaaatt cgtgcgtgac  1620
aatccagaat tccaagctga ctgggaacgt gtgaaaactg aagcatataa agtagctgga  1680
aacacagaag cgcttgctca tgccattcga tattttcaac gctgccttca atcacatcct  1740
gactataata ggtttccgtt caattttaga ccagcgaatg actacactag tttagatgat  1800
tttgttgact ccattaaaga caaattgttt atgatggaag aaactgctat taactggtcg  1860
tatgtgaggc aattagcaga agaaggaaca atttacttgt ttaaactcta caataaagat  1920
tatgccaaga atagagttgg cggtctaaa cccaacttgc atacgctcta ttgggaggcg  1980
atgttcagct ctgagaacct tcgtgaaaat aatataaagt tggaggaacc caaactcttc  2040
```

```
tatcgtgaag ttgcaactaa ccgtgatggt gaattgaata tgcgcttgat acctcacaga  2100
tatgcaacag accaacttga gctgcatgtt ccaattcact taaatgtgaa tgcaaccgct  2160
tcaagcgata taaatatgat ggtgttggat gcaatacgag aagggagtat tgaaaatgtc  2220
attggtattg accgtggaga gaggaacctt ctctactatt cagtcttgcg gttgtcagat  2280
ggtgaaattg ttgaccaaaa aagtttgaat attactttca atgatgttga ctaccacgcc  2340
aaactgtcga ctaaagagga ggaaatccat gacgaacaaa gagaatggaa agcaaaaaca  2400
agtattcgga aactgaaaga aggatacctt agtcaagcta tccaccaact aacatcgctg  2460
attgtcaagt accatgctgt ggtagtgcta gaagacttat cagaggactt ctattcgaag  2520
cgccagaaga taaacaagca aatctatcag atatttgaaa aaaggctgat agaaaaactg  2580
agttattttg tcgataagga tgctgcagaa ggtcaggcag gcaatatata ttcagcattg  2640
cagttgtcaa gccccaactt ggtgaggaaa gataataaaa aaatctttca gaacggcatc  2700
gtcttttttg tgccacctga atatacaagt gccattgacc ctgtaacagg gttctgcaat  2760
ctctttgaca agaatcgggt aagaaaatatt tgcgaacttc tctacagatt tgaaaacatc  2820
tgctataata ggaaaaatga ccgatttgag ttcacatggg actatcgtaa tgttatgact  2880
tatacgcgtc tggagcagga caatatttca catctttgga cagcatgctc tttaggaaac  2940
aggattgaat ggtctggtag cgaacgtaat aaaaacagaa ggtgcgaaat tgtaaacctt  3000
acgcaatcta tgaaagtttt gtttgaaaaa catggtatcc aataccaaac aggaaaagat  3060
gtaagggagg ctgtatgcag cataagaaac aacgatttta aaaaagaatt gaagcgcctg  3120
ttcttcttga tgttatcttt aaggaatagc attgttgatg gaaaagtgaa aaaagactat  3180
atattatccc ccgttcagaa ccaacgaggc agtttttttcg atagtagaga atatgaagag  3240
ttggacaatc caaaactccc taaatgtgga gatgcaaatg gcgcatataa tattgcaagg  3300
aaagggatac tgacaattag aaagttggaa aatggcaatg aaaaggcatt aacccttgat  3360
gagtgggtta tttctacgca aaaagggaat atacgcatgt aa                     3402
```

```
SEQ ID NO: 71          moltype = DNA  length = 3396
FEATURE                Location/Qualifiers
source                 1..3396
                       mol_type = other DNA
                       organism = synthetic construct
SEQUENCE: 71
gcctaccagg tggtgaaatg cctgattaac gactactgcc agaacgagat catcgcccct  60
cagctgcaaa aggtgagctg cgacaatacc tggatcgtga agctcagaga gttccaggag  120
gccgcaaact gggaagccca gaagatcatc cagcaggacc tgatcggcat tatcaataag  180
aaactgccta agaaattcaa ctctaaggcc ctgatcgagg ctatacctga ttacctccag  240
ggcaagagca aggaagatct gcagagaatg ctgtccggca tccacgacta tgagatcaag  300
gtgaagaacc agaacctgca ggtagcttgg aacaatggcc tggaagattt ctgtaacttg  360
tgctaccaac aatttagagg cttttccggc taccttgatg ctctgtcaga aaatctgaag  420
ttcctgttca gcggcagaaa aaacggcatc gcctacagga tcgtctacca gaacctggtg  480
accttcgagc ggaaccggag agcttacgag agcctgatcc tgatcaacga gacatttaga  540
gtgcaggacg aggccctgct gctcaactac tctagctctc tgacacagga gggaatcaac  600
acgtacaacg agcggatcgg ccagctggtg aagaacctga aggagttcgg cgacaccgac  660
cggagctttc ggaactggca cagacggttc aagaaactga acaagcagat cctgagccct  720
agagtggccc ctccttggct ggctcgtgcc tacagaagcg atgaggaaat ggtgatgagc  780
ctgcagagct tcctggatga gttcaaccct ctgaaaccta gactcaaaca gctgatcgcc  840
aatctggagt cctacgacga gcacatctac tacttcagaa agtccctgtc tctgctgtca  900
gtgacactga ggaacgacta taaggcactg gatgaagagc tgagcatccc tcaggagcag  960
gccaactgca gatctcttag cctgagctgg attcctttca gacaggaact gatcaacgag  1020
atcgagagaa tcatcgatag cagctacaca gacattgaga agtgcctggc cagcgcctcc  1080
gagtacctga acaccgagag agccaagaga aacgactacc ggctagataa taccgtgtcc  1140
ttcaccatca agaagctgat ggacgtgttc ctgagcctgt accgcgccgt gaagcctctg  1200
accggaacag gcgaagagga ggacagaaat gaagatttct acgacgagtt caccaccatc  1260
tgggatgtgc tgcaatacgt gcagaagctg tacaacgctg ttttcgcctg gctgaacaag  1320
aagccctacg agaacaatag ctaccctgcc tacctggatg aatttaccct gctgaagaac  1380
tggaaggaaa aggccgccta catcaagagg aatggaaaat tctacttcat catgttcaac  1440
ggcatcgacg agcaggatat catcgaacac agaggagatt ctgccatcct gtaccatgtg  1500
gaaagccaga gccctgatag aatcaaggcc aatctgacca agcagttcgt gttcagcaag  1560
aaagccaatg ccggcaaggg ccggcccaat cccagcaagg ccaagttcgt gagagataac  1620
cccgagtttc aggccgactg ggagcgggtg aaaaccgagg cctacaaggt ggccggaaac  1680
accgaggccc tggcccacgc catcagatac ttccaaagat gcctgcaaag ccacccccgat  1740
tataatcggt tcccccttcaa cttcagacct gccaacgact acacatctct ggatgacttc  1800
gtggacagca tcaaggacaa gctgttcatg atggaagaaa ccgccatcaa ctggagttat  1860
gtgagacagc tggccgaaga aggcacaatc tacctgttca agctgtataa caaagactac  1920
gccaagaacc gggtgggcgg cagcaagcct aacctgcaca ccctgtactg ggaggccatg  1980
ttcagctctg agaatctgag agaaaacaac atcaaactgg aagaacccaa actgttctac  2040
agagaggtgg ccacaaaccg ggacggcgag ctgaacatga gactgatccc ccacagatac  2100
gccaccgacc agctggaact gcacgtgcct atccacctga atgtgaacgc cacagccagc  2160
agcgacatca acatgatggt ccttgatgcc atccgggaag gatctattga gaacgtgatc  2220
ggcatcgacc ggggagaacg gaacctgctg tactacagcg tcctgcgact gtccgacggc  2280
gagatcgtgg accagaagag cctgaatatc acctttaacg atgtggacta ccacgcaaag  2340
ttgtctacca aggaggaaga aatccatgat gagcagagag agtggaaagc caagacctcc  2400
atcagaaagc tgaaggaagg ttacctgtct caggctatcc accagctgac cagcctgatc  2460
gtgaagtacc acgctgtggt agtgctggaa gatctgagcg aagatttcta cagcaagcgg  2520
cagaaaatca acaagcagat ctaccagatt ttcgagaaaa gacttatcga gaagctgagc  2580
tactttgtgg acaaagacgc cgccgagggc caggcaggca acatctacag cgccctgcag  2640
ctgagctccc caaatctggt gagaaaggac aacaagaaga tcttccagaa cggcatcgtg  2700
ttcttcgtgc cacctgagta cacgagtgcg attgaccccg tgaccggctt ctgcaacctg  2760
tttgacaaga acagagtgcg caatatctgt gagctgctct acagattcga aaacatttgc  2820
tacaacagaa agaatgaccg gtttgagttc acatgggact atagaaacgt gatgacctac  2880
accagacttg agcaggacaa catctctcac ctgtggaccg cttgtagcct cggcaaccgg  2940
```

```
atcgagtgga gcggctctga aagaaataag aacagaagat gcgagatcgt gaacctgaca  3000
caaagcatga aggtcctgtt tgagaagcac ggcatccagt accagaccgg caaggacgtg  3060
cgggaagctg tgtgtagtat cagaaacaac gactttaaga aagaactgaa gagactgttt  3120
ttcctgatgc tgagcctgcg taacagcatc gtggatggaa aggtgaaaaa ggactacatc  3180
ctgagcccag tgcaaaacca gcggggtagc tttttcgact ccagagaata tgaagaactg  3240
gacaacccga agttgcctaa gtgcggggac gccaacggcg cctacaacat cgccagaaaa  3300
ggaatcctga caatcagaaa gctggagaac ggcaacgaga aagccctgac cctggacgaa  3360
tgggtgatca gcacccagaa gggcaacatc agaatg                            3396

SEQ ID NO: 72          moltype = DNA  length = 3519
FEATURE                Location/Qualifiers
source                 1..3519
                       mol_type = other DNA
                       organism = synthetic construct
SEQUENCE: 72
atgggctccg gagcctacca ggtggtgaaa tgcctgatta acgactactg ccagaacgag  60
atcatcgccc ctcagctgca aaaggtgagc tgcgacaata cctggatcgt gaagctcaga  120
gagttccagg aggccgcaaa ctgggaagcc cagaagatca tccagcagga cctgatcggc  180
attatcaata agaaactgcc taagaaattc aactctaagg ccctgatcga ggctatacct  240
gattacctcc agggcaagag caaggaagat ctgcagagaa tgctgtccgg catccacgac  300
tatgagatca aggtgaagaa ccagaacctg caggtagctt ggaacaatgg cctggaagat  360
ttctgtaact tgtgctacca acaatttaga ggcttttccg gctaccttga tgctctgtca  420
gaaaatctga agttcctgtt cagcggcaga aaaaacggca tcgcctacag gatcgtctac  480
cagaacctgg tgaccttcga gcggaaccgg agagcttacg agagcctgat cctgatcaac  540
gagacattta gagtgcagga cgaggccctg ctgctcaact actctagctc tctgacacag  600
gagggaatca acacgtacaa cgagcggatc ggccagctgg tgaagaacct gaaggagttc  660
ggcgacaccg accggagctt tcggaactgg cacagacggt tcaagaaact gaacaagcag  720
atcctgagcc ctagagtggc ccctccttgg ctggctcgtg cctacagaag cgatgaggaa  780
atggtgatga gcctgcagag cttcctggat gagttcaacc ctctgaaacc tagactcaaa  840
cagctgatcg ccaatctgga gtcctacgac gagcacatct actacttcag aaagtccctg  900
tctctgctgt cagtgacact gaggaacgac tataaggcac tggatgaaga gctgagcatc  960
cctcaggagc aggccaactg cagatctctt agcctgagct ggattccttt cagacaggaa  1020
ctgatcaacg agatcgagag aatcatcgat agcagctaca cagacattga gaagtgcctg  1080
gccagcgcct ccgagtacct gaacaccgag agagccaaga gaaacgacta ccggctagat  1140
aataccgtgt ccttcaccat caagaagctg atggacgtgt tcctgagcct gtaccgcgcc  1200
gtgaagcctc tgaccggaac aggcgaagag gaggacagaa atgaagattt ctacgacgag  1260
ttcaccacca tctgggatgt gctgcaatac gtgcagaagc tgtacaacgc tgttttcgcc  1320
tggctgaaca agaagcccta cgagaacaat agctaccctg cctacctgga tgaatttacc  1380
ctgctgaaga actggaagga aaaggccgcc tacatcaaga ggaatggaaa attctacttc  1440
atcatgttca acggcatcga cgagcaggat atcatcgaac acagaggaga ttctgccatc  1500
ctgtaccatg tggaaagcca gagccctgat agaatcaagg ccaatctgac caagcagttc  1560
gtgttcagca agaaaagcaa tgccggcaag ggccggccca atcccagcaa ggccaagttc  1620
gtgagagata accccgagtt tcaggccgac tgggagcggg tgaaaaccga ggcctacaag  1680
gtggccggaa acaccgaggc cctggcccac gccatcagat acttccaaag atgcctgcaa  1740
agccaccccg attataatcg gttccccttc aacttcagac ctgccaacga ctacacatct  1800
ctggatgact tcgtggacag catcaaggac aagctgttca tgatggaaga aaccgccatc  1860
aactggagtt atgtgagaca gctggccgaa gaaggcacaa tctacctgtt caagctgtat  1920
aacaaagact acgccaagaa ccgggtgggc ggcagcaagc ctaacctgca caccctgtac  1980
tgggaggcca tgttcagctc tgagaatctg agagaaaaca acatcaaact ggaagaaccc  2040
aaactgttct acagagaggt ggccacaaac cgggacggcg agctgaacat gagactgatc  2100
ccccacagat acgccaccga ccagctggaa ctgcacgtgc ctatccacct gaatgtgaac  2160
gccacagcca gcagcgacat caacatgatg gtccttgatg ccatccggga aggatctatt  2220
gagaacgtga tcggcatcga ccggggagaa cggaacctgc tgtactacag cgtcctgcga  2280
ctgtccgacg gcgagatcgt ggaccagaag agcctgaata tcacctttaa cgatgtggac  2340
taccacgcaa agttgtctac caaggaggaa gaaatccatg atgagcagag agagtggaaa  2400
gccaagacct ccatcagaaa gctgaaggaa ggttacctgt ctcaggctat ccaccagctg  2460
accagcctga tcgtgaagta ccacgctgtg gtagtgctgg aagatctgag cgaagatttc  2520
tacagcaagc ggcagaaaat caacaagcag atctaccaga ttttcgagaa aagacttatc  2580
gagaagctga gctactttgt ggacaaagac gccgccgagg gccaggcagg caacatctac  2640
agcgccctgc agctgagctc cccaaatctg gtgagaaagg acaacaagaa gatcttccag  2700
aacggcatcg tgttcttcgt gccacctgag tacacgagtg cgattgaccc cgtgaccggc  2760
ttctgcaacc tgtttgacaa gaacagagtg cgcaatatct gtgagctgct ctacagattc  2820
gaaaacattt gctacaacag aaagaatgac cggtttgagt tcacatggga ctatagaaac  2880
gtgatgacct acaccagact tgagcaggac aacatctctc acctgtggac cgcttgtagc  2940
ctcggcaacc ggatcgagtg gagcggctct gaaagaaata agaacagaag atgcgagatc  3000
gtgaacctga cacaaagcat gaaggtcctg tttgagaagc acggcatcca gtaccagacc  3060
ggcaaggacg tgcgggaagc tgtgtgtagt atcagaaaca acgactttaa gaaagaactg  3120
aagagactgt ttttcctgat gctgagcctg cgtaacagca tcgtggatgg aaaggtgaaa  3180
aaggactaca tcctgagccc agtgcaaaac cagcggggta gctttttcga ctccagagaa  3240
tatgaagaac tggacaaccc gaagttgcct aagtgcgggg acgccaacgg cgcctacaac  3300
atcgccagaa aaggaatcct gacaatcaga aagctggaga acggcaacga gaaagccctg  3360
accctggacg aatgggtgat cagcacccag aagggcaaca tcagaatgtc tagaaagcgg  3420
acagcagacg gctccgaatt tgaaagccct aagaaaaaga gaaaggtggg atccggcaaa  3480
cctatcccca atcccctgct gggcctggac agcacctga                         3519

SEQ ID NO: 73          moltype = AA  length = 1283
FEATURE                Location/Qualifiers
source                 1..1283
                       mol_type = protein
```

```
                         organism = unidentified
SEQUENCE: 73
ERMYEEFRNC YSVRKTLSFK AIPTEETKKH LQLQWEVLGD EIRFENYDKM KMVLDQLHQS  60
YISRKLDNIG EENQKKIVEI LEKLVLVMKK IDTTHQKDKE KAQNQLQSLQ ASLRKEIGMF  120
FPKNEWQQLQ GKNVFKKDGV LSEYNISEEN KKNIQCYDGF MTFFKKYNET RANIYSTEEK  180
STAITFRIVN DNLPKYVRNA DNYEQIKKLI PEALEEVEKT YPNLTNYFSI KNYLKYWSQK  240
GIETYNTVIG EINKQVNLVV QQRKDSKFRK YKMQVLYQQI LSDREEQSFV YQQDQEVFAA  300
VNELAELVNG SAFNEAIELL KSPNINENEI FIPYAKLAEV SIKMKMGWNG LEEAFINDLQ  360
QQYPKKDHEK LVQKLKKEKK VFSLNEIKDV VMKIEHEEDW KFVSLLDCVE DYQKQLTETR  420
DAYVEYAKTY AGSTGTSLQG NDVAPIKAFL DSCLQLVRWC KLFEYSDLYG NRDKIFYGGA  480
ESIILALDSL ISVYNKTRNY VTMRPGQARK MHLMFNYPEF GDGFSNSKVD SYGTILLREG  540
KKYYLAVIKK GIKVLLEDTI NENDSYERLS YMLFPDVKKM IPKCSISTKK VKEHFENSDD  600
DYTIRKGESY AKELLVKKED YDLYFVNLYD DKKMFQKDYL SKTGDKKGYR QALERWIRFC  660
IRFLQAYKST KDYDLSELEP ISNFRSLDEF YDKLDTLLYK IEWKTISREQ IKQMESSGQL  720
FLFELYNKDF SEHAKGKKNL FTLYWEQIFC EENLKQPVIK LCGGAEMFYR KVAIQKKYVH  780
KKDSILVDKT YVDQNGVRKT LPDTIYKEWS DFMNKKITSV SQEASKYKGL VNCHEAKYDI  840
TKDKRYTEDQ FEFHVPITLN YSALGKGQLN DSVLDCLCQK EKYNVIGIDR GERNLLAYCV  900
VNQDGQILEQ GTFNKIVGGN KQEVDYKQKL QEKEVNRQQA RKEWKNIGKI KELKNGYLSQ  960
VIYQLTQMMV KYDAIVVMED LNVGFKRGRF KVERQVYQKF EKALIDKLNY LVTKKDENQY  1020
GIEGSVSNAY QLTEKIKSFK DIGKQNGMIF YVPAGYTSKI DPTTGFVDVL NRTGLTNAKA  1080
RKAFFENFDD INYSKEDNMF AFSFDYSKFK TFQEMHRKKW TVYTNGKKYI YSKKERKEKQ  1140
IDVTELMKEE LRKVGITEYD NLYSQITNVE DDKEHADFWK SLQFVFDRTM QLRSSQIDNG  1200
EDNLEDKIIS PVKNAEGVFY ESNGNYGDTS QPADADTNGA FHIARKGLLL AENVKKTGRG  1260
ANGKWNSSVK NISNKDWFAF VQK                                         1283

SEQ ID NO: 74            moltype = AA  length = 1284
FEATURE                  Location/Qualifiers
source                   1..1284
                         mol_type = protein
                         organism = unidentified
SEQUENCE: 74
MERMYEEFRN CYSVRKTLSF KAIPTEETKK HLQLQWEVLG DEIRFENYDK MKMVLDQLHQ  60
SYISRKLDNI GEENQKKIVE ILEKLVLVMK KIDTTHQKDK EKAQNQLQSL QASLRKEIGM  120
FFPKNEWQQL QGKNVFKKDG VLSEYNISEE NKKNIQCYDG FMTFFKKYNE TRANIYSTEE  180
KSTAITFRIV NDNLPKYVRN ADNYEQIKKL IPEALEEVEK TYPNLTNYFS IKNYLKYWSQ  240
KGIETYNTVI GEINKQVNLV VQQRKDSKFR KYKMQVLYQQ ILSDREEQSF VYQQDQEVFA  300
AVNELAELVN GSAFNEAIEL LKSPNINENE IFIPYAKLAE VSIKMKMGWN GLEEAFINDL  360
QQQYPKKDHE KLVQKLKKEK KVFSLNEIKD VVMKIEHEED WKFVSLLDCV EDYQKQLTET  420
RDAYVEYAKT YAGSTGTSLQ GNDVAPIKAF LDSCLQLVRW CKLFEYSDLY GNRDKIFYGG  480
AESIILALDS LISVYNKTRN YVTMRPGQAR KMHLMFNYPE FGDGFSNSKV DSYGTILLRE  540
GKKYYLAVIK KGIKVLLEDT INENDSYERL SYMLFPDVKK MIPKCSISTK KVKEHFENSD  600
DDYTIRKGES YAKELLVKKE DYDLYFVNLY DDKKMFQKDY LSKTGDKKGY RQALERWIRF  660
CIRFLQAYKS TKDYDLSELE PISNFRSLDE FYDKLDTLLY KIEWKTISRE QIKQMESSGQ  720
LFLFELYNKD FSEHAKGKKN LFTLYWEQIF CEENLKQPVI KLCGGAEMFY RKVAIQKKYV  780
HKKDSILVDK TYVDQNGVRK TLPDTIYKEW SDFMNKKITS VSQEASKYKG LVNCHEAKYD  840
ITKDKRYTED QFEFHVPITL NYSALGKGQL NDSVLDCLCQ KEKYNVIGID RGERNLLAYC  900
VVNQDGQILE QGTFNKIVGG NKQEVDYKQK LQEKEVNRQQ ARKEWKNIGK IKELKNGYLS  960
QVIYQLTQMM VKYDAIVVME DLNVGFKRGR FKVERQVYQK FEKALIDKLN YLVTKKDENQ  1020
YGIEGSVSNA YQLTEKIKSF KDIGKQNGMI FYVPAGYTSK IDPTTGFVDV LNRTGLTNAK  1080
ARKAFFENFD DINYSKEDNM FAFSFDYSKF KTFQEMHRKK WTVYTNGKKY IYSKKERKEK  1140
QIDVTELMKE ELRKVGITEY DNLYSQITNV EDDKEHADFW KSLQFVFDRT MQLRSSQIDN  1200
GEDNLEDKII SPVKNAEGVF YESNGNYGDT SQPADADTNG AFHIARKGLL LAENVKKTGR  1260
GANGKWNSSV KNISNKDWFA FVQK                                        1284

SEQ ID NO: 75            moltype = AA  length = 1323
FEATURE                  Location/Qualifiers
source                   1..1323
                         mol_type = protein
                         organism = synthetic construct
SEQUENCE: 75
MGSGERMYEE FRNCYSVRKT LSFKAIPTEE TKKHLQLQWE VLGDEIRFEN YDKMKMVLDQ  60
LHQSYISRKL DNIGEENQKK IVEILEKLVL VMKKIDTTHQ KDKEKAQNQL QSLQASLRKE  120
IGMFFPKNEW QQLQGKNVFK KDGVLSEYNI SEENKKNIQC YDGFMTFFKK YNETRANIYS  180
TEEKSTAITF RIVNDNLPKY VRNADNYEQI KKLIPEALEE VEKTYPNLTN YFSIKNYLKY  240
WSQKGIETYN TVIGEINKQV NLVVQQRKDS KFRKYKMQVL YQQILSDREE QSFVYQQDQE  300
VFAAVNELAE LVNGSAFNEA IELLKSPNIN ENEIFIPYAK LAEVSIKMKM GWNGLEEAFI  360
NDLQQQYPKK DHEKLVQKLK KEKKVFSLNE IKDVVMKIEH EEDWKFVSLL DCVEDYQKQL  420
TETRDAYVEY AKTYAGSTGT SLQGNDVAPI KAFLDSCLQL VRWCKLFEYS DLYGNRDKIF  480
YGGAESIILA LDSLISVYNK TRNYVTMRPG QARKMHLMFN YPEFGDGFSN SKVDSYGTIL  540
LREGKKYYLA VIKKGIKVLL EDTINENDSY ERLSYMLFPD VKKMIPKCSI STKKVKEHFE  600
NSDDDYTIRK GESYAKELLV KKEDYDLYFV NLYDDKKMFQ KDYLSKTGDK KGYRQALERW  660
IRFCIRFLQA YKSTKDYDLS ELEPISNFRS LDEFYDKLDT LLYKIEWKTI SREQIKQMES  720
SGQLFLFELY NKDFSEHAKG KKNLFTLYWE QIFCEENLKQ PVIKLCGGAE MFYRKVAIQK  780
KYVHKKDSIL VDKTYVDQNG VRKTLPDTIY KEWSDFMNKK ITSVSQEASK YKGLVNCHEA  840
KYDITKDKRY TEDQFEFHVP ITLNYSALGK GQLNDSVLDC LCQKEKYNVI GIDRGERNLL  900
AYCVVNQDGQ ILEQGTFNKI VGGNKQEVDY KQKLQEKEVN RQQARKEWKN IGKIKELKNG  960
YLSQVIYQLT QMMVKYDAIV VMEDLNVGFK RGRFKVERQV YQKFEKALID KLNYLVTKKD  1020
ENQYGIEGSV SNAYQLTEKI KSFKDIGKQN GMIFYVPAGY TSKIDPTTGF VDVLNRTGLT  1080
NAKARKAFFE NFDDINYSKE DNMFAFSFDY SKFKTFQEMH RKKWTVYTNG KKYIYSKKER  1140
```

```
KEKQIDVTEL MKEELRKVGI TEYDNLYSQI TNVEDDKEHA DFWKSLQFVF DRTMQLRSSQ  1200
IDNGEDNLED KIISPVKNAE GVFYESNGNY GDTSQPADAD TNGAFHIARK GLLLAENVKK  1260
TGRGANGKWN SSVKNISNKD WFAFVQKSRK RTADGSEFES PKKKRKVGSG KPIPNPLLGL  1320
DST                                                                1323

SEQ ID NO: 76          moltype = DNA  length = 3855
FEATURE                Location/Qualifiers
source                 1..3855
                       mol_type = unassigned DNA
                       organism = unidentified
SEQUENCE: 76
atggagagaa tgtacgaaga atttagaaat tgttattcag tacgaaaaac attgtcattt  60
aaggcaatcc caacagagga aacaaaaaaa catttacaat tacaatggga agtgttgggg  120
gatgagatac gttttgaaaa ctatgataaa atgaaaatgg ttttggatca acttcatcaa  180
tcatatattt cgagaaaatt agataaatata ggagaagaaa atcaaaaaaa gatagttgaa  240
atcttagaga aactcgtatt agttatgaaa aagatagata ctacgcatca aaaggataaa  300
gagaaagcgc aaaatcagct tcaatcgtta caagcttcat taaggaaaga aataggaatg  360
ttttttccta aaaacgaatg gcaacaatta cagggaaaaa atgtatttaa gaaggatggg  420
gtactaagcg agtataacat ttcggaagag aataagaaaa atattcaatg ttatgatggt  480
tttatgacat tctttaaaaa atataatgaa actagagcaa atatatatag tacagaggaa  540
aaaagcacgg caatcacttt tcgaattgtg aatgataatc ttccaaaata tgtgagaaat  600
gcggataatt acgaacagat taaaaaatta attcctgaag ctcttgaaga agtagaaaaa  660
acatacccaa atttgacgaa ttatttctcg attaaaaact atttgaagta ttggagtcag  720
aaggggattg aaacatacaa tactgttatt ggagaaataa ataagcaggt taatcttgta  780
gtacaacaaa gaaaagattc gaaatttaga aaatacaaga tgcaggtgtt gtatcaacaa  840
attctaagtg atagagagga acagtctttt gtgtatcaac aggatcagga agtttttgct  900
gctgttaatg aacttgcaga acttgtgaac ggtagtgctt ttaacgaggc aattgaattg  960
ttgaaatcac ctaatattaa cgaaaatgag atatttattc cctatgcaaa attagcagaa  1020
gtatccataa aaatgaaaat gggatggaat ggattagagg aggcttttat aaacgatttg  1080
caacagcagt atccaaagaa ggatcatgaa aaattggtgc aaaaattaaa aaaagagaaa  1140
aaagtttttt ctttgaatga aattaaagat gttgttatga aaattgaaca tgaagaagat  1200
tggaaatttg ttagtttgct ggattgtgtt gaggattatc aaaaacagtt gacagagaca  1260
agagatgcat atgtggaata tgcaaaaact tatgcaggtt caaccggtac atcattacaa  1320
ggaaatgatg tagcaccgat aaaagcattt ttagatagtt gtttgcaatt ggtacgatgg  1380
tgtaagttgt ttgaatattc tgatttgtat ggaaatcgag ataaaatatt ttatggagga  1440
gcagagtcga ttatacttgc attagattcc ttaatatctg tgtataataa aacaagaaat  1500
tatgtgacta tgcgaccggg gcaggctaga aaaatgcatt taatgtttaa ttatccggaa  1560
ttcggtgatg gctttagtaa tagtaaagtg gattcttatg gtacgatttt gcttcgtgaa  1620
ggaaagaaat attatttagc tgttattaaa aaaggcataa aagtcttgct ggaagatacc  1680
ataaatgaaa atgacagtta tgaacgtttg agttatatgt tgtttcctga tgtaaaaaaa  1740
atgataccga aatgttctat tagtacgaag aaagttaaag aacattttga aaattcggat  1800
gatgattata cgattcgtaa aggtgaatct tatgcaaaag aattacttgt gaaaaaagaa  1860
gattatgacc tttactttgt aaatctttat gatgataaga agatgtttca aaaggactat  1920
ttgagtaaaa ctggagataa aaaaggatat agacaggcgt tagaacgctg gatacgtttt  1980
tgcattcgat ttttacaagc ttataagagt acaaaggatt atgatctcag tgaattagag  2040
ccaatttcga attttcgttc cttagatgag ttttatgata aattggatac tttgttatac  2100
aagatagagt ggaaaacaat ttcaagagaa caaattaagc aaatggagtc atctggtcag  2160
ttgtttttat ttgaattata taacaaagat ttctctgaac atgcaaaagg aaagaaaaat  2220
ttatttacat tgtattggga acagattttc tgtgaagaga atttaaaaca gccagtgatt  2280
aaactttgtg gcggggcaga gatgttttat cgtaaggttg ccattcaaaa aaaatatgta  2340
cataaaaaag actccatttt ggtggataaa acgtatgtgg atcagaatgg agtcagaaaa  2400
acacttccgg atactatata taaagagtgg tcggatttta tgaataaaaa gataacatct  2460
gtcagccagg aggcaagtaa atataaaggt ttggttaatt gtcatgaggc aaaatatgat  2520
attacaaaag ataaaagata tacggaagat caatttgagt ttcatgtgcc aattacttta  2580
aattattcag cattaggaaa agggcaatta aatgatagtg ttctggattg tctatgtcag  2640
aaagaaaaat ataatgtgat aggaattgac cgtggagaaa gaaacttgtt ggcttactgt  2700
gtcgtaaatc aagatggaca gattttagaa caagggacat ttaataagat tgtaggtgga  2760
aataaacagg aagtagatta caaacagaag ttacaggaga aagaagtaaa tcgacaacaa  2820
gcaagaaaag agtggaaaaa tattggaaaa attaaagaat taaagaacgg ttatttgtct  2880
caggttattt atcaactgac gcaaatgatg gtaaaatatg atgctattgt tgttatggaa  2940
gatttgaatg ttggctttaa acgtggtcga tttaaggtgg aacgacaggt ttaccagaaa  3000
tttgaaaaag cgctgattga caaattaaat tatttagtaa ctaaaaaaga tgaaaatcaa  3060
tatggaatag agggtagcgt aagcaatgca tatcaactga cagaaaaaat caaatcattt  3120
aaagatattg gcaaacaaaa cgggatgata ttttatgtgc cagcgggata tacctctaaa  3180
atagatccta caacaggatt tgtggatgtg ctaaatcgaa caggattaac aaatgccaaa  3240
gccagaaaag cgttctttga aaattttgat gatattaact attcaaaaga agataatatg  3300
tttgcctttt cttttgatta tagcaagttt aagacatttc aagaaatgca tagaaaaaaa  3360
tggacagttt acacaaatgg taaaaagtac atttattcaa aaaaagaacg aaaagaaaaa  3420
caaattgatg ttactgagtt gatgaaagaa gaattgagaa aagtaggaat tacagagtat  3480
gataatcttt attcgcaaat tactaatgtg gaagatgata aagaacatgc agatttttgg  3540
aaatctttac agtttgtatt tgatagaacg atgcagttga gaagtagtca aattgacaat  3600
ggagaggata atcttgagga taagattata tctccggtga aaaatgcaga gggtgtattt  3660
tatgaatcaa atggaaatta tggtgacact tcacaacctg cagatgcaga tacaaatggt  3720
gcttttcata ttgcaaggaa gggattacta cttgcagaaa atgtgaaaaa aacaggtaga  3780
ggagcaaatg gaaaatggaa ttcttctgta aaaaatattt ctaataagga ttggtttgca  3840
tttgttcaaa aataa                                                   3855

SEQ ID NO: 77          moltype = DNA  length = 3849
FEATURE                Location/Qualifiers
```

```
source                 1..3849
                       mol_type = other DNA
                       organism = synthetic construct
SEQUENCE: 77
gaacggatgt acgaggagtt cagaaactgc tactccgtgc ggaaaacact gtccttcaaa  60
gccatcccta ccgaggagac aaagaagcac ctgcagctgc agtgggaagt gctcggcgac  120
gagattagat ttgagaatta tgataagatg aaaatggtgc tggaccagct gcaccagtct  180
tacatcagcc ggaagctgga caacatcggc gaggagaacc agaaaaagat tgtagaaatc  240
ctggagaagc tggtgctggt gatgaagaag atcgatacaa cccaccagaa ggacaaggag  300
aaggcccaga atcaactgca gagcctgcag gcttccctgc ggaaggaaat tggtatgttt  360
ttcccaaaga acgagtggca gcagctgcag ggcaaaaacg tgttcaagaa ggacggcgtt  420
ctcagcgaat acaacatcag cgaggaaaac aagaagaaca tccagtgtta cgacggcttt  480
atgaccttct tcaagaagta caacgagaca cgggccaata tctattctac ggaggaaaag  540
agcaccgcca tcaccttcag gatcgtgaat gataatctgc ctaagtatgt gcgaaacgct  600
gacaactacg agcagataaa gaagctgatc cccgaagctc tggaagaagt cgaaaagacc  660
tatcctaatc tgaccaacta cttcagcatc aagaactatc tgaagtactg gagccagaag  720
gggatcgaaa catacaacac cgtgatcggc gagatcaaca agcaggtgaa cctggtggtc  780
caacagagaa aggacagcaa gttcaggaag tacaaaatgc aggtgctgta ccagcagatc  840
ctatccgaca gagaggagca gagcttcgtg taccagcagg accaggaggt gttcgccgcc  900
gtgaacgagc tggccgagct ggtgaatggc agcgccttca atgaagctat cgaattgctg  960
aaaagcccaa acatcaacga gaatgagatt ttcatcccct acgccaagct cgccgaggtg  1020
tctatcaaga tgaaaatggg atggaacggc ctggaggagg ccttcatcaa cgatctgcag  1080
caacaatacc ccaagaaaga ccacgaaaaa ttggttcaga agctgaagaa agagaagaag  1140
gtgtttagcc tgaatgaaat caaggatgtg gtcatgaaga tcgaacacga ggaagattgg  1200
aaattcgtga gcctgctgga ctgcgtggag gattaccaga agcagcttac agagacaaga  1260
gatgcctacg tggagtacgc taagacatac gccggcagca caggcaccag cctgcagggc  1320
aacgacgtgg cccctatcaa ggccttcctg gactcctgcc tgcaactggt gcggtggtgc  1380
aagctgttcg agtacagcga cctgtacggc aacagagaca agatcttcta cggaggcgcc  1440
gagagcatca tcctggccct ggatagcctg atttccgtgt acaacaaaac cagaaactac  1500
gtgaccatgc ggcctggcca ggccagaaaa atgcacctga tgttcaacta ccccgagttt  1560
ggcgacggct tcagcaacag caaagtggat tcttacggca ccatcctgct gagagaaggc  1620
aagaagtact acctggctgt gatcaagaag ggcatcaaag tgctgctgga ggacaccatt  1680
aacgagaatg actcttacga gcggctgtcc tacatgctgt tccccgacgt gaaaaagatg  1740
atccctaagt gcagcatcag taccaagaag gtgaaagagc atttcgagaa cagcgacgac  1800
gactacacca tcagaaaggg cgagagctat gccaaggagc tgctggtgaa gaaggaagat  1860
tacgacctgt atttcgtgaa cctgtacgac gacaaaaaga tgttccagaa agactacctg  1920
agcaaaaccg gcgacaagaa gggatacaga caggccctgg agaggtggat cagattctgc  1980
atcagattcc tgcaggctta caagtctaca aaggattatg acctgtctga actggaacct  2040
atcagcaact tcagaagcct ggacgagttc tacgataagc tggacaccct actgtacaag  2100
atcgagtgga aaaccatctc cagagagcag atcaagcaaa tggaatcctc tggccagctc  2160
ttcctgttcg agttgtacaa caaggacttc tctgaacacg ccaagggaaa gaagaacctg  2220
ttcaccctgt actgggagca aatttttgt gaagagaacc tgaagcagcc tgtgatcaag  2280
ctgtgcggcg gagccgagat gttctacaga aaggttgcca tccagaaaaa gtacgtgcac  2340
aagaaggaca gcatcctggt agacaagacc tacgtggatc agaacggcgt tcgcaagacc  2400
ctgcctgata ccatctacaa ggaatggtcc gacttcatga acaaaaagat caccagcgtg  2460
tcccaagaag cctctaaata caagggcctg gtgaactgtc acgaggccaa gtacgacatc  2520
accaaggaca agagatacac cgaagatcaa ttcgaatttc acgtgccaat cacactgaac  2580
tacagcgccc tcggaaaagg tcagctgaac gacagcgtgc tggactgcct gtgtcagaaa  2640
gagaagtaca acgtgattgg aatcgaccgg ggagaaagaa acctgctggc ctactgcgtg  2700
gtgaaccagg atggccagat cctggaacag ggcaccttca acaagatcgt gggcggcaat  2760
aagcaggagg tggactataa gcagaaactg caggagaagg aggtgaatag acagcaggcc  2820
aggaaggagt ggaagaacat cggcaagatc aaggagttga aaaacggcta cctgagccaa  2880
gtaatctacc agctgacaca gatgatggtg aagtacgatg ccatcgtggt gatggaagat  2940
ctgaacgtgg gctttaagag aggcagattc aaggttgagc ggcaggtgta ccagaagttc  3000
gaaaaggctc tgatcgataa gctgaattat ctggtcacca agaaggacga gaaccaatac  3060
gggatcgagg gcagcgtttc gaatgcctac cagctgaccg agaaaatcaa gagcttcaaa  3120
gacatcggaa aacagaacgg catgatcttc tacgtgcctg ctggctatac aagcaaaatc  3180
gaccctacga ccggattcgt cgatgtgctg aacagaaccg gcctgacaaa cgccaaggct  3240
agaaaagcct tcttcgagaa ttttgacgac atcaactact ctaaggagga caacatgttc  3300
gccttcagct tcgattacag caagttcaag acctttcagg aaatgcatag aaaaaagtgg  3360
acagtgtaca caaacggaaa aaaatacatc tacagcaaga aggaacggaa ggaaaagcag  3420
atagacgtga ccgaactgat gaaagaagag ctgagaaagg tgggcataac cgagtacgac  3480
aacctctaca gccagatcac caacgtggaa gatgataagg agcacgccga cttttggaag  3540
tctctgcagt tcgtgttcga cagaacaatg cagctgagaa gcagccagat cgacaacggc  3600
gaggacaatc tggaagataa gatcatttca cctgtgaaaa acgccgaggg cgtgttctat  3660
gaaagcaacg gcaactacgg cgatacgagc cagcccgccg acgcggacac caacggcgcc  3720
ttccacatcg cgcggaaggg cctgctgctc gccgagaatg tgaagaaaac cggaagaggc  3780
gccaatggca aatggaatag cagcgtgaag aacatctcta acaaggattg gttcgccttt  3840
gtgcagaaa                                                          3849

SEQ ID NO: 78          moltype = DNA  length = 3972
FEATURE                Location/Qualifiers
source                 1..3972
                       mol_type = other DNA
                       organism = synthetic construct
SEQUENCE: 78
atgggctccg gagaacggat gtacgaggag ttcagaaact gctactccgt gcggaaaaca  60
ctgtccttca aagccatccc taccgaggag acaaagaagc acctgcagct gcagtgggaa  120
gtgctcggcg acgagattag atttgagaat tatgataaga tgaaaatggt gctggaccag  180
```

```
ctgcaccagt cttacatcag ccggaagctg gacaacatcg gcgaggagaa ccagaaaaag  240
attgtagaaa tcctggagaa gctggtgctg gtgatgaaga agatcgatac aacccaccag  300
aaggacaagg agaaggccca gaatcaactg cagagcctgc aggcttccct gcggaaggaa  360
attggtatgt ttttcccaaa gaacgagtgg cagcagctgc agggcaaaaa cgtgttcaag  420
aaggacggcg ttctcagcga atacaacatc agcgaggaaa acaagaagaa catccagtgt  480
tacgacggct ttatgacctt cttcaagaag tacaacgaga cacgggccaa tatctattct  540
acggaggaaa agagcaccgc catcaccttc aggatcgtga atgataatct gcctaagtat  600
gtgcgaaacg ctgacaacta cgagcagata aagaagctga tccccgaagc tctggaagaa  660
gtcgaaaaga cctatcctaa tctgaccaac tacttcagca tcaagaacta tctgaagtac  720
tggagccaga aggggatcga aacatacaac accgtgatcg gcgagatcaa caagcaggtg  780
aacctggtgg tccaacagag aaaggacagc aagttcagga agtacaaaat gcaggtgctg  840
taccagcaga tcctatccga cagagaggag cagagcttcg tgtaccagca ggaccaggag  900
gtgttcgccg ccgtgaacga gctggccgag ctggtgaatg gcagcgcctt caatgaagct  960
atcgaattgc tgaaaagccc aaacatcaac gagaatgaga ttttcatccc ctacgccaag  1020
ctcgccgagg tgtctatcaa gatgaaaatg ggatggaacg gcctggagga ggccttcatc  1080
aacgatctgc agcaacaata ccccaagaaa gaccacgaaa aattggttca gaagctgaag  1140
aaagagaaga aggtgtttag cctgaatgaa atcaaggatg tggtcatgaa gatcgaacac  1200
gaggaagatt ggaaattcgt gagcctgctg gactgcgtgg aggattacca gaagcagctt  1260
acagagacaa gagatgccta cgtggagtac gctaagacat acgccggcag cacaggcacc  1320
agcctgcagg gcaacgacgt ggcccctatc aaggccttcc tggactcctg cctgcaactg  1380
gtgcggtggt gcaagctgtt cgagtacagc gacctgtacg gcaacagaga caagatcttc  1440
tacggaggcg ccgagagcat catcctggcc ctggatagcc tgatttccgt gtacaacaaa  1500
accagaaact acgtgaccat gcggcctggc caggccagaa aaatgcacct gatgttcaac  1560
taccccgagt ttggcgacgg cttcagcaac agcaaagtgg attcttacgg caccatcctg  1620
ctgagagaag gcaagaagta ctacctggct gtgatcaaga agggcatcaa agtgctgctg  1680
gaggacacca ttaacgagaa tgactcttac gagcggctgt cctacatgct gttccccgac  1740
gtgaaaaaga tgatccctaa gtgcagcatc agtaccaaga aggtgaaaga gcatttcgag  1800
aacagcgacg acgactacac catcagaaag ggcgagagct atgccaagga gctgctggtg  1860
aagaaggaag attacgacct gtatttcgtg aacctgtacg acgacaaaaa gatgttccag  1920
aaagactacc tgagcaaaac cggcgacaag aagggataca gacaggccct ggagaggtgg  1980
atcagattct gcatcagatt cctgcaggct tacaagtcta caaaggatta tgacctgtct  2040
gaactggaac ctatcagcaa cttcagaagc ctggacgagt tctacgataa gctggacacc  2100
ctactgtaca agatcgagtg gaaaaccatc tccagagagc agatcaagca aatggaatcc  2160
tctggccagc tcttcctgtt cgagttgtac aacaaggact tctctgaaca cgccaaggga  2220
aagaagaacc tgttcaccct gtactgggag caaatttttt gtgaagagaa cctgaagcag  2280
cctgtgatca agctgtgcgg cggagccgag atgttctaca gaaaggttgc catccagaaa  2340
aagtacgtgc acaagaagga cagcatcctg gtagacaaga cctacgtgga tcagaacggc  2400
gttcgcaaga ccctgcctga taccatctac aaggaatggt ccgacttcat gaacaaaaag  2460
atcaccagcg tgtcccaaga agcctctaaa tacaagggcc tggtgaactg tcacgaggcc  2520
aagtacgaca tcaccaagga caagagatac accgaagatc aattcgaatt tcacgtgcca  2580
atcacactga actacagcgc cctcggaaaa ggtcagctga acgacagcgt gctggactgc  2640
ctgtgtcaga aagagaagta caacgtgatt ggaatcgacc ggggagaaag aaacctgctg  2700
gcctactgcg tggtgaacca ggatggccag atcctggaac agggcacctt caacaagatc  2760
gtgggcggca ataagcagga ggtggactat aagcagaaac tgcaggagaa ggaggtgaat  2820
agacagcagg ccaggaagga gtggaagaac atcggcaaga tcaaggagtt gaaaaacggc  2880
tacctgagcc aagtaatcta ccagctgaca cagatgatgg tgaagtacga tgccatcgtg  2940
gtgatggaag atctgaacgt gggctttaag agaggcagat tcaaggttga gcggcaggtg  3000
taccagaagt tcgaaaaggc tctgatcgat aagctgaatt atctggtcac caagaaggac  3060
gagaaccaat acgggatcga gggcagcgtt tcgaatgcct accagctgac cgagaaaatc  3120
aagagcttca aagacatcgg aaaacagaac ggcatgatct tctacgtgcc tgctggctat  3180
acaagcaaaa tcgaccctac gaccggattc gtcgatgtgc tgaacagaac cggcctgaca  3240
aacgccaagg ctagaaaagc cttcttcgag aattttgacg acatcaacta ctctaaggag  3300
gacaacatgt tcgccttcag cttcgattac agcaagttca agacctttca ggaaatgcat  3360
agaaaaaagt ggacagtgta cacaaacgga aaaaaataca tctacagcaa gaaggaacgg  3420
aaggaaaagc agatagacgt gaccgaactg atgaaagaag agctgagaaa ggtgggcata  3480
accgagtacg acaacctcta cagccagatc accaacgtgg aagatgataa ggagcacgcc  3540
gacttttgga agtctctgca gttcgtgttc gacagaacaa tgcagctgag aagcagccag  3600
atcgacaacg gcgaggacaa tctggaagat aagatcattt cacctgtgaa aaacgccgag  3660
ggcgtgttct atgaaagcaa cggcaactac ggcgatacga gccagcccgc cgacgcggac  3720
accaacggcg ccttccacat cgcgcggaag ggcctgctgc tcgccgagaa tgtgaagaaa  3780
accggaagag gcgccaatgg caaatggaat agcagcgtga agaacatctc taacaaggat  3840
tggttcgcct ttgtgcagaa atctagaaag cggacagcag acggctccga atttgaaagc  3900
cctaagaaaa agagaaaggt gggatccggc aaacctatcc ccaatcccct gctgggcctg  3960
gacagcacct ga                                                     3972
```

```
SEQ ID NO: 79          moltype = AA  length = 1288
FEATURE                Location/Qualifiers
source                 1..1288
                       mol_type = protein
                       organism = unidentified
SEQUENCE: 79
SFESFTNVYP VSKTLRFELR PVGATAEKLK ESGILEHDTK RGKEYATLKD LLDEQHKELL  60
ADALKPERVK NALKPNSGKS KKDKLVEENY ITEDGEIRWE TLAAAMEAFR AGEVEKNVLE  120
AIQTQFRKLI VTILKADERY PGLTASTPSA VIKTLLKQDV HPEAVETFAK FACYFTGFQE  180
NRKNIYAEEK QATAVATRVV HDNFAKFHTQ SKIIGVIKNK YPEILQSVEM ELMDELGGMK  240
ITDIFSINSY SKWMTQEGID FINKIIGGYS PSVGVKVRGL NEFINLYRQQ HEEANADRRN  300
LAKMPMLFKQ ILSDISTRSF IPVMFENDAE LKDSIEAFLT GLNDFELNAQ KFNVVVALGN  360
LFQKIVPCEG IFLDAALMEK VSKTATGDWS LLAQSMEAYA ETAFTRAKDR DAWLRKNYYS  420
LSELSQVPIL KNTDEGMLKF ELSAYWSGEK MESFVKGIMD AELAMKPVLA SIGQKTEEVR  480
```

```
LRDRIDDVVK IKGYLDSIQN FLHHLKPFCA PTELNRDADF YSDFDALYNQ LVLVIPLYNC  540
VRNYVTQKVT EVQKLRLKFD APTLADGWDA NKENDNKAVL FEKDGLYFLG ILNPNLKAKD  600
RPVFEHESNV TKKSCYRKIV YKLLPGPNKM LPKVFFADSN RTLYHPSKSL LDRYHNGEYK  660
KGDSFDIKFC HELIDYFKAS ISIHPDWKEF GFQFSATKTY ESIDGFYREV EEQGYKVNFA  720
FVRADLIDKY VESGSLFLFQ LYNKDFSCAS SGKPNLHTLY WKSLFAKENL DEPILKLCGG  780
AELFFRPVAI QKPYVHTLGE KLVNRRLGEH GKGEAIPERV HKELVDYYNH RVSVLSHDGK  840
AFKDKVVVRD VAHSITKDRR FSEAKFFFHV PIMFNRTASK SAKFNDKVVD YLKTTQNVNV  900
IGLDRGERNL IYLTMVNLHG KLIEQRSFNL VNGVDYHSKL DLREKERMDA RVNWENIGGI  960
KDLKTGYLSA VVHEIAKMMV TNNAIVVLED LNFGFKRGRF KVEKQVYQKF EKMLIDKLNF  1020
LMFKECNQAA LGGVRRAYQL TDKFVSFEKL GKQTGFLFYV PAGYTSKIDP TTGFTNLFNT  1080
KKCTNAEGRK VFFEAMNSII YDGSRKSFAF SFDYGNPVFR ASQTSFKKEW TVYSADTRIV  1140
YNRGEKTVNT IHPTQILHDA LCALGIDVHD GLNVLNVVRE TPADKIHAKF FSDLFYAFDR  1200
TLQMRNSVSG TDEDYIQSPV LNATGEFFDS RKADSTLPQD ADANGAYHIA LKGLLLLQRM  1260
KDIGSDIKLD LSIKHEDWFA FAQKRCQR                                    1288

SEQ ID NO: 80          moltype = AA  length = 1289
FEATURE                Location/Qualifiers
source                 1..1289
                       mol_type = protein
                       organism = unidentified
SEQUENCE: 80
MSFESFTNVY PVSKTLRFEL RPVGATAEKL KESGILEHDT KRGKEYATLK DLLDEQHKEL  60
LADALKPERV KNALKPNSGK SKKDKLVEEN YITEDGEIRW ETLAAAMEAF RAGEVEKNVL  120
EAIQTQFRKL IVTILKADER YPGLTASTPS AVIKTLLKQD VHPEAVETFA KFACYFTGFQ  180
ENRKNIYAEE KQATAVATRV VHDNFAKFHT QSKIIGVIKN KYPEILQSVE MELMDELGGM  240
KITDIFSINS YSKWMTQEGI DFINKIIGGY SPSVGVKVRG LNEFINLYRQ QHEEANADRR  300
NLAKMPMLFK QILSDISTRS FIPVMFENDA ELKDSIEAFL TGLNDFELNA QKFNVVVALG  360
NLFQKIVPCE GIFLDAALME KVSKTATGDW SLLAQSMEAY AETAFTRAKD RDAWLRKNYY  420
SLSELSQVPI LKNTDEGMLK FELSAYWSGE KMESFVKGIM DAELAMKPVL ASIGQKTEEV  480
RLRDRIDDVV KIKGYLDSIQ NFLHHLKPFC APTELNRDAD FYSDFDALYN QLVLVIPLYN  540
CVRNYVTQKV TEVQKLRLKF DAPTLADGWD ANKENDNKAV LFEKDGLYFL GILNPNLKAK  600
DRPVFEHESN VTKKSCYRKI VYKLLPGPNK MLPKVFFADS NRTLYHPSKS LLDRYHNGEY  660
KKGDSFDIKF CHELIDYFKA SISIHPDWKE FGFQFSATKT YESIDGFYRE VEEQGYKVNF  720
AFVRADLIDK YVESGSLFLF QLYNKDFSCA SSGKPNLHTL YWKSLFAKEN LDEPILKLCG  780
GAELFFRPVA IQKPYVHTLG EKLVNRRLGE HGKGEAIPER VHKELVDYYN HRVSVLSHDG  840
KAFKDKVVVR DVAHSITKDR RFSEAKFFFH VPIMFNRTAS KSAKFNDKVV DYLKTTQNVN  900
VIGLDRGERN LIYLTMVNLH GKLIEQRSFN LVNGVDYHSK LDLREKERMD ARVNWENIGG  960
IKDLKTGYLS AVVHEIAKMM VTNNAIVVLE DLNFGFKRGR FKVEKQVYQK FEKMLIDKLN  1020
FLMFKECNQA ALGGVRRAYQ LTDKFVSFEK LGKQTGFLFY VPAGYTSKID PTTGFTNLFN  1080
TKKCTNAEGR KVFFEAMNSI IYDGSRKSFA FSFDYGNPVF RASQTSFKKE WTVYSADTRI  1140
VYNRGEKTVN TIHPTQILHD ALCALGIDVH DGLNVLNVVR ETPADKIHAK FFSDLFYAFD  1200
RTLQMRNSVS GTDEDYIQSP VLNATGEFFD SRKADSTLPQ DADANGAYHI ALKGLLLLQR  1260
MKDIGSDIKL DLSIKHEDWF AFAQKRCQR                                   1289

SEQ ID NO: 81          moltype = AA  length = 1328
FEATURE                Location/Qualifiers
source                 1..1328
                       mol_type = protein
                       organism = synthetic construct
SEQUENCE: 81
MGSGSFESFT NVYPVSKTLR FELRPVGATA EKLKESGILE HDTKRGKEYA TLKDLLDEQH  60
KELLADALKP ERVKNALKPN SGKSKKDKLV EENYITEDGE IRWETLAAAM EAFRAGEVEK  120
NVLEAIQTQF RKLIVTILKA DERYPGLTAS TPSAVIKTLL KQDVHPEAVE TFAKFACYFT  180
GFQENRKNIY AEEKQATAVA TRVVHDNFAK FHTQSKIIGV IKNKYPEILQ SVEMELMDEL  240
GGMKITDIFS INSYSKWMTQ EGIDFINKII GGYSPSVGVK VRGLNEFINL YRQQHEEANA  300
DRRNLAKMPM LFKQILSDIS TRSFIPVMFE NDAELKDSIE AFLTGLNDFE LNAQKFNVVV  360
ALGNLFQKIV PCEGIFLDAA LMEKVSKTAT GDWSLLAQSM EAYAETAFTR AKDRDAWLRK  420
NYYSLSELSQ VPILKNTDEG MLKFELSAYW SGEKMESFVK GIMDAELAMK PVLASIGQKT  480
EEVRLRDRID DVVKIKGYLD SIQNFLHHLK PFCAPTELNR DADFYSDFDA LYNQLVLVIP  540
LYNCVRNYVT QKVTEVQKLR LKFDAPTLAD GWDANKENDN KAVLFEKDGL YFLGILNPNL  600
KAKDRPVFEH ESNVTKKSCY RKIVYKLLPG PNKMLPKVFF ADSNRTLYHP SKSLLDRYHN  660
GEYKKGDSFD IKFCHELIDY FKASISIHPD WKEFGFQFSA TKTYESIDGF YREVEEQGYK  720
VNFAFVRADL IDKYVESGSL FLFQLYNKDF SCASSGKPNL HTLYWKSLFA KENLDEPILK  780
LCGGAELFFR PVAIQKPYVH TLGEKLVNRR LGEHGKGEAI PERVHKELVD YYNHRVSVLS  840
HDGKAFKDKV VVRDVAHSIT KDRRFSEAKF FFHVPIMFNR TASKSAKFND KVVDYLKTTQ  900
NVNVIGLDRG ERNLIYLTMV NLHGKLIEQR SFNLVNGVDY HSKLDLREKE RMDARVNWEN  960
IGGIKDLKTG YLSAVVHEIA KMMVTNNAIV VLEDLNFGFK RGRFKVEKQV YQKFEKMLID  1020
KLNFLMFKEC NQAALGGVRR AYQLTDKFVS FEKLGKQTGF LFYVPAGYTS KIDPTTGFTN  1080
LFNTKKCTNA EGRKVFFEAM NSIIYDGSRK SFAFSFDYGN PVFRASQTSF KKEWTVYSAD  1140
TRIVYNRGEK TVNTIHPTQI LHDALCALGI DVHDGLNVLN VVRETPADKI HAKFFSDLFY  1200
AFDRTLQMRN SVSGTDEDYI QSPVLNATGE FFDSRKADST LPQDADANGA YHIALKGLLL  1260
LQRMKDIGSD IKLDLSIKHE DWFAFAQKRC QRSRKRTADG SEFESPKKKR KVGSGKPIPN  1320
PLLGLDST                                                          1328

SEQ ID NO: 82          moltype = DNA  length = 3870
FEATURE                Location/Qualifiers
source                 1..3870
                       mol_type = unassigned DNA
                       organism = unidentified
```

SEQUENCE: 82
atgagttttg aatcattcac taacgtttat cccgtttcca agactttgcg ctttgagctg 60
aggcccgttg gtgcaactgc agagaagctt aaggaaagtg gtatccttga gcatgatacg 120
aaacgaggta aggaatatgc gactctcaag gatctgcttg atgagcaaca taaggagtta 180
cttgctgacg ccctaaaacc tgaacgtgtg aagaatgcgc ttaagcccaa tagtggtaag 240
agtaaaaaag ataaattggt tgaagagaat tacattacgg aagacgggga gattcgatgg 300
gaaactcttg cggctgcgat ggaggcattt cgcgccggtg aggtagagaa aaatgtgctt 360
gaagcaatac agacgcaatt tagaaagctg attgtaacga tactgaaggc ggatgagcgg 420
tatccgggac tgacagcttc aacgccttcg gctgtcatta agactcttct taagcaggat 480
gttcatccag aagcagtaga gacatttgca aaatttgcct gttattttac cggttttcag 540
gaaaatcgga agaatatcta tgcggaagaa aagcaagcaa ctgcagttgc aacgcgagtt 600
gttcatgata atttcgcaaa gttccataca caatcgaaaa taataggtgt cataaagaat 660
aaatatccag aaatccttca gtcggtagaa atggaattga tggacgaatt aggtgggatg 720
aaaatcactg atatcttttc tatcaacagc tattccaaat ggatgacgca agaagggata 780
gactttatta ataagattat aggtggctat agcccatctg ttggtgtgaa ggtgcgtggt 840
ctgaacgagt tcattaatct ttatcggcag cagcatgaag aggcaaatgc agatcggcgg 900
aatctcgcaa aaatgccgat gctgtttaaa caaattttaa gtgatatttc gacacgatca 960
ttcattccgg tgatgtttga aaatgatgcg gaactaaagg attcaataga agcattcttg 1020
acaggtctga atgattttga gttgaatgct cagaagttta acgttgtcgt tgcattaggt 1080
aatcttttcc aaaaaattgt gccttgcgaa ggtattttct tggatgcagc attgatggaa 1140
aaagtttcga agacggctac aggagattgg agtcttcttg ctcagtcgat ggaggcgtat 1200
gcagagacag cattcacaag agcaaaagac cgagacgcat ggctaaggaa aaattattat 1260
tcgctgtccg agctgagcca agttccgatt ttgaagaaca ctgatgaagg aatgttgaag 1320
tttgaactat ctgcctattg gtcaggcgaa aagatggaaa gttttgttaa aggaatcatg 1380
gatgctgaat tggcaatgaa accagttctt gccagcattg gtcagaaaac cgaagaggtg 1440
cgtcttcgtg atcggattga cgatgtcgta aaaatcaagg gatatcttga ttcaattcag 1500
aatttttac atcacctaaa accgttttgt gctccaactg aattgaatcg tgatgcggat 1560
ttttattctg actttgacgc attgtataat cagcttgtac tggttatacc gctttataac 1620
tgtgtccgca attacgtgac acagaaagtg acagaggttc agaaactgag gctaaagttt 1680
gatgccccta cattggcgga cggatgggac gcgaataaag aaaatgataa taaggcagtt 1740
ctgtttgaaa aggacgggct atattttctt ggaatcctga atcctaacct gaaggcgaaa 1800
gatcgtccag tctttgagca tgaaagtaat gttacaaaga aatcttgtta tcgcaagatt 1860
gtctataaac ttttgccagg accaaataaa atgcttccca aggtcttttt tgctgattcc 1920
aataggacac tgtaccatcc ttccaagtcg ttgctggatc gttatcacaa cggtgaatac 1980
aagaaaggcg attcattcga catcaaattc tgtcatgaat tgattgatta ttttaaagcc 2040
tcgattagta ttcaccccga ttggaaggaa ttcggtttcc aattcagtgc gacaaaaaca 2100
tatgagagca ttgatggttt ttatcgtgag gttgaggagc aaggatataa agttaatttt 2160
gcttttgtaa gggcggattt aattgacaaa tatgtggaaa gtggaagttt gttccttttc 2220
caattgtata acaaggattt ctcttgtgcg tcatctggga agccaaacct ccacacgctt 2280
tactggaaga gcctctttgc aaaagaaaac cttgatgagc cgattctgaa gttgtgtggg 2340
ggtgcagagc tattcttccg cccagttgca atccagaagc cgtatgtaca taccttggga 2400
gaaaagttgg tcaatcgcag gcttggcgag cacggtaagg gagaggcaat cccggagaga 2460
gttcacaagg aactcgtgga ctactacaac catcgtgtgt cggtgctgag tcatgatggg 2520
aaggcattta aagacaaggt tgttgttcgg gatgtcgcac attcgattac aaaagatcgt 2580
cgattctcag aggcaaagtt ttttttccat gttccgatca tgtttaaccg tacagcatcg 2640
aagagtgcaa agtttaacga caaagttgtg gactatctca agaccactca gaatgtaaac 2700
gttatcgggt tggatcgagg agaaagaaat ctgatttatc tgacaatggt aaatttgcac 2760
ggaaagctga tagagcagcg tagtttcaac ctagttaatg gtgtggatta tcattcaaag 2820
ctagatttgc gagaaaagga gcgcatggac gcacgcgtta attgggagaa cattggggga 2880
attaaagatc ttaagaccgg atatctttcc gcggttgttc atgagattgc gaagatgatg 2940
gtgacgaata atgccattgt tgtcttggag gacttgaact tcggtttcaa acgtgggcgg 3000
ttcaaggttg agaaacaggt ctatcagaag tttgagaaga tgctgattga taaactgaat 3060
ttcctgatgt tcaaggaatg caatcaagcg gctctcggtg gtgttcgccg tgcatatcaa 3120
ttgacggata aattcgtgag ttttgaaaaa cttggtaaac aaacgggttt cctgttttat 3180
gttccggcgg gctacacatc gaagattgat ccaacaactg gattcaccaa cctcttcaac 3240
acgaaaaaat gcactaatgc cgaaggtcgg aaggtcttct ttgaggcgat gaactctatc 3300
atatatgacg gatcaaggaa gtcgtttgcg ttctcatttg attacggcaa cccagttttt 3360
agagcaagtc aaacgagttt taaaaaagaa tggaccgtct attccgctga tacgcgcatt 3420
gtctacaatc gtggcgagaa aactgttaat acgatccatc cgacacaaat tcttcatgat 3480
gctttgtgtg cactcggcat tgacgttcat gacggattga acgtcttgaa cgtagttcgt 3540
gagacgccag cggacaagat tcatgctaag tttttctcag acttgttcta tgcgtttgat 3600
cgtacacttc agatgcgtaa cagtgtttca ggaacagatg aagactatat ccaatcgcct 3660
gttttgaatg cgacaggtga gttttttgat tcgcggaaag cagacagtac tcttccgcag 3720
gatgccgatg ccaatggtgc ctaccacatc gcattaaagg gacttttgct gctacaacgc 3780
atgaaagata ttggcagtga tatcaagctt gatctatcca ttaagcatga ggactggttt 3840
gcgtttgcac aaaagcgttg ccagagataa 3870

SEQ ID NO: 83 moltype = DNA length = 3864
FEATURE Location/Qualifiers
source 1..3864
mol_type = other DNA
organism = synthetic construct
SEQUENCE: 83
agcttcgagt ctttcactaa cgtataccct gtgtctaaaa ccctgcgttt tgaactgcgg 60
cctgtgggcg ccactgccga gaagctgaag gagagcggca tcctggagca cgataccaag 120
cggggcaagg aatacgctac actgaaggac ctgctggacg agcagcacaa agagctactg 180
gccgacgccc tgaagccaga gagagtgaag aacgccctga agcccaacag cggcaagtcc 240
aaaaaggaca agctggtcga agagaactac attacagaag atggagagat cagatgggag 300
acactggccg ctgctatgga ggccttcaga gctggcgaag tggagaagaa cgtgctggaa 360

```
gcgatccaga cacagtttcg gaagctgatc gtgaccatcc tgaaagccga cgagagatac  420
cctggactga ccgcctctac acctagcgcc gtcatcaaga ccttgctgaa gcaggacgtg  480
caccccgagg ccgtagagac attcgctaaa tttgcctgtt acttcaccgg ctttcaggaa  540
aacagaaaga atatctacgc cgaagaaaaa caggccaccg ccgtggccac acgggttgtc  600
cacgacaact tcgccaaatt tcacacccag tctaagatta tcggcgtgat caaaaacaag  660
taccccgaga tcctgcagag cgtcgagatg gaactgatgg acgaacttgg gggaatgaag  720
atcaccgata tcttcagtat caacagctac agcaagtgga tgacccagga gggaatcgac  780
ttcatcaaca aaatcatcgg cggctacagc cctagcgtgg gcgtcaaagt gagaggcctg  840
aacgagttca tcaacctgta cagacagcag cacgaggaag ccaacgccga ccggcggaac  900
ctggctaaga tgcctatgct gtttaaacaa attctgagcg acatcagcac ccggagcttc  960
atccctgtga tgttcgagaa tgacgccgag ctcaaggaca gcatcgaggc cttcctgaca  1020
ggcctgaatg atttcgagct gaacgctcag aagttcaacg ttgtggtggc cctggggaac  1080
ctgtttcaga agattgtgcc ttgtgaaggc atcttcctgg acgctgccct gatggaaaag  1140
gtttccaaga cagctacagg cgactggagc ctgctcgcac agtctatgga agcctacgcc  1200
gaaacagcct ttacaagagc caaggaccgg gacgcctggc tgagaaagaa ttactacagc  1260
ctgtccgagc tgagccaggt gccaatcctg aagaacactg atgagggcat gctgaagttc  1320
gagctgagcg cctactggtc cggcgagaaa atggaatctt tcgtgaaggg catcatggac  1380
gccgagctgg ccatgaagcc agtgctggcc agcatcggcc agaaaaccga agaggtgcgg  1440
ctgagagata gaatcgacga cgtggtgaag atcaagggct acctggacag catccagaat  1500
ttcctgcacc acctgaagcc tttctgtgcc cctaccgagc tgaaccggga cgccgacttc  1560
tactctgact tcgatgctct gtacaatcaa ctggtgctgg tgattcccct gtacaactgc  1620
gtgagaaact acgtcaccca aaaggttacc gaggtgcaga agctgcgcct caagttcgat  1680
gcacctaccc tggccgatgg atgggacgcc aataaagaga atgacaacaa agccgtcctg  1740
ttcgagaaag acggcctgta tttcctcggc atcctcaacc ctaacctgaa agccaaggac  1800
cggcctgtgt tcgaacatga aagcaacgtg accaagaagt catgctaccg gaagattgtg  1860
tacaaactgc tgccaggccc taacaagatg ctgcctaagg tgttctttgc cgatagcaac  1920
aggacactgt accaccctag caagagcctg ctggaccggt atcacaacgg cgagtacaag  1980
aagggcgata gctttgatat caagttttgc cacgagctga tcgactactt caaggcctct  2040
atctctattc accctgactg gaaggagttc ggctttcaat ttctgccac aaagacctac  2100
gagtctatcg acggcttcta tagagaggtg gaagagcagg gctacaaggt gaacttcgcc  2160
tttgtgcgtg ctgacctgat cgataagtac gtggaaagcg gctccctgtt cctgttccag  2220
ctctataaca aggacttcag ctgtgcctct agcggcaagc cgaatcttca tacactgtac  2280
tggaaaagcc tgttcgccaa ggagaacctg gacgagccta tactgaagct gtgcggcggc  2340
gccgagctgt tcttcagacc cgtggcgatc cagaaaccct acgtgcacac attgggcgaa  2400
aagctggtga atagacggct cggcgagcac ggcaagggcg aggctatccc tgagcgggtg  2460
cacaaggaac tggtggacta ctacaaccac agagtgagcg tgctcagtca cgatggaaag  2520
gccttcaagg acaaggtggt ggttcgggac gtggcccaca gcatcaccaa ggaccgacgg  2580
tttagcgagg ccaagttctt cttccacgtg cccatcatgt ttaaccggac cgccagcaag  2640
agcgccaagt tcaacgacaa ggtggtggac tacctgaaaa ccacccaaaa cgtgaacgtg  2700
atcggactgg acagaggtga aagaaacctg atctacctca caatggtgaa cctgcatggc  2760
aagctcatcg agcagcggag cttcaacctg gtgaatggcg tggactacca ttctaagctg  2820
gatctgcgcg agaaggaacg tatggatgct agagtgaact gggagaatat cggcggcata  2880
aaggatctga aaaccggcta cctgagcgcc gtggtgcacg agatcgccaa aatgatggtg  2940
acaaacaacg ccatcgtggt gctggaagat ctgaactttg gattcaagag aggcagattc  3000
aaagtggaaa agcaggtgta ccagaaattc gagaagatgc tgatcgacaa actgaacttc  3060
ctgatgttca aagagtgcaa ccaggccgcc ctgggcggcg tgcggcgggc ctatcagctg  3120
accgacaagt tcgtgagctt cgagaagctg ggaaagcaga ccggcttcct gttctatgtg  3180
cccgccggct atacaagcaa aatcgatcct acaaccggtt tcaccaacct gttcaatacc  3240
aagaaatgca ccaacgccga gggaagaaag gtgttcttcg aggctatgaa cagcatcatc  3300
tacgacggct ccagaaaatc tttcgccttt agcttcgact acggcaaccc cgtgtttcga  3360
gcctcccaga ccagcttcaa gaaggaatgg accgtgtaca gcgccgatac aagaatcgtg  3420
tataatcggg gcgaaaagac cgtaaacacc atccacccta cccagatcct gcacgacgcc  3480
ctgtgcgcct tgggaatcga cgtgcacgat gggttaaatg tcttgaacgt cgtgagagag  3540
acacccgctg ataagatcca cgccaagttc ttcagcgatc tcttctacgc cttcgacaga  3600
accctgcaga tgaggaactc tgtgagcggg accgacgaag attacatcca gagccctgtg  3660
ctgaatgcta ccggcgagtt ctttgacagc agaaaagccg acagcaccct gccccaggac  3720
gcagacgcta atggagccta ccacatcgcc ctgaagggcc tgctgctcct gcagagaatg  3780
aaggatatcg gctcagatat caagctggat ctgtctatta agcacgagga ttggttcgcc  3840
ttcgctcaga agcggtgcca gaga                                         3864
```

```
SEQ ID NO: 84          moltype = DNA  length = 3987
FEATURE                Location/Qualifiers
source                 1..3987
                       mol_type = other DNA
                       organism = synthetic construct
SEQUENCE: 84
atgggctccg gaagcttcga gtctttcact aacgtatacc ctgtgtctaa aaccctgcgt  60
tttgaactgc ggcctgtggg cgccactgcc gagaagctga aggagagcgg catcctggag  120
cacgatacca agcggggcaa ggaatacgct acactgaagg acctgctgga cgagcagcac  180
aaagagctac tggccgacgc cctgaagcca gagagagtga agaacgccct gaagcccaac  240
agcggcaagt ccaaaaagga caagctggtc gaagagaact acattacaga agatggagag  300
atcagatggg agacactggc cgctgctatg gaggccttca gagctggcga agtggagaag  360
aacgtgctgg aagcgatcca gacacagttt cggaagctga tcgtgaccat cctgaaagcc  420
gacgagagat accctggact gaccgcctct acacctagcg ccgtcatcaa gaccttgctg  480
aagcaggacg tgcaccccga ggccgtagag acattcgcta aatttgcctg ttacttcacc  540
ggctttcagg aaaacagaaa gaatatctac gccgaagaaa aacaggccac cgccgtggcc  600
acacgggttg tccacgacaa cttcgccaaa tttcacaccc agtctaagat tatcggcgtg  660
atcaaaaaca agtaccccga gatcctgcag agcgtcgaga tggaactgat ggacgaactt  720
gggggaatga agatcaccga tatcttcagt atcaacagct acagcaagtg gatgacccag  780
```

```
gagggaatcg acttcatcaa caaaatcatc ggcggctaca gccctagcgt gggcgtcaaa  840
gtgagaggcc tgaacgagtt catcaacctg tacagacagc agcacgagga agccaacgcc  900
gaccggcgga acctggctaa gatgcctatg ctgtttaaac aaattctgag cgacatcagc  960
acccggagct tcatccctgt gatgttcgag aatgacgccg agctcaagga cagcatcgag  1020
gccttcctga caggcctgaa tgatttcgag ctgaacgctc agaagttcaa cgttgtggtg  1080
gccctgggga acctgtttca gaagattgtg ccttgtgaag gcatcttcct ggacgctgcc  1140
ctgatggaaa aggtttccaa gacagctaca ggcgactgga gcctgctcgc acagtctatg  1200
gaagcctacg ccgaaacagc ctttacaaga gccaaggacc gggacgcctg gctgagaaag  1260
aattactaca gcctgtccga gctgagccag gtgccaatcc tgaagaacac tgatgagggc  1320
atgctgaagt tcgagctgag cgcctactgg tccggcgaga aaatggaatc tttcgtgaag  1380
ggcatcatgg acgccgagct ggccatgaag ccagtgctgg ccagcatcgg ccagaaaacc  1440
gaagaggtgc ggctgagaga tagaatcgac gacgtggtga agatcaaggg ctacctggac  1500
agcatccaga atttcctgca ccacctgaag cctttctgtg cccctaccga gctgaaccgg  1560
gacgccgact tctactctga cttcgatgct ctgtacaatc aactggtgct ggtgattccc  1620
ctgtacaact gcgtgagaaa ctacgtcacc caaaaggtta ccgaggtgca gaagctgcgc  1680
ctcaagttcg atgcacctac cctggccgat ggatgggacg ccaataaaga gaatgacaac  1740
aaagccgtcc tgttcgagaa agacggcctg tatttcctcg gcatcctcaa ccctaacctg  1800
aaagccaagg accggcctgt gttcgaacat gaaagcaacg tgaccaagaa gtcatgctac  1860
cggaagattg tgtacaaact gctgccaggc cctaacaaga tgctgcctaa ggtgttcttt  1920
gccgatagca acaggacact gtaccaccct agcaagagcc tgctggaccg gtatcacaac  1980
ggcgagtaca agaagggcga tagctttgat atcaagtttt gccacgagct gatcgactac  2040
ttcaaggcct ctatctctat tcaccctgac tggaaggagt tcggctttca atttctgcc  2100
acaaagacct acgagtctat cgacggcttc tatagagagg tggaagagca gggctacaag  2160
gtgaacttcg cctttgtgcg tgctgacctg atcgataagt acgtggaaag cggctccctg  2220
ttcctgttcc agctctataa caaggacttc agctgtgcct ctagcggcaa gccgaatctt  2280
catacactgt actggaaaag cctgttcgcc aaggagaacc tggacgagcc tatactgaag  2340
ctgtgcggcg gcgccgagct gttcttcaga cccgtggcga tccagaaacc ctacgtgcac  2400
acattgggcg aaaagctggt gaatagacgg ctcggcgagc acggcaaggg cgaggctatc  2460
cctgagcggg tgcacaagga actggtggac tactacaacc acagagtgag cgtgctcagt  2520
cacgatggaa aggccttcaa ggacaaggtg gtggttcggg acgtggccca cagcatcacc  2580
aaggaccgac ggtttagcga ggccaagttc ttcttccacg tgcccatcat gtttaaccgg  2640
accgccagca agagcgccaa gttcaacgac aaggtggtgg actacctgaa aaccacccaa  2700
aacgtgaacg tgatcggact ggacagaggt gaaagaaacc tgatctacct cacaatggtg  2760
aacctgcatg gcaagctcat cgagcagcgg agcttcaacc tggtgaatgg cgtggactac  2820
cattctaagc tggatctgcg cgagaaggaa cgtatggatg ctagagtgaa ctgggagaat  2880
atcggcggca taaaggatct gaaaaccggc tacctgagcg ccgtggtgca cgagatcgcc  2940
aaaatgatgg tgacaaacaa cgccatcgtg gtgctggaag atctgaactt tggattcaag  3000
agaggcagat tcaaagtgga aaagcaggtg taccagaaat tcgagaagat gctgatcgac  3060
aaactgaact tcctgatgtt caaagagtgc aaccaggccg ccctgggcgg cgtgcggcgg  3120
gcctatcagc tgaccgacaa gttcgtgagc ttcgagaagc tgggaaagca gaccggcttc  3180
ctgttctatg tgcccgccgg ctatacaagc aaaatcgatc ctacaaccgg tttcaccaac  3240
ctgttcaata ccaagaaatg caccaacgcc gagggaagaa aggtgttctt cgaggctatg  3300
aacagcatca tctacgacgg ctccagaaaa tctttcgcct ttagcttcga ctacggcaac  3360
cccgtgtttc gagcctccca gaccagcttc aagaaggaat ggaccgtgta cagcgccgat  3420
acaagaatcg tgtataatcg gggcgaaaag accgtaaaca ccatccaccc tacccagatc  3480
ctgcacgacg ccctgtgcgc cttgggaatc gacgtgcacg atgggttaaa tgtcttgaac  3540
gtcgtgagag agacacccgc tgataagatc cacgccaagt tcttcagcga tctcttctac  3600
gccttcgaca gaaccctgca gatgaggaac tctgtgagcg ggaccgacga agattacatc  3660
cagagccctg tgctgaatgc taccggcgag ttctttgaca gcagaaaagc cgacagcacc  3720
ctgccccagg acgcagacgc taatggagcc taccacatcg ccctgaaggg cctgctgctc  3780
ctgcagagaa tgaaggatat cggctcagat atcaagctgg atctgtctat taagcacgag  3840
gattggttcg ccttcgctca gaagcggtgc cagagatcta gaaagcggac agcagacggc  3900
tccgaatttg aaagccctaa gaaaaagaga aaggtgggat ccggcaaacc tatccccaat  3960
cccctgctgg gcctggacag cacctga                                     3987
```

```
SEQ ID NO: 85          moltype = AA  length = 1309
FEATURE                Location/Qualifiers
source                 1..1309
                       mol_type = protein
                       organism = unidentified
SEQUENCE: 85
STINKFCGQG NGYSRSITLR NKLIPIGKTE ENLKWFLEKD LERAIAYPEI KNLIDNIHRS  60
VIEDTLSKVA LNWNEIFNTL AAYQNEKDKK KKAAIKKDLE KLQGCARKKI VDTFKKNPDY  120
EKLFKEGLFK ELLPELIKTA PVSEIEDKTK ALECFNRFST YFTGFHENRK NMYSEDAKST  180
AISYRIVNEN FPKFFANIKL YNYLKEKFPQ IIINTEESLK DYLKGKKLDS VFSIDGFNDV  240
LAQSGIDFYN TVIGGISGEA GTEKTQGLNE KINLARQQLP KDEKDKLRGK MVDLFKQILS  300
DRETSSFIPT GFENKKEVYS TVKKFSEIVV EKSVSKVKEI FTQNEEYNLN EIFVPAKSLT  360
NFSQNIFGNW SILSEGLFLL EKDNVKKQLS EKQIETLHKE IAKKDCSFTE LQNAYERWCA  420
ENSVDATKNI NRYFSIVDLR TKNDSFEKEE INILDEITNA FSKIDFDDIH DLQQEKEAAT  480
PIKNYLDEVQ NLYHHLKLVD YRGEERKDAN FYSKLDYILR KDRKDYLNLA EVVPLYNKVR  540
NFVTKKPGEV KKIKMMFDCS SLLGGWGTDY ETKEAHIFID SGKYYLGIIN EKLSKDDVEL  600
LKKSSERMIT KVIYDFQKPD NKNTPRLFIR SKGTNYAPAV FQYNLPIESV IDIYDRGLFK  660
TEYRKINSKV YKESLIKMID YFKMGFERHE SYKHYKFCWK ESSKYNDIGE FYKDVINSCY  720
QLNFEKVNYE NLLKLVENNK LFLFQIYNKD FAEKKSGKKN LHTLYWENLF SEENLKDVCL  780
KLNGEAELFW RKASLDKGKV IVHRMGSILV NRTTSEGKSI PEDIYQEIYQ YKNKMKDKIS  840
DEAKSLLDSG TVICKEATHD ITKDKRFTED TYLFHCPITM NFKATDKKNK EFNNHVLEVL  900
KENPDVKIIG LDRGERHLIY LSLINQKGEI ELQKTLNLVE QVRNDKTVKV DYQEKLVHKE  960
GDRDKARKNW QTIGNIKELK EGYLSAVVHE IAMLMVENNA IVVMEDLNFG FKRGRFAVER  1020
QIYQKFENML IEKLNYLVFK DKNATEPGGV LNAYQLTNKS ANVTDVYKQC GWLFYIPAAY  1080
```

```
TSKIDPKTGF ANLFITKGLT NVEKKKEFFD KFDSIRYDSK EDCFVFGFDY AKLCDNASFR  1140
KKWEVYTRGE RLVYNKDKHK NEPINPTEEL KGIFDAFDIN WNTDDNFIDS VQTIQAEKAN  1200
AKFFDILLRM FNATLQMRNS KTNSSASEDD YLISPVKAED GTFFDTREEL KKGKDAKLPI  1260
DSDANGAYHI ALKGLFLLEN DFNRDEKGVI QNISNADWFK FVQEKKYKD             1309

SEQ ID NO: 86          moltype = AA  length = 1310
FEATURE                Location/Qualifiers
source                 1..1310
                       mol_type = protein
                       organism = unidentified
SEQUENCE: 86
MSTINKFCGQ GNGYSRSITL RNKLIPIGKT EENLKWFLEK DLERAIAYPE IKNLIDNIHR  60
SVIEDTLSKV ALNWNEIFNT LAAYQNEKDK KKKAAIKKDL EKLQGCARKK IVDTFKKNPD  120
YEKLFKEGLF KELLPELIKT APVSEIEDKT KALECFNRFS TYFTGFHENR KNMYSEDAKS  180
TAISYRIVNE NFPKFFANIK LYNYLKEKFP QIIINTEESL KDYLKGKKLD SVFSIDGFND  240
VLAQSGIDFY NTVIGGISGE AGTEKTQGLN EKINLARQQL PKDEKDKLRG KMVDLFKQIL  300
SDRETSSFIP TGFENKKEVY STVKKFSEIV VEKSVSKVKE IFTQNEEYNL NEIFVPAKSL  360
TNFSQNIFGN WSILSEGLFL LEKDNVKKQL SEKQIETLHK EIAKKDCSFT ELQNAYERWC  420
AENSVDATKN INRYFSIVDL RTKNDSFEKE EINILDEITN AFSKIDFDDI HDLQQEKEAA  480
TPIKNYLDEV QNLYHHLKLV DYRGEERKDA NFYSKLDYIL RKDRKDYLNL AEVVPLYNKV  540
RNFVTKKPGE VKKIKMMFDC SSLLGGWGTD YETKEAHIFI DSGKYYLGII NEKLSKDDVE  600
LLKKSSERMI TKVIYDFQKP DNKNTPRLFI RSKGTNYAPA VFQYNLPIES VIDIYDRGLF  660
KTEYRKINSK VYKESLIKMI DYFKMGFERH ESYKHYKFCW KESSKYNDIG EFYKDVINSC  720
YQLNFEKVNY ENLLKLVENN KLFLFQIYNK DFAEKKSGKK NLHTLYWENL FSEENLKDVC  780
LKLNGEAELF WRKASLDKGK VIVHRMGSIL VNRTTSEGKS IPEDIYQEIY QYKNKMKDKI  840
SDEAKSLLDS GTVICKEATH DITKDKRFTE DTYLFHCPIT MNFKATDKKN KEFNNHVLEV  900
LKENPDVKII GLDRGERHLI YLSLINQKGE IELQKTLNLV EQVRNDKTVK VDYQEKLVHK  960
EGDRDKARKN WQTIGNIKEL KEGYLSAVVH EIAMLMVENN AIVVMEDLNF GFKRGRFAVE  1020
RQIYQKFENM LIEKLNYLVF KDKNATEPGG VLNAYQLTNK SANVTDVYKQ CGWLFYIPAA  1080
YTSKIDPKTG FANLFITKGL TNVEKKKEFF DKFDSIRYDS KEDCFVFGFD YAKLCDNASF  1140
RKKWEVYTRG ERLVYNKDKH KNEPINPTEE LKGIFDAFDI NWNTDDNFID SVQTIQAEKA  1200
NAKFFDILLR MFNATLQMRN SKTNSSASED DYLISPVKAE DGTFFDTREE LKKGKDAKLP  1260
IDSDANGAYH IALKGLFLLE NDFNRDEKGV IQNISNADWF KFVQEKKYKD             1310

SEQ ID NO: 87          moltype = AA  length = 1349
FEATURE                Location/Qualifiers
source                 1..1349
                       mol_type = protein
                       organism = synthetic construct
SEQUENCE: 87
MGSGSTINKF CGQGNGYSRS ITLRNKLIPI GKTEENLKWF LEKDLERAIA YPEIKNLIDN  60
IHRSVIEDTL SKVALNWNEI FNTLAAYQNE KDKKKKAAIK KDLEKLQGCA RKKIVDTFKK  120
NPDYEKLFKE GLFKELLPEL IKTAPVSEIE DKTKALECFN RFSTYFTGFH ENRKNMYSED  180
AKSTAISYRI VNENFPKFFA NIKLYNYLKE KFPQIIINTE ESLKDYLKGK KLDSVFSIDG  240
FNDVLAQSGI DFYNTVIGGI SGEAGTEKTQ GLNEKINLAR QQLPKDEKDK LRGKMVDLFK  300
QILSDRETSS FIPTGFENKK EVYSTVKKFS EIVVEKSVSK VKEIFTQNEE YNLNEIFVPA  360
KSLTNFSQNI FGNWSILSEG LFLLEKDNVK KQLSEKQIET LHKEIAKKDC SFTELQNAYE  420
RWCAENSVDA TKNINRYFSI VDLRTKNDSF EKEEINILDE ITNAFSKIDF DDIHDLQQEK  480
EAATPIKNYL DEVQNLYHHL KLVDYRGEER KDANFYSKLD YILRKDRKDY LNLAEVVPLY  540
NKVRNFVTKK PGEVKKIKMM FDCSSLLGGW GTDYETKEAH IFIDSGKYYL GIINEKLSKD  600
DVELLKKSSE RMITKVIYDF QKPDNKNTPR LFIRSKGTNY APAVFQYNLP IESVIDIYDR  660
GLFKTEYRKI NSKVYKESLI KMIDYFKMGF ERHESYKHYK FCWKESSKYN DIGEFYKDVI  720
NSCYQLNFEK VNYENLLKLV ENNKLFLFQI YNKDFAEKKS GKKNLHTLYW ENLFSEENLK  780
DVCLKLNGEA ELFWRKASLD KGKVIVHRMG SILVNRTTSE GKSIPEDIYQ EIYQYKNKMK  840
DKISDEAKSL LDSGTVICKE ATHDITKDKR FTEDTYLFHC PITMNFKATD KKNKEFNNHV  900
LEVLKENPDV KIIGLDRGER HLIYLSLINQ KGEIELQKTL NLVEQVRNDK TVKVDYQEKL  960
VHKEGDRDKA RKNWQTIGNI KELKEGYLSA VVHEIAMLMV ENNAIVVMED LNFGFKRGRF  1020
AVERQIYQKF ENMLIEKLNY LVFKDKNATE PGGVLNAYQL TNKSANVTDV YKQCGWLFYI  1080
PAAYTSKIDP KTGFANLFIT KGLTNVEKKK EFFDKFDSIR YDSKEDCFVF GFDYAKLCDN  1140
ASFRKKWEVY TRGERLVYNK DKHKNEPINP TEELKGIFDA FDINWNTDDN FIDSVQTIQA  1200
EKANAKFFDI LLRMFNATLQ MRNSKTNSSA SEDDYLISPV KAEDGTFFDT REELKKGKDA  1260
KLPIDSDANG AYHIALKGLF LLENDFNRDE KGVIQNISNA DWFKFVQEKK YKDSRKRTAD  1320
GSEFESPKKK RKVGSGKPIP NPLLGLDST                                   1349

SEQ ID NO: 88          moltype = DNA  length = 3933
FEATURE                Location/Qualifiers
source                 1..3933
                       mol_type = unassigned DNA
                       organism = unidentified
SEQUENCE: 88
atgtcaacta ttaacaaatt ttgtggacag gggaatgggt attctcgttc aattactttg  60
aggaataagt taattcctat tggaaaaact gaagaaaatt tgaaatggtt tttagaaaaa  120
gatttggaaa gggcaattgc ttatccggag ataaagaatc ttatagataa tattcatcgt  180
agtgtaattg aggatacttt atccaaagtt gctttgaatt ggaatgaaat attcaataca  240
cttgctgctt atcaaaatga aaaagataaa aaaaagaaag cagcaataaa aaaggatttg  300
gagaaattac aaggttgtgc aagaaagaaa atagttgata cttttaaaaa gaatcctgat  360
tatgaaaaat tgtttaagga aggattattc aaagaactat tacctgagtt aataaaaact  420
gctcctgtta gtgaaataga agataaaaca aaagctttgg aatgttttaa tagatttagt  480
acatatttta caggatttca tgaaaataga aaaaatatgt atagcgaaga tgcaaaatca  540
```

actgcaataa gttaccgtat tgtaaatgag aatttcccca aatttttttgc aaatataaag 600
ttatataatt atttaaaaga aaagtttcca caaattatta ttaatacaga agaatcttta 660
aaagattatc taaaaggtaa aaaacttgat tctgtattta gtattgatgg atttaatgat 720
gttttagctc aaagtggaat cgattttttat aatacagtaa ttggtggaat ttctggtgaa 780
gccggaacag aaaagactca aggattaaat gaaaaaatca atcttgcaag acaacaatta 840
ccaaaagatg aaaaagataa acttcgtgga aaaatggttg atttatttaa gcagatttta 900
agtgatagag aaacatcttc gtttattcca actggttttg aaaataaaaa agaagtttat 960
tctactgtaa agaaatttag tgaaattgtt gttgaaaagt ctgtttcaaa agtaaaagaa 1020
atttttacac aaaatgaaga atataatctt aatgaaatct ttgttccagc aaaatcatta 1080
acaaattttt ctcaaaatat ttttggaaat tggtctattt tatcagaagg gttatttttg 1140
cttgaaaaag ataatgttaa aaaacaatta tctgaaaaac aaattgaaac attacacaaa 1200
gaaattgcaa aaaaagattg ttcttttact gaactacaaa atgcttatga aagatggtgt 1260
gctgaaaata gtgttgatgc aacaaaaaat atcaataggt atttttcaat agttgattta 1320
agaacaaaaa atgattcgtt tgaaaaagaa gaaattaata ttttggatga aattacaaat 1380
gctttttcaa aaattgattt tgatgatatt catgatttac aacaagaaaa agaagctgca 1440
acaccaataa aaaattattt ggatgaagtt caaaatcttt atcatcactt aaaacttgtt 1500
gattatcgtg gtgaagaacg aaaggatgca aacttttatt caaagctaga ttatatatta 1560
aggaaagata ggaaagatta ccttaatctt gctgaagttg tacctttgta taacaaagtt 1620
cgtaattttg taacaaagaa acctggtgaa gtaaaaaaga ttaaaatgat gtttgattgt 1680
agttctttat tagggggggtg gggaactgat tacgaaacaa aagaagctca tatttttatt 1740
gattctggaa aatattattt gggaattata aacgaaaaat tatcaaaaga tgatgttgag 1800
ttattaaaaa aatcaagtga aagaatgata acaaaagtaa tttatgattt tcagaaacct 1860
gataataaaa atacacctcg tttatttatt cgttcaaaag gaacaaatta tgcacctgct 1920
gtttttcaat ataatttacc aatagaatct gttattgata tttatgatag aggattgttt 1980
aaaaccgaat atagaaaaat caattcaaaa gtttacaaag aatcattaat aaaaatgatt 2040
gattatttca agatgggctt tgaaagacat gaatcatata agcattataa attctgttgg 2100
aaggaatctt caaaatataa tgatattggt gaattttaca aggatgtgat aaattcatgc 2160
tatcaattaa atttcgaaaa agtgaattat gaaaatttat taaaattggt tgaaaacaat 2220
aaattattcc ttttccaaat atataacaaa gattttgcag aaaaaaaatc tggaaagaaa 2280
aatcttcata ctttgtattg ggaaaatctt tttagtgaag aaaacttgaa agatgtttgc 2340
ttaaaattga atggtgaagc tgaacttttc tggcgcaaag caagtttaga caaaggaaaa 2400
gttatagttc atagaatggg ttctattctt gtaaatagaa ctacatctga aggtaaatca 2460
attccagaag atatttatca ggaaatttat caatataaaa ataaaatgaa agataaaatt 2520
tctgatgaag caaaaagtct tttagattca ggaacagtta tttgtaaaga agcaactcac 2580
gatattacaa aagacaagcg ctttacagaa gatacatatc ttttccattg tccaattaca 2640
atgaacttta aagcaactga taaaaaaaat aaagaattta ataatcatgt tcttgaagtt 2700
ttaaaagaaa atccagatgt taaaattatt ggtcttgacc gtggtgaaag acatttgatt 2760
tatctttctt tgattaatca aaaaggtgaa attgaacttc aaaaaacatt gaatcttgta 2820
gaacaagtta gaaatgataa aactgtaaaa gtagattatc aagaaaaact tgtacataaa 2880
gaaggcgaca gagacaaagc tcgtaaaaac tggcaaacaa ttggaaatat caaagaacta 2940
aaagaaggtt atttatctgc tgttgttcat gaaattgcaa tgttgatggt agaaaataat 3000
gcaattgttg taatggaaga tttgaatttt ggatttaaac gtggtcgatt tgctgtagaa 3060
agacaaattt atcaaaagtt tgaaaatatg ctcattgaaa aacttaatta tcttgtgttt 3120
aaggataaaa atgctacaga accaggtggt gtccttaatg catatcaatt aacaaataaa 3180
tctgcaaatg taactgacgt ttataaacaa tgtggatggc ttttctatat tccagcagcg 3240
tatacttcaa aaattgatcc aaaaacaggt tttgcaaatt tattcataac aaaaggatta 3300
acaaatgtag aaaagaaaaa agaattcttt gataaattcg attccattcg ttatgactca 3360
aaagaagact gttttgtatt tggttttgat tatgcaaaac tttgtgataa tgcaagtttt 3420
agaaaaaaat gggaagtata cacaagaggg gaaagattag tttacaataa agataaacat 3480
aaaaatgaac ctattaatcc aacagaagaa ttaaaaggaa tttttgatgc attcgatata 3540
aattggaata cggatgataa ttttattgat tccgtacaga caatacaagc agaaaaagca 3600
aatgccaaat tctttgatat tcttttgcga atgtttaatg caactcttca aatgcgaaat 3660
tcaaaaaaaca attcttcagc atcagaagat gattatttga tatctccggt aaaagcagag 3720
gatggaacat tctttgatac tcgtgaagaa ttaaagaaag gcaaagatgc aaaacttcct 3780
atagattcag atgcaaacgg agcttatcat attgcactaa aaggactttt cttacttgaa 3840
aatgacttca atagagatga aaaaggtgtg attcagaata tctccaacgc cgattggttt 3900
aagtttgtgc aggagaaaaa atacaaagat taa 3933

SEQ ID NO: 89 moltype = DNA length = 3927
FEATURE Location/Qualifiers
source 1..3927
mol_type = other DNA
organism = synthetic construct
SEQUENCE: 89 agcaccatca acaaattctg cggccagggc aacggctaca gcagaagcat caccctgcgg 60
aacaaactga tccctatcgg caagactgag gagaacctga agtggttcct ggagaaggac 120
ctggagcggg ctatcgccta ccccgagatt aaaaacctta tcgacaatat ccacagaagc 180
gtgatagagg ataccctgag caaggtcgcc ctgaactgga atgagatctt caacaccctg 240
gccgcctacc agaacgagaa agataagaaa aagaaggccg ctatcaagaa ggacctggag 300
aagttgcaag gatgtgcgag aaagaaaatc gtggatacct tcaagaagaa ccctgattat 360
gagaaactgt ttaaagaggg actgttcaag gagctgctgc ctgaactgat caagaccgcc 420
cctgtgagcg aaattgaaga taaaaccaaa gccctggagt gcttcaaccg gttctccaca 480
tacttcaccg gcttccacga aaatcgcaaa aatatgtaca gcgaggacgc gaagagcacc 540
gccatctcct accggatcgt gaacgagaac ttccccaagt tcttcgctaa tatcaagctg 600
tacaactacc tcaaggaaaa atttccacag attatcatca acacagaaga gtctctgaag 660
gattacctga agggcaagaa gctggattcc gtgttctcca tcgacgggtt caatgacgtg 720
ctggcccaga gcggcataga cttctacaac accgtgatcg gtggcatctc aggagaggcc 780
ggcacagaaa agacccaggg cctgaatgag aagatcaacc tagccagaca gcagctgcct 840
aaggatgaga aggacaagct aagaggcaag atggtcgacc tgttcaagca gattctgagc 900

```
gatagagaaa ccagcagctt catccctact ggcttcgaga ataagaagga agtgtactct  960
accgtgaaga agttcagcga aatcgtggtc gaaaaaagcg tgtccaaggt gaaggagatc  1020
ttcactcaga acgaagagta caatctgaac gagatcttcg tgcctgcgaa gagcctgacc  1080
aattttagcc agaacatctt tggcaactgg agcatccttt ctgaaggcct gttcctgctg  1140
gaaaaggaca acgtgaagaa acagctgagt gagaaacaaa tcgagacact ccataaggag  1200
atcgccaaga aggactgcag ctttaccgaa ctgcagaacg cctacgagcg gtggtgcgcc  1260
gagaactccg tggacgccac caagaacatt aacagatact tcagcatcgt cgacctgaga  1320
accaagaatg actccttcga gaaggaagag atcaatatcc ttgatgagat aaccaacgcc  1380
ttctctaaga ttgacttcga cgatatccac gatctgcagc aagagaagga ggccgccacc  1440
cctatcaaga actacctgga cgaggttcaa aacctgtacc accacctgaa gctggtggac  1500
tacagaggtg aggaacgaaa ggacgctaac ttctactcta aactggacta tatcctgaga  1560
aaggacagaa aggactacct gaacctggcc gaagtggtgc cattgtacaa caaggttaga  1620
aacttcgtga ccaagaagcc tggcgaggtg aaaaagatca agatgatgtt cgactgcagc  1680
agcctgctgg gcggatgggg cacagattac gagacaaaag aggcccacat tttcatcgac  1740
tccggcaagt attaccttgg aatcatcaac gagaagttgt caaaagatga cgtggagctg  1800
ctgaagaaga gcagcgaacg gatgatcaca aaggtgatct acgatttcca aaagcccgat  1860
aacaagaata cacctagact gttcatcagg agcaagggca caaattatgc tcctgctgtt  1920
ttccaataca atctgccaat agagtctgtg atcgatattt acgaccgtgg cctgtttaag  1980
accgagtaca gaaaaatcaa cagcaaggtg tacaaggaga gcctgattaa gatgatcgat  2040
tacttcaaga tgggctttga gagacacgag agctacaagc actacaagtt ttgctggaag  2100
gaatctagca agtacaacga catcggcgaa ttttacaagg atgtgattaa ctcttgttac  2160
cagctgaact tcgagaaggt gaactatgag aacctcctga agttagtgga aaacaacaag  2220
ctgttcctgt ttcagatcta caacaaggat tttgccgaaa agaaaagcgg taagaagaac  2280
ctgcacaccc tgtactggga gaacctgttt tctgaggaga acctgaagga cgtttgtctg  2340
aagctgaatg gcgaggccga gctgttctgg cggaaggctt ctctggacaa gggcaaggtg  2400
atcgtgcaca gaatgggctc tatcctggtg aacagaacaa caagcgaggg caagtcaatc  2460
cctgaggaca tctaccagga gatctatcag tacaagaaca aaatgaagga taagatcagc  2520
gacgaagcca aaagcctgct ggacagcggc accgtgatct gtaaagaagc cacccacgac  2580
atcaccaagg acaaacggtt cacagaggac acctacctgt tccactgccc tatcaccatg  2640
aacttcaagg ccaccgacaa gaaaaacaaa gagttcaaca accacgtgct ggaagtgctg  2700
aaagagaatc ccgacgtgaa gatcatcggc ctggacagag gcgaacggca cctgatctac  2760
ctgagcctga tcaaccagaa gggcgagatc gagctgcaga aaccctgaa tctggtggaa  2820
caggtgcgga acgacaaaac cgtgaaggtg gactaccagg agaagctggt gcataaggaa  2880
ggcgaccgcg acaaagccag aaagaactgg cagacaatcg gaaacatcaa ggaactgaag  2940
gagggctacc tgtctgccgt ggtgcacgaa atcgccatgc tgatggtgga aaacaacgcc  3000
atcgtggtga tggaggacct gaacttcggc ttcaagagag gcagattcgc cgtggaacgg  3060
cagatctacc agaagttcga gaacatgctg atcgaaaagc tgaactacct agtgttcaag  3120
gacaagaacg ccaccgaacc tggcggcgtg ctgaatgcgt atcagctcac caacaagagc  3180
gccaacgtca ccgacgtgta caaacagtgc ggctggctgt tctacatccc cgccgcttat  3240
acaagcaaga tcgaccccaa gaccggattc gccaacctgt tcatcacaaa gggactgaca  3300
aacgtggaaa agaagaagga gttcttcgat aagttcgaca gcatccggta cgacagcaaa  3360
gaggactgct ttgtgttcgg cttcgactac gccaagctgt gcgacaacgc ctcctttaga  3420
aagaagtggg aagtttacac cagaggagag aggctggtct acaacaaaga caagcacaaa  3480
aacgaaccta tcaaccccac cgaggagctg aagggcatct tcgatgcttt tgatattaac  3540
tggaacaccg acgacaactt cattgattca gtgcagacca tccaggccga gaaggccaac  3600
gccaagttct ttgacatcct gctgagaatg ttcaacgcca cactgcagat gagaaacagc  3660
aagactaact cctctgccag cgaggacgac tacctgatca gccctgtcaa agccgaggat  3720
ggcaccttct tcgacacaag agaggaatta aagaagggca aagatgccaa gctgccgatc  3780
gacagcgacg ctaatggcgc ctaccacatc gccctgaaag gactgttcct gctggaaaat  3840
gactttaacc gggacgagaa gggagtgatc caaaatatca gcaacgctga ttggttcaag  3900
tttgtgcagg agaagaaata caaggat                                      3927
```

```
SEQ ID NO: 90          moltype = DNA  length = 4050
FEATURE                Location/Qualifiers
source                 1..4050
                       mol_type = other DNA
                       organism = synthetic construct
SEQUENCE: 90
atgggctccg gaagcaccat caacaaattc tgcggccagg gcaacggcta cagcagaagc  60
atcaccctgc ggaacaaact gatccctatc ggcaagactg aggagaacct gaagtggttc  120
ctggagaagg acctggagcg ggctatcgcc taccccgaga ttaaaaacct tatcgacaat  180
atccacagaa gcgtgataga ggataccctg agcaaggtcg ccctgaactg gaatgagatc  240
ttcaacaccc tggccgccta ccagaacgag aaagataaga aaaagaaggc cgctatcaag  300
aaggacctgg agaagttgca aggatgtgcg agaaagaaaa tcgtggatac cttcaagaag  360
aaccctgatt atgagaaact gtttaaagag ggactgttca aggagctgct gcctgaactg  420
atcaagaccg cccctgtgag cgaaattgaa gataaaacca aagccctgga gtgcttcaac  480
cggttctcca catacttcac cggcttccac gaaaatcgca aaaatatgta cagcgaggac  540
gcgaagagca ccgccatctc ctaccggatc gtgaacgaga acttccccaa gttcttcgct  600
aatatcaagc tgtacaacta cctcaaggaa aaatttccac agattatcat caacacagaa  660
gagtctctga aggattacct gaagggcaag aagctggatt ccgtgttctc catcgacggg  720
ttcaatgacg tgctggccca gagcggcata gacttctaca acaccgtgat cggtggcatc  780
tcaggagagg ccggcacaga aaagacccag ggcctgaatg agaagatcaa cctagccaga  840
cagcagctgc ctaaggatga gaaggacaag ctaagaggca agatggtcga cctgttcaag  900
cagattctga gcgatagaga aaccagcagc ttcatcccta ctggcttcga gaataagaag  960
gaagtgtact ctaccgtgaa gaagttcagc gaaatcgtgg tcgaaaaaag cgtgtccaag  1020
gtgaaggaga tcttcactca gaacgaagag tacaatctga acgagatctt cgtgcctgcg  1080
aagagcctga ccaattttag ccagaacatc tttggcaact ggagcatcct ttctgaaggc  1140
ctgttcctgc tggaaaagga caacgtgaag aaacagctga gtgagaaaca aatcgagaca  1200
ctccataagg agatcgccaa gaaggactgc agctttaccg aactgcagaa cgcctacgag  1260
```

```
cggtggtgcg ccgagaactc cgtggacgcc accaagaaca ttaacagata cttcagcatc  1320
gtcgacctga gaaccaagaa tgactccttc gagaaggaag agatcaatat ccttgatgag  1380
ataaccaacg ccttctctaa gattgacttc gacgatatcc acgatctgca gcaagagaag  1440
gaggccgcca cccctatcaa gaactacctg gacgaggttc aaaacctgta ccaccacctg  1500
aagctggtgg actacagagg tgaggaacga aaggacgcta acttctactc taaactggac  1560
tatatcctga gaaaggacag aaaggactac ctgaacctgg ccgaagtggt gccattgtac  1620
aacaaggtta gaaacttcgt gaccaagaag cctggcgagg tgaaaaagat caagatgatg  1680
ttcgactgca gcagcctgct gggcggatgg ggcacagatt acgagacaaa agaggcccac  1740
attttcatcg actccggcaa gtattacctt ggaatcatca acgagaagtt gtcaaaagat  1800
gacgtggagc tgctgaagaa gagcagcgaa cggatgatca caaaggtgat ctacgatttc  1860
caaaagcccg ataacaagaa tacacctaga ctgttcatca ggagcaaggg cacaaattat  1920
gctcctgctg ttttccaata caatctgcca atagagtctg tgatcgatat ttacgaccgt  1980
ggcctgttta agaccgagta cagaaaaatc aacagcaagg tgtacaagga gagcctgatt  2040
aagatgatcg attacttcaa gatgggcttt gagagacacg agagctacaa gcactacaag  2100
ttttgctgga aggaatctag caagtacaac gacatcggcg aattttacaa ggatgtgatt  2160
aactcttgtt accagctgaa cttcgagaag gtgaactatg agaacctcct gaagttagtg  2220
gaaaacaaca agctgttcct gtttcagatc tacaacaagg attttgccga aaagaaaagc  2280
ggtaagaaga acctgcacac cctgtactgg gagaacctgt tttctgagga gaacctgaag  2340
gacgtttgtc tgaagctgaa tggcgaggcc gagctgttct ggcggaaggc ttctctggac  2400
aagggcaagg tgatcgtgca cagaatgggc tctatcctgg tgaacagaac aacaagcgag  2460
ggcaagtcaa tccctgagga catctaccag gagatctatc agtacaagaa caaaatgaag  2520
gataagatca gcgacgaagc caaaagcctg ctggacagcg gcaccgtgat ctgtaaagaa  2580
gccacccacg acatcaccaa ggacaaacgg ttcacagagg acacctacct gttccactgc  2640
cctatcacca tgaacttcaa ggccaccgac aagaaaaaca aagagttcaa caaccacgtg  2700
ctggaagtgc tgaaagagaa tcccgacgtg aagatcatcg gcctggacag aggcgaacgg  2760
cacctgatct acctgagcct gatcaaccag aagggcgaga tcgagctgca gaaaaccctg  2820
aatctggtgg aacaggtgcg gaacgacaaa accgtgaagg tggactacca ggagaagctg  2880
gtgcataagg aaggcgaccg cgacaaagcc agaaagaact ggcagacaat cggaaacatc  2940
aaggaactga aggagggcta cctgtctgcc gtggtgcacg aaatcgccat gctgatggtg  3000
gaaaacaacg ccatcgtggt gatggaggac ctgaacttcg gcttcaagag aggcagattc  3060
gccgtggaac ggcagatcta ccagaagttc gagaacatgc tgatcgaaaa gctgaactac  3120
ctagtgttca aggacaagaa cgccaccgaa cctggcggcg tgctgaatgc gtatcagctc  3180
accaacaaga gcgccaacgt caccgacgtg tacaaacagt gcggctggct gttctacatc  3240
cccgccgctt atacaagcaa gatcgacccc aagaccggat tcgccaacct gttcatcaca  3300
aagggactga caaacgtgga aaagaagaag gagttcttcg ataagttcga cagcatccgg  3360
tacgacagca aagaggactg ctttgtgttc ggcttcgact acgccaagct gtgcgacaac  3420
gcctccttta gaaagaagtg ggaagtttac accagaggag agaggctggt ctacaacaaa  3480
gacaagcaca aaaacgaacc tatcaacccc accgaggagc tgaagggcat cttcgatgct  3540
tttgatatta actggaacac cgacgacaac ttcattgatt cagtgcagac catccaggcc  3600
gagaaggcca acgccaagtt ctttgacatc ctgctgagaa tgttcaacgc cacactgcag  3660
atgagaaaca gcaagactaa ctcctctgcc agcgaggacg actacctgat cagccctgtc  3720
aaagccgagg atggcacctt cttcgacaca agagaggaat taaagaaggg caaagatgcc  3780
aagctgccga tcgacagcga cgctaatggc gcctaccaca tcgccctgaa aggactgttc  3840
ctgctggaaa atgactttaa ccgggacgag aagggagtga tccaaaatat cagcaacgct  3900
gattggttca agtttgtgca ggagaagaaa tacaaggatt ctagaaagcg gacagcagac  3960
ggctccgaat ttgaaagccc taagaaaaag agaaaggtgg gatccggcaa acctatcccc  4020
aatcccctgc tgggcctgga cagcacctga                                    4050
```

```
SEQ ID NO: 91          moltype = AA  length = 1282
FEATURE                Location/Qualifiers
source                 1..1282
                       mol_type = protein
                       organism = unidentified
SEQUENCE: 91
GKFFETDEFI GQYSINKTLR FELIPQGKTK ELLNNYMNDN SKIKQDILRA DEKNNFKEVI  60
DEYYRELIHD ALTDEDIFSI TPLVKDAYEL YIASRKNTSD SSKKEYRDVK NKIRKEIANI  120
LNKYKTIYGL DKFANIYKSE SDKSVDDDES DNDDLDEKNT TNDDNAKSED KRIYKWLNKK  180
LRLKQISNEE YDRYYKSLNE YHGFTTGLQG LQNNKENMFS SENKSTAIAF RIIDDNMEKY  240
FSNILLLEFI KNKYKDLYEK IEEKANKMNV ECFTKYFTQE GIDEYNQMIG RSIEEEYAKG  300
INQEINLYKQ SKGLNNKEIR TLSPLYKQIL SKTSQNEIIV FKNDKETLEY IKNICDYIIE  360
EDIFGKMNHL IKTNLIDMCT GIYIKRNELS NISFKLYNDW GLLDRIICDY ANEFKTKKEK  420
NEFEKLNKEV ISLNLLNDIF NKYKETRGND TDLKEIVEYF KNVDEKMIED EYSKIKSILN  480
LERIDIDRRV PSKDEEKGGE GFEQICMIKT FLDLLLESIH IYKPLSLIKN GEKVEIYNYN  540
ENFYNEYDIL FSQLDNIINL YNKVRNYFSK KTYSKEKIKI YFSKPTLLNG WDVNKEISNY  600
SIILRKDEEY FLAIMNSDNK IFTNERLEEN CAITENNEEC YEKMVYKQIS DSNKMFSKVF  660
FSEKNKKIYM PSEEIKNIRK NKTHLKVANN KDSQTKWIKF MIECYYKHPE WSKYFDINFK  720
KPEEYESIVE FYNQVNEKIY NIKFVNIKCD YINSMVDSGE LYLFKIYNKD FSKNKKKSGT  780
DNLHTMYWKL LFSKENMNCG VYKLNGQAEV FFRKASLPDK ITHERNKEID NKNPIKDKKT  840
STFTYDLKKD KRFMEDKFFF HCPITINYKG LNAKDKEIRK YNEKINKFIA GNPDINIIGI  900
DRGERHLLYY TIINQKGEIL KQSTLNNVGI EGRDKDYQEL LSNKEKERHL ARKSWGTIGN  960
IKELKEGYLS IVVHELAKLV KEYNAIIVLE NLNAGFKRGR TKVEKQVYQK FELALIKKLN  1020
YLVFKNENIQ NKGGYLKGLQ LTQPFDTFKD IGNQSGIIYY VIPSYTSKIC PTTGFIDVIK  1080
PQYESVEKAK ELFSKFKRIY FDNNKKCFIF EFMYKDFGRD YGLDKIWSIC TLGEKRYYYD  1140
SKNKVSNVIN VTESIISILQ EKNINYINSD NIIDEILQYS DVKLYKELLF NLKVVLQMRY  1200
TKSGTNNEDD FILSPVLDEN DKAFCSLNAK ETEPQNADAN GAYHIAMKGL NAIMSIKNGN  1260
VDRDINNLEN WINFIQKFHI GK                                          1282
```

```
SEQ ID NO: 92          moltype = AA  length = 1283
FEATURE                Location/Qualifiers
```

-continued

```
source                  1..1283
                        mol_type = protein
                        organism = unidentified
SEQUENCE: 92
MGKFFETDEF IGQYSINKTL RFELIPQGKT KELLNNYMND NSKIKQDILR ADEKNNFKEV  60
IDEYYRELIH DALTDEDIFS ITPLVKDAYE LYIASRKNTS DSSKKEYRDV KNKIRKEIAN  120
ILNKYKTIYG LDKFANIYKS ESDKSVDDDE SDNDDLDEKN TTNDDNAKSE DKRIYKWLNK  180
KLRLKQISNE EYDRYYKSLN EYHGFTTGLQ GLQNNKENMF SSENKSTAIA FRIIDDNMEK  240
YFSNILLLEF IKNKYKDLYE KIEEKANKMN VECFTKYFTQ EGIDEYNQMI GRSIEEEYAK  300
GINQEINLYK QSKGLNNKEI RTLSPLYKQI LSKTSQNEII VFKNDKETLE YIKNICDYII  360
EEDIFGKMNH LIKTNLIDMC TGIYIKRNEL SNISFKLYND WGLLDRIICD YANEFKTKKE  420
KNEFEKLNKE VISLNLLNDI FNKYKETRGN DTDLKEIVEY FKNVDEKMIE DEYSKIKSIL  480
NLERIDIDRR VPSKDEEKGG EGFEQICMIK TFLDLLLESI HIYKPLSLIK NGEKVEIYNY  540
NENFYNEYDI LFSQLDNIIN LYNKVRNYFS KKTYSKEKIK IYFSKPTLLN GWDVNKEISN  600
YSIILRKDEE YFLAIMNSDN KIFTNERLEE NCAITENNEE CYEKMVYKQI SDSNKMFSKV  660
FFSEKNKKIY MPSEEIKNIR KNKTHLKVAN NKDSQTKWIK FMIECYYKHP EWSKYFDINF  720
KKPEEYESIV EFYNQVNEKI YNIKFVNIKC DYINSMVDSG ELYLFKIYNK DFSKNKKKSG  780
TDNLHTMYWK LLFSKENMNC GVYKLNGQAE VFFRKASLPD KITHERNKEI DNKNPIKDKK  840
TSTFTYDLKK DKRFMEDKFF FHCPITINYK GLNAKDKEIR KYNEKINKFI AGNPDINIIG  900
IDRGERHLLY YTIINQKGEI LKQSTLNNVG IEGRDKDYQE LLSNKEKERH LARKSWGTIG  960
NIKELKEGYL SIVVHELAKL VKEYNAIIVL ENLNAGFKRG RTKVEKQVYQ KFELALIKKL  1020
NYLVFKNENI QNKGGYLKGL QLTQPFDTFK DIGNQSGIIY YVIPSYTSKI CPTTGFIDVI  1080
KPQYESVEKA KELFSKFKRI YFDNNKKCFI FEFMYKDFGR DYGLDKIWSI CTLGEKRYYY  1140
DSKNKVSNVI NVTESIISIL QEKNINYINS DNIIDEILQY SDVKLYKELL FNLKVVLQMR  1200
YTKSGTNNED DFILSPVLDE NDKAFCSLNA KETEPQNADA NGAYHIAMKG LNAIMSIKNG  1260
NVDRDINNLE NWINFIQKFH IGK                                          1283

SEQ ID NO: 93           moltype = AA  length = 1322
FEATURE                 Location/Qualifiers
source                  1..1322
                        mol_type = protein
                        organism = synthetic construct
SEQUENCE: 93
MGSGGKFFET DEFIGQYSIN KTLRFELIPQ GKTKELLNNY MNDNSKIKQD ILRADEKNNF  60
KEVIDEYYRE LIHDALTDED IFSITPLVKD AYELYIASRK NTSDSSKKEY RDVKNKIRKE  120
IANILNKYKT IYGLDKFANI YKSESDKSVD DDESDNDDLD EKNTTNDDNA KSEDKRIYKW  180
LNKKLRLKQI SNEEYDRYYK SLNEYHGFTT GLQGLQNNKE NMFSSENKST AIAFRIIDDN  240
MEKYFSNILL LEFIKNKYKD LYEKIEEKAN KMNVECFTKY FTQEGIDEYN QMIGRSIEEE  300
YAKGINQEIN LYKQSKGLNN KEIRTLSPLY KQILSKTSQN EIIVFKNDKE TLEYIKNICD  360
YIIEEDIFGK MNHLIKTNLI DMCTGIYIKR NELSNISFKL YNDWGLLDRI ICDYANEFKT  420
KKEKNEFEKL NKEVISLNLL NDIFNKYKET RGNDTDLKEI VEYFKNVDEK MIEDEYSKIK  480
SILNLERIDI DRRVPSKDEE KGGEGFEQIC MIKTFLDLLL ESIHIYKPLS LIKNGEKVEI  540
YNYNENFYNE YDILFSQLDN IINLYNKVRN YFSKKTYSKE KIKIYFSKPT LLNGWDVNKE  600
ISNYSIILRK DEEYFLAIMN SDNKIFTNER LEENCAITEN NEECYEKMVY KQISDSNKMF  660
SKVFFSEKNK KIYMPSEEIK NIRKNKTHLK VANNKDSQTK WIKFMIECYY KHPEWSKYFD  720
INFKKPEEYE SIVEFYNQVN EKIYNIKFVN IKCDYINSMV DSGELYLFKI YNKDFSKNKK  780
KSGTDNLHTM YWKLLFSKEN MNCGVYKLNG QAEVFFRKAS LPDKITHERN KEIDNKNPIK  840
DKKTSTFTYD LKKDKRFMED KFFFHCPITI NYKGLNAKDK EIRKYNEKIN KFIAGNPDIN  900
IIGIDRGERH LLYYTIINQK GEILKQSTLN NVGIEGRDKD YQELLSNKEK ERHLARKSWG  960
TIGNIKELKE GYLSIVVHEL AKLVKEYNAI IVLENLNAGF KRGRTKVEKQ VYQKFELALI  1020
KKLNYLVFKN ENIQNKGGYL KGLQLTQPFD TFKDIGNQSG IIYYVIPSYT SKICPTTGFI  1080
DVIKPQYESV EKAKELFSKF KRIYFDNNKK CFIFEFMYKD FGRDYGLDKI WSICTLGEKR  1140
YYYDSKNKVS NVINVTESII SILQEKNINY INSDNIIDEI LQYSDVKLYK ELLFNLKVVL  1200
QMRYTKSGTN NEDDFILSPV LDENDKAFCS LNAKETEPQN ADANGAYHIA MKGLNAIMSI  1260
KNGNVDRDIN NLENWINFIQ KFHIGKSRKR TADGSEFESP KKKRKVGSGK PIPNPLLGLD  1320
ST                                                                 1322

SEQ ID NO: 94           moltype = DNA  length = 3852
FEATURE                 Location/Qualifiers
source                  1..3852
                        mol_type = unassigned DNA
                        organism = unidentified
SEQUENCE: 94
atgggtaaat tttttgaaac agatgaattt attggacagt attcaataaa taaaacatta  60
cgattcgaat tgataccaca aggtaagaca aaggaattac taaataatta tatgaatgat  120
aacagcaaaa ttaaacagga tattttaaga gcagatgaaa agaataattt taaagaagta  180
attgatgaat attatcgaga gttgattcat gatgctttaa cagatgaaga tattttttcc  240
attacaccat tagtaaagga tgcatatgaa ttatatattg cttctagaaa aaatacttct  300
gatagttcta aaaaagaata tagagatgtt aaaaataaaa ttaggaaaga aatagcaaac  360
attcttaata aatataagac gatttatgga ctagataaat ttgcaaatat atataaatcc  420
gagagtgata aaagtgtaga tgatgatgaa tctgataatg atgatttaga tgagaaaaat  480
actactaatg atgataatgc aaaatcagaa gataaaagga tatacaaatg gctaaataaa  540
aaattaagat taaaacaaat ttctaacgag gaatatgata gatactacaa atctttaaat  600
gaatatcatg gttttacaac aggtctgcaa ggattacaaa ataataaaga aaatatgttc  660
tcttcagaaa acaaaagtac ggcaatagca tttcgaataa tagatgacaa tatggaaaaa  720
tatttttcaa atatactgtt attagaattt attaaaaaca aatataaaga tttatatgaa  780
aaaattgaag aaaaagcaaa taaaatgaat gtggaatgtt ttactaaata ttttacacaa  840
gagggtatag atgaatataa tcaaatgata ggtagaagta tagaagaaga atatgcaaaa  900
ggtataaatc aagaaataaa tctttataaa caatcaaaag gattaaataa taaagaaatt  960
```

-continued aggacattat ctccattgta taagcaaata ttatcaaaga cttcacaaaa tgaaataata 1020
gtattcaaaa atgataaaga aactttagaa tacatcaaga atatatgtga ttatataata 1080
gaagaagata tatttggaaa gatgaatcat ttaattaaaa caaatttgat tgatatgtgt 1140
actggtatat atataaaaag aaatgaatta tcgaatattt catttaaact ttataatgat 1200
tggggattac tagatagaat aatatgtgat tatgcaaatg aatttaagac aaaaaaagaa 1260
aagaacgaat ttgaaaaatt aaataaagaa gtaatttcac ttaatctttt aaatgatata 1320
tttaataaat ataaggaaac aagagggaat gatacagatt taaaagaaat agtagaatat 1380
tttaaaaatg tagatgaaaa aatgatagag gatgaatact ctaaaataaa aagtatttta 1440
aatttagaaa gaatagatat tgatagaaga gtaccaagca aagatgaaga aaaaggtgga 1500
gaaggatttg aacaaatttg tatgataaaa acatttttag atttattgct tgagagtata 1560
catatttaca aaccattaag tttaattaaa aatggagaga aagtggagat atataattat 1620
aatgaaaatt tttacaatga atatgatata ttgttttcac aattagataa tataattaac 1680
ttatataata aagtcagaaa ttatttttct aaaaaaacat attcaaaaga aaaaatcaag 1740
atatattttt ctaagccaac gttattaaat ggatgggatg taaataaaga aatatcaaat 1800
tattcgatta ttttgagaaa agatgaagaa tatttcctag ccataatgaa tagtgataat 1860
aagattttta ctaatgaaag attggaagaa aattgcgcaa ttacagaaaa taatgaagag 1920
tgttatgaaa aaatggtata taaacaaata tccgattcaa ataagatgtt ttcaaaagtg 1980
ttttttttcag aaaaaaacaa aaaaatatat atgccttcag aagaaattaa aaatattaga 2040
aaaaataaaa cacatttgaa agtagcaaat aataaagact cacaaacaaa atggattaaa 2100
tttatgattg aatgctatta taaacatcct gaatggagta aatattttga tataaatttt 2160
aaaaagcctg aagaatatga atcaatagtt gaattttata atcaagtaaa tgaaaaaata 2220
tataatataa aatttgtaaa tattaaatgt gattatataa atagtatggt tgatagtgga 2280
gaattgtatt tgtttaaaat atataataag gatttttcaa aaaataagaa aaaatctgga 2340
acagataatt tacacactat gtattggaaa ttattatttt caaaagaaaa tatgaattgt 2400
ggtgtataca aattaaatgg acaagcagaa gtgtttttta ggaaagcttc tttacctgat 2460
aaaattacac atgaaagaaa taaagaaata gataataaaa atccaataaa agataaaaaa 2520
acaagtacat ttacttatga tttaaagaaa gataaaagat tcatggaaga taaattcttc 2580
tttcattgcc caataacaat aaattataaa ggattaaatg caaaagataa agaaataaga 2640
aaatataatg agaaaataaa caaatttatt gctggtaacc cagatataaa tattatcgga 2700
atagatcgtg gtgaacgaca tttgctatat tatacgataa taaatcaaaa gggtgaaata 2760
ttaaaacagt caacattaaa taatgttggt attgaagggc gtgataaaga ttatcaagaa 2820
ttattatcta ataaagagaa agaacgtcac ttagctagaa aaagttgggg aacaataggt 2880
aatataaaag aacttaaaga aggatattta tcaattgtag tacatgaatt agctaaatta 2940
gtaaaggaat ataatgcaat aattgttcta gaaaatttga atgctggatt taaaagggga 3000
agaactaaag ttgaaaaaca agtatatcaa aaatttgaac ttgcattgat aaagaaactt 3060
aattatttag tatttaaaaa cgaaaatatt caaaataaag gtggttattt aaaaggatta 3120
caattaactc agccatttga tacttttaaa gatattggaa atcaatctgg tataatttat 3180
tatgttattc catcatatac atcgaaaata tgtcctacta caggctttat agatgtaatt 3240
aagccacaat atgaaagtgt tgaaaaagcc aaagaattat tttctaaatt taagcgtata 3300
tatttcgata ataataaaaa atgttttata tttgaattta tgtataaaga ctttggtaga 3360
gattatggtt tagataaaat atggagtata tgtacacttg gagaaaaaag atattattat 3420
gattctaaaa ataaagtatc aaatgtaata aatgtaacag aatcaataat tagtatatta 3480
caagaaaaaa acataaatta tataaattca gacaatatca tagatgaaat tttacaatat 3540
agtgatgtta agttgtataa agaattatta tttaatttaa aagttgtttt acaaatgaga 3600
tatacgaaga gtggtacaaa taatgaagat gattttattc tatcaccagt attagatgaa 3660
aatgataagg cattttgttc acttaatgca aaagaaacag aacctcaaaa tgcagatgca 3720
aacggtgcat atcatattgc tatgaaaggt ttaaatgcaa taatgagcat taagaatggt 3780
aatgtagata gagatattaa caatttagaa aattggataa attttataca aaagtttcat 3840
ataggtaaat aa 3852

SEQ ID NO: 95 moltype = DNA length = 3846
FEATURE Location/Qualifiers
source 1..3846
mol_type = other DNA
organism = synthetic construct
SEQUENCE: 95
ggcaagttct ttgaaaccga cgagttcatc ggacagtaca gtatcaacaa aacactgagg 60
ttcgagctca tccctcaagg caagaccaag gaactgctga acaactatat gaacgacaac 120
agtaagatca agcaggacat cctgcgggcc gacgagaaga acaatttcaa ggaagtgatc 180
gacgagtatt atagagagtt gatccacgac gccctgaccg acgaggacat cttttccatc 240
acccctctcg tcaaggacgc ctacgagctg tacatcgcct ccagaaaaaa caccagcgac 300
tccagcaaga aggagtatcg ggacgtgaaa aataagatta gaaaagagat cgctaacatc 360
ctgaacaagt acaagacaat ctacggcctg gacaagttcg ccaatatcta caagtctgag 420
agcgacaaga gcgttgatga tgacgaatct gataacgatg acttggacga gaagaatacc 480
accaacgacg ataatgccaa gtctgaggac aagcggatct ataagtggct gaataagaag 540
ctgagactga agcagatctc caacgaagaa tacgaccggt actacaagtc cctgaacgaa 600
taccacgggt tcacaacagg actgcagggc ctgcagaaca acaaggaaaa catgttcagc 660
agcgagaaca agagcaccgc catcgccttt agaatcatcg atgacaacat ggaaaagtat 720
ttttctaaca tcctgctcct ggagttcatc aaaaacaagt acaaagatct gtacgagaag 780
atcgaggaga aggccaacaa gatgaacgtg gaatgcttca ccaagtactt cacccaggag 840
ggcatcgacg agtacaatca gatgattggc agaagcattg aggaagaata cgccaagggc 900
atcaaccagg agatcaacct gtataagcag agcaagggtc taaacaataa ggagatcaga 960
acactgagcc ccctgtacaa gcagatcctg tccaagacca gccagaacga aatcatcgtg 1020
ttcaaaaacg acaaggaaac cctggaatac atcaagaata tctgtgatta cattatcgag 1080
gaggacatct tcggaaagat gaaccacctg atcaaaacca acctgatcga catgtgcacc 1140
ggaatctaca ttaagagaaa cgagctgagc aacatctctt tcaagctcta caacgactgg 1200
ggcctgctgg acagaattat ctgtgactac gccaacgagt tcaagacaaa gaaggaaaag 1260
aatgagttcg agaagctgaa caaagaggtg atctctctga acctgctcaa cgatattttc 1320
aacaaataca aggaaaccag aggcaatgat acagacctga aggaaatcgt ggaatacttt 1380

```
aaaaacgtcg acgagaaaat gattgaggac gagtacagca agatcaagag catacttaat  1440
ctggaacgca tcgacatcga ccgtagagtg ccaagcaagg acgaggaaaa gggcggcgaa  1500
ggctttgagc agatctgcat gatcaagacg ttcctggatc tgctgttgga gagcatccac  1560
atctacaagc ctctgtctct gatcaagaac ggcgagaagg tggaaatcta caattataac  1620
gagaacttct acaacgagta cgacatcctg ttcagccagc tggataacat tataaatctg  1680
tacaataagg tgcggaacta cttcagcaag aaaacctaca gcaaagagaa aatcaaaatc  1740
tatttctcca aacccaccct gctgaacgga tgggacgtga acaaggagat cagcaactac  1800
tctatcatcc tgagaaaaga cgaagagtac tttctggcaa ttatgaacag cgacaacaag  1860
atcttcacga atgagaggct ggaagaaaac tgcgccatca ccgagaataa tgaagaatgt  1920
tacgagaaaa tggtgtacaa gcaaatctct gactctaaca agatgttcag caaggtgttt  1980
ttcagcgaga aaaacaagaa gatctacatg cccagcgaag agatcaagaa tatcagaaag  2040
aacaagaccc atctcaaggt ggccaacaat aaggattctc aaacaaagtg gatcaagttc  2100
atgatcgagt gctactataa acaccctgag tggagtaagt acttcgatat caacttcaag  2160
aaacctgaag aatatgaaag catcgtggaa ttttacaacc aggtgaacga gaagatctac  2220
aacatcaagt tcgtgaatat caaatgcgac tacatcaaca gcatggtgga ttcgggagag  2280
ctgtacctgt tcaagatcta caacaaggac ttctctaaga acaagaaaaa aagtggcaca  2340
gataacctgc acaccatgta ttggaagctg ctgtttagca aagaaaacat gaattgcggc  2400
gtgtacaagc tgaacggcca ggccgaggtg ttcttcagaa aggccagcct gcctgataag  2460
atcacacacg aaagaaataa ggagatcgac aacaaaaatc ctatcaagga caagaaaacc  2520
agcaccttca catacgacct gaagaaagat aagcggttca tggaagataa gttcttcttc  2580
cactgcccca taaccatcaa ctacaagggc cttaacgcca aggacaagga gatcagaaag  2640
tacaacgaaa agatcaacaa attcatcgct ggcaaccccg acatcaacat cataggcatc  2700
gaccggggcg aacggcacct gctgtactac accatcatca accagaaggg agagatcctg  2760
aagcaatcta cactgaacaa cgtgggcatc gagggcagag acaaagatta ccaggagctg  2820
ctgagcaaca aggaaaagga aagacacctc gctagaaaga gctggggcac catcggcaac  2880
ataaaagaac tgaaggaagg ctacctgagc atcgtggtgc acgagctggc caagctcgtg  2940
aaggagtaca acgccatcat cgtgctggag aatctgaacg ccggcttcaa gagaggcaga  3000
accaaggtgg aaaaacaggt ctaccagaag tttgagctgg ccctgatcaa gaagctgaac  3060
tacctcgtgt tcaagaacga gaacatccag aacaagggag gctacctgaa gggactgcaa  3120
ctgacacagc ctttcgacac ctttaaggat atcggcaacc agagcggcat catctactac  3180
gtgatcccca gctacacaag caaaatttgt ccaacaaccg gcttcatcga cgtgatcaaa  3240
cctcagtacg agtctgtgga aaaggccaag gagctgttct ccaaattcaa acggatttac  3300
ttcgacaaca acaagaagtg ctttatcttc gaatttatgt acaaagattt cggcagagat  3360
tacggtctgg acaagatctg gagcatctgt accctgggcg agaagagata ctactacgac  3420
agcaagaaca aggtttccaa tgtgatcaac gtgaccgaga gcatcatcag catcctgcag  3480
gagaagaaca tcaactacat caacagcgac aacatcatcg acgagatcct gcagtacagc  3540
gacgtgaagc tgtataagga gctgcttttt aacctgaagg tggtgctgca gatgcggtac  3600
accaagagcg gcaccaataa cgaggacgac ttcattctgt ctcctgtgct ggacgagaac  3660
gacaaggcct tctgcagcct gaacgctaag gaaacagagc ctcagaatgc tgatgctaat  3720
ggcgcctatc atatcgccat gaagggactg aacgccatca tgtccatcaa gaacggcaac  3780
gtggatagag atattaacaa cctggaaaac tggatcaact tcatccagaa attccacatc  3840
gggaag                                                             3846
```

```
SEQ ID NO: 96          moltype = DNA  length = 3969
FEATURE                Location/Qualifiers
source                 1..3969
                       mol_type = other DNA
                       organism = synthetic construct
SEQUENCE: 96
atgggctccg gaggcaagtt ctttgaaacc gacgagttca tcggacagta cagtatcaac  60
aaaacactga ggttcgagct catccctcaa ggcaagacca aggaactgct gaacaactat  120
atgaacgaca acagtaagat caagcaggac atcctgcggg ccgacgagaa gaacaatttc  180
aaggaagtga tcgacgagta ttatagagag ttgatccacg acgccctgac cgacgaggac  240
atcttttcca tcacccctct cgtcaaggac gcctacgagc tgtacatcgc ctccagaaaa  300
aacaccagcg actccagcaa gaaggagtat cgggacgtga aaaataagat tagaaaagag  360
atcgctaaca tcctgaacaa gtacaagaca atctacggcc tggacaagtt cgccaatatc  420
tacaagtctg agagcgacaa gagcgttgat gatgacgaat ctgataacga tgacttggac  480
gagaagaata ccaccaacga cgataatgcc aagtctgagg acaagcggat ctataagtgg  540
ctgaataaga agctgagact gaagcagatc tccaacgaag aatacgaccg gtactacaag  600
tccctgaacg aataccacgg gttcacaaca ggactgcagg gcctgcagaa caacaaggaa  660
aacatgttca gcagcgagaa caagagcacc gccatcgcct ttagaatcat cgatgacaac  720
atggaaaagt atttttctaa catcctgctc ctggagttca tcaaaaacaa gtacaaagat  780
ctgtacgaga agatcgagga gaaggccaac aagatgaacg tggaatgctt caccaagtac  840
ttcacccagg agggcatcga cgagtacaat cagatgattg gcagaagcat tgaggaagaa  900
tacgccaagg gcatcaacca ggagatcaac ctgtataagc agagcaaggg tctaaacaat  960
aaggagatca gaacactgag ccccctgtac aagcagatcc tgtccaagac cagccagaac  1020
gaaatcatcg tgttcaaaaa cgacaaggaa accctggaat acatcaagaa tatctgtgat  1080
tacattatcg aggaggacat cttcggaaag atgaaccacc tgatcaaaac caacctgatc  1140
gacatgtgca ccggaatcta cattaagaga aacgagctga gcaacatctc tttcaagctc  1200
tacaacgact ggggcctgct ggacagaatt atctgtgact acgccaacga gttcaagaca  1260
aagaaggaaa agaatgagtt cgagaagctg aacaaagagg tgatctctct gaacctgctc  1320
aacgatattt tcaacaaata caaggaaacc agaggcaatg atacagacct gaaggaaatc  1380
gtggaatact ttaaaaacgt cgacgagaaa atgattgagg acgagtacag caagatcaag  1440
agcatactta atctggaacg catcgacatc gaccgtagag tgccaagcaa ggacgaggaa  1500
aagggcggcg aaggctttga gcagatctgc atgatcaaga cgttcctgga tctgctgttg  1560
gagagcatcc acatctacaa gcctctgtct ctgatcaaga acggcgagaa ggtggaaatc  1620
tacaattata acgagaactt ctacaacgag tacgacatcc tgttcagcca gctggataac  1680
attataaatc tgtacaataa ggtgcggaac tacttcagca agaaaaccta cagcaaagag  1740
aaaatcaaaa tctatttctc caaacccacc ctgctgaacg gatgggacgt gaacaaggag  1800
```

```
atcagcaact actctatcat cctgagaaaa gacgaagagt actttctggc aattatgaac  1860
agcgacaaca agatcttcac gaatgagagg ctggaagaaa actgcgccat caccgagaat  1920
aatgaagaat gttacgagaa aatggtgtac aagcaaatct ctgactctaa caagatgttc  1980
agcaaggtgt ttttcagcga gaaaaacaag aagatctaca tgcccagcga agagatcaag  2040
aatatcagaa agaacaagac ccatctcaag gtggccaaca ataaggattc tcaaacaaag  2100
tggatcaagt tcatgatcga gtgctactat aaacaccctg agtggagtaa gtacttcgat  2160
atcaacttca agaaacctga agaatatgaa agcatcgtgg aattttacaa ccaggtgaac  2220
gagaagatct acaacatcaa gttcgtgaat atcaaatgcg actacatcaa cagcatggtg  2280
gattcgggag agctgtacct gttcaagatc tacaacaagg acttctctaa gaacaagaaa  2340
aaaagtggca cagataacct gcacaccatg tattggaagc tgctgtttag caaagaaaac  2400
atgaattgcg gcgtgtacaa gctgaacggc caggccgagg tgttcttcag aaaggccagc  2460
ctgcctgata agatcacaca cgaaagaaat aaggagatcg acaacaaaaa tcctatcaag  2520
gacaagaaaa ccagcacctt cacatacgac ctgaagaaag ataagcggtt catggaagat  2580
aagttcttct tccactgccc cataaccatc aactacaagg gccttaacgc caaggacaag  2640
gagatcagaa agtacaacga aaagatcaac aaattcatcg ctggcaaccc cgacatcaac  2700
atcataggca tcgaccgggg cgaacggcac ctgctgtact acaccatcat caaccagaag  2760
ggagagatcc tgaagcaatc tacactgaac aacgtgggca tcgagggcag agacaaagat  2820
taccaggagc tgctgagcaa caaggaaaag gaaagacacc tcgctagaaa gagctggggc  2880
accatcggca acataaaaga actgaaggaa ggctacctga gcatcgtggt gcacgagctg  2940
gccaagctcg tgaaggagta caacgccatc atcgtgctgg agaatctgaa cgccggcttc  3000
aagagaggca gaaccaaggt ggaaaaacag gtctaccaga agtttgagct ggccctgatc  3060
aagaagctga actacctcgt gttcaagaac gagaacatcc agaacaaggg aggctacctg  3120
aagggactgc aactgacaca gcctttcgac acctttaagg atatcggcaa ccagagcggc  3180
atcatctact acgtgatccc cagctacaca agcaaaattt gtccaacaac cggcttcatc  3240
gacgtgatca aacctcagta cgagtctgtg gaaaaggcca aggagctgtt ctccaaattc  3300
aaacggattt acttcgacaa caacaagaag tgctttatct tcgaatttat gtacaaagat  3360
ttcggcagag attacggtct ggacaagatc tggagcatct gtaccctggg cgagaagaga  3420
tactactacg acagcaagaa caaggtttcc aatgtgatca acgtgaccga gagcatcatc  3480
agcatcctgc aggagaagaa catcaactac atcaacagcg acaacatcat cgacgagatc  3540
ctgcagtaca gcgacgtgaa gctgtataag gagctgcttt ttaacctgaa ggtggtgctg  3600
cagatgcggt acaccaagag cggcaccaat aacgaggacg acttcattct gtctcctgtg  3660
ctggacgaga acgacaaggc cttctgcagc ctgaacgcta aggaaacaga gcctcagaat  3720
gctgatgcta atggcgccta tcatatcgcc atgaagggac tgaacgccat catgtccatc  3780
aagaacggca acgtggatag agatattaac aacctggaaa actggatcaa cttcatccag  3840
aaattccaca tcgggaagtc tagaaagcgg acagcagacg gctccgaatt tgaaagccct  3900
aagaaaaaga gaaaggtggg atccggcaaa cctatcccca atcccctgct gggcctggac  3960
agcacctga                                                          3969
```

```
SEQ ID NO: 97          moltype = AA  length = 1234
FEATURE                Location/Qualifiers
source                 1..1234
                       mol_type = protein
                       organism = unidentified
SEQUENCE: 97
EFDNSFVNRY PLSKTLSFSL LPVGSTEANF EKKLLLQEDE KRAAEYILVK SYIDRYHKAY  60
IESVLSKVVL DGINNYAQLY CKNNKTEQDI KRLEQLEGSF RKQISKSLKS DARYKLIYKK  120
EMLEKLLPEF LDNEEEKARV ISFENFTTYF TGFHTNRENM YTDEAKSTAV SFRCINDNLP  180
KFLDNISVFK WVTAFLSESD INELKADFSG LLGCSLEEMF TPDYFSFVLS QSGIERYNNV  240
IGGYTCSDGE KVKGLNEYIN LYNQKLQHGE KKLPLLKRLF KQILSDTESV SFIPEKLEND  300
DAVISAINGF CNIKIENETF FEILDKTKCL FSNLNEFDSA GVYITNGFAV TDISNAVFGT  360
WDVISEAWKK EYAKAIPLKN IAKADAYYEK QGKAYKAIKS FSVSELQRLA NTTEGKAAYK  420
HNGDISAYFS ETVCFAVQDI FEKYSSSKAL FASPYKNEKR LFKNNEAIAL IKDFLDSIKN  480
LEKLIKPFNG SGRENDKDES FYGEFTACYE RLSKIDLLYD KVRNYMTQKP YSGDKIKLNF  540
ENPQFLNGWD RNKERDYRTV LLRKGGYYYL AIMDKSNNRI FEDLPEPKNG EDCYEKIDYK  600
LLPGPNKMLP KVFFAASNID YFAPSEQILK IRQKETFKKG VNFNIDDCHA FIDFLKESIE  660
KHDEWCKYGF EFKDTSDYNN IGEFYKDVRE QGYSISFRNV PESYINSCVN SGSLYLFQIY  720
NKDFSPYSKG TKSLHTLYFE MLFDERNLKN VVYQLNGGAE MFYRKASIKE RDKIVHPANI  780
PIKNKNPDNP KAESVFEYDI IKDRRFTERQ FSLHIPVTLN FKGSGGSANL NADVRRAIRG  840
ADENYVIGID RGERNLLYIT VINSKGEIVE QIPGNVIING KQVVDYHKLL DAKEKERLAA  900
RQNWTTVENI KELKEGYLSV IIHNICELVK KYNAVIAMED LSSGFKNSRV KVEKQVYQKF  960
EKMLTEKLNF LVDKKADVQS RGGLLQAYQL TNSTKDYKRA GSQDGIVFYV PAWLTSKIDP  1020
VTGFVDLLKP KYTSVQEAKE LFSNFEAVEY IPEEDLFSFT FDYSKFPRCS VAYRNKWTVY  1080
SNGERIYTFR DKNSNNEYVS KTVALTTEFK SLFDEYSVYY RDNLKSQILC QDKVDFFKQL  1140
IRLLSLTMQM RNSISNSAVD YLISPVKDKN GNFFDSRKSI KNLPENADAN GAYNIAKKAL  1200
WAIGQIKEAD ENDLMKVKLS VSNKEWLKYV QEVE                              1234
```

```
SEQ ID NO: 98          moltype = AA  length = 1235
FEATURE                Location/Qualifiers
source                 1..1235
                       mol_type = protein
                       organism = unidentified
SEQUENCE: 98
MEFDNSFVNR YPLSKTLSFS LLPVGSTEAN FEKKLLLQED EKRAAEYILV KSYIDRYHKA  60
YIESVLSKVV LDGINNYAQL YCKNNKTEQD IKRLEQLEGS FRKQISKSLK SDARYKLIYK  120
KEMLEKLLPE FLDNEEEKAR VISFENFTTY FTGFHTNREN MYTDEAKSTA VSFRCINDNL  180
PKFLDNISVF KWVTAFLSES DINELKADFS GLLGCSLEEM FTPDYFSFVL SQSGIERYNN  240
VIGGYTCSDG EKVKGLNEYI NLYNQKLQHG EKKLPLLKRL FKQILSDTES VSFIPEKLEN  300
DDAVISAING FCNIKIENET FFEILDKTKC LFSNLNEFDS AGVYITNGFA VTDISNAVFG  360
TWDVISEAWK KEYAKAIPLK NIAKADAYYE KQGKAYKAIK SFSVSELQRL ANTTEGKAAY  420
```

-continued

KHNGDISAYF SETVCFAVQD IFEKYSSSKA LFASPYKNEK RLFKNNEAIA LIKDFLDSIK 480
NLEKLIKPFN GSGRENDKDE SFYGEFTACY ERLSKIDLLY DKVRNYMTQK PYSGDKIKLN 540
FENPQFLNGW DRNKERDYRT VLLRKGGYYY LAIMDKSNNR IFEDLPEPKN GEDCYEKIDY 600
KLLPGPNKML PKVFFAASNI DYFAPSEQIL KIRQKETFKK GVNFNIDDCH AFIDFLKESI 660
EKHDEWCKYG FEFKDTSDYN NIGEFYKDVR EQGYSISFRN VPESYINSCV NSGSLYLFQI 720
YNKDFSPYSK GTKSLHTLYF EMLFDERNLK NVVYQLNGGA EMFYRKASIK ERDKIVHPAN 780
IPIKNKNPDN PKAESVFEYD IIKDRRFTER QFSLHIPVTL NFKGSGGSAN LNADVRRAIR 840
GADENYVIGI DRGERNLLYI TVINSKGEIV EQIPGNVIIN GKQVVDYHKL LDAKEKERLA 900
ARQNWTTVEN IKELKEGYLS VIIHNICELV KKYNAVIAME DLSSGFKNSR VKVEKQVYQK 960
FEKMLTEKLN FLVDKKADVQ SRGGLLQAYQ LTNSTKDYKR AGSQDGIVFY VPAWLTSKID 1020
PVTGFVDLLK PKYTSVQEAK ELFSNFEAVE YIPEEDLFSF TFDYSKFPRC SVAYRNKWTV 1080
YSNGERIYTF RDKNSNNEYV SKTVALTTEF KSLFDEYSVY YRDNLKSQIL CQDKVDFFKQ 1140
LIRLLSLTMQ MRNSISNSAV DYLISPVKDK NGNFFDSRKS IKNLPENADA NGAYNIAKKA 1200
LWAIGQIKEA DENDLMKVKL SVSNKEWLKY VQEVE 1235

SEQ ID NO: 99 moltype = AA length = 1274
FEATURE Location/Qualifiers
source 1..1274
mol_type = protein
organism = synthetic construct
SEQUENCE: 99
MGSGEFDNSF VNRYPLSKTL SFSLLPVGST EANFEKKLLL QEDEKRAAEY ILVKSYIDRY 60
HKAYIESVLS KVVLDGINNY AQLYCKNNKT EQDIKRLEQL EGSFRKQISK SLKSDARYKL 120
IYKKEMLEKL LPEFLDNEEE KARVISFENF TTYFTGFHTN RENMYTDEAK STAVSFRCIN 180
DNLPKFLDNI SVFKWVTAFL SESDINELKA DFSGLLGCSL EEMFTPDYFS FVLSQSGIER 240
YNNVIGGYTC SDGEKVKGLN EYINLYNQKL QHGEKKLPLL KRLFKQILSD TESVSFIPEK 300
LENDDAVISA INGFCNIKIE NETFFEILDK TKCLFSNLNE FDSAGVYITN GFAVTDISNA 360
VFGTWDVISE AWKKEYAKAI PLKNIAKADA YYEKQGKAYK AIKSFSVSEL QRLANTTEGK 420
AAYKHNGDIS AYFSETVCFA VQDIFEKYSS SKALFASPYK NEKRLFKNNE AIALIKDFLD 480
SIKNLEKLIK PFNGSGREND KDESFYGEFT ACYERLSKID LLYDKVRNYM TQKPYSGDKI 540
KLNFENPQFL NGWDRNKERD YRTVLLRKGG YYYLAIMDKS NNRIFEDLPE PKNGEDCYEK 600
IDYKLLPGPN KMLPKVFFAA SNIDYFAPSE QILKIRQKET FKKGVNFNID DCHAFIDFLK 660
ESIEKHDEWC KYGFEFKDTS DYNNIGEFYK DVREQGYSIS FRNVPESYIN SCVNSGSLYL 720
FQIYNKDFSP YSKGTKSLHT LYFEMLFDER NLKNVVYQLN GGAEMFYRKA SIKERDKIVH 780
PANIPIKNKN PDNPKAESVF EYDIIKDRRF TERQFSLHIP VTLNFKGSGG SANLNADVRR 840
AIRGADENYV IGIDRGERNL LYITVINSKG EIVEQIPGNV IINGKQVVDY HKLLDAKEKE 900
RLAARQNWTT VENIKELKEG YLSVIIHNIC ELVKKYNAVI AMEDLSSGFK NSRVKVEKQV 960
YQKFEKMLTE KLNFLVDKKA DVQSRGGLLQ AYQLTNSTKD YKRAGSQDGI VFYVPAWLTS 1020
KIDPVTGFVD LLKPKYTSVQ EAKELFSNFE AVEYIPEEDL FSFTFDYSKF PRCSVAYRNK 1080
WTVYSNGERI YTFRDKNSNN EYVSKTVALT TEFKSLFDEY SVYYRDNLKS QILCQDKVDF 1140
FKQLIRLLSL TMQMRNSISN SAVDYLISPV KDKNGNFFDS RKSIKNLPEN ADANGAYNIA 1200
KKALWAIGQI KEADENDLMK VKLSVSNKEW LKYVQEVESR KRTADGSEFE SPKKKRKVGS 1260
GKPIPNPLLG LDST 1274

SEQ ID NO: 100 moltype = DNA length = 3708
FEATURE Location/Qualifiers
source 1..3708
mol_type = unassigned DNA
organism = unidentified
SEQUENCE: 100
atggaattcg acaatagctt tgttaaccga taccctttat caaaaacact aagcttcagt 60
ttgcttcctg ttggcagtac cgaagcaaat tttgagaaaa aactgttgct gcaggaggac 120
gaaaaaagag ccgcggaata tattttggtg aagtcataca ttgacagata ccataaagcc 180
tatattgaat cggttttatc aaaggttgtg cttgacggca taaataacta tgcacagctg 240
tactgcaaga acaacaaaac cgaacaggat atcaaacgac tggagcagct tgaaggttca 300
tttagaaagc agatttcaaa gagcttgaaa tccgatgccc gttataagtt gatttataaa 360
aaagaaatgc ttgaaaagct tttgcctgag tttcttgata atgaagaaga aaaggcgagg 420
gtaatatctt ttgaaaactt tacaacatat ttcacaggct ttcataccaa tagagaaaat 480
atgtataccg acgaagcaaa atccactgcg gtgtccttca gatgtataaa tgataattta 540
ccaaaatttc ttgataatat ttcagttttt aaatgggtta cggcattttt gagcgaaagt 600
gatatcaacg aattaaaggc ggatttttca ggtctgttag gttgttcgct tgaagaaatg 660
tttacaccgg attatttttc ctttgtgtta tctcaaagcg ggatagaaag atataacaat 720
gttatcggcg gttacacatg ttctgacggt gaaaaagtta agggactaaa tgaatacata 780
aatttataca accaaaagtt acaacacggt gaaaaaaagc tcccgctttt aaaacgcttg 840
ttcaagcaga tattgagtga taccgaaagt gtatccttta ttccggaaaa gcttgaaaac 900
gacgatgctg ttatttctgc gataaacgga ttttgtaata tcaaaattga aaacgaaaca 960
ttctttgaaa ttcttgataa aactaaatgc ttgttttcaa atttaaatga gtttgacagc 1020
gccggtgtat atattaccaa cggttttgct gtaaccgata tttcaaatgc tgttttcggt 1080
acttgggatg ttatttcgga agcgtggaaa aaggagtatg cgaaagcaat cccgcttaaa 1140
aatatcgcca aggcagatgc atattacgaa aagcagggca aggcgtataa ggcaattaaa 1200
agcttttcgg taagcgagct tcaaaggctg gccaacacaa cagaagggaa ggcggcatat 1260
aagcacaacg gagatatttc tgcatatttt tcggaaactg tttgctttgc ggttcaagat 1320
atatttgaaa aatacagtag ttcaaaagcc ctttttgcgt cgccctataa aaatgaaaag 1380
cggctcttca aaaacaatga ggctatagcg ctgattaagg atttcttgga cagcatcaaa 1440
aatctggaaa agcttattaa accatttaac ggctccggta gagaaaacga taaggacgaa 1500
agcttctacg gtgaatttac cgcttgctac gagaggcttt ctaaaattga cctgctatat 1560
gataaggttc gcaactatat gacacaaaaa ccttattccg ggacaagat aaagttgaat 1620
tttgaaaatc cgcaatttct aaatggttgg gacaggaaca aagagcggga ttacagaact 1680
gttctcttaa gaaaaggcgg gtattactac cttgctatta tggataaaag caacaacagg 1740

```
atttttgaag atttgccgga gcccaaaaac ggcgaggatt gttatgaaaa aatagactac  1800
aagcttctgc cgggaccgaa taagatgttg ccaaaggtgt tttttgccgc gagcaatatt  1860
gattattttg caccctctga gcaaattttg aaaattagac agaaagaaac ctttaagaag  1920
ggtgtgaatt ttaatattga tgattgccat gctttcatag acttccttaa agagtctata  1980
gaaaaacacg atgagtggtg caagtatggg ttcgaattta aagatacttc agattataac  2040
aacatcggtg aattttataa agatgtaagg gagcagggct attctatcag ctttagaaat  2100
gtgcctgagt cttatataaa ttcttgcgtt aattccggtt cactttacct tttccaaatc  2160
tacaacaagg atttttcacc ttacagcaaa gggaccaaga gtttgcacac attgtatttt  2220
gaaatgcttt ttgatgaaag gaaccttaag aatgttgttt atcagcttaa cggcggtgca  2280
gagatgtttt accgcaaagc aagtattaag gaaagggata aaatagtaca ccctgctaat  2340
attccgataa aaaataaaaa tcccgataac ccaaaagctg aaagtgtttt tgagtatgac  2400
atcataaagg acagacgctt tactgaaaga cagttctctt tgcatattcc tgttacgctc  2460
aattttaaag gctcgggcgg ctctgcaaat cttaatgctg atgtgcgcag agccataaga  2520
ggcgctgatg aaaactatgt tataggtata gacagaggag aaagaaattt gctttacatc  2580
accgtaataa acagtaaagg tgaaattgtt gagcagattc cgggcaatgt aataatcaac  2640
ggaaaacaag tggtcgatta tcacaagctg cttgatgcca aagaaaaaga gcgtcttgca  2700
gcacggcaaa actggacaac ggttgaaaat atcaaggagc ttaaagaggg ctatttgagc  2760
gtaatcatac acaatatttg tgaacttgta aaaaaataca atgctgttat tgctatggag  2820
gatctttctt ccggttttaa aaacagcagg gttaaagtag aaaaacaggt ttatcagaaa  2880
tttgaaaaaa tgcttaccga aaagcttaat ttttcttgttg ataaaaaagc tgatgttcaa  2940
agcaggggag gacttctgca ggcatatcag ttaacaaaca gcaccaagga ttataagcgg  3000
gcaggctcac aagacggtat tgttttctat gttccggcgt ggcttacaag caaaatcgat  3060
cccgttacgg gttttgttga tttgcttaag cctaagtata caagtgtgca ggaagcaaag  3120
gagctgtttt caaattttga agctgttgaa tatatccctg aggaggattt gttcagcttt  3180
acttttgatt attcgaaatt tccccgttgc tccgtagctt accgtaacaa atggactgta  3240
tactcaaacg gcgaaagaat ttatacattc agggataaaa acagcaataa tgaatatgtt  3300
agcaaaacag ttgctcttac aacggagttt aaatccttgt ttgacgaata cagcgtttat  3360
taccgcgata accttaaatc gcagattcta tgtcaagata aagtcgattt cttcaaacag  3420
ctaattcggt tactgtcttt gacaatgcaa atgcgaaaca gtatttcaaa ttcagcagta  3480
gattatctga tttctccggt taaggataaa aacggaaatt tctttgacag ccggaaaagt  3540
ataaaaaatc ttccggaaaa tgcagatgct aacggtgctt acaacattgc caaaaaggct  3600
ctttgggcaa tcgggcaaat aaaggaagcg gatgagaatg atttaatgaa ggtcaagctg  3660
tctgtttcaa acaaggaatg gcttaaatat gtgcaggagg tagaatga              3708
```

```
SEQ ID NO: 101          moltype = DNA  length = 3702
FEATURE                 Location/Qualifiers
source                  1..3702
                        mol_type = other DNA
                        organism = synthetic construct
SEQUENCE: 101
gaatttgata actctttcgt gaatagatat cctctgagca agaccctgag cttcagtctg  60
ctgccagtgg gcagcaccga agccaacttc gaaaaaaagc tgctgctgca ggaggacgaa  120
aagagagccg ccgagtacat cctggtgaaa agctacatcg acagatacca caaggcctac  180
atcgagagcg tgctgagcaa ggtggtgctg gacggcatca acaactatgc ccagctgtac  240
tgcaagaaca acaagaccga acaggacatc aagcggctgg agcagctgga gggcagcttc  300
agaaagcaga tctctaaaag cctgaagtcc gacgccagat acaagctgat ctacaaaaag  360
gagatgctgg aaaagctcct gcctgagttc ctggacaacg aggaagaaaa ggctagagtg  420
atcagcttcg agaactttac aacctacttc actggcttcc acaccaaccg ggaaaacatg  480
tacaccgatg aggccaagtc tacggccgtt tcctttaggt gtatcaacga taacctgcca  540
aagttcctgg acaacatcag cgtattcaag tgggtcaccg cctttctgag cgagtctgac  600
atcaacgaac tgaaggccga tttcagcggc ctgttgggct gctccctgga agagatgttc  660
acccctgatt acttcagctt cgtgctgtct cagagcggca tcgagagata caacaacgtg  720
atcggcggat acacctgtag cgatggcgag aaagtcaaag gacttaatga gtacatcaac  780
ctgtataacc agaagctgca acacggcgaa aagaaactgc ccctgctcaa gcggctgttc  840
aagcagattc tgtcagacac cgagagcgtg tccttcatcc ccgagaaact ggaaaatgat  900
gacgccgtga tctccgccat taacggattt tgtaatatca agatcgagaa tgaaacattc  960
ttcgagatcc tggacaagac caagtgcctg ttcagcaatc tgaacgagtt cgactctgcc  1020
ggagtgtaca tcaccaacgg cttcgcagtg acagacatca gcaacgccgt gttcggcacc  1080
tgggacgtca tcagcgaagc ctggaagaaa gagtacgcca aagctatccc cctgaagaac  1140
atcgctaagg ccgacgccta ctatgagaag cagggcaagg cctacaaggc catcaagagc  1200
ttctctgtaa gcgaactgca gagactggcc aacaccacgg agggaaaggc cgcctacaag  1260
cacaacggcg acatcagcgc ctatttcagc gagacagtct gcttcgctgt gcaggatatc  1320
ttcgagaagt atagcagcag caaggccctg ttcgccagcc cctataagaa cgagaagcgg  1380
ctgttcaaga acaatgaggc aatcgctctg attaaggact tcctggatag catcaagaac  1440
ctggagaagc tgattaagcc attcaacggc agcggcagag agaacgacaa ggacgagagc  1500
ttttacggcg agttcaccgc ctgctacgag cggctgagca aaatcgatct gctgtacgac  1560
aaggtgcgga actacatgac acagaaacct tacagcggcg ataagatcaa gctgaacttc  1620
gagaatcctc agttcctgaa cggatgggat agaaacaagg agcgggatta cagaacagtg  1680
ctgctgagaa agggaggtta ttactacctg gccatcatgg acaagagcaa caaccggatc  1740
ttcgaggatc tgcctgagcc taagaatggt gaggactgct acgaaaaaat cgattacaag  1800
ctgctgcctg gccctaacaa gatgctgccc aaagtgttct tcgccgctag taacatcgac  1860
tacttcgccc ctagcgaaca gatcctcaaa atccggcaga aggaaacctt caaaaagggc  1920
gtgaacttca acattgacga ctgtcacgcc ttcatcgact tcctgaagga atctatcgag  1980
aagcacgacg agtggtgcaa gtacggcttc gagtttaagg acaccagcga ctacaacaat  2040
ataggcgagt tctacaagga cgtgcgggaa cagggctaca gcatctcttt tcggaatgtg  2100
cccgagtcct acatcaacag ctgcgtgaac tctggctctc tgtacctgtt tcagatctac  2160
aacaaagatt ttagccctta ctctaagggc acaaagagcc tgcacaccct gtactttgaa  2220
atgctgtttg acgagcgcaa cctgaagaac gtggtgtatc agctgaatgg tggcgctgag  2280
atgttctaca gaaaggccag catcaaggaa agagacaaga tcgtgcaccc cgccaacatc  2340
```

```
cctatcaaga acaagaaccc cgacaaccct aaggccgaga gcgtgttcga atacgacatt  2400
atcaaggaca gaagattcac cgaacggcag ttctccctgc acatccctgt gaccctgaac  2460
ttcaaaggct ctggcggatc tgccaacctg aacgccgacg ttaggcgggc tatcagaggc  2520
gccgatgaga actacgtgat cggcatcgac cggggcgaga ggaacctgct gtacatcaca  2580
gtgatcaata gcaagggcga gatcgtggaa caaatcccag gcaacgtgat catcaacggc  2640
aagcaagtgg tggactacca caagctgctg gatgctaaag agaaggaaag actggctgcc  2700
agacagaact ggacaacagt tgaaaacatc aaggaactga aggaaggcta cctgtccgtg  2760
atcatccaca acatctgcga gctggtgaaa aagtacaacg ctgtgatcgc tatggaggac  2820
ctgagcagcg gcttcaagaa cagccgcgtg aaggtggaaa agcaggtata ccagaagttc  2880
gaaaaaatgc tgaccgagaa actgaacttc ctggtggaca agaaagccga tgtgcaaagc  2940
agaggcggcc tgctgcaggc ctaccagctg acaaatagca caaaggatta caagcgggcc  3000
ggcagccaag acggcatcgt gttctacgtg cctgcctggc tgacaagcaa aattgaccct  3060
gtgaccggct ttgtggacct gctgaaacct aaatacacca gcgttcagga ggccaaagag  3120
ctgttcagca acttcgaggc cgtcgagtac atccccgagg aggacctgtt cagcttcacc  3180
ttcgactaca gcaagttccc cagatgcagc gtggcctaca gaaacaagtg gaccgtgtac  3240
agtaacggag agagaatcta cacattcaga gataagaaca gcaacaacga atacgtgtcc  3300
aagacagttg ccctgaccac cgagtttaaa agcctcttcg acgaatatag cgtgtactac  3360
cgagacaacc tgaagagtca gattttgtgc caggataagg tggatttctt caagcaactt  3420
atcagactgc tgtccctgac catgcagatg agaaacagca tcagcaacag cgccgtggac  3480
tacctgatct cccctgtgaa ggataagaat ggcaattttt tcgacagcag aaaagagcatc  3540
aagaacctgc ctgagaacgc cgacgccaac ggcgcctaca acattgctaa gaaggctctg  3600
tgggccatcg gtcagatcaa agaggctgat gagaatgacc tgatgaaggt gaagctgtcc  3660
gtgtctaata aagagtggct gaagtacgtg caggaggtgg aa                    3702
```

```
SEQ ID NO: 102         moltype = DNA  length = 3825
FEATURE                Location/Qualifiers
source                 1..3825
                       mol_type = other DNA
                       organism = synthetic construct
SEQUENCE: 102
atgggctccg gagaatttga taactctttc gtgaatagat atcctctgag caagaccctg  60
agcttcagtc tgctgccagt gggcagcacc gaagccaact tcgaaaaaaa gctgctgctg  120
caggaggacg aaaagagagc cgccgagtac atcctggtga aagctacat cgacagatac  180
cacaaggcct acatcgagag cgtgctgagc aaggtggtgc tggacggcat caacaactat  240
gcccagctgt actgcaagaa caacaagacc gaacaggaca tcaagcggct ggagcagctg  300
gagggcagct tcagaaagca gatctctaaa agcctgaagt ccgacgccag atacaagctg  360
atctacaaaa aggagatgct ggaaaagctc ctgcctgagt tcctggacaa cgaggaagaa  420
aaggctagag tgatcagctt cgagaacttt acaacctact tcactggctt ccacaccaac  480
cgggaaaaca tgtacaccga tgaggccaag tctacggccg tttcctttag gtgtatcaac  540
gataacctgc caaagttcct ggacaacatc agcgtattca agtgggtcac cgcctttctg  600
agcgagtctg acatcaacga actgaaggcc gatttcagcg gcctgttggg ctgctccctg  660
gaagagatgt tcacccctga ttacttcagc ttcgtgctgt ctcagagcgg catcgagaga  720
tacaacaacg tgatcggcgg atacacctgt agcgatggcg agaaagtcaa aggacttaat  780
gagtacatca acctgtataa ccagaagctg caacacggcg aaaagaaact gcccctgctc  840
aagcggctgt tcaagcagat tctgtcagac accgagagcg tgtccttcat ccccgagaaa  900
ctggaaaatg atgacgccgt gatctccgcc attaacggat tttgtaatat caagatcgag  960
aatgaaacat tcttcgagat cctggacaag accaagtgcc tgttcagcaa tctgaacgag  1020
ttcgactctg ccggagtgta catcaccaac ggcttcgcag tgacagacat cagcaacgcc  1080
gtgttcggca cctgggacgt catcagcgaa gcctggaaga aagagtacgc caaagctatc  1140
cccctgaaga acatcgctaa ggccgacgcc tactatgaga agcagggcaa ggcctacaag  1200
gccatcaaga gcttctctgt aagcgaactg cagagactgg ccaacaccac ggagggaaag  1260
gccgcctaca agcacaacgg cgacatcagc gcctatttca gcgagacagt ctgcttcgct  1320
gtgcaggata tcttcgagaa gtatagcagc agcaaggccc tgttcgccag cccctataag  1380
aacgagaagc ggctgttcaa gaacaatgag gcaatcgctc tgattaagga cttcctggat  1440
agcatcaaga acctggagaa gctgattaag ccattcaacg gcagcggcag agagaacgac  1500
aaggacgaga gcttttacgg cgagttcacc gcctgctacg agcggctgag caaaatcgat  1560
ctgctgtacg acaaggtgcg gaactacatg acacagaaac cttacagcgg cgataagatc  1620
aagctgaact tcgagaatcc tcagttcctg aacggatggg atagaaacaa ggagcgggat  1680
tacagaacag tgctgctgag aaagggaggt tattactacc tggccatcat ggacaagagc  1740
aacaaccgga tcttcgagga tctgcctgag cctaagaatg gtgaggactg ctacgaaaaa  1800
atcgattaca agctgctgcc tggccctaac aagatgctgc ccaaagtgtt cttcgccgct  1860
agtaacatcg actacttcgc ccctagcgaa cagatcctca aaatccggca gaaggaaacc  1920
ttcaaaaagg gcgtgaactt caacattgac gactgtcacg ccttcatcga cttcctgaag  1980
gaatctatcg agaagcacga cgagtggtgc aagtacggct tcgagtttaa ggacaccagc  2040
gactacaaca atataggcga gttctacaag gacgtgcggg aacagggcta cagcatctct  2100
tttcggaatg tgcccgagtc ctacatcaac agctgcgtga actctggctc tctgtacctg  2160
tttcagatct acaacaaaga ttttagccct tactctaagg gcacaaagag cctgcacacc  2220
ctgtactttg aaatgctgtt tgacgagcgc aacctgaaga acgtggtgta tcagctgaat  2280
ggtggcgctg agatgttcta cagaaaggcc agcatcaagg aaagagacaa gatcgtgcac  2340
cccgccaaca tccctatcaa gaacaagaac cccgacaacc ctaaggccga gagcgtgttc  2400
gaatacgaca ttatcaagga cagaagattc accgaacggc agttctccct gcacatccct  2460
gtgaccctga acttcaaagg ctctggcgga tctgccaacc tgaacgccga cgttaggcgg  2520
gctatcagag gcgccgatga gaactacgtg atcggcatcg accggggcga gaggaacctg  2580
ctgtacatca cagtgatcaa tagcaagggc gagatcgtgg aacaaatccc aggcaacgtg  2640
atcatcaacg gcaagcaagt ggtggactac cacaagctgc tggatgctaa agagaaggaa  2700
agactggctg ccagacagaa ctggacaaca gttgaaaaca tcaaggaact gaaggaaggc  2760
tacctgtccg tgatcatcca caacatctgc gagctggtga aaaagtacaa cgctgtgatc  2820
gctatggagg acctgagcag cggcttcaag aacagccgcg tgaaggtgga aaagcaggta  2880
taccagaagt tcgaaaaaat gctgaccgag aaactgaact tcctggtgga caagaaagcc  2940
```

```
gatgtgcaaa gcagaggcgg cctgctgcag gcctaccagc tgacaaatag cacaaaggat  3000
tacaagcggg ccggcagcca agacggcatc gtgttctacg tgcctgcctg gctgacaagc  3060
aaaattgacc ctgtgaccgg ctttgtggac ctgctgaaac ctaaatacac cagcgttcag  3120
gaggccaaag agctgttcag caacttcgag gccgtcgagt acatccccga ggaggacctg  3180
ttcagcttca ccttcgacta cagcaagttc cccagatgca gcgtggccta cagaaacaag  3240
tggaccgtgt acagtaacgg agagagaatc tacacattca gagataagaa cagcaacaac  3300
gaatacgtgt ccaagacagt tgccctgacc accgagttta aaagcctctt cgacgaatat  3360
agcgtgtact accgagacaa cctgaagagt cagattttgt gccaggataa ggtggatttc  3420
ttcaagcaac ttatcagact gctgtccctg accatgcaga tgagaaacag catcagcaac  3480
agcgccgtgg actacctgat ctcccctgtg aaggataaga atggcaattt tttcgacagc  3540
agaaagagca tcaagaacct gcctgagaac gccgacgcca acggcgccta caacattgct  3600
aagaaggctc tgtgggccat cggtcagatc aaagaggctg atgagaatga cctgatgaag  3660
gtgaagctgt ccgtgtctaa taaagagtgg ctgaagtacg tgcaggaggt ggaatctaga  3720
aagcggacag cagacggctc cgaatttgaa agccctaaga aaaagagaaa ggtgggatcc  3780
ggcaaaccta tccccaatcc cctgctgggc ctggacagca cctga                  3825
```

```
SEQ ID NO: 103          moltype = AA  length = 1242
FEATURE                 Location/Qualifiers
source                  1..1242
                        mol_type = protein
                        organism = unidentified
SEQUENCE: 103
KAETNLTELV NLYSLQKTLR FELIPQGKTL ENIEKNGILT QDNQRADDYE KVKKLIDEYH  60
KHHIEISLDD CRLEGLEEYK ELYEKKDDLK KIQENLRKQI VKSLTENERY KDKRLFSDKL  120
FKEDLPNYLK DREQDKALVK KFEKFTTYFT GFNENRKNMY SSEDKPTSIA YRLIHENLPK  180
FIDNLHIFDK IKETTIKDDF DKIVEKLNKH LKIHIKSFDE IFSIEYFNKT LSQKQIDNYN  240
NIIGGMSFEN GTKIQGLNEY INRYNQKQED KHQKLPCVKT LYKQILSDRE KISWIPEQFD  300
DDKQMAESIS NLYNEMLPII KDDLLPLMAN IGDYDLSKIF ISNDSALTTI SQRIFGAYNV  360
YTLAIIEKLK SDKPKSKRQS ESKYLDEIDK NFKNMKSFSI AKLNNAVKGK YDKTIENYIK  420
VFGAFDEEEN LLQRLETAYN EAEPILNNIE DRCKNINQDK DAVEKIKTLL DALKDIQHFA  480
KLLLCDNDET EIDAEFYNKL HDIWVKLDKI TPIYNMVRNY VTKKPYSEEK IKLNFEKSTL  540
LGGWDLNKEK NNLSVILRKD NLYYLGIMKK DNNKIFDSTN IKTDGVCFEK MEYKLLPDPK  600
KMLPKVFFSK KCSKDFNPND KILEIKENES FKKTSSNFNI EQCRKLIDFY KESINKHKDW  660
QKFNFQFSDT KTYNDINEFY NEVEKQGYKI SFCKISEDYI NELVKDNKLY LFKIWNKDFS  720
KYSKGTPNTH TLYWKQIFAP ENINNVVYKL NGQAEIFFRQ ASISQKNVIK HLANKPVKNK  780
NIKNEKKEST FSYDLVKDKR FTMDKFHFHV PITINFKAKG INNTNPIVNN LIRQNKIEHI  840
IGIDRGERHL LYLSLIDLKG NIIEQKSLNE IINNYNGNEY KTDYHTLLDD KEKERKDARL  900
SWNTIENIKE LKDGYMSQVV HIISQMIVKY NAIVVLEDLN HGFVRGRQKI EKQVYEKFEH  960
KLIDKLNYYV DKNADSNAVG GLYNALQLTN PFDSFEKLGK QSGCLFYIPA WKTSKIDPVT  1020
GFINMFTNLK YESVEKSKKF FSKFDDIRYN KEKNRFEFDV SFDKFDSDFV RITQESKLHW  1080
TLCSVGQRIE LVKENNGYKP NEINLTDAFK SVFNTNKIEI NTAKLNREIG KINDTAFFKE  1140
LMRLMKLLLQ MRNSKPNSIE KNDDYIISPV ADENGVFFDS SKVEDNGNLP KDADANGAYN  1200
IARKGLYVIH QIKQSEDDKK IDFKDFNPRW LKFIQQKLYL ND                    1242

SEQ ID NO: 104          moltype = AA  length = 1243
FEATURE                 Location/Qualifiers
source                  1..1243
                        mol_type = protein
                        organism = unidentified
SEQUENCE: 104
MKAETNLTEL VNLYSLQKTL RFELIPQGKT LENIEKNGIL TQDNQRADDY EKVKKLIDEY  60
HKHHIEISLD DCRLEGLEEY KELYEKKDDL KKIQENLRKQ IVKSLTENER YKDKRLFSDK  120
LFKEDLPNYL KDREQDKALV KKFEKFTTYF TGFNENRKNM YSSEDKPTSI AYRLIHENLP  180
KFIDNLHIFD KIKETTIKDD FDKIVEKLNK HLKIHIKSFD EIFSIEYFNK TLSQKQIDNY  240
NNIIGGMSFE NGTKIQGLNE YINRYNQKQE DKHQKLPCVK TLYKQILSDR EKISWIPEQF  300
DDDKQMAESI SNLYNEMLPI IKDDLLPLMA NIGDYDLSKI FISNDSALTT ISQRIFGAYN  360
VYTLAIIEKL KSDKPKSKRQ SESKYLDEID KNFKNMKSFS IAKLNNAVKG KYDKTIENYI  420
KVFGAFDEEE NLLQRLETAY NEAEPILNNI EDRCKNINQD KDAVEKIKTL LDALKDIQHF  480
AKLLLCDNDE TEIDAEFYNK LHDIWVKLDK ITPIYNMVRN YVTKKPYSEE KIKLNFEKST  540
LLGGWDLNKE KNNLSVILRK DNLYYLGIMK KDNNKIFDST NIKTDGVCFE KMEYKLLPDP  600
KKMLPKVFFS KKCSKDFNPN DKILEIKENE SFKKTSSNFN IEQCRKLIDF YKESINKHKD  660
WQKFNFQFSD TKTYNDINEF YNEVEKQGYK ISFCKISEDY INELVKDNKL YLFKIWNKDF  720
SKYSKGTPNT HTLYWKQIFA PENINNVVYK LNGQAEIFFR QASISQKNVI KHLANKPVKN  780
KNIKNEKKES TFSYDLVKDK RFTMDKFHFH VPITINFKAK GINNTNPIVN NLIRQNKIEH  840
IIGIDRGERH LLYLSLIDLK GNIIEQKSLN EIINNYNGNE YKTDYHTLLD DKEKERKDAR  900
LSWNTIENIK ELKDGYMSQV VHIISQMIVK YNAIVVLEDL NHGFVRGRQK IEKQVYEKFE  960
HKLIDKLNYY VDKNADSNAV GGLYNALQLT NPFDSFEKLG KQSGCLFYIP AWKTSKIDPV  1020
TGFINMFTNL KYESVEKSKK FFSKFDDIRY NKEKNRFEFD VSFDKFDSDF VRITQESKLH  1080
WTLCSVGQRI ELVKENNGYK PNEINLTDAF KSVFNTNKIE INTAKLNREI GKINDTAFFK  1140
ELMRLMKLLL QMRNSKPNSI EKNDDYIISP VADENGVFFD SSKVEDNGNL PKDADANGAY  1200
NIARKGLYVI HQIKQSEDDK KIDFKDFNPR WLKFIQQKLY LND                   1243

SEQ ID NO: 105          moltype = AA  length = 1282
FEATURE                 Location/Qualifiers
source                  1..1282
                        mol_type = protein
                        organism = synthetic construct
SEQUENCE: 105
MGSGKAETNL TELVNLYSLQ KTLRFELIPQ GKTLENIEKN GILTQDNQRA DDYEKVKKLI  60
```

```
DEYHKHHIEI SLDDCRLEGL EEYKELYEKK DDLKKIQENL RKQIVKSLTE NERYKDKRLF  120
SDKLFKEDLP NYLKDREQDK ALVKKFEKFT TYFTGFNENR KNMYSSEDKP TSIAYRLIHE  180
NLPKFIDNLH IFDKIKETTI KDDFDKIVEK LNKHLKIHIK SFDEIFSIEY FNKTLSQKQI  240
DNYNNIIGGM SFENGTKIQG LNEYINRYNQ KQEDKHQKLP CVKTLYKQIL SDREKISWIP  300
EQFDDDKQMA ESISNLYNEM LPIIKDDLLP LMANIGDYDL SKIFISNDSA LTTISQRIFG  360
AYNVYTLAII EKLKSDKPKS KRQSESKYLD EIDKNFKNMK SFSIAKLNNA VKGKYDKTIE  420
NYIKVFGAFD EEENLLQRLE TAYNEAEPIL NNIEDRCKNI NQDKDAVEKI KTLLDALKDI  480
QHFAKLLLCD NDETEIDAEF YNKLHDIWVK LDKITPIYNM VRNYVTKKPY SEEKIKLNFE  540
KSTLLGGWDL NKEKNNLSVI LRKDNLYYLG IMKKDNNKIF DSTNIKTDGV CFEKMEYKLL  600
PDPKKMLPKV FFSKKCSKDF NPNDKILEIK ENESFKKTSS NFNIEQCRKL IDFYKESINK  660
HKDWQKFNFQ FSDTKTYNDI NEFYNEVEKQ GYKISFCKIS EDYINELVKD NKLYLFKIWN  720
KDFSKYSKGT PNTHTLYWKQ IFAPENINNV VYKLNGQAEI FFRQASISQK NVIKHLANKP  780
VKNKNIKNEK KESTFSYDLV KDKRFTMDKF HFHVPITINF KAKGINNTNP IVNNLIRQNK  840
IEHIIGIDRG ERHLLYLSLI DLKGNIIEQK SLNEIINNYN GNEYKTDYHT LLDDKEKERK  900
DARLSWNTIE NIKELKDGYM SQVVHIISQM IVKYNAIVVL EDLNHGFVRG RQKIEKQVYE  960
KFEHKLIDKL NYYVDKNADS NAVGGLYNAL QLTNPFDSFE KLGKQSGCLF YIPAWKTSKI  1020
DPVTGFINMF TNLKYESVEK SKKFFSKFDD IRYNKEKNRF EFDVSFDKFD SDFVRITQES  1080
KLHWTLCSVG QRIELVKENN GYKPNEINLT DAFKSVFNTN KIEINTAKLN REIGKINDTA  1140
FFKELMRLMK LLLQMRNSKP NSIEKNDDYI ISPVADENGV FFDSSKVEDN GNLPKDADAN  1200
GAYNIARKGL YVIHQIKQSE DDKKIDFKDF NPRWLKFIQQ KLYLNDSRKR TADGSEFESP  1260
KKKRKVGSGK PIPNPLLGLD ST                                          1282

SEQ ID NO: 106         moltype = DNA  length = 3732
FEATURE                Location/Qualifiers
source                 1..3732
                       mol_type = unassigned DNA
                       organism = unidentified
SEQUENCE: 106
atgaaagcag aaacaaatct gacagaatta gtgaatctgt attcattgca gaaaacactt  60
cgttttgaat taatcccaca gggcaaaaca ttagaaaaca ttgagaaaaa tggtattctt  120
acacaagata accaaagagc agacgattac gaaaaagtca aaaaacttat tgatgagtat  180
cataagcacc atattgaaat aagtcttgac gattgtcgcc ttgaaggttt agaggaatat  240
aaagaactct acgaaaagaa agatgatttg aaaaaaattc aagagaatct acgaaaacaa  300
atcgttaaaa gtttaacgga gaacgaaagg tataaagaca aacgtctatt ctctgataaa  360
ctcttcaaag aagatcttcc gaattatcta aaagatagag aacaagacaa agctcttgtt  420
aaaaaatttg aaaaattcac cacatatttt actggattta acgaaaacag aaaaaatatg  480
tattcttccg aagacaaacc tacctcaatt gcttatagat taatccatga aaatttacct  540
aagtttatag acaatttaca tatttttgat aaaattaaag aaacaacaat caaagatgat  600
tttgataaga ttgttgaaaa attaaacaag catctaaaaa ttcatatcaa atcatttgac  660
gaaatttctct ctattgaata tttcaataaa actcttagcc aaaaacaaat agacaattat  720
aacaatataa ttggaggaat gtcttttgag aatggtacaa agatacaagg cttaaacgaa  780
tatattaatc gttacaatca aaagcaggaa gataaacatc aaaaacttcc ttgcgtcaaa  840
acactttata agcaaatact cagtgataga gaaaaaatat cgtggattcc agaacaattt  900
gatgatgata aacaaatggc agaaagtatt tcgaatttgt acaatgaaat gcttccaatt  960
attaaagatg atctacttcc gctaatggct aatataggcg attatgatct tagcaaaata  1020
tttatctcca acgactctgc tttaacaaca atatctcaac gaatttttgg agcttacaac  1080
gtttacactc ttgcaataat agaaaaatta aaaagtgata aacctaaatc aaaaagacaa  1140
tccgagtcta agtatttaga cgaaattgac aaaaacttca aaaatatgaa aagtttcagt  1200
attgcaaaac taaacaatgc cgtaaaaggc aaatacgata aaacaataga aaattatatc  1260
aaggttttcg gggcttttga cgaagaagag aacttgctac aacgattaga aacagcctat  1320
aacgaagctg agcctatact taataatata gaagacagat gcaaaaatat taatcaagac  1380
aaagatgctg ttgaaaagat taaaacatta ttagatgctt tgaaagatat tcaacatttt  1440
gcaaaacttc tattatgtga taacgacgaa actgaaatag atgcggagtt ttataataaa  1500
ttacatgata tatgggtaaa attggacaag ataacaccta tatataatat ggtgagaaat  1560
tatgttacaa agaaacctta ttcagaagaa aaaatcaaat tgaattttga aaaatctaca  1620
ctattaggcg gctgggattt gaacaaagaa aaaaataatt tatcagttat actccgcaaa  1680
gataatttgt attacttagg gattatgaaa aaagataata acaaaatctt tgatagtaca  1740
aatatcaaaa ccgatggcgt ttgttttgag aaaatggaat acaaactact tcctgatcca  1800
aagaaaatgc tgccaaaggt attcttttca aaaaaatgtt caaaggactt taacccgaac  1860
gacaaaatat tagaaattaa ggaaaatgaa agtttcaaga aaacaagcag taatttcaat  1920
attgagcaat gtcgtaaatt aatagacttc tataaagaat ctatcaataa acataaagat  1980
tggcaaaaat ttaatttcca attctctgac actaaaactt acaatgacat aaacgaattt  2040
tacaacgaag ttgaaaaaca aggttataaa atatcttttt gtaaaatttc tgaggattat  2100
ataaatgagt tggtgaaaga caataaactt tatttgttta agatttggaa caaagacttt  2160
tcaaaatata gcaaaggaac tccaaatacg cacactcttt attggaaaca aatatttgca  2220
cctgaaaata tcaacaatgt cgtatataaa ctaaacggac aagccgaaat atttttttagg  2280
caagcaagta tttctcaaaa aaacgttatc aaacatttgg caaacaaacc tgttaaaaac  2340
aagaatataa aaaacgaaaa aaaggaaagt acgttcagtt atgatttagt aaaagataaa  2400
cgttttacta tggataaatt ccatttccac gtaccgatta ctattaattt caaggcaaaa  2460
ggaataaata ataccaatcc tattgtcaat aatctaattc gtcaaaacaa gatagaacat  2520
attattggta tagatagagg cgaaaggcat ttgctttatc tttctcttat agatttgaaa  2580
ggaaatatca ttgaacaaaa gtcgttgaat gaaatcataa acaactacaa tggcaatgaa  2640
tataaaaacag attaccatac cttgcttgat gataaggaaa aagaaagaaa agatgcccga  2700
ctttcgtgga atactattga aaatatcaaa gaactcaaag acgggtatat gagccaagtt  2760
gtgcatatta tctcacaaat gattgtgaag tacaatgcaa tagttgtttt ggaagacctt  2820
aatcatggct ttgttcgtgg tcgccagaag atagaaaaac aagtttatga aaaatttgag  2880
cataaactta ttgataaact aaactattat gtcgataaga atgccgatag caatgccgtt  2940
ggaggacttt acaatgcttt gcaactaaca aatccatttg atagttttga aaaattagga  3000
aaacaaagcg gctgtttatt ctatatccct gcttggaaaa caagtaagat tgatcccgtt  3060
```

```
actggattta ttaatatgtt tacaaatctc aaatacgaat cagtggaaaa atcaaagaag  3120
ttcttttcaa agtttgacga tattagatac aataaagaaa aaaataggtt tgaatttgat  3180
gtttcatttg ataaattcga tagtgatttt gtccgtatta cacaggaaag taaattacat  3240
tggacgcttt gcagtgttgg tcagcgtata gaattagtaa aagagaataa tggttataaa  3300
cctaatgaaa taaatttaac tgatgctttc aaatcagtgt ttaatactaa taaaatagag  3360
ataaacactg ctaaactgaa tagagagatt ggtaaaatca atgatacagc gtttttcaag  3420
gaacttatgc gtttaatgaa attgttatta caaatgagaa atagtaagcc aaattcaata  3480
gagaagaacg acgattatat tatctctcct gttgcagacg aaaatggagt attctttgac  3540
agcagtaaag ttgaagacaa tggcaatttg ccaaaagatg ccgatgccaa cggagcatac  3600
aatattgctc gcaaaggctt gtatgtaata caccaaataa agcaaagcga agatgataaa  3660
aaaatcgatt tcaaagattt caacccacgt tggttaaaat tcattcagca aaaactatat  3720
ttgaatgatt ga                                                      3732
```

```
SEQ ID NO: 107          moltype = DNA  length = 3726
FEATURE                 Location/Qualifiers
source                  1..3726
                        mol_type = other DNA
                        organism = synthetic construct
SEQUENCE: 107
aaggccgaga caaacctgac agaactcgtg aacctgtaca gcctgcaaaa aaccctgaga  60
tttgagctca tcccccaggg caagaccctt gagaacatcg agaagaacgg tatcctgacc  120
caggacaatc agagagccga cgactacgag aaggtgaaaa aactgatcga cgagtaccac  180
aagcaccaca tcgagatcag cctggacgat tgcagactgg aaggcctgga agaatacaag  240
gaactgtatg agaagaagga tgacctaaag aaaatccagg aaaacctgag aaagcagatc  300
gtgaagtccc tcactgagaa cgaacggtac aaggacaaaa gactcttctc agataagctg  360
ttcaaggaag atctgcctaa ttacctgaag gacagagaac aggacaaggc cctggtaaaa  420
aagttcgaga agttcaccac ctacttcacc ggcttcaacg aaaaccgcaa aaacatgtac  480
agcagcgagg ataagcccac cagcatcgct tatagactga tccacgagaa cctgcctaag  540
ttcatcgaca acctgcacat ctttgataag atcaaggaaa ccaccatcaa ggacgatttc  600
gataagatcg tggaaaagct gaataaacac ctgaagatcc acatcaaatc cttcgacgag  660
atcttttcta ttgaatactt caacaagaca ctgagtcaaa agcaaatcga caactacaac  720
aacatcatcg gcggaatgag cttcgagaat ggcaccaaga tccagggcct gaatgagtac  780
atcaacagat acaaccagaa acaagaggac aagcatcaaa agctgccttg cgtgaaaacc  840
ctgtacaagc agatcctgag cgacagagag aagatttcct ggattcctga acagttcgat  900
gacgacaaac agatggccga gagcatcagc aatctgtaca acgagatgct gccaatcatc  960
aaggacgacc tgctgcctct gatggccaac attggcgact acgacctgag caaaatcttc  1020
atcagcaatg acagcgccct gacaaccatc tcgcagcgga tcttcggagc ttacaacgtg  1080
tacaccctgg ccatcattga gaagctgaag tctgataagc ctaagagcaa gcggcagtct  1140
gagtctaagt acctggacga gatcgacaag aacttcaaga acatgaagtc ttttagcatc  1200
gccaagctga acaacgccgt gaagggcaag tatgacaaga caatcgaaaa ttacatcaag  1260
gtgtttggcg cctttgatga ggaggagaat ctcctgcaga ggctggaaac agcctataac  1320
gaggccgagc ctatcctgaa caacatcgag gacagatgca aaaacatcaa tcaagacaag  1380
gatgccgtgg aaaagatcaa gaccttactg gacgctctga aagatatcca gcactttgcc  1440
aagttactgc tgtgcgacaa tgacgaaacc gagattgacg ccgagttcta caacaagctg  1500
cacgacatct gggtgaagct ggacaaaatc acaccaatct acaacatggt gcggaactac  1560
gtgaccaaga agccctactc tgaagagaaa atcaagctga acttcgaaaa gtctacactg  1620
ctgggcggct gggatctgaa caaggaaaag aacaatctga gcgtgatcct gagaaaggac  1680
aacctgtact acctgggcat catgaagaaa gacaacaaca agatcttcga ctccacaaac  1740
atcaagaccg acggcgtttg tttcgagaag atggaatata agctgttacc tgaccctaaa  1800
aagatgctgc ccaaggtgtt cttctcaaag aaatgcagca aggatttcaa tcctaacgac  1860
aagatcctgg agatcaaaga gaacgaatct ttcaagaaaa cctctagcaa ctttaatatc  1920
gagcagtgca gaaaactgat cgacttttac aaggagtcca tcaataagca caaagactgg  1980
cagaaattca actttcagtt cagcgatacc aagacctaca acgatatcaa cgagttctac  2040
aacgaggtgg aaaaacaggg ctacaaaatt agcttctgca agatcagcga ggactacatc  2100
aatgagctgg ttaaggacaa caaactgtac ctgtttaaga tctggaacaa ggatttcagt  2160
aagtacagca aggggacccc taacacccac accctgtact ggaagcagat cttcgcccct  2220
gagaacatca acaacgtcgt gtacaagctg aacggacagg ccgagatctt cttcagacaa  2280
gcatctatct cccagaagaa cgtcatcaag cacctagcta ataagccagt gaaaaacaag  2340
aacatcaaga acgagaagaa ggagagcacc ttcagctacg atcttgttaa ggacaagcgg  2400
tttacaatgg acaagttcca cttccacgtg ccaatcacca taaactttaa ggccaagggc  2460
atcaacaaca ccaatcctat tgtcaacaac ctgatccggc agaacaagat tgaacacatc  2520
atcggcatcg acagaggcga gagacacctg ctgtatctga gcctgatcga tctgaagggc  2580
aacatcatag aacagaagag cctgaacgag atcatcaaca attacaacgg caatgagtac  2640
aagaccgatt accatacctt gctggatgac aaggaaaagg agagaaagga tgctagactg  2700
agctggaaca ccatcgaaaa tatcaaggaa ctgaaagatg gctacatgag ccaggtggtg  2760
cacatcatca gtcagatgat cgtgaaatac aacgccattg tggtcctgga ggatctcaac  2820
cacggcttcg tgcggggcag acagaagatc gagaagcagg tgtatgaaaa atttgaacac  2880
aagctgatcg acaagctgaa ttactacgtg gacaagaatg ctgacagcaa cgccgtggga  2940
ggactgtaca atgccctgca gctgacaaac cccttcgaca gcttcgagaa gctgggcaag  3000
cagagcggct gtctgtttta catccccgcc tggaaaacaa gtaagatcga tcctgtgacc  3060
ggattcatca acatgttcac caacctgaag tacgaatctg tggaaaagag caaaaagttc  3120
ttcagcaagt tcgatgacat cagatacaac aaggagaaaa accgattcga gttcgacgtg  3180
tccttcgaca agttcgactc cgacttcgtg cggatcaccc aggagagcaa actgcattgg  3240
accttgtgta gcgtgggcca gagaatcgaa ctggtcaagg aaaacaacgg atacaagcct  3300
aacgaaatca acctgacaga tgctttcaag agcgtgttca acacaaacaa gatcgagatc  3360
aacaccgcca aactgaatcg ggaaatcgga aaaatcaacg acacagcttt cttcaaggaa  3420
ctgatgcggc tgatgaagct gctcctgcag atgagaaaca gcaagcccaa ctccatcgaa  3480
aagaacgatg attacatcat cagccctgtg gccgatgaga acggcgtgtt ctttgacagc  3540
agcaaagtgg aggacaatgg caacctgcca aaggacgccg atgccaacgg cgcctacaac  3600
```

```
atcgccagga agggcctgta tgtgatccac cagattaagc agtctgagga cgacaagaag  3660
atcgacttta aggacttcaa ccccagatgg ctgaagttca tccagcagaa gctgtacctg  3720
aacgat                                                             3726

SEQ ID NO: 108         moltype = DNA  length = 3849
FEATURE                Location/Qualifiers
source                 1..3849
                       mol_type = other DNA
                       organism = synthetic construct
SEQUENCE: 108
atgggctccg gaaaggccga gacaaacctg acagaactcg tgaacctgta cagcctgcaa  60
aaaaccctga gatttgagct catcccccag ggcaagaccc ttgagaacat cgagaagaac  120
ggtatcctga cccaggacaa tcagagagcc gacgactacg agaaggtgaa aaaactgatc  180
gacgagtacc acaagcacca catcgagatc agcctggacg attgcagact ggaaggcctg  240
gaagaataca aggaactgta tgagaagaag gatgacctaa agaaaatcca ggaaaacctg  300
agaaagcaga tcgtgaagtc cctcactgag aacgaacggt acaaggacaa aagactcttc  360
tcagataagc tgttcaagga agatctgcct aattacctga aggacagaga acaggacaag  420
gccctggtaa aaaagttcga gaagttcacc acctacttca ccggcttcaa cgaaaaccgc  480
aaaaacatgt acagcagcga ggataagccc accagcatcg cttatagact gatccacgag  540
aacctgccta agttcatcga caacctgcac atctttgata agatcaagga aaccaccatc  600
aaggacgatt tcgataagat cgtggaaaag ctgaataaac acctgaagat ccacatcaaa  660
tccttcgacg agatcttttc tattgaatac ttcaacaaga cactgagtca aaagcaaatc  720
gacaactaca acaacatcat cggcggaatg agcttcgaga atggcaccaa gatccagggc  780
ctgaatgagt acatcaacag atacaaccag aaacaagagg acaagcatca aaagctgcct  840
tgcgtgaaaa ccctgtacaa gcagatcctg agcgacagag agaagatttc ctggattcct  900
gaacagttcg atgacgacaa acagatggcc gagagcatca gcaatctgta caacgagatg  960
ctgccaatca tcaaggacga cctgctgcct ctgatggcca acattggcga ctacgacctg  1020
agcaaaatct tcatcagcaa tgacagcgcc ctgacaacca tctcgcagcg gatcttcgga  1080
gcttacaacg tgtacaccct ggccatcatt gagaagctga agtctgataa gcctaagagc  1140
aagcggcagt ctgagtctaa gtacctggac gagatcgaca agaacttcaa gaacatgaag  1200
tcttttagca tcgccaagct gaacaacgcc gtgaagggca agtatgacaa gacaatcgaa  1260
aattacatca aggtgtttgg cgccctttgat gaggaggaga atctcctgca gaggctggaa  1320
acagcctata acgaggccga gcctatcctg aacaacatcg aggacagatg caaaaacatc  1380
aatcaagaca aggatgccgt ggaaaagatc aagaccttac tggacgctct gaaagatatc  1440
cagcactttg ccaagttact gctgtgcgac aatgacgaaa ccgagattga cgccgagttc  1500
tacaacaagc tgcacgacat ctgggtgaag ctggacaaaa tcacaccaat ctacaacatg  1560
gtgcggaact acgtgaccaa gaagccctac tctgaagaga aatcaagct gaacttcgaa  1620
aagtctacac tgctgggcgg ctgggatctg aacaaggaaa agaacaatct gagcgtgatc  1680
ctgagaaagg acaacctgta ctacctgggc atcatgaaga aagacaacaa caagatcttc  1740
gactccacaa acatcaagac cgacggcgtt tgtttcgaga agatggaata taagctgtta  1800
cctgacccta aaaagatgct gcccaaggtg ttcttctcaa agaaatgcag caaggatttc  1860
aatcctaacg acaagatcct ggagatcaaa gagaacgaat ctttcaagaa aacctctagc  1920
aactttaata tcgagcagtg cagaaaactg atcgactttt acaaggagtc catcaataag  1980
cacaaagact ggcagaaatt caactttcag ttcagcgata ccaagaccta caacgatatc  2040
aacgagttct acaacgaggt ggaaaaacag ggctacaaaa ttagcttctg caagatcagc  2100
gaggactaca tcaatgagct ggttaaggac aacaaactgt acctgtttaa gatctggaac  2160
aaggatttca gtaagtacag caaggggacc cctaacaccc acaccctgta ctggaagcag  2220
atcttcgccc ctgagaacat caacaacgtc gtgtacaagc tgaacggaca ggccgagatc  2280
ttcttcagac aagcatctat ctcccagaag aacgtcatca agcacctagc taataagcca  2340
gtgaaaaaca agaacatcaa gaacgagaag aaggagagca ccttcagcta cgatcttgtt  2400
aaggacaagc ggtttacaat ggacaagttc cacttccacg tgccaatcac cataaacttt  2460
aaggccaagg gcatcaacaa caccaatcct attgtcaaca acctgatccg gcagaacaag  2520
attgaacaca tcatcggcat cgacagaggc gagagacacc tgctgtatct gagcctgatc  2580
gatctgaagg gcaacatcat agaacagaag agcctgaacg agatcatcaa caattacaac  2640
ggcaatgagt acaagaccga ttaccatacc ttgctggatg acaaggaaaa ggagagaaag  2700
gatgctagac tgagctggaa caccatcgaa aatatcaagg aactgaaaga tggctacatg  2760
agccaggtgg tgcacatcat cagtcagatg atcgtgaaat acaacgccat tgtggtcctg  2820
gaggatctca accacggctt cgtgcggggc agacagaaga tcgagaagca ggtgtatgaa  2880
aaatttgaac acaagctgat cgacaagctg aattactacg tggacaagaa tgctgacagc  2940
aacgccgtgg gaggactgta caatgccctg cagctgacaa accccttcga cagcttcgag  3000
aagctgggca agcagagcgg ctgtctgttt tacatccccg cctggaaaac aagtaagatc  3060
gatcctgtga ccggattcat caacatgttc accaacctga agtacgaatc tgtggaaaag  3120
agcaaaaagt tcttcagcaa gttcgatgac atcagataca acaaggagaa aaaccgattc  3180
gagttcgacg tgtccttcga caagttcgac tccgacttcg tgcggatcac ccaggagagc  3240
aaactgcatt ggaccttgtg tagcgtgggc cagagaatcg aactggtcaa ggaaaacaac  3300
ggatacaagc ctaacgaaat caacctgaca gatgctttca agagcgtgtt caacacaaac  3360
aagatcgaga tcaacaccgc caaactgaat cgggaaatcg gaaaaatcaa cgacacagct  3420
ttcttcaagg aactgatgcg gctgatgaag ctgctcctgc agatgagaaa cagcaagccc  3480
aactccatcg aaaagaacga tgattacatc atcagccctg tggccgatga gaacggcgtg  3540
ttctttgaca gcagcaaagt ggaggacaat ggcaacctgc caaaggacgc cgatgccaac  3600
ggcgcctaca acatcgccag gaagggcctg tatgtgatcc accagattaa gcagtctgag  3660
gacgacaaga agatcgactt taaggacttc aaccccagat ggctgaagtt catccagcag  3720
aagctgtacc tgaacgattc tagaaagcgg acagcagacg gctccgaatt tgaaagccct  3780
aagaaaaaga gaaaggtggg atccggcaaa cctatcccca atcccctgct gggcctggac  3840
agcacctga                                                          3849

SEQ ID NO: 109         moltype = AA  length = 1248
FEATURE                Location/Qualifiers
source                 1..1248
```

```
                         mol_type = protein
                         organism = unidentified
SEQUENCE: 109
DMKSLNSFQN QYSLSKTLRF QLIPQGKTLD NINESRILEE DQHRSESYKL VKKIIDDYHK  60
AYIEQALGSF ELKIASDSKN DSLEEFYSQY IAERKEDKAK KLFEKTQDNL RKQISKKLKQ  120
GEAYKRLFGK ELIQEDLLEF VATDPEADSK KRLIEEFKDF TTYFIGFHEN RKNMYAEEAQ  180
STAIAYRIIH ENLPKFIDNI RTFEELAKSS IADVLPQVYE DFKAYLKVES VKELFSLDYF  240
NTVLTQKQLD IYNAVIGGKS LDENSRIQGL NEYINLYNQQ HKDKKLPFLK PLFKQILSDR  300
NSLSWLPEAF DNDKQVLQAV HDCYTSLLES VFHKDGLQQL LQSLPTYNLK GIYLRNDLSM  360
TNVSQKLLGD WGAITRAVKE KLQKENPAKK RESDEAYQER INKIFKQAGS YSLDYINQAL  420
EATDQTNIKV EDYFINMGVD NEQKEPLFQR VAQAYNQASD LLEKEYPANK NLMQDKESIE  480
HIKFLLDNLK AVQHFIKPLL GDGNEADKDN RFYGELTALW NELDQVTRLY NKVRNYMTRK  540
PYSVDKIKIN FKNSTLLNGW DRNKERDNTA VILRKDGKFY LAIMHKEHNK VFEKFPVGTK  600
DSDFEKMEYK LLPGANKMLP KVFFSKSRID EFKPSAELLQ KYQMGTHKKG ELFSLNDCHS  660
LIDFFKASIE KHDDWKQFNF HFSPTSSYED LSGFYREVEQ QGYKLTFKSV DADYINKMVD  720
EGKIFLFQIY NKDFSEHSKG TPNLHTLYWK MLFDERNLQN VVYKLNGEAE VFFRKKSLTY  780
TRPTHPKKEP IKNKNVQNAK KESIFDYDLI KNKRFTVDSF QFHVPITMNF KSEGRSNLNE  840
RVNEFLRQNN DAHIIGIDRG ERHLLYLVVI DRHGNIVEQF SLNSIINEYQ GNTYATNYHD  900
LLDKREKERE EARESWQSIE NIKELKEGYL SQVVHKIADL MVKYHAIVVL EDLNMGFMRG  960
RQKVEKQVYQ KFEKMLIDKL NYLVDKKQDA ETDGGLLKAY QLTNQFESFQ KLGKQSGFLF  1020
YVPAWNTSKI DPCTGFTNLL DTRYESIEKA KKFFQTFNAI RYNAAQGYFE FELDYNKFNK  1080
RADGTQTLWT LCTYGPRIET LRSTEDNNKW TSKEVDLTDE LKKHFYHYGI KLDADLKEAI  1140
GQQTDKPFFT NLLHLLKLTL QMRNSKIGTE VDYLISPIRN EDGTFYDSRQ GNKSLPANAD  1200
ANGAYNIARK GLWVINQIKQ TPQDQKPKLA ITNKEWLQFA QEKPYLKD            1248

SEQ ID NO: 110           moltype = AA  length = 1249
FEATURE                  Location/Qualifiers
source                   1..1249
                         mol_type = protein
                         organism = unidentified
SEQUENCE: 110
MDMKSLNSFQ NQYSLSKTLR FQLIPQGKTL DNINESRILE EDQHRSESYK LVKKIIDDYH  60
KAYIEQALGS FELKIASDSK NDSLEEFYSQ YIAERKEDKA KKLFEKTQDN LRKQISKKLK  120
QGEAYKRLFG KELIQEDLLE FVATDPEADS KKRLIEEFKD FTTYFIGFHE NRKNMYAEEA  180
QSTAIAYRII HENLPKFIDN IRTFEELAKS SIADVLPQVY EDFKAYLKVE SVKELFSLDY  240
FNTVLTQKQL DIYNAVIGGK SLDENSRIQG LNEYINLYNQ QHKDKKLPFL KPLFKQILSD  300
RNSLSWLPEA FDNDKQVLQA VHDCYTSLLE SVFHKDGLQQ LLQSLPTYNL KGIYLRNDLS  360
MTNVSQKLLG DWGAITRAVK EKLQKENPAK KRESDEAYQE RINKIFKQAG SYSLDYINQA  420
LEATDQTNIK VEDYFINMGV DNEQKEPLFQ RVAQAYNQAS DLLEKEYPAN KNLMQDKESI  480
EHIKFLLDNL KAVQHFIKPL LGDGNEADKD NRFYGELTAL WNELDQVTRL YNKVRNYMTR  540
KPYSVDKIKI NFKNSTLLNG WDRNKERDNT AVILRKDGKF YLAIMHKEHN KVFEKFPVGT  600
KDSDFEKMEY KLLPGANKML PKVFFSKSRI DEFKPSAELL QKYQMGTHKK GELFSLNDCH  660
SLIDFFKASI EKHDDWKQFN FHFSPTSSYE DLSGFYREVE QQGYKLTFKS VDADYINKMV  720
DEGKIFLFQI YNKDFSEHSK GTPNLHTLYW KMLFDERNLQ NVVYKLNGEA EVFFRKKSLT  780
YTRPTHPKKE PIKNKNVQNA KKESIFDYDL IKNKRFTVDS FQFHVPITMN FKSEGRSNLN  840
ERVNEFLRQN NDAHIIGIDR GERHLLYLVV IDRHGNIVEQ FSLNSIINEY QGNTYATNYH  900
DLLDKREKER EEARESWQSI ENIKELKEGY LSQVVHKIAD LMVKYHAIVV LEDLNMGFMR  960
GRQKVEKQVY QKFEKMLIDK LNYLVDKKQD AETDGGLLKA YQLTNQFESF QKLGKQSGFL  1020
FYVPAWNTSK IDPCTGFTNL LDTRYESIEK AKKFFQTFNA IRYNAAQGYF EFELDYNKFN  1080
KRADGTQTLW TLCTYGPRIE TLRSTEDNNK WTSKEVDLTD ELKKHFYHYG IKLDADLKEA  1140
IGQQTDKPFF TNLLHLLKLT LQMRNSKIGT EVDYLISPIR NEDGTFYDSR QGNKSLPANA  1200
DANGAYNIAR KGLWVINQIK QTPQDQKPKL AITNKEWLQF AQEKPYLKD           1249

SEQ ID NO: 111           moltype = AA  length = 1288
FEATURE                  Location/Qualifiers
source                   1..1288
                         mol_type = protein
                         organism = synthetic construct
SEQUENCE: 111
MGSGDMKSLN SFQNQYSLSK TLRFQLIPQG KTLDNINESR ILEEDQHRSE SYKLVKKIID  60
DYHKAYIEQA LGSFELKIAS DSKNDSLEEF YSQYIAERKE DKAKKLFEKT QDNLRKQISK  120
KLKQGEAYKR LFGKELIQED LLEFVATDPE ADSKKRLIEE FKDFTTYFIG FHENRKNMYA  180
EEAQSTAIAY RIIHENLPKF IDNIRTFEEL AKSSIADVLP QVYEDFKAYL KVESVKELFS  240
LDYFNTVLTQ KQLDIYNAVI GGKSLDENSR IQGLNEYINL YNQQHKDKKL PFLKPLFKQI  300
LSDRNSLSWL PEAFDNDKQV LQAVHDCYTS LLESVFHKDG LQQLLQSLPT YNLKGIYLRN  360
DLSMTNVSQK LLGDWGAITR AVKEKLQKEN PAKKRESDEA YQERINKIFK QAGSYSLDYI  420
NQALEATDQT NIKVEDYFIN MGVDNEQKEP LFQRVAQAYN QASDLLEKEY PANKNLMQDK  480
ESIEHIKFLL DNLKAVQHFI KPLLGDGNEA DKDNRFYGEL TALWNELDQV TRLYNKVRNY  540
MTRKPYSVDK IKINFKNSTL LNGWDRNKER DNTAVILRKD GKFYLAIMHK EHNKVFEKFP  600
VGTKDSDFEK MEYKLLPGAN KMLPKVFFSK SRIDEFKPSA ELLQKYQMGT HKKGELFSLN  660
DCHSLIDFFK ASIEKHDDWK QFNFHFSPTS SYEDLSGFYR EVEQQGYKLT FKSVDADYIN  720
KMVDEGKIFL FQIYNKDFSE HSKGTPNLHT LYWKMLFDER NLQNVVYKLN GEAEVFFRKK  780
SLTYTRPTHP KKEPIKNKNV QNAKKESIFD YDLIKNKRFT VDSFQFHVPI TMNFKSEGRS  840
NLNERVNEFL RQNNDAHIIG IDRGERHLLY LVVIDRHGNI VEQFSLNSII NEYQGNTYAT  900
NYHDLLDKRE KEREEARESW QSIENIKELK EGYLSQVVHK IADLMVKYHA IVVLEDLNMG  960
FMRGRQKVEK QVYQKFEKML IDKLNYLVDK KQDAETDGGL LKAYQLTNQF ESFQKLGKQS  1020
GFLFYVPAWN TSKIDPCTGF TNLLDTRYES IEKAKKFFQT FNAIRYNAAQ GYFEFELDYN  1080
KFNKRADGTQ TLWTLCTYGP RIETLRSTED NNKWTSKEVD LTDELKKHFY HYGIKLDADL  1140
KEAIGQQTDK PFFTNLLHLL KLTLQMRNSK IGTEVDYLIS PIRNEDGTFY DSRQGNKSLP  1200
```

```
ANADANGAYN IARKGLWVIN QIKQTPQDQK PKLAITNKEW LQFAQEKPYL KDSRKRTADG  1260
SEFESPKKKR KVGSGKPIPN PLLGLDST                                    1288

SEQ ID NO: 112          moltype = DNA  length = 3750
FEATURE                 Location/Qualifiers
source                  1..3750
                        mol_type = unassigned DNA
                        organism = unidentified
SEQUENCE: 112
atggatatga aaagtttaaa cagctttcag aaccagtatt ccctatccaa gaccctccgg  60
tttcagctaa taccccaggg taaaactttg gataacatta acgagagcag aatattggag  120
gaagaccaac accgaagcga aagctacaag ttggtcaaga aaatcattga cgactatcac  180
aaggcctaca tcgaacaagc cctgggcagt ttcgaactca aaattgccag tgactctaaa  240
aacgattcgt tagaggagtt ctactcgcag tatattgccg aacggaaaga agataaagcc  300
aaaaaacttt tcgaaaagac gcaagacaac ttgcgaaagc aaatctccaa gaaattaaag  360
cagggcgaag cctacaagcg gttgtttggc aaggaactca ttcaagaaga cctgctggag  420
tttgtagcta ccgaccctga ggctgatagc aaaaagcgtc tgattgaaga attcaaggac  480
ttcaccacct actttatcgg attccacgag aaccgaaaga acatgtatgc tgaggaagcc  540
caatccacag caattgccta ccgcatcatt cacgagaacc tgccgaagtt cattgataac  600
atacgcacct tcgaagaact tgctaaaagt tccattgccg acgtcctgcc acaggtttat  660
gaagatttca aagcgtactt aaaggtcgaa tcggtcaaag aacttttcag tctggactat  720
ttcaataccg tcttgaccca aaagcagctt gacatttaca atgcggttat cggcggtaag  780
tcgttagatg agaacagccg catccagggg ctcaacgagt atatcaacct gtacaaccag  840
cagcacaagg acaaaaagtt acccttctta aaaccccttgt tcaagcaaat tctgagcgac  900
cgcaacagcc tttcgtggtt gcccgaagct ttcgacaatg acaagcaggt acttcaggct  960
gtacacgact gctacacctc gctattggag agcgtattcc acaaagacgg cctgcaacag  1020
ttgctacagt cactgcctac ctacaacctg aagggcattt acctgcgcaa cgacctttcc  1080
atgaccaacg tttctcaaaa actattgggc gattggggag ctattacacg tgccgttaaa  1140
gaaaaactac aaaaagaaaa tcctgccaaa aaacgagagt cggacgaagc ctaccaagaa  1200
cgcatcaaca agatattcaa gcaagccggc agctactctt tagattacat caaccaagcg  1260
ctcgaagcaa cagaccagac caatatcaaa gtcgaagact acttcatcaa catgggcgta  1320
gacaacgagc aaaaagagcc cctgttccag cgtgtagcgc aagcctacaa tcaggccagc  1380
gatttgcttg aaaaggaata tcccgcaaac aaaaatctga tgcaggataa agaaaagcatc  1440
gagcacatca aattcttgct cgataacctc aaagccgttc aacactttat aaagcccctg  1500
ctcggcgatg gtaacgaggc tgataaagat aatcgttttt acggagaact tacagcgctg  1560
tggaacgaat tagaccaggt aacgcgcctg tataacaagg tgcgaaacta catgacccgc  1620
aagccctact cggttgataa aatcaagatt aactttaaga actcaactct acttaatggc  1680
tgggacagaa ataaggaacg tgacaatacc gctgttattc tgcgcaaaga cggcaagttc  1740
tatctggcca ttatgcataa agaacacaat aaggtgttcg aaaaattccc ggtcggaaca  1800
aaggattctg acttcgagaa aatggagtat aagttacttc cgggcgccaa taaaatgctt  1860
ccgaaggttt tcttctctaa atcgcgtatc gatgagttta agcccagcgc cgaacttctc  1920
caaaagtacc agatgggtac ccacaaaaag ggcgaactct tcagtctgaa cgactgccat  1980
tctctgattg acttctttaa ggcttctatt gaaaagcatg acgattggaa acagtttaac  2040
ttccatttct cacccacttc gagctacgaa gacttgagcg gattttacag agaggttgaa  2100
cagcaggggt acaaactgac cttcaaatcc gttgacgccg actatatcaa caaaatggtt  2160
gacgagggca aaatctttct cttccagatt tacaataaag acttctcgga acatagcaaa  2220
ggcaccccca acctgcatac gctctactgg aaaatgctct ttgacgaacg caacctgcag  2280
aacgtggtct acaaactgaa cggcgaggcc gaagtcttct tccggaagaa gagtcttacc  2340
tacacccgtc ctacgcaccc caagaaagag cctatcaaga acaagaacgt tcagaatgcc  2400
aaaaaggaaa gcatcttcga ctacgacctg attaaaaaca aacgctttac ggtcgactcc  2460
ttccagttcc acgttcccat cacgatgaac ttcaagagcg aaggacgctc caacctgaac  2520
gagcgggtca acgagttttt acgccagaac aacgatgccc acatcattgg cattgaccgg  2580
ggcgaacgcc atttgctcta cctggtggtt attgaccggc acggaaacat tgtggaacaa  2640
ttttcgctca actctatcat caacgaatat cagggtaata cgtacgccac caactaccac  2700
gacttgttgg ataagcgcga aaaggaaaga gaggaagcac gcgaaagctg gcagagtatt  2760
gagaatatta aagaactgaa agaaggatac ttgagccagg tggtgcataa aattgccgac  2820
ctcatggtaa agtatcatgc catcgtggtg ctcgaagact tgaatatggg cttcatgcgc  2880
ggacgccaga aggtagaaaa gcaggtctat cagaagtttg aaaaaatgct gatagacaag  2940
ttaaactatc tggttgacaa gaagcaagat gccgaaaccg acggcggtct gctcaaggca  3000
taccaactga ccaaccagtt cgaaagtttc cagaagttag gcaagcagag cggtttcctc  3060
ttctatgtgc ctgcctggaa caccagcaaa attgacccct gcaccggatt taccaacctg  3120
ctcgacactc gatacgagag catcgaaaag gccaaaaagt tctttcaaac tttcaatgcc  3180
atccgctaca atgctgcgca ggggtacttt gagttcgaac tggattacaa taaattcaac  3240
aagcgggccg atggtacaca aaccctatgg acgctctgca cctacggccc acgcatcgaa  3300
acactccgaa gcaccgagga taataacaag tggacaagca aagaggttga tttgaccgac  3360
gaattgaaaa agcacttcta ccactatggc attaagctgg atgccgacct gaaggaagcc  3420
atcggccaac aaaccgacaa acctttcttc accaacttgc tccatctgct caaactaaca  3480
ctgcaaatgc gaaacagcaa aatcggcacg gaggttgact acctcatttc gccaattcgc  3540
aatgaagacg gaacgttcta cgacagccga caaggcaaca aatcattgcc tgccaatgcc  3600
gatgccaatg gtgcctacaa cattgcccga aagggtttat gggtaattaa ccagataaaa  3660
caaacacctc aagaccaaaa gcccaagtta gctattacca acaaggaatg gctgcaattt  3720
gctcaagaga agccctacct taaggattga                                  3750

SEQ ID NO: 113          moltype = DNA  length = 3744
FEATURE                 Location/Qualifiers
source                  1..3744
                        mol_type = other DNA
                        organism = synthetic construct
SEQUENCE: 113
```

```
gacatgaaga gcctgaactc ttttcagaac caatactctc tgagcaaaac cctgcggttc  60
cagctgatcc ctcagggcaa gacactggat aatatcaacg agagcagaat cctggaagag  120
gatcagcaca gaagcgagtc atataaactg gtgaagaaga tcattgacga ctatcacaag  180
gcctacatcg agcaggccct gggcagcttc gagctgaaaa ttgcctccga tagcaagaac  240
gacagcctgg aggagttcta ctctcagtac attgcggaga gaaaggagga caaggccaag  300
aagctgttcg aaaagaccca ggacaatctg agaaagcaga tctccaagaa gctgaaacag  360
ggtgaagcct acaaacggct gttcggcaaa gaactgatcc aggaggacct gctggagttc  420
gtggccacag atcctgaggc cgactctaag aagagactga tcgaagagtt caaggacttt  480
accacctact tcatcggatt tcacgaaaat agaaagaaca tgtacgccga ggaggctcag  540
agcacagcta ttgcctacag aatcatccac gagaacctgc caaagtttat cgataatatc  600
agaaccttcg aggaactggc caagagcagc atcgccgacg tgctgcccca ggtctacgag  660
gactttaagg cctacctgaa ggtggaaagc gtgaaagaac tgttctctct ggattatttc  720
aacaccgtgc tgacacagaa acaactggac atctacaatg ccgtgatcgg cggaaaaagc  780
ctggacgaga acagcagaat ccagggcctg aacgagtaca tcaacctcta caaccagcag  840
cataaggaca agaagctgcc tttcctgaag cccctgttca agcaaatcct gtccgataga  900
aacagcctgt cctggctgcc tgaggccttc gacaacgaca agcaggtgct gcaggccgtg  960
cacgactgct acaccagcct gctggaatct gtgttccaca aggacggcct gcaacagctg  1020
ctgcagagcc tcccaaccta caacttaaaa ggcatctacc tgcggaacga ccttagcatg  1080
accaatgtgt cccagaaagct gctgggcgat tggggcgcta tcaccagagc cgtgaaggaa  1140
aagctgcaga aggaaaaccc tgccaagaag agagagtcgg acgaggccta ccaggagcgg  1200
atcaacaaga tcttcaagca ggccggctca tattcactgg attacatcaa ccaggccctc  1260
gaagccacag accagacaaa catcaaagtg gaggactact ttatcaacat gggcgtggat  1320
aatgagcaga aagagcctct gtttcaaagg gtggcccagg cctataacca ggccagcgac  1380
ctgctggaaa aagaataccc cgctaacaag aatctgatgc aggacaagga gagcatcgag  1440
cacatcaaat tcctgctcga caaccttaag gccgtgcagc acttcatcaa gcctctgctg  1500
ggagatggca acgaagccga caaggacaac agattctacg gcgagctaac cgccctgtgg  1560
aacgaacttg accaggtgac ccgcctgtac aacaaggtgc ggaattacat gaccaggaag  1620
ccttacagcg tggacaagat caaaatcaac ttcaagaaca gcaccctgct gaacggatgg  1680
gacagaaaca aggaacggga caacacagct gtcatcctga gaaaggacgg caagttctac  1740
ctcgccatca tgcacaagga acacaacaag gtctttgaga agtttcctgt gggcactaag  1800
gattctgact tcgagaagat ggaatacaag ctgctgcccg gcgccaacaa gatgctgcct  1860
aaggttttct ttagcaagag cagaatcgac gagttcaagc catctgccga gctgctgcag  1920
aagtaccaga tgggaactca caagaaggga gaactgttca gcctgaacga ttgccacagc  1980
ctgatcgact tcttcaaagc ctctatcgag aagcacgatg attggaagca gttcaacttc  2040
catttcagcc ctaccagcag ctacgaggac ctgagcggct tctaccggga ggtggaacag  2100
cagggctaca agctgacctt caagagcgtg gacgctgatt acatcaataa gatggtcgat  2160
gaaggcaaaa tcttcctgtt ccagatctac aacaaggatt ttagcgagca cagcaagggc  2220
acacctaacc tgcacaccct gtactggaag atgctgttcg acgagagaaa cctgcagaac  2280
gtggtgtaca agctgaacgg cgaagctgag gtgttctttc ggaagaagag cctgacctac  2340
acacgcccca cccaccctaa gaaggagcct atcaagaaca aaaacgtgca gaacgctaaa  2400
aaggaaagca tcttcgatta cgacctgatc aagaacaaaa gattcacagt ggattctttc  2460
cagttccacg tgcctatcac aatgaacttc aaatctgagg gcagaagcaa cctgaatgag  2520
agggtgaacg agttcctgag acaaaacaac gatgcccaca tcatcggaat cgacagaggc  2580
gaaaggcatc tgctgtacct ggtggtgatt gatagacacg gcaacatcgt ggaacaattt  2640
agcctgaaca gcataatcaa tgagtaccaa ggcaatacct acgccacaaa ctatcacgac  2700
ctcctggaca agagagagaa ggagcgggaa gaggccagag agtcctggca gtctatcgag  2760
aacatcaagg agctcaaaga aggctacctg agtcaggtgg tgcacaaaat cgccgacctg  2820
atggtgaagt atcacgccat cgtggtgctg gaggacctga acatgggctt catgagaggc  2880
cgacagaagg tagagaagca ggtttaccag aaattcgaga agatgctgat tgacaagctg  2940
aactatctgg tggacaaaaa gcaagatgct gaaaccgacg gcggcctgct caaggcctac  3000
caactgacca accagttcga gagcttccag aagctgggca aacagtctgg cttcctgttt  3060
tacgtgcccg cctggaacac cagcaagatc gatccctgta caggcttcac caacctgctg  3120
gacacccgat acgagagcat cgaaaaagca aagaagttct tccaaacatt caacgccata  3180
agatacaacg ctgctcaggg gtattttgag ttcgagctcg actacaacaa gtttaacaag  3240
cgggccgatg gcacccagac cctgtggaca ctgtgcacct acggacctag aatcgaaacc  3300
ctgcggagca cagaggacaa caacaagtgg accagcaaag aggtggacct gacagacgag  3360
ctgaagaaac acttctacca ctacggcatc aagttggatg ccgacctgaa agaggccatc  3420
ggccagcaaa cagacaagcc cttcttcacc aacctgctgc acctgctgaa gctgacactg  3480
cagatgagaa acagcaagat cggaaccgag gtggactacc tgattagccc catcagaaac  3540
gaagatggca ccttctacga cagcagacag ggaaacaaga gcctgcctgc taatgcggac  3600
gccaatggcg cctacaacat cgctagaaaa ggcctctggg tcatcaacca gatcaaacag  3660
acccctcagg atcagaaacc taagctggcc atcaccaata aggagtggct gcagttcgcc  3720
caggagaaac catacctgaa agac                                        3744
```

```
SEQ ID NO: 114          moltype = DNA  length = 3867
FEATURE                 Location/Qualifiers
source                  1..3867
                        mol_type = other DNA
                        organism = synthetic construct
SEQUENCE: 114
atgggctccg gagacatgaa gagcctgaac tcttttcaga accaatactc tctgagcaaa  60
accctgcggt tccagctgat ccctcagggc aagacactgg ataatatcaa cgagagcaga  120
atcctggaag aggatcagca cagaagcgag tcatataaac tggtgaagaa gatcattgac  180
gactatcaca aggcctacat cgagcaggcc ctgggcagct tcgagctgaa aattgcctcc  240
gatagcaaga acgacagcct ggaggagttc tactctcagt acattgcgga gagaaaggag  300
gacaaggcca agaagctgtt cgaaaagacc caggacaatc tgagaaagca gatctccaag  360
aagctgaaac agggtgaagc ctacaaacgg ctgttcggca aagaactgat ccaggaggac  420
ctgctggagt tcgtggccac agatcctgag gccgactcta agaagagact gatcgaagag  480
ttcaaggact ttaccaccta cttcatcgga tttcacgaaa atagaaagaa catgtacgcc  540
```

```
gaggaggctc agagcacagc tattgcctac agaatcatcc acgagaacct gccaaagttt  600
atcgataata tcagaacctt cgaggaactg gccaagagca gcatcgccga cgtgctgccc  660
caggtctacg aggactttaa ggcctacctg aaggtggaaa gcgtgaaaga actgttctct  720
ctggattatt tcaacaccgt gctgacacag aaacaactgg acatctacaa tgccgtgatc  780
ggcggaaaaa gcctggacga gaacagcaga atccagggcc tgaacgagta catcaacctc  840
tacaaccagc agcataagga caagaagctg cctttcctga agcccctgtt caagcaaatc  900
ctgtccgata gaaacagcct gtcctggctg cctgaggcct tcgacaacga caagcaggtg  960
ctgcaggccg tgcacgactg ctacaccagc ctgctggaat ctgtgttcca caaggacggc  1020
ctgcaacagc tgctgcagag cctcccaacc tacaacttaa aggcatcta cctgcggaac  1080
gaccttagca tgaccaatgt gtcccagaag ctgctgggcg attggggcgc tatcaccaga  1140
gccgtgaagg aaaagctgca gaaggaaaac cctgccaaga agagagagtc ggacgaggcc  1200
taccaggagc ggatcaacaa gatcttcaag caggccggct catattcact ggattacatc  1260
aaccaggccc tcgaagccac agaccagaca aacatcaaag tggaggacta ctttatcaac  1320
atgggcgtgg ataatgagca gaaagagcct ctgtttcaaa gggtggccca ggcctataac  1380
caggccagcg acctgctgga aaaagaatac cccgctaaca agaatctgat gcaggacaag  1440
gagagcatcg agcacatcaa attcctgctc gacaacctta aggccgtgca gcacttcatc  1500
aagcctctgc tgggagatgg caacgaagcc gacaaggaca acagattcta cggcgagcta  1560
accgccctgt ggaacgaact tgaccaggtg acccgcctgt acaacaaggt gcggaattac  1620
atgaccagga agccttacag cgtggacaag atcaaaatca acttcaagaa cagcaccctg  1680
ctgaacggat gggacagaaa caaggaacgg gacaacacag ctgtcatcct gagaaaggac  1740
ggcaagttct acctcgccat catgcacaag gaacacaaca aggtctttga gaagtttcct  1800
gtgggcacta aggattctga cttcgagaag atggaataca agctgctgcc cggcgccaac  1860
aagatgctgc ctaaggtttt ctttagcaag agcagaatcg acgagttcaa gccatctgcc  1920
gagctgctgc agaagtacca gatgggaact cacaagaagg gagaactgtt cagcctgaac  1980
gattgccaca gcctgatcga cttcttcaaa gcctctatcg agaagcacga tgattggaag  2040
cagttcaact tccatttcag ccctaccagc agctacgagg acctgagcgg cttctaccgg  2100
gaggtggaac agcagggcta caagctgacc ttcaagagcg tggacgctga ttacatcaat  2160
aagatggtcg atgaaggcaa aatcttcctg ttccagatct acaacaagga ttttagcgag  2220
cacagcaagg gcacacctaa cctgcacacc ctgtactgga agatgctgtt cgacgagaga  2280
aacctgcaga acgtggtgta caagctgaac ggcgaagctg aggtgttctt tcggaagaag  2340
agcctgacct acacacgccc cacccaccct aagaaggagc ctatcaagaa caaaaacgtg  2400
cagaacgcta aaaaggaaag catcttcgat tacgacctga tcaagaacaa aagattcaca  2460
gtggattctt tccagttcca cgtgcctatc acaatgaact tcaaatctga gggcagaagc  2520
aacctgaatg agagggtgaa cgagttcctg agacaaaaca acgatgccca catcatcgga  2580
atcgacagag gcgaaaggca tctgctgtac ctggtggtga ttgatagaca cggcaacatc  2640
gtggaacaat ttagcctgaa cagcataatc aatgagtacc aaggcaatac ctacgccaca  2700
aactatcacg acctcctgga caagagagag aaggagcggg aagaggccag agagtcctgg  2760
cagtctatcg agaacatcaa ggagctcaaa gaaggctacc tgagtcaggt ggtgcacaaa  2820
atcgccgacc tgatggtgaa gtatcacgcc atcgtggtgc tggaggacct gaacatgggc  2880
ttcatgagag gccgacagaa ggtagagaag caggtttacc agaaattcga gaagatgctg  2940
attgacaagc tgaactatct ggtggacaaa aagcaagatg ctgaaaccga cggcggcctg  3000
ctcaaggcct accaactgac caaccagttc gagagcttcc agaagctggg caaacagtct  3060
ggcttcctgt tttacgtgcc cgcctggaac accagcaaga tcgatccctg tacaggcttc  3120
accaacctgc tggacacccg atacgagagc atcgaaaaag caaagaagtt cttccaaaca  3180
ttcaacgcca taagatacaa cgctgctcag gggtattttg agttcgagct cgactacaac  3240
aagtttaaca agcgggccga tggcacccag accctgtgga cactgtgcac ctacggacct  3300
agaatcgaaa ccctgcggag cacagaggac aacaacaagt ggaccagcaa agaggtggac  3360
ctgacagacg agctgaagaa acacttctac cactacggca tcaagttgga tgccgacctg  3420
aaagaggcca tcggccagca aacagacaag cccttcttca ccaacctgct gcacctgctg  3480
aagctgacac tgcagatgag aaacagcaag atcggaaccg aggtggacta cctgattagc  3540
cccatcagaa acgaagatgg caccttctac gacagcagac agggaaacaa gagcctgcct  3600
gctaatgcgg acgccaatgg cgcctacaac atcgctagaa aggcctctgg ggtcatcaac  3660
cagatcaaac agacccctca ggatcagaaa cctaagctgg ccatcaccaa taaggagtgg  3720
ctgcagttcg cccaggagaa accatacctg aaagactcta gaaagcggac agcagacggc  3780
tccgaatttg aaagccctaa gaaaaagaga aaggtgggat ccggcaaacc tatccccaat  3840
cccctgctgg gcctggacag cacctga                                    3867

SEQ ID NO: 115          moltype = AA  length = 1251
FEATURE                 Location/Qualifiers
source                  1..1251
                        mol_type = protein
                        organism = unidentified
SEQUENCE: 115
KAFENFTGLY PLSKTLRFEL KPIGKTLEYI EKHGILDKDK HRANSYVKVK DIIDRYHKQF  60
IEDSLSDSDF KLKYENKGKK ESLEEYFYYY KLRNRDDKQK KDFDEIQKNL RKQIASQLKK  120
QDRFKKRIDKK ELIKEDLLEF VSDDNERNLI NEFKDFTTYF TGFHENRQNM YSDEAKSTAI  180
AYRLIHENLP KFIDNISVFE RVAATDVADC FAQIYSDFEE YLNVNDISEI FRLDYYTEIL  240
TQTQIDAYNL IIGGRSEGNI KIKGLNEYIN LYNQQQKDKS QRLPKLKSLF KQILSDRNAI  300
SWLPESFEND NQLLEKLESC YQSFNETYDD KKSIFVRFRE LLLTISDYEM DKIFLRNDLQ  360
LTDISQKMFG SYSIISRSLL EDLKRGTSRK SKKETDESFE ERLRNIIKNQ DSFAIGTIDS  420
SLQQMDVEEY KKSICDYFPN LSVDDKGDDI FDRIVKAYSE VKDLLNSPYP SDKNLAQEDD  480
DIDKIKNLLE SMKDLQKFVK PLCGKGNESD KDERFYGEFT ALYEELDKIT PLYNMVRNYL  540
TRKPYSTEKI KLNFDNAQLL NGWDLNKESD NTSVILRKDG LYYLAIMNKK HNKVFEKNKL  600
QSDGVCFEKM EYKLLPGANK MLPKVFFSKS RIDEFGPSQR LLDSYQNETH KKGDKFNIED  660
CHELIDFFKR SIDKHEDWSK FSFSFSDTKT YEDLSGFYRE VEHQGYILSF VNVSVDYVNS  720
LVDEGKIYLF QIYNKDFSPF SKGTPNMHTL YWKMLFDEEN LKDVVYKLNG QAEVFFRKSS  780
IKYDKPTHPA NLPIDNKNVS NHKKRSVFEY DLVKDKRYTV DKFQFHVPVT INFKSDGNGN  840
INPLVNDYIK KSDDLHVIGI DRGERHLLYL TVIDMKGNIK KQFSLNEIVN EYKGNTYSTN  900
YHDLLEKRED KRDKERKEWK TIETIKELKE GYLSQVIHKI TELMVEYNAI IVLEDLNLGF  960
```

```
MRGRQKVEKS VYQKFEKMLI DKLNYLADKK KEPEDLGGVL KAYQLANKFE SFQKMGKQSG  1020
FLFYTQAWNT SKIDPVTGFV NLFDTHYENI LKSKNFFSKF DLIKYNSDKD WFEFSFDYNN  1080
FTTKAEGTKT KWTLCTFGNR IISFRNPDNN MQWDGKEINL TEEFKLFFEK FGININSDLH  1140
AEILKQDKKD FFEGLLHLLK LTLQMRNSKT RTDIDYMQSP VADENGVLYN SNKCGKSLPE  1200
NADANGAYNI ARKGLMIIDK IKKSDNLNKI DLTISNKEWL VFAQNKPYLK N           1251

SEQ ID NO: 116          moltype = AA  length = 1252
FEATURE                 Location/Qualifiers
source                  1..1252
                        mol_type = protein
                        organism = unidentified
SEQUENCE: 116
MKAFENFTGL YPLSKTLRFE LKPIGKTLEY IEKHGILDKD KHRANSYVKV KDIIDRYHKQ  60
FIEDSLSDSD FKLKYENKGK KESLEEYFYY YKLRNRDDKQ KKDFDEIQKN LRKQIASQLK  120
KQDRFKRIDK KELIKEDLLE FVSDDNERNL INEFKDFTTY FTGFHENRQN MYSDEAKSTA  180
IAYRLIHENL PKFIDNISVF ERVAATDVAD CFAQIYSDFE EYLNVNDISE IFRLDYYTEI  240
LTQTQIDAYN LIIGGRSEGN IKIKGLNEYI NLYNQQQKDK SQRLPKLKSL FKQILSDRNA  300
ISWLPESFEN DNQLLEKLES CYQSFNETYD DKKSIFVRFR ELLLTISDYE MDKIFLRNDL  360
QLTDISQKMF GSYSIISRSL LEDLKRGTSR KSKKETDESF EERLRNIIKN QDSFAIGTID  420
SSLQQMDVEE YKKSICDYFP NLSVDDKGDD IFDRIVKAYS EVKDLLNSPY PSDKNLAQED  480
DDIDKIKNLL ESMKDLQKFV KPLCGKGNES DKDERFYGEF TALYEELDKI TPLYNMVRNY  540
LTRKPYSTEK IKLNFDNAQL LNGWDLNKES DNTSVILRKD GLYYLAIMNK KHNKVFEKNK  600
LQSDGVCFEK MEYKLLPGAN KMLPKVFFSK SRIDEFGPSQ RLLDSYQNET HKKGDKFNIE  660
DCHELIDFFK RSIDKHEDWS KFSFSFSDTK TYEDLSGFYR EVEHQGYILS FVNVSVDYVN  720
SLVDEGKIYL FQIYNKDFSP FSKGTPNMHT LYWKMLFDEE NLKDVVYKLN GQAEVFFRKS  780
SIKYDKPTHP ANLPIDNKNV SNHKKRSVFE YDLVKDKRYT VDKFQFHVPV TINFKSDGNG  840
NINPLVNDYI KKSDDLHVIG IDRGERHLLY LTVIDMKGNI KKQFSLNEIV NEYKGNTYST  900
NYHDLLEKRE DKRDKERKEW KTIETIKELK EGYLSQVIHK ITELMVEYNA IIVLEDLNLG  960
FMRGRQKVEK SVYQKFEKML IDKLNYLADK KKEPEDLGGV LKAYQLANKF ESFQKMGKQS  1020
GFLFYTQAWN TSKIDPVTGF VNLFDTHYEN ILKSKNFFSK FDLIKYNSDK DWFEFSFDYN  1080
NFTTKAEGTK TKWTLCTFGN RIISFRNPDN NMQWDGKEIN LTEEFKLFFE KFGININSDL  1140
HAEILKQDKK DFFEGLLHLL KLTLQMRNSK TRTDIDYMQS PVADENGVLY NSNKCGKSLP  1200
ENADANGAYN IARKGLMIID KIKKSDNLNK IDLTISNKEW LVFAQNKPYL KN          1252

SEQ ID NO: 117          moltype = AA  length = 1291
FEATURE                 Location/Qualifiers
source                  1..1291
                        mol_type = protein
                        organism = synthetic construct
SEQUENCE: 117
MGSGKAFENF TGLYPLSKTL RFELKPIGKT LEYIEKHGIL DKDKHRANSY VKVKDIIDRY  60
HKQFIEDSLS DSDFKLKYEN KGKKESLEEY FYYYKLRNRD DKQKKDFDEI QKNLRKQIAS  120
QLKKQDRFKR IDKKELIKED LLEFVSDDNE RNLINEFKDF TTYFTGFHEN RQNMYSDEAK  180
STAIAYRLIH ENLPKFIDNI SVFERVAATD VADCFAQIYS DFEEYLNVND ISEIFRLDYY  240
TEILTQTQID AYNLIIGGRS EGNIKIKGLN EYINLYNQQQ KDKSQRLPKL KSLFKQILSD  300
RNAISWLPES FENDNQLLEK LESCYQSFNE TYDDKKSIFV RFRELLLTIS DYEMDKIFLR  360
NDLQLTDISQ KMFGSYSIIS RSLLEDLKRG TSRKSKKETD ESFEERLRNI IKNQDSFAIG  420
TIDSSLQQMD VEEYKKSICD YFPNLSVDDK GDDIFDRIVK AYSEVKDLLN SPYPSDKNLA  480
QEDDDIDKIK NLLESMKDLQ KFVKPLCGKG NESDKDERFY GEFTALYEEL DKITPLYNMV  540
RNYLTRKPYS TEKIKLNFDN AQLLNGWDLN KESDNTSVIL RKDGLYYLAI MNKKHNKVFE  600
KNKLQSDGVC FEKMEYKLLP GANKMLPKVF FSKSRIDEFG PSQRLLDSYQ NETHKKGDKF  660
NIEDCHELID FFKRSIDKHE DWSKFSFSFS DTKTYEDLSG FYREVEHQGY ILSFVNVSVD  720
YVNSLVDEGK IYLFQIYNKD FSPFSKGTPN MHTLYWKMLF DEENLKDVVY KLNGQAEVFF  780
RKSSIKYDKP THPANLPIDN KNVSNHKKRS VFEYDLVKDK RYTVDKFQFH VPVTINFKSD  840
GNGNINPLVN DYIKKSDDLH VIGIDRGERH LLYLTVIDMK GNIKKQFSLN EIVNEYKGNT  900
YSTNYHDLLE KREDKRDKER KEWKTIETIK ELKEGYLSQV IHKITELMVE YNAIIVLEDL  960
NLGFMRGRQK VEKSVYQKFE KMLIDKLNYL ADKKKEPEDL GGVLKAYQLA NKFESFQKMG  1020
KQSGFLFYTQ AWNTSKIDPV TGFVNLFDTH YENILKSKNF FSKFDLIKYN SDKDWFEFSF  1080
DYNNFTTKAE GTKTKWTLCT FGNRIISFRN PDNNMQWDGK EINLTEEFKL FFEKFGININ  1140
SDLHAEILKQ DKKDFFEGLL HLLKLTLQMR NSKTRTDIDY MQSPVADENG VLYNSNKCGK  1200
SLPENADANG AYNIARKGLM IIDKIKKSDN LNKIDLTISN KEWLVFAQNK PYLKNSRKRT  1260
ADGSEFESPK KKRKVGSGKP IPNPLLGLDS T                                 1291

SEQ ID NO: 118          moltype = DNA  length = 3759
FEATURE                 Location/Qualifiers
source                  1..3759
                        mol_type = unassigned DNA
                        organism = unidentified
SEQUENCE: 118
atgaaagcat ttgagaattt tacaggattg tatcctcttt ctaaaacatt aagatttgag  60
ctgaaaccga ttggaaagac attggaatat attgagaagc atggtattct tgataaggat  120
aaacacagag caaatagtta tgttaaggtc aaggatataa ttgacagata tcataaacaa  180
tttattgaag actcgttaag tgatagtgat tttaaactta aatatgaaaa caaaggaaag  240
aaagaatcat tagaagaata tttctattat tataaattaa gaaatagaga cgacaaacag  300
aagaaagatt ttgatgaaat tcaaaagaat cttagaaaac agattgcaag tcaattaaag  360
aaacaagatc gttttaaaag aattgataaa aaggaactta taaaggaaga tcttttagaa  420
tttgttagtg atgataatga aaggaatctt attaatgaat ttaaagattt cacgacatat  480
tttacaggtt ttcacgaaaa cagacaaaat atgtattctg atgaagccaa atcaactgcg  540
atagcgtata gactgataca tgagaatctt cctaaattta tagataacat ttcagttttt  600
```

gaaagagttg ctgctacaga tgtggctgat tgttttgcac aaatctattc tgattttgag 660
gaatatctga atgtaaatga tatatctgaa atttttagat tagactatta tacggaaata 720
ttaactcaga cacagattga tgcttataat ctgataattg gaggacgttc tgagggcaat 780
attaaaataa aaggtttgaa cgaatatatt aatctgtata atcaacagca gaaagacaag 840
tctcaacggt tgccaaaact gaagtctttg tttaaacaga ttttgagtga tagaaatgct 900
atatcttggt tgccagaatc gtttgaaaat gataatcaac tcttggaaaa gttggagagt 960
tgttatcagt cttttaatga aacatatgac gataagaagt caatatttgt aaggtttaga 1020
gaattattgt tgactatatc tgattatgaa atggataaaa tatttcttcg taatgatttg 1080
cagttgacag atatttcaca aaagatgttc ggtagttata gtattatttc aaggtcttta 1140
ttggaagatt taaagagagg tacatctcgt aaatcaaaga aggaaactga tgaaagtttt 1200
gaagaaaggt tgagaaatat tatcaaaaac caagatagtt ttgccattgg aacaatagat 1260
tcgtctttgc aacaaatgga tgttgaagaa tacaagaaat ctatttgtga ttatttccct 1320
aatttatctg ttgatgacaa aggagatgat atttttgata gaatagtaaa agcgtattcg 1380
gaggttaaag acttgttgaa ttctccgtat ccgtcagata aaaaccttgc tcaagaagat 1440
gatgatattg ataagattaa aaatctttta gagtcaatga aagatcttca gaagtttgtg 1500
aaacctctct gtggaaaagg aaatgaatct gataaagatg agcgtttcta tggtgagttt 1560
acggctttat atgaagaatt agacaagata acaccattat ataatatggt gagaaattat 1620
cttactcgca aaccgtattc tacggaaaag ataaagttaa actttgacaa tgctcaactt 1680
ttgaatggat gggatttaaa taaagaaagt gataatacga gtgtcatatt gcgtaaagac 1740
ggattgtatt atcttgccat catgaacaag aagcataata aagtcttcga gaaaaataaa 1800
ttacagtcag atggtgtttg ctttgaaaaa atggagtata aattacttcc tggtgcaaac 1860
aagatgcttc caaaagtttt cttctctaaa tcaaggatag atgagtttgg accttctcaa 1920
agattgttgg acagttatca gaatgaaact cataaaaaag gtgataaatt caatattgaa 1980
gattgccatg aattgataga ttttttcaaa aggtctattg ataaacatga ggattggagt 2040
aaatttagct ttagtttctc agatactaag acatatgaag atttaagcgg attttacaga 2100
gaagttgagc atcagggtta tatactttct tttgtaaatg tttctgtaga ttatgtaaat 2160
agtttggtag atgaaggaaa gatatattta tttcaaattt ataataaaga tttctcgcca 2220
tttagcaaag gaactccaaa tatgcatact ttgtattgga aaatgctttt tgatgaagaa 2280
aatctgaaag atgtggtgta taaattgaat ggtcaggcag aagtgttttt caggaaatcc 2340
agtataaagt atgataaacc gactcatcct gctaatttgc ctattgataa taaaaatgta 2400
tctaaccata agaaacggag tgtctttgag tatgatttgg tcaaagataa gagatatacg 2460
gttgataaat tccagtttca tgttcctgta acaatcaatt ttaaaagtga tggaaatgga 2520
aatatcaatc ctctcgtcaa tgattatatc aaaaagtctg atgatttgca tgtgattggt 2580
atcgacaggg gagagcgtca tcttttgtat cttacggtca tagatatgaa aggtaatatc 2640
aagaagcagt tttcattgaa tgaaatcgtc aatgaatata aaggaaatac atatagtacc 2700
aattatcatg atttgttgga aaaacgcgag gacaaacgtg ataaggaaag aaaagaatgg 2760
aaaactatag aaaccatcaa ggagttgaaa gaaggttatc tcagccaggt tattcataaa 2820
ataacggaat tgatggttga atataatgca atcattgtgc tggaggatct taatttagga 2880
tttatgcgtg ggcgacaaaa ggtggagaag tctgtttatc aaaagtttga aaagatgttg 2940
attgataaac tgaattatct tgctgataaa aagaaagaac cggaagattt gggtggtgtg 3000
ttgaaggcat atcaactggc aaataagttt gaaagttttc aaaaaatggg aaaacaatca 3060
ggtttcttat tctataccca agcatggaat acaagtaaga tagatccggt tactggtttt 3120
gttaatcttt ttgacacaca ttatgagaat atcttaaagt ctaaaaattt cttctctaag 3180
tttgatttga taaagtataa ttctgataaa gattggttcg agttttcttt tgattataat 3240
aattttacaa ctaaagcaga aggtacaaaa acaaaatgga cattatgtac ctttggaaat 3300
agaataatat cattccgtaa tcctgataat aatatgcaat gggatggaaa agaaattaat 3360
cttactgaag aattcaagtt attctttgag aaatttggaa tcaatattaa ttctgatttg 3420
catgcggaaa tattaaaaca agataaaaaa gacttctttg aaggtctttt gcatttgttg 3480
aaattgacat tgcagatgcg taatagtaag actcgcactg atatagatta tatgcagtct 3540
cctgtagcag acgaaaacgg agtgttatac aatagtaata aatgtggtaa atccttgcca 3600
gaaaatgctg atgctaacgg tgcgtataat attgcaagaa aaggtcttat gataattgac 3660
aaaataaaga agtctgataa tctgaataaa atagatctta cgatctctaa taaggagtgg 3720
ttggtattcg cacaaaataa accatatttg aagaattga 3759

SEQ ID NO: 119 moltype = DNA length = 3753
FEATURE Location/Qualifiers
source 1..3753
mol_type = other DNA
organism = synthetic construct
SEQUENCE: 119
aaggccttcg agaacttcac cggcctgtat cccctctcta aaccctgag atttgagctg 60
aagccaatcg gcaagaccct cgaatacatt gagaagcacg gcatcctgga caaggacaag 120
cacagagcca atagctacgt gaaggtgaag gacatcatcg acagatacca caaacagttc 180
atcgaggact ctctgtctga tagcgacttc aagctaaagt acgagaacaa aggcaagaag 240
gagagcctgg aagagtactt ctactactac aagctgcgga accgggatga taagcaaaag 300
aaagattttg atgagatcca gaagaacctg agaaaacaaa tcgccagcca gctcaaaaaa 360
caggacagat tcaagcggat cgacaagaaa gaactgatca aggaagatct gctggagttc 420
gtgagcgacg acaatgaaag aaacctgatc aacgagttca aggattttac tacatacttt 480
accggcttcc acgagaaccg gcagaacatg tactctgatg aggccaagtc caccgccatc 540
gcttatagac tgattcacga gaatctgcct aagttcatcg ataacataag cgtgttcgag 600
cgggtcgcag ctacagatgt ggccgactgc ttcgcccaga tctactccga tttcgaggaa 660
tacctgaacg tgaacgacat cagcgagatc ttcagactgg actactatac agaaatcctg 720
acccagaccc agatcgacgc ctacaatctg atcattggcg gcagaagcga gggcaacatc 780
aaaattaaag gcttgaacga gtacatcaat ctgtacaacc agcagcagaa agacaagagc 840
caaagactgc ccaagctgaa gagcctgttt aaacagatcc tgagcgacag aaatgccata 900
tcttggttgc ctgagtcttt cgagaacgat aaccagctgc tggagaagct ggagagctgc 960
taccagagct tcaacgaaac ctacgacgac aagaagtcta tctttgttag atttagagaa 1020
ctgctgctga caatctctga ctacgagatg gacaaaatct tcctgagaaa tgacctgcag 1080
ctgaccgaca tctcccaaaa aatgttcgga tcttacagca tcatctcccg gagcctgtta 1140

```
gaggatctca agagaggaac cagccggaag tcaaagaagg aaacagacga gagcttcgaa  1200
gaacggctgc gcaacattat caagaatcag gactcctttg ccatcggcac catcgatagc  1260
agcctgcagc agatggacgt ggaagagtac aagaaatcca tctgcgacta tttccctaat  1320
ctgagtgttg acgacaaggg cgatgacata tttgacagaa tcgtgaaagc ctatagcgag  1380
gtgaaggacc tgctgaactc cccttaccct agcgacaaga acctggctca ggaggacgac  1440
gacatcgaca agatcaaaaa cctgctggaa agcatgaagg acctgcagaa gttcgtcaag  1500
cctctgtgtg gcaagggcaa cgagagcgat aaggatgaaa ggttctacgg cgagttcaca  1560
gccctgtacg aggaactgga caagatcacc cctctgtaca atatggtgcg gaactacctg  1620
acaagaaagc catactctac cgagaagatc aaactgaact tcgacaacgc ccagctgctg  1680
aacggatggg acctgaataa agagagcgac aacaccagcg tcatcctgcg taaggatggc  1740
ctgtactacc tggccatcat gaacaagaag cacaacaagg tgttcgagaa gaacaagctc  1800
caaagcgatg gcgtgtgctt cgagaagatg gagtacaagc tgctgcctgg cgccaacaag  1860
atgctgccaa aggtgttctt ctctaagagc agaatcgatg agttcggccc ttctcagaga  1920
ctgctggaca gctaccagaa cgaaacccac aagaagggcg acaaattcaa catcgaggac  1980
tgtcacgagc tgatcgactt tttcaaaaga agcatcgaca aacatgaaga ttggagcaag  2040
ttttctttta gcttcagcga caccaagacc tacgaggacc tgagcggctt ctacagagaa  2100
gtagaacacc agggctacat cctgagcttt gtgaacgtga gcgtggatta cgtgaacagc  2160
ctggtggacg agggaaagat ctacttattt cagatctaca acaaggattt cagccctttc  2220
tctaagggca cccctaacat gcacacactg tactggaaga tgctgttcga cgaggaaaac  2280
ctgaaggatg tggtgtacaa gctgaatggc caggccgaag tgttcttcag aaagtcctct  2340
atcaagtacg acaaacctac ccatcctgcc aatctcccca tcgataacaa gaacgtgagc  2400
aaccacaaga agcggagcgt gttcgagtac gacctggtga aggacaaacg ttacaccgtg  2460
gataagttcc agttccacgt gcccgtgacc atcaacttca agagcgatgg caacggcaat  2520
atcaaccccc tggtgaacga ctacatcaag aagagcgacg atctacacgt gatcggcatc  2580
gacagaggag aacggcacct gctgtacctg acggtgatcg acatgaaggg caacatcaag  2640
aaacaattta gcctgaacga gatcgtgaac gaatataagg gcaataccta cagcaccaac  2700
taccacgacc tgctggagaa acgggaagat aagagagata aggagagaaa ggaatggaaa  2760
accattgaaa caatcaagga actgaaagaa ggatatctga gccaggtgat ccacaagatc  2820
accgagctga tggtggagta caacgccatc atcgtcctgg aggacctgaa cctgggcttc  2880
atgagaggga gacagaaggt ggagaagtcc gtataccaga aatttgaaaa gatgctgatc  2940
gacaagctga actacctggc tgacaagaaa aaggaacctg aggaccttgg aggcgtcctg  3000
aaggcctacc agctggccaa caaattcgaa tctttccaaa agatgggcaa acagagcggc  3060
tttctgtttt acacccaggc ttggaacacc agcaagatcg accccgtgac gggcttcgtg  3120
aacctcttcg atacacatta cgagaacatc ctgaagagca agaatttctt cagcaagttc  3180
gatctcatca aatataacag cgataaagat tggttcgagt tctcgttcga ctacaacaat  3240
ttcaccacca aggccgaggg caccaaaaca aagtggacac tgtgcacctt cggaaacaga  3300
atcatcagct ttagaaaccc tgacaacaac atgcagtggg atggcaagga gatcaacctg  3360
acagaggagt tcaagctgtt cttcgagaag ttcggcatca acatcaactc cgacctgcac  3420
gctgagatcc tgaagcaaga caagaaggac ttcttcgagg gcctgctgca cctgctgaaa  3480
ctgacactcc agatgcggaa cagcaagacg aggaccgata tcgactacat gcagagcccc  3540
gtggccgacg agaatggggt gctgtacaac tccaacaaat gcggcaagag cctgcccgag  3600
aacgccgatg ccaacggagc ctacaacatc gctagaaagg gactgatgat cattgacaag  3660
atcaagaagt ctgacaacct gaacaagatc gatctgacta tctctaacaa ggaatggctg  3720
gtgttcgccc agaacaagcc ttacctgaaa aat                                3753

SEQ ID NO: 120          moltype = DNA  length = 3876
FEATURE                 Location/Qualifiers
source                  1..3876
                        mol_type = other DNA
                        organism = synthetic construct
SEQUENCE: 120
atgggctccg gaaaggcctt cgagaacttc accggcctgt atcccctctc taaaaccctg  60
agatttgagc tgaagccaat cggcaagacc ctcgaataca ttgagaagca cggcatcctg  120
gacaaggaca agcacagagc caatagctac gtgaaggtga aggacatcat cgacagatac  180
cacaaacagt tcatcgagga ctctctgtct gatagcgact tcaagctaaa gtacgagaac  240
aaaggcaaga aggagagcct ggaagagtac ttctactact acaagctgcg gaaccgggat  300
gataagcaaa agaaagattt tgatgagatc cagaagaacc tgagaaaaca aatcgccagc  360
cagctcaaaa aacaggacag attcaagcgg atcgacaaga aagaactgat caaggaagat  420
ctgctggagt tcgtgagcga cgacaatgaa agaaacctga tcaacgagtt caaggatttt  480
actacatact ttaccggctt ccacgagaac cggcagaaca tgtactctga tgaggccaag  540
tccaccgcca tcgcttatag actgattcac gagaatctgc ctaagttcat cgataacata  600
agcgtgttcg agcgggtcgc agctacagat gtggccgact gcttcgccca gatctactcc  660
gatttcgagg aatacctgaa cgtgaacgac atcagcgaga tcttcagact ggactactat  720
acagaaatcc tgacccagac ccagatcgac gcctacaatc tgatcattgg cggcagaagc  780
gagggcaaca tcaaaattaa aggcttgaac gagtacatca atctgtacaa ccagcagcag  840
aaagacaaga gccaaagact gcccaagctg aagagcctgt ttaaacagat cctgagcgac  900
agaaatgcca tatcttggtt gcctgagtct ttcgagaacg ataaccagct gctggagaag  960
ctggagagct gctaccagag cttcaacgaa acctacgacg acaagaagtc tatctttgtt  1020
agatttagag aactgctgct gacaatctct gactacgaga tggacaaaat cttcctgaga  1080
aatgacctgc agctgaccga catctcccaa aaaatgttcg gatcttacag catcatctcc  1140
cggagcctgt tagaggatct caagagagga accagccgga agtcaaagaa ggaaacagac  1200
gagagcttcg aagaacggct gcgcaacatt atcaagaatc aggactcctt tgccatcggc  1260
accatcgata gcagcctgca gcagatggac gtggaagagt acaagaaatc catctgcgac  1320
tatttcccta atctgagtgt tgacgacaag ggcgatgaca tatttgacag aatcgtgaaa  1380
gcctatagcg aggtgaagga cctgctgaac tccccttacc ctagcgacaa gaacctggct  1440
caggaggacg acgacatcga caagatcaaa aacctgctgg aaagcatgaa ggacctgcag  1500
aagttcgtca agcctctgtg tggcaagggc aacgagagcg ataaggatga aaggttctac  1560
ggcgagttca cagccctgta cgaggaactg gacaagatca cccctctgta caatatggtg  1620
cggaactacc tgacaagaaa gccatactct accgagaaga tcaaactgaa cttcgacaac  1680
```

```
gcccagctgc tgaacggatg ggacctgaat aaagagagcg acaacaccag cgtcatcctg  1740
cgtaaggatg gcctgtacta cctggccatc atgaacaaga agcacaacaa ggtgttcgag  1800
aagaacaagc tccaaagcga tggcgtgtgc ttcgagaaga tggagtacaa gctgctgcct  1860
ggcgccaaca agatgctgcc aaaggtgttc ttctctaaga gcagaatcga tgagttcggc  1920
ccttctcaga gactgctgga cagctaccag aacgaaaccc acaagaaggg cgacaaattc  1980
aacatcgagg actgtcacga gctgatcgac tttttcaaaa gaagcatcga caaacatgaa  2040
gattggagca agttttcttt tagcttcagc gacaccaaga cctacgagga cctgagcggc  2100
ttctacagag aagtagaaca ccagggctac atcctgagct ttgtgaacgt gagcgtggat  2160
tacgtgaaca gcctggtgga cgagggaaag atctacttat ttcagatcta caacaaggat  2220
ttcagccctt tctctaaggg caccccctaac atgcacacac tgtactggaa gatgctgttc  2280
gacgaggaaa acctgaagga tgtggtgtac aagctgaatg gccaggccga agtgttcttc  2340
agaaagtcct ctatcaagta cgacaaacct acccatcctg ccaatctccc catcgataac  2400
aagaacgtga gcaaccacaa gaagcggagc gtgttcgagt acgacctggt gaaggacaaa  2460
cgttacaccg tggataagtt ccagttccac gtgcccgtga ccatcaactt caagagcgat  2520
ggcaacggca atatcaaccc cctggtgaac gactacatca agaagagcga cgatctacac  2580
gtgatcggca tcgacagagg agaacggcac ctgctgtacc tgacggtgat cgacatgaag  2640
ggcaacatca agaaacaatt tagcctgaac gagatcgtga acgaatataa gggcaatacc  2700
tacagcacca actaccacga cctgctggag aaacgggaag ataagagaga taaggagaga  2760
aaggaatgga aaaccattga aacaatcaag gaactgaaag aaggatatct gagccaggtg  2820
atccacaaga tcaccgagct gatggtggag tacaacgcca tcatcgtcct ggaggacctg  2880
aacctgggct tcatgagagg gagacagaag gtggagaagt ccgtatacca gaaatttgaa  2940
aagatgctga tcgacaagct gaactacctg gctgacaaga aaaaggaacc tgaggacctt  3000
ggaggcgtcc tgaaggccta ccagctggcc aacaaattcg aatctttcca aaagatgggc  3060
aaacagagcg gctttctgtt ttacacccag gcttggaaca ccagcaagat cgaccccgtg  3120
acgggcttcg tgaacctctt cgatacacat tacgagaaca tcctgaagag caagaatttc  3180
ttcagcaagt tcgatctcat caaatataac agcgataaag attggttcga gttctcgttc  3240
gactacaaca atttcaccac caaggccgag ggcaccaaaa caaagtggac actgtgcacc  3300
ttcggaaaca gaatcatcag ctttagaaac cctgacaaca acatgcagtg ggatggcaag  3360
gagatcaacc tgacagagga gttcaagctg ttcttcgaga agttcggcat caacatcaac  3420
tccgacctgc acgctgagat cctgaagcaa gacaagaagg acttcttcga gggcctgctg  3480
cacctgctga aactgacact ccagatgcgg aacagcaaga cgaggaccga tatcgactac  3540
atgcagagcc ccgtggccga cgagaatggg gtgctgtaca actccaacaa atgcggcaag  3600
agcctgcccg agaacgccga tgccaacgga gcctacaaca tcgctagaaa gggactgatg  3660
atcattgaca agatcaagaa gtctgacaac ctgaacaaga tcgatctgac tatctctaac  3720
aaggaatggc tggtgttcgc ccagaacaag ccttacctga aaaattctag aaagcggaca  3780
gcagacggct ccgaatttga aagccctaag aaaaagagaa aggtgggatc cggcaaacct  3840
atccccaatc ccctgctggg cctggacagc acctga                            3876
```

```
SEQ ID NO: 121         moltype = AA  length = 1307
FEATURE                Location/Qualifiers
source                 1..1307
                       mol_type = protein
                       organism = synthetic construct
SEQUENCE: 121
MTQFEGFTNL YQVSKTLRFE LIPQGKTLKH IQEQGFIEED KARNDHYKEL KPIIDRIYKT  60
YADQCLQLVQ LDWENLSAAI DSYRKEKTEE TRNALIEEQA TYRNAIHDYF IGRTDNLTDA  120
INKRHAEIYK GLFKAELFNG KVLKQLGTVT TTEHENALLR SFDKFTTYFS GFYENRKNVF  180
SAEDISTAIP HRIVQDNFPK FKENCHIFTR LITAVPSLRE HFENVKKAIG IFVSTSIEEV  240
FSFPFYNQLL TQTQIDLYNQ LLGGISREAG TEKIKGLNEV LNLAIQKNDE TAHIIASLPH  300
RFIPLFKQIL SDRNTLSFIL EEFKSDEEVI QSFCKYKTLL RNENVLETAE ALFNELNSID  360
LTHIFISHKK LETISSALCD HWDTLRNALY ERRISELTGK ITKSAKEKVQ RSLKHEDINL  420
QEIISAAGKE LSEAFKQKTS EILSHAHAAL DQPLPTTLKK QEEKEILKSQ LDSLLGLYHL  480
LDWFAVDESN EVDPEFSARL TGIKLEMEPS LSFYNKARNY ATKKPYSVEK FKLNFQMPTL  540
ASGWDVNKEK NNGAILFVKN GLYYLGIMPK QKGRYKALSF EPTEKTSEGF DKMYYDYFPD  600
AAKMIPKCST QLKAVTAHFQ THTTPILLSN NFIEPLEITK EIYDLNNPEK EPKKFQTAYA  660
KKTGDQKGYR EALCKWIDFT RDFLSKYTKT TSIDLSSLRP SSQYKDLGEY YAELNPLLYH  720
ISFQRIAEKE IMDAVETGKL YLFQIYNKDF AKGHHGKPNL HTLYWTGLFS PENLAKTSIK  780
LNGQAELFYR PKSRMKRMAH RLGEKMLNKK LKDQKTPIPD TLYQELYDYV NHRLSHDLSD  840
EARALLPNVI TKEVSHEIIK DRRFTSDKFF FHVPITLNYQ AANSPSKFNQ RVNAYLKEHP  900
ETPIIGIDRG ERNLIYITVI DSTGKILEQR SLNTIQQFDY QKKLDNREKE RVAARQAWSV  960
VGTIKDLKQG YLSQVIHEIV DLMIHYQAVV VLENLNFGFK SKRTGIAEKA VYQQFEKMLI  1020
DKLNCLVLKD YPAEKVGGVL NPYQLTDQFT SFAKMGTQSG FLFYVPAPYT SKIDPLTGFV  1080
DPFVWKTIKN HESRKHFLEG FDFLHYDVKT GDFILHFKMN RNLSFQRGLP GFMPAWDIVF  1140
EKNETQFDAK GTPFIAGKRI VPVIENHRFT GRYRDLYPAN ELIALLEEKG IVFRDGSNIL  1200
PKLLENDDSH AIDTMVALIR SVLQMRNSNA ATGEDYINSP VRDLNGVCFD SRFQNPEWPM  1260
DADANGAYHI ALKGQLLLNH LKESKDLKLQ NGISNQDWLA YIQELRN                1307

SEQ ID NO: 122         moltype = AA  length = 18
FEATURE                Location/Qualifiers
source                 1..18
                       mol_type = protein
                       organism = synthetic construct
SEQUENCE: 122
KRTADGSEFE SPKKKRKV                                                18

SEQ ID NO: 123         moltype = AA  length = 7
FEATURE                Location/Qualifiers
source                 1..7
                       mol_type = protein
```

```
                        organism = synthetic construct
SEQUENCE: 123
PKKKRKV                                                                  7

SEQ ID NO: 124          moltype = AA  length = 7
FEATURE                 Location/Qualifiers
source                  1..7
                        mol_type = protein
                        organism = synthetic construct
SEQUENCE: 124
PKKKRRV                                                                  7

SEQ ID NO: 125          moltype = AA  length = 16
FEATURE                 Location/Qualifiers
source                  1..16
                        mol_type = protein
                        organism = synthetic construct
SEQUENCE: 125
KRPAATKKAG QAKKKK                                                        16

SEQ ID NO: 126          moltype = AA  length = 11
FEATURE                 Location/Qualifiers
source                  1..11
                        mol_type = protein
                        organism = synthetic construct
SEQUENCE: 126
YGRKKRRQRR R                                                             11

SEQ ID NO: 127          moltype = AA  length = 9
FEATURE                 Location/Qualifiers
source                  1..9
                        mol_type = protein
                        organism = synthetic construct
SEQUENCE: 127
RKKRRQRRR                                                                9

SEQ ID NO: 128          moltype = AA  length = 9
FEATURE                 Location/Qualifiers
source                  1..9
                        mol_type = protein
                        organism = synthetic construct
SEQUENCE: 128
PAAKRVKLD                                                                9

SEQ ID NO: 129          moltype = AA  length = 11
FEATURE                 Location/Qualifiers
source                  1..11
                        mol_type = protein
                        organism = synthetic construct
SEQUENCE: 129
RQRRNELKRS P                                                             11

SEQ ID NO: 130          moltype = AA  length = 8
FEATURE                 Location/Qualifiers
source                  1..8
                        mol_type = protein
                        organism = synthetic construct
SEQUENCE: 130
VSRKRPRP                                                                 8

SEQ ID NO: 131          moltype = AA  length = 8
FEATURE                 Location/Qualifiers
source                  1..8
                        mol_type = protein
                        organism = synthetic construct
SEQUENCE: 131
PPKKARED                                                                 8

SEQ ID NO: 132          moltype = AA  length = 8
FEATURE                 Location/Qualifiers
source                  1..8
                        mol_type = protein
                        organism = synthetic construct
SEQUENCE: 132
PQPKKKPL                                                                 8

SEQ ID NO: 133          moltype = AA  length = 12
FEATURE                 Location/Qualifiers
source                  1..12
```

```
                         mol_type = protein
                         organism = synthetic construct
SEQUENCE: 133
SALIKKKKKM AP                                                    12

SEQ ID NO: 134           moltype = AA  length = 7
FEATURE                  Location/Qualifiers
source                   1..7
                         mol_type = protein
                         organism = synthetic construct
SEQUENCE: 134
PKQKKRK                                                          7

SEQ ID NO: 135           moltype = AA  length = 10
FEATURE                  Location/Qualifiers
source                   1..10
                         mol_type = protein
                         organism = synthetic construct
SEQUENCE: 135
RKLKKKIKKL                                                       10

SEQ ID NO: 136           moltype = AA  length = 10
FEATURE                  Location/Qualifiers
source                   1..10
                         mol_type = protein
                         organism = synthetic construct
SEQUENCE: 136
REKKKFLKRR                                                       10

SEQ ID NO: 137           moltype = AA  length = 20
FEATURE                  Location/Qualifiers
source                   1..20
                         mol_type = protein
                         organism = synthetic construct
SEQUENCE: 137
KRKGDEVDGV DEVAKKKSKK                                            20

SEQ ID NO: 138           moltype = AA  length = 17
FEATURE                  Location/Qualifiers
source                   1..17
                         mol_type = protein
                         organism = synthetic construct
SEQUENCE: 138
RKCLQAGMNL EARKTKK                                               17

SEQ ID NO: 139           moltype = AA  length = 38
FEATURE                  Location/Qualifiers
source                   1..38
                         mol_type = protein
                         organism = synthetic construct
SEQUENCE: 139
NQSSNFGPMK GGNFGGRSSG PYGGGGQYFA KPRNQGGY                        38

SEQ ID NO: 140           moltype = AA  length = 42
FEATURE                  Location/Qualifiers
source                   1..42
                         mol_type = protein
                         organism = synthetic construct
SEQUENCE: 140
RMRIZFKNKG KDTAELRRRR VEVSVELRKA KKDEQILKRR NV                   42

SEQ ID NO: 141           moltype = AA  length = 14
FEATURE                  Location/Qualifiers
source                   1..14
                         mol_type = protein
                         organism = synthetic construct
SEQUENCE: 141
GKPIPNPLLG LDST                                                  14

SEQ ID NO: 142           moltype = AA  length = 9
FEATURE                  Location/Qualifiers
source                   1..9
                         mol_type = protein
                         organism = synthetic construct
SEQUENCE: 142
IPNPLLGLD                                                        9

SEQ ID NO: 143           moltype = AA  length = 166
FEATURE                  Location/Qualifiers
```

```
source                  1..166
                        mol_type = protein
                        organism = synthetic construct
SEQUENCE: 143
SEVEFSHEYW MRHALTLAKR ARDEREVPVG AVLVLNNRVI GEGWNRAIGL HDPTAHAEIM  60
ALRQGGLVMQ NYRLIDATLY VTFEPCVMCA GAMIHSRIGR VVFGVRNSKR GAAGSLMNVL  120
NYPGMNHRVE ITEGILADEC AALLCDFYRM PRQVFNAQKK AQSSIN                166

SEQ ID NO: 144          moltype = RNA  length = 31
FEATURE                 Location/Qualifiers
source                  1..31
                        mol_type = other RNA
                        organism = synthetic construct
SEQUENCE: 144
acgattagaa ataatttcta ctgttgtaga t                                31

SEQ ID NO: 145          moltype = RNA  length = 36
FEATURE                 Location/Qualifiers
source                  1..36
                        mol_type = other RNA
                        organism = synthetic construct
SEQUENCE: 145
ctttgaaaga atataatttc tactgaaagt gtagat                           36

SEQ ID NO: 146          moltype = RNA  length = 36
FEATURE                 Location/Qualifiers
source                  1..36
                        mol_type = other RNA
                        organism = synthetic construct
SEQUENCE: 146
gtttaataat aatacataat ttctactatt gtagat                           36

SEQ ID NO: 147          moltype = RNA  length = 36
FEATURE                 Location/Qualifiers
source                  1..36
                        mol_type = other RNA
                        organism = synthetic construct
SEQUENCE: 147
gtctataaga ctaatttaat ttctactatt gtagat                           36

SEQ ID NO: 148          moltype = RNA  length = 36
FEATURE                 Location/Qualifiers
source                  1..36
                        mol_type = other RNA
                        organism = synthetic construct
SEQUENCE: 148
gtttataaac cttatctaat ttctactgtt gtagat                           36

SEQ ID NO: 149          moltype = RNA  length = 35
FEATURE                 Location/Qualifiers
source                  1..35
                        mol_type = other RNA
                        organism = synthetic construct
SEQUENCE: 149
tctaaagctc tttaagaatt tctactttcg tagat                            35

SEQ ID NO: 150          moltype = RNA  length = 34
FEATURE                 Location/Qualifiers
source                  1..34
                        mol_type = other RNA
                        organism = synthetic construct
SEQUENCE: 150
ctaagaggct caaataattt ctactattgt agat                             34

SEQ ID NO: 151          moltype = RNA  length = 36
FEATURE                 Location/Qualifiers
source                  1..36
                        mol_type = other RNA
                        organism = synthetic construct
SEQUENCE: 151
cctttggaag tactaagaat ttctactgtt gtagat                           36

SEQ ID NO: 152          moltype = RNA  length = 36
FEATURE                 Location/Qualifiers
source                  1..36
                        mol_type = other RNA
                        organism = synthetic construct
SEQUENCE: 152
ggctataaaa gccatataat ttctactatt gtagat                           36
```

```
SEQ ID NO: 153          moltype = RNA  length = 36
FEATURE                 Location/Qualifiers
source                  1..36
                        mol_type = other RNA
                        organism = synthetic construct
SEQUENCE: 153
gactattaag tcttttgaat ttctactgtt gtagat                       36

SEQ ID NO: 154          moltype = RNA  length = 35
FEATURE                 Location/Qualifiers
source                  1..35
                        mol_type = other RNA
                        organism = synthetic construct
SEQUENCE: 154
tctagaatat ataggtaatt tctacttatg tagat                        35

SEQ ID NO: 155          moltype = RNA  length = 37
FEATURE                 Location/Qualifiers
source                  1..37
                        mol_type = other RNA
                        organism = synthetic construct
SEQUENCE: 155
ggcaataagc catatacaat ttctactgta tgtagat                      37

SEQ ID NO: 156          moltype = RNA  length = 36
FEATURE                 Location/Qualifiers
source                  1..36
                        mol_type = other RNA
                        organism = synthetic construct
SEQUENCE: 156
gtctgaaaga ctatataatt tctacttcgt gtagat                       36

SEQ ID NO: 157          moltype = RNA  length = 36
FEATURE                 Location/Qualifiers
source                  1..36
                        mol_type = other RNA
                        organism = synthetic construct
SEQUENCE: 157
gtctacggaa cgtctgtaat ttctactgtt gtagat                       36

SEQ ID NO: 158          moltype = RNA  length = 35
FEATURE                 Location/Qualifiers
source                  1..35
                        mol_type = other RNA
                        organism = synthetic construct
SEQUENCE: 158
tttaaacgaa ctattaaatt tctactgttg tagat                        35

SEQ ID NO: 159          moltype = RNA  length = 36
FEATURE                 Location/Qualifiers
source                  1..36
                        mol_type = other RNA
                        organism = synthetic construct
SEQUENCE: 159
gtttaatact tatatataat ttctactatt gtagat                       36

SEQ ID NO: 160          moltype = RNA  length = 35
FEATURE                 Location/Qualifiers
source                  1..35
                        mol_type = other RNA
                        organism = synthetic construct
SEQUENCE: 160
aataataatc ccttataatt tctacttttg tagat                        35

SEQ ID NO: 161          moltype = RNA  length = 36
FEATURE                 Location/Qualifiers
source                  1..36
                        mol_type = other RNA
                        organism = synthetic construct
SEQUENCE: 161
gtctataaga cgaactaaat ttctactatt gtagat                       36

SEQ ID NO: 162          moltype = RNA  length = 36
FEATURE                 Location/Qualifiers
source                  1..36
                        mol_type = other RNA
                        organism = synthetic construct
SEQUENCE: 162
```

```
ggctactaag cctttataat ttctactatt gtagat                         36

SEQ ID NO: 163          moltype = RNA  length = 36
FEATURE                 Location/Qualifiers
source                  1..36
                        mol_type = other RNA
                        organism = synthetic construct
SEQUENCE: 163
gtctataaag acgaatgaat ttctactatt gtagat                         36

SEQ ID NO: 164          moltype = RNA  length = 23
FEATURE                 Location/Qualifiers
source                  1..23
                        mol_type = other RNA
                        organism = synthetic construct
SEQUENCE: 164
tggcctggag gctatccagc gtg                                       23

SEQ ID NO: 165          moltype = RNA  length = 23
FEATURE                 Location/Qualifiers
source                  1..23
                        mol_type = other RNA
                        organism = synthetic construct
SEQUENCE: 165
ctcacgtcat ccagcagaga atg                                       23

SEQ ID NO: 166          moltype = RNA  length = 23
FEATURE                 Location/Qualifiers
source                  1..23
                        mol_type = other RNA
                        organism = synthetic construct
SEQUENCE: 166
actttccatt ctctgctgga tga                                       23

SEQ ID NO: 167          moltype = RNA  length = 23
FEATURE                 Location/Qualifiers
source                  1..23
                        mol_type = other RNA
                        organism = synthetic construct
SEQUENCE: 167
ctgaattgct atgtgtctgg gtt                                       23

SEQ ID NO: 168          moltype = RNA  length = 23
FEATURE                 Location/Qualifiers
source                  1..23
                        mol_type = other RNA
                        organism = synthetic construct
SEQUENCE: 168
aattctctct ccattcttca gta                                       23

SEQ ID NO: 169          moltype = RNA  length = 23
FEATURE                 Location/Qualifiers
source                  1..23
                        mol_type = other RNA
                        organism = synthetic construct
SEQUENCE: 169
agaatcaaaa tcggtgaata ggc                                       23

SEQ ID NO: 170          moltype = RNA  length = 23
FEATURE                 Location/Qualifiers
source                  1..23
                        mol_type = other RNA
                        organism = synthetic construct
SEQUENCE: 170
tgacacattt gtttgagaat caa                                       23

SEQ ID NO: 171          moltype = RNA  length = 23
FEATURE                 Location/Qualifiers
source                  1..23
                        mol_type = other RNA
                        organism = synthetic construct
SEQUENCE: 171
gagtctctca gctggtacac ggc                                       23

SEQ ID NO: 172          moltype = RNA  length = 23
FEATURE                 Location/Qualifiers
source                  1..23
                        mol_type = other RNA
                        organism = synthetic construct
```

```
SEQUENCE: 172
tctgtgatat acacatcaga atc                                          23

SEQ ID NO: 173         moltype = RNA  length = 23
FEATURE                Location/Qualifiers
source                 1..23
                       mol_type = other RNA
                       organism = synthetic construct
SEQUENCE: 173
attctcaaac aaatgtgtca caa                                          23

SEQ ID NO: 174         moltype = RNA  length = 23
FEATURE                Location/Qualifiers
source                 1..23
                       mol_type = other RNA
                       organism = synthetic construct
SEQUENCE: 174
ccttccgctc acctccgcct gag                                          23

SEQ ID NO: 175         moltype = RNA  length = 23
FEATURE                Location/Qualifiers
source                 1..23
                       mol_type = other RNA
                       organism = synthetic construct
SEQUENCE: 175
gcacgaagct ctccgatgtg ttg                                          23

SEQ ID NO: 176         moltype = RNA  length = 23
FEATURE                Location/Qualifiers
source                 1..23
                       mol_type = other RNA
                       organism = synthetic construct
SEQUENCE: 176
atctgcgcct tgggggccag gga                                          23

SEQ ID NO: 177         moltype = RNA  length = 23
FEATURE                Location/Qualifiers
source                 1..23
                       mol_type = other RNA
                       organism = synthetic construct
SEQUENCE: 177
gaactggccg gctggcctgg gtg                                          23

SEQ ID NO: 178         moltype = AA  length = 22
FEATURE                Location/Qualifiers
source                 1..22
                       mol_type = protein
                       organism = synthetic construct
SEQUENCE: 178
SSDDEATADS QHAAPPKKKR KV                                           22

SEQ ID NO: 179         moltype = AA  length = 8
FEATURE                Location/Qualifiers
source                 1..8
                       mol_type = protein
                       organism = synthetic construct
SEQUENCE: 179
PKKKRKVG                                                           8

SEQ ID NO: 180         moltype = AA  length = 24
FEATURE                Location/Qualifiers
source                 1..24
                       mol_type = protein
                       organism = synthetic construct
SEQUENCE: 180
GRSSDDEATA DSQHAAPPKK KRKV                                         24

SEQ ID NO: 181         moltype = RNA  length = 23
FEATURE                Location/Qualifiers
source                 1..23
                       mol_type = other RNA
                       organism = synthetic construct
SEQUENCE: 181
gtgtcaagct atatcaggca cca                                          23

SEQ ID NO: 182         moltype = RNA  length = 23
FEATURE                Location/Qualifiers
source                 1..23
                       mol_type = other RNA
```

```
                        organism = synthetic construct
SEQUENCE: 182
atgtgtcttt tcccgatatt cct                                             23

SEQ ID NO: 183          moltype = RNA  length = 21
FEATURE                 Location/Qualifiers
source                  1..21
                        mol_type = other RNA
                        organism = synthetic construct
SEQUENCE: 183
tggcctggag gctatccagc g                                               21

SEQ ID NO: 184          moltype = RNA  length = 23
FEATURE                 Location/Qualifiers
source                  1..23
                        mol_type = other RNA
                        organism = synthetic construct
SEQUENCE: 184
tcactggatt tagagtctct cag                                             23

SEQ ID NO: 185          moltype = RNA  length = 23
FEATURE                 Location/Qualifiers
source                  1..23
                        mol_type = other RNA
                        organism = synthetic construct
SEQUENCE: 185
gattctcaaa caaatgtgtc aca                                             23

SEQ ID NO: 186          moltype = RNA  length = 23
FEATURE                 Location/Qualifiers
source                  1..23
                        mol_type = other RNA
                        organism = synthetic construct
SEQUENCE: 186
aagagggaaa tgagatcatg tcc                                             23

SEQ ID NO: 187          moltype = RNA  length = 23
FEATURE                 Location/Qualifiers
source                  1..23
                        mol_type = other RNA
                        organism = synthetic construct
SEQUENCE: 187
accgattttg attctcaaac aaa                                             23

SEQ ID NO: 188          moltype = RNA  length = 23
FEATURE                 Location/Qualifiers
source                  1..23
                        mol_type = other RNA
                        organism = synthetic construct
SEQUENCE: 188
gtctgtgata tacacatcag aat                                             23

SEQ ID NO: 189          moltype = RNA  length = 20
FEATURE                 Location/Qualifiers
source                  1..20
                        mol_type = other RNA
                        organism = synthetic construct
SEQUENCE: 189
gagtctctca gctggtacac                                                 20

SEQ ID NO: 190          moltype = RNA  length = 21
FEATURE                 Location/Qualifiers
source                  1..21
                        mol_type = other RNA
                        organism = synthetic construct
SEQUENCE: 190
gagtctctca gctggtacac g                                               21

SEQ ID NO: 191          moltype = RNA  length = 22
FEATURE                 Location/Qualifiers
source                  1..22
                        mol_type = other RNA
                        organism = synthetic construct
SEQUENCE: 191
gagtctctca gctggtacac gg                                              22

SEQ ID NO: 192          moltype = RNA  length = 24
FEATURE                 Location/Qualifiers
source                  1..24
```

```
                         mol_type = other RNA
                         organism = synthetic construct
SEQUENCE: 192
gagtctctca gctggtacac ggca                                              24

SEQ ID NO: 193           moltype = RNA  length = 23
FEATURE                  Location/Qualifiers
source                   1..23
                         mol_type = other RNA
                         organism = synthetic construct
SEQUENCE: 193
atttgggcag ctcccctacc ccc                                               23

SEQ ID NO: 194           moltype = RNA  length = 23
FEATURE                  Location/Qualifiers
source                   1..23
                         mol_type = other RNA
                         organism = synthetic construct
SEQUENCE: 194
ggcagctccc ctacccccct tac                                               23

SEQ ID NO: 195           moltype = RNA  length = 23
FEATURE                  Location/Qualifiers
source                   1..23
                         mol_type = other RNA
                         organism = synthetic construct
SEQUENCE: 195
caggggtccg agagctcagc tag                                               23

SEQ ID NO: 196           moltype = RNA  length = 23
FEATURE                  Location/Qualifiers
source                   1..23
                         mol_type = other RNA
                         organism = synthetic construct
SEQUENCE: 196
atctgtcccc tccaccccac agt                                               23

SEQ ID NO: 197           moltype = RNA  length = 23
FEATURE                  Location/Qualifiers
source                   1..23
                         mol_type = other RNA
                         organism = synthetic construct
SEQUENCE: 197
tactttgtcc tccggttctg gaa                                               23

SEQ ID NO: 198           moltype = RNA  length = 23
FEATURE                  Location/Qualifiers
source                   1..23
                         mol_type = other RNA
                         organism = synthetic construct
SEQUENCE: 198
tcctccggtt ctggaaccac acc                                               23

SEQ ID NO: 199           moltype = RNA  length = 23
FEATURE                  Location/Qualifiers
source                   1..23
                         mol_type = other RNA
                         organism = synthetic construct
SEQUENCE: 199
agccatctca ctacagataa ctc                                               23

SEQ ID NO: 200           moltype = RNA  length = 23
FEATURE                  Location/Qualifiers
source                   1..23
                         mol_type = other RNA
                         organism = synthetic construct
SEQUENCE: 200
aagctagtct agtgcaagct aac                                               23

SEQ ID NO: 201           moltype = RNA  length = 23
FEATURE                  Location/Qualifiers
source                   1..23
                         mol_type = other RNA
                         organism = synthetic construct
SEQUENCE: 201
gcctctgatt agggtggggg cgt                                               23

SEQ ID NO: 202           moltype = RNA  length = 21
FEATURE                  Location/Qualifiers
```

```
source                  1..21
                        mol_type = other RNA
                        organism = synthetic construct
SEQUENCE: 202
tcacaggctc caggaagggt t                                            21

SEQ ID NO: 203          moltype = RNA  length = 23
FEATURE                 Location/Qualifiers
source                  1..23
                        mol_type = other RNA
                        organism = synthetic construct
SEQUENCE: 203
tctgccaccc acctcctcac ctt                                          23

SEQ ID NO: 204          moltype = RNA  length = 23
FEATURE                 Location/Qualifiers
source                  1..23
                        mol_type = other RNA
                        organism = synthetic construct
SEQUENCE: 204
caggtcatca cagttggggc cac                                          23

SEQ ID NO: 205          moltype = RNA  length = 21
FEATURE                 Location/Qualifiers
source                  1..21
                        mol_type = other RNA
                        organism = synthetic construct
SEQUENCE: 205
gagagtgagg acgtgtgtgt c                                            21

SEQ ID NO: 206          moltype = RNA  length = 20
FEATURE                 Location/Qualifiers
source                  1..20
                        mol_type = other RNA
                        organism = synthetic construct
SEQUENCE: 206
gggtgatcag acccaacagc                                              20

SEQ ID NO: 207          moltype = RNA  length = 21
FEATURE                 Location/Qualifiers
source                  1..21
                        mol_type = other RNA
                        organism = synthetic construct
SEQUENCE: 207
gggtgatcag acccaacagc a                                            21

SEQ ID NO: 208          moltype = RNA  length = 22
FEATURE                 Location/Qualifiers
source                  1..22
                        mol_type = other RNA
                        organism = synthetic construct
SEQUENCE: 208
gggtgatcag acccaacagc ag                                           22

SEQ ID NO: 209          moltype = RNA  length = 23
FEATURE                 Location/Qualifiers
source                  1..23
                        mol_type = other RNA
                        organism = synthetic construct
SEQUENCE: 209
gggtgatcag acccaacagc agg                                          23

SEQ ID NO: 210          moltype = RNA  length = 24
FEATURE                 Location/Qualifiers
source                  1..24
                        mol_type = other RNA
                        organism = synthetic construct
SEQUENCE: 210
gggtgatcag acccaacagc aggt                                         24

SEQ ID NO: 211          moltype = RNA  length = 20
FEATURE                 Location/Qualifiers
source                  1..20
                        mol_type = other RNA
                        organism = synthetic construct
SEQUENCE: 211
gaatttctac tgttgtagat                                              20

SEQ ID NO: 212          moltype = RNA  length = 20
```

```
FEATURE                 Location/Qualifiers
source                  1..20
                        mol_type = other RNA
                        organism = synthetic construct
SEQUENCE: 212
taatttctac tattgtagat                                         20

SEQ ID NO: 213          moltype = RNA  length = 20
FEATURE                 Location/Qualifiers
source                  1..20
                        mol_type = other RNA
                        organism = synthetic construct
SEQUENCE: 213
aatttctact tcgtgtagat                                         20

SEQ ID NO: 214          moltype = AA  length = 228
FEATURE                 Location/Qualifiers
source                  1..228
                        mol_type = protein
                        organism = synthetic construct
SEQUENCE: 214
SSETGPVAVD PTLRRRIEPH EFEVFFDPRE LRKETCLLYE INWGGRHSIW RHTSQNTNKH  60
VEVNFIEKFT TERYFCPNTR CSITWFLSWS PCGECSRAIT EFLSRYPHVT LFIYIARLYH  120
HADPRNRQGL RDLISSGVTI QIMTEQESGY CWRNFVNYSP SNEAHWPRYP HLWVRLYVLE  180
LYCIILGLPP CLNILRRKQP QLTFFTIALQ SCHYQRLPPH ILWATGLK           228

SEQ ID NO: 215          moltype = AA  length = 228
FEATURE                 Location/Qualifiers
source                  1..228
                        mol_type = protein
                        organism = synthetic construct
SEQUENCE: 215
SSKTGPVAVD PTLRRRIEPH EFEVFFDPRE LRKETCLLYE INWGGRHSIW RHTSQNTNKH  60
VEVNFIEKFT TERYFCPNTR CSITWFLSWS PCGECSRAIT EFLSRYPNVT LFIYIARLYH  120
LANPRNRQGL RDLISSGVTI QIMTEQESGY CWHNFVNYSP SNESHWPRYP HLWVRLYVLE  180
LYCIILGLPP CLNILRRKQS QLTSFTIALQ SCHYQRLPPH ILWATGLK           228

SEQ ID NO: 216          moltype = AA  length = 228
FEATURE                 Location/Qualifiers
source                  1..228
                        mol_type = protein
                        organism = synthetic construct
SEQUENCE: 216
SSETGPVAVD PTLRRRIEPH EFEVFFDPRE LRKETCLLYE INWGGRHSIW RHTSQNTNKH  60
VEVNFIEKFT TERYFCPNTR CSITWFLSWS PCGECSRAIT EFLSRYPHVT LFIYIARLYH  120
HADPENRQGL RDLISSGVTI QIMTEQESGY CWRNFVNYSP SNEAHWPRYP HLWVRLYVLE  180
LYCIILGLPP CLNILRRKQP QLTFFTIALQ SCHYQRLPPH ILWATGLK           228

SEQ ID NO: 217          moltype = AA  length = 162
FEATURE                 Location/Qualifiers
source                  1..162
                        mol_type = protein
                        organism = synthetic construct
SEQUENCE: 217
SFERNYDPRE LRKETYLLYE IKWGKSGKLW RHWCQNNRTQ HAEVYFLENI FNARRFNPST  60
HCSITWYLSW SPCAECSQKI VDFLKEHPNV NLEIYVARLY YHEDERNRQG LRDLVNSGVT  120
IRIMDLPDYN YCWKTFVSDQ GGDEDYWPGH FAPWIKQYSL KL                 162

SEQ ID NO: 218          moltype = AA  length = 237
FEATURE                 Location/Qualifiers
source                  1..237
                        mol_type = protein
                        organism = synthetic construct
SEQUENCE: 218
TSEKGPSTGD PTLRRRIESW EFDVFYDPRE LRKETCLLYE IKWGMSRKIW RSSGKNTTNH  60
VEVNFIKKFT SERRFHSSIS CSITWFLSWS PCWECSQAIR EFLSQHPGVT LVIYVARLFW  120
HMDQRNRQGL RDLVNSGVTI QIMRASEYYH CWRNFVNYPP GDEAHWPQYP PLWMMLYALE  180
LHCIILSLPP CLKISRRWQN HLAFFRLHLQ NCHYQTIPPH ILLATGLIHP SVTWRLK     237

SEQ ID NO: 219          moltype = AA  length = 191
FEATURE                 Location/Qualifiers
source                  1..191
                        mol_type = protein
                        organism = synthetic construct
SEQUENCE: 219
ADSSEKMRGQ YISRDTFEKN YKPIDGTKEA HLLCEIKWGK YGKPWLHWCQ NQRMNIHAED  60
YFMNNIFKAK KHPVHCYVTW YLSWSPCADC ASKIVKFLEE RPYLKLTIYV AQLYYHTEEE  120
NRKGLRLLRS KKVIIRVMDI SDYNYCWKVF VSNQNGNEDY WPLQFDPWVK ENYSRLLDIF  180
WESKCRSPNP W                                                  191
```

```
SEQ ID NO: 220          moltype = AA  length = 228
FEATURE                 Location/Qualifiers
source                  1..228
                        mol_type = protein
                        organism = synthetic construct
SEQUENCE: 220
SSETGPVAVD PTLRRRIEPH EFEVFFDPRE LRKETCLLYE IKWGTSHKIW RHSSKNTTKH  60
VEVNFIEKFT SERHFCPSTS CSITWFLSWS PCGECSKAIT EFLSQHPNVT LVIYVARLYH  120
HMDQQNRQGL RDLVNSGVTI QIMTAPEYDY CWRNFVNYPP GKEAHWPRYP PLWMKLYALE  180
LHAGILGLPP CLNILRRKQP QLTFFTIALQ SCHYQRLPPH ILWATGLK                228

SEQ ID NO: 221          moltype = AA  length = 198
FEATURE                 Location/Qualifiers
source                  1..198
                        mol_type = protein
                        organism = synthetic construct
SEQUENCE: 221
EASPASGPRH LMDPHIFTSN FNNGIGRHKT YLCYEVERLD NGTSVKMDQH RGFLHNQAKN  60
LLCGFYGRHA ELRFLDLVPS LQLDPAQIYR VTWFISWSPC FSWGCAGEVR AFLQENTHVR  120
LRIFAARIYD YDPLYKEALQ MLRDAGAQVS IMTYDEFKHC WDTFVDHQGC PFQPWDGLDE  180
HSQALSGRLR AILQNQGN                                                 198

SEQ ID NO: 222          moltype = AA  length = 198
FEATURE                 Location/Qualifiers
source                  1..198
                        mol_type = protein
                        organism = synthetic construct
SEQUENCE: 222
EASPASGPRH LMDPHIFTSN FNNGIGRHKT YLCYEVERLD NGTSVKMDQH RGFLHGQAKN  60
LLCGFYGRHA ELRFLDLVPS LQLDPAQIYR VTWFISWSPC FSWGCAGEVR AFLQENTHVR  120
LRIFAARIYD YDPLYKEALQ MLRDAGAQVS IMTYDEFKHC WDTFVDHQGC PFQPWDGLDE  180
HSQALSGRLR AILQNQGN                                                 198

SEQ ID NO: 223          moltype = AA  length = 381
FEATURE                 Location/Qualifiers
source                  1..381
                        mol_type = protein
                        organism = synthetic construct
SEQUENCE: 223
NPQIRNPMER MYRDTFYDNF ENEPILYGRS YTWLCYEVKI KRGRSNLLWD TGVFRGQVYF  60
KPQYHAEMCF LSWFCGNQLP AYKCFQITWF VSWTPCPDCV AKLAEFLSEH PNVTLTISAA  120
RLYYYWERDY RRALCRLSQA GARVKIMDYE EFAYCWENFV YNEGQQFMPW YKFDENYAFL  180
HRTLKEILRY LMDPDTFTFN FNNDPLVLRR RQTYLCYEVE RLDNGTWVLM DQHMGFLCNE  240
AKNLLCGFYG RHAELRFLDL VPSLQLDPAQ IYRVTWFISW SPCFSWGCAG EVRAFLQENT  300
HVRLRIFAAR IYDYDPLYKE ALQMLRDAGA QVSIMTYDEF EYCWDTFVYR QGCPFQPWDG  360
LEEHSQALSG RLRAILQNQG N                                             381

SEQ ID NO: 224          moltype = AA  length = 189
FEATURE                 Location/Qualifiers
source                  1..189
                        mol_type = protein
                        organism = synthetic construct
SEQUENCE: 224
NPQIRNPMKA MYPGTFYFQF KNLWEANDRN ETWLCFTVEG IKRRSVVSWK TGVFRNQVDS  60
ETHCHAERCF LSWFCDDILS PNTKYQVTWY TSWSPCPDCA GEVAEFLARH SNVNLTIFTA  120
RLYYFQYPCY QEGLRSLSQE GVAVEIMDYE DFKYCWENFV YNDNEPFKPW KGLKTNFRLL  180
KRRLRESLQ                                                           189

SEQ ID NO: 225          moltype = AA  length = 385
FEATURE                 Location/Qualifiers
source                  1..385
                        mol_type = protein
                        organism = synthetic construct
SEQUENCE: 225
NPQIRNPMER MYRDTFYDNF ENEPILYGRS YTWLCYEVKI KRGRSNLLWD TGVFRGPVLP  60
KRQSNHRQEV YFRFENHAEM CFLSWFCGNR LPANRRFQIT WFVSWNPCLP CVVKVTKFLA  120
EHPNVTLTIS AARLYYYRDR DWRWVLLRLH KAGARVKIMD YEDFAYCWEN FVCNEGQPFM  180
PWYKFDDNYA SLHRTLKEIL RNPMEAMYPH IFYFHFKNLL KACGRNESWL CFTMEVTKHH  240
SAVFRKRGVF RNQVDPETHC HAERCFLSWF CDDILSPNTN YEVTWYTSWS PCPECAGEVA  300
EFLARHSNVN LTIFTARLCY FWDTDYQEGL CSLSQEGASV KIMGYKDFVS CWKNFVYSDD  360
EPFKPWKGLQ TNFRLLKRRL REILQ                                         385

SEQ ID NO: 226          moltype = AA  length = 372
FEATURE                 Location/Qualifiers
source                  1..372
                        mol_type = protein
                        organism = synthetic construct
SEQUENCE: 226
```

```
KPHFRNTVER MYRDTFSYNF YNRPILSRRN TVWLCYEVKT KGPSRPRLDA KIFRGQVYSQ  60
PEHHAEMCFL SWFCGNQLPA YKCFQITWFV SWTPCPDCVA KLAEFLAEHP NVTLTISAAR  120
LYYYWERDYR RALCRLSQAG ARVKIMDDEE FAYCWENFVY SEGQPFMPWY KFDDNYAFLH  180
RTLKEILRNP MEAMYPHIFY FHFKNLRKAY GRNESWLCFT MEVVKHHSPV SWKRGVFRNQ  240
VDPETHCHAE RCFLSWFCDD ILSPNTNYEV TWYTSWSPCP ECAGEVAEFL ARHSNVNLTI  300
FTARLYYFWD TDYQEGLRSL SQEGASVEIM GYKDFKYCWE NFVYNDDEPF KPWKGLKYNF  360
LFLDSKLQEI LE                                                    372

SEQ ID NO: 227          moltype = AA  length = 383
FEATURE                 Location/Qualifiers
source                  1..383
                        mol_type = protein
                        organism = synthetic construct
SEQUENCE: 227
KPHFRNTVER MYRDTFSYNF YNRPILSRRN TVWLCYEVKT KGPSRPPLDA KIFRGQVYSE  60
LKYHPEMRFF HWFSKWRKLH RDQEYEVTWY ISWSPCTKCT RDMATFLAED PKVTLTIFVA  120
RLYYFWDPDY QEALRSLCQK RDGPRATMKI MNYDEFQHCW SKFVYSQREL FEPWNNLPKY  180
YILLHIMLGE ILRHSMDPPT FTFNFNNEPW VRGRHETYLC YEVERMHNDT WVLLNQRRGF  240
LCNQAPHKHG FLEGRHAELC FLDVIPFWKL DLDQDYRVTC FTSWSPCFSC AQEMAKFISK  300
NKHVSLCIFT ARIYDDQGRC QEGLRTLAEA GAKISIMTYS EFKHCWDTFV DHQGCPFQPW  360
DGLDEHSQDL SGRLRAILQN QEN                                        383

SEQ ID NO: 228          moltype = AA  length = 182
FEATURE                 Location/Qualifiers
source                  1..182
                        mol_type = protein
                        organism = synthetic construct
SEQUENCE: 228
ALLTAETFRL QFNNKRRLRR PYYPRKALLC YQLTPQNGST PTRGYFENKK KCHAEICFIN  60
EIKSMGLDET QCYQVTCYLT WSPCSSCAWE LVDFIKAHDH LNLGIFASRL YYHWCKPQQK  120
GLRLLCGSQV PVEVMGFPEF ADCWENFVDH EKPLSFNPYK MLEELDKNSR AIKRRLERIK  180
QS                                                               182

SEQ ID NO: 229          moltype = AA  length = 193
FEATURE                 Location/Qualifiers
source                  1..193
                        mol_type = protein
                        organism = synthetic construct
SEQUENCE: 229
KPQIRDHRPN PMEAMYPHIF YFHFENLEKA YGRNETWLCF TVEIIKQYLP VPWKKGVFRN  60
QVDPETHCHA EKCFLSWFCN NTLSPKKNYQ VTWYTSWSPC PECAGEVAEF LAEHSNVKLT  120
IYTARLYYFW DTDYQEGLRS LSEEGASVEI MDYEDFQYCW ENFVYDDGEP FKRWKGLKYN  180
FQSLTRRLRE ILQ                                                   193

SEQ ID NO: 230          moltype = AA  length = 279
FEATURE                 Location/Qualifiers
source                  1..279
                        mol_type = protein
                        organism = synthetic construct
SEQUENCE: 230
DPQRLRQWPG PGPASRGGYG QRPRIRNPEE WFHELSPRTF SFHFRNLRFA SGRNRSYICC  60
QVEGKNCFFQ GIFQNQVPPD PPCHAELCFL SWFQSWGLSP DEHYYVTWFI SWSPCCECAA  120
KVAQFLEENR NVSLSLSAAR LYYFWKSESR EGLRRLSDLG AQVGIMSFQD FQHCWNNFVH  180
NLGMPFQPWK KLHKNYQRLV TELKQILREE PATYGSPQAQ GKVRIGSTAA GLRHSHSHTR  240
SEAHLRPNHS SRQHRILNPP REARARTCVL VDASWICYR                       279

SEQ ID NO: 231          moltype = AA  length = 197
FEATURE                 Location/Qualifiers
source                  1..197
                        mol_type = protein
                        organism = synthetic construct
SEQUENCE: 231
DSLLMNRRKF LYQFKNVRWA KGRRETYLCY VVKRRDSATS FSLDFGYLRN KNGCHVELLF  60
LRYISDWDLD PGRCYRVTWF TSWSPCYDCA RHVADFLRGN PNLSLRIFTA RLYFCEDRKA  120
EPEGLRRLHR AGVQIAIMTF KDYFYCWNTF VENHERTFKA WEGLHENSVR LSRQLRRILL  180
PLYEVDDLRD AFRTLGL                                               197

SEQ ID NO: 232          moltype = AA  length = 175
FEATURE                 Location/Qualifiers
source                  1..175
                        mol_type = protein
                        organism = synthetic construct
SEQUENCE: 232
DPATFTYQFK NVRWAKGRRE TYLCYVVKRR DSATSFSLDF GYLRNKNGCH VELLFLRYIS  60
DWDLDPGRCY RVTWFTSWSP CYDCARHVAD FLRGNPNLSL RIFTARLYFC EDRKAEPEGL  120
RRLAEAGVQI AIMTFKDYFY CWNTFVENHE RTFKAWEGLH ENSVRLSRQL RRILQ      175

SEQ ID NO: 233          moltype = AA  length = 174
FEATURE                 Location/Qualifiers
```

```
source                  1..174
                        mol_type = protein
                        organism = synthetic construct
SEQUENCE: 233
DPATFTYQFK NVRWAKGRRE TYLCYVVKRR DSATSFSLDF GYLRNKNGCH VELLFLRYIS  60
DWDLDPGRCY RVTWFTSWSP CYDCARHVAD FLRGNPNLSL RIFTARLYYF QYPCYQEGLR  120
RLHRAGVQIA IMTFKDYFYC WNTFVENHER TFKAWEGLHE NSVRLSRQLR RILQ        174

SEQ ID NO: 234          moltype = AA  length = 174
FEATURE                 Location/Qualifiers
source                  1..174
                        mol_type = protein
                        organism = synthetic construct
SEQUENCE: 234
DPATFTYQFK NVRWAKGRRE TYLCYVVKRR DSATSFSLDF GYLRNKNGCH VELLFLRYIS  60
DWDLDPGRCY RVTWFTSWSP CYDCARHVAD FLRGNPNLSL RIFTARLYYF WDTDYQEGLR  120
RLHRAGVQIA IMTFKDYFYC WNTFVENHER TFKAWEGLHE NSVRLSRQLR RILQ        174

SEQ ID NO: 235          moltype = AA  length = 207
FEATURE                 Location/Qualifiers
source                  1..207
                        mol_type = protein
                        organism = synthetic construct
SEQUENCE: 235
TDAEYVRIHE KLDIYTFKKQ FFNNKKSVSH RCYVLFELKR RGERRACFWG YAVNKPQSGT  60
ERGIHAEIFS IRKVEEYLRD NPGQFTINWY SSWSPCADCA EKILEWYNQE LRGNGHTLKI  120
WACKLYYEKN ARNQIGLWNL RDNGVGLNVM VSEHYQCCRK IFIQSSHNQL NENRWLEKTL  180
KRAEKRRSEL SIMIQVKILH TTKSPAV                                      207

SEQ ID NO: 236          moltype = AA  length = 364
FEATURE                 Location/Qualifiers
source                  1..364
                        mol_type = protein
                        organism = synthetic construct
SEQUENCE: 236
SEVEFSHEYW MRHALTLAKR AWDEREVPVG AVLVHNNRVI GEGWNRPIGR HDPTAHAEIM  60
ALRQGGLVMQ NYRLIDATLY VTLEPCVMCA GAMIHSRIGR VVFGARDAKT GAAGSLMDVL  120
HHPGMNHRVE ITEGILADEC AALLSDFFRM RRQEIKAQKK AQSSTDSGGS SGGSSGSETP  180
GTSESATPES SGGSSGGSSE VEFSHEYWMR HALTLAKRAR DEREVPVGAV LVLNNRVIGE  240
GWNRAIGLHD PTAHAEIMAL RQGGLVMQNY RLIDATLYVT FEPCVMCAGA MIHSRIGRVV  300
FGVRNAKTGA AGSLMDVLHY PGMNHRVEIT EGILADECAA LLCYFFRMPR QVFNAQKKAQ  360
SSTD                                                               364

SEQ ID NO: 237          moltype = AA  length = 166
FEATURE                 Location/Qualifiers
source                  1..166
                        mol_type = protein
                        organism = synthetic construct
SEQUENCE: 237
SEVEFSHEYW MRHALTLAKR ARDEREVPVG AVLVLNNRVI GEGWNRAIGL HDPTAHAEIM  60
ALRQGGLVMQ NYRLIDATLY VTFEPCVMCA GAMIHSRIGR VVFGVRNSKR GAAGSLMNVL  120
NYPGMNHRVE ITEGILADEC AALLCDFYRM PRQVFNAQKK AQSSIN                 166

SEQ ID NO: 238          moltype = AA  length = 166
FEATURE                 Location/Qualifiers
source                  1..166
                        mol_type = protein
                        organism = synthetic construct
SEQUENCE: 238
SEVEFSHEYW MRHALTLAKR ARDEREVPVG AVLVLNNRVI GEGWNRAIGL HDPTAHAEIM  60
ALRQGGLVMQ NYRLIDATLY VTFEPCVMCA GAMIHSRIGR VVFGVRNAKT GAAGSLMDVL  120
HYPGMNHRVE ITEGILADEC AALLCYFFRM PRQVFNAQKK AQSSTD                 166

SEQ ID NO: 239          moltype = AA  length = 364
FEATURE                 Location/Qualifiers
source                  1..364
                        mol_type = protein
                        organism = synthetic construct
SEQUENCE: 239
SEVEFSHEYW MRHALTLAKR AWDEREVPVG AVLVHNNRVI GEGWNRPIGR HDPTAHAEIM  60
ALRQGGLVMQ NYRLIDATLY VTLEPCVMCA GAMIHSRIGR VVFGARDAKT GAAGSLMDVL  120
HHPGMNHRVE ITEGILADEC AALLSDFFRM RRQEIKAQKK AQSSTDSGGS SGGSSGSETP  180
GTSESATPES SGGSSGGSSE VEFSHEYWMR HALTLAKRAW DEREVPVGAV LVLNNRVIGE  240
GWNRSIGLHD PTAHAEIMAL RQGGLVMQNY RLIDATLYVT FEPCVMCAGA MIHSRIGRVV  300
FGVRNAKTGA AGSLMDVLHY PGMNHRVEIT EGILADECAA LLCYFFRMRR QVFNAQKKAQ  360
SSTD                                                               364

SEQ ID NO: 240          moltype = AA  length = 364
FEATURE                 Location/Qualifiers
```

```
source                  1..364
                        mol_type = protein
                        organism = synthetic construct
SEQUENCE: 240
SEVEFSHEYW MRHALTLAKR AWDEREVPVG AVLVHNNRVI GEGWNRPIGR HDPTAHAEIM  60
ALRQGGLVMQ NYRLIDATLY VTLEPCVMCA GAMIHSRIGR VVFGARDAKT GAAGSLMDVL  120
HHPGMNHRVE ITEGILADEC AALLSDFFRM RRQEIKAQKK AQSSTDSGGS SGGSSGSETP  180
GTSESATPES SGGSSGGSSE VEFSHEYWMR HALTLAKRAL DEREVPVGAV LVLNNRVIGE  240
GWNRAIGLHD PTAHAEIMAL RQGGLVMQNY RLIDATLYVT FEPCVMCAGA MIHSRIGRVV  300
FGVRNAKTGA AGSLMDVLHY PGMNHRVEIT EGILADECNA LLCYFFRMRR QVFNAQKKAQ  360
SSTD                                                              364

SEQ ID NO: 241          moltype = AA  length = 364
FEATURE                 Location/Qualifiers
source                  1..364
                        mol_type = protein
                        organism = synthetic construct
SEQUENCE: 241
SEVEFSHEYW MRHALTLAKR AWDEREVPVG AVLVHNNRVI GEGWNRPIGR HDPTAHAEIM  60
ALRQGGLVMQ NYRLIDATLY VTLEPCVMCA GAMIHSRIGR VVFGARDAKT GAAGSLMDVL  120
HHPGMNHRVE ITEGILADEC AALLSDFFRM RRQEIKAQKK AQSSTDSGGS SGGSSGSETP  180
GTSESATPES SGGSSGGSSE VEFSHEYWMR HALTLAKRAL DEREVPVGAV LVLNNRVIGE  240
GWNRAIGLHD PTAHAEIMAL RQGGLVMQNY RLIDATLYVT FEPCVMCAGA MIHSRIGRVV  300
FGVRNAKTGA AGSLMDVLHY PGMNHRVEIT EGILADECNA LLCYFFRMPR QVFNAQKKAQ  360
SSTD                                                              364

SEQ ID NO: 242          moltype = AA  length = 166
FEATURE                 Location/Qualifiers
source                  1..166
                        mol_type = protein
                        organism = synthetic construct
SEQUENCE: 242
SEVEFSHEYW MRHALTLAKR ARDEREVPVG AVLVLNNRVI GEGWNRAIGL HDPTAHAEIM  60
ALRQGGLVMQ NYRLIDATLY VTFEPCVMCA GAMIHSRIGR VVFGVRNAKT GAAGSLMDVL  120
HHPGMNHRVE ITEGILADEC AALLCRFFRM PRRVFNAQKK AQSSTD                166

SEQ ID NO: 243          moltype = AA  length = 364
FEATURE                 Location/Qualifiers
source                  1..364
                        mol_type = protein
                        organism = synthetic construct
SEQUENCE: 243
SEVEFSHEYW MRHALTLAKR AWDEREVPVG AVLVHNNRVI GEGWNRPIGR HDPTAHAEIM  60
ALRQGGLVMQ NYRLIDATLY VTLEPCVMCA GAMIHSRIGR VVFGARDAKT GAAGSLMDVL  120
HHPGMNHRVE ITEGILADEC AALLSDFFRM RRQEIKAQKK AQSSTDSGGS SGGSSGSETP  180
GTSESATPES SGGSSGGSSE VEFSHEYWMR HALTLAKRAR DEREVPVGAV LVLNNRVIGE  240
GWNRAIGLHD PTAHAEIMAL RQGGLVMQNY RLIDATLYVT FEPCVMCAGA MIHSRIGRVV  300
FGVRNAKTGA AGSLMDVLHH PGMNHRVEIT EGILADECAA LLCRFFRMPR RVFNAQKKAQ  360
SSTD                                                              364

SEQ ID NO: 244          moltype = AA  length = 166
FEATURE                 Location/Qualifiers
source                  1..166
                        mol_type = protein
                        organism = synthetic construct
SEQUENCE: 244
SEVEFSHEYW MRHALTLAKR ARDEREVPVG AVLVLNNRVI GEGWNRAIGL HDPTAHAEIM  60
ALRQGGLVMQ NYRLYDATLY VTFEPCVMCA GAMIHSRIGR VVFGVRNAKT GAAGSLMDVL  120
HHPGMNHRVE ITEGILADEC AALLCRFFRM PRRVFNAQKK AQSSTD                166

SEQ ID NO: 245          moltype = AA  length = 364
FEATURE                 Location/Qualifiers
source                  1..364
                        mol_type = protein
                        organism = synthetic construct
SEQUENCE: 245
SEVEFSHEYW MRHALTLAKR AWDEREVPVG AVLVHNNRVI GEGWNRPIGR HDPTAHAEIM  60
ALRQGGLVMQ NYRLIDATLY VTLEPCVMCA GAMIHSRIGR VVFGARDAKT GAAGSLMDVL  120
HHPGMNHRVE ITEGILADEC AALLSDFFRM RRQEIKAQKK AQSSTDSGGS SGGSSGSETP  180
GTSESATPES SGGSSGGSSE VEFSHEYWMR HALTLAKRAR DEREVPVGAV LVLNNRVIGE  240
GWNRAIGLHD PTAHAEIMAL RQGGLVMQNY RLYDATLYVT FEPCVMCAGA MIHSRIGRVV  300
FGVRNAKTGA AGSLMDVLHH PGMNHRVEIT EGILADECAA LLCRFFRMPR RVFNAQKKAQ  360
SSTD                                                              364

SEQ ID NO: 246          moltype = AA  length = 166
FEATURE                 Location/Qualifiers
source                  1..166
                        mol_type = protein
                        organism = synthetic construct
```

```
SEQUENCE: 246
SEVEFSHEYW MRHALTLAKR ARDEREVPVG AVLVLNNRVI GEGWNRAIGL HDPTAHAEIM  60
ALRQGGLVMQ NYRLIDATLY STFEPCVMCA GAMIHSRIGR VVFGVRNAKT GAAGSLMDVL  120
HYPGMNHRVE ITEGILADEC AALLCYFFRM PRRVFNAQKK AQSSTD                 166

SEQ ID NO: 247          moltype = AA  length = 364
FEATURE                 Location/Qualifiers
source                  1..364
                        mol_type = protein
                        organism = synthetic construct
SEQUENCE: 247
SEVEFSHEYW MRHALTLAKR AWDEREVPVG AVLVHNNRVI GEGWNRPIGR HDPTAHAEIM  60
ALRQGGLVMQ NYRLIDATLY VTLEPCVMCA GAMIHSRIGR VVFGARDAKT GAAGSLMDVL  120
HHPGMNHRVE ITEGILADEC AALLSDFFRM RRQEIKAQKK AQSSTDSGGS SGGSSGSETP  180
GTSESATPES SGGSSGGSSE VEFSHEYWMR HALTLAKRAR DEREVPVGAV LVLNNRVIGE  240
GWNRAIGLHD PTAHAEIMAL RQGGLVMQNY RLIDATLYST FEPCVMCAGA MIHSRIGRVV  300
FGVRNAKTGA AGSLMDVLHY PGMNHRVEIT EGILADECAA LLCYFFRMPR RVFNAQKKAQ  360
SSTD                                                               364

SEQ ID NO: 248          moltype = AA  length = 166
FEATURE                 Location/Qualifiers
source                  1..166
                        mol_type = protein
                        organism = synthetic construct
SEQUENCE: 248
SEVEFSHEYW MRHALTLAKR ARDEREVPVG AVLVLNNRVI GEGWNRAIGL HDPTAHAEIM  60
ALRQGGLVMQ NYRLYDATLY STFEPCVMCA GAMIHSRIGR VVFGVRNAKT GAAGSLMDVL  120
HHPGMNHRVE ITEGILADEC AALLCRFFRM PRRVFNAQKK AQSSTD                 166

SEQ ID NO: 249          moltype = AA  length = 364
FEATURE                 Location/Qualifiers
source                  1..364
                        mol_type = protein
                        organism = synthetic construct
SEQUENCE: 249
SEVEFSHEYW MRHALTLAKR AWDEREVPVG AVLVHNNRVI GEGWNRPIGR HDPTAHAEIM  60
ALRQGGLVMQ NYRLIDATLY VTLEPCVMCA GAMIHSRIGR VVFGARDAKT GAAGSLMDVL  120
HHPGMNHRVE ITEGILADEC AALLSDFFRM RRQEIKAQKK AQSSTDSGGS SGGSSGSETP  180
GTSESATPES SGGSSGGSSE VEFSHEYWMR HALTLAKRAR DEREVPVGAV LVLNNRVIGE  240
GWNRAIGLHD PTAHAEIMAL RQGGLVMQNY RLYDATLYST FEPCVMCAGA MIHSRIGRVV  300
FGVRNAKTGA AGSLMDVLHH PGMNHRVEIT EGILADECAA LLCRFFRMPR RVFNAQKKAQ  360
SSTD                                                               364

SEQ ID NO: 250          moltype = AA  length = 83
FEATURE                 Location/Qualifiers
source                  1..83
                        mol_type = protein
                        organism = synthetic construct
SEQUENCE: 250
TNLSDIIEKE TGKQLVIQES ILMLPEEVEE VIGNKPESDI LVHTAYDEST DENVMLLTSD  60
APEYKPWALV IQDSNGENKI KML                                          83

SEQ ID NO: 251          moltype = AA  length = 117
FEATURE                 Location/Qualifiers
source                  1..117
                        mol_type = protein
                        organism = synthetic construct
SEQUENCE: 251
ALSPQHSAVT QGSIIKNKEG MDAKSLTAWS RTLVTFKDVF VDFTREEWKL LDTAQQIVYR  60
NVMLENYKNL VSLGYQLTKP DVILRLEKGE EPWLVEREIH QETHPDSETA FEIKSSV     117

SEQ ID NO: 252          moltype = AA  length = 66
FEATURE                 Location/Qualifiers
source                  1..66
                        mol_type = protein
                        organism = synthetic construct
SEQUENCE: 252
SRTLVTFKDV FVDFTREEWK LLDTAQQIVY RNVMLENYKN LVSLGYQLTK PDVILRLEKG  60
EEPWLV                                                             66

SEQ ID NO: 253          moltype = AA  length = 323
FEATURE                 Location/Qualifiers
source                  1..323
                        mol_type = protein
                        organism = synthetic construct
SEQUENCE: 253
GTYGLLRRRE DWPSRLQMFF ANNHDQEFDP PKVYPPVPAE KRKPIRVLSL FDGIATGLLV  60
LKDLGIQVDR YIASEVCEDS ITVGMVRHQG KIMYVGDVRS VTQKHIQEWG PFDLVIGGSP  120
CNDLSIVNPA RKGLYEGTGR LFFEFYRLLH DARPKEGDDR PFFWLFENVV AMGVSDKRDI  180
```

```
SRFLESNPVM IDAKEVSAAH RARYFWGNLP GMNRPLASTV NDKLELQECL EHGRIAKFSK  240
VRTITTRSNS IKQGKDQHFP VFMNEKEDIL WCTEMERVFG FPVHYTDVSN MSRLARQRLL  300
GRSWSVPVIR HLFAPLKEYF ACV                                          323

SEQ ID NO: 254         moltype = AA  length = 385
FEATURE                Location/Qualifiers
source                 1..385
                       mol_type = protein
                       organism = synthetic construct
SEQUENCE: 254
AAIPALDPEA EPSMDVILVG SSELSSSVSP GTGRDLIAYE VKANQRNIED ICICCGSLQV  60
HTQHPLFEGG ICAPCKDKFL DALFLYDDDG YQSYCSICCS GETLLICGNP DCTRCYCFEC  120
VDSLVGPGTS GKVHAMSNWV CYLCLPSSRS GLLQRRRKWR SQLKAFYDRE SENPLEMFET  180
VPVWRRQPVR VLSLFEDIKK ELTSLGFLES GSDPGQLKHV VDVTDTVRKD VEEWGPFDLV  240
YGATPPLGHT CDRPPSWYLF QFHRLLQYAR PKPGSPRPFF WMFVDNLVLN KEDLDVASRF  300
LEMEPVTIPD VHGGSLQNAV RVWSNIPAIR SRHWALVSEE ELSLLAQNKQ SSKLAAKWPT  360
KLVKNCFLPL REYFKYFSTE LTSSL                                        385

SEQ ID NO: 255         moltype = AA  length = 714
FEATURE                Location/Qualifiers
source                 1..714
                       mol_type = protein
                       organism = synthetic construct
SEQUENCE: 255
NHDQEFDPPK VYPPVPAEKR KPIRVLSLFD GIATGLLVLK DLGIQVDRYI ASEVCEDSIT  60
VGMVRHQGKI MYVGDVRSVT QKHIQEWGPF DLVIGGSPCN DLSIVNPARK GLYEGTGRLF  120
FEFYRLLHDA RPKEGDDRPF FWLFENVVAM GVSDKRDISR FLESNPVMID AKEVSAAHRA  180
RYFWGNLPGM NRPLASTVND KLELQECLEH GRIAKFSKVR TITTRSNSIK QGKDQHFPVF  240
MNEKEDILWC TEMERVFGFP VHYTDVSNMS RLARQRLLGR SWSVPVIRHL FAPLKEYFAC  300
VSSGNSNANS RGPSFSSGLV PLSLRGSHMA AIPALDPEAE PSMDVILVGS SELSSSVSPG  360
TGRDLIAYEV KANQRNIEDI CICCGSLQVH TQHPLFEGGI CAPCKDKFLD ALFLYDDDGY  420
QSYCSICCSG ETLLICGNPD CTRCYCFECV DSLVGPGTSG KVHAMSNWVC YLCLPSSRSG  480
LLQRRRKWRS QLKAFYDRES ENPLEMFETV PVWRRQPVRV LSLFEDIKKE LTSLGFLESG  540
SDPGQLKHVV DVTDTVRKDV EEWGPFDLVY GATPPLGHTC DRPPSWYLFQ FHRLLQYARP  600
KPGSPRPFFW MFVDNLVLNK EDLDVASRFL EMEPVTIPDV HGGSLQNAVR VWSNIPAIRS  660
RHWALVSEEE LSLLAQNKQS SKLAAKWPTK LVKNCFLPLR EYFKYFSTEL TSSL        714

SEQ ID NO: 256         moltype = AA  length = 677
FEATURE                Location/Qualifiers
source                 1..677
                       mol_type = protein
                       organism = synthetic construct
SEQUENCE: 256
TLNIEDEYRL HETSKEPDVS LGSTWLSDFP QAWAETGGMG LAVRQAPLII PLKATSTPVS  60
IKQYPMSQEA RLGIKPHIQR LLDQGILVPC QSPWNTPLLP VKKPGTNDYR PVQDLREVNK  120
RVEDIHPTVP NPYNLLSGLP PSHQWYTVLD LKDAFFCLRL HPTSQPLFAF EWRDPEMGIS  180
GQLTWTRLPQ GFKNSPTLFN EALHRDLADF RIQHPDLILL QYVDDLLLAA TSELDCQQGT  240
RALLQTLGNL GYRASAKKAQ ICQKQVKYLG YLLKEGQRWL TEARKETVMG QPTPKTPRQL  300
REFLGKAGFC RLFIPGFAEM AAPLYPLTKP GTLFNWGPDQ QKAYQEIKQA LLTAPALGLP  360
DLTKPFELFV DEKQGYAKGV LTQKLGPWRR PVAYLSKKLD PVAAGWPPCL RMVAAIAVLT  420
KDAGKLTMGQ PLVILAPHAV EALVKQPPDR WLSNARMTHY QALLLDTDRV QFGPVVALNP  480
ATLLPLPEEG LQHNCLDILA EAHGTRPDLT DQPLPDADHT WYTDGSSLLQ EGQRKAGAAV  540
TTETEVIWAK ALPAGTSAQR AELIALTQAL KMAEGKKLNV YTDSRYAFAT AHIHGEIYRR  600
RGWLTSEGKE IKNKDEILAL LKALFLPKRL SIIHCPGHQK GHSAEARGNR MADQAARKAA  660
ITETPDTSTL LIENSSP                                                 677

SEQ ID NO: 257         moltype = AA  length = 506
FEATURE                Location/Qualifiers
source                 1..506
                       mol_type = protein
                       organism = synthetic construct
SEQUENCE: 257
ISSSKHTLSQ MNKVSNIVKE PELPDIYKEF KDITADTNTE KLPKPIKGLE FEVELTQENY  60
RLPIRNYPLT PVKMQAMNDE INQGLKGGII RESKAINACP VIFVPRKEGT LRMVVDYRPL  120
NKYVKPNVYP LPLIEQLLAK IQGSTIFTKL DLKSAYHQIR VRKGDEHKLA FRCPRGVFEY  180
LVMPYGIKTA PAHFQYFINT ILGEAKESHV VCYMDDILIH SKSESEHVKH VKDVLQKLKN  240
ANLIINQAKC EFHQSQVKFL GYHISEKGLT PCQENIDKVL QWKQPKNQKE LRQFLGQVNY  300
LRKFIPKTSQ LTHPLNKLLK KDVRWKWTPT QTQAIENIKQ CLVSPPVLRH FDFSKKILLE  360
TDVSDVAVGA VLSQKHDDDK YYPVGYYSAK MSKAQLNYSV SDKEMLAIIK SLEHWRHYLE  420
STIEPFKILT DHRNLIGRIT NESEPENKRL ARWQLFLQDF NFEINYRPGS ANHIADALSR  480
IVDETEPIPK DNEDNSINFV NQISIS                                       506

SEQ ID NO: 258         moltype = AA  length = 752
FEATURE                Location/Qualifiers
source                 1..752
                       mol_type = protein
                       organism = synthetic construct
SEQUENCE: 258
SFVAGVIRRL DETVVNRIAA GEVIQRPANA IKEMIENCLD AKSTSIQVIV KEGGLKLIQI  60
```

```
QDNGTGIRKE DLDIVCERFT TSKLQSFEDL ASISTYGFRG EALASISHVA HVTITTKTAD  120
GKCAYRASYS DGKLKAPPKP CAGNQGTQIT VEDLFYNIAT RRKALKNPSE EYGKILEVVG  180
RYSVHNAGIS FSVKKQGETV ADVRTLPNAS TVDNIRSIFG NAVSRELIEI GCEDKTLAFK  240
MNGYISNANY SVKKCIFLLF INHRLVESTS LRKAIETVYA AYLPKNTHPF LYLSLEISPQ  300
NVDVNVHPTK HEVHFLHEES ILERVQQHIE SKLLGSNSSR MYFTQTLLPG LAGPSGEMVK  360
STTSLTSSST SGSSDKVYAH QMVRTDSREQ KLDAFLQPLS KPLSSQPQAI VTEDKTDISS  420
GRARQQDEEM LELPAPAEVA AKNQSLEGDT TKGTSEMSEK RGPTSSNPRK RHREDSDVEM  480
VEDDSRKEMT AACTPRRRII NLTSVLSLQE EINEQGHEVL REMLHNHSFV GCVNPQWALA  540
QHQTKLYLLN TTKLSEELFY QILIYDFANF GVLRLSEPAP LFDLAMLALD SPESGWTEED  600
GPKEGLAEYI VEFLKKKAEM LADYFSLEID EEGNLIGLPL LIDNYVPPLE GLPIFILRLA  660
TEVNWDEEKE CFESLSKECA MFYSIRKQYI SEESTLSGQQ SEVPGSIPNS WKWTVEHIVY  720
KALRSHILPP KHFTEDGNIL QLANLPDLYK VF                                752

SEQ ID NO: 259          moltype = AA  length = 4
FEATURE                 Location/Qualifiers
source                  1..4
                        mol_type = protein
                        organism = synthetic construct
SEQUENCE: 259
GSGS                                                               4

SEQ ID NO: 260          moltype = RNA  length = 23
FEATURE                 Location/Qualifiers
source                  1..23
                        mol_type = other RNA
                        organism = synthetic construct
SEQUENCE: 260
cgtcgccgtc cagctcgacc agg                                          23

SEQ ID NO: 261          moltype = RNA  length = 23
FEATURE                 Location/Qualifiers
source                  1..23
                        mol_type = other RNA
                        organism = synthetic construct
SEQUENCE: 261
ctcagggcgg actgggtgct cag                                          23

SEQ ID NO: 262          moltype = DNA  length = 27
FEATURE                 Location/Qualifiers
source                  1..27
                        mol_type = other DNA
                        organism = synthetic construct
SEQUENCE: 262
agatcgtcgc cgtccagctc gaccagg                                      27

SEQ ID NO: 263          moltype = DNA  length = 27
FEATURE                 Location/Qualifiers
source                  1..27
                        mol_type = other DNA
                        organism = synthetic construct
SEQUENCE: 263
agatctcagg gcggactggg tgctcag                                      27

SEQ ID NO: 264          moltype = DNA  length = 27
FEATURE                 Location/Qualifiers
source                  1..27
                        mol_type = other DNA
                        organism = synthetic construct
SEQUENCE: 264
agattggcct ggaggctatc cagcgtg                                      27

SEQ ID NO: 265          moltype = DNA  length = 27
FEATURE                 Location/Qualifiers
source                  1..27
                        mol_type = other DNA
                        organism = synthetic construct
SEQUENCE: 265
agatctcacg tcatccagca gagaatg                                      27

SEQ ID NO: 266          moltype = DNA  length = 27
FEATURE                 Location/Qualifiers
source                  1..27
                        mol_type = other DNA
                        organism = synthetic construct
SEQUENCE: 266
agatactttc cattctctgc tggatga                                      27

SEQ ID NO: 267          moltype = DNA  length = 27
FEATURE                 Location/Qualifiers
```

```
source                  1..27
                        mol_type = other DNA
                        organism = synthetic construct
SEQUENCE: 267
agatctgaat tgctatgtgt ctgggtt                                     27

SEQ ID NO: 268          moltype = DNA  length = 27
FEATURE                 Location/Qualifiers
source                  1..27
                        mol_type = other DNA
                        organism = synthetic construct
SEQUENCE: 268
agataattct ctctccattc ttcagta                                     27

SEQ ID NO: 269          moltype = DNA  length = 27
FEATURE                 Location/Qualifiers
source                  1..27
                        mol_type = other DNA
                        organism = synthetic construct
SEQUENCE: 269
agatagaatc aaaatcggtg aataggc                                     27

SEQ ID NO: 270          moltype = DNA  length = 27
FEATURE                 Location/Qualifiers
source                  1..27
                        mol_type = other DNA
                        organism = synthetic construct
SEQUENCE: 270
agattgacac atttgtttga gaatcaa                                     27

SEQ ID NO: 271          moltype = DNA  length = 27
FEATURE                 Location/Qualifiers
source                  1..27
                        mol_type = other DNA
                        organism = synthetic construct
SEQUENCE: 271
agatgagtct ctcagctggt acacggc                                     27

SEQ ID NO: 272          moltype = DNA  length = 27
FEATURE                 Location/Qualifiers
source                  1..27
                        mol_type = other DNA
                        organism = synthetic construct
SEQUENCE: 272
agattctgtg atatacacat cagaatc                                     27

SEQ ID NO: 273          moltype = DNA  length = 27
FEATURE                 Location/Qualifiers
source                  1..27
                        mol_type = other DNA
                        organism = synthetic construct
SEQUENCE: 273
agatattctc aaacaaatgt gtcacaa                                     27

SEQ ID NO: 274          moltype = DNA  length = 27
FEATURE                 Location/Qualifiers
source                  1..27
                        mol_type = other DNA
                        organism = synthetic construct
SEQUENCE: 274
agatccttcc gctcacctcc gcctgag                                     27

SEQ ID NO: 275          moltype = DNA  length = 27
FEATURE                 Location/Qualifiers
source                  1..27
                        mol_type = other DNA
                        organism = synthetic construct
SEQUENCE: 275
agatgcacga agctctccga tgtgttg                                     27

SEQ ID NO: 276          moltype = DNA  length = 27
FEATURE                 Location/Qualifiers
source                  1..27
                        mol_type = other DNA
                        organism = synthetic construct
SEQUENCE: 276
agatatctgc gccttggggg ccaggga                                     27

SEQ ID NO: 277          moltype = DNA  length = 27
```

```
FEATURE                Location/Qualifiers
source                 1..27
                       mol_type = other DNA
                       organism = synthetic construct
SEQUENCE: 277
agatgaactg gccggctggc ctgggtg                                      27

SEQ ID NO: 278         moltype = DNA  length = 27
FEATURE                Location/Qualifiers
source                 1..27
                       mol_type = other DNA
                       organism = synthetic construct
SEQUENCE: 278
agatcagggg tccgagagct cagctag                                      27

SEQ ID NO: 279         moltype = DNA  length = 27
FEATURE                Location/Qualifiers
source                 1..27
                       mol_type = other DNA
                       organism = synthetic construct
SEQUENCE: 279
agatatctgt cccctccacc ccacagt                                      27

SEQ ID NO: 280         moltype = DNA  length = 27
FEATURE                Location/Qualifiers
source                 1..27
                       mol_type = other DNA
                       organism = synthetic construct
SEQUENCE: 280
agatggcagc tcccctaccc cccttac                                      27

SEQ ID NO: 281         moltype = DNA  length = 27
FEATURE                Location/Qualifiers
source                 1..27
                       mol_type = other DNA
                       organism = synthetic construct
SEQUENCE: 281
agatgtgtca agctatatca ggcacca                                      27

SEQ ID NO: 282         moltype = DNA  length = 27
FEATURE                Location/Qualifiers
source                 1..27
                       mol_type = other DNA
                       organism = synthetic construct
SEQUENCE: 282
agatatgtgt cttttcccga tattcct                                      27

SEQ ID NO: 283         moltype = DNA  length = 27
FEATURE                Location/Qualifiers
source                 1..27
                       mol_type = other DNA
                       organism = synthetic construct
SEQUENCE: 283
agattcactg gatttagagt ctctcag                                      27

SEQ ID NO: 284         moltype = DNA  length = 27
FEATURE                Location/Qualifiers
source                 1..27
                       mol_type = other DNA
                       organism = synthetic construct
SEQUENCE: 284
agatgattct caaacaaatg tgtcaca                                      27

SEQ ID NO: 285         moltype = DNA  length = 27
FEATURE                Location/Qualifiers
source                 1..27
                       mol_type = other DNA
                       organism = synthetic construct
SEQUENCE: 285
agataagagg gaaatgagat catgtcc                                      27

SEQ ID NO: 286         moltype = DNA  length = 27
FEATURE                Location/Qualifiers
source                 1..27
                       mol_type = other DNA
                       organism = synthetic construct
SEQUENCE: 286
agataccgat tttgattctc aaacaaa                                      27
```

```
SEQ ID NO: 287          moltype = DNA  length = 27
FEATURE                 Location/Qualifiers
source                  1..27
                        mol_type = other DNA
                        organism = synthetic construct
SEQUENCE: 287
agatgtctgt gatatacaca tcagaat                                        27

SEQ ID NO: 288          moltype = DNA  length = 27
FEATURE                 Location/Qualifiers
source                  1..27
                        mol_type = other DNA
                        organism = synthetic construct
SEQUENCE: 288
agatagccat ctcactacag ataactc                                        27

SEQ ID NO: 289          moltype = DNA  length = 27
FEATURE                 Location/Qualifiers
source                  1..27
                        mol_type = other DNA
                        organism = synthetic construct
SEQUENCE: 289
agatatttgg gcagctcccc taccccc                                        27

SEQ ID NO: 290          moltype = DNA  length = 27
FEATURE                 Location/Qualifiers
source                  1..27
                        mol_type = other DNA
                        organism = synthetic construct
SEQUENCE: 290
agattacttt gtcctccggt tctggaa                                        27

SEQ ID NO: 291          moltype = DNA  length = 27
FEATURE                 Location/Qualifiers
source                  1..27
                        mol_type = other DNA
                        organism = synthetic construct
SEQUENCE: 291
agattcctcc ggttctggaa ccacacc                                        27

SEQ ID NO: 292          moltype = DNA  length = 27
FEATURE                 Location/Qualifiers
source                  1..27
                        mol_type = other DNA
                        organism = synthetic construct
SEQUENCE: 292
agataagcta gtctagtgca agctaac                                        27

SEQ ID NO: 293          moltype = DNA  length = 27
FEATURE                 Location/Qualifiers
source                  1..27
                        mol_type = other DNA
                        organism = synthetic construct
SEQUENCE: 293
agatgcctct gattagggtg ggggcgt                                        27

SEQ ID NO: 294          moltype = DNA  length = 27
FEATURE                 Location/Qualifiers
source                  1..27
                        mol_type = other DNA
                        organism = synthetic construct
SEQUENCE: 294
agattctgcc acccacctcc tcacctt                                        27

SEQ ID NO: 295          moltype = DNA  length = 27
FEATURE                 Location/Qualifiers
source                  1..27
                        mol_type = other DNA
                        organism = synthetic construct
SEQUENCE: 295
agatcaggtc atcacagttg gggccac                                        27

SEQ ID NO: 296          moltype = DNA  length = 25
FEATURE                 Location/Qualifiers
source                  1..25
                        mol_type = other DNA
                        organism = synthetic construct
SEQUENCE: 296
agattcacag gctccaggaa gggtt                                          25
```

```
SEQ ID NO: 297          moltype = DNA  length = 25
FEATURE                 Location/Qualifiers
source                  1..25
                        mol_type = other DNA
                        organism = synthetic construct
SEQUENCE: 297
agatgagagt gaggacgtgt gtgtc                                         25

SEQ ID NO: 298          moltype = DNA  length = 25
FEATURE                 Location/Qualifiers
source                  1..25
                        mol_type = other DNA
                        organism = synthetic construct
SEQUENCE: 298
agattggcct ggaggctatc cagcg                                         25

SEQ ID NO: 299          moltype = DNA  length = 24
FEATURE                 Location/Qualifiers
source                  1..24
                        mol_type = other DNA
                        organism = synthetic construct
SEQUENCE: 299
agatgagtct ctcagctggt acac                                          24

SEQ ID NO: 300          moltype = DNA  length = 25
FEATURE                 Location/Qualifiers
source                  1..25
                        mol_type = other DNA
                        organism = synthetic construct
SEQUENCE: 300
agatgagtct ctcagctggt acacg                                         25

SEQ ID NO: 301          moltype = DNA  length = 26
FEATURE                 Location/Qualifiers
source                  1..26
                        mol_type = other DNA
                        organism = synthetic construct
SEQUENCE: 301
agatgagtct ctcagctggt acacgg                                        26

SEQ ID NO: 302          moltype = DNA  length = 28
FEATURE                 Location/Qualifiers
source                  1..28
                        mol_type = other DNA
                        organism = synthetic construct
SEQUENCE: 302
agatgagtct ctcagctggt acacggca                                      28

SEQ ID NO: 303          moltype = DNA  length = 24
FEATURE                 Location/Qualifiers
source                  1..24
                        mol_type = other DNA
                        organism = synthetic construct
SEQUENCE: 303
agatgggtga tcagacccaa cagc                                          24

SEQ ID NO: 304          moltype = DNA  length = 25
FEATURE                 Location/Qualifiers
source                  1..25
                        mol_type = other DNA
                        organism = synthetic construct
SEQUENCE: 304
agatgggtga tcagacccaa cagca                                         25

SEQ ID NO: 305          moltype = DNA  length = 26
FEATURE                 Location/Qualifiers
source                  1..26
                        mol_type = other DNA
                        organism = synthetic construct
SEQUENCE: 305
agatgggtga tcagacccaa cagcag                                        26

SEQ ID NO: 306          moltype = DNA  length = 27
FEATURE                 Location/Qualifiers
source                  1..27
                        mol_type = other DNA
                        organism = synthetic construct
SEQUENCE: 306
```

```
agatgggtga tcagacccaa cagcagg                                        27

SEQ ID NO: 307          moltype = DNA  length = 28
FEATURE                 Location/Qualifiers
source                  1..28
                        mol_type = other DNA
                        organism = synthetic construct
SEQUENCE: 307
agatgggtga tcagacccaa cagcaggt                                       28

SEQ ID NO: 308          moltype = DNA  length = 27
FEATURE                 Location/Qualifiers
source                  1..27
                        mol_type = other DNA
                        organism = synthetic construct
SEQUENCE: 308
aaaacctggt cgagctggac ggcgacg                                        27

SEQ ID NO: 309          moltype = DNA  length = 27
FEATURE                 Location/Qualifiers
source                  1..27
                        mol_type = other DNA
                        organism = synthetic construct
SEQUENCE: 309
aaaactgagc acccagtccg ccctgag                                        27

SEQ ID NO: 310          moltype = DNA  length = 27
FEATURE                 Location/Qualifiers
source                  1..27
                        mol_type = other DNA
                        organism = synthetic construct
SEQUENCE: 310
aaaacacgct ggatagcctc caggcca                                        27

SEQ ID NO: 311          moltype = DNA  length = 27
FEATURE                 Location/Qualifiers
source                  1..27
                        mol_type = other DNA
                        organism = synthetic construct
SEQUENCE: 311
aaaacattct ctgctggatg acgtgag                                        27

SEQ ID NO: 312          moltype = DNA  length = 27
FEATURE                 Location/Qualifiers
source                  1..27
                        mol_type = other DNA
                        organism = synthetic construct
SEQUENCE: 312
aaaatcatcc agcagagaat ggaaagt                                        27

SEQ ID NO: 313          moltype = DNA  length = 27
FEATURE                 Location/Qualifiers
source                  1..27
                        mol_type = other DNA
                        organism = synthetic construct
SEQUENCE: 313
aaaaaaccca gacacatagc aattcag                                        27

SEQ ID NO: 314          moltype = DNA  length = 27
FEATURE                 Location/Qualifiers
source                  1..27
                        mol_type = other DNA
                        organism = synthetic construct
SEQUENCE: 314
aaaatactga agaatggaga gagaatt                                        27

SEQ ID NO: 315          moltype = DNA  length = 27
FEATURE                 Location/Qualifiers
source                  1..27
                        mol_type = other DNA
                        organism = synthetic construct
SEQUENCE: 315
aaaagcctat tcaccgattt tgattct                                        27

SEQ ID NO: 316          moltype = DNA  length = 27
FEATURE                 Location/Qualifiers
source                  1..27
                        mol_type = other DNA
                        organism = synthetic construct
```

```
SEQUENCE: 316
aaaattgatt ctcaaacaaa tgtgtca                                         27

SEQ ID NO: 317         moltype = DNA  length = 27
FEATURE                Location/Qualifiers
source                 1..27
                       mol_type = other DNA
                       organism = synthetic construct
SEQUENCE: 317
aaaagccgtg taccagctga gagactc                                         27

SEQ ID NO: 318         moltype = DNA  length = 27
FEATURE                Location/Qualifiers
source                 1..27
                       mol_type = other DNA
                       organism = synthetic construct
SEQUENCE: 318
aaaagattct gatgtgtata tcacaga                                         27

SEQ ID NO: 319         moltype = DNA  length = 27
FEATURE                Location/Qualifiers
source                 1..27
                       mol_type = other DNA
                       organism = synthetic construct
SEQUENCE: 319
aaaattgtga cacatttgtt tgagaat                                         27

SEQ ID NO: 320         moltype = DNA  length = 27
FEATURE                Location/Qualifiers
source                 1..27
                       mol_type = other DNA
                       organism = synthetic construct
SEQUENCE: 320
aaaactcagg cggaggtgag cggaagg                                         27

SEQ ID NO: 321         moltype = DNA  length = 27
FEATURE                Location/Qualifiers
source                 1..27
                       mol_type = other DNA
                       organism = synthetic construct
SEQUENCE: 321
aaaacaacac atcggagagc ttcgtgc                                         27

SEQ ID NO: 322         moltype = DNA  length = 27
FEATURE                Location/Qualifiers
source                 1..27
                       mol_type = other DNA
                       organism = synthetic construct
SEQUENCE: 322
aaaatccctg gcccccaagg cgcagat                                         27

SEQ ID NO: 323         moltype = DNA  length = 27
FEATURE                Location/Qualifiers
source                 1..27
                       mol_type = other DNA
                       organism = synthetic construct
SEQUENCE: 323
aaaacaccca ggccagccgg ccagttc                                         27

SEQ ID NO: 324         moltype = DNA  length = 27
FEATURE                Location/Qualifiers
source                 1..27
                       mol_type = other DNA
                       organism = synthetic construct
SEQUENCE: 324
aaaactagct gagctctcgg acccctg                                         27

SEQ ID NO: 325         moltype = DNA  length = 27
FEATURE                Location/Qualifiers
source                 1..27
                       mol_type = other DNA
                       organism = synthetic construct
SEQUENCE: 325
aaaaactgtg gggtggaggg gacagat                                         27

SEQ ID NO: 326         moltype = DNA  length = 27
FEATURE                Location/Qualifiers
source                 1..27
                       mol_type = other DNA
```

```
                        organism = synthetic construct
SEQUENCE: 326
aaaagtaagg ggggtagggg agctgcc                                   27

SEQ ID NO: 327          moltype = DNA  length = 27
FEATURE                 Location/Qualifiers
source                  1..27
                        mol_type = other DNA
                        organism = synthetic construct
SEQUENCE: 327
aaaatggtgc ctgatatagc ttgacac                                   27

SEQ ID NO: 328          moltype = DNA  length = 27
FEATURE                 Location/Qualifiers
source                  1..27
                        mol_type = other DNA
                        organism = synthetic construct
SEQUENCE: 328
aaaaaggaat atcgggaaaa gacacat                                   27

SEQ ID NO: 329          moltype = DNA  length = 27
FEATURE                 Location/Qualifiers
source                  1..27
                        mol_type = other DNA
                        organism = synthetic construct
SEQUENCE: 329
aaaactgaga gactctaaat ccagtga                                   27

SEQ ID NO: 330          moltype = DNA  length = 27
FEATURE                 Location/Qualifiers
source                  1..27
                        mol_type = other DNA
                        organism = synthetic construct
SEQUENCE: 330
aaaatcactg gatttagagt ctctcag                                   27

SEQ ID NO: 331          moltype = DNA  length = 27
FEATURE                 Location/Qualifiers
source                  1..27
                        mol_type = other DNA
                        organism = synthetic construct
SEQUENCE: 331
aaaaggacat gatctcattt ccctctt                                   27

SEQ ID NO: 332          moltype = DNA  length = 27
FEATURE                 Location/Qualifiers
source                  1..27
                        mol_type = other DNA
                        organism = synthetic construct
SEQUENCE: 332
aaaatttgtt tgagaatcaa aatcggt                                   27

SEQ ID NO: 333          moltype = DNA  length = 27
FEATURE                 Location/Qualifiers
source                  1..27
                        mol_type = other DNA
                        organism = synthetic construct
SEQUENCE: 333
aaaaattctg atgtgtatat cacagac                                   27

SEQ ID NO: 334          moltype = DNA  length = 27
FEATURE                 Location/Qualifiers
source                  1..27
                        mol_type = other DNA
                        organism = synthetic construct
SEQUENCE: 334
aaaagagtta tctgtagtga gatggct                                   27

SEQ ID NO: 335          moltype = DNA  length = 27
FEATURE                 Location/Qualifiers
source                  1..27
                        mol_type = other DNA
                        organism = synthetic construct
SEQUENCE: 335
aaaagggggt aggggagctg cccaaat                                   27

SEQ ID NO: 336          moltype = DNA  length = 27
FEATURE                 Location/Qualifiers
source                  1..27
```

```
                         mol_type = other DNA
                         organism = synthetic construct
SEQUENCE: 336
aaaattccag aaccggagga caaagta                                              27

SEQ ID NO: 337           moltype = DNA  length = 27
FEATURE                  Location/Qualifiers
source                   1..27
                         mol_type = other DNA
                         organism = synthetic construct
SEQUENCE: 337
aaaaggtgtg gttccagaac cggagga                                              27

SEQ ID NO: 338           moltype = DNA  length = 27
FEATURE                  Location/Qualifiers
source                   1..27
                         mol_type = other DNA
                         organism = synthetic construct
SEQUENCE: 338
aaaagttagc ttgcactaga ctagctt                                              27

SEQ ID NO: 339           moltype = DNA  length = 27
FEATURE                  Location/Qualifiers
source                   1..27
                         mol_type = other DNA
                         organism = synthetic construct
SEQUENCE: 339
aaaaacgccc ccaccctaat cagaggc                                              27

SEQ ID NO: 340           moltype = DNA  length = 27
FEATURE                  Location/Qualifiers
source                   1..27
                         mol_type = other DNA
                         organism = synthetic construct
SEQUENCE: 340
aaaaaaggtg aggaggtggg tggcaga                                              27

SEQ ID NO: 341           moltype = DNA  length = 27
FEATURE                  Location/Qualifiers
source                   1..27
                         mol_type = other DNA
                         organism = synthetic construct
SEQUENCE: 341
aaaagtggcc ccaactgtga tgacctg                                              27

SEQ ID NO: 342           moltype = DNA  length = 25
FEATURE                  Location/Qualifiers
source                   1..25
                         mol_type = other DNA
                         organism = synthetic construct
SEQUENCE: 342
aaaaaaccct tcctggagcc tgtga                                                25

SEQ ID NO: 343           moltype = DNA  length = 25
FEATURE                  Location/Qualifiers
source                   1..25
                         mol_type = other DNA
                         organism = synthetic construct
SEQUENCE: 343
aaaagacaca cacgtcctca ctctc                                                25

SEQ ID NO: 344           moltype = DNA  length = 25
FEATURE                  Location/Qualifiers
source                   1..25
                         mol_type = other DNA
                         organism = synthetic construct
SEQUENCE: 344
aaaacgctgg atagcctcca ggcca                                                25

SEQ ID NO: 345           moltype = DNA  length = 24
FEATURE                  Location/Qualifiers
source                   1..24
                         mol_type = other DNA
                         organism = synthetic construct
SEQUENCE: 345
aaaagtgtac cagctgagag actc                                                 24

SEQ ID NO: 346           moltype = DNA  length = 25
FEATURE                  Location/Qualifiers
```

```
source                  1..25
                        mol_type = other DNA
                        organism = synthetic construct
SEQUENCE: 346
aaaacgtgta ccagctgaga gactc                                         25

SEQ ID NO: 347          moltype = DNA  length = 26
FEATURE                 Location/Qualifiers
source                  1..26
                        mol_type = other DNA
                        organism = synthetic construct
SEQUENCE: 347
aaaaccgtgt accagctgag agactc                                        26

SEQ ID NO: 348          moltype = DNA  length = 28
FEATURE                 Location/Qualifiers
source                  1..28
                        mol_type = other DNA
                        organism = synthetic construct
SEQUENCE: 348
aaaatgccgt gtaccagctg agagactc                                      28

SEQ ID NO: 349          moltype = DNA  length = 24
FEATURE                 Location/Qualifiers
source                  1..24
                        mol_type = other DNA
                        organism = synthetic construct
SEQUENCE: 349
aaaagctgtt gggtctgatc accc                                          24

SEQ ID NO: 350          moltype = DNA  length = 25
FEATURE                 Location/Qualifiers
source                  1..25
                        mol_type = other DNA
                        organism = synthetic construct
SEQUENCE: 350
aaaatgctgt tgggtctgat caccc                                         25

SEQ ID NO: 351          moltype = DNA  length = 26
FEATURE                 Location/Qualifiers
source                  1..26
                        mol_type = other DNA
                        organism = synthetic construct
SEQUENCE: 351
aaaactgctg ttgggtctga tcaccc                                        26

SEQ ID NO: 352          moltype = DNA  length = 28
FEATURE                 Location/Qualifiers
source                  1..28
                        mol_type = other DNA
                        organism = synthetic construct
SEQUENCE: 352
aaaaacctgc tgttgggtct gatcaccc                                      28

SEQ ID NO: 353          moltype = DNA  length = 81
FEATURE                 Location/Qualifiers
source                  1..81
                        mol_type = other DNA
                        organism = synthetic construct
SEQUENCE: 353
cctctaatac gactcactat agcctttgga agtactaaga atttctactg ttgtagatag  60
gtgaagttcg agggcgacga a                                             81

SEQ ID NO: 354          moltype = DNA  length = 81
FEATURE                 Location/Qualifiers
source                  1..81
                        mol_type = other DNA
                        organism = synthetic construct
SEQUENCE: 354
ttcgtcgccc tcgaacttca cctatctaca acagtagaaa ttcttagtac ttccaaaggc  60
tatagtgagt cgtattagag g                                             81

SEQ ID NO: 355          moltype = DNA  length = 80
FEATURE                 Location/Qualifiers
source                  1..80
                        mol_type = other DNA
                        organism = synthetic construct
SEQUENCE: 355
cctctaatac gactcactat aggctactaa gcctttataa tttctactat tgtagatagg  60
```

```
tgaagttcga gggcgacgaa                                              80

SEQ ID NO: 356          moltype = DNA  length = 80
FEATURE                 Location/Qualifiers
source                  1..80
                        mol_type = other DNA
                        organism = synthetic construct
SEQUENCE: 356
ttcgtcgccc tcgaacttca cctatctaca atagtagaaa ttataaaggc ttagtagcct  60
atagtgagtc gtattagagg                                              80

SEQ ID NO: 357          moltype = DNA  length = 80
FEATURE                 Location/Qualifiers
source                  1..80
                        mol_type = other DNA
                        organism = synthetic construct
SEQUENCE: 357
cctctaatac gactcactat agtctgaaag actatataat ttctacttcg tgtagatagg  60
tgaagttcga gggcgacgaa                                              80

SEQ ID NO: 358          moltype = DNA  length = 80
FEATURE                 Location/Qualifiers
source                  1..80
                        mol_type = other DNA
                        organism = synthetic construct
SEQUENCE: 358
ttcgtcgccc tcgaacttca cctatctaca cgaagtagaa attatatagt ctttcagact  60
atagtgagtc gtattagagg                                              80

SEQ ID NO: 359          moltype = DNA  length = 31
FEATURE                 Location/Qualifiers
source                  1..31
                        mol_type = other DNA
                        organism = synthetic construct
SEQUENCE: 359
cggcattcct gctgaaccgc tcttccgatc t                                 31

SEQ ID NO: 360          moltype = DNA  length = 30
FEATURE                 Location/Qualifiers
source                  1..30
                        mol_type = other DNA
                        organism = synthetic construct
SEQUENCE: 360
gatcggaaga gcggttcagc aggaatgccg                                   30

SEQ ID NO: 361          moltype = DNA  length = 55
FEATURE                 Location/Qualifiers
source                  1..55
                        mol_type = other DNA
                        organism = synthetic construct
SEQUENCE: 361
tcgtcggcag cgtcagatgt gtataagaga cagctgctga accgctcttc cgatc       55

SEQ ID NO: 362          moltype = DNA  length = 60
FEATURE                 Location/Qualifiers
source                  1..60
                        mol_type = other DNA
                        organism = synthetic construct
SEQUENCE: 362
tcgtcggcag cgtcagatgt gtataagaga cagtaagact gctgaaccgc tcttccgatc  60

SEQ ID NO: 363          moltype = DNA  length = 72
FEATURE                 Location/Qualifiers
source                  1..72
                        mol_type = other DNA
                        organism = synthetic construct
SEQUENCE: 363
tcgtcggcag cgtcagatgt gtataagaga caggctagac ctaatgtgat ctgctgaacc  60
gctcttccga tc                                                      72

SEQ ID NO: 364          moltype = DNA  length = 63
FEATURE                 Location/Qualifiers
source                  1..63
                        mol_type = other DNA
                        organism = synthetic construct
SEQUENCE: 364
gtctcgtggg ctcggagatg tgtataagag acagtctgcg ttctgattta atctgtatca  60
ggc                                                                63
```

```
SEQ ID NO: 365          moltype = AA  length = 6
FEATURE                 Location/Qualifiers
source                  1..6
                        mol_type = protein
                        organism = synthetic construct
SEQUENCE: 365
HHHHHH                                                                     6

SEQ ID NO: 366          moltype = DNA  length = 20
FEATURE                 Location/Qualifiers
source                  1..20
                        mol_type = other DNA
                        organism = synthetic construct
SEQUENCE: 366
catcacgagc agctggtttc                                                      20

SEQ ID NO: 367          moltype = DNA  length = 20
FEATURE                 Location/Qualifiers
source                  1..20
                        mol_type = other DNA
                        organism = synthetic construct
SEQUENCE: 367
ctctaacctg gcactgcgtc                                                      20

SEQ ID NO: 368          moltype = DNA  length = 20
FEATURE                 Location/Qualifiers
source                  1..20
                        mol_type = other DNA
                        organism = synthetic construct
SEQUENCE: 368
tggccagagt ggaaatggaa                                                      20

SEQ ID NO: 369          moltype = DNA  length = 20
FEATURE                 Location/Qualifiers
source                  1..20
                        mol_type = other DNA
                        organism = synthetic construct
SEQUENCE: 369
cactgcctct gtcactctcg                                                      20

SEQ ID NO: 370          moltype = DNA  length = 21
FEATURE                 Location/Qualifiers
source                  1..21
                        mol_type = other DNA
                        organism = synthetic construct
SEQUENCE: 370
cctcacgtag aaggaagagg c                                                    21

SEQ ID NO: 371          moltype = DNA  length = 20
FEATURE                 Location/Qualifiers
source                  1..20
                        mol_type = other DNA
                        organism = synthetic construct
SEQUENCE: 371
aatggtgacc ggcatctctg                                                      20

SEQ ID NO: 372          moltype = DNA  length = 20
FEATURE                 Location/Qualifiers
source                  1..20
                        mol_type = other DNA
                        organism = synthetic construct
SEQUENCE: 372
ccttatattc ccagggccgg                                                      20

SEQ ID NO: 373          moltype = DNA  length = 20
FEATURE                 Location/Qualifiers
source                  1..20
                        mol_type = other DNA
                        organism = synthetic construct
SEQUENCE: 373
actttgatgt ctgcaggcca                                                      20

SEQ ID NO: 374          moltype = DNA  length = 21
FEATURE                 Location/Qualifiers
source                  1..21
                        mol_type = other DNA
                        organism = synthetic construct
SEQUENCE: 374
atttcggact accctgagga g                                                    21
```

```
SEQ ID NO: 375         moltype = DNA  length = 20
FEATURE                Location/Qualifiers
source                 1..20
                       mol_type = other DNA
                       organism = synthetic construct
SEQUENCE: 375
tgctagactt gctgctcctt                                              20

SEQ ID NO: 376         moltype = DNA  length = 20
FEATURE                Location/Qualifiers
source                 1..20
                       mol_type = other DNA
                       organism = synthetic construct
SEQUENCE: 376
tgaacttcag ctcctgcaca                                              20

SEQ ID NO: 377         moltype = DNA  length = 24
FEATURE                Location/Qualifiers
source                 1..24
                       mol_type = other DNA
                       organism = synthetic construct
SEQUENCE: 377
gcatcacaac aggcagagaa tgtc                                         24

SEQ ID NO: 378         moltype = DNA  length = 20
FEATURE                Location/Qualifiers
source                 1..20
                       mol_type = other DNA
                       organism = synthetic construct
SEQUENCE: 378
tggcaatgga taaggccgag                                              20

SEQ ID NO: 379         moltype = DNA  length = 23
FEATURE                Location/Qualifiers
source                 1..23
                       mol_type = other DNA
                       organism = synthetic construct
SEQUENCE: 379
ggtgctagga catgcgaact tag                                          23

SEQ ID NO: 380         moltype = DNA  length = 21
FEATURE                Location/Qualifiers
source                 1..21
                       mol_type = other DNA
                       organism = synthetic construct
SEQUENCE: 380
tgtatttgtg caagtgctgc t                                            21

SEQ ID NO: 381         moltype = DNA  length = 17
FEATURE                Location/Qualifiers
source                 1..17
                       mol_type = other DNA
                       organism = synthetic construct
SEQUENCE: 381
tggggctccc atcctta                                                 17

SEQ ID NO: 382         moltype = DNA  length = 20
FEATURE                Location/Qualifiers
source                 1..20
                       mol_type = other DNA
                       organism = synthetic construct
SEQUENCE: 382
agagatgccg gtcaccattc                                              20

SEQ ID NO: 383         moltype = DNA  length = 20
FEATURE                Location/Qualifiers
source                 1..20
                       mol_type = other DNA
                       organism = synthetic construct
SEQUENCE: 383
aaggcacagt ggatcatgca                                              20

SEQ ID NO: 384         moltype = DNA  length = 20
FEATURE                Location/Qualifiers
source                 1..20
                       mol_type = other DNA
                       organism = synthetic construct
SEQUENCE: 384
```

```
gagaaaggga gtagaggcgg                                               20

SEQ ID NO: 385          moltype = DNA  length = 18
FEATURE                 Location/Qualifiers
source                  1..18
                        mol_type = other DNA
                        organism = synthetic construct
SEQUENCE: 385
gagcctcagc ccttccac                                                 18

SEQ ID NO: 386          moltype = DNA  length = 22
FEATURE                 Location/Qualifiers
source                  1..22
                        mol_type = other DNA
                        organism = synthetic construct
SEQUENCE: 386
ggaatctacc accccaggct ct                                            22

SEQ ID NO: 387          moltype = DNA  length = 20
FEATURE                 Location/Qualifiers
source                  1..20
                        mol_type = other DNA
                        organism = synthetic construct
SEQUENCE: 387
tgaagggatt gtgctggtgt                                               20

SEQ ID NO: 388          moltype = DNA  length = 20
FEATURE                 Location/Qualifiers
source                  1..20
                        mol_type = other DNA
                        organism = synthetic construct
SEQUENCE: 388
tgcagttccc agtacgttcc                                               20

SEQ ID NO: 389          moltype = DNA  length = 24
FEATURE                 Location/Qualifiers
source                  1..24
                        mol_type = other DNA
                        organism = synthetic construct
SEQUENCE: 389
tatgacgtca gggggaggca agtc                                          24

SEQ ID NO: 390          moltype = DNA  length = 31
FEATURE                 Location/Qualifiers
source                  1..31
                        mol_type = other DNA
                        organism = synthetic construct
SEQUENCE: 390
acgattagaa ataatttcta ctgttgtaga t                                  31

SEQ ID NO: 391          moltype = DNA  length = 36
FEATURE                 Location/Qualifiers
source                  1..36
                        mol_type = other DNA
                        organism = synthetic construct
SEQUENCE: 391
ctttgaaaga atataatttc tactgaaagt gtagat                             36

SEQ ID NO: 392          moltype = DNA  length = 36
FEATURE                 Location/Qualifiers
source                  1..36
                        mol_type = other DNA
                        organism = synthetic construct
SEQUENCE: 392
gtttaataat aatacataat ttctactatt gtagat                             36

SEQ ID NO: 393          moltype = DNA  length = 36
FEATURE                 Location/Qualifiers
source                  1..36
                        mol_type = other DNA
                        organism = synthetic construct
SEQUENCE: 393
gtctataaga ctaatttaat ttctactatt gtagat                             36

SEQ ID NO: 394          moltype = DNA  length = 36
FEATURE                 Location/Qualifiers
source                  1..36
                        mol_type = other DNA
                        organism = synthetic construct
```

```
SEQUENCE: 394
gtttataaac cttatctaat ttctactgtt gtagat                     36

SEQ ID NO: 395         moltype = DNA  length = 35
FEATURE                Location/Qualifiers
source                 1..35
                       mol_type = other DNA
                       organism = synthetic construct
SEQUENCE: 395
tctaaagctc tttaagaatt tctactttcg tagat                      35

SEQ ID NO: 396         moltype = DNA  length = 34
FEATURE                Location/Qualifiers
source                 1..34
                       mol_type = other DNA
                       organism = synthetic construct
SEQUENCE: 396
ctaagaggct caaataattt ctactattgt agat                       34

SEQ ID NO: 397         moltype = DNA  length = 36
FEATURE                Location/Qualifiers
source                 1..36
                       mol_type = other DNA
                       organism = synthetic construct
SEQUENCE: 397
cctttggaag tactaagaat ttctactgtt gtagat                     36

SEQ ID NO: 398         moltype = DNA  length = 36
FEATURE                Location/Qualifiers
source                 1..36
                       mol_type = other DNA
                       organism = synthetic construct
SEQUENCE: 398
ggctataaaa gccatataat ttctactatt gtagat                     36

SEQ ID NO: 399         moltype = DNA  length = 36
FEATURE                Location/Qualifiers
source                 1..36
                       mol_type = other DNA
                       organism = synthetic construct
SEQUENCE: 399
gactattaag tcttttgaat ttctactgtt gtagat                     36

SEQ ID NO: 400         moltype = DNA  length = 35
FEATURE                Location/Qualifiers
source                 1..35
                       mol_type = other DNA
                       organism = synthetic construct
SEQUENCE: 400
tctagaatat ataggtaatt tctacttatg tagat                      35

SEQ ID NO: 401         moltype = DNA  length = 37
FEATURE                Location/Qualifiers
source                 1..37
                       mol_type = other DNA
                       organism = synthetic construct
SEQUENCE: 401
ggcaataagc catatacaat ttctactgta tgtagat                    37

SEQ ID NO: 402         moltype = DNA  length = 36
FEATURE                Location/Qualifiers
source                 1..36
                       mol_type = other DNA
                       organism = synthetic construct
SEQUENCE: 402
gtctgaaaga ctatataatt tctacttcgt gtagat                     36

SEQ ID NO: 403         moltype = DNA  length = 36
FEATURE                Location/Qualifiers
source                 1..36
                       mol_type = other DNA
                       organism = synthetic construct
SEQUENCE: 403
gtctacggaa cgtctgtaat ttctactgtt gtagat                     36

SEQ ID NO: 404         moltype = DNA  length = 35
FEATURE                Location/Qualifiers
source                 1..35
                       mol_type = other DNA
```

```
                        organism = synthetic construct
SEQUENCE: 404
tttaaacgaa ctattaaatt tctactgttg tagat                         35

SEQ ID NO: 405          moltype = DNA  length = 36
FEATURE                 Location/Qualifiers
source                  1..36
                        mol_type = other DNA
                        organism = synthetic construct
SEQUENCE: 405
gtttaatact tatatataat ttctactatt gtagat                        36

SEQ ID NO: 406          moltype = DNA  length = 35
FEATURE                 Location/Qualifiers
source                  1..35
                        mol_type = other DNA
                        organism = synthetic construct
SEQUENCE: 406
aataataatc ccttataatt tctacttttg tagat                         35

SEQ ID NO: 407          moltype = DNA  length = 36
FEATURE                 Location/Qualifiers
source                  1..36
                        mol_type = other DNA
                        organism = synthetic construct
SEQUENCE: 407
gtctataaga cgaactaaat ttctactatt gtagat                        36

SEQ ID NO: 408          moltype = DNA  length = 36
FEATURE                 Location/Qualifiers
source                  1..36
                        mol_type = other DNA
                        organism = synthetic construct
SEQUENCE: 408
ggctactaag cctttataat ttctactatt gtagat                        36

SEQ ID NO: 409          moltype = DNA  length = 36
FEATURE                 Location/Qualifiers
source                  1..36
                        mol_type = other DNA
                        organism = synthetic construct
SEQUENCE: 409
gtctataaag acgaatgaat ttctactatt gtagat                        36

SEQ ID NO: 410          moltype = DNA  length = 31
FEATURE                 Location/Qualifiers
source                  1..31
                        mol_type = other DNA
                        organism = synthetic construct
SEQUENCE: 410
cctgccgtgt accagctgag agactctaaa t                             31

SEQ ID NO: 411          moltype = DNA  length = 31
FEATURE                 Location/Qualifiers
source                  1..31
                        mol_type = other DNA
                        organism = synthetic construct
SEQUENCE: 411
cctgccgtga gactctgtcc cggttgtgag a                             31

SEQ ID NO: 412          moltype = DNA  length = 27
FEATURE                 Location/Qualifiers
source                  1..27
                        mol_type = other DNA
                        organism = synthetic construct
SEQUENCE: 412
tttagagtct ctcagctggt acacggc                                  27
```